US011208697B2

(12) United States Patent
Davicioni et al.

(10) Patent No.: US 11,208,697 B2
(45) Date of Patent: Dec. 28, 2021

(54) MOLECULAR SUBTYPING, PROGNOSIS, AND TREATMENT OF BLADDER CANCER

(71) Applicants: DECIPHER BIOSCIENCES, INC., San Diego, CA (US); THE UNIVERSITY OF BRITISH COLUMBIA, Vancouver (CA)

(72) Inventors: Elai Davicioni, La Jolla, CA (US); Hussam Al-Deen Ashab, Ontario (CA); Nicholas Erho, Vancouver (CA); Peter Black, Vancouver (CA)

(73) Assignees: Decipher Biosciences, Inc., San Diego, CA (US); The University of British Columbia, Vancouver (CA)

( * ) Notice: Subject to any disclaimer, the term of this patent is extended or adjusted under 35 U.S.C. 154(b) by 155 days.

(21) Appl. No.: 15/875,871

(22) Filed: Jan. 19, 2018

(65) Prior Publication Data
US 2018/0216197 A1    Aug. 2, 2018

Related U.S. Application Data

(60) Provisional application No. 62/448,921, filed on Jan. 20, 2017.

(51) Int. Cl.
| C12Q 1/6886 | (2018.01) |
| G16H 50/20 | (2018.01) |
| G16H 20/10 | (2018.01) |
| G16H 50/70 | (2018.01) |
| G16H 20/40 | (2018.01) |
| G16H 50/50 | (2018.01) |
| G16H 50/30 | (2018.01) |
| C12Q 1/6811 | (2018.01) |
| C12Q 1/6809 | (2018.01) |

(52) U.S. Cl.
CPC .......... *C12Q 1/6886* (2013.01); *C12Q 1/6811* (2013.01); *G16H 20/10* (2018.01); *G16H 20/40* (2018.01); *G16H 50/20* (2018.01); *G16H 50/30* (2018.01); *G16H 50/50* (2018.01); *G16H 50/70* (2018.01); *C12Q 1/6809* (2013.01); *C12Q 2600/106* (2013.01); *C12Q 2600/112* (2013.01); *C12Q 2600/118* (2013.01); *C12Q 2600/158* (2013.01); *C12Q 2600/166* (2013.01)

(58) Field of Classification Search
None
See application file for complete search history.

(56) References Cited

U.S. PATENT DOCUMENTS

| 3,645,691 A | 2/1972 | Guenter et al. |
| 3,687,808 A | 8/1972 | Thomas, Jr. et al. |
| 4,323,546 A | 4/1982 | Crockfor et al. |
| 4,683,195 A | 7/1987 | Mullis et al. |
| 4,683,202 A | 7/1987 | Mullis et al. |
| 4,800,159 A | 1/1989 | Mullis et al. |
| 4,965,188 A | 10/1990 | Mullis et al. |
| 5,130,238 A | 7/1992 | Malek et al. |
| 5,143,854 A | 9/1992 | Pinung et al. |
| 5,225,326 A | 7/1993 | Bresser et al. |
| 5,270,184 A | 12/1993 | Walker et al. |
| 5,283,174 A | 2/1994 | Arnold et al. |
| 5,288,514 A | 2/1994 | Ellman |
| 5,384,261 A | 1/1995 | Winkle et al. |
| 5,399,491 A | 3/1995 | Kacian et al. |
| 5,455,166 A | 10/1995 | Walker |
| 5,480,784 A | 1/1996 | Kacian et al. |
| 5,494,810 A | 2/1996 | Barany et al. |
| 5,538,848 A | 7/1996 | Livak et al. |
| 5,545,524 A | 8/1996 | Trent et al. |
| 5,677,195 A | 10/1997 | Winkler et al. |
| 5,705,365 A | 1/1998 | Ryder et al. |
| 5,710,029 A | 1/1998 | Ryder et al. |
| 5,711,029 A | 1/1998 | Ryder et al. |
| 5,744,305 A | 4/1998 | Fodor et al. |
| 5,814,447 A | 9/1998 | Ishiguro et al. |
| 5,824,518 A | 10/1998 | Kacian et al. |
| 5,830,711 A | 11/1998 | Barany et al. |

(Continued)

FOREIGN PATENT DOCUMENTS

| EP | 0 684 315 | 11/1995 |
| EP | 1 409 727 | 11/2005 |

(Continued)

OTHER PUBLICATIONS

US 5,962,233 A, 10/1999, Livak et al. (withdrawn)
Choi et al. Identification of distinct basal and luminal subtypes of muscle-invasive bladder cancer with different sensitivities to frontline chemotherapy. Feb. 10, 2014. Cancer Cell. vol. 25, No. 2, pp. 152-165. (Year: 2014).*

(Continued)

*Primary Examiner* — Channing S Mahatan
(74) *Attorney, Agent, or Firm* — Knobbe, Martens, Olson & Bear, LLP

(57) ABSTRACT

The present invention relates to methods, systems and kits for the diagnosis, prognosis, and treatment of bladder cancer in a subject. The invention also provides biomarkers that define subgroups of bladder cancer, clinically useful classifiers for distinguishing bladder cancer subtypes, bioinformatic methods for determining clinically useful classifiers, and methods of use of each of the foregoing. The methods, systems and kits can provide expression-based analysis of biomarkers for purposes of subtyping bladder cancer in a subject. Further disclosed herein, in certain instances, are probe sets for use in subtyping bladder cancer in a subject. Classifiers for subtyping a bladder cancer are provided. Methods of treating bladder cancer based on molecular subtyping are also provided.

11 Claims, 40 Drawing Sheets

Specification includes a Sequence Listing.

(56) References Cited

U.S. PATENT DOCUMENTS

| | | |
|---|---|---|
| 5,846,717 A | 12/1998 | Brow et al. |
| 5,854,033 A | 12/1998 | Lizardi |
| 5,854,206 A | 12/1998 | Twardzik et al. |
| 5,888,779 A | 3/1999 | Kacian et al. |
| 5,925,517 A | 7/1999 | Tyagi et al. |
| 5,928,862 A | 7/1999 | Morrison |
| 5,965,360 A | 10/1999 | Zain et al. |
| 5,985,557 A | 11/1999 | Prudent et al. |
| 5,989,815 A | 11/1999 | Skolnick et al. |
| 5,994,069 A | 11/1999 | Hall et al. |
| 6,001,567 A | 12/1999 | Brow et al. |
| 6,022,692 A | 2/2000 | Coulie et al. |
| 6,027,887 A | 2/2000 | Zavada et al. |
| 6,034,218 A | 3/2000 | Reed et al. |
| 6,090,543 A | 7/2000 | Prudent et al. |
| 6,121,489 A | 9/2000 | Dorner et al. |
| 6,136,182 A | 10/2000 | Dolan et al. |
| 6,150,097 A | 11/2000 | Tyagi et al. |
| 6,198,107 B1 | 3/2001 | Seville |
| 6,218,523 B1 | 4/2001 | French |
| 6,225,051 B1 | 5/2001 | Sugiyama et al. |
| 6,251,639 B1 | 6/2001 | Kurn |
| 6,262,245 B1 | 7/2001 | Xu et al. |
| 6,268,142 B1 | 7/2001 | Duff et al. |
| 6,303,305 B1 | 10/2001 | Wittwer et al. |
| 6,410,278 B1 | 6/2002 | Notomi et al. |
| 6,436,642 B1 | 8/2002 | Gould-Rothberg et al. |
| 6,541,205 B1 | 4/2003 | Yokoyama et al. |
| 6,573,043 B1 | 6/2003 | Cohen et al. |
| 6,630,358 B1 | 10/2003 | Wagner et al. |
| 6,723,506 B2 | 4/2004 | Fletcher et al. |
| 6,828,429 B1 | 12/2004 | Srivastava et al. |
| 7,008,765 B1 | 3/2006 | Bussemakers et al. |
| 7,186,514 B2 | 3/2007 | Zavada et al. |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,280,922 B2 | 10/2007 | Mei et al. |
| 7,300,788 B2 | 11/2007 | Matsuzaki et al. |
| 7,319,011 B2 | 1/2008 | Riggins et al. |
| 7,323,305 B2 | 1/2008 | Leamon et al. |
| 7,335,762 B2 | 2/2008 | Rothberg et al. |
| 7,358,061 B2 | 4/2008 | Yamamoto et al. |
| 7,361,488 B2 | 4/2008 | Fan et al. |
| 7,378,233 B2 | 5/2008 | Sidransky et al. |
| 7,407,755 B2 | 8/2008 | Lubinski et al. |
| 7,541,169 B2 | 6/2009 | Freimuth et al. |
| 7,598,052 B2 | 10/2009 | Giordanos et al. |
| 7,662,553 B2 | 2/2010 | Lenz et al. |
| 7,767,391 B2 | 8/2010 | Scott et al. |
| 7,901,881 B2 | 3/2011 | Libutti et al. |
| 7,901,888 B2 | 3/2011 | Kebebew |
| 7,914,988 B1 | 3/2011 | Chudin et al. |
| 7,927,826 B2 | 4/2011 | Riggins et al. |
| 8,008,009 B2 | 8/2011 | Choquet-Kastylevsky et al. |
| 8,202,692 B2 | 6/2012 | Giordano et al. |
| 8,273,539 B2 | 9/2012 | Klee et al. |
| 8,293,880 B2 | 10/2012 | Cote et al. |
| 8,299,233 B2 | 10/2012 | Andre et al. |
| 8,338,109 B2 | 12/2012 | Vasmatzis et al. |
| 8,354,228 B2 | 1/2013 | Ron |
| 8,465,914 B2 | 6/2013 | Brown et al. |
| 8,541,170 B2 | 9/2013 | Kennedy et al. |
| 8,568,971 B2 | 10/2013 | Brown et al. |
| 8,669,057 B2 | 3/2014 | Kennedy et al. |
| 8,802,599 B2 | 8/2014 | Aharonov et al. |
| 8,828,656 B2 | 9/2014 | Bullerdiek et al. |
| 8,877,445 B2 | 11/2014 | Shackney |
| 8,945,829 B2 | 2/2015 | Keutgen et al. |
| 9,040,286 B2 | 5/2015 | Zon et al. |
| 9,074,258 B2 | 7/2015 | Davicion et al. |
| 9,096,906 B2 | 8/2015 | Aharonov et al. |
| 9,157,123 B2 | 10/2015 | Xing |
| 9,175,352 B2 | 11/2015 | Keutgen et al. |
| 9,206,481 B2 | 12/2015 | Srivastava et al. |
| 9,206,482 B2 | 12/2015 | Davicioni et al. |
| 9,234,244 B2 | 1/2016 | Zeiger et al. |
| 9,435,812 B2 | 9/2016 | Pestano et al. |
| 9,495,515 B1 | 11/2016 | Giulia et al. |
| 9,534,249 B2 | 1/2017 | Vasmatzis et al. |
| 9,587,279 B2 | 3/2017 | Fahey, III et al. |
| 9,617,604 B2 | 4/2017 | Davicion et al. |
| 9,708,667 B2 | 7/2017 | Yanai et al. |
| 9,714,452 B2 | 7/2017 | Davicioni et al. |
| 9,856,537 B2 | 1/2018 | Kennedy et al. |
| 9,994,907 B2 | 6/2018 | Davicioni et al. |
| 10,114,924 B2 | 10/2018 | Kennedy et al. |
| 10,407,731 B2 | 9/2019 | Klee et al. |
| 10,422,009 B2 | 9/2019 | Davicioni et al. |
| 10,494,677 B2 | 12/2019 | Vasmatzis et al. |
| 10,865,452 B2 | 12/2020 | Davicioni |
| 2001/0051344 A1 | 12/2001 | Shalon et al. |
| 2002/0076735 A1 | 6/2002 | Williams et al. |
| 2002/0090633 A1 | 7/2002 | Becker et al. |
| 2002/0119463 A1 | 8/2002 | Fads |
| 2002/0168638 A1 | 11/2002 | Schlegel et al. |
| 2002/0169137 A1 | 11/2002 | Reiner et al. |
| 2002/0182586 A1 | 12/2002 | Morris et al. |
| 2003/0119168 A1 | 6/2003 | Madison et al. |
| 2003/0152980 A1 | 8/2003 | Golub et al. |
| 2003/0175736 A1 | 9/2003 | Chinnaiyan et al. |
| 2003/0185830 A1 | 10/2003 | Xu et al. |
| 2003/0186248 A1 | 10/2003 | Erlander et al. |
| 2003/0190602 A1 | 10/2003 | Pressman et al. |
| 2003/0194734 A1 | 10/2003 | Jatkoe |
| 2003/0224399 A1 | 12/2003 | Reed et al. |
| 2003/0235820 A1 | 12/2003 | Mack et al. |
| 2004/0009481 A1 | 1/2004 | Schlegel et al. |
| 2004/0018493 A1 | 1/2004 | Anastasio et al. |
| 2004/0019466 A1 | 1/2004 | Minor et al. |
| 2004/0029114 A1 | 2/2004 | Mack et al. |
| 2004/0058378 A1 | 3/2004 | Kong et al. |
| 2004/0259086 A1 | 12/2004 | Schlegel et al. |
| 2005/0042222 A1 | 2/2005 | Yamamoto et al. |
| 2005/0042638 A1 | 2/2005 | Arnold et al. |
| 2005/0048533 A1 | 3/2005 | Sidransky et al. |
| 2005/0064455 A1 | 3/2005 | Baker et al. |
| 2005/0118625 A1 | 6/2005 | Mounts |
| 2005/0137805 A1 | 6/2005 | Lewin et al. |
| 2005/0202442 A1 | 9/2005 | Morris et al. |
| 2005/0227917 A1 | 10/2005 | Williams et al. |
| 2005/0240357 A1 | 10/2005 | Minor |
| 2005/0250125 A1 | 11/2005 | Novakoff |
| 2005/0260646 A1 | 11/2005 | Baker et al. |
| 2005/0266443 A1 | 12/2005 | Croce et al. |
| 2005/0266459 A1 | 12/2005 | Poulsen |
| 2006/0019256 A1 | 1/2006 | Clarke et al. |
| 2006/0019615 A1 | 1/2006 | Ditmer |
| 2006/0035244 A1 | 2/2006 | Riggins et al. |
| 2006/0046253 A1 | 3/2006 | Nakao |
| 2006/0046265 A1 | 3/2006 | Becker et al. |
| 2006/0083744 A1 | 4/2006 | Chen et al. |
| 2006/0088851 A1 | 4/2006 | Erlander et al. |
| 2006/0094061 A1 | 5/2006 | Brys et al. |
| 2006/0105360 A1 | 5/2006 | Croce et al. |
| 2006/0127907 A1 | 6/2006 | Matsubara et al. |
| 2006/0134663 A1 | 6/2006 | Harkin et al. |
| 2006/0204989 A1 | 9/2006 | Kopreski |
| 2006/0211017 A1 | 9/2006 | Chinnaiyan et al. |
| 2007/0010469 A1 | 1/2007 | Chan |
| 2007/0020657 A1 | 1/2007 | Grebe et al. |
| 2007/0031873 A1 | 2/2007 | Wang et al. |
| 2007/0037165 A1 | 2/2007 | Venter et al. |
| 2007/0037186 A1 | 2/2007 | Jiang et al. |
| 2007/0048738 A1 | 3/2007 | Donkena et al. |
| 2007/0065827 A1 | 3/2007 | Pauloski et al. |
| 2007/0065833 A1 | 3/2007 | Gupta |
| 2007/0083334 A1 | 4/2007 | Mintz et al. |
| 2007/0099197 A1 | 5/2007 | Afar et al. |
| 2007/0099209 A1 | 5/2007 | Clarke et al. |
| 2007/0105133 A1 | 5/2007 | Clarke et al. |
| 2007/0148667 A1 | 6/2007 | Williams et al. |
| 2007/0148687 A1 | 6/2007 | Bedingham et al. |
| 2007/0161004 A1 | 7/2007 | Brown et al. |

(56) References Cited

U.S. PATENT DOCUMENTS

| | | |
|---|---|---|
| 2007/0172841 A1 | 7/2007 | Wang |
| 2007/0172844 A1 | 7/2007 | Lancaster et al. |
| 2007/0212702 A1 | 9/2007 | Tomlins et al. |
| 2007/0220621 A1 | 9/2007 | Clarke et al. |
| 2007/0238119 A1 | 10/2007 | Yu et al. |
| 2007/0259352 A1 | 11/2007 | Bentwich et al. |
| 2007/0275915 A1 | 11/2007 | Hallenbeck et al. |
| 2008/0009001 A1 | 1/2008 | Bettuzzi et al. |
| 2008/0028302 A1 | 1/2008 | Meschkat |
| 2008/0044824 A1 | 2/2008 | Giordano et al. |
| 2008/0076674 A1 | 3/2008 | Litman et al. |
| 2008/0124344 A1 | 5/2008 | Combs et al. |
| 2008/0131892 A1 | 6/2008 | Becker et al. |
| 2008/0145841 A1 | 6/2008 | Libutti et al. |
| 2008/0254470 A1 | 10/2008 | Berlkin |
| 2008/0269157 A1 | 10/2008 | Srivastava et al. |
| 2008/0274457 A1 | 11/2008 | Eng et al. |
| 2008/0281568 A1 | 11/2008 | Kao et al. |
| 2009/0020433 A1 | 1/2009 | Cohen et al. |
| 2009/0036415 A1 | 2/2009 | Rubin et al. |
| 2009/0062144 A1 | 3/2009 | Guo |
| 2009/0075921 A1 | 3/2009 | Ikegawa |
| 2009/0149333 A1 | 6/2009 | Knudsen et al. |
| 2009/0191535 A1 | 7/2009 | Connelly et al. |
| 2009/0204333 A1 | 8/2009 | Friend et al. |
| 2009/0239221 A1 | 9/2009 | Chinnaiyan et al. |
| 2009/0280490 A1 | 11/2009 | Baker et al. |
| 2009/0298082 A1 | 12/2009 | Klee et al. |
| 2010/0055704 A1 | 3/2010 | Giordano et al. |
| 2010/0075384 A1 | 3/2010 | Kong et al. |
| 2010/0099093 A1 | 4/2010 | Weaver et al. |
| 2010/0130377 A1 | 5/2010 | Vasmatzis et al. |
| 2010/0131286 A1 | 5/2010 | Houlgatte et al. |
| 2010/0131432 A1 | 5/2010 | Kennedy et al. |
| 2010/0178653 A1 | 7/2010 | Aharonov et al. |
| 2010/0021538 A1 | 8/2010 | Iljin et al. |
| 2010/0215638 A1 | 8/2010 | Ijin et al. |
| 2010/0257617 A1 | 10/2010 | Ami et al. |
| 2010/0279327 A1 | 11/2010 | Ossovskaya |
| 2010/0285979 A1 | 11/2010 | Zeiger et al. |
| 2011/0009286 A1 | 1/2011 | Andre et al. |
| 2011/0045462 A1 | 2/2011 | Fu et al. |
| 2011/0092375 A1 | 4/2011 | Zamore et al. |
| 2011/0136683 A1 | 6/2011 | Davicioni |
| 2011/0152110 A1 | 6/2011 | Vierlinger et al. |
| 2011/0178163 A1 | 7/2011 | Chowdhury |
| 2011/0212855 A1 | 9/2011 | Rafnar et al. |
| 2011/0229894 A1 | 9/2011 | Levy et al. |
| 2011/0230372 A1 | 9/2011 | Willman et al. |
| 2011/0236903 A1 | 9/2011 | McClelland |
| 2011/0287946 A1 | 11/2011 | Gudmundsson et al. |
| 2011/0294123 A1 | 12/2011 | Nakamura et al. |
| 2011/0312520 A1 | 12/2011 | Kennedy et al. |
| 2012/0015839 A1 | 1/2012 | Chinnaiyan |
| 2012/0015843 A1 | 1/2012 | Von et al. |
| 2012/0041274 A1 | 2/2012 | Stone et al. |
| 2012/0108453 A1 | 5/2012 | Smit et al. |
| 2012/0115743 A1 | 5/2012 | Davicioni et al. |
| 2012/0122698 A1 | 5/2012 | Stacey et al. |
| 2012/0122718 A1 | 5/2012 | Reisman |
| 2012/0157334 A1 | 6/2012 | Beaudenon-Huibregtse et al. |
| 2012/0172243 A1 | 7/2012 | Davicioni et al. |
| 2012/0214165 A1 | 8/2012 | Walfish et al. |
| 2012/0220474 A1 | 8/2012 | Kennedy et al. |
| 2012/0304318 A1 | 11/2012 | Ohnuma et al. |
| 2013/0004974 A1 | 1/2013 | Klee et al. |
| 2013/0023434 A1 | 1/2013 | Van |
| 2013/0142728 A1 | 6/2013 | Beaudenon-Huibregtse et al. |
| 2013/0150257 A1 | 6/2013 | Abdueva et al. |
| 2013/0172203 A1 | 7/2013 | Yeatman et al. |
| 2013/0184999 A1 | 7/2013 | Ding |
| 2013/0196866 A1 | 8/2013 | Pestano et al. |
| 2013/0225662 A1 | 8/2013 | Kennedy et al. |
| 2013/0231258 A1 | 9/2013 | Wilde et al. |
| 2013/0273543 A1 | 10/2013 | Gudmundsson et al. |
| 2013/0302808 A1 | 11/2013 | Vasmatzis |
| 2013/0302810 A1 | 11/2013 | Latham et al. |
| 2013/0303826 A1 | 11/2013 | Jurisica et al. |
| 2014/0030714 A1 | 1/2014 | Paschke et al. |
| 2014/0066323 A1 | 3/2014 | Buerki et al. |
| 2014/0080731 A1 | 3/2014 | Davicioni et al. |
| 2014/0087961 A1 | 3/2014 | Sulem et al. |
| 2014/0099261 A1 | 4/2014 | Keutgen et al. |
| 2014/0121126 A1 | 5/2014 | Bivona et al. |
| 2014/0143188 A1 | 5/2014 | Mackey et al. |
| 2014/0228237 A1 | 8/2014 | Kennedy et al. |
| 2014/0243240 A1 | 8/2014 | Soldin et al. |
| 2014/0302042 A1 | 10/2014 | Chin et al. |
| 2014/0315199 A1 | 10/2014 | Rhodes et al. |
| 2014/0315739 A1 | 10/2014 | Aharonov et al. |
| 2014/0349856 A1 | 11/2014 | Schnabel et al. |
| 2014/0349864 A1 | 11/2014 | Kennedy et al. |
| 2014/0371096 A1 | 12/2014 | Umbright et al. |
| 2015/0011401 A1 | 1/2015 | Davicioni et al. |
| 2015/0038376 A1 | 2/2015 | Tian et al. |
| 2015/0099665 A1 | 4/2015 | Rosenfeld et al. |
| 2015/0141470 A1 | 5/2015 | Garraway et al. |
| 2015/0030794 A1 | 10/2015 | Basu et al. |
| 2015/0275306 A1 | 10/2015 | Bernards et al. |
| 2015/0292030 A1* | 10/2015 | McConkey ...... G01N 33/57407 424/649 |
| 2015/0299808 A1 | 10/2015 | Gonzalez et al. |
| 2015/0329915 A1 | 11/2015 | Davicioni et al. |
| 2015/0368724 A1 | 12/2015 | Aharonov et al. |
| 2016/0024586 A1 | 1/2016 | Delfour et al. |
| 2016/0032395 A1 | 2/2016 | Davicioni et al. |
| 2016/0032400 A1 | 2/2016 | Gomis et al. |
| 2016/0068915 A1 | 3/2016 | Kennedy et al. |
| 2016/0076108 A1 | 3/2016 | Davicioni et al. |
| 2016/0115546 A1 | 4/2016 | Rosenfeld et al. |
| 2016/0120832 A1 | 5/2016 | Rabinowitz et al. |
| 2016/0251729 A1 | 9/2016 | Chinnaiyan et al. |
| 2016/0312305 A1 | 10/2016 | Kennedy et al. |
| 2016/0312306 A1 | 10/2016 | Kennedy et al. |
| 2016/0312307 A1 | 10/2016 | Kennedy et al. |
| 2016/0312308 A1 | 10/2016 | Kennedy et al. |
| 2016/0348184 A1 | 12/2016 | Chinnaiyan |
| 2017/0016076 A1 | 1/2017 | Barnett-Ltzhaki et al. |
| 2017/0145513 A1 | 5/2017 | Kennedy et al. |
| 2017/0166980 A1 | 6/2017 | Fahey, III et al. |
| 2017/0329894 A1 | 11/2017 | Kennedy et al. |
| 2018/0016642 A1 | 1/2018 | Kennedy et al. |
| 2018/0030540 A1 | 2/2018 | Davicioni et al. |
| 2018/0068058 A1 | 3/2018 | Abdueva et al. |
| 2018/0112275 A1 | 4/2018 | Davicioni et al. |
| 2018/0122508 A1 | 5/2018 | Wilde et al. |
| 2018/0127832 A1 | 5/2018 | Kennedy et al. |
| 2018/0291459 A1 | 10/2018 | Al-Deen Ashab et al. |
| 2019/0017123 A1 | 1/2019 | Davicioni et al. |
| 2019/0204322 A1 | 7/2019 | Alshalalfa et al. |
| 2019/0218621 A1 | 7/2019 | Davicioni |
| 2020/0165682 A1 | 5/2020 | Chinnaiyan et al. |
| 2020/0224276 A1 | 7/2020 | Chinnaiyan et al. |

FOREIGN PATENT DOCUMENTS

| | | |
|---|---|---|
| EP | 2 366 800 A1 | 9/2011 |
| WO | WO 1990/015070 A1 | 12/1990 |
| WO | WO 1992/010092 A1 | 6/1992 |
| WO | WO 1993/009668 A1 | 5/1993 |
| WO | WO 1993/022684 A1 | 11/1993 |
| WO | WO 1998/045420 A2 | 10/1998 |
| WO | WO 2001/060860 A2 | 8/2001 |
| WO | WO 2001/066753 A1 | 9/2001 |
| WO | WO 2002/000929 A1 | 1/2002 |
| WO | WO 2002/083921 A2 | 10/2002 |
| WO | WO 2003/012067 A2 | 2/2003 |
| WO | WO 2004/037972 A2 | 5/2004 |
| WO | WO 2005/040396 A2 | 5/2005 |
| WO | WO 2005/085471 A2 | 9/2005 |
| WO | WO 2005/100608 A2 | 10/2005 |
| WO | WO 2006/047484 A2 | 5/2006 |
| WO | WO 2006/091776 A2 | 8/2006 |
| WO | WO 2006/110264 A2 | 10/2006 |

(56) References Cited

FOREIGN PATENT DOCUMENTS

| WO | WO 2006/127537 A2 | 11/2006 |
|---|---|---|
| WO | WO 2006/135596 A2 | 12/2006 |
| WO | WO 2007/056049 A2 | 5/2007 |
| WO | WO 2007/070621 A2 | 6/2007 |
| WO | WO 07/081740 | 7/2007 |
| WO | WO 2007/081720 A2 | 7/2007 |
| WO | WO 2008/023087 A2 | 2/2008 |
| WO | WO 2008/046911 A2 | 4/2008 |
| WO | WO 2008/086478 A2 | 7/2008 |
| WO | WO 2008/112283 A2 | 9/2008 |
| WO | WO 2009/009432 A2 | 1/2009 |
| WO | WO 2009/020521 A2 | 2/2009 |
| WO | WO 2009/020905 A2 | 2/2009 |
| WO | WO 09/029266 | 3/2009 |
| WO | WO 2009/045115 A1 | 4/2009 |
| WO | WO 2009/074968 A2 | 6/2009 |
| WO | WO 2009/143603 A1 | 12/2009 |
| WO | WO 10/018601 | 2/2010 |
| WO | WO 2010/056374 A2 | 5/2010 |
| WO | WO 10/073248 | 7/2010 |
| WO | WO 2010/056374 A3 | 9/2010 |
| WO | WO 2010/099598 A1 | 9/2010 |
| WO | WO 10/123626 | 10/2010 |
| WO | WO 2010/124372 A1 | 11/2010 |
| WO | WO 2011/150453 A1 | 12/2011 |
| WO | WO 2012/031008 A2 | 3/2012 |
| WO | WO 2012/068383 A2 | 5/2012 |
| WO | WO 2012/135008 A1 | 10/2012 |
| WO | WO 13/006495 | 1/2013 |
| WO | WO 2013/088457 A1 | 6/2013 |
| WO | WO 2013/090620 A1 | 6/2013 |
| WO | WO 2013/116742 A1 | 8/2013 |
| WO | WO 2014/028884 A2 | 2/2014 |
| WO | WO 2014/043803 A1 | 3/2014 |
| WO | WO 14/085666 | 5/2014 |
| WO | WO 14/151764 | 9/2014 |
| WO | WO 15/073949 | 5/2015 |
| WO | WO 2015/071876 A2 | 5/2015 |
| WO | WO 16/141127 | 9/2016 |
| WO | WO 2017/059549 A1 | 4/2017 |
| WO | WO 2017/062505 A1 | 4/2017 |
| WO | WO 2018/165600 A1 | 9/2018 |
| WO | WO 19/023517 | 1/2019 |

OTHER PUBLICATIONS

Kardos et al. Claudin-low bladder tumors are immune infiltrated and actively immune suppressed. Published online Mar. 17, 2016. JCI Insight. vol. 1, No. 3, e85902, 17 pages. (Year: 2016).*

Seiler et al. Impact of Molecular Subtypes in Muscle-invasive Bladder Cancer on Predicting Response and Survival after Neoadjuvant Chemotherapy. 2017. European Urology. vol. 72, pp. 544-554. (Year: 2017).*

Abdueva et al., "Quantitative Expression Profiting in Formalin-Fixed Paraffin-Embedded Samples by Affymetrix Microarrays," Journal of Molecular Diagnostics (Jul. 2010) vol. 12, No. 4, pp. 409-417.

Affymetrix: Data Sheet, "GeneChip® Exon Array System for Human, Mouse, and Rat," Internet Citation, [Online] Jan. 25, 2012 [Retrieved from the Internet] lntp://www.biainformatics.atickland.aciaz/workshops/1O_March_2011 1Exon_EOST_Datash eet.pdf, 8 pages.

Agell et al., "A 12-Gene Expression Signature Is Associated with Aggressive Histological in Prostate Cancer: SEC14L1 and TCEB1 Genes Are Potential Markers of Progression," Am J Pathol (2012) vol. 181 (5), pp. 1585-1594.

Alberts et al., "Vesicular traffic in the secretory and endocytic pathways," Molecular Biology of the Cell (1994) 3rd Ed., p. 465.

Aldred et al., "Papillary and follicular thyroid carcinomas show distinctly different microarray expression profiles and can be distinguished by a minimum of five genes," J Clin Oncol. (2004) 22(17):3531-9.

Amling et al.: "Long-term hazard of progression after radical prostatectomy for clinically EB localized prostate cancer continued risk of biochemical failure after 5 years," J Urol. (2000) 164:101-105.

Amundadottir et al., "A common variant associated with prostate cancer in European and African populations," Nat Genet. (2006) 38:652-658.

Amundson et al., "Integrating global gene expression and radiation survival parameters across the 60 cell lines of the National Cancer Institute Anticancer Drug Screen," Cancer Research (2008) 68(2):415-424.

Ausubel, et al. Current Protocols in Molecular Biology. Wiley & Sons, New York (1995) Table of Contents.

Baetke et al., "Molecular Pathways Involved in Prostate Carcinogenesis: Insights from Public Microarray Datasets," PLoS One (2012) 7(11):e49831, 1-11.

Baggerly et al., "Deriving Chemosensitivity from Cell Lines: Forensic Bioinformatics and Reproducible Research in High-Throughput Biology," The Annals of Applied Sciences (2009) vol. 3, No. 4, pp. 1309-1334.

Ballman et al., "Faster cyclic loess: normalizing RNA arrays via linear models," Bioinformatics, 2004, 20 :2778-2786.

Bannert et al., "Retroelements and the human genome: new perspectives on an old relation." PNAS (Oct. 5, 2004) vol. 101, Suppl. 2, pp. 14572-14579.

Bauer et al., "Identification of Markers of Taxane Sensitivity Using Proteomic and Genomic Analyses of Breast Tumor from Patients Receiving Neoadjuvant Paclitaxel and Radiation," Clin. Cancer Res. (2010) 16(2):681-690, American Association for Cancer Research.

Benner et al., "Evolution, language and analogy in functional genomics," Trends in Genetics, (Jul. 2001) vol. 17, pp. 414-418.

Bergstralh et al., "Software for optimal matching in observation al studies," Epidemiology (1996) 7(3):331-332.

Best et al., "Molecular differentiation of high- and moderate-grade human prostate cancer by cDNA microarray analysis", Diagn Mol Pathol. (2003) 12(2):63-70.

Bibikova et al., "Gene expression profiles in formalin-fixed, paraffin-embedded tissues obtained with a novel assay for microarray analysis," Clin Chem., 2004, 50:2384-2386.

Bibikova et al., "Quantitative gene expression profiling in formalin-fixed, paraffin-embedded tissues using universal bead arrays," Am J Pathol. (2004) 165:1799-1807.

Bibikova et al., "Expression signatures that correlated with Gleason score and relapse in prostate cancer," Genomics (2007) 89(6):666-672.

Birney et al., "Identification and analysis of functional elements in 1% of the human genome by the ENCODE pilot project." Nature (Jun. 14, 2007); 447(7146):799-816.

Boorjian et al., "Long-term risk of clinical progression after biochemical recurrence following radical prostatectomy: the mpact of time from surgery to recurrence." Eur Urol. (Jun. 2011) 59(6):893-9.

Boormans et al., "Identification of TDRD1 as a direct target gene of ERG in primary prostate cancer," Int J Cancer (2013) vol. 133 (2), pp. 335-345.

Bostwick et al., "Prognostic factors in prostate cancer: College of American Pathologists consensus statement," Arch Pathol Lab Med (2000) 124(7):995-1000.

Bott et al., "Prostate cancer management: (2) an update on locally advanced and metastatic disease", Postgrad Med J, Dec. 3, 2003, 79(937), 643-645.

Brase et al., "TMPRSS2-ERG—specific transcriptional modulation is associated with prostate cancer biomarkers and TGF-β signaling," BMC Cancer (2011) 11(507):1-8.

Breiman, "Random Forests," Machine Learning (2001) 45:5-32.

Brouha et al., "Hot L1s account for the bulk of retrotransposition in the human population." PNAS USA (Apr. 29, 2003) 100(9):5280-5.

Bull et al., "Identification of potential diagnostic markers of prostate cancer and prostatic intraepithelial neoplasia using cDNA microarray," British J Cancer (Jun. 1, 2001) 84(11):1512-1519.

Bussemakers et al., "DD3: a new prostate-specific gene, highly overexpressed in prostate cancer." Cancer Res. (Dec. 1, 1999) 59(23):5975-9.

(56) References Cited

OTHER PUBLICATIONS

Carninci et al., "The transcriptional landscape of the mammalian genome," Science (Sep. 2, 2005) 09(5740):1559-63.
Cerutti et al. "Diagnosis of suspicious thyroid nodules using four protein biomarkers," Clin Cancer Res. (2006) 12(11 Pt 1):3311-8.
Chalitchagorn et al., "Distinctive pattern of LINE-1 methylation level in normal tissues and the association with carcinogenesis." Oncogene (Nov. 18, 2004) 23(54):8841-6.
Che et al.: "Prognostic Value of Abnormal p53 Expression in Locally Advanced Prostate Cancer Treated With Androgen Deprivation and Radiotherapy: A Study Based on RTOG 9202"; International Journal of Radiation: Oncology Biology Physics (Nov. 15, 2007) vol. 69, No. 4, pp. 1117-1123.
Chen et al., "Hepsin and maspin are inversely expressed in laser capture microdissectioned prostate cancer," J Urol. (Apr. 2003) 169(4):1316-1319.
Chen et al.: "Molecular determinants of resistance to antiandrogen therapy"; Nature Medicine, Nature Publishing Group, New York, NY (Jan. 1, 2004) vol. 10, No. 1, pp. 33-39.
Chen et al., "Significance of noninvasive diagnosis of prostate cancer with cytologic examination of prostatic fluid," J Nippon Med Sch. (Jun. 2006) 73(3):129-135.
Chen et al., "Deregulation of a Hox Protein Regulatory Network Spanning Prostate Cancer Initiation and Progression," Clin Cancer Res (Jun. 2012) 18(16):4291-4302.
Cheng et al. "Cell Proliferation in Prostate Cancer Patients with Lymph Node Metastasis", Clin Cancer Res (Oct. 1999) 5(10): 2820-2823.
Cheung et al., "Natural variation in human gene expression assessed in lymphoblastoid cells," Nature Genetics (2003) vol. 33, pp. 422-425.
Cheville et at., "Gene Panel Model Predictive of Outcome in Men at High-Risk of Systemic Progression and Death From Prostate Cancer After Radical Retropubic Prostatectomy," Journal Of Clinical Oncology (Aug. 20, 2008) vol. 26, No. 24.
Chifman et al., "Conservation of immune gene signatures in solid tumors and prognostic implications," BMC Cancer (2016) 16:911, pp. 1-17. DOI 10.1186/S12885-016-2948-Z.
Cho et al., "Hypermethylation of CpG island loci and hypomethylation of LINE-1 and Alu repeats in prostate denocarcinoma and their relationship to clinicopathological features", J Pathol (Feb. 2007) 211(3):269-77.
Chow et al., "LINE-1 activity in facultative heterochromatin formation during X chromosome inactivation," Cell (Jun. 11, 2010) 141(6):956-69.
Cibas, et al. "The Bethesda System for Reporting Thyroid Cytopathology," Am J Clin Pathol. (Nov. 2009) 132(5):658-65. doi: 10.1309/AJCPPHLWMI3JV4LA.
Clancy et al., "Profiling networks of distinct immune-cells in tumors," BMC Bioinformatics (2016) 17:263, pp. 1-15. DOI 10.1186/s12859-016-1141-3.
Clark-Langone et al. "Riornarker discovery for colon cancer using a 761 gene RT-PCR assay 2007," BMC Genomics (2007) 8:279 pp. 1-18.
Cologne et al., "Optimal Case-Control Matching in Practice," Epidemiology Resources Inc. (1995) 6(3):271-275.
Cooperberg et al., "The CAPRA-S score: A straightforward tool for improved prediction of outcomes after radical prostatectomy," Cancer (2011) vol. 117 (22), pp. 5039-5046.
Cordaux et al., "The impact of retrotransposons on human genome evolution." Nat Rev Genet. (Oct. 2009) 10(10):691-703.
Couzin-Frankel, Jennifer, "As Questions Grow, Duke Halts Trials, Launches Investigation," Science (Aug. 6, 2010) vol. 329, pp. 614-615.
Cuzik et al., "Prognostic value of an RNA expression signature derived from cell cycle proliferation genes in patients with prostate cancer: a restrospective study," thelancet.com/oncology (Mar. 2011) vol. 12, pp. 245-255.

Dahlman et al., "Effect of androgen deprivation therapy on the expression of prostate cancer biomarkets MSMB and MSMB-binding protein CRISP3," Prostate Cancer and Prostatic Diseases (2010) 13:369-375.
Dalela et al., "Contemporary Role of the Decipher Test in Prostate Cancer Management: Current Practice and Future Perspectives," Rev. Urol. (2016), 18(1):1-9, MedReviews®, LLC.
Dalsgaard Sorensen et al.: "Discovery of prostate cancer biomarkers by microarray gene expression profiling"; Expert Review of Molecular Diagnostics, vol. 10, No. 1, Jan. 1, 2010, pp. 49-64.
D'Amico et al., "Cancer-specific mortality after surgery or radiation for patients with clinically localized prostate cancer managed during the prostate-specific antigen era," J Clin Oncol. (2003) 21:2163-2172.
D'Amico et al., "Determinants of prostate cancer-specific survival after radiation therapy for patients with clinically localized prostate cancer," J Clin Oncol. (2002) 20:4567-4573.
Dawood, Shaheenah, "Novel Biomarkers of Metastatic Cancer," Expert Rev. Mo/. Diagn. (2010) 10(5):581-590, Expert Reviews Ltd.
Day et al., "Estimating enrichment of repetitive elements from high-throughput sequence data." Genome Biol. (2010) 11 (6):R69.
De Klein et al., "A cellular oncogene is translocated to the Philadelphia chromosome in chronic myelocytic leukaemia." Nature (Dec. 23, 1982) 300(5894):765-7.
De Marzo et al., "Pathological and molecular mechanisms of prostate carcinogenesis: implications for diagnosis, detection, prevention, and treatment," J Cell Biochem. (Feb. 15, 2004) 91(3):459-477.
Dechassa et al., "Architecture of the SWI/SNF-nucleosome complex," Mol Cell Biol. (Oct. 2008) vol. 28, No. 19, pp. 6010-6021.
Demichelis et al., "TMPRSS2:ERG gene fusion associated with lethal prostate cancer in a watchful waiting cohort," Oncogene (2007) 26:4596-4599.
Dhanasekaran et al., "Delineation of prognostic biomarkers in prostate cancer," Nature (2001) 412:822-826.
Dougherty, "The fundamental role of pattern recognition for gene-expression/microarray data in bioinformatics," Pattern recognition (2005) 38:2226-2228.
Eder et al., "Genes differentially expressed in prostate cancer," BJU Int. (May 2004) 93(8): 1151-1155.
Edwards et al., "Expression analysis onto microarrays of randomly selected cDNA clones highlights HOXB13 as a marker of human prostate cancer," Br J Cancer. (Jan. 31, 2005) 92(2):376-381.
Edwards et al.: "MicroRNAs and Ultraconserved Genes as Diagnostic Markers and Therapeutic Targets in Cancer and Cardiovascular Diseases", Journal of Cardiovascular Translational Research (May 5, 2010) vol. 3, No. 3, pp. 271-279.
Englisch, et al., "Chemically Modified Oligonucleotides as Probes and Inhibitors," Angew. Chern. Int. Ed. Eng. (1991) 30:613-629.
Ernst et al., "Decrease and gain of gene expression are equally discriminatory markers for prostate carcinoma: a gene expression analysis on total and microdissected prostate tissue," Am J Pathol. (Jun. 2002) 160(6):2169-2180.
Etzioni et al. "The case for early detection", Nature Reviews | Cancer (Apr. 2003) vol. 3, pp. 1-10.
Fan et al., "Concordance among gene- expression-based predictors for breast cancer," N Engl J Med. (2006) 355:560-569.
Feng et al., "Luminal and basal subtyping of prostate cancer," J Clin Oncol (Feb. 20, 2017) vol. 35, No. 6, p. 3, Abstract.
Feroze-Merzoug et al., "Molecular profiling in prostate cancer," Cancer Metastasis Rev. 1 (2001) 20(3-4):165-71.
Finley et al., "Discrimination of benign and malignant thyroid nodules by molecular profiling," Ann Surg. (2004) 240(3):425-36; discussion 436-7.
Finley et al., "Advancing the molecular diagnosis of thyroid nodules: defining benign lesions by molecular profiling," Thyroid (2005) 15(6):562-8.
Fodor et al., "Light-directed, spatially addressable parallel chemical synthesis," Science (Feb. 15, 1991) 251(4995):767-773.
Foley et al., "Molecular pathology of prostate cancer: the key to identifying new biomarkers of disease," Endocrine-Related Cancer (2004) 11:477-488.

(56) References Cited

OTHER PUBLICATIONS

Fontaine, et al., "Increasing the number of thyroid lesions classes in microarray analysis improves the relevance of diagnostic markers," PLoS One (Oct. 29, 2009) 4(10):e7632. doi: 10.1371/journal.pone. 0007632.
Fryknas et al., "Molecular markers for discrimination of benign and malignant follicular thyroid tumors," Tumour Biol. (2006) 27(4):211-20.
Fu et al., "Regulation of apoptosis by a prostate-specific and prostate cancer-associated noncoding gene, PCGEM1." DNA Cell Biol. (Mar. 2006) 25(3): 135-41.
Fujarewicz et al., "A multi-gene approach to differentiate papillary thyroid carcinoma from benign lesions: gene selection using support vector machines with bootstrapping," Endocr Relat Cancer (Sep. 2007) 14(3):809-26.
Gait. Chapter 16: Oligoribonucleotides. Antisense Research and Applications, Crookeand Lebleu Eds., CRC Press (1993) pp. 289-302.
Galamb et al., "Diagnostic mRNA Expression Patterns of Inflamed, Benign, and Malignant Colorectal Biopsy Specimen and their Correlation with Peripheral Blood Results," Cancer Epidemiology, Biomarkers & Prevention (Oct. 2008) 17(10):2835-2845.
Gao et al., "VISTA is an inhibitory immune checkpoint that is increased after ipilimumab therapy in patients with prostate cancer," Nat Med. (May 2017) 23(5):551-555.
Garber et al., "Diversity of gene expression in adenocarcinoma of the lung," PNAS (Nov. 20, 2001) vol. 98, No. 24, pp. 13784-13789.
Genevieve de Saint Basile et al., "Severe Combined Immunodeficiency Caused By Deficiency In Either The Ii Or the E Subunit Of CD3," Journal of Clinical Investigation (2004) vol. 114, No. 10. p. 1512-1517.
Gibb et al., "The functional role of long non-coding RNA in human carcinomas", Molecular Cancer, Biomed Central, London, GB (Apr. 13, 2011) vol. 10, No. 1, p. 38.
Giordano et al., "Organ-Specific Molecular Classification of Primary Lung, Colon, and Ovarian Adenocarcinomas Using Gene Expression Profiles," Am J Pathol (2001) 159(4):1231-1238.
Gleave et al., "Randomized comparative study of 3 versus 8-month neoadjuvant hormonal therapy before radical orostatectomy : biochemical and pathological effects," J Urol. (2001) 166:500-507.
Glinsky et al., "Gene expression profiling predicts clinical outcome of prostate cancer," J Clin Investigation (2004) 113(6):913-923.
Glinsky et al., "Microarray analysis identifies a death-from-cancer signature predicting therapy i failure in patients with multiple types of cancer," J Clin Invest. (2005) 115: 1503-1521.
Gonzalgo et al: "Molecular pathways to prostate cancer"; J Urol. (2003) 170(6 Pt 1):2444-2452.
Greenbaum et al.: "Comparing protein abundance and mRNA expression levels on a genomic scale"; Genome Biology (2003) 4(9):117.1-117.8.
Griffith et al., "Meta-analysis and meta-review of thyroid cancer gene expression profiling studies identifies important diagnostic biomarkers," J Clin Oncol. (2006) 24(31):5043-51.
Griffith, et al. Biomarker panel diagnosis of thyroid cancer: a critical review. Expert Rev Anticancer Ther. (Sep. 2008) 8(9):1399-413. doi: 10.1586/14737140.8.9.1399.
Gupta et al., "Long non-coding RNA HOTAIR reprograms chromatin state to promote cancer metastasis," Nature (Apr. 15, 2010) 464(7291): 1071-6.
Guttman et al., "Chromatin signature reveals over a thousand highly conserved large non-coding RNAs in mammals", Nature (Mar. 12, 2009) 458(7235):223-7.
Guttman et al., "Ab initio reconstruction of transcriptomes of pluripotent and lineage committed cells reveals gene structures of thousands of lincRNAs," Nat Biotechnol. (May 2010) 28(5):503-10.
Haiman et al.: "Multiple regions within 8q24 independently affect risk for prostate cancer"; Nat Genet. (2007) 39:638-644.

Hamada et al., "Diagnostic usefulness of PCR profiling of the differentially expressed marker genes in thyroid papillary carcinomas," Cancer Lett. (Jun. 28, 2005) 224(2):289-301. Epub Nov. 18, 2004.
He et al., "The antisense transcriptomes of human cells", Science (Dec. 19, 2008) 322(5909): 1855-7.
Heemers, H. V. et al.: "Identification of a Clinically Relevant Androgen-Dependent Gene Signature in Prostate Cancer"; Cancer Research, vol. 71, No. 5 (2011) pp. 1978-1988.
Heidenreich et al., "EAU Guidelines on Prostate Cancer. Part 1: Screening, Diagnosis, and Treatment of Clinically Localised Disease," European Urology (2011) vol. 59, pp. 61-71.
Henrotin et al.: "Type II collagen peptides for measuring cartilage degradation," Biotheology (2004) 41 (3-4): Abstract.
Henshall et al., "Survival Analysis of Genome-Wide Gene Expression Profiles of Prostate ancers Identifies New Prognostic Targets of Disease Relapse," Cancer Research (Jul. 15, 2003) 63, 14196-4203.
Holzbeierlein et al., "Gene expression analysis of human prostate carcinoma during hormonal therapy identifies androgen-responsive genes and mechanisms of therapy resistance," Am. J . Pathol. (Jan. 2004) 164(1):217-227.
Hornberger et al., "A Multigene Prognostic Assay for Selection of Adjuvant Chemotherapy in Patients with T3, Stage II Colon Cancer: Impact on Quality-Adjusted Life Expectancy and Costs," Value In Health 15 (2012) pp. 1014-1021.
Huarte et al., "Large non-coding RNAs: missing links in cancer?" Human Molecular Genetics (Oct. 15, 2010) 19(2): R152-R161.
Hughes et al., "Molecular pathology of prostate cancer," J Clin Pathol. (Jul. 2005) 58(7):673-684.
Hughes et al., "Topoisomerase II—a expression increases with increasing Gleason score and with hormone insensitivity in prostate carcinoma," J Clin Pathol. (Jul. 2006) 59(7): 721-724.
Ida et al., "Topoisomerase II alpha protein expression Is predictive of outcome in Gleason score 7 prostate cancer patients treated surgically and is dependent on ERG status." Mod Pathol. (Feb. 2010) Abstract 1895, 23 : 424A-425A.
Ito et al., "Linkage of elevated ets-2 expression to hepatocarcinogenesis," Anticancer Research (2002) 22(4):2385-2389.
Jemal et al.: "Cancer statistics," CA Cancer J Clin. (2005) 55:10-30.
Jenkins et al., "Prognostic significance of ailetic imbalance of chromosome arms 71, 8p, 16q, and 18q in stage T3NOMO prostate cancer," Genes, Chromosomes & Cancer (1998) 21:131-143.
Jhavar et al., "Integration of ERG gene mapping and gene-expression profiling identifies distinct categories of human prostate cancer," BJUI (2008) vol. 103 (9), pp. 1256-1269.
Jhavar et al., "Technical Advance: Detection of TMPRSS2-ERG Translocations in Human Prostate Cancer by Expression Profiling Using GeneChip Human Exon 1.0 ST Arrays," J Mol. Diag (Jan. 2008) vol. 10, No. 1, pp. 50-57.
Jones et al., "Frequent mutations of chromatin remodeling gene ARID1A in ovarian clear cell carcinoma" Science (Oct. 8, 2010) 330(6001):228-31.
Kanehisa, "Use of statistical criteria for screening potential homologies in nucleic acid sequences," Nucleic Acids Res. (Jan. 11, 1984) 12(1 Pt 1):203-13.
Karan et al., "Current status of the molecular genetics of human prostatic adenocarcinomas," Int J Cancer, 2003, 103(3):285-293.
Karayi et al., "Molecular biology of prostate cancer," Prostate Cancer Prostatic Dis. (2004) 7(1):6-20.
Karnes et al., "Radical prostatectomy for high-risk prostate cancer," Jpn. J. Clin. Oneal. (Oct. 19, 2009) 40 (1): 3-9, Epub.
Karnes et al., "The ability of biomarkers to predict systemic progression in men with high-risk prostate cancer treated surgically is dependent on ERG status," Cancer Res. (Nov. 9, 2010) 70(22):8994-9002, Epub.
Kasraeian, et al., "A comparison of fine-needle aspiration, core biopsy, and surgical biopsy in the diagnosis of extremity soft tissue masses," Clin Orthop Relat Res. (Nov. 2010) 468(11):2992-3002.
Kawamorita et al., "Radical prostatectomy for high-risk prostate cancer: Biochemical outcome," International Journal of Urology (2009) 16:733-738.
Kebebew et al., "Diagnostic and extent of disease multigene assay for malignant thyroid neoplasms," Cancer (2006) 106(12):2592-7.

(56) References Cited

OTHER PUBLICATIONS

Kestin, "Potential survival advantage with early androgen deprivation for biochemical failure after external beam radiotherapy: the importance of accurately defining biochemical disease status," Int J Rad Oncol Biol Phys. (2004) 60:453-62.
Khor et al.: "Bcl-2 and Bax Expression Predict Prostate Cancer Outcome in Men Treated with Androgen Deprivation and Radiotherapy on Radiation Therapy Oncology Group Protocol 92-02"; Clinical Cancer Research (Jun. 15, 2007) vol. 13, No. 12, pp. 3585-3590.
Kiessling, et al., "D-TMPP: A novel androgen-regulated gene preferentially expressed in prostate and prostate cancer that is the first characterized member of an eukaryotic gene family," The Prostate (2005) 64:387-400.
Kikuchi et al., "Expression profiles of non-small cell lung cancers on cDNA microarrays: identification of genes for prediction of lymph-node metastasis and sensitivity to anti-cancer drugs," Oncogene (2003) 22, pp. 2192-2205.
Kishi et al., "Expression of the survivin gene in prostate cancer: correlation with clinicopathological characteristics, proliferative activity and apoptosis," J Urol. (May 2004) 171(5): 1855-1860.
Klee et al., "Candidate Serum Biomarkers for Prostate Adenocarcinoma identified by mRNA Differences in Prostate Tissue and Verified with Protein Measurements in Tissue and Blood," Clinical Chemistry (2012) 58(3):599-609.
Kosari et al., "Identification of biomarkers for prostate cancer," Clin. Cancer Res. (2008) 1734-1743.
Koshkin et al., "LNA (locked nucleic acids): An RNA mimic forming exceedingly stable LNA," LNA duplexes. J Am Chem Soc (1998) 120:13252-13253.
Koshkin et al., "LNA (locked nucleic acids): synthesis of the adenine, cytosine, guanine 5-methylcytosine, thymine and uracil bicyclonucleoside monomers, oligomerisation, and unprecedented nucleic acid recognition," Tetrahedron (1998) 54(14):3607-3630.
Kroschwitz The Concise Encyclopedia Of Polymer Science And Engineering (1990) (pp. 858-859).
Kube et al., "Optimization of laser capture microdissection and RNA amplification for gene expression profiling of prostate cancer," BMC Mol. Biol. (2007) 8:25.
Kumar, et al., "The first analogues of LNA (locked nucleic acids): phosphorothioate-LNA and 2'-thio-LNA," Bioorg Med Chem Lett. (Aug. 18, 1998) 8(16):2219-22.
Kumar-Sinha et al., "Molecular markers to identify patients al risk for recurrence after primary treatment for prostate cancer," Urology, 62 Suppl 1:19-35, Dec. 29, 2003.
Kunarso et al., "Transposable elements have rewired the core regulatory network of human embryonic stem cells," Nat Genet (Jul. 2010) 42(7):631-4.
Landers et al.: "Use of multiple biomarkers for a molecular diagnosis of prostate cancer"; Int. J. Cancer (May 10, 2005) 114 pp. 950-956.
Lapointe et al., "Gene expression profiling identifies clinically relevant subtypes of prostate cancer," PNAS USA (2004) 101:811-816.
Latulippe et al., "Comprehensive Gene Expression Analysis of Prostate Cancer Reveals Distinct Transcriptional Programs Associated with Metastatic Disease," Cancer Res. (2002) 62:4499-4506.
Lawton et al., "Updated results of the phase III Radiation Therapy Oncology Group (RTOG) trial 85-31 evaluating the potential benefit of androgen suppression following standard radiation therapy for unfavorable prognosis carcinoma of the prostate," Int J Rad Oncol Biol Phvs. (2001) 49:937-946.
Leyten et al., "Identification of a Candidate Gene Panel for the Early Diagnosis of Prostate Cancer," Clinical Cancer Research (2015) 21(13):3061-3070.
Lin et al., "Cox Regression with Incomplete Covariate Measurements," Journal of the American Statistical Association (1993) vol. 88 (424), pp. 1341-1349.
Liong et al., "Blood-Based Biomarkers of Aggressive Prostate Cancer," PLoS One (Sep. 2012) vol. 7, Issue 7, e45802, pp. 1-7.

Livingston et al., "*Homo sapiens* CDC20 Cell Division Cycle 20 Homolog (CDC20)," Gene (Apr. 24, 2006).
Lockstone, "Exon array data analysis using Affymetrix power tools and R statistical software," Briefings in bioinformatics (2011) vol. 12 (6), pp. 634-644.
Lunardi et al., "A co-clinical approach identified mechanisms and potential therapies for androgen deprivation resistance in prostate cancer," Nature Genetics (Jul. 2013) vol. 45, No. 7, pp. 747-757.
Luo et al., "Human Prostate Cancer and Benign Prostatic Hyperplasia : Molecular Dissection by Gene Expression Profiling," Cancer Res. (2001) 61:4683-4688.
Luo et al., "Gene expression analysis of prostate cancers," Molecular Carcinogenesis (Jan. 2002) 33(1):25-35.
Magee et al., "Expression Profiling Reveals Hepsin Overexpression in Prostate Cancer," Cancer Res. (2001) 61:5692-5696.
Martens-Uzunova, E. S. et al.: "Diagnostic and prognostic signatures from the small non-coding RNA transcriptome in prostate cancer", Oncogene (Jul. 18, 2011) vol. 31, No. 8, pp. 978-991.
Martin, "A New Access to 2'-O-Alkylated Ribonucleosides and Properties of 2'-O-Alkylated Oligoribonucleotides," Helv. Chim. Acta. (1995) 78:486-504. (in German with English abstract).
Mazzanti, et al., "Using gene expression profiling to differentiate benign versus malignant thyroid tumors," Cancer Res. (Apr. 15, 2004) 64(8):2898-903.
McCall et al., "Frozen robust multiarray analysis (fRMA)", Biostatistics (2010) vol. 11 (2), 242-253.
Mercer, DW, "Use of multiple markers to enhance clinical utility", Immunol Ser. (1990) 53: 39-54.
Mineva et al., "Differential expression of alphaB-crystallin and Hsp27-1 in anaplastic thyroid carcinomas because of tumor-specific alphaB-crystallin gene (CRYAB) silencing," Cell Stress Chaperones (Autumn 2005) 10(3):171-84.
Mitelman, "Recurrent chromosome aberrations in cancer," Mutation Research (2000) 462: 247-253.
Montironi et al., "Carcinoma of the prostate: inherited susceptibility, somatic gene defects and androgen receptors," Virchows Arch. (Jun. 2004) 444(6):503-508.
Moul, "Prostate specific antigen only progression of prostate cancer," J Urol. (2000) 163:1632-42.
Moul et al., "Early versus delayed hormonal therapy for prostate specific antigen only recurrence of prostate cancer after radical prostatectomy," J Urol. (2004) 171:1141-1147.
Mühlenbruch et al., "Multiple imputation was a valid approach to estimate absolute risk from a prediction model based on case—cohort data," Journal of Clinical Epidemiology (2017) 84:130-141.
Nakagawa et al., "A Tissue Biomarker Panel Predicting Systemic Progression after PSA Recurrence Post-Definitive Prostate Cancer Therapy," PLos One (2008) 3(5):e2318, 14 pages.
Newson, Roger, "Confidence intervals for rank statistics: Somers' D and extensions," The Stata Journal (Sep. 2006) 6(3):309-334.
Nielsen et al., "Sequence-selective recognition of DNA by strand displacement with a thymine-substituted polyamide," Science (1991) 254: 1497-1500.
Noordzij et al. "The prognostic value of CD44 isoforms in prostate cancer patients treated by radical prostatectomy", Clin Cancer Res (May 1997) 3(5): 805-815.
Norman, James, "Thyroid Nodule Ultrasound", Endocrine website (Updated Oct. 13, 2010) http://www.endocrineweb.com/noduleus.html.
Ohl et al., "Gene expression studies in prostate cancer tissue: which reference gene should be selected for normalization?," J. Mol. Med . (2005) 83(12):1014-1024.
Ong et al., "Expression Profiling Identifies a Novel-Methylacyl-CoA Racemase Exon with Fumarate Hydratase Homology," Cancer Research (Jun. 15, 2003) 63:3296-3301.
Oosumi et al., "Mariner transposons in humans", Nature (Dec. 14, 1995) 378 (6558): 672.
Parker et al., "High expression levels of surviving protein independently predict a poor outcome for patients who undergo surgery for clear cell renal cell carcinoma," Cancer (2006) 107:37-45.
Pascal et al., "Correlation of mRNA and protein levels: Cell type-specific gene expression of cluster designation antigens in the prostate," BMC Genomics (2008) 9:246 (13 pages).

(56) References Cited

OTHER PUBLICATIONS

Patel et al., "Preoperative PSA velocity is an independent prognostic factor for relapse after radical prostatectomy," J Clin Oncol. (2005) 23:6157-6162.
Paulo et al., "Molecular Subtyping of Primary Prostate Cancer Reveals Specific and Shared Target Genes of Different ETS Rearrangements," Neoplasia (Jul. 2012) 14(7):600-611.
Penney et al., "mRNA Expression Signature of Gleason Grade Predicts Lethal Prostate Cancer," J Clin Oncol (Jun. 10, 2011) vol. 29, No. 17, pp. 2391-2396.
Penney et al., "Appendix (online only) of Penney et al., J Clin Oncol 29:2391 (Jun. 2011; online May 2, 2011)" pp. 1-9.
Pereira et al., "Coagulation factor V and VIIIN ratio as predictors of outcome in paracetamol induced fulminant hepatic failure: relation to other prognostic indicators," Gut (1992) 33:98-102.
Perez et al., "Long, abundantly expressed non-coding transcripts are altered in cancer," Human Molecular Genetics (2008) vol. 17, No. 5, pp. 642-655. Published online Nov. 15, 207.
Pienta et al. "The current state of preclinical prostate cancer animal models"; Prostate (2008) 69: 629-639.
Pilepich et al., "Phase III radiation therapy oncology group (RTOG) trial 86-10 of androgen deprivation adjuvant to definitive radiotherapy in locally advanced carcinoma of the prostate," Int. J. Radiation Oncology Biol. Phys. (2001) vol. 50, No. 5, pp. 1243-1252.
Pinover et al., "Validation of a treatment policy for patients with prostate specific antigen failure after three-dimensional conformal prostate radiation therapy," Cancer (Feb. 15, 2003) vol. 97, No. 4, pp. 1127-1133.
Pittoni et al., "The Dark Side of Mast Cell-Targeted Therapy in Prostate Cancer," Cancer Res. (2012) 72(4):831-835.
Porkka et al: Molecular mechanisms of prostate cancer; Eur Urol. (2004) 45(6):683-691.
Porkka et al., "RAD21 and KIAA0196 at 8q24 are amplified and overexpressed in prostate cancer," Genes Chromosomes Cancer (2007) 39:1-10.
Pound et al., "Natural history of progression after PSA elevation following radical prostatectomy," JAMA (1999) 281:1591-1597.
Prasad et al., "Identification of genes differentially expressed in benign versus malignant thyroid tumors," Clin Cancer Res. (2008) 14(11):3327-37.
Prensner et al., "Transcriptome Sequencing Identifies PCAT-1, a Novel lincRNA Implicated in Prostate Cancer Progression," (2012) 29 (8): 742-749.
Puskas, et al., "Gene profiling identifies genes specific for well-differentiated epithelial thyroid tumors," Cell Mol Biol (Noisy-le-grand) (Sep. 5, 2005) 51(2):177-86.
Rabbits, "Chromosomal translocations in human cancer", Nature (Nov. 10, 1994) 372: 143-149.
Reis et al., "Antisense intronic non-coding RNA levels correlate to the degree of tumor differentiation in prostate cancer," Oncogene (2004) 23(39):6684-6692.
Rhodes et al., "Multiplex biomarker approach for determining risk of prostatespecific antigen-defined recurrence of prostate cancer," J Nat Cancer Inst. (May 7, 2003) vol. 95, No. 9, pp. 661-668.
Rhodes et al., "Oncomine: A Cancer Microarray Database and Integrated Data-Mining Platform," Neoplasia (2004) 6:1-6.
Rhodes et al., "Large-scale meta-analysis of cancer microarray data identifies common transcriptional profiles of neoplastic transformation and progression," Proc Nat Acad Sci USA (2004) 101:9309-9314.
Rinn et al., "Functional demarcation of active and silent chromatin domains in human HOX loci by noncoding RNAs," Cell (Jun. 29, 2007) 129(7):1311-23.
Roberts et al., "The SWI/SNF complex-chromatin and cancer." Nat Rev Cancer (Feb. 2004) 4(2):133-42.
Robertson et al., "DNA in radical prostatectomy specimens. Prognostic value of tumor ploidy," Acta Oncologica (1991) 30(2):205-207.

Robertson et al., "Reconstructing the ancient mariners of humans." Nat Genet. (Apr. 1996) 12(4):360-1.
Robinson, et al., "A comparison of Affymetrix gene expression arrays," BMC Bioinformatics (Nov. 15, 2007) 8:449.
Robinson et al., "A dynamic programming approach for the alignment of signal peaks in multiple gas chromatography-mass spectrometry experiments," BMC Bioinformatics (2007) 8.1:419.
Romanuik et al., "LNCaP Atlas: Gene expression associated with in vivo progression to castration-recurrent prostate cancer," GMB Medical Genomics (2010) 3:43, pp. 1-19.
Ross et al., "Tissue-based Genomics Augments Post-prostatectomy Risk Stratification in a Natural History Cohort of Intermediate- and High-Risk Men," European Urology 69 (2016) pp. 157-165.
Rotblat et al., "A Possible Role for Long Non-Coding RNA in Modulating Signaling Pathways," Med. Hvnotheses (2011) 77:962-965, Elsevier.
Rotunno et al., "A Gene Expression Signature from Peripheral Whole Blood for Stage I Lung Adenocarcinoma," Cancer Prevention Research (Jul. 8, 2011) 4(10) 1599-1607.
Rowley, "A new Consistent Chromosomal Abnormal ity in Chronic Myelogenous Leukaemia Identified by Quinacrine rluorescence and Giemsa Staining," Nature (Jun. 1, 1973) 243:290-293.
Rowley, "Chromosome translocations: dangerous liaisons revisited," Nature Reviews: Cancer (Dec. 2001) 1):245-250.
Rubin et al., "Molecular genetics of human prostate cancer," Modern Pathol. (2004) 17(3):380-388.
Saito-Hisaminato et al., "Genome-Wide Profiling of Gene Expression in 29 Normal Human Tissues with a cDNA Microarray," DNA Research (2002) vol. 9, pp. 35-45.
Saligan et al., "Supervised Classification by Filter Methods and Recursive Feature Elimination Predicts Rick of Radiotherapy-Related Fatigue in Patients with Prosate Cancer," Cancer Informatics (2014) 13: 141-152.
Sandler et al., "Overall survival after prostate-specific-antigen-detected recurrence following conformal radiation therapy," Int J Rad Oncol Biol Phvs. (2000) 48:629-633.
Sanghvi, "Heterocyclic base modifications in nucleic acids and their applications in antisense oligonucleotides in Antisense Research and Applications," Crooke, S. T. and Lebleu, B., ed., CRC Press. (1993) Ch 15 274-285.
Saramaki et al., "Amplification of EIF3S3 gene is associated with advanced stage in prostate cancer," Am J Pathol. (2001) 159:2089-2094.
Sato et al., "Clinical significance of alterations of chromosome 8 in high-grade, advanced, nonmetastatic prostate carcinoma," J Natl Cancer Inst. (1999) 91:1574-1580.
Savinainen et al., "Expression and copy number analysis of TRPS 1, EIF3S3 and MYC genes in breast and prostate cancer," Br J Cancer (2004) 90: 1041-1046.
Savinainen et al., "Over expression of EIF3S3 promotes cancer cell growth," The Prostate (2006) 66: 1144-1150.
Schmidt et al., "Lack of interferon consensus sequence binding protein (ICSBP) transcripts in human myeloid leukemias," Blood (1998) 91:22-29.
Schumacher et al., "A Common 8q24 Variant in Prostate and Breast Cancer from a Large Nested Case-Control Study," Cancer Res. (2007) 67:2951-2956.
Severi et al., "The Common Variant rs1447295 on Chromosome 8q24 and Prostate Cancer Risk: Results from an Australian Population-based Case-Control Study", Cancer Epidemiology, Biomarkers & Prevention (2007) 16:610-611.
Shariat et al., "Survivin expression is associated with features of biologically aggressive prostate carcinoma," Cancer (2004) 100(4): 751-757.
Shariat et al., "An updated catalog of prostate cancer predictive tools," Cancer (2008) 113(11):3062-6.
Shen et al., "The SWI/SNF ATPase Brm is a gatekeeper of proliferative control in prostate cancer," Cancer Res. (Dec. 15, 2008) 68(24):10154-62.
Shibru et al., "Does the 3-gene diagnostic assay accurately distinguish benign from malignant thyroid neoplasms?" Cancer (Sep. 1, 2008) 113(5):930-5. doi: 10.1002/cncr.23703.

(56) References Cited

OTHER PUBLICATIONS

Shipley et al., "Radiation therapy for clinically localized prostate cancer: a multi-institutional pooled analysis," JAMA (1999) 281:1598-1604.
Simmons et al., "Natural history of biochemical recurrence after radical prostatectomy: risk assessment for secondary herapy," Eur Urol. (May 2007) 51(5):1175-84.
Singh et al., "Synthesis of 2'-amino-LNA: A novel conformationally restricted high-affinity oligonucleotide analogues with a handle," J Org Chem (1998) 63:10035-10039.
Singh et al., "LNA (locked nucleic acids): synthesis and high-affinity nucleic acid recognition," Chem Common (1998) 4:455-456.
Singh et al., "Gene expression correlates of clinical prostate cancer behavior," Cancer Cell (Mar. 2002) vol. 1, pp. 1203-1209.
Slotkin et al., "Transposable elements and the epigenetic regulation of the genome." Nat Rev Genet. (Apr. 2007) 8(4):272-85.
Srikantan et al., "PCGEM1, a prostate-specific gene, is overexpressed in prostate cancer," PNAS (Oct. 24, 2000) 97(22): 12216-12221.
Stamey et al., "Molecular genetic profiling of Gleason grade 415 prostate cancers compared to benign prostatichyperplasia," J Urol. (2001) 166(6):2171-2177.
Stanbrough et al., "Increased Expression of Genes Converting Adrenal Androgens to Testosterone in Androgen-Independent Prostate Cancer," Cancer Res (Mar. 1, 2006) 66(5):2815-2825.
Stavenhagen et al., "An ancient provirus has imposed androgen regulation on the adjacent mouse sex-limited protein Jene." Cell (Oct. 21, 1988) 55(2):247-54.
Stephenson et al., "Integration of gene expression profiling and clinical variables to predict prostate carcinoma recurrence after radical prostatectomy," Cancer (Jul. 15, 2005) 104(2):290-298.
Subramanian et al., "Gene set enrichment analysis: A knowledge-based approach for interpreting genome-wide expression profiles," PNAS USA (2005) 102:15545-15550.
Sun et al., "Aberrant expression of SWI/SNF catalytic subunits BRG1/BRM is associated with tumor development and ncreased invasiveness in prostate cancers," Prostate (Feb. 1, 2007) 67(2):203-13.
Taft et al., "Non-coding RNAs: regulators of disease," J Pathol. (Jan. 2010) 220(2):126-39.
Takayama et al., "TACC2 Is an Androgen-Responsive Cell Cycle Regulator Promoting Androgen-Mediatged and Castration-Resistant Growth of Prostate Cancer," Mol Endocrinol (May 2012) 26(5):748-761.
Taylor et al., "Integrative genomic profiling of human prostate cancer," Cancer Cell (Jul. 13, 2010) vol. 18 (1), pp. 11-22.
Thompson et al., "Adjuvant and Salvage Radiotherapy After Prostatectomy: AUA/ASTRO Guideline," J Urol. (2013) 190(2):441-449.
Thorsen et al., "Alternative Splicing in Colon, Bladder, and Prostate Cancer Identified by Exon Array Analysis," Molecular & Cellular Proteomics (Mar. 18, 2008) vol. 7, No. 7, pp. 1214-1224.
Tockman et al., "Considerations in bringing a cancer biomarker to clinical application," Cancer Research (1992) 52:2711-2718.
Tollefson et al., "Stratification of Patient Risk Based on Prostate-Specific Antigen Doubling Time After Radical Retropubic Prostatectomy," Mayo Clin Proc. (2007) 82:422-427.
Tomlins et al., "Recurrent Fusion of TMPRSS2 and ETS Transcription Factor Genes in Prostate Cancer," Science (2005) 310(5748):644-648.
Tomlins et al., "TMPRSS2:ETV4 Gene Fusions Define a Third Molecular Subtype of Prostate Cancer," Cancer Res. (2006) 66:3396-3400.
Tomlins et al., "Distinct classes of chromosomal rearrangements create oncogenic ETS gene fusions in prostate cancer," Nature (Aug. 2, 2007) 448(7153):595-9.
Tomlins et al., "Integrative molecular concept modeling of prostate cancer progression," Nat Genet. (2007) 39:41-51.
Tricoli et al., "Detection of prostate cancer and predicting progression: current and future diagnostic markers," Clinical Cancer Research (Jun. 15, 2004) 10:3943-3953.
True et al., "A molecular correlate to the Gleason grading system for prostate adenocarcinoma," PNAS (Jul. 18, 2006) vol. 103, No. 29, pp. 10991-10996.
Tsuchiya et al., "Clinical significance in situ hybridization analysis in pathologic of alterations of chromosome 8 detected by fluorescence organ-confined prostate cancer," Genes Chromosomes Cancer (2002) 34:363-371.
Tsuchiya et al., "Mapping and gene expression profile of the minimally overrepresented 8q24 region in prostate cancer," Am J Pathol. (May 2002) 160(5):1799-1806.
Vanaja et al., "Transcriptional Silencing of Zinc Finger Protein 185 Identified Profiling Is Associated with Prostate Cancer Progression," Cancer Research (Jul. 15, 2003) 63:3877-3882.
Vanaja et al., "PDLIM4 Represseion by Hypermethylation as a Potential Biomarker for Prostate Cancer," Clin. Cancer Res. (2006) 12(4):1128-1136.
Varambally et al., "Integrative Genomic and Proteomic Analysis of Prostate Cancer Reveals Signatures of Metastatic Progression," Cancer Cell (Nov. 2005) 8(5):393-406.
Varela et al., "Exome sequencing identifies frequent mutation of the SWI/SNF complex gene PBRM1 in renal carcinoma," Nature (Jan. 27, 2011) 469(7331):539-42.
Varricchi et al., "Are Mast Cells MASTers in Cancer?" Front Immunol. ePub (Apr. 12, 2017) 8:424.
Versteege et al., "Truncating mutations of hSNF5/INI1 in aggressive paediatric cancer." Nature (Jul. 9, 1998) 394 6689):203-6.
Vickers et al., "Extensions to decision curve analysis, a novel method for evaluating diagnostic tests, prediction models and molecular markers," BMC Medical Informatics and Decision Making, (2008) 8(53):1-17.
Visakorpi, "The molecular genetics of prostate cancer," Urology (2003) 62(5 Suppl 1):3-10.
Wang et al., "Two common chromosome 8q24 variants are associated with increased risk for prostate cancer," Cancer Res. (2007) 67:2944-2950.
Wang et al., "RNA-Seq: a revolutionary tool for transcriptomics," Nature Reviews/Genetics (Jan. 2009) vol. 10, pp. 57-63.
Watson et al., "Future opportunities for the diagnosis and treatment of prostate cancer," Prostate Cancer Prostatic Dis. (2004) 7:S8-S13.
Weber et al., "The prognostic value of expression of HIF1[alpha], EGFR and VEGF-A, in localized prostate cancer for intermediate- and high-risk patients treated with radiation therapy with or without androgen deprivation therapy," Radiation Oncology (Apr. 30, 2012) vol. 7, No. 66, 8 pages.
Welsh et al., "Analysis of Gene Expression Identifies Candidate Markers and Pharmacological Targets in Prostate Cancer," Cancer Res. (Aug. 15, 2001) 61:5974-5978.
Wiegand et al., "ARID1A mutations in endometriosis-associated ovarian carcinomas," N Engl J Med. (Oct. 14, 2010) 363 (16):1532-43.
Willman et al., "Immunohistochemical staining for DNA topoisomerase II-alpha in benign, premalignant, and malignant lesions of the prostate," Prostate (Mar. 1, 2000) 42(4):280-286.
Winkler et al.: "Stage D1 prostatic adenocarcinoma: significance of nuclear DNA ploidy patterns studied by flow cytometry," Mayo Clin Proc. (1988) 63(2): 103-112.
Wyatt et al., "Heterogeneity in the inter-tumor transcriptome of high risk prostate cancer," Genome Biology (Aug. 26, 2014) vol. 15, No. 8, pp. 2-14.
Yap et al., "Molecular interplay of the noncoding RNA ANRIL and methylated histone H3 lysine 27 by polycomb CBX7 n transcriptional silencing of INK4a," Mol Cell. (Jun. 11, 2010) 38(5):662-74.
Yates et al., "X:Map: annotation and visualization of genome structure for Affymetrix exon array analysis," Nucleic Acids Res. (2008) vol. 36:D780-D786.
Yeager et al., "Genome-wide association study of prostate cancer identifies a second risk locus at 8q24," Nat Genet (2007) 39:645-649.

(56) References Cited

OTHER PUBLICATIONS

Yegnasubramanian et al., "DNA hypomethylation arises later in prostate cancer progression than CpG island hypermethylation and contributes to metastatic tumor heterogeneity," Cancer Res. (Nov. 1, 2008) 68(21): pp. 8954-8967.
Yeliin et al., "Widespread occurrence of antisense transcription in the human genome," Nat Biotechnol. (2003) 21(4):379-86.
Yu et al., "Gene expression alterations in prostate cancer predicting tumor aggression and preceding development of malignancy," J Clin Oncol. (Jul. 15, 2004) 22(14):2790-2799.
Yu et al., "An integrated network of androgen receptor, polycomb, and TMPRSS2-ERG gene fusions in prostate cancer progression," Cancer Cell. (May 18, 2010) 17(5):443-54.
Yukinawa et al., "A multi-class predictor based on a probabilistic model: application to gene expression profiling-based diagnosis of thyroid tumors," BMC Genomics (Jul. 27, 2006) 7:190.
Zanetta et al., "Flow-cytometric analysis of deoxyribonucleic acid content in advanced ovarian carcinoma: its importance in long-term survival," Am J Obstet Gynecol (1996) 175(5): 1217-1225.
Zelefsky et al., "Neoadjuvant hormonal therapy improves the therapeutic ratio in patients with bulky prostatic cancer treated with three-dimensional conformal radiation therapy," Int J Radiat Oncol Biol Phvs. (1994) 29:755-761.
Zelefsky et al., "High dose radiation delivered by intensity modulated conformal radiotherapy improves the outcome of localized prostate cancer," The Journal of Urology (Sep. 2001) 166(3):876-881.
Zhao et al., "Development and validation of a 24-gene predictor of response to postoperative radiotherapy in prostate cancer: a matched, retrospective analysis," Lancet Oncol (2016) 17, pp. 1612-1620.
GenBank Accession No. AA462934 dated Jun. 10, 1997, 2 pages.
GenBank Accession No. AA920095 dated Apr. 20, 1998, 2 pages.
GenBank Accession No. AB028840 dated Jan. 12, 2000, 2 pages.
GenBank Accession No. AB030836 dated Oct. 23, 1999, 2 pages.
GenBank Accession No. AB036741 dated Dec. 22, 2000, 3 pages.
GenBank Accession No. AF077349 dated Dec. 14, 2000, 2 pages.
GenBank Accession No. AF077351 dated Dec. 20, 2000, 3 pages.
GenBank Accession No. AF115517 dated Nov. 23, 2005, 4 pages.
GenBank Accession No. AI413910 dated Feb. 9, 1999, 2 pages.
GenBank Accession No. AI414999 dated Feb. 9, 1999, 2 pages.
GenBank Accession No. AI425960 dated Mar. 9, 1999, 2 pages.
GenBank Accession No. AI851940 dated Jul. 15, 1999, 2 pages.
GenBank Accession No. AK018022 dated Sep. 19, 2008, 4 pages.
GenBank Accession No. AK019341 dated Sep. 19, 2008, 3 pages.
GenBank Accession No. AK019342 dated Sep. 19, 2008, 3 pages.
GenBank Accession No. AK034387 dated Sep. 19, 2008, 4 pages.
GenBank Accession No. AK038229 dated Sep. 19, 2008, 4 pages.
GenBank Accession No. AK038434 dated Sep. 19, 2008, 4 pages.
GenBank Accession No. AK041534 dated Sep. 19, 2008, 4 pages.
GenBank Accession No. AK042683 dated Sep. 19, 2008, 4 pages.
GenBank Accession No. AK136096 dated Sep. 19, 2008, 4 pages.
GenBank Accession No. AK136101 dated Sep. 19, 2008, 4 pages.
GenBank Accession No. AK142768 dated Sep. 19, 2008, 3 pages.
GenBank Accession No. AL591433 dated Jan. 15, 2009, 56 pages.
GenBank Accession No. BC004702 dated Jul. 15, 2006, 3 pages.
GenBank Accession No. BC055737 dated Jul. 15, 2006, 2 pages.
GenBank Accession No. BC086799 dated Sep. 21, 2006, 3 pages.
GenBank Accession No. BF449664 dated Dec. 1, 2000, 1 page.
GenBank Accession No. BG063957 dated Jan. 26, 2001, 2 pages.
GenBank Accession No. BG077309 dated Dec. 17, 2003, 2 pages.
GenBank Accession No. BM114282 dated Jan. 30, 2002, 2 pages.
GenBank Accession No. BY023910 dated Dec. 6, 2002, 2 pages.
GenBank Accession No. CN724527 dated May 18, 2004, 2 pages.
GenBank Accession No. NM_000130 dated Oct. 18, 2009, 6 pages.
GenBank Accession No. NM_000493 dated Mar. 15, 2009, 4 pages.
GenBank Accession No. NM_000598, GI No. 62243067 , dated Jun. 6, 2010, 5 pages.
GenBank Accession No. NM_000688, GI No. 40316942, dated Apr. 11, 2010, 5 pages.
GenBank Accession No. NM_001013398; GI No. 62243247, dated Jun. 6, 2010, 5 pages.
GenBank Accession No. NM_001034 dated Oct. 5, 2009, 5 pages.
GenBank Accession No. NM_001 039573, GI No. 221316683, dated Mar. 4, 2010, 5 pages.
GenBank Accession No. NM_001049 dated Jun. 21, 2009, 4 pages.
GenBank Accession No. NM_001067 dated Oct. 18, 2009, 5 pages.
GenBank Accession No. NM_001098533, GI No. 237858579, dated May 7, 2010, 5 pages.
GenBank Accession No. NM_001130851; GI No. 195927024, dated Mar. 5, 2010, 4 pages.
GenBank Accession No. NM_001136154 dated Jan. 8, 2012, 6 pages.
GenBank Accession No. NM_001136155 dated Jan. 8, 2012, 6 pages.
GenBank Accession No. NM_001143998, GI No. 221316675, dated Mar. 4, 2010, 5 pages.
GenBank Accession No. NM_001143999, GI No. 221316679, dated Mar. 5, 2010, 5 pages.
GenBank Accession No. NM_001144001, GI No. 221316686, dated Mar. 4, 2010, 5 pages.
GenBank Accession No. NM_001160367, GI No. 237858581, dated May 7, 2010, 5 pages.
GenBank Accession No. NM_001786 dated Nov. 1, 2009, 4 pages.
GenBank Accession No. NM_001844 dated Sep. 28, 2009, 7 pages.
GenBank Accession No. NM_003003, GI No. 221316681, dated Mar. 4, 2010, 5 pages.
GenBank Accession No. NM_003014; GI No. 170784837, dated Mar. 13, 2010, 5 pages.
GenBank Accession No. NM_003184; GI No. 115527086, dated Mar. 4, 2010, 7 pages.
GenBank Accession No. NM_003873.3 dated Oct. 18, 2009, 4 pages.
GenBank Accession No. NM_004336; GI No. 211938448, dated Mar. 14, 2010, 6 pages.
GenBank Accession No. NM_004449 dated Jan. 8, 2012, 6 pages.
GenBank Accession No. NM_005025.2 dated Jul. 12, 2009, 4 pages.
GenBank Accession No. NM_005192, GI No. 195927023, dated Mar. 4, 2010, 4 pages.
GenBank Accession No. NM_005651.1 dated Oct. 27, 2009, 3 pages.
GenBank Accession No. NM_006265, GI No. 208879448, dated Apr. 11, 2010, 6 pages.
GenBank Accession No. NM_006558 dated 812109, 3 pages.
GenBank Accession No. NM_006727 dated Oct. 18, 2009, 3 pages.
GenBank Accession No. NM_006819; GI No. 110225356, dated May 17, 2010, 5 pages.
GenBank Accession No. NM_012152; GI No. 183396778, dated Apr. 5, 2010, 5 pages.
GenBank Accession No. NM_014846; GI No. 120952850, dated Mar. 4, 2010, 6 pages.
GenBank Accession No. NM_016623; GI No. 42734437, dated Mar. 29, 2009, 4 pages.
GenBank Accession No. NM_018930 dated Feb. 10, 2008, _pages.
GenBank Accession No. NM_031966 GI No. 34304372, dated Jun. 6, 2010, 5 pages.
GenBank Accession No. NM_032334; GI No. 223468686, dated Mar. 5, 2010, 3 pages.
GenBank Accession No. NM_052987, GI No. 237858574, dated May 17, 2010, 5 pages.
GenBank Accession No. NM_052988, GI No. 237858573, dated May 17, 2010, 5 pages.
GenBank Accession No. NM_080546; GI No. 112363101, dated May 17, 2010, 6 pages.
GenBank Accession No. NM_080607 dated Sep. 3, 2009, 2 pages.
GenBank Accession No. NM_133445 dated Sep. 20, 2009, 5 pages.
GenBank Accession No. NM_138455; GI No. 34147546, dated May 7, 2010, 3 pages.
GenBank Accession No. NM_182918 dated Jan. 8, 2012, 6 pages.
GenBank Accession No. NM_199166, GI No. 40316938, dated Apr. 11, 2010, 5 pages.
GenBank Accession No. NP_001058 dated Dec. 25, 2011, 9 pages.

(56) References Cited

OTHER PUBLICATIONS

GenBank Accession No. W34764 dated May 13, 1996, 2 pages.
Supplemental Table 1 of U.S. Appl. No. 61/057,698, filed May 30, 2008, 13 pages.
Supplemental Table 2 of U.S. Appl. No. 61/057,698, filed May 30, 2008, 15 pages.
Supplemental Table 3 of U.S. Appl. No. 61/057,698, filed May 30, 2008, 21 pages.
Supplemental Table 4 of U.S. Appl. No. 61/057,698, filed May 30, 12008, 1 page.
Supplemental Table 5 of U.S. Appl. No. 61/057,698, filed May 30, 12008, 2 pages.
Supplemental Table 6 of U.S. Appl. No. 61/057,698, filed May 30, 2008, 1 page.
Adamo and Ladomery, "The Oncogene ERG: A Key Factor in Prostate Cancer," *Oncogene*(2016), 35:403-414.
Affymetrix GeneChip Human Genome U133 Array Set HG-U133A, Geo, Mar. 11, 2002, retrieved on Mar. 11, 2002.
Anonymous, UCSC Genome Browser on Human Mar. 2006, NCBI36/hg18) Assembly, Mar. 2006, XP055587638, Retrieved from the Internet: URL:https://genome-euro.ucsc.edu/cgi-bin/hgTracks?db=hg18&lastVirtModeType=default&lastVirtModeExtraState=&virtModeType=default&virtMode=0&nonVirtPosition=&position=chr5%3A 14025126%2D14062770&hgsid=232148223_IYIy9VS0Lh0jhldEBQ3nViBrQuB5 [retrieved on May 10, 2019].
Bismar et al., "ERG Protein Expression Reflects Hormonal Treatment Response and is Associated with Gleason Score and Prostate Cancer Specific Mortality," *Eur. J. Cancer* (2012), 48:538-546,Elsevier Ltd.
Biton et al., Nov. 20, 2014, Independent component analysis uncovers the landscape of the bladder tumor transcriptome and reveals insights into luminal and basal subtypes, Cell Reports, 9(4):1235-1245.
Blute et al., "Use of Gleason score, prostate specific antigen, seminal vesicle and margin status to predict biochemical failure after radical prostatectomy," J Urol (2001) 165: 119-125.
Bueno et al., "A diagnostic test for prostate cancer from gene expression profiling data," J Urol, Feb. 2004; 171(2 Pt 1):903-6.
Choi et al., Feb. 2014, Identification of distinct basal and luminal subtypes of muscle-invasive bladder cancer with different sensitivities to frontline chemotherapy, Cancer Cell, 25(2):152-165.
Choi et al., Jun. 24, 2014, Intrinsic basal and luminal subtypes of muscle-invasive bladder cancer, Nature Reviews Urology, 11(7):400-410.
Cooper et al., "Mechanisms of Disease: biomarkers and molecular targets from microarray gene expression studies in prostate cancer," Nat Clin Pract Urol. (2007) Dee:4(12):677-87.
Cordon-Cardo et al., "Improved prediction of prostate cancer recurrence through systems pathology," The Journal of Clinical Investigation (Jul. 2007) vol. 117, No. 7, pp. 1876-1883.
Den et al., Mar. 10, 2015, Genomic classifier identifies men with adverse pathology after racial prostatectomy who benefit from adjuvant radiation therapy, Journal of Clinical Oncology, 33(8):944-951.
Dhani et al., 2011, Phase II study of cytarabine in men with docetaxel-refractory, castration-resistnt prostate cancer with evaluation of TMPRSS2-ERG and SPINK1 as serum biomarkers, BJUI, 110:840-845.
Epstein et al., "Prognostic factors and reporting of prostate carcinoma in radical AU prostatectomy and pelvic lymphadenectomy specimens," Scand. J. Urol. Nephrol. Suppl. (2005) 216:34-63.
Fine et al., "A Proportional Hazards Model for the Subdistribution of a Competing Risk," Journal of the American Statistical Association (1999) vol. 94 (446), pp. 496-509.
Galavotti et al., Apr. 2012, The autophagy-associated factors DRAM1 and p62 regulate cell migration and invasion in glioblastoma stem cells, Oncogene, 32:699-712.
Gleason: "Histologic grading and clinical staging of prostatic carcinoma", Urologic pathology: the prostate, (Tannenbaum, ed.) (1977) Lea & Febiger, Philadelphia, PA, pp. 171-197.
Gleason: "Histologic grading of prostate cancer: a perspective"; Hum. Pathol. (1992) 23(3):273-279.
Grambsch et al., "Proportional Hazards Tests and Diagnostics Based on Weighted Residuals," Biometrika (2013) vol. 81 (3), pp. 515-526.
Ha et al., Nov. 12, 2009, Comparison of affymetrix gene array with the exon array shows potential application for detection of transcript isoform variation, BMC Genomics, 19(1):519.
Heagerty et al., "Time-Dependent ROC Curves for Censored Survival Data and a Diagnostic Marker," Biometrics (2000) vol. 56 (2), pp. 337-344.
Humphrey et al: "Histologic grade, DNA ploidy, and intraglandular tumor extent as indicators of tumor progression of clinical Stage B prostatic carcinoma"; Am J Surg Pathol (1991) 15(12):1165-1170.
Knowles et al., Dec. 23, 2014, Molecular biology of bladder cancer: new insights into pathogenesis and clinical diversity, Nature Reviews Cancer, 15(1):25-41.
Lin et al., "Nuclear receptor-induced chromosomal proximity and DNA breaks underlie specific translocations in cancer," Cell (Dec. 11, 2009) 139(6):1069-83.
Liu et al., 2014, Synergistic killing of lung cancer cells by cisplatin and radiation via autophagy and apoptosis, Oncology Letters, 7:1903-1910.
McConkey et al., Apr. 2015, Therapeutic opportunities in the intrinsic subtypes of muscle-invasive bladder cancer, Hematology/Oncology Clinics of North America, 29(2):377-394.
McConkey et al., May 2016, A prognostic gene expression signature in the molecular classification of chemotherapy-naive urothelial cancer is predictive of clinical outcomes from neoadjuvant chemotherapy: a phase 2 trial of dose-dense methotrexate, vinblastine, doxorubicin, and cisplatin with bevacizumab in urothelial cancer, European Urology, 69(5):855-862.
Mendiratta et al., "Genomic signatures associated with the development, progression, rand outcome of prostate cancer," Molecular diagnosis & therapy (2007) 11(6):345-54.
Nelson, "Predicting prostate cancer behavior using transcript profiles," J Urol. (Nov. 2004) 172(5 Pt 2):S28-32; discussion S33.
Ozen et al., Sep. 24, 2007, Widespread deregulation of microRNA expression in human prostate cancer, Oncogene, 27:1788-1793.
Probe Set Listing for the Affymetrix Human Genome U133 Plus 2.0 array (Accessed from https://www.affymetrix.com/analysis/index.affx on Jul. 1, 2015) (Year: 2015).
Reddy et al., "Clinical utility of microarray-derived genetic signatures in predicting outcomes in prostate cancer," Clinical Genitourinary Cancer (2006) 5(3):187-189.
Schlomm et al., "Molecular staging of prostate cancer in the year 2007," World .J. Urol. (Mar. 2007) 25(1):19-30.
Seiler et al., Oct. 2017, Impact of molecular subtypes in muscle-invasive bladder cancer on predicting response and survival after neoadjuvant chemotherapy, European Urology, 72(4):544-554.
Smit et al., "High-Resolution ERG-Expression Profiling on GeneChip Exon 1.0 ST Arrays in Primary and Castration-Resistant Prostate Cancer," *BJU International* (2013), 111(5):836-842, BJU International.
Solo et al., "Prevalence of prostate cancer (PC) clinical states (CS) in the United States: Estimates using a dynamic progression model," ASCO Annual Meeting, Journal of Clinical Oncology (May 20, 2011) vol. 29, No. 15, Abstract 4637.
Stephenson et al., "Postoperative Nomogram Predicting the 10-Year Probability of Prostate Cancer Recurrence After Radical Prostatectomy," J Clin Oncol (2008) vol. 23 (28), pp. 7005-7012.
Talantov et al., "Gene Based Prediction of Clinically Localized Prostate Cancer Progression After Radical Prostatectomy," The Journal Of Urology (Oct. 2010) vol. 184, 1521-1528.
Thompson et al., "Is the GPSM scoring algorithm for patients with prostate cancer valid in the contemporary era?" J Urol. (Aug. 2007) vol. 178 (2), 459-463.
Warrick et al., 2016, FOXA1, GATA3 and PPARγ cooperate to drive luminal subtype in bladder cancer: a molecular analysis of established human cell lines, Scientific Reports, 6:38531, DOI: 10.1038, 15 pp.

(56) References Cited

OTHER PUBLICATIONS

Damrauer et al., Feb. 25, 2014, Intrinsic subtypes of high-grade bladder cancer reflect the hallmarks of breast cancer biology, Proc Natl Acad Sci USA, 111(8):3110-3115.
International Search Report and Written Opinion dated Jul. 26, 2018 in PCT/CA2018/050060.

* cited by examiner

MOLECULAR SUBTYPING, PROGNOSIS, AND TREATMENT OF BLADDER CANCER

CROSS-REFERENCE TO RELATED APPLICATIONS

This application claims benefit of priority under 35 U.S.C. § 119(e) of U.S. Ser. No. 62/448,921, filed Jan. 20, 2017, the entire contents of which is incorporated herein by reference in its entirety.

INCORPORATION OF SEQUENCE LISTING

The material in the accompanying sequence listing is hereby incorporated by reference into this application. The accompanying sequence listing text file, name GBX1270_1_Sequence_Listing, was created on Jan. 19, 2018, and is 1100 kb. The file can be assessed using Microsoft Word on a computer that uses Windows OS.

FIELD OF THE INVENTION

The present invention pertains to the field of personalized medicine and methods for treating bladder cancer. In particular, the invention relates to the use of genomic signatures to identify individuals in need of treatment for bladder cancer who will be responsive to neoadjuvant chemotherapy. The present invention also provides methods and compositions for treating bladder cancer.

BACKGROUND OF THE INVENTION

Cancer is the uncontrolled growth of abnormal cells anywhere in a body. The abnormal cells are termed cancer cells, malignant cells, or tumor cells. Many cancers and the abnormal cells that compose the cancer tissue are further identified by the name of the tissue that the abnormal cells originated from (for example, bladder cancer). Cancer cells can proliferate uncontrollably and form a mass of cancer cells. Cancer cells can break away from this original mass of cells, travel through the blood and lymph systems, and lodge in other organs where they can again repeat the uncontrolled growth cycle. This process of cancer cells leaving an area and growing in another body area is often termed metastatic spread or metastatic disease. For example, if bladder cancer cells spread to a bone (or anywhere else), it can mean that the individual has metastatic bladder cancer.

Standard clinical parameters such as tumor size, grade, lymph node involvement and tumor—node metastasis (TNM) staging (American Joint Committee on Cancer, cancerstaging.org) may correlate with outcome and serve to stratify patients with respect to (neo)adjuvant chemotherapy, immunotherapy, antibody therapy and/or radiotherapy regimens. Incorporation of molecular markers in clinical practice may define tumor subtypes that are more likely to respond to targeted therapy. However, stage-matched tumors grouped by histological or molecular subtypes may respond differently to the same treatment regimen. Additional key genetic and epigenetic alterations may exist with important etiological contributions. A more detailed understanding of the molecular mechanisms and regulatory pathways at work in cancer cells and the tumor microenvironment (TME) could dramatically improve the design of novel anti-tumor drugs and inform the selection of optimal therapeutic strategies. The development and implementation of diagnostic, prognostic and therapeutic biomarkers to characterize the biology of each tumor may assist clinicians in making important decisions with regard to individual patient care and treatment.

Neoadjuvant cisplatin-based chemotherapy (NAC) is standard treatment in muscle-invasive bladder cancer (MIBC) prior to radical cystectomy (Bajorin et al. (2011) J. Clin. Oncol. 29(16):2135-2137; Grossman et al. (2003) N. Engl. J. Med. 349(9):859-866; International Collaboration of Trialists et al. (2011) J. Clin. Oncol. 29(16):2171-2177). Although NAC improves pathological down-staging and improves patient survival, only approximately 40% of patients experience a major response (Zargar et al. (2015) Eur. Urol. 67(2):241-249). The non-responding patients are unlikely to derive clinical benefit, are exposed to substantial toxicity, and experience a delay in definitive local therapy (Grossman et al., supra; International Collaboration of Trialists et al., supra). The identification of molecular markers of non-responsiveness is essential for more precise delivery of care. Recent analyses suggest that specific mutations, especially in ERCC2 and DNA repair genes, may predict response to NAC (Liu et al. (2016) JAMA Oncol. 2(8):1094-1096).

Recent identification of molecular gene expression subtypes has advanced our understanding of the biology of bladder cancer (Biton et al. (2014) Cell Rep 9(4):1235-1245; Cancer Genome Atlas Research Network (2014) Nature 507(7492):315-232; Choi et al. (2014) Cancer Cell 25(2): 152-165; Damrauer et al. (2014) Proc. Natl. Acad. Sci. USA 111(8): 3110-3115; Sjodahl et al. (2012) Clin. Cancer Res. 18(12):3377-3386; Volkmer et al. (2012) Proc. Natl. Acad. Sci. USA 109(6):2078-2083). Molecular classification provides a framework for further study and has potential implications for the clinical management of MIBC. Four different molecular subtyping schemes have been previously described (Cancer Genome Atlas Research Network, supra; Choi et al., supra; Damrauer et al., supra; Sjodahl et al., supra). Each was developed on different patient populations, unique genomic platforms, and only one was based on integrative multiplatform genomic analysis (Cancer Genome Atlas Research Network, supra). Despite these differences, each identifies molecular phenotypes that share many similarities, and they represent a division into basal and luminal tumors at a higher level, with different subclassifications that are specific to each system.

Choi et al (MDA group) first introduced the concept that molecular subtypes may predict response to NAC. In three cohorts with a total of 100 patients, a subset classified as "p53-like" tumors demonstrated a lower response rate to cisplatin-based combination chemotherapy (Choi et al., supra). This finding has not been validated in additional larger patient cohorts and has not been investigated with the other subtyping methods. Furthermore, none of the four subtyping models is suitable for clinical implementation because each requires classification of an entire patient cohort in order to assign an individual patient sample to a subtype. Thus, improved methods are needed for subtyping bladder cancer that better predict a patient's response to NAC.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The present invention relates to methods, systems and kits for the diagnosis, prognosis, and treatment of bladder cancer in a subject. The invention also provides biomarkers that define subgroups of bladder cancer, clinically useful classifiers for distinguishing bladder cancer subtypes, bioinformatic methods for determining clinically useful classifiers, and methods of use of each of the foregoing. The methods, systems and kits can provide expression-based analysis of biomarkers for purposes of subtyping bladder cancer in a subject. Further disclosed herein, in certain instances, are probe sets for use in subtyping bladder cancer in a subject. Classifiers for subtyping a bladder cancer and methods of treating bladder cancer based on molecular subtyping are also provided.

In one embodiment, the present invention provides a method comprising: a) providing a biological sample from a subject having bladder cancer; b) detecting the presence or expression level in the biological sample for a plurality of targets selected from Table 3, Table 5, Table 13 or SEQ ID Nos: 1-4050; and c) subtyping the bladder cancer in the subject according to a genomic subtyping classifier based on the presence or expression levels of the plurality of targets, wherein said subtyping comprises assigning the bladder cancer to one of four subtypes selected from the group consisting of a claudin-low subtype, a basal subtype, a luminal-infiltrated subtype, and a luminal non-infiltrated subtype. In some embodiments, the method further comprises administering neoadjuvant chemotherapy to the subject if the subtyping indicates that the subject has the basal subtype and administering an anti-cancer treatment other than the neoadjuvant chemotherapy to the subject if the subtyping indicates that the subject has the luminal-infiltrated subtype, the luminal non-infiltrated subtype, or the claudin-low subtype, wherein the anti-cancer treatment other than neoadjuvant chemotherapy is selected from the group consisting of surgery, chemotherapy, radiation therapy, immunotherapy, biological therapy, hormonal therapy, radiation therapy, immunotherapy and photodynamic therapy. In certain embodiments the chemotherapy is selected from cisplatin, mitomycin, fluorouracil (5-FU), gemcitabine, methotrexate, vinblastine, doxorubicin, carboplatin, paclitaxel, docetaxel or a combination thereof.

In one embodiment, the present invention provides a method comprising: a) providing a biological sample from a subject having bladder cancer; b) detecting the presence or expression level in the biological sample for a plurality of targets selected from Table 10 and c) subtyping the bladder cancer in the subject according to a genomic subtyping classifier based on the presence or expression levels of the plurality of targets, wherein said subtyping comprises assigning the bladder cancer to one of four subtypes selected from the group consisting of a claudin-low subtype, a basal subtype, a luminal-infiltrated subtype, and a luminal non-infiltrated subtype.

In one embodiment, the present invention provides a method comprising: a) providing a biological sample from a subject having bladder cancer; b) detecting the presence or expression level in the biological sample for a plurality of targets selected from the group consisting of LAMC2, IFI30, SAA1, VIM, TGFBI, TIMP2, GBP1, SNAI2, GBP5, POSTN, TNC, F3, BGN, CCL5, SULF1, WARS, MMP3, CXCL10, TIMP3, SERPINB1, DDIT4, MET, MYADM, CD68, COL1A1, ENO1, THBS1, CD44, MT1L, ACER2, ACOX1, ACSL5, ACTA2, ACTG2, AHR, AKR1C2, ANXA1, BAMBI, BTG2, CASP14, CDH1, CLDN1, COL1A2, CPSF6, CSTA, CTSK, CXCL1, CXCL9, CYP1A1, DAPK1, DES, DUSP1, EFEMP1, ERP27, F11R, FCGR3A, FLNA, FN1, G0S2, GRHL1, HIST1H2AE, HIST1H2BF, HLA-DRA, HLA-DRB1, HLA-DRB5, HMGCS2, IFI16, IFI6, IFITM2, IGFL1, INA, ITGA6, KRT19, KRT8, LAPTM5, LUM, LYZ, MAL, MALL, MMP1, MMP12, MT1E, MYL9, OLFM4, PABPC1, PAQR7, PERP, PM20D1, PPARG, PSCA, PTMS, PTPN13, PTPRM, RALBP1, RNF128, RNF138P1, S100A10, S100A7, S100A8, SAMD9, SCCPDH, SCNN1A, SCNN1B, SCUBE2, SEMA5A, SERPINB13, SERPINB3, SERPINB4, SFN, SFRP2, SLITRK6, SNCG, SPINK1, SPP1, SPRR1B, STS, SYTL2, TACSTD2, TGM2, THBS2, TMEM45A, TMEM45B, TMPRSS2, TMSB10, TOX3, TPM2, TPX2, TWIST2, UPK1A, UPK1B, VCAN, VGLL1, VSIG2, ZNF486, UGT1A1, BEX4, UGT1A9, CXCL17, IGFBP3, UGT1A3, UGT1A5, SLC14A1, GPR110, TNFRSF21, FLRT3, ELF3, S100, PGATA3, UGT1A10, GABRP, GRHL3, MACC1, EHF, UGT1A8, MGP, and ERBB2; and c) subtyping the bladder cancer in the subject according to a genomic subtyping classifier based on the presence or expression levels of the plurality of targets, wherein said subtyping comprises assigning the bladder cancer to one of four subtypes selected from the group consisting of a claudin-low subtype, a basal subtype, a luminal-infiltrated subtype, and a luminal non-infiltrated subtype.

In one embodiment, the present invention provides a method comprising: a) providing a biological sample from a subject having bladder cancer and b) detecting the presence or expression level in the biological sample for a plurality of targets selected from Table 10. In some embodiments, the method further comprises subtyping the bladder cancer in the subject according to a genomic subtyping classifier based on the presence or expression levels of the plurality of targets, wherein said subtyping comprises assigning the bladder cancer to one of four subtypes selected from the group consisting of a claudin-low subtype, a basal subtype, a luminal-infiltrated subtype, and a luminal non-infiltrated subtype. In some embodiments, the method further comprises administering neoadjuvant chemotherapy to the subject if the subtyping indicates that the subject has the basal subtype and administering an anti-cancer treatment other than the neoadjuvant chemotherapy to the subject if the subtyping indicates that the subject has the luminal-infiltrated subtype, the luminal non-infiltrated subtype, or the claudin-low subtype, wherein the anti-cancer treatment is selected from the group consisting of surgery, chemotherapy, radiation therapy, immunotherapy, biological therapy, hormonal therapy, radiation therapy, immunotherapy and photodynamic therapy. In certain embodiments the chemotherapy is selected from cisplatin, mitomycin, fluorouracil (5-FU), gemcitabine, methotrexate, vinblastine, doxorubicin, carboplatin, paclitaxel, docetaxel or a combination thereof.

In one embodiment, the present invention provides a method comprising: a) providing a biological sample from a subject having bladder cancer and b) detecting the presence or expression level in the biological sample for a plurality of targets selected from the group consisting of LAMC2, IFI30, SAA1, VIM, TGFBI, TIMP2, GBP1, SNAI2, GBP5, POSTN, TNC, F3, BGN, CCL5, SULF1, WARS, MMP3, CXCL10, TIMP3, SERPINB1, DDIT4, MET, MYADM, CD68, COL1A1, ENO1, THBS1, CD44, MT1L, ACER2, ACOX1, ACSL5, ACTA2, ACTG2, AHR, AKR1C2, ANXA1, BAMBI, BTG2, CASP14, CDH1, CLDN1, COL1A2, CPSF6, CSTA, CTSK, CXCL1, CXCL9, CYP1A1, DAPK1, DES, DUSP1, EFEMP1, ERP27, F11R, FCGR3A, FLNA, FN1, G0S2, GRHL1, HIST1H2AE, HIST1H2BF, HLA-DRA, HLA-DRB1, HLA-DRB5, HMGCS2, IFI16, IFI6, IFITM2, IGFL1, INA, ITGA6, KRT19, KRT8, LAPTM5, LUM, LYZ, MAL, MALL, MMP1, MMP12, MT1E, MYL9, OLFM4, PABPC1, PAQR7, PERP, PM20D1, PPARG, PSCA, PTMS, PTPN13, PTPRM, RALBP1, RNF128, RNF138P1, S100A10, S100A7, S100A8, SAMD9, SCCPDH, SCNN1A, SCNN1B, SCUBE2, SEMASA, SERPINB13, SERPINB3, SERPINB4, SFN, SFRP2, SLITRK6, SNCG, SPINK1, SPP1, SPRR1B, STS, SYTL2, TACSTD2, TGM2, THBS2, TMEM45A, TMEM45B, TMPRSS2, TMSB10, TOX3, TPM2, TPX2, TWIST2, UPK1A, UPK1B, VCAN, VGLL1, VSIG2, ZNF486, UGT1A1, BEX4, UGT1A9, CXCL17, IGFBP3, UGT1A3, UGT1A5, SLC14A1, GPR110, TNFRSF21, FLRT3, ELF3, S100, PGATA3, UGT1A10, GABRP, GRHL3, MACC1, EHF, UGT1A8, MGP, and ERBB2.

In some embodiments, the method further comprises subtyping the bladder cancer in the subject according to a genomic subtyping classifier based on the presence or expression levels of the plurality of targets, wherein said subtyping comprises assigning the bladder cancer to one of four subtypes selected from the group consisting of a claudin-low subtype, a basal subtype, a luminal-infiltrated subtype, and a luminal non-infiltrated subtype. In some embodiments, the method further comprises administering neoadjuvant chemotherapy to the subject if the subtyping indicates that the subject has the basal subtype and administering an anti-cancer treatment other than the neoadjuvant chemotherapy to the subject if the subtyping indicates that the subject has the luminal-infiltrated subtype, the luminal non-infiltrated subtype, or the claudin-low subtype, wherein the anti-cancer treatment other than neoadjuvant chemotherapy is selected from the group consisting of surgery, chemotherapy, radiation therapy, immunotherapy, biological therapy, hormonal therapy, and photodynamic therapy.

In another embodiment, the present invention provides a method for treating a subject with bladder cancer, the method comprising: a) providing a biological sample from the subject; b) detecting the presence or expression level in the biological sample for a plurality of targets selected from Table 3, Table 5, Table 13 or SEQ ID Nos: 1-4050; and c) administering a treatment to the subject, wherein the treatment is selected from the group consisting of neoadjuvant chemotherapy or an anti-cancer treatment. In some embodiments, the anti-cancer treatment is selected from the group consisting of surgery, chemotherapy, radiation therapy, immunotherapy, biological therapy, hormonal therapy, and photodynamic therapy.

In other embodiments, the present invention provides a method for treating a subject with bladder cancer, the method comprising: a) providing a biological sample from the subject; b) detecting the presence or expression level in the biological sample for a plurality of targets selected from Table 3, Table 5, Table 13 or SEQ ID Nos: 1-4050; c) subtyping the bladder cancer in the subject according to a genomic subtyping classifier based on the presence or expression levels of the plurality of targets, wherein said subtyping comprises assigning the bladder cancer to one of four subtypes selected from the group consisting of a claudin-low subtype, a basal subtype, a luminal-infiltrated subtype, and a luminal non-infiltrated subtype; and d) administering neoadjuvant chemotherapy to the subject if the subtyping indicates that the subject has the basal subtype and administering an anti-cancer treatment other than the neoadjuvant chemotherapy to the subject if the subtyping indicates that the subject has the luminal-infiltrated subtype, the luminal non-infiltrated subtype, or the claudin-low subtype, wherein the anti-cancer treatment other than neoadjuvant chemotherapy is selected from the group consisting of surgery, chemotherapy, radiation therapy, immunotherapy, biological therapy, hormonal therapy, and photodynamic therapy.

In one aspect the invention includes a method for predicting benefit from neoadjuvant chemotherapy and treating a subject for bladder cancer, the method comprising: a) providing a biological sample from the subject; b) detecting the presence or expression level in the biological sample for a plurality of targets selected from Table 3, Table 5, Table 13 or SEQ ID Nos: 1-4050; and c) subtyping the bladder cancer in the subject according to a genomic subtyping classifier based on the presence or expression levels of the plurality of targets, wherein said subtyping comprises assigning the bladder cancer to one of four subtypes selected from the group consisting of a claudin-low subtype, a basal subtype, a luminal-infiltrated subtype, and a luminal non-infiltrated subtype; and d) administering neoadjuvant chemotherapy to the subject if the subtyping indicates that the subject has the basal subtype and administering an anti-cancer treatment other than the neoadjuvant chemotherapy to the subject if the subtyping indicates that the subject has the luminal-infiltrated subtype, the luminal non-infiltrated subtype, or the claudin-low subtype, wherein the anti-cancer treatment other than neoadjuvant chemotherapy is selected from the group consisting of surgery, chemotherapy, radiation therapy, immunotherapy, biological therapy, hormonal therapy, and photodynamic therapy. In one embodiment, the neoadjuvant chemotherapy comprises administering cisplatin. In another embodiment, the subject has muscle-invasive bladder cancer. In some embodiments, the biological sample comprises bladder cancer cells. In other embodiments, the biological sample comprises nucleic acids (e.g., RNA or DNA).

The method may be performed prior to treatment of the subject with neoadjuvant chemotherapy to determine if the subject will benefit from neoadjuvant chemotherapy or should be administered some other anti-cancer treatment. The method may also be performed while the subject is undergoing neoadjuvant chemotherapy to help evaluate whether continued treatment is likely to be efficacious.

The biological sample obtained from a patient is typically urine, a biopsy, blood or a tumor sample, but can be any sample from bodily fluids or tissue of the patient that contains cancerous cells or nucleic acids (e.g., RNA, DNA). In certain embodiments, nucleic acids (e.g., RNA transcripts) comprising sequences from targets selected from Table 3, Table 5, Table 13 or SEQ ID Nos: 1-4050, or complements thereof, are further isolated from the biological sample, and/or purified, and/or amplified prior to analysis.

The presence or expression level of biomarker nucleic acids can be determined by using a variety of methods including, but not limited to, in situ hybridization, a PCR-based method, an array-based method, an immunohistochemical method, a sequencing method (e.g., next-generation sequencing), an RNA assay method, or an immunoassay method.

In some embodiments, the invention provides a method of subtyping bladder cancer in a subject, comprising: providing a biological sample from the subject, and detecting the presence or expression level in the biological sample for a plurality of targets selected from Table 3, Table 5, Table 13 or SEQ ID Nos: 1-4050; wherein the presence or expression level of the plurality of targets provides an indication of the bladder cancer subtype. In some embodiments, the biological sample comprises bladder cancer cells. In other embodiments, the biological sample comprises nucleic acids. In some embodiments, the expression level of at least one target is reduced compared to a control. In other embodiments, the expression level of at least one target is increased compared to a control. In yet other embodiments, the level of expression of at least one target is determined by using a method selected from the group consisting of in situ hybridization, a PCR-based method, an array-based method, an immunohistochemical method, a sequencing method, an RNA assay method and an immunoassay method. In other embodiments, the level of expression of at least one target is detected using a reagent selected from the group consisting of a nucleic acid probe, one or more nucleic acid primers, and an antibody. In still other embodiments, determining the level of expression comprises measuring the level of a nucleic acid (e.g., RNA transcript).

In another aspect, the invention includes a method for determining a treatment for a subject who has bladder cancer, the method comprising: a) providing a biological sample from the subject; b) detecting the presence or expression level in the biological sample for a plurality of targets selected from Table 3, Table 5, Table 13 or SEQ ID Nos: 1-4050; c) subtyping the bladder cancer of the subject according to a genomic subtyping classifier based on the presence or expression levels of the plurality of targets, wherein said subtyping comprises assigning the bladder cancer to one of four subtypes selected from the group consisting of a claudin-low subtype, a basal subtype, a luminal-infiltrated subtype, and a luminal non-infiltrated subtype; and d) determining whether or not the subject is likely to be responsive to neoadjuvant chemotherapy based on the subtype of the bladder cancer in the subject; and prescribing neoadjuvant chemotherapy to the subject if the patient is identified as likely to be responsive to neoadjuvant chemotherapy, or prescribing a cancer treatment other than neoadjuvant chemotherapy to the subject if the subject is not identified as likely to be responsive to neoadjuvant chemotherapy. In some embodiments, the biological sample comprises bladder cancer cells. In other embodiments, the biological sample comprises nucleic acids.

In another aspect, the invention includes a probe set for predicting benefit from neoadjuvant chemotherapy in a subject who has bladder cancer, the probe set comprising a plurality of probes for detecting a plurality of targets, wherein the plurality of targets comprises one or more target sequences, or complements thereof, of targets selected from Table 3, Table 5, Table 13 or SEQ ID Nos: 1-4050, or a combination thereof. Probes may be detectably labeled to facilitate detection.

In another aspect, the invention includes a system for analyzing a bladder cancer to predict response of a subject to neoadjuvant chemotherapy, the system comprising: a) a probe set described herein; and b) a computer model or algorithm for analyzing an expression level or expression profile of the plurality of target nucleic acids hybridized to the plurality of probes in a biological sample from a subject who has bladder cancer and subtyping the bladder cancer of the subject according to a genomic subtyping classifier based on the expression level or expression profile, wherein said subtyping comprises assigning the bladder cancer to one of four subtypes selected from the group consisting of a claudin-low subtype, a basal subtype, a luminal-infiltrated subtype, and a luminal non-infiltrated subtype.

In another aspect, the invention includes a kit for predicting response of a subject to neoadjuvant chemotherapy, the kit comprising agents for detecting the presence or expression levels for a plurality of targets, wherein said plurality of targets comprises one or more targets selected from Table 3, Table 5, Table 13 or SEQ ID Nos: 1-4050. The kit may include one or more agents (e.g., hybridization probes, PCR primers, or microarray) for detecting the presence or expression levels of a plurality of targets, wherein said plurality of targets comprises one or more targets selected from Table 3, Table 5, Table 13 or SEQ ID Nos: 1-4050, a container for holding a biological sample isolated from a human subject for testing, and printed instructions for reacting the agents with the biological sample or a portion of the biological sample to determine whether or not the subject is likely to benefit from neoadjuvant chemotherapy. In some embodiments, the biological sample comprises bladder cancer cells. In other embodiments, the biological sample comprises nucleic acids (e.g., RNA or DNA). The agents may be packaged in separate containers. The kit may further comprise one or more control reference samples or other reagents for measuring gene expression (e.g., reagents for performing PCR, RT-PCR, microarray analysis, a Northern blot, an immunoassay, or immunohistochemistry). In one embodiment, the kit comprises agents for detecting the presence or expression levels of the targets listed in Table 3, Table 5, Table 13 or SEQ ID Nos: 1-4050. In another embodiment, the kit comprises agents for detecting the presence or expression levels of all the targets listed in Table 3, Table 5, Table 13 or SEQ ID Nos: 1-4050. For example, the kit may comprise a probe set, as described herein, for detecting a plurality of targets, wherein the plurality of targets comprises one or more target sequences, or complements thereof, of targets selected from Table 3, Table 5, Table 13 or SEQ ID Nos: 1-4050, or any combination thereof.

In another embodiment, the kit further comprises a system for analyzing a bladder cancer to predict response of a subject to neoadjuvant chemotherapy, wherein the system comprises: a) a probe set comprising a plurality of probes for detecting a plurality of target nucleic acids, wherein the plurality of target nucleic acids comprises one or more target sequences, or complements thereof, of targets selected from Table 3, Table 5, Table 13 or SEQ ID Nos: 1-4050, or any combination thereof; and b) a computer model or algorithm for analyzing an expression level or expression profile of the plurality of target nucleic acids hybridized to the plurality of probes in a biological sample from a subject who has bladder cancer and subtyping the bladder cancer of the subject according to a genomic subtyping classifier based on the expression level or expression profile, wherein said subtyping comprises assigning the bladder cancer to one of four subtypes selected from the group consisting of a claudin-low subtype, a basal subtype, a luminal-infiltrated subtype, and a luminal non-infiltrated subtype.

In another aspect, the invention includes a method of diagnosing, prognosing, determining the progression of cancer, or predicting benefit from therapy in a subject with bladder cancer, comprising: a) providing a biological sample from the subject; b) assaying an expression level in the biological sample from the subject for a plurality of targets using at least one reagent that specifically binds to said targets, wherein the plurality of targets comprises one or more targets selected from Table 3, Table 5, Table 13 or SEQ ID Nos: 1-4050; and c) diagnosing, prognosing, determining the progression of cancer, or predicting benefit from therapy in the subject based on the expression level of the plurality of targets. In some embodiments, the biological sample comprises bladder cancer cells. In other embodiments, the biological sample comprises nucleic acids (e.g., RNA or DNA).

The significance of the expression levels of one or more biomarker targets of the present invention may be evaluated using, for example, a T-test, P-value, KS (Kolmogorov Smirnov) P-value, accuracy, accuracy P-value, positive predictive value (PPV), negative predictive value (NPV), sensitivity, specificity, AUC, AUC P-value (Auc.pvalue), Wilcoxon Test P-value, Median Fold Difference (MFD), Kaplan Meier (KM) curves, survival AUC (survAUC), Kaplan Meier P-value (KM P-value), Univariable Analysis Odds Ratio P-value (uvaORPval), multivariable analysis Odds Ratio P-value (mvaORPval), Univariable Analysis Hazard Ratio P-value (uvaHRPval) and Multivariable Analysis Hazard Ratio P-value (mvaHRPval). The significance of the expression level of the one or more targets may be based on two or more metrics selected from the group comprising AUC, AUC P-value (Auc.pvalue), Wilcoxon Test P-value, Median Fold Difference (MFD), Kaplan Meier (KM) curves, survival AUC (survAUC), Univariable Analysis Odds Ratio P-value (uvaORPval), multivariable analysis Odds Ratio P-value (mvaORPval), Kaplan Meier P-value (KM P-value), Univariable Analysis Hazard Ratio P-value (uvaHRPval) or Multivariable Analysis Hazard Ratio P-value (mvaHRPval).

These and other embodiments of the subject invention will readily occur to those of skill in the art in view of the disclosure herein.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

FIG. 1A shows an overview of four previously described bladder cancer subtyping methods. UNC divides the cancers in two classes, luminal and basal. Claudin-low is a subtype within basal that has lost epithelial differentiation and has a high level of immune infiltration. The MDA subtyping method also divides into basal and luminal tumors, in addition to a third subtype with an active p53-signature (p53-like). The TCGA subtyping defines four clusters that are also basal (cluster III and IV) and luminal (cluster I and II). The Lund group discovered 5 subtypes that can be considered basal (Uro B and SCC-like), luminal (Uro A and genetically unstable) and infiltrated. FIG. 1B shows a heatmap of biologically relevant gene signatures (rows) in pre-NAC TUR samples from the discovery cohort. The column annotation across the top provides the subtype calls from each classification system. FIG. 1C shows a heatmap of two bidirectional epithelial-to-mesenchymal transition signatures (Tan et al. and Kardos et al.). FIG. 1D shows enrichment plots of the hallmark EMT signature in claudin-low versus basal tumors (left) and cluster IV versus III (right). FIG. 1E and FIG. 1F shows differential expression of immune markers CXCL9 (FIG. 1E) and CD8A (FIG. 1F) in the UNC subtypes (left) and the TCGA clusters (right).

FIG. 2A shows OS stratified according to the UNC subtypes. FIG. 2B shows OS stratified according to the MDA subtypes. FIG. 2C shows OS stratified according to the TCGA clusters. FIG. 2D shows OS stratified according to the Lund subtypes.

FIG. 3A shows the proposed GSC bladder cancer classes derived from a consensus of four models (UNC, MDA, TCGA, and Lund). FIG. 3B shows the GSC cross-validation scores for each sample in the NAC dataset. FIG. 3C shows the performance of the GSC in the discovery (10-fold cross validation for model performance) and two independent validation cohorts (NAC validation cohort and non-NAC validation cohort), respectively.

FIG. 4A shows Kaplan-Meier plots for OS in non-NAC (left) and NAC (right) datasets stratified according to the classes predicted by GSC. FIGS. 4B and 4C show OS of the NAC dataset according to major pathological downstaging stratified by luminal (FIG. 4B left), basal (FIG. 4B right), luminal-infiltrated (FIG. 4C left) and claudin-low subtype (FIG. 4C right), respectively.

FIG. 6A shows a heatmap of Lund classifier genes in all pre-NAC TUR samples. FIG. 6B shows a barplot indicating the number of tumors per subtype. FIG. 6C shows that characteristic genes for each subtype were expressed in the appropriate subtypes. FIG. 6D shows a heatmap of the genes in the TGAA ClaNC model.

FIG. 7A shows a heatmap of genes in BASE47 in the pre-NAC TURBT samples. FIG. 7B shows a plot of the prediction scores for basal tumors of the BASE47 model (y-axis) and the R values of Pearson correlation to the model centroids (x-axis). FIG. 7C shows a heatmap of genes in the claudin-low classifier. FIG. 7D shows a distribution of the prediction scores of all pre-NAC TURBT samples of the claudin-low classifier shown in the histogram. FIG. 7E shows a heatmap of basal, p53-like and luminal genes from the MDA classifier in all pre-NAC TURBT samples. FIG. 7F shows the distances of test samples to the samples in the training set measured with the one Nearest Neighbor (oneNN) model.

FIG. 8A shows the differences in expression of known chemokines and immune markers between the UNC subtypes. FIG. 8B shows a comparison of expression of chemokines and immune markers between tumors in TCGA cluster I-IV. FIG. 8C shows enrichment plots of immune signatures and signatures for epithelial-to-mesenchymal transition (EMT) in claudin-low versus basal tumors. FIG. 8D shows gene enrichment in cluster IV tumors. FIG. 8E shows enrichment plots of the Hallmark inflammatory response, KEGG chemokine signaling pathway and Tan EMT signature in cluster II versus I tumors.

FIG. 9A shows an OS analysis according to the UNC subtypes. FIG. 9B shows an OS analysis according to the MDA subtypes. FIG. 9C shows an OS analysis according to the TCGA clusters. FIG. 9D shows an OS analysis according to the Lund subtypes.

DETAILED DESCRIPTION OF THE INVENTION

Figure 1A:
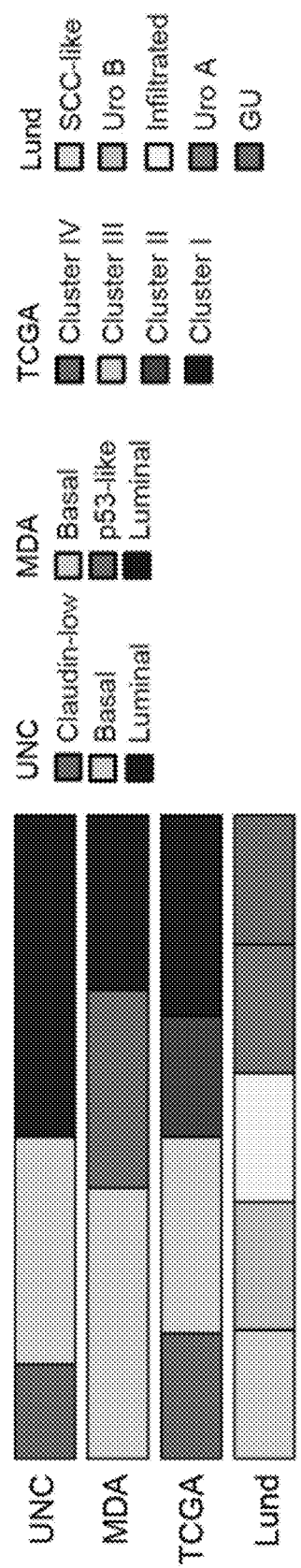
FIGS. 1A-1F show molecular subtypes in pre-NAC TURBT samples in discovery NAC cohort.

The present invention discloses systems and methods for diagnosing, predicting, and/or monitoring the status or outcome of bladder cancer in a subject using expression-based analysis of a plurality of targets. Generally, the method comprises (a) optionally providing a sample from a subject; (b) assaying the expression level of a plurality of targets in the sample; and (c) diagnosing, predicting and/or monitoring the status or outcome of a bladder cancer based on the expression level of the plurality of targets. Assaying the expression level for a plurality of targets in the sample may comprise applying the sample to a microarray. In some instances, assaying the expression level may comprise the use of an algorithm. The algorithm may be used to produce a classifier. Alternatively, the classifier may provide a probe selection region. In some instances, assaying the expression level for a plurality of targets comprises detecting and/or quantifying the plurality of targets. In some embodiments, assaying the expression level for a plurality of targets comprises sequencing the plurality of targets. In some embodiments, assaying the expression level for a plurality of targets comprises amplifying the plurality of targets. In some embodiments, assaying the expression level for a plurality of targets comprises quantifying the plurality of targets. In some embodiments, assaying the expression level for a plurality of targets comprises conducting a multiplexed reaction on the plurality of targets. In some instances, the plurality of targets comprises one or more targets selected from Table 3, Table 5, Table 13 or SEQ ID Nos: 1-4050. In some instances, the plurality of targets comprises at least about 2, at least about 3, at least about 4, at least about 5, at least about 6, at least about 7, at least about 8, at least about 9, or at least about 10 targets selected from Table 3, Table 5, Table 13 or SEQ ID Nos: 1-4050.

Further disclosed herein are methods for subtyping bladder cancer. Generally, the method comprises: (a) providing a sample from a subject; (b) assaying the expression level for a plurality of targets in the sample; and (c) subtyping the bladder cancer based on the expression level of the plurality of targets. In some instances, the plurality of targets comprises one or more targets selected from Table 3, Table 5, Table 13 or SEQ ID Nos: 1-4050. In some embodiments, the biological sample comprises bladder cancer cells. In other embodiments, the biological sample comprises nucleic acids (e.g., RNA or DNA). In some instances, the plurality of targets comprises at least about 2, at least about 3, at least about 4, at least about 5, at least about 6, at least about 7, at least about 8, at least about 9, or at least about 10 targets selected from Table 3, Table 5, Table 13 or SEQ ID Nos: 1-4050. In some instances, subtyping the bladder cancer comprises determining whether the cancer would respond to an anti-cancer therapy. Alternatively, subtyping the bladder cancer comprises identifying the cancer as non-responsive to an anti-cancer therapy. Optionally, subtyping the bladder cancer comprises identifying the cancer as responsive to an anti-cancer therapy.

Before the present invention is described in further detail, it is to be understood that this invention is not limited to the particular methodology, compositions, articles or machines described, as such methods, compositions, articles or machines can, of course, vary. It is also to be understood that the terminology used herein is for the purpose of describing particular embodiments only, and is not intended to limit the scope of the present invention.

Targets

In some instances, assaying the expression level of a plurality of genes comprises detecting and/or quantifying a plurality of target analytes. In some embodiments, assaying the expression level of a plurality of genes comprises sequencing a plurality of target nucleic acids. In some embodiments, assaying the expression level of a plurality of biomarker genes comprises amplifying a plurality of target nucleic acids. In some embodiments, assaying the expression level of a plurality of biomarker genes comprises conducting a multiplexed reaction on a plurality of target analytes.

The methods disclosed herein often comprise assaying the expression level of a plurality of targets. The plurality of targets may comprise coding targets and/or non-coding targets of a protein-coding gene or a non-protein-coding gene. A protein-coding gene structure may comprise an exon and an intron. The exon may further comprise a coding sequence (CDS) and an untranslated region (UTR). The protein-coding gene may be transcribed to produce a pre-mRNA and the pre-mRNA may be processed to produce a mature mRNA. The mature mRNA may be translated to produce a protein.

A non-protein-coding gene structure may comprise an exon and intron. Usually, the exon region of a non-protein-coding gene primarily contains a UTR. The non-protein-coding gene may be transcribed to produce a pre-mRNA and the pre-mRNA may be processed to produce a non-coding RNA (ncRNA).

A coding target may comprise a coding sequence of an exon. A non-coding target may comprise a UTR sequence of an exon, intron sequence, intergenic sequence, promoter sequence, non-coding transcript, CDS antisense, intronic antisense, UTR antisense, or non-coding transcript antisense. A non-coding transcript may comprise a non-coding RNA (ncRNA).

In some instances, the plurality of targets comprises one or more targets selected from Table 3, Table 5, Table 13 or SEQ ID Nos: 1-4050. In some instances, the plurality of targets comprises at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, or at least about 50 targets selected from Table 3, Table 5, Table 13 or SEQ ID Nos: 1-4050.

In some instances, the plurality of targets comprises one or more targets selected from CPSF6 and ELF3; CPSF6 and PTPN13; CPSF6 and SNCG; CPSF6 and VGLL1; CPSF6, PTPN13 and ELF3; CPSF6, PTPN13 and SNCG; CPSF6, PTPN13 and VGLL1; CPSF6, PTPN13, VGLL1 and ELF3; CPSF6, PTPN13, VGLL1 and SNCG; CPSF6, PTPN13, VGLL1, ELF3 and SNCG; CPSF6; EFEMP1 and CPSF6; EFEMP1 and ELF3; EFEMP1 and PTPN13; EFEMP1 and PTPRM; EFEMP1 and SNCG; EFEMP1 and VGLL1; EFEMP1, PTPRM and CPSF6; EFEMP1, PTPRM and ELF3; EFEMP1, PTPRM and PTPN13; EFEMP1, PTPRM and SNCG; EFEMP1, PTPRM and VGLL1; EFEMP1, PTPRM, CPSF6 and ELF3; EFEMP1, PTPRM, CPSF6 and PTPN13; EFEMP1, PTPRM, CPSF6 and SNCG; EFEMP1, PTPRM, CPSF6 and VGLL1; EFEMP1, PTPRM, CPSF6, PTPN13 and ELF3; EFEMP1, PTPRM, CPSF6, PTPN13 and SNCG; EFEMP1, PTPRM, CPSF6, PTPN13 and VGLL1; EFEMP1, PTPRM, CPSF6, PTPN13, VGLL1 and ELF3; EFEMP1, PTPRM, CPSF6, PTPN13, VGLL1 and SNCG; EFEMP1, PTPRM, CPSF6, PTPN13, VGLL1, ELF3 and SNCG; EFEMP1; ELF3 and SNCG; ELF3; GABRP and CPSF6; GABRP and EFEMP1; GABRP and ELF3; GABRP and PTPN13; GABRP and PTPRM; GABRP and SNCG; GABRP and VGLL1; GABRP and EFEMP1; GABRP, EFEMP1 and CPSF6; GABRP, EFEMP1 and ELF3; GABRP, EFEMP1 and PTPN13; GABRP, EFEMP1 and PTPRM; GABRP, EFEMP1 and SNCG; GABRP, EFEMP1 and VGLL1; GABRP, EFEMP1, PTPRM and CPSF6; GABRP, EFEMP1, PTPRM and ELF3; GABRP, EFEMP1, PTPRM and PTPN13; GABRP, EFEMP1, PTPRM and SNCG; GABRP, EFEMP1, PTPRM and VGLL1; GABRP, EFEMP1, PTPRM, CPSF6 and ELF3; GABRP, EFEMP1, PTPRM, CPSF6 and PTPN13; GABRP, EFEMP1, PTPRM, CPSF6 and SNCG; GABRP, EFEMP1, PTPRM, CPSF6 and VGLL1; GABRP, EFEMP1, PTPRM, CPSF6, PTPN13 and ELF3; GABRP, EFEMP1, PTPRM, CPSF6, PTPN13 and SNCG; GABRP, EFEMP1, PTPRM, CPSF6, PTPN13 and VGLL1; GABRP, EFEMP1, PTPRM, CPSF6, PTPN13, VGLL1 and ELF3; GABRP, EFEMP1, PTPRM, CPSF6, PTPN13, VGLL1 and SNCG; GABRP, EFEMP1, PTPRM, CPSF6, PTPN13, VGLL1, ELF3 and SNCG; GABRP; GBP1 and CPSF6; GBP1 and EFEMP1; GBP1 and ELF3; GBP1 and GABRP; GBP1 and PTPN13; GBP1 and PTPRM; GBP1 and SNAI2; GBP1 and SNCG; GBP1 and TMEM45A; GBP1 and VGLL1; GBP1, SNAI2 and CPSF6; GBP1, SNAI2 and EFEMP1; GBP1, SNAI2 and ELF3; GBP1, SNAI2 and GABRP; GBP1, SNAI2 and PTPN13; GBP1, SNAI2 and PTPRM; GBP1, SNAI2 and SNCG; GBP1, SNAI2 and TMEM45A; GBP1, SNAI2 and VGLL1; GBP1, SNAI2, TMEM45A and CPSF6; GBP1, SNAI2, TMEM45A and EFEMP1; GBP1, SNAI2, TMEM45A and ELF3; GBP1, SNAI2, TMEM45A and GABRP; GBP1, SNAI2, TMEM45A and PTPN13; GBP1, SNAI2, TMEM45A and PTPRM; GBP1, SNAI2, TMEM45A and SNCG; GBP1, SNAI2, TMEM45A and VGLL1; GBP1, SNAI2, TMEM45A, GABRP and CPSF6; GBP1, SNAI2, TMEM45A, GABRP and EFEMP1; GBP1, SNAI2, TMEM45A, GABRP and ELF3; GBP1, SNAI2, TMEM45A, GABRP and PTPN13; GBP1, SNAI2, TMEM45A, GABRP and PTPRM; GBP1, SNAI2, TMEM45A, GABRP and SNCG; GBP1, SNAI2, TMEM45A, GABRP and VGLL1; GBP1, SNAI2, TMEM45A, GABRP, EFEMP1 and CPSF6; GBP1, SNAI2, TMEM45A, GABRP, EFEMP1 and ELF3; GBP1, SNAI2, TMEM45A, GABRP, EFEMP1 and PTPN13; GBP1, SNAI2, TMEM45A, GABRP, EFEMP1 and PTPRM; GBP1, SNAI2, TMEM45A, GABRP, EFEMP1 and SNCG; GBP1, SNAI2, TMEM45A, GABRP, EFEMP1 and VGLL1; GBP1, SNAI2, TMEM45A, GABRP, EFEMP1, PTPRM and CPSF6; GBP1, SNAI2, TMEM45A, GABRP, EFEMP1, PTPRM and ELF3; GBP1, SNAI2, TMEM45A, GABRP, EFEMP1, PTPRM and PTPN13; GBP1, SNAI2, TMEM45A, GABRP, EFEMP1, PTPRM and SNCG; GBP1, SNAI2, TMEM45A, GABRP, EFEMP1, PTPRM and VGLL1; GBP1, SNAI2, TMEM45A, GABRP, EFEMP1, PTPRM, CPSF6 and ELF3; GBP1, SNAI2, TMEM45A, GABRP, EFEMP1, PTPRM, CPSF6 and PTPN13; GBP1, SNAI2, TMEM45A, GABRP, EFEMP1, PTPRM, CPSF6 and SNCG; GBP1, SNAI2, TMEM45A, GABRP, EFEMP1, PTPRM, CPSF6 and VGLL1; GBP1, SNAI2, TMEM45A, GABRP, EFEMP1, PTPRM, CPSF6, PTPN13 and ELF3; GBP1, SNAI2, TMEM45A, GABRP, EFEMP1, PTPRM, CPSF6, PTPN13 and SNCG; GBP1, SNAI2, TMEM45A, GABRP, EFEMP1, PTPRM, CPSF6, PTPN13 and VGLL1; GBP1, SNAI2, TMEM45A, GABRP, EFEMP1, PTPRM, CPSF6, PTPN13, VGLL1 and ELF3; GBP1, SNAI2, TMEM45A, GABRP, EFEMP1, PTPRM, CPSF6, PTPN13, VGLL1 and SNCG; GBP1, SNAI2, TMEM45A, GABRP, EFEMP1, PTPRM, CPSF6, PTPN13, VGLL1, ELF3 and SNCG; GBP1; IFI30 and CPSF6; IFI30 and EFEMP1; IFI30 and ELF3; IFI30 and GABRP; IFI30 and GBP1; IFI30 and PTPN13; IFI30 and PTPRM; IFI30 and SAA1; IFI30 and SNAI2; IFI30 and SNCG; IFI30 and TGFBI; IFI30 and TIMP2; IFI30 and TMEM45A; IFI30 and VGLL1; IFI30 and VIM; IFI30, SAA1 and CPSF6; IFI30, SAA1 and EFEMP1; IFI30, SAA1 and ELF3; IFI30, SAA1 and GABRP; IFI30, SAA1 and GBP1; IFI30, SAA1 and PTPN13; IFI30, SAA1 and PTPRM; IFI30, SAA1 and SNAI2; IFI30, SAA1 and SNCG; IFI30, SAA1 and TGFBI; IFI30, SAA1 and TIMP2; IFI30, SAA1 and TMEM45A; IFI30, SAA1 and VGLL1; IFI30, SAA1 and VIM; IFI30, SAA1, VIM and CPSF6; IFI30, SAA1, VIM and EFEMP1; IFI30, SAA1, VIM and ELF3; IFI30, SAA1, VIM and GABRP; IFI30, SAA1, VIM and GBP1; IFI30, SAA1, VIM and PTPN13; IFI30, SAA1, VIM and PTPRM; IFI30, SAA1, VIM and SNAI2; IFI30, SAA1, VIM and SNCG; IFI30, SAA1, VIM and TGFBI; IFI30, SAA1, VIM and TIMP2; IFI30, SAA1, VIM and TMEM45A; IFI30, SAA1, VIM and VGLL1; IFI30, SAA1, VIM, TGFBI and CPSF6; IFI30, SAA1, VIM, TGFBI and EFEMP1; IFI30, SAA1, VIM, TGFBI and ELF3; IFI30, SAA1, VIM, TGFBI and GABRP; IFI30, SAA1, VIM, TGFBI and GBP1; IFI30, SAA1, VIM, TGFBI and PTPN13; IFI30, SAA1, VIM, TGFBI and PTPRM; IFI30, SAA1, VIM, TGFBI and SNAI2; IFI30, SAA1, VIM, TGFBI and SNCG; IFI30, SAA1, VIM, TGFBI and TIMP2; IFI30, SAA1, VIM, TGFBI and TMEM45A; IFI30, SAA1, VIM, TGFBI and VGLL1; IFI30, SAA1, VIM, TGFBI, TIMP2 and CPSF6; IFI30, SAA1, VIM, TGFBI, TIMP2 and EFEMP1; IFI30, SAA1, VIM, TGFBI, TIMP2 and ELF3; IFI30, SAA1, VIM, TGFBI, TIMP2 and GABRP; IFI30, SAA1, VIM, TGFBI, TIMP2 and GBP1; IFI30, SAA1, VIM, TGFBI, TIMP2 and PTPN13; IFI30, SAA1, VIM, TGFBI, TIMP2 and PTPRM; IFI30, SAA1, VIM, TGFBI, TIMP2 and SNAI2; IFI30, SAA1, VIM, TGFBI, TIMP2 and SNCG; IFI30, SAA1, VIM, TGFBI, TIMP2 and TMEM45A; IFI30, SAA1, VIM, TGFBI, TIMP2 and VGLL1; IFI30, SAA1, VIM, TGFBI, TIMP2, GBP1 and CPSF6; IFI30, SAA1, VIM, TGFBI, TIMP2, GBP1 and EFEMP1; IFI30, SAA1, VIM, TGFBI, TIMP2, GBP1 and ELF3; IFI30, SAA1, VIM, TGFBI, TIMP2, GBP1 and GABRP; IFI30, SAA1, VIM, TGFBI, TIMP2, GBP1 and PTPN13; IFI30, SAA1, VIM, TGFBI, TIMP2, GBP1 and PTPRM; IFI30, SAA1, VIM, TGFBI, TIMP2, GBP1 and SNAI2; IFI30, SAA1, VIM, TGFBI, TIMP2, GBP1 and SNCG; IFI30, SAA1, VIM, TGFBI, TIMP2, GBP1 and TMEM45A; IFI30, SAA1, VIM, TGFBI, TIMP2, GBP1 and VGLL1; IFI30, SAA1, VIM, TGFBI, TIMP2, GBP1, SNAI2 and CPSF6; IFI30, SAA1, VIM, TGFBI, TIMP2, GBP1, SNAI2 and EFEMP1; IFI30, SAA1, VIM, TGFBI, TIMP2, GBP1, SNAI2 and ELF3; IFI30, SAA1, VIM, TGFBI, TIMP2, GBP1, SNAI2 and GABRP; IFI30, SAA1, VIM, TGFBI, TIMP2, GBP1, SNAI2 and PTPN13; IFI30, SAA1, VIM, TGFBI, TIMP2, GBP1, SNAI2 and PTPRM; IFI30, SAA1, VIM, TGFBI, TIMP2, GBP1, SNAI2 and SNCG; IFI30, SAA1, VIM, TGFBI, TIMP2, GBP1, SNAI2 and TMEM45A; IFI30, SAA1, VIM, TGFBI, TIMP2, GBP1, SNAI2 and VGLL1; IFI30, SAA1, VIM, TGFBI, TIMP2, GBP1, SNAI2, TMEM45A and CPSF6; IFI30, SAA1, VIM, TGFBI, TIMP2, GBP1, SNAI2, TMEM45A and EFEMP1; IFI30, SAA1, VIM, TGFBI, TIMP2, GBP1, SNAI2, TMEM45A and ELF3; IFI30, SAA1, VIM, TGFBI, TIMP2, GBP1, SNAI2, TMEM45A and GABRP; IFI30, SAA1, VIM, TGFBI, TIMP2, GBP1, SNAI2, TMEM45A and PTPN13; IFI30, SAA1, VIM, TGFBI, TIMP2, GBP1, SNAI2, TMEM45A and PTPRM; IFI30, SAA1, VIM, TGFBI, TIMP2, GBP1, SNAI2, TMEM45A and SNCG; IFI30, SAA1, VIM, TGFBI, TIMP2, GBP1, SNAI2, TMEM45A and VGLL1; IFI30, SAA1, VIM, TGFBI, TIMP2, GBP1, SNAI2, TMEM45A, GABRP and CPSF6; IFI30, SAA1, VIM, TGFBI, TIMP2, GBP1, SNAI2, TMEM45A, GABRP and EFEMP1; IFI30, SAA1, VIM, TGFBI, TIMP2, GBP1, SNAI2, TMEM45A, GABRP and ELF3; IFI30, SAA1, VIM, TGFBI, TIMP2, GBP1, SNAI2, TMEM45A, GABRP and PTPRM; IFI30, SAA1, VIM, TGFBI, TIMP2, GBP1, SNAI2, TMEM45A, GABRP and PTPN13; IFI30, SAA1, VIM, TGFBI, TIMP2, GBP1, SNAI2, TMEM45A, GABRP and SNCG; IFI30, SAA1, VIM, TGFBI, TIMP2, GBP1, SNAI2, TMEM45A, GABRP and VGLL1; IFI30, SAA1, VIM, TGFBI, TIMP2, GBP1, SNAI2, TMEM45A, GABRP, EFEMP1 and PTPRM; IFI30, SAA1, VIM, TGFBI, TIMP2, GBP1, SNAI2, TMEM45A, GABRP, EFEMP1 and CPSF6; IFI30, SAA1, VIM, TGFBI, TIMP2, GBP1, SNAI2, TMEM45A, GABRP, EFEMP1 and PTPN13; IFI30, SAA1, VIM, TGFBI, TIMP2, GBP1, SNAI2, TMEM45A, GABRP, EFEMP1 and VGLL1; IFI30, SAA1, VIM, TGFBI, TIMP2, GBP1, SNAI2, TMEM45A, GABRP, EFEMP1 and ELF3; IFI30, SAA1, VIM, TGFBI, TIMP2, GBP1, SNAI2, TMEM45A, GABRP, EFEMP1 and SNCG; IFI30, SAA1, VIM, TGFBI, TIMP2, GBP1, SNAI2, TMEM45A, GABRP, EFEMP1, PTPRM and CPSF6; IFI30, SAA1, VIM, TGFBI, TIMP2, GBP1, SNAI2, TMEM45A, GABRP, EFEMP1, PTPRM and PTPN13; IFI30, SAA1, VIM, TGFBI, TIMP2, GBP1, SNAI2, TMEM45A, GABRP, EFEMP1, PTPRM and VGLL1; IFI30, SAA1, VIM, TGFBI, TIMP2, GBP1, SNAI2, TMEM45A, GABRP, EFEMP1, PTPRM and ELF3; IFI30, SAA1, VIM, TGFBI, TIMP2, GBP1, SNAI2, TMEM45A, GABRP, EFEMP1, PTPRM and SNCG; IFI30, SAA1, VIM, TGFBI, TIMP2, GBP1, SNAI2, TMEM45A, GABRP, EFEMP1, PTPRM, CPSF6 and PTPN13; IFI30, SAA1, VIM, TGFBI, TIMP2, GBP1, SNAI2, TMEM45A, GABRP, EFEMP1, PTPRM, CPSF6 and VGLL1; IFI30, SAA1, VIM, TGFBI, TIMP2, GBP1, SNAI2, TMEM45A, GABRP, EFEMP1, PTPRM, CPSF6 and ELF3; IFI30, SAA1, VIM, TGFBI, TIMP2, GBP1, SNAI2, TMEM45A, GABRP, EFEMP1, PTPRM, CPSF6 and SNCG; IFI30, SAA1, VIM, TGFBI, TIMP2, GBP1, SNAI2, TMEM45A, GABRP, EFEMP1, PTPRM, CPSF6, PTPN13 and VGLL1; IFI30, SAA1, VIM, TGFBI, TIMP2, GBP1, SNAI2, TMEM45A, GABRP, EFEMP1, PTPRM, CPSF6, PTPN13 and ELF3; IFI30, SAA1, VIM, TGFBI, TIMP2, GBP1, SNAI2, TMEM45A, GABRP, EFEMP1, PTPRM, CPSF6, PTPN13 and SNCG; IFI30, SAA1, VIM, TGFBI, TIMP2, GBP1, SNAI2, TMEM45A, GABRP, EFEMP1, PTPRM, CPSF6, PTPN13, VGLL1 and ELF3; IFI30, SAA1, VIM, TGFBI, TIMP2, GBP1, SNAI2, TMEM45A, GABRP, EFEMP1, PTPRM, CPSF6, PTPN13, VGLL1 and SNCG;

IFI30, SAA1, VIM, TGFBI, TIMP2, GBP1, SNAI2, TMEM45A, GABRP, EFEMP1, PTPRM, CPSF6, PTPN13, VGLL1, ELF3 and SNCG; IFI30; LAMC2 and CPSF6; LAMC2 and EFEMP1; LAMC2 and ELF3; LAMC2 and GABRP; LAMC2 and GBP1; LAMC2 and IFI30; LAMC2 and PTPN13; LAMC2 and PTPRM; LAMC2 and SAA1; LAMC2 and SNAI2; LAMC2 and SNCG; LAMC2 and TGFBI; LAMC2 and TIMP2; LAMC2 and TMEM45A; LAMC2 and VGLL1; LAMC2 and VIM; LAMC2, IFI30 and CPSF6; LAMC2, IFI30 and EFEMP1; LAMC2, IFI30 and ELF3; LAMC2, IFI30 and GABRP; LAMC2, IFI30 and GBP1; LAMC2, IFI30 and PTPN13; LAMC2, IFI30 and PTPRM; LAMC2, IFI30 and SAA1; LAMC2, IFI30 and SNAI2; LAMC2, IFI30 and SNCG; LAMC2, IFI30 and TGFBI; LAMC2, IFI30 and TIMP2; LAMC2, IFI30 and TMEM45A; LAMC2, IFI30 and VGLL1; LAMC2, IFI30 and VIM; LAMC2, IFI30, SAA1 and CPSF6; LAMC2, IFI30, SAA1 and EFEMP1; LAMC2, IFI30, SAA1 and ELF3; LAMC2, IFI30, SAA1 and GABRP; LAMC2, IFI30, SAA1 and GBP1; LAMC2, IFI30, SAA1 and PTPN13; LAMC2, IFI30, SAA1 and PTPRM; LAMC2, IFI30, SAA1 and SNAI2; LAMC2, IFI30, SAA1 and SNCG; LAMC2, IFI30, SAA1 and TGFBI; LAMC2, IFI30, SAA1 and TIMP2; LAMC2, IFI30, SAA1 and TMEM45A; LAMC2, IFI30, SAA1 and VGLL1; LAMC2, IFI30, SAA1 and VIM; LAMC2, IFI30, SAA1, VIM and CPSF6; LAMC2, IFI30, SAA1, VIM and EFEMP1; LAMC2, IFI30, SAA1, VIM and ELF3; LAMC2, IFI30, SAA1, VIM and GABRP; LAMC2, IFI30, SAA1, VIM and GBP1; LAMC2, IFI30, SAA1, VIM and PTPN13; LAMC2, IFI30, SAA1, VIM and PTPRM; LAMC2, IFI30, SAA1, VIM and SNAI2; LAMC2, IFI30, SAA1, VIM and SNCG; LAMC2, IFI30, SAA1, VIM and TGFBI; LAMC2, IFI30, SAA1, VIM and TIMP2; LAMC2, IFI30, SAA1, VIM and TMEM45A; LAMC2, IFI30, SAA1, VIM and VGLL1; LAMC2, IFI30, SAA1, VIM, TGFBI and CPSF6; LAMC2, IFI30, SAA1, VIM, TGFBI and EFEMP1; LAMC2, IFI30, SAA1, VIM, TGFBI and ELF3; LAMC2, IFI30, SAA1, VIM, TGFBI and GABRP; LAMC2, IFI30, SAA1, VIM, TGFBI and GBP1; LAMC2, IFI30, SAA1, VIM, TGFBI and PTPN13; LAMC2, IFI30, SAA1, VIM, TGFBI and PTPRM; LAMC2, IFI30, SAA1, VIM, TGFBI and SNAI2; LAMC2, IFI30, SAA1, VIM, TGFBI and SNCG; LAMC2, IFI30, SAA1, VIM, TGFBI and TIMP2; LAMC2, IFI30, SAA1, VIM, TGFBI and TMEM45A; LAMC2, IFI30, SAA1, VIM, TGFBI and VGLL1; LAMC2, IFI30, SAA1, VIM, TGFBI, TIMP2 and CPSF6; LAMC2, IFI30, SAA1, VIM, TGFBI, TIMP2 and EFEMP1; LAMC2, IFI30, SAA1, VIM, TGFBI, TIMP2 and ELF3; LAMC2, IFI30, SAA1, VIM, TGFBI, TIMP2 and GABRP; LAMC2, IFI30, SAA1, VIM, TGFBI, TIMP2 and GBP1; LAMC2, IFI30, SAA1, VIM, TGFBI, TIMP2 and PTPN13; LAMC2, IFI30, SAA1, VIM, TGFBI, TIMP2 and PTPRM; LAMC2, IFI30, SAA1, VIM, TGFBI, TIMP2 and SNAI2; LAMC2, IFI30, SAA1, VIM, TGFBI, TIMP2 and SNCG; LAMC2, IFI30, SAA1, VIM, TGFBI, TIMP2 and TMEM45A; LAMC2, IFI30, SAA1, VIM, TGFBI, TIMP2 and VGLL1; LAMC2, IFI30, SAA1, VIM, TGFBI, TIMP2, GBP1 and CPSF6; LAMC2, IFI30, SAA1, VIM, TGFBI, TIMP2, GBP1 and EFEMP1; LAMC2, IFI30, SAA1, VIM, TGFBI, TIMP2, GBP1 and ELF3; LAMC2, IFI30, SAA1, VIM, TGFBI, TIMP2, GBP1 and GABRP; LAMC2, IFI30, SAA1, VIM, TGFBI, TIMP2, GBP1 and PTPN13; LAMC2, IFI30, SAA1, VIM, TGFBI, TIMP2, GBP1 and PTPRM; LAMC2, IFI30, SAA1, VIM, TGFBI, TIMP2, GBP1 and SNAI2; LAMC2, IFI30, SAA1, VIM, TGFBI, TIMP2, GBP1 and SNCG; LAMC2, IFI30, SAA1, VIM, TGFBI, TIMP2, GBP1 and TMEM45A; LAMC2, IFI30, SAA1, VIM, TGFBI, TIMP2, GBP1 and VGLL1; LAMC2, IFI30, SAA1, VIM, TGFBI, TIMP2, GBP1, SNAI2 and CPSF6; LAMC2, IFI30, SAA1, VIM, TGFBI, TIMP2, GBP1, SNAI2 and EFEMP1; LAMC2, IFI30, SAA1, VIM, TGFBI, TIMP2, GBP1, SNAI2 and ELF3; LAMC2, IFI30, SAA1, VIM, TGFBI, TIMP2, GBP1, SNAI2 and GABRP; LAMC2, IFI30, SAA1, VIM, TGFBI, TIMP2, GBP1, SNAI2 and PTPN13; LAMC2, IFI30, SAA1, VIM, TGFBI, TIMP2, GBP1, SNAI2 and PTPRM; LAMC2, IFI30, SAA1, VIM, TGFBI, TIMP2, GBP1, SNAI2 and SNCG; LAMC2, IFI30, SAA1, VIM, TGFBI, TIMP2, GBP1, SNAI2 and TMEM45A; LAMC2, IFI30, SAA1, VIM, TGFBI, TIMP2, GBP1, SNAI2 and VGLL1; LAMC2, IFI30, SAA1, VIM, TGFBI, TIMP2, GBP1, SNAI2, TMEM45A and CPSF6; LAMC2, IFI30, SAA1, VIM, TGFBI, TIMP2, GBP1, SNAI2, TMEM45A and EFEMP1; LAMC2, IFI30, SAA1, VIM, TGFBI, TIMP2, GBP1, SNAI2, TMEM45A and ELF3; LAMC2, IFI30, SAA1, VIM, TGFBI, TIMP2, GBP1, SNAI2, TMEM45A and GABRP; LAMC2, IFI30, SAA1, VIM, TGFBI, TIMP2, GBP1, SNAI2, TMEM45A and PTPRM; LAMC2, IFI30, SAA1, VIM, TGFBI, TIMP2, GBP1, SNAI2, TMEM45A and PTPN13; LAMC2, IFI30, SAA1, VIM, TGFBI, TIMP2, GBP1, SNAI2, TMEM45A and SNCG; LAMC2, IFI30, SAA1, VIM, TGFBI, TIMP2, GBP1, SNAI2, TMEM45A and VGLL1; LAMC2, IFI30, SAA1, VIM, TGFBI, TIMP2, GBP1, SNAI2, TMEM45A, GABRP and EFEMP1; LAMC2, IFI30, SAA1, VIM, TGFBI, TIMP2, GBP1, SNAI2, TMEM45A, GABRP and PTPRM; LAMC2, IFI30, SAA1, VIM, TGFBI, TIMP2, GBP1, SNAI2, TMEM45A, GABRP and CPSF6; LAMC2, IFI30, SAA1, VIM, TGFBI, TIMP2, GBP1, SNAI2, TMEM45A, GABRP and PTPN13; LAMC2, IFI30, SAA1, VIM, TGFBI, TIMP2, GBP1, SNAI2, TMEM45A, GABRP and VGLL1; LAMC2, IFI30, SAA1, VIM, TGFBI, TIMP2, GBP1, SNAI2, TMEM45A, GABRP and ELF3; LAMC2, IFI30, SAA1, VIM, TGFBI, TIMP2, GBP1, SNAI2, TMEM45A, GABRP and SNCG; LAMC2, IFI30, SAA1, VIM, TGFBI, TIMP2, GBP1, SNAI2, TMEM45A, GABRP, EFEMP1 and PTPRM; LAMC2, IFI30, SAA1, VIM, TGFBI, TIMP2, GBP1, SNAI2, TMEM45A, GABRP, EFEMP1 and CPSF6; LAMC2, IFI30, SAA1, VIM, TGFBI, TIMP2, GBP1, SNAI2, TMEM45A, GABRP, EFEMP1 and PTPN13; LAMC2, IFI30, SAA1, VIM, TGFBI, TIMP2, GBP1, SNAI2, TMEM45A, GABRP, EFEMP1 and VGLL1; LAMC2, IFI30, SAA1, VIM, TGFBI, TIMP2, GBP1, SNAI2, TMEM45A, GABRP, EFEMP1 and ELF3; LAMC2, IFI30, SAA1, VIM, TGFBI, TIMP2, GBP1, SNAI2, TMEM45A, GABRP, EFEMP1 and SNCG; LAMC2, IFI30, SAA1, VIM, TGFBI, TIMP2, GBP1, SNAI2, TMEM45A, GABRP, EFEMP1, PTPRM and CPSF6; LAMC2, IFI30, SAA1, VIM, TGFBI, TIMP2, GBP1, SNAI2, TMEM45A, GABRP, EFEMP1, PTPRM and PTPN13; LAMC2, IFI30, SAA1, VIM, TGFBI, TIMP2, GBP1, SNAI2, TMEM45A, GABRP, EFEMP1, PTPRM and VGLL1; LAMC2, IFI30, SAA1, VIM, TGFBI, TIMP2, GBP1, SNAI2, TMEM45A, GABRP, EFEMP1, PTPRM and ELF3; LAMC2, IFI30, SAA1, VIM, TGFBI, TIMP2, GBP1, SNAI2, TMEM45A, GABRP, EFEMP1, PTPRM and SNCG; LAMC2, IFI30, SAA1, VIM, TGFBI, TIMP2, GBP1, SNAI2, TMEM45A, GABRP, EFEMP1, PTPRM, CPSF6 and PTPN13; LAMC2, IFI30, SAA1, VIM, TGFBI, TIMP2, GBP1, SNAI2, TMEM45A, GABRP, EFEMP1, PTPRM, CPSF6 and VGLL1; LAMC2, IFI30, SAA1, VIM, TGFBI, TIMP2, GBP1, SNAI2, TMEM45A, GABRP, EFEMP1, PTPRM, CPSF6 and ELF3; LAMC2, IFI30, SAA1, VIM, TGFBI, TIMP2, GBP1, SNAI2, TMEM45A, GABRP, EFEMP1, PTPRM, CPSF6 and SNCG; LAMC2, IFI30, SAA1, VIM, TGFBI, TIMP2, GBP1, SNAI2, TMEM45A, GABRP, EFEMP1, PTPRM, CPSF6, PTPN13 and VGLL1; LAMC2, IFI30, SAA1, VIM, TGFBI, TIMP2, GBP1, SNAI2, TMEM45A, GABRP, EFEMP1, PTPRM, CPSF6, PTPN13 and ELF3; LAMC2, IFI30, SAA1, VIM, TGFBI, TIMP2, GBP1, SNAI2, TMEM45A, GABRP, EFEMP1, PTPRM, CPSF6, PTPN13 and SNCG; LAMC2, IFI30, SAA1, VIM, TGFBI, TIMP2, GBP1, SNAI2, TMEM45A, GABRP, EFEMP1, PTPRM, CPSF6, PTPN13, VGLL1 and ELF3; LAMC2, IFI30, SAA1, VIM, TGFBI, TIMP2, GBP1, SNAI2, TMEM45A, GABRP, EFEMP1, PTPRM, CPSF6, PTPN13, VGLL1 and SNCG; LAMC2, IFI30, SAA1, VIM, TGFBI, TIMP2, GBP1, SNAI2, TMEM45A, GABRP, EFEMP1, PTPRM, CPSF6, PTPN13, VGLL1, ELF3 and SNCG; LAMC2; PTPN13 and ELF3; PTPN13 and SNCG; PTPN13 and VGLL1; PTPN13, VGLL1 and ELF3; PTPN13, VGLL1 and SNCG; PTPN13, VGLL1, ELF3 and SNCG; PTPN13; PTPRM and CPSF6; PTPRM and ELF3; PTPRM and PTPN13; PTPRM and SNCG; PTPRM and VGLL1; PTPRM, CPSF6 and ELF3; PTPRM, CPSF6 and PTPN13; PTPRM, CPSF6 and SNCG; PTPRM, CPSF6 and VGLL1; PTPRM, CPSF6, PTPN13 and ELF3; PTPRM, CPSF6, PTPN13 and SNCG; PTPRM, CPSF6, PTPN13 and VGLL1; PTPRM, CPSF6, PTPN13, VGLL1 and ELF3; PTPRM, CPSF6, PTPN13, VGLL1 and SNCG; PTPRM, CPSF6, PTPN13, VGLL1, ELF3 and SNCG; PTPRM; SAA1 and CPSF6; SAA1 and EFEMP1; SAA1 and ELF3; SAA1 and GABRP; SAA1 and GBP1; SAA1 and PTPN13; SAA1 and PTPRM; SAA1 and SNAI2; SAA1 and SNCG; SAA1 and TGFBI; SAA1 and TIMP2; SAA1 and TMEM45A; SAA1 and VGLL1; SAA1 and VIM; SAA1, VIM and CPSF6; SAA1, VIM and EFEMP1; SAA1, VIM and ELF3; SAA1, VIM and GABRP; SAA1, VIM and GBP1; SAA1, VIM and PTPN13; SAA1, VIM and PTPRM; SAA1, VIM and SNAI2; SAA1, VIM and SNCG; SAA1, VIM and TGFBI; SAA1, VIM and TIMP2; SAA1, VIM and TMEM45A; SAA1, VIM and VGLL1; SAA1, VIM, TGFBI and CPSF6; SAA1, VIM, TGFBI and EFEMP1; SAA1, VIM, TGFBI and ELF3; SAA1, VIM, TGFBI and GABRP; SAA1, VIM, TGFBI and GBP1; SAA1, VIM, TGFBI and PTPN13; SAA1, VIM, TGFBI and PTPRM; SAA1, VIM, TGFBI and SNAI2; SAA1, VIM, TGFBI and SNCG; SAA1, VIM, TGFBI and TIMP2; SAA1, VIM, TGFBI and TMEM45A; SAA1, VIM, TGFBI and VGLL1; SAA1, VIM, TGFBI, TIMP2 and CPSF6; SAA1, VIM, TGFBI, TIMP2 and EFEMP1; SAA1, VIM, TGFBI, TIMP2 and ELF3; SAA1, VIM, TGFBI, TIMP2 and GABRP; SAA1, VIM, TGFBI, TIMP2 and GBP1; SAA1, VIM, TGFBI, TIMP2 and PTPN13; SAA1, VIM, TGFBI, TIMP2 and PTPRM; SAA1, VIM, TGFBI, TIMP2 and SNAI2; SAA1, VIM, TGFBI, TIMP2 and SNCG; SAA1, VIM, TGFBI, TIMP2 and TMEM45A; SAA1, VIM, TGFBI, TIMP2 and VGLL1; SAA1, VIM, TGFBI, TIMP2, GBP1 and CPSF6; SAA1, VIM, TGFBI, TIMP2, GBP1 and EFEMP1; SAA1, VIM, TGFBI, TIMP2, GBP1 and ELF3; SAA1, VIM, TGFBI, TIMP2, GBP1 and GABRP; SAA1, VIM, TGFBI, TIMP2, GBP1 and PTPN13; SAA1, VIM, TGFBI, TIMP2, GBP1 and PTPRM; SAA1, VIM, TGFBI, TIMP2, GBP1 and SNAI2; SAA1, VIM, TGFBI, TIMP2, GBP1 and SNCG; SAA1, VIM, TGFBI, TIMP2, GBP1 and TMEM45A; SAA1, VIM, TGFBI, TIMP2, GBP1 and VGLL1; SAA1, VIM, TGFBI, TIMP2, GBP1, SNAI2 and CPSF6; SAA1, VIM, TGFBI, TIMP2, GBP1, SNAI2 and EFEMP1; SAA1, VIM, TGFBI, TIMP2, GBP1, SNAI2 and ELF3; SAA1, VIM, TGFBI, TIMP2, GBP1, SNAI2 and GABRP; SAA1, VIM, TGFBI, TIMP2, GBP1, SNAI2 and PTPN13; SAA1, VIM, TGFBI, TIMP2, GBP1, SNAI2 and PTPRM; SAA1, VIM, TGFBI, TIMP2, GBP1, SNAI2 and SNCG; SAA1, VIM, TGFBI, TIMP2, GBP1, SNAI2 and TMEM45A; SAA1, VIM, TGFBI, TIMP2, GBP1, SNAI2 and VGLL1; SAA1, VIM, TGFBI, TIMP2, GBP1, SNAI2, TMEM45A and CPSF6; SAA1, VIM, TGFBI, TIMP2, GBP1, SNAI2, TMEM45A and EFEMP1; SAA1, VIM, TGFBI, TIMP2, GBP1, SNAI2, TMEM45A and ELF3; SAA1, VIM, TGFBI, TIMP2, GBP1, SNAI2, TMEM45A and GABRP; SAA1, VIM, TGFBI, TIMP2, GBP1, SNAI2, TMEM45A and PTPN13; SAA1, VIM, TGFBI, TIMP2, GBP1, SNAI2, TMEM45A and PTPRM; SAA1, VIM, TGFBI, TIMP2, GBP1, SNAI2, TMEM45A and SNCG; SAA1, VIM, TGFBI, TIMP2, GBP1, SNAI2, TMEM45A and VGLL1; SAA1, VIM, TGFBI, TIMP2, GBP1, SNAI2, TMEM45A, GABRP and CPSF6; SAA1, VIM, TGFBI, TIMP2, GBP1, SNAI2, TMEM45A, GABRP and EFEMP1; SAA1, VIM, TGFBI, TIMP2, GBP1, SNAI2, TMEM45A, GABRP and ELF3; SAA1, VIM, TGFBI, TIMP2, GBP1, SNAI2, TMEM45A, GABRP and PTPN13; SAA1, VIM, TGFBI, TIMP2, GBP1, SNAI2, TMEM45A, GABRP and PTPRM; SAA1, VIM, TGFBI, TIMP2, GBP1, SNAI2, TMEM45A, GABRP and SNCG; SAA1, VIM, TGFBI, TIMP2, GBP1, SNAI2, TMEM45A, GABRP and VGLL1; SAA1, VIM, TGFBI, TIMP2, GBP1, SNAI2, TMEM45A, GABRP, EFEMP1 and PTPRM; SAA1, VIM, TGFBI, TIMP2, GBP1, SNAI2, TMEM45A, GABRP, EFEMP1 and CPSF6; SAA1, VIM, TGFBI, TIMP2, GBP1, SNAI2, TMEM45A, GABRP, EFEMP1 and PTPN13; SAA1, VIM, TGFBI, TIMP2, GBP1, SNAI2, TMEM45A, GABRP, EFEMP1 and VGLL1; SAA1, VIM, TGFBI, TIMP2, GBP1, SNAI2, TMEM45A, GABRP, EFEMP1 and ELF3; SAA1, VIM, TGFBI, TIMP2, GBP1, SNAI2, TMEM45A, GABRP, EFEMP1 and SNCG; SAA1, VIM, TGFBI, TIMP2, GBP1, SNAI2, TMEM45A, GABRP, EFEMP1, PTPRM and CPSF6; SAA1, VIM, TGFBI, TIMP2, GBP1, SNAI2, TMEM45A, GABRP, EFEMP1, PTPRM and PTPN13; SAA1, VIM, TGFBI, TIMP2, GBP1, SNAI2, TMEM45A, GABRP, EFEMP1, PTPRM and VGLL1; SAA1, VIM, TGFBI, TIMP2, GBP1, SNAI2, TMEM45A, GABRP, EFEMP1, PTPRM and ELF3; SAA1, VIM, TGFBI, TIMP2, GBP1, SNAI2, TMEM45A, GABRP, EFEMP1, PTPRM and SNCG; SAA1, VIM, TGFBI, TIMP2, GBP1, SNAI2, TMEM45A, GABRP, EFEMP1, PTPRM, CPSF6 and PTPN13; SAA1, VIM, TGFBI, TIMP2, GBP1, SNAI2, TMEM45A, GABRP, EFEMP1, PTPRM, CPSF6 and VGLL1; SAA1, VIM, TGFBI, TIMP2, GBP1, SNAI2, TMEM45A, GABRP, EFEMP1, PTPRM, CPSF6 and ELF3; SAA1, VIM, TGFBI, TIMP2, GBP1, SNAI2, TMEM45A, GABRP, EFEMP1, PTPRM, CPSF6 and SNCG; SAA1, VIM, TGFBI, TIMP2, GBP1, SNAI2, TMEM45A, GABRP, EFEMP1, PTPRM, CPSF6, PTPN13 and VGLL1; SAA1, VIM, TGFBI, TIMP2, GBP1, SNAI2, TMEM45A, GABRP, EFEMP1, PTPRM, CPSF6, PTPN13 and ELF3; SAA1, VIM, TGFBI, TIMP2, GBP1, SNAI2, TMEM45A, GABRP, EFEMP1, PTPRM, CPSF6, PTPN13 and SNCG; SAA1, VIM, TGFBI, TIMP2, GBP1, SNAI2, TMEM45A, GABRP, EFEMP1, PTPRM, CPSF6, PTPN13, VGLL1 and ELF3; SAA1, VIM, TGFBI, TIMP2, GBP1, SNAI2, TMEM45A, GABRP, EFEMP1, PTPRM, CPSF6, PTPN13, VGLL1 and SNCG; SAA1, VIM, TGFBI, TIMP2, GBP1, SNAI2, TMEM45A, GABRP, EFEMP1, PTPRM, CPSF6, PTPN13, VGLL1, ELF3 and SNCG; SAA1; SNAI2 and CPSF6; SNAI2 and EFEMP1; SNAI2 and ELF3; SNAI2 and GABRP; SNAI2 and PTPN13; SNAI2 and PTPRM; SNAI2 and SNCG; SNAI2 and TMEM45A; SNAI2 and VGLL1; SNAI2, TMEM45A and CPSF6; SNAI2, TMEM45A and EFEMP1; SNAI2, TMEM45A and ELF3; SNAI2, TMEM45A and GABRP; SNAI2, TMEM45A and PTPN13; SNAI2, TMEM45A and PTPRM; SNAI2, TMEM45A and SNCG; SNAI2, TMEM45A and VGLL1; SNAI2, TMEM45A, GABRP and CPSF6; SNAI2, TMEM45A, GABRP and EFEMP1; SNAI2, TMEM45A, GABRP and ELF3; SNAI2, TMEM45A, GABRP and PTPN13; SNAI2, TMEM45A, GABRP and PTPRM; SNAI2, TMEM45A, GABRP and SNCG; SNAI2, TMEM45A, GABRP and VGLL1; SNAI2, TMEM45A, GABRP, EFEMP1 and CPSF6; SNAI2, TMEM45A, GABRP, EFEMP1 and ELF3; SNAI2, TMEM45A, GABRP, EFEMP1 and PTPN13; SNAI2, TMEM45A, GABRP, EFEMP1 and PTPRM; SNAI2, TMEM45A, GABRP, EFEMP1 and SNCG; SNAI2, TMEM45A, GABRP, EFEMP1 and VGLL1; SNAI2, TMEM45A, GABRP, EFEMP1, PTPRM and CPSF6; SNAI2, TMEM45A, GABRP, EFEMP1, PTPRM and ELF3; SNAI2, TMEM45A, GABRP, EFEMP1, PTPRM and PTPN13; SNAI2, TMEM45A, GABRP, EFEMP1, PTPRM and SNCG; SNAI2, TMEM45A, GABRP, EFEMP1, PTPRM and VGLL1; SNAI2, TMEM45A, GABRP, EFEMP1, PTPRM, CPSF6 and ELF3; SNAI2, TMEM45A, GABRP, EFEMP1, PTPRM, CPSF6 and PTPN13; SNAI2, TMEM45A, GABRP, EFEMP1, PTPRM, CPSF6 and SNCG; SNAI2, TMEM45A, GABRP, EFEMP1, PTPRM, CPSF6 and VGLL1; SNAI2, TMEM45A, GABRP, EFEMP1, PTPRM, CPSF6, PTPN13 and ELF3; SNAI2, TMEM45A, GABRP, EFEMP1, PTPRM, CPSF6, PTPN13 and SNCG; SNAI2, TMEM45A, GABRP, EFEMP1, PTPRM, CPSF6, PTPN13 and VGLL1; SNAI2, TMEM45A, GABRP, EFEMP1, PTPRM, CPSF6, PTPN13, VGLL1 and ELF3; SNAI2, TMEM45A, GABRP, EFEMP1, PTPRM, CPSF6, PTPN13, VGLL1 and SNCG; SNAI2, TMEM45A, GABRP, EFEMP1, PTPRM, CPSF6, PTPN13, VGLL1, ELF3 and SNCG; SNAI2; SNCG; TGFBI and CPSF6; TGFBI and EFEMP1; TGFBI and ELF3; TGFBI and GABRP; TGFBI and GBP1; TGFBI and PTPN13; TGFBI and PTPRM; TGFBI and SNAI2; TGFBI and SNCG; TGFBI and TIMP2; TGFBI and TMEM45A; TGFBI and VGLL1; TGFBI, TIMP2 and CPSF6; TGFBI, TIMP2 and EFEMP1; TGFBI, TIMP2 and ELF3; TGFBI, TIMP2 and GABRP; TGFBI, TIMP2 and GBP1; TGFBI, TIMP2 and PTPN13; TGFBI, TIMP2 and PTPRM; TGFBI, TIMP2 and SNAI2; TGFBI, TIMP2 and SNCG; TGFBI, TIMP2 and TMEM45A; TGFBI, TIMP2 and VGLL1; TGFBI, TIMP2, GBP1 and CPSF6; TGFBI, TIMP2, GBP1 and EFEMP1; TGFBI, TIMP2, GBP1 and ELF3; TGFBI, TIMP2, GBP1 and GABRP; TGFBI, TIMP2, GBP1 and PTPN13; TGFBI, TIMP2, GBP1 and PTPRM; TGFBI, TIMP2, GBP1 and SNAI2; TGFBI, TIMP2, GBP1 and SNCG; TGFBI, TIMP2, GBP1 and TMEM45A; TGFBI, TIMP2, GBP1 and VGLL1; TGFBI, TIMP2, GBP1, SNAI2 and CPSF6; TGFBI, TIMP2, GBP1, SNAI2 and EFEMP1; TGFBI, TIMP2, GBP1, SNAI2 and ELF3; TGFBI, TIMP2, GBP1, SNAI2 and GABRP; TGFBI, TIMP2, GBP1, SNAI2 and PTPN13; TGFBI, TIMP2, GBP1, SNAI2 and PTPRM; TGFBI, TIMP2, GBP1, SNAI2 and SNCG; TGFBI, TIMP2, GBP1, SNAI2 and TMEM45A; TGFBI, TIMP2, GBP1, SNAI2 and VGLL1; TGFBI, TIMP2, GBP1, SNAI2, TMEM45A and CPSF6; TGFBI, TIMP2, GBP1, SNAI2, TMEM45A and EFEMP1; TGFBI, TIMP2, GBP1, SNAI2, TMEM45A and ELF3; TGFBI, TIMP2, GBP1, SNAI2, TMEM45A and GABRP; TGFBI, TIMP2, GBP1, SNAI2, TMEM45A and PTPN13; TGFBI, TIMP2, GBP1, SNAI2, TMEM45A and PTPRM; TGFBI, TIMP2, GBP1, SNAI2, TMEM45A and SNCG; TGFBI, TIMP2, GBP1, SNAI2, TMEM45A and VGLL1; TGFBI, TIMP2, GBP1, SNAI2, TMEM45A, GABRP and CPSF6; TGFBI, TIMP2, GBP1, SNAI2, TMEM45A, GABRP and EFEMP1; TGFBI, TIMP2, GBP1, SNAI2, TMEM45A, GABRP and ELF3; TGFBI, TIMP2, GBP1, SNAI2, TMEM45A, GABRP and PTPN13; TGFBI, TIMP2, GBP1, SNAI2, TMEM45A, GABRP and PTPRM; TGFBI, TIMP2, GBP1, SNAI2, TMEM45A, GABRP and SNCG; TGFBI, TIMP2, GBP1, SNAI2, TMEM45A, GABRP and VGLL1; TGFBI, TIMP2, GBP1, SNAI2, TMEM45A, GABRP, EFEMP1 and CPSF6; TGFBI, TIMP2, GBP1, SNAI2, TMEM45A, GABRP, EFEMP1 and ELF3; TGFBI, TIMP2, GBP1, SNAI2, TMEM45A, GABRP, EFEMP1 and PTPN13; TGFBI, TIMP2, GBP1, SNAI2, TMEM45A, GABRP, EFEMP1 and PTPRM; TGFBI, TIMP2, GBP1, SNAI2, TMEM45A, GABRP, EFEMP1 and SNCG; TGFBI, TIMP2, GBP1, SNAI2, TMEM45A, GABRP, EFEMP1 and VGLL1; TGFBI, TIMP2, GBP1, SNAI2, TMEM45A, GABRP, EFEMP1, PTPRM and CPSF6; TGFBI, TIMP2, GBP1, SNAI2, TMEM45A, GABRP, EFEMP1, PTPRM and ELF3; TGFBI, TIMP2, GBP1, SNAI2, TMEM45A, GABRP, EFEMP1, PTPRM and PTPN13; TGFBI, TIMP2, GBP1, SNAI2, TMEM45A, GABRP, EFEMP1, PTPRM and SNCG; TGFBI, TIMP2, GBP1, SNAI2, TMEM45A, GABRP, EFEMP1, PTPRM and VGLL1; TGFBI, TIMP2, GBP1, SNAI2, TMEM45A, GABRP, EFEMP1, PTPRM, CPSF6 and PTPN13; TGFBI, TIMP2, GBP1, SNAI2, TMEM45A, GABRP, EFEMP1, PTPRM, CPSF6 and VGLL1; TGFBI, TIMP2, GBP1, SNAI2, TMEM45A, GABRP, EFEMP1, PTPRM, CPSF6 and ELF3; TGFBI, TIMP2, GBP1, SNAI2, TMEM45A, GABRP, EFEMP1, PTPRM, CPSF6 and SNCG; TGFBI, TIMP2, GBP1, SNAI2, TMEM45A, GABRP, EFEMP1, PTPRM, CPSF6, PTPN13 and VGLL1; TGFBI, TIMP2, GBP1, SNAI2, TMEM45A, GABRP, EFEMP1, PTPRM, CPSF6, PTPN13 and ELF3; TGFBI, TIMP2, GBP1, SNAI2, TMEM45A, GABRP, EFEMP1, PTPRM, CPSF6, PTPN13 and SNCG; TGFBI, TIMP2, GBP1, SNAI2, TMEM45A, GABRP, EFEMP1, PTPRM, CPSF6, PTPN13, VGLL1 and ELF3; TGFBI, TIMP2, GBP1, SNAI2, TMEM45A, GABRP, EFEMP1, PTPRM, CPSF6, PTPN13, VGLL1 and SNCG; TGFBI, TIMP2, GBP1, SNAI2, TMEM45A, GABRP, EFEMP1, PTPRM, CPSF6, PTPN13, VGLL1, ELF3 and SNCG; TGFBI; TIMP2 and CPSF6; TIMP2 and EFEMP1; TIMP2 and ELF3; TIMP2 and GABRP; TIMP2 and GBP1; TIMP2 and PTPN13; TIMP2 and PTPRM; TIMP2 and SNAI2; TIMP2 and SNCG; TIMP2 and TMEM45A; TIMP2 and VGLL1; TIMP2, GBP1 and CPSF6; TIMP2, GBP1 and EFEMP1; TIMP2, GBP1 and ELF3; TIMP2, GBP1 and GABRP; TIMP2, GBP1 and PTPN13; TIMP2, GBP1 and PTPRM; TIMP2, GBP1 and SNAI2; TIMP2, GBP1 and SNCG; TIMP2, GBP1 and TMEM45A; TIMP2, GBP1 and VGLL1; TIMP2, GBP1, SNAI2 and CPSF6; TIMP2, GBP1, SNAI2 and EFEMP1; TIMP2, GBP1, SNAI2 and ELF3; TIMP2, GBP1, SNAI2 and GABRP; TIMP2, GBP1, SNAI2 and PTPN13; TIMP2, GBP1, SNAI2 and PTPRM; TIMP2, GBP1, SNAI2 and SNCG; TIMP2, GBP1, SNAI2 and TMEM45A; TIMP2, GBP1, SNAI2 and VGLL1; TIMP2, GBP1, SNAI2, TMEM45A and CPSF6; TIMP2, GBP1, SNAI2, TMEM45A and EFEMP1; TIMP2, GBP1, SNAI2, TMEM45A and ELF3; TIMP2, GBP1, SNAI2, TMEM45A and GABRP; TIMP2, GBP1, SNAI2, TMEM45A and PTPN13; TIMP2, GBP1, SNAI2, TMEM45A and PTPRM; TIMP2, GBP1, SNAI2, TMEM45A and SNCG; TIMP2, GBP1, SNAI2, TMEM45A and VGLL1; TIMP2, GBP1, SNAI2, TMEM45A, GABRP and CPSF6; TIMP2, GBP1, SNAI2, TMEM45A, GABRP and EFEMP1; TIMP2, GBP1, SNAI2, TMEM45A, GABRP and ELF3; TIMP2, GBP1, SNAI2, TMEM45A, GABRP and PTPN13; TIMP2, GBP1, SNAI2, TMEM45A, GABRP and PTPRM; TIMP2, GBP1, SNAI2, TMEM45A, GABRP and SNCG; TIMP2, GBP1, SNAI2, TMEM45A, GABRP and VGLL1; TIMP2, GBP1, SNAI2, TMEM45A, GABRP, EFEMP1 and CPSF6; TIMP2, GBP1, SNAI2, TMEM45A, GABRP, EFEMP1 and ELF3; TIMP2, GBP1, SNAI2, TMEM45A, GABRP, EFEMP1 and PTPN13; TIMP2, GBP1, SNAI2, TMEM45A, GABRP, EFEMP1 and PTPRM; TIMP2, GBP1, SNAI2, TMEM45A, GABRP, EFEMP1 and SNCG; TIMP2, GBP1, SNAI2, TMEM45A, GABRP, EFEMP1 and VGLL1; TIMP2, GBP1, SNAI2, TMEM45A, GABRP, EFEMP1, PTPRM and CPSF6; TIMP2, GBP1, SNAI2, TMEM45A, GABRP, EFEMP1, PTPRM and ELF3; TIMP2, GBP1, SNAI2, TMEM45A, GABRP, EFEMP1, PTPRM and PTPN13; TIMP2, GBP1, SNAI2, TMEM45A, GABRP, EFEMP1, PTPRM and SNCG; TIMP2, GBP1, SNAI2, TMEM45A, GABRP, EFEMP1, PTPRM and VGLL1; TIMP2, GBP1, SNAI2, TMEM45A, GABRP, EFEMP1, PTPRM, CPSF6 and ELF3; TIMP2, GBP1, SNAI2, TMEM45A, GABRP, EFEMP1, PTPRM, CPSF6 and PTPN13; TIMP2, GBP1, SNAI2, TMEM45A, GABRP, EFEMP1, PTPRM, CPSF6 and SNCG; TIMP2, GBP1, SNAI2, TMEM45A, GABRP, EFEMP1, PTPRM, CPSF6 and VGLL1; TIMP2, GBP1, SNAI2, TMEM45A, GABRP, EFEMP1, PTPRM, CPSF6, PTPN13 and VGLL1; TIMP2, GBP1, SNAI2, TMEM45A, GABRP, EFEMP1, PTPRM, CPSF6, PTPN13 and ELF3; TIMP2, GBP1, SNAI2, TMEM45A, GABRP, EFEMP1, PTPRM, CPSF6, PTPN13 and SNCG; TIMP2, GBP1, SNAI2, TMEM45A, GABRP, EFEMP1, PTPRM, CPSF6, PTPN13, VGLL1 and ELF3; TIMP2, GBP1, SNAI2, TMEM45A, GABRP, EFEMP1, PTPRM, CPSF6, PTPN13, VGLL1 and SNCG; TIMP2, GBP1, SNAI2, TMEM45A, GABRP, EFEMP1, PTPRM, CPSF6, PTPN13, VGLL1, ELF3 and SNCG; TIMP2; TMEM45A and CPSF6; TMEM45A and EFEMP1; TMEM45A and ELF3; TMEM45A and GABRP; TMEM45A and PTPN13; TMEM45A and PTPRM; TMEM45A and SNCG; TMEM45A and VGLL1; TMEM45A, GABRP and CPSF6; TMEM45A, GABRP and EFEMP1; TMEM45A, GABRP and ELF3; TMEM45A, GABRP and PTPN13; TMEM45A, GABRP and PTPRM; TMEM45A, GABRP and SNCG; TMEM45A, GABRP and VGLL1; TMEM45A, GABRP, EFEMP1 and CPSF6; TMEM45A, GABRP, EFEMP1 and ELF3; TMEM45A, GABRP, EFEMP1 and PTPN13; TMEM45A, GABRP, EFEMP1 and PTPRM; TMEM45A, GABRP, EFEMP1 and SNCG; TMEM45A, GABRP, EFEMP1 and VGLL1; TMEM45A, GABRP, EFEMP1, PTPRM and CPSF6; TMEM45A, GABRP, EFEMP1, PTPRM and ELF3; TMEM45A, GABRP, EFEMP1, PTPRM and PTPN13; TMEM45A, GABRP, EFEMP1, PTPRM and SNCG; TMEM45A, GABRP, EFEMP1, PTPRM and VGLL1; TMEM45A, GABRP, EFEMP1, PTPRM, CPSF6 and ELF3; TMEM45A, GABRP, EFEMP1, PTPRM, CPSF6 and PTPN13; TMEM45A, GABRP, EFEMP1, PTPRM, CPSF6 and SNCG; TMEM45A, GABRP, EFEMP1, PTPRM, CPSF6 and VGLL1; TMEM45A, GABRP, EFEMP1, PTPRM, CPSF6, PTPN13 and ELF3; TMEM45A, GABRP, EFEMP1, PTPRM, CPSF6, PTPN13 and SNCG; TMEM45A, GABRP, EFEMP1, PTPRM, CPSF6, PTPN13 and VGLL1; TMEM45A, GABRP, EFEMP1, PTPRM, CPSF6, PTPN13, VGLL1 and ELF3; TMEM45A, GABRP, EFEMP1, PTPRM, CPSF6, PTPN13, VGLL1 and SNCG; TMEM45A, GABRP, EFEMP1, PTPRM, CPSF6, PTPN13, VGLL1, ELF3 and SNCG; TMEM45A; VGLL1 and ELF3; VGLL1 and SNCG; VGLL1, ELF3 and SNCG; VGLL1; VIM and CPSF6; VIM and EFEMP1; VIM and ELF3; VIM and GABRP; VIM and GBP1; VIM and PTPN13; VIM and PTPRM; VIM and SNAI2; VIM and SNCG; VIM and TGFBI; VIM and TIMP2; VIM and TMEM45A; VIM and VGLL1; VIM, TGFBI and CPSF6; VIM, TGFBI and EFEMP1; VIM, TGFBI and ELF3; VIM, TGFBI and GABRP; VIM, TGFBI and GBP1; VIM, TGFBI and PTPN13; VIM, TGFBI and PTPRM; VIM, TGFBI and SNAI2; VIM, TGFBI and SNCG; VIM, TGFBI and TIMP2; VIM, TGFBI and TMEM45A; VIM, TGFBI and VGLL1; VIM, TGFBI, TIMP2 and CPSF6; VIM, TGFBI, TIMP2 and EFEMP1; VIM, TGFBI, TIMP2 and ELF3; VIM, TGFBI, TIMP2 and GABRP; VIM, TGFBI, TIMP2 and GBP1; VIM, TGFBI, TIMP2 and PTPN13; VIM, TGFBI, TIMP2 and PTPRM; VIM, TGFBI, TIMP2 and SNAI2; VIM, TGFBI, TIMP2 and SNCG; VIM, TGFBI, TIMP2 and TMEM45A; VIM, TGFBI, TIMP2 and VGLL1; VIM, TGFBI, TIMP2, GBP1 and CPSF6; VIM, TGFBI, TIMP2, GBP1 and EFEMP1; VIM, TGFBI, TIMP2, GBP1 and ELF3; VIM, TGFBI, TIMP2, GBP1 and GABRP; VIM, TGFBI, TIMP2, GBP1 and PTPN13; VIM, TGFBI, TIMP2, GBP1 and PTPRM; VIM, TGFBI, TIMP2, GBP1 and SNAI2; VIM, TGFBI, TIMP2, GBP1 and SNCG; VIM, TGFBI, TIMP2, GBP1 and TMEM45A; VIM, TGFBI, TIMP2, GBP1 and VGLL1; VIM, TGFBI, TIMP2, GBP1, SNAI2 and CPSF6; VIM, TGFBI, TIMP2, GBP1, SNAI2 and EFEMP1; VIM, TGFBI, TIMP2, GBP1, SNAI2 and ELF3; VIM, TGFBI, TIMP2, GBP1, SNAI2 and GABRP; VIM, TGFBI, TIMP2, GBP1, SNAI2 and PTPN13; VIM, TGFBI, TIMP2, GBP1, SNAI2 and PTPRM; VIM, TGFBI, TIMP2, GBP1, SNAI2 and SNCG; VIM, TGFBI, TIMP2, GBP1, SNAI2 and TMEM45A; VIM, TGFBI, TIMP2, GBP1, SNAI2 and VGLL1; VIM, TGFBI, TIMP2, GBP1, SNAI2, TMEM45A and CPSF6; VIM, TGFBI, TIMP2, GBP1, SNAI2, TMEM45A and EFEMP1; VIM, TGFBI, TIMP2, GBP1, SNAI2, TMEM45A and ELF3; VIM, TGFBI, TIMP2, GBP1, SNAI2, TMEM45A and GABRP; VIM, TGFBI, TIMP2, GBP1, SNAI2, TMEM45A and PTPN13; VIM, TGFBI, TIMP2, GBP1, SNAI2, TMEM45A and PTPRM; VIM, TGFBI, TIMP2, GBP1, SNAI2, TMEM45A and SNCG; VIM, TGFBI, TIMP2, GBP1, SNAI2, TMEM45A and VGLL1; VIM, TGFBI, TIMP2, GBP1, SNAI2, TMEM45A, GABRP and CPSF6; VIM, TGFBI, TIMP2, GBP1, SNAI2, TMEM45A, GABRP and EFEMP1; VIM, TGFBI, TIMP2, GBP1, SNAI2, TMEM45A, GABRP and ELF3; VIM, TGFBI, TIMP2, GBP1, SNAI2, TMEM45A, GABRP and PTPN13; VIM, TGFBI, TIMP2, GBP1, SNAI2, TMEM45A, GABRP and PTPRM; VIM, TGFBI, TIMP2, GBP1, SNAI2, TMEM45A, GABRP and SNCG; VIM, TGFBI, TIMP2, GBP1, SNAI2, TMEM45A, GABRP and VGLL1; VIM, TGFBI, TIMP2, GBP1, SNAI2, TMEM45A, GABRP, EFEMP1 and CPSF6; VIM, TGFBI, TIMP2, GBP1, SNAI2, TMEM45A, GABRP, EFEMP1 and ELF3; VIM, TGFBI, TIMP2, GBP1, SNAI2, TMEM45A, GABRP, EFEMP1 and PTPN13; VIM, TGFBI, TIMP2, GBP1, SNAI2, TMEM45A, GABRP, EFEMP1 and PTPRM; VIM, TGFBI, TIMP2, GBP1, SNAI2, TMEM45A, GABRP, EFEMP1 and SNCG; VIM, TGFBI, TIMP2, GBP1, SNAI2, TMEM45A, GABRP, EFEMP1 and VGLL1; VIM, TGFBI, TIMP2, GBP1, SNAI2, TMEM45A, GABRP, EFEMP1, PTPRM and CPSF6; VIM, TGFBI, TIMP2, GBP1, SNAI2, TMEM45A, GABRP, EFEMP1, PTPRM and PTPN13; VIM, TGFBI, TIMP2, GBP1, SNAI2, TMEM45A, GABRP, EFEMP1, PTPRM and VGLL1; VIM, TGFBI, TIMP2, GBP1, SNAI2, TMEM45A, GABRP, EFEMP1, PTPRM and ELF3; VIM, TGFBI, TIMP2, GBP1, SNAI2, TMEM45A, GABRP, EFEMP1, PTPRM and SNCG; VIM, TGFBI, TIMP2, GBP1, SNAI2, TMEM45A, GABRP, EFEMP1, PTPRM, CPSF6 and PTPN13; VIM, TGFBI, TIMP2, GBP1, SNAI2, TMEM45A, GABRP, EFEMP1, PTPRM, CPSF6 and VGLL1; VIM, TGFBI, TIMP2, GBP1, SNAI2, TMEM45A, GABRP, EFEMP1, PTPRM, CPSF6 and ELF3; VIM, TGFBI, TIMP2, GBP1, SNAI2, TMEM45A, GABRP, EFEMP1, PTPRM, CPSF6 and SNCG; VIM, TGFBI, TIMP2, GBP1, SNAI2, TMEM45A, GABRP, EFEMP1, PTPRM, CPSF6, PTPN13 and VGLL1; VIM, TGFBI, TIMP2, GBP1, SNAI2, TMEM45A, GABRP, EFEMP1, PTPRM, CPSF6, PTPN13 and ELF3; VIM, TGFBI, TIMP2, GBP1, SNAI2, TMEM45A, GABRP, EFEMP1, PTPRM, CPSF6, PTPN13 and SNCG; VIM, TGFBI, TIMP2, GBP1, SNAI2, TMEM45A, GABRP, EFEMP1, PTPRM, CPSF6, PTPN13, VGLL1 and ELF3; VIM, TGFBI, TIMP2, GBP1, SNAI2, TMEM45A, GABRP, EFEMP1, PTPRM, CPSF6, PTPN13, VGLL1 and SNCG; VIM, TGFBI, TIMP2, GBP1, SNAI2, TMEM45A, GABRP, EFEMP1, PTPRM, CPSF6, PTPN13, VGLL1, ELF3 and SNCG; and VIM.

In some instances, the plurality of targets comprises a coding target, non-coding target, or any combination thereof. In some instances, the coding target comprises an exonic sequence. In other instances, the non-coding target comprises a non-exonic or exonic sequence. Alternatively, a non-coding target comprises a UTR sequence, an intronic sequence, antisense, or a non-coding RNA transcript. In some instances, a non-coding target comprises sequences which partially overlap with a UTR sequence or an intronic sequence. A non-coding target also includes non-exonic and/or exonic transcripts. Exonic sequences may comprise regions on a protein-coding gene, such as an exon, UTR, or a portion thereof. Non-exonic sequences may comprise regions on a protein-coding, non-protein-coding gene, or a portion thereof. For example, non-exonic sequences may comprise intronic regions, promoter regions, intergenic regions, a non-coding transcript, an exon anti-sense region, an intronic anti-sense region, UTR anti-sense region, non-coding transcript anti-sense region, or a portion thereof. In other instances, the plurality of targets comprises a non-coding RNA transcript.

The plurality of targets may comprise one or more targets selected from a classifier disclosed herein. The classifier may be generated from one or more models or algorithms. The one or more models or algorithms may be Naïve Bayes (NB), recursive Partitioning (Rpart), random forest (RF), support vector machine (SVM), k-nearest neighbor (KNN), high dimensional discriminate analysis (HDDA), or a combination thereof. The classifier may have an AUC of equal to or greater than 0.60. The classifier may have an AUC of equal to or greater than 0.61. The classifier may have an AUC of equal to or greater than 0.62. The classifier may have an AUC of equal to or greater than 0.63. The classifier may have an AUC of equal to or greater than 0.64. The classifier may have an AUC of equal to or greater than 0.65. The classifier may have an AUC of equal to or greater than 0.66. The classifier may have an AUC of equal to or greater than 0.67. The classifier may have an AUC of equal to or greater than 0.68. The classifier may have an AUC of equal to or greater than 0.69. The classifier may have an AUC of equal to or greater than 0.70. The classifier may have an AUC of equal to or greater than 0.75. The classifier may have an AUC of equal to or greater than 0.77. The classifier may have an AUC of equal to or greater than 0.78. The classifier may have an AUC of equal to or greater than 0.79. The classifier may have an AUC of equal to or greater than 0.80. The AUC may be clinically significant based on its 95% confidence interval (CI). The accuracy of the classifier may be at least about 70%. The accuracy of the classifier may be at least about 73%. The accuracy of the classifier may be at least about 75%. The accuracy of the classifier may be at least about 77%. The accuracy of the classifier may be at least about 80%. The accuracy of the classifier may be at least about 83%. The accuracy of the classifier may be at least about 84%. The accuracy of the classifier may be at least about 86%. The accuracy of the classifier may be at least about 88%. The accuracy of the classifier may be at least about 90%. The p-value of the classifier may be less than or equal to 0.05. The p-value of the classifier may be less than or equal to 0.04. The p-value of the classifier may be less than or equal to 0.03. The p-value of the classifier may be less than or equal to 0.02. The p-value of the classifier may be less than or equal to 0.01. The p-value of the classifier may be less than or equal to 0.008. The p-value of the classifier may be less than or equal to 0.006. The p-value of the classifier may be less than or equal to 0.004. The p-value of the classifier may be less than or equal to 0.002. The p-value of the classifier may be less than or equal to 0.001.

The plurality of targets may comprise one or more targets selected from a Random Forest (RF) classifier. The plurality of targets may comprise two or more targets selected from a Random Forest (RF) classifier. The plurality of targets may comprise three or more targets selected from a Random Forest (RF) classifier. The plurality of targets may comprise 2, 3, 4, 5, 6, 7, 8, 9, 10, 11, 12, 13, 14, 15, 20, 25, 30, 35, 40, 45, 50, or more targets selected from a Random Forest (RF) classifier. The RF classifier may be an RF2, and RF3, or an RF4 classifier. The RF classifier may be an RF22 classifier (e.g., a Random Forest classifier with 22 targets). For example, a RF classifier of the present invention may comprise two or more targets selected from Table 3, Table 5, Table 13 or SEQ ID Nos: 1-4050.

The plurality of targets may comprise one or more targets selected from an SVM classifier. The plurality of targets may comprise 2, 3, 4, 5, 6, 7, 8, 9, 10 or more targets selected from an SVM classifier. The plurality of targets may comprise 12, 13, 14, 15, 17, 20, 22, 25, 27, 30 or more targets selected from an SVM classifier. The plurality of targets may comprise 32, 35, 37, 40, 43, 45, 47, 50, 53, 55, 57, 60 or more targets selected from an SVM classifier. The SVM classifier may be an SVM2 classifier. A SVM classifier of the present invention may comprise two or more targets selected from Table 3, Table 5, Table 13 or SEQ ID Nos: 1-4050.

The plurality of targets may comprise one or more targets selected from a KNN classifier. The plurality of targets may comprise 2, 3, 4, 5, 6, 7, 8, 9, 10 or more targets selected from a KNN classifier. The plurality of targets may comprise 12, 13, 14, 15, 17, 20, 22, 25, 27, 30 or more targets selected from a KNN classifier. The plurality of targets may comprise 32, 35, 37, 40, 43, 45, 47, 50, 53, 55, 57, 60 or more targets selected from a KNN classifier. The plurality of targets may comprise 65, 70, 75, 80, 85, 90, 95, 100 or more targets selected from a KNN classifier. For example, a KNN classifier of the present invention may comprise two or more targets selected from Table 3, Table 5, Table 13 or SEQ ID Nos: 1-4050.

The plurality of targets may comprise one or more targets selected from a Naïve Bayes (NB) classifier. The plurality of targets may comprise 2, 3, 4, 5, 6, 7, 8, 9, 10 or more targets selected from an NB classifier. The plurality of targets may comprise 12, 13, 14, 15, 17, 20, 22, 25, 27, 30 or more targets selected from an NB classifier. The plurality of targets may comprise 32, 35, 37, 40, 43, 45, 47, 50, 53, 55, 57, 60 or more targets selected from a NB classifier. The plurality of targets may comprise 65, 70, 75, 80, 85, 90, 95, 100 or more targets selected from a NB classifier. For example, a NB classifier of the present invention may comprise two or more targets selected from Table 3, Table 5, Table 13 or SEQ ID Nos: 1-4050.

The plurality of targets may comprise one or more targets selected from a recursive partitioning (Rpart) classifier. The plurality of targets may comprise 2, 3, 4, 5, 6, 7, 8, 9, 10 or more targets selected from an Rpart classifier. The plurality of targets may comprise 12, 13, 14, 15, 17, 20, 22, 25, 27, 30 or more targets selected from an Rpart classifier. The plurality of targets may comprise 32, 35, 37, 40, 43, 45, 47, 50, 53, 55, 57, 60 or more targets selected from an Rpart classifier. The plurality of targets may comprise 65, 70, 75, 80, 85, 90, 95, 100 or more targets selected from an Rpart classifier. For example, an Rpart classifier of the present invention may comprise two or more targets selected from Table 3, Table 5, Table 13 or SEQ ID Nos: 1-4050.

The plurality of targets may comprise one or more targets selected from a high dimensional discriminate analysis (HDDA) classifier. The plurality of targets may comprise two or more targets selected from a high dimensional discriminate analysis (HDDA) classifier. The plurality of targets may comprise three or more targets selected from a high dimensional discriminate analysis (HDDA) classifier. The plurality of targets may comprise 5, 6, 7, 8, 9, 10, 11, 12, 13, 14, 15 or more targets selected from a high dimensional discriminate analysis (HDDA) classifier. For example, an Rpart classifier of the present invention may comprise two or more targets selected from Table 3, Table 5, Table 13 or SEQ ID Nos: 1-4050.

Probes/Primers

The present invention provides a probe set for predicting benefit from neoadjuvant chemotherapy and/or diagnosing, monitoring and/or predicting a status or outcome of bladder cancer in a subject, the probe set comprising a plurality of probes, wherein (i) the probes in the set are capable of detecting an expression level of at least one target selected from Table 3, Table 5, Table 13 or SEQ ID Nos: 1-4050; and (ii) the expression level determines the cancer status of the subject with at least about 40% specificity.

The probe set may comprise one or more polynucleotide probes. Individual polynucleotide probes comprise a nucleotide sequence derived from the nucleotide sequence of the target sequences or complementary sequences thereof. The nucleotide sequence of the polynucleotide probe is designed such that it corresponds to, or is complementary to the target sequences. The polynucleotide probe can specifically hybridize under either stringent or lowered stringency hybridization conditions to a region of the target sequences, to the complement thereof, or to a nucleic acid sequence (such as a cDNA) derived therefrom.

The selection of the polynucleotide probe sequences and determination of their uniqueness may be carried out in silico using techniques known in the art, for example, based on a BLASTN search of the polynucleotide sequence in question against gene sequence databases, such as the Human Genome Sequence, UniGene, dbEST or the non-redundant database at NCBI. In one embodiment of the invention, the polynucleotide probe is complementary to a region of a target mRNA derived from a target sequence in the probe set. Computer programs can also be employed to select probe sequences that may not cross hybridize or may not hybridize non-specifically.

In some instances, microarray hybridization of RNA, extracted from bladder cancer tissue samples and amplified, may yield a dataset that is then summarized and normalized by the fRMA technique. After removal (or filtration) of cross-hybridizing PSRs, and PSRs containing less than 4 probes, the remaining PSRs can be used in further analysis. Following fRMA and filtration, the data can be decomposed into its principal components and an analysis of variance model is used to determine the extent to which a batch effect remains present in the first 10 principal components.

These remaining PSRs can then be subjected to filtration by a T-test between CR (clinical recurrence) and non-CR samples. Using a p-value cut-off of 0.01, the remaining features (e.g., PSRs) can be further refined. Feature selection can be performed by regularized logistic regression using the elastic-net penalty. The regularized regression may be bootstrapped over 1000 times using all training data; with each iteration of bootstrapping, features that have non-zero co-efficient following 3-fold cross validation can be tabulated. In some instances, features that were selected in at least 25% of the total runs were used for model building.

The polynucleotide probes of the present invention may range in length from about 15 nucleotides to the full length of the coding target or non-coding target. In one embodiment of the invention, the polynucleotide probes are at least about 15 nucleotides in length. In another embodiment, the polynucleotide probes are at least about 20 nucleotides in length. In a further embodiment, the polynucleotide probes are at least about 25 nucleotides in length. In another embodiment, the polynucleotide probes are between about 15 nucleotides and about 500 nucleotides in length. In other embodiments, the polynucleotide probes are between about 15 nucleotides and about 450 nucleotides, about 15 nucleotides and about 400 nucleotides, about 15 nucleotides and about 350 nucleotides, about 15 nucleotides and about 300 nucleotides, about 15 nucleotides and about 250 nucleotides, about 15 nucleotides and about 200 nucleotides in length. In some embodiments, the probes are at least 15 nucleotides in length. In some embodiments, the probes are at least 15 nucleotides in length. In some embodiments, the probes are at least 20 nucleotides, at least 25 nucleotides, at least 50 nucleotides, at least 75 nucleotides, at least 100 nucleotides, at least 125 nucleotides, at least 150 nucleotides, at least 200 nucleotides, at least 225 nucleotides, at least 250 nucleotides, at least 275 nucleotides, at least 300 nucleotides, at least 325 nucleotides, at least 350 nucleotides, at least 375 nucleotides in length.

The polynucleotide probes of a probe set can comprise RNA, DNA, RNA or DNA mimetics, or combinations thereof, and can be single-stranded or double-stranded. Thus the polynucleotide probes can be composed of naturally-occurring nucleobases, sugars and covalent internucleoside (backbone) linkages as well as polynucleotide probes having non-naturally-occurring portions which function similarly. Such modified or substituted polynucleotide probes may provide desirable properties such as, for example, enhanced affinity for a target gene and increased stability. The probe set may comprise a coding target and/or a non-coding target. Preferably, the probe set comprises a combination of a coding target and non-coding target.

In some embodiments, the probe set comprise a plurality of target sequences that hybridize to at least about 5 coding targets and/or non-coding targets selected from Table 3, Table 5, Table 13 or SEQ ID Nos: 1-4050. Alternatively, the probe set comprise a plurality of target sequences that hybridize to at least about 10 coding targets and/or non-coding targets selected from Table 3, Table 5, Table 13 or SEQ ID Nos: 1-4050. In some embodiments, the probe set comprise a plurality of target sequences that hybridize to at least about 15 coding targets and/or non-coding targets selected from Table 3, Table 5, Table 13 or SEQ ID Nos: 1-4050. In some embodiments, the probe set comprise a plurality of target sequences that hybridize to at least about 20 coding targets and/or non-coding targets selected from Table 3, Table 5, Table 13 or SEQ ID Nos: 1-4050. In some embodiments, the probe set comprise a plurality of target sequences that hybridize to at least about 30 coding targets and/or non-coding targets selected from Table 3, Table 5, Table 13 or SEQ ID Nos: 1-4050.

The system of the present invention further provides for primers and primer pairs capable of amplifying target sequences defined by the probe set, or fragments or subsequences or complements thereof. The nucleotide sequences of the probe set may be provided in computer-readable media for in silico applications and as a basis for the design of appropriate primers for amplification of one or more target sequences of the probe set.

Primers based on the nucleotide sequences of target sequences can be designed for use in amplification of the target sequences. For use in amplification reactions such as PCR, a pair of primers can be used. The exact composition of the primer sequences is not critical to the invention, but for most applications the primers may hybridize to specific sequences of the probe set under stringent conditions, particularly under conditions of high stringency, as known in the art. The pairs of primers are usually chosen so as to generate an amplification product of at least about 50 nucleotides, more usually at least about 100 nucleotides. Algorithms for the selection of primer sequences are generally known, and are available in commercial software packages. These primers may be used in standard quantitative or qualitative PCR-based assays to assess transcript expression levels of RNAs defined by the probe set. Alternatively, these primers may be used in combination with probes, such as molecular beacons in amplifications using real-time PCR.

In one embodiment, the primers or primer pairs, when used in an amplification reaction, specifically amplify at least a portion of a nucleic acid sequence of a target selected from Table 3, Table 5, Table 13 or SEQ ID Nos: 1-4050 (or subgroups thereof as set forth herein), an RNA form thereof, or a complement to either thereof.

A label can optionally be attached to or incorporated into a probe or primer polynucleotide to allow detection and/or quantitation of a target polynucleotide representing the target sequence of interest. The target polynucleotide may be the expressed target sequence RNA itself, a cDNA copy thereof, or an amplification product derived therefrom, and may be the positive or negative strand, so long as it can be specifically detected in the assay being used. Similarly, an antibody may be labeled.

In certain multiplex formats, labels used for detecting different targets may be distinguishable. The label can be attached directly (e.g., via covalent linkage) or indirectly, e.g., via a bridging molecule or series of molecules (e.g., a molecule or complex that can bind to an assay component, or via members of a binding pair that can be incorporated into assay components, e.g. biotin-avidin or streptavidin). Many labels are commercially available in activated forms which can readily be used for such conjugation (for example through amine acylation), or labels may be attached through known or determinable conjugation schemes, many of which are known in the art.

Labels useful in the invention described herein include any substance which can be detected when bound to or incorporated into the biomolecule of interest. Any effective detection method can be used, including optical, spectroscopic, electrical, piezoelectrical, magnetic, Raman scattering, surface plasmon resonance, colorimetric, calorimetric, etc. A label is typically selected from a chromophore, a lumiphore, a fluorophore, one member of a quenching system, a chromogen, a hapten, an antigen, a magnetic particle, a material exhibiting nonlinear optics, a semiconductor nanocrystal, a metal nanoparticle, an enzyme, an antibody or binding portion or equivalent thereof, an aptamer, and one member of a binding pair, and combinations thereof. Quenching schemes may be used, wherein a quencher and a fluorophore as members of a quenching pair may be used on a probe, such that a change in optical parameters occurs upon binding to the target introduce or quench the signal from the fluorophore. One example of such a system is a molecular beacon. Suitable quencher/fluorophore systems are known in the art. The label may be bound through a variety of intermediate linkages. For example, a polynucleotide may comprise a biotin-binding species, and an optically detectable label may be conjugated to biotin and then bound to the labeled polynucleotide. Similarly, a polynucleotide sensor may comprise an immunological species such as an antibody or fragment, and a secondary antibody containing an optically detectable label may be added.

Chromophores useful in the methods described herein include any substance which can absorb energy and emit light. For multiplexed assays, a plurality of different signaling chromophores can be used with detectably different emission spectra. The chromophore can be a lumophore or a fluorophore. Typical fluorophores include fluorescent dyes, semiconductor nanocrystals, lanthanide chelates, polynucleotide-specific dyes and green fluorescent protein.

In some embodiments, polynucleotides of the invention comprise at least 20 consecutive bases of the nucleic acid sequence of a target selected from Table 3, Table 5, Table 13 or SEQ ID Nos: 1-4050 or a complement thereto. The polynucleotides may comprise at least 21, 22, 23, 24, 25, 27, 30, 32, 35, 40, 45, 50, or more consecutive bases of the nucleic acids sequence of a target selected from Table 3, Table 5, Table 13 or SEQ ID Nos: 1-4050, as applicable.

The polynucleotides may be provided in a variety of formats, including as solids, in solution, or in an array. The polynucleotides may optionally comprise one or more labels, which may be chemically and/or enzymatically incorporated into the polynucleotide.

In some embodiments, one or more polynucleotides provided herein can be provided on a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonates, or combinations thereof. Conducting polymers and photoconductive materials can be used.

The substrate can take the form of an array, a photodiode, an optoelectronic sensor such as an optoelectronic semiconductor chip or optoelectronic thin-film semiconductor, or a biochip. The location(s) of probe(s) on the substrate can be addressable; this can be done in highly dense formats, and the location(s) can be microaddressable or nanoaddressable.

Diagnostic Samples

A biological sample is collected from a subject in need of treatment for cancer to evaluate whether a patient will benefit from neoadjuvant chemotherapy. Diagnostic samples for use with the systems and in the methods of the present invention comprise nucleic acids suitable for providing RNAs expression information. In principle, the biological sample from which the expressed RNA is obtained and analyzed for target sequence expression can be any material suspected of comprising cancerous bladder tissue or cells. The diagnostic sample can be a biological sample used directly in a method of the invention. Alternatively, the diagnostic sample can be a sample prepared from a biological sample.

In one embodiment, the sample or portion of the sample comprising or suspected of comprising cancerous tissue or cells can be any source of biological material, including cells, tissue or fluid, including bodily fluids. Non-limiting examples of the source of the sample include an aspirate, a needle biopsy, a cytology pellet, a bulk tissue preparation or a section thereof obtained for example by surgery or autopsy, lymph fluid, blood, plasma, serum, tumors, and organs. In some embodiments, the sample is from urine comprising cancerous cells. Alternatively, the sample is from a bladder tumor biopsy.

The samples may be archival samples, having a known and documented medical outcome, or may be samples from current patients whose ultimate medical outcome is not yet known.

In some embodiments, the sample may be dissected prior to molecular analysis. The sample may be prepared via macrodissection of a bulk tumor specimen or portion thereof, or may be treated via microdissection, for example via Laser Capture Microdissection (LCM).

The sample may initially be provided in a variety of states, as fresh tissue, fresh frozen tissue, fine needle aspirates, and may be fixed or unfixed. Frequently, medical laboratories routinely prepare medical samples in a fixed state, which facilitates tissue storage. A variety of fixatives can be used to fix tissue to stabilize the morphology of cells, and may be used alone or in combination with other agents. Exemplary fixatives include crosslinking agents, alcohols, acetone, Bouin's solution, Zenker solution, Hely solution, osmic acid solution and Carnoy solution.

Crosslinking fixatives can comprise any agent suitable for forming two or more covalent bonds, for example an aldehyde. Sources of aldehydes typically used for fixation include formaldehyde, paraformaldehyde, glutaraldehyde or formalin. Preferably, the crosslinking agent comprises formaldehyde, which may be included in its native form or in the form of paraformaldehyde or formalin. One of skill in the art would appreciate that for samples in which crosslinking fixatives have been used special preparatory steps may be necessary including for example heating steps and proteinase-k digestion; see methods.

One or more alcohols may be used to fix tissue, alone or in combination with other fixatives. Exemplary alcohols used for fixation include methanol, ethanol and isopropanol.

Formalin fixation is frequently used in medical laboratories. Formalin comprises both an alcohol, typically methanol, and formaldehyde, both of which can act to fix a biological sample.

Whether fixed or unfixed, the biological sample may optionally be embedded in an embedding medium. Exemplary embedding media used in histology including paraffin, Tissue-Tek® V.I.P.™, Paramat, Paramat Extra, Paraplast, Paraplast X-tra, Paraplast Plus, Peel Away Paraffin Embedding Wax, Polyester Wax, Carbowax Polyethylene Glycol, Polyfin™, Tissue Freezing Medium TFMFM, Cryo-Gef™, and OCT Compound (Electron Microscopy Sciences, Hatfield, Pa.). Prior to molecular analysis, the embedding material may be removed via any suitable techniques, as known in the art. For example, where the sample is embedded in wax, the embedding material may be removed by extraction with organic solvent(s), for example xylenes. Kits are commercially available for removing embedding media from tissues. Samples or sections thereof may be subjected to further processing steps as needed, for example serial hydration or dehydration steps.

In some embodiments, the sample is a fixed, wax-embedded biological sample. Frequently, samples from medical laboratories are provided as fixed, wax-embedded samples, most commonly as formalin-fixed, paraffin embedded (FFPE) tissues.

Whatever the source of the biological sample, the target polynucleotide that is ultimately assayed can be prepared synthetically (in the case of control sequences), but typically is purified from the biological source and subjected to one or more preparative steps. The RNA may be purified to remove or diminish one or more undesired components from the biological sample or to concentrate it. Conversely, where the RNA is too concentrated for the particular assay, it may be diluted.

RNA Extraction

RNA can be extracted and purified from biological samples using any suitable technique. A number of techniques are known in the art, and several are commercially available (e.g., FormaPure nucleic acid extraction kit, Agencourt Biosciences, Beverly Mass., High Pure FFPE RNA Micro Kit, Roche Applied Science, Indianapolis, Ind.). RNA can be extracted from frozen tissue sections using TRIzol (Invitrogen, Carlsbad, Calif.) and purified using RNeasy Protect kit (Qiagen, Valencia, Calif.). RNA can be further purified using DNAse I treatment (Ambion, Austin, Tex.) to eliminate any contaminating DNA. RNA concentrations can be made using a Nanodrop ND-1000 spectrophotometer (Nanodrop Technologies, Rockland, Del.). RNA can be further purified to eliminate contaminants that interfere with cDNA synthesis by cold sodium acetate precipitation. RNA integrity can be evaluated by running electropherograms, and RNA integrity number (RIN, a correlative measure that indicates intactness of mRNA) can be determined using the RNA 6000 PicoAssay for the Bioanalyzer 2100 (Agilent Technologies, Santa Clara, Calif.).

Kits

Kits for performing the desired method(s) are also provided, and comprise a container or housing for holding the components of the kit, one or more vessels containing one or more nucleic acid(s), and optionally one or more vessels containing one or more reagents. The reagents include those described in the composition of matter section above, and those reagents useful for performing the methods described, including amplification reagents, and may include one or more probes, primers or primer pairs, enzymes (including polymerases and ligases), intercalating dyes, labeled probes, and labels that can be incorporated into amplification products.

In some embodiments, the kit comprises primers or primer pairs specific for those subsets and combinations of target sequences described herein. The primers or pairs of primers are suitable for selectively amplifying the target sequences. The kit may comprise at least two, three, four or five primers or pairs of primers suitable for selectively amplifying one or more targets. The kit may comprise at least 5, 10, 15, 20, 30, 40, 50, 60, 70, 80, 90, 100, 110, or more primers or pairs of primers suitable for selectively amplifying one or more targets.

In some embodiments, the primers or primer pairs of the kit, when used in an amplification reaction, specifically amplify a non-coding target, coding target, exonic, or non-exonic target described herein, a nucleic acid sequence corresponding to a target selected from Table 3, Table 5, Table 13 or SEQ ID Nos: 1-4050, an RNA form thereof, or a complement to either thereof. The kit may include a plurality of such primers or primer pairs which can specifically amplify a corresponding plurality of different amplify a non-coding target, coding target, exonic, or non-exonic transcript described herein, a nucleic acid sequence corresponding to a target selected from Table 3, Table 5, Table 13 or SEQ ID Nos: 1-4050, RNA forms thereof, or complements thereto. At least two, three, four or five primers or pairs of primers suitable for selectively amplifying the one or more targets can be provided in kit form. In some embodiments, the kit comprises from five to fifty primers or pairs of primers suitable for amplifying the one or more targets.

The reagents may independently be in liquid or solid form. The reagents may be provided in mixtures. Control samples and/or nucleic acids may optionally be provided in the kit. Control samples may include tissue and/or nucleic acids obtained from or representative of tumor samples from patients showing no evidence of disease, as well as tissue and/or nucleic acids obtained from or representative of tumor samples from patients that develop systemic cancer.

The nucleic acids may be provided in an array format, and thus an array or microarray may be included in the kit. The kit optionally may be certified by a government agency for use in prognosing the disease outcome of cancer patients and/or for designating a treatment modality.

Instructions for using the kit to perform one or more methods of the invention can be provided with the container, and can be provided in any fixed medium. The instructions may be located inside or outside the container or housing, and/or may be printed on the interior or exterior of any surface thereof. A kit may be in multiplex form for concurrently detecting and/or quantitating one or more different target polynucleotides representing the expressed target sequences.

Amplification and Hybridization

Following sample collection and nucleic acid extraction, the nucleic acid portion of the sample comprising RNA that is or can be used to prepare the target polynucleotide(s) of interest can be subjected to one or more preparative reactions. These preparative reactions can include in vitro transcription (IVT), labeling, fragmentation, amplification and other reactions. The mRNA can first be treated with reverse transcriptase and a primer to create cDNA prior to detection, quantitation and/or amplification; this can be done in vitro with purified mRNA or in situ, e.g., in cells or tissues affixed to a slide.

By "amplification" is meant any process of producing at least one copy of a nucleic acid, in this case an expressed RNA, and in many cases produces multiple copies. An amplification product can be RNA or DNA, and may include a complementary strand to the expressed target sequence. DNA amplification products can be produced initially through reverse translation and then optionally from further amplification reactions. The amplification product may include all or a portion of a target sequence, and may optionally be labeled. A variety of amplification methods are suitable for use, including polymerase-based methods and ligation-based methods. Exemplary amplification techniques include the polymerase chain reaction method (PCR), the lipase chain reaction (LCR), ribozyme-based methods, self-sustained sequence replication (3SR), nucleic acid sequence-based amplification (NASBA), and the use of Q Beta replicase, reverse transcription, nick translation, and the like.

Asymmetric amplification reactions may be used to preferentially amplify one strand representing the target sequence that is used for detection as the target polynucleotide. In some cases, the presence and/or amount of the amplification product itself may be used to determine the expression level of a given target sequence. In other instances, the amplification product may be used to hybridize to an array or other substrate comprising sensor polynucleotides which are used to detect and/or quantitate target sequence expression.

The first cycle of amplification in polymerase-based methods typically forms a primer extension product complementary to the template strand. If the template is single-stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that can produce an amplifiable segment; thus, each primer must hybridize so that its 3' nucleotide is paired to a nucleotide in its complementary template strand that is located 3' from the 3' nucleotide of the primer used to replicate that complementary template strand in the PCR.

The target polynucleotide can be amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity that can copy the target polynucleotide can be used, including DNA polymerases, RNA polymerases, reverse transcriptases, and enzymes having more than one type of polymerase or enzyme activity. The enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenase® Version 2.0 T7, Tub, Taq, Tth, Pfic, Pfu, Tsp, Tfl, Tli and *Pyrococcus* sp GB-D DNA polymerases; RNA polymerases such as *E. coil*, SP6, T3 and T7 RNA polymerases; and reverse transcriptases such as AMV, M-MuLV, MMLV, RNAse H MMLV (SuperScript®), SuperScript® II, ThermoScript®, HIV-1, and RAV2 reverse transcriptases. All of these enzymes are commercially available. Exemplary polymerases with multiple specificities include RAV2 and Tli (exo-) polymerases. Exemplary thermostable polymerases include Tub, Taq, Tth, Pfic, Pfu, Tsp, Tfl, Tli and *Pyrococcus* sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions (e.g., manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target polynucleotides or different regions of a particular target polynucleotide within the sample.

An amplification reaction can be performed under conditions which allow an optionally labeled sensor polynucleotide to hybridize to the amplification product during at least part of an amplification cycle. When the assay is performed in this manner, real-time detection of this hybridization event can take place by monitoring for light emission or fluorescence during amplification, as known in the art.

Where the amplification product is to be used for hybridization to an array or microarray, a number of suitable commercially available amplification products are available. These include amplification kits available from NuGEN, Inc. (San Carlos, Calif.), including the WT-Ovation™ System, WT-Ovation™ System v2, WT-Ovation™ Pico System, WT-Ovation™ FFPE Exon Module, WT-Ovation™ FFPE Exon Module RiboAmp and RiboAmp$^{Plus}$ RNA Amplification Kits (MDS Analytical Technologies (formerly Arcturus) (Mountain View, Calif.), Genisphere, Inc. (Hatfield, Pa.), including the RampUp Plus™ and SenseAmp™ RNA Amplification kits, alone or in combination. Amplified nucleic acids may be subjected to one or more purification reactions after amplification and labeling, for example using magnetic beads (e.g., RNAClean magnetic beads, Agencourt Biosciences).

Multiple RNA biomarkers can be analyzed using real-time quantitative multiplex RT-PCR platforms and other multiplexing technologies such as GenomeLab GeXP Genetic Analysis System (Beckman Coulter, Foster City, Calif.), SmartCycler® 9600 or GeneXpert® Systems (Cepheid, Sunnyvale, Calif.), ABI 7900 HT Fast Real Time PCR system (Applied Biosystems, Foster City, Calif.), LightCycler® 480 System (Roche Molecular Systems, Pleasanton, Calif.), xMAP 100 System (Luminex, Austin, Tex.) Solexa Genome Analysis System (Illumina, Hayward, Calif.), OpenArray Real Time qPCR (BioTrove, Woburn, Mass.) and BeadXpress System (Illumina, Hayward, Calif.).

Detection and/or Quantification of Target Sequences

Any method of detecting and/or quantitating the expression of the encoded target sequences can in principle be used in the invention. The expressed target sequences can be directly detected and/or quantitated, or may be copied and/or amplified to allow detection of amplified copies of the expressed target sequences or its complement.

Methods for detecting and/or quantifying a target can include Northern blotting, sequencing, array or microarray hybridization, serial analysis of gene expression (SAGE), by enzymatic cleavage of specific structures (e.g., an Invader® assay, Third Wave Technologies, e.g. as described in U.S. Pat. Nos. 5,846,717, 6,090,543; 6,001,567; 5,985,557; and 5,994,069) and amplification methods, e.g. RT-PCR, including in a TaqMan® assay (PE Biosystems, Foster City, Calif., e.g. as described in U.S. Pat. Nos. 5,962,233 and 5,538,848), and may be quantitative or semi-quantitative, and may vary depending on the origin, amount and condition of the available biological sample. Combinations of these methods may also be used. For example, nucleic acids may be amplified, labeled and subjected to microarray analysis.

In some instances, target sequences may be detected by sequencing. Sequencing methods may comprise whole genome sequencing or exome sequencing. Sequencing methods such as Maxim-Gilbert, chain-termination, or high-throughput systems may also be used. Additional, suitable sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, and SOLiD sequencing.

Additional methods for detecting and/or quantifying a target include single-molecule sequencing (e.g., Helicos, PacBio), sequencing by synthesis (e.g., Illumina, Ion Torrent), sequencing by ligation (e.g., ABI SOLID), sequencing by hybridization (e.g., Complete Genomics), in situ hybridization, bead-array technologies (e.g., Luminex xMAP, Illumina BeadChips), branched DNA technology (e.g., Panomics, Genisphere). Sequencing methods may use fluorescent (e.g., Illumina) or electronic (e.g., Ion Torrent, Oxford Nanopore) methods of detecting nucleotides.

Reverse Transcription for ORT-PCR Analysis

Reverse transcription can be performed by any method known in the art. For example, reverse transcription may be performed using the Omniscript kit (Qiagen, Valencia, Calif.), Superscript III kit (Invitrogen, Carlsbad, Calif.), for RT-PCR. Target-specific priming can be performed in order to increase the sensitivity of detection of target sequences and generate target-specific cDNA.

TanMan® Gene Expression Analysis

TaqMan®RT-PCR can be performed using Applied Biosystems Prism (ABI) 7900 HT instruments in a 5 1.11 volume with target sequence-specific cDNA equivalent to 1 ng total RNA.

Primers and probes concentrations for TaqMan analysis are added to amplify fluorescent amplicons using PCR cycling conditions such as 95° C. for 10 minutes for one cycle, 95° C. for 20 seconds, and 60° C. for 45 seconds for 40 cycles. A reference sample can be assayed to ensure reagent and process stability. Negative controls (e.g., no template) should be assayed to monitor any exogenous nucleic acid contamination.

Classification Arrays

The present invention contemplates that a probe set or probes derived therefrom may be provided in an array format. In the context of the present invention, an "array" is a spatially or logically organized collection of polynucleotide probes. An array comprising probes specific for a coding target, non-coding target, or a combination thereof may be used. Alternatively, an array comprising probes specific for two or more of transcripts of a target selected from Table 3, Table 5, Table 13 or SEQ ID Nos: 1-4050, or a product derived thereof, can be used. Desirably, an array may be specific for 5, 10, 15, 20, 25, 30 or more of transcripts of a target selected from Table 3, Table 5, Table 13 or SEQ ID Nos: 1-4050. Expression of these sequences may be detected alone or in combination with other transcripts. In some embodiments, an array is used which comprises a wide range of sensor probes for bladder-specific expression products, along with appropriate control sequences. In some instances, the array may comprise the Human Exon 1.0 ST Array (HuEx 1.0 ST, Affymetrix, Inc., Santa Clara, Calif.).

Typically the polynucleotide probes are attached to a solid substrate and are ordered so that the location (on the substrate) and the identity of each are known. The polynucleotide probes can be attached to one of a variety of solid substrates capable of withstanding the reagents and conditions necessary for use of the array. Examples include, but are not limited to, polymers, such as (poly)tetrafluoroethylene, (poly)vinylidenedifluoride, polystyrene, polycarbonate, polypropylene and polystyrene; ceramic; silicon; silicon dioxide; modified silicon; (fused) silica, quartz or glass; functionalized glass; paper, such as filter paper; diazotized cellulose; nitrocellulose filter; nylon membrane; and polyacrylamide gel pad. Substrates that are transparent to light are useful for arrays that may be used in an assay that involves optical detection.

Examples of array formats include membrane or filter arrays (for example, nitrocellulose, nylon arrays), plate arrays (for example, multiwell, such as a 24-, 96-, 256-, 384-, 864- or 1536-well, microtitre plate arrays), pin arrays, and bead arrays (for example, in a liquid "slurry"). Arrays on substrates such as glass or ceramic slides are often referred to as chip arrays or "chips." Such arrays are well known in the art. In one embodiment of the present invention, the Cancer Prognosticarray is a chip.

Data Analysis

In some embodiments, one or more pattern recognition methods can be used in analyzing the expression level of target sequences. The pattern recognition method can comprise a linear combination of expression levels, or a nonlinear combination of expression levels. In some embodiments, expression measurements for RNA transcripts or combinations of RNA transcript levels are formulated into linear or non-linear models or algorithms (e.g., an 'expression signature') and converted into a likelihood score. This likelihood score may indicate the probability that a biological sample is from a patient who will benefit from neoadjuvant chemotherapy. Additionally, a likelihood score may indicate the probability that a biological sample is from a patient who may exhibit no evidence of disease, who may exhibit systemic cancer, or who may exhibit biochemical recurrence. The likelihood score can be used to distinguish these disease states. The models and/or algorithms can be provided in machine readable format, and may be used to correlate expression levels or an expression profile with a disease state, and/or to designate a treatment modality for a patient or class of patients.

Assaying the expression level for a plurality of targets may comprise the use of an algorithm or classifier. Array data can be managed, classified, and analyzed using techniques known in the art. Assaying the expression level for a plurality of targets may comprise probe set modeling and data pre-processing. Probe set modeling and data pre-processing can be derived using the Robust Multi-Array (RMA) algorithm or variants GC-RMA, fRMA, Probe Logarithmic Intensity Error (PLIER) algorithm, or variant iterPLIER, or Single-Channel Array Normalization (SCAN) algorithm. Variance or intensity filters can be applied to pre-process data using the RMA algorithm, for example by removing target sequences with a standard deviation of <10 or a mean intensity of <100 intensity units of a normalized data range, respectively.

Alternatively, assaying the expression level for a plurality of targets may comprise the use of a machine learning algorithm. The machine learning algorithm may comprise a supervised learning algorithm. Examples of supervised learning algorithms may include Average One-Dependence Estimators (AODE), Artificial neural network (e.g., Back-propagation), Bayesian statistics (e.g., Naive Bayes classifier, Bayesian network, Bayesian knowledge base), Case-based reasoning, Decision trees, Inductive logic programming, Gaussian process regression, Group method of data handling (GMDH), Learning Automata, Learning Vector Quantization, Minimum message length (decision trees, decision graphs, etc.), Lazy learning, Instance-based learning Nearest Neighbor Algorithm, Analogical modeling, Probably approximately correct learning (PAC) learning, Ripple down rules, a knowledge acquisition methodology, Symbolic machine learning algorithms, Subsymbolic machine learning algorithms, Support vector machines, Random Forests, Ensembles of classifiers, Bootstrap aggregating (bagging), and Boosting. Supervised learning may comprise ordinal classification such as regression analysis and Information fuzzy networks (IFN). Alternatively, supervised learning methods may comprise statistical classification, such as AODE, Linear classifiers (e.g., Fisher's linear discriminant, Logistic regression, Naive Bayes classifier, Perceptron, and Support vector machine), quadratic classifiers, k-nearest neighbor, Boosting, Decision trees (e.g., C4.5, Random forests), Bayesian networks, and Hidden Markov models.

The machine learning algorithms may also comprise an unsupervised learning algorithm. Examples of unsupervised learning algorithms may include artificial neural network, Data clustering, Expectation-maximization algorithm, Self-organizing map, Radial basis function network, Vector Quantization, Generative topographic map, Information bottleneck method, and IBSEAD. Unsupervised learning may also comprise association rule learning algorithms such as Apriori algorithm, Eclat algorithm and FP-growth algorithm. Hierarchical clustering, such as Single-linkage clustering and Conceptual clustering, may also be used. Alternatively, unsupervised learning may comprise partitional clustering such as K-means algorithm and Fuzzy clustering.

In some instances, the machine learning algorithms comprise a reinforcement learning algorithm. Examples of reinforcement learning algorithms include, but are not limited to, temporal difference learning, Q-learning and Learning Automata. Alternatively, the machine learning algorithm may comprise Data Pre-processing.

Preferably, the machine learning algorithms may include, but are not limited to, Average One-Dependence Estimators (AODE), Fisher's linear discriminant, Logistic regression, Perceptron, Multilayer Perceptron, Artificial Neural Networks, Support vector machines, Quadratic classifiers, Boosting, Decision trees, C4.5, Bayesian networks, Hidden Markov models, High-Dimensional Discriminant Analysis, and Gaussian Mixture Models. The machine learning algorithm may comprise support vector machines, Naïve Bayes classifier, k-nearest neighbor, high-dimensional discriminant analysis, or Gaussian mixture models. In some instances, the machine learning algorithm comprises Random Forests.

Subtyping

Molecular subtyping is a method of classifying bladder cancer into one of multiple genetically-distinct categories, or subtypes. Each subtype responds differently to different kinds of treatments, and the presence of a particular subtype is predictive of, for example, chemoresistance, higher risk of recurrence, or good or poor prognosis for an individual. The inventors of the present invention discovered that classification of bladder cancer into four subtypes, including, basal, claudin-low, luminal-infiltrated, and luminal non-infiltrated subtypes is clinically useful for predicting patient outcome and response to neoadjuvant chemotherapy (see Examples). As described herein, each subtype has a unique molecular and clinical fingerprint. Differential expression analysis of one or more of the gene targets listed in Table 3, Table 5, Table 13 or SEQ ID Nos: 1-4050 allows for the identification of the molecular subtype of a bladder cancer. In some instances, the molecular subtyping methods of the present invention are used in combination with other biomarkers, like tumor grade and hormone levels, for analyzing the bladder cancer.

Prediction of Treatment Response to Neoadjuvant Chemotherapy

Bladder cancer subtyping can be utilized to predict whether or not a cancer patient will benefit from neoadjuvant chemotherapy. For example, patients with luminal, non-immune infiltrated tumors have the best prognosis, irrespective of the treatment strategy. Patients with luminal, immune-infiltrated tumors have a significantly worse prognosis than those with luminal non-infiltrated tumors with and without neoadjuvant chemotherapy. Patients with claudin-low tumors had the worst prognosis irrespective of treatment strategy. Patients with basal tumors derive the most benefit from neoadjuvant chemotherapy and have a poor prognosis compared to other subtypes when treated with surgery alone, but their prognosis dramatically improves with neoadjuvant chemotherapy. Thus, patients having the basal bladder cancer subtype benefit from neoadjuvant chemotherapy, whereas patients having other bladder cancer subtypes are better candidates for other anti-cancer treatment options.

Therapeutic Regimens

Diagnosing, predicting, or monitoring a status or outcome of bladder cancer may comprise treating the bladder cancer or preventing cancer progression. In addition, diagnosing, predicting, or monitoring a status or outcome of bladder cancer may comprise identifying or predicting which patients will be responders or non-responders to an anti-cancer therapy (e.g., neoadjuvant chemotherapy). In some instances, diagnosing, predicting, or monitoring may comprise determining a therapeutic regimen. Determining a therapeutic regimen may comprise administering an anti-cancer therapy. Alternatively, determining a therapeutic regimen may comprise modifying, recommending, continuing or discontinuing an anti-cancer regimen. In some instances, if the sample expression patterns are consistent with the expression pattern for a known disease or disease outcome, the expression patterns can be used to designate one or more treatment modalities (e.g., therapeutic regimens, such as neoadjuvant chemotherapy or other anti-cancer regimen). An anti-cancer regimen may comprise one or more anti-cancer therapies. Examples of anti-cancer therapies include surgery, chemotherapy, radiation therapy, immunotherapy/biological therapy, and photodynamic therapy.

For example, a patient is selected for treatment with neoadjuvant chemotherapy if the patient is identified as being likely to be responsive to neoadjuvant chemotherapy based on subtyping of the bladder cancer, as described herein. Neoadjuvant chemotherapy may be performed prior to other anti-cancer treatments such as, but not limited to, surgery (e.g., transurethral resection or cystectomy), radiation therapy, immunotherapy (e.g., *Bacillus* Calmette-Guerin (BCG) or anti-PDL1 immunotherapy), hormonal therapy, biologic therapy, or any combination thereof. Patients, especially those not identified as likely to benefit from neoadjuvant chemotherapy, may omit neoadjuvant chemotherapy and instead be administered other cancer treatments directly.

Examples of chemotherapeutic agents that may be used in treating bladder cancer include alkylating agents, anti-metabolites, plant alkaloids and terpenoids, vinca alkaloids, podophyllotoxin, taxanes, topoisomerase inhibitors, and cytotoxic antibiotics. Cisplatin, carboplatin, and oxaliplatin are examples of alkylating agents. Other alkylating agents include mechlorethamine, cyclophosphamide, chlorambucil, ifosfamide. Alkylating agents may impair cell function by forming covalent bonds with the amino, carboxyl, sulthydryl, and phosphate groups in biologically important molecules. Alternatively, alkylating agents may chemically modify a cell's DNA.

Anti-metabolites are another example of chemotherapeutic agents. Anti-metabolites may masquerade as purines or pyrimidines and may prevent purines and pyrimidines from becoming incorporated in to DNA during the "S" phase (of the cell cycle), thereby stopping normal development and division. Antimetabolites may also affect RNA synthesis. Examples of metabolites include azathioprine and mercaptopurine.

Alkaloids may be derived from plants and block cell division may also be used for the treatment of cancer. Alkyloids may prevent microtubule function. Examples of alkaloids are vinca alkaloids and taxanes. *Vinca* alkaloids may bind to specific sites on tubulin and inhibit the assembly of tubulin into microtubules (M phase of the cell cycle). The vinca alkaloids may be derived from the Madagascar periwinkle, *Catharanthus roseus* (formerly known as *Vinca rosea*). Examples of vinca alkaloids include, but are not limited to, vincristine, vinblastine, vinorelbine, or vindesine. Taxanes are diterpenes produced by the plants of the genus *Taxus* (yews). Taxanes may be derived from natural sources or synthesized artificially. Taxanes include paclitaxel (Taxol) and docetaxel (Taxotere). Taxanes may disrupt microtubule function. Microtubules are essential to cell division, and taxanes may stabilize GDP-bound tubulin in the microtubule, thereby inhibiting the process of cell division. Thus, in essence, taxanes may be mitotic inhibitors. Taxanes may also be radiosensitizing and often contain numerous chiral centers.

Alternative chemotherapeutic agents include podophyllotoxin. Podophyllotoxin is a plant-derived compound that may help with digestion and may be used to produce cytostatic drugs such as etoposide and teniposide. They may prevent the cell from entering the G1 phase (the start of DNA replication) and the replication of DNA (the S phase).

Topoisomerases are essential enzymes that maintain the topology of DNA. Inhibition of type I or type II topoisomerases may interfere with both transcription and replication of DNA by upsetting proper DNA supercoiling. Some chemotherapeutic agents may inhibit topoisomerases. For example, some type I topoisomerase inhibitors include camptothecins: irinotecan and topotecan. Examples of type II inhibitors include amsacrine, etoposide, etoposide phosphate, and teniposide.

Another example of chemotherapeutic agents is cytotoxic antibiotics. Cytotoxic antibiotics are a group of antibiotics that are used for the treatment of cancer because they may interfere with DNA replication and/or protein synthesis. Cytotoxic antibiotics include, but are not limited to, actinomycin, anthracyclines, doxorubicin, daunorubicin, valrubicin, idarubicin, epirubicin, bleomycin, plicamycin, and mitomycin.

Surgical oncology uses surgical methods to diagnose, stage, and treat cancer, and to relieve certain cancer-related symptoms. Surgery may be used to remove the tumor (e.g., excisions, resections, debulking surgery), reconstruct a part of the body (e.g., restorative surgery), and/or to relieve symptoms such as pain (e.g., palliative surgery). Surgery may also include cryosurgery. Cryosurgery (also called cryotherapy) may use extreme cold produced by liquid nitrogen (or argon gas) to destroy abnormal tissue. Cryosurgery can be used to treat external tumors, such as those on the skin. For external tumors, liquid nitrogen can be applied directly to the cancer cells with a cotton swab or spraying device. Cryosurgery may also be used to treat tumors inside the body (internal tumors and tumors in the bone). For internal tumors, liquid nitrogen or argon gas may be circulated through a hollow instrument called a cryoprobe, which is placed in contact with the tumor. An ultrasound or MRI may be used to guide the cryoprobe and monitor the freezing of the cells, thus limiting damage to nearby healthy tissue. A ball of ice crystals may form around the probe, freezing nearby cells. Sometimes more than one probe is used to deliver the liquid nitrogen to various parts of the tumor. The probes may be put into the tumor during surgery or through the skin (percutaneously). After cryosurgery, the frozen tissue thaws and may be naturally absorbed by the body (for internal tumors), or may dissolve and form a scab (for external tumors).

In some instances, the anti-cancer treatment may comprise radiation therapy. Radiation can come from a machine outside the body (external-beam radiation therapy) or from radioactive material placed in the body near cancer cells (internal radiation therapy, more commonly called brachytherapy). Systemic radiation therapy uses a radioactive substance, given by mouth or into a vein that travels in the blood to tissues throughout the body.

External-beam radiation therapy may be delivered in the form of photon beams (either x-rays or gamma rays). A photon is the basic unit of light and other forms of electromagnetic radiation. An example of external-beam radiation therapy is called 3-dimensional conformal radiation therapy (3D-CRT). 3D-CRT may use computer software and advanced treatment machines to deliver radiation to very precisely shaped target areas. Many other methods of external-beam radiation therapy are currently being tested and used in cancer treatment. These methods include, but are not limited to, intensity-modulated radiation therapy (IMRT), image-guided radiation therapy (IGRT), Stereotactic radiosurgery (SRS), Stereotactic body radiation therapy (SBRT), and proton therapy.

Intensity-modulated radiation therapy (IMRT) is an example of external-beam radiation and may use hundreds of tiny radiation beam-shaping devices, called collimators, to deliver a single dose of radiation. The collimators can be stationary or can move during treatment, allowing the intensity of the radiation beams to change during treatment sessions. This kind of dose modulation allows different areas of a tumor or nearby tissues to receive different doses of radiation. IMRT is planned in reverse (called inverse treatment planning). In inverse treatment planning, the radiation doses to different areas of the tumor and surrounding tissue are planned in advance, and then a high-powered computer program calculates the required number of beams and angles of the radiation treatment. In contrast, during traditional (forward) treatment planning, the number and angles of the radiation beams are chosen in advance and computers calculate how much dose may be delivered from each of the planned beams. The goal of IMRT is to increase the radiation dose to the areas that need it and reduce radiation exposure to specific sensitive areas of surrounding normal tissue.

Another example of external-beam radiation is image-guided radiation therapy (IGRT). In IGRT, repeated imaging scans (CT, MRI, or PET) may be performed during treatment. These imaging scans may be processed by computers to identify changes in a tumor's size and location due to treatment and to allow the position of the patient or the planned radiation dose to be adjusted during treatment as needed. Repeated imaging can increase the accuracy of radiation treatment and may allow reductions in the planned volume of tissue to be treated, thereby decreasing the total radiation dose to normal tissue.

Tomotherapy is a type of image-guided IMRT. A tomotherapy machine is a hybrid between a CT imaging scanner and an external-beam radiation therapy machine. The part of the tomotherapy machine that delivers radiation for both imaging and treatment can rotate completely around the patient in the same manner as a normal CT scanner. Tomotherapy machines can capture CT images of the patient's tumor immediately before treatment sessions, to allow for very precise tumor targeting and sparing of normal tissue.

Stereotactic radiosurgery (SRS) can deliver one or more high doses of radiation to a small tumor. SRS uses extremely accurate image-guided tumor targeting and patient positioning. Therefore, a high dose of radiation can be given without excess damage to normal tissue. SRS can be used to treat small tumors with well-defined edges. It is most commonly used in the treatment of brain or spinal tumors and brain metastases from other cancer types. For the treatment of some brain metastases, patients may receive radiation therapy to the entire brain (called whole-brain radiation therapy) in addition to SRS. SRS requires the use of a head frame or other device to immobilize the patient during treatment to ensure that the high dose of radiation is delivered accurately.

Stereotactic body radiation therapy (SBRT) delivers radiation therapy in fewer sessions, using smaller radiation fields and higher doses than 3D-CRT in most cases. SBRT may treat tumors that lie outside the brain and spinal cord. Because these tumors are more likely to move with the normal motion of the body, and therefore cannot be targeted as accurately as tumors within the brain or spine, SBRT is usually given in more than one dose. SBRT can be used to treat small, isolated tumors, including cancers in the lung and liver. SBRT systems may be known by their brand names, such as the CyberKnife®.

In proton therapy, external-beam radiation therapy may be delivered by proton. Protons are a type of charged particle. Proton beams differ from photon beams mainly in the way they deposit energy in living tissue. Whereas photons deposit energy in small packets all along their path through tissue, protons deposit much of their energy at the end of their path (called the Bragg peak) and deposit less energy along the way. Use of protons may reduce the exposure of normal tissue to radiation, possibly allowing the delivery of higher doses of radiation to a tumor.

Other charged particle beams such as electron beams may be used to irradiate superficial tumors, such as skin cancer or tumors near the surface of the body, but they cannot travel very far through tissue.

Internal radiation therapy (brachytherapy) is radiation delivered from radiation sources (radioactive materials) placed inside or on the body. Several brachytherapy techniques are used in cancer treatment. Interstitial brachytherapy may use a radiation source placed within tumor tissue, such as within a bladder tumor. Intracavitary brachytherapy may use a source placed within a surgical cavity or a body cavity, such as the chest cavity, near a tumor. Episcleral brachytherapy, which may be used to treat melanoma inside the eye, may use a source that is attached to the eye. In brachytherapy, radioactive isotopes can be sealed in tiny pellets or "seeds." These seeds may be placed in patients using delivery devices, such as needles, catheters, or some other type of carrier. As the isotopes decay naturally, they give off radiation that may damage nearby cancer cells. Brachytherapy may be able to deliver higher doses of radiation to some cancers than external-beam radiation therapy while causing less damage to normal tissue.

Brachytherapy can be given as a low-dose-rate or a high-dose-rate treatment. In low-dose-rate treatment, cancer cells receive continuous low-dose radiation from the source over a period of several days. In high-dose-rate treatment, a robotic machine attached to delivery tubes placed inside the body may guide one or more radioactive sources into or near a tumor, and then removes the sources at the end of each treatment session. High-dose-rate treatment can be given in one or more treatment sessions. An example of a high-dose-rate treatment is the MammoSite® system.

The placement of brachytherapy sources can be temporary or permanent. For permanent brachytherapy, the sources may be surgically sealed within the body and left there, even after all of the radiation has been given off. In some instances, the remaining material (in which the radioactive isotopes were sealed) does not cause any discomfort or harm to the patient. Permanent brachytherapy is a type of low-dose-rate brachytherapy. For temporary brachytherapy, tubes (catheters) or other carriers are used to deliver the radiation sources, and both the carriers and the radiation sources are removed after treatment. Temporary brachytherapy can be either low-dose-rate or high-dose-rate treatment. Brachytherapy may be used alone or in addition to external-beam radiation therapy to provide a "boost" of radiation to a tumor while sparing surrounding normal tissue.

In systemic radiation therapy, a patient may swallow or receive an injection of a radioactive substance, such as radioactive iodine or a radioactive substance bound to a monoclonal antibody. Radioactive iodine (131I) is a type of systemic radiation therapy commonly used to help treat cancer, such as thyroid cancer. Thyroid cells naturally take up radioactive iodine. For systemic radiation therapy for some other types of cancer, a monoclonal antibody may help target the radioactive substance to the right place. The antibody joined to the radioactive substance travels through the blood, locating and killing tumor cells. For example, the drug ibritumomab tiuxetan (Zevalin®) may be used for the treatment of certain types of B-cell non-Hodgkin lymphoma (NHL). The antibody part of this drug recognizes and binds to a protein found on the surface of B lymphocytes. The combination drug regimen of tositumomab and iodine I 131 tositumomab (Bexxar®) may be used for the treatment of certain types of cancer, such as NHL. In this regimen, nonradioactive tositumomab antibodies may be given to patients first, followed by treatment with tositumomab antibodies that have 131I attached. Tositumomab may recognize and bind to the same protein on B lymphocytes as ibritumomab. The nonradioactive form of the antibody may help protect normal B lymphocytes from being damaged by radiation from 131I.

Some systemic radiation therapy drugs relieve pain from cancer that has spread to the bone (bone metastases). This is a type of palliative radiation therapy. The radioactive drugs samarium-153-lexidronam (Quadramet®) and strontium-89 chloride (Metastron®) are examples of radiopharmaceuticals may be used to treat pain from bone metastases.

Photodynamic therapy (PDT) is an anti-cancer treatment that may use a drug, called a photosensitizer or photosensitizing agent, and a particular type of light. When photosensitizers are exposed to a specific wavelength of light, they may produce a form of oxygen that kills nearby cells. A photosensitizer may be activated by light of a specific wavelength. This wavelength determines how far the light can travel into the body. Thus, photosensitizers and wavelengths of light may be used to treat different areas of the body with PDT.

In the first step of PDT for cancer treatment, a photosensitizing agent may be injected into the bloodstream. The agent may be absorbed by cells all over the body but may stay in cancer cells longer than it does in normal cells. Approximately 24 to 72 hours after injection, when most of the agent has left normal cells but remains in cancer cells, the tumor can be exposed to light. The photosensitizer in the tumor can absorb the light and produces an active form of oxygen that destroys nearby cancer cells. In addition to directly killing cancer cells, PDT may shrink or destroy tumors in two other ways. The photosensitizer can damage blood vessels in the tumor, thereby preventing the cancer from receiving necessary nutrients. PDT may also activate the immune system to attack the tumor cells.

The light used for PDT can come from a laser or other sources. Laser light can be directed through fiber optic cables (thin fibers that transmit light) to deliver light to areas inside the body. For example, a fiber optic cable can be inserted through an endoscope (a thin, lighted tube used to look at tissues inside the body) into the lungs or esophagus to treat cancer in these organs. Other light sources include light-emitting diodes (LEDs), which may be used for surface tumors, such as skin cancer. PDT is usually performed as an outpatient procedure. PDT may also be repeated and may be used with other therapies, such as surgery, radiation, or chemotherapy.

Extracorporeal photopheresis (ECP) is a type of PDT in which a machine may be used to collect the patient's blood cells. The patient's blood cells may be treated outside the body with a photosensitizing agent, exposed to light, and then returned to the patient. ECP may be used to help lessen the severity of skin symptoms of cutaneous T-cell lymphoma that has not responded to other therapies. ECP may be used to treat other blood cancers, and may also help reduce rejection after transplants.

Additionally, photosensitizing agent, such as porfimer sodium or Photofrin®, may be used in PDT to treat or relieve the symptoms of esophageal cancer and non-small cell lung cancer. Porfimer sodium may relieve symptoms of esophageal cancer when the cancer obstructs the esophagus or when the cancer cannot be satisfactorily treated with laser therapy alone. Porfimer sodium may be used to treat non-small cell lung cancer in patients for whom the usual treatments are not appropriate, and to relieve symptoms in patients with non-small cell lung cancer that obstructs the airways. Porfimer sodium may also be used for the treatment of precancerous lesions in patients with Barrett esophagus, a condition that can lead to esophageal cancer.

Laser therapy may use high-intensity light to treat cancer and other illnesses. Lasers can be used to shrink or destroy tumors or precancerous growths. Lasers are most commonly used to treat superficial cancers (cancers on the surface of the body or the lining of internal organs) such as basal cell skin cancer and the very early stages of some cancers, such as cervical, penile, vaginal, vulvar, and non-small cell lung cancer.

Lasers may also be used to relieve certain symptoms of cancer, such as bleeding or obstruction. For example, lasers can be used to shrink or destroy a tumor that is blocking a patient's trachea (windpipe) or esophagus. Lasers also can be used to remove colon polyps or tumors that are blocking the colon or stomach.

Laser therapy is often given through a flexible endoscope (a thin, lighted tube used to look at tissues inside the body). The endoscope is fitted with optical fibers (thin fibers that transmit light). It is inserted through an opening in the body, such as the mouth, nose, anus, or vagina. Laser light is then precisely aimed to cut or destroy a tumor.

Laser-induced interstitial thermotherapy (LITT), or interstitial laser photocoagulation, also uses lasers to treat some cancers. LITT is similar to a cancer treatment called hyperthermia, which uses heat to shrink tumors by damaging or killing cancer cells. During LITT, an optical fiber is inserted into a tumor. Laser light at the tip of the fiber raises the temperature of the tumor cells and damages or destroys them. LITT is sometimes used to shrink tumors in the liver.

Laser therapy can be used alone, but most often it is combined with other treatments, such as surgery, chemotherapy, or radiation therapy. In addition, lasers can seal nerve endings to reduce pain after surgery and seal lymph vessels to reduce swelling and limit the spread of tumor cells.

Lasers used to treat cancer may include carbon dioxide ($CO_2$) lasers, argon lasers, and neodymium:yttrium-aluminum-garnet (Nd:YAG) lasers. Each of these can shrink or destroy tumors and can be used with endoscopes. $CO_2$ and argon lasers can cut the skin's surface without going into deeper layers. Thus, they can be used to remove superficial cancers, such as skin cancer. In contrast, the Nd:YAG laser is more commonly applied through an endoscope to treat internal organs, such as the uterus, esophagus, and colon. Nd:YAG laser light can also travel through optical fibers into specific areas of the body during LITT. Argon lasers are often used to activate the drugs used in PDT.

Immunotherapy (sometimes called, biological therapy, biotherapy, biologic therapy, or biological response modifier (BRM) therapy) uses the body's immune system, either directly or indirectly, to fight cancer or to lessen the side effects that may be caused by some cancer treatments. Immunotherapies include interferons, interleukins, colony-stimulating factors, monoclonal antibodies, vaccines, immune cell-based therapy, gene therapy, and nonspecific immunomodulating agents.

Interferons (IFNs) are types of cytokines that occur naturally in the body. Interferon alpha, interferon beta, and interferon gamma are examples of interferons that may be used in cancer treatment.

Like interferons, interleukins (ILs) are cytokines that occur naturally in the body and can be made in the laboratory. Many interleukins have been identified for the treatment of cancer. For example, interleukin-2 (IL-2 or aldesleukin), interleukin 7, and interleukin 12 have may be used as an anti-cancer treatment. IL-2 may stimulate the growth and activity of many immune cells, such as lymphocytes, that can destroy cancer cells.

Colony-stimulating factors (CSFs) (sometimes called hematopoietic growth factors) may also be used for the treatment of cancer. Some examples of CSFs include, but are not limited to, G-CSF (filgrastim) and GM-CSF (sargramostim). CSFs may promote the division of bone marrow stem cells and their development into white blood cells, platelets, and red blood cells. Bone marrow is critical to the body's immune system because it is the source of all blood cells. Because anticancer drugs can damage the body's ability to make white blood cells, red blood cells, and platelets, stimulation of the immune system by CSFs may benefit patients undergoing other anti-cancer treatment, thus CSFs may be combined with other anti-cancer therapies, such as chemotherapy.

Another type of immunotherapy includes monoclonal antibodies (MOABs or MoABs). These antibodies may be produced by a single type of cell and may be specific for a particular antigen. To create MOABs, a human cancer cells may be injected into mice. In response, the mouse immune system can make antibodies against these cancer cells. The mouse plasma cells that produce antibodies may be isolated and fused with laboratory-grown cells to create "hybrid" cells called hybridomas. Hybridomas can indefinitely produce large quantities of these pure antibodies, or MOABs. MOABs may be used in cancer treatment in a number of ways. For instance, MOABs that react with specific types of cancer may enhance a patient's immune response to the cancer. MOABs can be programmed to act against cell growth factors, thus interfering with the growth of cancer cells.

MOABs may be linked to other anti-cancer therapies such as chemotherapeutics, radioisotopes (radioactive substances), other biological therapies, or other toxins. When the antibodies latch onto cancer cells, they deliver these anti-cancer therapies directly to the tumor, helping to destroy it. MOABs carrying radioisotopes may also prove useful in diagnosing cancer.

Cancer vaccines are another form of immunotherapy. Cancer vaccines may be designed to encourage the patient's immune system to recognize cancer cells. Cancer vaccines may be designed to treat existing cancers (therapeutic vaccines) or to prevent the development of cancer (prophylactic vaccines). Therapeutic vaccines may be injected in a person after cancer is diagnosed. These vaccines may stop the growth of existing tumors, prevent cancer from recurring, or eliminate cancer cells not killed by prior treatments. Cancer vaccines given when the tumor is small may be able to eradicate the cancer. On the other hand, prophylactic vaccines are given to healthy individuals before cancer develops. These vaccines are designed to stimulate the immune system to attack viruses that can cause cancer. By targeting these cancer-causing viruses, development of certain cancers may be prevented. For example, cervarix and gardasil are vaccines to treat human papilloma virus and may prevent cervical cancer. Therapeutic vaccines may be used to treat bladder cancer. Cancer vaccines can be used in combination with other anti-cancer therapies.

Immune cell-based therapy is also another form of immunotherapy. Adoptive cell transfer may include the transfer of immune cells such as dendritic cells, T cells (e.g., cytotoxic T cells), or natural killer (NK) cells to activate a cytotoxic response or attack cancer cells in a patient. Autologous immune cell-based therapy involves the transfer of a patient's own immune cells after expansion in vitro.

Gene therapy is another example of a biological therapy. Gene therapy may involve introducing genetic material into a person's cells to fight disease. Gene therapy methods may improve a patient's immune response to cancer. For example, a gene may be inserted into an immune cell to enhance its ability to recognize and attack cancer cells. In another approach, cancer cells may be injected with genes that cause the cancer cells to produce cytokines and stimulate the immune system.

In some instances, biological therapy includes nonspecific immunomodulating agents. Nonspecific immunomodulating agents are substances that stimulate or indirectly augment the immune system. Often, these agents target key immune system cells and may cause secondary responses such as increased production of cytokines and immunoglobulins. Two nonspecific immunomodulating agents used in cancer treatment are bacillus Calmette-Guerin (BCG) and levamisole. BCG may be used in the treatment of superficial bladder cancer following surgery. BCG may work by stimulating an inflammatory, and possibly an immune, response. A solution of BCG may be instilled in the bladder. Levamisole is sometimes used along with fluorouracil (5-FU) chemotherapy in the treatment of stage III (Dukes' C) colon cancer following surgery. Levamisole may act to restore depressed immune function.

Target sequences can be grouped so that information obtained about the set of target sequences in the group can be used to make or assist in making a clinically relevant judgment such as a diagnosis, prognosis, or treatment choice.

A patient report is also provided comprising a representation of measured expression levels of a plurality of target sequences in a biological sample from the patient, wherein the representation comprises expression levels of target sequences corresponding to any one, two, three, four, five, six, eight, ten, twenty, thirty or more of the target sequences corresponding to a target selected from Table 3, Table 5, Table 13 or SEQ ID Nos: 1-4050, the subsets described herein, or a combination thereof. In some embodiments, the representation of the measured expression level(s) may take the form of a linear or nonlinear combination of expression levels of the target sequences of interest. The patient report may be provided in a machine (e.g., a computer) readable format and/or in a hard (paper) copy. The report can also include standard measurements of expression levels of said plurality of target sequences from one or more sets of patients with known disease status and/or outcome. The report can be used to inform the patient and/or treating physician of the expression levels of the expressed target sequences, the likely medical diagnosis and/or implications, and optionally may recommend a treatment modality for the patient.

Also provided are representations of the gene expression profiles useful for treating, diagnosing, prognosticating, and otherwise assessing disease. In some embodiments, these profile representations are reduced to a medium that can be automatically read by a machine such as computer readable media (magnetic, optical, and the like). The articles can also include instructions for assessing the gene expression profiles in such media. For example, the articles may comprise a readable storage form having computer instructions for comparing gene expression profiles of the portfolios of genes described above. The articles may also have gene expression profiles digitally recorded therein so that they may be compared with gene expression data from patient samples. Alternatively, the profiles can be recorded in different representational format. A graphical recordation is one such format. Clustering algorithms can assist in the visualization of such data.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLES

Example 1

Validation Study of Molecular Subtypes in Muscle-Invasive Bladder Cancer on Predicting Response and Survival Outcome to Neoadjuvant Chemotherapy Approximately 40% of patients with muscle-invasive bladder cancer respond to neoadjuvant cisplatin-based chemotherapy (NAC), an integral component of multimodal treatment for this highly lethal disease. Only these responders appear to gain a survival advantage from NAC, while the remaining 60% face the risk for adverse effects and a delay in definitive surgery without clinical benefit. Identification of likely responders is essential to achieve a more precise delivery of care.

The significance of four subtyping methods in muscle-invasive bladder cancer in the context of neoadjuvant cisplatin-based chemotherapy (NAC) was examined as follows. The outcome of NAC treated patients was compared to patients in TCGA who did not receive NAC. Patients with basal tumors showed the most marked improvement in overall survival when treated with NAC. The prognosis of patients with other tumor subtypes did not change significantly without or with NAC. A single sample consensus genomic subtyping classifier was developed based on biological data and had potential clinical significance. This classifier included claudin-low, basal, luminal-infiltrated and luminal subtypes. Importantly, the classifier was able to generate subtype calls and the prognostic significance could be validated in independent retrospectively acquired non-NAC and NAC datasets.

Patient Populations

For the discovery NAC cohort, 223 patients from five institutions were selected. In all patients MIBC was diagnosed by TUR prior to receiving at least 3 cycles of NAC. Variant histology other than glandular or squamous differentiation was excluded. Most patients (67%) received gemcitabine/cisplatin (GC), 24% received methotrexate, vinblastine, adriamycin and cisplatin (MVAC) and 9% received gemcitabine/carboplatin (GCa).

For the validation NAC cohort, 82 patients from two institutions were selected whose characteristics were similar to those of the discovery set. GC was administered in 63% patients, MVAC in 13%, GCa in 6%, and other regimens in 12%. In total, 69 patients had received cisplatin-based NAC. All patients underwent radical cystectomy.

For outcome and survival analysis in both cohorts, only patients that received cisplatin-based NAC were used. In patients with clinical suspicion of diseased lymph nodes chemotherapy might have been administered rather in an inductive than a neoadjuvant manner. We use the term neoadjuvant chemotherapy for all patients with chemotherapy in a curative intent and that underwent cystectomy thereafter. Importantly, also only those patients were used for outcome and survival analysis in both cohorts (discovery: n=200, validation: n=69).

All cystectomy and lymphadenectomy specimens were staged according to the seventh International Union Against Cancer classification of 2009 at each study site (Sobin L H W C. TNM Atlas: 7th ed. New York: Wiley-Lyss Inc. TNM Atlas; 2009). At cystectomy, major response to NAC was defined as absence of muscle-invasive disease and lymph node metastases (<pT2 and pN0) Follow up of all patients was performed according to routine practices at each study site. In general, follow-up with cross sectional imaging was conducted at 3 and 6 months postoperatively, then at 6-month intervals until 5 years and yearly thereafter.

Tissue Sampling and Gene Expression Profiling

After pathologic review, tissue was harvested from formalin-fixed, paraffin-embedded tumor blocks by 1 mm punch under RNAse-free conditions. Total RNA was extracted and purified using RNeasy FFPE kit (Qiagen, Valencia, Calif.). RNA was amplified and labeled using the Ovation WTA FFPE system (NuGen, San Carlos, Calif.) and hybridized to GeneChip Human Exon 1.0 ST oligonucleotide microarrays (Affymetrix, Santa Clara, Calif.) according to the manufacturer's recommendations. Human Exon arrays use over 1.4 million probe selection regions (PSRs) to interrogate exons throughout the genome. In total 223/250 (89%) and 82/93 (88%) of the discovery and validation NAC cohorts, respectively, passed QC. Microarray data was normalized and gene summarized using Single-Channel Array Normalization (SCAN, Piccolo et al. (2012) *Genomics* 100(6): 337-344).

Three datasets from the public domain were used for additional clinical validation. For investigation of the prognostic impact, the 397 patients without chemotherapy prior to sample collection were used. Because an unknown proportion may have subsequently received NAC, validation of the discovered single sample classifier was only performed in those 179 without chemotherapy prior to sample collection and without adjuvant chemotherapy. In addition, for the validation of the newly discovered classifier in non-NAC patients, the datasets from MD Anderson Cancer Center and Lund University were downloaded from Gene Expression Omnibus database. These two datasets contained 107 and 190 patients, respectively with invasive bladder cancer who did not receive NAC.

Assignment to Subtypes

In the NAC dataset, ComBat (Johnson et al. (2007) *Biostatistics* 8(1): 118-127) was used to reduce the batch effect from the array data in the discovery and the validation datasets. Median centered expression data on gene level was used to generate the calls for each subtype.

The group from Lund (G.S.) provided the centroid values for each subtype of their original model (Sjodahl et al. (2012) *Clin. Cancer Res.* 18(12):3377-3386). Of the original model, 902/1038 genes are annotated in the Affymetrix HuEx array. As previously described, highest pearson correlation to the centroids of this model was used to assign the tumors to SCC-like, urobasal B (Uro B), infiltrated, urobasal A (Uro A) and genomically unstable (GU) respectively.

A classification to nearest centroids (ClaNC) model was used to assign the tumors to the TCGA clusters (Cancer Genome Atlas Research Network *Nature* 2014; 507(7492): 315-d22). Of the original model only 702/720 genes are annotated in the Affymetrix HuEx array data. Therefore, a reduced model (ClaNC702) was trained in the original TCGA data provided by K.A.H. to generate the assignment to the TCGA clusters.

The group from UNC (W. K. and J. K.) provided the classifiers to assign UNC subtypes (Damrauer et al. (2014) *Proc. Natl. Acad. Sci. USA* 111(8):3110-3115). Pearson correlation to each of the BASE47 cluster centroids was used to generate distances for class calls to accommodate for differences in platforms (Illumina versus Affymetrix HuEx Arrays). The claudin-low classifier assigned the basal tumors to claudin-low versus others (Kardos et al., supra).

The MDA subtypes were generated using the one nearest neighbor (oneNN) prediction model provided by the developer (D. M. and W. C). Of the original model 1990/2249 genes are annotated in the Affymetrix HuEx array. As previously described by Choi et al. (Cancer Cell (2014) 25(2):152-165), the tumors were assigned to basal, p53-like and luminal.

Gene Signature Expression Analysis (GSEA)

GSEA software was used to generate enrichment plots and calculate significance of gene signatures (broad.mit.edu/gsea/, Subramanian et al. (2005) Proc. Natl. Acad. Sci. USA 102(43):15545-15550). Genes were ranked with Signal2Noise and a weighted enrichment statistic was used to calculate Normalized Enrichment Scores, p-values and false detection rate.

Discovery and Validation of the Single Sample Classifier

A single sample model was trained to predict subtypes (Genomic Subtyping Classifier, GSC) using all pre-NAC TUR samples that passed QC, irrespective of chemotherapy regimen (n=223). The model was trained to predict four classes (claudin-low, basal, luminal-infiltrated and luminal). The labels in the training set were determined as follows: tumors were first classified as basal or luminal according to the UNC classifier. Claudin-low tumors were labeled within the UNC basal tumors. UNC luminal tumors that were not TCGA cluster II were labeled luminal and those that were TCGA cluster II were labeled luminal-infiltrated.

To make the model applicable to several platforms, only genes on both Illumina HumanHT-12 V3.0 and Affymetrix Human Exon array 1.0 ST were selected as the initial gene list (17,007 genes). Using this initial gene set, the model development framework consisted of: 1) Feature selection, by which genes with low variance (variance <0.2) were removed, and significant genes were selected (p<0.001) using Kruskal-Wallis rank sum test; 2) Model training with a generalized linear model with elastic net regularization (GLMNET) using the significant genes. These two steps were assessed using 10-fold cross-validation. Using the full training set, the feature selection step resulted in 287 genes, which were used to train the GSC. GLMNET finally selected 149 genes to produce four scores. These scores, each ranging from 0 to 1, indicate the likelihood of the sample belonging to each of the four subtypes. The GSC was independently validated in our 82 patient NAC validation dataset as well as in the three non-NAC cohorts from the public domain (see above).

Statistical Analyses

Statistical analyses were conducted using R Software Package, version 3.2.1. All tests were two-sided with type I error probability of 5%. Discrimination abilities of classifiers were compared using area under the curve (AUC) on the receiver-operating characteristic (ROC) curves. For analysis of pathological response and overall survival after NAC, only patients receiving cisplatin-based NAC (i.e. GC or MVAC) and subsequently undergoing cystectomy were evaluated (n=269). Univariable (UVA) and multivariable analysis (MVA) adjusting for clinical tumor stage, age, gender and institution were performed using logistic regression when studying pathological response to NAC. Kaplan-Meier plots were used to estimate overall survival (OS) from the date of surgery and comparisons were made using the log-rank test. Patients who were lost to follow-up were censored at the date of last contact. Cox proportional hazards regression models were used to estimate the effect of GSC on survival in a multivariable setting. In non-NAC set, the MVA adjusted for age and gender, while in NAC set, clinical tumor stage, age, gender and institution were adjusted for. Bladder cancer specific mortality data were only available from five cohorts and therefore not evaluated in this analysis.

Results

Clinicopathological details of the discovery and validation NAC meta-datasets are provided below in Table 1 and Table 2.

TABLE 1

| Patient Characteristics table of the cisplatin-based NAC set (n = 269) | | | | | | | | | | |
|---|---|---|---|---|---|---|---|---|---|---|
| Variable | | Bern | NKI | UHS | UW | VGH | UCD* | EMC* | Total | p-value |
| n | | 40 | 49 | 22 | 41 | 48 | 26 | 43 | 269 | |
| Overall Survival Time (Censored Patients) | Median (IQR) | 48 (26-73) | 46 (31-87) | 49 (40-59) | 48 (26-61) | 31 (13-41) | 9 (4-23) | 24 (13-36) | 27 (11-49) | — |
| Age | (mean (sd)) | 64 (10) | 57 (11) | 67 (12) | 62 (11) | 61 (9) | 65 (8) | 59 (13) | 61 (11) | — |
| Gender (%) | Female | 12 (30.0) | 17 (34.7) | 7 (31.8) | 10 (24.4) | 14 (29.2) | 8 (30.8) | 12 (27.9) | 80 (29.7) | 0.97 |
| | Male | 28 (70.0) | 32 (65.3) | 15 (68.2) | 31 (75.6) | 34 (70.8) | 18 (69.2) | 31 (72.1) | 189 (70.3) | |
| Clinical tumor stage (%) | T1 | 1 (2.5) | 0 (0.0) | 0 (0.0) | 0 (0.0) | 0 (0.0) | 0 (0.0) | 0 (0.0) | 1 (0.4) | <0.001 |
| | T2 | 4 (10.0) | 10 (20.4) | 18 (81.8) | 20 (48.8) | 26 (54.2) | 25 (96.2) | 17 (39.5) | 120 (44.6) | |
| | T3 | 21 (52.5) | 26 (53.1) | 4 (18.2) | 13 (31.7) | 19 (39.6) | 1 (3.8) | 18 (41.9) | 102 (37.9) | |
| | T4 | 14 (35.0) | 13 (26.5) | 0 (0.0) | 8 (19.5) | 3 (6.2) | 0 (0.0) | 4 (9.3) | 42 (15.6) | |
| | NA | 0 (0.0) | 0 (0.0) | 0 (0.0) | 0 (0.0) | 0 (0.0) | 0 (0.0) | 4 (9.3) | 4 (1.5) | |

TABLE 1-continued

Patient Characteristics table of the cisplatin-based NAC set (n = 269)

| Variable | | Bern | NKI | UHS | UW | VGH | UCD* | EMC* | Total | p-value |
|---|---|---|---|---|---|---|---|---|---|---|
| Clinical lymph node stage (%) | N0 | 14 (35.0) | 21 (42.9) | 20 (90.9) | 33 (80.5) | 38 (79.2) | 0 (0.0) | 32 (74.4) | 158 (58.7) | — |
| | N1-3 | 26 (65.0) | 28 (57.1) | 2 (9.1) | 8 (19.5) | 10 (20.8) | 0 (0.0) | 7 (16.3) | 81 (30.1) | |
| | NA | 0 (0.0) | 0 (0.0) | 0 (0.0) | 0 (0.0) | 0 (0.0) | 26 (100.0) | 4 (9.3) | 30 (11.2) | |
| Pathologic tumor stage (%) | pT0/is/a | 13 (32.5) | 24 (49.0) | 9 (40.9) | 18 (43.9) | 19 (39.6) | 9 (34.6) | 13 (30.2) | 105 (39.0) | 0.618 |
| | pT1 | 3 (7.5) | 2 (4.1) | 0 (0.0) | 5 (12.2) | 2 (4.2) | 2 (7.7) | 6 (14.0) | 20 (7.4) | |
| | pT2 | 8 (20.0) | 7 (14.3) | 5 (22.7) | 6 (14.6) | 13 (27.1) | 3 (11.5) | 5 (11.6) | 47 (17.5) | |
| | PT3/4 | 16 (40.0) | 15 (30.6) | 8 (36.4) | 12 (29.3) | 14 (29.2) | 11 (42.3) | 18 (41.9) | 94 (34.9) | |
| | NA | 0 (0.0) | 1 (2.0) | 0 (0.0) | 0 (0.0) | 0 (0.0) | 1 (3.8) | 1 (2.3) | 3 (1.1) | |
| Pathologic lymph node stage (%) | pN0 | 24 (60.0) | 28 (57.1) | 18 (81.8) | 33 (80.5) | 41 (85.4) | 16 (61.5) | 35 (81.4) | 195 (72.5) | 0.04 |
| | pN1-3 | 16 (40.0) | 12 (24.5) | 4 (18.2) | 8 (19.5) | 6 (12.5) | 8 (30.8) | 7 (16.3) | 61 (22.7) | |
| | NA | 0 (0.0) | 9 (18.4) | 0 (0.0) | 0 (0.0) | 1 (2.1) | 2 (7.7) | 1 (2.3) | 13 (4.8) | |
| NAC Type (%) | GemCis | 40 (100.0) | 16 (32.7) | 22 (100.0) | 22 (53.7) | 48 (100.0) | 19 (73.1) | 33 (76.7) | 200 (74.3) | <0.001 |
| | MVAC | 0 (0.0) | 33 (67.3) | 0 (0.0) | 19 (46.3) | 0 (0.0) | 6 (23.1) | 5 (11.6) | 63 (23.4) | |
| | Other | 0 (0.0) | 0 (0.0) | 0 (0.0) | 0 (0.0) | 0 (0.0) | 1 (3.8) | 5 (11.6) | 6 (2.2) | |

TABLE 2

Comparison of patient characteristics from NAC discovery and validation sets

| Variable | | Discovery 223 | Validation 82 | p-value Fisher's Test |
|---|---|---|---|---|
| Overall Survival Time (Censored Patients) | Median (IQR) | 41 (24-64) | 18 (7-35) | — |
| Age | (mean (sd)) | 62 (11) | 62 (11) | — |
| Gender (%) | Female | 69 (30.9) | 21 (25.6) | 0.445 |
| | Male | 154 (69.1) | 61 (74.4) | |
| Clinical Stage (%) | T1 | 1 (0.4) | 0 (0.0) | <0.001 |
| | T2 | 89 (39.9) | 53 (64.6) | |
| | T3 | 90 (40.4) | 19 (23.2) | |
| | T4 | 43 (19.3) | 6 (7.3) | |
| | NA | 0 (0.0) | 4 (4.9) | |
| Clinical node (%) | 0 | 140 (62.8) | 33 (40.2) | — |
| | 1 | 83 (37.2) | 8 (9.8) | |
| | NA | 0 (0.0) | 41 (50.0) | |
| Pathologic Stage (%) | pT0/is/a | 90 (40.4) | 25 (30.5) | 0.274 |
| | pT1 | 13 (5.8) | 8 (9.8) | |
| | pT2 | 42 (18.8) | 12 (14.6) | |
| | pT3/4 | 74 (33.2) | 35 (42.7) | |
| | NA | 4 (1.8) | 2 (2.4) | |
| Lymph Node Involvement (%) | Negative | 157 (70.4) | 61 (74.4) | 0.631 |
| | Positive | 52 (23.3) | 18 (22.0) | |
| | NA | 14 (6.3) | 3 (3.7) | |
| NAC Type (%) | GemCis | 149 (66.8) | 52 (63.4) | <0.001 |
| | MVAC | 54 (24.2) | 11 (13.4) | |
| | GemCarbo | 20 (9.0) | 5 (6.1) | |
| | Other | 0 (0.0) | 9 (11.0) | |
| | NA | 0 (0.0) | 5 (6.1) | |
| GSC (%) | Luminal | 90 (40.4) | 37 (45.1) | 0.123 |
| | Inf-Luminal | 33 (14.8) | 6 (7.3) | |
| | Basal | 53 (23.8) | 25 (30.5) | |
| | Claudin-Low | 47 (21.1) | 14 (17.1) | |

Subtyping Calls of the Models in the Discovery NAC Dataset

Figure 1B:
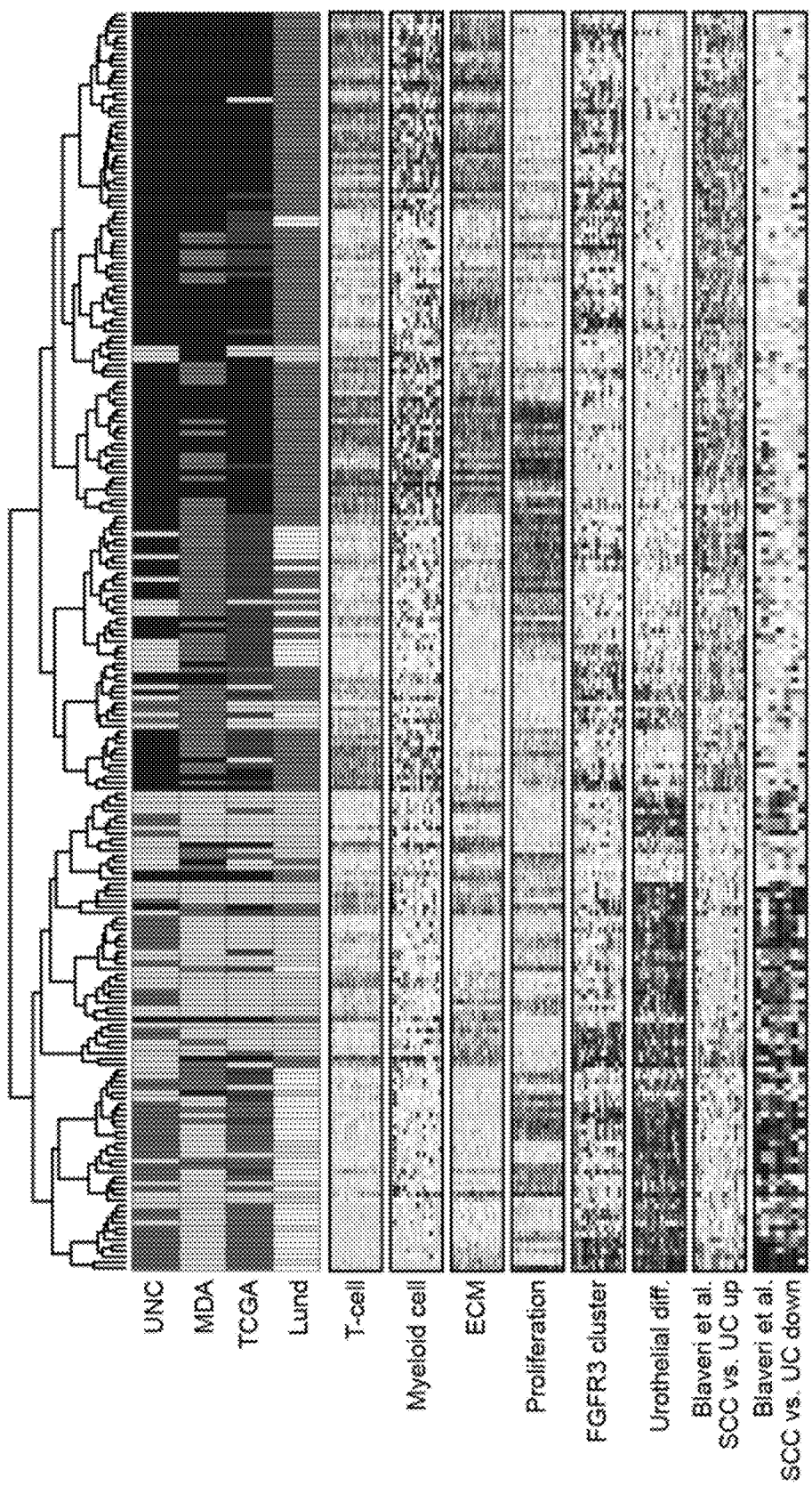
Figure 1C:
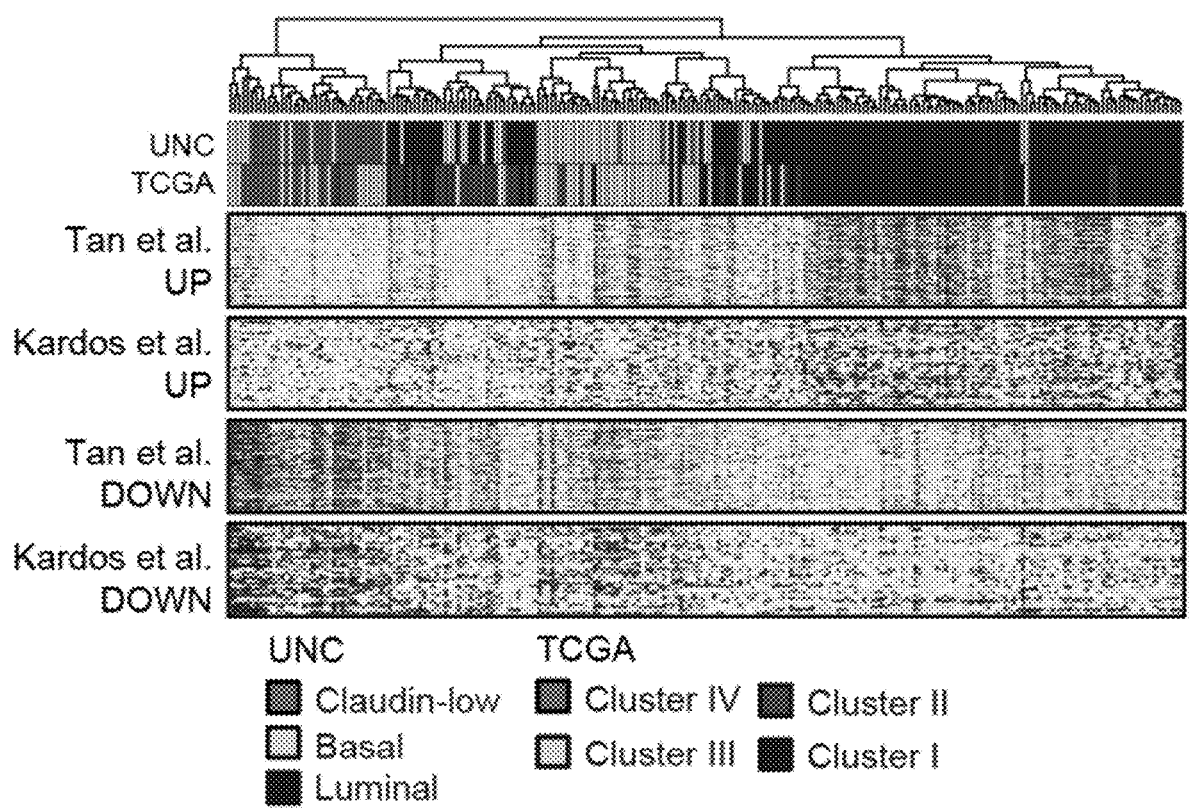
Figure 1D:
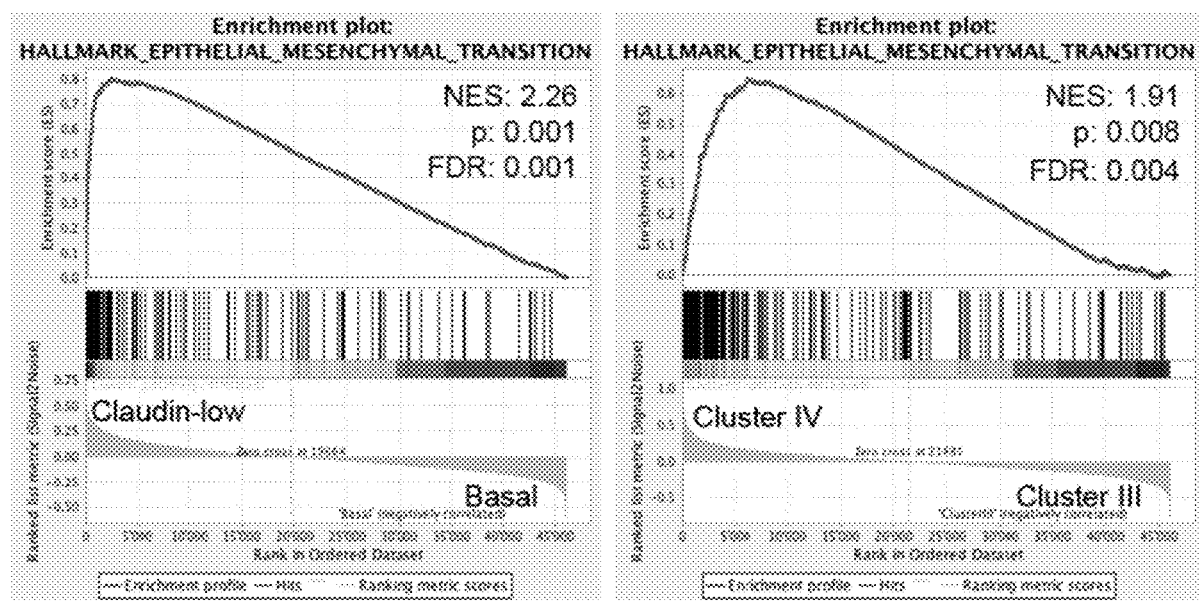
Figure 1E:
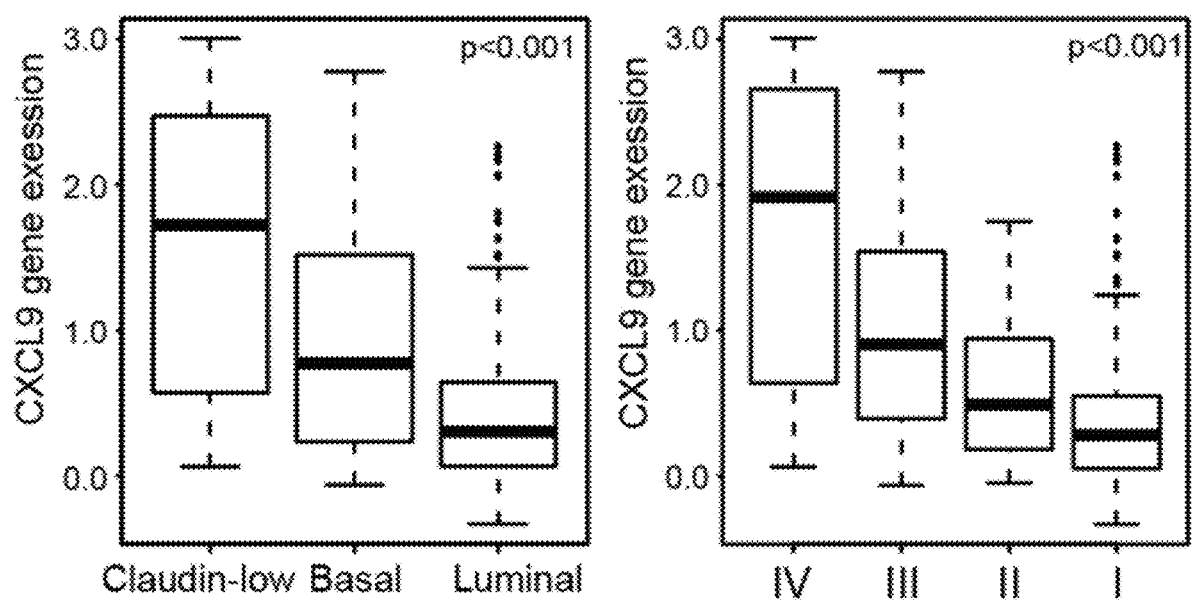
Figure 5:
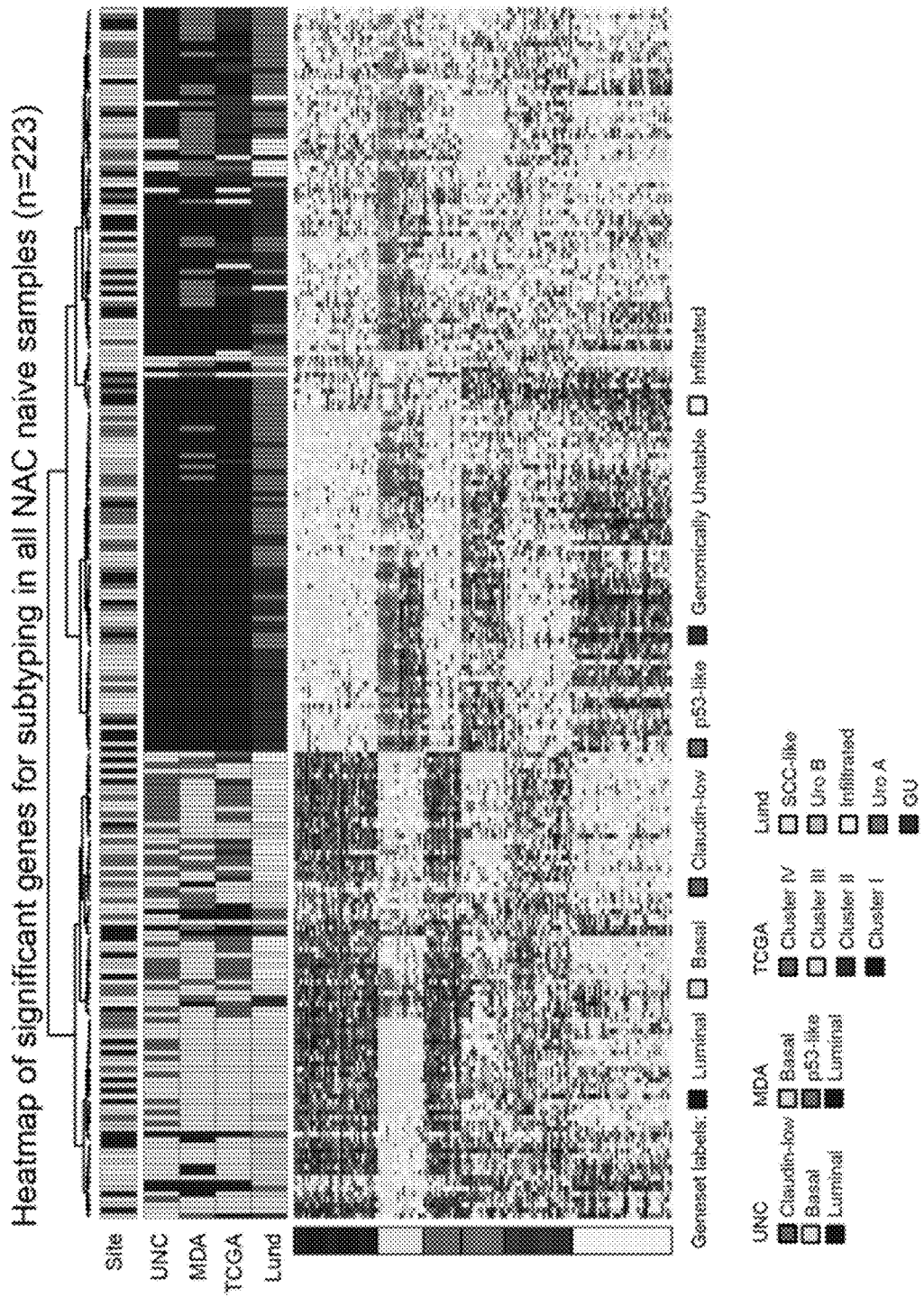
FIG. 5 shows a heatmap of gene signatures important for subtype calls.
Figure 6A:
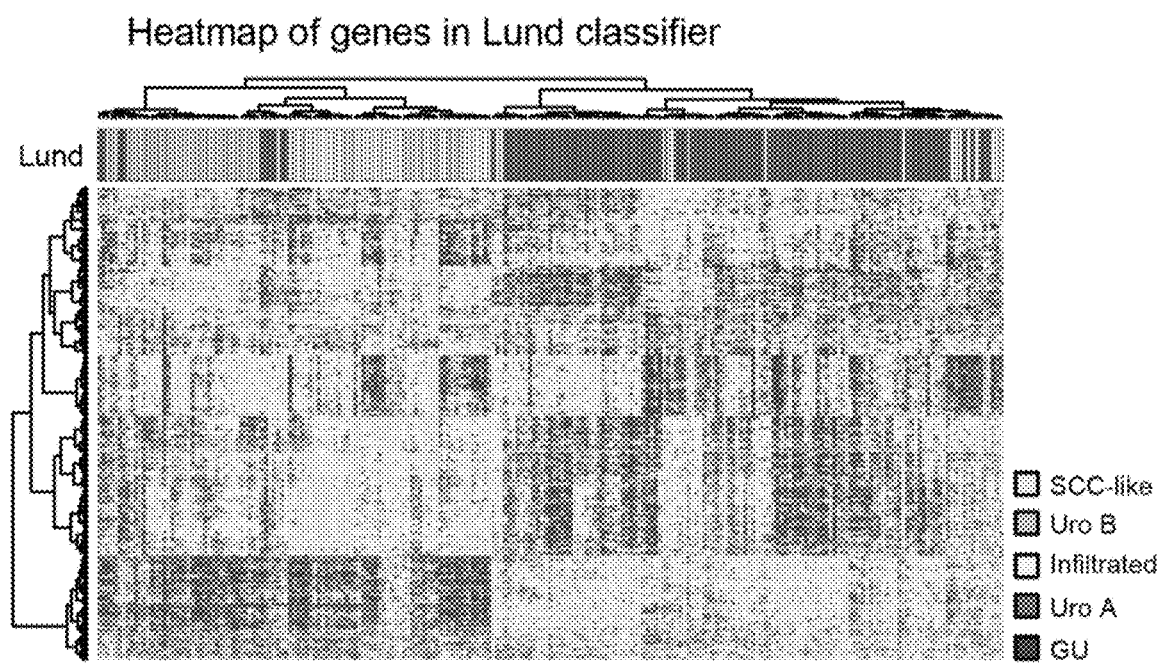
FIGS. 6A-6D show an analysis of the Lund and TCGA classifiers.
Figure 6B:
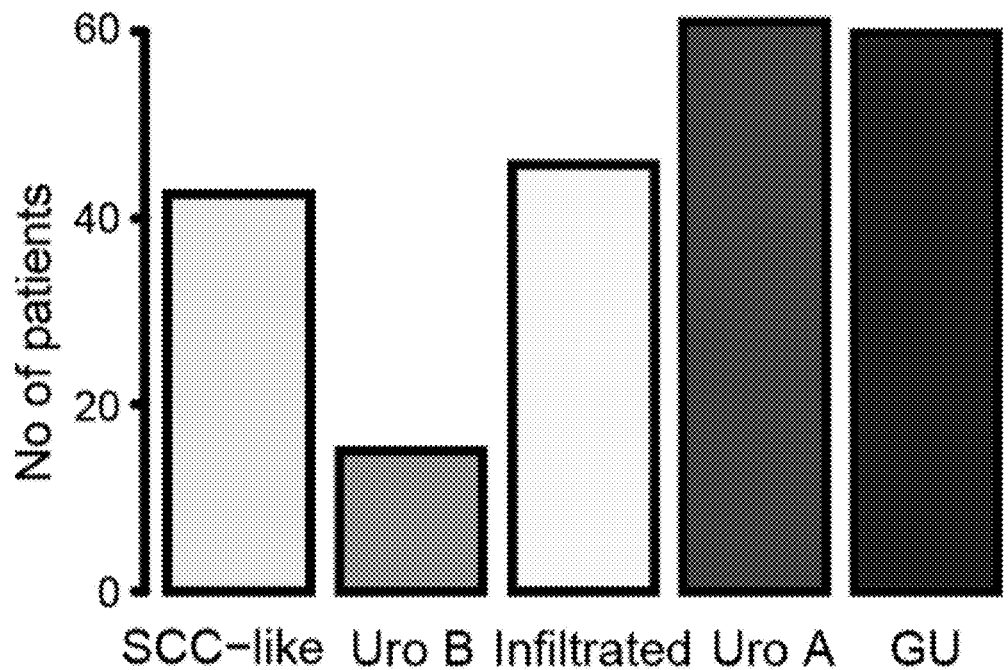
Figure 6C:
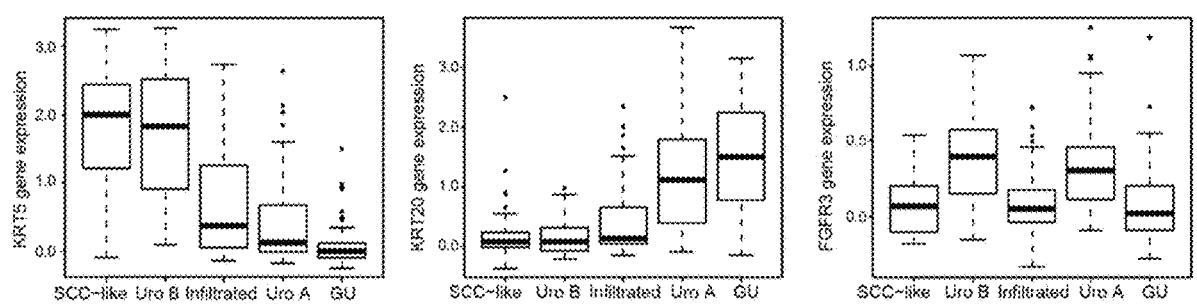
Figure 6D:
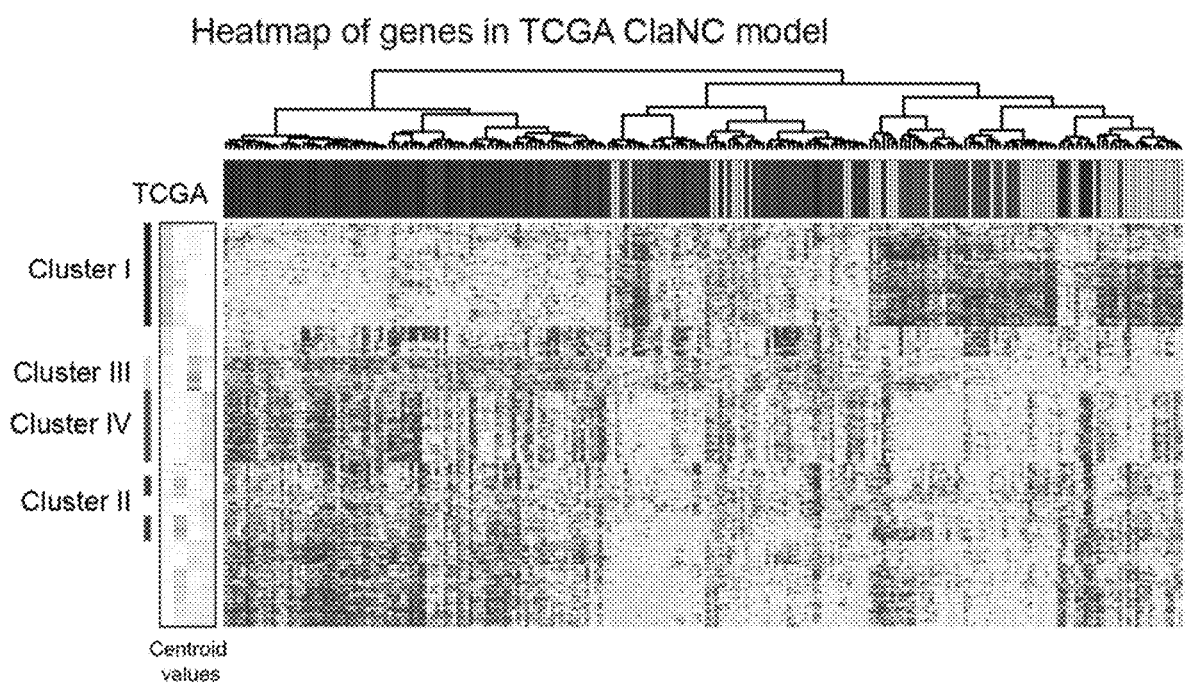
Figure 7A:
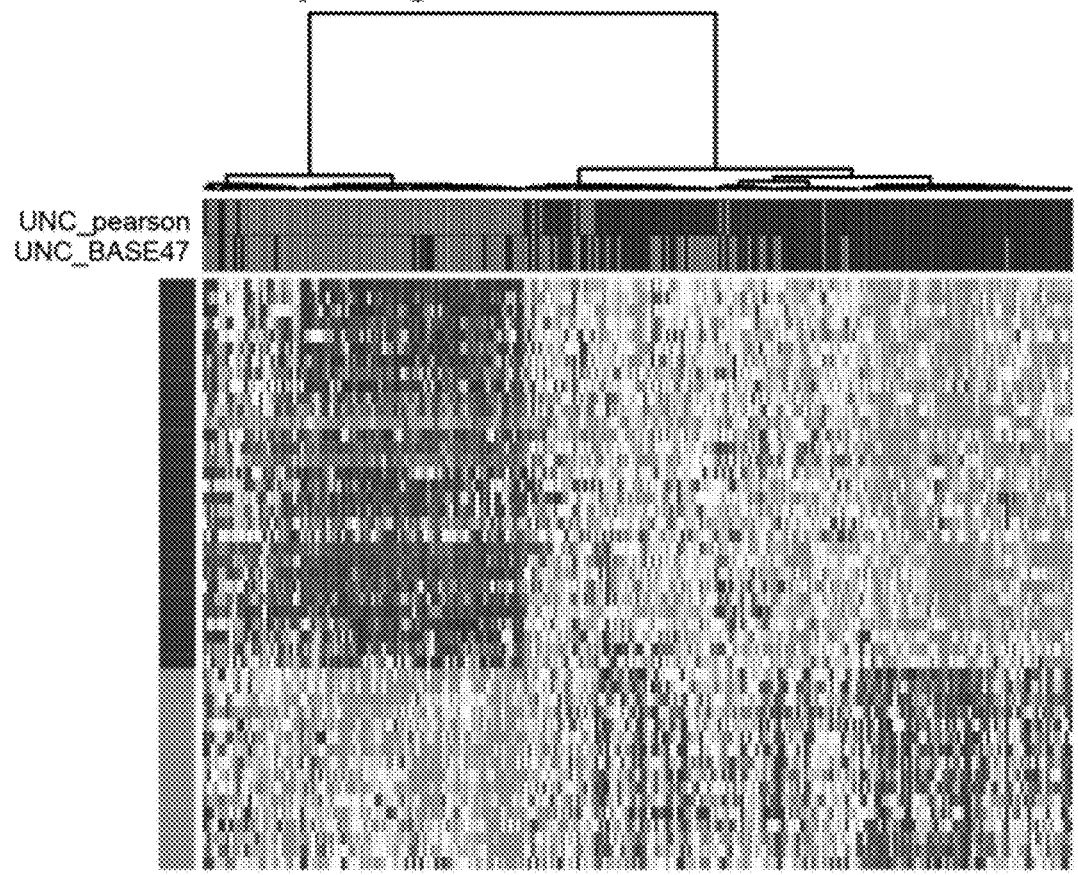
FIGS. 7A-7F show an analysis of the UNC and MDA classifiers.
Figure 7B:
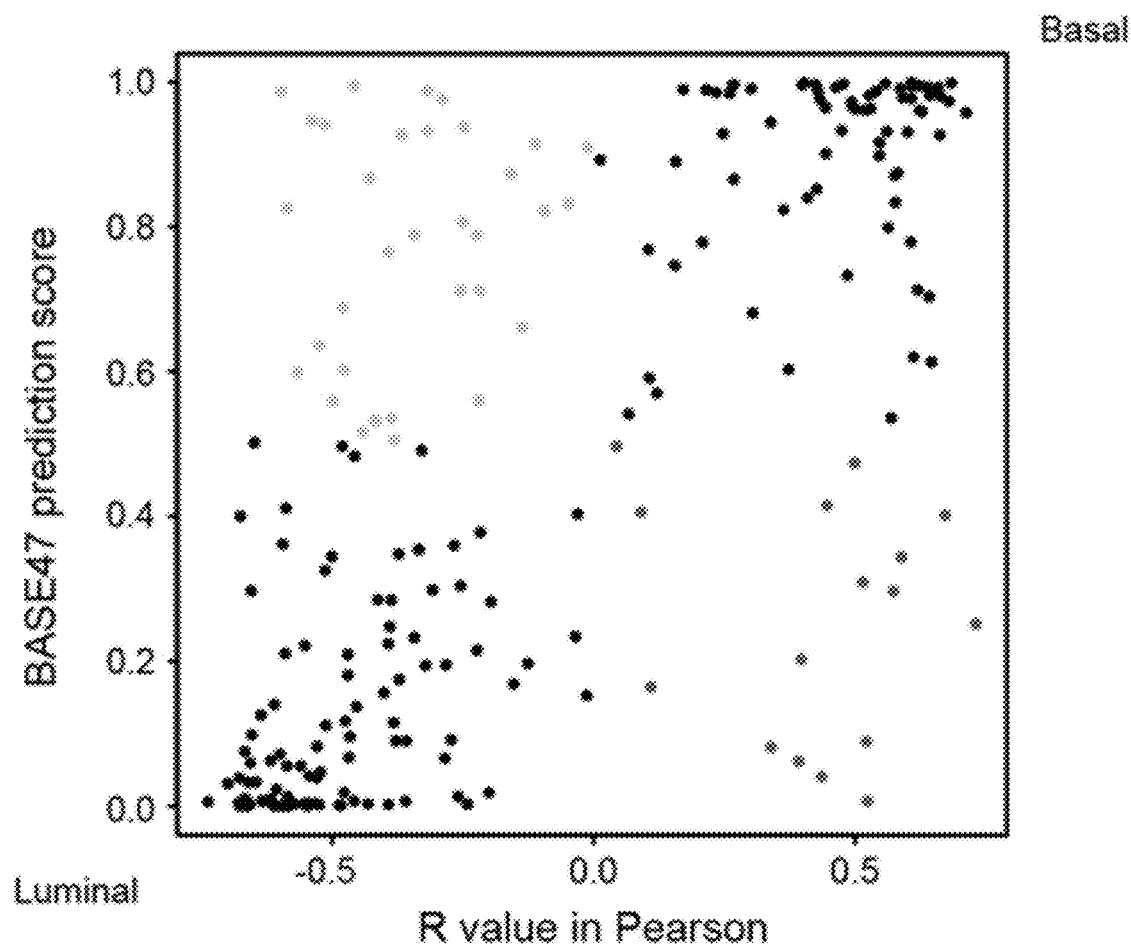
Figure 7C:
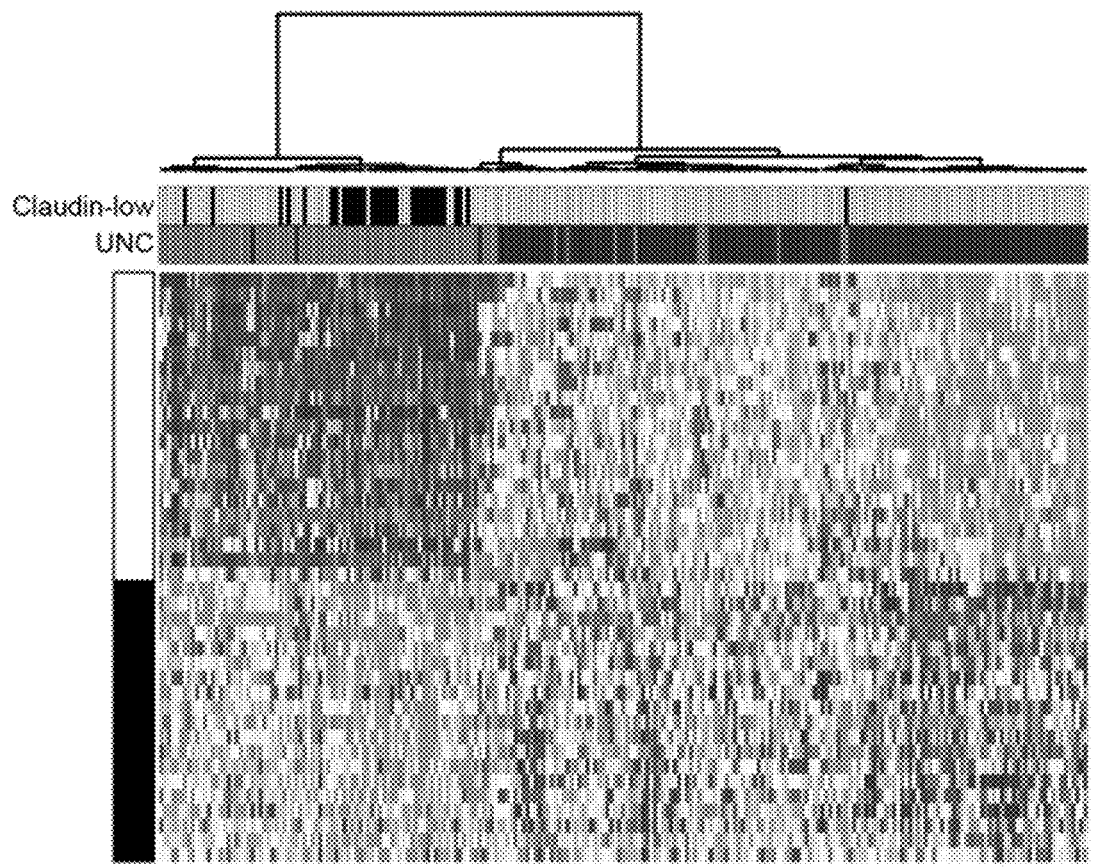
Figure 7D:
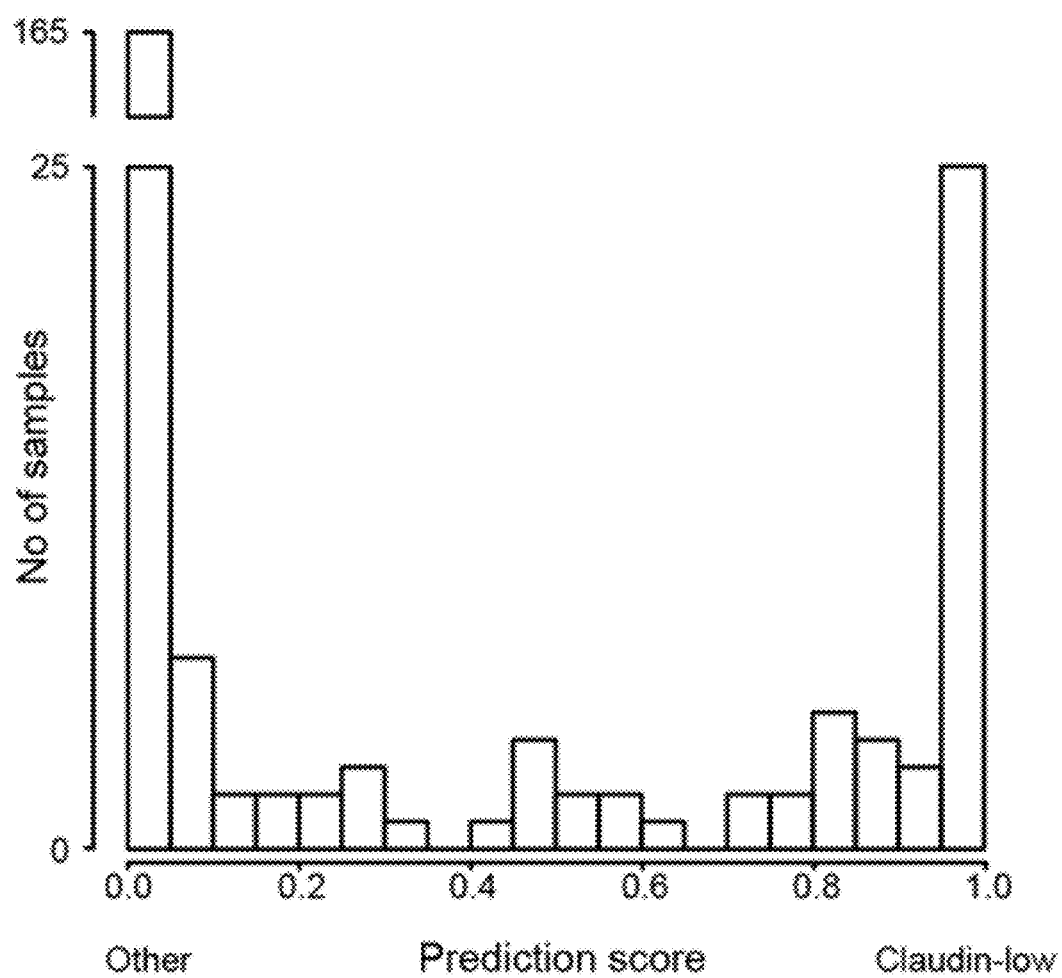
Figure 7E:
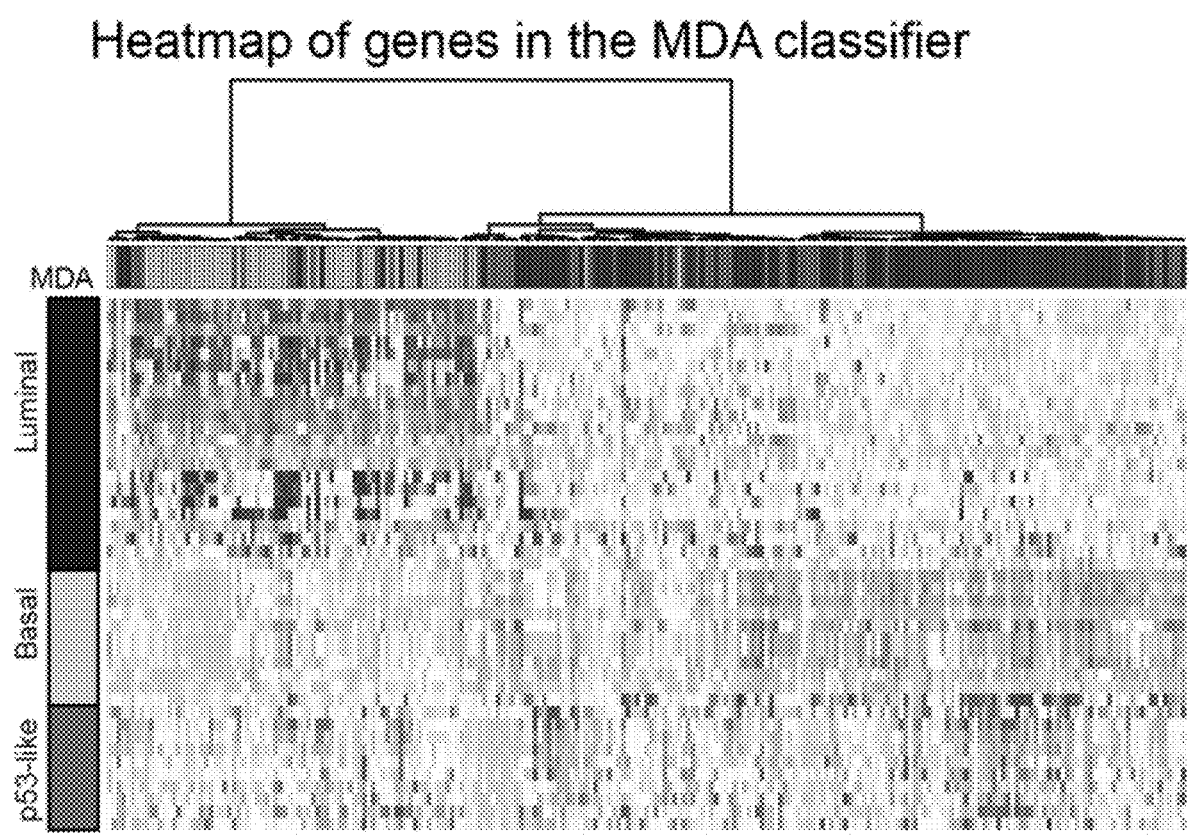
Figure 7F:
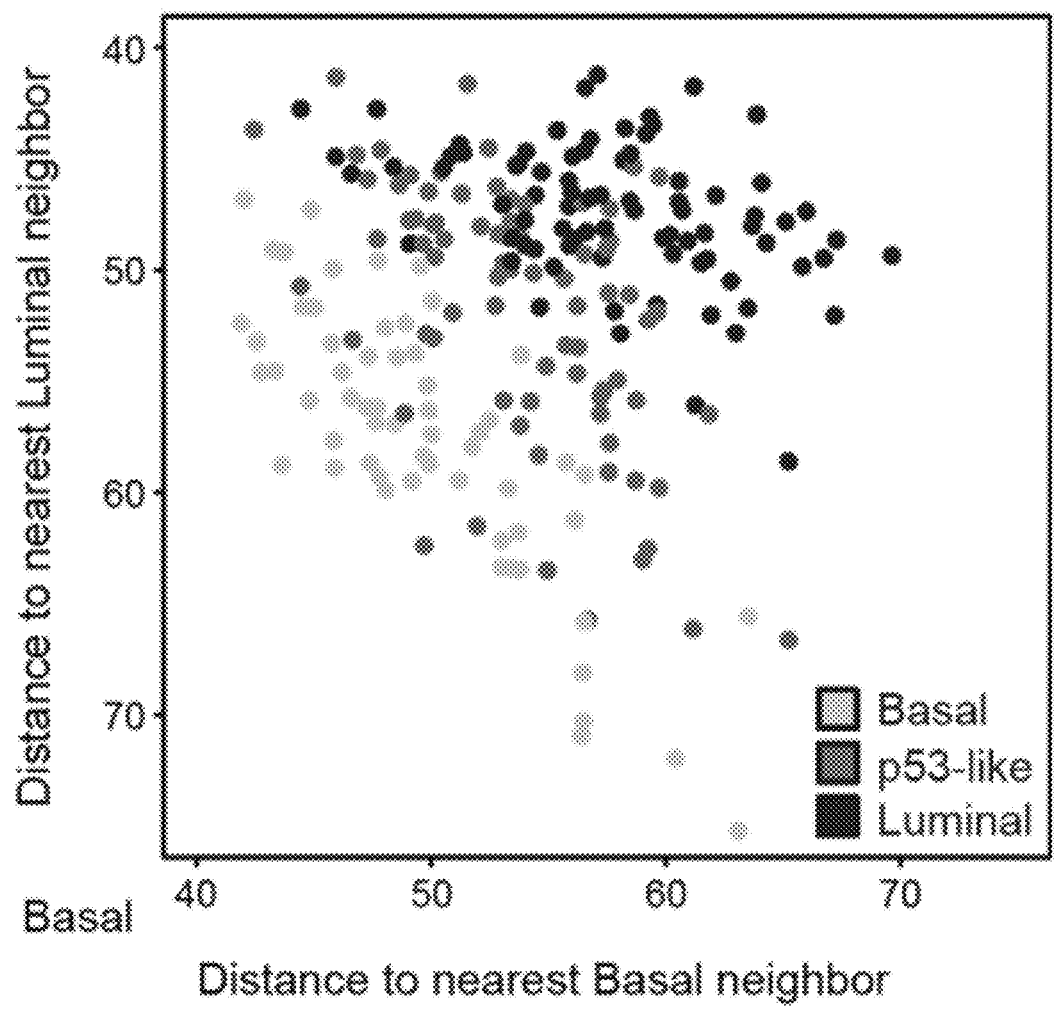

The frequency of each subtype in all pre-NAC samples (n=223) was in expected ratios (FIG. 1A). Gene expression of given biological functions confirmed the concordance between the different subtyping methods (FIG. 1B, FIG. 5 and Table 3). For example, all luminal subtypes showed a higher expression of genes for urothelial differentiation (FIGS. 1B, 7, and 10) compared to all basal subtypes. T- and myeloid cell signatures were highest in the expected subtypes (claudin-low (UNC) and cluster IV (TCGA)). Genes from the extracellular matrix (ECM) were highly expressed in p53-like (MDA, FIG. 7E) and infiltrated subtypes (Lund) (FIG. 1B).

TABLE 3

Highly Expressed Genes in Different Subtype Classes

| Gene Name | Subtype Class |
|---|---|
| UPK2 | Luminal |
| SCNN1B | Luminal |
| PPARG | Luminal |
| TOX3 | Luminal |
| GATA3 | Luminal |
| HMGCS2 | Luminal |
| RAB15 | Luminal |
| ADIRF | Luminal |
| SEMA5A | Luminal |
| TRAK1 | Luminal |
| SCNN1G | Luminal |
| TMPRSS2 | Luminal |
| VGLL1 | Luminal |
| TBX2 | Luminal |
| UPK1A | Luminal |
| GAREM | Luminal |
| BHMT | Luminal |
| SPINK1 | Luminal |
| GPD1L | Luminal |
| RNF128 | Luminal |
| CYP2J2 | Luminal |
| GDPD3 | Luminal |
| FBP1 | Luminal |
| SLC27A2 | Luminal |
| TMEM97 | Luminal |
| PLEKHG6 | Luminal |
| CYP4B1 | Luminal |
| CAPN5 | Luminal |
| SLC9A2 | Luminal |
| PPFIBP2 | Luminal |
| FAM174B | Luminal |
| KRT14 | Basal |
| DSG3 | Basal |
| KRT6B | Basal |
| KRT5 | Basal |
| KRT6A | Basal |
| KRT6C | Basal |
| PI3 | Basal |
| S100A7 | Basal |
| CD44 | Basal |
| CDH3 | Basal |
| KRT16 | Basal |
| GPX2 | Claudin |
| CACNA1D | Claudin |
| KLHDC7A | Claudin |
| CCSER1 | Claudin |
| BMP3 | Claudin |
| BCAS1 | Claudin |
| SNX31 | Claudin |
| CYP4F12 | Claudin |
| FAM3B | Claudin |
| SLC14A1 | Claudin |
| ALDH1L1 | Claudin |
| GRHL3 | Claudin |
| VSIG2 | Claudin |
| DHRS2 | Claudin |
| ACTG2 | p53 |
| CNN1 | p53 |
| MYH11 | p53 |
| MFAP4 | p53 |
| PGM5 | p53 |
| FLNC | p53 |
| ACTC1 | p53 |
| DES | p53 |
| PCP4 | p53 |
| DNM1 | p53 |
| RARRES1 | GU |

TABLE 3-continued

Highly Expressed Genes in Different Subtype Classes

| Gene Name | Subtype Class |
|---|---|
| MESP1 | GU |
| SH3GL2 | GU |
| LEAP2 | GU |
| FMO9P | GU |
| RASL11B | GU |
| CYP4F8 | GU |
| PHGDH | GU |
| SLC30A2 | GU |
| KCNG1 | GU |
| CNGA1 | GU |
| CRAT | GU |
| CDKN2A | GU |
| FAM78B | GU |
| NFIB | GU |
| ATP6V0E2 | GU |
| CRABP2 | GU |
| RASSF2 | GU |
| MCM3 | GU |
| RALBP1 | GU |
| DDAH1 | GU |
| MCM2 | GU |
| TESK2 | GU |
| EMX2 | GU |
| CCNE2 | GU |
| PTGDS | Infiltrated |
| IGLL1 | Infiltrated |
| CTSK | Infiltrated |
| SPON1 | Infiltrated |
| LUM | Infiltrated |
| HLA-DQA1 | Infiltrated |
| AEBP1 | Infiltrated |
| COL6A3 | Infiltrated |
| DCN | Infiltrated |
| SERPINE2 | Infiltrated |
| TAGLN | Infiltrated |
| HLA-DPA1 | Infiltrated |
| CDH11 | Infiltrated |
| RARRES2 | Infiltrated |
| CD48 | Infiltrated |
| ITGB2 | Infiltrated |
| CCL2 | Infiltrated |
| SRGN | Infiltrated |
| IRF8 | Infiltrated |
| COL1A2 | Infiltrated |
| TMEM119 | Infiltrated |
| RGS1 | Infiltrated |
| TYROBP | Infiltrated |
| PLEK | Infiltrated |
| FCN1 | Infiltrated |
| PODN | Infiltrated |
| C1QB | Infiltrated |
| PDLIM3 | Infiltrated |
| COL3A1 | Infiltrated |
| WAS | Infiltrated |
| MS4A6A | Infiltrated |
| ALOX5AP | Infiltrated |
| CSF1R | Infiltrated |
| DOCK2 | Infiltrated |
| COL8A1 | Infiltrated |
| LY96 | Infiltrated |
| RGS2 | Infiltrated |
| HLA-DRA | Infiltrated |
| ACTA2 | Infiltrated |

Similarities between Subtypes across Different Methods

Figure 1F:
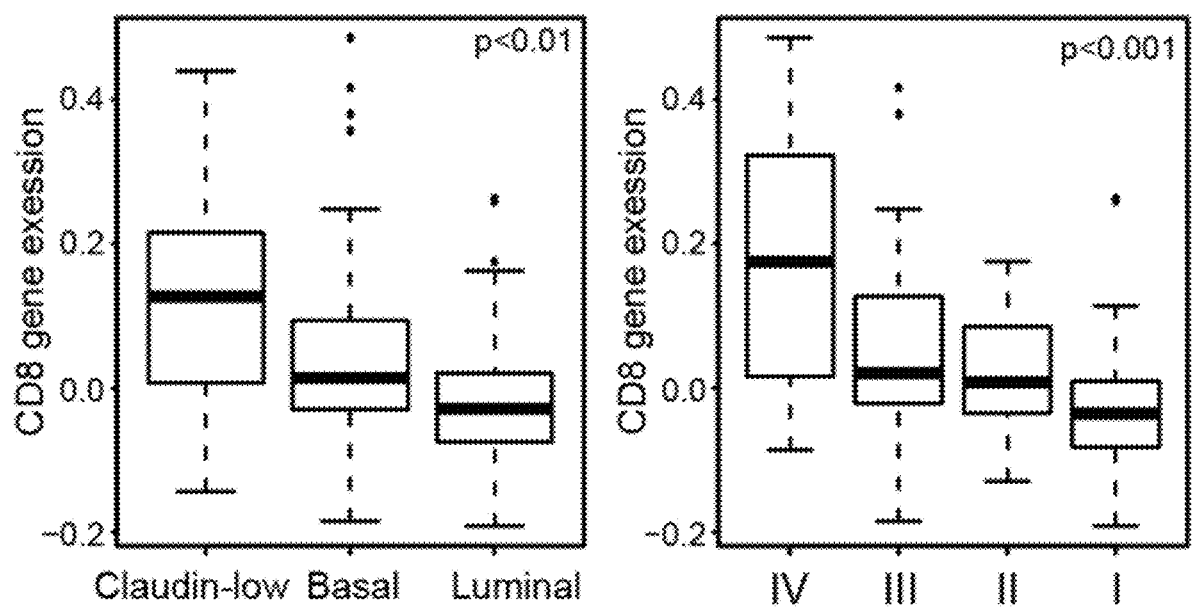
Figure 2A:
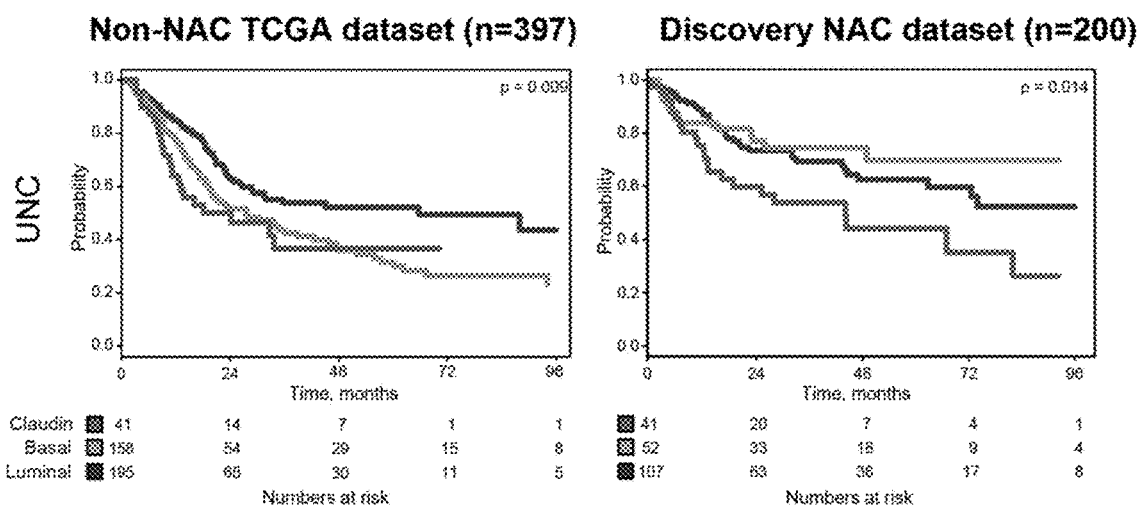
FIGS. 2A-2D show Kaplan Meier estimates of overall survival (OS) according to molecular subtype in the non-NAC (left) and NAC (right) discovery datasets.
Figure 2B:
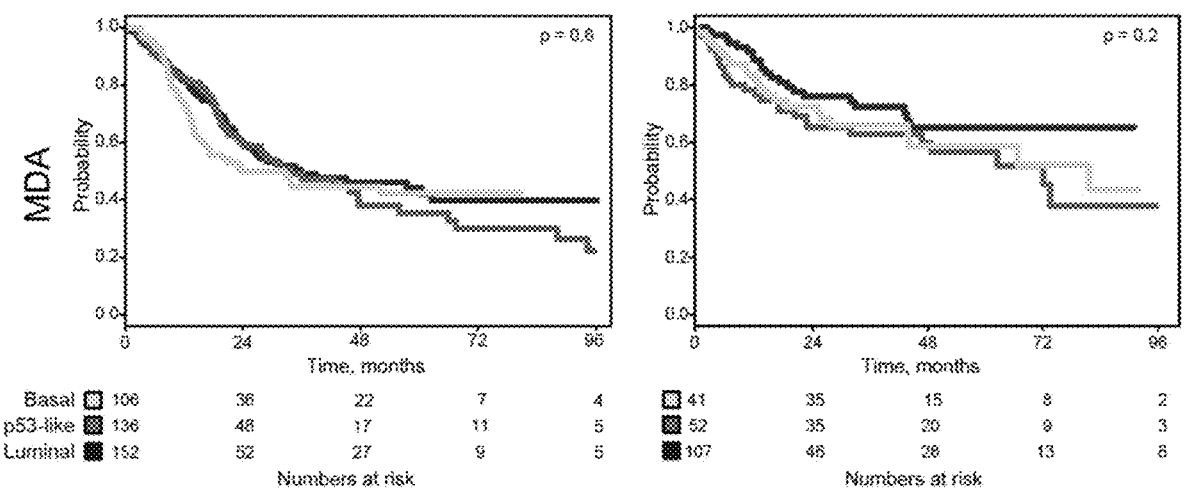
Figure 2C:
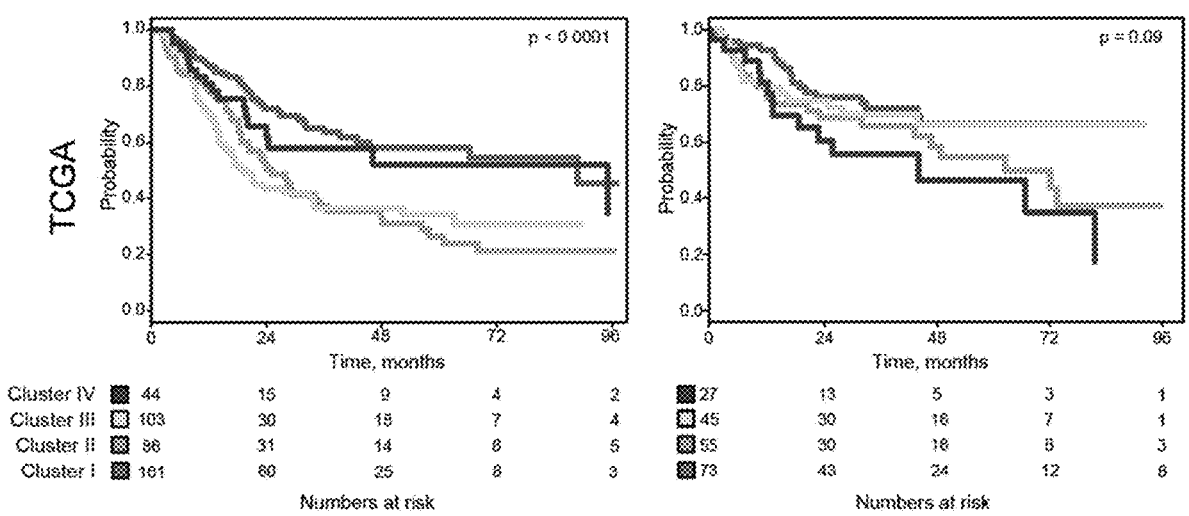
Figure 2D:
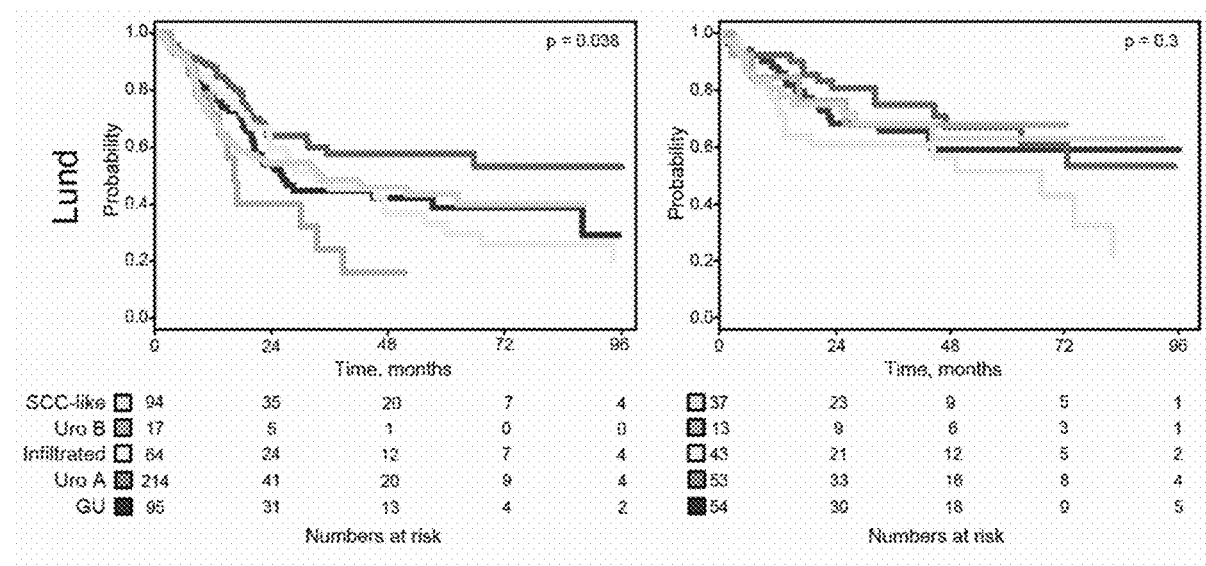
Figure 8A:
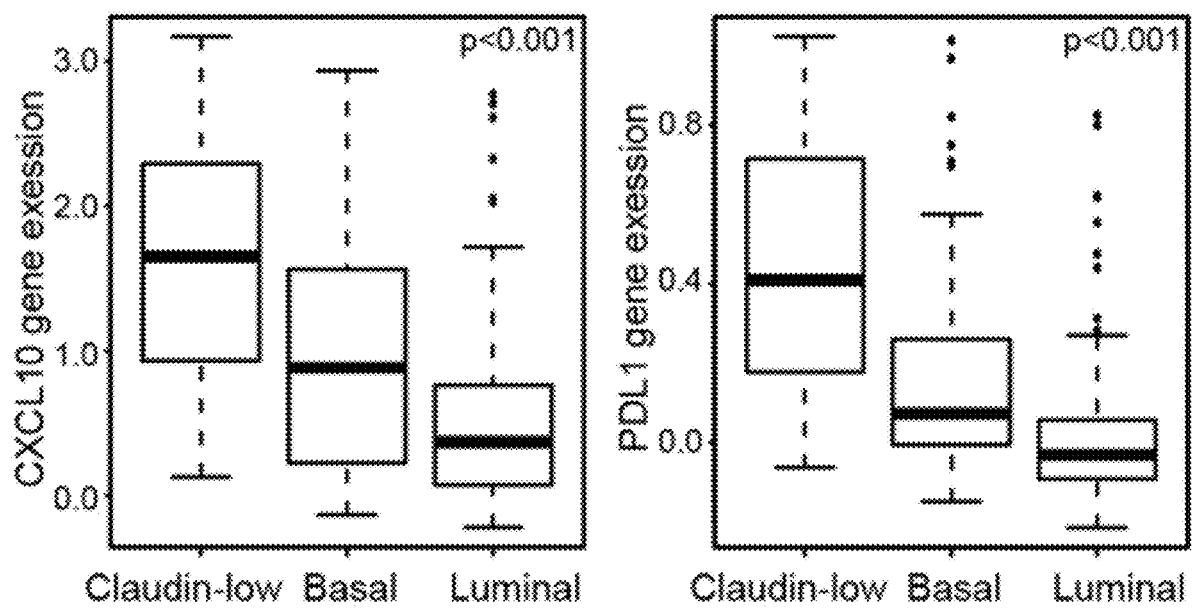
FIGS. 8A-8E show an analysis of immune infiltration and markers of epithelial-to-mesenchymal transition (EMT) in pre-NAC tumors classified according to the UNC and TCGA classifiers.
Figure 8B:
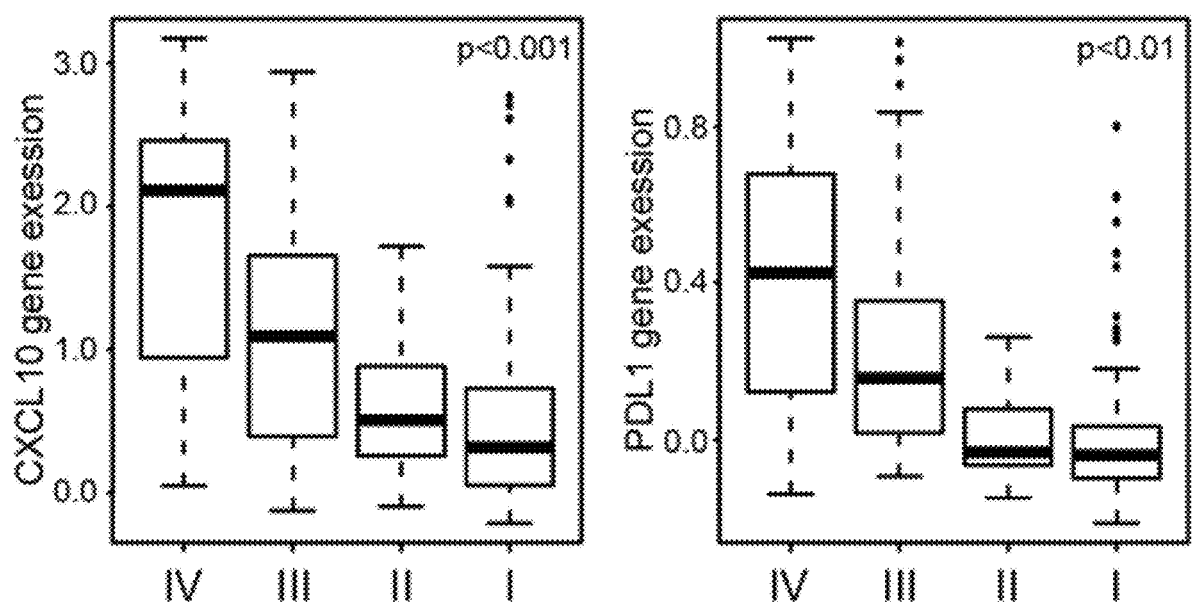
Figure 8C:
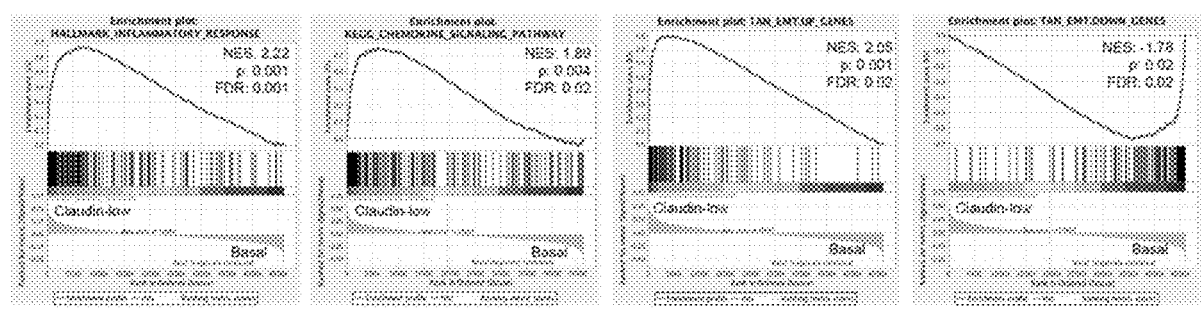
Figure 8D:
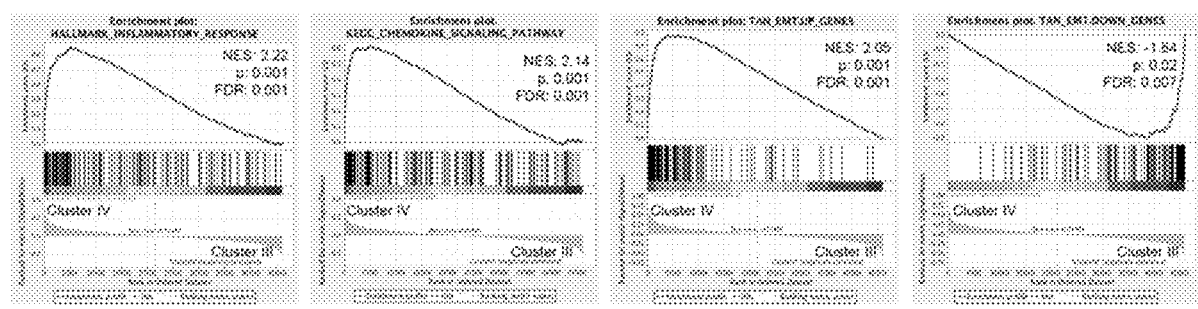
Figure 8E:
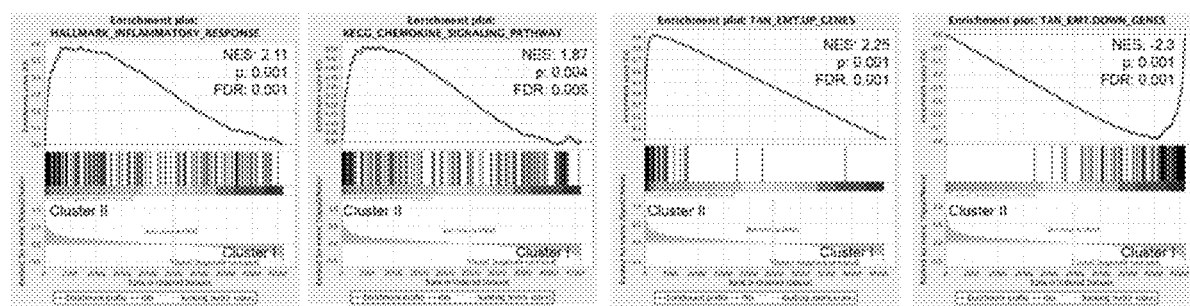
Figure 9A:
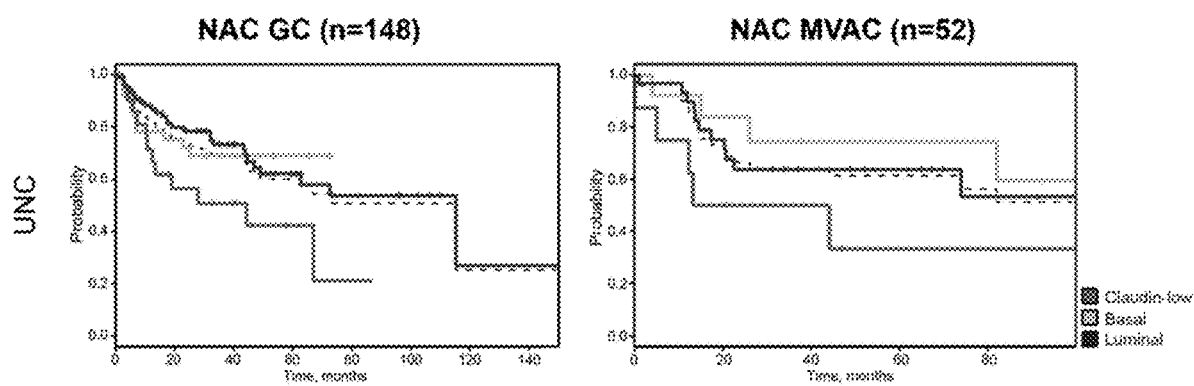
FIGS. 9A-9D show the overall survival (OS) analysis of the NAC cohort according to chemotherapy regimen stratified by subtype: gemcitabine/cisplatin (GC, left) and methotrexate, vinblastine, adriamycin and cisplatin (MVAC, right).
Figure 9B:
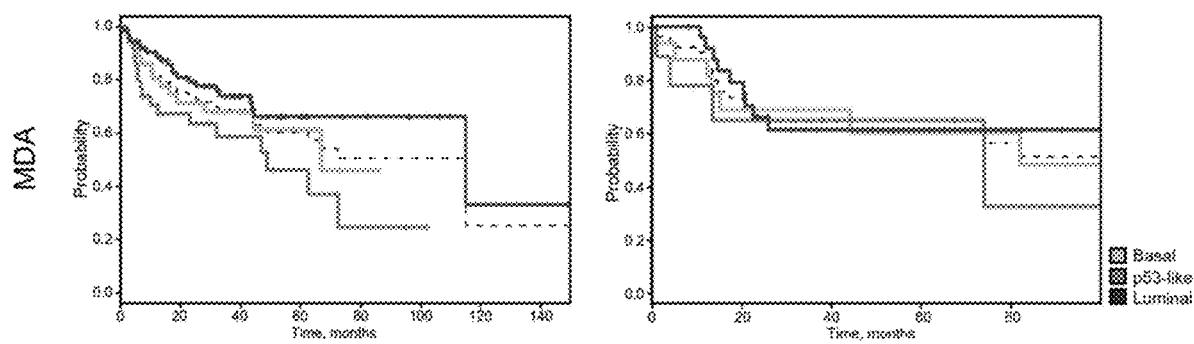
Figure 9C:
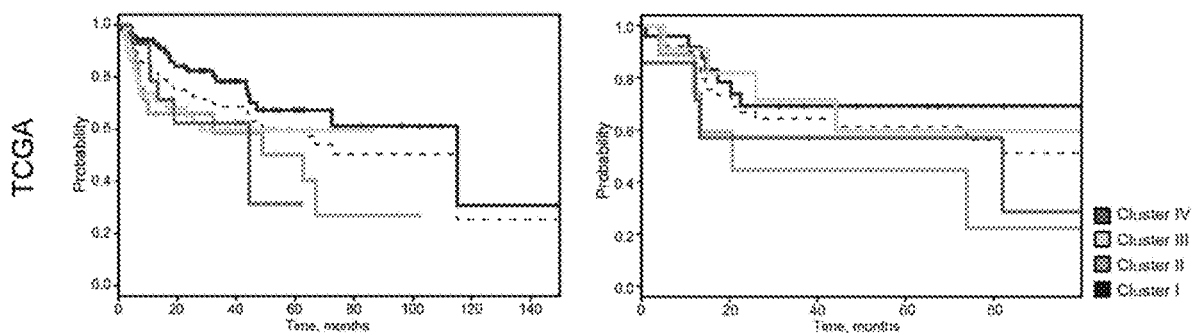
Figure 9D:
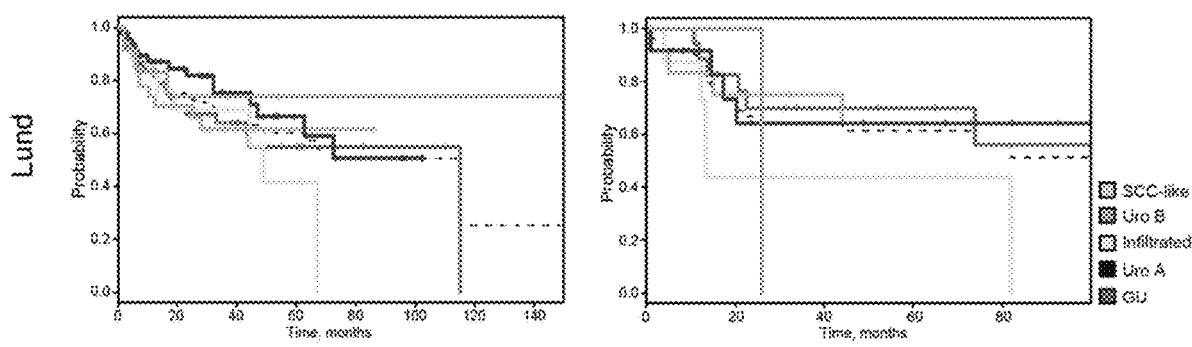

Claudin-low tumors have basal characteristics with high expression levels of genes indicative of epithelial-to-mesenchymal transition (EMT) and immune infiltration (FIGS. 1C-1E and FIGS. 8A and 8C). Tumors in TCGA cluster IV identify a similar subset of basal tumors: 21/28 cluster IV tumors were labeled claudin-low. Cluster IV showed enrichment for EMT, chemokine signaling and immune infiltration compared to cluster III tumors (FIGS. 1C, 1D, 1F, 8B, and 8D). Cluster II represents luminal tumors that are immune infiltrated. Compared to cluster I tumors, cluster II tumors were EMT-signature positive and enriched for inflammatory response and chemokine signaling (FIGS. 1F, 8B, and 8E).

Patient Benefit from NAC Differs between Subtypes

Extravesical extension of residual primary tumor (pT3/4) after NAC was observed more frequently in claudin-low (49%), p53-like (39%), and cluster II (40%) subtypes. None of the subtypes was associated with major response to NAC (ypT<2N0) on final pathology (Table 4).

TABLE 4

Subtypes, Pathological Tumor Stage, and Lymph Node Status

| Subtypes | Variables | Total n (%) | Pathologic Tumor Stage (n (%)) | | | | Lymph Node Status (n (%)) | | <pT2N0 (%) | |
|---|---|---|---|---|---|---|---|---|---|---|
| | | | pT0/is/a | pT1 | pT2 | pT3/4 | 0 | 1 | 0 | 1 |
| UNC (%) | Luminal | 197 (49.6) | 1 (0.6) | 2 (1.1) | 73 (41.0) | 102 (57.3) | 120 (60.9) | 77 (39.1) | 88 (97.8) | 2 (2.2) |
| | Basal | 159 (40.1) | 0 (0.0) | 1 (0.7) | 36 (24.5) | 110 (74.8) | 91 (57.2) | 68 (42.8) | 62 (100.0) | 0 (0.0) |
| | Claudin | 41 (10.3) | 0 (0.0) | 0 (0.0) | 7 (17.5) | 33 (82.5) | 27 (65.9) | 14 (34.1) | 16 (100.0) | 0 (0.0) |
| MDA (%) | Luminal | 153 (38.5) | 1 (0.7) | 1 (0.7) | 50 (37.3) | 82 (61.2) | 87 (56.9) | 66 (43.1) | 62 (98.4) | 1 (1.6) |
| | p53 | 137 (34.5) | 0 (0.0) | 1 (0.8) | 41 (31.5) | 88 (67.7) | 79 (57.7) | 58 (42.3) | 63 (98.4) | 1 (1.6) |
| | Basal | 107 (27.0) | 0 (0.0) | 1 (1.0) | 25 (24.8) | 75 (74.3) | 72 (67.3) | 35 (32.7) | 41 (100.0) | 0 (0.0) |
| TCGA (%) | Cluster I | 163 (41.1) | 1 (0.7) | 2 (1.4) | 72 (49.7) | 70 (48.3) | 114 (69.9) | 49 (30.1) | 76 (97.4) | 2 (2.6) |
| | Cluster II | 86 (21.7) | 0 (0.0) | 0 (0.0) | 12 (14.5) | 71 (85.5) | 29 (33.7) | 57 (66.3) | 34 (100.0) | 0 (0.0) |
| | Cluster III | 103 (25.9) | 0 (0.0) | 0 (0.0) | 22 (23.4) | 72 (76.6) | 66 (64.1) | 37 (35.9) | 34 (100.0) | 0 (0.0) |
| | Cluster IV | 45 (11.3) | 0 (0.0) | 1 (2.3) | 10 (23.3) | 32 (74.4) | 29 (64.4) | 16 (35.6) | 22 (100.0) | 0 (0.0) |
| Lund (%) | GU | 96 (24.2) | 1 (1.1) | 1 (1.1) | 27 (30.3) | 60 (67.4) | 46 (47.9) | 50 (52.1) | 41 (97.6) | 1 (2.4) |
| | Uro | 125 (31.5) | 0 (0.0) | 1 (0.9) | 49 (44.1) | 61 (55.0) | 84 (67.2) | 41 (32.8) | 54 (98.2) | 1 (1.8) |
| | Infiltrated | 65 (16.4) | 0 (0.0) | 0 (0.0) | 9 (14.3) | 54 (85.7) | 39 (60.0) | 26 (40.0) | 29 (100.0) | 0 (0.0) |
| | Uro B | 17 (4.3) | 0 (0.0) | 0 (0.0) | 3 (18.8) | 13 (81.2) | 10 (58.8) | 7 (41.2) | 5 (100.0) | 0 (0.0) |
| | SCC-like | 94 (23.7) | 0 (0.0) | 1 (1.2) | 28 (32.6) | 57 (66.3) | 59 (62.8) | 35 (37.2) | 37 (100.0) | 0 (0.0) |

NAC Cisplatin based (n = 200)

| Subtypes | Variables | Total n (%) | Pathologic Tumor Stage (n (%)) | | | | Lymph Node Status (n (%)) | | Major response (%) | |
|---|---|---|---|---|---|---|---|---|---|---|
| | | | pT0/is/a | pT1 | pT2 | pT3/4 | 0 | 1 | 0 | 1 |
| UNC (%) | Luminal | 107 (53.5) | 44 (41.5) | 8 (7.5) | 26 (24.5) | 28 (26.4) | 72 (72.7) | 27 (27.3) | 57 (57.6) | 42 (42.4) |
| | Basal | 52 (26.0) | 22 (42.3) | 3 (5.8) | 10 (19.2) | 17 (32.7) | 43 (84.3) | 8 (15.7) | 30 (58.8) | 21 (41.2) |
| | Claudin | 41 (20.5) | 17 (41.5) | 1 (2.4) | 3 (7.3) | 20 (48.8) | 29 (72.5) | 11 (27.5) | 23 (57.5) | 17 (42.5) |
| MDA (%) | Luminal | 78 (39.0) | 29 (37.7) | 5 (6.5) | 22 (28.6) | 21 (27.3) | 50 (69.4) | 22 (30.6) | 45 (62.5) | 27 (37.5) |
| | p53 | 66 (33.0) | 26 (39.4) | 4 (6.1) | 11 (16.7) | 25 (37.9) | 49 (77.8) | 14 (22.2) | 40 (63.5) | 23 (36.5) |
| | Basal | 56 (28.0) | 28 (50.0) | 3 (5.4) | 6 (10.7) | 19 (33.9) | 45 (81.8) | 10 (18.2) | 25 (45.5) | 30 (54.5) |
| TCGA (%) | Cluster I | 73 (36.5) | 30 (41.7) | 6 (8.3) | 21 (29.2) | 15 (20.8) | 50 (74.6) | 17 (25.4) | 38 (56.7) | 29 (43.3) |
| | Cluster II | 55 (27.5) | 22 (40.0) | 3 (5.5) | 8 (14.5) | 22 (40.0) | 36 (69.2) | 16 (30.8) | 34 (65.4) | 18 (34.6) |
| | Cluster III | 45 (22.5) | 19 (42.2) | 1 (2.2) | 8 (17.8) | 17 (37.8) | 38 (84.4) | 7 (15.6) | 26 (57.8) | 19 (42.2) |
| | Cluster IV | 27 (13.5) | 12 (44.4) | 2 (7.4) | 2 (7.4) | 11 (40.7) | 20 (76.9) | 6 (23.1) | 12 (46.2) | 14 (53.8) |

TABLE 4-continued

Subtypes, Pathological Tumor Stage, and Lymph Node Status

| | | | | | | | | | |
|---|---|---|---|---|---|---|---|---|---|
| Lund (%) | GU | 54 | 23 | 1 | 11 | 19 | 35 | 16 | 32 | 19 |
| | | (27.0) | (42.6) | (1.9) | (20.4) | (35.2) | (68.6) | (31.4) | (62.7) | (37.3) |
| | Uro | 53 | 22 | 5 | 14 | 11 | 39 | 10 | 27 | 22 |
| | | (26.5) | (42.3) | (9.6) | (26.9) | (21.2) | (79.6) | (20.4) | (55.1) | (44.9) |
| | Infiltrated | 43 | 18 | 4 | 4 | 17 | 29 | 11 | 21 | 19 |
| | | (21.5) | (41.9) | (9.3) | (9.3) | (39.5) | (72.5) | (27.5) | (52.5) | (47.5) |
| | Uro B | 13 | 4 | 2 | 3 | 4 | 11 | 2 | 8 | 5 |
| | | (6.5) | (30.8) | (15.4) | (23.1) | (30.8) | (84.6) | (15.4) | (61.5) | (38.5) |
| | SCC-like | 37 | 16 | 0 | 7 | 14 | 30 | 7 | 22 | 15 |
| | | (18.5) | (43.2) | (0.0) | (18.9) | (37.8) | (81.1) | (18.9) | (59.5) | (40.5) |

*Pathologic tumor stage and lymph node status are unavailable in the MDA and Lund sets Overall survival varied by molecular subtype and between non-NAC and NAC patients (FIG. 2). By all subtyping methods, non-NAC treated patients (TCGA cohort) with basal tumors had worse outcomes compared to luminal tumors (FIG. 2). Of both luminal TCGA clusters, patients with cluster II tumors experienced worse OS than those with cluster I tumors. Poor OS was also observed in patients with claudin-low tumors. The association between subtype and prognosis differed in our NAC cohort. The most pronounced difference was in patients with basal or equivalent subtypes (Cluster III, UroB, and SCC-like), who experienced an improvement in OS after NAC compared to the TCGA patients who received no NAC (FIG. 2). However, there was no such shift in survival in patients with claudin-low and cluster IV tumors, indicating that these patients fared poorly regardless of NAC even though they are subsets of the basal phenotype. Across the different subtyping methods, patients with luminal or equivalent tumors had the best OS with or without NAC, with the exception of cluster II patients, who fared poorly in both settings, as did patients with p53-like tumors. There was no noteworthy difference in these trends when the patients were analyzed according to NAC regimen (GC vs. MVAC; FIG. 9).

In summary, the differences in OS by subtype and the apparent impact of NAC suggest that a classification into four subtypes would have the greatest clinical relevance. Basal tumors warrant subclassification into tumors without and with EMT and immune infiltration (i.e., basal and claudin-low), since NAC has the greatest impact on the non-infiltrated basal tumors. Luminal tumors similarly warrant subclassification into tumors without and with EMT and immune infiltration (i.e., luminal and luminal-infiltrated), since OS differs between the two groups.

Single Sample Classifier to Predict Bladder Cancer Subtypes

Figure 3A:
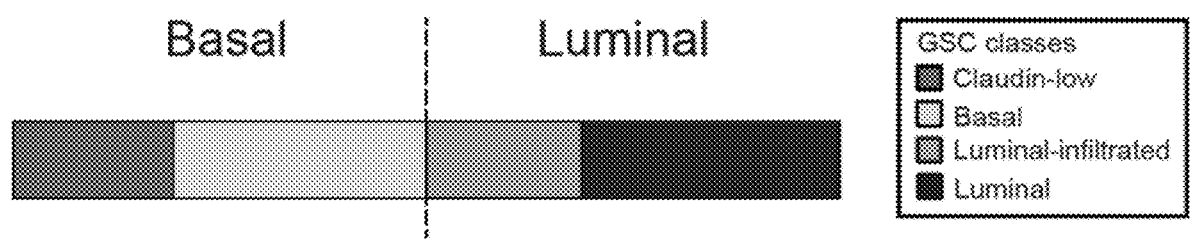
FIGS. 3A-3C show discovery and validation of the genomic subtyping classifier (GSC).
Figure 3B:
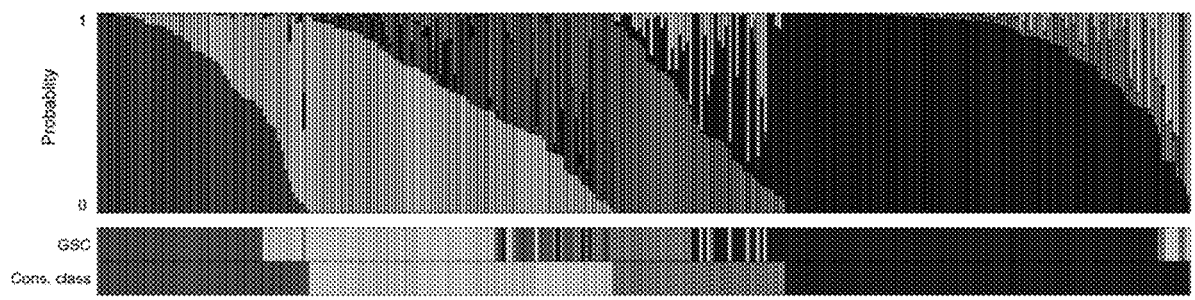
Figure 3C:
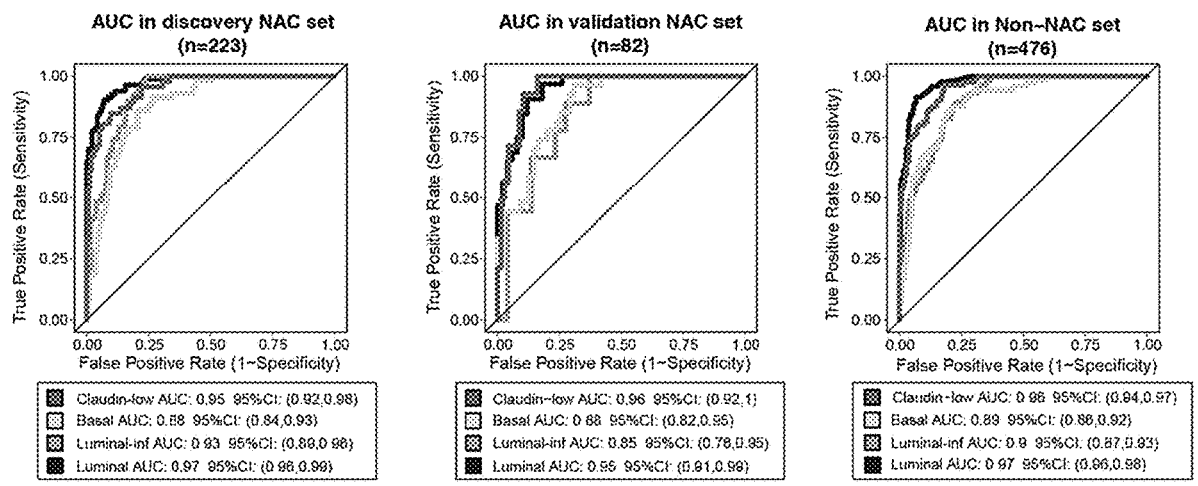
Figure 10:
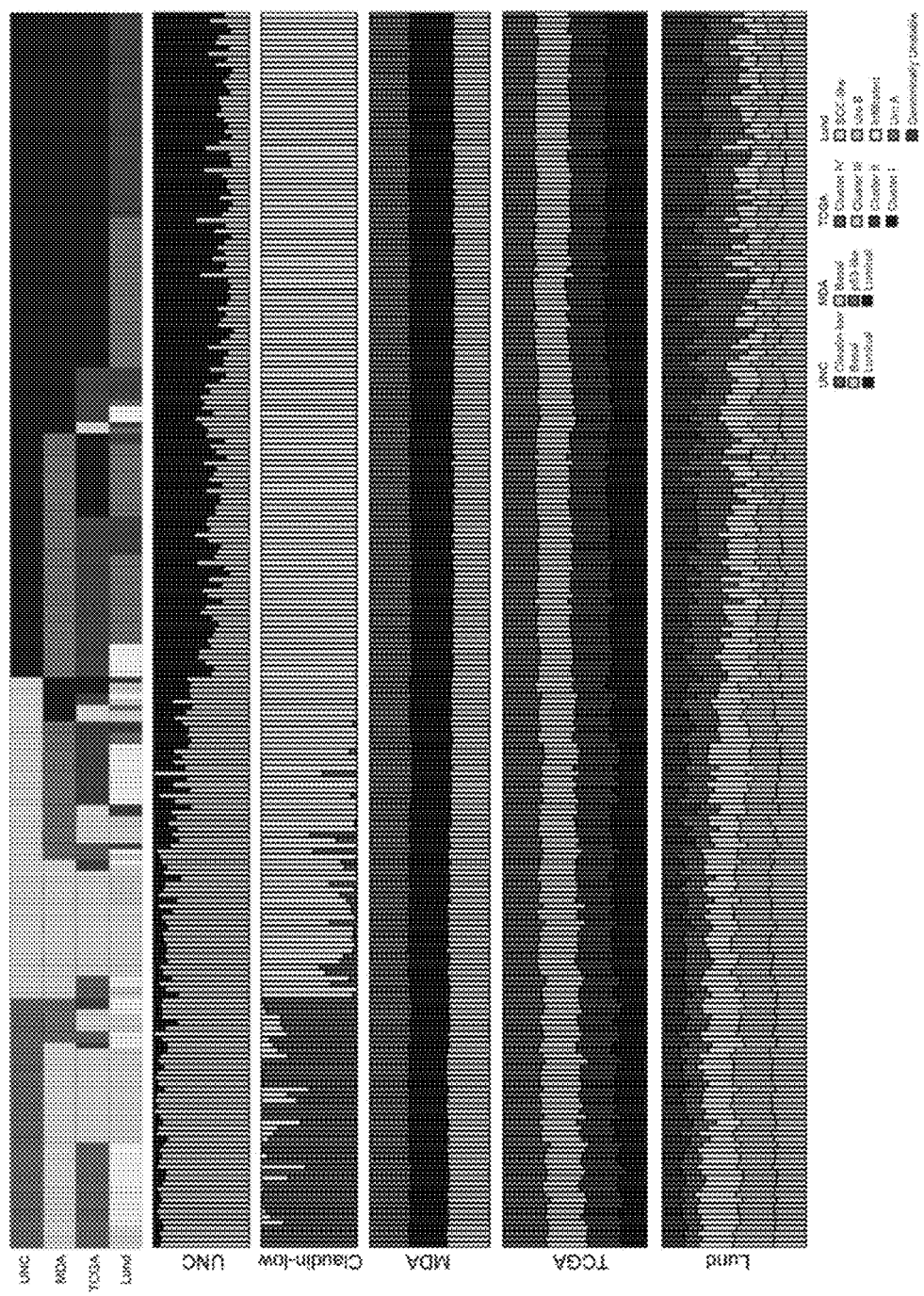
FIG. 10 shows the probability of subtype calls. This diagram shows across the top the subtype calls in the 223 TURBT samples of the discovery NAC dataset according to all subtyping methods. The probability of a tumor being assigned to each subtype within a given subtyping model is shown in the stacked barplot below.

Based on the biological characteristics and different impact on clinical outcome we trained a single sample genomic subtyping classifier (GSC) to predict 4 classes based on the consensus of the different classification schemes: claudin-low, basal, luminal-infiltrated and luminal (FIG. 3A and Table 5). Compared to previously published methods, the single sample GSC was more discriminate in assigning individual patients to a definitive subtype as seen by the number of patients that have a dominant subtype score (FIG. 3B and FIG. 10). The 10-fold cross-validation accuracy of GSC using the discovery cohort (n=223) was 83%. In the validation cohort (n=82), the accuracy was 73%. When we assign the subtype based on majority class the accuracy is 39% (p<0.001), which indicates that GSC is performing better than no-information rate. In both the NAC and non-NAC cohort (n=476), consensus subtype classes (i.e., those obtained using previously published clustering-based approaches) were all predicted with areas under the curve >0.85 (FIG. 3C).

TABLE 5

GSC Model

| GeneName/Intercept | Claudin-low | Basal | Luminal | Luminal-infiltrated |
|---|---|---|---|---|
| Intercept | -2.7422243 | 0.6042435 | 0.4472407 | 1.69074 |
| TMEM45B | -0.76380459 | . | . | . |
| ERBB2 | -0.41274889 | . | 0.150363923 | . |
| TNFRSF21 | -0.29642837 | . | . | 0.01953379 |
| FLRT3 | -0.29503283 | . | . | . |
| SPINK1 | -0.27540335 | . | . | . |
| LRRC37A2 | -0.27534664 | . | . | 0.31619037 |
| SCCPDH | -0.26879963 | . | . | . |
| UGT1A3 | -0.25832055 | . | . | . |
| ZNF486 | -0.25688633 | . | . | 0.2026522 |
| UGT1A8 | -0.24432959 | . | . | . |
| PPARG | -0.23354307 | . | . | . |
| UGT1A1 | -0.17875953 | . | . | . |
| AHR | -0.16157731 | . | . | . |
| EPCAM | -0.1575933 | . | . | . |
| PVRL4 | -0.15542842 | . | . | . |
| UGT1A4 | -0.15152295 | . | . | . |
| IGFBP3 | -0.12297767 | 2.17E-03 | . | . |
| S100P | -0.12075992 | . | . | . |
| PTPRM | -0.11969204 | . | . | . |
| NQO1 | -0.11797201 | . | . | . |
| RNF138P1 | -0.11438041 | . | . | . |
| CPSF6 | -0.10415486 | 7.95E-02 | 0.399489016 | -0.37481247 |
| GATA3 | -0.09830126 | . | . | . |
| UGT1A5 | -0.06289802 | . | . | . |
| UGT1A10 | -0.0614663 | . | . | . |
| ELF3 | -0.05358228 | . | . | . |
| AGR2 | -0.04732648 | . | . | . |
| EHF | -0.04346927 | . | 0.06822185 | . |
| SLC14A1 | -0.02475621 | . | . | . |
| CXCL17 | -0.01411846 | . | . | . |
| TMSB10 | 0.03420844 | . | . | -0.53821096 |
| CCL5 | 0.03720007 | . | . | . |
| MMP12 | 0.03846914 | . | . | . |
| SAT1 | 0.04934262 | . | . | . |
| CD68 | 0.06295573 | . | . | . |
| ANXA1 | 0.06652168 | . | . | . |
| IFITM2 | 0.08147351 | . | -0.241921432 | . |
| KRT5 | 0.09479006 | . | . | . |
| GJB2 | 0.09816201 | . | . | -0.33181587 |
| MT1L | 0.09851147 | . | . | . |
| NDRG1 | 0.10341095 | . | . | . |
| ASPN | 0.1211993 | . | . | . |
| SULF1 | 0.12310402 | -2.12E-02 | . | . |
| EFEMP1 | 0.12921654 | 1.82E-02 | -0.26599067 | . |
| G0S2 | 0.14303768 | . | . | . |
| TIMP3 | 0.1494699 | . | . | . |
| MUC16 | 0.16194856 | . | . | . |
| GBP1 | 0.18838626 | . | . | . |
| CGB2 | 0.19502279 | . | . | . |
| SNAI2 | 0.26861569 | . | . | . |
| DDIT4 | 0.29468037 | . | . | -0.0253577 |

TABLE 5-continued

GSC Model

| GeneName/Intercept | Claudin-low | Basal | Luminal | Luminal-infiltrated |
|---|---|---|---|---|
| CTSK | 0.31500848 | . | . | . |
| GBP5 | 0.33917204 | . | . | . |
| C3 | 0.34198121 | . | . | . |
| VIM | 0.34247125 | . | −0.333388459 | . |
| BGN | 0.38325778 | . | . | . |
| TGFBI | 0.41441125 | . | . | . |
| TIMP2 | 0.49419418 | . | −0.747524226 | . |
| SAA1 | 0.50978549 | −1.57E−01 | . | . |
| LAMC2 | 1.07099112 | . | . | . |
| FBP1 | . | −4.94E−01 | . | . |
| BAMBI | . | −4.65E−01 | . | 0.62521761 |
| PAQR7 | . | −4.28E−01 | . | 0.17060714 |
| IGFL1 | . | −3.99E−01 | . | . |
| TMPRSS2 | . | −3.47E−01 | . | 0.01052618 |
| PLXNB2 | . | −2.47E−01 | 0.118514328 | . |
| MAL | . | −2.11E−01 | . | . |
| TBX3 | . | −2.10E−01 | . | . |
| CRISP3 | . | −2.10E−01 | . | . |
| SCNN1B | . | −1.27E−01 | 0.062367003 | . |
| RNF128 | . | −1.08E−01 | . | . |
| KRT7 | . | −1.06E−01 | . | 0.21623783 |
| KRT8 | . | −1.04E−01 | 0.054120532 | . |
| ADAM10 | . | −1.01E−01 | . | . |
| SNX31 | . | −8.45E−02 | . | . |
| KRT18 | . | −6.26E−02 | . | . |
| UPK3A | . | −5.34E−02 | . | 0.14925342 |
| PSCA | . | −5.21E−02 | . | 0.08135977 |
| UPK2 | . | −4.67E−02 | . | . |
| AHNAK | . | −4.14E−02 | . | . |
| SPP1 | . | −1.45E−05 | . | . |
| TWIST2 | . | 5.93E−03 | . | −0.23104866 |
| SPARCL1 | . | 3.73E−02 | . | . |
| CASP14 | . | 4.48E−02 | . | −0.11998154 |
| MMP1 | . | 6.30E−02 | . | −0.19359346 |
| LAPTM5 | . | 6.63E−02 | −0.177011814 | . |
| MMP13 | . | 1.07E−01 | −0.069693132 | . |
| DUSP1 | . | 1.21E−01 | . | . |
| HIST1H2BF | . | 1.43E−01 | . | −0.25591353 |
| GABRP | . | 1.50E−01 | −0.070690688 | . |
| CFH | . | 1.60E−01 | . | . |
| SFRP2 | . | 1.82E−01 | . | . |
| SERPINB3 | . | 2.20E−01 | . | . |
| MGP | . | 2.45E−01 | . | . |
| FGFBP1 | . | 2.78E−01 | . | . |
| SAMD9 | . | 3.06E−01 | . | −0.06285417 |
| ITGA6 | . | 3.25E−01 | . | −0.09370337 |
| MALL | . | 3.31E−01 | . | . |
| MYL9 | . | . | −0.999232474 | . |
| IER3 | . | . | −0.687801478 | . |
| SPRR2F | . | . | −0.61048673 | . |
| MMP2 | . | . | −0.399399819 | . |
| HLA-DRA | . | . | −0.38019527 | . |
| DCN | . | . | −0.375988905 | . |
| TPM2 | . | . | −0.345807041 | . |
| HLA-A | . | . | −0.281158422 | 0.03357846 |
| LYZ | . | . | −0.187899622 | . |
| LUM | . | . | −0.157376466 | . |
| COL3A1 | . | . | −0.153285156 | . |
| POSTN | . | . | −0.141374249 | . |
| IFI30 | . | . | −0.133083286 | . |
| CD74 | . | . | −0.13175311 | . |
| VCAN | . | . | −0.091561626 | . |
| CALD1 | . | . | −0.091095352 | . |
| COL1A2 | . | . | −0.067763793 | . |
| HLA-DRB5 | . | . | −0.065668114 | . |
| OLFM4 | . | . | −0.05716249 | 0.06578151 |
| THBS2 | . | . | −0.04634627 | . |
| KRT23 | . | . | −0.044256964 | 0.46448906 |
| MYH11 | . | . | −0.017696254 | . |
| CLDN1 | . | . | −0.006052002 | . |
| RARRES1 | . | . | 0.023359372 | . |
| HPGD | . | . | 0.027477018 | . |
| ACER2 | . | . | 0.047288785 | . |
| RALBP1 | . | . | 0.052375622 | . |
| GSTM3 | . | . | 0.055776901 | . |
| BTBD16 | . | . | 0.100666013 | . |
| MACC1 | . | . | 0.103125969 | . |
| SEMA5A | . | . | 0.191690977 | . |
| ACOX1 | . | . | 0.204716367 | . |
| GSTM2 | . | . | 0.222507094 | −0.08536794 |
| CYP4Z2P | . | . | 0.229906712 | . |
| ZNF91 | . | . | 0.279026734 | . |
| STS | . | . | 0.288073414 | . |
| TOX3 | . | . | 0.292642628 | . |
| PLP2 | . | . | 0.555630814 | −0.17248888 |
| TACSTD2 | . | . | 0.711732783 | . |
| ATP8B1 | . | . | 0.888026967 | . |
| GRHL3 | . | . | 0.997892673 | . |
| TNC | . | . | . | −0.17479452 |
| TPX2 | . | . | . | −0.16128164 |
| DSP | . | . | . | −0.11656081 |
| TIMP1 | . | . | . | −0.11239522 |
| UPK1B | . | . | . | 0.02463108 |
| DHRS2 | . | . | . | 0.0442373 |
| PTN | . | . | . | 0.08733354 |
| SNCG | . | . | . | 0.13583842 |
| ACTG2 | . | . | . | 0.2287977 |
| SYTL2 | . | . | . | 0.31278763 |

Prediction of Clinical Endpoints Using GSC

Figure 4A:
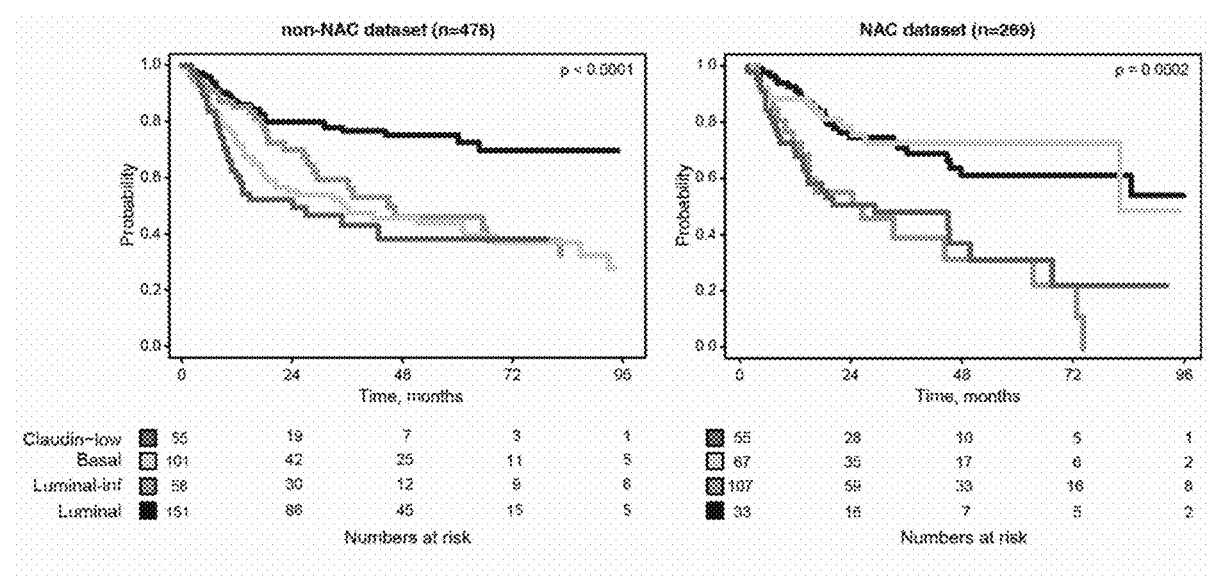
FIGS. 4A-4C show the clinical significance of GSC with and without cisplatin based NAC.

In both NAC datasets, we only used cases that were treated with cisplatin-based NAC for this analysis. The clinical significance of the predicted classes in the NAC datasets was compared with an independent non-NAC dataset that combined patients from TCGA, MD Anderson Cancer Center and the University of Lund datasets (n=476). We validated the relative changes in outcome by GSC subtype in patients treated with and without NAC (FIG. 4A). Patients with GSC basal tumors had a 3-year OS rate of 49.2% (95% confidence interval (CI) 39.5-61.2%; p<0.001) in the non-NAC cohort compared to 77.8% (95% CI 67.2-90.0%; p<0.001) in the NAC cohort.

In multivariable analysis adjusting for clinical tumor stage, age and gender in the non-NAC cohort, patients with a GSC basal subtype had a hazard ratio of 2.22 (p=0.002; Table 6) for OS compared to the luminal subtype. In the NAC cohort, GSC basal subtype patients did not fare differently than patients with luminal tumors (HR: 0.84, p=0.61; Table 6). Similar results were observed when considering only those patients from the independent NAC dataset (n=69) not used for GSC model training (Table 6). Overall, this analysis indicates that the outcome of patients with basal tumors can be improved most with NAC treatment.

TABLE 6

Results of Cox proportional hazard analysis of GSC's
ability to predict overall survival (NAC vs. Non-NAC)

| | MVA | | | MVA* | | | MVA* | | |
|---|---|---|---|---|---|---|---|---|---|
| | Non-NAC set (n = 476) | | | All NAC set (n = 269) | | | NAC Validation set (n = 69) | | |
| Variable | HR | 95% CI | p-value | HR | 95% CI | p-value | HR | 95% CI | p-value |
| Age | 1.02 | (1-1.05) | 0.066 | 1.01 | (0.99-1.04) | 0.235 | 0.98 | (0.93-1.03) | 0.433 |
| Female (Ref) | 1 | — | 1.000 | 1 | — | 1.000 | 1 | — | 1.000 |
| Male | 0.81 | (0.53-1.24) | 0.330 | 1.12 | (0.67-1.86) | 0.661 | 4.38 | (0.7-27.52) | 0.115 |
| Luminal (Ref) | 1 | — | 1.000 | 1 | — | 1.000 | 1 | — | 1.000 |
| Inf-Luminal | 2.38 | (1.33-4.28) | 0.004 | 2.46 | (1.29-4.7) | 0.006 | 5.68 | (0.4-81.3) | 0.201 |
| Basal | 2.22 | (1.34-3.68) | 0.002 | 0.84 | (0.42-1.68) | 0.614 | 0.88 | (0.16-4.94) | 0.881 |
| Claudin-Low | 3.06 | (1.71-5.47) | <0.001 | 2.16 | (1.22-3.81) | 0.008 | 3.73 | (0.81-17.25) | 0.092 |

*MVA models adjusted for institution and clinical stage

These results showed that NAC treatment in subjects with a basal subtype bladder cancer improves patient outcome. These results further showed that the subtyping methods of the present invention are useful for predicting benefit from neoadjuvant chemotherapy and treating a subject with bladder cancer. The results showed that the subtyping methods of the present invention may be used to determine a treatment for a subject with bladder cancer.

Example 2

Figure 4B:
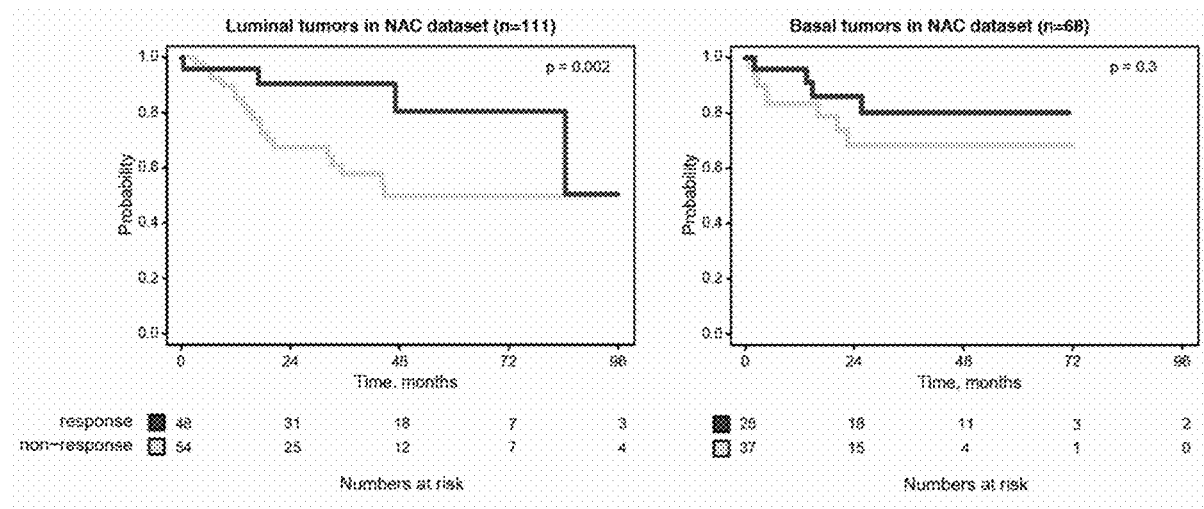
Figure 4C:
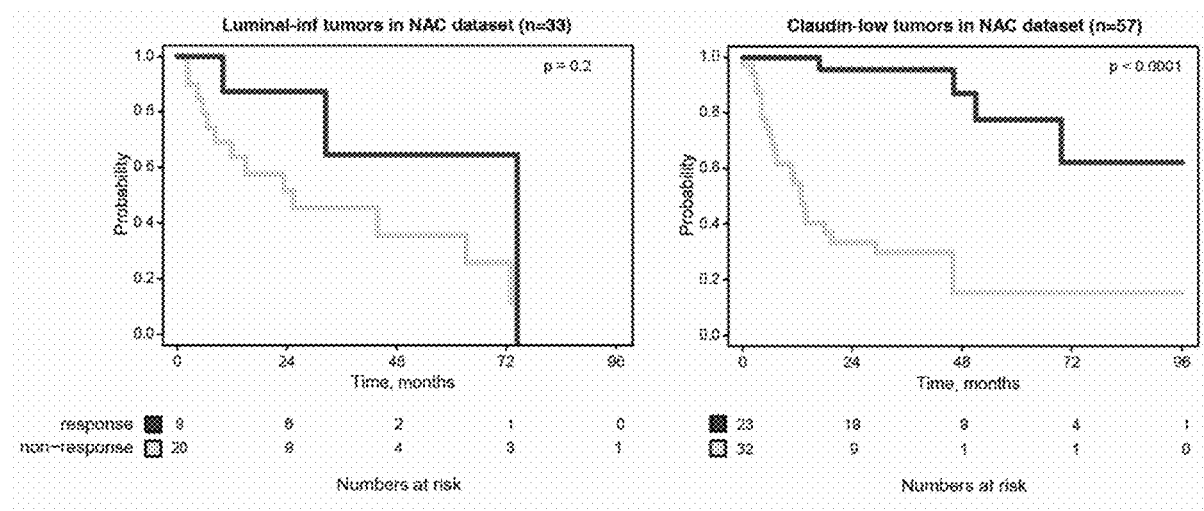
Figure 11:
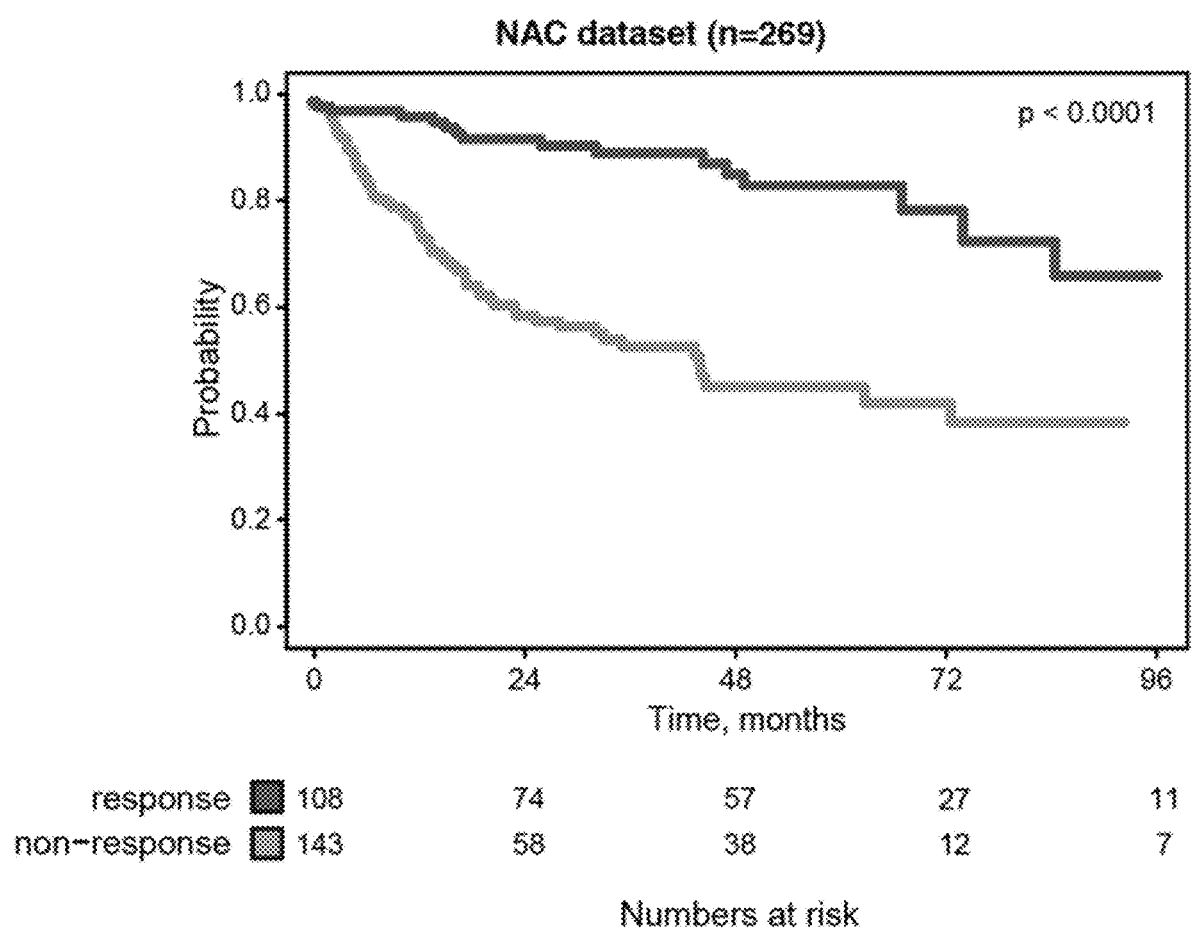
FIG. 11 shows the overall survival analysis in the NAC dataset according to response to NAC. A KM plot is shown of the OS according to response to NAC (response defined as <pT2N0).

NAC Survival Benefit in GSC Basal Tumors is Independent of Pathologic Response The relationship between NAC survival benefit in GSC basal tumors and pathological response was assessed as follows. The NAC cohort was analyzed using the subtyping methods described in Example 1. GSC was not significantly associated with major pathologic response (i.e., ypT<2N0) in the NAC cohort (Tables 4 and 7), even though major pathologic response was associated with improved OS (p<0.001) (FIG. 11 and Table 8). In an exploratory analysis, we further compared NAC responders (n=108) and non-responders (n=143) in each GSC subtype (FIG. 4B). Patients with luminal tumors who experienced a major response (n=46) had a 3-year OS of 95% (95% CI 89-100%) compared to 58% (95% CI 44-76%) in non-responders (n=47, p=0.002) (FIG. 4B upper left). In stark contrast, patients with GSC basal tumors did not show any significant differences in OS between major responders and non-responders (FIG. 4B upper right). The findings in the luminal infiltrated and claudin-low tumors were more similar to the luminal tumors (FIG. 4B lower panels).

TABLE 7

Logistic regression analysis of GSC's ability to predict
response to NAC (Cisplatin Based NAC set, n = 269)

| | UVA | | | MVA* | | |
|---|---|---|---|---|---|---|
| Variable | Odds Ratio | 95% CI | p-value | Odds Ratio | 95% CI | p-value |
| Age | 1 | (0.98-1.02) | 0.914 | 1 | (0.98-1.03) | 0.94 |
| Female (Ref) | 1 | — | 1.00 | 1 | — | 1.00 |
| Male | 1.52 | (0.87-2.64) | 0.139 | 1.48 | (0.82-2.64) | 0.192 |
| cT1&cT2 | 1 | — | 1 | 1 | (0.98-1.02) | 0.914 |
| cT3 | 0.77 | (0.44-1.32) | 0.336 | 0.76 | (0.4-1.45) | 0.404 |
| cT4 | 0.71 | (0.34-1.48) | 0.358 | 0.72 | (0.3-1.76) | 0.475 |
| Luminal (Ref) | 1 | — | 1 | 1 | — | 1.00 |
| Inf-Luminal | 0.53 | (0.22-1.28) | 0.161 | 0.61 | (0.24-1.57) | 0.307 |
| Basal | 0.93 | (0.5-1.73) | 0.82 | 0.93 | (0.48-1.81) | 0.834 |
| Claudin-Low | 0.83 | (0.43-1.6) | 0.572 | 0.92 | (0.46-1.85) | 0.821 |

*MVA model adjusted for institution

TABLE 8

Three-year overall survival rates for major responders
and non-responders within GSC subtypes

| | | Cisplatin-based NAC (n = 269) | | | |
|---|---|---|---|---|---|
| GSC Subtype | Non-NAC (n = 476) Overall | Overall | Re-sponders | Non-Responders | Log-rank p-value |
| Luminal | 76.60% | 74.7% | 95.2% | 57.6% | <0.001 |
| Inf-Luminal | 59.40% | 50.6% | 65.6% | 47.2% | 0.172 |
| Basal | 49.20% | 77.8% | 82.6% | 72.1% | 0.313 |
| Claudin-Low | 43.10% | 57.9% | 95.5% | 28.9% | <0.001 |

TABLE 9

Results of Cox proportional hazard analysis of GSC's
ability to predict overall survival in patients with NAC (n = 243)

| | MVA* | | |
|---|---|---|---|
| Variable | HR | 95% CI | p-value |
| Age | 1.01 | (0.99-1.03) | 0.483 |
| Female (Ref) | 1 | — | 1.000 |

TABLE 9-continued

Results of Cox proportional hazard analysis of GSC's ability to predict overall survival in patients with NAC (n = 243)

| | MVA* | | |
|---|---|---|---|
| Variable | HR | 95% CI | p-value |
| Male | 1.14 | (0.68-1.92) | 0.617 |
| Clinical Stage T1&T2 (Ref) | 1 | — | 1.000 |
| T3 | 1.48 | (0.83-2.65) | 0.185 |
| T4 | 1.69 | (0.82-3.47) | 0.152 |
| cN+ | 1.94 | (1.14-3.33) | 0.015 |
| Luminal (Ref) | 1 | — | 1.000 |
| Inf-Luminal | 2.5 | (1.3-4.8) | 0.006 |
| Basal | 0.9 | (0.44-1.83) | 0.767 |
| Claudin-Low | 2.26 | (1.24-4.1) | 0.008 |

*MVA models adjusted for institutions including Bern, NKI, UHS, UW, VGH, EMC; clinical node is not available in UCD.

These results showed that NAC survival benefit in GSC basal tumors is independent of pathologic response. These results further showed that the subtyping methods of the present invention are useful for predicting benefit from neoadjuvant chemotherapy and treating a subject with bladder cancer. The results showed that the subtyping methods of the present invention may be used to determine a treatment for a subject with bladder cancer.

Example 3

Development and Assessment of a Genomic Subtyping Classifier (GSC_RC) to Predict Molecular Subtypes in Muscle-Invasive Bladder Cancer A genomic subtyping classifier to predict molecular subtypes in muscle-invasive bladder cancer patients was developed and assessed as follows. A single sample model was trained to predict subtypes (Genomic Subtyping Classifier, GSC) using all pre-NAC TUR samples that passed QC, irrespective of chemotherapy regimen (n=223). The model was trained to predict four classes (claudin-low, basal, luminal-infiltrated and luminal). Unlike GSC_V1, these labels were generated using TURBT and RC samples.

To make the model applicable to several platforms, only genes on both Illumina HumanHT-12 V3.0 and Affymetrix Human Exon array 1.0 ST were selected as the initial gene list (17,007 genes). Using this initial gene set, the model development framework consisted of: 1) Feature selection, by which genes with low variance (variance <0.2) were removed, and significant genes were selected (p<0.001) using Kruskal-Wallis rank sum test; and 2) Model training with a generalized linear model with elastic net regularization (GLMNET) using the significant genes. These two steps were assessed using 10-fold cross-validation. Using the full training set, the feature selection step resulted in 298 genes, which were used to train the GSC_RC. GLMNET finally selected 162 genes to produce four scores. These scores, each ranging from 0 to 1, indicate the likelihood of the sample belonging to each of the four subtypes. The GSC_RC was independently validated in an 82 patient NAC validation dataset as well as in three non-NAC cohorts.

TABLE 10

The 162 Genes in the GSC_RC model with their coefficients

| Gene/Subtype | Claudin-low | Basal | Luminal | Luminal-infiltrated |
|---|---|---|---|---|
| Intercept | −6.95823 | 2.131339 | 3.175651 | 1.65124077 |
| LAMC2 | 0.976622 | 0 | 0 | 0 |
| IFI30 | 0.960598 | 0 | 0 | 0 |
| SAA1 | 0.82275 | −0.06162 | 0 | 0 |
| VIM | 0.787808 | 0 | 0 | 0 |
| TGFBI | 0.766984 | 0 | 0 | 0 |
| TIMP2 | 0.606912 | 0 | 0 | 0 |
| GBP1 | 0.526073 | 0 | −0.2393 | 0 |
| SNAI2 | 0.50705 | 0 | 0 | 0 |
| GBP5 | 0.457986 | 0 | 0 | 0 |
| POSTN | 0.379135 | −0.16632 | −0.00575 | 0 |
| TNC | 0.375036 | 0 | 0 | −0.235418787 |
| F3 | 0.363459 | −0.50552 | 0 | 0 |
| BGN | 0.359918 | −0.42863 | 0 | 0 |
| CCL5 | 0.233393 | 0 | −0.04296 | 0 |
| SULF1 | 0.229188 | 0 | 0 | 0 |
| WARS | 0.224574 | 0 | −0.25326 | 0 |
| MMP3 | 0.224215 | 0 | 0 | 0 |
| CXCL10 | 0.175088 | −0.05501 | 0 | 0 |
| TIMP3 | 0.154748 | −0.1268 | 0 | 0 |
| SERPINB1 | 0.146366 | 0 | 0 | 0 |
| DDIT4 | 0.134886 | 0 | 0 | 0 |
| MET | 0.089165 | −0.02577 | 0 | 0 |
| MYADM | 0.087209 | 0 | 0 | 0 |
| CD68 | 0.062788 | 0 | 0 | 0 |
| COL1A1 | 0.062049 | 0 | −0.11097 | 0 |
| ENO1 | 0.031846 | 0 | 0 | −0.388801186 |
| THBS1 | 0.031778 | 0 | 0 | 0 |
| CD44 | 0.029203 | 0 | 0 | 0 |
| MT1L | 0.007675 | 0 | −0.12182 | 0 |
| ACER2 | 0 | 0 | 0.254651 | 0 |
| ACOX1 | 0 | 0 | 0.344998 | 0 |
| ACSL5 | 0 | 0 | 0.056839 | 0 |
| ACTA2 | 0 | 0 | 0 | 0.184346006 |
| ACTG2 | 0 | 0 | 0 | 0.116816127 |
| AHR | 0 | 0 | 0 | 0.298753364 |
| AKR1C2 | 0 | −0.1062 | 0 | 0 |
| ANXA1 | 0 | 0.044244 | 0 | −0.023260537 |
| BAMBI | 0 | −0.05594 | 0 | 0.10127326 |
| BTG2 | 0 | −0.00806 | 0.169115 | 0 |
| CASP14 | 0 | 0.001236 | 0 | −0.333752276 |
| CDH1 | 0 | 0 | 0.488013 | 0 |
| CLDN1 | 0 | 0.113197 | 0 | 0 |
| COL1A2 | 0 | 0 | −0.02639 | 0 |
| CPSF6 | 0 | 0 | 0.54686 | 0 |
| CSTA | 0 | 0.068259 | 0 | 0 |
| CTSK | 0 | 0 | −0.76998 | 0 |
| CXCL1 | 0 | 0 | −0.18168 | 0 |
| CXCL9 | 0 | 0 | −0.35329 | 0 |
| CYP1A1 | 0 | 0 | 0 | 0.147248521 |
| DAPK1 | 0 | −0.41853 | 0 | 0 |
| DES | 0 | 0.00353 | 0 | 0 |
| DUSP1 | 0 | −0.19945 | 0 | 0.225606064 |
| EFEMP1 | 0 | 0.56878 | 0 | 0 |
| ERP27 | 0 | −0.0335 | 0 | 0.059116662 |
| F11R | 0 | 0 | 0.430938 | 0 |
| FCGR3A | 0 | 0 | −0.11616 | 0 |
| FLNA | 0 | 0 | −0.60018 | 0 |
| FN1 | 0 | 0 | −0.01906 | 0 |
| G0S2 | 0 | 0.231669 | 0 | 0 |
| GRHL1 | 0 | 0 | 0.181143 | 0 |
| HIST1H2AE | 0 | 0 | 0 | −0.204468813 |
| HIST1H2BF | 0 | 0.365323 | 0 | −0.332639794 |
| HLA-DRA | 0 | 0 | −0.00516 | 0 |
| HLA-DRB1 | 0 | 0 | −0.10826 | 0 |
| HLA-DRB5 | 0 | 0 | −0.1357 | 0.203470306 |
| HMGCS2 | 0 | 0 | 0.035475 | 0 |
| IFI16 | 0 | 0.282487 | −0.53556 | 0 |
| IFI6 | 0 | 0 | 0.21477 | 0 |
| IFITM2 | 0 | 0.168481 | −0.23749 | 0 |
| IGFL1 | 0 | 0 | 0 | 0.088865183 |
| INA | 0 | 0 | 0 | 0.269855096 |
| ITGA6 | 0 | 0 | 0 | −0.84448677 |
| KRT19 | 0 | 0 | 0.051028 | 0 |
| KRT8 | 0 | −0.07609 | 0 | 0 |

TABLE 10-continued

The 162 Genes in the GSC_RC model with their coefficients

| Gene/Subtype | Claudin-low | Basal | Luminal | Luminal-infiltrated |
|---|---|---|---|---|
| LAPTM5 | 0 | 0 | −0.14742 | 0 |
| LUM | 0 | 0 | 0 | 0.080477707 |
| LYZ | 0 | 0 | −0.14499 | 0.072869682 |
| MAL | 0 | 0 | 0 | 0.15591663 |
| MALL | 0 | 0.465878 | 0 | 0 |
| MMP1 | 0 | 0.052858 | 0 | 0 |
| MMP12 | 0 | 0.274163 | 0 | 0 |
| MT1E | 0 | 0 | −0.24211 | 0 |
| MYL9 | 0 | 0 | −0.79289 | 0 |
| OLFM4 | 0 | 0.092704 | −0.30198 | 0 |
| PABPC1 | 0 | −0.15484 | 0 | 0 |
| PAQR7 | 0 | −0.81694 | 0 | 0.085353834 |
| PERP | 0 | 0.119488 | 0 | −0.183724057 |
| PM20D1 | 0 | 0 | 0 | 0.334808319 |
| PPARG | 0 | 0 | 0.432215 | 0 |
| PSCA | 0 | 0 | 0 | 0.152192247 |
| PTMS | 0 | 0.155866 | −0.18937 | 0 |
| PTPN13 | 0 | 0 | 0.71945 | 0 |
| PTPRM | 0 | 0 | 0.799542 | 0 |
| RALBP1 | 0 | −0.33627 | 0.123879 | 0 |
| RNF128 | 0 | 0 | 0.355343 | 0 |
| RNF138P1 | 0 | 0 | 0.042225 | 0 |
| S100A10 | 0 | 0.036313 | 0 | 0 |
| S100A7 | 0 | 0 | −0.0635 | 0 |
| S100A8 | 0 | 0.061035 | −0.53246 | 0 |
| SAMD9 | 0 | 0.207082 | 0 | −0.093691035 |
| SCCPDH | 0 | 0 | 0.342716 | 0 |
| SCNN1A | 0 | 0.057514 | 0 | −0.31838232 |
| SCNN1B | 0 | −0.1988 | 0 | 0 |
| SCUBE2 | 0 | 0 | 0.014138 | 0 |
| SEMA5A | 0 | −0.233 | 0 | 0 |
| SERPINB13 | 0 | 0 | 0.015014 | 0 |
| SERPINB3 | 0 | 0.004895 | 0 | 0 |
| SERPINB4 | 0 | 0 | −0.0754 | 0 |
| SFN | 0 | 0 | 0.190208 | 0 |
| SFRP2 | 0 | 0 | −0.50451 | 0 |
| SLITRK6 | 0 | 0 | 0 | −0.066499889 |
| SNCG | 0 | 0 | 0 | 0.615705592 |
| SPINK1 | 0 | 0 | 0 | 0.142190603 |
| SPP1 | 0 | 0.041592 | 0 | −0.112347072 |
| SPRR1B | 0 | 0.309708 | 0 | 0 |
| STS | 0 | −0.0029 | 0.175825 | 0 |
| SYTL2 | 0 | 0 | 0 | 0.04313459 |
| TACSTD2 | 0 | −0.13378 | 0.340548 | 0 |
| TGM2 | 0 | 0.262799 | 0 | 0 |
| THBS2 | 0 | 0 | −0.37458 | 0 |
| TMEM45A | 0 | 0.9048 | 0 | 0 |
| TMEM45B | 0 | 0 | 0.392412 | 0 |
| TMPRSS2 | 0 | 0 | 0.071859 | 0 |
| TMSB10 | 0 | 0.015045 | 0 | −0.063996697 |
| TOX3 | 0 | −0.1094 | 0 | 0 |
| TPM2 | 0 | 0 | −0.68009 | 0 |
| TPX2 | 0 | 0.291045 | 0 | −0.113275851 |
| TWIST2 | 0 | 0.094704 | −0.57787 | 0 |
| UPK1A | 0 | −0.14054 | 0 | 0.18918717 |
| UPK1B | 0 | 0 | 0.05864 | 0 |
| VCAN | 0 | 0 | −0.57477 | 0 |
| VGLL1 | 0 | −0.45263 | 0.527312 | 0 |
| VSIG2 | 0 | 0 | 0.072273 | 0 |
| ZNF486 | 0 | 0 | 0 | 0.053892023 |
| UGT1A1 | −0.00506 | 0 | 0 | 0 |
| BEX4 | −0.00708 | 0 | 0 | 0 |
| UGT1A9 | −0.03392 | 0 | 0 | 0 |
| CXCL17 | −0.04011 | 0 | 0 | 0 |
| IGFBP3 | −0.04219 | 0 | 0.130155 | 0 |
| UGT1A3 | −0.04299 | 0 | 0 | 0 |
| UGT1A5 | −0.04733 | 0 | 0 | 0 |
| SLC14A1 | −0.05549 | 0 | 0 | 0.006087454 |
| GPR110 | −0.06705 | 0 | 0 | 0 |
| TNFRSF21 | −0.06924 | 0 | 0 | 0 |
| FLRT3 | −0.0772 | 0 | 0 | 0 |
| ELF3 | −0.07776 | 0 | 0.5981 | 0 |
| S100P | −0.13041 | 0 | 0 | 0 |
| GATA3 | −0.13428 | 0 | 0.005371 | 0 |
| UGT1A10 | −0.15895 | 0 | 0 | 0.014614392 |
| GABRP | −0.16184 | 0.823325 | 0 | 0 |
| GRHL3 | −0.1895 | −0.02293 | 0 | 0.377913673 |
| MACC1 | −0.26694 | 0 | 0.000789 | 0 |
| EHF | −0.26857 | 0 | 0 | 0 |
| UGT1A8 | −0.27341 | 0 | 0 | 0 |
| MGP | −0.29176 | 0.055706 | 0 | 0 |
| ERBB2 | −0.33678 | 0 | 0.083101 | 0 |

Validation of GSC RC to Predict Molecular Subtypes

Figure 12:
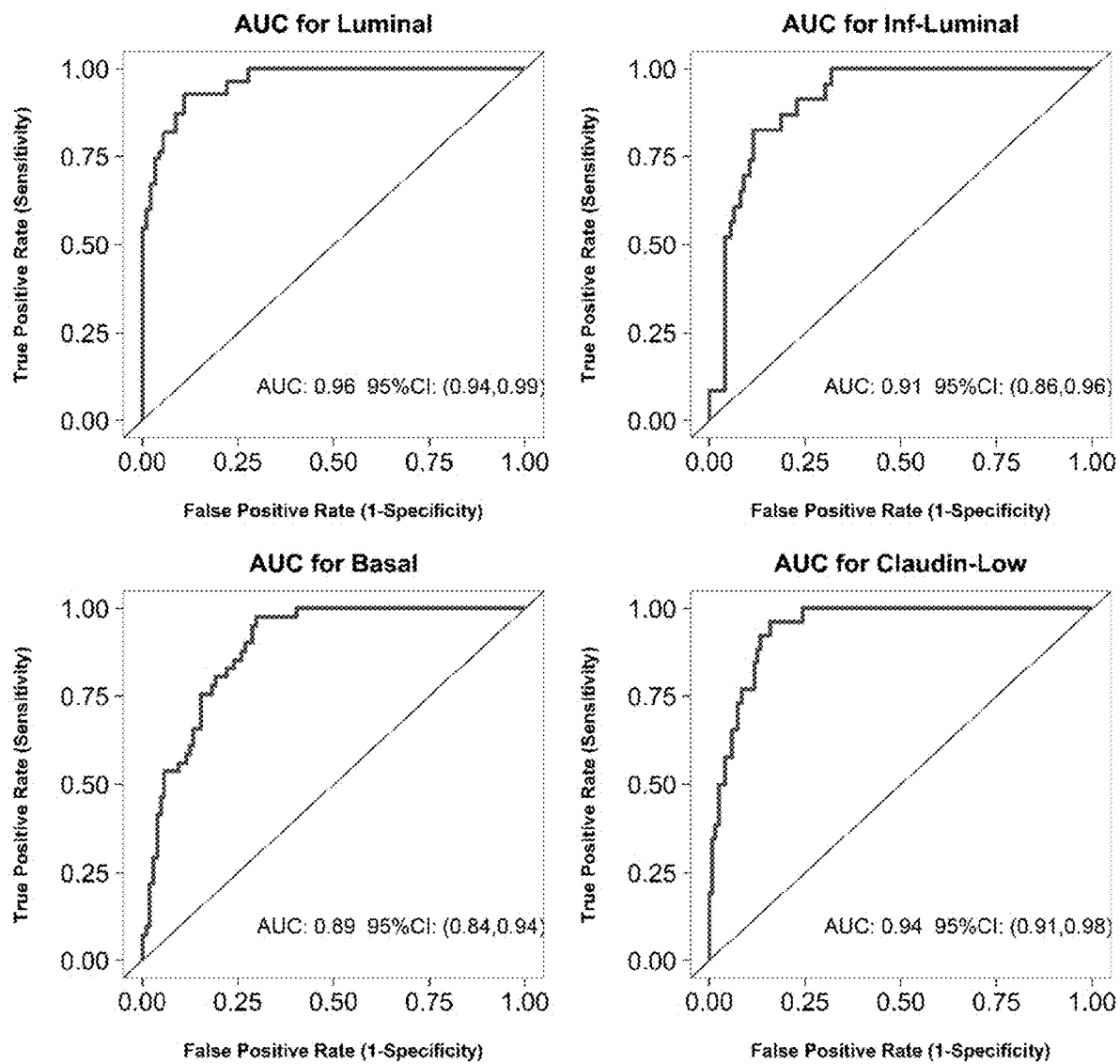
FIG. 12 shows the area under the curve (AUC) for four molecular subtypes of the present invention.

In the validation cohort, the average accuracy was 72% in predicting molecular subtypes (See Table 11). Moreover, as shown in FIG. 12 the Area Under Curve (AUC) for claudin-low, basal, luminal-infiltrated, and luminal was 0.94, 0.89, 0.91, and 0.96, respectively. These results showed that methods of the present invention are useful for predicting molecular subtypes for subject with muscle-invasive bladder cancer. These results suggested that the methods of the present invention may be useful for predicting benefit from neoadjuvant chemotherapy and treating a subject for bladder cancer.

TABLE 11

Confusion matrix showing GSC_RC predictions compared to labels of the validation data

| | | Reference | | | |
|---|---|---|---|---|---|
| | | Luminal | Inf_Luminal | Basal | Claudin_Low |
| Prediction | Luminal | 51 | 12 | 3 | 0 |
| | Inf_Luminal | 2 | 10 | 3 | 0 |
| | Basal | 2 | 1 | 29 | 11 |
| | Claudin_Low | 0 | 0 | 6 | 15 |

Accuracy: 0.72

Prediction of Response to NAC and Overall Survival

Figure 13:
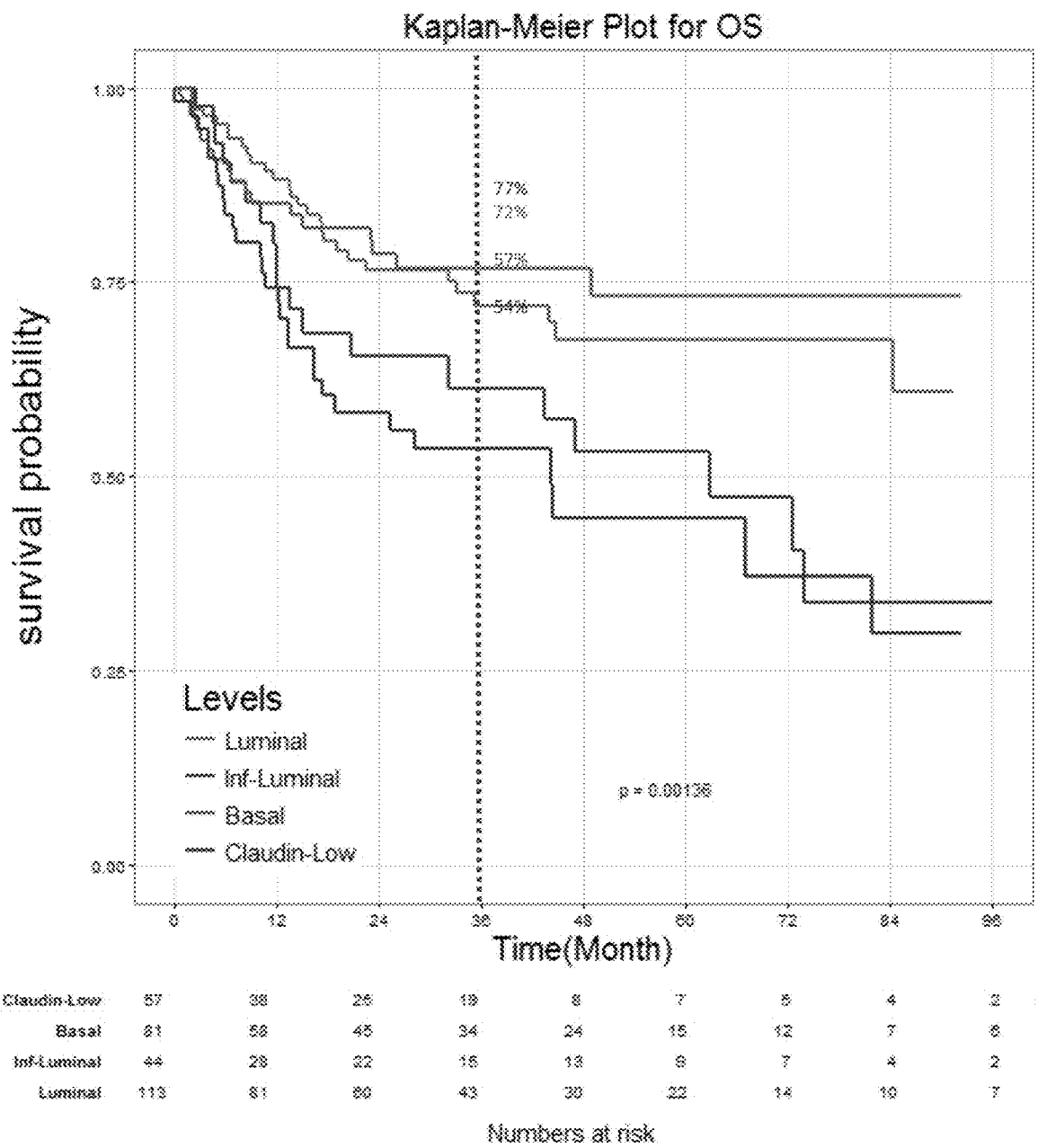
FIG. 13 shows survival analysis of a genomic subtyping classifier of the present invention. The Kaplan Meier curve shows survival probability for each subtype in NAC.

The relative changes in outcome by GSC_RC molecular subtype in bladder cancer patients treated with NAC is shown below in FIG. 13. Bladder cancer Patients with GSC had a 3-year OS rate of 77%, 72%, 57%, and 54% in the NAC cohort for basal, luminal, Inf-luminal, and Claudin-low. In multivariable analysis adjusting for clinical age and gender in the NAC cohort, patients had a hazard ratio of 1.71, 0.81, and 2.18 (p=0.08, p=0.49, p=0.004; Table 12), respectively. These results showed that the methods of the present invention are useful for predicting benefit from neoadjuvant chemotherapy and treating a subject for bladder cancer. These results further showed that the methods of the present invention are useful for determining a treatment for a subject who has bladder cancer.

TABLE 12

Cox Regression - Multivariable

| | HR | 95% CI | p-value |
|---|---|---|---|
| Luminal (ref) | 1 | — | 1 |
| Inf-Luminal | 1.71 | (0.94-3.1) | 0.08 |
| Basal | 0.81 | (0.44-1.48) | 0.49 |
| Claudin_Low | 2.18 | (1.28-3.71) | 0.004 |
| Age | 1.02 | (0.99-1.04) | 0.14 |
| Gender-F (ref) | 1 | — | 1 |
| Gender-M | 1.07 | (0.67-1.71) | 0.77 |

TABLE 12-continued

Cox Regression - Multivariable

|  | HR | 95% CI | p-value |
|---|---|---|---|
| Bern (ref) | 1 | — | 1 |
| NKI | 0.70 | (0.37-1.33) | 0.28 |
| UHS | 0.77 | (0.35-1.7) | 0.52 |
| UW | 0.67 | (0.34-1.29) | 0.23 |
| VGH | 0.72 | (0.37-1.43) | 0.35 |
| UCD | 0.77 | (0.31-1.94) | 0.59 |
| EMC | 0.67 | (0.3-1.48) | 0.32 |

While the preferred embodiments of the invention have been illustrated and described, it will be appreciated that various changes can be made therein without departing from the spirit and scope of the invention.

TABLE 13

Subtyping Target Sequences

| SEQ ID NO. | Gene | Affy Probeset ID | Sequence |
|---|---|---|---|
| 1 | GRHL3 | 2325371 | TGGGAACCTACCTGTCAGCAAAATCTCGACACCCAAACCTCAACATAAATCAAACACTTTCCC GGGCAGAGAATGTCTGTGTCAGGCAAGAATTAGAGACAAGCGGTCAGCAGAGCCTCA |
| 2 | GRHL3 | 2325372 | ACATCGGTGGATACCTGCCGCTCTCAGAGCGTGGAGGCTGGATGGGGTTTCCTGGAGGGGG AAGAGCGGGGAGGCCGGCACCGGGATTCACAGAGCAATTTGTAAGGGTAAATGAATGGGCT GACGATCTTACTTTGGCGTGTCAAGGCAAGC |
| 3 | GRHL3 | 2325374 | AGGAGATGTGCCAAACTGTTAAGAGTGGTTATTTCTGAGCAGAAGA |
| 4 | GRHL3 | 2325375 | ATGTGGATGAATTCCATTCTTCCTATTTTTC |
| 5 | GRHL3 | 2325382 | TGTGCGGCTGCTAAAGAACGACCCAGTCAACTTGCAGAAATTCTCTTACACTAGTGAGGATGA GGCCTGGAAGACGTACCTAGAAAACCCGTTGACAGCTGCCA |
| 6 | GRHL3 | 2325383 | GAGATGATGACAGTGTTGCGGCCTTGAGCTTCCTCTATGATTACTACA |
| 7 | GRHL3 | 2325385 | GAGAAGCGGATATTGTCCTCCAGCACTGGG |
| 8 | GRHL3 | 2325386 | TGAGACGGACCTCACTCCCCTTGAAAGCCCCACACACCTCATGA |
| 9 | GRHL3 | 2325387 | TCAAGAAGAATAACCTGATGAGCTTGGAGGGGGCCTTGCCCACCCCTGGCAAGGCAGCTCCC CTCCCTGCAGGCCCCAGCAAGCTGGAGGCCGGCTCTGTGGACAGCTACCTGTTACCCACCACT GATATGTATGATAATGGCTCCCTCAACTCCTTGTTTGAGAGCATTCATGGGGTGCCGCCCACA CAGCGCTGG |
| 10 | GRHL3 | 2325389 | AGCAAGTCTGTAACATAGCCTCAGGC |
| 11 | GRHL3 | 2325390 | TGACTTTGAATACACCCTGGGCTCCCCCAAAGCCATCCACATCAAGTCAGGCGAGTCACCCAT GGCCTACCTCA |
| 12 | GRHL3 | 2325391 | AGTGTGGTGATGGTTGTCTTCGACAATGAGAAGGTCCCAGTAGAGCAGCTGCGCTTCTGGAA GCACTGGCATTCCCGGCAACCCACTGCCAAGCAGCGGGTCATTGAC |
| 13 | GRHL3 | 2325392 | AAGAAAACTTCAACACTGTGGAGCACATTGAGGAGGTGGCCTATAATGCACTGTCCTTTG |
| 14 | GRHL3 | 2325394 | GTGTTCATCGGCGTAAACTGTCTGAGCACAGACTTTTCCTCACAAAAGGGGGTGAAGGGTGT CCCCCTGAACCTGCAGATTGACACCTATGACTGTGGCTTGGGCACTGAGCGCCTGGTACACCG TGCTGTCTGCCAGATCAAGATCTTCT |
| 15 | GRHL3 | 2325397 | AGGAAGATGCGCGATGACGAGCGGAAGCAGTTCCGGAGGAAGGTCAAG |
| 16 | GRHL3 | 2325398 | CAATGAGACGACCTACCTTCGGCCAGAGACTGACCTGGAGACGCCACCCGTGCTGTTCATCCC CAATGTGCACTTCTCCAGCCTGCAGCGCTCTGGAGGG |
| 17 | GRHL3 | 2325399 | TCAGCCAGTTTCAAGACCTTTATTGAATCATAGGGGTTTAAACATGTATATATGGTCCTATAGC TTCAGTGACCTATTGTATTGAAGAGAAGAATGTTATGAAGAAACAGATTTCGTAACCATTAAA ACGTTCATGCTTAGGGCA |
| 18 | GRHL3 | 2325403 | TTCTGCTGTATGTGCGGAGGGAGACTGAGGAGGTGTTTGACGCGCTCATGTTGAAGACCC |
| 19 | GRHL3 | 2325405 | CTTAGTCAACATGGACAACAACATCATTCAGCATTACAGCAACCACGTCGCCTTCCTGCTGGA CATGGGGGAGCTGGACGGCAAAATTCAGATCATCCTTA |
| 20 | GRHL3 | 2325406 | GCCTCAGCGCTGTTACTTGAATGCCTTCCCTGAGGGAAGAGGCCCTTGAGTCACAGACCCACA GACGTCAGGGCCAGGGAGAGACCTAGGGGGTCCCCTGGCCTGGATCCCCATGGTATGCTTG AATCTGCTCCCTGAACTTCCTGCCAGTGCCTCCCCGTACCCCAAAACAATGTCACCATGGTTAC CACCTACCCAGAAGACTGTTCCCTCCTCCCAAGACCCTTGTCTGCAGTGGTGCTCCTGCAGGCT GCCCGTTAAGATGGTGGCGGCACACGCTCCCTCCCGCAGCACCACGCCAGCTGGTGCGGCCC |

TABLE 13-continued

Subtyping Target Sequences

| SEQ ID NO. | Gene | Affy Probeset ID | Sequence |
|---|---|---|---|
|  |  |  | CCACTCTCTGTCTTCCTTCAACTTCAGACAAAGGATTTCTCAACCTTTGGTCAGTTAACTTGAAA ACTCTTGATTTTCAGTGCAAATGACTTTTAAAAGACACTATATTGGAGTCTCTTTCTCAGACTTC CTCAGCGCAGGATGTAAATAGCACTAACGATCGACTGGAACAAAGTGACCGCTGTGTAAAAC TACTGCCTTGCCACTCACTGTTGTATA |
| 21 | GRHL3 | 2325407 | CACCTGACTGTCTTGAATGTTCCCATCCTGTGACTCAAGTGAGGAACATGGGTTTTGGAGATG GATTTTGGAGGCAGAGGGACCTGGATTCAAATCCCAGCCCCACCACCGTCAACAGCCTGCAC TTCACTGTAAACTCGGAATGACACACCCACCTGGAGGAGAGGTGGAAGGACGACGGCAGGT CACATCTGAGAGCTCTCAGCTCAGAGTATGTGG |
| 22 | SFN | 2326775 | AGAGACACAGAGTCCGGCATTGGTCCCAGGCAGCAGTTAGCCCGCCGCCCG |
| 23 | SFN | 2326776 | CGCTATGAGGACATGGCAGCCTTCATGAAAGGCGCCGTGGAGAAGGGCGAGGAGCTCTCCT GCGAAGAGCGAAACCTGCTCTCAGTAGCCTATAAGAACGTGGTGGGCGGCCA |
| 24 | SFN | 2326777 | AGCTCCAGGGCGTGTGCGACACCGTGCTGGGCCTG |
| 25 | SFN | 2326778 | CACCGGTGACGACAAGAAGCGCATCATTGACTCAGCCCGGTCAGCCTACCAGGAGGCCATGG ACATCAGCAAGAAGGAGATGCCGCCCACCAACCCCATCCGCCTGGGCCTGGCCCTGAACTTTT CCGTCTTCCACTACGAGATCGCCAACAGCCCCGAGGAGGCCATCTCTCTGGCCAAGACCACTT TCGACGAGGCCATGGCTGATCTGCACACCCTCAGCGAGGACTCCTACAAAGACAGCAC |
| 26 | SFN | 2326779 | ACCCTGCCGAGAGGACTAGTATGGGGTGGGAGGCCCCACCCTTCTCCCCTAGGCGCTGTTCTT GCTCCAAAGGGCTCCGTGGAGAGGGACTGGCAGAGCTGAGGCCACCTGGGGCTGGGGATCC CACTCTTCTTGCAGCTGTTGAGCGCACCTAACCACTGGTCATGCCCCCACCCCTGCTCTCCGCA CCCGCTTCCTCCCGACCCCAGGACCAGGCTACTTCTCCCCTCCTCTTGCCTCCCTCCTGCCCCTG CTGCCTCTGATCGTAGGAATTGAGGAGTGTCCCGCCTTG |
| 27 | SFN | 2326780 | TGCGCGCGCGCCAGTGCAAGACCGAGATTGAGGGAAAGCATGTCTGCTG |
| 28 | CYP4Z2P | 2335016 | TCCTGGCTTCAGGAACTCATGGCTCACCCCTTCTTGCTGCTGATCCTCCTCTGCATGTCTCTGCT GCTGT |
| 29 | CYP4Z2P | 2335018 | CTTGTGGGTTGGACCCTTTACGATGTTCTTCA |
| 30 | CYP4Z2P | 2335028 | CGAGGACTTGTGACCCTGGATGGTTCTAAATGGAAAAAGCACCGCCAGATTGTGAAACCTGG CTTCAACATCAGCATTCTGAAAATATTCATCACCATGATG |
| 31 | CYP4Z2P | 2335030 | TGGGAGGAACACATTGCCCAAAACTCACGTCTGGAGCTCTTTCAACATGTCTCCCTGATGAC |
| 32 | CYP4Z2P | 2335031 | CCCTGGACTCATACCTGAAAGCAGTGTTCAACCTTAGCAAAATCTCCAACCAGCGCATGAACA ATTTTCTACATCACAACGACCTGGTTTTCAAATTCAGCTCTCAAGGCCAAATCTTTTCTA |
| 33 | CYP4Z2P | 2335032 | AGTAATCCAGGACCGGAAGGAGTCTCTTAAGGATAAGCTAAAACAAGATACTACTC |
| 34 | CYP4Z2P | 2335034 | ATGTGCATCAAGGAATGCCTCCGCCTCTACG |
| 35 | CYP4Z2P | 2335035 | TAGTAAACATATCCCGGTTACTCGACAA |
| 36 | CYP4Z2P | 2335042 | CTGTGTTTATCAATATTTGGGCTCT |
| 37 | GBP1 | 2345792 | TTCATCAGGAGTTCCTTCAAAGATGTGGACCATCTATTTCAAA |
| 38 | GBP1 | 2345852 | AGAGATCCACATGACAGGCCCAATGTGCCTCATTGAGAACACTAATGGGCGACTGATGGCGA ATCCAGAAGCTCTGAAGATCCTTTCTGCCATTAC |
| 39 | GBP1 | 2345856 | GTGCAGTCTCACACTAAAGGAATCTGGATGTGGTGTATGCCCCATCCCAAGAAGCCAGGCCA CATCCTAGTTCTGCTGGACACCGAGGGTCT |
| 40 | GBP1 | 2345862 | GACAAACAGGAACACCTGCTTACAGCC |
| 41 | GBP1 | 2345863 | CAGACATACTTGAAATCCAAGGAGTCTATGACTGATGCAATTCTCCAGACAGACCAGACTC |
| 42 | GBP1 | 2345864 | GAAAGCTGAGTCTGCACAGGCTTCAGCAAAAATGTTGCAGCAAATGCAAAGAAAGAATGAG CAGATGATGGAACAGAAGGAGAGGAGTTATCAGGAACACTTGAAACAACTGACTGAGAAGA TGGGAGAGCGACAGGGTCCAGTTGCTGGAAGAGCAAGAGAGGACCCTCGCTCTTAAACTTCAG |
| 43 | GSTM2 | 2350953 | TCTGGGCCTCTCACAAACGCTGAGCCCCGCCCCGCTGAGGCCTGTCTGCAGAATCCACAGCAA CCAGC |
| 44 | GSTM2 | 2350958 | GTAATGGCACCCTCGAGTCTGGGCCCTGCCCC |
| 45 | GSTM2 | 2350959 | CCCGTCTGGGTAATTATGATGGGTGTCCCTCAGGGCT |

TABLE 13-continued

Subtyping Target Sequences

| SEQ ID NO. | Gene | Affy Probeset ID | Sequence |
| --- | --- | --- | --- |
| 46 | GSTM2 | 2350960 | CTCCTGATTATGACAGAAGCCAGTGGCTGAATGAAAAATTCAAGCTGGGCCTG |
| 47 | GSTM2 | 2350963 | GGTACATTGCCCGCAAGCACAACCTG |
| 48 | GSTM2 | 2350964 | AGCAGATTCGCGAAGACATTTTGGAGAACCAGTTTATGGACAGCCGTATGCAGCTGGCCAAA<br>CTCTGCTATGACCCAGATT |
| 49 | GSTM2 | 2350965 | CCTTTCCCTGCAGAGTTTGTGTCCAAAATTGATTCCTTCTGGTGAGTTCTTGGTCTTGCTGACTC<br>TAAGAATGAAGCCGCGGTCCTACACGGTGAGTGTTACAGTTCTTAAAGATGGTGTGTCCGGA<br>GTTTGTTCCTTCAGATGTTCAGATGTGTCCGCAGTTTCTTCCTTCCGGTGGGTTTGTGGTCTTG<br>CTGACTTCAGGGGTGAAGCCGCAGACCTTCGCAGTGAGTGCTACAGCTCTTAAAGGTGGCGC<br>GTCTGGAGTTGTTTATTCCTCTTGGTGGGTTCATGGTCTGGCTGGCTTCAGGAGTGAAGCTGC<br>AGACCTTCATAGTGAATGTTATAGCTCATAAAGGTAGTTCAAACCCAAAGAGTGAGCAACAG<br>CAGGATTTATGGTGACGAGTGAA |
| 50 | GSTM2 | 2350970 | GAGAAACTGAAACCAGAATACCTGCAG |
| 51 | GSTM2 | 2350973 | GGATTTCATCGCTTATGATGTCCTTGAGAGAAA |
| 52 | GSTM2 | 2350975 | CTCCCAAGACCTGTGTTCACAAAGA |
| 53 | GSTM2 | 2350976 | CCTTCCTGTTAGTGGTTGTGTCTGCTTTAAAGGGCCTGCCTGGCCCCTCGCCTGTGGAGCTCA<br>GCCCCGAGCTGTCCCCGTGTTGCATGAAGGAGCAGCATTGACTGGTTTACAGGCCCTGCTCCT<br>GCAGCATGGTCCCTGCCTTAGGCCTACCTGATGGAA |
| 54 | GSTM2 | 2350978 | GTCTCTGATGATTACGCTCAAGGTATTCTCCTTCATATGTTAGCTTTTGAGAATGCGAACCATG<br>AGTGTAAAGTGGTCATGCGTTCTGTCTAATGACAAAATTTACCTGATCACGAGGTGTGCCTGC<br>ATATATTAAAGCTTGTGAAAGCATTGGATCAGAGACCCACAAAGCTATTCTGTGGGCACGGG<br>CCATGAAGGATGGCAATCAAACTGGCTTGACTGAATTCTTTTCTTGGAGCCTGCTATAATTGT<br>GGTCAACTTCATCATACCCAAAAAAATTGCACTGTTAAAAGCGGCCAAGCCAGCTCAACAAAC<br>ATGGCCAAATGCTCCTGCTACTGTTTGCCCTCATTGTCGTAAAGGTAAACACTGGGCAAGTAC<br>TTGCCACTCTAAGTCTGATATAGATGGCAATCCCTTGCCACAGAACCAGGGAAATGGGAAGC<br>AGGGCCAGTCCCAGGCCCCAGTATCAAATGGGACACCTCAGACTCAGACCAATATTGTGTTTC<br>TGCTTCAAGCGGTCCCAATACAGCCCCCAGCACAAGCAAATTTACCTACAGCCAACCCAGATG<br>GGTCCCAGTCGCTTCTTCTGTCTCAGTACAATGCTTGTCTACCTCCACAGTAGGGGCAGGGC<br>GGTCAATCTCTGTAGTACCACTCCTCTAAATTTACTACCGAATTCTTTGCCTTTAATTGTCCCCA<br>CGGGGGCCACTGGCCCTTTACCTCAAGGTTTGGTGGGCCTGGTGTTAGGTAGGGCATCCACC<br>TCTGCTAAAGGTATCATAGTTCATACTGGTCTCATTAATTCTGATTCCTCTGATGAGATTAAAA<br>TAATCGTGTCTGCCAAGGTTCCTGTTTCCATTCCGGCCAGTGAGTCAATTGCTCAACTACTTTT<br>ACTACCTAATATTGTTTTAAACAAAGGAGATAAGACAGGGGGCCCTGGGATGGGCTCTGGCG<br>GTGAAAAAGCCGCTTATTGGATTAAAGTAATTTCTAAACAACAGCCCACCTGCACCATACATA<br>TTAAAGGAAAAAAGTTTGAGGGCCTAGTAGATACTGGGGCTGATGTTTCTATTATTTCCTCTA<br>ATTTATGGCCTTCTTCCTGGCTTAAACATCCCACTAACATGGGACTAGTAAGGGTTGGAAAAG<br>CTGATGAAGTTCACCAAAGCACATTTATCTTGCCTTGCACTGGGCCTGATGGTCAAAAGGGAA<br>CAATTCAGCCTTATATCATGCCAATCCCCATTAATCTTTGGGGTAGATATTTGCTGGAACAATG<br>GGGGGCTGAAATTAATATTCCACATAACTCTTCTCGTGCTCCCAGTCAACATATAATGGAAAA<br>CGTGGGGACTGTTCCTGGACTCAGTCTCGGTCCAAAACATGAAGGAATTACTAAATTCCTTTA<br>TGGTTTAAAAGCATAATTTAACCACTCCCCACTCCCAATTCCATTTAGCATTGTTTACTTTAAAC<br>TTTCTAAATGTTCCTAAAGACAATACTCTGACTGCAGCCGAACACCATTATACAGGCAAAAAA<br>TTCTCCCTAAATGAAAGCAAGCCAGTGTTATGGAAAAACTCCCAGACAAATACCTGGGAACCT<br>GGAACAATTATAATGTGGGAAGAGGGTATGCTTGTGTTTCACCAGGAGATCATCAATCCCC<br>TGTCTGGGTGCCCACTAGAAGACTTTAACTTCGTGTGAATACTGACAATGAAAAACACAGGG<br>AAGAGATGTCCACGTCAGAGACTGCCCTCATACCTGGTGAGATCTGTGCCAACTCCTCAAAAA<br>CTGGCACACCAAATCAAATGGATCTCATTCAATCCTCCCTAATGGCAACAGAGACCCCTCTA<br>ACTAATCCCACTTCTCCTAATTACCTTTCTTTTTCTCCTTACAAACCTGAAAATCTCACCATTTCT<br>ATTAGCCTGAAAATAACATCCCTCTGTTCTTCTCTTCCTCCTTCAGCACTGGATCTCGCTTACAA<br>TAGGTTTTATTTAATAATTCTACTCCTTATACTTTCTGTCTCACCAGTTTCCCCTCACACTGATTT<br>GCCTGCTACACAAAATTATTCTTATTGGGCTTATGTGCCTTTTCCTCCACTTATTCGACCTCTCA<br>CCTGGATGAATGCTCCTGCGGAAATCTACACTAACGATAGTGTGTAGATGCCTGGAGCTATA<br>GATGACCATTGCCCTGCTCAACCAGGAGAAGAAGGCACTGCATTTAATGTTACTATGGGTTAT<br>AAATACCCTCCTCTGTGCCTCGGACATGCAACTCGTTGTATCCATCTAGAAACTCAAGTCTGGG<br>CTGCTTATCTTCTGGAGAGATTAGCTACAGGAAAATGGGGACATTTGGTCTCCGGCCTCTCCC<br>TTTGTCCTTTAAGACAAATGAAAGGGGAGTAATAGGAGATACCCCATACTTTCAATATAAAC<br>CTGTAGGAAAACTATGTCCTAAAAATTTTGAGGGCCCATCTAAAACTTTAATTTGGGGAGATT<br>GTGTTAACTCACATGCAGTAGTATTAAAAAATGACTCATATGCTTTAGTAATAGACTGGGCAC<br>CAAAGGGCTATTTAAAAAACACTTGCTCCTCTGGGGAGGGGAATTCCTGGAGGCTACTTATT<br>TTATTTCTTATTGGGAGGACGAGGATCATCATCCTACTTTGCATAGGTGGTTCGGCTCATT |
| 55 | GSTM2 | 2350979 | GAATCTGGATACTGTGTGCCGGACCAGCCAAAGAATCCTGTGTCAAAACCGAGAGAACGAATA |
| 56 | GSTM2 | 2350982 | AGCCCTGCTCGGTTTAGGCCTGTCTGCGGAATCCGCACCAACCAG |
| 57 | GSTM2 | 2350983 | TGCCCATGATACTGGGGTACTGGGACATCCGCG |

TABLE 13-continued

Subtyping Target Sequences

| SEQ ID NO. | Gene | Affy Probeset ID | Sequence |
|---|---|---|---|
| 58 | GSTM2 | 2350984 | CCCTCCATCTCTGACGCGACCTGCGGGCCATCT |
| 59 | GSTM2 | 2350985 | TGGAATACACAGACTCAAGCTATGAGG |
| 60 | GSTM2 | 2350986 | GTAATGGCACCCTCGTGTTCGGGCTCTGCCCACTCA |
| 61 | GSTM2 | 2350987 | TGCTGGAGCTGCAGGCTGTCTCTTCCCTGAGCC |
| 62 | GSTM2 | 2350990 | AAAGTGCAACGTGTCTCTGACTGCATCTCCTCTCCCAGCTTAGAGGTGTTAAGATCAGGAGT CTTCTGCCCAATTCCTCTCACTCCTGGCTGTCTAAACAGTCCTTCCATGATGTTCTGTGTCCACC TGCATTCGTTCATGTGACA |
| 63 | GSTM2 | 2350991 | AGCCTGGTGGCCCAACTGAGCTTCGCCGGTTTCCCATCCATCCAG |
| 64 | GSTM2 | 2350993 | CATGGACAACCATATGCAGCTGGGCATGATCTGCTACAATCCA |
| 65 | GSTM2 | 2350994 | AAACTGAAGCCAAAGTACTTGGAGGAACTCCCTGA |
| 66 | GSTM2 | 2350997 | CTCGTCTATGATGTCCTTGACCTCCACCG |
| 67 | GSTM2 | 2350998 | CTCCCAAGACCTGTGTTCTCAAAGATGGCTGTCTGGGGCAACA |
| 68 | GSTM2 | 2350999 | GAGTGAGGAGCCCATACTCAGCCTGCTGCCCAGGCTGTGCAGCGCAGCTGGACTCTGCATCC CAGCACCTGCCTCCTCGTTCCTTTCTCCTGTTTATTCCCATCTTTACTCCCAAGACTTCATTG |
| 69 | GSTM2 | 2351000 | CCTTCCTGTTAGTGGTTGTGTCTGCTTTAAAGGGCCTGCCTGGCCCCTCGCCTGTGGAGCTCA GCCCCGAGCTGTCCCCGTGTTGCATGAAGGAGCAGCATTGACTGGTTTACAGGCCCTGCTCCT GCAGCATGGTCCCTGCCTTAGGCCTACCTGATGGAA |
| 70 | SPRR1B | 2359522 | CCAGTTCTAAGGGACCATACAGAGTATTCCTCTCTTCACACC |
| 71 | SPRR1B | 2359523 | CCCACCCCCTCAGCTTCAGCAGCAGCA |
| 72 | SPRR1B | 2359525 | CCCAAAGTGCCCGAGCCCTGCCAGCCCAAGGTTCCAGAGCCATGCCACCCCAAG |
| 73 | SPRR1B | 2359526 | TGAGCCCTGCCCTTCAATAGTCACTCCAGCACCAG |
| 74 | SPRR1B | 2359527 | GCGTATGAGTCCCATTTGCCTTGCAATTAGCATTCTGTCTCCCCCAAAAAAGAATGTGCTATGA AGCTTTCTTTCCTACACACTCTGAGTCTCTGAATGAAGCTGAAGGTCTTAGTACCAGAGCTAGT TTTCAGCTGCTCAGAATTCATCTGAAGAGAGACTTAAGATGAAAGCAAATGATTCAGCTCCCT TATACC |
| 75 | S100A7 | 2359694 | GAGCAACACTCAAGCTGAGAGGTCCATAATAGGCATGATCGACATGTTTCACAAATACACCG GACGTGATGGCAAGATTGAGAAGCCAAGCCTGCTGACGATGATGAAGGAGAACTTCC |
| 76 | IFI16 | 2362396 | CCAAGTCTTGACTGAGAAACGGACCGGGCAGATGAGGGACTCCCACATATACCTGTTTCCTG CTCTTCCCGAAGACATTTTGCCACAAGCATATAATTCAGCTTCTGAAAAATACGGTCTTCCTCA CTGCAGACACCATGCCAGCGTTTTAAATCAAGTTGGCTACTCGTGCTGTTTA |
| 77 | IFI16 | 2362397 | AGTATGCAGTTTGCCTGTGGCAATATTAAACTCATCTGGAAGAAAGCACTTAAACCTATCCAG TTCCTCATCGGTGATGTTATCCAGGCTG |
| 78 | IFI16 | 2362398 | GTTAGCAAGAGTATCTCCTTATATTTACTCTCCATCTCACGACTTTTCAGCTTATAAGGGATCCA AACTATGTAAGATTATACCACCAAAAGTGATTCAACATTC |
| 79 | IFI16 | 2362403 | CACGCTAAAGGGCACCCACTGTCCTTAACAG |
| 80 | IFI16 | 2362404 | CTACCGGAAGTTCAGTGCATTTTCCAGGATTTTCAAGTCTTCGATGCTGTCATGTTGAGAGTCC ACTATCCACGTTTGTTTATCCAGGA |
| 81 | IFI16 | 2362405 | TGGGGCAATAGCAGAATAGGAGCAAGCCAGCACTAGTCAGCTAACTAAGTGACTCAACCAAG GCCTTTT |
| 82 | IFI16 | 2362406 | TTCTTAGCGTTTCTGGAGATTACAACATCCTGCGGTTCCGTTTCTGGGAACTTTACTGATTTAT CTCCCCCCTCACACAAATAAGCATTGATTCCTGCATTTC |
| 83 | IFI16 | 2362407 | TCTACTAAAAGGATTAGAGGTCATCAATGATTATCATTTTAGAATGGTTAAGTCCTTACTGAG |
| 84 | IFI16 | 2362408 | ATTTTCGAAGATATACCAACGCTTGAAGACCTGGCT |
| 85 | IFI16 | 2362409 | TGCTGGTCTCCTTAAGGCCAGGCTGGGCTAATGCAGTAGAGCTAGACTAAAGCACAGCTGAA CCCTCAAGCAGGAACTGAGAGCAAATTGTATTGAAACTGCTTCAG |
| 86 | IFI16 | 2362410 | CTGTCGGAGATCGTTTATATGTCTTCCTT |

TABLE 13-continued

Subtyping Target Sequences

| SEQ ID NO. | Gene | Affy Probeset ID | Sequence |
|---|---|---|---|
| 87 | IFI16 | 2362411 | CTCCACAAGCAGCACTGTCAAAACTGAAG |
| 88 | IFI16 | 2362413 | AAGGTGTCCGAGGAACAGACTCAGCCTCCCTCTCCTGCAGGAGCCGGCATGTCCACAGCCAT GGGCCGTTCCCCATCTCCCAAGACCTCATTGTCA |
| 89 | IFI16 | 2362416 | ACCCGAAAACAGTGGCCAAATGTCAGGTAACTCCCAGAAGAAATGTTCTCCAAAAACGCCCA GTGATAGTGAAGGTACTGAGTACAAC |
| 90 | IFI16 | 2362422 | ACCACAATCTACGAAATTCAGGATGATAGAGGAAAAATGGATGTAGTGGGGACAGGACAAT GTCACAATATCCCCTGTGAAGAAGGAGATAAGCTCCAACTTTTCTGCTTTCGACTTAGAA |
| 91 | IFI16 | 2362428 | CCCAAGAGCATGAAGCTACCCCAGGAACAGCGTCAGCTTCCATATCCTTCAGAGGCCA |
| 92 | IFI16 | 2362435 | CAGATACTGAAGGAAGGGAGTCATTTTCCAGGACCGTTCATGACCAGCATAGGCCCAGCTGA GAGCCATCCCCACACTCCTCAGATGCCTCCATCAACACCAAGCAGCAGTTTC |
| 93 | IFI16 | 2362439 | CAGATACTGAAGGAAGGGAGTCATTTTCCAGGACCGTTCATGACCAGCATAGGCCCAGCTGA GAGCCATCCCCACACTCCTCAGATGCCTCCATCAACACCAAGCAGCAGTTTC |
| 94 | IFI16 | 2362442 | CTGAAGAAGTTTCCATAGAAGACAGTGCCCAGAGTGACCTCAAAGAAGTGATGGTGCTGAAC GCAACAGAATCATTTGTATATGAG |
| 95 | IFI16 | 2362443 | TTTCATGCCACAGTGGCAACTGAGAATGAAGTCTTCCGAGTGAAG |
| 96 | IFI16 | 2362444 | TCACACTTGTGGCTGATGTGAATGCTGACCGAAACATGGAGATCCCAAAAGGATTGATTAGA AGTGCCAGCGTAACTCCTAAAATCAATCAGCTTTGCTCACAAACTAAAGGAAG |
| 97 | IFI16 | 2362445 | GTAAGCCCACACCATTGTTTTATAAAATTTCTCCTGCAACCTCCAATTTTTAAAGTCTTAACTTG TCAACTGGAGTTT |
| 98 | IFI16 | 2362446 | CTTGTCCAGGACAGTGCAGAGTTTATATCAACACACATATCCTTAGGATTTTGTTTCTTTGAGT TCTTCTCCATCTGTATCAATGACAACTTAATTTAATTGTGAATAAAAGAGTTGCTCTCCCAAGC CTGAATCCTGATTGTGACAACCAGAGTAAGAAATAAAATAGACTACTCTGCTTTAGAATGCAG CTATGTCTAACAGTTAGCTAGAATTCTGATCATTTGGACTCCAAAGTTTCTTGCCTCTTCTCATT CATTAATTCATCAGGAGACTGTAGAGCAACTAACTTCTGCATTAAATAATAAGAGAAATACGA AGCAAAAAGACTAAAAAAGTCACGTAGCTTAACTGCTCAATTTATAAATGGGGCAATAAAAT GCAAAAAAAGAAAAAAAGCTTGGTGAATTCTTAGGCTTACAGTGTGCCTTTCAGTCTCTACA CATCATGTAAATATTATGCTTAGCTGATTTAACTTCTTGTTTGAAGTACTGTTTCATACTCCATT ATACATGTCTTCTAGGGTGGCTTACTTTTAATTGTGCTGTTTTCTCTACACTCAGTTTAAATGAC TGTACATATATATGTGGTTGTAGAGTTAATGAATAATGAGCTACAAACCAGAACAATGTGACT AGATAGATAGGATGATCTAGATTTGAGATCTGGGCAGATTGGGAAAGAGTGACTATATGGA GAAGAAAGAAGTAGTTACATATTGAAATAACAGTCTACTTAATGAGGACGTGCAACATTCTTT CTCAAACTTACAAAGTGCCATAAAAAGCCTCTATTCTCTGCTCTTGGGCAGGTGTGAAAGAAA CCTACCAAATTAATCAGATTTTTCTGTATCCAGGCTCCTTA |
| 99 | IFI16 | 2362447 | GGTGCATGGACGACTGACCACAATCAACTGTGAGGAAGGAGATAAACTGAAACTCACCTGCT TTGAATTGGCACCGAAAAGTGGGAATACCGGGGAGTTGAGATCTGTAATTC |
| 100 | IFI16 | 2362450 | GTCATCAAGACCAGGAAAAACAAGAAAGACATACTCAATCCTGATTCAAGTATGGAAACTTC ACCAGACTTTTTC |
| 101 | IFI16 | 2362451 | TGGATGTCATTGACGATAATGTTTATGGAGATAAGGTCTAAGTGCCTAAAAAAATGTACATAT ACCTGGTTGAAATACAACACTATACATACACACCACCATATATACTAGCTGTTAATCCTATGGA ATG |
| 102 | IFI16 | 2362452 | TCTACAACTTCTATAATTTGAAAAA |
| 103 | LAMC2 | 2371146 | CTGCCTCTGCTTCTCGCTCCTCCTGCCC |
| 104 | LAMC2 | 2371152 | CTCTTAGTGCTCGATGTGACAACTCCGGACGGTGCAGCTGTAAACCAGGTGTGACAGGAGCC AGATGCGACCGATGTCTGCCAGGCTTCCACATGCTCACGGATGCG |
| 105 | LAMC2 | 2371153 | CAAGTGTGACTGTGACCCAGCTGGCATCGCAGGGCCCTGTGACGCGGGCCGCTGTGTCTGCA AGCCAGCTGTCACTGGAGAACG |
| 106 | LAMC2 | 2371155 | TCAGGTTACTATAATCTGGATGGGGGAACCCTGAGGGCTGTACCCAGTGTTTCTGCTATGG GCATTCAGCCAGCTGCCGCAGCTCTGCAGAATACAGTGTCCATAAGATCACCTCTACCTTTC |
| 107 | LAMC2 | 2371157 | CAACGAAATGGGTCTCCTGCAAAGCTCCAATGGTCACAGCGCCATCAAGATGTGTTTAGCTCA GCCCAACGACTAGACCCTGTCTA |

TABLE 13-continued

Subtyping Target Sequences

| SEQ ID NO. | Gene | Affy Probeset ID | Sequence |
|---|---|---|---|
| 108 | LAMC2 | 2371158 | GCCTGTCCTTTGACTACCGTGTGGACAGAGGAGGCAGACACCCATCTGCCCATGATGTGATTC<br>TGGAAGGTGCTGGTCTACGGATCACAGCTCCCTTGATGCCACTTGGCAAGACACTGCCTTGTG<br>GGCTCACCAAGACTTA |
| 109 | LAMC2 | 2371159 | AGCTGAGTTACTTTGAGTATCGAAGGTTACTGCGGAATCTCACAGCCCTCCGCATCCGAGCTA<br>CATATGGAGAATA |
| 110 | LAMC2 | 2371160 | ATGTCCTGTTGGGTACAAGGGGCAATTCTGCCAGGATTGTGCTTCTGGCTACAAGAGAGATTC<br>AGCGAGACTGGGGCCTTTTGGCACCTGTATTCCTTGTAACTGTCA |
| 111 | LAMC2 | 2371161 | AGAATCCTGACATTGAGTGTGCTGACTGCCCAATTGGTTTCTACAACGATCCGCACGACCCCC<br>GCAGCTGCAAGCCATGTCCCTGTCATAACGGGTTCAGCTGCTCA |
| 112 | LAMC2 | 2371162 | GTGTGCAATAACTGCCCTCCCGGGGTCAC |
| 113 | LAMC2 | 2371164 | CCCTTTGGTGAACATGGCCCAGTGAGGCCTTGTCAGCCCTGTCAATGCAACAACAATGTGGAC<br>CCCAGTGCCTCTGGGAATTGTGACCGGCTGACAGGCAGGTGTTTGAAGTGTATCCACAACAC<br>AGCCGGCATCTACTGCGACCAGTGCAAAGCAGGCTACTTCGGGGACCCA |
| 114 | LAMC2 | 2371165 | CCATGGGCTCAGAGCCTGTAGGATGTCGAAGTGATGGCACCTGTGTTTGCAAGCCAGGATTT<br>GGTGGCCCCAACTGTGAGCATGGAGCATTCAGCTGTCCAGCTTGCTATAATCA |
| 115 | LAMC2 | 2371166 | ATGGATCAGTTTATGCAGCAGCTTCAGAGAATGGAGGCCCTGATTTCAAAGGCTCAGGGTGG<br>TGATGGAGTAGTACCTGATACAGAGCTG |
| 116 | LAMC2 | 2371167 | GTGCTAGCAGATCCCTTGGTCTCCAGTTGGCCAAGGTGAGGAGCCAAGAGAACAGCTACCAG<br>AGCCGCCTGGATGACCTCAAGATGACTGTGGAAAGAGTTCGGGCTCTGGGAAGTCAGTACCA<br>GAACCGAGTTCGGGATACTCACA |
| 117 | LAMC2 | 2371169 | CCTCAGACCACTACGTGGGGCCAAATGGCT |
| 118 | LAMC2 | 2371170 | CCACGTTGAGTCAGCCAGTAACATGGAGCAACTGACAAGGGAAACTGAGGACTATTCCAAAC<br>AAGCCCTCTCACTGGTGCGCAAGGCCCTGCATGAAGGAGTCGGAAGCG |
| 119 | LAMC2 | 2371171 | CCCTGGCCCAGCAGTTGACAAGGGAGGCCACTCAAGCGGAAATTGAAGCAGATAGGTCTTAT<br>CAGCACAGTCTCCGCCTCCTGGATTCAGTGTCTCGGCTTCA |
| 120 | LAMC2 | 2371172 | AGAGGATCAAACAAAAAGCGGATTCACTCTCAAGCCTGGTAACCAGGCATATGGATGAGT |
| 121 | LAMC2 | 2371174 | CTGCTTTCCCGTGCCAATCTTGCTAAAAGCAGAGCACAAGAAGCACTGAGTATGGGCAATGC<br>CACTTTTTATGAAGTTGAGAGCATCCTTAAAAAC |
| 122 | LAMC2 | 2371175 | GGCCCTGGAAATCTCCAGTGAGATTGAACAG |
| 123 | LAMC2 | 2371176 | ATCGACATGTGTGTTGGTGCCAGTAGCACCAAACACAAGGGTGGTGTGGAGGGAAAAAGAA<br>CATTGAGCTTATTTTAACCTCTGAGGCTCAGAGCCCTGTTGTGGCCCATGGGAGCCCCAGATT<br>AAAAGACTATGGTAGCAAAGACGCATGACAGAGAATGATGTGTTTTTTTGTCCTCCGGGTTTT<br>CCCAAATGGTTCCTAACTCTGTTCAACATTTGGTGAGCATTGAACTGAGAGAAGCACTGTC<br>TGGCCGCTGACCTTCCTAGTCATACCCCCAGATTAGCTTGTTTGAGGCAGAGCTTGGCAAAGT<br>ACCCCTGTCCCTAAGTCTGATTCTCTCATTATTCATCTAATTTACTCCATCAGGGCCCGGCTGCC<br>GCTGTATTTTTTCTA |
| 124 | LAMC2 | 2371178 | CCCAGAAGGTTGATACCAGAGCCAAGAACGCTGGGGTTACAATCCAAGACACACTCAACACA<br>TTAGACGGCCTCCTGCA |
| 125 | LAMC2 | 2371179 | CCCTGTTTTACCGTTGCTAAGATGGGTCACTGAACACCTATTGCACTTGGGGGTAAAGGTCTG<br>TGGGCCAAAGAACAGGTGTATATAAGCAACTTCACAGAACACGAGACAGCTTGGGAATCCTG<br>CTAAAGAGTCTGGCCTGGACCCTGAGAAGCCAGTGGACAGTTTTAAGCAGAGGAATAACATC<br>ACCACTGTATATTTCAGAAAGATCACTAGGGCAGCCGAGTGGAGGAAAGCTTGAAGAGGGG<br>GTTAGAGAGAAGGCAGGTTGAGACTACTTAAGATATTGTTGAAATAATTGAAGAGAGAAATG<br>ACAGGAGCCTGCTCTAAGGCAGTAGAATGGTGGCTGGGAAGATGTGAAGGAAGATTTTCCC<br>AGTCTGTGAAGTCAAGAATCACTTGCCGGCCGGGTG |
| 126 | LAMC2 | 2371182 | GGAGCAGAAGCTTTCCCGAGCCAAGACCCAGATCAACAGCCAACTGCGGCCCATGATGTCAG<br>AGCTGGAAGAGAGGGCACGTCAGCAGAGGGCCACCTCCATTTGCTGGAGACAAGCATAGA<br>TGGGATTCTGGCTGATGTGAAGAACTTGGAGAACATTAGGGACAACCTGCCCCCAGGCTGCT<br>ACAATACCCAGGCTCTTG |
| 127 | LAMC2 | 2371183 | TCTCAACTGAGGTTCTTGGGATACAGATCTCAGGGCTCGGGAGCCATGTCAT |
| 128 | LAMC2 | 2371184 | GTTTAATGGGTATGCTCAGGTCAACTGACCTGACCC |
| 129 | LAMC2 | 2371185 | GTGGTTGTCTTATTGCACCATACTCCTTGCTTCCTGATGCTGGGCAATGAGGCAGATAGCACT<br>GGGTGTGAGAATGATCAAGGATCTGGACCCCAAAGAATAGACTGGATGG |

TABLE 13-continued

Subtyping Target Sequences

| SEQ ID NO. | Gene | Affy Probeset ID | Sequence |
|---|---|---|---|
| 130 | LAMC2 | 2371186 | TAAGTGGAGTCCTGGAATTTGGACAAGTGCTGTTGGGATATAGTCAACTTATTCTTTGAGTAATGTGAC |
| 131 | LAMC2 | 2371187 | TTCTTGCTGATCAGAGTTCCTCCTACTTACAACCCAGGGTGTGAACATGTTCTCCATTTTCAAGCTGGAAGAAGTGAGCAGTGTTGGAGTGAGGACCTGTAAGGCAGGCCCATTCAGAGCTATGGTGCTTGCTGGTGCCTGCCACCTTCAAGTTCTGGACCTGGGCATGACATCCTTT |
| 132 | LAMC2 | 2371188 | AAAGTGTGGCTTGGGCATTGAAAGAGGTAAAATTCTCTAGATTTATTAGTCCTAATTCAATCCTACTTTTCGAACACCAAAAATGATGCGCATCAATGTATTTTATCTTATTTTCTCAATCTCCTCTCTCTTTCCTCCACCCATAATAAGAGAATGTTCCTACTCACACTTCAGCTGGGTCACATCCATCCCTCCATTCATCCTTCCATCCATCTTTCCATCCATTACCTCCATCCATCCTTCCAACATATATTTATTGAGTACCTACTGTGTGCCAGGGGCTGGTGGGACAGTGGTGACATAGTCTCTGCCCTCATAGAGTTGATTGTCTA |
| 133 | LAMC2 | 2371189 | GAACATATGTTGCAAGACCCTCCCATGGGGGCACTTGAGTTTTGGCAAGGCTGACAGAGCTCTGGGTTGTGCACATTTCTTTGCATTCCAGCTGTCACTCTGTGCCTTTCTACAACTGATTGCAACAGACTGTTGAGTTATGATAACACCAGTGGGAATTGCTGGAGGAACCAGAGGCACTTCCACCTTGGCTGGGAAGACTATGGTGCTGCCTTG |
| 134 | CFH | 2373338 | ATTTGCCTTATGTTATGGGCTATTTGT |
| 135 | CFH | 2373340 | ATTCTGACAGGTTCCTGGTCTGACCAAACATATCCAGAAGGCACCCAGGCTATCTATAAATGCCGCCCTGGATATAGATCTCTTGGAAATGTAATAATGGTATGCAGGAAGGGAGAATGGGTTGCTCTTAATCCATTAAGG |
| 136 | CFH | 2373341 | TTAATATTGTAGCAATTATGCCTGAATTATATCACTATTGCCAGTC |
| 137 | CFH | 2373342 | TGGACATCCTGGAGATACTCCTTTTGGTACTTTTACCCTTACAGGAGGAAATGTGTTTGAATATGGTGTAAAAGCTGTGTATACA |
| 138 | CFH | 2373344 | CAATTGCTAGGTGAGATTAATTACCGTGAATGTGACACAGATGGATGGACCAAT |
| 139 | CFH | 2373345 | GTCAGTAGTGCAATGGAACCAGATCGGGAATACCATTTTGGACAAGCAGTACGGTTTGTATGTAACTCAGGCTACAAGATTGAAGGAGATGAAGAAATGCATTGTTCAGACGATGGTTTTTGGA |
| 140 | CFH | 2373346 | CTGAGGAAATCTTGGCTAAATAGTGATGACACAAAAACAGGTCAGTTACTTTTCAGAGATGTAATGACAATGAGTTAAATCAATGTCTTTGACAAAAAGTCCTGTTGATAATTCCTGTCTTATCAATAACTAGAAGATGTGTTATTTTTGCAGGTCATTCAGTGAAAACATCACAATAAAACTATATTTATGATCAATTTTATTTATACAGTTGATGAATGTTACTGGTCACTATTTATTTCAAGAAGGCTAATTTATCCTGAAACTAAATAAAATCAGAAGCATAATTTTAATCAGAATTTTAACTTTCTTCAGATAAATCATTTATTAAGCGGTCAAGTCAAAACAGAACTTTTGTTTGGTTGACTGATTTACCTGATGGAAACAACATTTCTGTTTTCATATAATTATGTCCTGGTCACAGTCCTTTAATTTGC |
| 141 | CFH | 2373347 | AATGGATCTCCTATATCTCAGAAGATTATTTATAAGGAGAATGAACGATTTCAATATAAATGTAACATGGGTTATGAATACAGTGAAAGAGGAGATGCTGTATGCACTGAATCTGGATGGCGTCCGTTGCCTTCATGTGAA |
| 142 | CFH | 2373349 | AAATGGTGACTACTCACCTTTAAGGATTAAACACAGAACTGGAGATGAAATCACGTACCAGTGTAGAAATGGTTTTTATCCTGCAACCCGGGGAAATACAGCAAAATGCACAAGTACTGGCTGGATACCTGCTCCGAGAT |
| 143 | CFH | 2373352 | GGTCTATATCATGAGAATATGCGTAGACCATACTTTCCAGTAGCTGTAGGAAAATATTACTCCTATTACTGTGATGAACATTTTGAGACTCCGTCAGGAAGTTACTGGGATCACATTCATTGCACACAAGATGGATGGTCGCCAGCAGTACCA |
| 144 | CFH | 2373353 | TTTGTACAGGGTAAATCTATAGACGTTGCCTGCCATCCTGGCTACGCTCTTCCAAAAGCGCAGACCACAG |
| 145 | CFH | 2373354 | ATGGCTGGTCTCCTACTCCCAGATG |
| 146 | CFH | 2373364 | CTTCTGATCGAAGGTCATCCCTCTCCAGCTTGAGTGGATCAAAGATGACAAGGGCCAATGGAACCAAGTTTGAGTCTTGCCAGGTCAATACTTGGGTCCTGAGTATGGTGACTAGTATCTGTTTTTGTTATGTGTGTATTATTCCAGCCAGAATGGGAAATGCTAATTCAGCTCCTCCAGG |
| 147 | CFH | 2373371 | AACAGCAGATGGTGAAACATCAGGAT |
| 148 | CFH | 2373373 | CCTGATCGCAAGAAAGACCAGTATAAAGTTGGAGAGGTGTTGAAATTCTCCTGCAAACCAGGATTTACAATAGTTGGACCTAATTCCGTTCAGTGCTACCACTTTGGATTGTCTCCTGACCTCCCAATATGTA |
| 149 | CFH | 2373377 | AGCAAGTACAATCATGTGGTCCACCTCCTGAACTCCTCAATGGGAATGTTAAGGAAAAACGAAAGAAGAATATGGACACAGTGAAGTGGTGGAATATTATTGCAATCCTAG |

TABLE 13-continued

Subtyping Target Sequences

| SEQ ID NO. | Gene | Affy Probeset ID | Sequence |
|---|---|---|---|
| 150 | CFH | 2373378 | TAATGAAGGGACCTAATAAAATTCA |
| 151 | CFH | 2373379 | CCTGTGGAGATATACCTGAACTTGAACATGGCTGGGCCCAGCTTTCTTCCCCTCCTTATTACTATGGAGATTCAGTGGAATTCAATTGCTCAGAATCATTTACAATGATTGGACACAGATCAATTACGTGTATTCATGGAGTATGGACCCAACTTCCC |
| 152 | CFH | 2373381 | CTTAAGAAGTGCAAATCATCAAATTTAATTATACTTGAGGAACATTTAAAAAACAAGAAGGAATTCGATCATAATTCTAACATAAGGTACAGATGTAGAGGAAAAGAAGGATGGATACACACAGTCTGCA |
| 153 | CFH | 2373382 | TGGCACAAATACAATTATGCCCACCTCCACCT |
| 154 | CFH | 2373383 | GAAGATGGCAGTCAATACCACTCTG |
| 155 | CFH | 2373384 | CCTCAGATAGAACACGGAACCATTAATTCATCCAGGTCTTCACAAGAAAGTTATGCACATGGGACTAAATTGAGTTATACTTGTGAGGGTGGTTTCA |
| 156 | CFH | 2373385 | GATTTCTCATGGTGTTGTAGCTCACATGTCAGACAGTTATCAGTATGGAGAAGAAGTTACGTACAAATGTTTTGAAGGTTTTGGAATTGATGGGCCTGCAATTGCAAAATGCTTAGGAGAAAA |
| 157 | CFH | 2373386 | TATTCTTCATTCAAAGTGTAAGTGGTACCAATAAGAAAGTAAACAGGGACTCTAGAAATTCATAAGGTTTTCTTGAATATTCTGGACTGCTGTGGGAAATTATAGCTGTAGTAATT |
| 158 | CFH | 2373387 | TGTGAACTTTAAGCATCCTCTGATGTATATTCTCAGACTTCTCATCTCTGTTCTTAGGGCACAGCTGCCTCTACTCATCAATCTCCACATTATTCAATCTTCTGTCAGTTTATCAACAATCTGCCTATAAGTACATTTTCTGAAATATTTTAAAAAATCATTATAAGTATTTCACATTTGATAGAAGCAAAAAATTTGGAAATGCACACACAATATAGGTGGTGTATTATTCCGTTTTCACACTGCTGTAAAGACCTTCCTGAGACTGGGTAATTTATAAAAGAAAAAATTTTAATTGATCACAGTTCCTCATGACTGAGGAGGTGTCATGAAACTTACCATTACCGCTGAAGGGAAGCAGGCACCTTCTTCACAAGGTGGCAGGAGAGAGAGGAGTGAGTGAAGGAGGAACTTCTAAACAGTTATTAAATCATCATATCTTGTGAGAACTCACTCACCATCGTGAGAACAGCATGTGGGAAACTGCCACCATGATCCAATCACTTCCCACCAGGTCTCTCTCTCAACACCTGGAGATTATTATTCAAGATGAGATTTGGGTGAGGACACAAAGCCTAACCATATCAGGTGGCAAGTATGGACAAAAATAATGTGAACAAAAAAATGTGTAATCTCAATTGCTACGGCTACCAATATTTCTTCAG |
| 159 | CFH | 2373388 | CAGATTGTCTCAGTTTACCTAGCTTTGAA |
| 160 | CFH | 2373389 | AGCAAGTGACTTACACTTGTGCAACATATTACAAAATGGATGGAGCCAGTAATGTAACATGCATTAATAGCAGATGGACAGGA |
| 161 | CFH | 2373391 | ACACCTCCTGTGTGAATCCGCCCACAG |
| 162 | CFH | 2373392 | ACGTTATCAATGTAGGAGCCCTTATGAAATGT |
| 163 | CFH | 2373394 | TCCCGTTGTCAGTATATGCTCCAGCTTCATCAGTTGAGTACCAATGCCAGAACTTGTATCAACTTGAGGGTAACAAGCGAATA |
| 164 | CFH | 2373396 | TCCGTGTGTAATATCCCGAGAAATTATGGAAAATTATAACATAGCATTAAGGTGGACAGCCAA |
| 165 | CFH | 2373397 | TTGAATTTGTGTGTAAACGGGGATA |
| 166 | CFH | 2373398 | AACTGGAGTATCCAACTTGTGCAAAA |
| 167 | CFH | 2373435 | TCCCGTTGTCAGTATATGCTCCAGCTTCATCAGTTGAGTACCAATGCCAGAACTTGTATCAACTTGAGGGTAACAAGCGAATA |
| 168 | CFH | 2373437 | AACTGGAGTATCCAACTTGTGCAAAA |
| 169 | CFH | 2373438 | TTATTCAGAACTTTAGTATTAAATCA |
| 170 | CFH | 2373439 | TATTCATACGTAAAATTTTGGATTAATTTGTGAAAATGTAATTATAAGCTGAGACCGGTGGCTCTCTTCTTAAAAGCACCATATTAAA |
| 171 | CFH | 2373445 | ACCATACTTTCCAGTAGCTGTAGGAA |
| 172 | ELF3 | 2375012 | GAAGCCGGTTCTCCCACATTCCTGGGTGAGGGACTGGGTGGAGGGTGTGCCTGCCTCAGGCTCCTTGGGGGAGGCCCCCTGAAGGGCTGGGAAAATCCTACTGAGCCCCAGGCTCTCCTGCCTGCACTGGCCCAGTGCGGGGCGGGGGGCGGGGGATCCTGGACATTAACTCTCTCCTAGGCACCTGGGAGCTTCAGAGAGGAAGAAGGTAAGGTAAGAAGCAGATTCTCTGCGCAGGACTTTCTTAGTCCTCAGGCTATAGAGTTAAAGAAAGAAGTATCTGTAGAAGGTGGAGTCACCTTTTGTTTGAGTAACCGTTTCACCCACCCTGGCTGAGGGTGGCCAGGAACTCCCCAAGTTGTGCATTAATGGAGGGGGTCACACAGATCCTACATTTTTTGTTTTGTTTTTTTTTTTGAGACGCAGTGATTACAGGTGTGAGCCACCGGATCCTACATTTCAAATGCATAAAAATCTAGATATGGGCTGGGCGCAGTAGCTCATGCCTGTAATCCCAGCACTTTGGGAGGCTGAGGCAGGCAGATCATGAGG |

TABLE 13-continued

Subtyping Target Sequences

| SEQ ID NO. | Gene | Affy Probeset ID | Sequence |
|---|---|---|---|
| | | | TCAGGAGATCGAGTCCATCCTGGCTAACATGGTGAAACCCCGTCTCTACTAAAAATACAGAAA
GCCGGGCATGGCAGCGGGCGCCTGTAATCCCAGCTACTCGGAAAGCTGAGGCAGGAGAATC
GCTTGAACCCAGGAGTCAGAGGTTGCAGTGAGCAGAGATCACGCCACTGCACTCCAACCTGG
GCGACAGAGCGAGACTCCACCTCAAAACAAAATAAACAAAATACTAGATCTGGAAGAGATCT
TAGGGATTATTAAATTCAGACAACCTCATTTTTTATAGATGGGGAAACAAGCACAGACTCCAA
GGGTCTCATCCAAGATCACACAGTTGCAGATGCTGGCTACAAGTCTCCTGCCTCAACCACCTG
TATTACCCCATTCAGGGTCTCAAGAAGGGTCTATAAGACACTATCCATTGTGTTTCGGGCTGA
GTCCATAGAGACAACCACAGACATGGGGGACTCTGCCCACAGGGAAGGCAAGGGCTCTGGC
CATGGAGCTGGATGGGAAGACTCTGAAGCCCGAAGACATTGAATCCTGTGCAGGGAAAGAG
CGAGGGTTTTGTGTACAACACACCTGCATACCTGGATGTGAATCTCAGCTCCACCCCTTCACCA
ACTCTGTGTGGCCTGGGCAAGCCATTCTAAGGGAACCCTCCACACTGCAACTTTCATGTCTAT
AAAATGGGAATAACCATGCATTCCTTACAGGACTTTTTTGGTGTGAGGATTAAATGAGAGAAT
ATGTTGAAAAGTGCTTGGTAAATATATTAATACTATGCATTCCCTCTTCTTTGAATGACGTGAC
CCAGGTAGTCAGGCTTCTGACCACTAGAGGGCAGCAGAAGGTACTGGAAAACTGGGCCGAG
TGAACCAGAGATTAGATGGGGTCCAGAGAGCAGGGATGAACTTACCCGTGTGGATTCTGGC
AACTC |
| 173 | ELF3 | 2375013 | GCCTCTTTGTTGCTGAATCTCTGGAATTT |
| 174 | ELF3 | 2375014 | TGACAATCATTAAACCAGCCGGGCCTGATTTCCCAGCACTGCCTGCTAAGATCCGGGCCAAGT
GGCACTGAATATGCAAATCACCTGGGGCCAGGAGCCCAGTCTAAAGGCCAGGAAATCCCCTC
CATCCAATGAGACACCAGCTCAGGTTACTGCAGGGGACACACTATAAAGCCCTGAGCTCAGG
GAGGAGCTCCCTCCAGGCTCTATTTAGAGCCGGGTAGGGGAGCGCAGCGGCCAGATACCTCA
GCGCTACCTGGCGGAACTGGATTTCTC |
| 175 | ELF3 | 2375015 | GGGTCCAGAGGATTTGCAGTTCTGAACCTGCACACTCCAGTCTAGGATCTCCGAGCAAGAGC |
| 176 | ELF3 | 2375016 | GAATGGCCATGACGCCGCTAGTCTGGCTCCAGGGCCCCAGAGATCTGAGGAGGGAAGCCCA
GCTGGAGGCTCCTGTGGTCCTGCCCTGGTCTGAGATCTTGGAGCCCTTCTTGAAGAGACGGT
GTCCGCAGAGTTGCTGATCTTCCTGCCCCTGGGGCTACTCTTGCCCAGGGTTGGGCAA |
| 177 | ELF3 | 2375017 | GCTGCAACCTGTGAGATTAGCAACATTTTTAGCAACTACTTCAGTGCGATGTACAGCTCGGAG
GACTCCACCCTGGCCTCTGTTCCCCCTGCTGCCACCTTTGGGGCCGATGACTTGGTACTGACCC
TGA |
| 178 | ELF3 | 2375018 | TCTAAGGGCCTGTTAGACAAATGGGGGAATAGGCAGGGAGGAGGGTCTCTAGGCAAATTCC
AGGGCTAGAGGCTGAGACTTAGTGACTGAGGTGCTGGGGGTTGTGGGCTGTGACAGGCAG
AGGGAGGTGTCAGATACCAGGACAAGGGTGTTGTGAATGCTACCTCC |
| 179 | ELF3 | 2375020 | CAGTTCTGGTCGAAGACGCAGGTTCTGGACTGGATCAGCTACCAAGTGGAGAAGAACAAGTA
CGACGCAAGCGCCATTGACTTCTCACGATGTGACATGGATGGCGCCACCCTCTGCAATTGTGC
CCTTGAG |
| 180 | ELF3 | 2375021 | CCACATGTTGAGCTGAGTCGAGTTCAGTGTGGCCGTAGGCAG |
| 181 | ELF3 | 2375022 | TTCCAGCTCTTCTGATGAGCTCAGTTGGATCATTGAGCTGCTGGA |
| 182 | ELF3 | 2375023 | CCCTCCACAGAGTGCTAGAGATGACCCCCTCCCCAGACTTCTTCCTCCCTCAATTAGAAA |
| 183 | ELF3 | 2375024 | GGGCAGCCCCTTTGCCCAGGAGCTGCTGGA |
| 184 | ELF3 | 2375025 | GCAGCTGTGGCGCAGGAGCCCCCTCC |
| 185 | ELF3 | 2375026 | TGAGAGCCAGCAGCGTGGTTGAGCAGAGGGTGGGCCGGCAGGGGACTTACTCTGACCCCGC |
| 186 | ELF3 | 2375027 | TGGTGCTTCTCGGAGCTCCCACTCCTCAGACTCCGGTGGAAGTGACGTGGACCTGGATCCCAC
TGATGGCAAGCTC |
| 187 | ELF3 | 2375028 | ATGGTTTTCGTGACTGCAAGAAGGGGGATCCCAAGCACGGGAAGCGGAAACGAGGCCGGCC
CCGAAAGCTGAGCAAAGAGTACTGGGACTGTCTCGAGGGCAAGAAGAGCA |
| 188 | ELF3 | 2375030 | AGAGGGGACACCTGGATGGCAAACTGATGGAGGCT |
| 189 | ELF3 | 2375031 | CCCACCTGTGGGAGTTCATCCGGGACATCCTCATCCACCCGGAGCTCAACGAGGGCCTCATGA
AGTGGGAGAATCGGCATGAAGGCGTCTTC |
| 190 | ELF3 | 2375033 | GTACTACTACAAACGGGAGATCCTGGAACGGGTGGATGGCCGGCGACTCGTCTACAAGTTTG
GCAAAAACTCAAGCGGCTGGAAGGAGGAAGAGGTTCTCCAGAGTCGGAACTGA |
| 191 | ELF3 | 2375034 | TCACGGACCACTCGAGGCCTGCAAACCTTCCTGGGAGGACAGGCAGGCCAGATGGCCCCTCC
ACTGGGAATGCTCCCAGCTGTGCTGTGGAGAGAAGCTGATGTTTTGGTGTATTGTCAGCCA
TCGTCCTGGGACTCGGAGACTATGGCCTCGCCTCCCCACCCTCCTCTTGGAATTACAAGCCCTG
GGGTTTGAAGCTGACTTTATAGCTGCAAGTGTATCTCCTTTTATCTGGTGCCTCCTCAAACCCA
GTCTCAGACACTAAATGCAGACAACACCTTCCTCCTGCAGACACCTGGACTGAGCCAAGGAG |

TABLE 13-continued

Subtyping Target Sequences

| SEQ ID NO. | Gene | Affy Probeset ID | Sequence |
|---|---|---|---|
| | | | GCCTGGGGAGGCCCTAGGGGAGCACCGTGATGGAGAGGACAGAGCAGGGGCTCCAGCACC TTCTTTCTGGACTGGCGTTCACCTC |
| 192 | ELF3 | 2375035 | GAAATTTGGGCCTTTGGATCGAATATGGTCAAGAGGTTGG |
| 193 | ELF3 | 2375036 | TGCTGTCATGACACCGCTCGAGTGACCTTGACCTTGACCAAGTCTGTCCTGTTTAGGACTGATT TTTCCTATTAGGCTAGGGTTTGGACCTGATGTTCTCAAGATGTCTAGAATTGCATGGCTGGCC TTGTGGAATAGATGGTTTTGCATTCCAGCCAAGTGTGCTGTAAACTGTATATCTGTAATATGA ATCCCAGCTTTTGAGTCTGACAAAATCAGAGTTAGGATCTTGTAAAGGAAAAAAAAAAAAAA ACAAAACAAAATGGAGATGAGTACTTGCTGAGAAAGAATGAGGGAAGGAGTTGGCATTTGT TGAAAGTGTAGTCTTTTTCTCTTTTTTTTTAATTGCAACTTTTACTTTAGATTTAGGAGGTCGT GCGCAGGTTTGTTACATGGGTATATTGTGTGATGCTGAGCTTGGGATGCGAATGATCCTGTCA CCCAGGTAGTGAGTATAGCACCCAGTGAAACTGTAGTCTCATGCCAGGCACTGTGCTAGCCC ACTCTGGCTCATTTAATCCTCTCCTAAGAAGAGAGGAGACACAGCGTCCCCATTTGACAGATG CAGAAAGAGGTTCCACAGGTGTGCCTTGATTCGTCCTAAAACCGTTTCCCGGAAGCTTTTCCT GGTGTGGGCGCTTCTAACCTAATCCTC |
| 194 | ELF3 | 2375037 | TGGAAATACCAATCAGATTGTTGGCTGAAGTGATGTG |
| 195 | BTG2 | 2375665 | CAGGGTAACGCTGTCTTGTGGACCCGCACTTCCCACCCGAGACCTCTCACTGAGCCCGAGCCGC |
| 196 | BTG2 | 2375666 | GGGAACCGACATGCTCCCGGAGATCGCCGCCGCCGTGGGCTTCCTCTCCAGCCTCCTGAGGA CCCGGGGCTGCGTGAGCGAGCAGAGGCTTAAGGTCTTCAGCGGGGCGCTCCA |
| 197 | BTG2 | 2375671 | CCCTATGAGGTGTCCTACCGCATTGGGGAGGACGGCTCCATCTGCGTCTTGTACGAGGAGGC CCCACTGGCCGCCTCCTGTGGGCTCCTCACCTGCAAGAACCAAGTGCTGCTGGGCCGGAGCA GCCCCTCCAAGAACTACGTGATGGCAGTCTCCAGCTA |
| 198 | BTG2 | 2375672 | CGTGCTCATGCTGCCGTGACAACAGGCCACCACATACCTCAACCTGGGGAACTGTATTTTTAA ATGAAGAGCTATTTATATATATTATTTTTTTTAAGAAAGGAGGAAAAGAAACCAAAAGTTTTT TTTAAGAAAAAAAATCCTTCAAGGGAGCTGCTTGGAAGTGGCCTCCCCAGGTGCCTTTGGAG AGAACTGTTGCGTGCTTGAGTCTGTGA |
| 199 | BTG2 | 2375673 | AGGGGCCTGTAGATGTTGCTTTCCAGCCAGGAATCTAAAGCTTTGGGTTTTCTGAGGGGGGG GAGGAGGGAACTGGAGGTTATTGGGGTTAGGATGGAAGGGAACTCTGCACAAAACCTTTGC TTTGCTAGTGCTGCTTTGTGTGTATGTGTGGCAAATAATTTGGGGGTGATTTGCAATGAAATT TTGGGACCCAAAGAGTATCCACTGGGGATGTTTTTTGGCCAAAACTCTTCCTTTTGGAACCAC ATGAAAGTCTTGATGCTGCTGCCATGATCCCTTTGAGAGGTGGCTCAAAAGCTACAGGGAAC TCCAGGTCCTTTATTACTGCCTTCTTTTCAAAAGCACAACTCTCCTCTAACCCTCCCCTCCCCCTT CCCTTCTGGTCGGGTCATAGAGCTACCGTATTTTCTAGGACAAGAGTTCTCAGTCACTGTGCA ATATGCCCCCTGGGTCCCAGGAGGGTCTGGAGGAAAACTGGCTATCAGAACCTCCTGATGCC CTGGTGGGCTTAGGGAACCATCTCTCCTGCTCTCCTTGGGATGATGGCTGGCTAGTCAGCCTT GCATGTATTCCTTGGCTGAATGGGAGAGTGCCCCATGTTCTGCAAGACTACTTGGTATTCTTG TAGGGCCGACACTA |
| 200 | BTG2 | 2375674 | CCCTGCCTTTTTAGAAGCAGCCTCATGGTCTCATGCTTAATCTTGTCTCTCTTCTCTTCTTTATGA TGTTCACTTTAAAAACAACAAAACCCCTGAGCTGGACTGTTGAGCAGGCCTGTCTCTCCTATTA AGTA |
| 201 | BTG2 | 2375675 | GGTTACTAATTGTATGATAGTGTTTTTATATGGAAGAATGTACAGCTTATGGACAAATGTACA CCTTTTTGTTA |
| 202 | G0S2 | 2378073 | GTCATTCCCGCCTCCGAGAGCCCAG |
| 203 | G0S2 | 2378074 | TGCTGGCCCTCTTCGGCGTGGTGCTCGGCCTGATGGAGACTGTGTGCAGCCCCTTCACGGCC GCCAGACGTCTGCGGGACCAGGAGGCAGCCGTGGCGGAGCTGCAGGCCGCCCTGGAGCGA CAGGCTCTCCAGAAGCAAGCCCTGCAGGAGAAAGGCAAGCAGCAGGACACGGTCCTCGGCG GCCGGGCCCTGTCCAACCGGCAGCACGCCTCCTA |
| 204 | G0S2 | 2378075 | CAGGAGCCTGACTCCGCTGGGAGAGTGCAGGAGCACGTGCTGTTTTTATTTGGACTTAACTT CAGAGAAACCGCTGACATCTAGAACTGACCTACCACAAGCATCCACCAAAGGAGTTTG |
| 205 | G0S2 | 2378076 | GCTGTGCAGCACTGCATTGTCATGACATTTCCAACACTGTGTGAATTATCTAAATGCGTCTACC ATTTTGCACTAGGGAGGAAGGATAAATGCTTTTTATGTTATTATTATTAATTATTACAATGACC ACCA |
| 206 | ENO1 | 2386864 | GGCAGCAAGGCTAAGTTTGCCGGCAGGAACTTCAGAAA |
| 207 | SCCPDH | 2389792 | CTGCAGAACAAACCGCCGCACGGAATTAGGGGCCGCCGTCCGCGCCTGCCAGGCTTGGAAG CGGACTCGCCCCCAGGGCCACCGCCCTAGGAAACCTCCCGTCGGAAGCCTCCCAAGCAAGCC GCTCACCCGCGCTCCCGCGCGAGGCGGCGTGGGCGTGGGCGCGGCCCTGCGCGGCGGC GCGCGCGGGGTGAAGGGAGCCCGGCGCGCTGGCTGCGGCGACGGCGGCCGTTGCTGCGCC GGGTACTGGGGTCGCTGCCTGAGGCGCAG |

TABLE 13-continued

Subtyping Target Sequences

| SEQ ID NO. | Gene | Affy Probeset ID | Sequence |
| --- | --- | --- | --- |
| 208 | SCCPDH | 2389793 | CCGGGGCCTGGGCTCGCTGTGGACTCGT |
| 209 | SCCPDH | 2389794 | GGCGACCGAGCAGAGGCCTTTCCACCTGGTGGTGTTCGGCGCGTCTGGCTTCACCGGCCAGT TCGTGACCGAGGAGGTGGCCCGGGAGCAGGTGGACCCGGAGCGGAGCTCCCGCCTGCC |
| 210 | SCCPDH | 2389802 | CAAAGGGGTTTATATCATTGGAAGCAGCGGCTTTGACTCCATTCCAGCAGATCTGGGAGTAAT ATATACCAGAAATA |
| 211 | SCCPDH | 2389807 | GGGTTGAGCATTCATGATGGTACCTGGAAGTCAGCAATTTATGGTTTTGGAGATCAGAGTAA TTTGAGAAAACTAAGAAATGTATCAAATCTGAAACCTGTCCCGCTCATTGG |
| 212 | SCCPDH | 2389809 | GCCAATTTCTTATTGTCGGGAACTCAAAGGTTATTCCATTCCTTTTATGGGATCTGATGTGTCT GTTGTAAGGAGGACTCAACGTTACTTGTATGAAAATTTAGAGGAATCACC |
| 213 | SCCPDH | 2389810 | GTTCAGTATGCTGCGTATGTAACTGTGGGAGGCATCACCTCTGTTATTAAGCTGATGTTTGCA GGACTTTTCTTT |
| 214 | SCCPDH | 2389811 | CCCATGGTTCTTCTCCTTTGGCTATTTTTCAAAACA |
| 215 | SCCPDH | 2389812 | GATGCTGCCTCATTCACGCTGACATTCTTT |
| 216 | SCCPDH | 2389813 | TACAGATAAGAACAAACCAAATATCAAAATTTG |
| 217 | SCCPDH | 2389814 | GTGGCTACCCCCATAGCTATGGTTCAGGCAGCCATGACTCTTCTAAGT |
| 218 | SCCPDH | 2389816 | AAAACAAAGTTGATTGACAGACTCAACAAACACGGTATTGAGTTTAGTGTTATTAGCAGCTCT GA |
| 219 | SCCPDH | 2389817 | CTGAAGTCATAACGTGCGTGAATTAACAGCTTCTCTATTTGATATTTGAAATTCTTCTGTAAGC CTGTCTGAGTGTATGTGGAAACGATTGTCAAATCTAAAATA |
| 220 | SCCPDH | 2389818 | TTTCACGAATGAGCTGGCAGGTCTAATGGGGGAGGCGGCGTCCCAGTCTGTGTTGCAGCAGC ATTCTCATCGGGGGTGCGCACACCATCGTTACTGTCGGGCAGTAACTGCCGCTTGCCTTGCCG CAGTAGGAGGGAA |
| 221 | SCCPDH | 2389819 | ATCTACACTGATTTTGGACTGTTACC |
| 222 | SCCPDH | 2389820 | GGTTTAATGTTTGGACCTGCCGATGTATTTGTATAG |
| 223 | SCCPDH | 2389821 | GTAGAAACATGCTGCTTAAGTGGCCTAACCTGTTTCTTGCCAATAAGTAGGCTTATCATTTTAT CTTTACGTAATTCTATATCTGTGACTAGGTTTTTAAGGATACAGCTTATAAGTTGCTATCA |
| 224 | ENO1 | 2395498 | CAGTCGTGTAATTGGCCCAAGTCAT |
| 225 | ENO1 | 2395499 | CCTTCGGTCACCTGTTGGCTACACAGACCCCTCCCCTCGTGTCAGCTCAGGCAGCTCGAGGCC CCCGACCAACACTTGCAGGGGTCCCTGCTAGTTAGCGCCCCACCGCCGTGGAG |
| 226 | ENO1 | 2395500 | GGCAGCAAGGCTAAGTTTGCCGGCAGGAACTTCAGAAA |
| 227 | ENO1 | 2395502 | ACTGGTGCCCCTTGCCGATCTGAGCGCTTGGCCAAGTACA |
| 228 | ENO1 | 2395503 | AATGGTTGGGGCGTCATGGTGTCTCATCGTTCGGGGGAGACTGAAGATACCTTCATCGCTGA CCTGGTTG |
| 229 | ENO1 | 2395504 | CCAACCCAAAGAGGATCGCCAAGGCCGTGAACGAGAAGTCCTGCAACTGCCTCCTGCTCAAA GTCAACCAGATTGGCTCCGTGACCGAGTC |
| 230 | ENO1 | 2395505 | CACTGATAAGGTGGTCATCGGCATGGACGTAGCGGCCTCCGAGTTCTTCAGGTCTGGGAAGT ATGACCTGGACTTCAAGTCTCCCGATGACCCCAGCAGGTACATCTCGCCTGACCAGCTGGC |
| 231 | ENO1 | 2395506 | TCCTCCCAGTCGGTGCAGCAAACTTC |
| 232 | ENO1 | 2395508 | TGCCATGCTTCTCTGCTCTGCTCTCCCCAG |
| 233 | ENO1 | 2395510 | TAAGTTTGGTGCGAACGCCATTCTGGGGGTGTCCCTTGCCGTCTGCAAAGCTGGTGCCGTTGA GAAGGGGGTCCCCCTGTACCGCCACATCGCTGACTTGGCTGGCAACTCTGAAGTCATCCTG |
| 234 | ENO1 | 2395516 | CAGGGGCTTTCCTGTTTATGGAAGAGCTTATTCTGAGAGCTGTAGAAGCCTATTGGATTCCCT GTCACGCACGAGAACAATCCATGCATGACATAATTCTAACCTGCCCGCTGCCTCACCCCACTTT TGGGAGCAGATGGAATTGCATCAGAAGAATGAGACACTTCGAGCCCTGAGGTTTCTTCCCCC CTGCAACTCTCTGGACCTTTGAAGAA |
| 235 | ENO1 | 2395518 | CAATAAAACTATTGCGCCTGCCCTGGTTAGCA |

TABLE 13-continued

Subtyping Target Sequences

| SEQ ID NO. | Gene | Affy Probeset ID | Sequence |
|---|---|---|---|
| 236 | ENO1 | 2395519 | CCTTTAGTCTGCAGTTGGCGTTTCCAGTGCATGGTCTTGCAAACTAACCTCCAGTCAGATCGTT<br>CTGAGCCAGCTGCTGTTTTGTGTGGCTCTAACCCTCTGGGGTCCTAGGTAGGAGCACTCAGAC<br>TGGGCCGGAAAGTCCTCCGATTCTGGGGGGAAAGGGGAGAGGGGGAAGAGGTCCCACAGA<br>AGGTCCCTTGGTGGGCTTCCGCGTCGGCCTCAACAGTGGTTCTCTCTAACAATGTGCTCAAG<br>CCTGTTTTAAAGTTA |
| 237 | ENO1 | 2395520 | GCGTCTCCAGACCCATTAAGTATATT |
| 238 | ENO1 | 2395522 | GCCCAGTGGTGCTTCAACTGGTATCTATGAGG |
| 239 | ENO1 | 2395524 | ATGTCTATTCTCAAGATCCATGCCAGGGAGATCTTTGACTCTCGCGGGAATCCCACTGTTGAG<br>GTTGATCTC |
| 240 | ENO1 | 2395526 | TCAACGACTCGACGCCAACGGGGTCTCTCGGATCGCGGCGCGAGGCAGGAGGGGCGGGGC<br>AGGAGGGCCGCGGCAGGCCCGGGCCGCCAAAGTTGTCAGCAAGGTCGAGGGCCGGACGTG<br>GGGCCCCAGAGCGACGCTGAGTGCGTGCGGGACTCGGAGTACGTGACGGAGCCCCGAGCTC<br>TCATGCCCGCCACGCCGCCCGGGCCATCCCCCGGAGCCCCGGCTCCGCACACCCCAGTTCGG<br>CTCACCGGTCCTATCTGGGGCCAGAGTTTCGCCCGCACCACTACAGGGCGCTGGGGAGTCG<br>GGGCCCCCAGATCTGCCCGCCTCAAGTCCGGGACGTCACCCCCCTTTCCACGCTACTGCA<br>GCCGTCGCAGTCCCACCCCTTTCCGGGAGGTGAGGGAATGAGTGACGGCTCTCCCGACGAAT<br>GGCGAGGCGGAGCTGAGGGGGCGTGCCCCGGAGGCGGGAAGTGGGTGGGGCTCGCCTTAG<br>CTAGGCAGGAAGTCGGCGCGGGCGGCGCGGACAGTATCTGTGGGTACCCGGAGCACGGAG<br>ATCTCGCCGGCTTTACGTTCACC |
| 241 | PAQR7 | 2402432 | CCCTGCTCACATTACTGGAGGTTTTCCGGAGGAAGCTGGGGCCCCTGGGAGTGGACACAGGG<br>TGCAGGGAGCAGTTCTTGTTTTATCTTTGCTGGGGGATGGGGTTGGGGCCTTATATACCCATAT<br>CTATATATACAAAATTTGTTTGGCAAGGGAGTGGGCGGCAGTTTTATTACTAAAGTTTTATAA<br>GTAGTTAAAATAATGTGTTTAAAATATGATAATCCCACT |
| 242 | PAQR7 | 2402433 | CAGAATGAACTGTCAAGGGAGGTGCTGGAGAGGGATTAACCTGTGCTGCCTGGGACCCTCA<br>GGGTCTTAGGTTGGGGAGTGTGAATAGGAGTTTGCAGATGGAGAATAGGAAGGGCATTCCA<br>GGCAGAGGGAAACCTGTCAGAGACCAAGAGGTGTGGAAGGAAAAGTGGGGTTGGGGCTG<br>GGTGGTCTGGATTATGGCCTGGATGCAATAAAGTAC |
| 243 | PAQR7 | 2402434 | CTTGTTGGCTAGGCTGGAGTAAAATGGTGC |
| 244 | PAQR7 | 2402435 | TCTGTGCACGACTCAACTGCCAAGGGCATCACTGGCCAATTCTTGGATTTAGGGATTGGCTAG<br>GAGTTGCTGGGGTCCACTCCTGGGCCTGCCCCAGCCTCTTGCCCAGGGAGAGGGAAAGAGTT<br>AACGGTGTGGGCCACTCCAGCTTGCCCTTCCACTGCCACTCACTGGGGTGAGGCTGGGGGTC<br>AGCTTGGTGAGGATTGGGGCTTCTAGATTGTCTAGGCAGGAGGTGAAACTTAGGCCAGAGTC<br>AGATTTGAGCTGAGCCAGGGGAGGCCTTGGCAACCTACTTCTACTCAGATTTCATTGCTGGAT<br>GCGGAAGGGTAGGCCCAAAATATATACAGGATCTTACTGTCCCTTGAAGCCCAGCCACAAG<br>TGTTGGAGCTGCAGAGAGACCCCAAAGGTAGTAGATTGTGCCAGATACAAATGGGTCCCATC<br>CAGTGCTTCATACTCCTTCAGTCACTATCCCAGACAGTGAGCCCCAGATCTCCTAGCTCTGGCT<br>TCTGTGTCCCACACGGCCTGTTCCCAGCTTCTCTCCTGGTTCCCTTGTTACGGATTCA |
| 245 | PAQR7 | 2402436 | CGCTCTTCTGGAAGCCGTACATCTATGCGGGCTACCGGCCGCTGCATCAGACCTGGCGCTTCT<br>ATTTCCGCACGCTGTTCCAGCAGCACAACGAGGCCGTGAATGTCTGGACCCACCTGCTGGCG<br>GCCCTGGTACTGCTGCTGCGGCTGGCCCTCTTTGTGGAGACCGTGGACTTCTGGGGAGACCC<br>ACACGCCCTGCCCCTCTTCATCATTGTCCTTGCCTCTTTCACCTACCTCTCCTTCAGTGCCTTGG<br>CTCACCTCCTGCAGGCCAAGTCTGAGTTCTGGCATTACAGCTTCTTCTTCCTGGACTATGTGGG<br>GGTGGCCGTGTACCAGTTTGGCAGTGCCTTGGCACACTTCTACTATGCTATCGAGCCCGCCTG<br>GCATGCCCAGGTGCAGGCTGTTTTTCTGCCCCATGGCTGCCTTTCTCGCCTGGCTTTCCTGCATT<br>GGCTCCTGCTATAACAAGTACATCCAGAAACCAGGCCTGCTGGGCCGCACATGCCAGGAGGT<br>GCCCTCCGTCCTGGCCTACGCACTGGACATTAGTC |
| 246 | PAQR7 | 2402438 | CAGTTACTCTGAATGGTCTTTGCTAAGAACAATTTAATGATTAAGTAAGGTCAGTGTCCTTGG<br>AAGTCCAAACTCTAGCCAGATTTCCCTGGTCTACACCCCTAGGGATAAGGTAAATGTTTAAGC<br>ACACAGTGAACTTCCTGAGGCCCCAAATCTAATGGAACTAGCTATTGAGGGCTAAAAGAGG<br>ATGGTTTTTTAGAAAAACTCGAAGCAAATCTCTCAGGCTGGGGATATTTCAAAGACTACTACT<br>ATTATTATTAATAACAATTGCAATATTTGTTGAGTCCCTAAATGAAGCTAAAACTTTGTTCTAAT<br>AAATTTAATCTTTACAGCAACCTATGAGGTAGATAATATTGTCATTCCCATGAGGGAGCTAAG<br>GATCAGAGAAGGTAAGTCACTTGTCTAAGGTCACATAGCTAGCATGTTATGCAATCAGGAGT<br>CAAACCTGGTTTGTCTGAATCTGAAGTCCATCTGCTCTGTGCACTTTTATACCGTCTG |
| 247 | IFI6 | 2403262 | GCTATTCACAGATGCGAACATAGTACACTGCAGCCTCCAACTCCTAGCCTCAAGTGATCCTCCT<br>GTCTCAACCTCCCAAGTAGGATTACAAGCATGCGCCGACGATGCCCAGAATCCAGAACTTTGT<br>CTATCACTCTCC |
| 248 | IFI6 | 2403263 | CTTCTTGGCCTAACTCTTCCAGTTAGG |
| 249 | IFI6 | 2403264 | GGCAGCAGCGTCGTCATAGGTAATATTGGTGCCCTGATGGGCTACGCCACCCACAAGTATCTC<br>GATAGTGAGGAGGA |

TABLE 13-continued

Subtyping Target Sequences

| SEQ ID NO. | Gene | Affy Probeset ID | Sequence |
|---|---|---|---|
| 250 | IFI6 | 2403265 | TCGCAGTCGCCGGGCTGCCCGCGCTGGGCTTCACCGGCGCCGGCATCGCGGCCAACTCGGTG<br>GCTGCCTCGCTGATGAGCTGGTCTGCGATCCTGAATGGGGGCGGCGT |
| 251 | IFI6 | 2403266 | TAAGAAAAAGTGCTCGGAGAGCTCGGACAGCGGCTCCGGGTTCTGGAAGGC |
| 252 | IFI6 | 2403269 | GTATCGCTTTTCTTGTGCTACCTGCTGCTCTTCACTTGCA |
| 253 | LAPTM5 | 2404159 | GCGACAGGGAGGAAGTTTCAATAAAGCAGC |
| 254 | LAPTM5 | 2404160 | TCACAACTGGGTCAACGCTTTAGGCTGAGTCACTCCTCGGGTCTCTCCATAATTCAGCCCAACA<br>ATGCTTGGTTTATTTCAATCAGCTCTGACACTTGTTTAGACGATTGGCCATTCTAAAGTTGGTG<br>AGTTTGTCAAGCAACTATCGACTTGATCAGTTCAGCCAAGCAACTGACAAATCAAAAACCCAC<br>TTGTCAGTTCAGTAAAATAATTTGGTCAAACAACAGTCTATTGCATTGATTTATAAATAGTTGT<br>CAGTTCACATAGCAATTTAATCAAGTAATCATTAATTAGTTACCCCCTATATATAAATATATGTA<br>ATCAATTTCTTCAAATAGCTTGCTTACATGATAATCAATTAGCCAACCATGAGTCATTTAGAAT<br>AGTGATAAATAGAATACACAGAATAGTGATGAAATTCAATTTAAAAAATCACGTTAGCCTCCA<br>AACCATTTAATTCAAATGAACCCATCAACTGGATGCCAACTCTGGCGAATGTAGGACCTCTGA<br>GTGGCTGTATAATTGTTAATTCAAATGAAATTCATTTAAACAGTTGACAAACTGTCATTCAACA<br>ATTAGCTCCAGGAAATAACAGTTATTTCATCATAAAACAGTCCCTTCAAACACACAATTGTTCT<br>GCTGAAGAGTTGTCATCAACAATCCAATGCTCACCTATTCAGTTGCTCTGTGGTCAGTGTGGC<br>TGCATAACAGTGGATTCCATGAAAGGAGTCATTTTAGTGATGAGCTGCCAGTCCATTCCCAGG<br>CCAGGCTGTCGCTGGCCATCCATTCAGTCGATTCAGTCATAGGCGAATCTGTTCTGCCCGAGG<br>CTTGTGGTCAAGCAAAAATTCAGCCCTGAAATCAGGCACATCTGTTCGTTGGACTAAACCCAC<br>AGGTTAGTTCAGTCAAAGCA |
| 255 | LAPTM5 | 2404161 | GGTGGAGCTGCCTCATAATCTGCTTTTTTGCTTTGGTGGCCCCTGTGGCCTGGGTGGGCCCTC<br>CCGCCCCTCCCTGGCAGGACAATCTGCTTGTGTC |
| 256 | LAPTM5 | 2404164 | GGCGGTGCTACAGATTGATCAAGTGCATGAACTCGGTGGAG |
| 257 | LAPTM5 | 2404167 | GCCAGGAGGATATGCCTCATAACCAGTTCATCAAGATGATGATCATCTTTTCCATCGCCTTCAT<br>CACTGTCCTTATCTTCAAG |
| 258 | LAPTM5 | 2404168 | GTTCCCCCTGATGACGCTGCAGCTGCTGGACTTCTGCCTGAGCATCCTGACCCTCTGCAGCTCC<br>TACATGGAAGTGCCCACCTATCTCAACTTCAAGTCCATGAACCACA |
| 259 | LAPTM5 | 2404169 | AAATCATGGACTATCTCCTGTGCCTGCTCACCCTGCTGGGCTCCTACATTGAGCTGCCCGCCTA<br>CCTCAAGTTGGCCTCCCGGAGCCGTGC |
| 260 | LAPTM5 | 2404170 | TCTTCATCATCAGCCTGAGCCTACTGATCGGCGTAGTCAAG |
| 261 | LAPTM5 | 2404171 | GGGCTTTCCTGTGCATCCTCATGTCCCCAAACCAGTGGTTCCCCAAGTGTGG |
| 262 | LAPTM5 | 2404183 | ACCCCCGCTTGTCCACTGTCCGCCAGACCTGCTGCTGCTTCAATGTCCGCATCGCAACCACCGCC |
| 263 | LAPTM5 | 2404184 | TGTCTCAGAGGAGGGGACGGCAGCACC |
| 264 | CYP4Z2P | 2411036 | CTATGCCTTCATACCATTCTCAGCT |
| 265 | CYP4Z2P | 2411038 | CCCTTGAGATTCTCCAGGGAAAGTTCTGAA |
| 266 | CYP4Z2P | 2411040 | CTGTGTTTATCAATATTTGGGCTCT |
| 267 | CYP4Z2P | 2411046 | ATGTGCATCAAGGAATGCCTCCGCCTCTACGCACCGGTAGTAAACATATCCCGGTTACTCGA |
| 268 | CYP4Z2P | 2411048 | GATGAAATCAGGGAACTCCTAGGGGATGGGTCTTCTATTACCTG |
| 269 | CYP4Z2P | 2411050 | TACCCTGAGCATCAGCAGAGATGCTGA |
| 270 | CYP4Z2P | 2411052 | CTGAAGTGAAAACGTTCATGTTTGCAGGACA |
| 271 | CYP4Z2P | 2411054 | TACTACTCAGAAAAGACGCCAGGATTTTCTGGACAT |
| 272 | CYP4Z2P | 2411056 | CCCTGGACTCATACCTGAAAGCAGTGTTCAACCTTAGCAAAATCTCCAACCAGCGCATGAACA<br>ATTTTCTACATCACAACGACCTGGTTTTCAAATTCAGCTCTCAAGGCCAATCTTTTCTA |
| 273 | CYP4Z2P | 2411058 | TGGGAGGAACACATTGCCCAAAACTCACGTCTGGAGCTCTTTCAACATGTCTCCCTGATGAC |
| 274 | CYP4Z2P | 2411060 | CGAGGACTTGTGACCCTGGATGGTTCTAAATGGAAAAAGCACCGCCAGATTGTGAAACCTGG<br>CTTCAACATCAGCATTCTGAAAATATTCATCACCATGATG |
| 275 | CYP4Z2P | 2411078 | CTTGTGGGTTGGACCCTTTACGATGTTCTTCA |

TABLE 13-continued

Subtyping Target Sequences

| SEQ ID NO. | Gene | Affy Probeset ID | Sequence |
|---|---|---|---|
| 276 | CYP4Z2P | 2411080 | AGGAGATGGACGATCAGAGCCATGCACCTGTTTCCTGCACCCCCTGCGCACTGGTTCTATGGC CACAAGG |
| 277 | CYP4Z2P | 2411082 | TCCTGGCTTCAGGAACTCATGGCTCACCCCTTCTTGCTGCTGATCCTCCTCTGCATGTCTCTGCT GCTGT |
| 278 | TACSTD2 | 2414960 | GACAACCCGGGATCGTTTGCAAGTAACTGAATCCATTGCGACATTGTGAAGGCTTAAATGAG TTTAGATGGGAAATAGCGTTGTTATCGCCTTGGGTTTAAATTATTTGATGAGTTCCACTTGTAT CATGGCCTACCCGAGGAGAAGAGGAGTTTGTTAACTGGGCCTATGTAGTAGCCTCATTTACCA TCGTTTGTATTACTGACCACATATGCTTGTCACTGGGAAGAAGCCTGTTTCAGCTGCCTGAAC GCAGTTTGGATGTCTTTGAGGACAGACATTGCCCGGAAACTCAGTCTATTTA |
| 279 | TACSTD2 | 2414961 | GTGAGTCACGCTTCCTGATTCCTCGGCGCAAAGGAGACGTTTATCCTTTCAAATTCCTGCCTTC CCCCTCCCTTTTGCGCACACACCAGGTTTAATAGATCCTGGCCTC |
| 280 | TACSTD2 | 2414962 | TACCGGATTTCGGTATCGTCCCAGACCCA |
| 281 | TACSTD2 | 2414963 | TCGGGGAAGTACAAGAAGGTGGAGATCAAGGAACTGGGGGAGTTGAGAAA |
| 282 | TACSTD2 | 2414964 | GTTCTCCATGAAGCGCCTCACCGCCGGCCTCATCGCCGTCATCGTGGTGGTCGTGGTGGCCCT CGTCGCCGGCATGGCCGTCCTGGTGATCACCAACCG |
| 283 | TACSTD2 | 2414965 | GTGGAGCGCACGCTCATCTATTACCTGGACGAGATTCCCCCGA |
| 284 | TACSTD2 | 2414966 | AACACGTCTCAGAAGGCCGCCGGTGACGTGGATATCGGCGATGCCGCCTACTACTTCGAGAG GGACATCAAGGGCGAGTCTCTATTCCAGGGC |
| 285 | TACSTD2 | 2414967 | CTGCACGTGTCCCACCAACAAGATGACCGTGTGCAGCCCCGACGGCCCCGGCGGCCGCTGCC AGTGCCGCGCGCTGGGCTCGGGCATGGCGGTCGACTGCTCCACGCTGACCTCCAAGTGTCTG CTGCTCAAGGCGCGCATGAGCGCCCCCAAGAACGCCCGCACGCTGGTGCGGCCGAGTGAGC ACGCGCTCGTGGACAACGATGGCCTCTACGACCCCGACTGCGACCCCGAGGGCCGCTTCAAG GCGCGCCAGTGCAACCAGACGTCGGTGTGCTGGTGCGTGAACTCGGTGGGCGTGCGCCGCA CGGACAAGGGCGACCTGAGCCTACGCTGCGATGA |
| 286 | TACSTD2 | 2414968 | CTTCCCTGTTCTGATCCTATCGCGGGCGGCGCAGGGCCGGCTTGGCCTTCCGTGGGACGGGG AGGGGGGCGGGATGTGTCACCCAAATACCAGTGGGGACGGTCGGTGGTGGAACCAGCCGG GCAGGTCGGGTAGAGTATAAGAGCCGGAGGGAGCGGCCGGGCGGCAGACGCCTGCAGACC ATCCCAGACGCCGGAGCCCGAGCCCCGACGAGTCCCCGCGCCTCATCCGCCCGCGTCCGGTC CGCGT |
| 287 | GBP1 | 2421885 | GGAAATCTCATAAGCTGGTACCACTCAGGAGAAGTTTATTCTTCCAGATGACCAGCAGTAGAC AAATGGATACTGAGCAGAGTCTTAGGTAAAAGTCTTGGGAAATATTTGGGCATTGGTCTGGC CAAGTCTACAATGTCCCAATATCAAGGACAACCACCCTAGCTTC |
| 288 | GBP1 | 2421890 | AAGCTGAGTCTGCACAGGCTTCAGCAAAAATGTTGCAGGAAATGCAAAGAAAGAATGAGCA GATGATGGAACAGAAGGAGAGGAGTTATCAGGAACACTTGAAACAACTGACTGAGAAGATG GAGAACGACAGGGTCCAGTTGCTGAAAGAGCAAGAGAGGACCCTCGCTCTTAAACTTCAG |
| 289 | GBP1 | 2421891 | GACTGGATAAACATGGGACCCTTTAACTAGAGCAAGATCCACAAAGGTGTGTCTTACTTGCCG AGGTCATCTCTGAGTAGGGCATATGCAGTCAGCAACAACGACAGGTAAGTGTA |
| 290 | GBP1 | 2421892 | TATGACTGATGCAATTCTCCAGACAG |
| 291 | GBP1 | 2421894 | TGGAAAGCTGCTGACCTGCCTCCTACAAACACCAAGGTGACCAAGCTTCACTGCATACAGATG TGCTTTTTTGTTTGCATAACATTCATGCTTTTATTCAATAACATATGCAAACAGGCTGTTATACC AGATATGTCCTAGGTGCTCATCAAAGAGAGTGCAGTCAATTAACTATTAAGTTATAAATTCAA TTAGCAGATGAAGCACAAAGTTATTATTGTCATCATTACAGCTGGGCTTTTCCTGTTGCAAGA GACAGGAACCCAATGATGGCTGCTTAAACAAAAATGTAATTCATTGATTTAGGCTGCAAACTG GCTTTACAGGTCAGGTGGGTCTAA |
| 292 | GBP1 | 2421900 | TGAAACTTTTAACCTGCCCAGACTCTGTATCCGGAAATTCTTCCCAAAGAAAAATGCTTTGTC TTTGATCGGCCCGTTCACCGCAGGAAGCTTGCCCAGCTCGAGAAACTACAAGATGAAGAGCT GGACCCCGAATTTGTGCAACAAGT |
| 293 | GBP1 | 2421902 | GGTTTGTGATCTTCTACTTAGCCATAGA |
| 294 | GBP1 | 2421903 | GAGAGCTTCAACTGATAAATGAGGATGAGAAAACACAAGAAATTATCATTTTTCAGTTTACTA TTGCTAGTTTTCCAGCATTTGCAGTTTTCTATGTCTTCAGCTGGCTATTCCTAGAAATTAATACT TGCTGAATATCCAAATTAATAGATGTTATTTAAATTACATTTGTCATTGTTCTAGAACAAGTTT CTTGTTCTTTCACCTTTGTGTATGCTGTGATTAGGTTAATTTTATCTCCCTG |
| 295 | GBP1 | 2421904 | GACACATAGAATCCGATCAAAATCCTCACCTGATGAGAATGAGAATGAGGTTGAGGATTCAG CTGACTTTGTGAGCTTCTTCCCAGACTTTGTGTGGACACTGAGAGATTTCTCCCTGGACTTGGA AGCAGATGGACAACCCCTCACACCAGATGAGTACCTGACATACTCCCTGAAGCTGAA |

TABLE 13-continued

Subtyping Target Sequences

| SEQ ID NO. | Gene | Affy Probeset ID | Sequence |
|---|---|---|---|
| 296 | GBP1 | 2421905 | ATCCCATGTATCCACTTTAGAACTGACACTGACACTTAGGTTAGGAG |
| 297 | GBP1 | 2421906 | CTGAGCAGCACCTTCGTGTACAATAGCAT |
| 298 | GBP1 | 2421907 | GTGCAGTCTCACACTAAAGGAATCTGGATGTGGTGTGTGCCCCACCCCAAGAAGCCAGGCCACATCCTAGTTCTGCTGGACACCGAGGGTC |
| 299 | GBP1 | 2421909 | AGCACAAATTATGCCTCTCCTAAAAGGAGTAA |
| 300 | GBP1 | 2421910 | ATCTACACAGTCAGCCTCCATTATG |
| 301 | GBP1 | 2421911 | GAGAACACTAATGGGCGACTGATGGCGAATCCAGAAGCTCTG |
| 302 | GBP1 | 2421912 | ATGGCATCAGAGATCCACATGACAGGCC |
| 303 | GBP1 | 2421951 | CTGAGCAGCACCTTCGTGTACAATAGCAT |
| 304 | GBP5 | 2422037 | GGCCATAGACTAGCTCTGATCTGTGGCCTCTTAGGAACCCGGCCACACAGCAGGAGGTGAGCAGCAGGTAAGTGAGCATTACAGCCTGAGCTCCACCTCCTGTCAGATCAGCAGTGACATTAGATTCTCACAGGAGTGGGAACCCTATTGTGAACTGTGCATGCAAAAGATCTAGGTTGTGTGATCCTTGTGGAACAATATAAACCAGAAACCAATAACGCCACCCCACCTCCAACCCCCGCCAACCCTCTGTGGAAAAATTACCTTCCACGAAACTGGTCCCTGATGCCAAATAGGTTGGGGGACCGCTGACCTAGAGGGAGTTATGCACATGGGCTTATAAGGTTAGCCAAGAGAAAGGACAAGAAGACCCAAAGTCGGCAAGCAAATTTATTAACCTGCTGGGCTGCTCTACAGAAATCTGAGGAGGCAGACACCCGGGCTTACAGGCTAAGGGGTATAAGTAGGTCTGCAGGGGTTTTGTGTGTGTGCGGGGGTGTCGGGGGGCAAGGCCATTTGTGGAGACTTTTCCTCCCAGTATGGCCACATCCTGCAGTTTGTCAGTTTTTGCCCCCGCCTGGCTCAGGGTACCAGGATGTGGTTTAGCTTAGGGGTGGTTATAGTGGCACCTAAGTTCTGGGAACTTGCGGTGGGGCGACCTTTTGGACGAAAATAAGCTGCAGGGCAGCTAGGGGAGGGGCTTGTTATATTCCTCTGGGGGCAGGGTGTCCCTAACTGGGTCAGTCGGAAGGAACTTGACCAAAGTCTGGGCTCAGTTGGGCATCACTCAGGCTAATGGTCG |
| 305 | GBP5 | 2422038 | AGTGCTAAATATGGGAGTTTCCTTTTTTTACTCTTTGTCACTGATGACACAACAGAAAAGAAACTGTAGACCTTGGGACAATCAACATTTAA |
| 306 | GBP5 | 2422039 | GCACAACATTCCAAGCTCAAAATAGAAGCCTTCTCAGTGAGCTCCAGCACGCCCAGAGGACTGTTAATAACGAT |
| 307 | GBP5 | 2422041 | GTATTCATCAATTGTTTCATCTCTCCCCTGCCTGTAACGATGAGAGTATGTAGCAGTGGCAAAGAGGGAGAGGCAGCAAGATCTTGTGGCTCTCAGC |
| 308 | GBP5 | 2422042 | AGCGCAAAGGTTGGCGGCGATTCAAAGGCAGAACGAGCAAATGATGCAGGAGAGGGAGAGACTCCATCAGGAACAAGTGAGACAAATG |
| 309 | GBP5 | 2422043 | CCCTCATGGGATGTTAAACTAGAGCAAGAATGGCAAAGATGCTTCTTAGCTCCTCAAGCATATCTGACTGGCATGATCCTGCATTGTGGTTACCTGGAAGGGAAAAACAACCCCTGGGAATTTTATCCAGGAAGTTGGAACAATCACAAACAAAAGTGGGA |
| 310 | GBP5 | 2422044 | TGCAATATTACAGACTGACCAGGCTCTCACAGAG |
| 311 | GBP5 | 2422045 | GTTGGTGTTCCTCGCACAGAATTTATATCTAATGGTAGCAGTGGGGTTAAACTGAACCATCACCATAATCACCAGACTTGCTTTGTGACCATCAACATTCATTGCAACAAAGAGGCCTTTTTGGTTACATTGGACAGAATGCCAATACTTGAAACTAACCTAAGAAACACCAGTAATTCATTGGCTTACACAAACTAAAAGCAAAGATTTTAATTTAGTTTCAAGTATAGATGCATTCAGAATTTTAAACAATATTATCCCTTTTCCTCCTTCTTTCTGTCATTTTTCTGTTTCATTTTCCTGACTATTGGCTTCATTTCCAGGCAGGCTCACCCCACATGACAATAAAGGTGACACCAACAGGTCCAAGCTTAACTAGTCCTTACTGCCCTCAGTCTCAGGGGAAAGAGAGCATCTTTTCTCCAGCATATATCTGTCATTCAAACACAAAAGCATCATCAATTTTCATACTCTTTGCAGTATTTTTCTCCCTGTGAACAAGTCCTTTGCATCTAGTGGACTTGCATGCTCTGACTGACCATGAGTCATGGCCAAACTTGTGACAGGAGCAGGTGTTCCACAAGCCTCTCCAGTCTCAATTGGCAGTTCCACCAAGTGCAGGGTGGAAGCCTGTATAGGCTCCACCTCTCCTATGGCAAGCCTCTCCTATGAGGAATAGATGCTGCTGGAAGGAACAAGACAAAGATGTTTACAACATTCCTAATCACCATTTCCTGCATCTAACTGCATGTTTTCCGGGTTGCTA |
| 312 | GBP5 | 2422046 | GGAACCTGGAAGCATCCTCGGATTATTGCTCGGCTTTACTTAAGGATATTTTTGGTCCTCTAGAAGAAGCAGTGAAGCAGGGAATTTATTCTAAGCCAGGAGGCCATAATCTCTTCATTCAGAAAACAGAAGAACTGAAGGCAAAGTACTATCGGGAGCCTCGGA |
| 313 | GBP5 | 2422049 | GCCTTGCATAGAGAATGCAGTCCTGGCCTTGGCTCAGAGAGAGAACTCAGCTGCAGTCAAAAGGCCATTGCCCACTATGACCAGCAAATGGGCCAGAAAGTGCAGCTGCCCATGGAAACCCTCCAGGAGCTGCTGGACCTGCACAGGACCAGTGAGAGGGAGGCCATTGAAGTCTTCATGAAAAACTCTTTCAAGGATGTAGACCAAAGTTTCCAGA |
| 314 | GBP5 | 2422050 | TGTTCCTACATCTTTAGCCATTCTATGACCAAGACTCTTCCAGGTGGCATCATGGTC |

TABLE 13-continued

Subtyping Target Sequences

| SEQ ID NO. | Gene | Affy Probeset ID | Sequence |
|---|---|---|---|
| 315 | GBP5 | 2422051 | TGATGAGCTAGAGCCTGAATTTGTGCAACAAGTG |
| 316 | GBP5 | 2422052 | AAATGCTTTATCTTTGACTTACCTGCTCACCAA |
| 317 | GBP5 | 2422053 | TCAAAATTTCAATTTGCCCCGTCTGTGTATACAG |
| 318 | GBP5 | 2422055 | CTGGAAATAGATGGGCAACTTGTCAC |
| 319 | GBP5 | 2422056 | ACTGACAGATCTGCTCAAGGCAAGAAACTCACCCGACCTTGACAGGGTTGAAGATCC |
| 320 | GBP5 | 2422058 | GATCTTTGCACTGGCACTCTTACTGAGCAGCACCTTTGTGTACAATACTGTGAACAAAATTGATCAGGGTGCTATCGACCTACTGCA |
| 321 | GBP5 | 2422059 | CTCTGTTGCATCTACGGTGCAGTCTCACACCAAGGGAATTTGGATATGGTGTGTGCCTCATCCCAACTGGCCAAATCACACATTAGTTCTGCTTGACACCGAGGGC |
| 322 | GBP5 | 2422062 | TCTGCCATTACGCAACCTGTAGTTGTGGTAGCGATTGTGGGCCTC |
| 323 | GBP5 | 2422063 | TGGCTTTAGAGATCCACATGTCAGACCCCATGTGCCTCATCGAGAACTTTAATGAGCAGCTGAAG |
| 324 | GBP5 | 2422064 | GGGTCAGGCTTGCACTAGGCATTTCCTGACTCCCATGTCCTAGTGCTACACCATTTGCAAATGGATATCCTATTTTCTGCTGCCAAGCAGTTTCTGTTTTAATTTATGTCAACATAATGATTTCCAGGGCATTAGCTATGAGGAAGCAGGGAGAATGGGTCTTCATAATTGTAAAATGACAGTTTTTGAAATTTGCTAGTAAAGAGATGGAGAATCCAAACCTTTTCATTGTAAGATTTTAGTGAAAGAACTCGTCAAGCGGATAGTGAAGTTTTAGCATCCTTAGTAAATAACCACCTTTAAAATGGAAGAAAACTATCCTTTATGATAAGGCAAAGTAGAAAAGCATATTTTTATGGCATTTGCTTTTTCTCATATAGCTCAAACATTTTTTTTAACCAGAGACTCTTTAGGTTATAGGGATTGATGCTCAGAAGTTAGAAAAAATAGGTTAAGTATTATTAAAGGAAGTTGTTTTACTCATTCAGTCAATCATAAAATAATCATGCTTTGAAGTTTTGGTTTAATAAAGCACATTAGTAACTATGTAAAAAATTTCAAGTATATCACTAAGAAGCAAACAGCTATGATTTGTTAGATAATGCTGCATAATGACTTGGTAGTATTTAATGTAATGCAGTTTGACTGGACATAGATCTAACTGAAAAAAATGAAGTTGACACAAAGTAAAAGGAACAGTGTAATATATTAATAAAGAACATCATAAAGAATTAATATAGGAACCCAGGGAGGTAAAAACTAAAAAACATAACTAAGCCAAAAACCAATGGAATAAGAGTTAGATTCAAACTAGTAGGTTAGACGCAGGAAATGGATTTTCGTATGCCTATCAAATATTTAAGAACCAGTAGAATGGCCTATAGTAGACATATAAAGGGCCTAGGACTTACTTTTGTTTTAAAATAAAGTCTCTCTATTTTACAGGACTCTTTTTATTTTAAAACTTTTTTTTTTCCAGAAACTTAGGCAGTGCTG |
| 325 | GBP5 | 2422065 | CTAATTGTTGTAGATCATCACTTCAAGGTGCCCATATCTTTCTAGTGGAAAAATTATTCTGGCCTCCGCTGCATACAAATCAGGCAACCAGAATTCTACATATA |
| 326 | GBP5 | 2422066 | TGCCCAACTGGATCCCTCAATACTGTCTGGCAACTGTTCACTCGTTGAAATTCTCTCCTTTGAATTTCTTACCATGACACATACTTCAAGCATTTTGTACTAGTTTGATTTCCATTTATATCCTTAATAGAGCCTTTTCCTTTTCCTTGAAATTCAAACCAGAAACTATGCAAATAAGCAAAAGCAAGCAATAACAACTACATATACAAATGCAGGCGCAAAACCCAAACTAGAATCATATGGCTGAAAACAGATGTTTTCTTTCAGAAATCCTTCCACTACCACTTCTGAGCATTTTCTCTTAGTATTTTTTTTGGGCATTTTCCTTCTTTGCACTTTTTAAAATCTCCTGCAGCTCGCTCACTCTCTTTCATAAGCCAGCAGTTATACTGATGTTAATAAATAGTTGTTTATTTACTTTTGCTTTTTTAGAAAACAAGCTGAAAGAATTGAGTGAAATGCCAGAGAGATACAGATAGCCAGTTGTAGGGCTGGGGTTGGAAATCAAGTCTAATTTAAGGCAAGGGCAAAATGTGCATTTTGTGTGTATTTTGAACCATTCTTGCATTGTTTTTATTTGCAAAGGTTATAGGGCTCAAGCAGTTAGGGAGAATGCATCCCAGAACACTAAGTTA |
| 327 | GBP5 | 2422067 | TGATAGCTATTATTTTCATGAGAAAGAACAATGAATATGATGCAAT |
| 328 | GBP5 | 2422068 | TCTACAAAGGATAGGATGCAGCTTATCCTGATGTGGTATATCAGACCTCAGTAAAGAATAAATTGTATTCTTATCAGACAGGCAGCAGAATTCATCAAGTACCAGCTGTGTCTGCC |
| 329 | F3 | 2423914 | AATATACTTTAAATAAAGGTGACTGG |
| 330 | F3 | 2423915 | GAGTAACCAGGTCGTCCAAGCAAAACAAATGGGAAAATGTCTTAAAAAATCCTGGGTGGACTTTTGAAAAGCTTTTTTTTTTTTTTTTTTTGAGACGGAGTCTTGCTCTGTTGCCCAGGCTGGAGTGCAGTAGCACGATCTCGGCTCACTGCACCCTCCGTCTCTCGGGTTCAAGCAATTGTCTGCCTCAGCCTCCCGAGTAGCTGGGATTACAGGTGCGCACTACCACGCCAAGCTAATTTTTGTATTTTTTAGTAGAGATGGGGTTTCACCATCTTGGCCAGGCTGGTCTTGAATTCCTGACCTCAGGTGATCCACCCACCTTGGCCTCCCAAAGTGCTAGTATTATGGGCGTGAACCACCATGCCCAGCCGAAAAGCTTTTGAGGGGCTGACTTCAATCCATGTAGGAAAGTAAAATGGAAGGAAATTGGGTGCATTTCTAGGACTTTTCTAACATATGTCTATAATATAGTGTTTAGGTTCTTTTTTTTTTCAGGAATACATTTTGGAAATTCAAACAATTGGCAAACTTTGTTATTAATGTGTTAAGTGCAGGAGACATTGGTATTCTGGGCACCTTCCTAATATGCTTTACA |
| 331 | F3 | 2423916 | TGGAGCTGTGGTATTTGTGGTCATCATCCTTGTCATCATCCTGGCTATATCTCTACACAAGTGT |

TABLE 13-continued

Subtyping Target Sequences

| SEQ ID NO. | Gene | Affy Probeset ID | Sequence |
|---|---|---|---|
| 332 | F3 | 2423918 | CTAATGAGTTTTTGATTGATGTGGATAAAGGAGAAAACTACTGTTTCAGTGTTCAAGCAGTGA<br>TTCCCTCCCGAACAGTTAACCGGAAGAGTACAGACAGCCCGGTAGAGTGTATGGGCCA |
| 333 | F3 | 2423919 | TTTATGACCTGTTTTAAATTGTGAATACTTGGG |
| 334 | F3 | 2423920 | CGGACAGCCAACAATTCAGAGTTTTGAACAGGTGGGAACAAAAGTGAATGTGACCGTAGAA<br>GATGAACGGACTTTAGTCAGAAGGAACAACACTTTCCTAAGCCTCCGGGATGTTTTTGGCAAG<br>GACT |
| 335 | F3 | 2423922 | AGACGTACTTGGCACGGGTCTTCTCCTACCCTGCAGGGAATGTGGAGAGCACCGGTTCTGCT<br>GGGGAGCCTCTGTATGAGAACTCCCCAGAGTT |
| 336 | F3 | 2423923 | GTGACCTCACCGACGAGATTGTGAA |
| 337 | F3 | 2423928 | CTACAAATACTGTGGCAGCATATAATTTAACTTGGAAATCAACTAATTTCAAGACAATTTTGGA<br>GTGGGAACCCAAACCCGTCAATCAAGTCTACACTGTT |
| 338 | F3 | 2423929 | TCCTGATCCAATACAGCCGACGGTGTGACAGGCCACACGTCCCCGTGGGTCTCTGTGGAAGTT<br>TCAGTGTAGCGACATTTCAGATAAAAAGTGGAAAAAGTGAAGTTTGGCTTTTTTCATTTGTATG<br>CAGTCCTAACTCTTGTCACACGTGTGGGATTTATCTTTTTCCATAACTTACTGAAAACCCTTCCT<br>GGCGGGCTGAACCTGACTCTTCCTGAGCTGAGTCCTGGACTGGCACACTGATGGCTCTGGGC<br>TCTTCCCGGTCAAGTTATAACAAGGCTTTGCCCATGAATAATTTC |
| 339 | F3 | 2423933 | CGAGACCGCCGTCGCTCGGACGCTCCTGCTCGGCTGGGTCTTCGCCCAGGT |
| 340 | F3 | 2423934 | ACGGGCGCCACGGAACCCGCTCGATCTCGCCGCCAACTGGTAGAC |
| 341 | GSTM3 | 2427209 | CCCTGGGGCTAGATCGATGATATGACCAGAAATCAAAAAGGGAATGCATTATTTATTGCTGT<br>GTAACACTGTTAAGAGAGGAGGTAGTTAAGGGATGGATAGGCACATAGAGAGGGAAGGTCT<br>CAGGAGAAGGGATAGAAAGGAACTATGTTCACAAGAACAACGGCAAGACAGTGCCTATACT<br>GCCTCTACAGTTAATAGGAAAAACGGAAGAAGTTACCCTTAAGCTAGGATGTTGCTCAGAAG<br>TGACCATCCCAACTTTGGTGCGGGCACAATAAATCAGCCTAAATGTCCCTAATTTAACCCAGCT<br>CATTATAATGTCATTAAACATGACATTAGCATTGTGGTTTTAGCACCCCATGGGTTTTGCTTA<br>GGCACTCATGGGTAATAACCAAGATGGAGTCCCTTTGGCAAAACTTAGGCATGCACAGCTGT<br>AGTACC |
| 342 | GSTM3 | 2427210 | GCCCAAATGGCAGGGATACCCAGTGATGTCAGGAGGAATAGTACAGACAGAAGGTGCTAAG<br>CAGACAATTCAACTGCCATGTTTTGCCACCCCTGTGAGCAGGGATTAGGTGTTCAGGCCAGT<br>ATCTTGGGCATGGGGGAGCCTTTGGCCAGAAGAGGTATAAAGCTC |
| 343 | GSTM3 | 2427211 | TATGCATTTCCTGCTGGTCAAGTTGTAAATTAGTATAGCTACTTTGGAGGACAATTGTAAAATT<br>TAAATCATATCCTATGACCCAGCAATTCCATGCTATAAAAACTCATCCATGGCCGGGCTTGGT<br>GGCTCACGCCTGTAATCCCAGCACTTTGGGAGGCTGAGGTGGGCAGATCACGAGGTCAAGA<br>GATCGAGACCATCCTGGCCAACATGATGAAACCCCGTTTCTACTAAAAATACAAAAATTAGCT<br>GGGCATGGTGGCATGTGCCTATAGTCCCAGCTACTCAGGAGGCTGAGGCAGGAGAATTGCTT<br>GAACCTGGGAGGCAGAGGTTGCAGTGAGCCGAGATCACGCCACTGCACTCCAGCCTGGCTAC<br>AGGGCGAGACTCTGTCTCAAAAAAAAAAAAAAAAAAAAAAAAAAACATTCAAAGAGACAT<br>ATACTAAGATGTTCACTGTGGCATTGTCTGTAATGACAAATAAGTGGAAACCGTGTAAATACC<br>TGTCAATACTATGGAGTACCATGTGGCAACGGAAGAATGAGACTGAACTGTGTGAACTAACA<br>TGCAAAGATCCCCAAAACAGGCCAGGTGTGGTTGCTCACAGCTGTAATAACAACACCTTCAGA<br>GGCTGAGGTGAGAGGATCAGTTGAGGCCAGGAGTTTAAGACCAGCCTGGGCAACATAGTGA<br>GACCCCTGTCTCCCAAAAATTTTTTTTAATTAGCTGTGCGCAATTGCTCATGCATAGTCCCAGC<br>TACCCAGGAGGCTGAGGTGGGAGGATCACTTGAGCCCAGGAATTTGAAGCTGCAGTGAGCT<br>GTGTTCTTGCCACTGCACTCCAATCTGGGTGACTGAGCAAGACCCTGTCTCTTAAAAAAATAA<br>AAAAGATCTCCAAGCATAGAGAAGAGTCTGGAGGGAAACACCAAACTCATAACAGTCTTACT<br>GCAGGCAAGTGGGATAAAGGCCCAGACTCCATGGTGGAAGTTAAAGGGCATTTCCAAGTTAA<br>GGCTAAGACTTGCTTTTCTAACTAAGAGAATGTGCTCATGCATTGCTTGTGTAGTAGAAACTA<br>GTTTTTAGAAAAGAAAGCAAACTTAAGAAACACTGACTCCTGTGGAGATGACTTGGCACCACT<br>CTCCTTTCACAGAGCAGAGTCTGAATAGTCTTCAGAGATAGGCCTGTGGGCCA |
| 344 | GSTM3 | 2427212 | TAAGGCCCAACATTAAACACAAAGCT |
| 345 | GSTM3 | 2427213 | CTGGTGTCCAGCTGAGTTTCTCTTGGGTATAAAGGCTAAAAGGGAAAAAGGATATGTGGAGA<br>ATCATCAAGATATGAATTGAATCGCTGCGATACTGGCATTTCCCTACTCCCCAACTGAGTTCAA<br>GGGCTGTAGGTTCATGCCCAAGCCCTGAGAGTGGGTACTAGAAAAAACGAGATTGCACAGTT<br>GGAGAGAGCAGGTGTGTTAAATGGGACTGGAGTCCCTGTGAAGACTGGGTGAGGATAACAC<br>AAGTAAAACTGTGGTACTGATGGACTTAACCGGAGTTC |
| 346 | GSTM3 | 2427214 | GTGGGGCAACAAGCCTGTATGCTGA |
| 347 | GSTM3 | 2427215 | GCTTTGGAGAAAATCGCTGCCTACTTACAGTCTGATCAGTTCTG |

TABLE 13-continued

Subtyping Target Sequences

| SEQ ID NO. | Gene | Affy Probeset ID | Sequence |
|---|---|---|---|
| 348 | GSTM3 | 2427216 | TGGGATCAATGGTTGGACACCTCTAGACCTTTAAGTCTTGGGAAGAGCCTAACTTCTATACCT TGGAGGCACTGTCTACAAAAAAATGGAGGAGGTAGACGCAGGCAACACGTGAATGTTGCTG TTCTGGTATGCATCTG |
| 349 | GSTM3 | 2427217 | TTCTCTTATAAAAACACTCACAGGCTCCCCTGGGACCTGCAGGATCCCATAGTGGAGGATTCT TCCCCGGCTTTTGC |
| 350 | GSTM3 | 2427218 | CCGTATATTTGACCCCAAGTGCCTGGATGAGTTCCCAAACCTGAAGGCTTTCATGTGCCGTTTT GAG |
| 351 | GSTM3 | 2427219 | GGATTTTCTCACCTATGATATCTTGGATCAG |
| 352 | GSTM3 | 2427220 | AAACTGAAGCCTCAGTACTTGGAAGAGCTACCTGGACAACTGAAACAATTCTCCATGTTTCTG GGGAAATTCTCATGGTTTGCCGGGGAAAAG |
| 353 | GSTM3 | 2427222 | ATTCGAGTGGACATCATAGAGAACCAAGTAATGGATTTCCGCACACAACTGATAAGGCTCTGT TACAGCTC |
| 354 | GSTM3 | 2427223 | CAATGCCATCTTGCGCTACATCGCTCGCAAGCACAACATGT |
| 355 | GSTM3 | 2427226 | CGCCTGCTCCTGGAGTTCACGGATACCTCTTATGAGGAGAAACGGTACACGTGCG |
| 356 | GSTM3 | 2427227 | TGAGTGCCGTCTCAACGGTAGAGCCGCTCGGTCAAAGAGACTGACGCGGAGAGGGCGGGTC TCTGGGTCCGCGATCTCCAGCAGGAGCAGCTCTACGCGGGAGCCTTTTCGAGCTGCCGAGCC ACGGATGTCGACCCCTGCCCAGCCTCTGGGATCGCGGGCCCTGTGGGGAGGGCGGAGGAG ACCACGCCGGAGCCGGGCCTAGGGGCCGCTTAACCACCGCCCCGGCAGGACGCAGGGACTC GGCAGCCCCGGGCCGGGGAACGTTAGCGGGCGGGGGTTGGGAATGGGTGGGAGCTGCGCA GTCGCTGAACCGCTGTCTT |
| 357 | GSTM3 | 2427228 | ATGTCGTGCGAGTCGTCTATGGTTCTCGGGTACTGGGATATTCGTGG |
| 358 | GSTM3 | 2427229 | AACGCCGGCATTAGTCGCGCCTGCGCACGGCCCTGTGGAGCCGCGGAGGCAAGGGACGGAG AACGGGGCGGAGGCGGAGTCAGGGCGCCCGCGCGTGGGCCCCGCCCCCTTATGTCGGGTAT AAAGCCCCTCCCGCTCACAGTTTCCCTA |
| 359 | HMGCS2 | 2431032 | CCTGCGTTTCTTGGAACCCAGAATACAAACCCAGCCTAACATGCAGCAAGCCTGCTAGACCTT GTGGGTCAGAGGGCTGGGTCCTTGCCTCACAGGCTGCCTCTGTCCCCTTGCAATTCCATTCTA TTTCTGCCACATGCCAAGTGCTATGACAGGTACAAGGCAAATAAGAACGGTAGAACACAGCT TCCCCCAGCCCACTTCCCTGTTCTAAAGACACCACATAGACAGAGAGCAGCAGACAGGGGCC AGCAGGAGCTGTAGTTCAGATCTTCTTGGTCATTCCTTGCCGCTGTTATTTGAACAAATAAACA CAGCGCAAAGGTTAACAAGTTTT |
| 360 | HMGCS2 | 2431033 | GCTTCCTGGGAAACGTATGCTAGCAGAGCTTCTCCCCGTGAATCATATTTTTAAGATCCCACTC TTAGCTGGTAAATGAATTTGAATCGACATAGTAGCCCCATAAGCATCAGCCCTGTAGAGTGAG GAGCCATCTCTAGCGGGCCCTTCATTCCTCTCCATGCTGCAATCACTGTCCTGGGCTTATGGTG CTATGGACTAGGGGTCCTTTGTGAAAGAGCAAGATGGAGCAATGGAGAGAAGACCTCTTCCT GAATCACTGGACTCCAGAAATGTGCATGCAGATCAGCTGTTGCCTTC |
| 361 | HMGCS2 | 2431035 | GTGACACAAACAGCCTTTTCCCAGGTACTTGGTACCTGGAGCGAGTGGACGAGCAGCATCGC CGAAAGTATGCCCGGCGTCC |
| 362 | HMGCS2 | 2431036 | TGGACAAGTTGGTGTCCAGCACATCAGACCTGCCAAAACGCCTAGCCTCCCGAAAGTGTGTG TCTCCTGAGGAGTTCACAGAAATAATGAACCAAAGAGAGCAATTCTACCATAAGG |
| 363 | HMGCS2 | 2431038 | TCCAGGATTGGTGCCTTCTCTTATGGCTCTGGTTTAGCAGCAAGTTTCTTTTCATTTCGAGTATC CCAGGATGCTGC |
| 364 | HMGCS2 | 2431041 | GTACGGGTGCCTGGCCTCGCTTCTGTCC |
| 365 | HMGCS2 | 2431042 | CAACAAGGACCTGGATAAAGCACTTCTAAAGGCCTCTCAGGACATGTTCGACAAGAAAACCA AGGCTTCCCTTTACCTCTCCACTCACAATGGGAACA |
| 366 | HMGCS2 | 2431044 | ACCCTTGACGATTTACAGTACATGATCTTTCATACACCCTTTTGCAAGATGGTCCAGAAGTCTC TGGCTCGCCTGATGTTCAATGACTTCCTGTCAGCCAGCAGTGACACACAAACCAGCTTATATA AGGGGCTGGA |
| 367 | HMGCS2 | 2431047 | CTACAAACCAAATTTGGCCTCGGAGTACCCAATAGTGGATGGGAAGCTTTCCATCCAGTGCTA CTTGCGGGCCTTGGATCGATGTTACACAT |
| 368 | HMGCS2 | 2431048 | GGGCATGGGACACAGATAATGACCAGAAACCTCCTTTATATGGTTCTCTCATCTTTTGTGCTCA AGGTAGGCTGCATTGTGTAGTCTCTGAAAC |
| 369 | HMGCS2 | 2431050 | GTGGCTATGCTGATTGGGCCCAAGGCCC |

TABLE 13-continued

Subtyping Target Sequences

| SEQ ID NO. | Gene | Affy Probeset ID | Sequence |
|---|---|---|---|
| 370 | HMGCS2 | 2431051 | TCTGTGGAGACATTGCCGTCTATCCCAGTGGTAATGCTCGTCCCACAG |
| 371 | HMGCS2 | 2431056 | ACCAATGCCTGCTACGGTGGTACTGCCTCCCTCTTCAATGCTGC |
| 372 | HMGCS2 | 2431057 | ACTCTTCCAGGATTCAGGCAATACTGATATTGAG |
| 373 | HMGCS2 | 2431058 | ACTTGGCCAAAGGACGTGGGCATCCTGGCCCTGGAGGTCTACTTCCCAGCCCAATATGTGGACCAAACTGACCTGGAGAAGTATAACAATGTGGAAGCAGGAAAGTATACAGTGGGCTTGGGCCAGACCCGTATGGGCTTCTGCTCAGTCCAAGAGGACATCAACTCCCTGTGCCTGACGGTGGTGCAACGGCTGATGGAGCGCATACAGCTCCCATGGGACTCTGTGGGCAGGCTGGAAGTAGGCACTGAGACCATCATTGACA |
| 374 | HMGCS2 | 2431059 | ATGCAGCGTCTGTTGACTCCAGTGAAGCGCATTCTGCAACTGACAAGAGCGGTGCAGGAAACCTCCCTCACACCTGCTCGCCTGCT |
| 375 | HMGCS2 | 2431060 | TTCTGCTGGGTTTCTGAACTGCTGGGTTTCTGCTTGCTCCTCTGGAG |
| 376 | CTSK | 2434611 | ATTTCTTCCACGATGGTGCAGTGTAACGATGCACTTTGGAAGGGAGTTGGTGTGCTATTTTGAAGCAGATGTGGTGATACTGAGATTGTCTGTTCAGTTTCCCCATTTGTTTGTGCTTCAAATGATCCTTCCTACTTTGCTTCTCTCCACCCATGACCTTTTTCACTGTGGCCATCAGGACTTTCCCTGACAGCTGTGTACTCTTAGGCTAAGAGATGTGACTACAGCCTGCCCCTGACTGTGTTGTCCCAGGGCTGATGCTGTACAGGTACAGGCTGGAGATTTTCACATAGGTTAGATTCTCATTCACGGGACTAGTTAGCTTTAAGCACCCTAGAGGACTAGGGTAATCTGACTTCTCA |
| 377 | CTSK | 2434612 | ACAAAGGATATATCCTCATGGCTCGAAATAAGAACAACGCCTGTGGCATTGCCAACC |
| 378 | CTSK | 2434614 | TGAAAGCTGCAATAGCGATAATCTGAACCATGCAGTTT |
| 379 | CTSK | 2434615 | AGAGTTGTATGTACAACCCAACAGGCAAGGCAGCTAAATGCAGAGGGTACAGAGAGATCCCCGAGGGGAATGAGAAAGCCCTGAAGAGGGCAGTGGCCCGAGTGGGACCTGTCTCTGTGGCCATTGATGCAAGCCTGACCTCCTT |
| 380 | CTSK | 2434617 | GGCTTTTAGCTCTGTGGGTGCCCTGGAGGGCAACTCAAGAAGAAAACTGGCAAACTCTTAAATCTGAGTCCCCAGAACCTAGTGGATTGTGTGTCTGAGAATGATGGCTGTGGAGGGGCTACATGACCAATGCCTTCCAATATGTGCAGAAGAACCGGGGTATTGACTCTGAAGATGCCTACCCATATGTGGGACA |
| 381 | CTSK | 2434618 | CCCTGTCTCATTCCCGCAGTAATGACACCGTTATATCCCAGAATGGGAAGGTAGAGCCCCAGACTCTGTCGACTATCGAAAGAAAGGATATGTTACTCCTGTC |
| 382 | CTSK | 2434622 | AGCTTTGCTCTGTACCCTGAGGAGATACTGGACACCCACTGGGAGCTATGGAAGAAGACCCACAGGAAGCAATATAACAACA |
| 383 | CTSK | 2434627 | AGCTGACTTCCGCAATCCCGATGGAATAAATCTAGCACCCCTGATGGTGTGCCCACACTTTGCTGCCGAAACGAAGCCAGACAACAGATT |
| 384 | S100A10 | 2435391 | GCAGAAATGAGCAGTTCGCTCCTCCCTGATAAGAGTTGTCCCAAAGGGTCGCTTAAGGAATCTGCCCCACAGCTTCCCCCATAGAAGGATTTCATGAGCAGATCAGGACACTTAGCAAATGTA |
| 385 | S100A10 | 2435392 | TCTTTTCCCTAATTGCGGGCCTCACCATTGCATGCA |
| 386 | S100A10 | 2435393 | ACCCTCTGGCTGTGGACAAAATAATGAAGGACCTGGACCAGTGTAGAGATGGCAAA |
| 387 | S100A10 | 2435400 | TGTTTACATTTCACAAATTCGCTGGGGATAAAGGCTACTTAACAAAGGAGGACCTGAGAGTACTCATGGAAAAGGA |
| 388 | S100A10 | 2435406 | CCAGACGGACCTCCTAGGGCTAATCTGATAGTGCCTCTGAGGTCGATAGGACTCCACGTGCCACTCCCTGCAGGGTCATCCAGCAAGTAATTCCTAGACCCGTAGGTGGCCGCAGAGCCGGTTACCTCTGGTTCTGCGCCAGCGTGCCCCACCCGCAGGACGGCCGGGTTCTTTGATTTGTACACTTTCTAAAACCAAACCCGAGAGGAAGGGCAGGCTCAGGGTGGGGATGCCCTGAAATATTCGAGAGCAGGACCGTTTCTACTGAAGAGA |
| 389 | SPRR2F | 2435876 | TTTCCTCTTAGCCTGTGATCGGCCTGTGATGATCTCTGATAGCAAAAGG |
| 390 | SPRR2F | 2435877 | TGCCCCGCGCCAAAGTGCCCAGAGCCAT |
| 391 | S100A8 | 2435993 | CTGAGTTACTGGGCCCAGAGGCTGGGCCCCTGGACATGT |
| 392 | S100A8 | 2435994 | AGTTGGATATCAACACTGATGGTGCAGTTAACTTCCAGGAGTTCCTCATTCTGGTGATAAAGATGGGCGTGGCAG |
| 393 | S100A8 | 2435997 | AGCCTTGAACTCTATCATCGACGTCTACCACAAGTACTCCCTGATAAAGGGGAATTTCCATGCCGTCTACAGGGATGACCTGAAGAAATTGCTAGAGACCGAGTGTCCTCAGTATATC |

TABLE 13-continued

Subtyping Target Sequences

| SEQ ID NO. | Gene | Affy Probeset ID | Sequence |
| --- | --- | --- | --- |
| 394 | S100A8 | 2435998 | ATGCAAATTCCCTGCCATGGGATTCCCCAGAAGGTTCTGT |
| 395 | S100A8 | 2435999 | TGTCTCTGTGTGAATGGACCCTTCCCCTTCCCACACGTGTATCCCTATCATCCCACCCTTCCCAC CAGAGCCATAGCCATCTGCTGGTTTGGTTATTTGGAGAGTGCAGGCCAGGACAAGGCCATCG CTTGGGGCATGAATCCTCTGCGTACTGCCCTGGC |
| 396 | S100A8 | 2436000 | ACTGTCTGGGTTGGCCCCGCACTTTGGGCTTCTCTTGGGGAGGGTCAGGGAAGTGGAGCAGC CTTCCTGAGAGAGGAGAGAGAAAGCTCAGGGAGGTCTGGAGCAAAGATACTCCTGGAGGTG GGGAGTGAGGCAGGGATAAGGAAGGAG |
| 397 | S100A8 | 2436001 | CTGGCCAAGCCTAACCGCTATAAAAAGGAGCT |
| 398 | S100A8 | 2436002 | ACTCTGGCAGGGAGAAGCTGTCTCTGATGGCCTGAAGCTGTGGGCA |
| 399 | S100A7 | 2436052 | CCCCACCAATGGGCCTCCAGAGACCCCAGGAACAATAAAATGTC |
| 400 | S100A7 | 2436053 | AAGGGCACAAATTACCTCGCCGATGTCTTTGAGAAAAAGGACAAGAATGAGGATAAGAAGA TTGATTTTTCTGAGTTTCTGTCCTTGCTGGGAGACATAGCCACAGACTACCACAAGCAGAGCC ATGGAGCAGCGCCCTGTTCCGGGGGCAG |
| 401 | S100A7 | 2436054 | GAGCAACACTCAAGCTGAGAGGTCCATAATAGGCATGATCGACATGTTTCACAAATACACCA GACGTGATGACAAGATTGAGAAGCCAAGCCTGCTGACGATGATGAAGGAGAACTTCC |
| 402 | S100A7 | 2436055 | CAGACTGACTACTGGCTGAAAGATCTGCTTTGGG |
| 403 | S100A7 | 2436056 | ACTCATCCTTCTACTCGTGACGCTTCCCAGCTCTG |
| 404 | F11R | 2440477 | GGACTCCTAGAGTGATTGGACATTCAAAATATTCCTGATAGTCTTGTTAATTAAGAGATTAGG ATATCTTTCCATTACCTTGATAATTACGTTTTAATTTAGCTTTTTTCATTGGCCTGTGTTTAAATG CAAATAACCCCACAATGGACATTTCCTATGTTAAAGTGACATTTAGGGGATAAAAAATGAGAG CAGTTCCATGGATTTTGGTGTTTCCCCTGAGACATGAACTCAGCATAATCTGGGATAAAATGA TTGAGTGTTAAGGATGTGTTTGTTGTTCCTGTCGTTTTTTATTTTCTTCAAAGTATACAACATG GTTTGATATGCACATACATTTGTGTAATGATTGCCATGGTCAATTAACACATCACCATTTTTGT GTGTGTGTGTGTGTGTGTGTGAGGGAGTCTTGCTCCGTTGCCAGGCTGGAGTGCAATGGT ACAACCTTGGCTCACTGCAACCTCCACCTCCTGGGTTCAAGCAATTCTCTTGCCTCAGCCTCCT AAGTAGCTGGGACTATAGGCGTGTGCCACCATGCCCAGCTAATTTTTGTATTTTTAGTAGAGA CGGGGTTTCACCATGTTGGCCAGGATGATCTCGATCCCTTGACCTCATGATCCGCCCACCTCG GCCTCCCAAAGTGCTGGGATTACAGGCGTGAGTCACTGCACCCGGCCACATCACCTCCCATGT TCTATCTTACGTATTCAGAACTTGTTCATCTTGTAACTGAAAGCGTGTACCCTTTGACCAACACT GTTTTTCCTGTCTTAACAGGATCTACAGATCAAGGACAGGGGAGGGGATAGTGGAGGAAAAC GGAGTTAGTCTGTTTCTAAATGAGGGGACAGTATGTTTCTTGGGGCCTGAGGACAGCTTAAT AAAGTA |
| 405 | F11R | 2440478 | GGTGATTCATGGCTCTGTGAATTTGAGGTGAATGGTTCCTTATTGTCTAGGCCACTTGTGAAG AATATGAGTCAGTTATTGCCAGCCTTGGAATTTACTTCTCTAGCTTACAATGGACCTTTTGAAC TGGAAAACACCTTGTCTGCATTC |
| 406 | F11R | 2440479 | TTCTGTGGAGGATATACTAAGTGCGACTTTGCCCTATCCTATTTGGAAATCCCTAACAGAATTG AGTTTTCTATTAAGGATCCAAAAAGAAAAACAAAATGCTAATGAAGCCATCAGTCAAGGGTC ACATGCCAATA |
| 407 | F11R | 2440480 | GGTTCCTAGGCTCCTTTGTACAACAGGAAAATGCCTCAAAGCCTTGCTTCCCAGCAACCTGGG GCTGGTTCCCAGTGCCTGGTCCTGCCCCTTCCTGGTTCTTATCTCAAGGCAGAGCTTCTGAATT TCAGGCCTTCATTCCAGAGCCCTCTTGTGGCCAGGCCTTCCTTTGCTGGAGGAAGGTACACAG GGTGAAGCTGATGCTGTACTTGGGGGATCTCCTTGGCCTGTTCCACCAAGTGAGAGAAGGTA CTTACTCTTGTACCTCCTGTTCAGCCAGGTGCATTAACAGACC |
| 408 | F11R | 2440481 | GCTGGTGGCTTAGGCCATCACCCTTCCCTTGGCTGGAACTACTGGACAGACCCTTTTGAGATG TGCCTGTGGTGCTGTGGAGATGTGTGTAGTGGTCTTAGCTCTTTGTTGAGCTTGTGTGTGTGT TGTGTAGTCTTAGCTGTATGC |
| 409 | F11R | 2440482 | GAAAAGAAAACTGGAGGCTGGGCGCAGT |
| 410 | F11R | 2440483 | CCTTGTGTACTGACGACCAGGGCCAGCTGTTCTAGAGCGGGAATTAGAGGCTAGAGCGGCTG AAATGGTTGTTTGGTGATGACACTGGGGTCCTTCCATCTCTGGGGCCCACTCTCTTCTGTCTTC CCATGGGAAGTGCCACTGGGATCCCTCTGCCCTGTCCTCCTGAATACAAGCTG |
| 411 | F11R | 2440484 | TATTTGTCTTCTACACCCCACAGGGCCCCCTACTTCTTCGGATGTGTTTTTAATAATGTCAGCTA TGTGCCCCATCCTCCTTCATGCCCTCCCTCCCTTTCCTACCACTGCTGAGTGGCCTGGAACTTGT TTAAAGTGTTTATTCCCCATTTCTTTGAGGGATCAGGAAGGAATCCTGGGTATGCCATTGACTT CCCTTCTAAGTAGACAGCAAAAAT |
| 412 | F11R | 2440485 | GCCTGGTCGGCTCACCGCCTATCATCTGCATTTGCCTTACTCAGGTGCTACCGGACTCTGGCC |

TABLE 13-continued

Subtyping Target Sequences

| SEQ ID NO. | Gene | Affy Probeset ID | Sequence |
|---|---|---|---|
| 413 | F11R | 2440486 | ATTCAAACAGACCTCGTCATTCCTGGTGTG |
| 414 | F11R | 2440490 | GTCATCGTGGCAGCCGTCCTTGTAACCCTGATTCTCCTGGGAATCTTGGTTTTTGGCATCTGGT TTGCCTATAGCCGAGGCCACTTTGACA |
| 415 | F11R | 2440491 | TTTGATCCCCTGTCAGCCTCTGATACTGGAGAATACAGCTGTGAGGCACGGAATGGGTATGG GACACCCATGACTTCAAATGCTGTGCGCATGGAAGC |
| 416 | F11R | 2440492 | CCACCATTGGGAACCGGGCAGTGCTGACATGCTCAGAACAAGATGGTTCCCCACCTTCTGAAT ACACCTGGTTCAAAGATGGGATAGTGATGCCTACGAATCCCAAAAGC |
| 417 | F11R | 2440493 | CCTTCTTGCCAACTGGTATCACCTTCAAGTCCGTGACACGGGAAGACACTGGGACATACACTT GTATGGTCTCTGAGGAAGGCGGCAACAGCTATGGGGAGGTCAAGGTCA |
| 418 | F11R | 2440494 | GAGTGGAAGTTTGACCAAGGAGACACCACCAGACTCGTTTGCTATAAT |
| 419 | F11R | 2440495 | GAAGTTGTCCTGTGCCTACTCGGGCTTTT |
| 420 | F11R | 2440496 | CCTTCGGCTCATTTTGACCCTGTCTGCAG |
| 421 | F11R | 2440497 | GGCATTGGGCAGTGTTACAGTGCACTCTTCTGAACCTG |
| 422 | F11R | 2440501 | ACAAAGGCGCAAGTCGAGAGGAAACTGTTGTGCCTCTTCATATTGGCGATCCT |
| 423 | F11R | 2440502 | TCCTTCGGCGGCTGTTGTGTCGGGAGCCTGATCGCG |
| 424 | F11R | 2440503 | TCAGTCCCCTCGCTGTAGTCGCGGAGCTGTGTCTGTTC |
| 425 | PVRL4 | 2440589 | GGAACCTGTCTCCTACCACTTCGGAGCCATGGGGCAAGTGTGAAGCAGCCAGTCCCTGGGT CAGCCAGAGGCTTGAACTGTTACAGAAGCCCTCTGCCCTCTGGTGGCCTCTGGGCCTGCTGCA TGTACATATTTTCTGTAAATATACATGCGCCGGGAGCTTCTTGCAGGAATACTGCTCCGAATCA CTTTTAATTTTTTCTTTTTTTTTCTTGCCCTTTCATTAGTTGTATTTTTTATTTATTTTTATTTTT ATTTTTTTTTAGAGATGGAGTCTCACTATGTTGCTCAGGCTGGCCTTGAACTCCTGGGCTCAAG CAATCCTCCTGCCTCAGCCTCCCTAGTAGCTGGGACTTTAAGTGTACACCACTGTGCCTGCTTT GAATCCTTTACGAAGAGAAAAAAAAAAATTAAAGAAAGCCTTTAGATTTATCCAATGTTTACTA CTGGGATTGCTTAAAGTGAGGCCCCTCCAACACCAGGGGGTTAATTCCTGTGATTGTGAAAG GGGCTACTTCCAAGGCATCTTCATGCAGGCAGCCCCTTGGGAGGGCACCTGAGAGCTGGTAG AGTCTGAAATTAGGGATGTGAGCCTCGTGGTTACTGAGTAAGGTAAAATTGCATCCACCATTG TTTGTGATACCTTAGGGAATTGCTTGGACCTGGTGACAAGGGCTCCTGTTCAATAGTGGTGTT GGGGAGAGAGAGAGCAGTGATTATAGACCGAGAGGAGTTGAGGTGAGGTGAAGGA GGTGCTGGGGGTGAGAATGTCGCCTTTCCCCCTGGGTTTTGGATCACTAATTCAAGGCTCTTC TGGATGTTTCTCTGGGTTGGGCTGGAGTTCAATGAGGTTTATTTTTAGCTGGCCCACCCAGA TACACTCAGCCAGAATACCTAGATTTAGTACCCAAACTCTTCTTAGTCTGAAATCTGCTGGATT TCTGGCCTAAGGGAGAGGCTCCCATCCTTCGTTCCCCAGCCAGCCTAGGACTTCGAATGT |
| 426 | PVRL4 | 2440590 | ACTCCACGCTGACCACGGTGAGGGAGATAGAAACACAGACTGAACTGCTGTCTCCAGGCTCT GGGCGGGCCGAGGAGGAGGAAGATCAGGATGAAGGCATCAAACAGGCCATGAACCATTTTG TTCAGGAGAATGGGACCCTACGGGCCAAGCCCACGGGCAATGGCATCTACATCAATGGGCG GGGACACC |
| 427 | PVRL4 | 2440592 | AGCCGAGGGCCACCCTGATAGTCTCAAGGACAACAGTAGCTGCTCTGTGATG |
| 428 | PVRL4 | 2440593 | GACCAGGGAGAACTCCATCCGGAGGCTGCATTCCCATCACACGGACCC |
| 429 | PVRL4 | 2440594 | TGGACCTAGTGTCAGCCTCGGTGGTGGTGGTGGGTGTGATCGCCGCACTCTTGTTCTGCCTTC TGGTGGTGGTGGTGCTCATGTCCCGATACCATCGGCGCAAGGC |
| 430 | PVRL4 | 2440596 | TGGATGGGGACACTTTGGGCTTTCCCCCACTGACCACTGAGCACAGCGGCATCTACGTCTGCC ATGTCAGCAATGAGTTCTCCTCAAGGGATTCTCAGGTCACTGT |
| 431 | PVRL4 | 2440597 | AGGCCTCTGTGAGGGGCCTTGAAGACCAAAATCTGTGGCACATTGGCAGAGAA |
| 432 | PVRL4 | 2440598 | TCCTGGTCCAGCACTAGAAGAGGGCCAGGGCCTGACCCTGGCAGCCTCCTGCACAGCTGAGG GCAGCCCAGCCCCCAGCGTGACCTGGGACACGGAGGTCAAAGGCACAACGTCCAGCCGTTCC TTCAAGCACTCCCGCTCTGCTGCCGTCACCTCAGAGTTCCACTTGGTGCCTAGCCGCAGCATG AATGGGCAGCCACTGACTTGTGTGGTGTCCATCCTGGCCTGCTCCAGGACCAAAGGATCACC CA |
| 433 | PVRL4 | 2440599 | CCTCAGACGTGGTAACTGTGGTGCTGGGCCAGGACGCAAAACTGCCCTGCTTCTACCGAGGG GACTCCGGCGAGCAAGTGGGGCAAGTGGCATGGGCTCGGTGGACGCGGGCGAAGGCGCC CAGGAACTAGCGCTACTGCACTCCAAATACGGGCTTCATGT |
| 434 | PVRL4 | 2440606 | CCCTGTCCCTGGGAGCCGAGATGTGGGGGCCTGAGGCCTGGCTGCTGCTGCTGCTACTGCTG GCATCATTTACAG |

TABLE 13-continued

Subtyping Target Sequences

| SEQ ID NO. | Gene | Affy Probeset ID | Sequence |
|---|---|---|---|
| 435 | PVRL4 | 2440607 | TCCCAGGTTTCTGCCGTCGTTGTTGGCCACAGCGTGGGAAGCAGCTCTGGGGGAGCTCGGAG<br>CTCCCGATCACGGCTTCTTGGGGGTAGCTACGGCTGGGTGTGTAGAACGGGGCCGGGGCTG<br>GGGCTGGGTCCCCTAGTGGAGACCCAAGTGCGAGAGGCAAGAACTCTGCAGCTTCCTGCCTT<br>CTGGGTCAGTTCCTTATTCAAGTCTGCAGCCGGCTCCCAGGGAGATCTCGGTGGAACT |
| 436 | FCGR3A | 2440950 | AACCATGGTAATAAAATATGAATGAT |
| 437 | FCGR3A | 2440951 | ATGCTACTCTTAGATAGAAGATGGGAA |
| 438 | FCGR3A | 2440952 | TACTAAATGTACTACTGAGCTTCGCTGAGTTAAGTTATGAAACTTTCAAATCCTTCATCATGTC<br>AGTTCCAATGAGGTGGGGATGGAGAAGACAATTGTTGCTTATGAAAGAAAGCTTTAGCTGTC<br>TCTGTTTTGTAAGCTTTAAGCGCAACATTTCTTGG |
| 439 | FCGR3A | 2440953 | TTGAGGCAGGACCATACAGAGTGTGGGAACTGCTGGGGATCTAGGGAATTCAGTGGGACCA<br>ATGAAAGCATGGCTGAGAAATAGCAGGTAGTCCAGGATAGTCTAAGGGAGGTGTTCCCATCT<br>GAGCCCAGAGATAAGGGTGTCTTCCTAGAACATTAGCCGTAGTGGAATTAACAGGAAATCAT<br>GAGGGTGACGTAGAATTGAGTCTTCCAGGGGACTCTATCAGAACTGGACCATCTCCAAGTAT<br>ATAACGATGAGTCCTCTTAATGCTAGGAGTAGAAAATGGTCCTAGGAAGGGGACTGAGGATT<br>GCGGTGGGGGGTGGGGTGGAAAAGAAAGTACAGAACAAACCCTGTGTCACTGTCCCAAGTT<br>GCTAAGTGAACAGA |
| 440 | FCGR3A | 2440954 | GGGAAAAGCCCATGATCTTCAAGCAGGGAAGCCC |
| 441 | FCGR3A | 2440955 | TCCCATGGGGGTAATAAGAGCAGTAGCAGCAGCATCTCTGAACATTTCTCTGGATTTGCAACC<br>CCATCATCCTCAGGCCTCTCTACAAGCAGCAGGAAACATAGAACTCAGAGCCAGATCCCTTAT<br>CCAACTCTCGACTTTTCCTTGGTCTC |
| 442 | FCGR3A | 2440956 | AGAGACTGGAAGGACCATAAATTTAAATGGAGAAAGGACCCTCAAGACAAATG |
| 443 | FCGR3A | 2440957 | TCATTCTTTCCACCTGGGTACCAAG |
| 444 | FCGR3A | 2440959 | TGACTTCTACATTCCAAAAGCCACACTCAAAGACAGCGGCTCCTACTTCTGCAGGGGGCTTTTTG |
| 445 | FCGR3A | 2440960 | TTCAAGGAGGAAGACCCTATTCACCTGAGGTGTCACAGCTGGAAGAACACTGCTCTGCATAA<br>GGTCACAT |
| 446 | FCGR3A | 2440961 | TAGAAACCACGAATTGCCAGGCTGAGCAATACCAGTCCCGCCCTTCCCCTCCCTGGTGTTTAC<br>ATTGAGTTCTCCTTCACAATTTCTGCAGCCACTCCGTGGCCACCGTCACCTTATTCCTGA |
| 447 | FCGR3A | 2440962 | ACTTCATTGACGCTGCCACAGTCGA |
| 448 | FCGR3A | 2440963 | CTCCCAAAGGCTGTGGTGTTCCTGGAGCCTCAATGGTACAG |
| 449 | FCGR3A | 2440965 | GCTGCTCCTCCCAACTGCTCTGCTACTTCTAG |
| 450 | FCGR3A | 2440966 | GGCTCCGGATATCTTTGGTGACTTGTCCACT |
| 451 | FCGR3A | 2440967 | GAAAGGCTGTTTACTTCCTCCTGTCTAGTCGGTTTGGTCCCT |
| 452 | PM20D1 | 2452725 | AGGGCACTCTTGCTGGGATGCTTTCTCCAGAGCTTATATATTTCTTCTTACTAGAACTTTCTTCC<br>CCCTTTTATTCCCCTCTCTTCTTGGACTCATGAGCTGTCTCTTCATCTCTCCTCTCTCTCCTGCAT<br>CTCTCCCCTTACTCTTCAATTTATTCTACTTCTGGACCTGGACTTACCCAAACTG |
| 453 | PM20D1 | 2452727 | ATGGAGACATTGTAGAACCTAACCCATCTACTGTCCTTATTGCCAGAGTCTCATTGTCACCCCC<br>TAGAATTTATGGAAATTGGCCCCTCTTTTACAAAGATGGAGATAATTGGGTGATTGGGGAGA<br>ACCTGGTGGAATCGGTACCCTTGGGTGCTAATCCCAGCTCTTCCTCTCTTTGGGAGAGGGCTT<br>ATCCTCTGGACCCCGTTTTCTCCACTTACAAAATGGGGAGACTCCTCAGCATTTTCTGAAATGC<br>AGACACATATGAGGTCAAAGGTGGATGCGTGTTTTGACTTCTCAGA |
| 454 | PM20D1 | 2452728 | AGCCGATTCTTTACAAACCTCACCACTGGCATCTACAGGTTCTACCCCATCTACATACAGCCTG<br>AAGACTTCAAA |
| 455 | PM20D1 | 2452730 | TCCATGTGTTGAGTGCCTTTGACCCCCTCCCCGTCAGCCCTTCTGATGACAAGGCCTTGGGCTA<br>CCAGCTGCTCCGCCAGACCGTACAGTCCGTCTTCCCGGAAGTCAATATTA |
| 456 | PM20D1 | 2452731 | AACTCACGAAGAACATTGTGGCTGA |
| 457 | PM20D1 | 2452734 | CCAGGCCACAGTCAACTTCCGGATTCACCCTGGACAGACAGTCCAA |
| 458 | PM20D1 | 2452736 | TCCCTTAACCAATGCAATAATCAGGACCACCACGGCACTCACCATATTCAAAGCAGGGGTCAAG |
| 459 | PM20D1 | 2452738 | GAGCAGACACCAATGCCTATCATATTTGGAAGCGGGACAGTGGTGACTGTATTGCAGCAACT<br>GGCAAATGA |

TABLE 13-continued

Subtyping Target Sequences

| SEQ ID NO. | Gene | Affy Probeset ID | Sequence |
|---|---|---|---|
| 460 | PM20D1 | 2452739 | GAGAAGGGTTCCATGAACCTCATGCTGCAAGTAAACATGACTTCAGGCCACTCTTCAG |
| 461 | PM20D1 | 2452740 | CCCTGCTACAGTCAAGGGGCGTCCAGCTAGCCTTCATTGTGGACGAGGGGGGCTTCATCTTG GATGATTTCATTCCTAACTTCAAGAAGCCC |
| 462 | PM20D1 | 2452742 | GCTGATCAGGAAGTACATCCCCCGAAGATCTTTCTTCATTT |
| 463 | PM20D1 | 2452743 | GTCAGCACCAGCTTTATCCAGCATGAAGTCGTGGAAGAGTATAGCCACCTGTTCACTATCCAA GGCTCGGACCCCAGCTTGCAGCCCTACCTGCTGATGGCTCACTTTGATGTGGTGCCTGCCCCT GAAGAAGGCTGGGAGGTGCCCCCATTCTCTGGGTTGGAGCGTGATGGCATCATCTATGGTCG GGGCACACTGGACGACAAGAACTC |
| 464 | PM20D1 | 2452744 | GCCATCCAGATTCCAACAGTGACTTTTAGCTCTGAGAAGTCCAATACTACAGCCCTGGCTGAG TTCGGAAAATACATTCA |
| 465 | PM20D1 | 2452748 | GGTGGCTATGCTGCTCCTAGTTTTCCCTACCGTCTCCAGATCGATGGGCCCGAGGAGCGGGG AGCATCAAAGGGCGTCGCGAATCCCTTCTCAGTTCAGCAAAGAGGAACGCGTC |
| 466 | PM20D1 | 2452749 | AGGTCAGAACTACCCCGGTAGCCTGACAGCAGGAG |
| 467 | GRHL1 | 2469161 | CAAACGGCCAGTGTTGGTTCTTCAG |
| 468 | GRHL1 | 2469162 | TGGAAAACCCTCTCACTGCAGCGACCAAAGCGATGATGAGCATCAATGGAGATGAAGAC |
| 469 | GRHL1 | 2469165 | AGAGAAGGTCATCAACAGCAAAGCC |
| 470 | GRHL1 | 2469166 | TTTGCCTCTGTTGCTCTGAAATTTCCTTTTTCTTTGGGCGTAGTAGTTGCCTTTTCTAGGATGA AGCACTAACATTCTCCTCCTCCAAAGGGATAGTTTTAGTAATAACTTCAGTATTTGCTTATTT GTTTTTGAGGTTTTCTTTAGAAGGATGTGTGGCAGTGGTCTATTAAAAAAATTAAGCACCAGT GACTCTTGAACAACTGCCTGAGTAAAATTGAATAAAGCAAGTTAAATTGTATTCAAATTCCTG TTGAAATTATTTGTGAAATATTTTAGATTAAAACTTTCAGAAAATTTAATTAACGTTTGGCTAG CCATGAAAAACTTTAAAAAGACACCTTTTAAATTGTCTTGTGTTTTATTATCAATCAAGGAATG AAACATATTTAAAGGAAGAATGATCATCACCCAGTATCCCATTATCGTGATGATTGCTTTATTC ATTGTTTTGATGTGTATGCAAATTTTATGTAGCGTAGTTGTGTTCACAGATAGGATTGGTAGT GTACTTTCTTCTACTTAGTTTGTTTCATAAACATTTTCTCTGTATTTTAATCTTCATAATTATCCTT TGGAAGAGGACTTGTGGCTTTTATCTTTTACTTTTCATTATGGGCATTTTCAAACATAATAAAA ATAGAAAAACAGTATAAGCCCACATGTATCCATGACCAGCCTCAACAGTTATCAACACAATTC CTCTTGTTTGATTTGTTCTTCCCTCTTCTTCAACTTTGAGATTAATTCATGTTTTTATTTTATTTAT TTTTGCTGGAACATTCTGAAGCAAACTGTAAATATCCTTACAATTGCTGCTATATCTAGTTTTCA CTATTAAGAAGTCTTAAGGAACAACTTTCTAGACTTTTTCCGTTTTAGGATAAATTCCTGGGAG TGAATTTATGGTTCAGGGTCAAACAGTTTTATTGATCTTGAAATGTACAGAATTCTCAATTTG CCTGTTTCTTGAAGCTTCAGCCTATATGATTTCTGGGGGCTTTGAAAATTCATTCATTTTACCCA CTGGAAATCATCTTGTATTGCTCAAATTATTTATCAAACCAAAATTTAATTTTATAAAAAGCAG ATGTGTCTACTGATGCAATGTAACAATAGGTTTTCTTGGGTGAAAGAGAAAGCCAGGCCCGG CACAGTGGCTCATGCCTGTAATCGCAGCGCTTTGGGAGGCTGAGGCAGGTGGATCACCTGAG GTCAGGAGTTCGAGACCAGCCTGGCCAACATGGTAAAACCCAGTCTCTACTAAAAATACAAA AATTAGCCAAGTGTGGTGGCGTGCGCCTGTAATCCCAGCTACTCGGGAGGCTGAGGTGGGA GAATCGCTTGAACCCGGGAGGCGGAGGTTGCAGTGAGCCTAGATCACGCCATTGCACACCAG CCTGGGCCATAAGGGCAAGACTCTGTCTCAAAAAAATAAAAATTAAAAAAAAAAAAAGGAG AAAGCCAAATGGCATAGGTGGTAGGAAAAGTGGTGACCAAGTAATAATAGCTCATACTTCTT GAAGACTGTGTGTCAGGCATTATTATACACCTTTTAGTGTATCATCTCATCTCAACCTGATGAG AATGGATGCCATTATTGTCCCCATTTTGCAGATGAGGATTCAGTTACTAAGAGATGAAGTAAC TTGCTCAGGTGACACAGAACTTGAACCCAGGCAATTTGACCCTGGCGTCTATGCTGTAACCCC AGTTGATCAGATCGCATAGCTTCAGGTTTCTAGTAAAACACAGTAATTGTTTTTAGGATTATG GAAAGTAAAGCTTGTTAGAGGAGAGCTCTGAGCCCTTAGTATTTCGAATGAAATTTTACTTAA TAGGTTTGGATTTTATTTGACCGATAACCAGAAAGCCTTTTTCCCTTTATCTAGTAATGGGTAG TTTTGATGTTTTCTGTTTATTCTGTCAAGTGTTATTGCACAGGACCCAA |
| 471 | GRHL1 | 2469167 | AAACAGCATACCAATTGTGACAGAGCAGCCCTCATCTCTGCTGGAGAAAACAGAGTGCAAG TACTGAAAAATGTGCCATTTAACATTGTCCTTCCCCAT |
| 472 | GRHL1 | 2469168 | CTGGGCATTGATAAGAGAGGCCATCTGACAGCTCCAGATACGACAGTCACTGTCT |
| 473 | GRHL1 | 2469169 | TGCCTACCCACTCCATCAAGACAGAAACCC |
| 474 | GRHL1 | 2469170 | GGTGGTGGTTTTCGATCGGAATCTCAATACTGACCAGTTCAGCTCTGGTGCTCAAGCCCCAAA TGCTCAAAGGCGAACTCCAGACTCGACCTTCT |
| 475 | GRHL1 | 2469172 | CCCTCGGATCTCAGTCTGCGGATGCCTGGCATGAATTCAGAGGACTATGTTTTGACAGTG |
| 476 | GRHL1 | 2469173 | GAACAACTTTGAATATACCCTAGAAGCTTCAAA |

TABLE 13-continued

Subtyping Target Sequences

| SEQ ID NO. | Gene | Affy Probeset ID | Sequence |
|---|---|---|---|
| 477 | GRHL1 | 2469174 | AGCCAGGAGACAGTACCATGACGTACCTGAACAAAGGCCAGTTCTATCCCATCACCTTGAAG GAGGTGAGCAGCAGTGAAGGAATCCATCATCC |
| 478 | GRHL1 | 2469175 | GCAGAGAAGATCAGTTAAGGCATTGGAAGTACTGGCACTCCCGGCAGCACACCGCTAAACAA AGATGCATTGACATA |
| 479 | GRHL1 | 2469176 | CAAGAGCCCGCTTTTATTCCCAGAGGTGCAGCCATCCAGTTTTCTAAATCCAATTATTTTTGGC AGTGATCAGCTTCCTGCCGAAAGCATTTGAATTTTTATGCCAGCTACTGATCTGTTCCAAACAC TGTCCTCGGCCTCCTGGAACCAGTGCTCTCACCATTGCTCCCATGCAGTAATGGGACATGTGC CCACGTGGTGGCTTTCCACAGGACACTAGGGCCAGAAGCCATGTAGCTGGCTAACCTGAGAA TGTCCCCACTGTTCAGTCTGCAATTGCTTTAAGGGGTAATATCTTCTTTAAAAGATTCTGATTAT TATTTGGAGATGATGGAGGTAGAGAAAAAAACAAGTAAAAGAAAGATATTGCTGCTGTGCA GTTGCCTAACAGTCTTCCCTAGTCACGTGCTAAACCGTGTAACTAACCTCTCTGTGGGCTGTAG TGGCAAACCTGTGCAAATCTGTATTTACTGAAGTAGCGTTACACAGACCTCTGTTCTTGCCATG TATGTAATTTTCATGTAAAACCATTGTCTGTATCACAGATGGCTGTTTAATATTAGTGTTACTTT TTTTCTTTACCTTTTGTAATGCTCTTGTTTCCTTTTCAGGAGAATGAGAACTCAGTTCTAATCTT GGTTCTACAGAGTAGTTTTGTGACCTTGGGACTGTTATTTAAACTTTTTAGACTTAAATTTCCTA ATTGTGACATAATGAGATTGAATTAAATATGTCTAAGCTTGCCTCTATTACAAAAACTCTGTGA TTCTTTTTCTTCGTATTTTGAACTTCTTCTAATCGAACAAAATGTTAATTTAAATTGTCCAGAGG TGATAATGCTAAAAACTAGATCTTATTTTGAACTGCTGGGATCCCA |
| 480 | GRHL1 | 2469177 | AAAGAAAGCTTCAACACTATCAGTAACATCGAGGAGATTGCGTATAACGCCATTTCCTTCACA |
| 481 | GRHL1 | 2469178 | GGGCGCCTTATGTCCAGCCATTTGAGAAATGGGAGGAGTTTAATGATTTGACAACTGATTTTT TTTTTTTCACAGTTTTATGTGTTTCATTCTCAGGTGTTATGAAACTATCCTCTTCCCTTTTTATTC TCCCCTCCTCCAAAACAGATCATTTTTGTTGCCATCCTTTGCACAGAGTCCAGTGTGTGAAACA TTGAGATTAAGTTGCACTCTGCCACTCCTGCCTGTTCAGCCTTGAGTCTGACTCCTCATTTGCTT TGCCTCATTTCCTCATTTGCACAGTGGAGGTGATATCTGTCTCCTCCCTCTATTGAAGGAGGTG TAAGGAGTAATGAAACAATGCCCATCAAACTGTTGGAGTGGCTTTGAGAAAGGCTCTTAAAT ATAAGTGATTATTAGTAGTACTCTGTTTCATATCATCACCTTGTAAATATGACTCTGTGTTAAG ATTCTTCTGTCTTGGGCTTTTCCCATTGAAGAGTTGCCTCCAGTTCAGTTGGAGTAACTCTAAT TGGCTAGAGTTACTCCTTGTGGGCGACTCTAA |
| 482 | GRHL1 | 2469185 | AGGGGTTGCCTCTTAACATTCAAGTTGATACCTATAGTTACAACAACCGCAGCAACAAGCCTG TGCACCGGGCCTACTGCCAGATCAAGGT |
| 483 | GRHL1 | 2469186 | GCGGAAAATCAGGGATGAAGAACGAAAG |
| 484 | GRHL1 | 2469188 | TGATGTTAAAGTGCCACTGCTTCCC |
| 485 | GRHL1 | 2469190 | TTCCCATTGCCTCTGAAGAATTGGAGGGTGAA |
| 486 | GRHL1 | 2469193 | GGCCGTACGGCACAGAAGATGACTTTGCTGTCCCTCCTTCTACCAAGCTGGCCCGGATAGAA GAACCAAAGA |
| 487 | GRHL1 | 2469194 | TGCTGCTCTACGTTCGAAAGGAGTCAGAAGAAGTCTTTGATGCCCTGATGCTCAAAACCCCAT CTTTGAAGGGCTTGATG |
| 488 | GRHL1 | 2469196 | ATCTCAGACAAATACGATGTTCCCCATGACAA |
| 489 | GRHL1 | 2469198 | AACATGGACGACAACATTGTGAAGCATTACTCCAATGAGGACACCTTCCAGCTGCAGATTGAA GAAGCCGGGGGGTCTTACAAGCTCACCCTGACGGAGATCTAA |
| 490 | GRHL1 | 2469199 | CATGTCGCCAGCACAGGTCTATGTCGAGGGAATGGGTTCCTTGCAGGTTGGAGGCGGGGCT GCATCTGGCTTGGTGGTAGCATTTAATCTATTGCATTGGTGTTTTTCAGATGAAAGAGAAATC CATATACCATTATGTTTGAATTTCCTGATATATACAGGATTTAAAGTGAAAACTTTATTCCAAG AGTTAACAGAGTCTCTGGGAAGCTTTAGGACATCTGCTACGTTATTTATCAAAATATTGGGAT CTCTGCCTTGTGCCTACAGTGTCGTGGGCCTGCTCGCTAGCAGAAGTCAGAAAAGGCGATAG GCTTGGCTTTAAGGATTTCGTGCCCTTGCCTGAATTCAGTACAACTCCACTGCCTCACGTTAGC GGGAGCGCACCTGAAGAGTACGGGGGGAGCCCTCTCTCCCTTACCCTCTCACTCTCCACCAGA TGTTTACTAAACAGGGCATGTTACTGAAATCTTCCTTTGCGACTTTCTCGGACATATCAACTG |
| 491 | EPCAM | 2480965 | GAGCAGCGCTCCTCCGGTTAAAAGGAAGTCTCAGCACAGAATCTTCAAACCTCCTCGGAGGC CACCAAAGATCCCTAACGCCGCCATGGAGACGAAGCACCTGGGGCGGGGCGGAGCGGGGC GCGCGGGCCCACACCTGTGGAGGGGCCGCCCAACTGCAGCGCCGGGGCTGGGGGAG GGGAGCCTACTCACTCCCCCAACTCCCGGGCGGTGACTCATCAACGAGCACCAGCGGCCAGA |
| 492 | EPCAM | 2480966 | GCGCACAGAGCGCTAGTCCTTCGGCGAGCGAGCACCTTCGACGCGGTCCGGGGACCCCCTCG TCGCTGTCCTCCCGACGCGGACCCGCGTGCCCCAGGCCTCGCGCTGCCCGGCCGGCTCCTCGT GTCCCACTCCCGG |
| 493 | EPCAM | 2480967 | GCCCCTCTTCTCGGCGCGCGCGCAG |
| 494 | EPCAM | 2480968 | CAGGTCCTCGCGTTCGGGCTTCTGCTTGCCGCGGCGACGGCGACTTTTGCCGCAGCTCAGG |

TABLE 13-continued

Subtyping Target Sequences

| SEQ ID NO. | Gene | Affy Probeset ID | Sequence |
|---|---|---|---|
| 495 | EPCAM | 2480969 | GTGAGGCGCGGATTGGAGCAGAGTTGT |
| 496 | EPCAM | 2480970 | CAAGAGGCCGCGCTTTCCAGCGTGGAG |
| 497 | EPCAM | 2480972 | CAAGCTGGCCGTAAACTGCTTTGTGAATAATAATCGTCAATGCCAGTGTACTTCAGTTGGTGCACAAAA |
| 498 | EPCAM | 2480973 | TGGCTGCCAAATGTTTGGTGATGAAG |
| 499 | EPCAM | 2480974 | GAAGGGGCCCTCCAGAACAATGATGGGCTTTATGATCCTGACTGCGATGAGAGCGGGCTCTTTAAGGCCAAGCAGTGCAACGGCACCTCCATGTGCTG |
| 500 | EPCAM | 2480975 | GTGTGTGAACACTGCTGGGGTCAGAAG |
| 501 | EPCAM | 2480980 | TATGAGAATAATGTTATCACTATTGATCTGGTTCAAAATTCTTCTCAA |
| 502 | EPCAM | 2480981 | TTAAAGGTGAATCCTTGTTTCATTCTAAGAAAATGGACCTGACAGTAAATGGGGAACAACTGGATCTGGATCCTGGTCAAACTTTAATTTA |
| 503 | EPCAM | 2480982 | GTCTAAAAGCTGGTGTTATTGCTGTTATTGTGGTTGTGGTGATAGCAGTTGTTGCTGGAATT |
| 504 | EPCAM | 2480987 | ATGGGTGAGATGCATAGGGAACTCAATGCATAA |
| 505 | EPCAM | 2480988 | TGCGTGGGACGAAGACATCTTTGAAGGTCATGAGTTTGTTAGTTTAACATCATATATTTGTAATAGTGAAACCTGTACTCAAAATATAAGCAGCTTGAAACTGGCTTTACCAATCTTGAAATTTGACCACAAGTGTCTTATATATGCAGATC |
| 506 | EPCAM | 2480989 | ACTGATTTGTGATTGAAAGCTGCCTTTCTATTTACTTGAGTCTTGTACATACATTTTTTATGAGCTATGAAATA |
| 507 | ACTG2 | 2489010 | CCCAGATGTCATTCGTGCTGAAAGAACCAGAACAACTCTCTGCTCCCTGCCAAGCATGAAGCGGTTGTGACCCCAGGAAACCACAGTGACTTTGACTCTGGTTCAGCTGACATGCTCGAGTC |
| 508 | ACTG2 | 2489013 | GCTCCAGTCCCCAGCTCACTCAGCCACACACACC |
| 509 | ACTG2 | 2489014 | AGGAGACCACCGCGCTCGTGTGTGACAATGGCTCGGCCTGTGCAAGGCAGGCTTCGCAGGAGATGATGCCCCCGGGCTGTCTTCCCCTCCATTGTGGGCCGCCCTCGCCA |
| 510 | ACTG2 | 2489015 | GGCTCAGAGCAAGCGAGGGATCCTAACTCTCAAATACCCCATTGAACACGGC |
| 511 | ACTG2 | 2489017 | CTGCGTGTAGCACCTGAAGAGCACCCCACCCTGCTCACAGAGGCTCCCCTAAATCCCAAGGCCAACAGGGAAAAGATGACCCAG |
| 512 | ACTG2 | 2489019 | CCTGCCATGTACGTCGCCATTCAAGCTGTGCTCTCCCTCTATGCCTCTGGCCGCACGACA |
| 513 | ACTG2 | 2489020 | GGATTCAGGTGATGGCGTCACCCACAATGTCCCCATCTATGAAGGCTATGCCCTGCCCCATGCCATCATGCGCCTGGACTTGGCTGGCCGTGACCTCACGGACTACCTCATGAAGATCCTCACAGAGAGAGGCTATTCCTTTGTGAC |
| 514 | ACTG2 | 2489021 | AGAGAGAAATTGTGCGAGACATCAAG |
| 515 | ACTG2 | 2489022 | GGCAATGAGCGCTTCCGCTGCCCTGAGACCCTCTTCCAGCCTT |
| 516 | ACTG2 | 2489025 | GCATGGAGTCCGCTGGAATTCATGAGACAACCTACAATTCCATCATGAAGTGTGACATTGACATCCGTAAGGACTTATATGCCAAC |
| 517 | ACTG2 | 2489026 | AAGGAGATCACAGCCCTGGCCCCCAGCACCATG |
| 518 | ACTG2 | 2489029 | CCCAGAGCGGAAGTACTCAGTCTGGATCGGGGGCTCTATCCTGGCCTCTCTCTCCACCTTCCAGCAGATGTGGATCAGCAAGCCTGAGTATGATGAGGCAGGGCCCTCCATTGTCCACAGGAAGTGCT |
| 519 | ACTG2 | 2489030 | CAAGGATCCCCTCGAGACTACTCTGTTACCAGTCATGAAACATTAA |
| 520 | ACTG2 | 2489031 | CTCTTTTTTCCTGGGCTATGTCTCATACACAGTGCTAAGGACTTTTCACACATTACTTTTAATCCATGCAATAGTGCTGTAAGGTAGGTGCTATCATTATACCCATATTACAGATGAGGAAATTGAGGCTCAGAGAAGTCAAGGACTTGCGAAGATCACACAGATTCCAGA |
| 521 | TMSB10 | 2491288 | TGGGAGCACCAGGATCTCGGGCTCGGAAC |
| 522 | TMSB10 | 2491295 | CCATTGAGCAGGAGAAGCGGAGTGAAATTTCCTAA |
| 523 | TMSB10 | 2491296 | AAGAGCCACCTGCAAGATGGACACGAGC |

TABLE 13-continued

Subtyping Target Sequences

| SEQ ID NO. | Gene | Affy Probeset ID | Sequence |
|---|---|---|---|
| 524 | TMSB10 | 2491297 | CCCCCCAATCGGACTGCCAAATTCTCCGGTTTGCCCCG |
| 525 | MAL | 2493859 | CAGGCCACTGGGCTCCGCGGAGCCAGCGAGAGGTCTGCGCGGAGTCTGAGCGGCGCTCGTC CCGTCCCAAGGCCGACGCCAG |
| 526 | MAL | 2493860 | TGCCCAGTGGCTTCTCGGTCTTCACCACCTTGCCCGACTTGCTCTTCATCTT |
| 527 | MAL | 2493865 | TGGGTGATGTTCGTGTCTGTGTTCTGCTTCGTGGCCACCACCACCTTGATCATCCTGTACATAA TTGGAGCCCACGGTGGAG |
| 528 | MAL | 2493866 | CACCGCTGCCCTCTTTTACCTCAGCGCCTCAGTCCTGGAGGCCCTGGCCACCATCACGATGCA AGACGGCTTCACCTACAGGCACTACCATGAAAAC |
| 529 | MAL | 2493868 | GTGTTCTCCTACATAGCCACTCTGCTCTACGTGGTCCATGCGGTGTTCTCTTTAATCA |
| 530 | MAL | 2493869 | TGCTGTGTTTACTCTCCCGTGTGCCTTCGCGTCCGGGTTGGGAGCTTGCTGTGTCTAACCTCCA ACTGCTGTGCTGTCTGCTAGGGTCACCTCCTGTTTGTGAAAGGGGACCTTCTTGTTCGGGGT GGGAAGTGGCGACCGTGACCTGAGAAGGAAAGAAAGATCCTCTGCTGACCCCTGGAGCAGC TCTCGAGAACTACCTGTTGG |
| 531 | RALBP1 | 2496248 | GATTGCACAAGAGATAGCCAGTCTTTCAAAAGAGG |
| 532 | ITGA6 | 2515628 | GCTCATTCAGCGGTCGCGAGCTGCCCGCGAGGGGAGCGGCCGGACGGAGAGCGCGACCC GTCCCGGGGGTGGGGCCGGGCGCAGCGGCGAGAGGAGGCGAAGGTGGCTGCGGTAGCAG CAGCGCGGCAGCCTCGGACCCAGCCCGGAGCGCAG |
| 533 | ITGA6 | 2515629 | GCTGTGCTTGCTCTACCTGTCGGCGGGGCTCCTGTCCCGGCTCGGCGCAGCCTTCAACTTGGA CACTCGGGAGGACAACGTGATCCGGAAATATGGAGACCCCGGGAGCCTCTTCGGCTTCTCGC TGGCCATGCACTGGCAACTGCAGCCCGAGGACA |
| 534 | ITGA6 | 2515643 | CGGGCAGAAGCGCTTCCACTGCAGAGAGCCAACAGAACGGGAGGGCTGTACAGCTGCGACA TCACCGCCCGGGGGCCATGCACGCGGATCGAGTTTGATA |
| 535 | ITGA6 | 2515645 | TGACCCCACGTCAGAAAGCAAGGAAGATCAGTGGATGGGGGTCACCGTCCAGAGCCAAGGT CC |
| 536 | ITGA6 | 2515646 | TGTGCTCACCGATATGAAAAAAGGCAGCATGTTAATACGAAGCAGGAATCCCGAGACATCTT TGGGCGGTGTTATGTCCTGAGTCAGAATCTCAGGATTGAAGACGATATGGATG |
| 537 | ITGA6 | 2515653 | GACCAGCGTTTCCTATACAGATCCTGATCAGTTTGTTTATAAAACACGGCCTCCCCGGGAGCA GCCTGACACATTCCCTGATGTGATGATGAATAGCTACCTA |
| 538 | ITGA6 | 2515654 | TCTGGTGCTCCCAGAGCCAATCACAGTGGAGCCGTGGTTTTGCTGAAGAGAGACATGAAGTC TGCACATCTCCTCCCTGAGCACATATTCGATGGAGAAGGTCTGGCCTCTTCATTT |
| 539 | ITGA6 | 2515655 | GTTGGAGGTGCAGTGTATGTCTACATGAACCAGCAAGGCAGATGGAATAATGTGAAGCCAAT TCGTCTTAATGGAACCAAAGATTCTATGTTTGGCATTGCAGTAAAAAATATTGGAGATATTAA TCAAGATGGCTA |
| 540 | ITGA6 | 2515656 | ATATTGCAGTTGGAGCTCCGTATGATGACTTGGGAAAGGTTTTTATCTATCATGGATC |
| 541 | ITGA6 | 2515657 | CACCTTATTTTGGATATTCAATTGCTGGAAACATGGACCTTGATCGAAATTCCTACCCTGATGT TGCTGTTGGTTCCCTCTCAGATTCAGTAACTATTT |
| 542 | ITGA6 | 2515658 | TCCCGGCCTGTGATTAATATTCAGAAAACCATCACAGTAACTCCTAACAGAATTGACCTCCGCC AGAAAACAGCGTGTGGGCGC |
| 543 | ITGA6 | 2515661 | AGAAAATCTGGGCTATCCTCAAGAGTTCAGTTTCGAAACCAAGGTTCTGAGCCCAAATATACT CAAG |
| 544 | ITGA6 | 2515662 | TCAGAGATAAACTGCGTCCCATTCCCATAACTGCCTCAGTGGAGATCCAAGAGCCAAGCTCTC GTAGGCGAGTGAATTCACTTCCAGAAGTTCTTCCAATTCTGAATTCAGATGAACCCAAGACAG CTCATATTG |
| 545 | ITGA6 | 2515663 | ACTTCTTAAAAGAGGGATGTGGAGACGACAATGTATGTAACAGCAACCTTAAACTAGAATAT AAATTTTGCACCCGAGAAGG |
| 546 | ITGA6 | 2515664 | CCCAAGGAATCCCACAAAAGATGGCGATGACGCCCATGAGGCTAAACTGATTGCAACGTTTC CAGACACTTTAACCTATTCTGCATATA |
| 547 | ITGA6 | 2515665 | GTTGTGTTGCCAACCAGAATGGCTCGCAAGCTGACTGTGAGCTCGGAAATCCTTTTAAA |
| 548 | ITGA6 | 2515666 | TTGGTTTTAAGTACAACTGAAGTCACCTTTGACACCCCAGATCTGGATATTAATCTGAAGT |

TABLE 13-continued

Subtyping Target Sequences

| SEQ ID NO. | Gene | Affy Probeset ID | Sequence |
|---|---|---|---|
| 549 | ITGA6 | 2515668 | TTCCCAGGTGTATTTTGGAGGTACAGTTGTTGGCGAGCAAGCTATGAAATCTGAAGATGAAG<br>TGGGAAGTTTAATAGAGTATGAATTC |
| 550 | ITGA6 | 2515669 | AAACCTCTTACAAACCTCGGCACAGCAACCTTGAACATTCAGTGGCCAAAAGAAATTAGCAAT<br>GGGAAATGGTTGCTTTATTTGGTGAAAGTAGAATCCA |
| 551 | ITGA6 | 2515670 | TAACTTGTGAGCCACAAAAGGAGATAAACTCCCTGAA |
| 552 | ITGA6 | 2515672 | CTTGCTGGTTTTACACTTACTTCTGTGCCTTTGGCAGGAGAGAGGCAAATATTGTTGATTATGT<br>GAATCTGGCACTGTTTGGGAGGATATGCTCAAGAGGCTTGTATGGTAATGACAAAG |
| 553 | ITGA6 | 2515673 | AACAGATAGATGATAACAGAAAATTTTCTT |
| 554 | ITGA6 | 2515674 | TGTGTGAACATCAGATGCCCGCTGCGGGGGCTGGACAGCAAGGCGTCTCTTATTTTGCGCTC<br>GAGGTTATGGAACAGCACATTT |
| 555 | ITGA6 | 2515675 | GGACATTCTCATGCGAGCCTTCATTGATGTGACTGCTGCTGCCGAAAATATCAGGCTGCCAAA<br>TGCAGGCACTC |
| 556 | ITGA6 | 2515677 | TTTCCCTCAAAGACTGTAGCTCAGTATTCGGGAGTACCTTGGTGGATCATCCTAGTGGCTATTC<br>TCGCTGGGATCTTGATGCTTGCTTTATTAG |
| 557 | ITGA6 | 2515679 | TATGATGCCACATATCACAAGGCTGAGATCCATGCTCAGCCATCTGATAAAGAGAGGCTTACT |
| 558 | ITGA6 | 2515683 | GTGGATTCTTTAAACGCTCTAGGTACGATGACAGTGTTCCCCGATACCATGCTGTAAGGATCC<br>GGAAAGAAGAGCGAGAGATC |
| 559 | ITGA6 | 2515684 | TCACAAAGTGGAACGAAAATGAAAGCTACTC |
| 560 | ITGA6 | 2515685 | TGCCCAGTTGCACTCAGGTGACATCCTCCAGATAGTGTAGCTGAGGAGGCACCTACACTCACC<br>TGCACTAACAGAGTGGCCGTCCTAACCTCGGGCCTGCTGCGCAGACGTCCATCACGTTAGCTG<br>TCCCACATCACAAGACTATGCCATTGGGGTAGTTGTGTTTCAACGGAAAGTGCTGTCTTAAAC<br>TAAATGTGCAATAGAAGGTGATGTTGCCATCCTACCGTCTTTTC |
| 561 | ITGA6 | 2515686 | GGTGAATGCCTATGGTGGATCCAAACTGATCCAGTATAAGACTACTGAATCTGCTACCAAAAC<br>AGTTAATCA |
| 562 | ITGA6 | 2515687 | AGTCTCAGTTTCTTGCTTGGGGAACTTGTGTCCCTAATGTGTTTAGATTGCTAGATTGCTAAGG<br>AGCTGATACTTTGACAGTGTTTTTAGACCTGTGTTACTAAAAAAAAGATGAATGTCCTGAAAA<br>GGGTGTTGGGAGGGTGGTTCAACAAAGAAACAAAGATGTTATGGTGTTTAGATTTATGGTTG<br>TTAAAAATGTCATCTCAAGTCAAGTCACTGGTCTGTT |
| 563 | COL3A1 | 2519582 | TGAGTTTTATGACGGGCCCGGTGCTGAAGGGCAGGGAACAACTTGATGGTGCTACTTTGAAC<br>TGCTTTTCTTTTCTCCTTTTTGCACAAAGAGTCTCATGTCTGATATTTA |
| 564 | COL3A1 | 2519583 | ATGAGCTTTGTGCAAAAGGGGAGCTGGCTACTTCTCGCTCTGCTTCATCCCACTATTATTTGG<br>CACAACAGGAA |
| 565 | COL3A1 | 2519585 | CTGTTGAAGGAGGATGTTCCCATCTTGGTCA |
| 566 | COL3A1 | 2519586 | GTTCTCTGCGATGACATAATATGTGACGATCAAGAATTAGACTGCCCCAACCCAGAAATTCCA<br>TTTGGAGAATGTTGTGCAGTTTGCCCACA |
| 567 | COL3A1 | 2519587 | CCTACTCGCCCTCCTAATGGTCAAGGACCTCAAGGCC |
| 568 | COL3A1 | 2519591 | ACCCCCTGGTGAACCTGGGCAAGCT |
| 569 | COL3A1 | 2519592 | GGACCTCCTGGTGCTATAGGTCCAT |
| 570 | COL3A1 | 2519594 | CAAAGGTCCAGCTGGGATACCTGGAT |
| 571 | COL3A1 | 2519596 | GGTGAAAATGGTCTTCCAGGCGAAAATGGAGCTCCT |
| 572 | COL3A1 | 2519597 | GGTGAGCGAGGACGGCCAGGACTTCCTGGGGC |
| 573 | COL3A1 | 2519599 | CTGGAACTGCCGGATTCCCTGGATCCCCTGGTGCTAA |
| 574 | COL3A1 | 2519600 | CCTGCAGGGTCTCCTGGTTCAAATGGTGCCC |
| 575 | COL3A1 | 2519604 | GTGAGGCTGGTATTCCAGGTGTTCCAGGAGCTAAAGGCGAAGATGGCAAGGAT |
| 576 | COL3A1 | 2519605 | GTGCCCCTGGGTTCCGAGGACCTGCTGGACCAAATGGCATCCCAGGAGAAA |

TABLE 13-continued

Subtyping Target Sequences

| SEQ ID NO. | Gene | Affy Probeset ID | Sequence |
|---|---|---|---|
| 577 | COL3A1 | 2519606 | CCTGCTGGAGAGCGTGGTGCTCCAG |
| 578 | COL3A1 | 2519607 | GAAGTGATGGGAAACCAGGGCCTCC |
| 579 | COL3A1 | 2519608 | TCAAGGAGAAAGTGGTCGACCAGGTCCTCCTGGGCCATCTGGTCCCCGAGGTCAGCCTGGTG TCATGGGCTTCCCCGGTCCTAAA |
| 580 | COL3A1 | 2519610 | TGGTAAGAATGGAGAACGAGGTGGCCCT |
| 581 | COL3A1 | 2519611 | GAAAGAATGGTGAAACTGGACCTCAGGGAC |
| 582 | COL3A1 | 2519612 | CCTGGTGGTGACAAAGGAGACACAGGACCCCCTGGTCCACAAGGATTACA |
| 583 | COL3A1 | 2519613 | GGCTTGCCTGGTACAGGTGGTCCTCCAGGAGA |
| 584 | COL3A1 | 2519614 | GGTCCAAAGGGTGATGCCGGTGCACCTGGA |
| 585 | COL3A1 | 2519615 | GTGCCCCTGGTGAACGTGGACCTCCTG |
| 586 | COL3A1 | 2519616 | GGAGGTCTTGGAAGTCCTGGTCCAAAG |
| 587 | COL3A1 | 2519617 | AACCAGGCGGTCCAGGTGCTGATGGTGTCCCA |
| 588 | COL3A1 | 2519618 | GGTCCTACTGGTCCTATTGGTCCTCCTGGCCCAG |
| 589 | COL3A1 | 2519620 | GTGAGAGAGGTGAAACTGGCCCTCCAGGACCTGCTGGTTTCCCTGGT |
| 590 | COL3A1 | 2519621 | GACAGAATGGTGAACCTGGTGGTAAAGGAGAAAGAGGGGCTCCGGGTGAGAAAGGTGAAG GAGGCCCTCCTG |
| 591 | COL3A1 | 2519623 | CCTGGTCCCCAAGGTGTCAAAGGTGAACGTGGCAGTCCTGGTGG |
| 592 | COL3A1 | 2519626 | GCTTCCCTGGTGCTCGTGGTCTTCC |
| 593 | COL3A1 | 2519627 | TTCTCATCATACACTTCAGAAAGAGCATTCATGTATGTATAGGATGAGAAACTTACACATTGCT ACTTATTTCTCTAGTAAGTCTCA |
| 594 | COL3A1 | 2519628 | TCCCAGCGGTTCTCCAGGCAAGGATGGGCCCCCAGGTCCTGCGGGTAACACTGGTGCTCCTG GCAGCCCTGGAGTGTCTGGACCAAAAGGTG |
| 595 | COL3A1 | 2519629 | GCCCACTTGGGATTGCTGGGATCACTGGAGCACGGGGTCTTGCAG |
| 596 | COL3A1 | 2519630 | ATGCCAGGTCCTAGGGGAAGCCCTG |
| 597 | COL3A1 | 2519631 | TGGGAAACCAGGAGCTAACGGTCTCAGTGGAGAACGTGGTCCCCCTGGACCCCAGGGTCTTC CTGGTCTGGCTGGTACAGCTGGTGAACCTG |
| 598 | COL3A1 | 2519635 | GCCCACCTGGTCCTGTCGGTCCAGC |
| 599 | COL3A1 | 2519636 | GCCCTGCTGGTGCTCCCGGTCCTGCTGGTTCCCGAG |
| 600 | COL3A1 | 2519637 | GTGACAAAGGTGAAACAGGTGAACGTGGAGCTGCTGGCATCAAAGGACATCGAGGATTCCC TGGTAATCCA |
| 601 | COL3A1 | 2519638 | CAGCAGGGTGCAATCGGCAGTCCAGGACCT |
| 602 | COL3A1 | 2519641 | CAGGTCCCATTGGACCACCAGGGCCTCGAGGTAACAGAG |
| 603 | COL3A1 | 2519642 | TGTCCACATTGCTATCCCACTAGAGATCTCAGAATTACAACATTCATAATTATCTGCGTTTATGT AGTGCATTTTACTTCTCAAACAGCTTCCATGGTTACTATTTTGTTAATGATACTATCATTCCTAA TACTTTCTATTCCATGCCTTTGGGTAAATGAAATAAAAACAATTATCCCAACAAATTACACTCC CCTCTGTCATGTCAATATTGGAATTGTAGCTCACAGGTGTTTGCTTACATCAGTCATCCAGAAG GAAGAATGATAGAGAAACTTGTGCTCTGACACTACTGATTCTTACATAGTGGAACAATATCT TTCTTGATAATGAATTGTAGTTATTATAAATCGGTGATCACGTGACCCTAAAGGCACCCAAAT AAATCTTTAGTAAAATAATTCTGATGACACAATGAATGAATTATTTTTAAGGCATTTTCTTGGA CTAGCAATGTATTCTTAGAGTGGCGACTGAATGTGCATACCTCA |
| 604 | COL3A1 | 2519643 | CACCCAGGGCAACCAGGCCCTCCTGGACCTCCTGGTGCCCCTGGTCCTTGCTGTG |
| 605 | COL3A1 | 2519644 | GTGGTGTTGGAGCCGCTGCCATTGCTGGG |
| 606 | COL3A1 | 2519645 | CACCGATGAGATTATGACTTCACTCAAGTCTGTTAATGGACAAATAGAAAGCCTCATTAGTCC TGATGGTTCTCGTAAAAACCCCGCTAGAAACTGCAGAGACCTGAAATTCTGCCATCCTGAAC |

TABLE 13-continued

Subtyping Target Sequences

| SEQ ID NO. | Gene | Affy Probeset ID | Sequence |
|---|---|---|---|
| 607 | COL3A1 | 2519647 | GAGAATACTGGGTTGACCCTAACCA |
| 608 | COL3A1 | 2519648 | TTGGATGCTATCAAGGTATTCTGTAATATGGAA |
| 609 | COL3A1 | 2519649 | TTTGAATGTTCCACGGAAACACTGGTGGACAGATTCTAGTGCTGAGAAGAAACACGTTTGGTT TGGAGAGTCCATGGATGGTGGTTTTCAG |
| 610 | COL3A1 | 2519650 | AATAAGTCACCTCTATATCCTTTGTATTCTTCCTATATGTTCATCACAAAGCAAAGTTACTAGGT TGGTACAAACATAATTGCAGTTTTTGCTACTGAAAGTGATGGCATGCAATAAAAATATTTTCA CACATAAAATACTCGTACATAAAATATATAAACAGCCCATATTACAATATGCATACACATACTA CATGAATCCCTCGCGTGCAG |
| 611 | COL3A1 | 2519651 | TTACAACTGAAATGTTTGATCTGTTTTATTTGTTCCCTATTACAG |
| 612 | COL3A1 | 2519652 | AGATGTCCTTGATGTGCATCTGGCATTCCTTCGACTTCTCTCCAGCCGAGCTTCCCAGAACATC ACATATCACTGCAAAAATAGCATTGCATACATGGATCAGGCCAGTG |
| 613 | COL3A1 | 2519653 | TGAATTCAAGGCTGAAGGAAATAGCAAATTCACCTACACAGTTCTGGAGGA |
| 614 | COL3A1 | 2519656 | TTTGAATATCGAACACGCAAGGCTGTGAGACTACCTATTGTAGATATTGCACCCTATGACATT GGTGGTCCTGATCAAGAATTTGGT |
| 615 | COL3A1 | 2519657 | CTCTTGTTCTAATCTTGTCAACCAGTGCAAGTGACCGACAAAATTCCAGTTATTTATTTCCAAA ATGTTTGGAAACAGTATAATTTGACAAAGAAAATGATACTTCTCTTTTTTTGCTGTTCCACCA AATACAATTCAAATGCTTTTTGTTTTATTTTTTTACCAATTCCAATTTCAAAATGTCTCAATGGT GCTATAATAAA |
| 616 | COL3A1 | 2519658 | GAGCAATGACTGTGCTCACCAGTAAAAGATAACCTTTCTTTCTGAAATAGTCAAATACGAAAT TAGAAAAGCCCTCCCTATTTTAACTACCTCAACTGGTCAGAAACACAGATTGTATTCTATGAGT CCCAGAAGATGAAAAAAATTTTATACGTTGATAAAACTTATAAATTTCATTGATTAATCTCCTG GAAGATTGGTTTAAAAAGAAAAGTGTAATGCAAGAATTTAAAGAAATATTTTTAAAGCCACA ATTATTTTAATATTGGATATCAACTGCTTGTAAAGGTGCTCCTCTTTTTTCTTGTCATTGCTGGT CAAGATTACTAATATTTGGGAAGGCTTTAAAGACGCATGTTATGGTGCTAATGTA |
| 617 | COL3A1 | 2519659 | GAAAGATTCATTGGCATGCCACAGGGGATTCTCCTCC |
| 618 | COL3A1 | 2519660 | AAATTATGGGGCTGCTTTTGTCACACTAGCATAGAGAATGTGTTGAAATTTAACTTTGTAAGC TTGTATGTGGTTGTTGATCTTTTTT |
| 619 | DES | 2528478 | ATGAGCCAGGCCTACTCGTCCAGCCAGCGCGTGTC |
| 620 | DES | 2528479 | TGAGTTCGCCCGTGTTCCCGCGGGCGGGTTTCGGCTCTAAGGGCTCCTCCAGCTCGGTGACGT CCCGCGTGTACCAGGTGTCGCGCA |
| 621 | DES | 2528480 | GGCCTGGGGTCGCTGCGGGCCAGCCGGC |
| 622 | DES | 2528481 | TGGACTTCTCACTGGCCGACGCGGTGAACCAGGAGTTTCTGACCACGCGCACCAACGAGAAG GTGGAGCTGCAGGAGCTCAATGACCGCTTCGCCAACTACATCGAGAAGGTGCGCTTCCTGGA GCAGCAGAACGCGGCGCTCGCCGCCGAAGTGAACCGGCTCAA |
| 623 | DES | 2528482 | TGCTCACTAACCAGCGCGCGCGCGTCGACGTCGAGCGCGACAACCTGCTCGACGACCTGCAG CGGCTCAA |
| 624 | DES | 2528483 | GCTACTCTAGCTCGCATTGACCTGGAGCGCAGAATTGAATCTCTCAACGAGGAGATCGCGTTC CTTAAGAAAGTGCA |
| 625 | DES | 2528484 | CCTCAGGGACATCCGGGCTCAGTATGAGACCATCGCGGCTAAGAACATTTCTGAAGCTGAGG AGTGGTACAAG |
| 626 | DES | 2528485 | GTGTCAGACCTGACCCAGGCAGCCAACAAGAACAACGACGCCCTGCGCCAGGCCAAGCAGG AGATGATGGAATACCGACACCAGATCCAGTCCTACACCTGCGAGATTGACGCCCTGAAG |
| 627 | DES | 2528486 | CGGGAATTGGAGGACCGATTTGCCAGTGAGGCCAGTGGCTACCAGGACAACATTGCGCGCCT GGAGGAGGAAATCCGGCACCTCAAGGATGAGATGGCCCGCCATCTG |
| 628 | DES | 2528488 | CCCATCCAGACCTACTCTGCCCTCAACTTCCGAG |
| 629 | DES | 2528489 | TTGGGGTCTGCTAGGGCTCTGCCCA |
| 630 | DES | 2528490 | AGCCTGGACTTGGTCAGGCTGAGTGTGCGATGGACCCTGTTACAG |
| 631 | DES | 2528491 | AAGGGGTTCTGAGGTCCATACCAAGAAGACGGTGATGATCAAGACCATCGAGACACGGGAT GG |

TABLE 13-continued

Subtyping Target Sequences

| SEQ ID NO. | Gene | Affy Probeset ID | Sequence |
|---|---|---|---|
| 632 | DES | 2528492 | GTCGTCAGTGAGGCCACACAGCAGCAGCATGAAGTGCTCTAA |
| 633 | DES | 2528493 | CTGCCACCAGAGACCGTCCTCACCCC |
| 634 | DES | 2528494 | TGGTCCCCAACAGCGACATAGCCCATCCCTGCCTGGTCACAGGGCATGCCCCGGCCACCT |
| 635 | DES | 2528495 | CAGGTAGCCAGGGGGACTAGCCCCTGTGGAGACTGGGGGGCTTGAAATTGTCCCCGTGGTCTCTTAC |
| 636 | DES | 2528496 | CTACAAGAGGGAATCCCCGAAGGTGCTGGAG |
| 637 | DES | 2528497 | GAAAGTGGGTGAGATGCTGGAGAAGAGAGGAGAGGAGAGAGGCAGAGAGCGGTCTCAGGC |
| 638 | UGT1A8 | 2533024 | CAGCTTAGAATCCCAGCTGCTGGCTCGGGCTGCAGTTCTCTC |
| 639 | UGT1A8 | 2533025 | ATGGCTCGCACAGGGTGGACCAGCCCCATTCCCCTATGTGTTTCTCTGCTGCTGAC |
| 640 | UGT1A8 | 2533026 | TGGGAGTCACTGGTTCACCATGCAG |
| 641 | UGT1A8 | 2533027 | TATTTCTGAGTTCATCCAATGGTTTT |
| 642 | UGT1A8 | 2533028 | GAGTACGGAACCACATCATGCACTTGGAGGAACATTTATTTTGCCAGTATTTTTCCAAAAATGCCCTAGAAATAGCCTCTGAAATTCTCCAAACACCTGTCACAGCATATGATCTCTACAGCCACACATCAATTTGGTTGTTGCGAACAGACTTTGTTTTGGACTATCCCAAACCCGTGATGCCCAATATGATCTTCATTGGTGGTATCAACTGCCATC |
| 643 | UGT1A8 | 2533035 | CAGCTTAGAATCCCAGCTGCTGGCTCGGGCTGCAGTTCTCTC |
| 644 | UGT1A8 | 2533036 | ATGGCTCGCGCAGGGTGGACCAGCCCCGTTCCTTTATGTGTGTGTCTACTGC |
| 645 | UGT1A10 | 2533036 | ATGGCTCGCGCAGGGTGGACCAGCCCCGTTCCTTTATGTGTGTGTCTACTGC |
| 646 | UGT1A8 | 2533037 | TGGGAGTCACTGGTTCACCATGCAG |
| 647 | UGT1A8 | 2533038 | GTGAGTTGGCAACTGGAAAGATCACTGAATTGCACA |
| 648 | UGT1A10 | 2533038 | GTGAGTTGGCAACTGGAAAGATCACTGAATTGCACA |
| 649 | UGT1A8 | 2533039 | CTCTGGAAGATCAGAACCGGGAATTCATGGTTTTCGCCCATGCTCAATGGAAAGCACA |
| 650 | UGT1A10 | 2533039 | CTCTGGAAGATCAGAACCGGGAATTCATGGTTTTCGCCCATGCTCAATGGAAAGCACA |
| 651 | UGT1A8 | 2533040 | CTCTATTAATGAGTTCATCCAGTGGT |
| 652 | UGT1A10 | 2533040 | CTCTATTAATGAGTTCATCCAGTGGT |
| 653 | UGT1A8 | 2533041 | TCTGGATCCTTTTGATACCTGTGGCTTAATTGTTGCTAAATATTTCTCCCTCCCCTCTGTGGTCTTCACCAGGGGAATATTTTGCCACCATCTTGAAGAAGGTGCACAGTGC |
| 654 | UGT1A10 | 2533041 | TCTGGATCCTTTTGATACCTGTGGCTTAATTGTTGCTAAATATTTCTCCCTCCCCTCTGTGGTCTTCACCAGGGGAATATTTTGCCACCATCTTGAAGAAGGTGCACAGTGC |
| 655 | UGT1A8 | 2533042 | TCAATTTGGTTGTTGCGAACGGACTTTGTTTTGGACTATCCCAAACCCGTGATGCCCAACATGATCTTCA |
| 656 | UGT1A10 | 2533042 | TCAATTTGGTTGTTGCGAACGGACTTTGTTTTGGACTATCCCAAACCCGTGATGCCCAACATGATCTTCA |
| 657 | UGT1A8 | 2533047 | TAAGGAACCACATCTTCTACTTAGAGGAGCATTTATTTTGCCCATATTTTTTCAAAAATGCCTTAAACATAGCCTCTGAAATTC |
| 658 | UGT1A10 | 2533047 | TAAGGAACCACATCTTCTACTTAGAGGAGCATTTATTTTGCCCATATTTTTTCAAAAATGCCTTAAACATAGCCTCTGAAATTC |
| 659 | UGT1A8 | 2533048 | CATCAATTTGGTTGCTGCGAATGGA |
| 660 | UGT1A10 | 2533048 | CATCAATTTGGTTGCTGCGAATGGA |
| 661 | UGT1A8 | 2533050 | GCTTAGATTCCCAGCTGCTTGCTCT |
| 662 | UGT1A10 | 2533050 | GCTTAGATTCCCAGCTGCTTGCTCT |
| 663 | UGT1A9 | 2533050 | GCTTAGATTCCCAGCTGCTTGCTCT |

TABLE 13-continued

Subtyping Target Sequences

| SEQ ID NO. | Gene | Affy Probeset ID | Sequence |
|---|---|---|---|
| 664 | UGT1A8 | 2533051 | ATGGCTTGCACAGGGTGGACCAGCCCCCTTCCTCTATGTGTGTGTCTGCTGCTGACCTGTGGC<br>TTTGCCGAG |
| 665 | UGT1A10 | 2533051 | ATGGCTTGCACAGGGTGGACCAGCCCCCTTCCTCTATGTGTGTGTCTGCTGCTGACCTGTGGC<br>TTTGCCGAG |
| 666 | UGT1A9 | 2533051 | ATGGCTTGCACAGGGTGGACCAGCCCCCTTCCTCTATGTGTGTGTCTGCTGCTGACCTGTGGC<br>TTTGCCGAG |
| 667 | UGT1A8 | 2533054 | TATTCAACTTCATATACCCTGGAGGATCTGGACCGGGAGTTCAAGGCTTTTGCCCATGCTCAA<br>TGGAAAGCACAAGTACGAAGTATATATTCTCTATTAATGGGTTCATACAATGACATT |
| 668 | UGT1A10 | 2533054 | TATTCAACTTCATATACCCTGGAGGATCTGGACCGGGAGTTCAAGGCTTTTGCCCATGCTCAA<br>TGGAAAGCACAAGTACGAAGTATATATTCTCTATTAATGGGTTCATACAATGACATT |
| 669 | UGT1A9 | 2533054 | TATTCAACTTCATATACCCTGGAGGATCTGGACCGGGAGTTCAAGGCTTTTGCCCATGCTCAA<br>TGGAAAGCACAAGTACGAAGTATATATTCTCTATTAATGGGTTCATACAATGACATT |
| 670 | UGT1A8 | 2533057 | TTTCAAGGAGAGAGTACGGAACCACATCATGCACTT |
| 671 | UGT1A8 | 2533058 | CTCCAAACACCTGTTACGGAGTATGATCTCTACAGC |
| 672 | UGT1A10 | 2533058 | CTCCAAACACCTGTTACGGAGTATGATCTCTACAGC |
| 673 | UGT1A9 | 2533058 | CTCCAAACACCTGTTACGGAGTATGATCTCTACAGC |
| 674 | UGT1A8 | 2533065 | ATGGCTCGTGCAGGGTGGACTGGCCTCCTTCCCCTATATGTGTGTCTACTGCTGAC |
| 675 | UGT1A10 | 2533065 | ATGGCTCGTGCAGGGTGGACTGGCCTCCTTCCCCTATATGTGTGTCTACTGCTGAC |
| 676 | UGT1A9 | 2533065 | ATGGCTCGTGCAGGGTGGACTGGCCTCCTTCCCCTATATGTGTGTCTACTGCTGAC |
| 677 | UGT1A8 | 2533067 | TGCAGTCGGTGGTGGAGAAACTCATCCTCAGGGGGCATGAGGTGGTCGTAGTCATGCCAGA |
| 678 | UGT1A10 | 2533067 | TGCAGTCGGTGGTGGAGAAACTCATCCTCAGGGGGCATGAGGTGGTCGTAGTCATGCCAGA |
| 679 | UGT1A9 | 2533067 | TGCAGTCGGTGGTGGAGAAACTCATCCTCAGGGGGCATGAGGTGGTCGTAGTCATGCCAGA |
| 680 | UGT1A8 | 2533068 | AGTTCATGGTTTTTGCCGATGCTCGCTGGACGGCACCATTGCGAAGTGCATTTTCTCTATTAAC<br>AAGTTC |
| 681 | UGT1A10 | 2533068 | AGTTCATGGTTTTTGCCGATGCTCGCTGGACGGCACCATTGCGAAGTGCATTTTCTCTATTAAC<br>AAGTTC |
| 682 | UGT1A9 | 2533068 | AGTTCATGGTTTTTGCCGATGCTCGCTGGACGGCACCATTGCGAAGTGCATTTTCTCTATTAAC<br>AAGTTC |
| 683 | UGT1A8 | 2533072 | GGGTCTCCAGCGGAGCTACTCTTTAGGGATCGTCATTATGACGAACAGACATGCCAGATTCCT<br>CTGGCTAGTGTCCAGTGCAGACATACACACACACACATACACACACACACACACACACA<br>CCATTCTTAGTACAGTCAAAGCTCACAGGAGAAAGAAAAATGTTTTCTAATACCTTCTTAATTT<br>GCAAGAAGGTGTTAGGAATTCAAGGGATGGTATGCATAGTGATGTTAGTTTCATTTCTTCAGC<br>TCCTTCCTCCAACTCATGTTCTGTAGGGACTTCTGGGACTAAGAACAGGACCCACATATGAGC<br>AACAGGATTTTCAGAGCAAGGCTGTGGTTGGAAGGGCTCAGACCAACGTCCACAGCAGAGT<br>GGAGGTCTAGTATAAAGAATGTGAAGTTTGTAGCATCTCTTGATCCCGCTATTCCTACATGCTTG |
| 684 | UGT1A10 | 2533072 | GGGTCTCCAGCGGAGCTACTCTTTAGGGATCGTCATTATGACGAACAGACATGCCAGATTCCT<br>CTGGCTAGTGTCCAGTGCAGACATACACACACACACATACACACACACACACACACACA<br>CCATTCTTAGTACAGTCAAAGCTCACAGGAGAAAGAAAAATGTTTTCTAATACCTTCTTAATTT<br>GCAAGAAGGTGTTAGGAATTCAAGGGATGGTATGCATAGTGATGTTAGTTTCATTTCTTCAGC<br>TCCTTCCTCCAACTCATGTTCTGTAGGGACTTCTGGGACTAAGAACAGGACCCACATATGAGC<br>AACAGGATTTTCAGAGCAAGGCTGTGGTTGGAAGGGCTCAGACCAACGTCCACAGCAGAGT<br>GGAGGTCTAGTATAAAGAATGTGAAGTTTGTAGCATCTCTTGATCCCGCTATTCCTACATGCTTG |
| 685 | UGT1A9 | 2533072 | GGGTCTCCAGCGGAGCTACTCTTTAGGGATCGTCATTATGACGAACAGACATGCCAGATTCCT<br>CTGGCTAGTGTCCAGTGCAGACATACACACACACACATACACACACACACACACACACA<br>CCATTCTTAGTACAGTCAAAGCTCACAGGAGAAAGAAAAATGTTTTCTAATACCTTCTTAATTT<br>GCAAGAAGGTGTTAGGAATTCAAGGGATGGTATGCATAGTGATGTTAGTTTCATTTCTTCAGC<br>TCCTTCCTCCAACTCATGTTCTGTAGGGACTTCTGGGACTAAGAACAGGACCCACATATGAGC<br>AACAGGATTTTCAGAGCAAGGCTGTGGTTGGAAGGGCTCAGACCAACGTCCACAGCAGAGT<br>GGAGGTCTAGTATAAAGAATGTGAAGTTTGTAGCATCTCTTGATCCCGCTATTCCTACATGCTTG |
| 686 | UGT1A8 | 2533073 | GCCTAATGTCTGCCTGCTCAAGAAGGTGGACCTGAGCTCTGTTCCCTTTGCAACCTTCCTGGA<br>GTCTTATTGCTATCTAGATGAACTCAAAGCAAGATGCTGCCGCCC |

TABLE 13-continued

Subtyping Target Sequences

| SEQ ID NO. | Gene | Affy Probeset ID | Sequence |
|---|---|---|---|
| 687 | UGT1A10 | 2533073 | GCCTAATGTCTGCCTGCTCAAGAAGGTGGACCTGAGCTCTGTTCCCTTTGCAACCTTCCTGGA<br>GTCTTATTGCTATCTAGATGAACTCAAAGCAAGATGCTGCCGCCC |
| 688 | UGT1A9 | 2533073 | GCCTAATGTCTGCCTGCTCAAGAAGGTGGACCTGAGCTCTGTTCCCTTTGCAACCTTCCTGGA<br>GTCTTATTGCTATCTAGATGAACTCAAAGCAAGATGCTGCCGCCC |
| 689 | UGT1A8 | 2533074 | GCTGAGTCTTCGCATGCCTTGAACAATGAATTTGCATCCTGGTTATGTTCCCCATGGGGGCCA<br>GCCCTGTCCTTGGAGTGGCCCCTCTAATCATGTTGCTCAGGCTTCTTCTCCCTTCCTGGGCCCC<br>AGAACACCTCCGGTGCCAAACTTGTGGGTGGGAACAGGAACTCGCGTGCCAGCCAGGTGTG<br>CATGACTAGCTCTGGGCAAGTCTGTTCTAGTAATTCAAGGTACCACCTCTCACTGGGACAGCC<br>TAGTTTCTACACAGGTCTTGCTCTGGGACCGCCCTCAGCAGTGTGGTTAGCAGGCAGGGCCA<br>GTGTGACCCTCCCTTTCTGGGCCTCAGTTGAGAAACCTGAAGCTCAGGAGAGGAGTCACTCCC<br>CTGGCAGATGGGTGGCTGGGCCAGAAGCAGATACCAGGCTTTCTGACTCCTGCTCTAGGATT<br>CTCACCACGTACTG |
| 690 | UGT1A10 | 2533074 | GCTGAGTCTTCGCATGCCTTGAACAATGAATTTGCATCCTGGTTATGTTCCCCATGGGGGCCA<br>GCCCTGTCCTTGGAGTGGCCCCTCTAATCATGTTGCTCAGGCTTCTTCTCCCTTCCTGGGCCCC<br>AGAACACCTCCGGTGCCAAACTTGTGGGTGGGAACAGGAACTCGCGTGCCAGCCAGGTGTG<br>CATGACTAGCTCTGGGCAAGTCTGTTCTAGTAATTCAAGGTACCACCTCTCACTGGGACAGCC<br>TAGTTTCTACACAGGTCTTGCTCTGGGACCGCCCTCAGCAGTGTGGTTAGCAGGCAGGGCCA<br>GTGTGACCCTCCCTTTCTGGGCCTCAGTTGAGAAACCTGAAGCTCAGGAGAGGAGTCACTCCC<br>CTGGCAGATGGGTGGCTGGGCCAGAAGCAGATACCAGGCTTTCTGACTCCTGCTCTAGGATT<br>CTCACCACGTACTG |
| 691 | UGT1A9 | 2533074 | GCTGAGTCTTCGCATGCCTTGAACAATGAATTTGCATCCTGGTTATGTTCCCCATGGGGGCCA<br>GCCCTGTCCTTGGAGTGGCCCCTCTAATCATGTTGCTCAGGCTTCTTCTCCCTTCCTGGGCCCC<br>AGAACACCTCCGGTGCCAAACTTGTGGGTGGGAACAGGAACTCGCGTGCCAGCCAGGTGTG<br>CATGACTAGCTCTGGGCAAGTCTGTTCTAGTAATTCAAGGTACCACCTCTCACTGGGACAGCC<br>TAGTTTCTACACAGGTCTTGCTCTGGGACCGCCCTCAGCAGTGTGGTTAGCAGGCAGGGCCA<br>GTGTGACCCTCCCTTTCTGGGCCTCAGTTGAGAAACCTGAAGCTCAGGAGAGGAGTCACTCCC<br>CTGGCAGATGGGTGGCTGGGCCAGAAGCAGATACCAGGCTTTCTGACTCCTGCTCTAGGATT<br>CTCACCACGTACTG |
| 692 | UGT1A8 | 2533075 | TCTCTAAGGATGAGGGCTAGTTGCCAGGGAACAAAACCCTTGCGATTAGAGGGAAGAAAGG<br>AGAGAGAGATTGAAGATTGATTTGATCACCGATGGGCAACAATCTAATCAATCATGCCTACTA<br>TGTATGGAAGCCTACATAAAAACTCAGAAGGGCAGGGTTCAGAGAGCTTTCAGGTTGCTGAA<br>GGTGTGGAGGGTGGGGCACCCAGAGATGGCAGATGGGGCTCCATGGCCATACCCCCATATC<br>TTGTTCTTTGTACTTTTTCCTCTGGCTATTCATCCGTATTGTTTG |
| 693 | UGT1A10 | 2533075 | TCTCTAAGGATGAGGGCTAGTTGCCAGGGAACAAAACCCTTGCGATTAGAGGGAAGAAAGG<br>AGAGAGAGATTGAAGATTGATTTGATCACCGATGGGCAACAATCTAATCAATCATGCCTACTA<br>TGTATGGAAGCCTACATAAAAACTCAGAAGGGCAGGGTTCAGAGAGCTTTCAGGTTGCTGAA<br>GGTGTGGAGGGTGGGGCACCCAGAGATGGCAGATGGGGCTCCATGGCCATACCCCCATATC<br>TTGTTCTTTGTACTTTTTCCTCTGGCTATTCATCCGTATTGTTTG |
| 694 | UGT1A9 | 2533075 | TCTCTAAGGATGAGGGCTAGTTGCCAGGGAACAAAACCCTTGCGATTAGAGGGAAGAAAGG<br>AGAGAGAGATTGAAGATTGATTTGATCACCGATGGGCAACAATCTAATCAATCATGCCTACTA<br>TGTATGGAAGCCTACATAAAAACTCAGAAGGGCAGGGTTCAGAGAGCTTTCAGGTTGCTGAA<br>GGTGTGGAGGGTGGGGCACCCAGAGATGGCAGATGGGGCTCCATGGCCATACCCCCATATC<br>TTGTTCTTTGTACTTTTTCCTCTGGCTATTCATCCGTATTGTTTG |
| 695 | UGT1A8 | 2533077 | TGAAAAGCAGTGGTTAGTTTAGGGAAAATACCTAGGAGCCCTGTGATTTGGAGAGTGAAAAC<br>TCTTTATTACC |
| 696 | UGT1A10 | 2533077 | TGAAAAGCAGTGGTTAGTTTAGGGAAAATACCTAGGAGCCCTGTGATTTGGAGAGTGAAAAC<br>TCTTTATTACC |
| 697 | UGT1A9 | 2533077 | TGAAAAGCAGTGGTTAGTTTAGGGAAAATACCTAGGAGCCCTGTGATTTGGAGAGTGAAAAC<br>TCTTTATTACC |
| 698 | UGT1A8 | 2533078 | ATGGCCTGCCTCCTTCGCTCATTTCAG |
| 699 | UGT1A10 | 2533078 | ATGGCCTGCCTCCTTCGCTCATTTCAG |
| 700 | UGT1A9 | 2533078 | ATGGCCTGCCTCCTTCGCTCATTTCAG |
| 701 | UGT1A8 | 2533079 | AGAATTTCTGCAGGGGTTTTCTTCTTAGCACTTTG |
| 702 | UGT1A10 | 2533079 | AGAATTTCTGCAGGGGTTTTCTTCTTAGCACTTTG |
| 703 | UGT1A9 | 2533079 | AGAATTTCTGCAGGGGTTTTCTTCTTAGCACTTTG |
| 704 | UGT1A8 | 2533080 | TCCCTCAGGACGGAAGCCACTGGCTTAGTATGAAGGATATAGTTGAGGTTCTCAGTGACCGG<br>GGTCATGAGATTGTAGTGGTGGTGCCTGAAGTTAATTTGCTTTTGAAAGAATCCAAATACTAC |

TABLE 13-continued

Subtyping Target Sequences

| SEQ ID NO. | Gene | Affy Probeset ID | Sequence |
|---|---|---|---|
| | | | ACAAGAAAAATCTATCCAGTGCCGTATGACCAAGAAGAGCTGAAGAACCGTTACCAATCATTT GGAAACAATCACTTTGCTGAGCGATCATTCCTAACTGCTCCTCAGACAGAGTACAGGAATAAC ATGATTGTTATTGGCCTGTACTTCATCAACTGCCAGAGCCTCCTGCAGGACAGGGACACCCTG AACTTCTTTAAGGAGAGCAAGTTTGATGCTCTTTTCACAGACCCAGCCTTACCCTGTGGGGTG ATCCTGGCTGAGTATTGGGCCTACCATCTGTGTACCTCTTCAGGGGTTTTCCGTGTTCCCTGG AGCATACATTCAGCAGAAGCCCAGACCCTGTGTCCTACATTCCCAGGTGCTACACAAAGTTTT CAGACCACATGACTTTTTCCCAACGAGTGGCCAACTTCCTTGTTAATTTGTTGGAGCCCTATCT ATTTTATTGTCTGTTTTCAAAGTATGAAGAACTCGCATCAGCTGTCCTCAAGA |
| 705 | UGT1A10 | 2533080 | TCCCTCAGGACGGAAGCCACTGGCTTAGTATGAAGGATATAGTTGAGGTTCTCAGTGACCGG GGTCATGAGATTGTAGTGGTGGTGCCTGAAGTTAATTTGCTTTTGAAAGAATCCAAATACTAC ACAAGAAAAATCTATCCAGTGCCGTATGACCAAGAAGAGCTGAAGAACCGTTACCAATCATTT GGAAACAATCACTTTGCTGAGCGATCATTCCTAACTGCTCCTCAGACAGAGTACAGGAATAAC ATGATTGTTATTGGCCTGTACTTCATCAACTGCCAGAGCCTCCTGCAGGACAGGGACACCCTG AACTTCTTTAAGGAGAGCAAGTTTGATGCTCTTTTCACAGACCCAGCCTTACCCTGTGGGGTG ATCCTGGCTGAGTATTGGGCCTACCATCTGTGTACCTCTTCAGGGGTTTTCCGTGTTCCCTGG AGCATACATTCAGCAGAAGCCCAGACCCTGTGTCCTACATTCCCAGGTGCTACACAAAGTTTT CAGACCACATGACTTTTTCCCAACGAGTGGCCAACTTCCTTGTTAATTTGTTGGAGCCCTATCT ATTTTATTGTCTGTTTTCAAAGTATGAAGAACTCGCATCAGCTGTCCTCAAGA |
| 706 | UGT1A9 | 2533080 | TCCCTCAGGACGGAAGCCACTGGCTTAGTATGAAGGATATAGTTGAGGTTCTCAGTGACCGG GGTCATGAGATTGTAGTGGTGGTGCCTGAAGTTAATTTGCTTTTGAAAGAATCCAAATACTAC ACAAGAAAAATCTATCCAGTGCCGTATGACCAAGAAGAGCTGAAGAACCGTTACCAATCATTT GGAAACAATCACTTTGCTGAGCGATCATTCCTAACTGCTCCTCAGACAGAGTACAGGAATAAC ATGATTGTTATTGGCCTGTACTTCATCAACTGCCAGAGCCTCCTGCAGGACAGGGACACCCTG AACTTCTTTAAGGAGAGCAAGTTTGATGCTCTTTTCACAGACCCAGCCTTACCCTGTGGGGTG ATCCTGGCTGAGTATTGGGCCTACCATCTGTGTACCTCTTCAGGGGTTTTCCGTGTTCCCTGG AGCATACATTCAGCAGAAGCCCAGACCCTGTGTCCTACATTCCCAGGTGCTACACAAAGTTTT CAGACCACATGACTTTTTCCCAACGAGTGGCCAACTTCCTTGTTAATTTGTTGGAGCCCTATCT ATTTTATTGTCTGTTTTCAAAGTATGAAGAACTCGCATCAGCTGTCCTCAAGA |
| 707 | UGT1A8 | 2533081 | GTCTTCATTGGAGGTATCAACTGTAAGAAGAGGAAAG |
| 708 | UGT1A10 | 2533081 | GTCTTCATTGGAGGTATCAACTGTAAGAAGAGGAAAG |
| 709 | UGT1A9 | 2533081 | GTCTTCATTGGAGGTATCAACTGTAAGAAGAGGAAAG |
| 710 | UGT1A8 | 2533085 | ACAGGACTCCAGGTTCCCCTGCCGCAG |
| 711 | UGT1A10 | 2533085 | ACAGGACTCCAGGTTCCCCTGCCGCAG |
| 712 | UGT1A9 | 2533085 | ACAGGACTCCAGGTTCCCCTGCCGCAG |
| 713 | UGT1A5 | 2533085 | ACAGGACTCCAGGTTCCCCTGCCGCAG |
| 714 | UGT1A8 | 2533086 | AGGTGCTGGTGGTGCCCACTGATGG |
| 715 | UGT1A10 | 2533086 | AGGTGCTGGTGGTGCCCACTGATGG |
| 716 | UGT1A9 | 2533086 | AGGTGCTGGTGGTGCCCACTGATGG |
| 717 | UGT1A5 | 2533086 | AGGTGCTGGTGGTGCCCACTGATGG |
| 718 | UGT1A8 | 2533087 | ACCTCCATGCGAGAGGCCACCAGGTG |
| 719 | UGT1A10 | 2533087 | ACCTCCATGCGAGAGGCCACCAGGTG |
| 720 | UGT1A9 | 2533087 | ACCTCCATGCGAGAGGCCACCAGGTG |
| 721 | UGT1A5 | 2533087 | ACCTCCATGCGAGAGGCCACCAGGTG |
| 722 | UGT1A8 | 2533088 | GCTGGGTCACACTCAATCGTTCTTTGAAACAGAACATCTTCTGATGAAATTTTCTAGAAGAAT GGCAATTATGAACAATATGTCTTTGATCATACATAGGTCTTGTGTGGAGC |
| 723 | UGT1A10 | 2533088 | GCTGGGTCACACTCAATCGTTCTTTGAAACAGAACATCTTCTGATGAAATTTTCTAGAAGAAT GGCAATTATGAACAATATGTCTTTGATCATACATAGGTCTTGTGTGGAGC |
| 724 | UGT1A9 | 2533088 | GCTGGGTCACACTCAATCGTTCTTTGAAACAGAACATCTTCTGATGAAATTTTCTAGAAGAAT GGCAATTATGAACAATATGTCTTTGATCATACATAGGTCTTGTGTGGAGC |
| 725 | UGT1A5 | 2533088 | GCTGGGTCACACTCAATCGTTCTTTGAAACAGAACATCTTCTGATGAAATTTTCTAGAAGAAT GGCAATTATGAACAATATGTCTTTGATCATACATAGGTCTTGTGTGGAGC |

TABLE 13-continued

Subtyping Target Sequences

| SEQ ID NO. | Gene | Affy Probeset ID | Sequence |
|---|---|---|---|
| 726 | UGT1A8 | 2533089 | GTGCTGGCTAAGTACCTGTCGATTCCTGCTGTGTTTTCTTGAGGAACATTCCATGTGATTTAGACTTTAAGGGCACACAGTGTCCAAACCCTTCCTCCTATATTCCTAGATTACTAACGACCAATTCAGACCACATGACATTCCTGCAAAGGGTCAAGAACA |
| 727 | UGT1A10 | 2533089 | GTGCTGGCTAAGTACCTGTCGATTCCTGCTGTGTTTTCTTGAGGAACATTCCATGTGATTTAGACTTTAAGGGCACACAGTGTCCAAACCCTTCCTCCTATATTCCTAGATTACTAACGACCAATTCAGACCACATGACATTCCTGCAAAGGGTCAAGAACA |
| 728 | UGT1A9 | 2533089 | GTGCTGGCTAAGTACCTGTCGATTCCTGCTGTGTTTTCTTGAGGAACATTCCATGTGATTTAGACTTTAAGGGCACACAGTGTCCAAACCCTTCCTCCTATATTCCTAGATTACTAACGACCAATTCAGACCACATGACATTCCTGCAAAGGGTCAAGAACA |
| 729 | UGT1A5 | 2533089 | GTGCTGGCTAAGTACCTGTCGATTCCTGCTGTGTTTTCTTGAGGAACATTCCATGTGATTTAGACTTTAAGGGCACACAGTGTCCAAACCCTTCCTCCTATATTCCTAGATTACTAACGACCAATTCAGACCACATGACATTCCTGCAAAGGGTCAAGAACA |
| 730 | UGT1A8 | 2533092 | TGGATGAATGGATACTTCAGTCTCTATGCAGACTTGCAGAAGACTGGAGCCTTTGGCATTCAGAAGAGGAATTCAG |
| 731 | UGT1A10 | 2533092 | TGGATGAATGGATACTTCAGTCTCTATGCAGACTTGCAGAAGACTGGAGCCTTTGGCATTCAGAAGAGGAATTCAG |
| 732 | UGT1A9 | 2533092 | TGGATGAATGGATACTTCAGTCTCTATGCAGACTTGCAGAAGACTGGAGCCTTTGGCATTCAGAAGAGGAATTCAG |
| 733 | UGT1A5 | 2533092 | TGGATGAATGGATACTTCAGTCTCTATGCAGACTTGCAGAAGACTGGAGCCTTTGGCATTCAGAAGAGGAATTCAG |
| 734 | UGT1A8 | 2533094 | ATGGCCAGAGGACTCCAGGTTCCCCTGCCGC |
| 735 | UGT1A10 | 2533094 | ATGGCCAGAGGACTCCAGGTTCCCCTGCCGC |
| 736 | UGT1A9 | 2533094 | ATGGCCAGAGGACTCCAGGTTCCCCTGCCGC |
| 737 | UGT1A5 | 2533094 | ATGGCCAGAGGACTCCAGGTTCCCCTGCCGC |
| 738 | UGT1A4 | 2533094 | ATGGCCAGAGGACTCCAGGTTCCCCTGCCGC |
| 739 | UGT1A8 | 2533095 | GACTGCTGCTCCTCCTCAGTGTCCAG |
| 740 | UGT1A10 | 2533095 | GACTGCTGCTCCTCCTCAGTGTCCAG |
| 741 | UGT1A9 | 2533095 | GACTGCTGCTCCTCCTCAGTGTCCAG |
| 742 | UGT1A5 | 2533095 | GACTGCTGCTCCTCCTCAGTGTCCAG |
| 743 | UGT1A4 | 2533095 | GACTGCTGCTCCTCCTCAGTGTCCAG |
| 744 | UGT1A8 | 2533096 | GAGAGTGGAAAGGTGTTGGTGGTGCCCACTGATGGCAGCCCCTGGCTCAGCATGCGGGAGGCCTTGCGGGAGCTCCATGCCAGAGGCCACCAGGCGGTGGTCCTCACCCCAGAG |
| 745 | UGT1A10 | 2533096 | GAGAGTGGAAAGGTGTTGGTGGTGCCCACTGATGGCAGCCCCTGGCTCAGCATGCGGGAGGCCTTGCGGGAGCTCCATGCCAGAGGCCACCAGGCGGTGGTCCTCACCCCAGAG |
| 746 | UGT1A9 | 2533096 | GAGAGTGGAAAGGTGTTGGTGGTGCCCACTGATGGCAGCCCCTGGCTCAGCATGCGGGAGGCCTTGCGGGAGCTCCATGCCAGAGGCCACCAGGCGGTGGTCCTCACCCCAGAG |
| 747 | UGT1A5 | 2533096 | GAGAGTGGAAAGGTGTTGGTGGTGCCCACTGATGGCAGCCCCTGGCTCAGCATGCGGGAGGCCTTGCGGGAGCTCCATGCCAGAGGCCACCAGGCGGTGGTCCTCACCCCAGAG |
| 748 | UGT1A4 | 2533096 | GAGAGTGGAAAGGTGTTGGTGGTGCCCACTGATGGCAGCCCCTGGCTCAGCATGCGGGAGGCCTTGCGGGAGCTCCATGCCAGAGGCCACCAGGCGGTGGTCCTCACCCCAGAG |
| 749 | UGT1A8 | 2533097 | GCCTATGCTGTTCCATGGACCCAGAAGGAATTTGATCGCGTTACGCTGGGCTACACTCAAGGGTTCTTTGAAACAGAACATCTTCTGAAGAGATATTCTAGAAGTATGGCAATTATGAACAATGTATCTTTGGCCCTTCATAGG |
| 750 | UGT1A10 | 2533097 | GCCTATGCTGTTCCATGGACCCAGAAGGAATTTGATCGCGTTACGCTGGGCTACACTCAAGGGTTCTTTGAAACAGAACATCTTCTGAAGAGATATTCTAGAAGTATGGCAATTATGAACAATGTATCTTTGGCCCTTCATAGG |
| 751 | UGT1A9 | 2533097 | GCCTATGCTGTTCCATGGACCCAGAAGGAATTTGATCGCGTTACGCTGGGCTACACTCAAGGGTTCTTTGAAACAGAACATCTTCTGAAGAGATATTCTAGAAGTATGGCAATTATGAACAATGTATCTTTGGCCCTTCATAGG |

TABLE 13-continued

Subtyping Target Sequences

| SEQ ID NO. | Gene | Affy Probeset ID | Sequence |
|---|---|---|---|
| 752 | UGT1A5 | 2533097 | GCCTATGCTGTTCCATGGACCCAGAAGGAATTTGATCGCGTTACGCTGGGCTACACTCAAGG<br>GTTCTTTGAAACAGAACATCTTCTGAAGAGATATTCTAGAAGTATGGCAATTATGAACAATGT<br>ATCTTTGGCCCTTCATAGG |
| 753 | UGT1A4 | 2533097 | GCCTATGCTGTTCCATGGACCCAGAAGGAATTTGATCGCGTTACGCTGGGCTACACTCAAGG<br>GTTCTTTGAAACAGAACATCTTCTGAAGAGATATTCTAGAAGTATGGCAATTATGAACAATGT<br>ATCTTTGGCCCTTCATAGG |
| 754 | UGT1A8 | 2533101 | TTGGTGGTGCCCATTGATGGCAGCCACTGGCTCAGCATGCGGGAGGTCTTGCGGGAGCTCCA<br>TGCCAGA |
| 755 | UGT1A10 | 2533101 | TTGGTGGTGCCCATTGATGGCAGCCACTGGCTCAGCATGCGGGAGGTCTTGCGGGAGCTCCA<br>TGCCAGA |
| 756 | UGT1A9 | 2533101 | TTGGTGGTGCCCATTGATGGCAGCCACTGGCTCAGCATGCGGGAGGTCTTGCGGGAGCTCCA<br>TGCCAGA |
| 757 | UGT1A5 | 2533101 | TTGGTGGTGCCCATTGATGGCAGCCACTGGCTCAGCATGCGGGAGGTCTTGCGGGAGCTCCA<br>TGCCAGA |
| 758 | UGT1A4 | 2533101 | TTGGTGGTGCCCATTGATGGCAGCCACTGGCTCAGCATGCGGGAGGTCTTGCGGGAGCTCCA<br>TGCCAGA |
| 759 | UGT1A3 | 2533101 | TTGGTGGTGCCCATTGATGGCAGCCACTGGCTCAGCATGCGGGAGGTCTTGCGGGAGCTCCA<br>TGCCAGA |
| 760 | UGT1A8 | 2533102 | CTATCATAGGTCTTGTGTGGAGCTACTACATAATGAGGCCCTGATCAGGCACCTGAATGCTAC<br>TTCCTTTGATGTGGTTTTAACAGACCCCGTTAACCTCTGCGCGGCAGTGCTGGCTAAGTACCTG<br>TCGATTCCTACTGTGTTTTTTTTGAGGAACATTCCATGTGATTTAGACTTTAAGGGCACACAGT<br>GTCCAAACCCTTCCTCCTATATTCCTAGATTACTAACAACCAATTCAGACCACATGACATTCAT<br>GCAAAGGGTCAAGAACATGCTCTACCCTCTGGCCCTGTCCTACATTTGCCATGCTTTTTCTGCT<br>CCTTATGCAAGC |
| 761 | UGT1A10 | 2533102 | CTATCATAGGTCTTGTGTGGAGCTACTACATAATGAGGCCCTGATCAGGCACCTGAATGCTAC<br>TTCCTTTGATGTGGTTTTAACAGACCCCGTTAACCTCTGCGCGGCAGTGCTGGCTAAGTACCTG<br>TCGATTCCTACTGTGTTTTTTTTGAGGAACATTCCATGTGATTTAGACTTTAAGGGCACACAGT<br>GTCCAAACCCTTCCTCCTATATTCCTAGATTACTAACAACCAATTCAGACCACATGACATTCAT<br>GCAAAGGGTCAAGAACATGCTCTACCCTCTGGCCCTGTCCTACATTTGCCATGCTTTTTCTGCT<br>CCTTATGCAAGC |
| 762 | UGT1A9 | 2533102 | CTATCATAGGTCTTGTGTGGAGCTACTACATAATGAGGCCCTGATCAGGCACCTGAATGCTAC<br>TTCCTTTGATGTGGTTTTAACAGACCCCGTTAACCTCTGCGCGGCAGTGCTGGCTAAGTACCTG<br>TCGATTCCTACTGTGTTTTTTTTGAGGAACATTCCATGTGATTTAGACTTTAAGGGCACACAGT<br>GTCCAAACCCTTCCTCCTATATTCCTAGATTACTAACAACCAATTCAGACCACATGACATTCAT<br>GCAAAGGGTCAAGAACATGCTCTACCCTCTGGCCCTGTCCTACATTTGCCATGCTTTTTCTGCT<br>CCTTATGCAAGC |
| 763 | UGT1A5 | 2533102 | CTATCATAGGTCTTGTGTGGAGCTACTACATAATGAGGCCCTGATCAGGCACCTGAATGCTAC<br>TTCCTTTGATGTGGTTTTAACAGACCCCGTTAACCTCTGCGCGGCAGTGCTGGCTAAGTACCTG<br>TCGATTCCTACTGTGTTTTTTTTGAGGAACATTCCATGTGATTTAGACTTTAAGGGCACACAGT<br>GTCCAAACCCTTCCTCCTATATTCCTAGATTACTAACAACCAATTCAGACCACATGACATTCAT<br>GCAAAGGGTCAAGAACATGCTCTACCCTCTGGCCCTGTCCTACATTTGCCATGCTTTTTCTGCT<br>CCTTATGCAAGC |
| 764 | UGT1A4 | 2533102 | CTATCATAGGTCTTGTGTGGAGCTACTACATAATGAGGCCCTGATCAGGCACCTGAATGCTAC<br>TTCCTTTGATGTGGTTTTAACAGACCCCGTTAACCTCTGCGCGGCAGTGCTGGCTAAGTACCTG<br>TCGATTCCTACTGTGTTTTTTTTGAGGAACATTCCATGTGATTTAGACTTTAAGGGCACACAGT<br>GTCCAAACCCTTCCTCCTATATTCCTAGATTACTAACAACCAATTCAGACCACATGACATTCAT<br>GCAAAGGGTCAAGAACATGCTCTACCCTCTGGCCCTGTCCTACATTTGCCATGCTTTTTCTGCT<br>CCTTATGCAAGC |
| 765 | UGT1A3 | 2533102 | CTATCATAGGTCTTGTGTGGAGCTACTACATAATGAGGCCCTGATCAGGCACCTGAATGCTAC<br>TTCCTTTGATGTGGTTTTAACAGACCCCGTTAACCTCTGCGCGGCAGTGCTGGCTAAGTACCTG<br>TCGATTCCTACTGTGTTTTTTTTGAGGAACATTCCATGTGATTTAGACTTTAAGGGCACACAGT<br>GTCCAAACCCTTCCTCCTATATTCCTAGATTACTAACAACCAATTCAGACCACATGACATTCAT<br>GCAAAGGGTCAAGAACATGCTCTACCCTCTGGCCCTGTCCTACATTTGCCATGCTTTTTCTGCT<br>CCTTATGCAAGC |
| 766 | UGT1A8 | 2533103 | TTCCGAGGGGACTTTGTGATGGACT |
| 767 | UGT1A10 | 2533103 | TTCCGAGGGGACTTTGTGATGGACT |
| 768 | UGT1A9 | 2533103 | TTCCGAGGGGACTTTGTGATGGACT |

TABLE 13-continued

Subtyping Target Sequences

| SEQ ID NO. | Gene | Affy Probeset ID | Sequence |
|---|---|---|---|
| 769 | UGT1A5 | 2533103 | TTCCGAGGGGACTTTGTGATGGACT |
| 770 | UGT1A4 | 2533103 | TTCCGAGGGGACTTTGTGATGGACT |
| 771 | UGT1A8 | 2533104 | GCCCAACATGGTCTTCATTGGGGGC |
| 772 | UGT1A10 | 2533104 | GCCCAACATGGTCTTCATTGGGGGC |
| 773 | UGT1A9 | 2533104 | GCCCAACATGGTCTTCATTGGGGGC |
| 774 | UGT1A5 | 2533104 | GCCCAACATGGTCTTCATTGGGGGC |
| 775 | UGT1A8 | 2533108 | AGGACCCCAGGTTCCCCTGCTGTGGCTGGCCACAG |
| 776 | UGT1A10 | 2533108 | AGGACCCCAGGTTCCCCTGCTGTGGCTGGCCACAG |
| 777 | UGT1A9 | 2533108 | AGGACCCCAGGTTCCCCTGCTGTGGCTGGCCACAG |
| 778 | UGT1A5 | 2533108 | AGGACCCCAGGTTCCCCTGCTGTGGCTGGCCACAG |
| 779 | UGT1A4 | 2533108 | AGGACCCCAGGTTCCCCTGCTGTGGCTGGCCACAG |
| 780 | UGT1A3 | 2533108 | AGGACCCCAGGTTCCCCTGCTGTGGCTGGCCACAG |
| 781 | UGT1A8 | 2533109 | GAGTGCTACTCCTTCTCAGTGCCCAGCCCTG |
| 782 | UGT1A10 | 2533109 | GAGTGCTACTCCTTCTCAGTGCCCAGCCCTG |
| 783 | UGT1A9 | 2533109 | GAGTGCTACTCCTTCTCAGTGCCCAGCCCTG |
| 784 | UGT1A5 | 2533109 | GAGTGCTACTCCTTCTCAGTGCCCAGCCCTG |
| 785 | UGT1A4 | 2533109 | GAGTGCTACTCCTTCTCAGTGCCCAGCCCTG |
| 786 | UGT1A3 | 2533109 | GAGTGCTACTCCTTCTCAGTGCCCAGCCCTG |
| 787 | UGT1A8 | 2533110 | AGAGGCCACCAGGCGGTGGTCCTCACCCCAGAG |
| 788 | UGT1A10 | 2533110 | AGAGGCCACCAGGCGGTGGTCCTCACCCCAGAG |
| 789 | UGT1A9 | 2533110 | AGAGGCCACCAGGCGGTGGTCCTCACCCCAGAG |
| 790 | UGT1A5 | 2533110 | AGAGGCCACCAGGCGGTGGTCCTCACCCCAGAG |
| 791 | UGT1A4 | 2533110 | AGAGGCCACCAGGCGGTGGTCCTCACCCCAGAG |
| 792 | UGT1A8 | 2533111 | CCTTGTGCTGGGCCACACTCAACTGTACTTTGAAACAGAACATTTTCTGAAGACATTTTCTAAA AGTATGGCAATTTTGAAAAATTCATCTTTGGTCTTTCATAGGTCTTGTGTGGAGCTACTGCATA ATGAGGCCCTGATCAGGCACCTGAATGCTACTTCCTTCGATGTGGTTTTAATAGACCCAATTTA CCTCTGTGGGGCAGTG |
| 793 | UGT1A10 | 2533111 | CCTTGTGCTGGGCCACACTCAACTGTACTTTGAAACAGAACATTTTCTGAAGACATTTTCTAAA AGTATGGCAATTTTGAAAAATTCATCTTTGGTCTTTCATAGGTCTTGTGTGGAGCTACTGCATA ATGAGGCCCTGATCAGGCACCTGAATGCTACTTCCTTCGATGTGGTTTTAATAGACCCAATTTA CCTCTGTGGGGCAGTG |
| 794 | UGT1A9 | 2533111 | CCTTGTGCTGGGCCACACTCAACTGTACTTTGAAACAGAACATTTTCTGAAGACATTTTCTAAA AGTATGGCAATTTTGAAAAATTCATCTTTGGTCTTTCATAGGTCTTGTGTGGAGCTACTGCATA ATGAGGCCCTGATCAGGCACCTGAATGCTACTTCCTTCGATGTGGTTTTAATAGACCCAATTTA CCTCTGTGGGGCAGTG |
| 795 | UGT1A5 | 2533111 | CCTTGTGCTGGGCCACACTCAACTGTACTTTGAAACAGAACATTTTCTGAAGACATTTTCTAAA AGTATGGCAATTTTGAAAAATTCATCTTTGGTCTTTCATAGGTCTTGTGTGGAGCTACTGCATA ATGAGGCCCTGATCAGGCACCTGAATGCTACTTCCTTCGATGTGGTTTTAATAGACCCAATTTA CCTCTGTGGGGCAGTG |
| 796 | UGT1A4 | 2533111 | CCTTGTGCTGGGCCACACTCAACTGTACTTTGAAACAGAACATTTTCTGAAGACATTTTCTAAA AGTATGGCAATTTTGAAAAATTCATCTTTGGTCTTTCATAGGTCTTGTGTGGAGCTACTGCATA ATGAGGCCCTGATCAGGCACCTGAATGCTACTTCCTTCGATGTGGTTTTAATAGACCCAATTTA CCTCTGTGGGGCAGTG |
| 797 | UGT1A3 | 2533111 | CCTTGTGCTGGGCCACACTCAACTGTACTTTGAAACAGAACATTTTCTGAAGACATTTTCTAAA AGTATGGCAATTTTGAAAAATTCATCTTTGGTCTTTCATAGGTCTTGTGTGGAGCTACTGCATA |

TABLE 13-continued

Subtyping Target Sequences

| SEQ ID NO. | Gene | Affy Probeset ID | Sequence |
|---|---|---|---|
| | | | ATGAGGCCCTGATCAGGCACCTGAATGCTACTTCCTTCGATGTGGTTTTAATAGACCCAATTTACCTCTGTGGGGCAGTG |
| 798 | UGT1A8 | 2533112 | TCCGAGGGGACTTTGTGATGGATTACCCCAGGCCGATCATGCCCAACATGGTCTTCATTGGGGGC |
| 799 | UGT1A10 | 2533112 | TCCGAGGGGACTTTGTGATGGATTACCCCAGGCCGATCATGCCCAACATGGTCTTCATTGGGGGC |
| 800 | UGT1A9 | 2533112 | TCCGAGGGGACTTTGTGATGGATTACCCCAGGCCGATCATGCCCAACATGGTCTTCATTGGGGGC |
| 801 | UGT1A5 | 2533112 | TCCGAGGGGACTTTGTGATGGATTACCCCAGGCCGATCATGCCCAACATGGTCTTCATTGGGGGC |
| 802 | UGT1A8 | 2533116 | TCCTCTGACCCCCCAAAATATTCTCCAG |
| 803 | UGT1A10 | 2533116 | TCCTCTGACCCCCCAAAATATTCTCCAG |
| 804 | UGT1A9 | 2533116 | TCCTCTGACCCCCCAAAATATTCTCCAG |
| 805 | UGT1A5 | 2533116 | TCCTCTGACCCCCCAAAATATTCTCCAG |
| 806 | UGT1A4 | 2533116 | TCCTCTGACCCCCCAAAATATTCTCCAG |
| 807 | UGT1A3 | 2533116 | TCCTCTGACCCCCCAAAATATTCTCCAG |
| 808 | UGT1A8 | 2533117 | CGGCCGCCAAAGAACTCCCTGAAGACCTCGGCGGGGTCACGGAAGCTGAAGACCTACTCGAAGGGGTCCTTGAAGGGCCTGCCGCCTGCGCAGCCGCCCTCCGCCCTCGCCTCGCCATAGCGGTCATAGATATCGCGTTTCTACGCGTCCGACAACACCTCGTAGGCCTCAGCCACCTGCTTGAATCTTCTCACCGCTTCCTCCCTGTCCTCGGGGTTTTTGTCGGGGTGCCACTTGAGCGCCAGCTTGCGGTACGCCTTCTTGATACCCTCGGACGAGGCCTACCGGGGTACTCCCAGCACCTCGTAGTAGTCCACTATG |
| 809 | UGT1A10 | 2533117 | CGGCCGCCAAAGAACTCCCTGAAGACCTCGGCGGGGTCACGGAAGCTGAAGACCTACTCGAAGGGGTCCTTGAAGGGCCTGCCGCCTGCGCAGCCGCCCTCCGCCCTCGCCTCGCCATAGCGGTCATAGATATCGCGTTTCTACGCGTCCGACAACACCTCGTAGGCCTCAGCCACCTGCTTGAATCTTCTCACCGCTTCCTCCCTGTCCTCGGGGTTTTTGTCGGGGTGCCACTTGAGCGCCAGCTTGCGGTACGCCTTCTTGATACCCTCGGACGAGGCCTACCGGGGTACTCCCAGCACCTCGTAGTAGTCCACTATG |
| 810 | UGT1A9 | 2533117 | CGGCCGCCAAAGAACTCCCTGAAGACCTCGGCGGGGTCACGGAAGCTGAAGACCTACTCGAAGGGGTCCTTGAAGGGCCTGCCGCCTGCGCAGCCGCCCTCCGCCCTCGCCTCGCCATAGCGGTCATAGATATCGCGTTTCTACGCGTCCGACAACACCTCGTAGGCCTCAGCCACCTGCTTGAATCTTCTCACCGCTTCCTCCCTGTCCTCGGGGTTTTTGTCGGGGTGCCACTTGAGCGCCAGCTTGCGGTACGCCTTCTTGATACCCTCGGACGAGGCCTACCGGGGTACTCCCAGCACCTCGTAGTAGTCCACTATG |
| 811 | UGT1A5 | 2533117 | CGGCCGCCAAAGAACTCCCTGAAGACCTCGGCGGGGTCACGGAAGCTGAAGACCTACTCGAAGGGGTCCTTGAAGGGCCTGCCGCCTGCGCAGCCGCCCTCCGCCCTCGCCTCGCCATAGCGGTCATAGATATCGCGTTTCTACGCGTCCGACAACACCTCGTAGGCCTCAGCCACCTGCTTGAATCTTCTCACCGCTTCCTCCCTGTCCTCGGGGTTTTTGTCGGGGTGCCACTTGAGCGCCAGCTTGCGGTACGCCTTCTTGATACCCTCGGACGAGGCCTACCGGGGTACTCCCAGCACCTCGTAGTAGTCCACTATG |
| 812 | UGT1A4 | 2533117 | CGGCCGCCAAAGAACTCCCTGAAGACCTCGGCGGGGTCACGGAAGCTGAAGACCTACTCGAAGGGGTCCTTGAAGGGCCTGCCGCCTGCGCAGCCGCCCTCCGCCCTCGCCTCGCCATAGCGGTCATAGATATCGCGTTTCTACGCGTCCGACAACACCTCGTAGGCCTCAGCCACCTGCTTGAATCTTCTCACCGCTTCCTCCCTGTCCTCGGGGTTTTTGTCGGGGTGCCACTTGAGCGCCAGCTTGCGGTACGCCTTCTTGATACCCTCGGACGAGGCCTACCGGGGTACTCCCAGCACCTCGTAGTAGTCCACTATG |
| 813 | UGT1A3 | 2533117 | CGGCCGCCAAAGAACTCCCTGAAGACCTCGGCGGGGTCACGGAAGCTGAAGACCTACTCGAAGGGGTCCTTGAAGGGCCTGCCGCCTGCGCAGCCGCCCTCCGCCCTCGCCTCGCCATAGCGGTCATAGATATCGCGTTTCTACGCGTCCGACAACACCTCGTAGGCCTCAGCCACCTGCTTGAATCTTCTCACCGCTTCCTCCCTGTCCTCGGGGTTTTTGTCGGGGTGCCACTTGAGCGCCAGCTTGCGGTACGCCTTCTTGATACCCTCGGACGAGGCCTACCGGGGTACTCCCAGCACCTCGTAGTAGTCCACTATG |
| 814 | UGT1A8 | 2533118 | GTCTGACCGGGGCTGAAGACATCCTGTTGTTTAGGACTGCGGTTCTCCAACGTTCCAGC |
| 815 | UGT1A10 | 2533118 | GTCTGACCGGGGCTGAAGACATCCTGTTGTTTAGGACTGCGGTTCTCCAACGTTCCAGC |
| 816 | UGT1A9 | 2533118 | GTCTGACCGGGGCTGAAGACATCCTGTTGTTTAGGACTGCGGTTCTCCAACGTTCCAGC |

TABLE 13-continued

Subtyping Target Sequences

| SEQ ID NO. | Gene | Affy Probeset ID | Sequence |
|---|---|---|---|
| 817 | UGT1A5 | 2533118 | GTCTGACCGGGGCTGAAGACATCCTGTTGTTTAGGACTGCGGTTCTCCAACGTTCCAGC |
| 818 | UGT1A4 | 2533118 | GTCTGACCGGGGCTGAAGACATCCTGTTGTTTAGGACTGCGGTTCTCCAACGTTCCAGC |
| 819 | UGT1A3 | 2533118 | GTCTGACCGGGGCTGAAGACATCCTGTTGTTTAGGACTGCGGTTCTCCAACGTTCCAGC |
| 820 | UGT1A8 | 2533119 | AGTCCCAGGGCGGACGCCCACTTGTCCTGGGCCTGCTGCTGTGTGTGCTGGGCCCAGTGGTG<br>TCCCATGCTGGGAAGATACTGTTGATCCCAGTGGA |
| 821 | UGT1A10 | 2533119 | AGTCCCAGGGCGGACGCCCACTTGTCCTGGGCCTGCTGCTGTGTGTGCTGGGCCCAGTGGTG<br>TCCCATGCTGGGAAGATACTGTTGATCCCAGTGGA |
| 822 | UGT1A9 | 2533119 | AGTCCCAGGGCGGACGCCCACTTGTCCTGGGCCTGCTGCTGTGTGTGCTGGGCCCAGTGGTG<br>TCCCATGCTGGGAAGATACTGTTGATCCCAGTGGA |
| 823 | UGT1A5 | 2533119 | AGTCCCAGGGCGGACGCCCACTTGTCCTGGGCCTGCTGCTGTGTGTGCTGGGCCCAGTGGTG<br>TCCCATGCTGGGAAGATACTGTTGATCCCAGTGGA |
| 824 | UGT1A4 | 2533119 | AGTCCCAGGGCGGACGCCCACTTGTCCTGGGCCTGCTGCTGTGTGTGCTGGGCCCAGTGGTG<br>TCCCATGCTGGGAAGATACTGTTGATCCCAGTGGA |
| 825 | UGT1A3 | 2533119 | AGTCCCAGGGCGGACGCCCACTTGTCCTGGGCCTGCTGCTGTGTGTGCTGGGCCCAGTGGTG<br>TCCCATGCTGGGAAGATACTGTTGATCCCAGTGGA |
| 826 | UGT1A1 | 2533119 | AGTCCCAGGGCGGACGCCCACTTGTCCTGGGCCTGCTGCTGTGTGTGCTGGGCCCAGTGGTG<br>TCCCATGCTGGGAAGATACTGTTGATCCCAGTGGA |
| 827 | UGT1A8 | 2533120 | TGTCCTAGCACCTGACGCCTCGTTGTACATCAGAGACGGAGCATTTTACACCTTGAAGACGTA<br>CCCTGTGCCATTCCAAAGGGAGGATGTGAAAGAGTCTTTTGTTAGTCTCGGGCATAATGTTTT<br>TGAGAATGATTCTTTCCTGCAGCGTGTGATCAAAACATACAAGAAAATAAAAAAGGACTCTGC<br>TATGCTTTTGTCTGGCTGTTCCCACTTACTGCACAACAAGGAGCTCATGGCCTCCCTGGCAGAA<br>AGCAGCTTTGATGTCATGCTGACGGACCCTTTCCTTCCTTGCAGCCCCATCGTGGCCCAGTACC<br>TGTCTCTGCCCACTGTATTCTTCTTGCATGCACTGCCATGCAGCCTGGAATTTGAGGCTACCCA<br>GTGCCCCAACCCATTCTCCTACGTGCCCAGGCCTCTCTCCTCTCATTCAGATCACATGACCTTCC<br>TGCAGCGGGTGAAGAACATGCTCATTGCCTTTTCACAGAACTTTCTGTGCGACGTGGTTTATT<br>CCCCGTATGCAACCCTTGCCTCAGAATTCCTTCAGAGAGAGGTGACTGTCCA |
| 828 | UGT1A10 | 2533120 | TGTCCTAGCACCTGACGCCTCGTTGTACATCAGAGACGGAGCATTTTACACCTTGAAGACGTA<br>CCCTGTGCCATTCCAAAGGGAGGATGTGAAAGAGTCTTTTGTTAGTCTCGGGCATAATGTTTT<br>TGAGAATGATTCTTTCCTGCAGCGTGTGATCAAAACATACAAGAAAATAAAAAAGGACTCTGC<br>TATGCTTTTGTCTGGCTGTTCCCACTTACTGCACAACAAGGAGCTCATGGCCTCCCTGGCAGAA<br>AGCAGCTTTGATGTCATGCTGACGGACCCTTTCCTTCCTTGCAGCCCCATCGTGGCCCAGTACC<br>TGTCTCTGCCCACTGTATTCTTCTTGCATGCACTGCCATGCAGCCTGGAATTTGAGGCTACCCA<br>GTGCCCCAACCCATTCTCCTACGTGCCCAGGCCTCTCTCCTCTCATTCAGATCACATGACCTTCC<br>TGCAGCGGGTGAAGAACATGCTCATTGCCTTTTCACAGAACTTTCTGTGCGACGTGGTTTATT<br>CCCCGTATGCAACCCTTGCCTCAGAATTCCTTCAGAGAGAGGTGACTGTCCA |
| 829 | UGT1A9 | 2533120 | TGTCCTAGCACCTGACGCCTCGTTGTACATCAGAGACGGAGCATTTTACACCTTGAAGACGTA<br>CCCTGTGCCATTCCAAAGGGAGGATGTGAAAGAGTCTTTTGTTAGTCTCGGGCATAATGTTTT<br>TGAGAATGATTCTTTCCTGCAGCGTGTGATCAAAACATACAAGAAAATAAAAAAGGACTCTGC<br>TATGCTTTTGTCTGGCTGTTCCCACTTACTGCACAACAAGGAGCTCATGGCCTCCCTGGCAGAA<br>AGCAGCTTTGATGTCATGCTGACGGACCCTTTCCTTCCTTGCAGCCCCATCGTGGCCCAGTACC<br>TGTCTCTGCCCACTGTATTCTTCTTGCATGCACTGCCATGCAGCCTGGAATTTGAGGCTACCCA<br>GTGCCCCAACCCATTCTCCTACGTGCCCAGGCCTCTCTCCTCTCATTCAGATCACATGACCTTCC<br>TGCAGCGGGTGAAGAACATGCTCATTGCCTTTTCACAGAACTTTCTGTGCGACGTGGTTTATT<br>CCCCGTATGCAACCCTTGCCTCAGAATTCCTTCAGAGAGAGGTGACTGTCCA |
| 830 | UGT1A5 | 2533120 | TGTCCTAGCACCTGACGCCTCGTTGTACATCAGAGACGGAGCATTTTACACCTTGAAGACGTA<br>CCCTGTGCCATTCCAAAGGGAGGATGTGAAAGAGTCTTTTGTTAGTCTCGGGCATAATGTTTT<br>TGAGAATGATTCTTTCCTGCAGCGTGTGATCAAAACATACAAGAAAATAAAAAAGGACTCTGC<br>TATGCTTTTGTCTGGCTGTTCCCACTTACTGCACAACAAGGAGCTCATGGCCTCCCTGGCAGAA<br>AGCAGCTTTGATGTCATGCTGACGGACCCTTTCCTTCCTTGCAGCCCCATCGTGGCCCAGTACC<br>TGTCTCTGCCCACTGTATTCTTCTTGCATGCACTGCCATGCAGCCTGGAATTTGAGGCTACCCA<br>GTGCCCCAACCCATTCTCCTACGTGCCCAGGCCTCTCTCCTCTCATTCAGATCACATGACCTTCC<br>TGCAGCGGGTGAAGAACATGCTCATTGCCTTTTCACAGAACTTTCTGTGCGACGTGGTTTATT<br>CCCCGTATGCAACCCTTGCCTCAGAATTCCTTCAGAGAGAGGTGACTGTCCA |
| 831 | UGT1A4 | 2533120 | TGTCCTAGCACCTGACGCCTCGTTGTACATCAGAGACGGAGCATTTTACACCTTGAAGACGTA<br>CCCTGTGCCATTCCAAAGGGAGGATGTGAAAGAGTCTTTTGTTAGTCTCGGGCATAATGTTTT<br>TGAGAATGATTCTTTCCTGCAGCGTGTGATCAAAACATACAAGAAAATAAAAAAGGACTCTGC<br>TATGCTTTTGTCTGGCTGTTCCCACTTACTGCACAACAAGGAGCTCATGGCCTCCCTGGCAGAA<br>AGCAGCTTTGATGTCATGCTGACGGACCCTTTCCTTCCTTGCAGCCCCATCGTGGCCCAGTACC<br>TGTCTCTGCCCACTGTATTCTTCTTGCATGCACTGCCATGCAGCCTGGAATTTGAGGCTACCCA |

TABLE 13-continued

Subtyping Target Sequences

| SEQ ID NO. | Gene | Affy Probeset ID | Sequence |
|---|---|---|---|
| | | | GTGCCCCAACCCATTCTCCTACGTGCCCAGGCCTCTCTCCTCTCATTCAGATCACATGACCTTCC<br>TGCAGCGGGTGAAGAACATGCTCATTGCCTTTTCACAGAACTTTCTGTGCGACGTGGTTTATT<br>CCCCGTATGCAACCCTTGCCTCAGAATTCCTTCAGAGAGAGGTGACTGTCCA |
| 832 | UGT1A3 | 2533120 | TGTCCTAGCACCTGACGCCTCGTTGTACATCAGAGACGGAGCATTTTACACCTTGAAGACGTA<br>CCCTGTGCCATTCCAAAGGGAGGATGTGAAAGAGTCTTTTGTTAGTCTCGGGCATAATGTTTT<br>TGAGAATGATTCTTTCCTGCAGCGTGTGATCAAAACATACAAGAAAATAAAAAAGGACTCTGC<br>TATGCTTTTGTCTGGCTGTTCCCACTTACTGCACAACAAGGAGCTCATGGCCTCCCTGGCAGAA<br>AGCAGCTTTGATGTCATGCTGACGGACCCTTTCCTTCCTTGCAGCCCCATCGTGGCCCAGTACC<br>TGTCTCTGCCCACTGTATTCTTCTTGCATGCACTGCCATGCAGCCTGGAATTTGAGGCTACCCA<br>GTGCCCCAACCCATTCTCCTACGTGCCCAGGCCTCTCTCCTCTCATTCAGATCACATGACCTTCC<br>TGCAGCGGGTGAAGAACATGCTCATTGCCTTTTCACAGAACTTTCTGTGCGACGTGGTTTATT<br>CCCCGTATGCAACCCTTGCCTCAGAATTCCTTCAGAGAGAGGTGACTGTCCA |
| 833 | UGT1A1 | 2533120 | TGTCCTAGCACCTGACGCCTCGTTGTACATCAGAGACGGAGCATTTTACACCTTGAAGACGTA<br>CCCTGTGCCATTCCAAAGGGAGGATGTGAAAGAGTCTTTTGTTAGTCTCGGGCATAATGTTTT<br>TGAGAATGATTCTTTCCTGCAGCGTGTGATCAAAACATACAAGAAAATAAAAAAGGACTCTGC<br>TATGCTTTTGTCTGGCTGTTCCCACTTACTGCACAACAAGGAGCTCATGGCCTCCCTGGCAGAA<br>AGCAGCTTTGATGTCATGCTGACGGACCCTTTCCTTCCTTGCAGCCCCATCGTGGCCCAGTACC<br>TGTCTCTGCCCACTGTATTCTTCTTGCATGCACTGCCATGCAGCCTGGAATTTGAGGCTACCCA<br>GTGCCCCAACCCATTCTCCTACGTGCCCAGGCCTCTCTCCTCTCATTCAGATCACATGACCTTCC<br>TGCAGCGGGTGAAGAACATGCTCATTGCCTTTTCACAGAACTTTCTGTGCGACGTGGTTTATT<br>CCCCGTATGCAACCCTTGCCTCAGAATTCCTTCAGAGAGAGGTGACTGTCCA |
| 834 | UGT1A8 | 2533123 | TTGAAGCCTACATTAATGCTTCTGGAGAACATGGAATTGTGGTTTTCTCTTTGGGATCAATGGT<br>CTCAGAAATTCCAGAGAAGAAAGCTATGGCAATTGCTGATGCTTTGGGCAAAATCCC |
| 835 | UGT1A10 | 2533123 | TTGAAGCCTACATTAATGCTTCTGGAGAACATGGAATTGTGGTTTTCTCTTTGGGATCAATGGT<br>CTCAGAAATTCCAGAGAAGAAAGCTATGGCAATTGCTGATGCTTTGGGCAAAATCCC |
| 836 | UGT1A9 | 2533123 | TTGAAGCCTACATTAATGCTTCTGGAGAACATGGAATTGTGGTTTTCTCTTTGGGATCAATGGT<br>CTCAGAAATTCCAGAGAAGAAAGCTATGGCAATTGCTGATGCTTTGGGCAAAATCCC |
| 837 | UGT1A5 | 2533123 | TTGAAGCCTACATTAATGCTTCTGGAGAACATGGAATTGTGGTTTTCTCTTTGGGATCAATGGT<br>CTCAGAAATTCCAGAGAAGAAAGCTATGGCAATTGCTGATGCTTTGGGCAAAATCCC |
| 838 | UGT1A4 | 2533123 | TTGAAGCCTACATTAATGCTTCTGGAGAACATGGAATTGTGGTTTTCTCTTTGGGATCAATGGT<br>CTCAGAAATTCCAGAGAAGAAAGCTATGGCAATTGCTGATGCTTTGGGCAAAATCCC |
| 839 | UGT1A3 | 2533123 | TTGAAGCCTACATTAATGCTTCTGGAGAACATGGAATTGTGGTTTTCTCTTTGGGATCAATGGT<br>CTCAGAAATTCCAGAGAAGAAAGCTATGGCAATTGCTGATGCTTTGGGCAAAATCCC |
| 840 | UGT1A1 | 2533123 | TTGAAGCCTACATTAATGCTTCTGGAGAACATGGAATTGTGGTTTTCTCTTTGGGATCAATGGT<br>CTCAGAAATTCCAGAGAAGAAAGCTATGGCAATTGCTGATGCTTTGGGCAAAATCCC |
| 841 | UGT1A8 | 2533124 | GTCCTGTGGCGGTACACTGGAACCCGACCATCGAATCTTGCGAACAACACGATACTTGTTAAG<br>TGGCTACCCCAAAACGATCTGCTT |
| 842 | UGT1A10 | 2533124 | GTCCTGTGGCGGTACACTGGAACCCGACCATCGAATCTTGCGAACAACACGATACTTGTTAAG<br>TGGCTACCCCAAAACGATCTGCTT |
| 843 | UGT1A9 | 2533124 | GTCCTGTGGCGGTACACTGGAACCCGACCATCGAATCTTGCGAACAACACGATACTTGTTAAG<br>TGGCTACCCCAAAACGATCTGCTT |
| 844 | UGT1A5 | 2533124 | GTCCTGTGGCGGTACACTGGAACCCGACCATCGAATCTTGCGAACAACACGATACTTGTTAAG<br>TGGCTACCCCAAAACGATCTGCTT |
| 845 | UGT1A4 | 2533124 | GTCCTGTGGCGGTACACTGGAACCCGACCATCGAATCTTGCGAACAACACGATACTTGTTAAG<br>TGGCTACCCCAAAACGATCTGCTT |
| 846 | UGT1A3 | 2533124 | GTCCTGTGGCGGTACACTGGAACCCGACCATCGAATCTTGCGAACAACACGATACTTGTTAAG<br>TGGCTACCCCAAAACGATCTGCTT |
| 847 | UGT1A1 | 2533124 | GTCCTGTGGCGGTACACTGGAACCCGACCATCGAATCTTGCGAACAACACGATACTTGTTAAG<br>TGGCTACCCCAAAACGATCTGCTT |
| 848 | UGT1A8 | 2533125 | GTCACCCGATGACCCGTGCCTTTATCACCCATGCTGGTTCCCATGGTGTTTATGAAAGCATATG<br>CAATGGCGTTCCCATGGTGATGATGCCCTTGTTTGGTGATCAGATGGACAATGCAAAGCGCAT<br>GGAGACTAAGGGAGCTGGAGTGACCCTGAATGTTCTGGA |
| 849 | UGT1A10 | 2533125 | GTCACCCGATGACCCGTGCCTTTATCACCCATGCTGGTTCCCATGGTGTTTATGAAAGCATATG<br>CAATGGCGTTCCCATGGTGATGATGCCCTTGTTTGGTGATCAGATGGACAATGCAAAGCGCAT<br>GGAGACTAAGGGAGCTGGAGTGACCCTGAATGTTCTGGA |

TABLE 13-continued

Subtyping Target Sequences

| SEQ ID NO. | Gene | Affy Probeset ID | Sequence |
|---|---|---|---|
| 850 | UGT1A9 | 2533125 | GTCACCCGATGACCCGTGCCTTTATCACCCATGCTGGTTCCCATGGTGTTTATGAAAGCATATG<br>CAATGGCGTTCCCATGGTGATGATGCCCTTGTTTGGTGATCAGATGGACAATGCAAAGCGCAT<br>GGAGACTAAGGGAGCTGGAGTGACCCTGAATGTTCTGGA |
| 851 | UGT1A5 | 2533125 | GTCACCCGATGACCCGTGCCTTTATCACCCATGCTGGTTCCCATGGTGTTTATGAAAGCATATG<br>CAATGGCGTTCCCATGGTGATGATGCCCTTGTTTGGTGATCAGATGGACAATGCAAAGCGCAT<br>GGAGACTAAGGGAGCTGGAGTGACCCTGAATGTTCTGGA |
| 852 | UGT1A4 | 2533125 | GTCACCCGATGACCCGTGCCTTTATCACCCATGCTGGTTCCCATGGTGTTTATGAAAGCATATG<br>CAATGGCGTTCCCATGGTGATGATGCCCTTGTTTGGTGATCAGATGGACAATGCAAAGCGCAT<br>GGAGACTAAGGGAGCTGGAGTGACCCTGAATGTTCTGGA |
| 853 | UGT1A3 | 2533125 | GTCACCCGATGACCCGTGCCTTTATCACCCATGCTGGTTCCCATGGTGTTTATGAAAGCATATG<br>CAATGGCGTTCCCATGGTGATGATGCCCTTGTTTGGTGATCAGATGGACAATGCAAAGCGCAT<br>GGAGACTAAGGGAGCTGGAGTGACCCTGAATGTTCTGGA |
| 854 | UGT1A1 | 2533125 | GTCACCCGATGACCCGTGCCTTTATCACCCATGCTGGTTCCCATGGTGTTTATGAAAGCATATG<br>CAATGGCGTTCCCATGGTGATGATGCCCTTGTTTGGTGATCAGATGGACAATGCAAAGCGCAT<br>GGAGACTAAGGGAGCTGGAGTGACCCTGAATGTTCTGGA |
| 855 | UGT1A8 | 2533126 | AAGAAGCAGCAGTCAGGAAGACAGATGTGA |
| 856 | UGT1A10 | 2533126 | AAGAAGCAGCAGTCAGGAAGACAGATGTGA |
| 857 | UGT1A9 | 2533126 | AAGAAGCAGCAGTCAGGAAGACAGATGTGA |
| 858 | UGT1A5 | 2533126 | AAGAAGCAGCAGTCAGGAAGACAGATGTGA |
| 859 | UGT1A4 | 2533126 | AAGAAGCAGCAGTCAGGAAGACAGATGTGA |
| 860 | UGT1A3 | 2533126 | AAGAAGCAGCAGTCAGGAAGACAGATGTGA |
| 861 | UGT1A1 | 2533126 | AAGAAGCAGCAGTCAGGAAGACAGATGTGA |
| 862 | UGT1A8 | 2533127 | TTCAGATGAGAGGAGACGGAACACGGGGACACACCAGCTTGAGCAAGGGACAACAGGGGA<br>GGACTGATGACTGACTTCCCACCTTTGAGGTGCTAATGTGTGTGTGGTGGCACTGGATAAAA<br>GATCAATGTTGGCTAGGCACCATGGCACACGCCTGTAGTCCCAGCCACTCTGGAGGCTAAGG<br>CGGGAGGATTGCTTGAGCCCAGAAGTTGGAGGCTGCTATGAGCCGTGATCATGCCACTGCAC<br>TCCAGCAACCTGGGCAACAGAGTGAGACCCTGTCTCAAAAAAAAAAAAAAAATGAAAAGTC<br>CACATAACCTGAGCATCATGTGCCCAGAGCGTTGGGTGGTGTGGTCCCATTCCTTCCTTCCAG<br>CGGCTTCTTCTGGCCACCTCAATGTCAGGATGTC |
| 863 | UGT1A10 | 2533127 | TTCAGATGAGAGGAGACGGAACACGGGGACACACCAGCTTGAGCAAGGGACAACAGGGGA<br>GGACTGATGACTGACTTCCCACCTTTGAGGTGCTAATGTGTGTGTGGTGGCACTGGATAAAA<br>GATCAATGTTGGCTAGGCACCATGGCACACGCCTGTAGTCCCAGCCACTCTGGAGGCTAAGG<br>CGGGAGGATTGCTTGAGCCCAGAAGTTGGAGGCTGCTATGAGCCGTGATCATGCCACTGCAC<br>TCCAGCAACCTGGGCAACAGAGTGAGACCCTGTCTCAAAAAAAAAAAAAAAATGAAAAGTC<br>CACATAACCTGAGCATCATGTGCCCAGAGCGTTGGGTGGTGTGGTCCCATTCCTTCCTTCCAG<br>CGGCTTCTTCTGGCCACCTCAATGTCAGGATGTC |
| 864 | UGT1A9 | 2533127 | TTCAGATGAGAGGAGACGGAACACGGGGACACACCAGCTTGAGCAAGGGACAACAGGGGA<br>GGACTGATGACTGACTTCCCACCTTTGAGGTGCTAATGTGTGTGTGGTGGCACTGGATAAAA<br>GATCAATGTTGGCTAGGCACCATGGCACACGCCTGTAGTCCCAGCCACTCTGGAGGCTAAGG<br>CGGGAGGATTGCTTGAGCCCAGAAGTTGGAGGCTGCTATGAGCCGTGATCATGCCACTGCAC<br>TCCAGCAACCTGGGCAACAGAGTGAGACCCTGTCTCAAAAAAAAAAAAAAAATGAAAAGTC<br>CACATAACCTGAGCATCATGTGCCCAGAGCGTTGGGTGGTGTGGTCCCATTCCTTCCTTCCAG<br>CGGCTTCTTCTGGCCACCTCAATGTCAGGATGTC |
| 865 | UGT1A5 | 2533127 | TTCAGATGAGAGGAGACGGAACACGGGGACACACCAGCTTGAGCAAGGGACAACAGGGGA<br>GGACTGATGACTGACTTCCCACCTTTGAGGTGCTAATGTGTGTGTGGTGGCACTGGATAAAA<br>GATCAATGTTGGCTAGGCACCATGGCACACGCCTGTAGTCCCAGCCACTCTGGAGGCTAAGG<br>CGGGAGGATTGCTTGAGCCCAGAAGTTGGAGGCTGCTATGAGCCGTGATCATGCCACTGCAC<br>TCCAGCAACCTGGGCAACAGAGTGAGACCCTGTCTCAAAAAAAAAAAAAAAATGAAAAGTC<br>CACATAACCTGAGCATCATGTGCCCAGAGCGTTGGGTGGTGTGGTCCCATTCCTTCCTTCCAG<br>CGGCTTCTTCTGGCCACCTCAATGTCAGGATGTC |
| 866 | UGT1A4 | 2533127 | TTCAGATGAGAGGAGACGGAACACGGGGACACACCAGCTTGAGCAAGGGACAACAGGGGA<br>GGACTGATGACTGACTTCCCACCTTTGAGGTGCTAATGTGTGTGTGGTGGCACTGGATAAAA<br>GATCAATGTTGGCTAGGCACCATGGCACACGCCTGTAGTCCCAGCCACTCTGGAGGCTAAGG<br>CGGGAGGATTGCTTGAGCCCAGAAGTTGGAGGCTGCTATGAGCCGTGATCATGCCACTGCAC<br>TCCAGCAACCTGGGCAACAGAGTGAGACCCTGTCTCAAAAAAAAAAAAAAAATGAAAAGTC<br>CACATAACCTGAGCATCATGTGCCCAGAGCGTTGGGTGGTGTGGTCCCATTCCTTCCTTCCAG<br>CGGCTTCTTCTGGCCACCTCAATGTCAGGATGTC |

TABLE 13-continued

Subtyping Target Sequences

| SEQ ID NO. | Gene | Affy Probeset ID | Sequence |
|---|---|---|---|
| 867 | UGT1A3 | 2533127 | TTCAGATGAGAGGAGACGGAACACGGGGACACACCAGCTTGAGCAAGGGACAACAGGGGA<br>GGACTGATGACTGACTTCCCACCTTTGAGGTGCTAATGTGTGTGGTGGCACTGGATAAAA<br>GATCAATGTTGGCTAGGCACCATGGCACACGCCTGTAGTCCCAGCCACTCTGGAGGCTAAGG<br>CGGGAGGATTGCTTGAGCCCAGAAGTTGGAGGCTGCTATGAGCCGTGATCATGCCACTGCAC<br>TCCAGCAACCTGGGCAACAGAGTGAGACCCTGTCTCAAAAAAAAAAAAAAAAATGAAAAGTC<br>CACATAACCTGAGCATCATGTGCCCAGAGCGTTGGGTGGTGTGGTCCCATTCCTTCCTTCCAG<br>CGGCTTCTTCTGGCCACCTCAATGTCAGGATGTC |
| 868 | UGT1A1 | 2533127 | TTCAGATGAGAGGAGACGGAACACGGGGACACACCAGCTTGAGCAAGGGACAACAGGGGA<br>GGACTGATGACTGACTTCCCACCTTTGAGGTGCTAATGTGTGTGGTGGCACTGGATAAAA<br>GATCAATGTTGGCTAGGCACCATGGCACACGCCTGTAGTCCCAGCCACTCTGGAGGCTAAGG<br>CGGGAGGATTGCTTGAGCCCAGAAGTTGGAGGCTGCTATGAGCCGTGATCATGCCACTGCAC<br>TCCAGCAACCTGGGCAACAGAGTGAGACCCTGTCTCAAAAAAAAAAAAAAAAATGAAAAGTC<br>CACATAACCTGAGCATCATGTGCCCAGAGCGTTGGGTGGTGTGGTCCCATTCCTTCCTTCCAG<br>CGGCTTCTTCTGGCCACCTCAATGTCAGGATGTC |
| 869 | UGT1A8 | 2533128 | GAAGCTCCTTCTTGAGGCTCACATTATGGATATAATTTTGATTCTTTCTTCAGTGGTATAGATA<br>ACTACTTGTAACCTAAGAACAACTTGGTGAAAGTCCTCTAATACATTATTTTTAAAAAAACAC<br>AAATCAATGAGCTCAACTTATTAACTAACTTTCATCTATTCATTTTTGAGCCATCCCTGTCTGAT<br>TGTGAATCTCCATGATTCCAACACTCTGAGCTG |
| 870 | UGT1A10 | 2533128 | GAAGCTCCTTCTTGAGGCTCACATTATGGATATAATTTTGATTCTTTCTTCAGTGGTATAGATA<br>ACTACTTGTAACCTAAGAACAACTTGGTGAAAGTCCTCTAATACATTATTTTTAAAAAAACAC<br>AAATCAATGAGCTCAACTTATTAACTAACTTTCATCTATTCATTTTTGAGCCATCCCTGTCTGAT<br>TGTGAATCTCCATGATTCCAACACTCTGAGCTG |
| 871 | UGT1A9 | 2533128 | GAAGCTCCTTCTTGAGGCTCACATTATGGATATAATTTTGATTCTTTCTTCAGTGGTATAGATA<br>ACTACTTGTAACCTAAGAACAACTTGGTGAAAGTCCTCTAATACATTATTTTTAAAAAAACAC<br>AAATCAATGAGCTCAACTTATTAACTAACTTTCATCTATTCATTTTTGAGCCATCCCTGTCTGAT<br>TGTGAATCTCCATGATTCCAACACTCTGAGCTG |
| 872 | UGT1A5 | 2533128 | GAAGCTCCTTCTTGAGGCTCACATTATGGATATAATTTTGATTCTTTCTTCAGTGGTATAGATA<br>ACTACTTGTAACCTAAGAACAACTTGGTGAAAGTCCTCTAATACATTATTTTTAAAAAAACAC<br>AAATCAATGAGCTCAACTTATTAACTAACTTTCATCTATTCATTTTTGAGCCATCCCTGTCTGAT<br>TGTGAATCTCCATGATTCCAACACTCTGAGCTG |
| 873 | UGT1A4 | 2533128 | GAAGCTCCTTCTTGAGGCTCACATTATGGATATAATTTTGATTCTTTCTTCAGTGGTATAGATA<br>ACTACTTGTAACCTAAGAACAACTTGGTGAAAGTCCTCTAATACATTATTTTTAAAAAAACAC<br>AAATCAATGAGCTCAACTTATTAACTAACTTTCATCTATTCATTTTTGAGCCATCCCTGTCTGAT<br>TGTGAATCTCCATGATTCCAACACTCTGAGCTG |
| 874 | UGT1A3 | 2533128 | GAAGCTCCTTCTTGAGGCTCACATTATGGATATAATTTTGATTCTTTCTTCAGTGGTATAGATA<br>ACTACTTGTAACCTAAGAACAACTTGGTGAAAGTCCTCTAATACATTATTTTTAAAAAAACAC<br>AAATCAATGAGCTCAACTTATTAACTAACTTTCATCTATTCATTTTTGAGCCATCCCTGTCTGAT<br>TGTGAATCTCCATGATTCCAACACTCTGAGCTG |
| 875 | UGT1A1 | 2533128 | GAAGCTCCTTCTTGAGGCTCACATTATGGATATAATTTTGATTCTTTCTTCAGTGGTATAGATA<br>ACTACTTGTAACCTAAGAACAACTTGGTGAAAGTCCTCTAATACATTATTTTTAAAAAAACAC<br>AAATCAATGAGCTCAACTTATTAACTAACTTTCATCTATTCATTTTTGAGCCATCCCTGTCTGAT<br>TGTGAATCTCCATGATTCCAACACTCTGAGCTG |
| 876 | UGT1A8 | 2533130 | GTACCAGTACCATTCCTTGGACGTGATTGGTTTCCTCTTGGCCGTCGTGCTGACAGTGGCCTTC<br>ATCACCTTTAAATGTTGTGCTTATGGCTACCGGAAATGCTTGGGGAAAAAAGGGCGAGTTAA<br>GAAAGCCCACAAATC |
| 877 | UGT1A10 | 2533130 | GTACCAGTACCATTCCTTGGACGTGATTGGTTTCCTCTTGGCCGTCGTGCTGACAGTGGCCTTC<br>ATCACCTTTAAATGTTGTGCTTATGGCTACCGGAAATGCTTGGGGAAAAAAGGGCGAGTTAA<br>GAAAGCCCACAAATC |
| 878 | UGT1A9 | 2533130 | GTACCAGTACCATTCCTTGGACGTGATTGGTTTCCTCTTGGCCGTCGTGCTGACAGTGGCCTTC<br>ATCACCTTTAAATGTTGTGCTTATGGCTACCGGAAATGCTTGGGGAAAAAAGGGCGAGTTAA<br>GAAAGCCCACAAATC |
| 879 | UGT1A5 | 2533130 | GTACCAGTACCATTCCTTGGACGTGATTGGTTTCCTCTTGGCCGTCGTGCTGACAGTGGCCTTC<br>ATCACCTTTAAATGTTGTGCTTATGGCTACCGGAAATGCTTGGGGAAAAAAGGGCGAGTTAA<br>GAAAGCCCACAAATC |
| 880 | UGT1A4 | 2533130 | GTACCAGTACCATTCCTTGGACGTGATTGGTTTCCTCTTGGCCGTCGTGCTGACAGTGGCCTTC<br>ATCACCTTTAAATGTTGTGCTTATGGCTACCGGAAATGCTTGGGGAAAAAAGGGCGAGTTAA<br>GAAAGCCCACAAATC |
| 881 | UGT1A3 | 2533130 | GTACCAGTACCATTCCTTGGACGTGATTGGTTTCCTCTTGGCCGTCGTGCTGACAGTGGCCTTC<br>ATCACCTTTAAATGTTGTGCTTATGGCTACCGGAAATGCTTGGGGAAAAAAGGGCGAGTTAA<br>GAAAGCCCACAAATC |

TABLE 13-continued

Subtyping Target Sequences

| SEQ ID NO. | Gene | Affy Probeset ID | Sequence |
|---|---|---|---|
| 882 | UGT1A1 | 2533130 | GTACCAGTACCATTCCTTGGACGTGATTGGTTTCCTCTTGGCCGTCGTGCTGACAGTGGCCTTC ATCACCTTTAAATGTTGTGCTTATGGCTACCGGAAATGCTTGGGGAAAAAAGGGCGAGTTAA GAAAGCCCACAAATC |
| 883 | UGT1A8 | 2533131 | AAATTTTGAACCATTCCCTAGTCATTTCCAAACTTGAAAACAGAATCAGTGTTAAATTCATTTT ATTCTTATTAAGGAAATACTTTGCATAAATTAATCAGCCCC |
| 884 | UGT1A10 | 2533131 | AAATTTTGAACCATTCCCTAGTCATTTCCAAACTTGAAAACAGAATCAGTGTTAAATTCATTTT ATTCTTATTAAGGAAATACTTTGCATAAATTAATCAGCCCC |
| 885 | UGT1A9 | 2533131 | AAATTTTGAACCATTCCCTAGTCATTTCCAAACTTGAAAACAGAATCAGTGTTAAATTCATTTT ATTCTTATTAAGGAAATACTTTGCATAAATTAATCAGCCCC |
| 886 | UGT1A5 | 2533131 | AAATTTTGAACCATTCCCTAGTCATTTCCAAACTTGAAAACAGAATCAGTGTTAAATTCATTTT ATTCTTATTAAGGAAATACTTTGCATAAATTAATCAGCCCC |
| 887 | UGT1A4 | 2533131 | AAATTTTGAACCATTCCCTAGTCATTTCCAAACTTGAAAACAGAATCAGTGTTAAATTCATTTT ATTCTTATTAAGGAAATACTTTGCATAAATTAATCAGCCCC |
| 888 | UGT1A3 | 2533131 | AAATTTTGAACCATTCCCTAGTCATTTCCAAACTTGAAAACAGAATCAGTGTTAAATTCATTTT ATTCTTATTAAGGAAATACTTTGCATAAATTAATCAGCCCC |
| 889 | UGT1A1 | 2533131 | AAATTTTGAACCATTCCCTAGTCATTTCCAAACTTGAAAACAGAATCAGTGTTAAATTCATTTT ATTCTTATTAAGGAAATACTTTGCATAAATTAATCAGCCCC |
| 890 | UGT1A8 | 2533132 | CAGACAGGCTGGCATTCTAGATTACTTTTCTTACTCTGAAACATGGCCTGTTTGGGAGTGCGG GATTCAAAGGTGGTCCCACGGCTGCCCCTACTGCAAATGGCAGTTTTAATCTTATCTTTTGGCT TCTGCAGATGGTTGCAATTGATCCTTAACCAATAATGGTCAGTCCTCATCTCTGTCGTGCTTCA TAGGTGCCACCTTGTGTGTTTAAAGAAGGGAAGCTTTGTACCTTTAGAGTGTA |
| 891 | UGT1A10 | 2533132 | CAGACAGGCTGGCATTCTAGATTACTTTTCTTACTCTGAAACATGGCCTGTTTGGGAGTGCGG GATTCAAAGGTGGTCCCACGGCTGCCCCTACTGCAAATGGCAGTTTTAATCTTATCTTTTGGCT TCTGCAGATGGTTGCAATTGATCCTTAACCAATAATGGTCAGTCCTCATCTCTGTCGTGCTTCA TAGGTGCCACCTTGTGTGTTTAAAGAAGGGAAGCTTTGTACCTTTAGAGTGTA |
| 892 | UGT1A9 | 2533132 | CAGACAGGCTGGCATTCTAGATTACTTTTCTTACTCTGAAACATGGCCTGTTTGGGAGTGCGG GATTCAAAGGTGGTCCCACGGCTGCCCCTACTGCAAATGGCAGTTTTAATCTTATCTTTTGGCT TCTGCAGATGGTTGCAATTGATCCTTAACCAATAATGGTCAGTCCTCATCTCTGTCGTGCTTCA TAGGTGCCACCTTGTGTGTTTAAAGAAGGGAAGCTTTGTACCTTTAGAGTGTA |
| 893 | UGT1A5 | 2533132 | CAGACAGGCTGGCATTCTAGATTACTTTTCTTACTCTGAAACATGGCCTGTTTGGGAGTGCGG GATTCAAAGGTGGTCCCACGGCTGCCCCTACTGCAAATGGCAGTTTTAATCTTATCTTTTGGCT TCTGCAGATGGTTGCAATTGATCCTTAACCAATAATGGTCAGTCCTCATCTCTGTCGTGCTTCA TAGGTGCCACCTTGTGTGTTTAAAGAAGGGAAGCTTTGTACCTTTAGAGTGTA |
| 894 | UGT1A4 | 2533132 | CAGACAGGCTGGCATTCTAGATTACTTTTCTTACTCTGAAACATGGCCTGTTTGGGAGTGCGG GATTCAAAGGTGGTCCCACGGCTGCCCCTACTGCAAATGGCAGTTTTAATCTTATCTTTTGGCT TCTGCAGATGGTTGCAATTGATCCTTAACCAATAATGGTCAGTCCTCATCTCTGTCGTGCTTCA TAGGTGCCACCTTGTGTGTTTAAAGAAGGGAAGCTTTGTACCTTTAGAGTGTA |
| 895 | UGT1A3 | 2533132 | CAGACAGGCTGGCATTCTAGATTACTTTTCTTACTCTGAAACATGGCCTGTTTGGGAGTGCGG GATTCAAAGGTGGTCCCACGGCTGCCCCTACTGCAAATGGCAGTTTTAATCTTATCTTTTGGCT TCTGCAGATGGTTGCAATTGATCCTTAACCAATAATGGTCAGTCCTCATCTCTGTCGTGCTTCA TAGGTGCCACCTTGTGTGTTTAAAGAAGGGAAGCTTTGTACCTTTAGAGTGTA |
| 896 | UGT1A1 | 2533132 | CAGACAGGCTGGCATTCTAGATTACTTTTCTTACTCTGAAACATGGCCTGTTTGGGAGTGCGG GATTCAAAGGTGGTCCCACGGCTGCCCCTACTGCAAATGGCAGTTTTAATCTTATCTTTTGGCT TCTGCAGATGGTTGCAATTGATCCTTAACCAATAATGGTCAGTCCTCATCTCTGTCGTGCTTCA TAGGTGCCACCTTGTGTGTTTAAAGAAGGGAAGCTTTGTACCTTTAGAGTGTA |
| 897 | TWIST2 | 2535028 | AGTCAGCCTGGAATTCTTACTTTCACGCCGCTATTCTTTTCCTTTCTCCGTGATTGCTTGGCTAG CCATTTAAAAAAAATATTCTCTGTTCAGTGTATATGTTGCTTGTTTGTTTTATTTATTGAGATA TTTTTACAAGCTAAGTGACTGCAGTG |
| 898 | EFEMP1 | 2554034 | TCTAAACCACATTGGAACTGACCTGAAGAAGCAAACTCGGAAAATATAATAACATCCCTGAAT TCAGGACTTCCACAAGATGCAGAACAAATGGATAAAAGGTATTTCACTGGAGAAGTTTTAAT TTCTAAGTAAAATTTAAATCCTAACACTTCACTAATTTATAACTAAAATTTCTCATCTTCGTACTT GATGCTCACAGAGGAAGAAAATGATGATGGTTTTTATTCCTGGCATCCAGAGTGACAGTGAA CTTAAGCAAATTACCCTCCTACCCAATTCTATGG |
| 899 | EFEMP1 | 2554035 | TATTTTCATATCCAGCCTAAAGGTGGTTGTTTATTATATAGTAATAAATCATTGCTGTA |

TABLE 13-continued

Subtyping Target Sequences

| SEQ ID NO. | Gene | Affy Probeset ID | Sequence |
|---|---|---|---|
| 900 | EFEMP1 | 2554036 | TCTTTTCTAAGAGTCAACCACAGGCATTTAAGTCAGCCAAAGAATATTGTTACCTTAAAGCACT<br>ATTTTATTTATAGATATATCTAGTGCATCTACATCTCTATACTGTACACTCACCCATAATTCAAA<br>CAATTACACCATGGTATAAAGTGGGCATTTAATATGTAAAGATTCAAAGTTTGTCTTTATTACT<br>ATATGTAAATTAGACATTAATCCACTAAACTGGTCTTCTTCAAGAGAGCTAAGTATACACTATC<br>TGGTGAAACTTGGATTCTTTCCTATAAAAGTGGGACCAAGCAATGATGATCTTCTGTGGTGCT<br>TAAGGAAACTTACTA |
| 901 | EFEMP1 | 2554037 | TGCAATGCTTGTGCTCGTGAAGTCATTATCAGGACCAAGAGAACATATCGTGGACCTGGAGA<br>TGCTGACAGTCAGCAGTATAGGGACCTTCCGCACAAGCTCTGTGTTA |
| 902 | EFEMP1 | 2554040 | ACAAATACATGAGCATCCGATCTGATAGGTCTGTGCCATCAGACATCTTCCAGATACAGGCCA<br>CAACTATTTATGCCAACACCATCAATACTTTTCGGATTAAATCTGGA |
| 903 | EFEMP1 | 2554041 | ACCACAAATGAATGCCGGGAGGATGAAATGTGTTGGAATTATCATGGCGGCTTCCGTTGTTA<br>TCCACGAAATCCTTGTCAAGATC |
| 904 | EFEMP1 | 2554042 | GAACCTCAAGCTACCTGTGTCAATATCAATGTGTCAATGAACCTGGGAAATTCTCATGTATGT<br>GCCCCCAGGGATACCAAGTGGTGAGAAGTAGAACATG |
| 905 | EFEMP1 | 2554045 | GTGCTACAACATTCTTGGTTCATTCATCTGTCAGTGCAATCAAGGATATGAGCTAAGCAGTGA<br>CAGGCTCAACTGTGAAG |
| 906 | EFEMP1 | 2554046 | TGAATGTACCATCCCTCCATATTGCCACCAAAGATGCGTGAATACACCAGGCTCATTTTATTGC<br>CAGTGCAGTCCTGGGTTTCAATTGGCAGCAAACAACTATACCTGCGTA |
| 907 | EFEMP1 | 2554047 | CATAGACGAGTGCACTGCAGGGACGCACAACTGTAGAGCAGACCAAGTGTGCATCAATTTAC<br>GGGGATCCTTTGCATGTCAGTG |
| 908 | EFEMP1 | 2554056 | CTGCTGCAGTCGCAGGCCCTGAAATGCAGACTGGCCGAAATAACTTTGTCATCCGGCGGAAC<br>CCAGCTGACCCTCAGCGCATTCCCTCCAACCCTTCCCACCGTATCCAGTGTGCAGCAGGCTAC<br>GAGCAAA |
| 909 | EFEMP1 | 2554057 | GCAACCACCGGGGTTGTAGCTGCCAGCAGC |
| 910 | EFEMP1 | 2554058 | GTGACATTGTCCCAGACGCTTGTAAAGGTGGAATGAAGTGTGTCAACCACTATGGAGGATAC<br>CTCTGCCTTCCGAAAACAGCCCAGATTATTGTCAATAATGAACAGCCTCAGCA |
| 911 | EFEMP1 | 2554059 | AATGCACTGACGGATATGAGTGGGATCCTGTGAGACAGC |
| 912 | EFEMP1 | 2554062 | CGGTTCAGCGGGATTCTGTGACAAAAAAAGACTTTACACACCCCTGCCAGTGTATTTGGGCTA<br>TACTCTGCTGAGGGTGATAAATTAAACAACACTTCATTCATGCTTCATATCTAAGATTCGTTGT<br>AAAATTGCCCCCTTGATCCTTTCAAAAGTTCATTGGGCTCACCACCTAAGATAGGAACCAACAT<br>GTAATCATTTGTGCAGGGCTAAAAATGGGATCCGTTCA |
| 913 | EFEMP1 | 2554063 | ACACCGAAGAAACCATCACGTACACG |
| 914 | EFEMP1 | 2554064 | TGCAGCCTGCTTTGTAGGTGCAGTATAAAATGCACGCTGAATGTCTTTTGTATGTAAACAGCG<br>TAGCAGGATGGAGTAACGTGAAATGCAATTCTACAGCAGTTTTTACGTCTTTGCTGCCTCGTT<br>CGTTGGCTACCGAGAAGGTTCAGGAGGGGAGGGGAGATGAGAAAGCAGATTGGAAGTTG<br>AGTATGGTGGAGCCTCAGCCTCTCCCACCCTCCTTTCCTCGCTTGTGCTCACTGCTAAAG |
| 915 | EFEMP1 | 2554067 | CGCTGCCGGACTTCGCCAGATCAGACCCACGGGGCTGCCCTC |
| 916 | MALL | 2570194 | TTGAGGCCTTACAGTTTTGTATCTACATTTTTCCCTCCTGGGGTTTGCGGGGACAGGGACAG<br>AACTACAGGAGTCATGGGAAAGAAAATTCTGGCTTCACTACTGCTCACTGCTCACTTTCTGAT<br>CACTCTGATACTTTTTTTTTTTTTTTTTTTTGCAACCTGATACCTTGAAAAGCTTCTATGTGTC<br>TCTCCTTTTGTTGCCTGGCAGCTGTCTAGGATGATCACTGATTACTATTTACTAAGTAGCCACA<br>TGC |
| 917 | MALL | 2570195 | GACTGAGCGATGACACCACACTTTGTTTGGACATTTAAATTCACTCTGCTGAATAGGAGGAAG<br>CTTTTCTTTTTCCTGGGAAAACAACTGTCTCTTGGAATTATCTGACCATGAACTTGCTCTTCTAG<br>ACAACTCACATCAAAGCCCTCACTCCACTAATGGAGAATCCTAGCCCCACTAATGCCAAGTCT<br>GTTTGGGATTTTGCCTCAGCTATGGGCTTCCTAGAGTAGGTCTAGGGGAATACTCAGTCTG<br>ATCTTTTTTTGTTTGTTTTATTTTGTTTTTTTGAGACGGAGTCTCGCTCTTCCTCCAAGGCTGG<br>AGTGCAGTGACGCGATCTCCACTCACTGCAGGCTCCGCCTCCCGGGTTCCCGCCATTCTCCTG<br>CCTCAGCCTCCCGAGTAGCCGGGACTACAGGCGCCCACCACCGTGCCCGGCTAATTTAGTTGT<br>ATTTTTAGTAGAGATGGGGTTTCACCGTATTAGCCAGGATGGTCTCGATCTCCTGACCTCGTG<br>ATCCGCCCGCCTCGGCCTCCCAAAGTGCTGGGATTACAGGCGTGAGCCACCGCGCCCGGCCT<br>GATTCTCTTAAAATTGAAGAGGTGCTGCCAAGGCCTTCAGATCTAACGCAGATGCATAGACCT<br>TGTTCCTGGTACTTGTTCAGCCTGTGCTGGGGAGCCGTGGTCCCGAGTTCCCTGGGAGGCTG<br>ACAGGGTCAAGCCACCCTGCCCACCACCCTCCCACTTCCCCTCCCCTTTCCTCTCCAGCATTAG<br>GATTCAAGGGAAATTTGCATGAAGCCAATTTTGAGGGTAGACGTGTGGGGAAAATAAATCAT<br>TATACAGTAAGACCTGGGGCTTGAGGGGTGGGGAATGGGAGGGAAGGGCATAGCCTGCT<br>CCTCCATGAGTCTGACATCTCGGAAACTGAGCAGCTGCCGGACGCCTGGGTCAGGAATCCAA |

TABLE 13-continued

Subtyping Target Sequences

| SEQ ID NO. | Gene | Affy Probeset ID | Sequence |
|---|---|---|---|
| | | | GACCCCACCTCTTAAGGACTGGTTCCTCAGAAAGCACCCTCAGGGAAAAAGGTGAAAACATT ACATCCGTGGATTCTCCTGCCACAACCGCATTGGAAGAAAAGGCTGCCGCAACATCTCAGCGA GGAGTGAAGGACCCATGTCCCAGGAACCGCGCTGCGCCACCTGCACTCACCCCCCTCACATTC TCTTAAGCACCCGGTGCCCTCCGAGGCCTGGCGGAATGGTGGTGCCCACGGGGTTGGGCA AGGGCTCACCAGGACCTCAACGGGCAAGTTGTGCACACTAAAATATCAAATCAAGGTGCTT GGTTTTAAAGTAAATGTTTTTCTAAAGAAAGCTGTGCTCTTCTGTTGACCCAGACGAATAGGG CACAGCCCTGTAACTGCACGTGCCTTCTG |
| 918 | MALL | 2570197 | TCCTGTACATGAGCGCTGCCGTCCTACAAGTACATGCCACGATTGTTTCTGAGAAACTGCTGG ACCCAAGAATTTACTACATTAATTCGGCAGCCTCG |
| 919 | MALL | 2570200 | ATGGTAGCCGCCACCCACATAGTATACCCCTTGCTGCAA |
| 920 | MALL | 2570204 | CCGCCACCAGCTACGCCCCGTCCGACGTGCCCTCGGGGGTCGCGCTGTTCCTCACCATCCCT |
| 921 | MALL | 2570205 | CTGTCTGCAGATAGCTTGGCTCATTGTTGGTCCTCAGTACGCAGCCCTCGTAGCCAAGCAGCT TGGGCCTACACTCTGGGCCCAGGGGAGTGGCTGTCGCTGGCATCCCCTGGAATAACATGCTC CGGGGGTCAAAGATTCCTTAGCTGGAAAGGTCTAGGAGGAGACTCCCGCTCTGCTCCCTCCT GCACCAGCGCTGTGCCCCCGCCGGCCAGGCAGAGCCATCCGATGCCGCTGGGCCGCCCACT GAGGATCTGCTGGCTGCAGCGAGTGGAAGGACCTGCTCGGCTGGAACGTTTTTTTTTTTTC CCTCCCAGGCGACGTCCGATGGGTGTGTCGGGCAGGAGGTGATATTTGACAGGCTGCGCGC |
| 922 | MALL | 2570235 | ATGAGGGGCTTCCAGCTGCTCTGTGCAG |
| 923 | FN1 | 2598262 | CCTGCAAGGGAAATAAAAATGACTAAGATATTA |
| 924 | FN1 | 2598263 | TAAAATTGCTAGTTTACCGTTCAGAAGTATAATAGAAATAATCTTTAGTTGCTCTTTTCTAACC ATTGTAATTCTTCCCTTCTTCCCTCCACCTTTCCTTCATTGAATAAACCTCTGTTCAAAGA |
| 925 | FN1 | 2598264 | TTTGATATAAGACACCTTCGGGGGAAATAATTCCTGTGAATATTCTTTTTCAATTCAGCAAACA TTTGAAAATCTATGATGTGCAAGTCTAATTGTTGATTTCAGTACAAGATTTTCTAAATCAGTTG CTACAAAAACTG |
| 926 | FN1 | 2598265 | ACTTAGTATGCAGTTGATAAGAGGAATTTGGTATAATTATGGTGGGTGATTATTTTTATACTG TATGTGCCAAAGCTTTAC |
| 927 | FN1 | 2598266 | TTGGGATCAATAGGAAAGCATATGCAGCCAACCAAGATGCAAATGTTTTGAAATGATATGAC CAAAATTTTAAGTAGGAAAGTCACCCAAACACTTCTGCTTTCACTTAAGTGTCTGGCCCGCAAT ACTGTAGGAACAAGCATGATCTTGTTACTGTGATATTTTAAATATCCACAGTACTCACTTTTTC CAAATGATCCTAGTAATTGCCTA |
| 928 | FN1 | 2598267 | GTTCTGCTTCGAAGTATTCAATACCGCTCAGTATT |
| 929 | FN1 | 2598268 | TGTTAGCAGACCCAGCTTAGAGTTCTT |
| 930 | FN1 | 2598269 | TCTCTGCCAAGATCCATCTAAACTGGAGTGA |
| 931 | FN1 | 2598270 | CTGACAGAGAAGATTCCCGAGAGTAA |
| 932 | FN1 | 2598271 | TGTTAATTGCCCAATTGAGTGCTTCATGCCTT |
| 933 | FN1 | 2598273 | GCTGTGACAACTGCCGCAGACCTGGGGGTGAACCCAGTCCCGAAGGCACTACTGGCCAGTCC TACAACCAGTATTC |
| 934 | FN1 | 2598274 | CTGACCTCCATGAGCTTGCTTTACCCCCTGCCAGCTTAAGAACAGTAGTGAAAGAGAACATGT GTGTCCTCCCATTTCCAGTAAAAACTTCAGGCAGGAGCCTCACTGGCTCAGCTTGGTCCCGTTT CCATCTCCCATGCCATCTCCGGCCAGGTGACAGGCTAC |
| 935 | FN1 | 2598275 | GCCAGGCTCCCTACAAGTTAGATAAGATAAAGGGTGGGCTCCTGCAAGGATGTGTCGTACAC ACAGGAGGGGCAGAGACCCTTCGGAAGTATTAAAATACCACATTTCCTGTTGGCATACAACT GCTGACATAGAGCTCTAGAGCAGCTCTATGTCTACCTTACATGCCATTCATTCTTTCTATTACTC TTAGTAGAAAGAATGAATGAATGGCATGTAGAGTACCAAAAACACAAGTCTTGAGTCATTCTT AATAGCAACACCTGTCATTTATATGATGTTAGAATCATTTTCCTAAGCTCCCTAGCATGTCAGA GATACTA |
| 936 | FN1 | 2598276 | TGATGGGAAGACATACCACGTAGGAGAACAGTGGCAGAAGGAATATCTCGGTGCCATTTGCT CCTGCACATGCTTTGGA |
| 937 | FN1 | 2598277 | GATGGTGCCATGACAATGGTGTGAACTA |
| 938 | FN1 | 2598280 | AAACTGTTGTGCCAGTGCTTAGGCTTTGGAAGTGGTCA |
| 939 | FN1 | 2598284 | CACTCTGACAGGCCTCACCAGAGGTGCCACCTACAACGTCATAGTGGAGGCACTGAAAGACC AGCAGAGGCATAAGGTTCGGGAAGAGGTTGTTACCGTGGGCAACTCTG |

TABLE 13-continued

Subtyping Target Sequences

| SEQ ID NO. | Gene | Affy Probeset ID | Sequence |
|---|---|---|---|
| 940 | FN1 | 2598286 | CAAGAAGCTCTCTCTCAGACAACCATCTCATGGGCCCCATTCCAGGACACTTCTGAGTACATC<br>ATTT |
| 941 | FN1 | 2598287 | AGGAAATCCAAATTGGTCACATCCCCAGGGAAGATGTAGACTATCACCTGTACCCACACGGTC<br>CGGGACTCAATCCAAA |
| 942 | FN1 | 2598288 | CACCCACCCTGGGTATGACACTGGAAATGGTATTCAGCTTCCTGGCACTTCTGGTCAGCAACC<br>CAGTGTTGGGCAACAAATGATCTTTGAGGAACATGGTTTTAGGCGGACCACACCGCCCACAA<br>CGGCCACCCCCATAAGGCATAGGCCAAGACCATACCCGC |
| 943 | FN1 | 2598289 | CTTCATGGACCAGAGATCTTGGATGTTCCTTCCA |
| 944 | FN1 | 2598290 | CCGGGAACCGAATATACAATTTATGTCATTGCCCTGAAGAATAATCAGAAGAGCGAGCCCCT<br>GATTGGAAGGAAAA |
| 945 | FN1 | 2598294 | CACACCCAATTCCTTGCTGGTATCATGGCAGCCGCCACGTGCCAGGATTACCGGCTACATCAT<br>CAAG |
| 946 | FN1 | 2598296 | TTACAACCAGGCACTGACTACAAGATCTACCTGTACACCTTGAATGACAATGCTCGGAGCTCC<br>CCTGTGGTCATCGACGCCTCCACTG |
| 947 | FN1 | 2598299 | CAAGAAGGGCTCGTGTGACAGATGCTACTGAGACCACCATCACCATTAGCTGGAGAACCAAG<br>ACTGAGACGATCACTGGCTTCCAAGTTGATGCCGTTCCAGCCA |
| 948 | FN1 | 2598301 | GTGAGTGTCTATGCTCTTAAGGACACTTTGACAAGCAGACCAGCTCAGGGAGTTGTCACCACT<br>CT |
| 949 | FN1 | 2598302 | CTATTCCTGCACCAACTGACCTGAAGTTCACTCAGGTCACACCCACAAGCCTGAGCGCCCAGT<br>GGACACCACCCAATGTTCAGCTCACTGGATATCGAGTGCGGGTGACCCCCAAGGAGAAGACC<br>GGACCAATGAAAGAAATCAACCTTGCTCCTGACAGCTCATCCGTGGTTGTATCAGG |
| 950 | FN1 | 2598303 | CAAACTCGGGCATTTCATAGCAGCATGATTCTGAGCACACGTGGGTAAGACCTTTCTTCTCTG<br>GTTAGATATCATATGCTGGTGTATAATTAGCTTAAATGATTGTGATTTAGCACCTAGGAAAT<br>AATCAATAGGGCAATTGCTTTCCATAATACTTTATCTTCTTGTGCTTTATTTCTGAAGCAGAGTA<br>GAATGCTAAAGATGTATCCTAGTGACAGCATAAACCCTAGAGGTGACAGTCTGTATTATTGCT<br>TTTCGCTTCTCTTTTCTGCTTCTGTTGGGAGCCAGTTTTCTTCTTACGCCGCATTACAGAGAGAA<br>CGTCAAATTTAGCAGCCATATCTGCCATAGGGTCCAAATAAAGAGACAATAAAAACATTATTC<br>TCTCTTTTTTGGATGGAATACTGCGTGAAATGGTTATCCATACAAAGATACTTTATGTAGAATA<br>GAAAAAGGAGGCCGGGTGCAGTGGCTCACACATGTAATCCTAGTGCTTTGGGAGGCTAAGC<br>CGGGAGCACTGATTGAGGCCAGGAGTTCATGATCAGCCTGGGCAATGAAGTGAGACCCCGT<br>CTCTACAAAAAAATATGAAAAAATTAGCGAGGTGTGGTGACACATGCCTGTAGTCCCAGCTAC<br>TCAAGAGGCTGAGGTAGAGGATCACTTGAGCCTACGAGTTCAAGGCTGCAGTGAGCTATGAT<br>AACTCCACTGCACTGCCGCCTGGATGACACAGAGAGACCGTTTCTAAATTAATTAATTAACAA<br>TTTTAAGAAAGAAAAAGGGCCATTGCTTATTTTTCCATACAAAAGTAAAATAAATCATAATGG<br>CCAATAAGCCAATGTAACTTTTTTTTTTAAGGGAAAGCAAAACTTGTAAAACCTAAAATCTCTT<br>AGAGTTTTGGCATTTACCCAAATGTTTTCAGTGATTCTGAGAATTGGTGGATATAAAACACATT<br>TCTCAGCAAACACTTTCTTCATTTTGCATCCCTTACTGTACGTACTTTCTTGTACTGAATCTTTGC<br>TTGACCAGGGAACC |
| 951 | FN1 | 2598304 | TGATCGCCCTAAAGGACTGGCATTCACTGATGTGGATGTCGATTCCATCAAAATTGCTTGGGA<br>AAGCCCACAGGGGCAAGTTTCCAGGTACAGGGTGACCTACTCGAGCCCTGAGGATGGAATCC<br>ATGAGCTATTCCCTGCACCTGATGGTGAAGAAGACACTGCAGAGCTGCAAGGCCTCAGACCG<br>GGTTCTGAGTACACAGTCAGTGTGGTTGCCTTGCACGATGATATGGAGAGCCAGCC |
| 952 | FN1 | 2598305 | GTCTGAATGCCCACGACATGTCTTTTGCAATTACACATAGGGAAAGTGAACTTGTTGGTTAGT<br>TTATGTCTTGAGCTGAGCCCTTTACGAACATCTTTTTTCCTTCTCAGTGCCAAGCGAGGAATTT<br>ACAGAGAAAGAAGTTGTGAAACCACCATAGTTAGTTGCTGTGCTTTGAATTTCTTTTGCTCAA<br>ATGGCCTCAGCGAAATCTTATTTGC |
| 953 | FN1 | 2598306 | GCCCACAGTGGAGTATGTGGTTAGTGTCTATGCTCAGAATCCAAGCGGAGAGAGTCAGCCTCT |
| 954 | FN1 | 2598307 | TTGACAAACCATCCCAGATGCAAGTGACCGATGTTCAGGACAACAGCATTAGTGTCAAGTGG<br>CTGCCTTCAAGTTCCCCTGTTACTGGTTACAGAGTAACCACCACTCCCAAAAATGGACCAGGA<br>CCAACA |
| 955 | FN1 | 2598308 | TGGGAGCAAGTCTACAGCTACCATCAGCGGCCTTAAACCTGGAGTTGATTATACCATCACTGT<br>GTATGCT |
| 956 | FN1 | 2598309 | TCTGTTGTGGATAACCTGAAAGCCCAACAGTGAACAAAGAATTAAAGAAACTTTGGCAAGTC<br>CATTCAACGGAGCCCTTGTTTTTTCCAAGAAAATACGTAAGATATAGATGATATAATTTGTTCT<br>AAAACCCAAATAAAAAGTTGTTTATATACTACAACTAGAGGGGGAACGGCAGAGCTGAGGAA<br>ATAAAAGGATTGTAAATTCACAAACATATTATCAGTGGTGGAAATAAGTGATTTTTATTTTTC<br>TTCTCTTTACTTTTCTGTATTTTCCAAATTTTATTTAAAAGGAATGTATTCTGTTAAAAGTTTTAA |

TABLE 13-continued

Subtyping Target Sequences

| SEQ ID NO. | Gene | Affy Probeset ID | Sequence |
|---|---|---|---|
| | | | AAAGGACACAATGCATGCAATCCTGGGTTGAGGGCTTACCTTCTCCCACTTCTAATGCTACTCT ACTACTCAGTGACATTTTAAAGCTGAAATGTTAAAACAGCGCTAACTGTAATTTTCTCTCAATG TTTATACACTTACCAAGGTTTGCTACATGCATA |
| 957 | FN1 | 2598310 | GGACCTGGAAGTTGTTGCTGCGACCCCCACCAGCCTACTGATCAGCTGGGATGCTCCTGCTGT CACAGTGAGATATTACAGGATCACTTACGGAGA |
| 958 | FN1 | 2598313 | CCAACTGGCATTGACTTTTCTGATATTACTGCCAACTCTTTTACTGTGCACTGGATTGCTCCTCG AGCCACCATCACTGGCTACAGGATCCGCCATCATCCCGAGCACTTCAGTGGGAGACCTCGAG AAGATCGGGTGCCCCACTCTCGGAATTCCATCACCCTCACCAACCTCACTCCAGGCACAGAGT ATGTGGTCAGCATCGTTGCTCTTAATGGCAGA |
| 959 | FN1 | 2598314 | CAGAATATGTAGTGAGTGTCTCCAGTGTCTACGAACAACATGAGAGCACACCTCTTAGAGGA AG |
| 960 | FN1 | 2598318 | CTGACCTGCGATTCACCAACATTGGTCCAGACACCATGCGTGTCACCTGGGCTCCACCCCCAT CCATTGATTTAACCAACTTCCTGGTGCGTTACTCACCTGTGAAAAATGAGGAAGATGTTGCAG AGTTGTCAATTTCTCCTTCAGACAATGCAGTGGTCTTAACAA |
| 961 | FN1 | 2598319 | TCACTGAATGGAACTGTAGCTCTAGATATCTCACATGGGGGAAGTTTAGGACCCTCTTGTCT TTTTGTCTGTGTGCATGTATTTCTTTGTAAAGTACTGCTATGTTTCTCTTTGCTGTGTGGCAACT TAAGCCTCTTCGGCCTGGGATAAAATAATCTG |
| 962 | FN1 | 2598320 | ACATAGATGGTGTTGCATGCTGCCACCAGTTACTCCGGTTAAATATGGATGTTTCATGGGGGA AGTCAGCAATTGGCCAAAGATTCAGATAGGGTGGATTGGGGGGATAAGGAATCAAATGCAT CTGCTAAACTGATTGGAGAAAAACACATGCAAGTATTCTTCAGTACACTCTCATTTAAACCACA AGTAGATATAAAGCTAGAGAAATACAGATGTCTGCTCTGTTTAAATATAAAATAGCAAATGTTC ATTCAATTTGAAGACCTAGAATTTTTCGTCTTAAATACCAAACACGAATACCAAATTGCGTAAG TACCAATTAATTATAAGAAATATATCACCAAAATGTACCATCATGATCTTCCTTCTACCCTTTGA TAAACTCTACCATGCTCCTTCTTTGTAGCTAAAAACCCATCAAAATTTAGGGTAGAGTGGATG GGCATTGTTTTGAGGTAGGAGAAAAGTAAACTTGGGAGCATTCTAGGTTTTGTTGCTGTCACT AGGTAAAGAAACACCTCTTTAACCACAGTCTGGGGACAAGCATGCAACATTTT |
| 963 | FN1 | 2598321 | TTGGGTACCGCATCACAGTAGTTGCGGCAGGAGAAGGTATCCCTATTTTTGAAGATTTTGTGG ACTCCTCAGTAGGATACTACACAGTCACAGGGCTGGAGCCGGGCATTGACTATGATATCAGC GTTATCACTCTCATTAATGGCGG |
| 964 | FN1 | 2598322 | CTTCAGATATTATGTCTAGGCTCTAAGAATGGTTTTGACATCCTAAACAGCCATATGATTTTTA GGAATCTGAACAGTTCAAATTGTACCCTTTAAGGATGTTTTCAAAATGTAAAAAATATATATAT ATATATATTCCCTAAAAGAATATTCCTGTTTATTCTTCTAGGGAAGCAAACTGTTCATGATGCT TAGGAAGTCTT |
| 965 | FN1 | 2598324 | GTGTCCCTATCTCTGATACCATCATCCCAG |
| 966 | FN1 | 2598325 | CCTACAAACGGCCAGCAGGGAAATTCTTTGGAAGAAGTGGTCCATGCTGATCAGAGCTCCTG CACTTTTGATAACCTGAGTCCCGGCCTGGAGTACAATGTCAGTGTTTACACTGTCAAGGATGAC |
| 967 | FN1 | 2598328 | GCAAACCCTGACACTGGAGTGCTCAC |
| 968 | FN1 | 2598330 | GAGGCACCACGAGAAGTGACTTCAGACTCAGGAAGCATCGTTGTGTCCGGCTTGACTCCAGG AGTAGAATACGTCTACACCATCCAAGTCCTGAGAGATGGACAGGAAAGAGATGCGCCAATTG TAAACAAAGT |
| 969 | FN1 | 2598331 | TCTATTCCACCTTACAACACCGAGGTGACTGAGACCACCATTGTGATCACATGGACGCCTGCT CCAAGAATTGGTTTTA |
| 970 | FN1 | 2598334 | GAAACTGATTCTACTGTCCTGGTGAGATGGACTCCACCTCGGGCCCAGATAACAGGATACCG ACTGACCGTGGGCCTTACCCGAAGAGGACAGCCCAGGCAGTACAATGTGGGTCCCTCTGTCT CCAAGTACCCACTGAGGAATCTGCAGCCTGCATCTGAGTACACCGTATCCCTCGTGGCCATAAA |
| 971 | FN1 | 2598338 | GACAGACGTGAAGGTCACCATCATGTGGACACCGCCTGAGAGTGCAGTGACCGGCTACCGTG TGGATGTGATCCCCGTCAACCTGCCTGGCGAGCACGGGCAGAGGCTGCCCATCAGCAGGAAC ACCTTTGCAGAAGTCACCGGGCTGTC |
| 972 | FN1 | 2598339 | TATTCGCCATCAGTAGAAGGTAGCAGCACAGAACTCAACCTTCCTGAAACTGCAAACTCCGTC ACCCTCAGTGACTTGCAACCTGGTGTTCAGTATAACATCACTA |
| 973 | FN1 | 2598340 | TGATGCCCCTCCTGACACGACTGTGGACCAAGTTGATGACACCTCAATTGTTGTTCGCTGGAG CA |
| 974 | FN1 | 2598342 | TCCAAGCACAGCCACTTCTGTGAACATCCCTGACCTGCTTCCTGGCCGAAAATACATTGTAAAT GTCTATCAGATATCTGAGGATGGGGA |

TABLE 13-continued

Subtyping Target Sequences

| SEQ ID NO. | Gene | Affy Probeset ID | Sequence |
|---|---|---|---|
| 975 | FN1 | 2598344 | ACAGGAGAGACGACTCCCTTTTCTCCTCTTGTGGCCACTTCTGAATCTGTGACCGAAATCACA GCCAGTAGCTTTGTGGTCTCCTGGGTCTCAGCTTCCGACACCGTGTCGGGATTCCGGGTGGAA TATGAGCTGAGT |
| 976 | FN1 | 2598345 | AGGCTCTCCTGAGGCAATGCTTTCCTTCTCAATTCATATTCTTCCAGGAGGGGCACCAACGTTT TTTAAAATGATGTTGGCGACGAGGACGGTAAATTTTCTAGATGACTGAAGGCTGACTTTCC |
| 977 | FN1 | 2598346 | TGGAAGGAAGCTACCATACCAGGCCACTTAAAACTCCTACACCATCAAAGGCCTGAAGCCTGGT GTGGTATACGAGGGCCAGCTCATCAGCATCCAGCAGTACGGCCACCAAGAAGTGACTCGCTT TGACTTCACCACCA |
| 978 | FN1 | 2598350 | ATCTTATCAATTCTGATGGTTTCTTTTTTTCCCAGCTTTTGAGCCAACAACTCTGATTAACTATTC CTATAGCATTTACTATATTTG |
| 979 | FN1 | 2598351 | GTGAGTATCCCACCCAGAAACCTTGGATACTGA |
| 980 | FN1 | 2598353 | GACGTTTTATCAAATTGGAGATTCATGGGAGAAGTATGTGCATGGTGTCAGATACCAGTGCT ACTGCTATGGCCGTGGCATTGGGGAGTGGCATTGCCAAC |
| 981 | FN1 | 2598354 | TGACATCACTTACAATGTGAACGACACATTCCACAAGCGTCATGAAGAGGGGCACATGCTGA ACTGTACATGCTTCGGTCAGGG |
| 982 | FN1 | 2598355 | GGCTTCTCACAGGAAAGTGTATTTTACCACATTCTTTACTTGAGCATACTGTAACCTCTGCAAA AGTTACACATTTTGGGAAGAAAAAAATTTTTTTGGCAAAAATTGTATTACTGACCAAACTTTGA AAAAAATGTTATTCTATGCTTGTAGAAAAGTTATTTTAGTGGAAGGTGTTGATAATTAAGTGG AAGTAGTTGTATGCTTTGAGAA |
| 983 | FN1 | 2598356 | GGAAATCTGCACAACCAATGAAGGGGTCATGTACCGCATTGGAGATCAGTGGGATAAGCAG CATGACATGGGTCACATGATGAGGTGCACGTGTGTTGGGAATGGTCGTGGGGAATGGACAT GCATTGCCTACTCGCAGCTTCGA |
| 984 | FN1 | 2598357 | CCTTCCTATACAACAACCACAATTACACTGATTGCACTTCTGAGGGCAGAAGAGACAACATGA AGTGGTGTGGGACCACACAGAACTATGATGCCGACCAGAAGTTTGGG |
| 985 | FN1 | 2598358 | CATCTTTGGTGCAGCACAACTTCGAATTATGAGCAGGACCAGAAATACTCTTTCTGCACAGAC CA |
| 986 | FN1 | 2598359 | TGGCAGGACGTTCTACTCCTGCACCACAGAAG |
| 987 | FN1 | 2598360 | CAGACTTACGGTGGCAACTCAAATGGAGAGCCATGTGTCTTACCATTCACCTACAA |
| 988 | FN1 | 2598362 | CCACTGTGTCACAGACAGTGGTGTGGTCTACTCTGTGGGGATGCAGTGGCTGAAGCACAAG GAAATAAGCAAATGCTTTGCACGTGCCTGGGCAACGGAGTCAGCTGCCAAGAGACA |
| 989 | FN1 | 2598363 | TCTGGCCCCTTCACCGATGTTCGTGCAGCTGTTTACCAACCGCAGCCT |
| 990 | FN1 | 2598367 | ATGCAACGATCAGGACACAAGGACATCCTATAGAATTGGAGACACCTGGAGCAAGAAGGAT AATCGAGGAAACCTGCTCCAGTGCATCTGCACAGGCAACGGCCGAGGAGAGTGGAAGTGTG AGAGGCACACCTCTGTGCAGA |
| 991 | FN1 | 2598371 | GACTTCCTATGTGGTCGGAGAAACGTGGGAGAAGCCCTACCAAGGCTGGATGATGGTAGATT GTACTTGCCTGGGAGAAGGCAGCGGACGCATCACTTGCACTTCTAGAA |
| 992 | FN1 | 2598372 | CCATGAAGGGGGTCAGTCCTACAAGATTGGTGACACCTGGAGGAGACCACATGAGACTGGT GGTTACATGTTAGAGTGTGTGTCTTGGTAATGGAAAAGGAGAATGGACCTGCAAGCCCAT AG |
| 993 | FN1 | 2598373 | ACACTTACCGAGTGGGTGACACTTATGAGCGTCCTAAAGACTCCATGATCTGGGACTGTACCT GCATCGGGGCTGGGCGAGGGAGAATAAGCTGTACCATC |
| 994 | FN1 | 2598374 | ATCAACAGTGGGAGCGGAACCTACCTAGGCAATGCGTTGGTTTGTACTTGTTATGGAGGAAGC CGAGGTTTTAACTGCGAGAGTA |
| 995 | FN1 | 2598375 | GAGGCAGGCTCAGCAAATGGTTCAGCCCCAGTCCCCGGTGGCTGTCAGTCAAAG |
| 996 | FN1 | 2598376 | GCGACAACCCCCGGGAGGCATTAGAAGGGATTTTTCCCGCAGGTTGCGAAGGGAAGCAAAC TTGGTGGCAACTTGCCTCCCGGTGCGGGCGTCTCTC |
| 997 | FN1 | 2598377 | GACCGTCCCATATAAGCCCCGGCTCCCGGCGCTCGGACGCCCGCGCCGGCTGTGCTGCA |
| 998 | PPARG | 2611057 | CCTGGGGCGCTTGGGTCGGCCTCGAGGACACCGGAGAGGGGCGCCACGCC |

TABLE 13-continued

Subtyping Target Sequences

| SEQ ID NO. | Gene | Affy Probeset ID | Sequence |
|---|---|---|---|
| 999 | PPARG | 2611059 | AGTCGTGGTACTTTACGCCTCGGTGTTTAGGGAGGAGCCTAAGGTAAGGAGTCAGAAACGG GGAGTAACCGAGCTGCGGCTTTTATATAAGGTCAGTGGTAGGTAAGGAAGGGGCCTTAACCT CTGCTGGTGACCAGAAGCCTGCATTTC |
| 1000 | PPARG | 2611073 | GTGTAGGAAGAATGTTTATTTTTCAG |
| 1001 | PPARG | 2611074 | TTAGAGAAGCAGCAAATAGCGAAGAAA |
| 1002 | PPARG | 2611080 | ACAGCAAACCCCTATTCCATGCTGTT |
| 1003 | PPARG | 2611081 | CTCTGGGAGATTCTCCTATTGACCCAGAAAGCGATTCCTTCACTGATACACTGTCTGCAAACA |
| 1004 | PPARG | 2611086 | CCAACTTTGGGATCAGCTCCGTGGATCTCTCCGTAATGGAAGACCACTCCCACTCCTTTGATAT CAAGCCCTTCACTACTGTTGACTTCTCCAGCATTTCTACTCCACATTACGAAGCATTCCATTCA CAAGAACAGATCCAGTGGTTGCAGATTACAAGTATGA |
| 1005 | PPARG | 2611087 | GTGCAATCAAAGTGGAGCCTGCATCTCCACCTTATTATTCTGAGAAGACTCAGCTCTACAATA AGCCTCATGAAGAGCCTTCCAACTCCCTCATGGCAATTGAATGTCGTGTCTGTGGAGATAAAG CTTCTGGATTTCACTATGGAGTTC |
| 1006 | PPARG | 2611089 | TTTCTTCCGGAGAACAATCAGATTGAAGCTTATCTATGA |
| 1007 | PPARG | 2611090 | GATGTGATCTTAACTGTCGGATCCACAAAAAAAGTAGAAATAAATGTCAGTACTGTCGGTTTC AGAAATGCCTTGCAGTGGGGATGTCTCATAAT |
| 1008 | PPARG | 2611094 | CTGTTGGCGGAGATCTCCAGTGATATCGACCAGCTGAATCCAGAGTCCGCTGACCTCCGGGC CCTGGCAAACATTTGTATGACTCATACATAAAGTCCTTCCCGCTGACCAAAGCAAAG |
| 1009 | PPARG | 2611095 | TAAATGGTTTACTGCGCTACAAATGCACACACAGAATATTGTTCAACTGTTGGCTGTTAACATA TTGCAGGCTGAGTCTGAAACGCAGGAAGTGTTTTCAGATAGCACAAGTCAACATTATTTTGAA AAGGGAGAAAAGTCCATAAAGTTTTTGAGAATAGTGTAACAATGTATTGGTCATCCTAACTTT AATGAATGAACTTAAGCCCCCTGAGCCTATCACCCTCTTTTAGG |
| 1010 | PPARG | 2611101 | TGGAGTCCACGAGATCATTTACACAATGCTGGCCTCCTTGATGAATAAAGATGGGGTTCTCAT ATCCGAGGGCCAAGGCTTCATGACAAGGGAGTTTCTAAAGAGCCTGCGAAAGCCTTTTGGTG ACTTTA |
| 1011 | PPARG | 2611111 | GACAACCTGCTACAAGCCCTGGAGCTCCAGCTGAAGCTGAACCACCCTGAGTCCTCACAGCTG TTTGCCAAGCTGCTCCAGAAAATGACAGACCTCAGACAGATTGTCACGGAACACGTGCAGCT ACTG |
| 1012 | PPARG | 2611112 | GTGATCAAGAAGACGGAGACAGACATGAGTCTTCACCCGCTCCTGCAG |
| 1013 | PPARG | 2611113 | TCCAGTTGCACTATTCTGAGGGAAAATCTGA |
| 1014 | TMEM45A | 2633692 | CCAAAGAAGCGACTAGGGACCCAAGTTTAAAAATTCCTCCCCCCACCCAATGCGAGACGTGG CCAGATCCCATCCAACACACGGTTTAATTTTCATGGGGCTCTGGGATCAAAAGAACAGAAACA GCAACAACAAAAGCCCAGCCGCTGTCTGATTTTAAGCT |
| 1015 | TMEM45A | 2633698 | GAGCATTAAGCAGTATCTCCCAGCATTGTTAGCTACTGAGTGGCACATCTTCAGTACGCATGA TTCGTGGGG |
| 1016 | TMEM45A | 2633699 | AACTTTTCAGCATTACCTAAGAAGCAAAGGC |
| 1017 | TMEM45A | 2633700 | TTCTAACGTGCCTGATCTACTGAGACCAAGGATGACCAATGACTCAGAAG |
| 1018 | TMEM45A | 2633706 | AGAGGTCATGCCCTCCCTGGAACCTTCTTTTTTATTATTGGTCTTTGGTGGTGTACAAAGAGTA TTCTGAAGTATATCTGCAAAAAGCAAAAGCGAACCTGCTATCTTGGTTCCAAAACATTATTCTA TCGATTGGAAATTTTGGAGGGAATTACAATAGTTGGCATGGC |
| 1019 | TMEM45A | 2633707 | TAAACAAGGTCACTGGAATCAACTCCTGGG |
| 1020 | TMEM45A | 2633708 | TTGGGTGTGGCAGATATCTTATGTTTCACCATCAGTTCACTTCCTGTGTCCTTAACCAAGTTAA TGTTGTCAAATGCC |
| 1021 | TMEM45A | 2633710 | ACTCATGGCCGGGAAATGCTGGACATCTTTGTGCACCAGCTGCTGGTTTTGGTCGTCTTTCTG ACAGGCCTCGTTGCCTTCCTAGAGTTCCTTGTTCGGAACAATGTACTTCTGGAGCTATTGCGGT CAAGTCTCATTCTGCTTCAGGGG |
| 1022 | TMEM45A | 2633712 | TTGGATTTGTCCTGTATCCCCCAGTGGAGGTCCTGCATGGGATCTGATGGATCATGAA |
| 1023 | TMEM45A | 2633715 | GCTGACTTCTGGGCCTCATCTCCTTAG |

TABLE 13-continued

Subtyping Target Sequences

| SEQ ID NO. | Gene | Affy Probeset ID | Sequence |
|---|---|---|---|
| 1024 | TMEM45A | 2633716 | GCCAGCATCCAAGGAAATGCTCTTCCTCATGTCAGCTCCCCTCCAGAGCCAAAAGAAGACTAC<br>TGTCTCTTCCTGTTTCAAAACGCTTCATACCCCTAATGGGCCTCTTATCCACTTATA |
| 1025 | TMEM45A | 2633717 | CCTCCACCTGGCATATTCACATTAAATGCACGTCTTTTCTATGAAAACTTCTGTGGTGACTCTA<br>GCTCTTGCTCATCTCCCTTTAAGAGTTTTTGTTTTTTTTTCAAATACACCACAAAAGATTTTATT<br>ATGAAAAACATATGGGTAAAATGTAGCAACTATGCGGTTTACAAAATGTTCTATTATTGCATA<br>AAACTATCTTTGGTCTATCACCTTCTAAAACTTCTTACACTCTTTCTTGGTGTTAGGTCAAATCT<br>GCAAATGCTTTATCTGTTCTCCATATCATTAGAGCTCCATCTTCCACAAATATTTTAAGATAGAC<br>CTTCCCTCCACAATCATTACTCCCACAGTCTTAATGTAACCAGTGAACATGGACAGCAGCCGTC<br>CAATATACATTCACA |
| 1026 | TMEM45A | 2633718 | CAACAAGTATTGTTTACTGCACATATATAAAGATGATTTAATATTGAAAAATTTATTAATTAAA<br>TGCACCCTAATGATAGGTCCAGTTTCTTATGATTAAGAAACACCATAAGGTGATCTTAATAGCT<br>ACTTAAGAAACATTCGATACAATTTAAACTGATTTGTTTACCTCTTAGAAAACAAGAATGAAGT<br>TTTTGTATGATAAGCAATATTCTTTTTTTAAAAATTTTATTATTATTATACTTTAAGTTTTAGGGT<br>ACATGTGCACAACATGCAGGTTTGTTACATATGTATACATGTGCCATGTTGGTGTGCTGCACC<br>CGTTAACTCATCATTTAGTGTTAGGTATATCTCCTAATGCTATCCCTCCCCCCTATCGACACCCC<br>ACAACAGTCCCCGGTGTGTGATGTTCCCCTTCTTGTGTCCATGTGTTCTCATTGTTCAATTCCCA<br>CCTATGAGTGAGAATATGCGGTGTTTGGTTTTTTGTTCTTGCGATAGTTTGCTGAGAATGATG<br>GTTTCCAGTTTCATCCATGTCCCTACAAAGGACATGAACTCATCATTTTTTATGGCTGCATAGT<br>ATTCCATGGTGTATATGTGCCACATTTTCTTAATCCAATCTATCGTTGTTGGACATTTAGGTTG<br>GTTCCAAGTCTTTGCTATTGTGAATAGTGCCACAGTAAACATACATGTGCATGTGTCTTTATAG<br>CAGCATGATTTATAATCCTTTGGGTATATACCCAGTAATGGGATGGCTGGATCAAATGGTATT<br>TCTAGTTCTAGATCCCTGAGGAATCGCCACACTGACTTCCACAATGGTTGAACTAGTTTACAGT<br>CCCACCAACAGTGTAAAAGTGTTCCTATTTCTCCACAACCTCTCCAGCACCTGTTGTTTCCTGAC<br>TTTTTAATGATCGCCATTCTAACTGGTGTGAGATGGTATCTCATTGTGGTTTTGATTTGCATTTC<br>TCTGATGGCCAGTGATGGTGAGCATTTTTTCATGTGTTTTTTGGCTACATAAATGTCTTCTTTTG<br>AGAAGTGTCTGTTCATATCCTTCGCCCACTTTTTGATGGGGTTGTTTGTTTTTTTCTTGTAAATT<br>TGTTTGAGTTCATTGTAGATTCTGGATACTAGCCCTTTGTCAGATGAGTAGGTTGTGAAAATTT<br>TCTCCCATTCTGTAGGTTGCCTGTTCACTCTCATGGTAGTTTCTTTTGCTGTGCAGAAGCTCTTT<br>AGTTTAATTAGATCCCATTTGTCAATTTTGTCTTTTGTTGCCATTGCTTTTGGTGTTTTCGACAT<br>GAAGTCCTTGCCCATGCCTATGTCCTGAATGGTATTGCCTAGGTTTTCTTCTAGGGTTTTTATG<br>GTTTTAGGTCTAACATGTAAGTCTTTAATCCATCTTGAATTAATTTTTGTATAAGGTGTAAGGA<br>AGGGATCCAGTTTCAGCTTTCTACATATGGCTAGCCAGTTTTCCCAGCACCATTTATTAAATAG<br>GGAATCCTTTCCCCATTGCTTGTTTTTCTCAGGTTTGTCAAAGATCAGATAGTTGTAGATATGT<br>GGCATTATTTCTGAGGGCTCTGTTCTGTTCCATTGGTCTATATCTCTGTTTTGGTACCAGTACCA<br>TGCTGTTTTGGTGACTGTAGCCTTGTAGTATAGTTTGAAGTCAGGTAGCATGATGCCTCCAGC<br>TTTGTTCTTTTGGCTTAGGATTGACTTGGCGATGCGGCTCTTTTTTGGTTCCATATGAACTTTA<br>AAGCAGTTTTTTCCAATTCTGTGAAGAAAGTCATTGGTAGCTTGATGGGGATGGCATTGAATC<br>TATAAATTACCTTGGGCAGTATGGCCATTTTCACGATATTGATTCTTCCTACCCATGAGCATGG<br>AATGTTCTTCCATTTGTTTGTATCCTCTTTTATTTCCTTGAGCAGTGGTTTGTAGTTCTCCTTGAA<br>GAGGTCCTTCACATCCCTTGTAAGTTGGATTCCTAGGTATTTTATTCTCTTTGAAGCAATTGTG<br>AATGGGAGTTAATTCATGATTTGGCTCTCTGTTTGTCTGTTATTGGTGTATAAGAATGCTTGCG<br>ATTTTTGTACATTGATTTTGTATCCTGAGACTTTGCTGAAGTTGCTTATCAGCTTAAGGAGCTTT<br>TGGGCTGAGCTGATGGGGTTTTCTAGATATACAATCACGTCATCTGCAAACAGGGACAATTTG<br>ACCTCCTGTTTTCCTAATTGAATACCCTTTATTTCCTTCTCCTGCCTGATTGCCCTGGCCAGAAC<br>TTCCAACACTATGTTGAATAGGAGTGGTGAGAGAGGGCATCCCTGTCTTGTGCCAGTTTTCAA<br>AGGGAATGCTTCCAGTTTTTGCCCATTCAGTATGGATATTGGCTATGGGTTTCATAGATAGCTTT<br>TATTATTTTGAGATACGTCCCATCAATACCTAATTTATTGAGAGTTTTTAGCATGAAGGGTTGT<br>TGAATTTTGTCAAAGGCCTTTTCTGCATCTATTGAGATAATCATGTGGTTTTTGTCGTTGGTTCT<br>GTTATATGCTGGATTACATTTATTGATTTGTGTATGTTGAACCAGCCTTGCATCCCAGGGATGA<br>AGCCCACTTGATCATGGTGGATAAGCTTTTTGATGTGCTGCTGGATTCGGTTTGCCAGTATTTT<br>ATTGAGGATTTTTGCATCCATGTTCATCAAGGATATTGGTCTAAAATTTTCTTTTTTGGTTATGT<br>CTCTGCCAGCCTTTGGTATCAGGATGATGCTGGCCTCATGAAATGAGTTAGGGAGGATTCCCT<br>CTTTTTCTATTGATTGGAATAGTTTCAGAAGGAATGGTACAAAAAACCTTTCAAAAAATTAATG<br>AATCCAGGAGCTGGTTTTTGAAAACATCAACAAAATTGATAGACTGCTAGCAAGACTAATAA<br>AGAAGAAAAGAGAAGAATCAAATAGAGCAATAAAAAATGATAAAGGGGATGTCACCAC<br>CGATCCCACAGAAATACAAACTACCATCAGAGAGTACTATAAACACCTGTATGCAAATAAACT<br>AGAAAATCCTGAAGAAATGGATAAATTCCTCGACACATACATCCTCCCAAGACTAAACCAGGA<br>AGAAGTTGAATCTCTGAATAGACCAATAACAGGCTCTGAAATTGAGGCAATAATCAATAGCTT<br>ACCAACCAAAAAAGTCCAGGACAGATGGATTCACAGCCGAATTCTACCAGAGGTCCCTCC<br>AAGAATTTTTACAGCCCGTCGTCTTCACCATGCATTTTAACAATTGGGATCTCTCCTGTGATGT<br>TCACTATTAGGTC |
| 1027 | TMEM45A | 2633720 | TTGGTTAAATCTAGACTTAAGAGGCTCTGCTCCTCAGAAGTTGGACTTCTGAAAAATGCTGAA<br>CGAGAACAAGAATC |
| 1028 | TMEM45A | 2633721 | TGGCTAAGGATGACTCTAAGTGTACTGTTTGCATTTCCAATTTGGTTAAAGTATTTGAATTTAA<br>ATATTTTCTTTTTAGCTTTGAAAATATTTTGGGTGATACTTTCATTTTGCACATCATGCACATCA<br>TGGTATTCAGGGGCTAGAGTGATTTTTTTCCAGATTATCTAAAGTTTGGATGCCCACACTATGA<br>AAGAAATATTTGTTTTATTTGCCTTATAGATATGCTCAAGGTTACTGGGCTTGCTACTA |
| 1029 | UPK1B | 2637835 | ATCCTACCTTAAGTTGAAGCAGACCAGCAATTGTTGTGACCTACAATCTCCACACCCATCTT |

TABLE 13-continued

Subtyping Target Sequences

| SEQ ID NO. | Gene | Affy Probeset ID | Sequence |
|---|---|---|---|
| 1030 | UPK1B | 2637838 | TGCCTTCAGCTTGTGGGAAATCCCGAAG |
| 1031 | UPK1B | 2637839 | ATGGCCAAAGACAACTCAACTGTTCGTTGCTTCCAGGGCCTGCTGATTTTTGGAAA |
| 1032 | UPK1B | 2637841 | CCCTGACTGCGGAGTGCATCTTCTTTGTATCTGACCAACACAGCCTCTACCCACTGCTTGAAGCCACCGACAACGATGACATCTATGGGGCTGCCTGGATCGGCATATTT |
| 1033 | UPK1B | 2637842 | GCATCTTGTATCACAGCAGCAACAC |
| 1034 | UPK1B | 2637843 | TAGAGAGGTACCAAAACAACAGCCCTCCAAACAATGATGAC |
| 1035 | UPK1B | 2637844 | GACAATTGCTGTGGCGTAAATGGTCCATCAGACTGGCAAAAATACACATCTGCCTTCCGGACTGAG |
| 1036 | UPK1B | 2637845 | TGCTGACTATCCCTGGCCTCGTCAATGCTGTGTTATGAACAATCTTAAAGAACCTCTCAACCTGGAGGCTTGTAAACTAGGCGTGCCTGGT |
| 1037 | UPK1B | 2637848 | GCTGCTATGAACTGATCTCTGGTCCAATGAACCGACACGCCTGGGGGGT |
| 1038 | UPK1B | 2637850 | GGGTTCTCCTGGGTACCATGTTCTACTGGAGCAGAATTGAAT |
| 1039 | UPK1B | 2637851 | GCTCTCTCCTAATATTCCACGTTTGTGCCCCACACTAACGTGTGTGTCTTACATTGCCAAGTCAGATGGTACGGACTTCCTTTA |
| 1040 | UPK1B | 2637852 | TTGGCTAGCAATCTGCCTGTATCTCTCACTATTATCTAAAAGAAACCTTCCAATGCTTCTGTTGATCTCAGTATTGTCAGGGGAACAGAGAAGTTGGGAAAAGATTACTGAAATATACCTTTTGCATTTCTTTCTAGAGTAGCTCCCATATATGGAGATGGGTGATTCTCTTGATGCCACCTTCAGATCCTTTTATTCTCCAGAATAATTCTTAACAGTGGTTCAAATTTCCTTTCATACCTTGAAGTATGTGTTTAGTAGCCTCAATTCTCCATTAATTAAAAGTGTGGGCTGGGCGTGGGGGCTCATGCCTGTAATCCCAGCACTTTGGGAGGCCGAGGTGGGCAGATCACCTGAGGTCAGGAGTTCAAGACCAGCCTGGCCAACATGGTGAAACCCCGTCTCTACAAAAATACAAAAATTAGCCAGGCGTGATGGCAGGTGCCTGTAATCCTAGCTACTTGGCAGGCTAACGCAGGAGAATCACTTGACCGGGAGACGAGGTTGCAGTGAGCTGAGATCGTACCTATTGCACTCCATCCTGGATGAAAGAGCCAGACTCTGTCTCAAAACAAACAAAAAAGCGTGGGGACTTCTGGGGACAGACAAGGTGCCTGTTATATATTTACTCAGTCTTTGCCCTGAATGGTCTCAGCTTGAGACCATTTCAAACTGGAGAGAAGCAAGCCAGCCAATAGAATGGGGTGATTTACAGGGATTTCTGTTTACTGTCAAAA |
| 1041 | CSTA | 2638872 | CATCCTGTCCAGCAAAGAAGCAATCAGCCAAA |
| 1042 | CSTA | 2638873 | TGGAGGCTTATCTGAGGCCAAACCCGCCACTCCAG |
| 1043 | CSTA | 2638876 | ACAAATGAGACTTACGGAAAATTGGAAGCTGTGCAGTATAAAACTCAAGTTGTTGCTGG |
| 1044 | CSTA | 2638877 | GAGTTCAGCACCTACTTTAGCGCCAAAAGATGTATTTCTCATTTTATGTAAAATATTCCCTGATTTCCCTACCACATAATTCCTTCCTTACGGTTGTCCTAAATTAAGATGCCCAGCATGATTCCTTCCAAGTGGTGGACTCTCAAATTTGGTAGATGATGTGACACCATTTTTTTTCTTGTGAATTCAGAAGTTTTATTACATTGATTCTTGATTTCTGGAAATTGTATAGAAAAGATTTCATAACAGTTCAGGGCATGCTGGATTTGTGGCTGTGCTGCTGCTTAGGTAAGGAGGGAGGATCACGTCTCATCTGCCTGAAGGTGTGGGGCTGGACCACATGGTATCTTGAAGCTGATTCTACCTCAAAGCTGTATGATTCTCTATGTCTAAATTAAATAAATTAAGTAACGACTCAAATCATTAGCTGGGAAAATAATTTAAACCTTTTTTGCCCTTCAATTAATATAATGTAAATACTATTTTGTAACTCAAATTAGATTTAACTTGTGGCACTCTAGGCATAGTTTA |
| 1045 | CSTA | 2638879 | CAAAAGTCTTCCCGGACAAAATGAGGACTTGGTACTTACTGGATACCAGGTTGACAAAAACAAGGATGACGAGCTGACGGGCTTTTA |
| 1046 | CSTA | 2638880 | AAGTGTTCTGATTCCTTCAACTGGCTACTGAGTCATGATCCTTGCTGATAAATATAACCATCAATAAAGAAGCATTCTT |
| 1047 | CSTA | 2638881 | GTCAAGCCTAATGCAACTGGCTAAAGGATAGTACCACCCTCACCCCCACCATAGGCAGGCTGGATCGTGGACTATCAATTCACCAGCCTCCTTG |
| 1048 | RALBP1 | 2654257 | TGCAGGAATTCCAGCGTTTACTCAAAGAACTGCCAGA |
| 1049 | KRT18 | 2698437 | GCCCAGGAGTATGAGGCCCTGCTGAACATCAAG |
| 1050 | RARRES1 | 2702753 | TGTGTTGAATGTTCTCGTGAAGATTTGTATACAAAGGAAAAATTTGTGCTAAACTGGAATTAAATGAATGGTAATATTGCTTAACTTAAATTTTACAAATAATAGAACGTCTGTCTCACCAGATAAAGCTGTCTGCAAACATGCATCAAAAG |
| 1051 | RARRES1 | 2702754 | TTTTAACTCTGGAAGCGCATGCACACTGAACTCTGCTCAGTGCTAAACAGTCACCAGCAGGTTCCTCAGGGTTTCAGCCCTAAAATGTAAAACCTGGATAATCAGTGTATGTTGCACCAGAATCAGCATTTTTTTTTTAACTGCAAAAAATGATGGTCTCATCTCTGAATTTATA |

TABLE 13-continued

Subtyping Target Sequences

| SEQ ID NO. | Gene | Affy Probeset ID | Sequence |
|---|---|---|---|
| 1052 | RARRES1 | 2702755 | CCTGTCGCATTCACTTGGTCTGGTACCCTGGCAAACCTCTTAAAGTGAAGTACCACTGTCAAG AGCTACAGACACCAGAAGAAGCCTCCGGAACTGAAGAAGGATCAGCTGTAGTACCAACAGA GCTTAGTA |
| 1053 | RARRES1 | 2702756 | GATGATACAATTGATTTTGATTATAC |
| 1054 | RARRES1 | 2702757 | GTGACAGACATTCAACCAGACTTTCATATAACTCAGTGACAAGACAA |
| 1055 | RARRES1 | 2702760 | ACTTGTGCCACAAGAGTTACAATCAAAGTGGTCTCCTTAGACTGAATTCATGCGAACTTCTAAT TTCATATCAAGAGTTGTAATCACATTT |
| 1056 | RARRES1 | 2702761 | GGCTTTCCTTGGAAGCTCTTACGTGATGTGGGAAATGACAACACAGGTGTCACACTACTACTT GGCACAGCTCACTAGTGTG |
| 1057 | RARRES1 | 2702764 | GGACGTTTGGGGAAATGTTCTGCTCGAGTGTTTTTCAAGAATCAGAAACCCAGACCAACCATC AATGTAACTTGTACACGGCTCATCGAGA |
| 1058 | RARRES1 | 2702767 | TCCAAAAGAGGGATGTAAAGTTCACGTGGTCTTCAGCACAGAGCGCTACAACCCAGAG |
| 1059 | RARRES1 | 2702775 | GCGCGCGGCGCTTCACTTCTTCAACTTCCGGTCCGGCTCGCCCAGCGCGCTACGAGTGCTGGC CGA |
| 1060 | RARRES1 | 2702776 | CCTCAGGATGCTGGGGTCCCGCGCAG |
| 1061 | RARRES1 | 2702777 | CGCCGGCAACGGCTGCCTGCTCCCTGGTCCGGGCCCAGGGGCCCGCGCCCCACCGCCCCGCT GCTCGCGCTGCTGCTGTTGCTCGCCCCGGTGGCGGC |
| 1062 | CLDN1 | 2710603 | CTCATAAGGTGCTATCTGTTCAGTGATGCCCTCAGAGCTCTTGCTGTTAGCTGGCAGCTGACG CTGCTAGGATAGTTAGTTTGGAAATGGTACTTCATAATAAACTACACAAGGAAAGTCAGCCAC TGTGTCTTATGAGGAATTG |
| 1063 | CLDN1 | 2710604 | GCCTTAACCAGTCTCTCAAGTGATGAGACAGTGAAGTAAAATTGAGTGCACTAAACAAATAA GATTCTGAGGAAGTCTTATCTTCTGCAGTGAGTATGGCCCGATGCTTTCTGTG |
| 1064 | CLDN1 | 2710605 | AGCTTTGGGTGCCTTTGCCACAAGACCTAGCCTAATTTACCAAGGATGAATTCTTTCAATTCTT CATGCGTGCCCTTTTCATATACTTATTTTATTTTTTACCATAATCTTATAGCACTTGCATCGTTAT TAAGCCCTTATTTGTTTTGTGTTTCATTGGTCTCTATCTCCTGAATCTAACACATTTCATAGCCT ACATTTTAGTTTCTAAAGCCAAGAAGAATTTATTACAAATCAGAACTTTGGAGGCAAATCTTTC TGCATGACCAAAGTGATAAATTCCTGTTGACCTTCCCACACAATCCCTGTACTCTGACCCATAG CACTCTTGTTTGCTTTGAAAATATTTGTCCAATTGAGTAGCTGCATGCTGTTCCCCCAGGTGTT GTAACACAACTTTATTGATTGAATTTTTAAGCTACTTATTCATAGTTTTATATCCCCCTAAACTA CCTTTTTGTTCCCCATTCCTTAATTGTATTGTTTTCCCAAGTGTAATTATCATGCGTTTTATATCT TCCTAATAAGGTGTGGTCTGTTTGTCTGAACAAAGTGCTAGACTTTCTGGAGTGATAATCTGG TGACAAATATTCTCTCTGTAGCTGTAAGCAAGTCACTTAATCTTTCTACCTCTTTTTTTCTATCTGC CAAATTGAGATAATGATACTTAACCAGTTAGAAGAGGTAGTGTGAATATTAATTAGTTTATAT TACTCTCATTCTTTGAACATGAACTATGCCTATGTAGTGTCTTTATTTGCTCAGCTGGCTGAGA CACTGAAGAAGTCACTGAACAAAACCTACACACGTACCTTCATGTGATTCACTGCCTTCCTCTC TCTACCAGTCTATTTCCACTGAACAAAACCTACACACATACCTTCATGTGGTTCAGTGCCTTCCT CTCTCTACCAGTCTATTTCCACTGAACAAAACCTACGCACATACCTTCATGTGGCTCAGTGCCT TCCTCTCTCTACCAGTCTATTTCCATTCTTTCAGCTGTGTCTGACATGTTTGTGCTCTGTTCCATT TTAACAACTGCTCTTACTTTTCCAGTCTGTACAGAATGCTATTTCACTTGAGCAAGATGATGTA ATGGAAAGGGTGTTGGCATTGGTGTCTGGAGACCTGGATTTGAGTCTTGGTGCTATCAATCA CCGTCTGTGTTTGAGCAAGGCATTTGGCTGCTGTAAGCTTATTGCTTCATCTGTAAGCGGTGG TTTGTAATTCCTGATC |
| 1065 | CLDN1 | 2710606 | CGAAAATGGACATTGAGATACTATCATTAACATTAGGACCTTAGAATTTTGGGTATTGTAATC TGAAGTATGGTATTACAAAACAAACAAACAAACAAAAAACCCATGTGTTAAAATACTCAGTGC TAAACATGGCTTAATCTTATTTTATCTTCTTTCCTCAATATAGGAGGGAAGATTTTTCCATTTGT ATTACTGCTTCCCATTGAGTA |
| 1066 | CLDN1 | 2710607 | TCTTACCCAACACCAAGGCCCTATCCAAAACCTGCACCTTCCAGCGGGAAAGACTA |
| 1067 | CLDN1 | 2710609 | GTTGCCACAGCATGGTATGGCAATAGAATCGTTCAAGAATTCTATGACCCTATGACCCCAGTCA |
| 1068 | CLDN1 | 2710611 | TTGGCATCCTCCTGGGAGTGATAGCAATCTTTGTGGCCACCGTTGGCATGAAGTGTATGAAGT GCTTGGAAGACGATGAGGTGCAGAAGATGAGGATGGCTGTCATTGGGGGTGCGATATTTCTT CTTG |
| 1069 | CLDN1 | 2710612 | GCACATTGCAAGCAACCCGTGCCTTG |
| 1070 | CLDN1 | 2710618 | TTGGGCTTCATTCTCGCCTTCCTGGGATGGATCGGCGCCATCGTCAGCACTGCCCTGCCCCAG TGGAGGATTTACTCCTATGCCGGCGACAACATCGTGACCGCCCAGGCCATGTACGAGGGGCT GTGGATGTCCTGCGTGTCGCAGAGCACCGGGCAGATCCAGTGCAAAGTCTTTGACTCCTTGCT GAATCTGAGC |

TABLE 13-continued

Subtyping Target Sequences

| SEQ ID NO. | Gene | Affy Probeset ID | Sequence |
|---|---|---|---|
| 1071 | CLDN1 | 2710619 | TGCGTCTCAGTTCCCGAGCCTGGGAGCAACCGCAGCTTCTAGTATCCAGACTCCAGCGCCGCC CCGGGCGCGGACCCCAACCCCGACCCAGAGCTTCTCCAGCGGCGGCGCAGCGAGCAGGGCT CCCCGCCTTAACTTCCTCCGCGGGCCCAGCCACCTTCGGGAGTCCGGGTTGCCCACCTGCAAA |
| 1072 | S100P | 2717083 | TCCTCTTGGTCTGTGAGCATCCAGCCTTACTTTTTGTATCCAATCATATTTCCATACTTCGCTGAA CTGTGTTTATGGATAGTTTCCACCAGATCTTTGGATCTTCATCTTGAAGGCTGCCGTGCCACAT AAGCTATGATCAAATACATCTGTTATGCTCTTCTCCTATTCATCTGCCTTCTGCCCGTTGATTTT CAGCAAACTCCCAGAGGATGAAGGGGAGTTTTCTGTTTGGCCCCACAGGGGAGGAGCGAGC GAGATTGACGTGGAAGCTGGGCCTCTGAAGGACACAGAGTGCTCTAAGAAAGGGACGATGG GGCAGATCCATGTTCACAAACACGCCCATGTGAATTCACTCTCAGATGTCTCCTCGTGTCAGC ACGCTGGGTGCCAGCACGCTCTGATATTGACA |
| 1073 | S100P | 2717087 | CAAGGATGCCGTGGATAAAATTGCTCAAGGACCTGGATGCCAATGGAGATGCCCAGGTGGACT TCAGTGAGTTCATAGTGTTCGTGGCTGCAATCACGTCTGCCTGTCACAAGTACTTTGAGAAGG CAG |
| 1074 | S100P | 2717088 | CATGGTCCCAGGCTTCCCAAAAGTGTTTGTTGGCAATTATTCCCCTAGGCTGAGCCTGCTCATG TACCTCTGATTAA |
| 1075 | CXCL1 | 2731382 | CACAGCCGCCAGACCCGCCTGCTGAGCC |
| 1076 | CXCL1 | 2731387 | AATGGGCGGAAAGCTTGCCTCAATCCTGCATCC |
| 1077 | CXCL1 | 2731388 | CTCACTGGTGGCTGTTCCTGAAGGAGGCCCTGCCCTTATAGGAACAGAAGAGGAAAGAGAG ACACAGCTGCAGAGGCCACCTGGATTGTGCCTAATGTGTTTGAGCATCGCTTA |
| 1078 | CXCL1 | 2731389 | GATTAACTCTACCTGCACACTGTCCTATTATATTCATTCTTTTTGAAATGTCAACCCCAAGTTAG TTCAATCTGGATTCATATTTAATTTGAAGGTAGAATGTTTTCAAATGTTCTCCAGTCATTATGTT AATATTTCTGAGGAGCCTGCAACATGCCAGCCACTGTGATAGAGGCTGGCGGATCCAAGCAA ATGGCCAATGAGATCATTGTGAAGGCAGGGGAATGTATGTGCACATCTGTTTTGTAACTGTTT AGATGAATGTCAGTTGTTATTTATTGAAATGATTTCACAGTGTGTGGTCAACATTTCTCATGTT GAAACTTTAAGAACTAAAATGTTCTAAATATCCCTTGGACATTTTATGTCTTTCTTGTAAGGCA TACTGCCTTGTTTAATGGTAGTTTTACAGTGTTTCTGGCTTAGAACAAAGGGGC |
| 1079 | PTPN13 | 2734630 | GAGGGTGACACACCATGCTCACGGCCCCTGGAGACCGTCGTGCTGGCGAGCCGTGCTCCGTA GCTCCCCGGTCCGCCTCGGCAGCGGTCAGAGTCGCCTACAGGAGTTGAGCGCCCGCGCCAG AAGGTTTTGGCGAAGCTCTTGGAGAGGCGTCGAGCACAGTAGGGCGGCGGGGGTGCGTTGA GCGCTCGGGGGTCAGGCAGTCGGCCGGAGATCGCCGCTGGGGAGCGTTTCCGAGGCGAGGA GGAGGAGGAGGAGATGCTGCTCCTCTTCTCCCCCCTCCCCAGGCTCCTTCTACAGCTCCTTCAG CCCACGCCCGCAGCCGCTTGTGGGAGAAGTGGTGGTGGCTCTCGGCGCCCGCGGCGGCTGC CGGCGGCCCGCCCCGACGCCGCGTCCCTGCAGCCCTCGCCCGGCGCTCCAGTAGCAGGACCC GGTCT |
| 1080 | PTPN13 | 2734634 | ATGCACGTGTCACTAGCTGAGGCCCTGGAGGTTCGGGGTGGACCACTTCAGGAGGAAGAAA TATGGGCTGTATTAAATCAAAGTGCTGAAAGTCTCCAAGAATTATTCA |
| 1081 | PTPN13 | 2734644 | TGCTGTTGCTGCCATCTGGTAGTGTGTCA |
| 1082 | PTPN13 | 2734645 | TTCCAATCAGGATCTTCGAGCATTCACTGCACCAGAGGTTCTTCAAAATCAGTCACTAACTTCT CTCTCA |
| 1083 | PTPN13 | 2734650 | GGAGATCATCTCAACAGCATACTGCTTGGAATGTGTGAGGATGTTATTTACGCTCGAGTTTCT GTTCGGACTGTGCTGGATGCTTGCAGTGCCCACATTAGGAATAGCAATTGTGCACCC |
| 1084 | PTPN13 | 2734651 | AAACTGGTTCTGGGAAATCTTTCTG |
| 1085 | PTPN13 | 2734652 | TGCTACCAGTGTATCCAGGGAATCCATGCTTGTATCCCTGCCAGATTTCCCCAAGACCTGGAC TCTTCTAGTTTTTCTCTTGTTTTGGATATGAAGAATCCCAAGAATAACCAATGCTATATATTACC TGAAAGTCCCACCTCTGTTCTGCATTTCTAAGGCTGTATTTTATCTTGTTTGCCCTATCTGATCT GGATCTATACTTTATCTGCTCTTATCCTTAGGGTTGTAGTCCTGGAGTGTTGGTCCCTCTTCCTT GCACAGGTTACAAATTTACCACTGCCACACAGTGTTCTTGTTGACTTCCTCAGAATTCCTCATC GGTAGGGGTTTAGTTCCCATCTTAACCAGGATGTCAGATGGCTGCCAGGAATGTATTCAAATT CTGCACAGTTTTTCAGTTGATAACAAACAGGCCCACAGATCTTCTAGACAAATG |
| 1086 | PTPN13 | 2734655 | CAGATCAGCTTTCCTGTAACAGTGAACAAAAGCCTGATCGAAGCCAGGCTATTCGAGATCGAT TGCGAGGAAAAGGATTACCA |
| 1087 | PTPN13 | 2734657 | AAGCTCTACTTCTGATGTACTAGACATACAAAAGCCTCCACTCTCTCATCAGACCTTTCTTAAC AAAG |

TABLE 13-continued

Subtyping Target Sequences

| SEQ ID NO. | Gene | Affy Probeset ID | Sequence |
|---|---|---|---|
| 1088 | PTPN13 | 2734658 | GCTTCATCCATGGACTTGCTTTGTACAGCTGACAGAGACTTCTCTTCAGGAGAGACTGCCACA TATCGTCGTTGTCACCCTGAGGCAGTAACAGTGCGGACTTCAACTACTCCTAGAAAAAAGGA GGCAAGATACTCAGATGGAAGTATAGCCTTGGATATCTTTGGCCCTCAGAAAATGGATCCAAT ATATCACACTCGAGAATTGCCCACCTCCTCAGCAATATCAAGTGCTTTGGACCGAATCCGAGA |
| 1089 | PTPN13 | 2734665 | TGAATCCAGCAGTGGTCTCCCAGGGGTAGATGAAACCTTAAGTCAAGGCCAGTC |
| 1090 | PTPN13 | 2734667 | GCCAAAATGGCCCTTAGACAGTCTCGGTTGAGCCTATATCCAGGAGACACAATCAAAGCGTCC ATGCTTGACATCACCAGGGATCCGTTAAGAGAAATTGCCCTA |
| 1091 | PTPN13 | 2734669 | GGAAGAATGAGGATAACCGAAGGAAAGTAAACATAATGCTTCTGAACGGGCAAAGACTGGA ACTGACCTGTGATACCAAAACTATATGTAAAGATGTGTTTGATATGGTTGTGGCACATATTGG CTTAGTAGAGCATC |
| 1092 | PTPN13 | 2734672 | GTTCATGGTGTGTCTTACTTTAGAATGGAGCACTATTTGCCCGCCAGA |
| 1093 | PTPN13 | 2734673 | GAAACTTGATTTATCCTATATCAAAGAAGAGTTACCCAAATTGCATAATACCTATGTGGGAGC TTCTGAAAA |
| 1094 | PTPN13 | 2734676 | ACCGAGTGCACCCTGAGAAGAAGTCACAAACAGGAATATTGCTTGGAGTCTGTTCTAAAGGT GTCCTTGTGTTTGAAGTTCACAATGGAGTGCGCACATTGGTCCTTCGCTTTCCATGGAGGGA |
| 1095 | PTPN13 | 2734677 | ACATTGCAAAATACATCAGATGGAATAAAACATGGCTTCCAGACAGACAACAGTAAGATATG CCAGTACCTGCTGCACC |
| 1096 | PTPN13 | 2734678 | CATAAGTTCCAGCTACAGATGAGAGCAAGACAGAGCAACCAAGATGCC |
| 1097 | PTPN13 | 2734679 | AGAGCTTCGTTTAGGAGCCTGAATCTCCAAGCAGAGTCTGTTAGAGGATTTAATATGGGACG AGCAATCAGCACTGGCAGTCTGGCCAGCAGCACCCTCAACAAACTTGCTGTTCGACCTTTATC AGTTCAAGCTGAGATTCTGAAGAGGCTATCCTGCTCAGAGCTGTCGCTTTACCAGCCATTGCA AAACAGTTCAAAAGAGAAGAATGACAAAGCTTCATGGGAGGAAAAGCCTAGAGAGATGAGT AAATCATACCATGATCTCAGTCAGGCCTCTCTCTATCCACATCGGAAAAATGTCATTGTTAACA TGGAACCCCACCACAAACCGTTCAGAGTTGG |
| 1098 | PTPN13 | 2734680 | GTTGCGAGTTTAAATAGAAGTCCTGAAAGGAGGAAACATGAATCAGACTCCTCATCCATTGA AGACCCTGGGCAAGCATATGTTC |
| 1099 | PTPN13 | 2734681 | GAATGACTATGCATAGTTCTGGAAACTCT |
| 1100 | PTPN13 | 2734684 | TCTTCACCAGAAAGGGAGATCACCTTAGT |
| 1101 | PTPN13 | 2734685 | GATTTCAAATTATTGGTGGGGAGAAG |
| 1102 | PTPN13 | 2734686 | TATTTATCAGTTCAGTTGCCCCTGGAGGACCAGCTGACTTGGATGGATGC |
| 1103 | PTPN13 | 2734687 | GCCACCATGCTGCAATTGAAATTTTGCAAAATGCACCTGAAGATGTGACACTTGTTATCTCTCA GCCAAAA |
| 1104 | PTPN13 | 2734689 | TCTTCCTACATGCAAGACAGTGCTATAGATTCTTCTTCCAAGGATCACCACTGGTCACGTGGTA CCCTGAGGCACATCTCGGAGAACTCCTTTGG |
| 1105 | PTPN13 | 2734690 | TGCCAGCCATTTAGGTGACCAAACCTGGCAGGAATCACAGCATGGCAGCCCTTCCCCATCTGT AATATCCAAAGCCACCGAGAAAGAGACTTTCACTGATAGTAACCAA |
| 1106 | PTPN13 | 2734693 | TCCTCTTCAGTGAATACATCCAACAAG |
| 1107 | PTPN13 | 2734694 | AACTTTTTCTTCATCACCTCCTAAG |
| 1108 | PTPN13 | 2734695 | CCTGGAGATATCTTTGAGGTTGAACTGGCTAAAAATGATAACAGCTTGGGGATAAGTGTCACG |
| 1109 | PTPN13 | 2734697 | GGAGGTGTGAATACGAGTGTCAGACATGGTGGCATTTATGTGAAAGCTGTTATTCCCCAGGG AGCAGCAGAGTCTGATGGTAGAATTCAC |
| 1110 | PTPN13 | 2734699 | GTGATCGCGTCCTAGCTGTCAATGGAGTTAGTCTAGAAGGAGCCACCCATAAGCAAGCTGTG GAAACACTGAGAAATACAGGA |
| 1111 | PTPN13 | 2734701 | CTGTTATTAGAAAAGGGACAATCTCCAACATCTAAAGAACATGTCCCGGTAAC |
| 1112 | PTPN13 | 2734702 | TGTACCCTTTCAGATCAGAATGCCC |
| 1113 | PTPN13 | 2734704 | GGATTCAGTTTTTCTCGAGAAGATAATCTTATACCGGAGCAAATTAATGCCAGCATAGTAAGG GTTAAAAAGC |

TABLE 13-continued

Subtyping Target Sequences

| SEQ ID NO. | Gene | Affy Probeset ID | Sequence |
|---|---|---|---|
| 1114 | PTPN13 | 2734707 | TTCAGTCTCCAGCACAAGTACTTCCAAACAGCAGTAAAGACTCTTCTCAGCCATCATGTGTGG AGCAAAGCACC |
| 1115 | PTPN13 | 2734708 | GCAAAAAACAGTGCAAGTCCCCATCCAGAAGAGACAGTTAC |
| 1116 | PTPN13 | 2734709 | GTGACAGCTCCAGCAAACATATCAAATTCGACCTGGAGTTCAGCTTTGCATCAGACTCTAAGC AACATGGTATCACAGGCACAGAGTCATCATGAAGCACCCAAGAGTCAAGAAGATACCATTTG TACCATGTTT |
| 1117 | PTPN13 | 2734710 | TTCCCCTCTACCACCGGATATGGCTCCTGGGCAG |
| 1118 | PTPN13 | 2734711 | ATCAGAATCTGCTTCCTCTAGTTCGATGGATAAGTATCATATACATCACATTTCTGAACCAACT AGACAAGAAA |
| 1119 | PTPN13 | 2734712 | CTCCTCATTACCCTAATTAAATCAGAAAAGGAAGCCTGGGTTTTACAGTAACCAAAGGCAAT CAGAGAATTGGTTGTTATGTTCATGATGTCATACAGGATCCAGCC |
| 1120 | PTPN13 | 2734713 | GATACAGATGTTACTAATATGACTCATACAGATGCAGTTAATCTGCTCCGGGCTGCATCCAAA ACAGTCAGATTAGTTATTGGACGAGTTCTAGAATTACCCAGAATACCAATGTTGCCTCATTTGC TACCGGACATA |
| 1121 | PTPN13 | 2734715 | TCCTTATGTGGAGGTCATGACAGCCTTTATCAAGTGGTATATA |
| 1122 | PTPN13 | 2734716 | AATCCAAGGTCCGTCGCAGCCATTGAGGGTAATCTCCAGCTATTAGATGTCATCCATTATGTG AACGGAGTCAGCACACAAGGAATGACCTTGGAGGAAGTTAACAGAGCATTAGACATGTCACT TCCTTC |
| 1123 | PTPN13 | 2734720 | AAGAGGTCTGCTGTTTCAGCTCCAAAGTCAACCAAAGGCAAT |
| 1124 | PTPN13 | 2734721 | GTTCCTACAGTGTGGGGTCTTGCAGCCAGCCTGCC |
| 1125 | PTPN13 | 2734723 | ATAAATGAAATATCGTACCCCAAAGGAAAATGTTCTACTTATCAGATAAAGGGATCACCAAAC TTGACTCTGC |
| 1126 | PTPN13 | 2734725 | CAAGAAGCTGAAGTTATCCAGTCTCTGCTGGATGTTGTGGATGAGGAAGCCCAGAATCTTTTA AACGAAAATAATG |
| 1127 | PTPN13 | 2734726 | AAGATGAATGGAAGTTATCAGAAGAGAGAACA |
| 1128 | PTPN13 | 2734727 | AAGATACAGACTGCGATGGTTCACCTTTACC |
| 1129 | PTPN13 | 2734730 | TGGCTGTGAAGAATATTGTGAAGAAAAAGTAA |
| 1130 | PTPN13 | 2734731 | ATGATGATGAAATAACATGGGGAAATGATGAGTTGCCAATAGAGAGAACAAACCATGAAGA TTCTG |
| 1131 | PTPN13 | 2734737 | CCTTTCTGACAAACGATGAGCTCGCTGTACTCCCTGTCGTCAAAGTGCTTCCCTCTGGTAAATA CACGGGTGCCAACTTAAAATCAGTCATTCGAGTCCTGCGGGGTTTGCTAGATCAA |
| 1132 | PTPN13 | 2734739 | AATTAAAACCTTTGGATCAGTGTCTAATTGGGCAAACTAAGGAA |
| 1133 | PTPN13 | 2734741 | GAGTTCGTTTACATTGCCTGCCAAGGACCACTGCCTACAACTGTTGGAGACTTCTGGCAGATG ATTTGGGAGCAAAAATCCACAGTGATAGCCATGATGACTCAAGAAGTAGAAGGAGAAAAA TCAAATGCCAGCGCTATTGGCCCAACATCCTAGGCAAAACAACAATGGTCAGCAACAGACTTC GACTGGCTCTTGTGAGAATGCA |
| 1134 | PTPN13 | 2734743 | TGGCCAGACCATGATACACCTTCTCAACCAGATGATCTGCTTACTTTTATCTCCTACATGAGAC ACATCCACAGATCAGGCCCAATCATTACGCACTGCAGTGCTGGCATTGGACGTTCAGGGACCC TGATTTGCATAGATGTGGTTCTGGGATTAATCAGTCAGGATCTTG |
| 1135 | PTPN13 | 2734744 | CATCTCTGATTTGGTGCGCTGCATGAGACTACAAAGACACGGAATGGTTCAGACAGA |
| 1136 | PTPN13 | 2734748 | TATATTTTCTGCTATCAAGTCATCCTTTATGTCCTGACACGTCTTCAAGCAGAAGA |
| 1137 | PTPN13 | 2734749 | CTTAGGGATGATTAAAGGCAGCATTTGATGATAGCAGACATTGTTACAAGGACATGGTGAGT CTATTTTTAATGCACCAATCTTGTTTATAGCAAAAATGTTTTCCAATATTTTAATAAAGTAGTTA TTTTATAGGGGATACTTGAAACAGTATTTAAGCTTTAAATGACAGTAATATTGGCATAGAAA AAAGTAGCAAATGTTTACTGTATCAATTTCTAATGTTTACTATATAGAATTTCCTGTAATATATT TATACTTTTTCATGAAAATGGAGTTATCAGTTATCTGTTTGTTACTGCATCATCTGTTTGTAA TCATTA |
| 1138 | SPP1 | 2735055 | TAAATTCTGGGAGGGCTTGGTTGTCAGCAGCAGCAGGAGGAGGCAGAGCACAGCATCGTCG GGACCAGACTCGTCTCAGGCCAGTTGCAGCCTTCTCAGCCAAA |

TABLE 13-continued

Subtyping Target Sequences

| SEQ ID NO. | Gene | Affy Probeset ID | Sequence |
|---|---|---|---|
| 1139 | SPP1 | 2735057 | TGAGAATTGCAGTGATTTGCTTTTGCCTCCTA |
| 1140 | SPP1 | 2735058 | GTTAAACAGGCTGATTCTGGAAGTT |
| 1141 | SPP1 | 2735059 | CCACAACAGATGAAACTGTGCCAGCCAAACAACAAATGGGCATTGTCCCCAGAAGCTTGGAC AAAAAGGCACACAGAGTTCAATTCCAGTTGAACAGAATAAAGGCCAAAATAGAGCTGCCTTG GGGGTCACTGCAATTAGACTGCTTA |
| 1142 | SPP1 | 2735062 | CATCTCAGAAGCAGAATCTCCTAGCCCCACAG |
| 1143 | SPP1 | 2735063 | AACTTCTCATAATTAAACTACAGTGATGAAAG |
| 1144 | SPP1 | 2735064 | AATGCTGTGTCCTCTGAAGAAACCAATGACTTTAAACAAGAG |
| 1145 | SPP1 | 2735066 | TTCCAAGTAAGTCCAACGAAAGCCATGACCACATGGA |
| 1146 | SPP1 | 2735067 | GACTCCATTGACTCGAACGACTCTGATGATGTAGATGACACTG |
| 1147 | SPP1 | 2735068 | CTCACCAGTCTGATGAGTCTCACCATTCTGATGAATCTGATGAACTGGTCACTGATTTTCCCAC GGACCTGCCAGCAACCGAAGTTTTCACTCCAGTTGTCCCCACAGTAGACACATATGATGGCCG AGGTGATAGTGTGGTTTATGGACTGAGGTCAAAATCTAAGAAGTTTCGCAGACCTGACA |
| 1148 | SPP1 | 2735070 | TGAATGGTGCATACAAGGCCATCCCCGTTGCCCAGGACCTGAACGCGCCTTCTGATTGGGAC AGCCGTGGGAAGGACAGTTATGAAACGAGTCAGCTGGATGACCAGAGTGCTGAAACCCACA GCCACAAGCAGTCCAGATTATATAAGCGGAAAGCCAATGATGAGAGCAATGAGCATTCCGAT GTGATTGATAGTCAGGAACTTTCCAAAGTCAGCCGTGAATTCCACAGCCATGAATTTCACAGC CATGAAGATATGCTGGTTGTAGACC |
| 1149 | SPP1 | 2735071 | TCTCACTTTGCATTTAGTCAAAAGAAAAAATGCTTTATAGCAAAATGAAAGAGAACATGAAAT GCTTCTTTCTCAGTTTATTGGTTGAATGTGTATCTATTTGAGTCTGGAAATAACTAATGTGTTT GATAATTAGTTTAGTTTGTGGCTTCATGGAAACTCCCTGTAAACTAAAAGCTTCAGGGTTATGT CTATGTTCA |
| 1150 | SPP1 | 2735072 | TTTGGTGGTGTCAATTGCTTATTTGTTTTCCCACGGTTGTCCAGCAATTAATAAAA |
| 1151 | EPCAM | 2753287 | TTAAAGGTGAATCCTTGTTTCATTC |
| 1152 | EPCAM | 2753288 | ATCTGGATCCTGGTCAAACTTTAATTTA |
| 1153 | FGFBP1 | 2761830 | ATGTCATGTCGTAAGTCCCTCTGTATACTTTAAAGCTCTCTACAGTCCCCCCAAAATATGAACT TTTGTGCTTAGTGAGTGCAACGAAATATTTAAACAAGTTTTGTATTTTTGCTTTTGTGTTTTGG AATTTGCCTTATTTTTCTTGGATGCGATGTTCAGAGGCTGTTTCCTGCAGCATGTATTTCCATG GCCCACACA |
| 1154 | FGFBP1 | 2761831 | TGAGTGCACTCAATTGGACCATGAATTTTCCTGTGTCTTTGCTGGCAATCCAACCTCATGCCTA AGCTCAAGGATGAGAGAGTCTATTGGAAACAAGTTGCCCGGAATCTGCGCTCACAGAAAGA CATCTGTAGATATTCCAAGACAGCTGTGAAACCAGAGTGTGCAGAAAGGATTTTCCAGAATC CAGTCTTAAGCTAGTCAGCTCCACTCTATTTGGGAACACAAAGCCCAGGAAGGAGAAAACAG AGATGTCCCCCAGGGAGCACATCAAAGGCAAAGAGACCACCCCCTCTAGCCTAGCAGTGACC CAGACCATGGCCACCAAAGCTCCCGAGTGTGTGGAGGACCCAGATATGGCAAACAGAGGA AGACTGCCCTGGAGTTCTGTGGAGAGACTTGGAGCTCTCTGCACATTCTTCCTCAGCATAG TGCAGGACACGTC |
| 1155 | FGFBP1 | 2761832 | ATGAAGATCTGTAGCCTCACCCTGCTCTCCTTCCTCCTACTGGCTGCTCAGGTGCTCCTGGTGG AGGGGAAAAAAAAAGTGAAGAATGGACTTCACAGCAAAGTGGTCTCAGAA |
| 1156 | FGFBP1 | 2761833 | GAGGAGCTGTGAGTAACGTGCCACAGTGTTGTAAAAACCCAGTGAGTGTTATAAAAACCCAG TCAGCCTGGCTCCTGTTGAATAGTCTACCCCCCTTGCACTCTACCTGACACAGCTGCAGCCTGC AATTCACTCGCACTGCCTGGGATTGCACTGGATCCG |
| 1157 | FGFBP1 | 2761834 | AGAGCGGATGTGATGAGGGAAAAGGAGAACTCAG |
| 1158 | CXCL9 | 2773948 | TCTCTTGAATGTACCCTTCAACTGTTGAATGTTTAATAGTAAATCTTATATGTCCTTATTTACTTT TTAGCTTTCTCTCAAATAAAGTGTAACACTAGTTGAGATAA |
| 1159 | CXCL9 | 2773949 | AGCCCTAGGCTTCCACGTACTGCAGCCTCCAGAGAGTATCTGAGGCACATGTCAGCAAGTCCT AAGCCTGTTAGCATGCTGGTGAGCCAAGCAGTTTGAAATTGAGCTGGACCTCACCAAGCTGC TGTGGCCATCAACCTCTGTATTTGAATCAGCCTACAGGCCTCACACACAATGTGTCTGAGAGA TTCATGCTGATTGTTATTGGGTATCACCACTGCAGAGCCTCC TTTCTGGCTTTGGAAGCCATGTGATTCCATCTTGCCCGCTCAGGCTGACCACTTTATTTCTTTTT GTTCCCCTTTGCTTCATTCAAGTCAGCTCTTCTCCATCCTACCACAATGCAGTGCCTTTCTTCTCT CCAGTGCACCTGTCATATGCTCTGATTTATCTGAGTCAACTCCTTTCTCATCTTGTCCCCAACAC CCCACAGAAGTGCTTTCTTCTCCCAATTCATCCTCACTCAGTCCAGCTTAGTTCAAGTCCTGCCT CTTAAATAAACCTTTTTGGACACACAAATTATCTTAAAACTCCTGTTTCACTTGGTTCAGTACCA |

TABLE 13-continued

Subtyping Target Sequences

| SEQ ID NO. | Gene | Affy Probeset ID | Sequence |
|---|---|---|---|
| | | | CATGGGTGAACACTCAATGGTTAACTAATTCTTGGGTGTTTATCCTATCTCTCCAACCAGATTG<br>TCAGCTCCTTGAGGGCAAGAGCCACAGTATATTTCCCTGTTTCTTCCACAGTGCCTAATAATAC<br>TGTGGAACTAGGTTTTAATAATTTTTTAATTGATGTTGTTATGGGCAGGATGGCAACCAGACC<br>ATTGTCTCAGAGCAGGTGCTGGCTCTTTCCTGGCTACTCCATGTTGGCTAGCCTCTGGTAACCT<br>CTTACTTATTATCTTCAGGACACTCACTACAGGGACCAGGGATGATGCAACATCCTTGTCTTTT<br>TATGACAGGATGTTTGCTCAGCTTCTCCAACAATAAGAAGCACGTGGTAAAACACTTGCGGAT<br>ATTCTGGACTGTTTTTAAAAAATATACAGTTTACCGAAAATCATATAATCTTACAATGAAAAGG<br>ACTTTATAGATCAGCCAGTGACCAACCTTTTCCCAACCATACAAAAATTCCTTTTCCCGAAGGA<br>AAAGGGCTTTCTCAATAAGCCTCAGCTTTCTAAGATCTAACAAGATAGCCACCGAGATCCTTA<br>TCGAAACTCATTTTAGGCAAATATGAGTTTTATTGTCCGTTTACTTGTTTCAGAGTTTGTATTGT<br>GATTATCAATTACCACACCATCTCCCATGAAGAAAGGGAACGGTGAAGTACTAAGCGCTAGA<br>GGAAGCAGCCAAGTCGGTTAGTGGAAGCATGATTGGTGCCCAGTTAGCCTCTGCAGGATGTG<br>GAAACCTCCTTCCAGGGGAGGTTCAGTGAATTGTGTAGGAGAGGTTGTCTGTGGCCAGAATT<br>TAAACCTATACTCACTTTCCCAAATTGAATCACTGCTCACACTGCTGATGATTTAGAGTGCTGT<br>CCGGTGGAGATCCCACCCGAACGTCTTATCTAATCATGAAACTCCCTAGTTCCTTCATGTAACT<br>TCCCTGAAAAATCTAAGTGTTTCATAAATTTGAGAGTCTGTGACCCACTTACCTTG |
| 1160 | CXCL9 | 2773950 | AAGTTCTGAAAGTTCGAAAATCTCAACGTTCTCGTCAAAAGAAGACTACATA |
| 1161 | CXCL9 | 2773951 | CTGAAGAATGGAGTTCAAACATGTCTAAACCCAGATTCAGCAGATGTGA |
| 1162 | CXCL9 | 2773952 | AGAAAGGGTCGCTGTTCCTGCATCAGCACCAACCAAGGGACTATCCACCTACAATCCTTGAAA<br>GACCTTAAACAATTTGCCCCAAGCCCTTCCTGCGAGAAAATTG |
| 1163 | CXCL9 | 2773953 | CCTCTTGGGCATCATCTTGCTGGTTCTGATTGGAGTGCAAG |
| 1164 | CXCL10 | 2773961 | TTCCAAGGATGGACCACACAGAGGCTGCCTCTCCCATCACTTCCCTACATGGAGTATATGTCA<br>AGCCATAATTGTTCTTAGTTTGCAGTTACACTAAAAGGTGACCAATGATGGTCACCAAATCAG<br>CTGCTACTACTCCTGTAGGAAGGTTAATGTTCATCATCCTAAGCTATTCAGTAATAACTCTACC<br>CTGGCACTATAATGTAAGCTCTACTGAGGTGCTATGTTCTTAGTGGATGTTCTGACCCTGCTTC<br>AAATATTTCCCTCACCTTTCCCATCTTCCAAGGGTACTAAGGAATCTTTCTGCTTTGGGGTTTAT<br>CAGAATTCTCAGAATCTCAAATAACTAAAAGGTATGCAATCAAATCTGCTTTTTAAAGAATGCT<br>CTTTACTTCATGGACTTCCACTGCCATCCTCCCAAGGGGCCCAAATTCTTTCAGTGGCTACCTA<br>CATACAATTCC |
| 1165 | CXCL10 | 2773963 | AAGAGATGTCTGAATCCAGAATCGAAGGCCATCAAGAATTTACTGAAAGCAGTTAGCAAGGAA |
| 1166 | CXCL10 | 2773966 | AACTTGAAATTATTCCTGCAAGCCAATTTTGTCCACGTGTTGAG |
| 1167 | CXCL10 | 2773967 | TACCTGCATCAGCATTAGTAATCAACCTGTTAATCCAAGGTCTTTAG |
| 1168 | CXCL10 | 2773970 | TGCCATTCTGATTTGCTGCCTTATCTTTCTGACTCTAAGTGGCATTCAAG |
| 1169 | CXCL10 | 2773971 | ATTGCTTAGACATATTCTGAGCCTACAGCAGAGGAACCTCCAGTCTCAGCAC |
| 1170 | SPARCL1 | 2777118 | CAGCTGTGATACTTGTAGATTTATATTTAGCAAAATGTTAGCATGTATGACAAGACAATGAGA<br>GTAATTGCTTGACAACAACCTATGCACCAGGTATTTAACATTAACTTTGGAAACAAAAATGTA<br>CAATTAAGTAAAGTCAACATATGCAAAATACTGTACATTGTGAACAGAAGTTTAATTCATAGT<br>AATTTCACTCTCTGCATTGACTTATGAGATAATTAATGATTAAACTATTAATGATAAAAATAAT<br>GCATTTGTATTGTTCATAATATCATGTGCACTTCAAGAAAATGGAATGCTACTCTTTTGTGGTT<br>TACGTGTA |
| 1171 | SPARCL1 | 2777124 | TGCTCCTCTGCGAGCATCTCTGGTGCCCATGGAACACTGCATAACCCGTTTCTTTGAGGAGTG<br>TGACCCCAACAAGGATAAGCACATC |
| 1172 | SPARCL1 | 2777125 | TGATCTTCTCTTAAGGGACTTTAAGAAAAACTACCACATGTATGTGTATCCTGTGCACTGGCA<br>GTTTAGTGAACTTGACCAACACCCTATGGATA |
| 1173 | SPARCL1 | 2777126 | CCTACTTGTACGGACTTTGAAGTGATTCAGTTTCCTCTACGGATGAGAGACTGGCTCAAGAAT<br>ATCCTCATGCAGCTTTATGAAGCCAACTCTGAACACGCTGGTTATCTAAATGAGA |
| 1174 | SPARCL1 | 2777131 | TGTGGCACTGACAATCAGACCTATGCTAGTTCCTGTCATCTATTCGCTACTAAATGCAGACTGG<br>AGGGGACCAAAAAGGGGCATCAACTCCAGCTGGATTATTTTGGAGCCTGCA |
| 1175 | SPARCL1 | 2777132 | TCTTGCATGAGCTTCCAGTGTAAAAGAGGCCACATCTGTAAGGCAGACCAACAGGGAAACC<br>TCACTGTGTCTGCCAGGATCCAGTGACTTGTCCTCCAACA |
| 1176 | SPARCL1 | 2777133 | AGCAGAGAACTCATCAAATGAGGAGGAAACGTCAAGTGAAGGCAACATGAGGGTGCATGCT |
| 1177 | SPARCL1 | 2777136 | CCACGCCCAGAAATCATGGAGTTGATGATGATGGCGATGATGATGGCGATGATGGCGGCACT<br>GATGGCCCCAGGCACAGTGCAAGTGATGACTACTTCATCCCAAGCCAGGCCTTTCTGGAGGC<br>CGAGAGAGCTCAATCCATTGC |

TABLE 13-continued

Subtyping Target Sequences

| SEQ ID NO. | Gene | Affy Probeset ID | Sequence |
|---|---|---|---|
| 1178 | SPARCL1 | 2777137 | GAAGCTATCAGCAACCACAAAGAGACAGAAGAAAAGACTGTTTCTGAGGCTCTGCTCATGGA ACCTACTGATGATG |
| 1179 | SPARCL1 | 2777138 | TAGCCAAGGCCTAAGGGATCAAGGAAACCAAGAGCAGGATCCAAATATTTCCAATGGAGAA GAGGAAGAAGAAAAAGAGCCAGGTGAAGTTGGTACCCACAATGATAACCAAGAAAGAAAG ACAGAATTGCCCAGGGAGCATGCTAACAGCAAGCAGGAGGAAGACAATACCCAATCTGATG ATATTTTGGAAGAGTCTGATCAACCAACTCAAGTAAGCAAGATGCAGGAGGATGAATTTGAT CAGGGTAACCAAGAACAAGAAGATAACTCCAATGCAGAAATGGAAGAGGAAAATGCATCGA ACGTCAATAAGCACATTC |
| 1180 | SPARCL1 | 2777139 | TGGAGTATGCACCAACTGAAGGTACATTGGACATAAAAGAAGATATGAGTGAGCCTCAGGA GAAAAAACTCTCAGAGAACACTGATTTTTTGGCTCCTGGTGTTAGTTCCTTC |
| 1181 | SPARCL1 | 2777140 | TCATCAGTACTAAAGTCAAAAGAGGAAAGCCATGAACAGTCAGCAGAACAGGGCAAGAGTT CTAGCCAAGAGCTGGGATTGAAGGATCAAGAGGACAGTGATGGTCACTTAA |
| 1182 | SPARCL1 | 2777141 | CAGTATCCACAGAAGACGATTCCCACCATAAG |
| 1183 | SPARCL1 | 2777142 | CAACTGCTGAAACGGTAGCACCTGACAACACTGCAATCCCCAGTTTAAGGGCTG |
| 1184 | SPARCL1 | 2777143 | CAAGATTATTATCTGATCATTCCAAAC |
| 1185 | SPARCL1 | 2777144 | CCTATGTCTCTTGGGAACTGCAGCTG |
| 1186 | SPARCL1 | 2777159 | TGGCTCTGGGTCCAGCCCCTTACTTAA |
| 1187 | SPARCL1 | 2777160 | TTCCCTTTTGGTTTGCAAGCACTGCCTGTAAAGCCCTCGCATGAGAGGCCAGCCTGCTAGGGA AATCCAGGAATCTGCAACAAAAACGATGACAGTCTGAAATACTCTCTGGTGCCA |
| 1188 | SFRP2 | 2790370 | ATTGACTTGAGTACTTTAAGCCTTGTT |
| 1189 | SFRP2 | 2790371 | TAGGTGCAACTGTGACTTGGGTCTGGTTGGTTGTTGTTTGTTGTTTTGAGTCAGCTGATTTTCA CTTCCCACTGAGGTTGTCATAACATGCAAATTGCTTCAATTTTCTCTGTGGCCCAAACTTGTGG GTCACAAACCCTGTTGAGATAAAGCTGGCTGTTATCTCAACATCTTC |
| 1190 | SFRP2 | 2790372 | GCTGACCATTTCTGCTCCGGGATCTCAGCTCCCGTTCCCAAGCACACTCCTAGCTGCTCCAGT CTCAGCCTGGGCAGCTTCCCCCTGCCTTTTGCACGTTTGCATCCCCAGCATTTCCTGAGTTATA AGGCCACAGGAGTGGATAGCTGTTTTCACCTAAAGGAAAAGCCCACCCGAATCTTGTAGAAA TA |
| 1191 | SFRP2 | 2790373 | TGATCACCTCGGTGAAGCGGTGGCAGAAGGGGCAGAGAGAGTTCAAGCGCATCTCCCGCAG CATCCGCAAGCTGCAGTGCTA |
| 1192 | SFRP2 | 2790374 | AGGAGATAACCTACATCAACCGAGATACCAAAATCATCCTGGAGACCAAGAGCAAGACCATT TACAAGCTGAACGGTGTGTCCGAAAGGGACCTGAAGAAATCGGTGCTGTGGCTCAAAGACA GCTTGCAGTGCACCTGTGAGGAGATGAACGACATCAACGCGCCCTATCTGGTCATGGGACA |
| 1193 | SFRP2 | 2790378 | TGATGACAACGACATAATGGAAACGCTTTGTAAA |
| 1194 | SFRP2 | 2790379 | CTGTGCCACGGCATCGAATACCAGAACATGCGGCTGCCCAACCTGCTGGGCCACGAGACCAT GAAGGAGGTGCTGGAGCAGGCCGGCGCTTGGATCCCGCTGGTCATGAAGCAGTGCCACCCG GACACCAAGAAGTTCCTGTGCTCGCTCTTCGCCCCCGTCTGCCTCGATGACCTAGACGAGACC ATCCAGCCATGCCACTCGCTCTGCGTGCAGGTGAAGGACCGCTGCGCCCCGGTCATGTCCGCC TTCGGCTTCCCCTGGCCCGACATGCTTGAGTGCGACCGTTTC |
| 1195 | SFRP2 | 2790380 | TGCTGCAGGGCCCTGGCTCGCTGCTGCTGCTCTT |
| 1196 | SFRP2 | 2790381 | AGCGGGCCCGGGACAAGCTCGAACTCCGGCCGCCTC |
| 1197 | SFRP2 | 2790382 | AGCTGCGCGCGGGCTTGCAGCGCCTCGCCCGCGCTGTCCTCCCGGTGTCCCGCTTCTCCGCGC CCCAGCCGCCGGCTGCCAGCTTTTCGGGGCCCCGAGT |
| 1198 | HPGD | 2794410 | TCTCTGGTGTATACTGATTGAGAAAATAATTAAACTGA |
| 1199 | HPGD | 2794411 | ATACACCTGCTTTGGGTAAAACTCTTTGCAAGCAGTAATTAACACTAGTAACAGTGAAAGCAC AAGATTTCCAAATCAGTCGTTTTCTCAAAAAAATATCGTATAAGTGACTCATCCTGTCTGCTAA CTCCAGACCTCCCAGCTTGAAGCCAAATCTTTCCATGTGAGATTGATATGGATTCCTAGAAGT ACTGGAATGTTGTCATATCTTGCCCTATTTTAATTCTGCTATAGAAAACAATTGCCTTCACTTTT AAGGAGTAATTTGAATATTAATAACTCTGGTCTAGATTTTCATATAATGTATTAAAGACAAAGT AGTGAACATCAATGAACATCTGATAGAGATAAACTGTAATCAGGCATAAGCTTGTTTGTATGT TCTGGCAGTGACTAATCAGTAAATGATGTCGGTTTGCCCAGTATCACTTATC |
| 1200 | HPGD | 2794412 | TTACTTAGTCTTCTATGTATAGCTATCAAGGA |

TABLE 13-continued

Subtyping Target Sequences

| SEQ ID NO. | Gene | Affy Probeset ID | Sequence |
|---|---|---|---|
| 1201 | HPGD | 2794413 | TGCACTTGGTGATAAACGTTTTCTAAATTTTTAGTTAAGTATATGGATAAAAAGTTATGAACTA<br>TTAAAAATGTGATGTGGACCAAAGGCTAGGTTGTAATCTTGATAGTCTAAAAAATGATCAAAA<br>CAAATGATTTTCAAGGAATATTCAATATTCTGCCTTTCAGAAAGTGTATTTATATCTGTGCTTCA<br>TAAATATTAATGTTCTTCAGAACATCATTTTAAAGGAGATACTTGAATTGTTATTTAAATCAAA<br>CCAGATGTAAAACACTCACATACAAGTTCATACTTTAAAAGAGGAAAGCTACTTAACAATGAC<br>AAATATTTCACAATAATAATTTTTACTTATATACCATCTTTCAACTGAACATTTCAGTTCTTCCAA<br>GAGCTTCTTAGAGTAGTATATTTTGGGGGCAGTCAAGGAATAAACTACAGTGTAAACATATCC<br>CAGATGAAAACTGCTGTATGGAAAAATGACAGAAAGTAACTGATTGACACTGTTGATTCACA<br>GTTCAGCCTCCTATCTG |
| 1202 | HPGD | 2794414 | TGCCAATGGATTGATAACACTCATTGAAGATGATGCTTTAAATGGTGCTATTATGAAGATCAC<br>AACTTCTAAGGGAATTCATTTTCAAGACTATGATACAACTCCATTTCAAG |
| 1203 | HPGD | 2794416 | TCTTATGAACAGTGGTGTGAGACTGAATGCCATTTGTCCAGGCTTTGTTAACACAGCCATCCTT<br>GAATCAATTGAAAAGAAGAAAACATGGGACAATATATAGAATATAAGGATCATATCAAGG |
| 1204 | HPGD | 2794417 | ATGCCCGTTGCACAGCAGCCGGTTTATTGTGCTTCAAAGCA |
| 1205 | HPGD | 2794423 | GACGATCTGGGAGAAATTCTTTACCATAA |
| 1206 | HPGD | 2794424 | AGCAAAGCTTGGAGTACCATGAATATTCTACAAGGAG |
| 1207 | HPGD | 2794425 | GGGCTGTGATCAAGATTGATAATTCTCTGTATTC |
| 1208 | HPGD | 2794426 | GTACCTGTGATTGAACCTCTGTCTGATTCTCAGCATTTGTCTCATCCCTCTAGGAATGATTATCA<br>AATGGTTCTTTTATATCACTGTAAAGCTGCCACCAGAGGAGATTTAGAAATCTCCTTTAGAAGT<br>TCTCAAAAATAGACTAGCATCTCATTTTCTGGGTCGCTTAAAGTCAAAATCATGTCCCTAAAGC<br>TATTACAAACCTATTTCTATAAATTTTTCAGGGTAATCAGATTCTTTTTCCTAGTGGTACAACTA<br>CTTATAAATTATAACATTTTAATCCTAATGATACTTTAAAAGGTGAGCGCACGGGCAATATTTG<br>AAAG |
| 1209 | HPGD | 2794427 | AGCTCCCAGGGTTACTTTAGAACTGCTGGATTCCTTTTTCTCTAGCAGAAAGAGAAGAAGAAC<br>ATGGAGGAGGCATGGCTACTCTTTTAAGAACCCCAGCCCAGTAATGGCAGACCTTCTGCTCAC<br>ATTTCAGTATAGAACTTGAGCTCATGTTTCACCTAACTGTAAGCGAGTCTGTCTGGGAAATGC<br>AGTCTAGCTGTGTGCCTAAGAGAAGAATGGATTTCAGAGGGCAGCTAATCATCTTTTC |
| 1210 | HPGD | 2794428 | ATCAGTGGAACCTATCTTGGTTTGGATTACATGAGTAAGCAAAATGGAGGTGAAGGCGGCAT<br>CATTATCAATATGTCATC |
| 1211 | HPGD | 2794432 | TAATGCTGGAGTGAATAATGAGAAA |
| 1212 | HPGD | 2794435 | TAGCGCTGGTGGATTGGAATCTTGAAGCAGGTGTACAGTGTAAAGCTGCCCTGGATGAGCAG<br>TTTGAACCTCAGAAGACTCTGTTCATCCAGTGCGATGTGGCTGACCAGCAACAACTGAGAG |
| 1213 | HPGD | 2794436 | TTGCCAAATTTCAGGTCCAGGAGGGGAGCCTCTTGTGTGTTTATTGTTTGTCCGTCTATTTCGT<br>GAGCTGCGCAGGCCCGCGATTCCTCTCCTCTTGTCTATA |
| 1214 | HPGD | 2794438 | ATGCACGTGAACGGCAAAGTGGCGCTGGTG |
| 1215 | HPGD | 2794439 | CTATCCAGTTGGTCTTTAGGGCACTGAAGGAAACTCTTCTTCAGAAATAACCTTTTAACTTTTC<br>TTCTGTCAGCTGCCTGCCAATCACGGAGCCAGAGGCTGAGGGGAGGCTTTGAGCCGGTCTGC<br>GAGTCCGGAAGGCAAAGATCGCGAAGCTTGGCGCTCCAGAACGCTCA |
| 1216 | VCAN | 2818523 | TCTTCTCGCTGAGTCTCCTCCTCGGCTCTGACGGTACAGTGATATAATGATGATGGGTGTCAC<br>AACCCGCATTTGAACTTGCA |
| 1217 | VCAN | 2818524 | CCGAGAACATTAGGTGTTGTGGACAGGAGCTGGGACCAAGATCTTCGGCCAGCCCCGCATCC<br>TCCCGCATCTTCCAGCACCGTCCCGCACCCTCCGCATCCTTCCCCGGGCCACCACGCTTCCTAT<br>GTGACCCGCCTGGGCAACGCCGAACCCAGTCGCGCA |
| 1218 | VCAN | 2818525 | TTCCCCCCAAACTGCAATAAGCCGCCTTCC |
| 1219 | VCAN | 2818529 | TAAAGAGCATCTTATGGATGTGTTCAACCTTAATAGTAACCCATGCGCTACATAAAG |
| 1220 | VCAN | 2818532 | TGGAAAAGTCAGCCTACCTTGTCATTTT |
| 1221 | VCAN | 2818533 | TGCCTACTTTGCCACCCAGTTACAACACCAGTGAATTTCTCCGCATCAAATGGTCTAAGATTGA<br>AGTGGACAAAAATGGAAAAGATTTGAAAGAGACTACTGTCCTTGTGGCCCAAAATGGAAATA<br>TCAAGATTGGTCAGGACTACAAAGGGAGAGTGTCTGTGCCCACACATCCCGAGGCTGTGGGC<br>GATGCCTCCCTCACTGTGGT |
| 1222 | VCAN | 2818534 | TGATGCGGGTCTTTACCGCTGTGACGTCATGTACGGGATTGAAGACACACAAG |

TABLE 13-continued

Subtyping Target Sequences

| SEQ ID NO. | Gene | Affy Probeset ID | Sequence |
|---|---|---|---|
| 1223 | VCAN | 2818535 | CAGGGCGGCAACCAGCAGGTACACACTGAATTTTGAGGCTGCTCAGAAGGCTTGTTTGGACG TTGGGGCAGTCATAGCAACTCCAGAGCA |
| 1224 | VCAN | 2818536 | ATCCCATCCGGGCTCCCAGAGTAGGCTGTTATGGAGATAAGATGGGAAAGGCAGGAGTCAG GACTTATGGATTCCGTTCTCCCCAGGAAACTTACGATGTGTATTGTTATGTGGATCATCTGGA |
| 1225 | VCAN | 2818543 | GGAACGGCTTTGACCAGTGCGATTACGGGTGGCTGTCGGATGCCAGCGTGCGCCACCCTGTG ACTGTGGCCAGGGCCCAGTGTGGAGGTGGTCTACTTGGGGTGAGAACCCTGTATCGTTTTGA GAACCAGACAGGCTTCCCTCCCCCTGATAGCAGATTTGATGCCTAC |
| 1226 | VCAN | 2818544 | CAACTAGCCGTTGGAGTGGATTCCATGTCTTGCAGTGTGTGCACGGAATGGAAACAGTTCAG TGATTTTCAAAAGCAAGCAAACTGAACAGCAGTGATATGGTTAAAACCACAGGAATTTTGGC AAATGGATTTTTAGAGGGGTGAGGAAATATCAGGTTAAGCTGTAACTGTGCTCTGTTGTGTCC AGAGCCACAGAGCATTTTTCTAAGTATTTTATATTAATTGCAGTCCTTAAGTTTTGCAATTTGTT TATTGGTGTTACAATGCCAAGGCCAACTGAGGCTGAGTTAAATCCTTA |
| 1227 | VCAN | 2818549 | CCTCCCGTGGGAAATATTGTCAGTTTTGAACAGAAAGCCACAGTCCAACCTCAGGCTATCACA GATAGTTTAGCCACCAAATTACCCACACCTACTGGCAGTACCAAGAAGCCCTGGGATATGGAT GACTACTCACCTTCTGCTTCAGGACCTCTTGGAAAGCTAGACATATCAGAAATTAAGGAAGAA GTGCTCCAGAGTACAACTGGCGTCTCATTATGCTACGGATTCATGGGATGGTGTCGTGGAA GATAAACAAACACAAGAATCGGTTACACAGATTGAACAAATAGAAGTGGGTCCTTTGGTAAC ATCTATGGAAATCTTAAAGCACATTCCTTCCAAGGAATTCCCTGTAACTGAAACACCATTGGTA ACTGCAAGAATGATCCTGGAATCCAAAACTGAAAAGAAAATGGTAAGCACTGTTTCTGAATT GGTAACCACAGGTCACTATGGATTCACCTTGGGAGAAGAGGATGATGAAGACAGAACACTTA CAGTTGGATCTGATGAGAGCACCTTGATCTTTGACCAAATTCCTGAAGTCATTACGGTGTCAA AGACTTCAGAAGACACCATCCACACTCATTTAGAAGACTTGGAGTCAGTCTCAGCATCCACAA CTGTTTCCCCTTTAATTATGCCTGATAATAATGGATCATCCATGGATGACTGGGAAGAGAGAC AAACTAGTGGTAGGATAACGGAAGAGTTTCTTGGCAAATATCTGTCTACTACACCTTTTCCATC ACAGCATCGTACAGAAATAGAATTGTTCCTTATTCTGGTGATAAAATATTAGTAGAGGGAAT TTCCACAGTTATTTATCCTTCTCTACAAACAGAAATGACACATAGAAGAGAAAGAACAGAAAC ACTAATACCAGAGATGAGAACAGATACTTATACAGATGAAATACAAGAAGAGATCACTAAAA GTCCATTTATGGGAAAAACAGAAGAAGAAGTCTTCTCTGGGATGAAACTCTCTACATCTCTCT CAGAGCCAATTCATGTTACAGAGTCTTCTGTGGAAATGACCAAGTCTTTTGATTTCCCAACATT GATAACAAAGTTAAGTGCAGAGCCAACAGAAGTAAGAGATATGGAGGAAGACTTTACAGCA ACTCCAGGTACTACAAAATATGATGAAAATATTACAACAGTGCTTTTGGCCCATGGTACTTTA AGTGTTGAAGCAGCCACTGTATCAAAATGGTCATGGGATGAAGATAATACAACATCCAAGCC TTTAGAGTCTACAGAACCTTCAGCCTCTTCAAAATTGCCCCCTGCCTTACTCACAACTGTGGGG ATGAATGGAAAGGATAAAGACATCCCAAGTTTCACTGAAGATGGAGCAGATGAATTTACTCT TATTCCAGATAGTACTCAAAAGCAGTTAGAGGAGGTTACTGATGAAGACATAGCAGCCCATG GAAAATTCAACAATTAGATTTCAGCCAACTACATCAACTGGTATTGCAGAAAAGTCAACTTTGA GAGATTCTACAACTGAAGAAAAAGTTCCACCTATCACAAGCACTGAAGGCCAAGTTTATGCAA CCATGGAAGGAAGTGCTTTGGGTGAAGTAGAAGATGTGGACCTCTCTAAGCCAGTATCTACT GTTCCCCAATTTGCACACACTTCAGAGGTGGAAGGATTAGCATTTGTTAGTTATAGTAGCACC CAAGAGCCTACTACTTATGTAGACTCTTCCCATACCATTCCTCTTTCTGTAATTCCCAAGACAGA CTGGGGAGTGTTAGTACCTTCTGTTCCATCAGAAGATGAAGTTCTAGGTGAACCCTCTCAAGA CATACTTG |
| 1228 | VCAN | 2818550 | CAGAAACCGATATTGATAGAGAGTATTTCACGACTTCAAGTCCTCCTGCTACACAGCCAACAA GACCACCCACTGTGGAAGACAAAGAGGCCTTTGGACCTCAGGCGCTTTCTACG |
| 1229 | VCAN | 2818556 | GGGTTGGCTCCGTCATAATGATTTCTCCTAAACACTTCTCAGGTTTGGCCTATGCATGTGTGTT ATAGATTGGGGATAGTTTGAAAACTCATTCTGTAGTATTATTCCTATGGGCAGGGTGGTGAGT AGTGTGTAAATTCTTTGTCTTCTTTATGGGTCAGTATATCCACAGGCACATTTTCATACTGCTTT GTCACTGAAAGTAAGGCAGCTGCAGTGGCAGGACCCTGTTCTAGGACAGTTGAATGCCTCTA TGATGAGACCTCAGA |
| 1230 | VCAN | 2818557 | AAAAGGCCATTGAGCTTAGTGGTTGGTACCATATGGCAATTTACAATCTGGGAAATATTCTGA TGATACATACTTTTCGAGGAATGCTA |
| 1231 | VCAN | 2818558 | ATCAGCCTAATCTGGGTCACATCCCAGGAAGGATAAAGGTCTATAGGTGTGGAAGGCTCTTT CTGGTCCTTTCAGTGAGCTATTTCAATAGAGCCCGCCTATCCAGAGCTTCCCACTCTTGTGCA TAGGATGTGGTTAAGCTCATGTCTCAGTGCCACAGTAGGTAGAGGATGCCATT |
| 1232 | VCAN | 2818559 | TCGAATGAGTGATTTGAGTGTAATTGGTCATCCAATAGATTCAGAATCTAAAGAAGATGAACC TTGTAGTGAAGAACAGA |
| 1233 | VCAN | 2818560 | GTGCATGATCTAATGGCTGAAATTTTACCTGAATTCCCTGACATAATTGAAATAGACCTATACC ACAGTGAAGAAAATGAAGAAGAAGAAGAAGAGTGTGCAAATGCTACTGATGTG |
| 1234 | VCAN | 2818561 | TGGGAAGCATCTCGTTACCACTGTGCCCAAGGACCCAGAAGCTGCAGAAGCTAGGCGTGGCC AGTTTGAAAGTGTTGCACCTTCTCAGAATTTCTCGGACAGCTCTGAAAGTGATACTCATCCATT TGTAATAGCCAAAACGGAATTGTCTACTGCTGTGCAACCTAATGAATCTACAGAAACAACTGA GTCTCTTGAAGTTACATGGAAGCCTGAGACTTACCCTGAAACATC |

TABLE 13-continued

Subtyping Target Sequences

| SEQ ID NO. | Gene | Affy Probeset ID | Sequence |
|---|---|---|---|
| 1235 | VCAN | 2818562 | GCTCTCAGGGAGTTCTTCGATTCCAATTACAGAAGGCTCTGGAGAAGCAGAAGAAGATGAAGATACAATGTTCACCATGGTAACTGATTTATCACAGAGAAATACTACTGATACACTCATTACTTTAGACACTAGCAGGATAATCACAGAAAGCTTTTTTGAGGTTCCTGCAACCACCATTTATCCAGTTTCTGAACAACCTTCTGCAAAAGTGGTGCCTACCAAGTTTGTAAGTGAAACAGACACTTCTGAGTGGATTTCAGTACCACTGTTGAGGAAAAGAAAAGGAAGGAGGAGGAGGGAACTACAGGTACGGCTTCTACATTTGAGGTATATTCATCTACACAGAGATCGGATCAATTAATTTTACCCTTTGAATTAGAAAGTCCAAATGTAGCTACATCTAGTGATTCAGGTACCAGGAAAAGTTTTATGTCCTTGACAACACCAACACAGTCTGAAAGGGAAATGACAGATTCTACTCCTGTCTTTACAGAAACAAATACATTAGAAAATTTGGGGGCACAGACCACTGAGCACAGCAGTATCCATCAACCTGGGGTTCAGGAAGGGCTGACCACTCTCCCACGTAGTCCTGCCTCTGTCTTTATGGAGCAGGGCTCTGGAGAAGCTGCTGCCGACCCAGAAACCACCACTGTTTCTTCATTTTCATTAAACGTAGAGTATGCAATTCAAGCCGAAAAGGAAGTAGCTGGCACTTTGTCTCCGCATGTGGAAA |
| 1236 | VCAN | 2818563 | CCCTGGGAAGAGTTTACATCCTCAGCTGAGGGCTCAG |
| 1237 | VCAN | 2818564 | TGAGCAACTGGTCACAGTCAGCAGCTCTGTTGTTCCAGTGCTTCCCAGTGCTGTGCAAAAGTTTTCTGGTACAGCTTCCTCCATTATCGACAAGGATTGGGAGAAGTGGGTACTGTCAATGAAATTGATAGAAGATCCACCATTTTACCAACAGCAGAAGTGGAAGGTACGAAAGCTCCAGTAGAGAAGGAGGAAGTAAAGGTCAGTGGCACAGTTTCAACAAACTTTCCCCAAACTATAGAGCCAGCCAAATTATGGTCTAGGCAAGAAGTCAACCCTG |
| 1238 | VCAN | 2818565 | GGTCCACAGACGGTAGTTTCCAAGACCGTTTCAGGGAATTCGAGGATTCCACCTTAAAACCTAACAGAAAAAAACCCACTGAAAATATTATCATAGACCTGGACAAAGAGGACAAGGATTTAATATTGACAATTACAGAGAGTACCATCCTTGAAATTCTACCTGAGCTGACATCGGATAAAAATACTATCATAGATATTGATCATACTAAACCTGTGTATGAAGACATTCTTGGAATGCAAACAGATATAGATACAGAGGTACCATCAGAACCACATGACAGTAATGATGAAAGTAATGATGACAGCACTCAAGTTCAAGAGATCTATGAGGCAGCTGTCAACCTTTCTTTAACTGAGGAAACATTTGAGGGCTCTGCTGATGTTCTGGCTAGCTACACTCAGGCAACACATGATGAATCAATGACTTATGAAGATAGAAGCCAACTAGATCACATGGGCTTTCACTTCACAACTGGGATCCCTGCTCCTAGCACAGAAACAGAATTAGACGTTTTACTTCCCACGGCAACATCCCTGCCAATTCCTCGTAAGTCTGCCACAGTTATTCCAGAGATTGAAGGAATAAAAGCTGAAGCAAAAGCCCTGGATGACATGTTTGAATCAAGCACTTTGTCTGATGGTCAAGCTATTGCAGACCAAAGTGAAATAATACCAACATTGGGCAATTTGAAAGGACTCAGGAGGAGTATGAAGACAAAAAACATGCTGGTCCTTCTTTTCAGCCAGAATTCTCTTCAGGAGCTGAGGAGGCATTAGTAGACCATACTCCCTATCTAAGTATTGCTACTACCCACCTTATGGATCAGAGTGTAACAGAGGTGCCTGATGTGATGGAAGGATCCAATCCCCCATATTACACTGATACAACATTAGCAGTTTCAACATTTGCGAAGTTGTCTTCTCAGACACCATCATCTCCCCTCACTATCTACTCAGGCAGTGAAGCCTCTGGACACACAGAGATCCCCCAGCCCAGTGCTCTGCCAGGAATAGACGTCGGCTCATCTGTAATGTCCCCACAGGATTCTTTTAAGGAAATTCATGTAAATATTGAAGCGACTTTCAAACCATCAAGTGAGGAATACCTTCACATAACTGAGCCTCCCTCTTTATCTCCTGACACAAAATTAGAACCTTCAGAAGATGATGGTAAACCTGAGTTATTAGAAGAAATGGAAGCTTCTCCCACAGAACTTATTGCTGTGGAAGGAACTGAGATTCTCCAAGATTTCCAAAACAAAACCGATGGTCAAGTTTCTGGAGAAGCAATCAAGATGTTTCCCACCATTAAAACACCTGAGGCTGGAACTGTTATTACAACTGCCGATGAAATTGAATTAGAAGGTGCTACACAGTGGCCACACTCTACTTCTGCTTCTGCCACCTATGGGGTCGAGGCAGGTGTGGTGCCTTGGCTAAGTCCACAGACTTCTGAGAGGCCCACGCTTTCTTCTTCTCCAGAAATAAACCCTGAAACTCAAGCAGCTTTAATCAGAGGGCAGGATTCCACGATAGCAGCATC |
| 1239 | VCAN | 2818568 | CTGATCGCTGCAAAATGAACCCGTGCCTTAACGGAGGCACCTGTTATCCTACTGAAACTTCCTACGTATGCACCTGTGTGCCAGGATACAGCGGAGACCAGT |
| 1240 | VCAN | 2818571 | TTGATGAATGTCACTCTAATCCCTGTCGTAATGGAGCCACTTGTGTTGATGGTTTTAACACATTCAGGTGCCTCTGCCTTCCAAGTTATGTTGGTGCACTTT |
| 1241 | VCAN | 2818572 | AAGGGCAGTGCTACAAATACTTTGCCCATCGACGCACATGGGATGCAGCTGAACGGGAATGCCGTCTGCAGGGTGCCCATCTCACAAGCATCCTGTCTCACGAAGAACAAATGTTTG |
| 1242 | VCAN | 2818573 | CCATGATTATCAGTGGATAGGCCTCAATGACAAGATGTTTGAGCATGACTTCCGTTGGACTGATGGCA |
| 1243 | VCAN | 2818577 | TACGAGAATTGGAGACCCAACCAGCCAGACAGCTTCTTTTCTGCTGGAGAAGACTGTGTTGTAATCATTTGGCATGAGAATGGCCAGTGGAATGATGTTCCCTGCAATTACCATCTCACCTATACGTGCAAGAAAGGAACA |
| 1244 | VCAN | 2818578 | ACCTCGTTATGAAATCAACTCCCTGATTAGATACCACTGCAAAGATGGTTTCATTCAACGTCACCTTCCAACTATCCGGTGCTTAGGAAATGGAAGATGGGCTATACCTAAAATTACCTGCATG |
| 1245 | VCAN | 2818579 | GTGGTCCTTTAGAAAGAATGGACTACCGTGCTATAACAACTACTA |
| 1246 | VCAN | 2818580 | TTTTACGGCTGTGGTATCGGCAGTTTAGGGTATGGAGCAA |
| 1247 | VCAN | 2818581 | ATACCAAAGGACTTATTCTATGAAATACTTTAAAAATTCCTCATCAGCAAAGGACAATTCAATAAATACATCCAAACATGATCATCGTTGGAGCCGGAGGT |

TABLE 13-continued

Subtyping Target Sequences

| SEQ ID NO. | Gene | Affy Probeset ID | Sequence |
|---|---|---|---|
| 1248 | VCAN | 2818582 | CCTATCACCTCGAGAAGTAATTATCAGTTGGTTTGGATTTTTGGACCACCGTTCAGTCATTTTG GGTTGCCGTGCTCCCAAAACATTTTAAATGAAAGTATTGGCATTCAAAAAGACAGCAGACAAA ATGAAAGAAAATGAGAGCAGAAAGTAAGCATTTCCAGCCTATCTAATTTCTTTAGTTTTCTATT TGCCTCCAGTGCAGTCCATTTCCTAATGTATACCAGCCTACTGTACTATTTAAAATGCTCAATTT CAGCACCGATGGCCATGTAAATA |
| 1249 | VCAN | 2818583 | CTCAGCCATAGGTGCAGTTTGCTTCTACATGATGCTAAAGGCTGCGAATGGGATCCTGATGGA ACTAAGGACTCCAATGTCGAACTCTTCTTTGCTCATTCCTTTTTCTTCACTTACAAGAAAGGCC TGAATGGAGGACTTTTCTGTAACCAGGAACATTTTTTAGGGGTCAAAGTGCTAATAATTAACT CAACCAGGTCTACTTTTTAATGGCTTTCATAACACTAACTCATAAGGTTACCGATCAATGCATT TCATACGGATATAGACCTAGGGCTC |
| 1250 | VCAN | 2818584 | GTGTTAGCCTTTTACTTTCCTCACACAATTTGGAATCATATAATATAGGTACTTTGTCCCTGATT AAATAATGTGACGGATAGAATGCATCAAGTGTTTATTATGAAAAGAGTGGAAAAGTATATAG CTTTTAGCAAAAGGTGTTTGCCCATTCTAAGAAATGAGCGAATATATAGAAATAGTGTGGGCA TTTCTTCCTGTTAGGTGGAGTGTA |
| 1251 | VCAN | 2818585 | GGCACAAAGGGATTGGCCCAATATTGATTCTTTTTTTATAAAACCTCCTTTGGCTTAGAAGGA ATGACTCTAGCTACAATAATACACAGTATGTTTAAGCAGGTTCCCTTGGTTGTTGCATTAAATG TAATCCACCTTTAGGTATTTTAGAGCACAGAACAACACTGTGTTGATCTAGTAGGTTTC |
| 1252 | TGFBI | 2829948 | GGAGGCGCTCTCACTTCCCTGGAGCCGCCCGCTTGCCCGTCGGTCGCTAGCTCGCTCGGTGCG CGTCGT |
| 1253 | TGFBI | 2829949 | CTCTTCGTGCGGCTGCTGGCTCTCGCCCTGGCTCTG |
| 1254 | TGFBI | 2829950 | GCCGCGACCCTGGCGGGTCCCGCCAAG |
| 1255 | TGFBI | 2829951 | GTGCTGCAGCACAGCAGGCTCCGGGGCCGCCAGC |
| 1256 | TGFBI | 2829952 | GTGCAGAAGGTTATTGGCACTAATAGGAAGTACTTCACCAACTGCAAGCAGTGGTACCAAAG GAAAAT |
| 1257 | TGFBI | 2829958 | GTCATCAGCTACGAGTGCTGTCCTGGATATGAAAGGTCCCTGGGGA |
| 1258 | TGFBI | 2829959 | CTACCACTCTCAAACCTTTACGAGACCCTGGGAGTCGTTGGATCCACCACCACTC |
| 1259 | TGFBI | 2829960 | GAGGGGCCCGGCAGCTTCACCATCTTCGCCCCTAGCAACGAGGCCTGGGCC |
| 1260 | TGFBI | 2829961 | ATGACCTCCGTCTGCCCGGGGACT |
| 1261 | TGFBI | 2829962 | TCTTACCAGGTTGCGTCTAATGCCCCCGTTCCCTACTGGGCAGAAAGACTTGGGTGCTTCCT GAGGAGGGATCCTTGGCAGAAGAGAGGCCTGGGCTCACGAGGGCTGAGAACATGTTTCCCA GAGTTGCAAGGACCCATCTCTTAAACACAGAGTCTGCAGCC |
| 1262 | TGFBI | 2829963 | GCAATGTCAACATTGAGCTGCTCAATGCCCTCCGCTACCATATGGTGGGCAGGCGAGTCCTGA CTGATGAGCTGAAACACGGCATGACCCTCACCTCTATGTA |
| 1263 | TGFBI | 2829964 | TGCTGAAAGCCGACCACCATGCAACCAACGGGGTGGTGCACCTCATCGATAAGGTCATCTCC ACCATCACCAACAACATCCAGCAGATCATTGAGATCGAGGACACCTTTG |
| 1264 | TGFBI | 2829965 | GACATTCAGCTTGACCTAACCTGTGAAATTCTCCATCTTCTTTATAAAGTGTTCCCTTCCTTGCC TCCCCTGGAAAGGTCAGTGGTGTGTGGCTGCAGCAGCACAGTGTCCTCTGAGCCCTGGACCT GCACTGTGGCTTCCAGAGGTGGCAGTTCCCACATGGGGTACTAGAATAAATG |
| 1265 | TGFBI | 2829966 | AGAAAATGATGTTCCCACATAGTTGGCAGCACGTGAACAGCAATTGATCCC |
| 1266 | TGFBI | 2829967 | CATCAGGGCTCAACACGATGCTTGAAGGTAACGGCCAGTACACGCTTTTGGCCCCGACCAAT GAGGCCTTCGAGAAGATCCCTAGTGAGACTTTGAACCGTATCCTGGGCGACCCAGA |
| 1267 | TGFBI | 2829968 | TGCCTCATTTGTGCAGCTAGATTGAGCCCAAGACCTGCTCTGGTCCAAGATGAACATACCACC TGCCATGAGGTGACCCTCAGGATATCCACTGCAGCCATGGGCTGGGGTCATCCTGTCCTGTTG CTTCAGCTAACCGTGTCTCTAGCAGCCACACTACTCTGAGGG |
| 1268 | TGFBI | 2829973 | GCAGCGGGACATGCTCACTATCAACGGGAAGGCGATCATCTCCAATAAAGACATCCTAGCC ACCAACGGGGTGATCCACTACATTGATGA |
| 1269 | TGFBI | 2829974 | GAGTCTGATGTGTCCACAGCCATTGACCTTTTCAGACAAGCCGGCCTCGGCAATCATCTCTCT GGAAGTGAGCGGTTGACC |
| 1270 | TGFBI | 2829975 | ATCTCTCTGGACCTAACCATCACCCTT |
| 1271 | TGFBI | 2829976 | ACAAGGAATTTGCTTCGGAACCACATAATTAAAGACCAGCTGGCCTCTAAGTATCTGTACCAT GGACAGACCCTGGAAACTCTGGGCGGCAAAAAACTGAGAGTT |

TABLE 13-continued

Subtyping Target Sequences

| SEQ ID NO. | Gene | Affy Probeset ID | Sequence |
|---|---|---|---|
| 1272 | TGFBI | 2829977 | GTTCTGGGTCCTAAATCATGCTCCTGGGAAGCTCCTTACTGTGGGACTTGTATTAGTGTAAAA AAAAATGTCCTCAATAAGCAGGAGTTTGC |
| 1273 | TGFBI | 2829978 | AAGTACAACTCAACATAGCTCTTGCCTGGGACCAACCAGCACCATTTGGCTAA |
| 1274 | TGFBI | 2829979 | CAGCCTTAATAACCCATCCCAGTGTATACTCCTTCATCTTCATGGATAATGACCCTGCTACATG CTCTGAACAAATCAGGAGGCCCCTCGTGGAAGTATAACCA |
| 1275 | TGFBI | 2829980 | AGAACAGCTGCATCGCGGCCCACGACAAGAGGGGGAGGTACGGGACCCTGTTCACGATGGA CCGGGTGCTGACCCCCCCAATGGGGACTGTCATGGATGTCCTGAAGGGAGACAATCGCTTTA |
| 1276 | TGFBI | 2829982 | GCTGGTAGCTGCCATCCAGTCTGCAGGACTGACGGAGACCCTCAACCGGGAAGGAGTCTACA CAGTCTTTGCTCCCACAAATGAAGCCTTCCGAGCCCTGCCA |
| 1277 | TGFBI | 2829983 | AGATTTGTGGTCATGAACATGTGCTTTGTGTCCTCTGACCATTAGACAGATT |
| 1278 | TGFBI | 2829984 | AGATGCCAAGGAACTTGCCAACATCCTGAAATACCACATTGGTGATGAAATCCTGGTTAGCG GAGGCATCGGGGCCCTGGTGCGGCTAAAGTCTCTCCAAGGTGACAAGCT |
| 1279 | TGFBI | 2829986 | GTGTCAACAAGGAGCCTGTTGCCGAGCCTGACATCATGGCCACAAATGGCGTGGTCCATGTC ATCACCAATGTTCTGCAGCCTC |
| 1280 | TGFBI | 2829988 | TGCCTCTCCTCATGTGTGCATTCACCTTTCTTGGTGCTCTCTCCCCATGGGCCAAGTTCTACCAT GAGTTATGAAACATTATGGAGAAAACATGTCTTTGGAAATGTGAGCCAGAAAGCCCACCAGT GCCCCTCAGTCACGGTTGTTATGAATGACATGCTAATGGTTTCACTCTGGTCAAACCTGCCTTT |
| 1281 | TGFBI | 2829989 | CCAACAGACCTCAGGAAAGAGGGGATGAACTTGCAGACT |
| 1282 | TGFBI | 2829992 | GGAGGAATGCACCACGGCAGCTCTCCGCCAATTTCTCTCAGATTTCCACAGAGACTGTTTGAA TGTTTTCAAAACCAAGTATCACACTTTAATGTACATGGGCCGCACCATAATGAGATGTGAGCC TTGTGCATGTGGGGGAGGAGGGAGAGAGATGTACTTTTTAAATCATGTTCCCCCTAAACATG GCTGTTAACCCACTGCATG |
| 1283 | TGFBI | 2829993 | TTCCAGAGAGGACCTATCCCAAATGTGGAATTGACTGCCTATGCCAAGTCCCTGGAAAAGGA GCTTCAGTATTGTGGGGCTCATAAAACATGA |
| 1284 | TGFBI | 2829994 | TTTTGTAAAGCCCTTGCACAGCTGGAGAAATGGCATCATTATAAGCTATGAGTTGAAATGTTC TGTCAAATGTGTCTCACATCTACACGTGGCTTGGAGGCTTTTA |
| 1285 | TGFBI | 2829995 | TGGTATGTAGAGCTTAGATTTCCCT |
| 1286 | GABRP | 2840395 | TGCGGCTGCAGTCCAGGAATAGTCA |
| 1287 | GABRP | 2840398 | CTGCGTGTCCACATACGAGGGGACAGGGCTGAGGATGAGGAGAACCCTGGGGACCCAGAA GACCGTGCCTTGCCTGGAAGTCCTGCCTGTAGGCCTGAAGGACTTGCCCTAACAGAGCCTCAA CAACTA |
| 1288 | GABRP | 2840400 | CCTACTTCAGCCCCTTGGTGTGAGCAGCTTCTC |
| 1289 | GABRP | 2840401 | GGCCTTCGTGTGTCTGAGTCTCTTCACTG |
| 1290 | GABRP | 2840402 | AGTCAGTTCAACGTCGAGGTCGGCAGAAGTGACAAGCTTTCCCTGCCTGGCTTTGAGAACCTC ACAGCAGGATATAACAAATTTCTCAGGCCCAATTTTGG |
| 1291 | GABRP | 2840404 | GAGAACCCGTACAGATAGCGCTGACTCTGGACATTGCAAGTATCTCTAGCATT |
| 1292 | GABRP | 2840405 | GTAAGCGCTGTTCCTTTGTACTCTACCCAAGTAGTCCCTCTCTGTGTG |
| 1293 | GABRP | 2840406 | TACACAGCCACCATATACCTCCGACAGCGCTGGATGGACCAGCGGCTG |
| 1294 | GABRP | 2840407 | TCCTCTGGGTGCCAGATACTTACATTGTGGAGTCC |
| 1295 | GABRP | 2840408 | TGGGAAACAGGCTCATCCGCCTCTTCTC |
| 1296 | GABRP | 2840411 | CTGTTGCATGTAACATGGATCTGTCTAAATACCC |
| 1297 | GABRP | 2840415 | ACGACTCTGTGCGTGGACTGGAACACCTGCGGCTTGCTCAGTACACCATAGAGCGGTATTTCA CCTTAGTCACCAGATCGCAGCAGGAGA |
| 1298 | GABRP | 2840418 | TACACTAGATTGGTCTTACAGTTTGAGCTTCGGAGGAATGTTCTGTATTTCATTTTGGAAACCT ACGTTCCTTCCACTTTCCTGGTGGTGTTGTCCTGGGTTTCATTTTGGATCTCTCTCGATTCAGTC CCTGCA |

TABLE 13-continued

Subtyping Target Sequences

| SEQ ID NO. | Gene | Affy Probeset ID | Sequence |
|---|---|---|---|
| 1299 | GABRP | 2840419 | ACCACACTGATGATCGGGTCCCGCACTTCTCTTCCCAACACCAACTGCTTCATCAAGGCCATCG<br>ATGTGTACCTGGGGATCTGCTTTAGCTTTGTGTTTGGGGCCTTGCTAGAATATGCAGTTGCTC<br>ACTACAGTTCCTTACAGCAGATGGCA |
| 1300 | GABRP | 2840420 | CTCCAGCTTTAAACGGAAGATCAGCTTTGCCAGCATTGAAATTTCCAGCGACAACGTTGACTA<br>CAGTGACTTGACAATGAAAACCAGCGACAAGTTCAAGTTTGTCTTCCGAGAAAAGATGGGCA<br>GGATTGTTGATTATTTCACA |
| 1301 | GABRP | 2840421 | TTGATTTTTATGCTAGCCAATGTATTTTACTGGGCATACTACAT |
| 1302 | GABRP | 2840422 | CTCAGGGCTGTTTATTCGGTGGCTCCCTGGTTTGCATTTACCTCATATAAAGAATGGGAAGGA<br>GACCATTGGGTAACCCTCAAGTGTCAGAAGTTGTTTCTAAAGTAACTATACATGTTTTTTACTA<br>AATCTCTGCAGTGCTTATAAAATACATTGTTGCCTATTTAGGGAGTAACATTTTCTAGTTTTTGT<br>TTCTGGTTAAAATGAAATATGGGCTTATGTCAATTCATTGGAAGTCAATGCACTAACTAATAC<br>CAAGATGAGTTTTTAAATAATGAATATTATTTAATACCAACACAGAATTATCCCCAATTTCCAA<br>TAAGTCCTATCATTGAAAATTCAAATATAAGTGAAGAAAAAATTAGTAGATCAACAATCTAAA<br>CAAATCCCTCGGTTCTAAGATACAATGGATTCCCCATACTGGAAGGACTCTGAGGCTTTATTCC<br>CCCACTATGCATATCTTATCATTTTATTATTATACACACATCCATCCTAAACTATACTAAAGCCC<br>TTTTCCCATGCATGGATGGAAATGGAAGATTTTTTTTTAACTTGTTCTAGAAGTCTTAATATGG<br>GCTGTTGCCATGAAGGCTTGCAGAATTGAGTCCATTTTCTAGCTGCCTTTATTCACATAGTGAT<br>GGGGTACTAAAAGTACTGGGTTGACTCAGAGAGTCGCTGTCATTCTGTCATTGCTGCTACTCT<br>AACACTGAGCAACACTCTCCCAGTGGCAGATCCCTGTATCATTCCAAGAGGAGCATTCATCC<br>CTTTGCTCTAATGATCAGGAATGATGCTTATTAGAAAACAAACTGCTTGACCCAGGAACAAGT<br>GGCTTAGCTTAAGTAAACTTGGCTTTGCTCAGATCCCTGATCCTTCCAGCTGGTCTGCTATGAG<br>TGGCTTA |
| 1303 | SEMA5A | 2847975 | GCTATGCCGCTTGATGTAACTTTTAAAGATGTTATCAAATGTTAAATGCCTCATTCTGCGTTAA<br>TTTGCTGTTGGCTGTTTTGTGAACACAAAATAAACTTGAGATTTTTTTTTTTTTTTTTGTGA<br>AACTCCTCCAAAGCCAATTTCAGCCCTTGGTAAGCTTGCAGACAGTTACTGATCTTAAATTTAA<br>TTTTAAAAGACAATGTATCTTAATTATAATTTAGCTTTTTAAAACAATGAGATAGCTTTACATTT<br>CCCCTTTGTTTGAATGAGAAATGGATCTTGGGTTGCTATGCTAGAACACTTGTAGATTGCTG<br>GGTCCTTTGTAAGGGGGCCATGGACACACCACACTTTCTTTCAATCCTTACATTTGAAGCATTG<br>ATATTCTTCAAAACCTTCTTGTTACATGTGCGCAATAGAAATTTCTAATGTTCATGACTTTTATC<br>TTTCCTGTCCATCAATTCACTGGTTGTAAATGCTTCCTGAGAGCTGTCTAGGTCTGTATCCCAG<br>ATTGTTGCTTAATGACATCTGACAGATGCATTGTTTTCTGAAATCAGCTTAAGACACCAATTGT<br>GGCAACTGGAAACTCATTACCTGCTGCATTGGATCAACTATGGAAGTTGGAGCAGGGGTGGG<br>CGGAGGTCACCTAACCAATCAATGGAAGGCAACTCACACCTGCTCCAAGCCTCAGCTTTGAGA<br>AACAAACACGTTTATAAGAAAAAATATATAGCTATTATTACAGAAGTGAATATGTTGTGCTCT<br>CTTACTGCTCTTGG |
| 1304 | SEMA5A | 2847976 | TTGGCGCAATGGCAGGAACTAGTCAAGGGCACTTTCAGATCTGGAAAGAGGAAAGAGGAGG<br>TAGAAAATCACTCTTTTGTGTTTCTTAAACTGTCAATCAAGCAAGAAAATTTATTCCACCCCTTC<br>ATATTTGCTCTAAAATCTGGGGCCAGTAGTTGAAATGTGATCTTGTTCTTTCTCAGCCTTTTGG<br>CAATTTAATGCCAAATATTCCAAATGTTAGATGAATGGCAGTAATAAAATGATTCAAATGTTT<br>GATAAATACAAGCTGAGAGCAAAATCTGGACTCTGAAAAATCGGAACTATTTTATCATGTTGC<br>TAAAATGAGAGCATCATTTTCTTCCCTCTCTGTAAGTGCGGTAGTTTA |
| 1305 | SEMA5A | 2847977 | TGCCCAGAGTGCCAGAGTTTTAGCCAAAGGTGTACTTACTTCCTTATTTATCTGCAAAAGGAT<br>GGAAACTGTGGGAGTCAAAGCCTATTTTGCTGAGTGTTCCCACTGGAGTCTCTGGTAGAATTA<br>GCAGGTCATGCTGTCAAAATCATGGACAAAGGCTGGGTGCAGTGGCTCATGCCTATAATCCC<br>AGCACTTTGGGAGGCCAAGGTGGGCGGATCACCTGAGCTCAGGAGTTTGAGACCAGCCTGG<br>GCAACATGGGGAAACTCCATCTCTACAAAATATACAAAATATTAGCCAGCATCGTGGTGCGT<br>GCCTGTGGTCCCAGTTTCTTGGGAGGCTGAGGCGGGAGTATCATTTGAGCCAGGAGGTTGAG<br>GTTGCAGTGAGCTGAGATCACATCACTGCACTCCATCCTGGGTGACAGAGAGAGACCCTGTC<br>TCAAAAAAAAAAAAAAAGAACAAAGTCTTAGCGGGGGTCTCTATGTCCCCAAGTGGCTCTC<br>TAAGGGGATCCATTAGCGTATAATTGAATATCAAAGGGAATTTTACCTTAAACATATATCAAG<br>TCTATACTCAGCTAATCGTTTTGTCTAAACACAGCCTTGTTAGCATTTGAATTTACAAATATTCA<br>TTTGCTTATTTGCAGTGTTCCTTTTGCTTTTAGAATAAATCATAAATATTTCCCCAATACTGTCA<br>AGATACTTCTTCAACTTTGTCCCTGAACCATCAGCTTTCTTTAGGGTCCGGGTATCCTTTACACT<br>TCAATG |
| 1306 | SEMA5A | 2847978 | GAAGAGTCCGTTCATGTCATGTGGTTTGGGATGAACCAGGGGTCTGGCCCCATCGGGTCACA<br>GGTGATGGCAAATAGAAAAGAAGCAAATGGAGGGAAATAGTCGGATAAGTA |
| 1307 | SEMA5A | 2847979 | GCTGGCTTGGCTTTAGTCTTACATTTAAATTCTTTGAAAGTGGCTCCCAGTGCTATTCAGGGTC<br>CTTTCTTGAGGCCAGACTCATCACCATCTACTATTGATTTTACAGTGCACTGACAGTTTACAGG<br>AAGGAGAAGAACAGAATTTCTGCACACTACACAACATGTGGGCTTCCTGTAGCTCCAGGGAC<br>ATGTAGCTTTGGTGAAACTGGGGTTTTGTAACCTCTGAATGATATGGACTTAGTGAATTCTAA<br>GGAACTCAGGGGGCACGTGGTCAGGCTCCACCGCACAGAAGAGCCACAGTCTCCAGACTCAT<br>GGCGTTCCCTCCAGAACTCCCCATTCCCCTCTGAGCATATTTCTATGCTGCTGCTTCTTGTGACT<br>TACATGAGGCATCTCAGCTTCTTCATGTTTGTAGGGATGGTTCCCTAAGCCTGTTCAAGTA |
| 1308 | SEMA5A | 2847980 | ACCTGGTCCACACCGGCAGAAGTTACAGTAGACTGTGAGGCACCCCACCTTGCTCCTGATGCA<br>GTTTCTGTGCCATTGCTGGTGCTGGTGGAGGCAGCGGAGCAGAGGCTCAGGCACAATGAAG |

TABLE 13-continued

Subtyping Target Sequences

| SEQ ID NO. | Gene | Affy Probeset ID | Sequence |
|---|---|---|---|
| | | | CGTGGATGTGTTCTGCAGGTTGCTGCAAAACTCACCTTATTCTGACTTTTGGATTTCATGGCAT<br>TCCAGGAAGCTCCTTGCCATGCTGTTGGCCTGGAAGTCCACCTGTCTGGTCCATAGTGACGTC<br>CTGAAGAGCCAGTCTGTAAAATAACCAACCACTTACTTAGCGTTTGGATAGACTCCATGCCTT<br>CTCTCTCCCTGCAAAGAAAATCTTGAACATTTATGATGTCAATTAGTGAAAGTATTGAAAATA<br>CTAAATTATAACTAAAAGCAACTTTTTATGTTATTGAAAATATTGAAAGAACTGATATTAATGA<br>TAATCATTTTATTTTTCATCTCTCTGATATACCCAATGTGTGGCAATCAGCCCCTACCACGAGCA<br>TTAATACCATGTAAAGCTGGCTTTCTGGAGTCTGCCAGGTCCACACGAAGTGCTACCCCCAGT<br>TTCTGCTGTTACTTGCTGCCTCCAGGCCAGGGGAGCAGGAGATGCTCAGCTCTGGTGCCTTTT<br>CTTTTATTTCAGTGCTGCCTTCCCACCCACCCAGTCCATTCACCCTCACCTCTCCCTGCATGGAG<br>GCAACAGCATTTCAAGATGTACCTTGGGAAGTCAGGATAGCTGGAAGTAAGGGTTTTTGGGA<br>TCCCTGTGGTCTCTTCACTGATCATCGATAAGCATTTAAGAGTGTGCTAACACCATTCACAGAG<br>GTCCCTGGAAAAAATATATAATTTTCTCACAAACAACCAATACATAACCTATGGCAGTTGGTT<br>GAATAATTATTGAAAAAAGAACACGACTGAAAAAGTTCATCTGATGCCTCTGAGCATGTGAT<br>AAAGTCCTGGGTAGACACGAAACGTGTTCTTACAAATGAACCTTCGGATCTATGAAAGAAA<br>ATATAGTAGGGGGACTAAGGAACATAGAATTTTATTAGCATATGTGATTTTACCCTTATCTTTG<br>TTTCTAATTTAAAGAAACAATTTCAGAAAGTGTTAGAAGAATTCTATGTTTAATAATGAATATT<br>GTTGAGTTCAAAATATTCTCATATACCCAGATTTACAGAGATGACACAGTATTGAAATGGCAG<br>GTGGGCTCTGTAAGTTATTTTGGATTAATGACATTCAGGGTCTTTGCAGTGGGGACTTCATGT<br>TGCCTCTCACTCATTCCTCATATGTCAGAGTCTTCTGTCTATATGCACATGCTCAAAGTCCTAC<br>TCAGTAGGGGAAATCTAGCCGGATGGTTCTCCAATTGTTCC |
| 1309 | SEMA5A | 2847981 | CAAAAACAACTTGATCCTAGAGGAAAGAAACAAATACTTCAACCCACATCTCACTGGGAAGA<br>CCTATTCTAATGCCTACTTTACAGATCTCAATAATT |
| 1310 | SEMA5A | 2847983 | ACATGTTCCACATGATCGCCGTGGGGCTGAGCAGCTCCATCCTCGGCTGCCTCCTCACCCTGC<br>TCGTCTATACTTACTGCCAGCGGTACCAGCAGCAATCCCACGATGCGACTGTCATCCACC |
| 1311 | SEMA5A | 2847987 | ATCGTGGCAAGATCCAGTAGCGTAGAAGAGAAAAG |
| 1312 | SEMA5A | 2847988 | TGTGAAGCCTCTGGCGTCCAAGTCCGCGCCCGCCAGTGCATCCTCCTGTTCCCCATGGGCAGC<br>CAGTGCTCCGGGAACACCACGGAGAGCCGGCCGTGTGTGTTTGACTCTAATTTCATCCCAG |
| 1313 | SEMA5A | 2847989 | GCACACAGAAGAGGCACTCTGCAACACGCAGCC |
| 1314 | SEMA5A | 2847990 | TGAGGACCCGCTCTTGCTCCAATCCAG |
| 1315 | SEMA5A | 2847991 | ATGGCGTGTGGTCTTGCTGGTCCCCCTGGACAAAATGTTCAGCAACATGCGGCGGTGGACAC<br>TAT |
| 1316 | SEMA5A | 2847996 | TGGGAGATACTCTGCCCACACGGTCAACGGGCTTGGTCAGCCTGGACGTCGTGGTCACAGT<br>GCAGCCGTGACTGCAGCAGGGGCATTCGGAACCGGAAGCGTGTTTGCAACAACCCCGAACCC<br>AAGTATGGGGGAATGCCTTGCCTTGGCCCATCTCTGGAATACCAGG |
| 1317 | SEMA5A | 2847997 | GGCGGCCACTATGAGCAACGATTCCGATACACATGCAAAGCCCGCCTGGCTGATCCGAATTT<br>GCTGGAAGTGGGAAGACAGAGAATCGAAATGCGGTACTGTTCTAGCGACGGCACCA |
| 1318 | SEMA5A | 2848011 | TGGGAACGGTGCACAGCCCAATGCGGGGGTGGCATTCAAGCTCGCCGCAGGATCTGTGAGA<br>ATGGGCCTGACTGTGC |
| 1319 | SEMA5A | 2848012 | CTATGTCCCCCACACATGTTCTGGAC |
| 1320 | SEMA5A | 2848021 | ATCGGCTTCCAGGTGCGGCAGCGCTCCTGCAGCAACCCCACTCCCAGGCACGGGGGCCGGGT<br>GTGCGTGGGACAGAACCGCGAGGAAAG |
| 1321 | SEMA5A | 2848024 | TCTCACCGTGGATGGGCACTTTGGTGTGTGGTCTCCGTGGACGCCTTGCACGCACACAGATG<br>GCAGCGCCGTGGGATCCTGCCTCTGTCGAACCCGCTCCTGCGACAGCCCGGCCCCGCAGTGT<br>GGTGGCTGGCAGTGCGAGGGCCCTGGCATGGAGATCGCCAACTGTTC |
| 1322 | SEMA5A | 2848029 | AGGAGAGCCTGAGCATGACGCAGTGGGAACA |
| 1323 | SEMA5A | 2848031 | CCCTGAATCAGACCTCAAGCAGCTGTTTGCTGGAAGAGATTGAGCTCTTCCCTGAGAGGCGG<br>AGGGAGCCCATCAGGAGCCTGCAGATCCTGCACAGCCAGAGTGTCCTGTTCGTGGGCCTGCG<br>GGAGCACGTGGTCAAGATCCCCCTGAAGAGGTGCCAGTTCTACCG |
| 1324 | SEMA5A | 2848041 | GTGAACCTGACCGAGAGAAATCTGCAGGATGCTCAGAAGTTCATTCTGATGCATGAGGTGGT<br>ACAGCCAGTGACCACAGTGCCCTCCTTCATGAGGACAATAGCCGCTTTTCCCACGTGGCAGT<br>CGACGTGGTGCAGGGCAGAGAAGCGCTCGTCCACATCATCTA |
| 1325 | SEMA5A | 2848044 | TTTTTCCGAGAAAATGCAGTAGAGCATGACTGTGGGAAAACAGTGTTCTCCAGAGCTGCCCG<br>GGTGTGCAAGAACGATATTGGTGGGCGCTTCCTGCTGGAAGACACCTGGACCACATTCATGA<br>AGGCTCGCCTGAACTGCTCCCGT |

TABLE 13-continued

Subtyping Target Sequences

| SEQ ID NO. | Gene | Affy Probeset ID | Sequence |
|---|---|---|---|
| 1326 | SEMA5A | 2848050 | TGATCAGATCAGTGGCATGGCCCGCTGTCCCTACAGTCCCCAGCACAATTCCACAGCGCTCCT CACAGCTGGTGGGGAGCTCTATGCTGCTACAGCCATGGATTTTCCAGGACGTGATCCTGCCAT TTACCGAAGCCTAGGCATTTTACCTCCTCTCCGCACGGCGCAGTACAACTCCAAATG |
| 1327 | SEMA5A | 2848051 | GGTGGCGACCGGTTATTCACCTGTGGGACCAATGCATTCACGCCTGTCTGCA |
| 1328 | SEMA5A | 2848052 | TGTGATGAAGCTACCAAAAAGGCCTGTTACAGCAAAGGCAAATCAAAG |
| 1329 | SEMA5A | 2848064 | AACTACCTCTTCAGGTTACAGCTTGAGGATCTGT |
| 1330 | SEMA5A | 2848067 | CCCTGGTTACGGGAGTTCAGAGCGAAGAATGCTGTGGATTTCTCGCAGTTAACATTTGACCCA GGACAGA |
| 1331 | SEMA5A | 2848077 | ACCTGTGTTATAGCATGGCTGTTCTCAAGCCTGGGGCTGTGGAGACTCGCCCACCCAGAGGC CCAGGGTACGACTCAGTGCCAGAGAACCGAGCATCCAGTCATC |
| 1332 | SEMA5A | 2848078 | AAGACACGTGCCCAGAGTCAGAGGCCCCTTGCCCA |
| 1333 | SEMA5A | 2848083 | GTTGGTGTGTGAGACTTGGGCTGGAGTGCCCACGTGGCTGTGGAGTCAGTGTGATTCATGAT TGAGGAAACGCGTCCTCCATCCTC |
| 1334 | SEMA5A | 2848088 | GAGCTGGCTTGGACACCCAACTTTGCCACCTCGAGGGTCGTCTCTGCTGGGCGCGAACCTGCC CACCCACCGGTTGGCCGCGCGCTCGGGGACCGTGCTCGTGGCCCCCAAGCCGGTGCCCCCAT TCTGGAACTCAGCGAGTAGGGGGCGGCTCTGGGGAAGTGGCAGGGGGCGGCTGCAGCTGC TGCCTCCACTTCCCTAGCCAGGTGCTGAAGAGGATCCTCGGAGCCGCTCTGGCCCCCAGGCGC TGGATGACTGGCACCAGCGCTCCTC |
| 1335 | SEMA5A | 2848106 | CGTGCTCATGGGAAACAAACGACTCCAGGGTGTGTGCCGCCGATTTGCAATATGAGGCTGAT CTACTGTTCCCACTGTTTTATTCCCTGCTGCTATATCTCGGCTGGGAAATGTACGCTGTGGACC CCGCATCTTCATAATGATGGTCCCTCAATGATCAACCACCTTCCACGTAGCATCCATACAGTAG TC |
| 1336 | RNF138P1 | 2857253 | AAGAAACTCAATGTCAAACTGCTGTTGAA |
| 1337 | PPARG | 2878248 | ACAACATCCGGGAGATGCTGATGGC |
| 1338 | SPINK1 | 2880429 | GGCCTTATTGTTGAATAAATGTATCTGAATA |
| 1339 | SPINK1 | 2880430 | AACCAAGGTTTTGAAATCCCATCAGGTCACC |
| 1340 | SPINK1 | 2880433 | AGCAACTGAAACCTTAGCATGTCTCAAGCATCATGCTAATATTCCCTGTCTTACTTGTGCTTAT GACTAAGAAAACATCATGAGCATGTATAGGATGGCTTCTTATAACTTGGGGCAAATGCCAGA AGATGAGGTGTAAATAAAGTGCAACAGGAGTGAAGCAGAGATACATATTTTTTATTAAAAGG GGCCAAGAAAGGATCCATGAAAAGAATAGAATGCCAGCCGGGTGC |
| 1341 | SPINK1 | 2880434 | CAATGAACTTAATGGATGCACCAAGATATATGACCCTGTCTGTGGGACTGATGGAAATACTTA TCCCAATGAATGCGTGTTATG |
| 1342 | SPINK1 | 2880435 | TAACACTGGAGCTGACTCCCTGGGAAGAGA |
| 1343 | SPINK1 | 2880439 | ATGAAGGTAACAGGCATCTTTCTTCTCAGTGCCTTGGCCCTGTTGAGTCTATCTG |
| 1344 | SPINK1 | 2880452 | TGGAGGCCAGGCTATGACACAGAGTCAATCAATAACCAGGGAGATCTGTGATATAGCCCAGT AGGTGGGGCCTTGCTGCCATCTGCCATATGACCCTTCCAGTCCCAGGCTTCTGAAGAGACGTG GTAAGTGCGGTGCAGTTTTCAACTGACCTCTGGACGCAG |
| 1345 | CD74 | 2881377 | ATAATCCTTTCTGCCGACCCCTAGT |
| 1346 | CD74 | 2881378 | TTTCTAGCCTATTTACCTGCAGGCTGAGCC |
| 1347 | CD74 | 2881379 | AGTGGCCAAAAGCTAGACAGATCCCCGTTCCTGACATCACAGCAGCCTCCAACACAAGGCTCC AAGACCTAGGCTCATGGACGAGATGGGAAGGCACAGGGAGAAGGGATAACCCTACACCCAGA |
| 1348 | CD74 | 2881380 | CTGGCTCTTTCGTCACCCTTGGACAAGACAAACCAAGTCGGAACAGCAGATAACAATGCAGC AAGGCCCTGCTGCCCAATCTCCATCTGTCAACA |
| 1349 | CD74 | 2881381 | GCAGCAGAGGCGGTCTTCAACATCCTG |
| 1350 | CD74 | 2881382 | GTGGGGAGTTACACAAATCCATGATGGTCATTATTGGACCTGAGCAGGGGGCAGGGGAGGG TGGACAGTCCTTAACTGCTCTGCAGGTCCAGGATGTTAGAAAGGGGCAGGGACAACAAATG GGTGACCCCAACCTCAACCTG |
| 1351 | CD74 | 2881383 | TGGGCCACTCTCCAACATTCCTGGGATGTCCATTTCA |

TABLE 13-continued

Subtyping Target Sequences

| SEQ ID NO. | Gene | Affy Probeset ID | Sequence |
|---|---|---|---|
| 1352 | CD74 | 2881384 | GAACTGGAGGACCCGTCTTCTGGGC |
| 1353 | CD74 | 2881386 | CCCAAGTGCGACGAGAACGGCAACTATCTGCCACTCCAGTGCTATGGGAGCATCGGCTACTG CTGGTGTGTCTTCCCCAACGGCACGGAGGTCCCCAACACCAGAAGCCGCGGGCACCATAACT GCAGTG |
| 1354 | CD74 | 2881387 | AGTGCCAGGAAGAGGTCAGCCACATCCCTGCTGTCCACCCGGGTTCATTCAG |
| 1355 | CD74 | 2881391 | TTTGAGAGCTGGATGCACCATTGGCTCCTGTTTGAAATGAGCAGGCACTCCTTGGAGCAAAA GCCCACTGACGCTCCA |
| 1356 | CD74 | 2881393 | TACCCGCCACTGAAGGGGAGCTTCCCGGAGAACCTGAGACACCTTAAGAACACCATGGAGAC CATAGACTGGAA |
| 1357 | CD74 | 2881395 | CTCTGGATTACTGAATACAAGGGTGACCCTTAAATGTTATATGTAGTCTGGCCTCTGCATTTTT GAGATAAACAGGCTCGGCTGGGT |
| 1358 | CD74 | 2881396 | AATGCCACCAAGTATGGCAACATGACAGAGGACCATGTGATGCACCTGCTC |
| 1359 | CD74 | 2881398 | AGCCTGTGAGCAAGATGCGCATGGCCACCCCGCTGCTGATGCAGGCGCTGCCCATGGGAGC |
| 1360 | CD74 | 2881399 | TCTCCCTCCGGTTTGGAATTCCAGCCCTTCCTCATCTGGGTCTGATACCCTCCTCCCTGGGCAC CGGGGCCACACTTACCCTCGTTCCTGTCC |
| 1361 | CD74 | 2881400 | CCGCCTACTTCCTGTACCAGCAGCAGGGCCGGCTGGACAAACTGACAGTCACCTCC |
| 1362 | CD74 | 2881401 | AGGCTTTTCCATCCTGGTGACTCTGCTCCTCG |
| 1363 | CD74 | 2881407 | GATGACCAGCGCGACCTTATCTCCAACAATGAGCAACTGCCCATGCTGGGCCGGCGCCC |
| 1364 | CD74 | 2881408 | AGCAGGAGCTGTCGGGAAGATCAGAAGCCAGTC |
| 1365 | CD74 | 2881409 | CGGAGTGGCCTTCTGTGGACGAATCAGATTCCTCTCC |
| 1366 | DUSP1 | 2887311 | TGGGACTCCATGCTCCTTGAGAGGAGAAATGCAATAACTCTGGGAGGGGCTCGAGAGGGCT GGTCCTTATTTATTTAACTTCACCCGAGTTCCTCTGGGTTTCTAAGCAGTTATGGTGATGACTT AGCGTCAAGACATTTGCTGAACTCAGCACATTCGGGACCAATATATAGTGGGTACATCAAGTC CATCTGACAAAATGGGGCAGAAGAGAAAGGACTCAGTGTGTGATCCGGTTTCTTTTTGCTCG CCCCTGTTTTTTGTAGAATCTCTTCATGCTTGACATACCTACCAGTATTATTCCCGACGACACAT ATACATATGAGAATATACCTTATTTATTTTTGTGTAGGTGTCTGCCTTCACAAATGTC |
| 1367 | DUSP1 | 2887312 | CAGGCAGGCATTTCCCGGTCAGCCACCATCTGCCTTGCTTACCTTATGAGGACTAATCGAGTC AAGCTGGACGAGGCCTTTGAGTTTGTGAAGCAGAGGCGAAGCATCATCTCTCCCAACTTCAG CTTCATGGGCCAGCTGCTGCAGTTTGAGTCCCAGGTGCTGGCTCCGACTGTTCGGCAGAGG CTGGGAGCCCCGCCATGGCTGTGCTCGACCGAGGCACCTCCACCACCACCGTGTTCAACTTCC CCGTCTCCATCCCTGTCCACTCCACGAACAGTGCGCTG |
| 1368 | DUSP1 | 2887314 | CTGGTTCAACGAGGCCATTGACTTCATAG |
| 1369 | DUSP1 | 2887315 | GCCTTGATCAACGTCTCAGCCAATTGTCCCAACCATTTTGAGGGTCACTACCAGTACAAGAGC ATCCCTGTG |
| 1370 | DUSP1 | 2887316 | TGCCCTTTCTGTACCTGGGCAGTGCGTATCACGCTTCCCGCAAGGA |
| 1371 | DUSP1 | 2887318 | GATACGAAGCGTTTTCGGCTTCCTGCCCGGAGCTGTGCAGCAAACAGTCGACCCCCATGGGG CTCAGCCTTCCCCTGAGTACTAGCGTCCCTGACAGCGCGGAATCTGGGTGCA |
| 1372 | DUSP1 | 2887320 | TGGACTGCCGCTCCTTCTTCGCTTTCAACGCCGGCCACATCGCCGGCTCTGTCAACGTGCGCTT CAGCACCATCGTGCGGCGCCGGGCAAGGGCGCCATGGGCCTGGAGCACATCGTGCCCAAC GCCGAGCTCCGCGGCCGCCTGCTGGCCGGCGCCTACCACGCCGTGGTGTTG |
| 1373 | DSP | 2893795 | AGCGAGCAGCGACCTCGCGAGCCTTCCGCACTCCCGCCCGGTTCCCCGGCCGTCCGCCTATCC TTGGCCCCCTCCGCTTTCTCCGCGCCGGCCCGCCTCGCTTATGCCTCGGCGCTGAGCCGCTCTC CCGATTGCCCGCCGA |
| 1374 | DSP | 2893796 | ACGGAGGCTCCCACCCGCGGATCAACACTCTGGGCCGCATGATCCGCGCCGAGTCTGGCCCG GACCTGCGCTACGAGGTGACCAGCGGC |
| 1375 | DSP | 2893797 | CAGGATGTACTATTCTCGGCGCGGCGTGATCACCGACCAGAACTCGGACG |
| 1376 | DSP | 2893800 | TCAAACCGGCACGATGTCCAGGCACCAGAACCAGAACACCATCCAGGAGCTGCTGCAGAACT GCTCCGACTGCTTGATGCGAGCAGAGCTCATCGTGCA |

TABLE 13-continued

Subtyping Target Sequences

| SEQ ID NO. | Gene | Affy Probeset ID | Sequence |
|---|---|---|---|
| 1377 | DSP | 2893801 | GGAGATGGAATACAACTGACTCGGAGTCGAGAATTGGATGAGTGTTTTGCCCAGGCCAATGACCAAATGGAAATCCTCGACAGCTTGATCAGAGAGATGCGGCAGATGGGCCAGCCCTGTGATGCTTACCAGAAAA |
| 1378 | DSP | 2893802 | GAGCAAATGCGAGCCCTTTATAAAGCCATCAGTGTCCCTCGAGTCCGCAGGGCCAGCTCCAAGGGTGGTGGAGGCTACACTTGTCAGAGTGGCTCTGGCTGGGATGAGTTCACCAAACATGTCACCAGTG |
| 1379 | DSP | 2893805 | CGCGAGAAATCTGCTATCTACCAGTTGGAGGAGG |
| 1380 | DSP | 2893807 | GAACATCATTCAGGCCACGTCCAGGGAGATCATGTGGATCAATGACTGCGAGGAGGAGGAGCTGCTGTACGACTGGAGCGACAAGAACACCAACATCGCTCAGAAACAGGA |
| 1381 | DSP | 2893808 | AAAGAGCTCAATAAGCTGAAACAAGAA |
| 1382 | DSP | 2893809 | GTTGGATTCTTCAGATCACCAAGTGCATTGATGTTCA |
| 1383 | DSP | 2893810 | TTTGAAGAGGCGCAGTCTACTGAAGCATACCTGAAGGGGCTCCAGGACTCCATCAGGAAGAAGTACCCCTGCGACAAGAACATGCC |
| 1384 | DSP | 2893811 | TCCTTGAATACAAGCGTCAGGTGCAGAACTTGGTAAACAAGTCTAAGAAGATTGTACAGCTGAAGCCTCGTAACCCAGACTACAGAAGCAATAAACCCATTATTCTCAGAGCTCTC |
| 1385 | DSP | 2893812 | TGCATAAGGGGGATGAGTGTATCCTGAAGGACAACAACGAGCGCAGCAAGTGGTACGTGACGGGCCCGGGAGGCGTTGACATGCTTGTTCCCTCTGTGGGGCTGATCATCCCTCCTCCGAACCCA |
| 1386 | DSP | 2893813 | GATTGAGCAGTACTACGAAGCCATCTTGGCTCTGTGGAACCAGCTCTACATCAACATGAAGAGCCTGGTGTCCTGGCACTACTGCATGATTGACATA |
| 1387 | DSP | 2893814 | CGATAGCCGACCTTGAGTTACATTACCAAGAGTTCATCAGAAATAGCCAAGGCTCAGAGATGTTTGGAGATGATGACAAGCGGAAAATACAGTCTCAGTTCACCGATGCCCGAAAGCATTACCAGACCCTG |
| 1388 | DSP | 2893816 | TTCACAAGCAATTGCTGAGGTTCTCAACCAGCTTAAAGATATGCTTGCCAACTTCAGAGGTTCTGAAAAGTACTGCTATTTACAGAATGAAGTATTTGGACTA |
| 1389 | DSP | 2893817 | GACATGTTAAAGGTTTATGAAGCCAGGCTCACTGAGGAGGAAACTGTCTGCCTGGACCTGGATAAAGTGGAAGCTTACCGCTGTGGACTGAA |
| 1390 | DSP | 2893818 | ACTTGAAGAAGTCGTTGTTGGCCACTATGAAGACAGAACTACAGAAAGCCCAGCAGATCCACTCTCAGACTTCACAGCAGTATCCACTTTATGATCTGGACTTGGGCAAGTTCGGTGAAAAAGTCACACAGCTGACAGACCGCTGGCAAAGGATA |
| 1391 | DSP | 2893819 | CGTGATAACTATCAGGCTTTCTGCAAGTGGCTCTATGATGCTAAACGCCGCCAGGATTCCTTAGAATCCATGAAATTTGGAGATTCCAACACAGTCATGCGGTTTTTGAATGAGCA |
| 1392 | DSP | 2893821 | GCTGGCCTCATACACCTCAGGACTGGAAACTCTGCTGAACATACCTATCAAGAGGACCATGATTCAGTCCCCTTCTGG |
| 1393 | DSP | 2893822 | TGCAGATGTTCATGCTCGGTACATTGAACTACTTACAAGATCTGGAGACTATTACAGGTTCTTAAGTGAGATGCTG |
| 1394 | DSP | 2893823 | TCAGACTGGCCCGAGATGCCAACTCGGAAAACTGTAATAAGAACAAATTCCTGGATCAGAACCTGCAGAAATACCAGGCAGAGTGTTCCCAGTTCAAAGCGAAGCTTGCGAGCCTGGAGGAGCTGAAGAGACAGGCTGAGCTGGATGGAAGTCGGCTAAGCAAAATCTAGACAAGTGCTACGGCCAAATAAAAGAACTCAATGAGAAGATCACCCGACTGACTTATGAGATTGAA |
| 1395 | DSP | 2893824 | GGCGAGCTGAAGAAAACGCCCTTCAGCAAAAGGCCTGTGGCTCTGAGATAATGCAGAAGAAGCAGCATCTGGAGATAGAACTGAAGCAGGTCATGCAGCAGCGCTCTGAGGACAATGCCCGGCACAAGCAGTCCCTGGAGGAGGCTGCCAAGACCATTCAGGACAAAAATAAGGAGATCGAGAGACTCAAAGCTGAGTTTCAGGAGGAGGCCAAGCGCCGCTGGGAATATGAAA |
| 1396 | DSP | 2893825 | GTAAGAAACAATTATGATGAGGAGATCATTAGCTTAAAAAATCAG |
| 1397 | DSP | 2893826 | TTTGAGACCGAGATCAACATCACCAAGACCACCATCC |
| 1398 | DSP | 2893827 | GCTACCGGGCTCAGATAGACAATCTCACCCGAGAAAACAGGAGCTTATCTGAAGAAATAAAGAGGCTGAAGAACACTCTAACCCAGACCACAGAGAATCTCAGGAGGGTGGAAGAAGACATCCAACAGCAAAAGGCCACTGGCTCTGAGGTGTCTCAGAGGAAACAGCAGCTGGAGGTTGAGCTGAGACAAGTCACTCAGATGCGAACAGAGGAGAGCGTAAGATATAAGCAATCTCTTGATGATGCTGCCAAAACCATCCAGGATAAAAACAAGGAGATAGAAAGGTTAAAACAACTGATCGACAAAGAAACAAATGACCGGAAATGCCTGGAAGATGAAAACGCGAGATTACAAAGGGTCCAGTATGACCTGCAGAAAGCAAACAGTAGTGCGACGGAGACAATAAACAAACTGAAGGTTCAGGAGCAAGAACTGACACGCCTGAGGATCGACTATGAAAGGGTTTCCCAGGAGAGGACTGTGAAGGAC |

TABLE 13-continued

Subtyping Target Sequences

| SEQ ID NO. | Gene | Affy Probeset ID | Sequence |
|---|---|---|---|
| | | | CAGGATATCACGCGGTTCCAGAACTCTCTGAAAGAGCTGCAGCTGCAGAAGCAGAAGGTGG AAGAGGAGCTGAATCGGCTGAAGAGGACCGCGTCAGAAGACTCCTGCAAGAGGAAGAAGCT GGAGGAAGAGCTGGAAGGCATGAGGAGGTCGCTGAAGGAGCAAGCCATCAAAATCACCAA CCTGACCCAGCAGCTGGAGCAGGCATCCATTGTTAAGAAGAGGAGTGAGGATGACCTCCGG CAGCAGAGGGACGTGCTGGATGGCCACCTGAGGGAAAAGCAGAGGACCCAGGAAGAGCTG AGGAGGCTCTCTTCTGAGGTCGAGGCCCTGAGGCCGCAGTTACTCCAGGAACAGGAAAGTG TCAAACAAGCTCACTTGAGGAATGAGCATTTCCAGAAGGCGATAGAAGATAAAAGCAGAAGC TTAAATGAAAGCAAAATAGAAATTGAGAGGCTGCAGTCTCTCACAGAGAA |
| 1399 | DSP | 2893828 | AATCCAGCCATTCCTTCGGGGTGCAGGATCTATCGCTGGAGCATCTGCTTCTCCTAAGGAAAA ATACTCTTTGGTAGAGGCCAAGAGAAAGAAATTAATCAGCCCAGAATCCACAGTCATGCTTCT GGAGGCCCAGGCAGCTACAGGTGGTATAATTGATCCCCATCGGAATGAGAAGCTGACTGTCG ACAGTGCCATAGCTCGGGACCTCATTGACTTCGATGACCGTCAGCAGATATATGCAGCAGAA AAAGCTATCACTGGTTTTGATGATCCATTTTCAGGCAAGACAGTATCTGTTTCAGAAGCCATCA AGAAAAATTTGATTGATAGAGAAACCGGAATGCGCCTGCTGGAAGCCCAGATTGCTTCAGGG GGTGTAGTAGACCCTGTGAACAGTGTCTTTTTGCCAAAAGATGTCGCCTTGGCCCGGGGGCT GATTGATAGAGATTTGTATCGATCCCTGAATGATCCCCGAGATAGTCAGAAAAACTTTGTGGA TCCAGTCACCAAAAGAAGGTCAGTTACGTGCAGCTGAAGGAACGGTGCAGAATCGAACCAC ATACTGGTCTGCTCTTGCTTTCAGTACAGAAGAGAAGCATGTCCTTCCAAGGAATCAGACAAC CTGTGACCGTCACTGAGCTAGTAGATTCTGGTATATTGAGACCGTCCACTGTCAATGAACTGG AATCTGGTCAGATTTCTTATGACGAGGTTGGTGAGAGAATTAAGGACTTCCTCCAGGGTTCAA GCTGCATAGCAGGCATATACAATGAGACCACAAAACAGAAGCTTGGCATTTATGAGGCCATG AAAATTGGCTTAGTCCGACCTGGTACTGCTCTGGAGTTGCTGGAAGCCCAAGCAGCTACTGG CTTTATAGTGGATCCTGTTAGCAACTTGAGGTTACCAGTGGAGGAAGCCTACAAGAGAGGTC TGGTGGGCATTGAGTTCAAAGAGAAGCTCCTGTCTGCAGAACGAGCTGTCACTGGGTATAAT GATCCTGAAACAGGAAACATCATCTCTTTGTTCCAAGCCATGAATAAGGAACTCATCGAAAAG GGCCACGGTATTCGCTTATTAGA |
| 1400 | DSP | 2893829 | AAATGTCTGTTCAGGAGGCCTACAAGAAGGGCCTAATTGATTATGAAACCTTCAAAGAACTGT GTGAGCAGGAATGTGAATGGGAAGAAATAACCATCACGGGATCAGATGGCTCCACCAGGGT GGTCCTGGTAGATAGAAAGACAGGCAGTCAGTATGATATTCAAGATGCTATTGACAAGGGCC TTGTTGACAGGAAGTTCTTTGATCAGTACCGATCCGGCAGCCTCAGCCTCACTCAATTTGCTGA CATGATCTCCTTGAAAAATGGTGTCGGCACCAGCAGCAGCATGGGCAGTGGTGTCAGCGATG ATGTTTTTAGCAGCTCCCGACATGAATCAGTA |
| 1401 | DSP | 2893830 | AGATTTCCACCATATCCAGCGTCAGGAATTTAACCATAAGGAGCAGCTCTTT |
| 1402 | DSP | 2893831 | TACAGAAGGTATAGAGCGGGGCATCGTTGACAGCATCACGGGTCAGAGGCTTCTGGAGGCT CAGGCCTGCACAGGTGGCATCATCCACCCAACCACGGGCCAGAAGCTGTCACTT |
| 1403 | DSP | 2893832 | CCAGGGTGTGATTGACCAAGACATGGCCACCAGGCTGAAGCCTGCTCAGAAAGCCT |
| 1404 | DSP | 2893833 | AGAAAAATGGCTCCCGTATGAGGCTGGCCAGCGCTTCCTGGAGTTCCAGTACCTCACGGGAG |
| 1405 | DSP | 2893834 | TGGGAGGATAAGCACCGAAGAAGCCATCCGGAAGGGGTTCATAGATGGCCGCGCCGCACAG AGGCTGCAAGACACCAGCAGCTATGCCAAAATCCTGACCTG |
| 1406 | DSP | 2893835 | TAGAAGATATCACTGGGCTGCGCCTTC |
| 1407 | DSP | 2893836 | TTACAACATGTCTTCGGCTCCGGGTCCCGCTCCGGCTCCCGCTCGGGATCTCGCTCCGGATC TCGCTCCGGGTCCCGCAGTGGGTCCCGGAGAGGAAGCTTTGACGCCACAGGGAATTCTTCCT ACTCTTATTCCTACTCATTTAGCAGTAGTTCTATTGGGCACTA |
| 1408 | DSP | 2893837 | AGTTGGGAGTGGTTGCTATACCTTGACTTC |
| 1409 | DSP | 2893838 | TCCCGGTGCTTGCAGTAGAGTGATAGGACATTCTATGCTTACAGAAAATATAGCCATGATTGA AATCAAATAGTAAAGGCTGTTCTGGCTTTTTATCTTCTTAGCTCATCTTAAATAAGCAGTACAC TTGGATGCAGTGCGTCTGAAGTGCTAATCAGTTGTAACAATAGCACAAATCGAACTTAGGATT TGTTTCTTCTCTTCTGTGTTTCGATTTTTGATCAATTCTTTAATTTTGGAAGCCTATAATACAGTT TTCTATTCTTGGAGATAAAAATTAAATGGATCACTGATATTTTAGTCATTCTGCTTCTCATCTAA ATATTTCCATATTCTGTATTAGGAGAAAATTACCCTCCCAGCACCACCAGCCCCCCTCTCAACCCC CAACCCAAAACCAAGCATTTTGGAATGAGTCTCCTTTAGTTTCAGAGTGTGGATTGTATAACC CATATACTCTTCGATGTACTTGTTTGGTTTGGTATTAATTTGACTGTGCATGACAGCGGCAATC TTTT |
| 1410 | DSP | 2893839 | TTTATCATAGGTCTAAAAATATTTGT |
| 1411 | HIST1H2BF | 2899208 | TGCTAAGTCCGCTCCTGCTCCAAAAAAGGGC |
| 1412 | HIST1H2AE | 2899225 | GGCGGCAAAGCTCGGGCAAAAGCTAAAACGCGTTCTTCCAGGGCCGGTCTTCAGTTTCCAGT TGGCCGTGTGCACCGCTCCTCCGCAAAGGCAACTACTCCGAACGAGTCGGGGCCGGCGCTC CAGTGTACCTGGCAGCGGTGCTGGAATATCTGACGGCCGAGATCTTAGAGCTAGCTGGCAAC GCGGCTCGCGACAATAAGAAGACCCGCATCATCCCGCGCCACCTGCAGCTAGCCATCCGCAA CGACGAGGAGCTAAATAAGCTTCTAGGTCGCGTGACCATC |

TABLE 13-continued

Subtyping Target Sequences

| SEQ ID NO. | Gene | Affy Probeset ID | Sequence |
|---|---|---|---|
| 1413 | HLA-A | 2901162 | ACCCCCCCAAGACACATATGACCCA |
| 1414 | HLA-A | 2901181 | CCGTCATGGCGCCCCGAACCCTCCTCCTGCTACTCTCGGGGGCCCTGGCCCT |
| 1415 | HLA-A | 2901182 | CAGCGACGCCGCGAGCCAGAGGATGGAGCCGCGGGCGCCGTGGATAGAGCAGGAGGGGCCGGAGTATTGGGACCAGGAGACACGGAATGTGAAGGCCCAGTCACAGACTGAC |
| 1416 | HLA-A | 2901183 | TGGGGACCCTGCGCGGCTACTACAAC |
| 1417 | HLA-A | 2901184 | ACGGACGGGCCAGGTCGCCCACAGTCTCCGGGTCCGAGATCCACCCCGAAGCCGCGGGA |
| 1418 | HLA-A | 2901191 | TGTGCAGCATGAGGGTCTGCCCAAGCCC |
| 1419 | HLA-A | 2901193 | GGCCTGGTTCTCCTTGGAGCTGTGATCACTGGAGCTGTGGTCGCTGCCGTGATGTGGAGGAGGA |
| 1420 | HLA-A | 2901194 | AGATTTCTTGTCTCACTGAGGGTTCCAAGCCCCAGCTAGAAATGTGCCCTGTCTCATTACTGGGAAGCACCGTCCACAATCATGGGCCTACCCAGTCTGGGCCCTGTGTGCCAGCACTTACTCTTTTGTAAAGCACCTGTTAAAATGAAGGACAGATTTATCACCTTGATTACG |
| 1421 | HLA-A | 2901196 | GCAGTGACAGTGCCCAGGGCTCTGATGTGTCCCTCACAGCTTGTAAA |
| 1422 | HLA-A | 2901201 | TTACTTTCTCAAATTCTTGCCATGAGAGGTTGATGAGTTAATTA |
| 1423 | HLA-DRA | 2903191 | TGCCTCACTCCCGAGCTCTACTGACTCCCAACAG |
| 1424 | HLA-DRA | 2903195 | ATGTGATCATCCAGGCCGAGTTCTATCTGAATCCTGACCAATCAGGCGAGTTTATGTTTGACTTTGATGGTGATGAGATTTTCCATGTGGATATGGCAAAGAAGGAGACGGTCTGGCGGCTTGAAGAATTTGGACGATTTGCCAGCTTTGAGGCTCAAGGTGCATTGGCCAACATAGCTGTGGACAAAGCCAACCTGGAAATCATGACAAAGCGCTCCAACTATACTCCGATCA |
| 1425 | HLA-DRA | 2903196 | ACTGAGAGAGCCCAACGTCCTCATCTGTTTC |
| 1426 | HLA-DRA | 2903197 | GTCAATGTCACGTGGCTTCGAAATGGAAAACCTGTCAC |
| 1427 | HLA-DRA | 2903200 | CCCAGAGACTACAGAGAACGTGGTGTGTGCCCTGGGCCTGACTGTGGGTCTGGTGGGCATCATTATTGGGACCATCTTCATCATCAAGGGATTGCGCAAAAGCAATGCAGCAGAACGCAGGGGGCCT |
| 1428 | HLA-DRA | 2903202 | ATGGTGTTTCTTAGAGAGAAGATCACTGAAGAAACTTCTGCTTTAATGGCTTTACAAAGCTGGCAATATTACAATCCTTGACCTCAGTGAAAGCAGTCATCTTCAGCATTTTCCAGCCCTATAGCCA |
| 1429 | HLA-DRA | 2903203 | CACCATGCAATGCCTCTGGAATAAAACATACAGGAGTCTGTCTCT |
| 1430 | HLA-DRA | 2903204 | TGCCCCATGGGGCATCTCTTGTGTACTTATTGTTTAAGGTTTCCTCAAACTGTGA |
| 1431 | SERPINB1 | 2938983 | AATATATAGTTCATGTGGCGCTGCATGAAATCAAGAAGTGGGTGTCTTAGGATAAAAGATACCAAGAGTCTACAAAAATAACCATGTAGTAAGATAAACTGCTGAACAAAGGTTTTACTGTTAGCCACCTTCTCATGTGTTTTCTTTTCTCTTTTTCTTTTTCTTTCTTTCTTTTTTTTTTTTTGAGACAGAGTCTTGCTCTGTTACCCAGGCTGGAGTGCAGTGGCACGATCTCAGCTCACCGCAACCTCTGCCTCCTGGGTTCAAGTGATTCTCTTGCTTCAGCCTCCTGAGTAGCTGGGATTATAGGCATGCACCACTAGGCCTGGCTAATTTTTGTATTTTTAGTAGAGATGGGGTTTTTCCATGTTGGCCAGGCTGGTCCCGAACTCCTGACCTCAGGTGATCCGCGCACCTCAGCCTCCCAAAGTGCTGGGATTACAGGCATGAGCTACCATGCCTGGCCTTCTCATGTGTTTTCTGATTAAGGCTCTTGACTTCCAAGGCTGTGTGGGAGATGGGTGGGGCTCTTGGACTGATATAAAACTTTGTCAAATGTAGTTCTTTGAATGGAGCTTGAAACGCCACATATTCTTGCTCCCACAAGGATAGTGGGCATCATGA |
| 1432 | SERPINB1 | 2938984 | AGTATTCTGTTACAGACCTCTAGTTTTTAGACTCTTCAAT |
| 1433 | SERPINB1 | 2938985 | ACAGACACCCTGACTGTTGAAGGGAGGTTTAAAAACAGATATTCAATTGAAATGTAAGAGAGCACCCCAATTGAGAGCCCAGGTTACGAAGACAAGCTTGCCTCGCCTGACTTTTCTGTC |
| 1434 | SERPINB1 | 2938986 | TTAGAATTTTGGAAGCCACAAAATAG |
| 1435 | SERPINB1 | 2938987 | TGGCTGTTTACACCCATGAATTTTGGCATGGGTATCTATTTTCTTTTTTACATTGAAAAAAATCCAGTGGTTGCTTTTGAATGCATCAAGTAAAGAAGAAGAAAAGAATACATCCGATGCGTAGATTCTTGACCATGTAGTAATCTATAAAATTGCTATATCCTCCTGATAGCCATGGGAAAAC |
| 1436 | SERPINB1 | 2938988 | AAGAGACTGTAGCAATACAAAAATCAAGCTTAGTGCTTTATTACCTGAGTTTTTA |
| 1437 | SERPINB1 | 2938989 | GTAGCATCCTATTCTTGGGGAGATTTTCTT |
| 1438 | SERPINB1 | 2938990 | AAAATTTCACTGCCGACCATCCATTCCTTTTCTTTATTCGGCATAATTCCTCAG |

TABLE 13-continued

Subtyping Target Sequences

| SEQ ID NO. | Gene | Affy Probeset ID | Sequence |
|---|---|---|---|
| 1439 | SERPINB1 | 2938991 | CACAGCAGGCATCGCAACTTTCTGCATG |
| 1440 | SERPINB1 | 2938992 | CATGAGTGGACTAAACCTGAGAATCTCGATTTCATTGAAGTTAATGTCAGCTTGCCCAGGTTC AAACTGGAAGAGAGTTACACTCTCAACTCCGACCTCGCCCGCCTAGGTGTGCAGGATCTCTTT AACAGTAGCAAGGCTGATC |
| 1441 | SERPINB1 | 2938994 | TTTGCATATGGCTACATCGAGGACCTTAAGTGCCGTGTGCTGGAACTGCCTTACCAAGGCGAG GAGCTCAGCATGGTCATCCTGCTGCCGGATGACATTGAGGACGAGTCCA |
| 1442 | SERPINB1 | 2938996 | TTCGGGCATGGTTGATAACATGACCAAACTTGTGCTAGTAAATGCCATCTATTTCAAGGGAAA CTGGAAGGATAAATTCATGAAAGAAGCCACGACGAATGCACCATTCAGA |
| 1443 | SERPINB1 | 2938999 | GAAGATGCAAGGAAGACCATAAACCAGTGGGTCAAA |
| 1444 | SERPINB1 | 2939001 | CTTTCCATTTCAACACGGTTGAAGAGGTTCATTCAAGATTCCAGAGTCTGAATGCTGATATCAA CAAACGTGGAGCGTCTTATATTCTGAAACTTGCTAATAGATTATA |
| 1445 | SERPINB1 | 2939004 | GGACCAGAGGTAACACGGCAGCACAGCTGTCCAA |
| 1446 | SERPINB1 | 2939005 | AGCAAACACCCGCTTCGCCTTGGACCTGTTCCTGGCGTTGAGTGAGAACAATCCGGCTGGA |
| 1447 | SERPINB1 | 2939010 | GAGAGGCCAGGCTCCCTCGCTCAGCTTCCAGCCCGGCACCCCCCACCCCCCAGGCTCAGGCCC CTCAGACCCGCAGCTCCCTGCGCTCGCCCTCCCCGCCAGCTTCGCGCCCCCATCCCTTCCGGGC GCCCCGACGGAGACAGACGACCTCTGAT |
| 1448 | SERPINB1 | 2939011 | TTGCACTTAGGCGACCTCGGGAGCTCGGACTCCTACGCAGTCACCGGGAAGGGCCGCCGCCC CGCCCGCGGCTGCTGGCCCGGGTGACGCTTCCGCCTGCTATAAGAGCAGCGGCCCTCGGT |
| 1449 | IER3 | 2948631 | TGTGAACACAAATAAAATTGATTTACTGT |
| 1450 | IER3 | 2948632 | CTGGGACTTCCGAGGCAACTTGAACTCAGAACACTACAGCGGAGACGCCACCCGGTGCTTGA GGCGGGACCGAGGCGCACAGAGACCGAGGCGCATAGAGACCGAGGCACAGCCCAGCTGGG GCTAGGCCCGGTGGGAAGGAGAGCGTCGTTAATTTATTTCTTATTGCTCCTAATTAATATTTAT ATGTATTTATGTACGTCCTCCTAGGTGATGGAGATGTGTACGTAATATTTATTTTAACTTATGC AAGGGTGTGAGATGTTCCCCCTGCTGTAAATGCAGGTCTCTTGGTATTTATTGAGCTTTGTGG GACTGGTGGAAGCAGGACACCTGGAACTGCGGCAAAGTAGGAGAAGAAATGGGGAGGACT CGGGTGGGGAGGACGTCCCGGCTGGGATGAAGTCTGGTGGTGGGTCGTAAGTTTAGGAG GTGACTGCATCCTCCAGCATCTCAACTCCGTCTGTCTACTGTGTGAGACTTCGGCGGACCATTA GGAATG |
| 1451 | IER3 | 2948633 | CCCTTTAATCTGACTTCGGAGCCCTCGGACTACGCTCTGGACCTCAGCA |
| 1452 | IER3 | 2948634 | CTGCCTCCAGAGGACGCCCCTAACGCCGCATCCCTGGCGCCCA |
| 1453 | IER3 | 2948635 | CCGGCGCCAGCTGCCAGTCGAGGAACCGAACCCAGCCAAAAGGCTTCTCTTTCTGCTGCTCAC CATCGTCTTCTGCCAGATCCTGAT |
| 1454 | IER3 | 2948636 | ACTGGGGAACGACCCGACTCCAGAGGCCTCGAC |
| 1455 | IER3 | 2948637 | CTGCCACCCGACCATGACCATCCTGCAGGCCCCGACCCCGGCCCCCTCCACCATCCCGGGACC CCGGCGGGGCTCCGGTCCTGAGATCTTCACCTTCGACCCTCTCCCGGAGCCCGCAGCGGCCC TGCCGGGCGCCCCAGCGCCTCTCGCGGGCACCGAAAGCGCAGCCGCAGGGTTCTCTACCCTC GAGTG |
| 1456 | HLA-DRB1 | 2950021 | TGAAGTCCCAGCATTGATGGCAGCGCCTCA |
| 1457 | HLA-DRB1 | 2950023 | — |
| 1458 | HLA-DRB1 | 2950035 | TGATGGCAGCGCCTCATCTTCAACTTTTG |
| 1459 | HLA-DRB1 | 2950041 | — |
| 1460 | HLA-DRB1 | 2950042 | CTGCGGTGGTCTCCATAGGCCTGATCCAGAATGGA |
| 1461 | HLA-DRB1 | 2950043 | — |
| 1462 | HLA-DRB5 | 2950046 | — |
| 1463 | HLA-DRB1 | 2950052 | AATGTCCTCCCTTGTGGCTTCCTCAG |
| 1464 | HLA-DRB1 | 2950057 | — |
| 1465 | HLA-DRB5 | 2950067 | — |

TABLE 13-continued

Subtyping Target Sequences

| SEQ ID NO. | Gene | Affy Probeset ID | Sequence |
|---|---|---|---|
| 1466 | HLA-DRB1 | 2950068 | GGAGGGGTTCATAGTTCTCCCTGAGTGAGAC |
| 1467 | HLA-DRB5 | 2950095 | — |
| 1468 | GPR110 | 2955944 | GTGTGTTTCCCATGAACCATAGTGAGACATGCAAGAGTGAAGGTCAGCATGGGGCTCTTTTA<br>GGTCCTCTCTGATAGGGTTGTCCAAAGAGGTGGAGGGAACCCAGCATCAAGAAGTGGGAGG<br>TGAAGCCAGATTGTGGGATGAGGAAGGAGTCACAAATGACCACCTGGAATACAAAAAAATCT<br>ACACAAGCTAAAGATGAGAAGTCAGGGCTATGAGAATTTCTATGGGAGTTCTTGAATGCTCC<br>CTCTCTTATTACACACAATTACTATCCAGAGAACCCTGACACCATGTGAAGGCAGCCCTATCTC<br>ATAAGACAGATTTCTTTTTTTGGGGACCTTGGGGAAAGGGAGGCCAGAAACCTCCGTGTCCA<br>AGGTGGGGTGGAAGGAGAGGGAGAAATCTTAGCAAAAATGTCAACCAGCAAGGGAAGATG<br>TGCTAGCGCAAGTAGGCAACTCA |
| 1469 | GPR110 | 2955945 | AGGCACTTCCATCTGGTCCTAAACCCTGCAAACAAAAGTGTCAAGGCAGACCCTAGTGCAGAG<br>ATGAGGGCATGGGGGCTCAGAGAGGTAAAGTGACTTGCCAAAGATTGTGAAGCCAGTTAAG<br>GGAAATTGGGGATTTTTAGGACATTTGTCTCCCAGACCATTTCTACAGCCAATA |
| 1470 | GPR110 | 2955946 | TGTTGGAAATCGTGTCAGTTGTACCCTGACCATAAAATATGGTTTCTATTTTCATAAAACAGCA<br>TTATTCACATGGCATTTCCAATAATCTGGATTGAAGGAAGAAAATTTTATGAAATAGCTTTAG<br>ATAAATTAATAGGCCACGTTCATTTTCTTGTCAAAAAGTTACTGGTGGGGGATGGTGGGAA<br>AAAGTTATTAGTGCAAATTTCCTAGAGAAAAAACCATTTCTCTTTCAAATTTTCCAGTTGAATTT<br>TATGTTCGCTTTTGCTTCTTAGGTTC |
| 1471 | GPR110 | 2955947 | ATTATGCTCAGTATTCGATCGGGTTTTCTGATTTAGG |
| 1472 | GPR110 | 2955948 | TACTGGAGATTCCTCCGACAACATCATGCTAACTCAGTTTGTCTCAAATGA |
| 1473 | GPR110 | 2955949 | CTCATCAGATTTATCTGCCAAACCCAAATTCTCAAAGCCTTTCAACCCACTGCAAACAA |
| 1474 | GPR110 | 2955950 | TAGTCAGAGCACTGTTTTTCCTCCATTTTCCTCCATGGGTTTCTCTTCCAGTAACAAATGTGATC<br>CAAAGAAATGTAAGCATAGACATGAAAAGGGATAATGCCGCCTTTAAAACTGTTTTCTAGTTT<br>GTTGTTAGAAGTTATAAAAATACACAGGAACACAGCATTCACTTGAAAATAAATTTTTAGGCA<br>TTTTAAATAGATTAAAGCAGAAGAAAGAGTGAGAAAGTAACCATTCTAAATTCTTAAAAAGA<br>GAATAGCACCTATGAAAATGAAATAAAGAATCATGAATAACATCAGGAAGTCAGG |
| 1475 | GPR110 | 2955957 | TGCTTTGGAATACTCTTGGACAGTAAG |
| 1476 | GPR110 | 2955960 | TAGCCCTGTCCCTCTTGATTGCTGATGTCTGGTTTATTGTTGGTGCCACAGTGGACACCACGGT<br>GAACCCTTCTGGAGTCTGCACAGCTGCTGTGTTCTTTACACACTTCTTCTACCTCTCTCTTTGTTCT<br>TCTGGATGCTCATGCTTGGCATCCTGCTGGCTTACCGGATCATCCTCGTGTTCCATCACATGGC<br>CCAGCATTTGATGATGGCTGTTGGATTTTGCCTGGGTTATGGGTGCCCTCTCATTATATCTGTC<br>ATTACCATTGCTGTCACGCAACCTAGCAATACCTACAAAAGGAAAGATGTGTGTTGGCTTAAC<br>TGGTCCAATGGAAGCAAACCACTCCTGGCTTTTGTTGTCCCTGCACTGGCTATTG |
| 1477 | GPR110 | 2955961 | GGACCTGTGATATCCACGGTTATTCAAAACTATTCCATAAATGAAGTTTTCCTATTTTTTTCCAA<br>GATAGAGTCAAACCTGAGCCAGCCTCATTGTGTGTTTTGGGATTTCAGTCATTTGCAGTGGAA<br>CGATGCAGGCTGCCACCTAGTGAATGAAACTCAAGACATCGTGACGTGCCAATGTACTCACTT<br>GACCTCCTTCTCCATATTGATGTCACCTTTTGTCCCCTCTACAATCTTCCCCGTTGTAAAATGGA<br>TCACCTATG |
| 1478 | GPR110 | 2955962 | CTCAAAAGGGGTTACAGCTATCAGATTAAAATGTGTCCCCAAAATACATCTATTCCCATCAGA<br>GGCCGTGTGTTAATTGGGTCAGACCAATTCCAGAGATCCCTTCCAGAAACTATTATCAGCATG<br>GCCTCGTTGACTCTGGGGAACATTCTA |
| 1479 | GPR110 | 2955963 | AGCTGTGTCATCCTTCGTGCAAAATCTTTCTGTCATCATTCGGCAAAACCCATCAACCACAGTG<br>GGGAATCTGGCTTCGGTGGTGTCGATTCTGAGCAATATTTCATCTCTGTCACTGGCCAGCCAT<br>TTCAGGGTGTCCAATTCAAC |
| 1480 | GPR110 | 2955964 | AATGTTAGTTCTATATGGCCAAGACATCTGATTTAAATTTGATGAAACACAGCATGTCA |
| 1481 | GPR110 | 2955965 | ACTTGCCCTGGTCTTGAGTTTCAGAGTGGCAATATCCCAGTGAGCATGGCTAGGTGGAGGGT<br>AAGTATACCTACGTGCATCATTGGCCAGTATGCAAAGAGCAAGGATGACATCAGACCCTGGT<br>GAACCCGTGGAGTCGTGCATGAGTGGTAGCGTCTGGGCAGCAGAGTCTAGGTTGCAGCTCA<br>AAAGACAGAGTTGATAGTTTTGTCAGGCAGAGGTGTTGTGGAGGAGTGTATCATTGCTGAGG<br>AGGTCTATGATGGATGGTAGAGCAGCAACTAAGCTGGCCTCAGAAGTCCAGAAGACCTGGG<br>AATTAAAGAAGAGTGAAGGTGTGAGTCATAAGCCAGCAGGCTTAGTACAAGTAAGGATA<br>TATCTATACCAGAAATTAGGGCAAGGAGTGGGTCAGACAAAGGTGAACCATATAAAATGACT<br>GAACTGCAATGACCTTAAGGGGCATCTGGTTTACCAACCTCATTTTGCAGATCAGAAAACAA<br>AAGACCAAGGGCCAATAGTTCCTCTGGTAGCAATAGTTTTGAATTAGAAGCATGGTCACTTG<br>ATTCCTAGTCCAGTGCTGTATTAGTCTGTTCTCACATTGTTATAAAGAACTATTTGAGACTGGG<br>TAGTTTATAAAGAAAAGAGGTTTGACTCACAGTTATGCAGGATGTACAAAAGGCATATCTGG<br>GGAGGCCTCAGGAAACTTACAATCATGGTGGGAGGCGAAAGGGAAGTAAGCACATCCTTAT<br>ATGGTGACAGGAGAGAGAGAGAGAGAGAGAGAGAGAGAAAGAGAGAGATGGAGAGAGAATG |

TABLE 13-continued

Subtyping Target Sequences

| SEQ ID NO. | Gene | Affy Probeset ID | Sequence |
|---|---|---|---|
| | | | GGGGAGATGCTACACACTTTTAAACAACCAGATCTTGTGAGAACTGTATCATGAGACAGCACT TGGGGGATGGTGCTAAACCATTAGAAACCACCTCCATGATCCAATCATCTCCCACCAAGCCCC ACCTCCAACATTGGGAATTATAACTCGACATAAGATTTGGGTGGGGACACAGAGCCAAACCA CATCAGGTGCTATGCCCTCCACATGATGCTCTCTTAGGAAGGTTCAAGTATTAAGACAAGTAA GACAGAAAGAAGGAAATAAATATCTAGGAATCAGAAGAACTCAAGTCACAGAAAGAAGGA CCCCAAGACCAGTTCACAGATACTGTTCAGCAAGTAGATTTCCATATTGAGCAGAACTTCTATT CCAGCCAGAGACCTTGCTTCTGCTGCTGTGAGTAGAAAACCCCAGAATAGTATTCATCAGAGGA CTGTGGAATGTTTACTTCTCCCTTTGTGGATCTCAGTTTCCTCATCTGTAAACTGGGGAAGGGG ATTAGATTCTGGGGTTTCTTCTTGCTCTTGCCTTCGTTGCCTCAATTCTGGACATGAGCAATAG TTGAGACTAGTTCGCTCCAGGCAGATCCCAGGTGGCTTGAACAGAAAACAGCATTGTCAGTT GAGAAGAACAAGAAGGAAAATGGCGGGCACTTGGGCGCCTGAGTGGACTTAATGTTGAGTG GAAGGGGACTGCCTTCCTTTGCTGCTTTCCAAGTTAGCCTGGTGTAGTAAAAGTAGATGGGA GCCTCAAGAAAGAAGTAAAATTCCAAATCTAGGGCCGGGTGCA |
| 1482 | GPR110 | 2955966 | GGTCCAAGGATGATGAATATACCCTGCCCTGCAGCAGTGGCTACAGGGGAAACATCACAGCC AAGTGTGAGTCCTCTGGGTGGCAGGTCATCAGGGAGACTTGTGTGCTCTCTCTGCTTGAAGA ACTG |
| 1483 | GPR110 | 2955968 | AGCATCGTTGCTGGGTATGAAGTTGTTGGCTCCAGCAGTGCATCTGAACTGCTGTCAGCCATT GAACATGTTGCCGAGAAGGCTAAGACAGCCCTTCACAAGCTGTTTCCATTAGAAGACGGCTCT TTCAGAGTGTTCGGAAA |
| 1484 | GPR110 | 2956000 | CTGTGGAACCTGGTTTAACTTCACTAAATCAAACCTATAACAAGCAGGAAAA |
| 1485 | GPR110 | 2956001 | GCAACTACAGGAGATATGATGCCTCATAATTCGGAGCCAGAAGTGGGGCTTTGGGTGAGATA TCTTTGCACAGATAACATGTATACATCATAGTTCAAAACCCAGTAGTCATTGTTTACAGCA |
| 1486 | GPR110 | 2956002 | AATGTCACTCTTGTCGCCCAAGTTGGAGTG |
| 1487 | GPR110 | 2956003 | GAATTCAAGGTTTTGAGTCGGTTCAGGTCACCCAATT |
| 1488 | GPR110 | 2956004 | TTTGGGGCACTTTCAAAATTAATGAAAGGTTTACAAATGACCTTTTGAATTCATCTTCTGCTAT ATACTCCAAATATGCAAA |
| 1489 | GPR110 | 2956005 | GTACCTGTGAAGACAGCTACACCTGGTTTCCTCCCTCATGCCTTGATCCCCAGAACTGCTACCT TCACACGGCTGGAGCACTCCCAAGCTGTGAATGTCATCTCAACAACCTCAGCCAGAGTGTCAA TTTCTG |
| 1490 | GPR110 | 2956006 | ACTGCAACAGCCTGAATGGAGTCCTGCAG |
| 1491 | GPR110 | 2956007 | CTTCAGGTGACCTATAGAGATTCCAAGGAGAAAAGAGATTTGAGAAATTTTCTGAAGCTCTTG AAGCCTCCATTATTATGGTCACATGGGCTAATTAGAATTATCAGAGCAAAGGCTACCACAG |
| 1492 | GPR110 | 2956008 | AATGATGGCATCAAAACAAAAAAAGAACTCATTGTGAATAAGAAAAAACATC |
| 1493 | GPR110 | 2956009 | TCTTCACCTTCACTGACGGCCACGGTGGCTT |
| 1494 | GPR110 | 2956010 | ACTATGCACCCGACTGCTGCTGTTCA |
| 1495 | GPR110 | 2956016 | GCTCAGATACTGATACTTTCTTTCCAAACAGCATAAGAAGTGATTGAGCCACAAGTATACTGA AGGAAGGGCTCCCTCGAGTTCTGGTGTGAAGAGA |
| 1496 | TNFRSF21 | 2956054 | CTTATGCTAATATGCTCTGGGCTGGAGAAATGAAATCCTCAAGCCATCAGGATTTGCTATTTA AGTGGCTTGACAACTGGGCCACCAAAGAACTTGAACTTCACCTTTTAGGATTTGAGCTGTTCT GGAACACATTGCTGCACTTTGGAAAGTCAAAATCAAGTGCCAGTGGCGCCCTTTCCATAGAG AATTT |
| 1497 | TNFRSF21 | 2956055 | ATATGTCTTGTATAGTTCATATTCATGGCTGAAACTTGACCACACTATTGCTGATTGTATGGTT TTCAC |
| 1498 | TNFRSF21 | 2956056 | ACATAGGGATACTGCATTCTGGAAATTACTCAATTTAGTGGCAGGGTGGTTTTTAATTTTCTT CTGTTTCTGATTTTGTTGTTTGGGGTGTGTGTGTGTTTGTGTGTGTGTGTGTGTGT TGTGTGTGTGTTTAACAGAGAATATGGCCAGTGCTTGAGTTCTTTCTCCTTCTCTCTCTCTTTT TTTTTTAAATAACTCTTCTGGGAAGTTGGTTTATAAGCCTTTGCCAGGTGTAACTGTTGTGAA ATACCCACCACTAAAGTTTTTAAGTTCCATATTTTCTCCATTTTGCCTTCTTATGTATTTTCAAG ATTATTCTGTGCACTTTAAATTTACTTAACTTACCATAAATGCAGTGTGACTTTTCCCACACACT GGATTGTGAGGCTCTTA |
| 1499 | TNFRSF21 | 2956057 | GTGACTTGCAGCCTATCTTTGATGACATGCTCCACTTTCTAAATCCTGAGGAGCTGCGGGTGA TTGAAGAGATTCCCCAGGCTGAGGACAAACTAGACCGGCTATTCGAAATTATTGGAGTC |
| 1500 | TNFRSF21 | 2956058 | ACAAGGGCTTCTTCGTGGATGAGTCGGAGCCCCTTCTCCGCTGTGACTCTACATCCAGCGGCT CCTCCGCGCTGAGCAGGAACGGTTCCTTT |

TABLE 13-continued

Subtyping Target Sequences

| SEQ ID NO. | Gene | Affy Probeset ID | Sequence |
|---|---|---|---|
| 1501 | TNFRSF21 | 2956059 | CCCAACGCGAAACTTGAGAATTCCGCTCTCCTGACGGTGGAGCCTT |
| 1502 | TNFRSF21 | 2956064 | GATATCCTGAAGCTTGTAGCAGCCCAAGTGGGAAGCCAGTGGAAAGATATCTATCAGTTTCTT<br>TGCAATGCCAGTGAGAGGGAGGTTGCTGCTTTCTCCAATGGGTACACAGCCGACCACGAGCG<br>GGCCTACGCAGCTCTGCAGCACTGGACCATCCGGGGCCCCGAGGCCAGCCTCGCCCAGCTAA<br>TTAGCGCCCTGCGCCAGCACCGGAGAAACGATGTTG |
| 1503 | TNFRSF21 | 2956076 | GGGGACATCCTAGACAGAACCTACACAAGCATTTTGACATCAATGAGCATTTGCCCTGGATGA<br>TTGTGCTTTTCCTGCTGCTGGTGCTTGTGGTGATTGTGGTGTGCAGTATCCGGAAAAGCTCGA<br>GGACTCTGAAAAAGGGGCCCCGGCAGGATCCCAGTGCCATTGTGGAAAAGGCAGGGCTGAA<br>GAAATCCATGACTCCAACCCAGAACCGGGAGAAATGGATCTACTACTGCAATGGCCATG |
| 1504 | TNFRSF21 | 2956077 | AGAATCCAACTCTTCTGCCTCTGTTAGACCAAAGGTACTGAGTAGCATCCAG |
| 1505 | TNFRSF21 | 2956079 | TGGTGGTGATCAAGCCGGGGACCAAGGAGACAGACAACGTCTGTGGCACACTCCCGTCCTTC<br>TCCAGCTCCACCTCACCTTCCCCTGGCACAGCCATCTTTCCACGCCCTGAGCACATGGAAACCC<br>ATGAAGTCCCTTCCTC |
| 1506 | TNFRSF21 | 2956080 | GAAGGCCTCGAATCTCATTGGCACATACCGCCATGTTGACCGTGCCACCGGCCAGGTGCTAAC<br>CTGTGACAAGTGTCCAGCAGGAACCTATGTCTCTGAGCATTGTACCAACACAAGCCTGCGCGT<br>CTGCAGCAGTTGCCCTGTGGGGACCTTTACCAGGCATGAGAATGGCATAGAGAAATGCCATG<br>ACTGTAGTCAGCCATGCCCATGGCCAATGATTGAGAAATTACCTTGTGCTGCCTTGACTGACC<br>GAGAATGCACTTGCC |
| 1507 | TNFRSF21 | 2956094 | CGAGCCACAGCCACGATGATCGCGGGCTCCCTTCTCC |
| 1508 | TNFRSF21 | 2956095 | TGCACATGGGGTGTTGGAGGTAGATGGGCTCCCGGCCCGGGAGGCGGCGGTGGATGCGGC<br>GCTGGGCAGAAGCAGCCGCCGATTCCAGCTGCCCCGCGCGCCCCGGGCGCCCCTGCGAGTCC<br>CCGGTTCA |
| 1509 | TNFRSF21 | 2956096 | GTGCTGAGCGCCCCTAGAGCCTCCCTTGC |
| 1510 | TNFRSF21 | 2956097 | CTGGAAGCTTCGCTATGGGAAGTCGTTCCTTTGCTCTCTCGCGCCCAGTCCTCCTCCCTGGTTC<br>TCCTCAGCCGCTGTCGGAGGAGAGC |
| 1511 | CRISP3 | 2956567 | ACGCATTACACACCGAGTAGGGCTATGTAGAGAGGAGTCAGATTATCTACTTAGATTTGGCAT<br>CTACTTAGATTTAACATATACTAGCTGAGAAATTGTAGGCATGTTTGATACACATTTGATTTCA<br>AATGTTTTTCTTCTGGATCTGCTTTTTATTTTACAAAATATTTTTCATACAAATGTTAAAAAG<br>AAACAAAATCTATAACAACAACTTTGGATTTTATATATAAACTTTGTGATTTAAATTTACTGAA<br>TTTAATTAGGGTGAAAATTTTGAAAGTTGTATTCTCATATGACTAAGTTCACTAAAACCCTGGA<br>TTGAAAGTGAAAATTATGTTCCTAGAACAAAATGTACAAAAAGAACAATATAATTTTCACATG<br>AACCCTTGGCTGTAGTTGCCTTTCCTAGCTCCACTCTAAGGCTAAGCATCTTCAAAGACGTTTT<br>CCCATATGCTGTCTTAATTCTTTTCACTCATTCACCCTTCTTCCCAATCATCTGGCTGGCATCCTC<br>ACAATTGAGTTGAAGCTGTTCCTCCTAAAACAATCCTGACTTTTATTTTGCCAAAATCAATACA<br>ATCCTTTGAATTTTTTATCTGCATAAATTTTACAGTAGAATATGATCAAACCTTCATTTTTAAAC<br>CTCTCTTCTCTTTGACAAAACTTCCTTAAAAAGAATACAAGATAATATAGGTAAATACCCTCC<br>ACTCAAGGAGGTAGAACTCAGTC |
| 1512 | CRISP3 | 2956568 | CAGTTGCAAGGCCTCCTGCAATTGTTCAAACAGCA |
| 1513 | CRISP3 | 2956571 | TGAACAAGGAGCACCTTGTGCCAGTTGCCCAGATAACTGTGACGATGGACTATGCA |
| 1514 | CRISP3 | 2956574 | GCAGCAAATGCCCAAAAGTGGGCAAACCAGTGCAATTACAGACACAGTAACCCAAAGGATCG<br>AATGACA |
| 1515 | CRISP3 | 2956575 | ACCCAAACACAAGTGCAAAGGGAGATTGTGAATAAGCACAATGAACTGAGGAGAGCAGTAT<br>CTCCCCCTGC |
| 1516 | CRISP3 | 2956576 | CCAGTGCTGTTGTTCCTGGTTGCTG |
| 1517 | CRISP3 | 2956577 | GCAGATCCCTGTTCCACCGGTTTTGT |
| 1518 | CRISP3 | 2956578 | CTTCATCCTGCTCTGGAAACCACTG |
| 1519 | GSTM2 | 2969579 | AGACCTGTGTTCACAAAGATGGCTGTCTGGGGCAACAAGTAG |
| 1520 | PERP | 2976366 | AGCCAGACATGCTAAGTGGCACTTACTGCTGATTGTAACAAAGAAGTAATATATCAAGGTCTT<br>TCCATGTTCACACAAGGTAGCTTGTGTGTAATAACTTAGCTTCAAAACCATAGACTGCAGAAC<br>TCACAAGTTCAACAGCCTTTCCTTTTTTAAGGAAATGAAAACAATGGAAAATATAGTCATCATA<br>ACTTAATTCGGTTTATTTTTTTTTTCTGTAAACTCCCCCTGAAAGACATTCCTATTAATACAGTA<br>AATGTGAACACTGACTTGTTTTTATAAGCACATCTGAAAGGGCATATTTGAGTCTCATCCCAAC<br>TTTGGTCCTTGCTATCTGTGCAGGCTTGGGCAGGTCATCTCCCTGCTGGTCTCAATATCCTCAC<br>CTGTAAAATGATTGTAAATGATCCCCCTACCTTCAAGATTCTCTGATTGATAGAATTTTTTCTTT<br>AATTAAAAAATTTTAAATATTCCTTGAGTTGGAAGCACTGATCAATAAGTGGATTGCTTAGGG |

TABLE 13-continued

Subtyping Target Sequences

| SEQ ID NO. | Gene | Affy Probeset ID | Sequence |
|---|---|---|---|
| | | | AGGTTGGAACGAATAGATTCAGTCCCAACTTCCTCTTTTAAATTCCCTCTTCCTCACTCTTCCTG<br>CAACACTTATTTTTACAGTTGAGTTTTAAAAATAAGTAATATATAAAATAATTTCTGTAGTGTG<br>GTTTCAGATTTAAAAATTCCTGCAGACAGGCTGGGCTTGCAACCCCATCAGTCGATGGTCAGA<br>GCCCTTTGCTTTTTGAGACCATTTTTAGGTGAGCTTGGCTTGCCTGGATACAGTGTGCAGTGC<br>ATTCTTCCTGAATTTTGCAATTCTGGTATCTGGGTGTATTTTCTAGGTGTGTCAGGGTGAGTGT<br>AATCCACCTAGGGTGTGGAAAAAGCCAAGAAAGGGAAATTAAAAGAGGTTCCTATCCAGTCA<br>TGTTAATGATCTTCCACTTGTACTATCCTGTGCTTCGTTGTTAACC |
| 1521 | PERP | 2976367 | TGTGCAGTGTAGCTGAAGCCTCCTCCTTGTGCTGGGGTCCCCTTCCATTCAGGTGGTGGGGTA<br>GCAGTCTCTCTATTTTCCCCTTGCCCTCCTTCCCATTTTATCATTTGTTATTTTTTTCCCACCATA<br>AGTCATATGTTACTTCCACTATGGTGTATGTCATTGTGAGGATGGGTGCAGAGAGGCTGGGT<br>GGGAGAACGGAAATATATCTCCCTAGGGCTACTGTTGGCCAGCTAGTCCTTGGCAGTGAATTTT |
| 1522 | PERP | 2976368 | TATATATGATGCATCGGATAGGTCATTATGATTTTTTACCATTTCGACTTACA |
| 1523 | PERP | 2976369 | GCTAAGGCTTCATGTTGACTCGATATGTCATCTAGGAAAGTACTATTTCATGGTCCAAACCTGT<br>TGCCATAGTTGGTAAGGCTTTCCTTTAAGTGTGAAATATTTAGATGAAATTTTCTCTTTTAAAG<br>TTCTTTATAGGGTTAGGGTGTGGGAAAATGCTATATTAATAAATCTGTAGTGTTTTGTGTTTAT<br>ATGTTCAGAACCAGAGTAGACTGGATTGAAAGATGGACTGGGTCTAATTTATCATGACTGAT<br>AGATCTGGTTAAGTTGTGTAGTAAAGCATTAGGAGGGTCATTCTTGTCA |
| 1524 | PERP | 2976370 | TTTCTCCAGGCGACTTTGAACCCATTT |
| 1525 | PERP | 2976371 | TTCATGCCAACCCTGCTGTCACTTAC |
| 1526 | PERP | 2976378 | TCATCATCCTGGTGATCTGTTTCATCCTCTCCTTCTTCGCCCTCTGTGGACCCCAGATGCTGTC<br>TTCCTGAGAGTGATTGGAGGTCTCC |
| 1527 | PERP | 2976389 | CAGCGGGTCCTACGAGGAGGGCTGTC |
| 1528 | PERP | 2976390 | CACGGCCAGACGTCCTCGCTGTGGTGGAAATG |
| 1529 | PERP | 2976393 | CCGCGGCCTCTTCGCTTTTGTGGCGGCGCCCGCGCTCGCAGGCCACTCTCTGCTGTCGCCCGT<br>CCCGCGCGCTCCTCCGACCCGCT |
| 1530 | THBS2 | 2985810 | GTGTTGTGGGTCAACCGTACAATGGTGTGGGAGTGACGATGATGTGAGTATTTAGAATGTA<br>CCATATTTTTTGTAAATTATTTATGTTTTTCTAAACAAATTTATCGTATAGGTTGATGAAACGTC<br>ATGTGTTTTGCCAAAGACTGTAAATATTTATTTATGTGTTCACATGGTCAAAATTTCACCACTG<br>AAACCCTGCACTTAGCTAGAACCTCATTTTTA |
| 1531 | THBS2 | 2985811 | TCACGATGAAGCATGCTAGAAGCTGTAACAGAATACATAGAGAATAATGAGGAGTTTATGAT<br>GGAACCTTAAATATATAATGTTGCCAGCGATTTTAGTTCAATATTGTTACTGTTATCTATCTGC<br>TGTATATGGAATTCTTTTAATTCAAACGCTGAAAAGAATCAGCATTTAGTCTTGCCAGGCACAC<br>CCAATAATCAGTCATGTGTAATATGCACAAGTTTGTTTTTGTTTTTGTTTTTTTTGTTGGTTGGT<br>TTGTTTTTTGCTTTAAGTTGCATGATCTTTCTGCAGGAAATAGTCACTCATCCCACTCCACATA<br>AGGGGTTTAGTAAGAGAAGTCTGTCTGTCTGATGATGGATAGGGGGCAAATCTTTTTCCCCTT<br>TCTGTTAATAGTCATCACATTTCTATGCCAAACAGGAACAATCCATAACTTTAGTCTTAATGTA<br>CACATTGCATTTTGATAAAATTAATTTTGTTGTTTCCTTTGAGGTTGATCGTTGTTGTTGTTT<br>TGCTGCACTTTTTACTTTTTTGCGTGTGGAGCTGTATTCCCGAGACCAACG |
| 1532 | THBS2 | 2985812 | CATCCTTGCAAATGGGTGTGACGCGGTTCCAGATGTGGATTTGGCAAAACCTCATTTAAGTAA<br>AAGGTTAGCAGAGCAAAGTGCGGTGCTTTAGCTGCTGCTTGTGCCGCTGTGGCGTCGGGGAG<br>GCTCCTGCCTGAGCTTCCTTCCCCAGCTTTGCTGCCTGAGAGGAACCAGAGCAGACGCACAGG<br>CCGGAAAAGGCGCATCTAACGCGTATCTAGGCTTTGGTAACTGCGGACAAGTTGCTTTTACCTG |
| 1533 | THBS2 | 2985813 | TGGGCATGCCATTACATTGCTTTTTCTTGTTTGTTTAAAAAGAATGACGTTTACATATAAAATG<br>TAATTACTTATTGTATTTATGTGTATATGGAGTTGAAGGGAATACTGTGCATAAGCCATTATGA<br>TAAATTAAGCATGAAAAATATTGCTGAACTACTTTTGGTGCTTAAAGTTGTCACTATTCTTGAA<br>TTAGAGTTGCTCTA |
| 1534 | THBS2 | 2985814 | TCCTGTCCCTTGACCTTAACTCTGATGGTTCTTCAC |
| 1535 | THBS2 | 2985815 | ATGCCATGGTCCCTAGACACCTCAGTTCATTGTGG |
| 1536 | THBS2 | 2985816 | CAGACTCAGGACCTATCTATGACCAAACCTACGCTGGCGGGCGGCTGGGTCTATTTGTCTTCT<br>CTCAAGAAATGGTCTATTTCTCAGACCTCAAGTACGAATGCAGAG |
| 1537 | THBS2 | 2985817 | TGCGAACCTTATGGCACGACCCCAGGAACATTGGCTGGAAGGACTACACGGCCTATAGGTGG<br>CACCTGACTCACAGGCCCAAGACTGGCTACATC |
| 1538 | THBS2 | 2985818 | TTCAGTGGCACATTCTACGTAAACACTGACCGGGACGACGACTATGCCGGCTTCGTCTTTGGT<br>TACCAGTCAAGCAGCCGCTTC |

TABLE 13-continued

Subtyping Target Sequences

| SEQ ID NO. | Gene | Affy Probeset ID | Sequence |
|---|---|---|---|
| 1539 | THBS2 | 2985819 | TGATGGACGGGGTGATATTTGTAAAGATGATTTTGACAATGACAACATCCCAGATATTGATGA TGTGTGTCCTGAAAACAATGCCATCAGTGAGACAGACTTCAGGAACTTCCAGATGGTCCCCTT GGATCCCAAAGGGACCACCCAAATTGATCCCAACTGGGTCATTCGCCATCAAGGCAAGGAGC TGGTTCAGACAGCCAACTCGGACC |
| 1540 | THBS2 | 2985824 | TGTCTTCAATGAACGAGACAATTGTCCCTACGTCTACAACACTGACCAGAGGGACACGGATGG |
| 1541 | THBS2 | 2985825 | TTCAATCCCCGCCAGGCTGACTATGACAAGGATGAGGTTGGGGACCGCTGTGACAACTGCCC TTACGTGCACAACCCTGCCCAGATCGACACAGACAACAATGGAGAGGGTGACGCCTGCTCCG TGGACATTGATGG |
| 1542 | THBS2 | 2985827 | ACAAGGACGGGATTGGCGATGCCTGTGATGAT |
| 1543 | THBS2 | 2985830 | TGAGCCCGAAAACCCATGCAAGGACAAGACACACAACTGCCACAAGCACGCGGAGTGCATCT ACCTGGGCCACTTCAGCGACCCCATGTACAAGTGCGAGTGCCAGACAGGCTACGCGGGCGAC GGGCTCATCTGCGGGGAGGACTCGGACCTGGACGGCTGGCCCAACCTCAATCTG |
| 1544 | THBS2 | 2985833 | TCCACCAGCAAGGTGCCTCGCTGTGTCAACACTCAGCCTGGCTTCCACTGCCTGCCCTGCCCG CCCCGATACAGAGGGAACCAGCCCGTCGGGGTCGGCCTGGAAGCAG |
| 1545 | THBS2 | 2985836 | TGAAACCCGGGCTTCCATTCTGATGAAAGCACAAACGCTTTGGGAAACTAGATGAAAAACA CAGAAAAGAAAAATCAATTTTAGTTGCACACGCAAAGATAACTACTTTTAACATCTGTGTTTCA GTCCTCCTGTATTTCTAATGTAAAAACAAAAAAGATGCCAGGTGGCGTGGCCT |
| 1546 | THBS2 | 2985837 | GGTCCCCGTGGTCGGCCTGCACTGTCACCTGTGCCGGTGGGATCGGGAGCGCACCCGGGTC TGCAACAGCCCTGAGCCTCAGTACGGAGGGAAGGCCTGCGTGGGGATGTGCAGGAGCGTC AGATGTGCAACAAGA |
| 1547 | THBS2 | 2985838 | TCTGTGACCTGTGGAGTTGGCAATATCACACGCATCCGTCTCTGCAACTCCCCAGTGCCCCAG ATGGGGGGCAAGAATTGCAAA |
| 1548 | THBS2 | 2985839 | TCCGGCAGGACGGCGGCTGGAGCCACTGGT |
| 1549 | THBS2 | 2985840 | AAATACCCCTCTAGGCGGCACAGCCTGATCTCTCT |
| 1550 | THBS2 | 2985841 | TGGACCCAGTGCTCCGTGACGTGTGGCTCTGGGACCCAGCAGAGAGGCCGGTCCTGTGACGT CACCAGCAACACCTGCTTGGGGCCCTCCATCCAGACACGGGCTTGCAGTCTGAGCAAGTGTG ACACC |
| 1551 | THBS2 | 2985844 | AAACCATTTGCCACCAAATCACCTGCCCGCCTGCAACCTGCGCCAGTCCATCCTTTGTGGAAG GCGAATGCTGCCCTTCCTGCC |
| 1552 | THBS2 | 2985846 | TCATTGGTGGCCCTCCTAAGACAAGGAACATGTCAGCTTGCTGGCAGGATGGCCGGTTCTTTG CGGAAAATGAAACGTGGGTGGTGGACAGCTGCACCACGTGTACCTGCA |
| 1553 | THBS2 | 2985849 | TCCGCATGTCACCACCGAGTACGTGGGCCCCAGCTCGGAGAGGAGGCCCGAGGTGTGCGAA CGCTCGTGCGAGGAGCTGGGAAACATGGTCCAGGAGCTCTCGGGGCTCCACGTCCTCGTGAA CCAGCTCAGCGAGAACCTCAAGA |
| 1554 | THBS2 | 2985854 | AAATGCATTTTATATACTGGCTTGGATGGATTTCTATTGTGACATGGTGTATGTGTGTGTGTGT ATGTGTGTGCATTCATGCTTGTA |
| 1555 | THBS2 | 2985855 | GCTTCAGAACGTCCACCTAGTGTTTGAAAACTCTGTGGAAGATATTCTAAGCAAGAAGGGTTG CCAGCAAGGCCA |
| 1556 | THBS2 | 2985856 | CGCTTCGTGCGCTTTGACTACATCCCACCGGTGAACGCAGATGACCTCAGCAAGATCACCAAG ATCATGCGGCAGAAGGAGGGCTTCTTCCTCACGGCCCAGCTCAAGCAGGACGGCAAGTCCAG GGGCACGCTGTTGGCTCTGGAGGGCCCCGGTCTCTCCCAGAGGCAGTTCGAGATCGTCTCCA ACGGCCCCGCGGACACGCTGGATCTCACCTACTGGATTGA |
| 1557 | THBS2 | 2985857 | TGGTCTGGAGGCTGGTCCTGCTGGCTCTGTGGGTGTGGCCCAGCACGCAAG |
| 1558 | THBS2 | 2985860 | CCCTGGTGAAGTTTCATTTGCCGAATTCATCTCTCATGACAACCCGATGAGGTGGGCATTTTAC ATGACGCTACGTTTCATTCTACGGATGAGGA |
| 1559 | THBS2 | 2985863 | CCTGCACAGGAGAAGCGGCATATAAAGCCGCGCTGCCCGGGAGCCGCTCGGCCACGTCCACC GGAGCATCCTGCACTGCAGGGCCGGTCTCTCGCTCCAGCAGAGCCTGCGCCTTTCTGACTCGG TCCGAACACTGAAACCAGTCATCACTGCATCTTTTTGGCAA |
| 1560 | THBS2 | 2985864 | GAGACGGCATCCAGTACAGAGGGGCTGGACTTGGACCCCTGCAGCAG |
| 1561 | AHR | 2991234 | TCCCGTCGACGCTCTGTTCCGAGAGCGTGCCCCGGACCGCCAGCTCAGAACAGGGGCAGCCG TGTAGCCGAACGGAAGCTGGGAGCAGCCGGGACTGGTGGCCCGCGCCCGAGCTCCGCAGGC GGGAAGCACCCTGGATTTAGGAAGTCCCGGGAGCAGCGCGGCGGCACCTCCCTCACCCAAG |

TABLE 13-continued

Subtyping Target Sequences

| SEQ ID NO. | Gene | Affy Probeset ID | Sequence |
|---|---|---|---|
| | | | GGGCCGCGGCGACGGTCACGGGGCGCGGCGCCACCGTGAGCGACCCAGGCCAGGATTCTAA
ATAGACGGCCCAGGCTCCTCCTCCGCCCGGGCCGCCTCACCTGCGGGCATTGCCGCGCCGCT
CCGCCGGTGTAGACGGCACCTGCGCCGCCTTGCTCGCGGGTCTCCGCCCCTCGCCCACCCTCA
CTGCGCCAGGCCCAGGCAGCTCACCTGTACTGGCGCGGGCTGCGGAAGCCTGCGTGAGCCG
AGGCGTTGAGGCGCGGCGCCCACGCCACTGTCCCGAGAGGACGCAGGTGGAGCGGGCGCG
GCTTCGCGGAACCCGGCGCCGGCCGCCGCAGTGGTCCCAGCCTACACCGGGT |
| 1562 | AHR | 2991238 | GTCAAATCCTTCCAAGCGGCATAGAGACCGACTTAATACAGAGTTGGACCGTTTGGCTAGCCT
GCTGCCTTTCCCACAAGATGTTATTAATAAGTTGGACAAACTTTCAGTTCTTAGGCTCAGCGTC
AGTTA |
| 1563 | AHR | 2991240 | AGGATAACTGTAGAGCAGCAAATTTCAGAGAAGGCCTGAACTTACAAGAA |
| 1564 | AHR | 2991244 | TCTGAATGGCTTTGTATTAGTTGTCACTACAGATGCTTTGGTCTTTTATGCTTCTTCTACTATAC
AAGATTATCTAGGGTTTCAGCA |
| 1565 | AHR | 2991245 | ATCAGTCCTTTTGTTGTATTCCTTGTATC |
| 1566 | AHR | 2991246 | ACCGAAGACCGAGCTGAATTTCAGCGTCAGCTACACTGGGCATTAAATCCTTCTCAGTGTACA
GAGTCTGGACAAGGAATTG |
| 1567 | AHR | 2991247 | AGACAGTAGTCTGTTATAACCCAGACCAGATTCCTCCAGAAAACTCTCCTTTAATGGAGAGGT
GCTTCATATGTCGTCTAAGGTGTCTGCTGGATAA |
| 1568 | AHR | 2991249 | TTTAGGATATACTGAAGCAGAGCTGTGCACGAGAGGCTCAGGTTATCAGTTTATTCATGCAGC
TGATATGCTTTATTGTGCCGAGTC |
| 1569 | AHR | 2991252 | AACCGATGGACTTGGGTCCAGTCTAATGCACGCCTGCTTTATAAAAATGGAAGACCAGATTAT
ATCATTGTAACTCAGAGACCACTA |
| 1570 | AHR | 2991253 | ATAAGTCCTCTTATGTGAAAGCATAAAAATAATTCAAGCAGACTTTAGTCTGTAAATAAAAATT
GAAAAGTTTAATTCATCTAGAAAGAAGAGCACAGGTGAGAGACATTGAGAAGATAGAATTG
ACGAACTTGATTGAGAGCTACATGTGCAGAGCTATAGAAAGAATAATAAAACTCTAGGGTTTT
ATCTTGGGCATATGAAAGACACA |
| 1571 | AHR | 2991254 | AGGAAGGAACAGAGCATTTACGAAAACGAAATACGAAGTTGCCTTTTATGTTTACCACTGGA
GAAGCTGTGTTGTATGAGGCAACCAACCCTTTTCCTG |
| 1572 | AHR | 2991255 | TGCACCGATGGGAAATGATACTATCCTGAAACATGAGCAAATTGACCAGCCTCAGGATGTGA
ACTCATTTGCTGGAGGTCACCCAGGGCTCTTTCAAGATAGTAAAAACAGTGACTTGTACAGCA
TAATGAAAAACCTAGGCATTGATTTTGAAGCATCAGACACATGCAGAATGAAAAATTTTTCA
GAAATGATTTTTCTGGTGAGGTTGACTTCAGAGACATTGACTTAACGGATGAAATCCTGACGT
ATGTCCAAGATTCTTTAAGTAAGTCTCCCTTCATACCTTCAGATTATCAACAGCAACAGTCCTT
GGCTCTGAACTCAAGCTGTATGGTA |
| 1573 | AHR | 2991256 | TGAAGCACATGCAAGTTAATGGCATGTTTGAAAATTGGAACTCTAACCAATTCGTGCCTTTCA
ATTG |
| 1574 | AHR | 2991257 | TGTACAGAGCTGGACTACCCTATGGGGAGTTTTGAACCATCCCCATACCCCACTACTTCTAGTT
TAGAAGATTTTGTCACTTGTTTACAACTTCCTGAAAACCAAAAGCATGGATTAAATCCACAGTC
AGCCATAATAACTCCTCAGACATGTTATGCTGGGGCCGTGTCGATGTATCAGTGCCAGCCAGA
ACCTCAGCACACCCACGTGGGTCAGATGCAGTACAATCCAGTA |
| 1575 | AHR | 2991262 | GAAACATATCCAGCTGAATTAAATAACATAAATAACACTCAGACTACCACACATCTTCAGCCA
CTTCATCATCCGTCAGA |
| 1576 | AHR | 2991263 | AAACTGTCACTGTTGGACGTCAGCAAGTTCACATGGAGGCATTGATGCATGCTATTCACAATT
ATTCCAAACCAAATTTTAATTTTTGCTTTTAGAAAAGGGAGTTTAAAAATGGTATCAAAATTAC
ATATACTACAGTCAAGATAGAAAGGGTGCTGCCACGGAGTGGTGAGGTACCGTCTACATTTC
ACATTATTCTGGGCACCACAAAATATACAAAACTTTATCAGGGAAACTAAGATTCTTTTAAATT
AGAAAATATTCTCTATTTGAATTATTTCTGTCACAGTAAAAATAAAACTTTGAGTTTTGAGC
TACTGGATTCTTATTAGTTCCCCAAATACAAAGTTAGAGAACTAAACTAGTTTTTCCTATCATG
TTAACCTCTGCTTTTATCTCAGATGTTAAATAAATGGTTTGGTGCTTTTTATAAAAAGATAATC
TCAGTGCTTTCCTCCTTCACTGTTTCATCTAAGTGCCTCACATT |
| 1577 | AHR | 2991264 | GTTGCTATGTGCCTTATGTTGAAAAAATTTAAAAGTAAAATGTCTTTCCAAATTATTTCTTAATT
ATTATAAAAATATTAAGACAATAGCACTTAAATTCCTCAACAGTGTTTTCAGAAGAAATAAATA
TACCACTCTTTACCTTTATTGATATCTCCATGATGATAGTTGAATGTTGCAATGTGAAAAATCT
GCTGTTAACTGCAACCTTGTTTATTAAATTGCAAGAAGCTTTATTTCTAGCTTTTTAATTAAGCA
AAGCACCCATTTCAATGTGTATAAATTGTCTTTAAAAACTGTTTTAGACCTATAATCCTTGATA
ATATATTGTGTTGACTTTATAATTTCGCTTCTTAGAACAGTGGAAACTATGTGTTTTTCTCATA
TTTGAGGAGTGTTAAGATTGCAGATAGCAAGGTTTGGTGCAAAGTATTGTAATGAGTGAATT
GAATGGTGCATTGTATAGATATAATGAACAAAATTATTTGTAAGATATTTGCAGTTTTTCATTT
TAAAAAGTCCATACCTTATATATGCACTTAATTTGTTGGGGCTTTACATACTTTATCAATGTGTC |

TABLE 13-continued

Subtyping Target Sequences

| SEQ ID NO. | Gene | Affy Probeset ID | Sequence |
| --- | --- | --- | --- |
| | | | TTTCTAAGAAATCAAGTAATGAATCCAACTGCTTAAAGTTGGTATTAATAAAAAGACAACCAC ATAGTTCGTTTACCTTCAAACTTTAGGTTTTTTTAATGATATACTGATCTTCATTACCAATAGGC AAA |
| 1578 | AHR | 2991265 | TATGAGAGCTGAAGAGCTTAGACACATTTTGCATGTATTATTTGAAAATCTGATGGAATCCCA AACTGAG |
| 1579 | AHR | 2991266 | GAATAGCCTGAACCTGGGAATCGGAG |
| 1580 | AHR | 2991267 | ATGGCTTCGGACAAAATATCTCTGAGTTCTGTGTATTTTCAGTCAAAACTTTAAACCTGTAGAA TCAATTTAAGTGTTGGAAAAAATTTGTCTGAAACATTTCATAATTTGTTTCCAGCATGAGGTAT CTAAGGATTTAGACCAGAGGTCTAGATTAATACTCTATTTTTACATTTAAACCTTTTATTATAAG TCTTACATAAACCATTTTTGTTACTCTCTTCCACATGTTACTGG |
| 1581 | AHR | 2991268 | AACTAAAATGTATCTAAGAATAATAAAATCACGTTAA |
| 1582 | AHR | 2991269 | CGTTTGTCTGTATTGTTAAGTGCCAAACAAAGGATACTTAGTGCACTGCTACATTGTGGGATTT ATTTCTAGATGATGTGCACATCTAAGGATATGGATGTGTCTAATTTAGTCTTTTCCTGTACCAG GTTTTTCTTACAATACCTGAAGACTTACCAGTATTCTAGTGTATTATGAAGCTTTCAACATTACT ATGCACA |
| 1583 | COL1A2 | 3013077 | TATGCAGACAACGAGTCAGAGTTTCCCCTTGAAAGCCTCAAAAGTGTCCACGTCCTCAAAAAG AATGGAACCAATTTAAGAAGCCAGCCCCGTGGCCACGTCCCTTCCCCCATTCGCTCCCTCCTCT GCGCCCCCGCAGGCTCCTCCCAGCTGTGGCTGCCCGGGCCCCAGCCCCAGCCCTCCCATTGG TGGAGGCCCTTTTGGAGGCACCCTAGGGCCAGGGAAACTTTTGCCGTATAAATAGGGCAGAT CCGGGCTTTATTATTTTAGCACCACGGCAGCAGG |
| 1584 | COL1A2 | 3013078 | GTGATACCTCCGCCGGTGACCCAGGGGCTCTGCGACACAAGGAGTCTGCATGTCTAAGTGCT AGA |
| 1585 | COL1A2 | 3013083 | GGCCCAGCCGGAGATAGAGGACCACGTGGA |
| 1586 | COL1A2 | 3013084 | AGATGGTCCCACAGGCCCTCCTGGTC |
| 1587 | COL1A2 | 3013091 | GGCTTAATGGGACCTAGAGGCCCACCTGGT |
| 1588 | COL1A2 | 3013092 | GCCCTCAAGGTTTCCAAGGACCTGCTG |
| 1589 | COL1A2 | 3013093 | GTGAGCCTGGTGAACCTGGTCAAAC |
| 1590 | COL1A2 | 3013098 | TCTGGATGGATTGAAGGGACAGCCCGGTGCTCC |
| 1591 | COL1A2 | 3013102 | CCTGGTGAGAGAGGACGTGTTGGTG |
| 1592 | COL1A2 | 3013103 | GGTGCCCGTGGCAGTGATGGAAGTG |
| 1593 | COL1A2 | 3013104 | GGTCCCATTGGGTCTGCTGGCCCTCCAGGC |
| 1594 | COL1A2 | 3013105 | AAATTGGAGCTGTTGGTAACGCTGGTCCTGCTGGTCCCGCCGGTCCCCGTGGTGAAGTGGGT CTTCCAGGC |
| 1595 | COL1A2 | 3013106 | GTAATCCTGGAGCAAACGGCCTTACTGGTGCCAAGGGTG |
| 1596 | COL1A2 | 3013107 | CTCCCTGGACCCCGCGGTATTCCTGGCCCTGTTGGTGCTGCCGGTGCTACTGGTGCCAGAGGAC |
| 1597 | COL1A2 | 3013109 | GCCCTAATGGGGAAGCTGGATCTGCCGG |
| 1598 | COL1A2 | 3013110 | GGTAGTCCTGGTTCTCGTGGTCTTCCTG |
| 1599 | COL1A2 | 3013111 | GGCCCTCCTGGTAGTCGTGGTGCAAGTGGCCCTGCTGGAGTCCGAGGACCTAATGGAGATGC TGGTCGCCCTGGGGAGCCTGGTCTCATGGGACCCA |
| 1600 | COL1A2 | 3013113 | TCCCCTGGAAATATCGGCCCCGCTGGAAAAGA |
| 1601 | COL1A2 | 3013114 | TCCCTGGCATCGACGGCAGGCCTGGCCCAATTGGCCCAGCTGGAGCAAGAGGAGAGCCTGG CAACATTGGATTCCCTG |
| 1602 | COL1A2 | 3013115 | GGTGATCCTGGCAAAAACGGTGATAAAGGTCATGC |
| 1603 | COL1A2 | 3013116 | TCCAGGTCCTGATGGAAACAATGGTGCTCAGGGACCTCCTGG |
| 1604 | COL1A2 | 3013118 | CCTCAGGTCCCGCTGGTGAAGTTGGCAAACCAGG |
| 1605 | COL1A2 | 3013119 | GGTCTCCATGGTGAGTTTGGTCTCCC |

TABLE 13-continued

Subtyping Target Sequences

| SEQ ID NO. | Gene | Affy Probeset ID | Sequence |
|---|---|---|---|
| 1606 | COL1A2 | 3013120 | TGAGAGTGGTGCTGCCGGTCCTACTGGTCCTATTGGAAGCCGAGGTCCTTCTGGACCC |
| 1607 | COL1A2 | 3013121 | CTGCCTGGAATAAGTAGACCCTTTACAATAGAAAGATAATTGTTTTTCAGATTTTTATTTATTTC CAGTTCTGTGATGACTTCCCTCTCAGTAAACAGCAATCCGATTCCAGTGGACCTGAATTATTCT AAA |
| 1608 | COL1A2 | 3013123 | GAATCGCAGCTGTGCACTCCCACTACCCTCATCTCTTCAGTCACCATGTCATTAACAGCATCTC TCTCTGCTATATTCTCCCTCCTTTCAATAGCCCAGCCTTCTTTGTGTTTCAAAGCAGGCAAGAAG CCTGTCTAGCTAGCTGTTTAAATTGGAATTC |
| 1609 | COL1A2 | 3013124 | GGTTGGTGCTGTGGGCACTGCTGGTCCATCTGGTCCTAGTGGACTCCCAGGAGAGGGGT GCTGCTGGCATACCTGGAGGCAA |
| 1610 | COL1A2 | 3013125 | GGTGAACCTGGTCTCAGAGGTGAAATTGGTAACCCTGGCAGAGAT |
| 1611 | COL1A2 | 3013126 | AGACATGTTTCCTTTTTGGTACTAG |
| 1612 | COL1A2 | 3013127 | TCCTGGTGCTGTAGGTGCCCCTGGTCCTGCTGGAGCCACAGGTGACC |
| 1613 | COL1A2 | 3013129 | GGTGAACGTGGTGAGGTCGGTCCTGCTGGCCCCAATGGATTTGCTGG |
| 1614 | COL1A2 | 3013130 | TGCTGCTGGTCAACCTGGTGCTAAAGGAGAAAGAGGAGCCAAAGGGCCTAAGGGTGAAAAC GGTGTTGTTGGTCCCACAGGCCCCGTTGGAGCTGCTGGCCCA |
| 1615 | COL1A2 | 3013131 | TATATCCGTCAAGTGCCTGCTATGCAACAGGGAATATACCAGATAGAAGATGGAAAATAACG GAAGGATTAACATTTGCACACTGCTTTACAAAGTATAAAAGTTTCATGAATATTGTTTTATTTT AATTCTCTGATAACCTCATAAGGGTGGTAATATTGAAGAACATTCTGACACAGATAGTCATTTT TTATTTCTATATTTTCTTCTAAGAGATGCGGGAATGATCC |
| 1616 | COL1A2 | 3013132 | CCAAATGGTCCCCCCGGTCCTGCTGGAAGTCGTGGT |
| 1617 | COL1A2 | 3013133 | TTACAATGGACTCTCGCCGCTTTTCTTTTTTCAGAATCTATTAAGGACACTTGAAAGTTTTGAA ATTTTTGGTAAATTTGGACTACCATGAGGAAACTTTTGAGATTCAAGTTCATTCTATTCAGAGC AATTCCGATATTGATGTTAACTTGAACTCAGCTGGAACTCAGTGTATGTTGCTATCAGCTCACT TG |
| 1618 | COL1A2 | 3013135 | TGGTGCTGCTGGACGGACTGGTCCCCCAGGAC |
| 1619 | COL1A2 | 3013137 | AAAGAAGGGCTTCGTGGTCCTCGTGGTGACCAAGGTCCAGTTGGCCGAACTGGAGAAGTAG GTGCAGTTGGTCCCCCTGGCTTCGCTGGTGAGAAGGGTCCCTCT |
| 1620 | COL1A2 | 3013138 | AGCCAGGAAATCTGTCCAGCACACACTGAGGGGCTGTGGCTTCCAAGATGCTCAGAAAGCAC AAAATCGGGAAGACAATAAATGAGGGAACTCAGTTTTATCACAAAGCCCTTAAAGCTATTGA AGGCACCTTACTGGTACCAGGATTAGAACAGAGTCCCATTGCTGTGGCCATCCTACTACATAT TAATCAATCTCAGTAGGCTACCAATTTCTTAAACATACACTGTCCAGTATTAGTGCTACTCTGA AAGGTGCCC |
| 1621 | COL1A2 | 3013139 | GGTCTCCCTGGCTCGAGAGGTGAACGTGGTCTACCA |
| 1622 | COL1A2 | 3013140 | TGGGATACTGAATGACACGAGGCTCACTTTTTACAGAGCAACATCCCGTGATTACATAAAGCT GGCCATCTACATGTGGAGAAGGAGGGCAGAGATGATACTAATGATACTTCTTACCATTGTGT GACCCATTCACATTCAATTTACCTTCTTCCTTCAAACTAGAATCTCCTGAGTAGGGTTGTTTTGG AGGGGAAGGTTAGCATTCCATCGAATA |
| 1623 | COL1A2 | 3013141 | GTCCTCTTGGCATTGCCGGCCCTCCTGGGGCCCGTGGTCCTCCTGGTGCTGTGGGTAGTCCTG GAGTCAACGGTGCTCCTGGTGAAGCT |
| 1624 | COL1A2 | 3013143 | AGAGCGCGGTTACCCTGGCAATATTGGTCCCGTTGGTGCTGCAGGTGCACCTGGTCCTCATG GCCCCGTGGGTCCTGCTGGCAAACATGGAAACCGTGGTGA |
| 1625 | COL1A2 | 3013146 | ACAAGGCATTCGTGGCGATAAGGGAGAGCCCGGTGAAAAGGGGCCCAGAGGTCTTCCTGGC TTAAAGGGACACAATGGATTGCAAGGTCTGCCTGGTATCGCT |
| 1626 | COL1A2 | 3013147 | CTGTAGCCATCTCGCACATAAACTGATCCTGAAGGCCTTCAGCTCAGAAGGATTTTCATATTTT CACTGCTATTGTTCCAGTATAGCCTATATAATATCCATTTCCCATTCTCTGGCTAACTCCATCTC ACTCTTGGAGGTAATGCTATTTCATACCAACATGAAAGGTGAGGATTAAGGGAGATAGAAAT AGACATACAATAAAATCTCCTGGTAACAATGTCCTTCAACCCCACTTAAAATAAACATAATTAG AGGAATGACTAATATTGCACTGCTGA |
| 1627 | COL1A2 | 3013148 | CCATGGTGATCAAGGTGCTCCTGGCT |
| 1628 | COL1A2 | 3013151 | GATGGTCGCACTGGACATCCTGGTACAGTTGGACCTGCTGGCATTCGAGGCCCTCAGGGTCA CCAAGGCCCTGCT |

TABLE 13-continued

Subtyping Target Sequences

| SEQ ID NO. | Gene | Affy Probeset ID | Sequence |
|---|---|---|---|
| 1629 | COL1A2 | 3013152 | GATCACGGACCTAAGGAATGTTTTCTTCAGACTAAACCAAGACAACTTTGACAACCCATTAAA GTTAGCCCCATTTCAATATATCCTCTAAAATATCTGGAAATTGTCTATATGCAATGGGCTTGTT AAGTCCATCCCTGCAAGTGTGCCTGGGGGCTCGTTATTTATTTATGTGAACTTGATTATTTTTT ACTGATGAGAACATGCTTCCGTGTGAAGCTCAACTGAAAATCTGCTGCCATGGATGTCTCTCA CTGTAACAAAATA |
| 1630 | COL1A2 | 3013153 | ACTTTGGTTACGATGGAGACTTCTACAGGGCTGACCAGCCTCGCTCAGCACCTTCTCTCAGAC CCAAGGACTATGAAGTTGATGCTACTCTGAAGTCTCTCAACAACCAGATTGAGACCCTTCTTA CTCCTGAAGGCTCTAGAAAGAACCCAGCTCGCACATGCCGTGACTTGAGACTCA |
| 1631 | COL1A2 | 3013155 | CCAAGGATGCACTATGGATGCTATCAAAGTATACTGTGATTTCTCTACTGGCGAAACCTGTAT CCGGGCCCAACCTGAAAACATCCCAGCCAAGAACTGGTATAGGAGCTCCAAGGACAAGAAAC ACGTCTGGCTAGGAGAAACTATCAATGCTGGCAGCC |
| 1632 | COL1A2 | 3013156 | GGAGTGACTTCCAAGGAAATGGCTACCCAACTTGCCTTCATGCGCCTGCTGGCCAACTATGCC TCTCA |
| 1633 | COL1A2 | 3013157 | TTGCATACATGGATGAGGAGACTGGCAACCTG |
| 1634 | COL1A2 | 3013158 | GCTGTCATTCTACAGGGCTCTAATGATGTTGAACTTGTTGCTGAGGGCAACAGCAGGTTCACT TACACTGTTCTTGTAGATGGC |
| 1635 | COL1A2 | 3013159 | TTCTTGAGACTTCAGTGGCCTAAACTATAATTTATAGTTATGTGTATTTTATTTTACTTATTAGT ATGGCCTACATTTAACTTTTAATGCTTTTTCTACAATATGCTATAAATATAAGAAAAATTAAAT TCACTAACAGCAAGACTACATACCCACCCAGGTCCCGCTCCCAAAGACACACATAGAGGGAC ATACACACAACAATCCTAAAAATGACTTTGTAGAGATAGGTCACTTGGAATGTGTGTTGAAAT GTTGTTGGTTTTTTGGTTTGTTTGTTTGTTTGTTTTTTGTTAGACTGATAGGGAGCCCCTCCCA CTAAAGACACCCTTGATACTGTTATTTCAAGGATGAACTTATTTATCTGGGACAGACATCTTCA GAATGACACATGCCAAACAGTGGTTCTTA |
| 1636 | COL1A2 | 3013160 | GGGGAAAGACAATCATTGAATACAAAACAAATAAGCCATCACGCCTGCCCTTCCTTGATATTG CACCTTTGGACATCGGTGGTGCTGACCAGGAATTCTTTGTGGACATTG |
| 1637 | COL1A2 | 3013161 | ACATCTACTTGCTTAAATTGTGGGCAAAAGAGAAAAAGAAGGATTGATCAGAGCATTGTGCA ATACAGTT |
| 1638 | COL1A2 | 3013162 | TTCAACACTCTTACACCTGTTATGGAAAA |
| 1639 | COL1A2 | 3013163 | TTTCCCATGAGTGTGATCCACATTGTTAGGTGCTGACCTAGACAGAGATGAACTGAGGTCCTT GTTTTGTTTTGTTCATAATACAAAGGTGCTAATTAATAGTATTTCAGATACTTGAAGAATGTTC ATGGTGCTAGAAGAATTTGAGAAGAAATACTCCTGTATTGAGTTGTATCGTGTGGTGTATTTT TTAAAAAATTTGATTTAGCATTCATATTTTCCATCTTATTCCCAATTAAAAGTATGCAGATTATT TGCCCAAATCTTCTTCAGATTCAGCATTTGTTCTTTGCCAGTCTCATTTTCATCTTCTTCCATGGT TCCACAGAAGCTTTGTTTCTTG |
| 1640 | MET | 3020344 | GAGCCGAGTGGAGGGCGCGAGCCAGATGCGGGGCGACAGCTGACTTGCTGAGAGGAGGCG GGGAGGCGCGGAGCGCGCGTGTGGTCCTTGCGCCGCTGAC |
| 1641 | MET | 3020348 | CGCGGAAACACCCCATCCAGAATGTCATTCTACATGAGCATCACATTTTCCTTGGTGCCACTAAC TACATTTATGTTTTAAATGAGGAAGACCTTCAGAAGGTTGCTGAGTACAAGACTGGGCCTGTG CTGGAACACCCAGATTGTTTCCCATGTCAGGACTGCAGCAGCAAAGCCAATTTATCAGGAGGT GTTTGGAAAGATAACATCAACATGGCTCTAGTTGTCGACACCTACTATGATGATCAACTCATT AGCTGTGGCAGCGTCAACAGAGGGACCTGCCAGCACATGTCTTT |
| 1642 | MET | 3020349 | GTTCACTGCATATTCTCCCCACAGATAGAAGAGCCCAGCCA |
| 1643 | MET | 3020350 | CGCCCTGGGAGCCAAAGTCCTTTCATCTGTAAAGGACCGGTTCATCAACTTCTTTGTAGGCAA TACCATAAATTCTTCTTATTTCCCAGATCATCCATTGCATTCGATATCAGTGAGAAGGCTAAAG GAAACGAAAGATGGTTTTATGTTTTTGACGGACCAGTCCTACATTGATGTTTTACCTGAGTTCA GAGATTCTTACCCCATTAAGTATGTCCATGCTTTGAAAGCAACAATTTTATTTACTTCTTGACG GTCCAAAGGGAAACTCTAGATGCTCAGACTTTTCACACAAGAATAATCAGGTTCTGTTCCATA AACTCTGGATTGCATTCCTACATGGAAATGCCTCTGGAGTGTATTCTCACAGAAAAGAGAAAA AAGAGATCCACAAAGAAGGAAGTGTTTAATATACTTCAGGCTGCGTATGTCAGCAAGCCTGG GGCCCAGCTTGCTAGACAAATAGGAGCCAGCTGAATGATGACATTCTTTTCGGGGTGTTCGC ACAAAGCAAGCCAGATTCTGCCGAACCAATGGATCGATCTGCCATGTGTGCATTCCCTATCAA ATATGTCAACGACTTCTTCAACAAGATCGTCAACAAAAACAATGTGAGATGTCTCCAGCATTTT TACGGACCCAATCATGAGCACTGCTTTA |
| 1644 | MET | 3020363 | AGCGCGCCGTGATGAATATCGAACAGAGTTTACCACAGCTTTGCAGCGCGTTGACTTATTCAT GGGTCAATTCAGCGAAGTCCTCTTAACATCTATATCCACCTTCATTAAAGGAGACCTCACCATA GCTAATCTTG |
| 1645 | MET | 3020365 | TTGTGGTTTCTCGATCAGGACCATCAACCCCTCATGTGAATTTTCTCC |

TABLE 13-continued

Subtyping Target Sequences

| SEQ ID NO. | Gene | Affy Probeset ID | Sequence |
|---|---|---|---|
| 1646 | MET | 3020366 | TCACGAAGATCCCATTGAATGGCTTGGGCTGC |
| 1647 | MET | 3020367 | TGGCTGGTGCCACGACAAATGTGTGCGATCGGAGGAATGCCTGAGCGGGACATGGACTCAACAGATCTGTCT |
| 1648 | MET | 3020374 | ATATGTGGCTGGGACTTTGGATTTCGGAGGAATAATAAATTTGATTTAAAGAAAACTAGAGTTCTCCTTGGAAATGAGAGCTGCACCTTGACTTTAAGTGAGAGCACGATG |
| 1649 | MET | 3020377 | ATTGAAATGCACAGTTGGTCCTGCC |
| 1650 | MET | 3020378 | AATTATTTCAAATGGCCACGGGACAACACAATACAGTACATTCTCCTATG |
| 1651 | MET | 3020379 | TAATAACAAGTATTTCGCCGAAATACGGTCCTATGGCTGGTGGCACTTTACTTACTTTAACTGGAAATTACCTAAACAGTGGGAATTCTAGACACATTTCA |
| 1652 | MET | 3020380 | AACAGTATTCTTGAATGTTATACCCCAGCCCAAACCATTTCAACTGAGTTTGCTGTTAAATTGAAAATTGACTTAGCCAACCGAGAGACAAGCATCTTCAGTTACCGTGAAGATCCCATTGTC |
| 1653 | MET | 3020381 | TACTTGGTGGAAAGAACCTCTCAACATTGTCAGTTTTC |
| 1654 | MET | 3020382 | TGGTGGGAGCACAATAACAGGTGTTGGGAAAAACCTGAATTCAGTTAGTGTCCCGAGAATGGTCATAAATGTGCATG |
| 1655 | MET | 3020384 | GCATGTCAACATCGCTCTAATTCAGAGATAATCTGTTGTACCACTCCTTCCCTGCAACAG |
| 1656 | MET | 3020385 | CATGTTAGATGGGATCCTTTCCAAATACTTTGATCTCATTTATGTACATAATCCTGTGTTTAAGCCTTTTGAAAAGCCAGTGATGATCTCAATGGGCAATG |
| 1657 | MET | 3020387 | TGAAGCAGTTAAAGGTGAAGTGTTAAAAGTTGGAAATAAGAGCTGTGAGAATATACACTTACATTCTGAAGCCGTTTTATGCACGGTCCCCAATGACCTGCTGAAATTGAACAGCGAGCTAAATA |
| 1658 | MET | 3020388 | ATTCCTCTCATGATGTAAATAAGGAAGCCA |
| 1659 | MET | 3020389 | GTAATTATGTTATTCTCAGGCTTAAAATAAATCATTAAAGCTCATTTATGTGT |
| 1660 | MET | 3020390 | AAGCAATTTCTTCAACCGTCCTTGGAAAAGTAATAGTTCAACCAGATCAGAATTTCACAGGATTGATTGCTGGTGTTGTCTCAATATCAACAGCAC |
| 1661 | MET | 3020391 | TGGGCAGTGAATTAGTTCGCTACGATGCAAGAGTACACACTCCTCATTTGGATAGGCTTGTAAGTGCCCGAAGTGTAAGCCCAACTACAGAAATGGTTTCAAATGAATCTGTAGACTACCGAGCTACTTTTCCAGAA |
| 1662 | MET | 3020392 | TCAGAACGGTTCATGCCGACAAGTGCAGTATCCTCTGACAGACATGTCCCCATCCTAACTAGTGGGGACTCTGATATATCCAGTCCATTACTGCAAAATACTGTCCACATTGACCTCAGTGCTCTAAATCCAGAGCTGGTCCAGGCAGTCAGCATGTAGTGATTGGGCCCAGTAGCCTGATTGTG |
| 1663 | MET | 3020395 | GGCATTTTGGTTGTGTATATCATGGGACTTT |
| 1664 | MET | 3020396 | ATTTCTGACCGAGGGAATCATCATGAAAGATTTTAGTCATCCCAATGTCCTCTCGCTCCTGGGAATCTGCCTGCGAAGTGAAGGGTCTCCGCTGGTGGTCCTACCATACATG |
| 1665 | MET | 3020397 | GTAAAAGATCTTATTGGCTTTGGTCTTCAAGTAGCCAAAGGCATGAAATATCTTGCAAGCAAAAAGTTTGTCCACAGA |
| 1666 | MET | 3020399 | ACAGTCAAGGTTGCTGATTTTGGTCTTGCCAGAGACATGTATGATAAAGAATACTATAGTGTACACAACAAAACAGGTGCAAAGCTGCCAGTGAAGTGGATGGCTTTGGAAAGTCTGCAAACTCAAAAGTTTACCA |
| 1667 | MET | 3020401 | CCTTATCCTGACGTAAACACCTTTGATATAACTGTTTACTTGTTGCAAGGGAGAAGACTCCTACAACCCGAATACTGCCCAGACCC |
| 1668 | MET | 3020402 | TGCTGGCACCCTAAAGCCGAAATGCGCCCATCCTTTTCTGAACTGGTGTCCCGGATATCAGCGATCTTCTCTACTTTCATTGGGGAGCACTATGTCCATGTGAAC |
| 1669 | MET | 3020403 | GTGTCGCTCCGTATCCTTCTCTGTTGTCATCAGAAGATAACGCTGATGATGA |
| 1670 | MET | 3020404 | GTGGACACACGACCAGCCTCCTTCTGGG |
| 1671 | MET | 3020405 | GCAACAGTCCACACTTTGTCCAATGGTTTTTTCACTGCCTGACCTTTAAAAGGCCATCGATATTCTTTGCTCTTGCCAAAATTGCACTATTATAGGACTTGTATTGTTATTTAAATTACTGGATTCTAAGGAATTTCTTATCTGA |

TABLE 13-continued

Subtyping Target Sequences

| SEQ ID NO. | Gene | Affy Probeset ID | Sequence |
|---|---|---|---|
| 1672 | MET | 3020406 | ACCAGAGGCTTGGTCCCACAGGCCACGGACCAATGGCCTGCAGCCGTGACAACACTCCTGTCATA |
| 1673 | MET | 3020407 | CCAAAACTTGAATTCTGGGTTGAATT |
| 1674 | MET | 3020408 | GTACCACTTGATTTCATATGGGAAATTGAAGCAGGAAATATTGAGGGCTTCTTGATCAC |
| 1675 | MET | 3020409 | ACACTTTTGTGTGTTGTATGGTCAATAACATTTTTCATTACTGATGGTGTCATTCACCCATTAGGTAAACATTCCCTTTTAAATGTTTGTTTGTTTTTTGAGACAGGATCTCACTCTGTTGCCAGGGCTGTAGTGCAGTGGTGTGATCATAGCTCACTGCAACCTCCACCTCCCAGGCTCAAGCCTCCCGAATAGCTGGGACTACAGGCGCACACCACCATCCCCGGCTAATTTTTGTATTTTTTGTAGAGACGGGGTTTTGCCATGTTGCCAAGGCTGGTTTCAAACTCCTGGACTCAAGAAATCCACCCACCTCAGCCTCCCAAAGTGCTAGGATTACAGGCATGAGCCACTGCGCCCAGCCCTTATAAATTTTTGTATAGACATTCCTTTGGTTGGAAGAATATTTATAGGCAATACAGTCAAAGTTTCA |
| 1676 | MET | 3020410 | AGTTGTCATATAAAAACCCACTGTTTGAGAATGATGCTAC |
| 1677 | MET | 3020411 | AAGATTAGCCTCTGTCTCGGTGGCAGGTTCCCACCTCGCAAGCAATTGGAAACAAAACTTTTGGGGAGTTTTATTTTGCATTAGGGTGTGTTTTATGTTAAGCAAAACATACTTTTAGAAACAAATGAAAAAGGCAATTGAAAATCCCAGCTATTTCACCTAGATGGAATAGCCACCCTGAGCAGAACTTTGTGATGCTTCATTCTGTGGAATTTTGTGCTTGCTACTGTATAGTGCATGTGGTGTAGGTTACTCTAACTGGTTTTGTCGACGTAAACATTTAAAGTGTTATATTTTTATAAAAATGTTTATTTTAATGATATGAGAAAAATTTTGTTAGGCCACAAAAACACTGCACTGTGAACATTTTAGAAAAGGTATGTCAGACTGGGATTAATGACAGCATGATTTTCAATGACTGTAAATTGCGATAAGGAAATGTACTGATTGCCAATACACCCCACCCTCATTACATCATCAGGACTTGAAGCCAAGGGTTAACCCAGCAAGCTACAAAGAGGGTGTGTCACACTGAAACTAATAGTTGAGTTTGGCTGTTGTTGCAGGAAAATGATTATAACTAAAAGCTCTCTGATAGTGCAGAGACTTACCAGAAGACACAAGGAATTGTACTGAAGAGCTATTACAATCCAAATATTGCCGTTTCATAAATGTAATAAGTAATACTAATTCACAGAGTATTGTAAATGGTGGATGACAAAAGAAAATCTGCTCTGTGGAAAGAAAGAACTGTCTCTACCAGGGTCAAGA |
| 1678 | MET | 3020412 | TCATGCAATTAAAGTAAAGTGATGC |
| 1679 | CALD1 | 3025546 | GAGCTGAGAGTTAAGCTGAACAAAA |
| 1680 | CALD1 | 3025553 | TCCTGAGCATGCCTAGGGAATGACAGGCATCTCCACAGGCAGGCTGCATCCACCTTGGCTGGGGTGTCGTCATTGGCTGCCTATTAGAAAAACGACAGGACAATGCATACCACCGCCTCCCGACTGTAAACATAGGGGATATGTGTTCACTTAGCATGGACTTCTGGGAGGG |
| 1681 | CALD1 | 3025554 | TCCTCGGGAAGAAGTTTCAGACTACA |
| 1682 | CALD1 | 3025581 | AGATCATCAAATCAAATTCCACAGGGATTGGTGACCAA |
| 1683 | CALD1 | 3025586 | TGGCACAGAAACGCAGGGGAAACGGGCTCCTCATTTAAAGAGCTGGAAGGGGAAGGTCTTTCCGGAATTAAAACCATCACA |
| 1684 | CALD1 | 3025587 | TCCAGACATCATCTGGTCTCCCTGAACCTGAAATCACACC |
| 1685 | CALD1 | 3025588 | TGGATGATTTTGAGCGTCGCAGAGAACTTAGAAGGCAA |
| 1686 | CALD1 | 3025589 | AAGGATCTAGGGTGAAAAATACTTGTAT |
| 1687 | CALD1 | 3025590 | CTTTTGAGAGGCCAAATGTGGTCATATCGCACACCAAACTGTTCGCAAAAGTAGTT |
| 1688 | CALD1 | 3025591 | TGAGAGGAATCAATTGATAACTGCATATTGATAATTGCATTTAATCAATACCTTTCACATTGGAATGTTTTAAATGACAAAAGTAATGTGTGAATGAAGGTTTAAAAAGCTTATATAATAAGAAATGACAAAAAAATGTCAAGTATTGAATATTGGAACCACTTAGGACATG |
| 1689 | CALD1 | 3025612 | GGATCCGGATCGCATGGAAGACGCAGCCTGGCCGCGCTCT |
| 1690 | CALD1 | 3025614 | GGAATGTCTACATTCACCTTTTCTAGGAGTCAGTTCTCCAAATCACTCTACCTTTCACTTTGTAAG |
| 1691 | CALD1 | 3025621 | ATTGAGTATCTCAGTTACCAGCCTGAAATCTCCATCGACCAACACTGCCTTCTCTCAAATGACTTCTTATATGAAAGTGGACAGACAGTGGAATGCAGAAATTTTAGAGCTGATCTTGGGGACCGGTCAACTGT |
| 1692 | CALD1 | 3025626 | GCCGCCGAGCCCGACAGGAACGGCTGCGGCAGAAGCA |
| 1693 | CALD1 | 3025628 | ATGATGAGGCCGCATTCCTGGAGCGCCTGGCTCGGCGTGAGGAAAGACGCCAAAAACGCCTTCAGGAGGCTCTGGAGCGGCAGAAGGAGTTCGACCCAACAATAACAGATGCAAGTCTGTCGCTCCCAAGCAGAAGAATGC |
| 1694 | CALD1 | 3025629 | CTACCAGAAGAATGATTGGAGGGATGCTGAAG |

TABLE 13-continued

Subtyping Target Sequences

| SEQ ID NO. | Gene | Affy Probeset ID | Sequence |
|---|---|---|---|
| 1695 | CALD1 | 3025630 | GAGGAGAAGCCAAAGCGAGGGAGCATTGGAGAAAAT |
| 1696 | CALD1 | 3025631 | GGCAGATCAGTTCAGAAGAGCCTAAACAAGAGGAGGAGAGGGAACAAGGTTCAGATGAGATT |
| 1697 | CALD1 | 3025632 | AGAGAAAGAATTAAAGCCGAGCAAGACAAAAAGATAGCAGATGAACGAGCAAGAATTGAAGCA |
| 1698 | CALD1 | 3025633 | AGAGAGGGAAAGGATGAGGGAGGAAGAGAAA |
| 1699 | CALD1 | 3025634 | AGGAGAGGCAGAGGATAAAAGAGGAAGAGA |
| 1700 | CALD1 | 3025635 | AGAGCAGAAACGTAACAAGCAGCTAGAAGAGAAAAAACATGCCATGCAAGAGACAAA |
| 1701 | CALD1 | 3025638 | GAGAAGAGAAGGGAACTAAAGTGCAAGCTAAAAGAGAAAAGCTCCAAGAAGACAAGCCTACCTTCAAAA |
| 1702 | CALD1 | 3025644 | GTTAAGAGCTTCATGGATCGAAAGAAGGGATTTACAGAAGTTAAGTCGCAGAATGGAGAATTCATGACCCACAAACTTAAACATA |
| 1703 | CALD1 | 3025649 | GAGGGAGGGCCAGCGTGGACACCAAGGAGGCTGAGGGCGC |
| 1704 | CALD1 | 3025650 | AAGGCTGGAGGAGCTTCGTCGTCGTCGCGGGGAGACCGAGAGCGAAGAGTTCGAGAAGCTCAAACAGAAGCAGCAGGAGGCGGCTTTGGAGCTGGAGGAACTCAAGAAAAAGAGGGAGGAGAGAAGGAAGGTCCTGGAGGAGGAAGAGCAGAGGAGGAAGCAGGAGGAAGCCGATCGAAAACTCAGAGAGG |
| 1705 | CALD1 | 3025651 | CTAGCCCACTGAGAACGTTGCCCGGGAAAATTCCCTAGTGCCGTGCGGCTGTTCTTTTGAGCATGGGCTCTCAAAAATATTTTTTTAAGAATAATAAACTTACCATGTGCTAGGTACTGTTTTATAACTTGTAGATGTATTAATTTGTCCACTGCTTCAAGAACTCGCTGACCTAGGTACTAATCCCCATTTTACAGATGAGAAAACTGAGGCACAGAGAGGTTTTGTTTTTGTTTTTGTTTTGTTTGTAACTTTCCCAAGGTCTCCCTTGAGTCTGCCTGACATG |
| 1706 | CALD1 | 3025654 | TAGAAGAGCGAGCAGAATTTTTGAATA |
| 1707 | CALD1 | 3025658 | AAGCGCAAAACCTACAAAGCCGGCAGCCTCGGATCTTCCTGTTCCTGCTGAAGGTGTACGCAACATCAAGAGTA |
| 1708 | CALD1 | 3025659 | GCATGTCGATTTTGATTTAGGAATCACACTAGTAAATAATAAAAGCAGTGAAGAAGGTGCAATTTGTACTTTGTTTTGCAATGACCACAAAAGCAAGCTCAGAGAGAATGTGTTTGTGAGGTTGCATGAGGTACTAAGCCCGGGCCATCTTACTCCAAATAAAGTGCCTGGGCTGAAATGTCCACCCTTGGAGTT |
| 1709 | CALD1 | 3025660 | TTGAAGGTAGGGGTTTCTAGCCGCATCAATGAATGGCTAACTAAAACCCCAGATGGAAACAAGTCACCTGCT |
| 1710 | CALD1 | 3025661 | TCTGAGTTTCTTTGATCTCCCAGCT |
| 1711 | CALD1 | 3025662 | CAGATTTACAACAGTTCTAAGAAGCTGCATCTCAGTTACTCAGAGGGTAAAATGGAACCAAATAATCACCTCTACACCCTAACTGAGAGGAGGAATCAGCTAGAATACTGA |
| 1712 | CALD1 | 3025663 | CCTAGGCCTCTGTGCATTTAATTGCATCCATTGGCTCCATGCCATTTAATTGCATTTGTTGGCTCCATATATAATCTCCAAAGTCATTAAATTTTGTCACTTTCCAATTTAAAAAGGAAGAAATGGAAATGTTCACAAATCCTTCTTGGGCACAACTCCTTGAACCGTTTAATTAATCTACACCCCGAGATTCTTTGCATAAAGGCTCACAGGAGGTATACACTAATGTCAACCCAATTTACAATTGGAAAATCTTTATACATTGAAAAAGCAACTTTTCCTCCCCCTCTCAATAGGTACAAGAATGCGGGTTTATAAAAGGACACAGTTGAGGCAAGAGACCGGACCCAAAAGTTATGTGCTCTTTAGTGCCTCAAGTTTTCCAAGCATCTCTGGTAACATAAGGAGTAGAAATTATTTTCAAAAACAAAATAATCACTGGTTCCAGACCAGTGATTATTAACCCTTTTTGAATTATGAACCCCTTTAAAACCTAATGAAATTTAAGGACCCTCTCCCCAAAATATACATATAAAAAAACAAGGCAGTCTATGGACCTACTGAGTAACTCTCAAGATAGTAAGTAAGGAGAAAAGATCTATGTTTCCCTCTTTGATAAGTATGAAATATTTGGAGGAGATGCTAATTTTTGCACGTTTATGATATTTGCAATCTTTCATTTTTGTAGCAGATTATACTCAAAAATTTGATCCAGAACTTGGCCCCTATTCTTTTATCAGCACTTTAACTTGTAAACTGAAAAGTTTACCATCATCTGTATGACATCCTAATGAGGTTAAAAAGATAAAATGCAGTTATGATTATGATAGGTATAACTGTATCCAGGTTTCCACAGCAAAAACAAAACAAAACATACACCATGTTCTGGGGTTATTGACA |
| 1713 | CALD1 | 3025664 | TGACCTTCTGTTCCTCACTCTTTGGTCTCTGGTTGATTGGAAACCTGCTTCTCCTGCCTTCATTTCTCCCTCTTCTTCCGGAGTGGGTCTTTCTC |
| 1714 | CALD1 | 3025668 | TTGAGACCAGGAGAGACGTATCCAGCAAGCGGAACCTCTGGGAAAAGCAATCTGTGG |

TABLE 13-continued

Subtyping Target Sequences

| SEQ ID NO. | Gene | Affy Probeset ID | Sequence |
|---|---|---|---|
| 1715 | CALD1 | 3025673 | GACGAGCTCAGTTGTAGAGGGCTAATTCGCTCTGTTTTGTATTTATGTTGATTTACTAAATTGG GTTCATTATCTTTTATTTTTCAATATCCCAGTAAACCCATGTATATTATCACTATATTTAATAATC ACAGTCTAGAGATGTTCATGGTAAAAGTAC |
| 1716 | CALD1 | 3025674 | GCTGTGAAATAGAGACTTTTCTACTGATCATCATAACTCTGTATCTGAGCAGTGATACCAACCA CATCTGAAGTCAACAGAAGATCCAAGTTTAAAATTGCCTGCGGAATGTGTGCAGTATCTA |
| 1717 | CALD1 | 3025675 | TTTAGTAGTGATAGTAGCCTGAACCACATTTTAGATAACTCAATTATGTATGTATGTGCATACA CATATACAAACACACTAATGGTAGAATGCTTTTTTATGTGCTAGACTATTATATTTAGTAGTAT GTCATTGTAACTAGCCAATATCACAGCTTTTGAAAAATTAAAAAATCACACTATATTAATATTT TATATTTGCCAACAGAAACATGGCAGATAGGTATCAATATGTTTTCAATGCCTGATGACCTAT AAGAAGAAAGTA |
| 1718 | CALD1 | 3025676 | TCACAATAGGTCATAAGGTCTCTTCCTTTTCTAAAATTGAAAGACAAGAAATTTAGTGCCAATA TTGTACAGACAGAAATTCCATGTATGAGTCTCAACAAAGACTACCTTTGGCTAAATGTCTAGA AGCAGAGAAGTAAAGTGAGCAAAATCCAGTGTTGAGGAGTCATGACAGTACTTTGATCTTTA TATACTCTGAAGCATTTCTTCAAACTTTTCTACTTTTATTTGTCATTGATACCTGTAGTAAGTTG ACAATGTGGTGAAATTTCAAAATTATATGTAACTTCTACTAGTTTTACTTTCTCCCCCAAGTCTT TTTTAACTCATGATTTTTACACACAATCCAGAACTTATTATATAGCCTCTAAGTCTTTATTCTT CACAGTAGATAATGAAAGAGTCCTCCAGTGTCTTGGCAAAATGTTCTAGTATAGCTGGATACA TACAGTGGAGTTCTATAAACTCATACCTCAGTGGACTTAACCAAAATTGTGTTAGTCTCAATTC CTACCACACTGAGGGAGCCTCCCAAATAACTATTTTCTTATCTGCAGTATTCCTCCAGAAGAGC TAACCAGGGCAGGGCTGGCATGAGAAGTGACATCTGCGTTACAAAGTCTATCTTCCTCATAA GTCTGTAAAGAGCAATTGAATCTTCTAGCTTTAGCAAACCTAAGCCAAAGGAAGGAAAGCCA TGAAGAATGCAGAAGTCAAACCCTCATGACAAAGTAGGCACAAGTCTACAATAAGCTAAATC AGAATTTACAAATACAAGTGTCCCAGGTAGCATTGACTCCCGTCATTGGAGTGAAATGGATCA AAGTTTGAATTAAGGCCTATGGTAAGGTAACATTGCTTTGTTGTACTTTTGAACAAGAGCTCCT CCTGATCACTATTACA |
| 1719 | CALD1 | 3025677 | ATATTGATAGTGAGAGGTATGTCTATTATAA |
| 1720 | AGR2 | 3039796 | CTCTGGCCAGGAACTCTAAGGTACACACTTTCATTTAGTAATTAAATTTTAGTCAGATTTTGCC CAACCTAATGCTCTCAGGGAAAGCCTCTGGCAAGTAGCTTTCTCCTTCAGAGGTCTAATTTAGT AGAAAGGTCATCCAAAGAACATCTGCACTCCTGAACACACCCTGAAGAAATCCTGGGAATTG ACCTTGTAATCGATTTGTCTGTCAAGGTCCTAAAGTACTGGA |
| 1721 | AGR2 | 3039797 | TCTCCAAGCCCTTCTGTCTGTCAGGCCTTGAGACTTGAAACCAGAAGAAGTGTGAGAAGACTG GCTAGTGTGGAAGCATAGTGAACACACTGATTAGGTTATGGTTTAATGTTACAACAACTATTT TTTAAGAAAAACAAGTTTTAGAAATTTGGTTTCAAGTGTACATGTGTGAAAACAATATTGTAT ACTACCATAGTGAGCCATGA |
| 1722 | AGR2 | 3039798 | GAAAGCTCTCAAGTTGCTGAAGACTGAATTGTAA |
| 1723 | AGR2 | 3039800 | AGAGAGCTAGGCTTAGGGACGCCTCGGACTCAGTTTGACCCTAACTAGCCTTGCATCTTCAGG CAAATCACACTCTTTC |
| 1724 | AGR2 | 3039801 | GTAAGTGTGACCTTCAATTCGGATGTTGCCCAAGAGTTGAACACCTCTATTGCTGTAGTGATG GGACTA |
| 1725 | AGR2 | 3039809 | ACAACTGACAAACACCTTTCTCCTGATGGCCAGTATGTCCCCAGGATTATGTTTGTTG |
| 1726 | AGR2 | 3039810 | TTAAAGAAAGTGTTTGCTGAAAATAAAGAAATCCAGAAATTGGCAGAGCAGTTTGTCCTCCTC AATCTG |
| 1727 | AGR2 | 3039812 | AAGAAGCTCTATATAAATCCAAGACAAG |
| 1728 | AGR2 | 3039813 | TAGGAGTCAGCTTCTTGTTGGCTTCCAACTGCTACTTAATTGGAAAAGATTTC |
| 1729 | AGR2 | 3039814 | TCAGCATTCTTGCTCCTTGTGGCCCTCTCCTACACTCTGGCCAGAGATACCACAGTCAAACCTG GAGCCAAAAAGGACACAAAGGACTCTCGACCCAAACTGC |
| 1730 | AGR2 | 3039819 | GCCACGATGAATTAGGAGAACAAGATGTCAAATTACACTGATGCTGAGTCAAGCTTCTCAAAG |
| 1731 | MACC1 | 3040557 | GGTGATCGGATGTTCTTTCTAAGGATCATATTCCACATTTAAAGAGATGGTGACTGAGAAGAG GTGGCAAGCTGAACCATCTCACTTTGAGATTGACGTATCACGTTTTATCCTCTGCCATCATTTC CTTGTTAATTGTTTTTCTTTGGGTGATTGGAAGAATCTATGGCTTCCTTTTCTCTGTTCTTAAAG ATATCAAGACTCTGCCCTTTTGTGACTGGAAGTAGATTTAAATGTCCCTAATGTTTATATGCT CACTTAAACTCAATACATGGAATTTACTGGGCATTTAACTTGTTCATG |
| 1732 | MACC1 | 3040558 | CATTGGTTTCACTAGGAGCTTCTCAAAGCACGCTGCCAAACATGCTCCAGTCTCATTGTCAAG GCCTTAGACCAGGCAATCATTACGGCAGTGGTTCTTCAACTTCAGCAGCAGCAAAACGATCTG GCGGGGGCTTGGTGAAACAGACTGCTGGGCTCGACCACCAGAATTTCTCATTCAGAGGGTCT GGCCTGATCACTTGCATTT |

TABLE 13-continued

Subtyping Target Sequences

| SEQ ID NO. | Gene | Affy Probeset ID | Sequence |
|---|---|---|---|
| 1733 | MACC1 | 3040559 | TTCATGGCCTGTAATGTAGAACATACTATATAAAGTTCTCAGTTTGGGGATGACTAGGTTTCT GGAAGGAATAGAATGCTAAATCAATGGATGGCATTGGGCTGAGAAACACTGCTGCTACTAAT CAGCCTTGAATGTGTAATGTGAACATGCAAAAGAGAACATGCATACACTCAAATTTGTACAAT GCTATAACTGGAAGTTGAAGGACTTGAATTTTTATATTGTGCTATTGTTATGTTTTCTGTAATT GTTTATATCTAAGGAATTTTTGAGGTAATATAAAAGAAAAAGAGAATAATGAACAATGATGTC ACTGGAGGGTTTTTACATTAAATTAGATCATTTTTCTTCTTATTCACAATAATAATCTTAATCTTT AAGAATTAATTATAATTTAATATTATAATTCATAATCTTTAAGAATTAATAATTATAATTTAATA TTATAATTAATAATCTTTAAGAATTAATAATATAATTTAATATTATAATTAATAATCTTTAAGAA TTAATAATTACAATTAATAATTAATAATAATCTTAATCTTTAAGAATTAATAATAATCCTTAATC GCAATAATAATCGCAAGGAGGAGAAGTAAGTCCCTCCTCCTTCTGTATGAACTTTTCTCCCAC ATGCTGCTGTATGGTTTAGTGAGAGTGAAGTTCTAAAGAACATCAATATGATTGGTGGGATA ATCCAAAGACATTTTTTCAGAATCAAATGGCATGTCGAAGGTTTGTTTCTTGCATATGTATTTA CTGGTCCACAGC |
| 1734 | MACC1 | 3040560 | CACCCTGGGATATTTGGTATGCTGGCAATGGTAATTCAAATTGGCGTTTAAGAATAATCTTGG CCG |
| 1735 | MACC1 | 3040561 | GGACCCTGGGTCAGTATAAATGCTAATGGCTGACAAAGTTCACAAAGAGATGTATTTTGCTTA CTCCTCTGTTCAATCCTCTGGTTGCCTGCCAGTGTTTATGTGTGTATTTGGACAGACATTCATTT ATTGTCATTCAGTCAATAGGTAGAGTATATGTGTCTATTTTTTGGCAGGCATATAGATGCTTGA GGCTAATGGGAAAAAACCAGCATGAACTCTGACTTTAGTAGTGCTAAGTAATAGATAATTTTA AAAAATGACACCGTTAAATAGAAAATGGCATGCATACTAACAGTTGCAATGGAGAGGCTGTG ATGCTACAGAGATATAAACGTAGAGATGCCATCATGTGAAACTGGAAGTGGGGGTGGGTCAG GGAAATTTGTTCTTGGAAAGAAATAATGAACCTCAAGGAAGAGTAGGCATTGTCCTGGTGTG GTGGGGTGTAAGCGGTGATCCCACAAAGCACT |
| 1736 | MACC1 | 3040562 | AACAGTTGCCGTTTCATTTTAAGTGAGACTTGCTACTCTTTTTCATCGTCTCTTGAAAGACTGAC AGAAGGAAAATATGACTTATCAGAAATCTGTTGTCTGCATGCATGGACCTAGTGTTTTCATCA GCTCCCTTCAGCATCTTGGG |
| 1737 | MACC1 | 3040563 | CAAGCACACACCCTGTGGCCAGTCACGGCTGCCCGCTTTCCACACCTGACCTCTTCAGTTCATC AGTGGGTTCACCAGCATCACCCCCATTTTTTCATGGGGAGAAACTCAGAAGTGGAGAGAACG TCTGAGGCTACATAGCC |
| 1738 | MACC1 | 3040564 | CTGATGAAAGCACAGCCTAACTGATAACCAAGATGGGTTTTATCCTC |
| 1739 | MACC1 | 3040565 | GAAAATGAGGTAATGGTGTGTGTGT |
| 1740 | MACC1 | 3040566 | GAGATGTGTTACAAGACCTTCAGTCAGCTTTGGACAGAATGAAAAACCCTGTGACTAAACACT GGAGAGAATTAACTGGAGTTTTAATACTAGTAAATTCTTTGGAGGTTTTGAGAGTAACTGCAT TCTCCACTTCTGAGGAAGTATA |
| 1741 | MACC1 | 3040568 | TAGTCGCACGTCTCATCCAAGAAGCTGCTGTTCTGACTTCAGCTGTCAAGCTTGGAAAAGGCT GGAGGGAACTAGCTGAAAAGTTAGTACGACTCACAAAGCAACAAATGGAGGCATATGAAAT TCCTCATCGAGGA |
| 1742 | MACC1 | 3040569 | CAGAAAAGTTTATGATTGGAAAGTTTTAGCTGATGTCCTGGGTTACTCACATCTGTCCCTGG AAGATTTTGATCAAATTCAAGCAGACAAAGA |
| 1743 | MACC1 | 3040570 | TTTCAAAGGGGACACAATAGCTCTCCTCGGGGAAGGTAAGGTAAAAGCTATTGGTCAGTCCA AAGTGAAAGAATGGTATGTAGGAGTCCTCAGAGGTAAGATTGGACTTGTACACTGCAAAAAT GTCAAGGTGATTTCAAAGGAGCAAGTAATGTTTATGTCAGATAGTGTCTTTACAACCAGAAAT CTTCTTGAACAGATTGTCCTGCCTTTA |
| 1744 | MACC1 | 3040571 | TTTTGTGTTCAAGTGGAGCCTCCCAATGGTGAACCAGTTGCACAGTTCTCTATCACTACTCCTG ATCCAACCCCAAACCTAAAAAGACTCTCGAATCTGCCAGGCTATTTGCAGAAGAAGGAGGAA ATCAAGTCTGCTCCTTTATCACCAAAAATTCTTGTTAAATATCCTACATTTCAAGATAAAACATT GAACTTTAGCAACTATGGGGTAACCCTG |
| 1745 | MACC1 | 3040572 | GCCCGCTCCTGCCTTGATTTGAATACAATTAGTCAGAGCCCTGGATGGGCCCAGACACAACTT GCGGAGGTCACCATAGCTTGCAAAGTAAACCATCAAGGAGGGTCAGTACAATTACCTGAATC AGACATCACTGTTCATGTGCCCCAAGGTCATGTGGCTGTGGGAGAATTCCAAGAGGTGTCTCT AAGGGCTTTCCTTGATCCGCCACACATGCTTAACCATGATCTTTCGTGCACTGTGAGCCCGTTG TTGGAAATC |
| 1746 | MACC1 | 3040573 | CAAATCCATTCTGGAATCAACTGTCTGCTTCTAACCCATTTTTGGATGACATAACTCAACTAAG AAATAAC |
| 1747 | MACC1 | 3040574 | AGGACCCAGACTTGCTTCACAATTGGCCGGATGCTTTCACCCTTCGTGGTAATAATGCTTC |
| 1748 | MACC1 | 3040576 | AACATTTTCGGTCAGGAAGAATTGCACAAAGTAT |
| 1749 | MACC1 | 3040577 | AGGAGGGGTCACAGGTGAACGAGATGTGGTC |

TABLE 13-continued

Subtyping Target Sequences

| SEQ ID NO. | Gene | Affy Probeset ID | Sequence |
| --- | --- | --- | --- |
| 1750 | MACC1 | 3040579 | GTAGCCTTGTCAGATGATATGCAAA |
| 1751 | MACC1 | 3040587 | GAAGAAATTATAGGCGAGGCTGAGATCTAAAAGGAGAGCTCCAGAATGGAGGCTTGGACCA GGGGCAGACCAGGAGCTTATCAAGATACAATTGAATAATCAAAGGGTGGAGCCTGGACAAA |
| 1752 | MACC1 | 3040590 | CCGGGTTTGGTAGAGTGACTTCTATTCACTAAAACCATGTGTCTGAACTGAAGAAGCTTGGGC TCACTTCCA |
| 1753 | IGFBP3 | 3049293 | CTGGGCTTTGTATCACTAATTATTT |
| 1754 | IGFBP3 | 3049294 | GAGAAGTTTGTCTTGCAATGTATTTA |
| 1755 | IGFBP3 | 3049295 | TGCTGCAGACCTCGGTGTGGACACACGCTGCATAGAGCTCTCCTTGAAAACAGAGGGGTCTC AAGACATTCTGCCTACCTATTA |
| 1756 | IGFBP3 | 3049296 | GATGCTATATGATACAACTGTGGCCATGACTGAGGAAAGGAGCTCACGCCCAGAGACTGGGC TGCTCTCCCGGAGGCCAAA |
| 1757 | IGFBP3 | 3049297 | AGCGGCCGACCACTGACTTTGTGACTTAGGCGGCTGTGTTGCCTATGTAGAGAACACGCTTCA CCCCCACTCCCCGTACAGTGCGCACAGGCTTTATCGAGAATAGGAAAACCTTTAAACCCCGGT CATCCGGACATCCCAACGCATGCTCCTGGAGCTCACAGCCTTCTGTGGTGTCATTTCTGAAAC AAGGGCGTGGATCCCTCAACCAAGAAGAATGTTTATGTCTTCAAGTGACCTGTACTGCTTGGG GACTATT |
| 1758 | IGFBP3 | 3049299 | GTGTGGATAAGTATGGGCAGCCTCTCCCAGGCTACACCACCAAGGGGAAGGAGGACGTGCA CTGCTACAGCATG |
| 1759 | IGFBP3 | 3049303 | ACAGCCAGCGCTACAAAGTTGACTACGAGTCTCAGAGCACAGATACCCAGAACTTCTCCTCCG AGTCCAAGCGGGAGACAGA |
| 1760 | IGFBP3 | 3049304 | AAATGCTAGTGAGTCGGAGGAAGACCGCAG |
| 1761 | IGFBP3 | 3049306 | GTCAACGCTAGTGCCGTCAGCCGCCTG |
| 1762 | IGFBP3 | 3049307 | TGTGGCTCCGGCCTTCGCTGCCAGCCGTCGCC |
| 1763 | IGFBP3 | 3049308 | GTGCGACGCGCGTGCACTGGCCCAGTG |
| 1764 | IGFBP3 | 3049309 | GCGCGACCCACGCTCTGGGCCGCTGCG |
| 1765 | IGFBP3 | 3049310 | GCCCAGCCTGCCAAGCAGCGTGCCCCG |
| 1766 | IGFBP3 | 3049311 | CTGGGCGCTGAGGATCAGCCGCTTCCTGCCTGGATTCCACAGCTTCGCGCCGTGTACTGTCGC CC |
| 1767 | SAMD9 | 3061439 | CAGTCTTCTGAAGGTCATGCCCACAGAAGTCATCAGACCTTACCAAAGTAGGTTGGAGAATTA GATTGCCTTTTCATGCAGTGAGATTCAGTTAAGCAAAAATGAAATTTGTCTCTATAGCTAATTA GCTTATCAACTCCCCTCCAAACAAACAATTAAAAAAAAAACATACAGACACTCAAATTCCACAA GCTAATGAACAAAAGGGACTCTTGTGAGAAGACTAATGAGTCCCTCATCCAGAAGATGCCAA TGTACTGGCAGATTAACATACAACCTATGTTTTGAACAAAAACAACCAGCGATACGTAATCAA AATGTAATTTTCCCCTAATAAAATTATGGATATGGGCAGTCATCAATGGCTGCCAAAACCATT AAGTGGAAAGCTGATTAAAAAACAAAAATTTCTAATGGATTTATCAAACTGTCCCAAATCCTG ATAAATATTAACATCACAGAGGAAGACCAGACATTATGGGCCTGGAAGTACTATAGGAGTGC ACACATCACCCGTGACATGGTCTTGCCAAATAATTAAACCTGAATTTGATCAGGTCTCTGGATC TTATTTGCAATTCAAAAGAAATTTTAAAAAAATCCTACTAACACCACCACAAATATGCAATCAG CAATATCCAGAAAGGGGAAATTCACAGGACAAAAACCTGGTTTTCTTTTTTGGTTTCTTCAACC AAAAAAGAAAGAAATTGCAAAGGACCAAAAAAATGTTGGGGAATCTATACATTATAAGGGA CTTAACAACTAAAGGGCAACATATAGACTTTAGATCCTAATTTGAGCAAAATCTAAAATCAATT ATTAGGCAATCAGAAAAATTGAACACAGACTAGATATTTGAGGATATTAAGGTACTATATTA TTGAAGATTCCATGGTTATGTTTTTTAAAGAGTTCATGCCTTTTAGAGATACATACTAAAGTAT TTGTAAATAAATGACATGATCTAGAATCAGTAATTTTGTGTTTGGGGTGTGGGGGTGGTGAA AGGGAAGTAGAACCGAAACAAGATTAGTCCTGAGTTAACAATGGCTGCAAGCTGGATACATG GAATTC |
| 1768 | SAMD9 | 3061440 | CTGGGATTTTCCATTGGAGGCCCACTTGCTTATGACA |
| 1769 | SAMD9 | 3061441 | GCTCTTTTGGATTTAGCAGAACATGCCTCAAGTGCATTCAAAGAATCTCAACAGCAAAGTGAA GATAGAGAGTATGAAGTGAAGGAAAGATTGTATCCGAAGTCAAAAAGGCGGTATGATACTT ACAATATAGCTGGTTATCAAGGAGAGATAGAAGTTGGGCTTTACACAATCCAAATTCTCCAGC TCATTCCTTTTTTTGATAATAAAAATGAGCTATCTAAAAGATATATGGTCAATTTTGTATCAGG AAGTAGTGATATTCAGGGGATCCAAACAATGAATATAAATTAGCCCTCAAAACTATATTCC TTATTTAACTAAATTGAAATTTCTTTGAAAAAGTCCTTTGATTTTTTTGATGAATACTTTGTCCT GCTAAAACCCAGGAACAATATTAAGCAAAATGAAGAGGCCAAAACTCGGAGAAAGGTGGCT GGATATTTTAAGAAATATGTAGATATATTTTGTCTCTTAGAAGAATCACAAAACAACACAGGT |

TABLE 13-continued

Subtyping Target Sequences

| SEQ ID NO. | Gene | Affy Probeset ID | Sequence |
| --- | --- | --- | --- |
| | | | CTTGGATCAAAGTTCAGTGAGCCACTTCAAGTAGAGAGATGCAGGAGAAACCTAGTAGCTTT<br>AAAAGCAGACAAGTTTTCTGGGCTCTTGGAATATCTTATCAAAAGTCAAGAGGATGCTATAAG<br>CACTATGAAATGTATAGTGAACGAATATACTTTTCTCTTAGAACAATGCACTGTCAAAATCCAG<br>TCAAAAGAAAAGCTAAATTTCATCTTGGCCAACATTATTCTCTCCTGTATCCAACCTACCTCCA<br>GATTAGTAAAGCCAGTTGAAAAACTAAAAGATCAGCTTCGAGAAGTCTTGCAACCAATAGGA<br>CTGACTTATCAGTTTTCAGAACCGTATTTTCTAGCTTCCCTCTTATTCTGGCCAGAAAATCAACA<br>ACTAGATCAACATTCTGAACAAATGAAAGAGTATGCTCAAGCACTAAAAAATTCTTTCAAGGG<br>GCAATATAAACATATGCATCGTACAAAGCAACCAATTGCATATTTCTTTCTTGGAAAAGGTAA<br>AAGACTGGAAAGACTTGTTCACAAAGGAAAAATTGACCAGTGCTTTAAGAAGACACCAGATA<br>TTAATTCCTTGTGGCAGAGTGGAGATGTGTGGAAGGAGGAAAAAGTCCAAGAACTTTTGCTT<br>CGTTTACAAGGTCGAGCTGAAA |
| 1770 | SAMD9 | 3061442 | CAGAGGTCATCGAATGTGGGAACTACTGTGGAGTACGCATCATTCACTCTTTGATTGCAGAGT<br>TCTCACTGGAAGAATTGAAGAAAAGCTATCACCTGAATAAAAGTCAAATTATGTTGGATATGC<br>TAACTGAGAATTTGTTCTTCGATACTGGTATGGGAAAAAGTAAATTTTTGCAAGATATGCACA<br>CACTCCTACTCACAAGACACCGCGATGAACATGAAGGTGAAACAGGAAATTGGTTTTCCCCAT<br>TTATTGAAGCATTACATAAAGATGAAGGAAATGAAGCAGTTGAAGCTGTATTGCTTGAAAGT<br>ATCCATCGGTTCAACCCAAATGCATTCATTTGCCAAGCGTTGGCAAGACATTTCTACATTAAAA<br>AGAAGGACTTTGGCAATGCTCTAAACTGGGCA |
| 1771 | SAMD9 | 3061443 | AAGGATCCCAGACAGTATTGCCGTAATACAGCAACTCTCTCCCAAAGAACAGAGAGCTTTTGA<br>GCTTAAATTGAAAGAAATCAAAGAACAGCATAAAAACTTTGAGGATTTTTATTCCTTTATGATC<br>ATGAAAACCAATTTTAATAAAGAATACATAGAAAATGTGGTCCGGAATATCCTGAAAGGGCA<br>GAATATTTTCACCAAGGAAGCAAAGCTCTTTTCTTTTCTGGCTCTTCTTAATTCATATGTGCCTG |
| 1772 | SAMD9 | 3061444 | CCTTGGCTATGCACATTCTCTGGGAACTAAGGAAGAAATTCAGATGTGCTGTGCTGAAAAACA<br>AGACAGTGGATTTTTCTGAAATTGGAGAACAGGTAACCAGTTTAATCACCTATGGGGCAATG<br>AACCGTCAGGAATACGTACCTGTACTACTCCTTGTTGATGA |
| 1773 | SAMD9 | 3061445 | AAAACTGTGCAGATTCTTCTAAACCAACAAGTACCAAAATTATTCATC |
| 1774 | SAMD9 | 3061446 | AGGAAGACTTCTATCGAGGTGGCAAAGTGTCATGGTGGAACTTCTACTTCTCTTCTGAAAGTT<br>ATTCTTCACC |
| 1775 | SAMD9 | 3061447 | GCACCCACACATATTTCAGGGATGGAAAGATCTACTTGAAGCAAGATTAATAAAACACCAAG<br>ATGAAATTTCAAGCCAATGTATTTCTGCTTTAAGCCTTGAAGAGATCAATGGCACTATTCTTAA<br>ACTAAAATCTGTGACTCAATCTTCAAAAAGGCTTTTGCCATCTATTGGTTTATCGACTGTCCTTC<br>TGA |
| 1776 | SAMD9 | 3061448 | AGCCGAGTAGCAAACCTTCACTTTCCAAGTGTATATGTAGAACAGAAAACCACACCAAATGAG<br>ACGATTTCTACTCTAAATCTTTACCATCAACCCAGCTGGATTTTCTGCAATGGCAGGTTAGACC<br>TTGACAGTGAAAATATAAACCCTTTGATCCAAGTTCCTGGCAAAGAGAAAGAGCTTCTGATG<br>TCAGGAAACTGATTTCATTTCTTACACATGAAGACATAATGCCAAGAGGGAAGTTTTTGGTGG<br>TATTTCTATTACTGTCCTCTGTGGATGACCCAAGAGATCCCCTCATTGAGACTTTCTGTGCTTTC<br>TACCAGGATCTCAAAGGAATG |
| 1777 | SAMD9 | 3061449 | TTCTCTGAATGCCAATATGATTATTTCCAGATTAAAATGCAAAATTACAACAACAAAATATGGG<br>AACAAAGTAAAAAATTCTCACTATTTGTGCGAGATGGGACCAGCTCTAAGGACATTACGAAA<br>AATAAAGTTGATTTCAGAGCATTTAAAGCAGATT |
| 1778 | SAMD9 | 3061450 | GGCAATCTCATTGATCCGATACATGAATTCAAAGCCTTCACAAATACAGCAACAGCCACAGAA<br>GAGGATGTCAAGATGAAATTTAGCAATGAGGTTTTCCGATTTGCTTCAGCTTGTATGAATTCA<br>CGTACCAATGGCACTATTCATTTTGGAGTCAAAGACAAACCCCATGGGAAAATTGTTGGCATC<br>AAAGTCACCAATGATACCAAGGAAGCCCTCATTAACCATTTCAATCTGATGATAAACAAGTAT<br>TTTGAAGACCATCAAGTCCAACAAGCAAAGAAGTGCATTCGAGAGCCAAGATTTGTG |
| 1779 | SAMD9 | 3061451 | TTGATATGGGCATCACACATGGACCAGCTATTCAAATAGAAGAACTATTCAAAGAATTGCGGA<br>AAACAGCCATTGAAGATTCGATTCAGACATCTAAGATGGGAAAGCCCAGTAAAAATGCTCCT<br>AAAGACCCAAACTGTGTCTCAAAAGGAACGTAGAGAAACTTCAAAGCAAAAACAAAAGGGTA<br>AAGAGAACCCAGATATGGCTAATCCGTCTGCAATGAGTACAACTGCTAAAGGTTCTAAGTCAC<br>TAAAAGTTGAGCTCATAGAAGATAAAATAGATTATACAAAGGAAAGGCAACCATCCATAGAC<br>CTGACATGTGTATCATATCCATTTGATGAATTCAGTAATCCATATCGTTACAAGTTGGATTTTA<br>GTCTACAGCC |
| 1780 | SAMD9 | 3061452 | GAATAGGTGGCCTTTTGTGATCTCCTACATCACCCTGGAAGTGAGACTTCTTCGGTTTCTTCTA<br>GAGTC |
| 1781 | SAMD9 | 3061453 | TACTTTTCTCTAGCATCGTAGGAGGAAGAAAACAAACACATCAGATATTTTCAGCACTAAAAG<br>AGATGGTTTTCCCCACATATA |
| 1782 | PTN | 3074858 | GAAATTATTTTCCATCTGAGGAAAAAAATACTAGGAAAATAAATCAAGGTGATGCTG |
| 1783 | PTN | 3074859 | GGAAGCAGAGCATGTCCTAGTTCAATGTT |

TABLE 13-continued

Subtyping Target Sequences

| SEQ ID NO. | Gene | Affy Probeset ID | Sequence |
|---|---|---|---|
| 1784 | PTN | 3074860 | ATGTCACCTGTGGAACATAAAAAGGACATCAGCAAACAGGATCAGTTAACTATTGCATTTATA<br>TGTACCGTAGGCTTTGTATTCAAAAATTATCTATAGCTAAGTACACAATAAGCAAAAACAAAA<br>AGAAAAGAAAATTTTTGTAGTAGCGTTTTTTAAATGTATACTATAGTACCAGTAGGGGCTTAT<br>AATAAAGGACTGTAATCTTATTTAGGAAGTTGACTTATAGTACATGATAAATGATAGACAATT<br>GAGGTAAGTTTTTTGAAATTATGTGACATTTTACATTAAATTTTTTTACATTTTTTGGGCAGCA<br>ATTTAAATGTTATG |
| 1785 | PTN | 3074861 | AAAGGAAGGCAAGAAACAGGAGAAGATGCTGGATTA |
| 1786 | PTN | 3074862 | ATGGATTCGTCTACTGATGCAACTG |
| 1787 | PTN | 3074863 | AAGATGGTAGAGAGGAGTGTTTGGGTG |
| 1788 | PTN | 3074872 | CCAGTTCCAGGCCTGGGGAGAATGTGACCTGAACACAGCCCTGAAGACCAGAACTGGAAGTC<br>TGAAGCGAGCCCTGCACAATGCCGAATGCCAGAAGACTGTCACCATCTCCAAGCCCTGTGGC<br>AAACTGACCAAGCCCAAACC |
| 1789 | PTN | 3074873 | GTGTGTGCCCACCAGTGGAGACTGTGGGCTGGGCACACGGGAGGGCACTCGGACTGGAGCT<br>GAGTGCAAGCAAACCATGAAGACCCAGAGATGTAAGATCCCCTGCAA |
| 1790 | PTN | 3074874 | TGCAGGCTCAACAGTACCAGCAGCAGCGTCGAAAATTTGCAGCTGCCTTCTTGGCATTCATTT<br>TCATACTGGCAGCTGTGGA |
| 1791 | PTN | 3074901 | AGTGAGTCATCCGTCCAGAAGGCGGGGAGAGCAGCAGCGGCCCAAGCAGGAGCTGCAGCG<br>AGCCGGGTACCTGGACTCAGCGGTAGCAACCTCGCCCCTTGCAACAAAGGCAGACTGAGCGC<br>CAGAGAGGACGTTTC |
| 1792 | PTN | 3074902 | TTGAGTCAAAGGCAGGATCAGGTTCCCCGCCTTCCAG |
| 1793 | KRT8 | 3100564 | CCTTCTAGGATCTCCGCCTGGTTCGGCCCGCC |
| 1794 | SULF1 | 3102371 | CATCAGCATTCTACCAGCTGTGAAAGTGTTTGAGCACACGGGATATCCCTTCCAG |
| 1795 | SULF1 | 3102373 | CTCAGCCTCCAATCCGTAAGAGACACCCAGCCCCAGCAATTGGATTGGGCAGCCCGTCTTGAC<br>ACACCACTGTGCTGAGTGCTTGAGGACGTGTTTCAACAGATGGTTGGGGTTAGTGTGTGTCAT<br>CACATTCGAGTGGGGATTAAGAGAAGGAAGGCTGCCTTGCTGGAGCTGTGTGGTCTTCTCCA<br>AGTGAGAGTCGCAGGCA |
| 1796 | SULF1 | 3102380 | TGACTCTCCCCCTTCGGAGGAGGAAGGAAGTCCCGCTGCCACCTTATCTCTGCTCCTCTGCCTC<br>CTCCCTGTTCCCAGAGCTTTTTCTCTAGAAGATTTTGAAGGCGGCTTT |
| 1797 | SULF1 | 3102381 | TCTTCACTTCTCTTGAACAAGGAACTCACTCAGAGACTAACACAAAGGAAGTAATTTCTTACCT<br>GGTCATTATTTAGTCTACAATAAGTTCATCCTTCTTCAGTGTGACCAGTAAATTCTTCCCATACT<br>CTTGAAGAGAGCATAA |
| 1798 | SULF1 | 3102386 | ACGGCCACCCACCATCATCTAAAGAAGATAAACTTGGCAAATGACATGCAGGTTCTTCA |
| 1799 | SULF1 | 3102391 | TCTGCAGATGTTCTGAATACCTCTGAGAATAGAGATTGATTATTCAACCAGGATACCTAATTCA<br>AG |
| 1800 | SULF1 | 3102392 | TTGTCAGTTTTGCAACATTGGACCAAA |
| 1801 | SULF1 | 3102393 | GGGAAGCCTCTGTTCGACTGTCAGATCCCCGAGGTTCAGAGGACGGATACAGCAGGAACGA<br>AAAAACATCCGACCCAACATTATTCTTGTGCTTACCGATGATCAAGATG |
| 1802 | SULF1 | 3102404 | GCTACATCCCCCCTGGGTGGCGAGAATGGCTTGGATTAATCAAGAATTCTCGCTTCTATAATT<br>ACACTGTTTGTCGCAATGGCATC |
| 1803 | SULF1 | 3102405 | TACTTCACAGACTTAATCACTAACGAGAGCATTAATTACTTCAAAATGTCTAAGAGAATGTATC<br>CCCATAGGCCCGTTATGATGGTGATCAGCCACGCTGCGCCCACGGCCCCGAGGACTCAGCC<br>CCACAGTTTTCTAAACTGTACCCCAATGCTTCC |
| 1804 | SULF1 | 3102407 | AACAGACAGGGTAAGGACCAATCTGGACTGTGTTATCTTTT |
| 1805 | SULF1 | 3102410 | AACTCCTAGTTATAACTATGCACCAAAT |
| 1806 | SULF1 | 3102411 | AGGACCAATGCTGCCCATCCACATGGAATTTACAAACATTCTACAGCGCAAAAGGCTCCAGAC<br>TTTGATGTCAGTGGATGATTC |
| 1807 | SULF1 | 3102412 | CTGTATAACATGCTCGTGGAGACGGGGAGCTGGAGAATACTTACATCATTTACACCGCCGA<br>CCATGGTTACCATATTGGGCAGTTTGGACTGGTCAAGGGGAAATCCATGCCA |
| 1808 | SULF1 | 3102414 | GTCCCACAGATCGTTCTCAACATTGACTTGGCCCCCACGATCCTGGATATTGCTGGGCTCGAC<br>ACACCTCCTGATGTGGACGGCAAGTCTG |

TABLE 13-continued

Subtyping Target Sequences

| SEQ ID NO. | Gene | Affy Probeset ID | Sequence |
|---|---|---|---|
| 1809 | SULF1 | 3102417 | AAGAAGGCCAAAATTTGGCGTGATACATTCCTAGTG |
| 1810 | SULF1 | 3102419 | TTTCTACGTAAGAAGGAAGAATCCAGCAAGAATATCCAACAG |
| 1811 | SULF1 | 3102430 | GCAATGCATTGAGGATACATCTGGCAAGCTTCGAATTCACAAGT |
| 1812 | SULF1 | 3102431 | GTCCGGCAGAGCACGCGGAACCTCTACGCTCGCGGCTTCCATGACAAAGACAAAGAGTGCAGTTGTAGGGAGTCTGGTTACCGTGCCAGCAGAAGCCAAAGAAAGAGTCAACGGCAATTCTTGAGAAACCA |
| 1813 | SULF1 | 3102434 | TCCATACTCGGCAGACACGTTCCTTGTCCGTCGAATTTGAAGGTGAAATATATGACATAAATCTGGAAGAAGAAGAAGAATTGCAAGTGTTGCAACCAAGAAACATTGCTAAGCGTCATGATGAAGGCCACAAGGGGCCAAGAGATCTCCAGGCTTCCAGTGGTGGCAACAGGGGCAGGATGCTGGCAGATAGCAGCAACGCCGTGGGCCCA |
| 1814 | SULF1 | 3102435 | ATGACTCTATCCATTGTGAGAGAGAACTGTACCAATCGGCCAGAGCGTGGAAGGACCATAAGGCATACATTGACAAA |
| 1815 | SULF1 | 3102437 | ATTGAAGCTCTGCAAGATAAAATTAAGAATTTAAGAGAAGTGAGAGGACATCTGAAGAGAAGGAAGCCTGAGGAATGTAGCTGCAGTAAACAA |
| 1816 | SULF1 | 3102439 | GCTCAGGAAGTAGATAGCAAACTGCAACTTTTCAAGGAGAACAACCGTAGGAGGAAGAAGGAGAGGAAGGAGAAGAGACGGCAGAGGAAGGGGGAAGAGTGCAGCCTGCCTGGCCTCACTTGCTTCACGCATGACAACAACCACTGGCAGACAGCC |
| 1817 | SULF1 | 3102442 | TCTACAAGTTAACCAGAGGGCTATGTGGTATAAAAGATGTTTGTGGTCACAGCCTAGCTCAGGCTAGAGTGTTGCAGAGACCATCCCAAATCCTCCAGGCTGGGCTCAAGGCTTCTCTAAACCCTTCTTTGTTGCAAAATCCCATCTTTTCATGCTTCATTGGTGACATGTGGCCATCTGCCACATAGAACAAGTGAGAGTACTAGTTCCATATCTTTATTAAATAACCATTTTTCTTTTGTACAAAGAATAAATAGAAATTCTGATATTTTTCTTCTCATACTTCCGTCACTCACCCCTCTTTGGAAACCACTGCATAACAGAGCTAAGGGGAGGATAAACTAATGTGCTGAAATTTTACTTTAGTCTTCAGCCTATAAGAGATCACTATCTTTTTTCCCATTTTCACCTAGTTTCACAGCAAATTTACCTACGGGGGGAAAGGTATTATTATTCTTAACATGAAACCACAATATTTATAAGAAAGAAATTGTGAACTTTAAAGTGTAAAGATAAGGGAACACTGGAATGGCAAGCCTGCCTAAGGTTTTTCA |
| 1818 | SULF1 | 3102443 | GAGTTCTAACAATAACACCTACTGGTGTTTGCGTACAGTTAATGAGACGCATAATTTTCTTTTCTGTGAGTTTGCTACTGGCTTTTTGGAGT |
| 1819 | SULF1 | 3102445 | CACACGGTAGAACGAGGCATTTTGAATCAGCTACACGTACAACTAATGGAGCTCAGAAGCTGTCAAGGATATAAGCAGTGCAACCCAAGACCTAAGAATCTT |
| 1820 | SULF1 | 3102447 | GAAATAAAGATGGAGGAAGCTATGACCTA |
| 1821 | SULF1 | 3102450 | AATGTTGCTGTTCCTGGTACCCTGTTCGGCCCCTCTAACCTCCAGAGCTATGGTCTCAGATGCTTCCTTT |
| 1822 | SULF1 | 3102451 | GAGAAGGTCATTAGTCCACCAAGAAGCC |
| 1823 | SULF1 | 3102460 | AGGACAGTTATGGGATGGATGGGAAGGTTAA |
| 1824 | SULF1 | 3102461 | TTGCACTGCTGAAGAGTCACTATGAGCAAAATAAAACAAATAAGACTCAAACTGCTCAAAGTGACGGGTTCTTGGTTGTCTCTGCTGAGCACGCTGTGTCAATGGAGATGGCCTCTGCTGACTCAGATGAAGACCCAAGGCATAAGGTTGGGAAAACACCTCATTTGACCTTGCCAGCTGACCTTCAAACCCTGCATTTGAACCGACCAACATTAAGTCCAGAGAGTAAACTTGAATGGAATAACGACATTCCAGAAGTTAATCATTTGAATTCTGAACACTGGAGAAAAACCGAAAATGGACGGGGCATGAAGAGACTAATCATCTGGAAACGATTTCAGTGGCGATGGCATGACAGAGCTAGAGCTCGGGCCCAGCCCCAGGCTGCAGCCCATTCGCAGGCACCCGAAAGAACTTCCCCAGTATGGTGGTCCTGGAAAGGACATTTTTGAAGATCAACTATATCTTCCTGTGCATTCCGATGGAATTTCAGTTCATCAGATGTTCACCATGGCCACCGCAGAACACCGAAGTA |
| 1825 | SULF1 | 3102462 | ACTAATAAAGGTAATCACAGCCACCAA |
| 1826 | SULF1 | 3102463 | CCCTGGGTACCTTTGTGCAGTAGAAGCTAGTGAGCATGTGAGCAAGCGGTGTGCACACGGAGACTCATCGTTATAATTTACTATCTGCCAAGAGTAGAAAGAAAGGCTGGGGATATTTGGGTTGGCTTGGTTTTGATTTTTTGCTTGTTTGTTTGTTTTGTACTAAAACAGTATTATCTTTTGAATATCGTAGGGACATAAGTATATACATGTTATCCAATCAAGATGGCTAGAATGGTGCCTTTCTGAGTGTCTAAAACTTGACACCCCTGGTAAATCTTTCAACACACTTCCACTGCCTGCGTAATGAAGTTTTGATTCATTTTTAACCACTGGAATTTTTCAATGCCGTCATTTTCAGTTAGATGATTTTGCACTTTGAGATTAAAATGCCATGTCTATTTGATTAGTCTTATTTTTTATTTTTACAGGCTTATCAGTCTCACTGTTGGCTGTCATTGTGACAAAGTCAAATAAACCCCAAGGACGACACACAGTATGGATCACATATTGTTTGACATTAAGCTTTTGCCAGAAAATGTTGCATGTGTTTTACCTCGACTTGCTAA |

TABLE 13-continued

Subtyping Target Sequences

| SEQ ID NO. | Gene | Affy Probeset ID | Sequence |
|---|---|---|---|
| 1827 | SULF1 | 3102464 | GTGCCTAGCCTCAAAGCGTTCATCATACATCATACCTTTAAGATTGCTATATTTTGGGTTATTTT<br>CTTGACAGGAGAAAAAGATCTAAAGATCTTTTATTTTCATCTTTTTTGGTTTTCTTGGCATGACT<br>AAGAAGCTTAAATGTTGATAAAATATGACTAGTTTTGAATTTACACCAAGAACTTCTCAATAAA<br>AGAAAATCATGAATGCTCCACAATTTCAACATACCACAAGAGAAGTTAATTTCTTAACATTGTG<br>TTCTATGATTATTTGTAAGACCTTCACCAAGTTCTGATATCTTTTAAAGACATAGTTCAAAATTG<br>CTTTTGAAAATCTGTATTCTTGAAAATATCCTTGTTGTGTATTAGGTTTTTAAATACCAGCTAAA<br>GGATTACCTCACTGAGTCATCAGTACCCTCCTATTCAGCTCCCCAAGATGATGTGTTTTTGCTT<br>ACCCTAAGAGAGGTTTTCTTCTTATTTTTAGATAATTCAAGTGCTTAGATAAATTATGTTTTCTT<br>TAAGTGTTTATGGTAAACTCTTTTAAAGAAAATTTAATATGTTATAGCTGAATCTTTTTGGTAA<br>CTTTAAATCTTTATCATAGACTCTGTACATATGTTCAAATTAGCTGCTTGCCTGATGTGTGTATC<br>ATCGGTGGGATGACAGAACAAAC |
| 1828 | SULF1 | 3102465 | TTAGGAAGCATACTCTGTTTTTTAATCATGTATAATATTCCATGATACTTTTATAGAACAATTCT<br>GGCTTCA |
| 1829 | PSCA | 3119201 | ATCAGCCCAGGACGGTCTTCCCGGTGCAGTTTCTGATGCGGGAGGGCAGTGCTGCCTTCCG<br>GTCACCAGGACCAGTGCTCAGCCCGCTGCTTGACCCCCTTACTTAGCTGGGGTCCAATCCA |
| 1830 | PSCA | 3119206 | GGCTGTGCTGCTTGCCCTGTTGATGGCAGGCTTGGCCCTGCAGC |
| 1831 | PSCA | 3119207 | CCCTGCTGTGCTACTCCTGCAAAGCCCAGGTGAGCAACGAGGACTGCCTGCAGGT |
| 1832 | PSCA | 3119208 | CTTTCTGGCCATCTGTCCGCATCTGTGTGCTGTTTTCCTTCCACCTGTCCCGACCCGTCCCGCA<br>CCTGCACCCCCAACAATCACCCAGCATCTGTCCCTCCAGCCATCCTCCTCCATCTGCCACTCCTC<br>CACTCATCTGTCCCTCCCCATCCTCCATCTTCCACTCCTCCACCCATCTGTCCCTCCCCATCCCTG<br>AGCTCACTTACTCACTCACCCCATTTCTGACGCTCAGCGGGTGGTCCATCTGCCTCGGACATCT<br>GGATAGGGCTGAGACCAGGGCCGAGACCAGGCCCTCGCACTGCTTGCAATCCTGAGGCCA |
| 1833 | PSCA | 3119209 | AGCTTGAACTGCGTGGATGACTCACAGGACTACTACGTGGGCAAGAAGAACATCACGTGCTG<br>TGACACCGACTTGTGCAACGCCAGCGGGGCCCAT |
| 1834 | PSCA | 3119210 | GAGGCACATCCTAACGCAAGTCTGACCATGTATGTCTGCGCCCCTGTCCCCCACCCTGACCCTC<br>CCATGGCCCTCTCCAGGACTCCCACCCGGCAGATCGGCTCTATTGACACAGATCCGCCTGCAG<br>ATGGCCCCTCCAACCCTCTCTGCTGCTGTTTCCATGGCCCAGCATTCTCCACCCTTAACCCTGTG<br>CTCAGGCACCTCTTCCCCCAGGAAGCCTTCCCTGCCCACCCCATCTATGACTTGAGCCAGGTCT<br>GGTCCGTGGTGTCCCCCGCACCCAGCAGGGGACAGGCACTCAGGAGGGCCCGGTAAAGGCT<br>GAGATGAAGTGGACTGAGTAGAACTGGAGGACAGGAGTCGACGTGAGTTCCTGGGAGTCTC<br>CAGAGATGGGGCCTGGAGGCCTGGAGGAAGGGGCCAGGCCTCACATTCGTGGGGCTCCCTG<br>AATGGCAGCCTCAGCACAGCGTAGGCCCCTTAATA |
| 1835 | SNAI2 | 3134549 | TCCTGTGCTGACCAACCAAATAATATGTATAGACACACACACATATGCACACACACACACACA<br>CACCCACAGAGAGAGAGCTGCAAGAGCATGGAATTCATGTGTTTAAAGATAATCCTTTCCATG<br>TGAAGTTTAAAATTACTATATATTTGCTGATGGCTAGATTGAGAGAATAAAAGACAGTAACCT<br>TTCTCTTCAAAGATAAAATGAAAAGCACATTGCATCTTTTCTTCCTAAAAAAATGCAAAGATTT<br>ACATTGCTGCCAAATCATTTCAACTGAAAAGAACAGTATTGCTTTGTAATAGAGTCTGTAATA<br>GGATTTCCCATAGGAAGAGATCTGCCAGACGCGAACTCAGGTGCCTTAAAAAGTATTCCAAG<br>TTTACTCCATTACATGTCGGTTGTCTGGTTGCCATTGTTGAACTAAAGCCTTTTTTTGATTACCT<br>GTAGTGCTTTAAAGTATATTTTTAAAAGGGAGGAAAAAAATAACAAGAACAAAACACAGGAG<br>AATGTATTAAAAGTATTTTTGTTTTGTTTTGTTTTTGCCAATTAACAGTATGTGCCTTGGGGGA<br>GGAGGGAAAGATTAGCTTTGAACATTCCTGGCGCATG |
| 1836 | SNAI2 | 3134550 | TTTCTTGCCCTCACTGCAACAGAGCATTTGCAGACAGGTCAAATCTGAGGGCTCATCTGCAGA<br>CCCATTCTGATGTAAAGAAATACCAGTGCAAAAACTGCTCCAAAACCTTCTCCAGAATGTCTCT<br>CCTGCACAAACATGAGG |
| 1837 | SNAI2 | 3134552 | TGCGATGCCCAGTCTAGAAAATCTTTCAGCTGTAAATACTGTGACAAGGAATATGTGAGCCTG<br>GGCGCCCTGAAGATGCATATTCGGACCCACACATTACCTTGTGTTTGCAAGATCTGCGGCAAG<br>GCGTTTTCCAGACCCTGGTTGCTTCAAGGACA |
| 1838 | SNAI2 | 3134553 | TGAGAGTTACTCCATGCCTGTCATACCACAACCAGAGATCCTCAGCTCAGGAGCATACAGCCC<br>CATCACTGTGTGGACTACCGCTGCTCCATTCCACGCCCAGCTACCCAATGGCCTCTCTCCTCTTT<br>CCGGATACTCCTCATCTTTGGGGCGAGTGAGTCCCCCTCCTCCATCTGACACCTCCTCCAAGGA<br>CCACAGTGGCTCAGAAAAGCCCCATTAGTGATGAAGAGGAAAGACTACAGTCCAAGCTTTCAG<br>ACCCCCATGCCATTGAAGCTGAAAAGTT |
| 1839 | SNAI2 | 3134554 | CAAGAAGCATTTCAACGCCTCCAAAAAGCCAAACTACAGCGAACTGGACACACATACAG |
| 1840 | SNAI2 | 3134555 | TCCCAGCCAAAACGGGCTCAGTTCGTAAAGGAGCCGGGTGACTTCAGAGGCGCCGGCCCGTC<br>CGTCTGCCGCACCTGAGCACGGCCCCTGCCCGAGCCTGGCCCGCCGCGATGCTGTAGGGACC<br>GCCGTGTCCTC |
| 1841 | SNAI2 | 3134557 | TCCTGCGCCCCTCCTAGCTCCCAGAGAGCGTGGATCGCGGGCGGGGCTCACCGAGCGAG |

TABLE 13-continued

Subtyping Target Sequences

| SEQ ID NO. | Gene | Affy Probeset ID | Sequence |
|---|---|---|---|
| 1842 | SNX31 | 3146725 | TCAGGTGGGCTACCTACCATCAGTGGAGGAAATTTGACCTCTTCCCATTTTTTTGGCATTAACA TGGACTGTATTCATCAAGGTATTATACCACAGCACTCTATGGAAATCTCAAGATTAGAAAAAA AAAAAGAACCAAGTTATAGAGTTAGTTTTTATTTTATTTTTGCACTTCGTCATGACAGTATAGA GTTTGTTTTTAATGTCTCATAAATGACAAGTGGCAAATTCAAATCAACTCATATAAAACTCATT CTATTTTTTCTCTAAAATAGATCTTTATATGGCTTCATGAAGTCTTTTATGTGTTTTGAATTTACA TAAATGAAAGTCTCATAAAATATCATAAAGATATTTTGGATCGATTTCTAAAGATGTGACTCTT CAACGGAGGAGAATAGGGCTCTGAGAAATGGAATCACTGAAAAAGAAACCTGGGTTCTCTG ATCTATCCACACAGAACTAGAGCAAGGAGGTGATGAAATACTGATCTCTTTCCTCACATAAGT CTGAGCCTACCAATATGGATGTACTCAAAGTGAAACGCTGCCCTGTTCTCTGCTTGACCATTGT TA |
| 1843 | SNX31 | 3146726 | AGACTATTCTAGTTTTCTATCAAGAAAAAGCAAGATTAAGATAGCTAAAGATGACTGCGTTTT TGGGAACATAAAG |
| 1844 | SNX31 | 3146729 | TGGTGACTGAACAATTCAAGATGTGCTAGAGAGTAGTAAATCAAAGCAATAAAAGAATCAAG GAAACTCTTTTTAAAAGAGTAATATAATAAAATCCAACCTCTCAGGCAGGATGGACCCTCTTA GGCTGAGATTA |
| 1845 | SNX31 | 3146732 | GAACTCTGCTGGATACGGATGGGCCCCAGAGAACTCTCAACCAGAACTTAGAGCTCAGATTT CAATACAGTGAGGATAGTTGC |
| 1846 | SNX31 | 3146736 | CGGGAGGTACGGCACTATGGATACCTGCAGCTGGATCCTTGTACCTGTGACTACCCAGAATC AGGCTCTGGAGC |
| 1847 | SNX31 | 3146741 | CATCCCTCGACTCCGTGCTGATGGACTGCAGGGTGGCGGTAGATTTGCTCTACATGCAG |
| 1848 | SNX31 | 3146743 | ACTTTGAACTCCCTTATGTTAGTCTTGGAAGTTCTGAGGTG |
| 1849 | SNX31 | 3146744 | GTGTCACACAAAATTGGACTGTGTCGAGAGCTCTTGGGCTACTTCGGCCTCTTTCTCATTCGGT TTGGCAAGGAGG |
| 1850 | SNX31 | 3146749 | ATTTGACATCGCCACCAAGAAAGCTTATCTGGACATATTTCTGCCCAATGAACAGAGTATTAG AATCGAAATTATAACATCAGACACTGC |
| 1851 | SNX31 | 3146750 | AAAAATCAGGGATATGGGCTTTAGGG |
| 1852 | SNX31 | 3146759 | ATGGACCCAAACGTGTTGAGAAGTGATGTCTTCGTTGAGTTTTAA |
| 1853 | SNX31 | 3146761 | CTTCCCACCAAAGTACTATCTGGCAATGACCACAGCTATGGCTGATGAGAGGAGGGACCAAC TGGAACAATATTTG |
| 1854 | SNX31 | 3146764 | TGCATTTCTGTATCCCGGTGTCCCAGCAGCGGTCCGACGCGCTGGGGGGCCG |
| 1855 | SNX31 | 3146765 | TTCGCTCTGAGTCGCGTGGCAGGCCGCGCTGCGTCCACCGCTGCCGAGTTCAGAGCCGCGCA CCGCCCGCCGCCGCAGGTCGGGTTCCCAGCGCTACTCCCAAGAC |
| 1856 | SNX31 | 3146767 | CTCCCAAGTAGTCCACTTCATTCTTCACCTCTGGA |
| 1857 | SNX31 | 3146768 | CCAGTTGTACTGTCGAGAAAAGAGCTATTTCTGTCTTTTAACTCTCAAATACAAAGATACTGCT CAGTGGGAATCAAACATTCCTAATTTTCATTTATTTATCTTTTCATTTTAATTTTGGATTGGGGG GGGTATCTGCGCAGCTCTGTTAGACGGAGTATATTGCATGGTGCTGAGGTCTGGGCTTCTGA TGGTCCCGTCGTTCAAGTAGCAAACGCGCTGCGCGA |
| 1858 | PABPC1 | 3146782 | TGACACCGCCATGAAAACGATCAGCACCGTCGAATCCTCACGCCCCACTCAAGTTCCTTGATT GCTTCAATAATGTCCTCCGTAGCAAAAGGATCTAGTTCAAAATCGGGAGTTACATTTCATTGTC ATGCCTAAAACGTAAGAATTGCTCATTCACTTTGGAGCAGTTCTTCAGTCTATCCTTGATTTTC ATGACCTTGACACTTTTGAACATTATAGACCAGTTATTCAATAGAAATATCTTTCAATCTGGGTT TGTCCGATACCTCTTTATTATTAGATTGAAATGACATTTTGGTGGAACTATCACAGAATTGA CATTGCATTCTTCTCATTACATCCTGTCTGGTGGCCTG |
| 1859 | PABPC1 | 3146788 | CCTTATGTACCGAGCAAATGCCAGGTCTAGCAAACATAATGCTAGTCCTAGATTACTTATTGAT TTAAAAACAAAAAAACACAAAAAAATAGTAAAATATAAAAACAAATTAATGTTTTATAGACCC TGGGAAAAAGAATTTTCAGCAAGTACAAAAATTTAAAGCATTCCTTTCTTTAATTTTGTAATT CTTTACTGTGGAATAGCTCAGAA |
| 1860 | PABPC1 | 3146789 | TGATCAGGGACCATGAAAAGAAACTTGTGCTTCACCGAAGAAAAATATCTAAACATCGAAAA ACTTAAATATTATGG |
| 1861 | PABPC1 | 3146791 | ATGAAGCTGTAGCTGTACTACAAGCCCACCAAGCTAAAGAGGCTGCCCAGAAAGCAGTTAAC AGTGCCACCGGTGTTCCAACTGTTT |
| 1862 | PABPC1 | 3146793 | GCCATGCACCCTACTCTTGCTGGTA |
| 1863 | PABPC1 | 3146794 | TCCTCAAGAGCAAAAGCAAATGTTG |

TABLE 13-continued

Subtyping Target Sequences

| SEQ ID NO. | Gene | Affy Probeset ID | Sequence |
|---|---|---|---|
| 1864 | PABPC1 | 3146795 | AATGGGTCCACGTCCTGCAGCTGCA |
| 1865 | PABPC1 | 3146797 | TGCAAACCTCAGATCGAAGAAGACAGCATAAACACTTTTCACTCAGTAAGTTTTCCCAGTTAATGTA |
| 1866 | PABPC1 | 3146799 | AACCGTGCTGCATACTATCCTCCTA |
| 1867 | PABPC1 | 3146802 | TTATGATGGAGGGTGGTCGCAGCAAA |
| 1868 | PABPC1 | 3146805 | GATGATGGTATTGATGATGAACGTCTCCGGAAAGAGTTTTCTCCAT |
| 1869 | PABPC1 | 3146806 | TTATGTTGGTCGAGCTCAGAAAAAGGTGGAACGGCAGACGGAACTTAAGCGCAAATTTGAACAGATGAAACAAGATAGGATCACCAGAT |
| 1870 | PABPC1 | 3146809 | TTTGTTGGACGATTTAAGTCTCGTAAAGAACGAGAAGCTGAACTTGGAGCTAGGGCAAAAGAATTCACCAATG |
| 1871 | PABPC1 | 3146812 | TGAAAATGGTTCCAAGGGCTATGGATTTGTACACTTTGAGACGCAGGAAGCAGCTGA |
| 1872 | PABPC1 | 3146813 | GCTACATTTAGTTTAGTGCTTGAAATAGGAACTGTGCAGTAATGGATATCTTTATTTCACAAATATCCAGGTTAGATGGCTAACAGATTGTCTCTCAACA |
| 1873 | PABPC1 | 3146815 | GGAGCGTGCTTTGGACACCATGAATTTTG |
| 1874 | PABPC1 | 3146819 | CTACGAGAAGTTCAGCCCGGCCGGGCCCATCCTCTCCATCCGGGTCTGCAGGGACATGATCACCCGCCGCTCCTTGGGCTACGCGTATGTGAACTTCCAGCAGC |
| 1875 | PABPC1 | 3146820 | GTCGCGGCCTGTGGCCCTGCGGGCAGC |
| 1876 | PABPC1 | 3146821 | CCCGGCACTCGCTCTCCTCCTCTCACGGAAAG |
| 1877 | PABPC1 | 3146822 | GATTTTTGTCCCTCTGCGCTTGCTCCCCGCTCCCCT |
| 1878 | PABPC1 | 3146823 | TCGCTCCCCGCCGGCAGCCGGCAGCCAGCGGCAGTGGATCGACCCC |
| 1879 | PABPC1 | 3146824 | CCAAGAAGGAACCAAGAGACCGAGGCCTTCCCGCTGCCCGGACCCGACACCGCCACC |
| 1880 | PABPC1 | 3146825 | GCTGGCTCCATCTACGCACGTTTCGGAAACCGGGCCCGGAGGGGACCACGCCCGCTCACCCGTGCCCGGCGTCCCCCGGAGCTGGGGCTAGAGGAGCCGGGCCGGCCGCAGCGGGAAGGAGGCCACAGGCGGCCGCGCACGTGGGGGGTGGTTAGCGCGGAGGAACCCGGAAGCCCTTTGCACCGCCCACCGCCGCGGTGACGGGTTAACGCTCCTCCTGGTGGAGGCAGGGGCGGGCGGGGCGGAAGGCGGGGACGCCTCAGCCAACACCCCGAGGACCGCCCGCGAGCCGTCCTCCCCACCCCCACGGACGCGACGCAGCGCGGGCTCCGCTTCCCGGCCGCGGCGCCTGCGCAAAAGCCCCGCCCCCTTCGCCCGAGCCCCACCCCCACACCGCAGCCTCCACCGCCGCCACCTCTCCCTTCCTCTCTGCTCTTTCCTCCTGTTTTCTCTTCCCTCCTCCCCCTGGCCTCCGCGTCTCCTCCTACTCCGGCGCTGACGCTCGCGTAGGGCCCTGGCGTCAGACGCGCGGGGCGGGCGAGTGCGGCGCGGGGTATAAGTAGAGGGTGCAGGAGGCGGTGCTTCCCCTTCTCCCCGGCGGTTAGTGCTGAGAGTGCGGAGTGTGTGCTCCGGGCTCGGAACACACATTTATT |
| 1881 | PABPC1 | 3146826 | AGGCACCGCTTCTGCGGCCGACGCGCGTGGCGGCGGTGCCGGCTGGGACTCGTAGTGCGGTCCGG |
| 1882 | NDRG1 | 3154318 | GATCGGGGCAAGAGAGGCTGAGTACGGATGGGAAACTATTGTGCACAAGTCTTTCCAGAGGAGTTTCTTAATGAGATATTTGTATTTAT |
| 1883 | NDRG1 | 3154319 | GCTCACCGTGGATTTTCTCATAGGAAGTTTGGTCAGAGTGAATTGAATATTGTAAGTCAGCCACTGGGACCCGAGGATTTCTGGGACCCCGCAGTTGGGAGGAGGAAGTAGTCCAGCCTTCCAGGTGGCGTGAGAGGCAATGACTCGTTACCTGC |
| 1884 | NDRG1 | 3154320 | AGGTCTATTACGTGGGTGCCCTCTCCAAAGGCGGGGTGGCGGTGGACCAAAGGAAGGAAGCAAGCATCTCCGCATCGCATCCTCTTCCATTAACCAGTGGCCGGTTGCCACTCTCCTCCCCTCCCTCAGAGACACCAAACTGCCAAAAACAAGACGCGTAGCAGCACACACTTCACAAAGCCAAGCCTAGGCCGCCCTGAGCATCCTGGTTCAAACGGGTGCCTGGTCAGAAGGCCAGCCGCCCACTTCCCGTTTCCTCTTTAACTGAGGAGAAGCTGATCCAGTTTCCGGAAACAAAATCCTTTTCTCATTTGGGGAGGGGGTAATAGTGACATGCAGGCACCTCTTTTAAACAGGCAAAACAGGAAGGGGGAAAAGGTGGGATTCATGTCGAGGCTAGAGGCATTTGGAACAACAAATCTACGTAGTTAACTTGAAGAAACCGATTTTTAAAGTTGGTGCATCTAGAAAGCTTTGAATGCAGAAGCAAACAAGCTTGATTTTTCTAGCATCCTCTTAATGTGCAGCAAAAGCAGGCGACAAAATCTCCTGGCTTTACAGACAAAAATATTTCAGCAAACGTTGGGCATCATGGTTTTTGAAGGCTTTAGTTCTGCTTTCTGCCTCTCCTCCACAGCCCCAACCTCCCACCCCTGATACATGAGCCAGTGATTATTCTTGTTCAGGGAGAAGATCATTTAGATTTGTTTTGCATTCCTTAGAATGGAGGGCAACATTCCACAGCTGCCCTGGCTGTGATGAGTGTCCTTGCAGGGGCGGAGTAGGAGCACTGGGGTGGGGTGGAATTGGGGTTACTCGATGTAAGGGATTCCTTGTTGTTGTGTTGAGATCCAGTCAGTTGTGATTTCTGT |

TABLE 13-continued

Subtyping Target Sequences

| SEQ ID NO. | Gene | Affy Probeset ID | Sequence |
|---|---|---|---|
| | | | GGATCCCAGCTTGGTTCCAGGAATTTTGTGTGATTGGCTTAAATCCAGTTTTCAATCTTCGACA GCTGGGCTGGAACGTGAACTCAGTAGCTGAACCTGTCTGACCCGGTCACGTTCTTGGATCCTC AGAACTCTTTGCTCTTGTCGGGGTGGGGGTGGGAACTCACGTGGGGAGCGGTGGCTGAGAA AATGTAAGGATTCTGGAATACATATTCCATGGGACTTTCCTTCCCTCTCCTGCTTCCTCTTTTCC TGCTCCCTAACCTTTCGCCGAATGG |
| 1885 | NDRG1 | 3154321 | TTCCAGCGTCACTTCTCTGGATGGCACCCGCAGCCGCTCCCACACCAGCGAGGGCACCCGAA GCCGCTCCCACACCAGCGAGGGCACCCGCAGCCGCTCGCACACCAGCGAGGGGCCCACCT GGACATCACCCCCAACTCGGGTGCTGCTGGGAACAGCGCCGGGCCCAAGTCCATGGAGGTCTC |
| 1886 | NDRG1 | 3154322 | CTCGGCTAGCATGACCCGCCTGATGCGGTCCCGCACAGCCTC |
| 1887 | NDRG1 | 3154323 | AATTCGTGTGTCCTCCCTTACTAGGAAGTTATTGAACTTCTGATCCCTTTTATCATTTCCTTAAA CTGTTTGCCCATGTATAGTAAGAGTATGCTTGGTAAGCTGACTGCAGTCCTAGCATTGGCCTT AGCCATGATTAGCTCTAGCAAGGCGAGGCTGGCAGGTTTGATTTCCATGCCTCAGGCTCAGG CAGGATCCACATCCCCAGGTGCCCTCTTCCAACAGAAGCTATCTGCTAGTGGGGCTCCTGCCT TTCTAGCCTGCTTTCCCCGACGGAAGTTGCAGGCAAAGGTTGTCATTGGAGACAGCCATGGA GACAGCCGCGGGGCAGTCCTGCTTTACCCTGCACGGTGTGA |
| 1888 | NDRG1 | 3154324 | GCATGTGTCGGAATTGGAAGTGCTCTGTCCTGAGCCAGGTTTGGATGAGCAATTCTGTGTC |
| 1889 | NDRG1 | 3154325 | CAAGTACTTCGTGCAGGGCATGGGATACA |
| 1890 | NDRG1 | 3154328 | ATGGCGGACTGTGGCGGCCTCCCGCAGA |
| 1891 | NDRG1 | 3154333 | GGAGTGCAACTCAAAATTGGACCCAACAAAGACCACTCTCCTCAAG |
| 1892 | NDRG1 | 3154335 | GGTGGTTGGGGACAGCTCGCCTGCAGTGGATGCCG |
| 1893 | NDRG1 | 3154339 | GCGCAAAGAGATCCTGTGTTCTCCCCAAGGCCACACAGCTAGAAAGTGGCAGAGCATGATTT GGATCCTGCTTGTCTAACTCCAGGCTGTGAGCTGGGAAAGAGCTTCTCATGTTGGGAGC |
| 1894 | NDRG1 | 3154340 | TGCAGAGTAACGTGGAAGTGGTCCACACCTACCGCCAGCACATTGTGAATGACATGAACCCC GGCAAC |
| 1895 | NDRG1 | 3154341 | ATGGACCCAAGCTCTGCCGGACATGGTG |
| 1896 | NDRG1 | 3154342 | AGGAGCCCTTCCGTCCAGCCTGTATGACGTTCTGGAGTGGAACACACTCCCTGTTTTTATTTG ATTTTCCAGCAAAGGAAGTGACATTCCAGTCAACCCGCTGGGCTTCATGATAGCTGTCCTGAG TGAGACTCGAAGGTCTGGGGATGTCGACCACTGGCTAATGTGAAGCCTGAGGATTGTCTTTA ATAGCTGTACTATTCCCTTCAGTACAGCTTTAATAGCTGTACTATTCCCTTCTTTTTCAACTCCA GCCTTTCGATTACCAGGCATTGGTATTAGATACTGTGATGTGTGCAGTTACTTCTTGCAGTCCT TCCCTTGACCTTGTGGCCTTGAAGTTCCTGGCACTCCCAGTTCCAGATTAGAAGTCTGAGACCC AGAGGTATGCAGACTGCCCAGTGCCACACAGCTAGGCTGTGGCAGGCAAGGGCCAGCCAAA GACCCTTAGGTCTAGAGCTTCTCTCCTACTCATTTTTGCCTAATGCTTAGGTCAGCACACATTTA TGGAGCTTCTGCTGTATACTAGGACTTATAGAGCTCCTGCTGCAAACCTAGTCACTGGGGAGA GGTAGGAAAGAAGATTGTCAGTGTCTTTGGTAATATCAGTATACTTAGAAAGGGGAAACTG GCTTGGAGATGAGAGAGGAGGGATAGTTGGGAGCCAAGCATATCTTGGGGTATAGACTGGG GAGCTCAGTGTGTTTTTAGAAGAGGTGAATGGATGGCCCTCTTTGCTGAGGACTTGGTGAAT GTTTGGAGCAGGGTAAGCTAGCAGTAGCTGGGTCTTTATTCAGCACTTATTTGCTGTGCATCT TGTGCATGGGCCTCTGAA |
| 1897 | NDRG1 | 3154344 | TGGAGGGCCTTGTCCTTATCAACGTGAACCCTTGTGCGGAAGGCTG |
| 1898 | NDRG1 | 3154346 | CTGAAAAGCATTATTGGCATGGGAACAG |
| 1899 | NDRG1 | 3154347 | TGGTTTCTAGCATCTTCCTGCCCCTTGGCTTTGATCTGGACTGACCACTAAAATTAAGGTTGCA ATTTAGAGATGAGGCAAGAAATTAGCTCGTCACTCTGTGAACACT |
| 1900 | NDRG1 | 3154348 | GCTTCCTGGAGTCCTTCAACAGTTTGG |
| 1901 | NDRG1 | 3154349 | ACCCAGCACTTTGCCGTCTGCCACGTGGACGCCCCTGGCCAGCAGGACGGCGCAGCCTCCTTC CC |
| 1902 | NDRG1 | 3154350 | CCGAGACACCTAATTTTTTCTCATCTTACTTTTTTCTCTTCTCTCCCTCACTGCTGTTCTTCAG |
| 1903 | NDRG1 | 3154352 | AGCAGGACATCGAGACTTTACATGGCTCTGTTCACGTCACGCTGTGTGGGACTCCCAAGGGA AACCGGCCTGTCATCCTCACCTACCATGACATCGGCATGAA |
| 1904 | NDRG1 | 3154353 | CCCACTGTCTGCTGTGTCTCCTCAG |
| 1905 | NDRG1 | 3154361 | TCTCGGGAGATGCAGGATGTAGACCTCGCTGAGGTGAAGCCTT |

TABLE 13-continued

Subtyping Target Sequences

| SEQ ID NO. | Gene | Affy Probeset ID | Sequence |
|---|---|---|---|
| 1906 | NDRG1 | 3154364 | GGCGATGAGACGGTCCGAAAAAATACCAGGATAGCGTTTCCTGGCGTCGTCTCCGAATCCCAGCTGGCGCCGCTGGCA |
| 1907 | NDRG1 | 3154365 | CGGAGCTGCAAGTGCGCGGTCACCCCGGGGCGCGGGCGCGAGGGGGCTTTGGGTGCAGACACCGCTGAAGTGGGGGGTT |
| 1908 | NDRG1 | 3154366 | AGGGGCCGCCCGTGCGGTGCCGCTGGAGCGCCAGGACCGCCCTTTGTAG |
| 1909 | NDRG1 | 3154367 | GTAAGCCCGCGCCCTCTTCTCCCAG |
| 1910 | NDRG1 | 3154368 | GCTTGCGCAACAGGCGGCGGCTCCAGTGGGCGCCCGCCGCGCGCTGCCGGAGCCCAGCCCAGCCCGGCGCGCCCGGGAGGAGGGAGCAGGGAGCGGGAAGGGGTGTGTCCCGGCTGCGTGCTGGGACTGCGAGGGTCTGGGAGGGGCGAGGCGCGGGGGCGGGGCCGCGGCGCCTATAAAGTCGCCCTCCGCCCGGACGTAAACAAACCTCGCCTGGCTCCCAGCTGGTGCTGAAGCTCGTCAGTTCACCATCCGCCCTCGG |
| 1911 | NDRG1 | 3154369 | ATGGACGAGATTAAACGGGAGCGAGGATTTCAGCGAGAGCTTTGGCGACACGGAAGGCTGAGAATCGGAGGGAGCCTGTCGGGCGAAAGCGAAGGCGGCTGCTGGGCAGGCAGCCGAATCCGGCTGGAGA |
| 1912 | ACER2 | 3164328 | TGGTCAGTGTCCTGTCTGCGGTTACGACGT |
| 1913 | ACER2 | 3164335 | AAGTTCTGGCCCAATGAGAAATGGGC |
| 1914 | ACER2 | 3164336 | GAAGACAGCCAAGGGAGTTCGAATAGTTGG |
| 1915 | ACER2 | 3164337 | CTCCTCCTCCCTAATGTGTCTGTGGACCACCTGGATTCCACTGTACAAGGGGAAAAGTGTCTATTCCTTTCCCAAAGATGGAAAATGGAGGGCTTAGGGACACTAGATGCATCTTTCTCAGCATCACTTCCAGATGCAGTGACTTGTTGGGCTGCGTCCTTAATGGCCATG |
| 1916 | ANXA1 | 3174821 | GAAGGCAGCCAATTACTAACTTCTGGTTGCTAGGTGTGGCTTCCTTTAAAATCCTATAAAATCAGAAGCCCAAGTCTCCACTGCCAGTGTGAAATCTTCAGAGAAGAATTTCTCTTTAGTTCTTTGCAAGAAGGTAGAGATAAA |
| 1917 | ANXA1 | 3174824 | CATATTCGAGGAAAAACTATGCACAAGGCCGTGCATTTAAAAATAAACTCCCTAAGGCTGGGGTGAAACCTGCTACGGTCTGCGCAAGTTGACTGTTAATG |
| 1918 | ANXA1 | 3174829 | CAGCCAGGGCCTACTCTAAGAAGTTTCTTTAGCCCTTATGTTTTCCTATGGAGAGCACACACTAGCTTTAAGTCCTGAGGGTACTTAAGATGATATTTCAATGTTTTTGTACTCTTAGTGCTTGGCATATGGTGGGTGGTCTACAAATTTAGAACAATGTAGTGAACCACAAACTCCTCTCTTCAGCCTGTGTGCTTACTTGTAGTAGTTGTCTGATCTCTAAAATTTAGAACTGAATATGCCAAGAAAGAGTTCAATTTCAGAGAGGAGGGTATGGTTTCATTTTAAGTATAAAAGCTTCCTTTAAAAAAAATTACGTCTTACATTTTGTTATGCTCCTAAGTGTAATTGATCCTGGAAAGTAAGCGCAAGGCTACTCTCTAATG |
| 1919 | ANXA1 | 3174830 | GGTATCAGAATTCCTCAAGCAGGCCTGGTTTATTGAAAATG |
| 1920 | ANXA1 | 3174831 | GTCATCCAAAGGTGGTCCCGGATCAGCGGTGAGCCCCTATCCTACCTTCAATCCATCCTCGGATGTCGCTGCCTTGCATAAGGCCATAATG |
| 1921 | ANXA1 | 3174832 | GGATGAAGCAACCATCATTGACATTCTAACTAAGCGAAACAATGCACAGCGTCAACAGATCAAGCAGCATATC |
| 1922 | ANXA1 | 3174833 | CTTAACCATGGATTCGGAAGCACAGTTACCTAGTTCTTTAAGGTTCTAACCACTGTTTTCTCATTACATCTATGATTGGGATTGCAGTGTTTATCCACTTTGTTGCAATTTAATCATTTTATCAAATTTCCTATTTTTATACATTAGTCATCTTGGTGTATATTGTTTGCAGATGTGGTGCTCTGGGGACAAATTTTTAATTTGAACGTAAACATCGAGATTGCTGCTGTCAATAAAGAATATGGTC |
| 1923 | ANXA1 | 3174834 | CCCCTGGATGAAACACTGAAGAAAG |
| 1924 | ANXA1 | 3174835 | CCCTTACAGGTCACCTTGAGGAGGTTGTTTTAGCTCTGCTAAAAACTCCAGCGCAATTTGATGCTGATGAACTTCGTGCTGCCATGA |
| 1925 | ANXA1 | 3174836 | AGATACTCTAATTGAGATTTTGGCATCAAGAACTAACAAAGAAATCAGAGACATTAACAGGGTCTACAGAGA |
| 1926 | ANXA1 | 3174838 | TGAAGAGAGATCTGGCCAAAGACATAACCTCAGACACATCTGGAGATTTTCGGAACGCTTTGCTTTCTCT |
| 1927 | ANXA1 | 3174840 | GTGACCGATCTGAGGACTTTGGTGTGAATGAA |
| 1928 | ANXA1 | 3174845 | GGGACAGACGTAAACGTGTTCAATACCATCCT |
| 1929 | ANXA1 | 3174847 | CACCAAGTACAGTAAGCATGACATGAACAAAGTTCTGGACCTGGAGTTGAAAGGTGACAT |

TABLE 13-continued

Subtyping Target Sequences

| SEQ ID NO. | Gene | Affy Probeset ID | Sequence |
|---|---|---|---|
| 1930 | ANXA1 | 3174850 | TGAAGTGCGCCACAAGCAAACCAGCTT |
| 1931 | ANXA1 | 3174852 | GCTAGGTACTGCTCTGTAGTGGTTAGCATAGTTGCTGCCCCCTTTCTGCCATAGTCTAGTGTGA TATTTCGTTGGGTAATGATGAATACCTGGTGCCATGGAAGAGAAAAGTGGGACATATACTCC AGACTTTGGAAATCCAGGTAGCATTGCTGTCAGCTAAATTAACACCTGAAGTTTAAATAGAAA TGAGCCAGATGAGGGCAAGAGTGGAAGAGATGGGGATAAAGCAAGGGTGGTCCAAGAGGA AGAAGTAACCCACACACAGGCTTGAAGGCAAAAGGTAACATAACCTTCTCAAGACAGTAAGT ATAGAGTGATGGTGCACACTGGAAGAGATGGTAGAATTAGGCAGGATATTGTAAGCCTTGA AAAAGAATTAGGCAGGATATCGGAAGCCCTGATTAGATTCTATC |
| 1932 | ANXA1 | 3174853 | CGCCATAAGGCATTGATCAGGATTATGGTTTCCCGTTCTGAAATTGACATGAATGATATCAAA GCATTCTATCAGAAGATGTATGGTATCTCCCTTTGCCAAGCCATC |
| 1933 | ANXA1 | 3174856 | GATGAAACCAAAGGAGATTATGAGAAAATCCTGGTGGCTCTTTGTGGAGGAA |
| 1934 | ANXA1 | 3174857 | ACATTCCCTTGATGGTCTCAAGCTATGATCAGAAGACTTTAATTATATATTTTCATCCTATAAGC TTAAATAGGAAAGTTTCTTCAACAGGATTACAGTGTAGCTACCTACATGCTGAAAAATATAG |
| 1935 | DAPK1 | 3177901 | CAGAACCCGCAGCGCCGGCCTGGCAGGGCA |
| 1936 | DAPK1 | 3177902 | CGCCGCCAGCCCGCTTGCAGGGTCCCCATTGGCCGCCTGCCGGCCGCCCTCCGCCCAAAGG CGGCAAGGAGCCGAGA |
| 1937 | DAPK1 | 3177903 | TTCCCTCCGCGGAGGGGACTCGGCAACTCGCAGCGGCAGGGTCTGGGGCCGGCGCCTGGGA GGGATCTGCGCCCCCCACTCACTCCCTA |
| 1938 | DAPK1 | 3177904 | TAGTCTCCGGCGCTGGCGCCTATGGTCGGCCTCCGACAGCGCTCCGGAGGGACCG |
| 1939 | DAPK1 | 3177905 | CTGGGCGAGGGCTTCATTCTTCCGCGGCGTCCCT |
| 1940 | DAPK1 | 3177906 | GAGCGGTGGTGATGGTCTGGGAAGCGGAGCTGAAGTGCCCTGG |
| 1941 | DAPK1 | 3177907 | AGGAAAACGTGGATGATTACTACGACACCGGCGAGGAACTTGGCAG |
| 1942 | DAPK1 | 3177918 | CAGTTTGCGGTTGTGAAGAAATGCCGTGAGAAAAGCACCGGCCTCCAGTATGCCGCCAAATT CATCAAGAAAGGAGGACTAAGTCCAGCCGGCGGGGTGTGAGCCGCGAGGACATCGAGCG GGAGGTCAGCATCCTGAAGGAGATCCAGCACCCCAATGTCATCACCCTGCACGAGGTCTATG AGAACAAGACGGACGTCATCCTGATCTTGGA |
| 1943 | DAPK1 | 3177925 | CCTGAGAACATAATGCTTTTGGATAGAAATGTCCCCAAACCTCGGATCAAGATCATTGACTTT |
| 1944 | DAPK1 | 3177926 | CTCCTGAGATAGTCAACTATGAACCTCTTGGTCTTGAGGCAGATATGTG |
| 1945 | DAPK1 | 3177927 | GAGTATCGGGGTAATAACCTATATC |
| 1946 | DAPK1 | 3177928 | GAAACGTTAGCAAATGTATCCGCTGTCAACTACGAATTTGAGGATGAATACTTCAGTAATACC AGTGCCCTAGCCAAAGATTTC |
| 1947 | DAPK1 | 3177929 | TGACAATTCAAGATAGTTTGCAGCATCCCTGG |
| 1948 | DAPK1 | 3177930 | CCTAAAGATACACAACAGGCACTTAGTAGAAAAGCATCAGCAGTAAACATGGAGAAATTCAA GAAGTTTGCAGCCCGGAAAAAATG |
| 1949 | DAPK1 | 3177932 | AATCCGTTCGCTTGATATCACTGTGCCAAAGATTATCCAGGTCATTCCTGTCCAGAAGTAACAT GAGTGTTGCCAGAAGCGATGATACTCT |
| 1950 | DAPK1 | 3177933 | AGACTCCTTTGTGATGAAAGCCATCATCCATGCCATCAACGATGACAATGTCCCAGGCCTGCA GCACCTTCTGGGCTCATTATCCAACTATGATGTTAACCAACC |
| 1951 | DAPK1 | 3177936 | GGGTCCAATGCCGTCTACTGGGCTGCTCGGCATGGCCACGTCGATACCTTGAAATTTCTC |
| 1952 | DAPK1 | 3177938 | TCCACGTGGCAGCTCGCTATGGCCATGCTGACGTGGCTCAGTTACTGTGCAGCTTCGGCTCAA ATCCCAATATCCAGGACA |
| 1953 | DAPK1 | 3177940 | TGCTGCTTGGCACGGCTATTACTCTGTGGCCAAAGCCCTTTGTGAAGCCGGCTGTAACGTGAA CATCAAGAACCGAGAAGGAGAGACGCCCCTCCTGACAGCCTCTGCCAGGGGCTACCACGACA TCGTGGAGTGTCTGGCCGAACATGGAGCCGACCTTA |
| 1954 | DAPK1 | 3177942 | CTTCATCTGGCTGTAAGACGGTGTCAGATGGAGGTAATCAAGACTCTCCTCAGCCAAGGGTG TTTCGTCGATTATCAAGACAGGCACGGCAATACTCCCCTCCATGTGGCATGTAAAGATGGCAA CATGCCTATCGTGGTGGCCCTCTGTGAAGCAAACTGCAAT |

TABLE 13-continued

Subtyping Target Sequences

| SEQ ID NO. | Gene | Affy Probeset ID | Sequence |
|---|---|---|---|
| 1955 | DAPK1 | 3177943 | CAGTTCCCTGGGTTACCTTGGCACACAATTTGGGAACCATAGGCACAAACAAGGCTTATGGGCTTGTCCTGGTATTTTCACTAATTAGGATGTCTTCAATATCTGTCTTCCATGTCTTCCCTGGCTGTGTCTAAATTTGAACTATGGTGCAGATCTTGCTGGAACTCTGGACCTTGAGCCCTTGACTCCTGTCTCTTTCAGGCCAGCACAGCAGGAAACTTACTTAAGTTATCTTTGAAGTTGTATTTTGAAGCTCCTCTTTTAATTGCAAAGTACTTGGAAAGGTTCTGCCTGGCTG |
| 1956 | DAPK1 | 3177944 | TCCTTAACCTTGTGTCTCCGGAATGTCATCCTCAGCAACTGCGTGAGAAGAACGACCTTTGGCCTT |
| 1957 | DAPK1 | 3177947 | CCTCTCAGGGGTGACTTCAAGGACTGAGGCTTGCAGAGAGCACTGAGAGCTGGGTCGAGCACATATTATGAGGTGGTGTTCAATAAATACTTGCTGTCATCGTGTATGTTCATGGTGTAGA |
| 1958 | DAPK1 | 3177948 | TGGCTTGCTTCTCACACCTGCTATGCTTGTTTCTGCCTCAGACCCACGGAATTGGCGTATGGAACACACA |
| 1959 | DAPK1 | 3177949 | ACGGAAAGACGGCAGAAGATCTTGCTAGATCGGAACAGCACGAGCACGTAGCAGGTCTCCTTGCAAGACT |
| 1960 | DAPK1 | 3177950 | CTCTAGACAGCCAGGTTTTAGGAACAGTGGTCCCTGTCCTGTGGTTTACATGTCAGTCGGTATAAATGCATCAGCTCCCTATCTGTTTTCTTCTCTATTTGGACTTGGAAATCATTTAGCATGTTTGCAGTTGCCGTGCC |
| 1961 | DAPK1 | 3177952 | ACCGAGGACTCTTCATCCAGCAGCTCCGACCCACACAGAACCTGCAGCCAAGAATTAAGCTCAAGCTGTTTGGCCACTCGGGATCCGGGAAAACCACCCTTGTAGAATCTCTCAAGTGTGGGCTGCTGAGGAGCTTTTTCAGAAGGCGTCGGCCCA |
| 1962 | DAPK1 | 3177954 | TCTCAGTGAGCATCAACAACCTGTACCCAG |
| 1963 | DAPK1 | 3177955 | AGGAGCCGCAGCATGATGTTCGAGCCGGGTCTTACCAAAGGGATGCTGGAGGTGTTTGTGGCCCCGACCCACCACCCGCACTGCTCGGCCGATGACCAGTCCACCAAGGCCATCGACATCCAGAACGCTTA |
| 1964 | DAPK1 | 3177956 | CGATTTCAGCGTGTGGGAGTTCTCTGGAAATCCTGTGTATTTCTGCTGTTATGACTATTTTGCTGCAAATGATCCCACGTCAATCCATGTTGTTGTCTTTAGTCTAGAAGAGCCCTATGAGATCCAGCTGAACCAAGTGATTTTCTGGCTCAGTTTCCTGAAGTCCCTTGTCCCAGTTGAAGAACCCATA |
| 1965 | DAPK1 | 3177957 | CCTTGTGGCCTAGGAGATAGGCTTATCCTGTCGTTGGCCATGCTGGGGCCTTCTAGGGTCACAGTGCACAGCAGGCGTGGGCCTTCATCTCTGTGGCATGTTGCACTTGTACC |
| 1966 | DAPK1 | 3177958 | TGGCCACCCACGCTGACATCATGAATGTTCCTCGACCGGCTGGAGGCGAGTTTGGATATGACAAAGACACATCGTTGCTGAAAGAGA |
| 1967 | DAPK1 | 3177959 | AAGGACATGAAGGTACTTCGAAATCATCTGCAAGA |
| 1968 | DAPK1 | 3177960 | CGAGGAGGACCTCAGGCGCATTGCTCAGCAGC |
| 1969 | DAPK1 | 3177961 | CTCCTGACCGTGAAGCATTACCTGAGCCCCCAGCAGCTGCGGGAGCACCATGAGCCCGTCATGATCTACCAGCCACGGGACTTCTTCCGGGCACAGACTCTGAAGGAAACCTCACTGACCAACACCATGGGGGGTACAAGGAAAGCTTCAGCAGCATCATGTGCTTCGGGTGTCACGACGTCTACTCACAGGCCAGCCTCGGCATGGACATCCATGCATCAGACCTGAACCTCCTCACTCGGAGGAAACTGAGTCGCCTGCTGGACCCGCCCGACCCCCTGGGGAAGGACTGGTGCCTTCTCGCCATGAACTTAGGCCTCCCTGACCTCGTGGCAAAGTACAACACCAGTAACGGGGCTCCCAAGGATTCCTCCCCAGCCCCCTCCACGCCCTGCTGCGGGAATGGACCCACCTACCCTGAGAGCACAGTGGGCACCCTCATGTCCAAACTGA |
| 1970 | DAPK1 | 3177962 | TAGTGTACCTCCTCTCAGTGTTTTGGACTCCATCTCTCATCCTCCAGTACCTTGCTTCTTACTGATAATTTTGCTGGAATTCCTAACTTTTCAATGACATTTTTTTAACTACTATATTGATTGTCCTTTAAAAAAGAAAAGTGCATATTTATCCAAAATGTGTATTTCTTATACGCTTTTCTTTGTTATACCATTTCCTCAGCTTATCTCTTTTATATTTGTAGGAGAAACTCCCATGTATGGAATCCCACTGTATGATTTATAAACAGACAATATGTGAGTGCCTTTTGCAGAAGAGGGTGTGTTTGAAATCATCGGAGTCAGCCAGGAGCTGTCACCAAGGAAACGTACCTCTCTGTCCCTTGCTGTATGCTGATCATCGCCAGAGGTGCTTCACCCTGAGTTTTGTTTTGTATTGTTTTCTGACAGTTTTTCTGTTTTGTTTGGCAAGGAAAGGGGAGAAGGGAATCCTCCTCCAGGGTGATTTTATGATCAGTGTTGTTGCTCTAGGAAGACATTTTTCCGTTTGCTTTTGTTCCAATGTCAATGTGAACGTCCACATGAAACCTACACACTGTCATGCTTCATCATTCCCTCTCATCTCAGGTAGAAGGTTGACACAGTTGTAGGGTTACAGAGACCTATGTAAGAATTCAGAAGACCCCTGACTCATCATTTGTGGCAGTCCCTTATAATTGGTGCATA |
| 1971 | DAPK1 | 3178013 | AAGAAGTTGACACTCCGATTTTCCACATCATCTAACTAAAATGGATTTAAACTAACTTTCTCTAACTATTAAATCTTTCTTAGGTAAGTACAGTTGTATCCCAGCTCTAGAGTTAATGTGCTGGG |
| 1972 | DAPK1 | 3178023 | CGCTCTTGTTGCGTGTGTTCAAACAACCGGCACGGTC |
| 1973 | DAPK1 | 3178055 | TCGGTCTGTTGCCCAGGCGGGTGTGCA |

TABLE 13-continued

Subtyping Target Sequences

| SEQ ID NO. | Gene | Affy Probeset ID | Sequence |
|---|---|---|---|
| 1974 | DAPK1 | 3178057 | CCCGATCGGGAAACTCTGCTGTCAACTAAGCAAACTCTAAATTTAACATTTGGGGGACCCCCT<br>TGGAGAGTAGTTGAGAGCTATGTGCTCCCCTTTTCAGAAAAATGCTCTCAAATACTCAGTGCA<br>TAAGCCCACAGCCTTAGCAGGTTCCCAGACCTTAGGTCAGCAATCCTGTTCTAAGGCATACAT<br>CACGAGCAGCATTTTGATTTTCATCTGGGGAACTTATAGTTCATAAAGACCTACTGATCCATTA<br>AATTTCCACTTGATTTTGCCATTAGTAATCTCTTAAACAAGTCCAAGGAAGCCAGAGGAAGT<br>TATTTCTTGAATGCTTTTATACTAGTGCTTTCAAGAGTTCGTGTTGCTGACTCCAGTTTTTAAAA<br>TTATTATTCTCATCTTCTGCAATGCCTCGAGGCATGTTTTTAGCTGAATA |
| 1975 | TPM2 | 3204722 | CCCAGCCAGGCTATGGTTGCCACCCCAACCCAATAAAACTGATGT |
| 1976 | TPM2 | 3204723 | GCCAAGGAGGAGAACGTCGAGATTCACCAGACCTTGGACCAG |
| 1977 | TPM2 | 3204724 | CTCTATGACCCCAAGGCCTTGAGTGAGGCATCCACGTCCGTCCTGTTCCCCTCATCCTAGTCAG<br>TCCATCTGTTTGTCCCTGCCAAGGGGCCCTGAGGTCCGTGAATGCATGTGTCTTCCTTGACCCA<br>CTCCATGTCTATATGTCACCTTCC |
| 1978 | TPM2 | 3204725 | ACGGAGCACTGGTTCACTCCTGACACCCTGGCACTTACTGACACCCCCAGCCCCTGCACTGAG<br>CCCACCCACAAAACACCATGGCCCACGCTGAAACCCCTCTGCACAGGCACTCCCTGGCTGTCG<br>CTCTCTGATTCACCACTGCATGTGGGCACGTGTGGCCCCATCAAACCATGACCGCCTCTGGTG<br>CCAATCCCTGACCTCAGAGCACTTAGCTGGGGTTCCAGGATCAAACAGAGTGACTGGAAAGG<br>AAGTAGGGTGGTGAGGTGCAGGACAGGGGCAAGAAGGTTGCAAAAGGTCTGGAATGGAGC<br>TTGGAAAAATGTTGGATATCAGCAACATGGGCTTTCACTG |
| 1979 | TPM2 | 3204726 | TCCTTTGCTGCTTAATAAATTCTGAACTTGG |
| 1980 | TPM2 | 3204727 | CCACGCCAGCGTGGCCACCTCAGCTCTCTTCTCTCCTCTCCTTTCCATTCTCTCTATGGGGAGG<br>GGAGCAGGCAGGAGGAGCAGAAATTGCCAACATTGCA |
| 1981 | TPM2 | 3204728 | AGGAACTGGACAACGCACTCAATGACATCACCT |
| 1982 | TPM2 | 3204729 | GACCCGAGCAGAGTTTGCCGAGAGGTCTG |
| 1983 | TPM2 | 3204730 | GAAGAGGAGATCAAACTGTTGGAGGA |
| 1984 | TPM2 | 3204731 | CAAGATGACCAGGAGCCTACGGGGTACAATGGAGAAATGAAGGATCTGTGGTAGCGCTGTA<br>CTGATGGCGTGTGTGTGTCCC |
| 1985 | TPM2 | 3204732 | TGAAAATTGTTACCAACAACTTGAA |
| 1986 | TPM2 | 3204733 | TTTCTGGGCAATGGCGCCTTCTCTCAGCTCACCTTCCCTCCGTCTCAGCACCGCAGGCTGCTCT<br>TTCTCAGCTGCTGGGGATCAGGAAGGGCCTGGGGCTTCTGAGCCCTGCCTGCTGTCACTCTCA<br>CAACTTTGCTCTTCTCTTCTCCTCCACCCGTCCCTGCTGTGCCATCTCCACTGTCTGGCTTCG<br>CTGTGCCCTCACA |
| 1987 | TPM2 | 3204734 | TGGAGGAGGAACTTCGAACCATGGACCAGGCC |
| 1988 | TPM2 | 3204735 | GGGTGACAAGTGAGCCCATTGGCCCTGGGGCCTTCCACACAGTGGGAAGGTAGCATCCTAG<br>GCTTGGGGC |
| 1989 | TPM2 | 3204736 | TGGCCAGGAAGCTGGTGATCCTGGAAGGAGAGCTGGAGCGCTCGGAGGAGAGGGCTGA |
| 1990 | TPM2 | 3204737 | GGAGGCCAAGCACATCGCTGAGGATTCAG |
| 1991 | TPM2 | 3204738 | AGAAGGCGGCTGATGAGAGCGAGAG |
| 1992 | TPM2 | 3204739 | GATGTGGCCTCCCTGAACCGCCGCATTCAGCTGGTTGA |
| 1993 | TPM2 | 3204740 | AGAAACTGGAGCAGGCCGAGAAGAAGGCCACT |
| 1994 | TPM2 | 3204741 | GATGAGGTGGAAAAGTATTCTGAATCC |
| 1995 | TPM2 | 3204742 | ATCGACCGCGCCGAGCAGGCCGAAGCCGACAAGAAGCAAGCTGAGGACCGCTGCAAGCAG |
| 1996 | TPM2 | 3204743 | TTCAGCATAAAGTTGGCCCACTGGGAAAGAGAGGAGCGTCCGCGGGGAGCGGGGGAGAAG<br>AGGGAAGGCGCGCGGAGGGGAGTGGGGCCAGGCGGAGCCAGGGGCGGGGAGCGGAGGG<br>GCTCGGGACGCGTCCGGGTGGGAGCGGGGGCGGGAACGCGCGGTGACCAGCCTGGCCGC<br>AGCCGCGTGGAAAATATGCGGGGCACGTGGGGGCGGGGCGGGGAGCTGGGTCCTGAGCC<br>GCCGGGTGCTCGCAGGAAGGGCCTGGCTCCAGGGGCAGGGGCTGGGAGGGGAGGCGAGG<br>GGATGAGAGGTCAGGCCGGTCCTGGGGGCAGCAAGCCGGCCACACTCCCCACCGCGACCG<br>GGGCTCTGGGCTCGCTTCCTGCTTCAGTTTCCCCAAGCTCCCGATGAGACTCCGCTACTACCAC<br>CACGTCGATAACGCAAACCTAGAGGGACTCAGGGTAAACTGAGGCACTCAAACTGCCGAGG<br>AGCTCCGCCTCCCGAGAGACATTTAA |

TABLE 13-continued

Subtyping Target Sequences

| SEQ ID NO. | Gene | Affy Probeset ID | Sequence |
|---|---|---|---|
| 1997 | ASPN | 3214846 | TCATGTCTTAGAGCCCGTCTTTATGTTTAAAACTAATTTCTTAAAATAAAGCCTTCAGTAAATGTTCATTACCAACTTGATAAATGCTACTCATAAGAGCTGGTTTGGGGCTATAGCATATGCTTTTTTTTTTTTAATTATTACCTGATTTAAAAATCTCTGTAAAAACGTGTAGTGTTTCATAAAATCTGTAACTCGCATTTTAATGATCCGCTATTATAAGCTTTTAATAGCATGAAAATTGTTAGGCTATATAACATTGCCACTTCAACTCTAAGGAATATTTTGAGATATCCCTTTGGAAGACCTTGCTTGGAAGAGCCTGGACACTAACAATTCTACACCAAATTGTCTCTTCAAATACGTATGGACTGGATAACTCTGAGAA |
| 1998 | ASPN | 3214847 | CTAATTCAATTGCAAGAGTGGGAGTAAATGACTTCTGTCCAACAGTGCCAAAGATGAAGAAATCTTTATACAGTGCAATAAGTTTATTCAACAACCCGGTGAAATACTGGGAAATGCAACCTGCAACATTTCGTTGTGTTTTGAGCAGAATGAGCGTTCAGCTTGGGAAC |
| 1999 | ASPN | 3214850 | ATCACAGATATCGAAAATGGGAGTCTTGCTAACATACCACGTGTGAGAGAAATACATTTGGAAAACAATAAACTAAAAAAAATCCCTTCAGGATTACCAGAGTTGAAATACCTCCAG |
| 2000 | ASPN | 3214856 | TAATAATGGGATAGAGCCAGGGGCATTTGAAGGGGTGACGGTGTTCCATATCAGAATTGCAGAAGCAAAACTGACCTCAGTTCCTA |
| 2001 | ASPN | 3214857 | CCTGAACAACAACAAGCTAACGAAGATTCACCCAAAAGCCTTTCTAACCACAAAGAAGTTGCGAAGGCTGTATCTGTCCCACAATCAACTAAGTGAAATACCACTTAATCTTCCCAAATCATTAGCAGAACTC |
| 2002 | ASPN | 3214859 | ATTCCATTTGATACTCGAATGCTTGATC |
| 2003 | ASPN | 3214862 | TTTGATCTGTTTCCAATGTGTCCATTTGGATGTCAGTGCTATTCACGAGTTGTACATTGC |
| 2004 | ASPN | 3214863 | TGTGCTCCTATTATTCCTGGCTTTGTGCTCTGCCAAACCCTTCTTTAGCCCTTCACACATCGCACTGAAGAATATGATGCTGAAGGATATGG |
| 2005 | ASPN | 3214866 | TGGACTAATCTGTGGGAGCAGTTTATTCCAGTATCACCCAGGGTGCAGCCACACCAGGACTGTGTTGAAGGGTGTTTTTTTCTTTTAAATGTAATACCTCCTCATCTTTTCTTCTTACACAGTGTCTGAGAACATTTACATTATAGATAAGTAGTACATGGTGGATAACTTCTACTTTTAGGAGGACTACTCTCTTC |
| 2006 | FBP1 | 3215572 | ATGCTTGGCACTCCCTAACCAAATGCTGTCTCCATAATGCCACTGGTGTTAAGATATATTTTGAGTGGATGGAGGAGAAATAAACTTATTCCTC |
| 2007 | FBP1 | 3215573 | GCCTGCATCCGGAGAATTGCCTCTACCTGGACCTTTTGTCTCACACAGCAGTACCCTGACCTGCTGTGCACCTTACATTCCTAGAGAGCAGAAATAAAAAGCATGACTATTTCCACCA |
| 2008 | FBP1 | 3215574 | TCCTGAAGGTGTATGAGAAGCACTCTGCCCAGT |
| 2009 | FBP1 | 3215575 | AAGGAGGCCGTGTTAGACGTCATTCCCACAGACATTCACCAGAGGGCGCCGGTGATCTTGGGATCCCCCGACGA |
| 2010 | FBP1 | 3215577 | ATTCAGCTCCTTATGGGGCCCGGTATGTGGGCTCCATGGTGGCTGATGTTCATCGCACTCTGGTCTACGAGGGATATTTCTGTACCCCGCTAACA |
| 2011 | FBP1 | 3215579 | CTTAACGAGGGCTACGCCAGGGACTTTGACCCTGCCGTCACTGAGTACATC |
| 2012 | FBP1 | 3215584 | CTGAGAAGGATGCTCTGCAACCAGGCCGGAACCTGGTGGCAGCCGGCTACGCACTGTATGGCAGTGCCACCATGCTGGTCCTTGCCATGGACTGTGGGGTCAACTGCTTCATGCT |
| 2013 | FBP1 | 3215586 | GTGGTCTGTTTTGATCCCCTTGATGGATCTTCCAACATCGATTGCCTTGTGTCCGTTGGAACCATTTTTG |
| 2014 | FBP1 | 3215587 | CTGGTTCTACCAACGTGACAGGTGATCAAGTTAAGAAGCTGGACGTCCTCTCCAACGACCTGGTTATGAACATGTTAAAGTCATCCTTTGCCACGTGTGTTCTCGTGTCAGAAGA |
| 2015 | FBP1 | 3215590 | AGGCGCCCTTCGACACGGACGTCAACACCCTGACCCGCTTCGTCATGGAGGAGGGCAGGAAGGCCCGCGGCACGGGCGAGTTGACCCAGCTGCTCAACTCGCTCTGCACAGCAGTCAAAGCCATCTCTTCGGCGGTGCGCAAGGCG |
| 2016 | FBP1 | 3215591 | CCCCGCACCTGCCGCTTGCACCTGC |
| 2017 | FBP1 | 3215592 | TGCGGCCAGTGCCTACTGCCCTCTCTTGCCGCCCGCACCT |
| 2018 | TNC | 3222171 | GTAAGTATTGTTACCACACATGGGCTAAGATCCCCAGAGGCAGACTGCCTGAGTTCAATTCTTGGCTCCACCATTCCCAAGTTCCCTAACCTCTCTATGCCTCAGTTTCCTCTTCTGTAAAGTAGGGACACTCATACTTCTCATTTCAGAAACATTTTTTGTGAAGAATAAATTATGTTATCCATTTGAGGCCCTTAGAATGGTACCCGGTGTATATTAAGTGC |
| 2019 | TNC | 3222172 | TTCACCAAAGCCAATCATTTGAACAAAGCGGGGAATGTTGGGATAGGAAAGGTAAGTAGGGATAGTGGTCAAGTGGGAGGG |

TABLE 13-continued

Subtyping Target Sequences

| SEQ ID NO. | Gene | Affy Probeset ID | Sequence |
|---|---|---|---|
| 2020 | TNC | 3222173 | AAACATTTCTGGACAGTACCTGATTGTA |
| 2021 | TNC | 3222174 | TACATTTCATACAACAGAAACCAGAAAAGCAATACTGTTTCCATTTTAAGGAT |
| 2022 | TNC | 3222175 | CCAGTGACAACATCGCAATAGTTTTTTACTTCTCTTAGGTGGCTCTGGGAATGGGAGAGGGGTAGGATGTACAGGGGTAGTTTGTTTTAGAACCAGCCGTATTTTACATGAAGC |
| 2023 | TNC | 3222176 | AACCAGCCCAACCATCGGTCCACACCTGGGCATTTGGTGAGAGTCAAAGCTGACCATGGATCCCTGGGGCCAACGGCAACAGCATGGGCCTCACCTCCTCTGTGATTTCTTTCTTTGCACCAAAGACATCAGTCTCCAAC |
| 2024 | TNC | 3222177 | TTAACTGGTTCCACTGGAAGGGCCACGAACACTCAATCCAGTTTGCTGAGATGAAGCTGAGACCAAGCAACTTCAGAAATCTTGAAGGCAGGCGCAAACGGG |
| 2025 | TNC | 3222181 | CAGATTCAGCCATCACCAACTGTGCTCTGTCCTACAAAGGGGCTTTCTGGTACAGGAACTGTCACCGTGTCAACCTGATGGGAGATATGGGACAATAACC |
| 2026 | TNC | 3222183 | ACAGCCCAGGGGCAGTACGAGCTCCGGGTGGACCTGCGGGACCATGGGGAGACAGCCTTTGCTGTCTATGACAAGTTCAGCGTGGGAGATGCCAAGACT |
| 2027 | TNC | 3222186 | CCAAGGACTGCTCCCAAGCAATGCTGAATGGAGACACGACCTCTGGCCTCTACACCATTTATCTGAATGGTGATAAGGCTGAGGCGCTGGAAGTCTTCTGTGA |
| 2028 | TNC | 3222187 | TGGGTCCAGATACCACCTCCTACAGCCTGGCAGACCTGAGCCCATCCACCCACTACACAGCCAAGATCCAGGCACTCAATGGGCCCCTGAGGAGCAATATGATCCAGAC |
| 2029 | TNC | 3222188 | TCCAAGAGACTTGACTGCTACTGAGGTTCAGTCGGAAACTGCCCTCCTTACCTGGCGACCCCCCCGGGCATCAGTCACCGGTTACCTGC |
| 2030 | TNC | 3222189 | CTGGCCCTAAACCTAGTATTTAATGATCCACGTTCCAGGCAGGAAAATATTTTTGAAGAGGCATATTTTTTAGGCAATTTTTCCTAGATGTTTGTTAGGTTTCTATACATTGAGAGCTTTTTACAAACTATAGCAAGCAGGGAAAC |
| 2031 | TNC | 3222192 | GCCACTGTGGACAGTTATGTCATCTCCTACACAGG |
| 2032 | TNC | 3222194 | CTGTGGACGGAACCAAGACTCAGACCAGGCTGGTGAAACTCATACCTGGCGTGGAGTACCTTGTCAGCATCATCGCCATGAAGGGCTTT |
| 2033 | TNC | 3222195 | CATCACTGAAAATTCGGCTACTGTCAGCTGGAGGGCACCCACAGCCCAAGTGGAGAGCTTCCGGATTACCTATGTGCCCATTACAGGA |
| 2034 | TNC | 3222198 | CGAACCGGAAGTTGACAACCTTCTGGTTTCAGATGCCACCCCAGACGGTTTCCGTCTGTCCTGGACAGCTGATGAAGGGGTCTTCGACAATTTTGTTCTCAAAATACAGAGATACCAAAAAGCAGTCTGAGCCACTGGAAATAACCCTACTTGCCCCCGAACGTACCAGGGACATAACAGGTCTCAGAGAGGCTACTGAATACGAAATTGAACTCTATGGAATAAGCAAAGGAAGGCGATCCCAGACAGTCAGTGC |
| 2035 | TNC | 3222205 | CGGGTTCACAGTTTCCTGGATGGCATCGGAGAATGCCTTTGACAGCTTTCTAGTAACGGTGGTGGATTCTGGGAAGCTGCTGGACCCCCAGGAATTCACACTTTCAGGAACCCAGAGGAAGCTGGAGCTTAGAGGCCTCATAACTGGCATTGGCTATG |
| 2036 | TNC | 3222207 | CCACAGTTGGGCACGCTAATCTTTAGCAATATTACTCCAAAAAGCTTCAACATGTCATGGACCACTCAAGCTGGGCTTTTTGCAAAGATTGTTATCAATGTGAGTGACGCTCACTCACTGCATGAGTCCCAGCAATTCACAGTCTCAGGAGATGCAAAGCAAGCTC |
| 2037 | TNC | 3222208 | GTGTCTCGCAGCTCTGTCATCACCAACCTCAAAGCTTCTTCCTAATTACACTGCCCACCTTCATGGGCTGATTGGCGGGCAGCGTGCTCAGACCCTGATGGTC |
| 2038 | TNC | 3222209 | TCACTGTCTCAAACATGACCTGGGGCAGTGTGTCCATCTCGTGGGAAGCTCAGGAGTCTGCCTTTGATAGCTTTCTTATAGAAGTTAGTAATTCCGATCACCC |
| 2039 | TNC | 3222210 | GTTTCTGACATAACTCCCGAGAGCTTCAATCTCTCCTGGATGGCTACCGATGGGATCTTCGAGACCTTTACCATTGAAATTATTGATTCCAATAGGTTGCTGGAGACTGTGGAATATAATATCTCTGGTGCTGAACGAACTGCCCATATCTCAGGGCTACCCCCTAGTACTGATTTATTGTCTACCTCTCTGGACTTGCTCCCAGCATCCGGACCAAAACCATCAGTG |
| 2040 | TNC | 3222212 | CACAGCTGGAGATTTAGCCGTGTCTGAGGTTGGCTGGGATGGCCTCAGACTCAACTGGACCGCAGCTGACAATGCCTATGAGCACTTTGTCATTCAGGTGCAGGAGGTCAACAAAGTGGAGGCAGCCCAGAACCTCACGTTGCCTGGCAGCCTCAGGGCTGTGGACATCCCGGGCCTCGAGGCTGCCACGCCTTATAGAGTCTCCATCTATGGGGTGATCCGGGGCTATAGAACACCAGT |

TABLE 13-continued

Subtyping Target Sequences

| SEQ ID NO. | Gene | Affy Probeset ID | Sequence |
|---|---|---|---|
| 2041 | TNC | 3222214 | ACCGAGGTTAGCTGGGATGCTCTCAGACTGAACTGGACCACGCCAGATGGAACCTATGACCAGTTTACTATTCAGGTCCAGGAGGCTGACCAGGTGGAAGAGGCTCACAATCTCACGGTTCCTGGCAGCCTGCGTTCCATGGAAATCCCAGGCCTCAGGGCTGGCACTCCTTACACAGTCA |
| 2042 | TNC | 3222215 | GAAGGGGCCTATGAGTACTTTTTCATTCAGGTGCAGGAGGCTGACACAGTAGAGGCAGCCCAGAACCTCACCGTCCCAGGAGGACTGAGGTCCACAGACCTGCCTGGGCTCAAAGCAGCCACTCATTATACCATCACCATCCGCGGGGTC |
| 2043 | TNC | 3222216 | GCTGACCAGGCCTATGAGCACTTTATCATTCAGGTGCAGGAGGCCAACAAGGTGGAGGCAGCTCGGAACCTCACCGTGCCTGGCAGCCTTCGGGCTGTGGACATACCGGGCCTCAAGGCTGCTACGCCTTATACAGTCTCCATCTATGGGGTGATCCAGGGCTATAGAACACCAGT |
| 2044 | TNC | 3222219 | CTGCTCTGGAAGACACCGTTGGCCAAATTTGACCGCTACCGCCTCAATTACAGTCTCCCCACAGGCCAGTGGGTGGGAGTGCAGCTTCCAAGAAACACCACTTCCTATGTCCTGAGAGGCCTGGAACCAGGACAGGAGTACAATGTCCTCCTGACAGCCGAGAAAGGCAGACACAAGAGCAAGCCCGCACGTGTGAAGGCATCCA |
| 2045 | TNC | 3222220 | CTGAGGCCGGGAACTGAATATGGGATTGGAGTTTCTGCTGTGAAGGAAGACAAGGAGAGCAATCCAGCGACCATCAACGCAGCCAC |
| 2046 | TNC | 3222221 | CCAGACAGATAACAGCATCACCCTGGAATGGAGGAATGGCAAGGCAGCTATTGACAGTTACAGAATTAAGTATGCCCCCATCTCTGGAGGGGACCACGCTGAGGTTGATGTTCCAAAGAGCCAACAAGCCACAACCAAAA |
| 2047 | TNC | 3222222 | CCCAGCCAGATCGAGGTGAAAGATGTCACAGACACCACTGCCTTGATCACCTGGTTCAAGCCCCTGGCTGAGATCGATGGCATTGAGCTGACCTACGGCATCAAAGACGTGCCAGGAGACCGTACCACCATCGATCTCACAGAGGACGAGAACCAGTACTCCATCGGGAACCTGAAGCCTG |
| 2048 | TNC | 3222225 | AGGCCAGAGACCTCTTACCGGCAAACTGGTCTAGCTCCTGGGCAAGAGTATGAGATATCTCTGCACATAGTGAAAAACAATACCCG |
| 2049 | TNC | 3222226 | GATCCTCTAGACATTGCTTTTGAAA |
| 2050 | TNC | 3222227 | AATTCAAGTCCATCAAGGAGACATCTGT |
| 2051 | TNC | 3222228 | TGAGATGCGGGTCACAGAGTACCTTGTCGTGTACACGCCCACCCACGAGGGTGGTCTGGAAATGCAGTTCCGTGTGCCTGGGGACCAGACGTCCACCATCATCCAGGAGCTGGAGCCTGGTGTGGAGTACTTTATCCGTGTATTTGCCATCCTGGAGAACAAGAAGAGCATTCCTGTCAGCGCCA |
| 2052 | TNC | 3222229 | TTATGGGCAAAGACTGCAAGGAGCAAAGATGTCCCAGTGACTGTCATGGCCAGGGCCGCTGCGTGGACGGCCAGTGCATCTGCCACGAGGGCTTCACAGGCCTGGACTGTGGCCAGCACTCCTGCCCCAGTGACTGCAACAACTTAGGACAATGCGTCTCGGGCC |
| 2053 | TNC | 3222230 | TTGCTACAACCGTGGACGATGCGTGGAGAATGAGTGCGTGTGTGATGAGGGTTTCACGGGCGAAGACTGCAGTGAGCTCATCTGCCCCAATGACTGCTTCGACCGGGGCCGCTGCATCAATGGCACCTGCTACTGCGAAGAAGGCTTCACAGGTGAAGACTGCGGGAAACCCACCTGCCCACATGCCTGCCACACCCAGGGCCGGTGTGAGGAGGGGCAGTGTGTATGTGATGAGGGCTTTGCCGGTGTGGACTGCAGCGAGAAGAGGTGTCCTGCTGACTGTCACAATCGTGGCCGCTGTGTAGACGGGCGGTGTGAGTGTGATGATGGTTTCACTGGAGCTGACTGTGGGGAGCTCAAGTGTCCCAATGGCTGCAGTGGCCATGGCCGCTGTGTCAATGGGCAGTGTGTGTGATGAGGGCTATACTGGGGAGGACTGCAGCCAGCTACGGTGCCCCAATGACTGTCACAGTCGGGGCCGCTGTGTCGAGGGCAAATGTGTATGTGAGCAAGGCTTCAAGGGCTATGACTGCAGTGACATGAGCTGCCCTAATGACTGTCA |
| 2054 | TNC | 3222231 | CTGTGTCTGCGAACCTGGCTGGAAAGGCCCCAACTGCTCTGAGCCCGAATGTCCAGGCAACTGTCACCTTCGAGGCCGGTGCATTGATGGGCAGTGCATCTGTGACGACGGCTTCACGGGCGAGGACTGCAGCCAGCTGGCTTGCCCCAGCGACTGCAATGACCAGGGCAAGTGCGTAAATGGAGTCTGCATCTGTTTCGAAGGCTACGCCGGGGCTGACTGCAGCCGTGAAATCTGCCCAGTGCCCTGCAGTGAGGAGCACGGCACATGTGTAGATGGCTTGTGTGTGTGCCACGATGGCTTTGCAGGCGATGAC |
| 2055 | TNC | 3222234 | TCCTTGCCCTCGCTACCGAAGGTGGGGTCCTCAAGAAAGTCATCCGGCACAAGCGACAGAGTGGGGTGAACGCCACCCTGCCAGAAGAGAACCAGCCAGTGGTGTTTAACCACGTTTACAACATCAAGCTGCCAGTGGGATCCCAGTGTTCGGTGGATCTGGAGTCAGCCAGTGGGGAGAAAGACCTGGCACCGCCTTCAGAGCCCAGCGAAAGCTTTCAGGAGCACACA |
| 2056 | TNC | 3222235 | ATTCTGCTGAAAGTGAGATACCCTAGAGCCCTAGAGCC |
| 2057 | TNC | 3222248 | TTTCTATAGACACCTAGCTGTGCTTTCTTACAAGAAAACATATCCACTGGACCAAAG |
| 2058 | TNC | 3222253 | AACCGCCGCAGCTCCACACTCCAGGTACTTCTTCAAGGACCTAGGTCTCTCGCCCATCGGAAA |
| 2059 | TNC | 3222254 | CCCCGCCTCCGTGGGCACAAAGGCAGCGCTGCTGGGGAACTCGGGGGAACGCGCA |

TABLE 13-continued

Subtyping Target Sequences

| SEQ ID NO. | Gene | Affy Probeset ID | Sequence |
|---|---|---|---|
| 2060 | TNC | 3222255 | CGAGGCGTCCCATTACAGAGGAAGGAGCTCGCTATATAAGCCAGCCAAAGTTGGCTGCACCG GCCACAGCCTGCCTACTGT |
| 2061 | AKR1C2 | 3232993 | GGAACTGATCCTCAGACAAGCCAGGACTCAAGTACAAGCCCATCTACAACCAGATGAGCCCTT AGGGCCACT |
| 2062 | AKR1C2 | 3232994 | TTGTTCAGTATGTTGTGCTTTAATT |
| 2063 | AKR1C2 | 3232998 | GTAAGAAACGGTTGAACTGGATGCAATTTTTATCACAGCTTGTGTAAGACTGCCTCTGTCCCT CCTCTCACATGCCATTGGTTAACCAGCAGACAGTGTGCTCAGGGGCGTTGCCAGCTCATTGCTC |
| 2064 | AKR1C2 | 3233005 | GTTGGACTGGCCATCCGAAGCAAGATTGCAGATGGCAGTGTGAAGAGAGAAGACATATTCTA CACTTCA |
| 2065 | AKR1C2 | 3233006 | GCAATTCCCATCGACCAGAGTTGGTCCGACCA |
| 2066 | AKR1C2 | 3233007 | CCAGGTGAGGAAGTGATCCCAAAAGATGAAAATGGAAAAATACTATTTGACACAGTGGATCT CTGTGCCACATG |
| 2067 | AKR1C2 | 3233012 | TGGATTTCTGCAAGTCAAAAGACAT |
| 2068 | AKR1C2 | 3233013 | GAGGACCCAGTCCTTTGTGCCTTGGCAAAAAAGCACAAGCGAACCCCAGCCCTGATTGCCCT GCGCTACCAGCTACAGCGTGGGGTTGTGGTCCTGGCCAAGAGCTACAATGAGCAGCGCATCA GACAGAACGTG |
| 2069 | AKR1C2 | 3233018 | TAGATGGCCTAAACAGAAATGTGCG |
| 2070 | AKR1C2 | 3233020 | TTGCTGGCCCCCCTAATTATCCATTT |
| 2071 | AKR1C2 | 3233063 | GTTGGACTGGCCATCCGAAGCAAGATTGCAGATGGCAGTGTGAAGAGAGAAGACATATTCTA CACTTCA |
| 2072 | AKR1C2 | 3233074 | GAGGACCCAGTCCTTTGTGCCTTGGCAAAAAAGCACAAGCGAACCCCAGCCCTGATTGCCCT GCGCTACCAGCTGCAGCGTGGGGTTGTGGTCCTGGCCAAGAGCTACAATGAGCAGCGCATCA GACAGAACGTG |
| 2073 | AKR1C2 | 3233086 | GATTCACATCTTGGAGTAGTCACAACTTGCAGTGCCCTGATTGCTTCTATTTGCTT |
| 2074 | AKR1C2 | 3233127 | GAGAGAAGACATATTCTACACTTCAA |
| 2075 | AKR1C2 | 3233133 | ACAGTGCTCTGGGAACCCAACGACAT |
| 2076 | GATA3 | 3234279 | CCGGGGTGCCCATTGCGCAGAGCGTGGCCTGGAGACCCGCGAGCCGGGGAAGGTCGCCGTG GAGTCCCGACCAGAGGCCGGGGTTGGGGTCGGTGCAGACCGAGGGCTGGTTTCCTTGACTG TGGGAGAAACGCCGGGAGCCGG |
| 2077 | GATA3 | 3234281 | CTGGCGCCGTCTTGATACTTTCAGAAAGAATGCATTCCCTGTAAAAAAAAAAAAAAAATACTG AGAGAGGGAGAGAGAGAGAAGAAGAGAGAGACGGAGGGAGAGCGAGACAGAGCG AGCAACGCAATCTGACCGAGCAGGTCGTACGCCGCCG |
| 2078 | GATA3 | 3234282 | GTGACCCGAGGAGGGACTCCGCCTCCGAGCGGCTGAGGACCCCGGTGCAGAGGAGCCTGGC TCGCAGAATTGCAGAGTCGTCGCCCCTTTTTACAACCTGGTCCCGTTTTATTCTGCCGTACCCA GTTTTTGGATTTTTGTCTTCCCCTTCTTCTCTTTGCTAAACGACCCCTCCAAGATAATTTTTAAAA AACCTTCTCCTTTGCTCACCTTTGCTTCCCAGCCTTCCCATCCCCCCACCGAAAGCAAATCATTC AACG |
| 2079 | GATA3 | 3234283 | CGAGAGGGCGCGAGCACAGCCGAGG |
| 2080 | GATA3 | 3234284 | GAGGTGACGGCGGACCAGCCGCGCTGGGTGAGCCACCACCACCCCGCCGTGCTCAACGGGC AGCACCCGGACACGCACCACCCGGG |
| 2081 | GATA3 | 3234285 | ATGTGCTTTTTAACATCGACGGTCAAGGCAACCACGTCCCGCCCTACTACGGAAACTCGGTCA GGGCCACGGTGCAGAGGTACCCTCCGACCCACCA |
| 2082 | GATA3 | 3234286 | CCTACCCTGGCTGGACGGCGGCAAAGCCCTGGGCAGCCACCACACCGCCTCCCCCTGGAATC TCAGCCCCTTCTCCAAGACGTCCATCCACCACGGCTCCCCGGGGCCCCTCTCCGTCTACCCCCC GGCCTCGTCCTCCTCCTTGTCGGGGGGCCACGCCAGCCCGCACCTCTTCACCTTCCCGCCCACC CCGCCGAAGGACGTCTCCCCGGACCCATCGCTGTCCACCCCAGGCTCGGCCGGCTCGGCCCG GCAGGACGAGAAAGAGTGCCTCAAGTACCAGGTGCCCCTGCCCGACAGCATGAAGCTGGAG TCGTCCCACTCCCGTGGCAGCATGACCGCCCTGGGTGGAGCCTCCTCGTCGACCCACCACCCC ATCACCACCTACCCGCCCTACGTGCCCGAGTACAGCTCCGGACTCTTCCCCCCCAGCAGCCTGC TGGGCGGCTCCCCCACCGGCTTCGGATGCAAGTCCAGG |

TABLE 13-continued

Subtyping Target Sequences

| SEQ ID NO. | Gene | Affy Probeset ID | Sequence |
|---|---|---|---|
| 2083 | GATA3 | 3234291 | AGTGTGTGAACTGTGGGGCAACCTCGACCCCACTGTGGCGGCGAGATGGCACGGGACACTA CCTGTGCAACGCCTGCGGGCTCTATCACAAAATGAACGGACAGAACCGGCCCCTCA |
| 2084 | GATA3 | 3234293 | AGAGCAGGGACGTCCTGTGCGAACTGTCAGACCACCACAACCACACTCTGGAGGAG |
| 2085 | GATA3 | 3234298 | AGGCATCCAGACCAGAAACCGAAAAATGTCTAGCAAATCCAAAAAGTGCAAAAAAGTGCATG ACTCACTGGAGGACTTCCCCAAGAACAGCTCGTTTAACCCGGCCGCCCTCTCCAGACACATGT CCTCCCTGAGCCACATCTCGCCCTTCAGCCACTCCAGCCACATGCTGACCACGCCCACGCCGAT GCACCCGCCATCCAGCCTGTCC |
| 2086 | GATA3 | 3234299 | AGCCCTGCTCGATGCTCACAGGGCCCCCAGCGAGAGTCCCTGCAGTCCCTTTCGACTTGCATT TTTGCAGG |
| 2087 | GATA3 | 3234300 | GTGTCTGTGTTCCAACCACTGAATCTGGACCCCATCTGTGAATAAGCCATTCTGACTCATATCC CCTATTTAACAGGGTCTCTAGTGCTGTGAAAAAAAAAATGCTGAACATTGCATATAACTTATA TTGTAAGAAATACTGTACAATGACTTTATTGCATCTGGGTAGCTGTAA |
| 2088 | GATA3 | 3234301 | AAGAAGAAACTAGGTCTGATATTCAAATGGACAAACTGCCAGTTTTGTTTCCTTTCACTGGCC ACAGTTGT |
| 2089 | GATA3 | 3234302 | GTTCAAAGCTGTTGGCCTCTGCAAAGGAAATACCAGTTCTGGGCAATCAGTGTTACCGTTCAC CAGTTGCCGTTGAGGGTTTCAGAGAGCCTTTTTCTAGGCCTACATG |
| 2090 | GATA3 | 3234303 | TAGCTTCTAAGAGTCCGGCGGCATCTGTCTTGTCCCTATTCCTGCAGCCTGTGCTGAGGGTAG CAGTGTATGAGCTACCAGCGTGCATGTCAGCGACCCTGGCCCGACAGGCCACGTCCTGCAAT CGGCCCGGCTGCCTCTTCGCCCTGTCGTGTTCTGTGTTAGTGATCACTGC |
| 2091 | VIM | 3236965 | GCTAACAAAAAGTCCGCACATTCGAGCAAAGACAGGCTTTAGCGAGTTATTAAA |
| 2092 | VIM | 3236966 | GGCCCGACCGCACACAGCAAGGCGATGGCCC |
| 2093 | VIM | 3236967 | ACTGAGAACTAGCAGCGCGCGCGGAGCCCGCTGAGACTTGAATCA |
| 2094 | VIM | 3236968 | GAGCCCTCAATCGGCGGGACAGCAGGG |
| 2095 | VIM | 3236969 | CTTTCCTCTGCCACCGCCGTCTCGCAACTCCCGCCGTCCGAAGCTGGACTGAGCCCGTTAGGT CCCTCGACAGAA |
| 2096 | VIM | 3236971 | CCCGCGCCAGAGACGCAGCCGCGCTCCCACCACCCACACCCACCGCGCCCTCGTTCGCCTCTT CTCCGGGAGCCAGTCCGCGCCACCGCC |
| 2097 | VIM | 3236972 | TCCAGCCGGAGCTACGTGACTACGTCCACCCGCACCTACAG |
| 2098 | VIM | 3236973 | CTGGGCAGCGCGCTGCGCCCCAGCACCAGC |
| 2099 | VIM | 3236974 | GTGCGCCTGCGGAGCAGCGTGCCCG |
| 2100 | VIM | 3236975 | TGCAGGACTCGGTGGACTTCTCGCTGGCCGACGCCATCAACACCGAGTTCAAGAACACCCGC ACCAACGA |
| 2101 | VIM | 3236976 | GCAGGAGCTGAATGACCGCTTCGCCAACTAC |
| 2102 | VIM | 3236977 | CAGAATAAGATCCTGCTGGCCGAGCTCGAGCAGCTCAAGGGCCAAGGCAAGTCGCGCCTGG GGGACCTCTACGAGGAGGAGATGCGGGAGCTGCGCCGGCAGGTGGACCAGCTAACCAACG ACAAAGCCCGCGTCGA |
| 2103 | VIM | 3236978 | GTGGAGCGCGACAACCTGGCCGAGGAC |
| 2104 | VIM | 3236979 | AGGACGCTCCGTTTCAAGTTACAGATTTCTTAAAACTACCACTTTGTGTGCAGTTGAAGGCCCT TGGGCACAATGAGAGCCAGTCCTCCAAACTTTCAGAAAGTTTCCTGCCCCTTCTGGCAGGCTG CCAATCACCGGGCGGGAGAAGGAAGGAGGGGAAGGCGGTGGAGGGAGCGAGACAAAGGG ATGGTCCCTCGGGGCGGGATGGCGGGGCTGTCCTGTAGGTCTGTGCGGCCACCGTGATT GCCCCTCTGCGCGGTCCCGAAGTCCCGCTGAAACCTGCCGAGGGCAGCAGGTCTGAAAGCT GCAGGCGCTAGTTGCGCGGAGGTGGCGCAGCTGCTCTGGAGGCGCAGAGCGAATACGTGGT GTTTGGGTGTGGCCGCCCCGCCCCTGGCGGTTTCCTCGTTCCCCTTTGGTTAATGCGCAACTGT TTC |
| 2105 | VIM | 3236980 | CGAAAACACCCTGCAATCTTTCAGACAG |
| 2106 | VIM | 3236981 | CACAACCCACGAGCAATTCTAAAAGTTGCTTAACTCACGTCTAAAAAGTGCAAAACTTCAGGG CTGCGCGTAAAGCCCTCTAGTGGCGGGAAGACCACAGGT |

TABLE 13-continued

Subtyping Target Sequences

| SEQ ID NO. | Gene | Affy Probeset ID | Sequence |
|---|---|---|---|
| 2107 | VIM | 3236984 | CAGTCATGATTGAGTGCAGTTTACCATGTGTGTGGACATTTATTTATTTTAAAATTGTCTGATC ACCACCTTGAGTAAAACACAAGCAGTCACAATTAAAATATATTAGTGAGCAGGAGAAAGCAC AGCATATTATAGCACTGAATG |
| 2108 | VIM | 3236985 | TCATAAAATGTGTCAACGGCTTTTCTATA |
| 2109 | VIM | 3236986 | GTAAGGAGACTAGGTTCAGATGGTTAATCTAAGACAAATAAATGAGATAAGCCATACACTTTT ACATCCTCCATGTCCTGTCTTT |
| 2110 | VIM | 3236987 | GATGTTGACAATGCGTCTCTGGCACGTCTTGACCTTGAACGCAAAGTGGAATCTTTGCAAGA |
| 2111 | VIM | 3236988 | CAGGAACAGCATGTCCAAATCGATGTGGATGTTTCCAAGCCTGACCTCACGGCTGCCCTGCGT GACGTACGTCAGCAATATGAAAGTG |
| 2112 | VIM | 3236991 | CTCTGAGGCTGCCAACCGGAACAATGACGCCCTGCGCCAGGCAAAGCAGGAGTCCACTGAGT ACCGGAGACAGGTG |
| 2113 | VIM | 3236993 | GAGAACTTTGCCGTTGAAGCTGCTAACTACCAAGACACTATTGGCCGCCTGCAGGATGAGATT CAGAATATGAAGGAGGAAATGGCTCGTCACCTTCGTAATACCAAGACCTGCTCAATGTTAA GATGGCCCTTG |
| 2114 | VIM | 3236994 | CTCAGACTTGGATGCGTGAACTAATGGTGACCATTTGTTAGGCCCTGTGCCACTGGGCTCTAA GCAGTGTCACATTTAATCTTTAGAAAGTTTCTTTGAGGTAACTGCTTTCCACTTTTTGTAGAGG AGGAATTTGAATTGAGAGAGAGTAAGTGACTTGCTGAAAAAGGGTTAATCAACAGCAGAGCT GGGATTTGAACCCATAACTCTGTCAAAGCCTCCACTCCTAACTCCTGTTCATGCTCCTGTGGA |
| 2115 | VIM | 3236995 | GATTTCTCTGCCTCTTCCAAACTTTTCCTCCCTGAACCTGAG |
| 2116 | VIM | 3236996 | CTTTAGGAAAAACGTCAGCTGCTTGTAACCACTGTGTTTATGTCAAAGCATTCATTTTTTTAG GATATCTGAAAAAATGCCATATAAGAGAAAACTCTATAAAACATCTATAATTTTCGAACCCAA GTACACTCTTGCATTCTATGCTTTAAGTTAAATGCAAACTCCTTTTTCCTTCTTCCTGCTGCAAG TACTATCTCATCCTGATGCTCAAGAGTGTCAGGGCCTGGGTTTCCAAACAGAGACTACCCTAA AATTATTTGGCGAGTAGTACTTTACACAATTGC |
| 2117 | VIM | 3236999 | CTCAGCATCACGATGACCTTGAATAA |
| 2118 | VIM | 3237000 | CACTCAGTGCAGCAATATATTACCAGCA |
| 2119 | VIM | 3237001 | GCAGTTTTTCAGGAGCGCAAGATAGATTTGGAATAGGA |
| 2120 | VIM | 3237002 | TCTAGTTCTTAACAACCGACACTCCTACAAGATTTAGAAAA |
| 2121 | VIM | 3237003 | GTATTTTGAATACCATTAAAACTGC |
| 2122 | BAMBI | 3240453 | AGCTGCGGCGGATACCCTTGCGTGCTGTGGAGACCCTACTCTCTTCGCTGAGAACGGCCGCTA GCGGGGACTGAAGGCCGGGAGCCCACTCCCGACCCGGGGCTAGCGTGCGTCCCTAGAGTCG AG |
| 2123 | BAMBI | 3240454 | ATGGATCGCCACTCCAGCTACATCTTCATCTGGCTGCAGCTGG |
| 2124 | BAMBI | 3240461 | TTCGATGCTACTGTGATGCTGCCCACTGTGTAGCCACTGGTTATATGTGTAAATCTGAGCTCA GCGCCTGCTTCTCTAGACTTCTTGATCCTCAG |
| 2125 | BAMBI | 3240462 | TGCCTGGACTCTCTTGCAAGCACGACAGACATCTGCCAAGCCAAACAGGCCCGAAACCACTCT GGCACCACCATACCCACATTGGAATGCTGTCATGAAGACATGTGCAATTACAGAGGGCTGCA CGATGTTCTCTCTCC |
| 2126 | BAMBI | 3240463 | GCCTGCCTGATCTATAGACTTGTGACAGCCACGACTTTGTATGTCTGCTATTGATTTTGTTGTT AATGTAATTAGAGACACCAGAGGGAGAAGCCTGGCTGGATGCAAAGATGCATCTTGATTGAG TGGCTTTTATGTCTGAGCATTAGATGTCTGTC |
| 2127 | BAMBI | 3240464 | TTGCTTATTATGTTGGCCCTGAGGATGCTTCGAAGTGAAAATAAGAGGCTGCAGGATCAGCG GCAACAGATGCTCTCCCGTTTGCACTACAGCTTTCACGGACA |
| 2128 | BAMBI | 3240465 | GCAGACCTCAGCAACGATAAGATCCTCTCGCTTGTTCACTGGGGCATGTACAGTGGGCACGG GAAGCTGGAATTCGTATGA |
| 2129 | BAMBI | 3240466 | CGGAGTCTTATCTGAACTACACTTACTGAACAGCTTGAAGGCCTTTTGAGTTCTGCTGGACAG GAGCACTTTATCTGAAGACAAACTCATTTAATCATCTTTGAGAGACAAAATGACCTCTGCAAA CAGAATCTTGGATATTTCTTCTGAAGGATTATTTGCACAGACTTAAATCAGTTAAATGTGTTA TTTGCTTTTAAAATTATAAAAAGCAAAGAAGACTTTGTACACACTGTCACCAGGGTTATTT GCATCCAAGGGAGC |

TABLE 13-continued

Subtyping Target Sequences

| SEQ ID NO. | Gene | Affy Probeset ID | Sequence |
|---|---|---|---|
| 2130 | DDIT4 | 3251402 | GGTCCTAGAGCTCGCGGTCTGGTCTGGTCTGGTCCCCAGACTGACGCCTGGTCGGTCCCCCTCTT |
| 2131 | DDIT4 | 3251403 | GGCTTCTACGCTCCGGCACTCTGAGTTCATCAGCAAACGCCCTGGCGTCTGTCCTC |
| 2132 | DDIT4 | 3251404 | CTAGCCTTTGGGACCGCTTCTCGTCGTCGTCCACCTCCTCTTCGCCCTCGTCCTTGCCCCGAACTCCCACCCCAGATCGGCCGCCGCGCTCAGCCTGGGGGTCGGCGACCCGGGAGGAGGGGTTTGACCGCTCCACGAGCCTGGAGAGCTCGGACTGCGAGTCCCTGGA |
| 2133 | DDIT4 | 3251406 | TTGCCCGACTTCGAGCTGCTCAGTGACCCTGAGGATGAACACTTGTGTGCCAACCTGATGCAGCTGCTGCAGGAGAGCCTGGCCCAGGCGCGGCTGGGCTCTCGACGCCCTGCGCGCCTGCTGATGCCTAGCCAGTTGGTAAGCCAGGTGGGCAAAGAACTACTGCGCCTGGCCTACAGCGAGCCGTGCGGCCTGCGGGGGCGCTGCTGGACGTCTGCGTGGAGCAGGGCAAGAGCTGCCACAGCGTGGGCCAGCTGGCACTCGACCCCAGCCTGGTGCCCACCTTCCAGCTGACCCTCGTGCTGCGCCTGGACTCACGACTCTGGCCCAAGATCCAGGGGCTGTTTAGCTCCGCCA |
| 2134 | DDIT4 | 3251407 | CAGAGACGACTGAACTTTTGGGGTGGAGACTAGAGGCAGGAGCTGAGGGACTGATTCCTGTGGTTGGAAAACTGAGGCAGCCACCTAAGGTGGAGGTGGGGGAATAGTGTTTCCCAGGAAGCTCATTGAGTTGTGTGCGGGTGGCTGTGCATTGGGGACACATACCCCTCAGTACTGTAGCATGAAACAAAGGCTTAGGGGCCAACAAGGCTTCCAGCTGGATGTGTGTGTAGCATGTACCTTATTATTTTTGTTACTGACAGTTAACAGTGGTGTGACATCCAGAGAGCAGCTGGGCTGCTCCCGCCCCAGCCCGGCCCAGGGTGAAGGAAGAGGCACGTGCTCCTCAGAGCAGCCGGAGGGAGGGGGAGGTCGGAGGTCGTGGAGGTGGTTTGTGTATCTTACTGGTCTGAAGGGACCAAGTGTGTTTGTTGTTTGTTTTGTATCTTGTTTTTCTGATCGGAGCATCACTACTGACCTGTTGTAGGCAGCTATCTTACAGACGCATG |
| 2135 | DDIT4 | 3251408 | CACTTGAAAAATTACACCTGGCAGCTGCGTTTAAGCCTTCCCCCATCGTGTACTGCAGAGTTGAGC |
| 2136 | DDIT4 | 3251409 | CCTCCCCGGGAGGAGTGCCATCTGGGTCTTCCATCTAGAACTGTTTACATGAAGATAAGATACTCACTGTTC |
| 2137 | DDIT4 | 3251410 | TTCAAGTATTAAGACCTATGCAATATTTTT |
| 2138 | SNCG | 3256173 | CCGCAGCTCGCAGGGAGATCCAGCTCCGTCCT |
| 2139 | SNCG | 3256174 | GAAGGGCTTCTCCATCGCCAAGGAGGGCGTGGTGGGTGCGGTGGAAAAGACCAAGCAGGGGGTGACGGAAGC |
| 2140 | SNCG | 3256175 | GGTCTAGCCAGTGTCCCTACCTCAGGCCTGCTCTCTCTTGTCCCCCACATTCTGTCCTGTCCCCTTCCCATCCATCCACTTCTTCCAGACACAGCAGGAAGAGGCCCTCTGAAGGGGCCGCCGGCCCCCAGACACCATCCTTACCCCCCCACCGACCCCACAGTTTGTCCAGCTGTTCTGTTGTGTTTGTCCTGACCGCCCCCAACACCTCGAGGGAGGTCTGG |
| 2141 | SNCG | 3256178 | GGGCTGGGGTGGAGGCCAGCCAGTGTCC |
| 2142 | SNCG | 3256179 | AGGAGCAGGCCAACGCCGTGAGCGAGGCTGTGGTGAGCAGCGTCAACACTGTGGCCACCAAGACCGTGGAGGAGGCGGAGAACATCGCGGTCACCTCCGGGGTGGT |
| 2143 | SNCG | 3256183 | GACTTGAGGCCATCTGCCCCCCAACAGGAGG |
| 2144 | SNCG | 3256184 | GTGAGGCATCCAAAGAGAAAGAGGAAGTGGCAGAGGAG |
| 2145 | SNCG | 3256186 | GGCTACAGGCCAGCGTGGATGACCTGAAGAGCGCTCCTCTGCCTTGGACACCATCCCCTCCTAGCACAAGGAGTGCCCGCCTTGAGTGA |
| 2146 | SNCG | 3256187 | CCTCGTCTCCCTGGCCACCCTTGGCCTGTCCACCTGTGCTGCTGCACCAACCTCACTGCCCTCCCTCGGCCCCACCCACCCTCTGGTCCTTCTGACC |
| 2147 | INA | 3262137 | CGCACGTCCGGCCCCGATCCCGGCAC |
| 2148 | INA | 3262138 | ATGAGCTTCGGCTCGGAGCACTACCTGTGCTCCT |
| 2149 | INA | 3262139 | CCGCCTCTCTGGGGCCGGCGGCGCG |
| 2150 | INA | 3262140 | GGCGCGCACCAACGAGTACAAGATCATCCGCACCAACGAGAAGGAGCAGCTGCAGGGCCTCAACGACCGCTTCGCCGTGTTCATCGAGAAGGTGCATCAGCTGGAGACGCAGAACCGCGCGTTGGAGGCCGAGCTGGCCGCGCTGCGACAGCGCCACGCTGAGCCGTCGCGCGTCGGCGAGCTCTTCCAGCGCGAGCTGCGCGACCTGCGCGCGCAGCTGGAGGCCCAGCTCGGCTCGCTCGCAGGCCCTGCTGGAGCGCGACGGGCTGGCGGAGGAGGTGCAGCGGCTGCGGGCGCGCTGCGAGGAGGAGAGCCGCGGACGCGAAGGCGCCGAGCGCGCCCTGAAGGCGCAGCAGCGCGACGTGGACGCGCCACGCTGGCCCGCCTGGACCTGGAGAAGAAGGTGGAGTCGCTGCTGGACGAGCTGGCCTTCGTACGCCAGGTGCACGACGAGGAGGTAGCCGAGCTGCTGGCCACGCTGCAGGCGTCGTCGCAGGCCGCGGCCGAGGTGGACGTGACTGTGGCTAAACCAGACCTGACCTCGG |

TABLE 13-continued

Subtyping Target Sequences

| SEQ ID NO. | Gene | Affy Probeset ID | Sequence |
|---|---|---|---|
| | | | CTCTGAGGGAGATCCGCGCCCAGTATGAGTCCCTGGCCGCTAAGAACCTGCAGTCCGCGGAA GAATGGTACAAGTCCAAGTTTGCCAACCTGAACGAGCAGGCGGCGCGCAGCACCGAGGCCA TCCGGGCCAGCCGCGAGGAGATCCACGAGTATC |
| 2151 | INA | 3262146 | CACCAAGAGTGAGATGGCACGCCACCTTCGGGAATACCAGG |
| 2152 | INA | 3262149 | GACACGTTTTAGCACCAGTGGGTTAAGCATTTCGGGGCTGAATCCACTTCCCAATCCAAGTTA CCTGCTCCCACCTAGAATCCTCAGTGCTACAACCTCCAA |
| 2153 | INA | 3262150 | ATCCACTGGGCTATCACTTAAGAAAGAGGAGGA |
| 2154 | INA | 3262151 | GTAGCCTCTAAGAAAACCTCCCAGATAGGGGAAAGTTTTGAAGAAATATTAGAGGAGACAGT AATATCTACTAAGAAAACCGAGAAATCAAATAT |
| 2155 | INA | 3262152 | AGCTCACGCTTCACAGTGATCGATGATTCAGGTGCAGAGGAAGTACAAACTAAGGTGCTAAA TCTGCGATCATCGTCATTTGCTGTGAACTGAAATTAAAACTATTCATGCTACCCAGCCATTACC CAGCTAAATAATCTTACTCTAGATACCTAAAACATAAGATCACTGCCAGAGATAAACTAATGG TCCACACCCAATTCCACTCTGATAGAATTATTTCACAAATAATAGGTGTTTGTTTAATGGACAC TTTTCACCTCCTTCAATTCCATATATCCTTTTCTTCTATGTAGGAAAAAAATAGTCTAGTGTAGT ATTCTTCCCTTTTAAACACATTTTGGTTCTTCTCAAAAGAACTTACCCCCATTCGCGCTCTGCTC AGTGGGTAAAATTAGATGCATGTTGACCATGTCTATGATTCGTGTAATTACTTATCCCTGCCCA TTTCATATTCTTTCAATTCTGTAGGTTAAAAAAATGGCAGTGATGAATTTTAAGGGTTTCCCCC AACATATAAAATAATGCAAAGAATCCCTAGACTTTAGGCTTTCAGCTTACACAAATCTATTTAA TTAGGAAAAAAACTATTAAGGATGTAGCTTTTCACCTTTACTTTAGAAGCACAGTAAATATCCC AAACTGTGATGAAGCCGACCTTAGATTTA |
| 2156 | INA | 3262153 | ATGCCTTTTACGAGTGCTAAGTGTAGGATATTTTGTCACCAGAACACAATGCTACCGCCCCAA AGTAAAAGAAACCACTTCTGGTCAATCAACACTACCAGCGTATATATAAGAAAGACATCTTTC TCTTTTTCTAAAAGACTTCCCTAACACTTACCCCATGGCTGCACAGTTGGTGGGGTCCTGCCGGA GAGGAAGAGACACTCAGACCAGAGAAGGGGTGTGCATGCGCCTACTCGCTTGCTA |
| 2157 | INA | 3262154 | GCCCAACTGTGTAGCATCTGCATTGCCCAGTCTTTCATGTGTGCCAAGGCTGATGCAGGATTT GTTCTCTGTCCAGCAGTCACTTCGGCCAGAGCTGAAGAGTTGCCC |
| 2158 | ACSL5 | 3264338 | ACAAGTGTTTGAACAGGTAACTTCTACCTTTGAA |
| 2159 | ACSL5 | 3264339 | ATTCAAAGGTTCCAGGGGAGTGTGTTGGCCACTCTCAG |
| 2160 | ACSL5 | 3264340 | ACAGTACACAGTAGCTTCGGGTGTGTCCCAGTCAGTCCTAGGAGCTGTGGAAAGAGTAGAAG TGCCTGAATGTGGTGCTGA |
| 2161 | ACSL5 | 3264341 | CAGAGGATGGAATGCCACAGGCCCCACTTCGTCTCCCAGCCCTTCATCTTTCTTCCATGTCCAA AGGCGGCTCCCCAGAGGCCAAGGGCTCAGCTCTTGTGTTCTCTGAGA |
| 2162 | ACSL5 | 3264342 | AGCTTTTAAGAACTGCTCTGTAGAAAGAACAAACCCTAATCTAGCTCCAGCAAAGAGCCAGG ATCATGCTGAACTTCCTGTGAGCCTTCGTG |
| 2163 | ACSL5 | 3264344 | CCAGGAAGTGAAGTCCCCGAGCACGTTAGAAAGCCTGACATGGCCTGACTCGGGACAGCTCA GAGCAGGGCAGAACTGGGGACACTCTGGGCCGGCCTTCT |
| 2164 | ACSL5 | 3264345 | ATGGACGCTCTGAAGCCACCCTGTCTCTGGAGGAACCACGAGCGAGGGAAGAAGGACAGGG ACTCGTGTGGCAGGAAGAACTCAGAGCCGGGAAGCCCCCATTCACTAGAAGCACTGAGAGAT GCGGCCC |
| 2165 | ACSL5 | 3264352 | GTCTGAATTTCCTGCTGCTGTTCACAAAG |
| 2166 | ACSL5 | 3264353 | CGGCGTTGATCTGCATCCTGACATTTGGAGCTGCCATCTTCTTGTGGCTGATCACCAGACCTCA ACCCGTCTTACCTCTTCTTGACCTGAACAATCAGTCTGTGGGAATT |
| 2167 | ACSL5 | 3264358 | CAATGGGCCCTGCTTGGGATATAGAAAACCAAACCAGCCCTACAGATGG |
| 2168 | ACSL5 | 3264359 | GTGTCTGATAGAGCAGAGTACCTGGGTTCCTGTCTCTTGCATAAAGGTTATAAATCATCACCA GACCAGTTTGTCGGCATCTT |
| 2169 | ACSL5 | 3264361 | GGATCATCTCCGAATTGGCTTGTTACACGTACTCTATGGTAGCTGTACCTCTGTATGACACCTT GGGACCAGAAGCCATCGTACATA |
| 2170 | ACSL5 | 3264363 | CATGGTGATCTGTGACACACCCCAAAA |
| 2171 | ACSL5 | 3264367 | CTCCTAGCCCAGAAGACCTGAGCGTCATCTGCTTCACCAGTGGGAC |
| 2172 | ACSL5 | 3264368 | GCTACCTATTAGCTACATAAAGTATCT |
| 2173 | ACSL5 | 3264369 | CCAAAGGAGCCATGATAACCCATCAAAA |

TABLE 13-continued

Subtyping Target Sequences

| SEQ ID NO. | Gene | Affy Probeset ID | Sequence |
|---|---|---|---|
| 2174 | ACSL5 | 3264371 | TGTGGAGCCAGAGTTGGATTCTTCCAAGGGGATATTCGGTTGCTGGCTGACGACATGAAGAC TTTGAAGCCCACATTGTTTCCCGCGGTGCCTCGACTCCTTAACAGGA |
| 2175 | ACSL5 | 3264373 | AGGGTATCATCAGGCATGATAGTTTCTGGGACAAGCTCATCTTT |
| 2176 | ACSL5 | 3264374 | GGCGGAAGGGTTCGTGTAATTGTCACTGGAGCTGCCCCCATGTCCACTTCAGTCATGACATTC TTCCGGGCAGCA |
| 2177 | ACSL5 | 3264376 | TCACGTTGGGGTGCCCCTGGCTTGCAATTACGTGAAGCTGGAAGATGTGGCTGACATGAACT ACTTTACAG |
| 2178 | ACSL5 | 3264378 | TGAAGATCATCGACCGTAAAAAGAACATTTTCAAGCTGGCCCAAGGAGAATACATTGCACCA GAGAAGATAGAAAATATCTACAACAGGAGTCAACCAGTGTTACAAATTTTTGTACACG |
| 2179 | ACSL5 | 3264379 | GGTTCCTGACACAGATGTACTTCCCTCATTTGCAGCCAAGCTTGGGGTGAAGGGCTCCTTTGA GGAACTGTGCCAAAACCA |
| 2180 | ACSL5 | 3264380 | TGTAAGGGAAGCCATTTTAGAAGACTTGCAGAAA |
| 2181 | ACSL5 | 3264382 | TTCATCCAGAGCCATTTTCCATTGAAAATGGGCTCTTGACACCAACATTGAAAGCAAAGCGAG GAGAGCTTTCCAAATACTTTCGGACCCAAATTGACAGCCTGTATGAGCACATCCA |
| 2182 | ACSL5 | 3264383 | AGTACCTGCCGGCCCACTGTGCACTGCTTGTGAGAAAATGG |
| 2183 | ACSL5 | 3264384 | AACCTGTTAAACTCTAAAGCCATAGCTTTTGTTTTATATTGAGACATATAATGTGTAAACTTAGT |
| 2184 | ACSL5 | 3264385 | TTCAGGGCTACTTTTATCAACATGCCTGTCTTCAAGATCCCAGTTTATGTTCTGTGTCCTTCCTC ATGATTTCCAACCTTAATACTATTAGTAACCACAAGTTCAAGGGTCAAAGGGACCCTCTGTGC CTTCTTCTTTGTTTTGTGATAAACATAACTTGCCAACAGTCTCTATGCTTATTTACATCTTCTACT GTTCAAACTAAGAGATTTTTAAATTCTGAAAAACTGCTTACAATTCATGTTTTCTAGCCACTCC ACAAACCACTAAAATTTTAGTTTTAGCCTATCACTCATGTCAATCATATCTATGAGACAAATGT CTCCGATGCTCTTCTGCGTAAATTAAATTGTGTACTGAAGGGAAAAGTTTGATCATACCCAAAC ATTTCCTAAACTCTCTAGTTAGATATCTGACTTGGGAGTATTAAAAATTGGGTCTATGACATAT TGTCCAAAAGGAATGCTGTTCTTAAAGCATTATTTACAGTAGGAACTGGGGAGTAAATCTGTT CCCTACAGTTTGCTGCTG |
| 2185 | ACSL5 | 3264386 | CTGTGAAGGAACCAACTGATCTCCCCCACCCTTGGATTAGAGTTCCTGCTCTACCTTACCCACA GATAACACATGTTGTTTC |
| 2186 | BTBD16 | 3268223 | AGCTCCCCCTGTCAAAGCACCTTGGCCCATAAGAAGAAAAGGGGGAGCCCCAGATGTGATGA GCGCTTCCAGGCTTCAGGCTCAGAAGGCGCCCCCAGCTCTCCTGTAACTCAGAGGCCAGTGT GATGGGAGTTCCTCCACTCAGCACACTTCCCCTGTAAACACGCCTGTGGTGGGCAAAAGG |
| 2187 | BTBD16 | 3268224 | TTTCTCTCCTGCGTAATTTCCACTTTC |
| 2188 | BTBD16 | 3268226 | TCACTGGCTCAACCAACCGGTGGCGTTTGCCCAAACAGCCTTTCTCTGGGGACCTGCTCTCACT TTCCCAGATGTGCAAGGCTCTGAGCATAGACTTTGAGGAAGCT |
| 2189 | BTBD16 | 3268229 | ACAAGGACATCCAAAGTGGGGAAGCA |
| 2190 | BTBD16 | 3268231 | ATGTGATTCTCGAGTGCCTGGGCTTCAAATGGGAGCTCCATCAGCCCCAGCTTTTTCAGTCTG AGACCTTGGCCAAGCTCTACCTGAAAGCCCTGGCGCA |
| 2191 | BTBD16 | 3268236 | CACGGCCCTGAAGAACCTCTACATGAGTGAGGTGGAGATTAACTTGGAAGACCTACTGGGAG TGCTGGCTTCCGCCCACATCCTCCAG |
| 2192 | BTBD16 | 3268238 | AGCAGCTCACCACCGGCTGCGAGAAGTGGCTGGAAATGAACTTGGTTCCTCTAGGGGGGAC GCAGATCCACCTCCACAAAATCCCACAGGACCTGCTCCACAAAGTGCTG |
| 2193 | BTBD16 | 3268241 | GCTTTTGTGGGTCTTCTTGCAACTGAACTACAAGATTCAGGCAATTCCGACTTATGAAACCGT GATGACATTTTT |
| 2194 | BTBD16 | 3268245 | CTTTCCTGAGAACTGTTGCTTTCTGGACCGGGACATAG |
| 2195 | BTBD16 | 3268246 | TCTTCCTCTGCTTGCGTCTGCACGGCATCAC |
| 2196 | BTBD16 | 3268248 | GGGGCGACATGGTCCACCTGAAAGATCTTAACACCCAG |
| 2197 | BTBD16 | 3268249 | GAGAATACAACTTATTCGAAAACGATTGCTCTATATGGATTCTTCTTTAAGATAAAGGGACTC AAACATGATACTACCTCTTATAG |
| 2198 | BTBD16 | 3268250 | GGAATCTCCCTCTGCGGTCTACGAGCACAACCACGTCAGCCTGCGAGCGGCACGCCT |

TABLE 13-continued

Subtyping Target Sequences

| SEQ ID NO. | Gene | Affy Probeset ID | Sequence |
|---|---|---|---|
| 2199 | BTBD16 | 3268251 | GCAGAGGCCCTGGTTGACGGCAAGTGGC |
| 2200 | BTBD16 | 3268252 | AAAATCCAAACTGTGGGCATCCCAATCTATGTAAGTTTTGCATTC |
| 2201 | BTBD16 | 3268253 | CCAGAAGAATCTATGGGATTTTCCCCCCACTGGTCTGCATAAAAGAAAATAA |
| 2202 | AKR1C2 | 3274763 | TCTCTCCTGCTTGGCGACTTCAGTAAGCTACAGCTAAGCCCATCGGCCGGAAAAGAAAGACAATA |
| 2203 | AKR1C2 | 3274764 | TGAGGTCTGCCAGAAGGCCCTGCGTG |
| 2204 | AKR1C2 | 3274765 | TTGCTGGCCCCCCTAATTATCCATTT |
| 2205 | AKR1C2 | 3274771 | GAGGACCCAGTCCTTTGTGCCTTGGCAAAAAGCACAAGCGAACCCCAGCCCTGATTGCCCTGCGCTACCAGCTGCAGCGTGGGGTTGTGGTCCTGGCCAAGAGCTACAATGAGCAGCGCATCAGACAGAACGTG |
| 2206 | AKR1C2 | 3274772 | GGTTGCCTATAGTGCTCTGGGATCC |
| 2207 | AKR1C2 | 3274773 | CCAACTTCAACCACAGGCTGCTGGA |
| 2208 | AKR1C2 | 3274775 | GTGAGGAAGTGATCCCAAAAGATGAAAATGGAAAAATACTATTTGACACAGTGGATCTCTGTGCCACATGGGA |
| 2209 | AKR1C2 | 3274776 | GGAGCGCTGCATCACCTACCTCATG |
| 2210 | AKR1C2 | 3274777 | GCAATTCCCATCGACCAGAGTTGGTCCGACCAGCCTTGGAAAGGTCA |
| 2211 | AKR1C2 | 3274778 | GAGAGAAGACATATTCTACACTTCAA |
| 2212 | AKR1C2 | 3274779 | AAAGTAAAGCTCTAGAGGCCGTCAAATTGGCAATAGAAGCCGGGTTC |
| 2213 | AKR1C2 | 3274782 | CAGTGTGTGAAGCTGAATGATGGTCACTTCATGCCTGTCCTGGGATTTGGCACCTATGCGCCTGCA |
| 2214 | AKR1C2 | 3274783 | GGAGGAAGAAACATTTGCTAACCAGGCCAGTGACAG |
| 2215 | AKR1C2 | 3274784 | GTAAGAAACGGTTGAACTGGATGCAATTTTTATCACAGCTTGTGTAAGACTGCCTCTGTCCCTCCTCTCACATGCCATTGG |
| 2216 | AKR1C2 | 3274785 | TGTGCTATCCCTATGTGTATTGATTAT |
| 2217 | AKR1C2 | 3274786 | TGCGATGGTGCAATCCCAACTCACTG |
| 2218 | AKR1C2 | 3274787 | ACCATTGGAATGACATACTGCATCCTATAGTTATACCATCCAC |
| 2219 | AKR1C2 | 3274788 | AGCCCTAGCCAACGCCGCATGAGAGGGAGTGTGCCGAGGGCTTCTGAGAAGGTTTCTCTCACATCTAGAAAGAAGCGCTTAAGATGTGGCAGCCCCTCTTCTTCAAGTGGCTCTTGTCCTGTTGCCCTGGGAGTTCTCAAA |
| 2220 | AKR1C2 | 3274789 | TGCCAGCCAAGTGAAGACATGCTTACTTCCC |
| 2221 | AKR1C2 | 3274800 | GATTCACATCTTGGAGTAGTCACAACTTGCAGTGCCCTGATTGCTTCTATTTGCTT |
| 2222 | AKR1C2 | 3274814 | GTGGGGCAGGACATCGAAGATATCATTGACTCATCACATTCCCCTGAATAGCTCATATTTAGAAAATATTCTTAGATTGTAAAAATGTACTGTTCATTTGTTATATGCAATCTTTTAAATGTTTTATACTTTAAACAAGGCATAGTTACAAGTATAAAACATAAATATCCCAAAGCCATTATGCATGGCACTCAAGATTAAAATGGGAAATAATACATCTAATAAATCAAATGTTCCAAGACTTCAAATGTCTTTTGGAAACAGGCTATGTAAAACAGCACACTGGTTTCAAACTTTGGTAAATTTTAAGAAGAACTCTTACAAAGGCATTTAATTCTTATACATAATTTTCAGGGGAACTAATCAAATCAGCTAATCATGAAGACATGATTTTCGTTTTAGAAAACACTTTTGAAAACTTGGGATAATCTCATGTCTTAATGATCAAAGCATTATGAGAAGGACAGTGGTTTTTACCTGGGCACACTTTCTAACACATTTACTCTCCACTATTCGTACTCTGGTAGCCATGTTAACCCCATCAGAGATTCCTTCTCAAGCCATGTCTCAGAGCTGATAGGCATCCCAGCAAGTTTTGCAGCTCACAATTTTCTGTAAATTACTTATTCTATAAAATTGGAAGAGGCCATAAACTTTGGAGGGCCCTAGACCAATTTTTTGGATTATTTCTGGTCTACTCTCATTCCGTTGATGATCTTAGATATTCTCTGCATTAAATATCACCTCTAGGCTGAGAAATCCACCAAAAAATATTTCTAGCTCAGCGTTTTCCTCCAAATCTTC |
| 2223 | AKR1C2 | 3274820 | TTGTTCAGTATGTTGTGCTTTAATT |
| 2224 | AKR1C2 | 3274821 | TGCAGGTTTAACCAGGTCCATCAGG |
| 2225 | AKR1C2 | 3274822 | ACTCTCTTGGAGGTAATAGCTGCAAGAACTCTCCCAACAGGGACTTCTGTGCAAAAGGCTGAGTAAATTGCCCTTATGAGAGCCTT |

TABLE 13-continued

Subtyping Target Sequences

| SEQ ID NO. | Gene | Affy Probeset ID | Sequence |
|---|---|---|---|
| 2226 | AKR1C2 | 3274831 | AAAGCCATTGACAGCCTCAACGGAAATCTCCGACATGCTAAGTTAC |
| 2227 | AKR1C2 | 3274832 | GGCTGTGGTCCTGGTCAAGAGCTCCAATGAACAGCAGATCA |
| 2228 | AKR1C2 | 3274835 | ACAGTGCTCTGGGAACCCAACGACAT |
| 2229 | AKR1C2 | 3274836 | GATTCTGCTCATTTATACAATAATGAGGAG |
| 2230 | ACTA2 | 3299507 | TCCAAATCATTCCTAGCCAAAGCTCTGACTCGTTACCTATGTGTTTT |
| 2231 | ACTA2 | 3299508 | TCAGCAAACAGGAATACGATGAAGCCGGGCCTTCCA |
| 2232 | ACTA2 | 3299513 | GGCATCCATGAAACCACCTACAACAGCATCATGAAGTGTGATATTGACATCAGGAAGGACCTCTATGCTAACAATGTCCTATCAGGGGGCACCACTATGTAC |
| 2233 | ACTA2 | 3299517 | TCATCCTCCCTTGAGAAGAGTTACGAGTTGCCTGATGGGCAAGTGATCACCATCGGAAATGAACGTTTCCGCTGCCCAGAGACC |
| 2234 | ACTA2 | 3299520 | CTGGCTGGCCGAGATCTCACTGACTACCTCATGAAGATCCTGACTGAGCGTGGCTATTCCTTCGTTACTACTG |
| 2235 | ACTA2 | 3299521 | ATGTATGTGGCTATCCAGGCGGTGCTGTCTCTATGCCTCTGGACGCACAACT |
| 2236 | ACTA2 | 3299527 | CTCTTTCTACAATGAGCTTCGTGTTGCCCCTGAAGAGCATCCCACCCTGCTCACGGAGGCACCCCTGA |
| 2237 | ACTA2 | 3299530 | CAGGATGCATAATCCCTGTGTTCTCTGATACAGAACACCACACTACTGCTGGGGAAATAACTGGCTCACATTGCTCAACTGTACTTTTACTTG |
| 2238 | ACTA2 | 3299531 | ACAGCTACGTGGGTGACGAAGCACAGAGCAAAAGAGGAATCCTGACCCTGAAGTACCCGATAGAACATGGCATCAT |
| 2239 | ACTA2 | 3299534 | TGGGCTCTGTAAGGCCGGCTTTGCTGGGGACGATGCTCCCAGGGCTGTTTTCCCATCCATTGTGGGACGTCCCAGACATCA |
| 2240 | IFITM2 | 3315664 | GAACCACATTGTGCAAACCTTCTCTCCTGTCA |
| 2241 | IFITM2 | 3315665 | AGCAGGAAGTGGCTATGCTGGGGGTGC |
| 2242 | IFITM2 | 3315671 | TGGGCCCTGATTTTGGGCATCTTCATGACCATTCTGC |
| 2243 | IFITM2 | 3315672 | GTTGGTCGTCCAGGCCCAGCGATAG |
| 2244 | IFITM2 | 3315673 | CGTGACCTGTATCCCACGTACTCTATCTTCCATTCCTCGCCCTGCCCCCAGAGGCCAGGAGCTCTGCCCTTGACCTGTATTCCACTTACTCCAC |
| 2245 | IFITM2 | 3315674 | GAGTCCTGCATCAGCCCTTTATCCTCACACGCT |
| 2246 | IFITM2 | 3315678 | TTGGGGCAGGAAACTTTGGCCACCAGGCCTCTGACCTGCACCAGGAGACACTGGGAGGTTTAGTCCCCAAACCCGCACAGAGCAGGACTGCAGCCTG |
| 2247 | IFITM2 | 3315679 | TTAAACCACACCTCATTGGTCCCTGGCTAATTCACCAATTTAC |
| 2248 | IFITM2 | 3315680 | GTCTCACTGAGCACCGTCCCAGCATCCGGACACCACAGCGGCCCTTCGCTCCACGCAGAAAACCACACTTCTCAAACCTTCACTCAACACTTCC |
| 2249 | IFITM2 | 3315681 | ATCCTTCCAAGGTCCACCGTGATCAACATCCACAGCGAGACCTCCGTGCCCGACCATGTCGTCTGGTCCCTGTTCAACACCCTCTTCTTGAACTGGTGCTGTCTGGGCTTCATAGC |
| 2250 | IFITM2 | 3315684 | ATCCTCATGACCATTGGATTCATCCTGTTACTG |
| 2251 | IFITM2 | 3315685 | GTATTCGGCTCTGTGACAGTCTACCATATTATGTTACA |
| 2252 | IFITM2 | 3315686 | TAGCCGCCCATAGCCTGCAACCTTTGCACTCCACTGTGCAA |
| 2253 | IFITM2 | 3315687 | TTGGTCCTGCCCCTAGATACAGCAGTTTATACCCACACACCTGTCTACAGTGTCATTCAATAAAG |
| 2254 | SAA1 | 3322701 | TAAATAGCAGCCACCGCTCCCTGGCA |
| 2255 | SAA1 | 3322709 | GAGAATATCCAGAGATTCTTTGGCCATGGT |
| 2256 | SAA1 | 3322710 | ATCTGGCTGTGAGGCCCTCAGGGCAGGGATACAAAGCGGGGAGAGGGTACACAATGGGTATCTAATAAATACT |

TABLE 13-continued

Subtyping Target Sequences

| SEQ ID NO. | Gene | Affy Probeset ID | Sequence |
|---|---|---|---|
| 2257 | EHF | 3326462 | GGCTCAGACTTGATAACACCCGTGGTGCCCCATCCCTATAGGAGCTGGTGAGATTGCAGCCT GCTGCCTCCCCTCCAACAGCCACAGCTATTGGATTTCCCACCCAGAA |
| 2258 | EHF | 3326477 | GTGCTGCCACCAGCTTGGATTTTCATTGTTTGAAATTGCACTTTAAATACTTTA |
| 2259 | EHF | 3326479 | GAAGGAGGTGGTGTAATGAATCTCAACCCCGGCAACAACCTCCTTCACCAGCCGCCAGC |
| 2260 | EHF | 3326483 | ACCAACCAGCTGGATGCCAATTGTATCCCTTTCCAAGAGTTCGACATCAACGGCGAGCACCTC TGCAGCATGAGTTTGCAGG |
| 2261 | EHF | 3326485 | GCCAGTGCAGTAGTGACCTGTTCCAGTCCACACACAATGTCATTGTCAAGACTGAACAAACT |
| 2262 | EHF | 3326488 | TGGACAGCAAAACTTTCTGCCGGGCTCAGATCTCCATGACAAC |
| 2263 | EHF | 3326491 | TGAAAAAGGAGCAAGACCCCCCTGC |
| 2264 | EHF | 3326493 | CGAGAGGGACTCACTTATGGGAATTCATCCGCGACATCCTCTTGAACCCAGACAAGAACCCA GGATTAATAAAATGGGAAGACCGATCTGAGGGCGTCTTCAGGTTCTTGAAATCAGAGGCAGT GGCTCAGCTATGGGTAAAAAGAAGAACAACAGCAGCATGACCTATGAAAAGC |
| 2265 | EHF | 3326494 | ATTCTGGAGCGTGTGGATGGACGAAGACTGGTATATAAAT |
| 2266 | EHF | 3326495 | CAAAGAACTCCTGGACGTAAATATTTCAAAGACTACTTTTCTCTGATATTTATGTACCATGAG |
| 2267 | EHF | 3326496 | CAAGGTTGGCTATAATCTCTGCATAACCACATGACTTGGAATGCTTAAATCAGCAAGAAGAAT AATGGTGGGGTCTTTATACTCATTCAGGAATGGTTTATCTGATGCCAGGGCTGTCTTCCTTTCT CCCCTTTGGATGGTTGGTGAAATACTTTAATTGCCCTGTCTGCTCACTTCTAGCTATTTAAGAG AGAACCCAGCTTGGTTCTTTTTTGCTCCAAGTGCTTAAAAATAAGTTGGAAAAAGGAGACGGT GGTGTGGAAATGGCTGAAGAGTTTGCTCTTGTATCCCTATAGTCCAAGGTTTCTCAATCTGCA CAATTGACATTTTTGGCCGGAGTGTTCTTTGTGGTGAGGGCTTTCCTGTGCATTGTAAGATGTT CAGCAGTATCCACTCATGGTCTCTAACCACTTGACACCAGAAACCCCCCAGCTGTGATAACGC AAAATGTCTCTAGACATCACCAAATGTTCCCTGGGGGTGGCAAATTTGCCCTTGATTGAGAAC CACCAGTTTAGCTAGTCAATATGAGGATGGTGGTTTATTCTCAGAAGAAAAGATATGTAAG GTCTTTTAGCTCCTTAGAGTGAAGCAAAAGCAAGACTTCAACCTCAACCTATCTTTATGTTTTA AATGTTAGGGACAATAAGTTGAAATAGCTAGAGGAGCTTCTTTTCAGAACCCCAGATGAGAG CCAATGTCAGATAAAGTAAGCATAGTAATGTAGCAGGAACTACAATAGAAGACATTTTCACTG GAATTACAAAGCAGAATTAAAATTATATTGTAGAAGGAAACACCAAGAAAAGAATTTCCAGG GAAAATCCTCTTTGCAGGTATTAATTCTTATAATTTTTTGTCTTTTGGATTATCTGTTTACTGTCT CATCTGAACTGATCCCAGGTGAACGGTTTATTGCCTAGATTTGTACTCAGAGGAATTTTTTTTG TTTTGTTTTGTCTTTTAAGAAAGGAAAGAAAGGATGAAAAAATAAACAGAAAACTCAGCTCA GGCACAATTGTCACCAAGGAGTTAAAAGCTTCTTCTTCAATAGAGGAATTGTTCTGGGGGTCC TGGAGACTTACCATTGAGCCATGCAATCTGGGAAGCACAGGAATAAGTAGACACTTTGAAAA TGGATTTGAATGTTCTCATCCCTTTTGCAGCTTTTCTTTTTGGCTCTCTCATGTCCTTGGCTTGCT CCTCTATTCTA |
| 2268 | EHF | 3326497 | CATGTATCCATAAGAAGGAGTGCTCTTCATCAACTAATAGAGCACCTACCACAGTGTCAT |
| 2269 | CD44 | 3326636 | CCCGATTATTTACAGCCTCAGCAGAGCACGGGGCGGGGGCAGAGGGGCCCGCCCGGGAGG GCTGCTACTTCTTAAAACCTCTGCGGGCTGCTTAGTCACAGCCCCCCTTGCTTGGGTGTGTCCT TCGCTCGCTCCCTCCCTCCGTCTTAGGTCACTGTTTTCA |
| 2270 | CD44 | 3326637 | TGGACAAGTTTTGGTGGCACGCAGCCTGGGGACTCTGCCTCGTGCCGCTGAGCCTGGCGCAG AT |
| 2271 | CD44 | 3326652 | ATTTGAATATAACCTGCCGCTTTGCAG |
| 2272 | CD44 | 3326653 | AATGGTCGCTACAGCATCTCTCGGACGGAGGCCGCTGACCTCTGCAAGGCTTTCAATAGCACC TTGCCCACAATGGCCCAGATGGAGAAAGCTCTGAGCATCGGATTTGAGACCTG |
| 2273 | CD44 | 3326654 | GTAAGAGACCAGCACCCGACCACTGGGGAAAGCTGGCGGCCTGGGACCAGGCAGCTGGGCT TAGAACTGGAAGGCTCCTTTCCCACAGCTGAATGGATTATTGCCTAAGGAGTCAACCCCACGT ATTAATTTGGCCAAGTCAATCTGCAACCTGTATGACAACTGGAGTTTAAAGTCAGCTAAAGAC ACCTTTGTGAATCATAGAGCGGGAACCCAGAGGAAGCCATTAGGGGTCCTCTCGGCTGGAAT CCTCTTGT |
| 2274 | CD44 | 3326658 | AGGGCACGTGGTGATTCCCCGGATCCACCCCAACTCCATCTGTGCAGCAAACAACACAGGGG TGTACATCCTCACATCCAACACCTCCCAGTATGACACATATTGCTT |
| 2275 | CD44 | 3326666 | TATTGTTAACCGTGATGGCACCCGCTATGTCCAGAAAGGAGAATACAGAACGAATCCTGAAG ACATCTACCCCAGCAACCCTACTGATGATGA |
| 2276 | CD44 | 3326667 | CAGCGGCTCCTCCAGTGAAAGGAGCAGCACTTCAGGAG |

TABLE 13-continued

Subtyping Target Sequences

| SEQ ID NO. | Gene | Affy Probeset ID | Sequence |
|---|---|---|---|
| 2277 | CD44 | 3326668 | CTTTTCTACTGTACACCCCATCCCAG |
| 2278 | CD44 | 3326669 | ACAGTCCCTGGATCACCGACAGCACAGACAGAATCCCT |
| 2279 | CD44 | 3326670 | GTAAGGAGAATAAATCACTGTGCTTCCCAA |
| 2280 | CD44 | 3326671 | TTCCCTGGCAAAATGTCTCTGACCTTCCTGAGCATTGCACACTCACGTGCTGATTTTCTCGTCTCTAG |
| 2281 | CD44 | 3326672 | ACAGCTGGAAGCTGGTGATGCCATTCAGGGAG |
| 2282 | CD44 | 3326685 | GCGTCCAGCTCAGCCACTAATGCAAGTCACCACAACAG |
| 2283 | CD44 | 3326686 | CCTCAGTTTTTCTGGATCAGGCATTGATGATGATGAAGATTTTATCTCCAGCACCA |
| 2284 | CD44 | 3326696 | AATGGCACCACTGCTTATGAAGGAAACTGGAACCCAGAAGCACACCCTCCCCTCATTCACCATGAGCATCATGAGGA |
| 2285 | CD44 | 3326700 | CCAGGCAACTCCTAGTAGTACAACGGAAGAAACAGCTACCCAGAAGGAACAGTGGTTTGGCAACAGATGGCATGAGGGATATCGCCAAACACCCAAAGAAGACTCCCATTCGACAACAGGG |
| 2286 | CD44 | 3326701 | CACTGGAGGAATTGTCACGAGATGTTAGGTTACTTAATAAATTATGCTGCAGTTCACACAGAGCCAAACCTTAAAGGCTCATAACAAGTCACCTGAACAGGAATGGATACAAGCCAGTTATGAATAAGAACAGG |
| 2287 | CD44 | 3326703 | GGTAACTCATCCTTTCTGCACTGCGGGAGTTGTTAATGCTTTTGTGTCCTCCAGTTCACATGCTGATTGCTAAGAAGAAAATGAGCATGAGTGAACCCAAAGCTGCTGAAACATTCTGCGTTTATGCAACTTCCTTGCCCTCTATACAAGGAAGATGGTT |
| 2288 | CD44 | 3326704 | TCGGTGTATCCCTGACCAAGCGTCCATTAACACTTTGACAATTGCTCAAACTGCATGG |
| 2289 | CD44 | 3326705 | GCTCATACCAGCCATCCAATGCAAGGAAGGACAACACCAAGCCCAGAGGACAGTTCCTGGACTGATTTCTTCAACCCAATCTCACACCCCATGGGACGAGGTCATCA |
| 2290 | CD44 | 3326711 | GACTCCAGTCATAGTATAACGCTTCAGCCTACTGCAAATCCAAACACAGGTTTGGTGGAAGATTTG |
| 2291 | CD44 | 3326712 | CTTCTCTACATCACATGAAGGCTTGGAAGAAGATAAAGACCATCCAACAACTTCTACTCTGACATCAAGC |
| 2292 | CD44 | 3326714 | CTGAAGGCTCAACTACTTTACTGGAAGGTTATACCTCTCATTACCCACACACGAAGGAAAGCAGGACCTTCATCCCAGTGACCTCAGCTAAGACTGGGTCCTTTGGAGTTACTGCA |
| 2293 | CD44 | 3326716 | CCCATTCAAGGCTGTTTTGCCATCATTTTTTGGAATACCTTAAAAAGACTAAACTTTGTGATAGGCTGTATAAGAATGCAAAGGTAAAGAAATGCAGATGGGAGTGTAAGTGAAAACATGCAGTACTGACCTTCCTGATTGCTCATTACA |
| 2294 | CD44 | 3326717 | CCAGTGGGGGGTCCCATACCACTCATGGATCTG |
| 2295 | CD44 | 3326720 | AGCAAACACAACCTCTGGTCCTATAAGGACACCCCAAAT |
| 2296 | CD44 | 3326721 | AATGGCTGATCATCTTGGCATCCCTCTT |
| 2297 | CD44 | 3326723 | CGTCTTCTTGCTGTTAGGAGGTCTATGAAGCAGAGAAGAACTTTCCTTTGGAAAACAACTAAATGAAGACAGTCACCTCGCTAGAACTGACACATGGGCTGTTTTTATATTCTTGAAGGCCACTCTCTCCCTACCTGAACCAAGACCTATAGGTTTACATGTTATTTACATTTTATATATAATATATATATATATATACACATACATTATATATACACAATAGTAATTCTAGCAACAGAGGAAATGACCTTTAACAGGGGTATAAATCTAAATTTATAAAAGTATAAATCTAAATTTCTTACCCAAGCACTTTAAAGATACATTATTTTTCTCCAGGACGTAATTCATAGGAATATTAAGCCTTTTGTAAATGTCCCTTTAGATGGTTTCTCATAAGGTAAAAGAAACTTATTTCCAAGCAGGACCACCTTTATTGTGTCCCCAGATCACCTCACAGGGCAGAAAAATGCCCCTCAGTCTGGGAGAAGACCTAGAGAGAATTATGGACTCCTTACTGGTTTTTGGAAAGCAACCAACAGCTAATTCCAACACCATGGGCAGCCCATACAGTCTCTAATTATCTGAGAAAATCAAATGATGCTGTTACAATAATTACGCTGGTACAAGTTAATAAAAGTGCCATGTTACAGTCAAACAGCTATGTTGCTATCTATACCATTGAGGGCATAGTTTTAAAAGTAGTTATGCTACCTGATTGTATAAGGAACAAAACTGAGAGAAAAAATCTAAAAGGCCGCCTATGATTGAATGGAAAGA |
| 2298 | CD44 | 3326726 | CCAAGTGGACTCAACGGAGAGGCCAGCAAGTCTCAGGAAATGGTGCATTTGGTGAACAAGGAGTCGTCAGAAACTCCAGACCAGTTTATGACAGCTG |
| 2299 | CD44 | 3326727 | ACAAGGAACCTGCAGAATGTGGACATGAAGATTGGGGTGTAA |
| 2300 | CD44 | 3326728 | CCATTACAGGGAGCTGGGACACTTAACAGATGCAATGTGCTACTGATTGTTTCATTGCGAATCTTTTTTAGCATAAAATTTTCTACTCTTTTTGTTTTTTGTGTTTTGTTCTTTAAAGTCAGGTCCAAT |

TABLE 13-continued

Subtyping Target Sequences

| SEQ ID NO. | Gene | Affy Probeset ID | Sequence |
|---|---|---|---|
| | | | TTGTAAAAACAGCATTGCTTTCTGAAATTAGGGCCCAATTAATAATCAGCAAGAATTTGATCG<br>TTCCAGTTCCCACTTGGAGGCCTTTCATCCCTCGGGTGTGCTATGGATGGCTTCTAACAAAAAC<br>TACACATATGTATTCCTGATCGCCAACCTTTCCCCCACCAGCTAAGGACATTTCCCAGGGTTAA<br>TAGGGCCTGGTCCCTGGGAGGAAATTTGAATGGGTCCATTTTGCCCTTCCATAGCCTAATCCC<br>TGGGCATTGCTTTCCACTGAGGTTGGGGGTTGGGGTGTACTAGTTACACATCTTCAACAGACC<br>CCCTCTAGAAATTTTTCAGATGCTTCTGGGAGACACCCAAAGGGTGAAGCTATTTATCTG |
| 2301 | CD44 | 3326729 | TTTGCATGACCTGTTATCCCTGGGGCCCTATTTCATAGAGGCTGGCCCTATTAGTGATTTCCAA<br>AAACAATATGGAAGTGCCTTTTGATGTCTTACAATAAGAGAAGAAGCCAATGGAAATGAAAG<br>AGATTGGCAAAGGGAAGGATGATGCCATGTAGATCCTGTTTGACATTTTTATGGCTGTATTT<br>GTAAACTTAAACACACCAGTGTCTGTTCTTGATGCAGTTGCTATTTAGGATGAGTTAAGTGCCT<br>GGGGAGTCCCTCAAAAGGTTAAAGGGATTCCCATCATTGGAATCTTATCACCAGATAGGCAA<br>GTTTATGACCAAACAAGAGAGTACTGGCTTTATCCTCTAACCTCATATTTTCTCCCACTTGGCA<br>AGTCCTTTGTGGCATTTATTCATCAGTCAGGGTGTCCGATTGGTCCTAGAACTTCCAAAGGCT<br>GCTTGTCATAGAAGCCATTGCATCTATAAAGCAACGGCTCCTGTTAAATGGTATCTCCTTTCTG<br>AGGCTCCTACTAAAAGTCATTTGTTACCTAAACTTATGTGCTTAACAGGCAATGCTTCTCAGAC<br>CACAAAGCAGAAGAAGAAGAAAAGCTCCTGACTAAATCAGGGCTGGGCTTAGACAGAGTT<br>GATCTGTAGAATATCTTTAAAGGAGAGATGTCAACTTTCTGCACTATTCCCAGCCTCTGCTCCT<br>CCCTGTCTACCCTCTCCCCTCCCTCTCCCTCCACTTCACCCCACAATCTTGAAAAACTTCCTTT<br>CTCTTCTGTGAACATCATTGGCCAGATCCATTTTCAGTGGTCTGGATTTCTTTTTATTTTCTTTTC<br>AACTTGAAAGAAACTGGACATTAGGCCACTATGTGTTGTTACTGCCACTAGTGTTCAAGTGCC<br>TCTTGTTTTCCCAGAGATTTCCTGGGTCTGCCAGAGGCCCAGACAGGCTCACTCAAGCTCTTTA<br>ACTGAAAAGCAACAAGCACTCCAGGACAAGGTTCAAAATGGTTACAACAGCCTCTACCTGTC<br>GCCCCAGGGAGAAAGGGGTAGTGATACAAGTCTCATAGCCAGAGATGGTTTTCCACTCCTTC<br>TAGATATTCCCAAAAAGAGGCTGAGACAGGAGGTTATTTTCAATTTTATTTTGGAATTAAATA<br>CTTTTTTCCCTTTATTACTGTTGTAGTCCCTCACTTGGATATACCTCTGTTTTCACGATAGAAAT<br>AAGGGAGGTCTAGAGCTTCTATTCCTTGGCCATTGTCAACGGAGAGCTGGCCAAGTCTTCACA<br>AACCCTTGCAACATTGCCTGAAGTTTATGGAATAAGATGTATTCTCACTCCCTTGATCTCAAGG<br>GCGTAACTCTGGAAGCACA |
| 2302 | CD44 | 3326731 | AGACAAAGCCCCTTACACTCCTTAGTTCTTTATTCAGCATTGTTCTGCTCTCATTTATTAAAAAT<br>TCCAAGTACCATTGTCAGTATTCTTCAGAAAATCTTATAGTGCTGTCTCATTTCTCTTGGCAAAA<br>GAAAGCCTGTTGTGCAACCCAATGAATTT |
| 2303 | CD44 | 3326732 | TCTCTTCAATATAGTTACACAGGTGACTAAGTGTCACCCGCTTCCACCTTCTCTAATCAAGGAA<br>ATGGTGACGATCAGGTTACTATAGATTCCTTATAAGGTGCCTTCATAATGGATAACTGTA |
| 2304 | UPK2 | 3351695 | TGGGCTGCAATGCATTATGCTGATGGGTGTCCACACCAAGTTCAGCATCGATATGGTGACCTC<br>CTAGGAGTGGGAGACCGCCAGGTTGACTAAGGAAGGGTGAGCTGGCCCAGGTCAGAATGG<br>AACAGATTGAAACTCTGGTGCTGATCATGGTGGGATTGGGCACACAAGCCTGACAACACCAG<br>GACACCCTGTCTCT |
| 2305 | UPK2 | 3351698 | TCCAGCCTCAGGTCTCAAGGATAGAGGTGCCACCACTTCCCAAT |
| 2306 | UPK2 | 3351700 | AGCCTGCCAGCACCTATTCCACCTCCCAGC |
| 2307 | UPK2 | 3351701 | CCCTGCTGCCCATCCGGACCTTGCCCTTGATCCTGATTCTGC |
| 2308 | UPK2 | 3351702 | TTCAACATCTCAAGCCTCTCTGGTCTGCTGTCCCGGCGCTAACGGAGAGCTGCTGGTTGCC<br>TTGCCCCCCTGTCACCTCACAGGAGGCAATGCCACACTGATGGTCCGGAGAGCCAAT |
| 2309 | UPK2 | 3351703 | TGGTGACGTCCAGCTTTGTGGTGCCTCCGTGCCGTGGGCGCAGGGAACTGGTGAGTGTGGTG<br>GACAGTGGTGCTGGCTTCACAGTCACTCGGCTCAGTGCATACCAG |
| 2310 | UPK2 | 3351704 | GTGACAAACCTCGTGCCAGGAACCA |
| 2311 | UPK2 | 3351705 | CATTTCCTACCTAGTGAAGAAGGGGACAGCCACTGAGTCCAGCAGAGAGATCCCAATGTCCA<br>CACTCCC |
| 2312 | UPK2 | 3351706 | GCATGGTGGTCATCACGGTGCTGCTCTCTGTCGCCATGTTCCTGCTG |
| 2313 | UPK2 | 3351707 | GTGCTGGGCTTCATCATTGCCCTGGCACTGGGCTCCCGCAA |
| 2314 | UPK2 | 3351708 | AGTGCCTCACCTTCCAACACTCCATTATTCCTCTCACCCCACTCCTGTCAGAGTTGACTTTCCTC<br>CCATTTTACCACTTTAAACACCCCCATAACAATTCCCCCATCCTTCAGTGAACTAAGTCCCTATA<br>ATAAAGGCTGAGGCTGCATC |
| 2315 | TMEM45B | 3356039 | TGCAGACGGCTGCGAGGCGCTGGGC |
| 2316 | TMEM45B | 3356044 | GCAGGGCTGAGACTATCTTCTGCTCAGGAA |
| 2317 | TMEM45B | 3356053 | TCTCATGTTTTTCTATAAGCAGTTAAGAGAAGCCACACAGCATCCTGAACACTTTGCTTTCT |

TABLE 13-continued

Subtyping Target Sequences

| SEQ ID NO. | Gene | Affy Probeset ID | Sequence |
|---|---|---|---|
| 2318 | TMEM45B | 3356054 | ATGGCAAATTTCAAGGGCCACGCGCTTCCAGGGAGTTTCTTCCTGATCATTGGGCTGTGTTGG<br>TCAGTGAAGTACCCGCT |
| 2319 | TMEM45B | 3356055 | GTACTTTAGCCACACGCGGAAGAACAGCCCACTACATTACTATCAG |
| 2320 | TMEM45B | 3356056 | CGTCTCGAGATCGTCGAAGCCGCAATTAGGACTTTGTTTTCCGTCACTG |
| 2321 | TMEM45B | 3356057 | GTCATTTGGTCTAGGGAATCTCCTCATCATACCCAGAACCTTTAATTCATTTTCTGAGCCCTGT<br>GAAATAGATGTTCCCACTGGCAGAGATAATAGGGCAACAATTTCCTGATGGCCACTAGACTAT<br>TTTATCGTAACATCCATTGTGTACAGAGCTTTATAATACTAACGGTTGACAGCTCTCACATCATG |
| 2322 | TMEM45B | 3356058 | CACCATGTACCTATTCTTTGCAGTCTCAGGAATTGTTGACATGCTCACCTATCTGGTCAGCCAC<br>GTTCCCTTGG |
| 2323 | TMEM45B | 3356061 | AACCGGCCTCCGCTGGACCAGCACATCCACTCACTCCTGCTGTATGCTCTGTTCGGAGGGTGT<br>GTTAGTATCTCCCTAGAGGTGATCTTCCGGGACCACATTGTGCTGGAACTTTTCCGAACCAGT<br>CTCATC |
| 2324 | TMEM45B | 3356063 | ATTGGGTTTGTGCTGTTCCCACCTTTTGGAACACCCGAATGGGACCAGAAGGATGATGCCAAC<br>CTCATGTTCATCACCATGTGCTTCTGCTGGCACTACCTGGCTGCCCTCAGCATTGTGGCCGTCA<br>ACTATTCTCTTG |
| 2325 | TMEM45B | 3356065 | CCTTTTGACTCGGATGAAGAGACACGGAAGGGGAGAAATCATTGGAATTCAGAAGCTGAATT<br>CAGATGACACTTACCAGACCGCCCTCTTGAGTGGCTCAGA |
| 2326 | TMEM45B | 3356066 | TAAAGTCTGTGTTGGTATAGTACCCTTCATAAGGAAAAATGAAGTAATGCCTATAAGTAGCAG<br>GCCTTTGTGCCTCAGTGTCAAGAGAAATCAAGAGATGCTAAAAGCTTTACAATGGAAGTGGC<br>CTCATGGATGAATCCGGGGTATGAGCCCAGGAGAACGTGCTGCTTTTGGTAACTTATCCCTTT<br>TTCTCTTAAGAAAGCAGGTACTTTCTTATTAGAAATATGTTAGAATGTGTAAGCAAACGACAG<br>TGCCTTTAGAATTACAATTCTAACTTACATATTTTTTGAAAGTAAAATAATTCACAAGCTTTGGT<br>ATTTTAAAATTATTGTTAAACATATCATAACTAATCATACCAGGGTACTGCAATACCACTGTTT<br>ATAAGTGACAAAATTAGGCCAAAGGTGATTTTTTTTTAAATCAGGAAGCTGGTTACTGGCTCT<br>ACTGAGAGTTGGAGCCCTGATGTTCTGATTCTTCAAAGTCACCCTAAAAGAAGATCTGACAGG<br>AAAGCTGTATAATGAGATAGAAAAACGTCAGGTATGGAAGGCTTTCAGTTTTAATATGGCTG<br>AAAGCAAAGGATAACGAATTCAGAATTAGTAATGTAAAATCTTGATACCCTAATCTTGCTTCT<br>GGATCTGTTCTTTTTTTAAAAAAACTTCCTTCACCGCGCCTATAATCCTAGCACTTTGGGAGGC<br>CGAGGCAGGCAGATCACGGGGTCAGGAGATCAAGACCATCCTGGCTAACATGGTGAAACCC<br>CGTCTCTACTGAAAATACAAAAAATTAGCCGGGTGTGGTGGCGGGCGCCTGTAGTTCCAGCT<br>ACTCGGGAGGCTGAGGCAAGAGAATGGCATGAACCCGGTAGGGGAGCTTGCAGTGAGCCCA<br>GATCATGCCACTGTACTCCAGCCTAGGTGACAGAGCAAGACTCTGTCTCAAAAACAAGCAAAC<br>AGACTTCCTTCAACAAATATTTATTAAATATCCACTTTGCAACAGCACTGAAATGGCTGTAAGG<br>ACTCCTGAGATATGTGTCCAGCAAGG |
| 2327 | SCUBE2 | 3362192 | CGTGCCACTCAATACAAATGTTCTGCTATAGGGTTGGTGGGACAGAGCTGTCTTCCTTCTGCA<br>TGTCAGCACAGTCGGGTATTGCTGCCTCCCGTATCAGTGACTCATTAGAGTTCAATTTTTATAG<br>ATAATACAGATATTTTGGTAAATTGAACTTGGTTTTTCTTTCCCAGCATCGTGGATGTAGACTG<br>AGAATGGCTTTGAGTGGCATCAGCTTCTCACTGCTGTGGGCGGATGTCTTGGATAGATCACG<br>GGCTGGCTGAGCTGGACTTTGGTCAGCCTAGGTGAGACTCACCTGTCCTTCTGGGGTCTTA |
| 2328 | SCUBE2 | 3362193 | AGAAACTTATCAAGGCTCTGTTTGATGTCCTGGCCCATCCCCAGAACTATTTCAAGTACACAGC<br>CCAGGAGTCCCGAGAGATGTTTCCAAGATCGTTCATCCGATTGCTACGTTCCAAA |
| 2329 | SCUBE2 | 3362195 | GACTACCAGGAACTCATTGAAGACATAGTTCGAGATGGCAGGCTCTATGCATCTGAGAACCA<br>TCAGGAA |
| 2330 | SCUBE2 | 3362196 | TGGAAGCAACTAAATCATAAGAATGCAAAACATGTTCTTTATTCCAAC |
| 2331 | SCUBE2 | 3362200 | CACCCAAGACAAGGAGTTTTAGTATCTCTTGGGGTGGACCCAAATGCCTCCCACATGGCTCTG<br>CTGAGAGAGACAGAGAGCCTCATCTACCCAAAAGCAACCAACTGGCAACCTCTCCTATCTGGA<br>ATCAGG |
| 2332 | SCUBE2 | 3362201 | CAGCACATGGAAAGAGCGTCTCTGCTTTGAACAGAGCCAACTTCGGAGCCAGCTGGCAAACT<br>GCTGACAAGCACACATGCTCAGAAAGGCAGGCAAGATGAGGGGAAAAGACATTGCTGACTC<br>ACAAGTGCCAAATTTTA |
| 2333 | SCUBE2 | 3362202 | ATCGCCTTCACCTCCAGGTCAAAGAAGCTGTGGATTCAGTTCAAGTCCAATGAAGGGAACAG<br>CGCTAGAGGGTTCCAGGTCCCATACGTGACATATG |
| 2334 | SCUBE2 | 3362203 | TACTAGTTCTATGATCTCGGGCACACATTCTGAATCTTTCTGCACTTGTCTTCTCATCTGTTAAA<br>ATGGGGCTAGTAACAGTTGCTACCTTATAAGGTTATAAGGGCTAAAGGAGTTCATAGATGTG<br>AAACACTTAGAATAGGCCAGGCACAGTGGCTCACACCTGTAATCCCAGGCTGAGGGAGGAG<br>GCTGAACCAGGATTTTGTGACCAGGCTCGGTGAGACCCTGTCTCTATACATTTTTTTTTTTTA<br>ATTAGCTGGGCATGATGGTGCATGCCTGTGGTTCCGGCTACTCGGGAGGCTGAGATGGGTGA<br>ATCGCTTAAGCCTGGGAGGTGGAGGATGCAGTGAGCCGTGATCATGCCACTGCACTCCAGCC |

TABLE 13-continued

Subtyping Target Sequences

| SEQ ID NO. | Gene | Affy Probeset ID | Sequence |
|---|---|---|---|
| | | | TGGTAGACAGAGCCAGACCTTGTCTCAAAAAACAAACAAACAAACAAACAAACAAACA AGAATGATGATGACACATGGAGCCACTATATAAACGTTTGCTCTTCTTATTAGTGGTTAAAA TGTCTGAAGTCAAGTATAGGTTTAAATCCTTGTTTTACCACATACTGGCTATATGACCCTGGGC AAGTATTTAATCTCTCTATTAAAAAGGTAACGGTTGCACCAACTTTCTGTGGTTTTCAGAAGAT TAAATGAGACAAAGTCCATAAATTGCCTAGCATGCTGCCTGATCTTAGGCAGCAAATGGTGGT GATGACAATTAGATGACAGCAGGTCAGTTCTGGAATGGGAGGCCCTCACCCAGCTCCTACAG TGAACGGTACAGCCTGGGCTGCTGCTGCTTGCCAAGCCCCAGGTCTTTCAGGTGTAGCCTCCC CTGGGGGTCCACAATTACCAGCTGAATC |
| 2335 | SCUBE2 | 3362205 | GCTGGGAGATTTCACTGGGTACATTGAATCCCCAAACTACCCAGGCAATTACCCAGCCAACAC CGAGTGTACGTGGACCATCAACCCACCCCCCAAGCGCCGCATCCTGATCGTGGTCCCTGAGAT CTTCCTGCCCATAGAGGACGACTGTG |
| 2336 | SCUBE2 | 3362206 | TCACCGATGTATTCGTTGCCCAGTGGGAACATACCAGCCTGAATTTGGAAAAAATAATTGTGT TTCTTGCCCAGGAAATACTACGACTGACTTTGATGGCTCCACAAACATAACCCAGTGTA |
| 2337 | SCUBE2 | 3362207 | GTCAACCTGGTGAATATTCTGCAGATGGCTTTGCACCTTGCCATCTCTGTGCCCTGGGCACGTT CCAGCCTGAAGCTGGTCGAACTTCCTGCTTCCCCTGTGGAGGAGGCCTTGCCACCAAACATCA GGGAGCTACTT |
| 2338 | SCUBE2 | 3362208 | CTGGGACCTATTATGATGGAGCACGAGAACGCTGCATTTTATGTCCAAATGGAACCTTCCAAA ATGAGGAAGGACAAATGACTTGTGAACCATGCC |
| 2339 | SCUBE2 | 3362211 | CCTGAGCTGCATCGTAAAGCGAACCGAGAAGCGGCTCCGTAAAGCCATCCGCACGCTCAGAA AGGCCGTCCACAGGGAGCAGTTTCACCTCCAGCTCTCAGGCATGAACCTCGACGTGGCTAAAA |
| 2340 | SCUBE2 | 3362212 | GAGAGCTTCCGCTACGTAAACCTTACATGCAGCTCTGGCAAGCAAGTCCCAGGAGCCCCTGG CCGACCAAGCACCCCTAAGGAAATGTTTATCACTGTTGAGTTTGAGCTTGAAACTAACCAAAA GGAGGTGACA |
| 2341 | SCUBE2 | 3362213 | CCACCATCAGGACAAGTGTAACCTTTAAGCTAAATGAAGGCAAGTGTAGTTTGAAAAATGCT GAGCTGTTTCCCGAGGGTCTGCGACCAGCACTACCA |
| 2342 | SCUBE2 | 3362215 | CCTACTCTGTCACCTGTGGCTCTTCCT |
| 2343 | SCUBE2 | 3362216 | TGGTGGAGGAGACGGGTGCTTCCTCAGATG |
| 2344 | SCUBE2 | 3362217 | TGCCCACAAGTGTGTCACCCCGTGTGTCCCTGCACTGCG |
| 2345 | SCUBE2 | 3362218 | ACCAATGAGTGTCAGCATCAACAACGGAGGCTGTCAGCAGGTCTGTGTGAACACAGTGGGCA GCTATGAATGCCAGTGCCACCCTGGGTACAAGCTCCACTGGAATAAAA |
| 2346 | SCUBE2 | 3362221 | ACCACCCTGGCACATTTGCTTGTGCTTGCAACCGAGGGTACACCCTGTATGGCTTCACC |
| 2347 | SCUBE2 | 3362222 | ATGAGTGCCAGACCCGCAATGGAGGTTGTGATCATTTCTGCAAAAACATCGTGGGCAGTTTT GACTGCGGCTGCAAGAAAGGA |
| 2348 | SCUBE2 | 3362223 | AACGTGTGCTGTCAACAATGGAGGCTGTGACCGCACCTGTAAGGATACTTCGACAGGTGTCC ACTGCAGTTGTCCTGTTGGATTCACTCTCCAGTTGGATG |
| 2349 | SCUBE2 | 3362226 | GGTGACAGAGAGCAACACCACATCAGTGGTGGATGGGGATAAACGGGTGAA |
| 2350 | SCUBE2 | 3362234 | TGCATGAATAAGGATCACGGCTGTAGTCACATCTGCAAGGAGGCCCCAAGGGGCAGCGTCG CCTGTGAGTGCAGGCCTGGTTTT |
| 2351 | SCUBE2 | 3362235 | GGCTGCCAGCATACCTGTGTCAACGTCATGGGGAGCTATGAGTGCTGCTGCAAGGAGGGGTT TTTCCTGAGTGACAATCAGCACACCTGCATTCACCGCTCGGAA |
| 2352 | SCUBE2 | 3362240 | TGTGGAAATGAGCTCAATGGAGGCTGTGTCCATGACTGTTTGAATATTCCAGGCAATTATCGT TGCACTTGTTTTGATGGCTTCATGTTGGCTCATGACGGTCA |
| 2353 | SCUBE2 | 3362242 | TGTGCCCAAGGGCTAGATGACTGCCATGCCGACGCCCTGTGTCAGAACACACCCACCTCCTAC AAGTGCTCCTGCAAGCCTGGCTACCAAGGGGAAGGC |
| 2354 | SCUBE2 | 3362243 | CCGGGGCGGCCTGGGCGGTGCTGCTGCTGCTGCTGCTGCCGCCACTGCTGCTGCTGGCG GGGGCCGTCCCGCCGGGTCGGGGCCGTGCCGCGGGGCCGCAGG |
| 2355 | SCUBE2 | 3362244 | CGCCACCGCCCGCACTCCGCCGCCTCTGCCCGCAACCGCTGAGCCATCC |
| 2356 | SCUBE2 | 3362262 | GGCCCAGAGAGCTGCAGCGCAGCGTCCTGCCTGCAGAGGGGGTGAGAGGCCACACTGCAGC CGTCTGCCTGGAGCCCACGGACAGAGCTTTAGTTCTCTCGGAGAAGGCCGAGG |
| 2357 | AHNAK | 3375736 | CACCTGCAGTTAAAGGAATACCTTCCGCGAGGCGGCTTTTCGGAGCATGCATGTTTATAGCTC CAGCCAGGCCAGACCGAGGGCTGCTGCATAAGCCCTGCTTGGTGCATTTCTTTACTTGCAAGG |

TABLE 13-continued

Subtyping Target Sequences

| SEQ ID NO. | Gene | Affy Probeset ID | Sequence |
|---|---|---|---|
| | | | GGACAGAGTGTGGGCTTAGGTTTGGGACTAGAGGGGCTTTGGCAACTATGGTGCTCAGGT GATTATCCTTCGCTCGTTTA |
| 2358 | AHNAK | 3375738 | CAGCAGCCAAGCCGGGGCAGTTTCAGTCTCCACC |
| 2359 | AHNAK | 3375739 | CCAGCCAGTTTGGTGCTGACGGTGAGAGGAAATTAGAATCTGTTTGCAAATTGTCCAACCCAC CCCCTCAACATGAGGGGCTTCCATTTTCTGTGTTTTGTAAGGGAACTGTTTCCTTCATGCCGCC ATGTTCCTGATATTAGTTC |
| 2360 | AHNAK | 3375740 | GGGAAACACACCGACTGCCTCAGCAATCATGCAAAGACCTTGCCTGGCCCGGTGGCAAGCGC TGAAAAACCGACCGCCTGTAGGCTCCTGGAACTATACAGATAGGTAAAGAGTTCCAAGTTCG TCCAGCCCATGTGCAAAGTCAACAGTATTTGCCTTAAGATTTCATATATATATATTTTTTTGCAT TGACTGCTGAGAGCTCC |
| 2361 | AHNAK | 3375741 | GCTGAAATTCGGTACCTTTGGTGGATTGGGGTCAAAGAGCAAAGGTCATTATGAGGTGACTG GGAGCGATGATGAGACAGGCAAGTTACAGGGGAGTGGGGTGTCCCTGGCCTCTAAGAAGTC CCGACTGTCCTCCTCTTCTAGCAATGACAGTGGG |
| 2362 | AHNAK | 3375742 | CACGTCTGGATTTCGAAGGCCCTGATGCCAAACTCAGTGGCCCATCTTTGAAGATGCCATCGC TGGAGATATCTGCTCCTAAAGTAACTGCTCCTGATGTTGATTTGCATCTCAAGGCACCAAAAA TTGGATTTTCAGGTCCGAAGTTAGAAGGTGGTGAAGTGGACCTCAAGGGACCCAAAGTTGAA GCTCCAAGCTTAGATGTACACATGGACAGCCCAGATATTAACATCGAAGGGCCAGATGTTAA AATCCCCAAATTTAAGAAACCCAAGTTTGGATTTGGGGCAAAAAGCCCCAAAGCTGACATCAA GTCACCTTCACTGGATGTCACTGTTCCTGAGGCAGAGCTGAACCTTGAGACTCCTGAAATTAG TGTTGGTGGCAAGGGCAAGAAAGTAAGTTTAAAATGCCTAAAATTCATATGAGTGGTCCTA AGATTAAGGCCAAAAACAGGGATTTGACCTGAATGTTCCTGGGGGTGAAATTGATGCCAGC CTCAAGGCTCCGGATGTAGATGTCAACATCGCAGGGCCGGATGCTGCACTCAAAGTCGACGT GAAATCGCCCAAAACCAAGAAAACGATGTTTGGAAAAATGTACTTCCCAGATGTAGAGTTTG ACATTAAATCACCTAAATTTAAAGCTGAGGCCCCTCTCCCTAGCCCCAAACTGGAGGGTGAAC TCCAGGCACCTGATCTGGAACTTTCTTTGCCAGCGATTCACGTCGAAGGTCTTGACATCAAGG CGAAGGCTCCCAAGGTCAAGATGCCAGATGTGGACATCTCAGTGCCAAAAATAGAGGGTGAC CTGAAAGGCCCAAAGTGCAGGCAAACTTGGGTGCACCTGACATCAACATCGAAGGCCTAGA TGCTAAAGTCAAAACACCGTCCTTCGGCATTTCTGCCCCTCAAGTCTCCATCCCTGATGTGAAT GTAAACTTGAAAGGACCAAAGATAAAGGGTGATGTCCCCAGCGTGGGACTGGAAGGACCAG ATGTAGATCTGCAAGGTCCAGAAGCAAAAATTAAGTTCCCCAAGTTTTCCATGCCCAAGATCG GCATCCCAGGTGTGAAAATGGAGGGTGGGGGAGCCGAGGTCCATGCCCAGCTACCCTCTCTT GAAGGAGACTTGAGAGGACCAGATGTTAAGCTCGAAGGGCCCGATGTTTCTCTAAAGGGGC CAGGAGTAGACTTGCCTTCAGTGAACCTCTCTATGCCAAAAGTCTCTGGGCCTGACCTTGATC TGAACTTGAAAGGACCAAGTTTGAAGGGAGACCTGGATGCATCTGTTCCCAGCATGAAGGTG CATGCTCCAGGGCTCAACCTCAGTGGTGTCGGTGGCAAAATGCAGGTGGGAGGAGACGGTG TGAAAGTGCCAGGGATCGATGCCACAACAAAGCTTAACGTTGGGGCACCAGATGTGACACTG AGGGGACCAAGCCTGCAGGGAGATCTGGCTGTCTCTGGTGACATCAAATGCCCTAAAGTATC CGTAGGAGCTCCTGATCTAAGCTTGGAGGCATCCGAAGGCAGCATTAAACTTCCCAAAATGA AGCTGCCCCAATTTGGCATCTCTACTCCGGGGTCCGACTTGCACGTCAATGCCAAGGGGCCAC AGGTTTCTGGCGAACTGAAGGGGCCAGGTGTGGATGTGAACCTGAAAGGGCCTCGGATTTC AGCACCGAATGTGGACTTTAACTTGGAAGGACCAAAAGTGAAAGGGAGCCTTGGGGCCACT GGTGAGATCAAAGGCCCCACTGTCGGAGGAGGTCTTCCAGGCATTGGTGTTCAAGGCCTAGA AGGAAACCTCCAGATGCCTGGAATTAAGTCCTCTGGATGTGATGTGAACCTGCCAGGCGTGA ATGTGAAACTCCC |
| 2363 | AHNAK | 3375743 | GTCCAGACGCAAAACTGAAGGGCCCCAAGTTCAAGATGCCTGAAATAAATATC |
| 2364 | AHNAK | 3375744 | GCCCAAGGCCGACATCGATGTCTCGGGACCCAAG |
| 2365 | AHNAK | 3375745 | ATGTGGATGTTCATGGCCCAGACTGGCACCTGAAGATGCCCAAGGTGAAAATGCCCAAATTC AGCATGCCTGGCTT |
| 2366 | AHNAK | 3375746 | TGGATGTGAACCTGCCCAAGGCTGACATTGATGTCTCAGGACCCAAAGTGGACGTTGATGTT CCTGATGTGAATATCGAAGGTCCAGATGCGAAACTAAAGGGCCC |
| 2367 | AHNAK | 3375747 | TAAAAATGCCCAAAGTGAAAATGCCCA |
| 2368 | AHNAK | 3375748 | GTGGGCATTGACACTCCTGATATTGACATTCATGGTCCAGAAGGGAAACTGAAGGGCCCCAA ATTTAAAATGCCTGACTTACACCTCAAGGCACCGAAGATCTCTATGCCTGAAGTTGACCTGAA TCTGAAAGGTCCAAAGGTGAAGGGCGACATGGACAT |
| 2369 | AHNAK | 3375749 | AAAGGAGATATGGACATTTCCGTTCCTAAACTGGAGGGAGATC |
| 2370 | AHNAK | 3375750 | TAGACATTGAAGGTCCTGAAGGGAA |
| 2371 | AHNAK | 3375751 | AAGGGCCCTGAAATTGACATAAAAGGCCCCAGTTTGGACATTGACACACCTGATGTCAATATT GAAGGTCCGGAAGGGAAA |

TABLE 13-continued

Subtyping Target Sequences

| SEQ ID NO. | Gene | Affy Probeset ID | Sequence |
|---|---|---|---|
| 2372 | AHNAK | 3375752 | TTCCTAAGGCTGACATTGAGATTTCTGGCCCCAAAGTGGACATTGATGCCCCTGATGTCAGTA<br>TCGAAGGTCCAGATGCAAAACTCAAGGGTCCAAAGTTCAAGATGC |
| 2373 | AHNAK | 3375753 | ATGTGGACGTTCAAGGCCCAGACTGGCACTTAAAAATGCCCAAAGTGAAAATGCCCAAGTTC<br>AGCATGCCTGGCTTCAAAGGAGAGGGCCCAGATGTGGATGTGAACCTGCCCAAGGCTGACCT<br>TGACGTCTCAGGACCCA |
| 2374 | AHNAK | 3375754 | AGATGTGGATGTTTCTCTGCCTAAGATGGAAGGTGATCTAAAGGCCCCTGAAGTTGACATCA<br>AGGGCCCCAAAGTGGACATTGATGCCCCAGATGTGGATGTTCATGGCCCAGACTGGCACCTG<br>AAGATGCCCAAGGTGAAAATGCCCAAATTCAGCATGCCAGGATTTAAAGGAGAGGGCCCAG<br>AAGTGGATGTTAATTTGCCCAAAGCTGA |
| 2375 | AHNAK | 3375755 | GTGACATGCAAGTTCCTGACTTGGATATTAAAG |
| 2376 | AHNAK | 3375756 | GGCCCAGACTGGCACCTGAAGATGCCCAAGGTGAAAATGCCCAAGTTCAGCATGCCTGGCTT<br>CAAAGGAGAGGGCCCAGATGTGGATGTGAACCTGCCCAAGGCTGA |
| 2377 | AHNAK | 3375757 | GTGACCTCAAGGGTCCTGAAGTTGACATCAAGGGCCCCAAAGTGGACATTAATGCTCCAG |
| 2378 | AHNAK | 3375758 | AAGGGCGATGTGGATGTTTCTCTGCC |
| 2379 | AHNAK | 3375759 | AAATTTAAGATACCAGAGATGCACCTGAAGGCTCCCAAAATATCGATGCCTGACA |
| 2380 | AHNAK | 3375760 | CATTGACACTCCTGACATTAACATCGAAG |
| 2381 | AHNAK | 3375761 | CCAGAGGTTGATATCAAAGGCCCTAAAGTGGACATCAATGCCCCAGATGTGGATGTTCATGG<br>TCCAGACTGGCATCTGAAGATGCCCAAAGTGAAAATGCCCAAGTTCAGCATGCCTGGCTTCAA<br>AGGAGAAGGCCCTGAAGTCGATGTTACCCTCCCTAAAGCTGACATTGACATTTCTGGTCCCAA<br>TGTAGACGTTGATGTTC |
| 2382 | AHNAK | 3375762 | GTGATGTGGATATTTCTCTTCCCAAACTTGAAGGGGATCTGAAAG |
| 2383 | AHNAK | 3375763 | GCCCAAAGATAGATGTAGATGCTCCAGATATTGACATTCATGGCCCAGATGCCAAATTAAAAG<br>GTCCAAAACTGAAGATGCCTGACATGCATGTAAACATGCCCAAGATCTCCATGCCAGAAATTG<br>ACTTGAATTTGAAAGGCTCAAAGCTTAAGGGAGATGTTGATGTCTCTGGGCCCAAGTTGGAA<br>GGTGACATTAAAGCTCCCAGTTTGGATATAAAGGGCCCAGAGAGTGGACGTTTCCGGTCCTAA<br>GCTTAATATCGAAGGCAAGTCAAAGAAATCTCGTTTTAAGCTTCCCAAATTTAATTTTTCGGGC<br>TCTAAAGTTCAGACACCTGAAGTGGATGTCAAAGGTAAAAAGCCAGATATTGACATAACAGG<br>TCCAAAAGTTGATATTAATGCTCCTGATGTCGAGGTCCAAGGAAAAGTGAAAGGATCCAAGT<br>TTAAAATGCCTTTCCTGAGTATTTCATCTCCCAAAGTTTCTATGCCTGACGTGGAGCTAAATTT<br>GAAA |
| 2384 | AHNAK | 3375764 | CCAAGATCAGCATGCCTGGCTTCAAAGGAGAAGGTCCAGAAGTGGACGTGAACCTGCCCAAG<br>GCTGACCTTGACGTCTCAGGACCCAAGGTGGACGTTGATGTTC |
| 2385 | AHNAK | 3375765 | GCCCAAATTCAGCATGCCTGGCTTCAAAGGAGAGGGCCCAGATGTGGATGTGAACCTGCCCA<br>AGGCTGACCTTGATGTCTCAGGACCCAAGGTGGACATTGATGTTCCAGATGTGAATATCGAA<br>GGCCCAGAGGGAAAGTTGAAAGGTCCCAAATTCAAAATGCCTGAGATGAACATCAAAGCCCC<br>CAAGATCTCCATGCCTGACATTGATCTTAACCTGAAA |
| 2386 | AHNAK | 3375766 | TGGACATTGACGCACCTGATGTTGATGTTCATGGCCCAGACTGGCACCTAAAGATGCCCAAG<br>ATAAAAATGCCCAAGATCAGCATGCCTGGCTTCAAAGGAGAAGGTCCAGATGTGGACGTGAA<br>CCTGCCCAAGGCTGACATTGATGTCTCAGGACCGAAAGTGGATGTTGAATGTCCCGATGTGA<br>ATATCGAAGGACCTGAAGGAAAGTGGAAAAGTCCAAAGTTTAAGATGCCAGAGATGCATTTT<br>AAGACTCCAAAGATATCCATGCCAGATATTGACCTGAATCTCACAGGTCCAAAAATAAAGGA<br>GATGTGGATGTTACAGGCCCTAAGGTAGAGGGAGATCTGAAAGGTCCTGAAGTTGACCTCAA<br>AGGCCCCAAAGTGGACATTGATGTCCCAGATGTTAATGTTCAGGGTCCAGACTGGCACCTGA<br>AGATGCCCAAGATGAAAATGCCCAAGTTCAGCATGCCTGGCTTCAAAGCAGAGGGCCCTGAA<br>GTGGATGTGAACCTGCCCAAGGCTGACGTTGATGTCTCAGGCCCCAAAGTGGACGTTGAAGG<br>CCCTGATGTTA |
| 2387 | AHNAK | 3375767 | GTGGAAGGTGACCTCAAGGGCCCAG |
| 2388 | AHNAK | 3375768 | AAAGGACCCAAAGTGAAGGGTGATG |
| 2389 | AHNAK | 3375769 | AGAGGGCCCTGAAGTAGACGTCAACTTGCCTAAGGCTGACGTTGACATCTCAGGACCCAAGG<br>TGGACATTGAAGGCCCTGATGTTAATATTGAAGGACCAGAGGGA |
| 2390 | AHNAK | 3375770 | AAGTACCAGATATGAACATCAGGGGCCCCAAAGTTGATGTAAATGCCCCCGATGTCCAAGCT<br>CCAGACTGGCACCTGA |
| 2391 | AHNAK | 3375771 | ACTCCTAAGTTCAAGATGCCAGATATGCACTTTAAAGCTCCCAAAATCTCTATGCCAGACCTCG<br>ATCTACACTTGAAGAGCCCCAAGGCAAAAGGAGAGGTGGATGTAGATGTTCCCAAATTGGAA<br>GGGGACCTTAAAGGGCCACATGTGGATGTC |

TABLE 13-continued

Subtyping Target Sequences

| SEQ ID NO. | Gene | Affy Probeset ID | Sequence |
|---|---|---|---|
| 2392 | AHNAK | 3375772 | CAGAATTGGATGTCAAAGGTCCCAAATTAGATGCTGACATGCCAG |
| 2393 | AHNAK | 3375773 | CTCCATGCCTGATGTTGATTTCAATTTAAAGGGACCCAAAATCAAAGGAGATGTTGATGTTTC<br>TGCCCCAAAG |
| 2394 | AHNAK | 3375774 | GTTCCCAAGGTAGAAGGTGAAATGAA |
| 2395 | AHNAK | 3375775 | TGAGATGCACTTCAAGGCCCCCAAGATCTCCATGCCTGATGTGGACTTACACTTGAAAGGCCC<br>CAAAGTCAAAGGGGATGTGGATGTGTCTTTGCCAAAATTGGAGGGAGATTTAACAGGCCCCA<br>GTGTGGATGTGGAGGTGCCTGATGTTGAGCTGGAGTGTCCT |
| 2396 | AHNAK | 3375776 | GCCCAAGTTCAGCATGCCTGGCTTCAAA |
| 2397 | AHNAK | 3375777 | CATTGATGCCCCAGATGTGGATGTTCATGGCC |
| 2398 | AHNAK | 3375778 | CCGCAAGTTGATGTCAAAGGTCCTTTTGTGGAAGCGGAGGTGCCCGATGTTGATCTGGAGTG<br>TCCTGATGCAAAGTTGAAAGGGCCCAAGTTTAAGATGCCTGAGATGCACTTCAAGGCCCCCA<br>AGATCTCCATGCCTGATGTGGACTTACACCTGAAAGGCCCCAAAGTCAAAGGGGATGTCGGAT<br>GTGTCGGTGCCAAAATTGGAGGGAGATTTAACAGGCCCCAGTGTGGGTGTGGAGGTGCCTG<br>ATGTTGAGCTGGAGTGTCCTGATGCAAAGTTGAAAGGCCCTAAATTTAAGATGCCAGACATG<br>CACTTC |
| 2399 | AHNAK | 3375779 | ATGTGGAGGTTCACGACCCAGATTGGCACCTGAAAATGCCCAAGATGAAAATGCCCAAGTTC<br>AGTATGCCTGGCTTCAAAGCAGAGGGCCCTGAAGTGGATGTGAATCTGCCAAAGGCTGACAT<br>TGATGTGTCTGGACCCAGTGTGGACACTGATGCTCCTGATTTGGATATTGAGGGACCAGAAG<br>GAAAGTTGAAAGGCTCCAAATTTAAGATGCCCAAGTTGAATATAAAAGCTCCCAAGGTCTCCA<br>TGCCAGATGTGGACTTGAATTTGAAGGGACCCAAACTGAAGGGAGAGATAGATGCTTCTGTG<br>CCA |
| 2400 | AHNAK | 3375780 | GCCTGATGTGGACCTGAATCTTAAGGGGCCAAAATTGAAGGGAGATGTGGATGTGTCCTTGC<br>CTGAGGTAGAAGGTGAAATGAAAGTGCCAGATGTTGACATTAAAGGGCCCAAAGTTGACATT<br>AGTGCTCCAGATGTGGATGTTCATGGCCCAGATTGGCACCTGAAGATGCCCAAGGTGAAAAT<br>GCCCAAGTTCAGCATGCCCGGCTTCAAAGGAGAGGGCCCTGAAGTGGATGTGAAGCTGCCCA<br>AGCTGACGTTGATGTCTCAGGACCCAAAATGGATGCTGAAGTTCCAGATGTGAATATTGAA<br>GGTCCAGACGCAAAACTAAAAGGTCCCAAATTCAAGATGCCAGAAATGAGTATAAAAGCCTCA<br>GAAGATATCCATACCAGATGTTGGTTTGCATTTGAAAGGTCCTAAAATGAAAGGAGATTATG<br>ATGTAACAGTTCCAAAAGTAGAAGGAGAGATAAAAGCTCCTGATGTTGACATCAAAGGCCCC<br>AAAGTTGATATTAATGCACCAGATGTGGAGGTTCATGGCCCAGACTGGCACCTGAAGATGCC<br>CAAGGTAAAAATGCCCAAGTTCAGCATGCCTGGCTTTAAAGGAGAGGGCCCAGAGGTGGAT<br>ATGAACCTGCCCAAGGCTGACCTTGGTGTTTCAGGACCCAAGGTGGACATTGATGTTCCAGAT<br>GTGAATCTTGAAGCTCCAGAGGGGAAACTAAAAGGCCCTAAGTTCAAGATGCCAAGCATGAA<br>TATACAGACGCACAAAATCTCTATGCCTGATGTTGGACTTAATTTGAAAGCCCCTAAACTGAA<br>AACTGATGTAGATGTTTCCCTTCCCAA |
| 2401 | AHNAK | 3375781 | GACCCAGAGCCGTACCATCACAGTGACCAGAAGGGTCACGGCCTACACTGTGGATGTGACTG<br>GCCGGGAAGGAGCCAAGGACATAGACATCAGTAGCCCTGAATTCAAGATCAAGATTCCAAGA<br>CATGAACTGACTGAAATCTCCAATGTGGATGTGGAGACCCAGTCTGGGAAGACCGTGATCAG<br>ACTGCCCTCGGGCTCGGGGGCAGCCTCTCCGACAGGCTCTGCTGTGGATATCCGAGCAGGGG<br>CCATTTCTGCTTCAGGACCAGAGCTCCAAGGTGCTGGCCACTCGAAGCTCCAGGTCACCATGC<br>CTGGGATAAAGGTGGGAGGCTCAGGTGTCAATGTCAATGCAAAGGGCTTGGACTTGGGTGG<br>CAGAGGAGGGGTCCAAGTTCCAGCAGTGGACATTTCATCTTCTCTTGGGGGTAGGGCAGTAG<br>AGGTACAGGGCCCATCTCTGGAGAGTGGTGATCATGGCAAAATTTAAATTTCCCACCATGAAA<br>GTGCCGAAATTTGGTGTCTCAACAGGGCGTGAGGGCCAGACACCAAAGGCAGGGCTGAGGG<br>TTTCTGCACCTGAAGTCTCTGTGGGGCACAAGGGCGGCAAGCCAGGCTTGACTATCCAAGCC<br>CCTCAGCTGGAAGTCAGTGTGCCCTCTGCCAATATTGAGGGCCTTGAGGGGAAGCTGAAGGG<br>CCCCCAAATCACTGGGCCATCACTTGAGGGTGACCTAGGCCTGAAAGGTGCCAAGCCACAGG<br>GGCACATTGGGGTGGATGCCTCTGCTCCCCAAATTGGGGGTAGCATCACTGGCCCCAGTGTG<br>GAAGTTCAGGCCCCTGACATTGATGTTCAGGGGCCTGGGAGCAAACTGAATGTGCCCAAGAT<br>GAAAGTCCCCAAGTTCTCTGTATCAGGTGCAAAGGGAGAGGAAACTGGGATTGATGTGACAC<br>TGCCTACAGGTGAAGTGACTGTTCCTGGGGTCTCTGGGGATGTCAGCCTGCCTGAGATTGCTA<br>CTGGTGGGCTGGAAGGAAAGATGAAAGGTACTAAAGTGAAGACTCCTGAAATGATTATTCAG<br>AAACCTAAAATCTCCATGCAGGATGTGGATCTGAGCCTTGGGTCTCCTAAACTGAAAGGAGA<br>TATTAAGGTTTCTGCTCCTGGGGTGCAAGGTGATGTTAAAGGCCCTCAAGTGGCACTTAAAG<br>GCTCCAGAGTGGACATAGAGACACCAAACCTAGAGGGAACCTTGACAGGCCCTAGGCTTGGC<br>AGTCCTTCCGGGAAAACCGGAACCTGTAGGATCTCTATGTCAGAAGTAGACTTAAATGTGGC<br>CGCACCTAAAGTGAAAGGGGTGTAGATGTCACACTCCCCAGAGTAGAAGGGAAAGTCAAA<br>GTCCCTGAAGTTGATGTCAGAGGCCCCAAAGTGGATGTCAGTGCCCCAGATGTCGAAGCGCA<br>TGGCCCCAGAATGGAACCTGAAAATGCCCAAGATGAAAATGCCCACGTTCAGCACTCCAGGAG<br>CCAAAGGGGAAGGTCCAGATGTTCATATGACTCTACCCAAAGGAGATATCAGTATTTCAGGG<br>CCCAAGGTCAATGTGGAAGCCCAGATGTCAACTTGAGGGTCTGGGGGAAAACTTAAAG<br>GCCCCGATGTTAAGCTGCCTGATATGAGTGTCAAGACACCAAAGATCTCCATGCCTGATGTAG<br>ATTTGCACGTGAAAGGTACAAAGGTGAAGGAGAGTATGATGTAACTGTACCAAAGCTGGA<br>AGGAGAACTCAAAGGCCCAAAAGTGGACATTGATGCCCCAGATGTGGATGTTCATGGCCCAG |

TABLE 13-continued

Subtyping Target Sequences

| SEQ ID NO. | Gene | Affy Probeset ID | Sequence |
|---|---|---|---|
| | | | ACTGGCACTTGAAGATGCCCAAGATGAAAATGCCCAAATTCAGTGTGCCAGGGTTCAAAGCA GAGGGCCCAGAAGTGGATGTGAACCTGCCCAAGGCTGATGTGGACATTTCCGGGCCCAAGA TAGATGTTACTGCTCCTGATGTGAGCATTGAGGAACCAGAAGGGAAATTGAAAGGGCCCAAG TTTAAGATGCCTGAGATGAACATCAAAGTCCCCAAGATCTCCATGCCTGATGTGGACTTACAT CTGAAAGGCCCTAACGTAAAGGGAGAATATGATGTCACAATGCCAAAGGTTGAAAGTGAGAT TAAAGTTCCTGATGTTGAACTTAAAAGTGCCAAAATGGACATTGATGTCCCAGATGTGGAGGT TCAAGGCCCAGACTGGCACCTGAAGATGCCCAAGATGAAAATGCCCAAGTTCAGCATGCCTG GCTTCAAAGCAGAGGGCCCAGAAGTGGATGTGAACCTGCCCAAGGCTGATGTGGACATCTCA GGACCCAAGGTGGGTGTTGAAGTTCCAGATGTGAATATTGAAGGACCTGAAGGAAAGCTGA AGGGCCCCAAGTTCAAGATGCCAGAGATGAATATCAAGGCCCCCAAGATCTCCATGCCTGAT GTGGACTTGCATATGAAAGGTCCTAAAGTAAAGGGAGAATATGATATGCAGTGCCAAAGCT GGAAGGGGACCTGAAAGGCCCAAAAGTAGATGTCAGTGCCCCAGATGTTGAAATGCAGGGT CCTGACTGGAACTTGAAGATGCCAAAGATTAAAATGCCCAAATTTAGCATGCCCAGCCTCAAA GGAGAGGGGCCAGAATTTGATGTGAACCTGTCCAAAGCGAATGTG |
| 2402 | AHNAK | 3375783 | GGGTGCCACCATCTACTTTGACAACCTGCAGTCGGGTGAGGTGACCCAGCTGCTGAACACCA TGGGGCACCACACGGTGGGCCTGAAGCTGCACCGCAAGGGGGACCGCTCTCCCGAGCCTGG CCAGACCTGGACCCGTGAAGTCTT |
| 2403 | AHNAK | 3375784 | AAGGAGGAGACAACCCGGGAGCTGCTGCTGCCCAACTGGCAGGGTAGTGGCTCCCACGGGC TGACCATCGCCCAGAGGGACGACGGCGTCTTTGTGCAGGAGGTGACGCAG |
| 2404 | SYTL2 | 3385044 | CCAGAGCATTAAACATGGGGTATTGTTAAGAAGCAAAATGTTCTTGTTTGCCATCATGTGTTT CACACCACAATTCTGTGCCACAGTTAAGAGGGTCTGGTACCCTTGCAGGACCTTTGTAGGTTG TGGGAAAAAGTCGCAGAAAGATACTCAAAGTGGAGCAGGGAATGGAGACAGACATCAGTGA TGATAAAAAAAAAAATGGACCTTAAGAAACTATTTACTCTGTAATCTCTAATAAAATATGGAA TTCCATATTAGGGCAATGAGACTGAAACTACTGGTGTTTTCTGCCTTGAGAAAACAAACAGT TAAAACAAGCCTCAAATGTATTTTAGTGCCACCCACTGGCCATAGGTACAATTCAGTTGTTGG CTTGTTTTGACTTAATTCTAAAATAGGTCTCAAGCCTGTATTTTTATGA |
| 2405 | SYTL2 | 3385045 | CTACTAAACCGGTGGAATCTGATCTTGAAAATCTGAGTAGGTGGACAAATATCCTCACTTTCT ATCTATTGCACCTAAGGAATACTACACAGCATGTAAAAGTCAATCTGCATGTGCTTCTTTGATT ACA |
| 2406 | SYTL2 | 3385046 | TGGACTCTACTTCAGAGGAAGTTGCTCTCTGGGAGAAGATGGTAAACTCCCCCAATACTTGGA TTGAAGCAACACTGCCTCTCAGAATGCTTTTGATTGCCAAGATTTCCA |
| 2407 | SYTL2 | 3385048 | CTATGGTGTATGATGGGTTCAGGCCTGAAGATCTGATGGAAGCCTGTGTAGAGCTTACTGTCT GGGACCATTACAAATTAACCAACCAATTTTTGGGAGGTCTTCGTATTGGCTTTGGAACA |
| 2408 | SYTL2 | 3385052 | AAGCTTCCTACAACTGGAGAAGTGCACATCTGGGTGAAGGAATGCCTTGATCTACCACTGCTA AGGGGAAGTCATCTAAATTC |
| 2409 | SYTL2 | 3385055 | AATGAAACTAGCTCTCCAGTATGTCCCA |
| 2410 | SYTL2 | 3385060 | CACAGAAATTGAACCTGTCCATTTGGCATCGGGATACATTTAAGCGCAATAGTTTCCTAGGGG AGGTGGAACTTGATTTGGAAACATGGGACTGGGATAACAAACAGAATAAACAATTGAGATG GTACCCTCTGAAGCGGAA |
| 2411 | SYTL2 | 3385064 | TTGCCCAGGCTGGCACGATCTCAGC |
| 2412 | SYTL2 | 3385065 | GTGATGAGTGTTTATAGTGGAGACTTTGGCAATCTGGAAGTTAAAGGAAATATTCAGTTTGCA ATTGAATATGTGGAGTCACTGAAGGAGTTGCATGTTTTTGTGGCCCAGTGTAAGGACTTAGCA GCAGCGGATGTAAAAAAACAGCGTTCAGA |
| 2413 | SYTL2 | 3385067 | GAGCTCTTTAACCAATCTTAGCAGCTCCTCTGGCATGACGTCCTTGTCTTCT |
| 2414 | SYTL2 | 3385071 | ATGAGCAAGTCTGTTCCAGCATTTCTCCAA |
| 2415 | SYTL2 | 3385072 | TGCCTACACAACCTGATAATCCATTTTCTCACCCTGACAAACTC |
| 2416 | SYTL2 | 3385073 | ACCATTCTAACTTTGCCTTGGGATATTGAAAATTCTGAATCAGTGAGGTATCTAAATAATTTAT ATTTTCAAAAAATAATGTTTATTTTATAATTCTGAGTGTAAAACACTATCAGAAAAGTAATCCT CATGCTCACTAAACAAACCTACTCTAAGACACTCAACAACCAGAACAGTTTTATTATTGAGTTG TGTACAAAAATCTTGACTGTCCAGATGAAATAGTTTTTCAGCCTGCAGTGTGTTAGTGATATAT CTCAAGGAGATGAACCAATAAAGTACAGACTTTGTGGTCTGAAGCTCTGTTGTGAAAAAATA AGCTAAACCAATTCACACTGACAGTATAATTTGATTCAAGTGCAGCTCCAGTTCAATAAAAACT AATGTTTTTAAAATTAACTTTGTTTTGTATTTGGTTCAACTCCTTGCTAGTTCTCTCTATATAA TTTATAAAAACTGCATGTTGCTAATCTCATGATCCTGTGCATGTGGACTACTCTGCCTTTAACTTT |
| 2417 | SYTL2 | 3385076 | AGTTACAAATGAATGCGTACCAAGAA |
| 2418 | SYTL2 | 3385077 | CCTGTCAGATGTATTCTGCTGTCTCAGTTGTGAAACTGACATTTGAGCTTTACTTTCATGTCTCT TTAATCCTTCTGTTAAAATGGTATTTATTCTCAATGTTGCCCTCCTGAGTA |

TABLE 13-continued

Subtyping Target Sequences

| SEQ ID NO. | Gene | Affy Probeset ID | Sequence |
|---|---|---|---|
| 2419 | SYTL2 | 3385080 | AAGTAGATAATCAGCCAGAAGAATTAGTGCGTAGTGCTGAA |
| 2420 | SYTL2 | 3385081 | GGTTGCACCCCTCATTGCATCTTGACTAATTGCTTCCAACTCCGGGGGCTTCCAGGGACAATCTCATTGTTCTTTTCTCTCCAAGGGTCAGCCATG |
| 2421 | SYTL2 | 3385083 | TGCCAAGATTCCACTTAGCAGCTGGTCCCCAGTTACATCTCTTCAGTTGACTTCCCAAGCAAGCCTCCCAGAGGCATATGTGAATGATGATGC |
| 2422 | SYTL2 | 3385086 | AAACTTTGGAAAGGAGTGCCGCTAGGAAAATGCCTTCCAAAAGTCTAGAAGACATTTCATCAGATTCATCAA |
| 2423 | SYTL2 | 3385092 | ATGGAAACACCAGTTCTAATGCAGAGAGCTGGAG |
| 2424 | SYTL2 | 3385093 | GTAAAGTTGAATTGACTCTAGCATCGCCATATATGAAACAAGAGAAAGAGGAAGAAAAAGAAGGTTTCTCTGAGTCTGATT |
| 2425 | SYTL2 | 3385094 | CTGAAGCAATTAGTGTGTCCAGAAATAGGCAACCCATTCCTCTCC |
| 2426 | SYTL2 | 3385095 | AGATTTTTGTGGTTCCAGAAGTGGAGTTGAGATCCCTAGAACCCCACAACTTTATGTGGCTCATGAAATAGGGACCATTAAAACTGTAACCCCCCAGAGGACAGGGACAGTGAAAGTGGGGTTGC |
| 2427 | SYTL2 | 3385096 | GTAATGGTTTGGAATCTCAAGTCAACCAATGTGATAAAATGTTGGGAGGAGACGCACTTGTGACTGATTTAT |
| 2428 | SYTL2 | 3385097 | CTCACAGACCTCTGAAATGAAGGATAAAA |
| 2429 | SYTL2 | 3385098 | ATAGGTAGTACAGAGGAGCCCAGGCGAGCCACTTCTGAATGCCATCCTGAGGAATTAAAAGAAACAGTAGAAAAGGCCGAGGCTCCGTTAATAACTGAGAGTGCTTTTGATGCTGGTTTTGAGAAACTTCTTAAAGAAATAACTGAAGCTCCTCCTTATCAGCCCCAGGTGTCAGTGAGAGAAGAAACTCACGAGAAGGAGTCCTCACAGTCAGAGCA |
| 2430 | SYTL2 | 3385099 | GTGAGGGAAACAATTGTTCAACCCAAATCAGAG |
| 2431 | SYTL2 | 3385100 | TGGGCTACGATGGACACCATAGTTCCAGACAGGAAGGATTTTTATTCCTCCAATGTAGTTCCTGATAAAACTCATGAAGTTGGATCTTATTTAGCTGCCCAAATGTCTCCATCAGACCAGACGCTTAGCTCATTTGCTTCCATTGTTGCTCAATATGGCAAAGGCC |
| 2432 | SYTL2 | 3385101 | AAGTATGGTTAAGTTATCCAGCTGGAAGGGAAGTAGGTCCTGGAGAAGTGAACCCAGAATTTCCTGAAGCAGTACAGCCAGTATGTAGCCCCCTAAATCC |
| 2433 | SYTL2 | 3385102 | TCCATTGGATCCAACTTCCCAGCTTTCCAGAAAGGGTTCTTTTGGGGATGTGGCCAGCCCTCCCCAAGATATGCTTTTTCCCCAGGATGCTCATCTTGTTCCCCAGGCTAGGGTACACCCTTCTCAAACGGAAATTTCGGAGACTGTAGAGAAAGTCATTCTTCCACCCAGACCTGTATTGAATGA |
| 2434 | SYTL2 | 3385103 | TTCAAAGGGCATACTCCAGGTGCTACCAGATGAAATCACATTTCCTTTGAGTCCACTTAGAAAGTATACTTATCAGTTGCCAGGAAATGAGTCATCAAAGGAAAATGTGGAAAAGAATACGGAAGGGATTGTTACTCCAGTGTTTAAGGAAGAAAAGGATTACTCAGAACAAGAGATTCAAGAATCCATAATAAAAACCAATGTTTTGTCTAAAGACTGCAAAGACACTTTTAATGACAGCTTGCAGAAACTGCTTTCAGAAACCTCAACACCAGCAATTCAACCCTCTGGTGGAAAAGTTCATGGAAAACAAGTGCTTGAACCAAGTGTTTCTGAAAATAGGACATGGCCTCAAAAAACAGATTTTGCTGATACTGAGGAAGAAGTCAAAGGACCTGAGAAGATCATTAATGAGCATGTTGACAAAACAGTAGTTCATCCAAAGGTTAAACGGAACTCTTTGACTGCTAGTCTAGACAAACTCCTGAAGGAAGCAACTGGAACTTCACCCTCTCCCTTGCAAGCCAAGTTGGCGCCTGTTATCACTGGAACCAACTCTAAGCTGGAAGAGGGGAGATTTTTTGGAAAAGGGATAGAACAGAGTCACAATACTTCAGCTGATAAGAGAGAAATACTAGCTCCTTTTCCAGTGAGAGA |
| 2435 | SYTL2 | 3385104 | TTCTGCTAAAGCATATCAGCCTGTGAAGAAGTCACAGGGTGTATCATCCATGGACAGTTTATCTACAGACCAGAGTGAATATAATCAGGCCATTCCCAAACGAGTGGTCTTAGATGAGGATGATCAAGCATCCCAGCTCTCCAATTCTTATTCCTCAAATAAATCTAAAGAGACCAAGCCACAAATAGCAGGTCCATCCAGATACTATCTTTCAGCTGAGCAATCAGATAAAGTGTCTCTGTTTCAGAATAAGAAAAATGAGCCTATAAAAGATCACAAGTGGCAGACAGTTTGCCTTCTAGAAGAACATTACTTTACCAGCACTGCAACCTCCCTCAAATGTCGGGAGTGAACGACATGCTCCATTGGAGAAAGACAGACCTCTAGTTCGTGAATCA |
| 2436 | SYTL2 | 3385105 | AACCAAGTGCAGAGAGAGAAATACAAAAGAGTGAGTGACAGAATATCCTTTTGGGAAGGA |
| 2437 | SYTL2 | 3385106 | CACGTTCTGGTCCATATGCCACTGAGATAAAGAAGTCAACTGATGATTCCATATTTAAAGTTCTAGACTGGTTTAACCGAAGTTCTTATTCAGATGACAATAAGTCATTCCTCCAACATCCCCGAGGAATAGAGTCCAAGAAAAAACAGACTCAAAATCACAGGTTGCTGTTGACTTGGTGACAGATGACACTACTTTAAGAGAAAATGGCTCAAAGACCCTATCACCCAGCAAAATTGAATTGAAGCCTGTGAGATCTGACTCACCATTCCAAGCAGAGGGAGATATGCTGGTTTCTGAAAGTTGCCAAGATAATAATGTGAATATCAAATCCAAATTCATGAATTTGTCCCAAAAAGGCACCCCAAAGGAAGGC |

TABLE 13-continued

Subtyping Target Sequences

| SEQ ID NO. | Gene | Affy Probeset ID | Sequence |
|---|---|---|---|
| | | | CCAGGTATATTGCAACCATTTGAAAGCTATGGCACCCCAAGTCAAGGGAGTAAAAATATGGA CTATAGCCAAGATTCAAAAAGCCCAGGAAAAGGGAATGGGGCATCTCCTTCAAATAGTAACT |
| 2438 | SYTL2 | 3385107 | TAAGCCCCCTCCTCTCCCGGCTCTA |
| 2439 | SYTL2 | 3385108 | ATGAACTGTCTCATTGTGTTGAGCCTGAGCCATCTCAGGTGCCAGGTGGCAGTTCTAGAGACC GTCAGCAAG |
| 2440 | SYTL2 | 3385110 | GTTGTCACTACTAGATTATAAAAAC |
| 2441 | SYTL2 | 3385111 | GTGACCCTAAGCCTTCTCAATACAGAAAGCCTTCGCTTTTTCATCAATCAACCTCAAGCCCATA TGTATCAAAAAGTGAAACACATCAGCCAATGACTTCTGGTTCTTTTCCAATTAATGGGCTGCAT TCTCATTCAGAAGTTTTAACTGCAAGACCACAGTCTATGGAGAATTCACCAACCATCAATGA |
| 2442 | SYTL2 | 3385112 | GAATTTAGTGTTTTAGAATCTGACAGAT |
| 2443 | SYTL2 | 3385113 | AGAGGGATCCTCAAGCGCAACTCCAGTTCCAGTAGCACAGACTCAGAAACCCTTCGTTATAAT CACAACTTTGAACCCAAAAGCAAAATTGTGTCACCTGGCCTAACCATCCATGAGAGAATTTCT GAGAAGGAGCATTCTTTAGAAGACAACTCTTCCCCAAACTCCCTGGAGCCATTAAAGCATGTG AGATTCTCTGCAGTGAAGGATGAGCTTCCACAGAGTCCTGGGCTAATCCATGGTCGGGAA |
| 2444 | SYTL2 | 3385114 | GAAAAGTCAACTGTCGCAGATACTTCAATCCAAAAGTTAGAGAAATCAAAGCAGACTTTGCCA GGCCTTTCAAATGGGTCCCAAATCAAGGCTCCAATCC |
| 2445 | SYTL2 | 3385116 | AGGAAGAATCCGTTTAATAGCTCCAAGTTGCCAGAAGGTCACTCATCACAACAAACTAAAA |
| 2446 | SYTL2 | 3385117 | CAGTGTGGTAAATCCAGCTTCCAGTGTGATTGATATGTCCCAGGAAAACACAAGGAAACCAA ATGTGTCT |
| 2447 | SYTL2 | 3385119 | TCCAGAGCTGGCTGGCGTTGTAGAAGAGCCAGAAGAAGATGCAGCACCAGCAAGCCCGAG |
| 2448 | SYTL2 | 3385120 | GAAAAAATTAAGGATGACCAGCAGCTGAAGAATATGAGTGGCCAATGGTTTTATGAAGCCAA GGCAAAAAGGCACAGGGACAAAATCCATGGCGCAGATATCATCAGAGCATCTATGAGAAA |
| 2449 | SYTL2 | 3385121 | ATGAAGGTTTTGCAGCGGGATGCTGCTCTGAAGAGGGCCGAAGAAGAGAG |
| 2450 | SYTL2 | 3385122 | ATGATTGACTTAAGCTTCCTGACTGA |
| 2451 | SYTL2 | 3385123 | TGCTGCCTCTTATGAATTGACGACAGGTGCAGAGAGAGAATAAACTGTGTCTAAGACTGGAC CAGAGAGTGAGTGTGCTGGAAGCCACCATAGGAACAAGCGACCTGTTTGGCAAGGAATACA GCATCCTTCTGAGAGCCTCTTCTCGACACTATCCCACAGACCAGGACTTCCTCATGGGAAAGA GCACTTAGGATCTTGCTATCAGCTGCCCTAAACTTTTGCTGAGCCAAAATAAGACTTTGATGCA GAACTGAACAAGATATTTCATTTTTGTGTGTTTTAATCTTCCTGGTTGCAGTCTTAGTTGTTCAG CCCTGAGAATTTTGAGCCACATTT |
| 2452 | SYTL2 | 3385127 | AGCGTCCGTCGGGAGAGTGAAGGCTCGCAACGCCTTGCCCGGGGGAAGGTAACGCGCCGCG CCCGGGGCTGCGCGGTTTGCACCGCCAGGCCGAGGGCTGGGGGCCAGAAGACAAGAGAGA CGGCGAGGC |
| 2453 | MMP1 | 3388808 | ATGGATTCATATAGGCCAGAGTTGCAAAGATCTTTTCCAGAGTATGCAACTCTGACGTTGATC CCAGAGAGCAGCTTCAGTGACAAACATATCCTTTCAAGACAGAAAGAGACAGGAGACATGAG TCTTTGCCGGAGGAAAAGCAGCTCAAGAACACATGTGCAGTCACTGGTGTCACCCTGGATAG GCAAGGGATAACTCTTCTAACACA |
| 2454 | MMP1 | 3388809 | AAAGCTAATAGCTGGTTCAACTGCAGGAAAAATTGA |
| 2455 | MMP1 | 3388810 | AACGATCTATGGATCCAGGTTATCCCAAAATGATAGCACATGACTTTCCTGGAATTGGCCACA AGTTGATGCAGTTTTCATGAAAGATG |
| 2456 | MMP1 | 3388812 | ATAAGTACTGGGCTGTTCAGGGACAGAATGTGCTACACGGATACCCCAAGGACATCTACAGC TCCTTTGGCTTCCCTAGAACTGTGAAGCATATCG |
| 2457 | MMP1 | 3388813 | TTCTACCCGGAAGTTGAGCTCAATTTCATTTCTGTTTTCTGGCCACAACTGCCAAATGGGCTTG AAGCTGCTTACGAATTTGCCGACAGAGATGAAGTCCGGTTTTTC |
| 2458 | MMP1 | 3388814 | GCTAACCTTTGATGCTATAACTACGATTCGGGGAGAAGT |
| 2459 | MMP1 | 3388815 | CGTTCCCAAAATCCTGTCCAGCCCATCGGCCCACAAACCCCAAAAGCGTGTGACA |
| 2460 | MMP1 | 3388817 | ACTTACATCGTGTTGCAGCTCATGAACTCGGCCATTCTCTTGGACTCTCCCATTCTACTGATATC GGGGCTTTGATGTACCCTAGCTACACCTTCAGTGGTGATGTTCAGCTAGCTCAGGATGACATTG |
| 2461 | MMP1 | 3388818 | GGGACAACTCTCCTTTTGATGGACCTGGAGGAAATCTTGCTCATGCTTTTCAACCAGGCCCAG GTATTGGAGGGGATGCTCATTTTGATGAAGATGAAAGGTGGACCAACAATTTC |

TABLE 13-continued

Subtyping Target Sequences

| SEQ ID NO. | Gene | Affy Probeset ID | Sequence |
|---|---|---|---|
| 2462 | MMP1 | 3388820 | CCTCACTGAGGGGAACCCTCGCTGGG |
| 2463 | MMP1 | 3388821 | GAATTCTTTGGGCTGAAAGTGACTGGGAAACCAGATGCTGAAACCCTGAAGGTGATGAA |
| 2464 | MMP1 | 3388822 | GCAAGTTGAAAAGCGGAGAAATAGTGGCCCAGTGGTTGAAAAATTG |
| 2465 | MMP1 | 3388825 | AAGAGCAAGATGTGGACTTAGTCCAG |
| 2466 | MMP1 | 3388826 | ATGCACAGCTTTCCTCCACTGCTGCTGCTGCTGTTCTGGGGTGTGGTGTCTCA |
| 2467 | MMP3 | 3388839 | TGAAATGTTCGTTTTCTCCTGCCTGTGCTGTGACTCGAGTCACACTCAAGGGAACTTGAGCGTGAATCTGTATCTTGCCGGTCATTTTTATGTTATTACAGGGCATTCAAATGGGCTGCTGCTTAGCTTGCACCTTGTCACATAGA |
| 2468 | MMP3 | 3388840 | ACAGTTGGAGTTTGACCCAAATGCA |
| 2469 | MMP3 | 3388842 | GGCTTTCCCAAGCAAATAGCTGAAGACTTTCCAGGGATTGACTCAAAGATTGATGCTGTTTTTG |
| 2470 | MMP3 | 3388845 | GCGTGGATGCCGCATATGAAGTTACTAGCAAGGACCTCGTTTTCATTTT |
| 2471 | MMP3 | 3388846 | AACCTGAATTGCATTTGATCTCTTCATTTTGGCCATCTCTTCCT |
| 2472 | MMP3 | 3388847 | TCCTGCTTTGTCCTTTGATGCTGTCA |
| 2473 | MMP3 | 3388848 | TACCCACGGAACCTGTCCCTCCAGAACCTGGGACGCCAGCC |
| 2474 | MMP3 | 3388849 | GATGTACCCACTCTATCACTCACTCACAGACCTGACTCGGTTCCGCCTGTCTCAAGATGATATAAA |
| 2475 | MMP3 | 3388850 | ATTTATTTCTCGTTGCTGCTCATGA |
| 2476 | MMP3 | 3388852 | CAGGGATTAATGGAGATGCCCACTTTGATGAT |
| 2477 | MMP3 | 3388854 | CTGGCATCCCGAAGTGGAGGAAAAC |
| 2478 | MMP3 | 3388855 | ATATCTAGAAAACTACTACGACCTCAAAAAGATGTGAAACAGTTTGTTAGGAGAAAGGACAGTGGTCCTGTTGTTAAAAAAATCCGAGAAATGCAGAAGTTCCTTGGATTGGAGGTGACGGGGAAGCTGGACTCCGACACTCTGGAGGTG |
| 2479 | MMP3 | 3388856 | CAGCCTATCCATTGGATGGAGCTGCAA |
| 2480 | MMP3 | 3388857 | CCAATCCTACTGTTGCTGTGCGTGGCAG |
| 2481 | MMP3 | 3388858 | AGGTTGGACCTACAAGGAGGCAGGCAAGACAGCAAGGCATAGAGACAACATAGAGCTAAGTAAAGCCAGTGGA |
| 2482 | MMP12 | 3388860 | GTCCTCAGTGTACCACTACTTAGAGATATGTATCATAAAAATAAAATCTGTAAACCATAGGTAATGATTATATAAAATACATAATATTTTTCAATTTTGAAAACTCTAATTGTCCATTCTTGCTTGACTCTACTATTAAGTTTGAAAATAGTTACCTTCAAAGGCCAAGAGAATTCTATTTGAAGCATGCTCTGTAAGTTGCTTCCTAACATCCTTGGACTGAGAAATT |
| 2483 | MMP12 | 3388861 | TACTACTATTTCTTCCAAGGATCTAACCAATTTGAATATGACTTCCTACTCCAACGTATCACCAAAACACTGAAAAGCAATAGCTGGTTTG |
| 2484 | MMP12 | 3388864 | GGAGACAGATGATGGACCCTGGTTATCCCAAACTGATTACCAAGAACTTCCAAGGAATCGGGCCTAAAATTGATG |
| 2485 | MMP12 | 3388865 | CTGGTTAATTAGCAATTTAAGACCAGAGCCAAATTATCCCAAGAGCATACATTCTTTTGGTTTTCCTAACTTTGTGAAAAAAATTGATGCAGCTGTTTTTAACCCACGTTTTTATAGGACCTACTTCTTTGTAGATAACCA |
| 2486 | MMP12 | 3388866 | TCCTTATGGCCAACCTTGCCATCTGGCATTGAAGCTG |
| 2487 | MMP12 | 3388870 | TGATGCTGTCACTACCGTGGGAAATAAGATCTTT |
| 2488 | MMP12 | 3388871 | CCAAAAGAGAACCAACGCTTGCCAAATCCTGACAATTCAGAACCAGCTCTC |
| 2489 | MMP12 | 3388872 | TAGTGATCCAAAGGCCGTAATGTTCCCCACCTACAAATATGTTGACATCAACACATTTCGCCTCTCTGCTGATGACATACGTGGCATTCA |
| 2490 | MMP12 | 3388873 | TCCTCACTGCTGTTCACGAGATTGGCCATTCCTTAG |

TABLE 13-continued

Subtyping Target Sequences

| SEQ ID NO. | Gene | Affy Probeset ID | Sequence |
|---|---|---|---|
| 2491 | MMP12 | 3388874 | GCTTTTGATGGCAAAGGTGGAATCCTAGCCCATGCTTTTGGACCTGGATCTGGCATTGGAGG GGATGCACATTTCGATGAGGACGAATTCTGGACTACACATTCA |
| 2492 | MMP12 | 3388876 | CACCTGACATGAACCGTGAGGATGTTGACTACGCAATCCGGAAAGCTTTCCAAGTATGGAGT AATGTTACCCCCTTGAAATTCAGCAAGATTAACACAGGCATGG |
| 2493 | MMP12 | 3388877 | TGGGTCTGAAAGTGACCGGGCAACTGGACACATCTACCCTGGAGATGATGCACGCACCTCGA TGTGGAGTCCCCGATGTCCATCATTTC |
| 2494 | MMP12 | 3388878 | ATGAAATATAGTGGAAACTTAATGAAGGAAA |
| 2495 | MMP12 | 3388879 | AGATAAACAAACTTCCAGTGACAAA |
| 2496 | MMP12 | 3388880 | GTTTCTTCTAATACTGCTCCTGCAGGCC |
| 2497 | MMP12 | 3388881 | ACACAGTAAACTGAATTGATCCGTTTAGAAGTTTACA |
| 2498 | MMP13 | 3388894 | AGTCTACTAGATTGTGATCCCTTGAGATATGGAAGGATGCCTTTTTTTCTCTGCATTTAAAAAA ATCCCCCAGCACTTCCCACAGTGCCTATTGATACTTGGGGAGGGTGCTTGGCACTTATTGAAT ATATGATCGGCCATCAAGGGAAGAACTATTGTGCTCAGAGAC |
| 2499 | MMP13 | 3388895 | GGATATTCAGATGTATGTGCCCTTCTTCACACAGACACTAACGAAATATCAAAGTCATTAAAG ACAGGAGACAAAAGAGCAGTGGTAAGAATAGTAGATGTGGCCTTTGAATTCTGTTTAATTTTC ACTTTTGGCAATGACTCAAAGTCTGCTCTCATATAAGACAAATATTCCTTTGCATATTATAAAG GATAAAGAAGGATGATGTCTTTTTATTAAAATATTTCAGGTTCTTCAGAAGTCACACATTACAA AGTTAAAATTGTTATCAAAATAGTCTAAGGCATGGCATCCCTTTTTCATAAATTATTTGATTAT TTAAGACTAAAAGTTGCATTTTAACCCTATTTTACCTAGCTAATTATTTAATTGTCCAGTTTGTC TTGGATATATAGGCTATTTTCTAAAGACTTGTATAGCATGA |
| 2500 | MMP13 | 3388896 | ATATGACTATGCGTGGCTGGAACCACATTGAAGAATGTTAGAGTAATGAAATGGAGGATCTC TAAAGAGCATCTGATTCTTGTTGCTGTACAAAAGCAATGGTTGATGATACTTCCCACACCACA AATGGGACACATGGTCTGTCAATGAGAGCATA |
| 2501 | MMP13 | 3388897 | TACAGCATCTGGAGTAACCGTATTGTTCGCGTCATGCCAGCAAATTCCAT |
| 2502 | MMP13 | 3388898 | ATATCTATTTTTTCAACGGACCCATACAGTTTGA |
| 2503 | MMP13 | 3388899 | CTGGAGTTCATTGTCGCAATCTGAGCTCGCTGCA |
| 2504 | MMP13 | 3388900 | GGATAAAGACTATCCGAGACTAATAGAAGAAGACT |
| 2505 | MMP13 | 3388901 | AAAATATCTGAACTGGGTCTTCCAAAAGAAGTTAAGAAGATAAGTGCAGCTGTTCACTTTGAG GATACAGGCAAGACTCTCCTGT |
| 2506 | MMP13 | 3388902 | CCTCAGCAGGTTGATGCGGAGCTGTTTTTAACGAAATCATTTTGGCCAGAACTTCCCAACCGT ATTGATGCTGCATATGAGCACCCTTCTCATG |
| 2507 | MMP13 | 3388903 | CCTAAACATCCAAAAACGCCAGACAAATGTGACCCTTCCTTATCCCTTGATGCCATTACCAGTC TCCGAGGAGAAACAATGATCTTTAA |
| 2508 | MMP13 | 3388905 | AGTTCGGCCACTCCTTAGGTCTTGACCACTCCAAGGACCCTGGAGCACTCATGTTTCCTATCTA CACCTACACCGGCAAAAGCCACTTTATGCTTCCTGATGACGATGTA |
| 2509 | MMP13 | 3388907 | CATTCTGAAGTCGAAAAGGCATTCAAAAAAGCCTTCAAAGTTTGGTCCGATGTAACTCCTCTG AATTTTACCAGACTTCACGATGGCATTGCTGACATCATGATCTCTTTTGGAA |
| 2510 | MMP13 | 3388908 | GCTCCATGACTGAGAGGCTCCGAGAAATGCAGTCTTTCTTCGGCTTAGAGGTGACTGGCAAA CTTGACGATAACACCTTAGATGTCATGAAAAAGCCAAGATGCGGGGTTCCTGA |
| 2511 | MMP13 | 3388910 | AGATGATTTGTCTGAGGAAGACCTCCAGTTTGCAGAG |
| 2512 | MMP13 | 3388911 | TCTTCTTGAGCTGGACTCATTGTCGGGCCCTGCC |
| 2513 | MMP13 | 3388912 | CAACAGTCCCCAGGCATCACCATTCAAG |
| 2514 | VSIG2 | 3396085 | TTCTCCCGATCCCTGAGGGCGGTGAGGGGGAATATCAATAATTAAAGTCTGTGGGTACC |
| 2515 | VSIG2 | 3396086 | GGGATCTCTGAGCACACTTGTATGAGGGCTGATTCTAGCAAGGGGTTCCTGGAAAGACCCTC GTCTGCCAGCACCGTGACGACCACCAAGTCCAAGCTCCCTATGGTCGTGTGA |
| 2516 | VSIG2 | 3396090 | AGCGGGTGCCTGCAACCCTCAAACTCCGACATCATTCAGTGTGTTTAGGGGCAGGAGGTGTT GTTCAGCCGTGGAATTTGCTGGTGGCAGCAGTGTAACCTGTGTATTTGAGGGTACAGGCAAG CGGTACAGGGTGGAGTGGCTGGTCCACAAGCTGTGGCAGGGAAGCTGTTTGCAGGACTGCC CTGCC |

TABLE 13-continued

Subtyping Target Sequences

| SEQ ID NO. | Gene | Affy Probeset ID | Sequence |
|---|---|---|---|
| 2517 | VSIG2 | 3396091 | CTGGGCGTGCTGTTGCTGTCAGTTGCTGCGTTCTGCCTGGTCAGGTTCCAGAAAGAGAGGGG GAAGAAGCCCAAGGAGACATATGGGGGTAGTGACCTTCG |
| 2518 | VSIG2 | 3396095 | AGTAATCCCTTATGCAGTCAGAGTGGACAAACCTCTGTGGGAGGCTCTACTGCACTGAGATG CAGCTCTTCCGAGGGGGCTCCTAAGCCAGTGTACAACTGGGTGCGTCTTGGAACTTTTCCTACA |
| 2519 | VSIG2 | 3396096 | TGTACTTCACCAATGGCCATCTGTATCCAACTGGTTCTAAGTCAAAGCGGGTCAGCCTGCTTCA GAACCCCCCCACAGTGGGGGTGGCCACACTGAAACTGACTGACGTCCACCCCTCAGATACTG GAACCTACCTCTGCCAAGTCAACAACCCCACCAGATTTCTACACCAATGGGTTGGGGCTAATCA ACCTTACTGTGCTG |
| 2520 | VSIG2 | 3396098 | TACAGCACGTCGGTGGGAGACAGCTTCGCCCTGGAGTGGAGCTTTGTGCAGCC |
| 2521 | VSIG2 | 3396099 | CCGTGGAGGTGAAGGTACCCACAGAGCCGCTGAGCACGCCCCTGGGGAAGACAGCCGAGCT GACCTGCA |
| 2522 | VSIG2 | 3396101 | CCGAGCTCCCGGGGCCCTTTCTCTGCGGGGCCCTGCTAGGCTT |
| 2523 | VSIG2 | 3396102 | ACCGACCTTGACCGCCCACCTGGCAGGAGCAGGACAGGACGGCCGGACGCG |
| 2524 | VSIG2 | 3396103 | GGCGGCTGCCCTTGGGTGCTCCCTTCCCTGCCCGACACCCAG |
| 2525 | PTMS | 3402742 | AGGGGCCTGAGGATTAGGGAGACACAG |
| 2526 | PTMS | 3402744 | GAGGAGAAGGCAAGCCGGAAAGAGCGAAAGAAAGA |
| 2527 | PTMS | 3402745 | TGGGCAAGGCATGCAGCCAGCCTGAGGCTACTCCCTCTCCTGGTCC |
| 2528 | PTMS | 3402746 | AGAAGAAGAAACTGCCGAGGATGGAGAGGAG |
| 2529 | PTMS | 3402747 | ATGAGGAAGAAGAAGAAGAGGATGATGAAGGGCCCGCGCTGA |
| 2530 | PTMS | 3402749 | TGAAGCGGATCCCAAACGGCAGAAGACAGAAA |
| 2531 | PTMS | 3402750 | CAGCCTTCTCATTTCCGCCTCTCCAGACACTGCGCCCTCCACCCTCACTCTGCCATTGTTCCACC TCCTGACCTGCTCCATCTGAGCTCTCCAGCTGGCCCCCAATTGCTCCTCTC |
| 2532 | PTMS | 3402751 | CTCTCCCACCTAACCTCTGCATCCCCCAGCCTCATGTCCTGCCCCATCCCTATCCTGCCTGATCC CTGGATCTCCCTCAGATCCC |
| 2533 | PTMS | 3402752 | TTGGGGCCGAGCCCCACAGCTGCCCCCCTCCCCTCCCTTTTTGTATAATTTAATAAAGAAATGG TCGCG |
| 2534 | KRT7 | 3415323 | ATGTCCATCCACTTCAGCTCCCCGGTATTCACCTCGCGCTCA |
| 2535 | KRT7 | 3415324 | AGCCTCTACGGCCTCGGCGCCTCACG |
| 2536 | KRT7 | 3415325 | GCCGGCATCCGCGAGGTCACCATTAACCAGAGC |
| 2537 | KRT7 | 3415326 | GGCTGGACGCCGACCCCTCCCTCCAGCGGGTGCGCCAGGAGGAGAGC |
| 2538 | KRT7 | 3415329 | GTGCGGTTTCTGGAGCAGCAGAACAA |
| 2539 | KRT7 | 3415330 | GCAGAAGTCGGCCAAGAGCAGCCGCCTCCCAGACATCTTTGAGGCCCAGATTGCTGGCCTTC GGGGTCAGCTTGAGGCACTGCAGGTGGAT |
| 2540 | KRT7 | 3415333 | GATGAAATTAACCACCGCACAGCTGCTGAGAATGAGTTTGTGGTGCTGAAGAA |
| 2541 | KRT7 | 3415334 | TGAGTGGGAAAGACAGGCTCGAGGAGGGTTGTCTGAAAACATGGGACAAAGGACCACAGG ATCCTCTCACCTGA |
| 2542 | KRT7 | 3415337 | AGTCGCTCCCTGGACCTGGACGGCATCATCGCTGAGGTCAAGGCGCAGTATGAGGAGATGG CCAAATGCAGCCGGGCTGAGGCTGAAGCCTGGTACCAGACC |
| 2543 | KRT7 | 3415339 | CGACCTCCGGAATACCCGGAATGAGATTTCAGAGATGAACCGGGCCATCCAGAGGCT |
| 2544 | KRT7 | 3415340 | GGCTTCCCCTGCTACTTGGGGCATGCAGGG |
| 2545 | KRT7 | 3415341 | CCAGCTGAGGCCAAACTCAGGATGTGGAGCAGGAGGTTCCCATCTCCCGGCCAAAGCTGGTG CCACTGTCTCAGACCCCCTTGTGAGATCTCCAGCACAGAATGTT |
| 2546 | KRT7 | 3415343 | GGCAGGCAGGAAGGCAGACTGGTGAGCCCCAGCTTACAGCTGCACTGCTGCCC |

TABLE 13-continued

Subtyping Target Sequences

| SEQ ID NO. | Gene | Affy Probeset ID | Sequence |
|---|---|---|---|
| 2547 | KRT7 | 3415344 | CTGGCGCTCAAGGATGCTCGTGCCAAGCAGGAG |
| 2548 | KRT7 | 3415349 | TGATGAATTCCACTGGTGGCAGTAGCA |
| 2549 | KRT7 | 3415350 | AAGGCTTATTCCATCCGGACCGCATCCGCCAGTCGCAGGAGTGCCCGCGACTGA |
| 2550 | KRT7 | 3415351 | CAGTCTGGAAAGTGATGTCAGAATAGCTT |
| 2551 | KRT18 | 3415581 | CTGTCCGTGTCCATGCCCGGTTGGCCACCCCG |
| 2552 | KRT18 | 3415582 | GGCTCCGAGCCGTCCACCTGTGGCTCCGGCTTCCGAAGCGGCTCCGGGGCGGGGCGGGGC CTCACTCTGCGATATAACTCGGGTCGCGCGGCTCGC |
| 2553 | KRT18 | 3415583 | CGGCGCCCGGCCGGTCAGCAGCGCGGCCAGCG |
| 2554 | KRT18 | 3415584 | GCTCCACCAGCTTCAGGGGCGGCATGGGGT |
| 2555 | KRT18 | 3415585 | CACCGGGATAGCCGGGGGTCTGGCAGGA |
| 2556 | KRT18 | 3415586 | CTGAACGACCGCCTGGCCTCTTACCTGGACAGAGTGAGGAGCCTGGAGACCGAGAACCGGA GGCTGG |
| 2557 | KRT18 | 3415588 | GCTAAGGCTGAGTCATCTAGGAGTAAACAAGAGGCCTTCCTTTGGGAGGAGCCAATCCAGGG TGTAGGGGGCCCAGAGTGACCAGGTGCACTAGGGAAAAAATGCCAGGAGAGGGCCAGGAA GAGGACTTGTTAGTAGCGACTCACTTCTGGGCAGGCAGGCCAGCCAGCTAGCCAGCCTGCTG AGGCTTCCCAAGAGGGGCAGAGTGCTGGGATCTGGGAATCCAGGAAAGGAGGGAATGGGG TGGGGCTAGATGAAAAGGGATAGGTGTCCAGGGAGAGCCTCTGGCTATTCCTGGGACCAGG AAGTTTTCACTAGGATACATAACACTTTTTACACACTCACCCCACCCATCCCTGGCTTTCTATTC ATGGAACAA |
| 2558 | KRT18 | 3415589 | ATGCCCGCATCGTTCTGCAGATTGACAATG |
| 2559 | KRT18 | 3415590 | GGTGGAGCTAAGAAGGATCTGCTCCCCAGGCTGGGTCAGTTAGGGGCTCACAGTGGGATCCT GTTAGGTGTGGGTGGATGAGAGTCAGGGTCCATCAGTGTATTCATTTAACTGTTCATTTGTAT AACCCCGTTTAAGAATACTGTCCTCCAAGTGCCAAGAATGGTGCTCAGGGGATTACCACCTAA TTGCTGACTCAAGTTGCTGGTTTGCAATGGGCACAGAACTTCTCTTAGTAGGTG |
| 2560 | KRT18 | 3415591 | GCCATGCGCCAGTCTGTGGAGAACGACATCCATGGGCTCCGCAAG |
| 2561 | KRT18 | 3415592 | TGATGACACCAATATCACACGACTGCAGCTGGAGA |
| 2562 | KRT18 | 3415596 | GGCTCGGAAGAACCGAGAGGAGCTAGACAAGTACTGGT |
| 2563 | KRT18 | 3415597 | AGGGAGGCAGACGGAATGAGGGGCCTGAT |
| 2564 | KRT18 | 3415598 | GGTCACCACACAGTCTGCTGAGGTTGGAGCTGCTGAGACGACGCTCACAGAGCTGAGACGT |
| 2565 | KRT18 | 3415599 | CACATAGCAGGTGCCCAAAAAAGTTTCCAAAAGTGAAGGGATGAGCAG |
| 2566 | KRT18 | 3415600 | TCCTGGGACTCTGGGCTCACCCTGCCCCTCC |
| 2567 | KRT18 | 3415601 | CCCGCTACGCCCTACAGATGGAGCAGCTC |
| 2568 | KRT18 | 3415602 | TGCTGGAAGATGGCGAGGACTTTAA |
| 2569 | KRT18 | 3415603 | TCCTACCCACACGTGCTGGGATCAGGAGATCACTTCTCCCCAAAGTCTGAGCTTTTGGAAGCA CCCCATGTGTCTGTTCACTGGTATCCACTGAGCACTGGGCCGTTGCTCCGTGGGTGCTCCTGT GTCTTCAAGGGAGTAACAGTTACAGAGGTCTCCCCCTTGAAGAAAGCAAACTAAGTATTGTCC CTAGCTGTACTTAGTATGCAAATGAAGTTTGGCCTTGAGTTTCCCTTTTCTGGAGGAAGAGGC TGAGGGTGATTTGGAGATAAAGGTAGAGGTCAGGAGGCTTTTTCCCTCTACCTTTCTTGTCTC CCTTCTACTCCACGGGGCTGTTTATAACTTG |
| 2570 | KRT18 | 3415604 | GCCTTGGACAGCAGCAACTCCATGCAAACCATCCAAAAGACCACCACCCGCCGGATAGTGGA TGGCAAAGT |
| 2571 | KRT18 | 3415606 | GGAGCAGGAGGCCAATAAAAAGTTCAGAGT |
| 2572 | CPSF6 | 3421447 | TGCTGCCGCGGCGGGCAGACCTGCAGGAG |
| 2573 | CPSF6 | 3421458 | ATGGAGATGCCCCAGAAGACCGAGATTACATGGATACTCTCCCACCAACTGTTGGTGATGAT GTGGGTAAAGGAGCAGCACCAA |
| 2574 | CPSF6 | 3421459 | TTGAAAATCGGGCAAATGGCCAGTCAAAGG |

TABLE 13-continued

Subtyping Target Sequences

| SEQ ID NO. | Gene | Affy Probeset ID | Sequence |
|---|---|---|---|
| 2575 | CPSF6 | 3421462 | TGCCCTTGTTGGTGTTGGATCTGAAGCATCTTCAAAAAAGTTAATGGATCTGTTACCTAAAAG<br>AGAACTTCATGGTCAGAATCCTGTTGTAACTCCATGCAATAAACAGTTCCTGAGTCAATTTGA<br>AATGCA |
| 2576 | CPSF6 | 3421466 | CTACACAATCAGGACAAATGTCTGGGG |
| 2577 | CPSF6 | 3421467 | CAGGAGGCAGTTCCCGTGCAGCATTTCCACAAGGTGGTAGAGGACGGGGC |
| 2578 | CPSF6 | 3421468 | TTACCATGGATAAAACATGTCTACCTAATACCTCTTTTCCTTTTCTCTCTTTTTCAAGTAATGCAT<br>TATTAATGTGACTTACTCTCCTTGTTATGCT |
| 2579 | CPSF6 | 3421469 | AGCATCTTGTTAAAGGAACTCGGCCTTTGTTCCTGGAAACTAGGATTCCATGGCATATGGGGC<br>ACAGCATAGAGGAAATACCCATTTTTGGC |
| 2580 | CPSF6 | 3421471 | CCACGTCCACCCTTAGGTCCTCCAG |
| 2581 | CPSF6 | 3421472 | CTCTAGCTGGGCCTCCTAATCGAGGAGATCGCCCTCCACCACCAGTTCTTTTTCCTGGACAACC<br>TTTTGGGCAGCCTCCATTGGGTCCACTTCCT |
| 2582 | CPSF6 | 3421473 | TCCGCATGTGAACCCAGCTTTCTTTCCTCCACCAACTAACAGTGGCATGCCTACATCAGATAGC<br>CGAGGTCCACCACCAACAGATCCATATGGGCGACCTCCACCATATGATAGG |
| 2583 | CPSF6 | 3421474 | GGAAATGGATACTGCAAGAACGCCATTGAGTGAAGCTGAATTTGAAGAAATCATGAATAGAA<br>ATAGGGCAATCTCAAGCAGTGCTATTTCGAGAGCTGTGTCTGATGCCA |
| 2584 | CPSF6 | 3421475 | TGATTATGGGAGTGCTATTGAGACACTGGTAACTGCAATTTCTTTAATTAAACAATCCAAAGT<br>ATCTGCTGATGATCGTTGCAAAGTTCTTATTAGTTCTTTGCAAGATTGCCTTCATGGAATTGAG<br>TCCAAGTCT |
| 2585 | CPSF6 | 3421477 | AGAGGGACCATAGTAGATCACGAGAAAAGAGTCGACGTCATAAATCCCGTAGTAGAGACCG<br>TCATGACGATTATTACA |
| 2586 | CPSF6 | 3421478 | TGACCGAGAGCGCGAATATCGTCATC |
| 2587 | CPSF6 | 3421489 | GAAGAGGATCACCTTCCAAGACAAAACAGTCTTCATGGGGGAAAAATGACGCTTGTCCAGCA<br>GTTTGCTTCTTGTGATTGAACTGAACCTGTAAGGATTCATGGATAAAATGAACAGGA |
| 2588 | CPSF6 | 3421490 | TTTATTTGAAGGAAACCTGTGTGATTTAAAAAGTTATAGCTTTTGCAACTTTATTACTGGTTAT<br>ATACATTTGGCCATTATGATGTGCAAGCAATTGGAAAAAAAGTCAAGTAAATGCTTGTTTTTG<br>TAGTAGTTTGTTCTTGTTAAAAATGTTTATATGATAATGTCTGTAAACAGCATCACTTTGAT |
| 2589 | CPSF6 | 3421491 | TACAATAGATGTAGTGTTGTAATAAACTGTTTAA |
| 2590 | CPSF6 | 3421492 | CTCAGGGAAAGTCTTGTGTTCAGCAATATCTAAAGATAATGTTACTATGACAACATTTTTACTG<br>TCCTTTAAAGCATTGCAATAGCGTTTTTGGATATGCCTCAATCTAATCTTGCGTTCAGTGAATT<br>AAACATAGTA |
| 2591 | CPSF6 | 3421493 | GCACCTGACTAGCATGTGTTCTTGATTGCAAAATTGGCAGAGGCAGGGTGTCAACTTGATTAG<br>GTGTTTTTATGGGAATGTAATTTGAAATCACTACTTCAGAAATTTGACTTAAAATTCTTGAGCA<br>CGTTAATATGTTTTTAAGATCTGATTATCTTTGAGAGATCTTCTGTTAATACACATTGGTTGTTA<br>AAGAGTACCCAAATTCTAGGACAATGCTTAAAGTGTTAAAATACCCTAGATACTGTGTTATGT<br>GCAACTGTAGAAACCCTCCAGAAATTTCCACTGCTGTTCTTCACTTTCATCTTGTCTGCTATCAA<br>ACCACTTCTGACAAAATTAGCTGTTTTGAATTACCCATATCACTGCCAGTTTTATTTTAAAATAT<br>TTTGTGTTTGAAGTATCTGTGCATGGGATCGTTGATGTTTATCAGAACTGTTCACTTTCAGAAA<br>TGATTTTTTAAAGCATTTTGTTGAAAATGCGGTTGCTTTTTTAACATTATTTTAGAGTTGTATCA<br>AAATTTTCCTGTTTTCTGTATATTGTTGTGTCATTTCTTGGCTTTTTAATATTTTGACTACAATGC<br>CCTAATGCGAAGAAGTATGGAC |
| 2592 | CPSF6 | 3421494 | ACTTTCGTTACAGACAGTGTGAGTGTACTAGATTTGTTTGCTGCTAATCCGTTATTTTAAGTGT<br>TGTCAGAAGGAAATAACTTCTTGGTTTGACCAAGTAATTTTGCAAAGTCCTTCTCTACCTGATA<br>ACACGTGAATGTATA |
| 2593 | CPSF6 | 3421495 | ACAAGACTTTTCTGTTGGAGTGCTCTCGACATTTTGGTTTTCATACCTGAATGATCATTGCATTT<br>TCTGTATTTTCTAAAATGGCTCCAATTTTGTGTTTTAAGCTTCAGCTTAAGAGGAAGTTTATGTT<br>CTAATTCTTGACTGAGAATACAGTATTGAGATTCTCTGTTTTACAGATAACAACTGGTTTTTATT<br>ACTCATTAAGTTCATTTGCATCCCGTAGCCCTCTGTAAATGTTTCCCCTAGTTGTATGTACGTAA<br>ATGCACGCTTATCCAGTGTATATTAGACATTTTTGTGCTAAAATATATTAAGTGGGATTTTGT<br>AGCAAAGCATTCTATTTTTCTGTTCTTACAGTGTGTGTGTGTGTGTGTGTGTATGCGT<br>TTTTTAACCTTAACTTCAGTTTAAACACTTGTATTTATTTTTTTAAGCAACTTGACTCTTAGA<br>AGCCTTAGACTGATTTTTTCAATAAATATTCAACCAAAAATTATAAATTTATTAAGATGTGGCC<br>TTACATATGGCATTCCTTGTGTTCGTAATGTGAGATTTTTGATTTAGATAAATCAAGATTCAGG<br>ATTAAAGTTTCATTGTAAGTTGAAATAGAAAATGTATTAAAATGTCTAGGCTTCGGGAGGAA<br>GTTCTTATACTCTTCTTCTTGGCATTAGAAAGAAGCAATATGAATTTTTGTGAATATTCTAAAT<br>ATTCAGGCAACACTGTTCAGATTGATTTAGGTTTGTCTTAACCAATGTTCTTTTTTTAGAATTTC |

TABLE 13-continued

Subtyping Target Sequences

| SEQ ID NO. | Gene | Affy Probeset ID | Sequence |
|---|---|---|---|
| | | | AGGTTGTGTGGCATTCACTGAGTATGCAGCTACTATGGTTTTTGTATGGGACGTATAAATACTTG ATTATATACGACAGATTTTAATGTCTTTAAAGACTTCCTGCTGTATTAACATATTGTAATGGAG TCTTTTAAATACTAGGTTGAATTTAATTGAAGTCACACACATCTTGAAGTGGTAACTGCATAGT AAATACTACCAAGAGTTTTTTTCACGTGGGAGTATCCTAAAACTCTGCCATGGGTGTAAATGT TTTACATTAATTTCATAATTGGACAGACCCTGCATTTAGCGAAAA |
| 2594 | LYZ | 3421512 | GGTCAGCCTAGCACTCTGACCTAGCA |
| 2595 | LYZ | 3421513 | GCTTGTCCTCCTTTCTGTTACGGTCCAGGGCAAGGTCTTTGAAAGGTGTGAGTTGGCCAGAAC TCTGAAAAGATTGGGAATGGATGGCTACAGGGGAATCAGCCTAGCAAAC |
| 2596 | LYZ | 3421515 | AATGGGAGAGTGGTTACAACACACGAGCTACAAACTACAATGCTGGAGACA |
| 2597 | LYZ | 3421516 | TTCAGATCAATAGCCGCTACTGGTGTAATGATGGCAAAACCCCAGGAGCAGTTAATGCCTGTC ATT |
| 2598 | LYZ | 3421519 | CTGCAAGATAACATCGCTGATGCTGTAGCTTGTGCAAAGAGGGTTGTCCGTGATCCACAAGG CATTAGAGCA |
| 2599 | LYZ | 3421520 | GGTGGCATGGAGAAATCGTTGTCAAAACAGAGATGTCCGTCAGTATGTTCAAGGT |
| 2600 | LYZ | 3421521 | GTGAAAGGTCACACTACCATTATTTCCCCTTCAAACAAATAATATTTTTACAGAAGCAGGAGC AAAATATGGCCTTTCTTCAAGAGATATAATGTTCACTAATGTGGTTATTTTACATTAAGCCTA CAACATTTTTCAGTTTGCAAATAGAACTAATACTGGTGAAAATTTACCTAAAACCTTGGTTATC AAATACATCTCCAGTACATTCCGTTCTTTT |
| 2601 | LYZ | 3421522 | CCGGCCACATTCAGTTCTTATCAAAGAAATAACCCAGACTTAATCTTGAATGATACGATTATGC CCAATATTAAGTAAAAAATATAAGAAAAGGTTATCTTAAATAGATCTTAGGCAAAATACCAGC TGATGAAGGCATCTGATGCCTTCATCTGTTCAGTCATCTCCAAAAACAGTAAAAATAACCACTT TTTGTTGGGCAATATGAAATTTTTAAAGGAGTAGAATACCAAATGATAGAAACAGACTGCCTG AATTGAGAATTTTGATTTCTTAAAGTGTGTTTCTTTCTAAATTGCTGTTCCTTAATTTGATTAAT TTAATTCATGTATTATGATTAAATCTGAGGCAGATGAGCTTACAAGTA |
| 2602 | SCNN1A | 3441886 | AGAGCCGCCCAAACTGCCGTTGATGTGTGGAGGGAAGCAAGATGGGTAAGGGCTCAGGAA GTTGCTCCAAGAACAGTAGCTGATGAAGCTGCCCAGAAGTGCCTTGGCTCCAGCCTGTACCC CTTGGTACTGCCTCTGAACACTCTGGTTTCCCCACCCAACTGCGGCTAAGTCTCTTTTTCCCTTG GATCAGCCAAGCGAAACTTGGAGCTTTGACAAGGAACTTTCCTAAGAAACCGCTGATAACCA GGACAAAACACAACCAAGGGTACACGCAGGCATGCACGGGTTTCCTGCCCAGCGACGGCTTA AGCCAGCCCCCGACTGGCCTGGCCACACTGCTCTCCAGTAGCACAGATGTCTGCTCCTCCTCTT GAACTTGGGTGGGAAACCCCACCCAAAAGCCCCCTTTGTTACTTAGGCAATTCCCCCTTCCCTG ACTCCCGAGGGCTAGGGCTAGAGCAGACCCGGGTAAGTAAAGGCAGACCCAGGGCTCCTCT AGCCTCATACCCGTGCCCTCACAGAGCCATGCCCCGGCACCTCTGCCCTGTGTCTTTCATCCT CTACATGTCTGCTTGAGATATTTCCTCAGCCTGAAAGTTTCCCCAACCATCTGCCAGAGAACTC CTATGCATCCCTTAGAACCCTGCTCAGACACCATTACTTTTGTGAACGCTTCTGCCACATCTTGT CTTCCCCAAAATTGATCACTCCGCCTTCTCCTGGGCTCCCGTAGCACACTATAACATCTGCTGG AGTGTTGCTGTTGCACCATACTTTCTTGTACATTTGTGTCTCCCTTCCCAACTAGACTGTAAGTG CCTTGCGGTCAGGGACTGAATCTTGCCCGTTTATGTA |
| 2603 | SCNN1A | 3441887 | CCCACCCCATGTCTCTGTCCTTGTCCCAGCCAGGCCCTGCTCCCTCTCCAGCCTTGACAGCCCCT CCCCCTGCCTATGCCACCCTGGGCCCCCGCCCATCTCCAGGGGGCTCTGCAGGGGCCAGTTCC TCCACCT |
| 2604 | SCNN1A | 3441888 | GGCTGAGCTCGTCTTTGACCTGCTGGTCATCATGTTCCTCATGCTGCTCCGAAGGTTCCGAAG CCGATACTGGTCTCCAGG |
| 2605 | SCNN1A | 3441889 | GAACTACAAAACCAATTCTGAGTCTCCCTCTG |
| 2606 | SCNN1A | 3441890 | ATGCTATCGCGACAGAACAATTACACCGTCAACAACAAGAG |
| 2607 | SCNN1A | 3441891 | TCTCTGCTGGTTACTCACGATGGCCCTCGGTGACATCC |
| 2608 | SCNN1A | 3441892 | CTGGGCTGTTTCACCAAGTGCCGGAAGCCATGCA |
| 2609 | SCNN1A | 3441895 | GAGTGTGGCTGTGCCTACATCTTCTATCCGCGGCCCCAGAACGTGG |
| 2610 | SCNN1A | 3441896 | GATGTTCCTGTTGAGAACCTTTACCCTTCAAAGTACACACAGCAG |
| 2611 | SCNN1A | 3441897 | TGGACAGACTTGGGGGCGATTATGGCGACTGCAC |
| 2612 | SCNN1A | 3441898 | TGGAGACCTCCATCAGCATGAGGAA |
| 2613 | SCNN1A | 3441899 | TGATGGTGGCTTAACTTGCGGCCTGGC |
| 2614 | SCNN1A | 3441900 | GTCTGTCCCTGATGCTGCGCGCAGAGCAGAATGACTTCATTC |

TABLE 13-continued

Subtyping Target Sequences

| SEQ ID NO. | Gene | Affy Probeset ID | Sequence |
|---|---|---|---|
| 2615 | SCNN1A | 3441902 | TTACTCTCACTTCCACCACCCGATGTATGGAAACTGCTATACTTTCAATGAC |
| 2616 | SCNN1A | 3441904 | TCGGACTGCTTCTACCAGACATACTCATCAGGGGTGGATGCGGTGAGGGAGTGGTACCGCTT CCACTACATCAACATCCTGTCGAGGCTGCCAGAGACTCTGCCATCCCTGGAGGAGGACACGCT GGGCAACTTCATCTTC |
| 2617 | SCNN1A | 3441906 | TGGACCGCATCACAGAGCAGACGCTCTTTGACCTGTACAAATACAGCTCCTTCACCACTCTCGT GGCCGGCTCCCGCAGCCGTCGCGACCTGCGGGGGACTCTGCCGCACCCCTTGCAGCGCCTGA GGGTCCCGCCCCCGCCTCACGGGGCCCGTCGAGCCCGTAGCGTGGCCTCCAGCTTGCGGGAC AACAA |
| 2618 | SCNN1A | 3441907 | ACCGACACTCGCCTGCGGGGATCAGGGCGGGATGACCTGGGTACCGCGGTCACGCCAAGGC CGAGGCCCTCACCCTTCCCCTCTTTGGGAAAGGGCAGACAAGTTCCGGGTTCCCTTCTAGGTC CGGGCGAGGGGGAGAGCGCCCCACAGACGACGAGGCGCCTCCTGCCTCTCTCCTTCAATAAAC AGTCCACAGTGTCCCGGCTGGGCTCGCCGTGGCCTCCGCCTTCCCGGCGGACACACCTGTTTA CCCTTCACCGCCGGACGGCCAGGAGGCGCCACGACGACCCCAGCCCCGCCCAGGCTTCTCCG GGATGGACCGGCCTCCCGGGGCACAGATGAGGACCCTGACCCCGGAGGGGCCAGACACTCG CTCCAGGGC |
| 2619 | SCNN1A | 3441910 | GAGGCCCTGATCGAGTTCCACCGCTCCTACCGAGAGCTCTTCGAGTTCTTCTGCAACAACACC ACCATCCACGGCGCCATCCGCCTGGTGTGCTCCCAGCACAACCGCATGAAGACGGCCTTCTGG GCAGTGCTGTGGCTCTGCACCTTTGGCATGATGTACTGGCAATTCGGCCTGCTTTTCGGAGAG TACTT |
| 2620 | SCNN1A | 3441911 | GGAGGAGCAGGACCCTAGACCTCTGCAGCCCATACCAG |
| 2621 | SCNN1A | 3441913 | CCGGCCAGCGGGCGGGCTCCCCAGCCAGGCCGCTGCACCTGTCAG |
| 2622 | SCNN1A | 3441915 | CAAGGGAACCTGGTTTGGAATCCTGGTTGACACCGGCTTTCACTTTAAGAAGTCGCAAGAGA CTGCCGCAAGAGAGG |
| 2623 | MGP | 3445744 | GAGAGTCAACATATGTGATTGTTCCATAATAAACTTCTGGTGTGA |
| 2624 | MGP | 3445745 | GCAGCATTACAGAAATACATAGGCTTATATACAATGCTTCTTTCCTGTATATTCTCTTGTCTGG CTGCACCCCTTTTTCCCGCCCCAGATTGATAAGTAATG |
| 2625 | MGP | 3445749 | CAGAGATGGAGAGCTAAAGTCCAAGAGAG |
| 2626 | MGP | 3445750 | TCCCTTCATTAACAGGAGAAATGCAAATACCTTCATATCCCCTCAG |
| 2627 | MGP | 3445751 | TGGGATTTAAGCTACAGGCGACATATTTAGAAGCCATAAAATCTCATTTGGAAATTTTAAATT GGCACCACGTCAACTGCACAGATGGAAAACGAGGAGTAATGACAAATGGTAAAGCACAGAG CTGGACGCCAAGTCAGCTGGGAGACCACAGGCGCCACGTTAAGCTGAGTGCTGTTTTGGTTT TTTTGTGTTTTTCTTTCTTGTTTTTTTTTTGAGACAGTGTCTCACTCTGTCGCCCAGGCTAGAGT GCAGTGGTGTGATCTCGGCTCGCCGCAACCTCCACCTCCCAGGTTCAGGCAATTCTCATGCCT CAGCCTCCTGAGTAGCTGGGATTACAGGCCCATGACATCATGCCTGGCTAATTTTTGTATTTTT AGTAGAGATGGGGTTTCACCATGTTGTCCAGGCTGGTCTCGAACTCCTGGCCTCAAGTGATCC ACCCACCACAGCCTCCCAAAGTGCCGGGATTACAGGCATGAGCCACCACACCCAGCCAGCTG ATTGCTGTTGAATAGCTGGATTTATAAAGACTGAGCATAGGAGGAAATGGCACATCACTCTCA TTTTTAATTTATTCATTATTTTTATAGTGTTTAAACTGTTCATGTATCGGCAATCTAGTTATGCTT CATAAATCCTCAGGACAGAGAATTTCTCCTCAAAAGGAATTTAAAATCTACCAAGTAGAAATA CAGAAATTAAGAAAGGCAAAGTGATCGTCCAAACTCAAAACCAACAAAGCCTATATGACAAG TCTCTAAGACACATGGATTGATTACTGATTTCATTTGATCAGGAAGTTAATGAAATCTACTTTA TACTCTCCTTTAATTTTTGCCAATCTCCGTTTATATGAGTTGCATAAGTTAAGGCACTTTCAAAT ATATTTGTGTCAAGGAATATTCACGGAAATATTTCCAGCTATGTGTCGCTAAAACTGC |
| 2628 | MGP | 3445754 | AGAAGAAAACTTCGGCTTTGATATCGTTTCAGTTCTCTCTCTGAACTGGCATCGTGCCCAGG |
| 2629 | MGP | 3445755 | CCTGGCCGCCTTAGCGGTAGTAACTTTGTGTTATG |
| 2630 | MGP | 3445756 | CTGCTGCTACACAAGACCCTGAGACTGACCTGCAG |
| 2631 | MGP | 3445757 | CCTCACAGCCTTCCACTAACATCCCGTAG |
| 2632 | ERP27 | 3445769 | ATCTCCAACTCCCTATGTAAATCAACAACCTGCATAATAAA |
| 2633 | ERP27 | 3445770 | AGTTAAAGGCTGTCTCCAAGTCCCTGAACTCAGCAGAAATAGACCATGTGAAAACTCCATGCT TGGTTAG |
| 2634 | ERP27 | 3445771 | TATCGTGCATTCATACTCTGTAAGCCCATCTGTAACACACCTAGATCAAGGCTTTAAGAGACTC ACTGTGATGCCTCTATGAAAGAGAGGCATTCCTAGAGAAAGATTGTTCCAATTTGTCATTTAA TATCAAGTTTGTATACTGCACATGACTTACACACAACATAGTTCCTGCTCTTTTAAGGTTACCTA AGGGTTGAAACTCTACCTTCTTTCATAAGCACATGTCCGTCTCTGACTCAG |

TABLE 13-continued

Subtyping Target Sequences

| SEQ ID NO. | Gene | Affy Probeset ID | Sequence |
|---|---|---|---|
| 2635 | ERP27 | 3445772 | AAGAAAATCGTGAATCAGAAGGAAAGACTCCAAAGGTGGAACTCTGA |
| 2636 | ERP27 | 3445773 | AGGAGTCTCAACTGCCAGCTTTGGCAATTTACCAGACTCTAGATGACGAGTGGGATACACTGCCCACAGCAGAAGTTTCCGTAGAGCATGTGCAAAACTTTTG |
| 2637 | ERP27 | 3445774 | GATTTCAATTTCATGGTGCAGACCATAAATTCAATCAGTGTGAGCTGCAACAATTACAAGGTATCTCTTTATCCCTGGACGTCACCTCAGATAGAACTTTT |
| 2638 | ERP27 | 3445775 | ATGAACAAGGCCTCCCCAGAGTATGAAGAGAACATGCACAGATACCAGAAGGCAGCCAAGCTCTTCCAGGGG |
| 2639 | ERP27 | 3445776 | GGTTATTCAACAGCGTAATTCAGATTCATCTCCT |
| 2640 | ERP27 | 3445777 | ACAACTGAATTTAGAGGACGAAGACATTGAAAGCATTGATGCCACCAAATTGAGCCGTTTCATTGAGATC |
| 2641 | ERP27 | 3445778 | CACATCAAATGTTAAACGAGTCCTGATTATGATGATAATGATGATGATTTTGGTGGTTGCAATAGCAAAGCCTTAAGTATGAAGGAGACTTGCCAGCTGG |
| 2642 | ERP27 | 3445780 | CCATACTCCATAGCATGGTGCAAAAATTCCCAGGCGTGTCATTTGGGATCAGCACTGATTCTGAGGTTCTGACACACTACAACATCACTGGGAACACCATCTGCCTCTTT |
| 2643 | ERP27 | 3445781 | CACTGAGGTGGCTGTCATAGGCTTCT |
| 2644 | ERP27 | 3445783 | GTGAGCTGGCTGCAGAAGTTGCTGCAGAAGTTGAGAAATCCTCAG |
| 2645 | ERP27 | 3445784 | GGTTCATGTTCCTCTTATTTCTCCTCACGT |
| 2646 | ERP27 | 3445785 | TTCTACCTTGTGTTGCCTGGCAAAATCTTACTTACCCAGAACTCTGCTCCGGCATCCTCCGCAGGAAGAACACTTTCATTGAACCCTAGCATTGTCCCTAATACCCTTAATATGTATTGTCATAGCACCCTATGAATTTTCTATATCACTTTCCATCTTATATTTAAATAATCTTTTTACTTGCCCATCTCTCCCACTGATAATCTAAGCTGGCAGAGGCTGGATCAGATCATAATTATCTTTCTATTCTTAGCGCTAGGATCAATGCCTGG |
| 2647 | KRT5 | 3455207 | CCTTTTCTGGAGAGTAGTCTAGACCAAGCCAATTGCAGAACCACATTCTTTGGTTCCCAGGAGAGCCCCATTCCCAGCCCCTGGTCTCCCGTGCCGCAGTTCTATATTCTGCTTCAAATCAGCCTTCAGGTTTCCCACAGCATGGCCCCTGCTGACACGAGAACCCAAAGTT |
| 2648 | KRT5 | 3455208 | TCTTGCCGGAGGTAGCAGTGGAAGCTACTACTCCAGCAGCAGTGGGGGTGTCGGCCTAGGTGGTGGGCTCAGTGTGGGGGCTCTGGCTTCAGTGCAAGCAGTGGCCGAGGGCTGGGGGTGGGCTTTGGCAGTGGCGGGGTAGCAGCTCCAGCGTCAAATTTGTCTCCAC |
| 2649 | KRT5 | 3455211 | ACTCAGTGGAGAAGGAGTTGGACCAGTCAACATCT |
| 2650 | KRT5 | 3455212 | AGGTCAATCCCTCTTCATTGGAAAATCCCTCTGGAGAGTTCTCCCTTCCTTTAACTTAAGCAGCTTTTGGGTGTACAGACTCCTGGCTTATGGAATGAACTCGAATCATGAGGATGGGAGTTAGCCACATAGACTAATGCTGTCTTTTTGGGAGCTGTTAACCCTTAATTCA |
| 2651 | KRT5 | 3455214 | CAAGATGGCCTTCAGCTGATAAAGCGAAGCTGCTCTACTGTGGGGTGTACAACACACATACATGAGATCAGTGACTTGTGCGTGATAATGACACATCATCAACACTATTTCAGTCTGACTCATGGCCATATAGCTGACCTCAACTCACTTTTCTGGTCTCTTTTCCCCCACCGGTGTTCCTGGGCACTGGCTGTCCTCCAAGCACCTGAGCAACTCAGCAATCTTCTTGACACTTGTGCCTTTTCTGCTTTTGCTCACGTCCTTTGCTCAACCTCAATATCCATGTCATG |
| 2652 | KRT5 | 3455215 | TGCGCCAATCTGCAGAACGCCATTGCGGATGCCGAGC |
| 2653 | KRT5 | 3455216 | CTTTTGCTAAACACACGCAGCTAGATCCAGTACCAGTGTTTCAGTGTCCTGCCACCCACGATGTACTGGTTTCTCTCTGGGATTCATGATAGTTTGGTTTGTCTGACCCAGAAACTCAG |
| 2654 | KRT5 | 3455217 | AGCTGGCCGGCATGGCGATGACCTCCGCAACACCAAGCATGAGATCTCTGAGATGAACCGGATGATCCAGAGGCTGAGAGCCGAGATTGACAATGTCAAGA |
| 2655 | KRT5 | 3455219 | CAGATGCAGACGCATGTCTCTGACACCTCAGTGGTCCTCTCCATGGACAACAACCGCAACCTGGACCTGGATAGCATCATCGCTGAGGTCAAGGCCCAGTATGAGGAGATTGCCAACCGCAGCCGGACAGAAGCCGAGTCCTGGTATCAGACCAAG |
| 2656 | KRT5 | 3455220 | CAGAACCAGATGACCGACTCCAAATCTCCCTG |
| 2657 | KRT5 | 3455222 | GGCCAAGGTTGATGCACTGATGGATGAGATTAACT |
| 2658 | KRT5 | 3455223 | GCAGCCTGCAGCTATGCTCTCTAAGCGTGGAGCTCACTTGAGTAGGGTGACGGTGTGT |
| 2659 | KRT5 | 3455224 | TGAAATCAACAAGCGTACCACTGCTGAGAATGAG |

TABLE 13-continued

Subtyping Target Sequences

| SEQ ID NO. | Gene | Affy Probeset ID | Sequence |
|---|---|---|---|
| 2660 | KRT5 | 3455225 | AAAAGAACACTAGAGAAATTGACTAG |
| 2661 | KRT5 | 3455228 | GTGGACACGTTCTGAATTAGACTGGCAGCTGGGAAG |
| 2662 | KRT5 | 3455229 | CAACCTGCAAATCGACCCCAGCATCCAGAGGGTGAGGACCGAGGAGCGCGAGCAGATCAAGA |
| 2663 | KRT5 | 3455230 | GAGGTGGTGCCGGTAGTGGATTTGGTTTCGGCGGTGGAGCTGGTGGT |
| 2664 | KRT5 | 3455231 | GGCAGCTTCAGGAACCGGTTTGGTGCTGGTGC |
| 2665 | KRT5 | 3455232 | GGGCTCCAAGAGGATATCCATCAGCACTAGTG |
| 2666 | KRT5 | 3455233 | TGTGGAGTGGGTGGCTATGGCAGCCGGAGCCTCTACAACCTGGG |
| 2667 | KRT5 | 3455234 | TGGTGGCTTCGGCAGGGTCAGCCTTGCGG |
| 2668 | KRT5 | 3455235 | TCAAGTGTGTCCTTCCGGAGCGGGGGCAGTCGTAGCTTCAGCACCGCCTCTGCCATCACCCCGTCTGTCTCCCGCACCAG |
| 2669 | KRT5 | 3455236 | ACAGCTCGACAGCTCTCTCGCCCAGCCCAGTTCTGGAAGGGATAAAAAGGGGGCATCACCGTTCCTGGGTAACAGAGCCACCTTCTGCGTCCTGCTGAGCTCTGTTCTCTCCAGCACCTCCCAACCCACTAGTGCCT |
| 2670 | KRT5 | 3455237 | CCCAGCCTCTATGGTGAAGACATACTTGCTAGCAGCGTCACCAACTTGCTGCCAAGAGATCAGTGCTGCAAGGCAAGGTTATTTCTAACTGAGCAGAGCCTG |
| 2671 | KRT8 | 3455567 | GGCTCAGCCCTAGCCCTCAGCCCACCTGGGGAGTTTACTAC |
| 2672 | KRT8 | 3455568 | CCGCTATGCAGGGTAGCACTGGGAACA |
| 2673 | KRT8 | 3455569 | CCTCCCAGCCTACCCCTCCTGCGCTGCCCCAG |
| 2674 | KRT8 | 3455570 | TCTGAGTCCTCTGACGTCCTGCCCA |
| 2675 | KRT8 | 3455571 | AGCTCCTCCAGGGCCGTGGTTGTGAAG |
| 2676 | KRT8 | 3455575 | GGATGCAGAACATGAGTATTCATACGAAGACCACCAGCGGCTATGCAG |
| 2677 | KRT8 | 3455576 | TGGGACTTGGGGTCCTGTTGTTCTGGGCCAAGAAGGGCTAGGAGTTGGTCCTGACACCCCA |
| 2678 | KRT8 | 3455577 | GTGGGTACCTCTGACCGGACCTGCTTCCCTATCCCT |
| 2679 | KRT8 | 3455578 | CGCCATTGCAGATGCCGAGCAGCGTGGAGAGCTGGCCA |
| 2680 | KRT8 | 3455580 | CGGGGATGACCTGCGGCGCACAAAGACTGAGATCTCTG |
| 2681 | KRT8 | 3455581 | GTACCAGATCAAGTATGAGGAGCTGCAG |
| 2682 | KRT8 | 3455582 | ACAGTACGAGGATATTGCCAACCGCAGCCGGG |
| 2683 | KRT8 | 3455584 | TCTCGCCTGGAAGGGCTGACCGACGAGATCAACTTCCT |
| 2684 | KRT8 | 3455585 | TTGGACAGAACTCTTGACATCGGTGTTGGGACATGGTTCAGAAAACAGAGCAGTAGAACTGGAGATCTGGCTCTAGAAGGCTCCCTAGAGAAGGAGGTGGAAGAGGGTGTGTTGCAGGAAGCAGAGGTGAAGGTGTGTGGGCTGAGAATGCACATGTGATGGGCAGAGGCTGGGCTGGAAGATCAATCCACAAAGTGGGCAACTAGAAAGTCCTGTGACC |
| 2685 | KRT8 | 3455586 | ATAAGCGTACAGAGATGGAGAACGAATTTGTCCTCAT |
| 2686 | KRT8 | 3455587 | GGTGACCACCTGATGAGGTTTGCTCGGAACAGTCTGTGTTTATGCCCAGGTTCCTAGCACAATTGTTGATAGTACCCACCCCCTTTCAATCTCAACTGTCTGGATTTGAAGAACAAATTATGTGTCAATGTTGACATGGTAAACCTGAGACGGGAGAGATAGGCAGCCTGTGGGCCTCACTTTTGTACTTAACATTCTGGCCCCTCTTTAGTCTTGACCCTTGACCTCTAGC |
| 2687 | KRT8 | 3455589 | CAGAAGACGGCTCGAAGCAACATGGACAAC |
| 2688 | KRT8 | 3455590 | CTGGAGACCTTACTGCTTGAGGAGTGAATTAAGAGAAAAGACTGCTTGCTTTCCTCCAGACTTTGAGCCCTGGCCTGATGTAGACCTTTTTGC |
| 2689 | KRT8 | 3455591 | GCGGCCCCGAGGATTGGGCCCTTCACGCTGACTG |
| 2690 | KRT8 | 3455593 | AGCAACTTTCGCGGTGGCCTGGGCGGC |

TABLE 13-continued

Subtyping Target Sequences

| SEQ ID NO. | Gene | Affy Probeset ID | Sequence |
|---|---|---|---|
| 2691 | KRT8 | 3455594 | GATCTCCGCCTGGTTCGGCCCGCCTGCCTCC |
| 2692 | KRT8 | 3455596 | GGATCTGGCTGTCATCTGTTGGTCCTCTGAGTTCAGTTTCATCCAGTCCCCACATCACACCCTG CAGTATCTTCCAGAGA |
| 2693 | KRT8 | 3455597 | TAAGTTTGTCTGTCCTCCAAGGAGGGGGCTTCTGGGTCTCTCTGTCCTTCTGGGTAGGGGTCC TATGTGCCTGTCTTTCTGTGAGCCTGGGTGTCTCTCCTAGAGAAGGATGGGGAAGAAACTGTA CATCTGTCCTCCCAGTAGGTGGTCACCCCCTTCCCTGGGTCAGGGCTATGTCACCTGTC |
| 2694 | KRT8 | 3455607 | AGGAGGTGCTGGCGAGTTTGAAATTTGG |
| 2695 | KRT8 | 3455608 | AGCGCCTGCATAGACGCTGGCCGCGCTGCTGACCGGCCGGGCGCCGTA |
| 2696 | KRT8 | 3455609 | CTGGGGTCCCTTCTTCTCCAAGTGCTCCCGGATTTTGCTCTCCAGCCTCCGGTTCTCGGTCTCC AGGCTCCTCAC |
| 2697 | KRT8 | 3455610 | TAGGGGTTGGGTGGTTATGGAATGACGGAAAGAGGCAAAGGAGTGTATAATTGGAGGGTCA GACAAGGCTGGGA |
| 2698 | KRT8 | 3455611 | CCTCTGTAAAGCTCTCAACCCTGTCCCCTTCCCCCTCTCTCCTGGGAAAGAGCCCTCCCATGCCT AGCTGCTGCTCTTAGGGACCCTGTGGCTAGGTGCGCGGATGGAAATCCAG |
| 2699 | LUM | 3465249 | TGGTACAGCGGCCTTTCATCAGAGGATCATCATTGAGACTGAGTTGACTGGCAGATATGTGC GATGGATATTACATTAGGTACAATGTGTATTTTTGATTTTCATGAGTTTTCTACATTAAGGTAA ATTCCTTAGAGTGTGATAGCAGCCTCAGTTTA |
| 2700 | LUM | 3465250 | GAAATCAAAAGATATCTCTGGCCTGCAATATTTTACTGATGTGAACATAGGATTTTCCACTAAA TAATTTGTCTACTTCTAGCATTCACTTACAAAGAGTTCTTAAAAACACCTATAATAGGTACTTA GATTTCACAACTTACTTAGATATTTGTCATTATTCCCATTCCTGGTGTTTTTACTGGTTCATATA CAATGGTATTCTATTAGATAAGAAGCTGCTATGTGATCTCAGCACTCACTCCTTGGTTGTCAAG AAATGGTGGATAACTCACAGGATTAAAAATGAATGAATATAAAATTTTCTGAAATAGATATTT AAAAAATCATTTTAGCTTGAAGCCAATATGTCTGGATCATAGGTTTTGAGTTCATAATCCAGTA ATAACAGCTTTCAGCTTTCTATGAGTATATACAATTCTATACAATGATAAATACTCTGCATATA ATTTATAAAAATAACTTCTGTTTTACCTAGTTAACAATAAAACCTATGTGTGGAGCCAAATGTT ATGCAGACAAAGGTCTGCTCATCCCATACCAGTG |
| 2701 | LUM | 3465251 | ACCTTTTACTGGTTGCATGGAAATCAGCCAAGTTTTATAATCCTTAAATCTTAATGTTCCTCAAA GCTTGGATTAAATACATATGGATGTTACTCTCTTGCACCAAATTATCTTGATACATTCAAATTT GTCTGGTTAAAAAATAGGTGGTAGATATTGAGGCCAAGAATATTGCAAATACATGAAGCTT CATGCACTTAAAGAAGTATTTTTAGAATAAGAATTTGCATACTTACCTAGTGAAACTTTTC |
| 2702 | LUM | 3465252 | GTGTCAGTTTTCATAGTATCCATATTTTATTACTGTTTATTACTTCCATGAATTTTAAAATCTGA GGGAAATGTTTTGTAAACATTTATTTTTTTAAAGAAAAGATGAAAGGCAGGCCTATTTCATC ACA |
| 2703 | LUM | 3465253 | ATGAATGTCTACGTGTTGCTAACGAAGTCACTCTTAATTAA |
| 2704 | LUM | 3465254 | AGATCCTGGGGCCATTATCCTACTCCAAGATCAAGCATTTGCGTTTGGATGGCAATCGCATCT CAGAAACC |
| 2705 | LUM | 3465257 | CCTGACAGAGTCTGTGGGCCCACTTCCCAAATCTCTGGAGGATCTGCAGCTTACTCATAACAA GATCACAAAGCTGGGCTCTTTTGAAGGATTGGTAAACCTGACCTTCATCCATCTCCAGCACAA TCGGCTGAAAGAGGATGCTGTTTCAGCTGCTTTTAAAGGTCTTAAATCACTCGAATACCTTGA CTTGAGCTTCAATCAGATAGCCAGACTGCCTTCTGGTCTCCCTGTCTCTCTTCTAACTCTCTACT TAGACAACAATAAGATCAGCAACATCCCTGATGAGTATTTCAAGCGTTTTAATGCATTGCAGT ATCTGCGTTTATCTCACAACGAACTGGCTGATAGTGGAATACCTGGAAATTCTTTCAATGTGTC ATCCCTGGTTGAGCTGGATCTG |
| 2706 | LUM | 3465258 | TGATTGGTGGTACCAGTGGCCAGTACTATGATTATGATTTTCCCCTATCAATTTATGGGCAATC ATCACCAAACTGTGCACCAGAATGTAACTGCCCTGAAAGCTACCCAAGTGCCATGTACTGTGA TGAGCTGAAATTGAAAAGTGTACCAATGGTGCCTCCTGGAATCAAGTATCTTTACCTTAGGAA TAACCAGATTG |
| 2707 | LUM | 3465259 | GTGCATCTGCTTTAAGAATTAACGAAAGCAGTGTCAAG |
| 2708 | LUM | 3465260 | TGGCAGCCAGTTCCGTCCTGACAGAGTTCACAGCATATATTGGTGG |
| 2709 | LUM | 3465261 | GCCACAGATGTAAAGAGGCTTGTAAGAAAAATGTTCTCACAGTGAGCTTCCTTATTTGAAGCA GGACTCAATTCTTGGTTAAAAGCTATGGTATTTGAGCTAGTTAAACACATATCTCTCTCCCATT CCATAGGGAATGAGCTGGGCTGTCCTTTCTCCCCACGTTCACCTGCACTTCGTTAGAGAGCAG TGTTCACATGCCACACCACAAGATCCCCACAATGACATAACTCCATTCAGAGACTGGCGTG |
| 2710 | DCN | 3465265 | CAACTTCCATATGGAGGTGTCAAGGAGGATTTAGATCTAGAATTTTGGAGCTCAAGGGAAAG GGTTGAGCTGTAGACATAAATTCTAGAGATGCCGGAATATAGATTGTGATCCTTCTTTATCAG |

TABLE 13-continued

Subtyping Target Sequences

| SEQ ID NO. | Gene | Affy Probeset ID | Sequence |
|---|---|---|---|
| | | | CACAGAAATGACTTGACTTTGTCCAAACTAAGCAATCATACTGTACATGTTAGCAACACATTTT<br>ACAGGGCCAATTTG |
| 2711 | DCN | 3465267 | ACTGTGAGGGCTGAATGAATGCTTCCAGGCCATCAGGAACAAGCATAGAAACACAAATCAAT<br>TTTAAAATACACTCAAAAATGTCAAAATAATCCAACTTTTTTGTCTTGATCAGATATATCTACTA<br>GCACATATTACTTCATTTTTTCAGCCAATATTTATTAATAACCTACTGTGTGCTTGACAGTGTTC<br>TAGTGGCAGAGACACAGCAGTGCATAATGCCTTGCCCTCTGAAGCAGATGTTGCAGCAGGAG<br>GAGACATTCCAGGACATGACA |
| 2712 | DCN | 3465269 | GGTGTTGCTACTGCCATTGTTATTACAGGCACACAGTTCGAGCTATAATCATTTCAAGGGAAA<br>TTCTTATGTGTCAGTTCTGGATCGAGGTCTGAGATTCTGCATTTCAAACAAACTTCCAGGAATG<br>CTGCTGCTTCTTGGTCCACACTTGGAGAAATAAGTCAGCAGAGAGTCCTCTCGTTTCCTATTGT<br>ACCATGTCTGTCTTTTGTCTCCTGCTTATTGGCCTCTGTAAGG |
| 2713 | DCN | 3465271 | AGCCTTCAATGATGCACACTCCATGTTATAGCCTTGAATGATATACCCTTTATGCTGCAGCCTT<br>TCTCTTATGGGAAAAGCCTGCAGATATCCTGCTGCTTAACTGACAAGTGTGGTGAGAAATAA<br>GTAGAAATCTAAAGAGGGGAAGACCATTTTGGACACTTATCTGCAAGGCAGATCCAACACAC<br>TTTTCCAGTAGTCAAGCTACTTCTAATTTTGTTCAGTATCAAAATGAGAAACAGGCCTGATTCT<br>CCAGCACTCTTGTC |
| 2714 | DCN | 3465273 | ATGAGTGCAGTGGAACATGAAAAACTTGAGGAGATAACAGTTGAG |
| 2715 | DCN | 3465275 | TTCATGTAATCAGGCTGAACATTTCTACAATTACTAGATGTATTAGACGTAAGTATTTTCTTTA<br>GTTAAACCACCCATGTTAGAAATGTTTTCTGTAGAATTTATAAACAACTATCAATGCAGACAAT<br>TTAATAAGCCTGGGGATGATTTACTTACAGTAAACATTTATCAAATTGTACATTTGTGCTATCA<br>ACAATT |
| 2716 | DCN | 3465276 | CCTCTCCCTATCTTACATTTGAGTATGGTAACTTATGTCATCTATGTTGAATGTAAGCTTATAAA<br>GCACAAAGCATACATTTCCTGACTGGTCTAGAGAACTGATGTTTCAATTTACCC |
| 2717 | DCN | 3465277 | TACAGGCTATGTAAAATTTTTACTAATGTCATTA |
| 2718 | DCN | 3465278 | CAGTTAGCTCATTTGAGATAAAGTCAAATGCCAAACACTAGCTCTGTATTAATCCCCATCATTA<br>CTGGTAAAGCCTCATTTGAATGTGTGAATTCA |
| 2719 | DCN | 3465279 | TCTGTTGATGTTAACTGAGCTACTAGAGATATT |
| 2720 | DCN | 3465280 | CATAAAGCCAAATTTCCAGTTTAAG |
| 2721 | DCN | 3465281 | CTGCAATGTGGATGTTTTACCCACATGAC |
| 2722 | DCN | 3465282 | TATAACCTGGCAAAATCTTGTTAATG |
| 2723 | DCN | 3465283 | GTGCGCTCTGCCATTCAACTCGGAAACTATA |
| 2724 | DCN | 3465284 | TCTCTGTAGTTGGATCAAGTGACTTCTGCCCACCTGGACACAACACCAAAAAGGCTTCTTATTC<br>GGGTGTGAGTCTTTTCAGCAACCCGGTCCAGTACTGGGAGATACAGCCATCCACCTTCAG |
| 2725 | DCN | 3465286 | GCTTCTTTGGTCTAGCTCCTGATTCTTTTTGACATGGCCTCATCATTTTTCTTTATTTCCTCTAAA<br>AAAAAAATGAGATACGTTTGCAGAATGTGCAGGTTTGTTATATAGGTATACGTGTGCCATGGT<br>GGTTTGCTGGCCCTACTGACCCATCCTCTAAGTTCGCCCGCTCACCCCCTACCCCCTGTTGTGT<br>GTTTTGTTACCCTCTCTGTG |
| 2726 | DCN | 3465287 | CCACTGCTTATGTGAGGAATATCCAAA |
| 2727 | DCN | 3465288 | CTGCTGTTGACAATGGCTCTCTGGCCAACACGCCTCATCTGAGGGAGCTTCACTTGGACAACA<br>ACAAGCTTACCAGAGTACCTGGTGGGCTGGCAGAGCATAA |
| 2728 | DCN | 3465290 | CCTTCCCTTACGGAATTACATCTTGATGGCAACAAAATCAGCAGAGTTGATGCAGCTAGCCTG<br>AAAGGACTGAATAATTTGGC |
| 2729 | DCN | 3465293 | CCTGGAGCATTTACACCTTTGGTGAAGTTGGAACGACTTTATCTGTCCAAGAATCAGCTGAAG<br>GAATTGCCAGAAAAAATGCCCAAAACTCTTCAGGAGCTGCGTGCCCATGAGAATGAGATC |
| 2730 | DCN | 3465295 | GACAAAGTGCCAAAGGATCTTCCCCCTGACACAACTCTGCTAGACCTGCAAAACAACAAAATA<br>ACCGAAATCAAAGATGGAGACTTTAAGAACCTGAAGAAC |
| 2731 | DCN | 3465297 | GCGCCCGGCCTCAATATGTCTTCTAATCTTAAAGATAAAGAAGAGGAACCAGAATTGAAATTC<br>ACATAACAGTCTTATAAAAAAATGTTATTATAGGAGCATGTTTAAATATGA |
| 2732 | DCN | 3465299 | ATGCATGGCTTGGTTCTTGAATTAATGCTTGGATGAATATTCTACAATATTCTTGACTCTAGCA<br>AGCTGCAAAGAGAAGGGAACATGCCTGATTGAGAAACAAAAGTGATTTCTCAGTGCATCCTT<br>GCTCCTTCCCTTTAAGGACAACTGTAAAACCAGGAAGCTTAGAAATTCCTTGAGTTTGACTGG<br>AAAGAGAATAGAATTAAAGAGAAGAATCATCTATGTATGAAGCCTGGTCTAACTGATAACGC |

TABLE 13-continued

Subtyping Target Sequences

| SEQ ID NO. | Gene | Affy Probeset ID | Sequence |
|---|---|---|---|
| | | | AGTCAGATTGCCATTTTTAAGATGGAAAAAGGGGAACATGCTTGCCTTGAGCAGAAAAGTTT<br>TTGGTGGGGCTGGAGCTCCTAAATATTATTTTGGTCATTTGCCCAAAAACTGAAGTACACCAC<br>CAATGTCCCAATTATGAAGTTGAATACAGAATTATAAAAAAAAATTGTTGAAAGTCAATAAGA<br>ATAAATCTTAGAATTTGGACTCCTGCCACATGGCAGAAAAAAAGCATGATGTTTTAAGACAAC<br>CTGGCCTTTGTCCAACATG |
| 2733 | DCN | 3465302 | TCTGCAGGATAATTTGATGCCTCTGGAAAAATGCATGGACTGTTTTAGTCCCTAATTCTAATTT<br>ATCACAGTAGTATTAACACGTGCTTTTTTTTTTTTTAAGAGGATGAGGGATTGAGACAGTAA<br>ACATGAATTCCTCATAGATATTGGCCAAGTTGTTTCATTGAACTTGTTGCAACTTACCTTGTAA<br>TTGGAACCACAATTTTATGAGACCCATATCTTGTCTTCTTTTATCTATCATGTTAAGAAATAAAC<br>CAGTTCCCTCTTAATTATAGCA |
| 2734 | DCN | 3465303 | TCCTATTAATCGTGTGAGGTACCTGGGTCATAGTAGCAGCTTCATGCAGTGTTAAAATTATAT<br>GATGATTATATGCAGTAACAGATGAAGAAAAAAGAAAGAAAGCAGGAGAAATGCACCACC<br>TCATTCATTGTAAATGCAGTATAGTTGATTTTTTAATTTGTTTTATGTCCTCTAGTGATCTAAGC<br>ATGAAGCTTGAATTATTATAATAAAGAAAATAAATGCAATGCAGTTGGGGATGGCAAATGTT<br>AATGCTTATCTGTATCAAAGACTAACACTGTCTTCAGGATTATCCTTGGTGGATTATCCTTGGC<br>AGACACTTA |
| 2735 | DCN | 3465304 | TGTAGTCTTAGGAAGCAGCAAGTTCACTGACTTGGGATCTTTATGACAGTTTTGTTGTTGCCAT<br>TGATATTGTTTTGTTTATTTTTGTTTTCAGATGAGAAAGTTTTCTACATGTTATCTTTTTTCTAG<br>GAGCTCAAAGTGTACATCATTCCTTTATTATAGCTAGGTTTACTGACTCATATACTAAGGAAGT<br>AGCTAAAATTATAAAAATAATTTGTTTTTAAAACCATATTTAACTAAGGGAACTAAGTAAGTTC<br>CAATGAGCAGTGGTCTCATGCAAGGTATTTTCAATATTTTAAAATTTACAGATGAATATTTAAA<br>TATATTATAAAAGTTTTAATCAGCTATCTCTAAGAAAATACATTTCTTAAAGGGAAATGAAATT<br>CACTTGACTTTAAATAAAACAAATGAACTCATTTCATGTTTTTAACTATTATCTAACTCTTCCTT<br>ACTTTATGATGCTGGCAAGCTGTTGAGAGCCTTGACATC |
| 2736 | DCN | 3465305 | TGATTCCGCCATGTGTACTTCCTTCTGGAAGAAATTCCATACTATGATCAGGCACTTCTTTCAG<br>AAGTCCTATATTTACTCAGAACATGCTTTCTAGCAGTAGTTTGCAGAAGAAAAATGCAACTTCT<br>ACAATTGGAATAAACTGCCTATAGGAACCCAGAAAAAATATAAAGTATATTCAGTAGTAACG<br>ACTGAAAAACACTTGAAATAGCTTCTTCAACACATATATTGTATAGCTATTTAAAACCCAAATA<br>CAAATGTTATATGAAGACTTTCAAAAGGCCGCAGGATAATTCCAATGGATCTATTTGTTCAGT<br>CATTCAGAAGCTATATCGGGAACCCATCATGGATGAGCTCTGCTCTAGGCATGGGGAGAAAG<br>GATGAGGAAGACAAATATGGCCCTAGTTCTTGTGGATCTTATGTTCTAGTGGTGGTGACTATT<br>ACTTTTTGAATTGTGTATTTGCCACAGGGGAGATTGGATTACTC |
| 2737 | DCN | 3465306 | CCAGAAAGATTGAAGCTCAGTGGATGGG |
| 2738 | DCN | 3465307 | TTCCTGGGCTGGACCGTTTCAACAGAGAGGCTTATTTGACTTTATGCTAGAAGATGAGGCTTC<br>TGGGATAGGCCCAGAAGTTCCTGATGACCGCGACTTCGAGCCCTCCCTAGGCCCAGTGTGCC<br>CCTTCCGCTGTCAATGCCATCTTCGAGTGGTCCAGTGTTCTGATTTG |
| 2739 | DCN | 3465308 | ATCATCCTCCTTCTGCTTGCACAAG |
| 2740 | DCN | 3465310 | GGAGTACATCGTCTAGTGAGGGACAGACCAAGCACGCAAAACAAATTGCAATATAATGTGAT<br>AAGTTCTTTAAAAGAGGTAAGAGCAACGTGCTTTGGGAGCAGAGAAGAGGGAGAAAGCAGC<br>ATCTTGCCTGGATGAGCCAGG |
| 2741 | DCN | 3465311 | GATAATGACTCAAAACAGCTGTAAGATTCTACTTACGAACGTACAGCTTTAATATGGATTCGT<br>CTAAG |
| 2742 | DCN | 3465312 | CTTCTCTAGAGAATCTAGGCAAAAATTCCCAGAAGATAC |
| 2743 | DCN | 3465314 | ATCTAATGTGGGTGTCAGCCGGATTGTGTTCATTGAGGGAAACCTTATTTTTAACTGTGCTAT<br>GGAGTAGAAGCAGGAGGTTTTCAACCTAGTCACAGAGCAGCACCTACCCCCTCCTCCTTTCCA<br>CACCTGCAAACTCTTTTACTTGGGCTGA |
| 2744 | TBX3 | 3472758 | CAGAGGCTGCGTTTGACTTTTTAATTTTTCTTTTGTTATTTGTATTTGCTAGTCTCTGATTTCCT<br>CAAAACGAAGTGGAATTTACTACTGTTGTCAGTATCGGTGTTTTGAATTGGTGCCTGCCTATA<br>GAGATATATTC |
| 2745 | TBX3 | 3472759 | GCTGCCGTGCACTTTGTCGGATATAAAATAAACCACGGGCCCGCCATGGCGTTAGCCCTTCCT<br>TTTGCAGTTGCGTCTGGGAAGGGGCCCCGGACTCCCTCGAGAGAATGTGCTAGAGACAGCCC<br>CTGTCTTCTTGGCGTGGTTTATATGTCCGGGATCTGGATCAGATTCTGGGGGCTCAGAAACGT<br>CGGTTGCATTGAGCTACTGGGGGTAGGAGTTCCAACATTTATGTCCAGAGCAACTTCCAGCAA<br>GGCTGGTCTGGGTCTCTGCCCACCAGGCGGGGAGGTGTTCAAAGACATCTCCCTCAGTGCGG<br>ATTTATATATATATTTTTCCTTCACTGTGTCAAGTGGAAACAAAAACAAAATCTTTCAAAAAAA<br>AATCGGAACAAGTGAACACATTAACATGATTCTGTTTGTGCAGATTAAAAACTTTATAGGGA<br>CTTGCATTATCCGGTTCTCAATAAATTACTGAGCAGCTTTGTTTGGGGAGGGAAGTCCCTACCA<br>TCCTTGTTTAGTCTATATTAAGAAAATCTGTGTCTTTTTAATATTCTTGTGATGTTTTCAGAGCC<br>GCTGTAGGTCTCTTCTTGCATGTCCACAGT |
| 2746 | TBX3 | 3472760 | TTGGTTAGCGGCTTGGAAGCCAAGCCGGACAGGTCCCGCAGCGCGTCCCCGTA |

TABLE 13-continued

Subtyping Target Sequences

| SEQ ID NO. | Gene | Affy Probeset ID | Sequence |
|---|---|---|---|
| 2747 | TBX3 | 3472761 | GGACTCGGGCTCTGAACTCAACAGCCGCTCCTCCACGCTCTCCTCCAGCTCCATGTCCTTGTCG CCCAAACTCTGCGCGGAGAAAGAGGCGGCCACCAGCGAACTGCAGAGCATC |
| 2748 | TBX3 | 3472762 | GGCCCCTGGACGGCAAAGTCGCCGCCCTG |
| 2749 | TBX3 | 3472763 | CCTTCCTCAATCTGAACACCATGCGCCCGCGGCTGCGCTACAGCCCCTACTCCATCCCGGTGCC GGTCCCGGACGGCAGCAGTCTGCTCACCA |
| 2750 | TBX3 | 3472764 | CCTTACCCCTACACGTACATGGCCGCAGCGGCG |
| 2751 | TBX3 | 3472767 | GCCTGGCGGGCCAACAGTTCTTCAACGGGCACCCGCTCTTCCTGCACCCCAGCCAGTTTGCCA TGGGGGGCGCCTTCTCCAGCATGGCGGCCGCTGGCATGGGTCCCCTCCTGGCCACGGTTTCT GGGGCCTCCACCGGTGTCTCGGGCCTGGATTCCACGGCCATGGC |
| 2752 | TBX3 | 3472768 | GAGCCCTGCCGTGACAAGGGCAGCCCCGCGGTCAAGGCTCACCTTTTCGCTGCTGAGCGGCC CCGGGACAGCGGGCGGCTGGACAAAGCGTCGCCCGACTCACGCCATAGCCCCGCCACCATCT CGTCCAGCACTCGCGGCCTGGGCGCGGAGGAGCGCAGGAGCCCGGTTCGCGAGGGCACAGC GCCGGCCAAGGTGGAAGAGGCGCGCGCGCTCCCGGGCAAGGAGGCCTTCGCGCCGCTCACG GTGCAGACGGA |
| 2753 | TBX3 | 3472771 | AATGGGACCTCTGATGAGTCCTCCAGTGAACAAGCAGCTTTCAACTGCTTCGCCCAGGCTTCT TCTCCAGCCGCCTCCACTGTAGGGACATCGA |
| 2754 | TBX3 | 3472772 | TGCAAAAGGTTTCCGGGACACTGGAAATGGCCGAAGAGAAAAAAG |
| 2755 | TBX3 | 3472773 | GACATCTTGAAACTCCCTTATAGTACATTTCGGACATACTTGTTCCCCGAAACTGAATTCATCG CTGTGACTGCATACCAGAATGA |
| 2756 | TBX3 | 3472774 | CTAGGGTTCAAGGTATGAATGATCCTTAGATGGTGAGGGTGGGGGGGCCCTTTGGCAACT GAGGAGCAATTTGGATTCTCCAGAAGATAACATCTGTGGAGCGAAACGTACCCAGGGGGTAC TCCAAGGAGGTGGGCTCGGTACAAGCGTGGTACCCTGCGGTGGGGAAGATTTCAGCCTGGC AGGGGTCCTAAGATCCCGTTTGTTCTGCTAAATCCTTG |
| 2757 | TBX3 | 3472775 | CTTTGGCCTTCCCAAGTGATCACGCTACGTGGCAGGGGAATTA |
| 2758 | TBX3 | 3472776 | CCAAATAATGGAAGGCCTGGCGTTCTAAAAGAAATGGGGCAAGAAAACTTACCGGCTTGTGT TCTATAGCAATTCCAGCTCTTTGGTAGATTCCTGACCTGAGAGTGAAGTTAAAAACCATTTTTT AAGAGCTAAAATCAATTTCAAGGCTATGTATTCCTAAAGGATTTGTTTTGTTTTAAAATATCAT ACTTCTGTTTTGAAACCAGTGATATTATTTTCTCAGGAGAGTTTACGTTTCGGAGCCTTGACTC TGTTGGTTAAATGGTGTGAATACATTTTTAAAAACTCGTTCTTTTACTAAAAAAAGAATTGGGC TTAGGTGGGAGTCCGGCTTACCCTAAATGA |
| 2759 | TBX3 | 3472777 | ATGTTCTGGGCTGGATAAAAAAGCCAAATACATTTTATTGATGGACATTATAGCTGCTGATGA CTGTCGTTATAAATTTCACAATTCTCGGTGGATGGTGGCTGGTAAGGCCGACCCCGAAATGCC AAAGAGGATGTACATTCACCCGGACAGCCCCGCTACTGGGGAACAGTGGATGT |
| 2760 | TBX3 | 3472780 | AAAGAACTTTGGGATCAGTTTCACAAGCGGGGCACCGAGATGGTCATTACCAAGTCGGGAAG |
| 2761 | TBX3 | 3472781 | GGCCGAGACCGGCATCCCGTTCTCCTCCCTGGGG |
| 2762 | TBX3 | 3472782 | ATGGCCTACCATCCGTTCCTACCTCACCGGGCGCCGGACTTCGCCATGAGCGCGGTGCTGGGT CACCAGCCGCCGTTCTTCCCCGCGCTGACGCTGCCTCCCAACGGCGCGGCGGCGCTCTCGCTG CCGGGCGCCCTGGCCAAGCCGATCATGGAT |
| 2763 | TBX3 | 3472783 | AGCCTCTCCATGAGAGATCCGGTCATTCCTGGGACAAGC |
| 2764 | OLFM4 | 3490901 | AAGCTGCAGGGGATTTGGGGGATGTGGGACCTCCAATTCCCAGCCC |
| 2765 | OLFM4 | 3490902 | CAGCTCCAGGTCGGGCTCCAGCTCCAGCCGCAGCTTAGGCAGCGGAGGTT |
| 2766 | OLFM4 | 3490907 | TTTCCAATTTCACCGGCTCCGTGGATGACCGTGGGACCTGCCA |
| 2767 | OLFM4 | 3490908 | CACCTTTCCCGTGGACAGAGTGGAACGCTTGGAATTCACAGCTCATGTTCTTTC |
| 2768 | OLFM4 | 3490910 | GTGAGGGAATATGTCCAATTAATTAGTGTGTATGAAAAGAAACTGTTAAACCTAACTGTCCGA ATTGACATCATGGAGAAGGATACCATTTCTTACACTG |
| 2769 | OLFM4 | 3490911 | TGGAAAAACTGGTCATACAGCTGAAGGAGAGTTTTGGTGGAAGCTCAGAAATTGTTGACCAG CTGG |
| 2770 | OLFM4 | 3490912 | AAATATGACTCTCTTGGTAGAGAAGCTTGAGACACTAGACAAAAACAATGTCCTTGCCATTCGC CGAGAAATCGTGGCTCTGAAGACC |

TABLE 13-continued

Subtyping Target Sequences

| SEQ ID NO. | Gene | Affy Probeset ID | Sequence |
|---|---|---|---|
| 2771 | OLFM4 | 3490913 | GTGAGGCCTCTAAAGATCAAAACACCCCTGTCGTCCACC |
| 2772 | OLFM4 | 3490916 | ATCAGCAAACCGTCTGTGGTTCAGCTCAACTGGAGAGGGTTTTCTTATCTATATGGTGCTTGG GGTAGGGATTACTCTCCCCAGCATCCAAACAAAGGACTGTATTGGGTGGCGCCATTGAATAC AGATGGGAGACTGTTGGAGTATTATAGACTGTACAACACACTGGATGATTTGCTATTGTATAT AAATGCTCGAGAGTTGCGGATCACCTA |
| 2773 | OLFM4 | 3490917 | GTAGTGGTACAGCAGTTTACAACAACAAC |
| 2774 | OLFM4 | 3490918 | CACCGGGAATATTGCCAGAGTTAACCTGACCACCAACACGATTGCTGTGACTCAAACTCTCCC TAATGCTGCCTATAATAACCGCTTTTCATATGCTAATGTTGCTTGGCAAGATATTGACTTTGCT GTGGATGAGAATGGATTGTGGGTTATTTATTCAACTGAAGCCAGCACTGGTAACATGGTGAT TAGTAAACTCAATGACACCACACTTCAGGTGCTAAACACTTGGTATACCAAGCAGTATAAACC ATCTGCTTCTAACGCCTTCATGGTATGTGGGGTTCTGTATGCCACCCGTACTATG |
| 2775 | OLFM4 | 3490919 | TACCTTCTGAATTATGATCTTTCTGTCT |
| 2776 | OLFM4 | 3490920 | TGCAGGGGTGTCTAAAAGTGTGTTCATTTTGCAGCAATGTTTAGGTGCATAGTTCTACCACAC TAGAGATCTAGGACATTTGTCTTGATTTGGTGAGTTCTTGGGAATCATCTGCCTCTTCAGGC GCATTTTGCAATAAAGTCTGTCTAGGGTGGGATTGTCAGAGGTCTAGGGGCACTGTGGGCCT AGTGAAGCCTACTGTGAGGAGGCTTCACTAGAAGCCTTAAATTAGGAATTAAGGAACTTAAA ACTCAGTATGGCGTCTAGGGATTCTT |
| 2777 | OLFM4 | 3490921 | TTCTTTTCTCTCATTGTCCACCTTACTAAAAGTCAGTAGAATCTTCTACCTCATAACTTCCTTCCA AAGGCAGCTCAGAAGATTAGAACCAGACTTACTAACCAATTCCACCCCCCACCAACCCCCTTCT ACTGCCTACTTTAAAAAAATTAATAGTTTTCTATGGAACTGATCTAAGATTAGAAAAATTAATT TTCTTTAATTTCATTATGAACTTTTATTTACATGACTCTAAGACTATAAGAAAATCTGATGGCAG TGACAAAGTGCTAGCATTTATTGTTA |
| 2778 | OLFM4 | 3490922 | TCTAGGACGAGCTATAGAAAAGCTATTGAGAGTATCTAGTTAATCAGTGCAGTAGTTGGAAA CCTTGCTGGTGTATGTGATGTGCTTCTGTGCTTTTGAATGACTTTATCATCTAGTCTTTGTCTAT TTTTCCTTTGATGTTCAAGTCCTAGTCTATAGGATTGGCAGTTTAA |
| 2779 | GJB2 | 3504194 | TGCTTGTAACTAAAATAATTTTGTAATGTATCAAATACATTTAAAACATTA |
| 2780 | GJB2 | 3504195 | AGCAGATCTATAGGAAGATTGAACCTGAATATTGCCATTATGCTTGACATGGTTTCCAAAAAA TGGTACTCCACATATTTCAGTGAGGGTAAGTATTTTCCTGTTGTCAAGAATAGCATTGTA |
| 2781 | GJB2 | 3504196 | CGCATTGCCCAGTTGTTAGATTAAGAAATAGACAGCATGAGAGGGATGAGGCAACCCGTGCT CAGCTGTCAAGGCTCAGTCGCTAGCATTTCCCAACACAAAGATTCTGACCTTAAATGCAACCA TTTGAAACCCCTGTAGGCCTCAGGTGAAACTCCAGATGCCACAATGGAGCTCTGCTCCCCTAA AGCCTCAAAACAAAGGCCTAATTCTATGCCTGTCTTAATTTTCTTTCACTTAAGTTAGTTCCACT GAGACCCCAGGCTGTTAGGGGTTATTGGTGTAAGGTACTTTCATATTTTAAACAGAGGATATC GGCATTTGTTTCTTTCTCTGAGGACAAGAGAAAAAAGCCAGGTTCCACAGAGGACACAGAGA AGGTTTGGGTGTCCTCCTGGGGTTCTTTTTGCCAACTTTCCCCACGTTAAAGGTGAACATTGGT TCTTTCATTTGCTTTGGAAGTTTTAATCTCTAACAGTGGACAAAGTTACCAGTGCCTTAAACTCT GTTACACTTTTTGGAAGTGAAAACTTTGTAGTATGATAGGTTATTTTGATGTAAAGATGTTCTG GATACCATTATATGTTCCCCCTGTTTCAGAGGCTCAGATTGTAATATGTAAATGGTATGTCATT CGCTACTATGATTTAATTTGAAATATGGTCTTTTGGTTATGAATACTTTGCAGCACAGCTGAGA GGCTGTCTGTTGTATTCATTGTGGTCATAGCACCTAACAACATTGTAGCCTCAATCGAGTGAG ACAGACTAGAAGTTCCTAGTGATGGCTTATGATAGCAAATGGCCTCATGTCAAATATTTAGAT GTAATTTTGTGTAAGAAATACAGACTGGATGTACCACCAACTACTACCTGTAATGACAGGCCT GTCCAACACATCTCCCTTTTCCATGACTGTGGTAGCCAGCATCGGAAAGAACGC |
| 2782 | GJB2 | 3504197 | CTTCACAGTGTTCATGATTGCAGTGTCTGGAATTTGCATCCTGCTGAATGTCACTGAATTGTGT TATTTGCTAATTAGATATTGTTCTGGGAAGTCAAAAAAGCCA |
| 2783 | GJB2 | 3504198 | GCAGCTGATCTTCGTGTCCACGCCAGCGCTCCTAGTGGCCATGCACGTGGCCTACCGGAGAC ATGAGAAGAAGAGGAAGTTCATCAAGGGGGAGATAAAGAGTGAATTTAAGGACATCGAGG AGATCAAAACCCAGAAGGTCCGCATCGAAGGCTCCCTGTGGTGGACCTACACAAGCAGCATC TTCCTTCCGGGTCATCTTCGAAGCCGCCTTCATGTACGTCTTCTATGTCATGTACGACGGCTTCT CCATGCAGCGGC |
| 2784 | GJB2 | 3504199 | GATTGGGGCACGCTGCAGACGATCCTGGGGGGTGTGAACAAACACTCCA |
| 2785 | GJB2 | 3504200 | ATCCTATGACAAACTAAGTTGGTTCTGTCTTCACCTGTTTTGGTGAGGTTGTGTAAGAGTTGGT GTTTGCTCAGGAAGAGATTTAAGCATGCTTGCTTACCCAGACTCAGAGAAGTCTCCCTGTTCT GTCCTAGCTAGTGATTCCTGTGTTGTGTGCATTCGTCTTTTTCCA |
| 2786 | POSTN | 3510067 | ATTACTTCAAATTGAGTAATTCAGAAA |
| 2787 | POSTN | 3510068 | ATCGAAGAGTTGTGAACTGTTATCCCATTGAAAAGACCGAGCCTTGTATGTATGTTATGGATA CATAAAATGCACGCAAGCCATTATCTCTCCATGGGAAGCTAAGTTATAAAA |

TABLE 13-continued

Subtyping Target Sequences

| SEQ ID NO. | Gene | Affy Probeset ID | Sequence |
|---|---|---|---|
| 2788 | POSTN | 3510069 | ATGTTTATACAACCCTAAGTCAATAACCTGACCTTAGAAAATTGTGAGAGCCAAGTTGACTTC AGGAACTGAAACATCAGCACAAAGAAGCAATCATCAAATAATTCTGAACACAAATTTAATATT TTTTTTTCTGAATGAGAAACATGAGGGAAATTGTGGAGTTAGCCTCCTGTGGTAAAGGAATTG AAGAAAATATAACACCTTACACCCTTTTTCATCTTGACATTAAAAGTTCTGGCTAACTTTGG |
| 2789 | POSTN | 3510070 | TCTAGAAGACGATTAAGGGAAGGTCGTTCTCAGTGA |
| 2790 | POSTN | 3510072 | ACACACCCGTGAGGAAGTTGCAAGCCAACAAAAAAG |
| 2791 | POSTN | 3510073 | GTGGCTAACTCTGGGAAGATACTTGTGTTAAACTTTATATGACATTTAATAACCCTTCATCATA AGGCAATGTTTTTTACAAAAAGATTGAAAAAATCATGTAAGTCATTTACTCTGCAAAAATGGC ACATTAGGTGGGGTTCCAAAATCCATAATGAAACAATGTGTTTTGCAACTAAGAAACATTCAT TATGATATATGGAAAACACTGTCTGTCTACTTGTCCTTTACGAAAAAATGTAAAACTCTGAGG ATCATAAAATTTAACTACTAAAAATAATCTTCGTGTTTAAGTGATACTTATTTAAGACTTTACAC TGTTCTGTTTAACCATGGTCTCCTGTCTGATTTTAGCCATA |
| 2792 | POSTN | 3510074 | AAAACTGGACTTCATGCTGAGTATAGATGATACATATAAAAGAAGTCAAAATTTGGAGAAAA AATTTAAAAAGATAAGTAGAAAAATGAAGTAACTGTAGAAAACCATACTTACTCTTTGATCTCA AATGCCCAAAAACTGAATGAAAATGTGAATTTAGGCCGACCAGGTAGTCTTGTCAATA |
| 2793 | POSTN | 3510078 | TCTGTCTGTGGCATTAAATGAACCTTAAGAACA |
| 2794 | POSTN | 3510079 | CCCTTAACAGGTTCTAGTGACTGAGTTCAACTTTTTAAAGACTGAGCAAGCAGATTTTTTCTTT TAATTGGGTTAAAAAAAAAAAGACAACATCCACTGTTGTCTTAATAGATGGATTGGTTCAAT GGTAGTTAATAGTTATGAAGAAATGATTACTAGTTTAAACAGTCTTTAAAAAGTTCTATGGTA TAAAGTTTGGGGAGCAATGAATATTTTTTTGCTTTGATTCAGATAATTTTAAGGGCCTTTTAA GTATGCAAAGGGAAATAATTGTTAAATTGCTAGCTGTTAAACAAGCCCAAATTTGATATACT TTTTATATTTAAAAAATTATATTCACTGCCCCCATAAGAGCAATCAAGGCATGTCTTTAAATTC |
| 2795 | POSTN | 3510080 | ACCAAGGTCACCAAATTCATTGAAGGTGGTGATGGTCATTTATTTGAAGATG |
| 2796 | POSTN | 3510081 | AATACACTAGGATTTCTACTGGAGGTG |
| 2797 | POSTN | 3510082 | GAGACACGAGAAGAACGAATCATTACAG |
| 2798 | POSTN | 3510083 | GGGCCGACTACCTTCGCTGTGATTATTTTGAAATAGTGTTGGTTTAGAAATATTGAACATCTG ATATTTTCTCTTAGTTCTTATTTTATAAAAATTGTGGGAATTATTTCCTCAGCTATGAGTTCTTAT TAGCTGGTCAGAAATAAAACATAGTTAGCTTTTAATGGATCTAGTTGGAATTAATTTATCTATT AAGTCACTGGGCCCAACAAAATGTCATGATTTTTGCATATACAAGTGAGGATTGTGGAATAAA ATTGTAACATTAATGTCAGTATAAAAGGAAATATTAGAAACAGTAGGAAAAAATGACCATTGT ATAAGTCTCTGTCTAATAAGCCACTCCACTACTAGGATTTATGATAGGGCTCCCATTCCAATGA TATAGAACTCCCTGGATTCTCACTAAGTATTTATTCCACATCCAGAAAACAAGTATGACATGGA GAGTTAGGATGTCAAATGGCCCTCTCTC |
| 2799 | POSTN | 3510084 | AAGTCAAAATTGAAGGTGAACCTGAATTCAGACTGATTAAAGAAGGTGAAACAATAACTGAA GTGATCC |
| 2800 | POSTN | 3510085 | AAAGGACTGTTTTAACATGATAATTTGTCTCCTA |
| 2801 | POSTN | 3510089 | ATTAAAGTGATTGAAGGCAGTCTTCAGCCTATTATCAAAAC |
| 2802 | POSTN | 3510092 | TCAACTGCTGGAAATACTTAATAAAT |
| 2803 | POSTN | 3510093 | TGATACACTTCTGGTGAATGAATTGAAATCAAAAGAATCTGACATCATGACAACAAATGGTGT AATTCATGTTGTAGATAAACTCCTCTATCCAGCAG |
| 2804 | POSTN | 3510094 | CACCTGACACCAGGAGTTTTCATTGGAAAAGGATTTGAACCTGGTGTTACTAACAT |
| 2805 | POSTN | 3510095 | GCTCCTGACACAACCTGGAGACTGGACATTATTTGTGCCAACCAATGATGCTTTTAAGGGAAT GACTAGTGA |
| 2806 | POSTN | 3510096 | AGGGAGAAACGGTGCGATTCACATATTCCGCGAGATCATCAAGCCAGCAGAGAAATCCCTCC ATGAAAGTT |
| 2807 | POSTN | 3510097 | GATCAGCGCCTCCTTAAATTAATTCTGCAGAATCACATATTGAAAGTAAAAGTTGGCCTTAAT GAGCTTTACAACGGGCAAATACTGGAAACCATCGGAGGCAAACAGCTCAGAGTCTTCGTATA TCGTACA |
| 2808 | POSTN | 3510098 | CAAACAAGTTATTGAGCTGGCTGGAAAACAGCAAACCACCTTCACGGATCTTGTGGCCCAATT AGGCTTGGCATCTGCTCTGAGGCCAGATGGAGAATACACTTTGCTGGCACC |
| 2809 | POSTN | 3510099 | GTCTATTATGGGAGGAGCAGTCTTTGAGACGCTGGAAGGAAATACAATTGAGATAGGATGTG ACGGTGACAGTATAACAGTAAATGGAATCAAAATGGTGAACAAAAGGATATTGTGACAAAT AATGGTGTGATCCATTTGATTGATCAGGTCCTA |

TABLE 13-continued

Subtyping Target Sequences

| SEQ ID NO. | Gene | Affy Probeset ID | Sequence |
|---|---|---|---|
| 2810 | POSTN | 3510100 | AGCTGCCATCACATCGGACATATTGGAGGCCCTTGGAAGAGACGGTCACTTCACACTCTTTGC TCCCACCAATGAGGCTTTTGAGAAACTTCCACGAGGTGTCCTAGAAAGGATCATGGGAGACA AA |
| 2811 | POSTN | 3510101 | TTGTGCTCGAATCATCCATGGGAACCAGATTGCAACAAATGGTGTTGTCCATGTCATTGACCG TGTGCTTACACAAATTGGTACCTCAATT |
| 2812 | POSTN | 3510102 | GGAGAGCAACGTGAATGTTGAATTACTGAATGCTTTACATAGTCACATGATTAATAAGAGAAT GTTGACCAAGGACTTAAAAAATGGCATGATTATTCCTTCAATGTATAACAATTTGGGCTTTTC ATTAACCATTATCC |
| 2813 | POSTN | 3510103 | GTAATGAGGCTTGGGACAACTTGGA |
| 2814 | POSTN | 3510104 | CATGTTTATGGCACTCTGGGCATCGTGGGAGCCACCACAACGCAGCGCTATTCTGACGCCTCA AAACTGAGGGAGGAGATCGAGGGAAAGGGATCCTTCACTTACTTTGCACCGA |
| 2815 | POSTN | 3510109 | AAAGAAATACTTCAGCACTTGTAAGAACTGGTATAAAAAGTCCATCTGTGGACAG |
| 2816 | POSTN | 3510110 | CTATTGCTGCTTATTGTTAACCCTATAAACGCCAACAATCATTATGACAAGATCTTGGCTCATA GTCGTATCAGGGGTC |
| 2817 | POSTN | 3510111 | TTCTCTTCGGGGACTAACTGCAACGGAGAGACTCAA |
| 2818 | SLITRK6 | 3519841 | GTTGCAATTATATAGGCCATGGGTGGCTCAAAACTTTGAACATTTGAGCTTAAACAAATGCCA CTCTCATGCATTCTAAATTAAAAAGTTAAAATGATTAATAGTTCAGGTGGAAGAAATAAGCAT ACTTTTTGGGTTTTCTACACATTTTGTGTAGACAATTTTAATGTCAGTGCTGCTGTGAACTAAA GTATGTCATTTATGCTCAAAGTTTAATTCTTCTTCTTGGGATATTTTAAAAATGCTACTGAGATT CTGCTGTAAATATGACTAGAGAATATATTGGGTTTGCTTTATTTCATAGGCTTAATTCTTTGTA AATCTGAATGACCATAATAGAAATACATTTCTTGTGGCAAGTAATTCACAGTTGTAAAGTAAA TAGGAAAAATTATTTTATTTTTATTGATGTACATTGATAGATGCCATAAATCAGTAGCAAAAG GCACTTCTAAAGGTAAGTGGTTTAAGTTGCCTCAAGA |
| 2819 | SLITRK6 | 3519842 | AGTTTGAGGGCTTTCGCAGAAATGCTGTGATTCTGTTTTAAGTCCATACCTTGTAAATAAGTGC CTTACGTGAGTGTGTCATCAATCAGAACCTAAGCACAGCAGTAAACTATGGGGAAAAAAAA GAAGAAGAAAAAGAAACTCAGGGATCACTGGGAGAAGCCATGGCATTATCTTCAGGCAATTT AGTCTGTCCCAAATAAAATAAATCCTTGCATGTAAATCATTCAAGGATTATAGTAATATTTCAT ATACTGAAAAGTGTCTCATAGGAGTCCTCTTGC |
| 2820 | SLITRK6 | 3519843 | CCTTTGGTCCAAAGCATCTGGAAGAGGAAGAAGAGAGGAATGAGAAAGAAGGAAGTGATGC AAAACATCTCCAAAGAAGTCTTTTGGAACAGGAAAATCATTCACCACTCACAGGGTCAAATAT GAAATACAAAACCACGAACCAATCAACAGAATTTTTATCCTTCCAAGATGCCAGCTCATTGTAC AGAAACATTTTAGAAAAAGAAAGGGAACTTCAGCAACTGGGAATCACAGAATACCTAAGGAA AACATTGCTCAGCTCCAGCCTGATATGGAGGCACATTATCCTGGAGCCCACGAAGAGCTGA AGTTAATGGAAACATTAATGTACTCACGTCCAAGGAAGGTATTAGTGGAACAGACAAAAAAT GAGTATTTTGAACTTAAAGCTAATTTACATGCTGAACCTGACTATTTAGAAGTCCTGGAGC |
| 2821 | SLITRK6 | 3519844 | GGTTCTTGTTCTTCACCGCAGGAGAAGATACAAAAAGAAACAAGTAGATGAGCAAATGAGAG ACAACAGTCCTGTGCATCTTCAGTACAGCATGTATGGCCATAAAACCACTCATCACACTACTGA AAGACCCTCTGCCTCACTCTATGAACAGCACATGG |
| 2822 | SLITRK6 | 3519845 | AAAGGCATGTTCCTTGGTCTCCATAATCTTGAATACTTATATCTTGAATACAATGCCATTAAGG AAATACTGCCAGGAACCTTTAATCCAATGCCTAAACTTAAAGTCCTGTATTTAAATAACAACCT CCTCCAAGTTTTACCACCACATATTTTTTCAGGGGTTCCTCTAACTAAGGTAAATCTTAAAACA AACCAGTTTACCCATCTACCTGTAAGTAATATTTTGGATGATCTTGATTTGCTAACCCAGATTG ACCTTGAGGATAACCCCTGGGACTGCTCCTGTGACCTGGTTGGACTGCAGCAATGGATACAA AAGTTAAGCAAGAACACAGTGACAGATGACATCCTCTGCACTTCCCCCGGGCATCTCGACAAA AAGGAATTGAAAGCCCTAAATAGTGAAATTCTCTGTCCAGGTTTAGTAAATAACCCATCCATG CCAACACAGACTAGTTACCTTATGGTCACCACTCCTGCAACAACAACAAATACGGCTGATACT ATTTTACGATCTCTTACGGACGCTGTGCC |
| 2823 | SLITRK6 | 3519846 | TTCACTTTGGAAATGCTTCACTTGGGAAACAATCGTATTGAAGTTCTTGAAGAAGGATCGTTT ATGAACCTAACGAGATTACA |
| 2824 | SLITRK6 | 3519847 | GGCTGACGATGCTTCACACAAATGACTTTTCTGGGCTTACCAATGCTATTTCAATACACCTTG GATTTAACAATATTGCAGATATTGAGATAGGTGCATTTAATGGCCTTGGCCTCCTGAAACAAC TTCATATCAATCACAATTCTTTAGAAATTCTTAAAGAGGATACTTTCCATGGACTGGAAAACCT GGAATTCCTGCAAGCAGATAACAATTTTATCACAGTGATTGAACCAAGTGCCTTTAGCAAGCT CAACAGACTCAAAGTGTTAATTTTAAATGACAATGCTATTGAGAGTCTTCCTCCAAACATCTTC CGATTGTTCCTTTAACCCATCTAGATCTTCGTGGAAATCAATTACAAACATTGCCTTATGTTG GTTTTCTCGAACACATTGGCCGAATATTGGATCTTCAGTTGGAGGACAACAAATGGGCCTGCA ATTGTGACTTA |

TABLE 13-continued

Subtyping Target Sequences

| SEQ ID NO. | Gene | Affy Probeset ID | Sequence |
|---|---|---|---|
| 2825 | SLITRK6 | 3519848 | TGCTAATAAATTGTGAAGCAAAAGGTATCAAG |
| 2826 | SLITRK6 | 3519849 | AGGCTCTTGTGATTCTCTTTGCAATTGTGAGGAAAAAGATGGCACA |
| 2827 | SLITRK6 | 3519850 | AGCTGTGGATTCATCTCTTTTATTCATCTCTCCTTGCCTGTATATCTTTACACTCCCAAACTCCAGTGCTCTCATC |
| 2828 | SLITRK6 | 3519851 | ATAACGTCAGGAAGAGTCTCTGCTTTACAG |
| 2829 | SLITRK6 | 3519852 | GGAGAACATTGCTGTAGCTTGGATCTACAACCTAAGAAAGCAAGAGTGATCAATCTCAGCTCTGTTAAACATCTTGTTTACTTACTGCATTCAGCAGCTTGCAAATGGTTAACTATATGCAAAAAAGTCAGCATAGCTGTGAAGTATGCCGTGAATTTTAATTGAGGGAAAAAGGGACAATTGCTTCAGGATGCTCTAGTATGCACTCTGCTTGAAATATTTTCAATGAAATGCTCAGTATTCTATCTTTGACCAGAGGTTTTAACTTTATGAAGCTATGGGACTTGACAAAAAGTGATATTTGAGAAGAAAGTACGCAGTGGTTGGTGTTTTCTTTTTTTAATAAAGGAATTGAATTACTTTGAACACCTCTTCCAGCTGTGCATTACAG |
| 2830 | DHRS2 | 3529241 | CTGACAGAAGGGCTGCCAAACTGCACTCCAGACA |
| 2831 | DHRS2 | 3529244 | GCCTGATTCAGCAGGAAGCATCTCAGACACCAA |
| 2832 | DHRS2 | 3529245 | GCTACCAGGGCTGGTTTCATCCCTGTGCTAGGCTTTCTGTGAGGATGAGCAGCACCGGGATAGACAGGAAGGGCGTCCTGGCTAACCGGGTAGCCGTGGTCA |
| 2833 | DHRS2 | 3529246 | ATCGGCTTTGCCATCGCCCGACGTCTGGCCCGGGACGGGGCCCACGTGGTCATCAGCAGCCGGAAGCAGCAGAACGTGGACCGGGCCATGGCCAAGCTGCAGGGGGAGGGGCTGAGTGTGGCGGGCATTGTGTGCCACGTGGGGA |
| 2834 | DHRS2 | 3529247 | GTGTGCAGCGCAGGGGTCAACCCTCTGGTAGGGAGCACTCTGG |
| 2835 | DHRS2 | 3529248 | TCTCTCCTAGAAGGGGGCTCCTCACTGAGTCCCACACAAACTTGCCGACAGGACCAGATCCAGCCATCAGCATTCCGGGGGCTTAGACATCCCAGCCT |
| 2836 | DHRS2 | 3529249 | GTGCGCCCTCTTTCAGGCTCATGGATAGTTCTCTGCTCAGAACTACTTGGCACACTGAGCTACTCTCTCTTACTTTCTAATGGGGCAGTTTTCTTCATCAAGGGAGGGAGTCTCACCTTTTCTTTGGCTTGGTTTTTGTTCCTGAGTCCAGGAGGGGTCTTACCTCAGCCCCTCACTCAGCCTGATGCACATGGAGTATTGGACAGATATCCTGTGGGCTGGTGGGGTCTGTTTTGACCAGGAAACCCTTACAGCTAACCTAATCCTCAATTCCTTCTTATTAGGGACCTCAGGGTGGTACCCACTTCTGACATCTGGACCACTTCTTGCAGTCATTGGGGGTCATCCCCCACACTGGTAACCTGTCATCAAATGGGCCAGCAACATTCAGCTTAAGTATTTCTCCTTCCCACATCCAAGGGATTGAGTGGGAGTGAGATTGGGGGGTGGAAAAAACAGTGAACAGTCCTGGTGAGTTGCAGATGTGGTCTCATTCCCTAGAGATGCAGGATGCAGCTGACCTGAATCAGGACAGATCCCTGCAGGAGGGACTCCTGGTGCCATGTCAGTCCCACCTGGCACTGCCCTAGCTCCCAGGCTCCGCCTCTGCATCTTTCCTTGCTACTTCCTCTTTCACTTCTCCCCCGTTCCCAGACCCACCAGACAGAGCTTCCAGAGTGTCAGGACATGTGTGACTTAGCCCAGA |
| 2837 | DHRS2 | 3529250 | GCCAGTTGCTGCCCTACATGGAGAACAG |
| 2838 | DHRS2 | 3529251 | CTTGGCCTTGACATCAGCAGGTTTGGGACAAGGCTATGCTTTAACTCCTTGACCTTGTGGGCTGGTCATTGTCACCTTACCTGCTCTCTGTTCTTACCAACTTAAAACCAATGACAGGGTTAGCCCCATTCCTCTCCATAGGAAAAAGCCTGTCCCAGACCTCTCCTCATGCCTGCGCTTGGTCTCCAGGGACCCTGCCTGTGTTCCAGGTCCTGCAGATCTGACTGTACCCCTCACAGACACACCCTTAGGAACTGGCCAGGGGCTGTCTTCAGTAGAAGGAAAGTTCCTGACTGTCACTTCTGGTCTCCCTTACCCCATCTGCTCCTTAGAGGTTGCTCATTGATAGGCACTCACCATCAGCCTTGGGTGCCTCTTCACAAAGCCCACCCTGCCCTCTCCTTCAAGCACCTGGCAAGAGAGGAAGCAGAAGATAAGGGTTCTGAGCATGGACATCGTATTTATGAGAAATAGGCATGGAATCCTAGCTCTGCCGTGTATTGGCTGGTACTA |
| 2839 | DHRS2 | 3529252 | AGGGGTGCTGTCATCCTGGTCTCTTCCATTG |
| 2840 | DHRS2 | 3529253 | ATAGGGTGAGGGGCAACTTTGTTCTTTTCCTCAGAGCCTTACAGACAAAGTGCCTGGGACAGACCCCCACCATCCTCCTGCTGCCCTGGGCTGAGCTTGTCTCCATGTGGGTGGGAGGGCTGCTGGGCCTGTGAGATCCCTGTAGGTGAGAAATCC |
| 2841 | DHRS2 | 3529254 | GCGCTGGGTGTCTACAATGTCAGCAAGACAGCGCTGCTGGGTCTCACTAGAACACTGGCATTGG |
| 2842 | DHRS2 | 3529255 | GTAAACTGCGTGGTTCCAGGAATTATC |
| 2843 | DHRS2 | 3529256 | CTGAATCCTTAGGTCAGCATGCCTATGACTGAGGTCCTCATTGTTCTCTGAACTCAGCCATGGTGCAGTCCATCCATCCTGAAAAGATGCTCCTTCTTTTGAGAAGGGCAAAGCTGCCCTAGGTGTTCTGCCTGGTGGCCTTCCCGGGGCCCTGCCCATCTTGTTTTAGTAGCACTGAC |
| 2844 | DHRS2 | 3529257 | TCATGGGAATGAGTCTCTCTGGAAGAACTTCAAGGAACATCATCAGCTG |

TABLE 13-continued

Subtyping Target Sequences

| SEQ ID NO. | Gene | Affy Probeset ID | Sequence |
|---|---|---|---|
| 2845 | DHRS2 | 3529258 | GTTGAGTCTATTGCAAGAGCAGACCCCTCCCTGTCATCTGGCCATTGTTTTTGCTGAAATCTGG<br>AGTCCACATGGCCCTGGAGGGTGCAAGTAGCCCTGCTGCATCCACCTTGTTCCCCATGGAGCC<br>CACTCCCACCTGTCATCCGTGAGCCCCAGAGCAGCAGAATCAGAGTACAAG |
| 2846 | DHRS2 | 3529259 | GGACTGTGCAGGAATCGTGTCCTTCCTGTGCTCTCCAGATGCCAGCTACGTCAACGGGGAGA<br>ACATTGCG |
| 2847 | DHRS2 | 3529260 | GTGGCAGGCTACTCCACTCGGCTCTGA |
| 2848 | DHRS2 | 3529261 | GCGGCTGCGTAGCTGTGGTCCCAGGC |
| 2849 | DHRS2 | 3529262 | GCCATTCTGCCAGACTAGCAATTTGGGGGCTTACTCATGCTAGGCTTGAGGAAGAAGAAAAA<br>CGCTTCGGCATTCTCCTTAGGACTTATCTGCTTGTAGATTTGGCTGATCCA |
| 2850 | WARS | 3579547 | CTCCTGTCACCCAGTAGAGTAAATAAACT |
| 2851 | WARS | 3579548 | TGGTTGATGTATCTGGGTCTCCTCTG |
| 2852 | WARS | 3579549 | CCTGGCCTCTGTAAGCCTGTGTATGTTATCAATACTGTTTCTTCCTGTGAGTTCCATTATTTCTA<br>TCTCTTATGGGCAAAGCATTGTGGGTAATTGGTGCTGGCTAACATTGCATGGTCGGATAGAG<br>AAGTCCAGCTGTGAGTCTCTCCCCAAAGCAGCCCCACAGTGGAGCCTTTGGCTGGAAGTCCAT<br>GGGCCACCCTGTTCTTGTCCATGGAGGACTCCGAGGGTTCCAAGTATACTCTTAAGACCCACT<br>CTGTTTAAAATATATATTCTATGTATGCGTATATGGAATTGAAATGTCATTATTGTAACCTAG<br>AAAGTGCTTTGAAATATTGATGTGGGGAGGTTTATTGAGCACAAGATGTATTTCAGCCCATGC<br>CCCCTCCCAAAAAGAAATTGATAAGTAAAAGCTTCGTTATACATTTGACTAAGAAATCACCCA<br>GCTTTAAAGCTGCTTTTAACAATGAAGATTGAACAGAGTTCAGCAATTTTGATTAAATTAAGA<br>CTTGGGGGTGAAACTTTCCAGTTTACTGAACTCCAGACCATGCATGTAGTCCACTCCAGAAAT<br>CATGCTCGCTTCCCTTGGCACACCAGTGTTCTCCTGCCAAATGACCCTAGCCCTCTGTCCTGC<br>AGAGTCAGGGTGGCTTTTCCCCTGACTGTGTCCGATGCCAAGGAGTCCTGGCCTCCGCAGAT<br>GCTTCATTTTGACCCTTGGCTGCAGTGGAAGTCAGCACAGAGCAGTGCCCTGGCTGTGTCCCT<br>GGACGGGTGGACTTAGCTAGGGAGAAAGTCGAGGCAGCAGCCCTCGAGGCCCTCACAGATG<br>TCTAGGCAGGCCTCA |
| 2853 | WARS | 3579550 | ATTACACCAGCGGAGCCATGCTCACCGGTGAGCTCAAGAAGGCACTCATAGAGGTTCTGCAG<br>CCCTTGATCGCAGAGCACCAGGCCCGGCGCAAGGAGGTCACGGATGAGATAGTGAAAGAGT<br>TCATGACTCCCCGGAAGCTGTCCTTCGACTTTCAGTA |
| 2854 | WARS | 3579552 | CAATAAGCATGCGTTTTCTGGAGGGAGAGACACCATCGAGGAGCACAGGCAGTTTGGGGGC<br>AACTGTGATGTGGACGTGTCTTTCATGTACCTGACCTTCTTCCTCGAGGACGACGACAAGCTC<br>GAGCAG |
| 2855 | WARS | 3579554 | AGCCAGCGGGATCAGAAACATGCCCTGGGGGGCACACGCACACACACCACTGCGCAGTG<br>CTTTGGGCCTCAGCCACCCAGCCACCGTAGCAATGCTGAACTCCAGGATTGCCAACTTTGCT<br>CCTGCAGAACTCAAGGCAGCCTGTCCTTCCCACATGAATCAGGTGAATTTGTTTTGTGTCCTTT<br>CATTTAGGTAAAATTTTGAATTTTTTTTCTTTTTTTCCTTTTCTGCTTTTCTTATCAGCACTGTTCT<br>GCAGGCAAAGTCA |
| 2856 | WARS | 3579555 | GATCGGCTATCCTAAACCAGCCCTGCTGCACTCCACCTTCTTCCCAGCCCTGCAGGGCGCCCA<br>GACCAAAATGAGTGCCAGCGACCCCAACTCCTCCATCTTCCTCACCGACACG |
| 2857 | WARS | 3579557 | CCCTCCTTCAGCAACTCATTCCCACAGATCTTCCGAGACAGGACGGATATCCA |
| 2858 | WARS | 3579559 | ATGAGCTCAGGTTTCTACAAAAATGTGGTGAAGATTCAAAAGCATGTTACCTTCAACCAAGTG<br>AAAGGCATTTTCGGCTTCACTGACAGCGACTGCATTG |
| 2859 | WARS | 3579560 | TCTTGCCAAGGATAGTCAGTCTTCCAGAGTTATGTCTTCCTCCTTTTCAACGCACCTTTTCCTCA<br>CAGAGAAAAGACTCAGTGGTTACACAGTTTCCTCAG |
| 2860 | WARS | 3579561 | CCAAGGACATCATCGCCTGTGGCTTTGACATCAACAAGACTTTCATATTCTCTGACCT |
| 2861 | WARS | 3579562 | GTGGCTCCAGGATGTATTTAACGTGCCCTTGGTCATCCAGATGACGGATGACGAGAAGTATCT<br>GTGGAA |
| 2862 | WARS | 3579563 | TGGGCTCACTTTAGAGGACCATGGAGTGATGGGAGAGCGCAGCTTTGGAGTCAGCCAGGC<br>CTGCTCCTCTTCTCATCCTGCTCCCTGTCTGCATGGCCATGGGCCTGCTACTTCTCTGAGCCTAA<br>GTTTCCACATCTGCAAGATGAGAATGAAGATACCTACCTCATAGAACTACTGTAAAGCTTCAA<br>AACAAAGTGTGTAGAGCAGCTAACACAGAGCACACAGGGCCACCTGGTCGATAAATGGTAGT<br>AGACCTTATCATTATCCATAGTCAAATTCATATCACAATTCAAATTGTGATTTTGTAGGCAAGG<br>AAGTTTTAACATACGTTGTAAGTAGGAGCTGTGTTTTCAGATGCACGATGGCGTTCCTCC |
| 2863 | WARS | 3579564 | ATCAGGTTCTTGATGCCTATGAAAATAAGAAGCCATTTTATCTGTACACGGGCCGGGCCCCT<br>CTTCTGAAGCAATGCATGTAGGTCACCTCATTCCATTTA |

TABLE 13-continued

Subtyping Target Sequences

| SEQ ID NO. | Gene | Affy Probeset ID | Sequence |
|---|---|---|---|
| 2864 | WARS | 3579568 | GCTAATAAACCGAATAGAGAGAGCCACCGGCCAAAGACCACACCACTTCCTGCGCAGAGGCA TCTTCT |
| 2865 | WARS | 3579569 | GGGAGGATTACAAGGCTGACTGTCCTCCAGGGAACCCAGCACCTACCAGTAATCATGGCCCA GATGCCACAGAAGCTGAAGAGGATTTTGTGGACCCATGGACAGTACAGACAAGCAGTGCAA AAGGCATAGACTACGATAAGCTCATTG |
| 2866 | WARS | 3579571 | TGAGTTCGAGCGATTCTCCTGCCCTGGCCT |
| 2867 | WARS | 3579576 | TAAGGTCCCTCAAAGCGGGAAATGCGTCAAAG |
| 2868 | WARS | 3579577 | ACAGTGAGCCCGCATCTCTGCTGGAGCTGTTCAACAGCATCGCCACACAAGGGGAGC |
| 2869 | WARS | 3579578 | GCCGGCTGTGAACGTAGTTCCTGAGAGATA |
| 2870 | WARS | 3579579 | GTCTGCTGAACAAATCCTCTGACCTCA |
| 2871 | WARS | 3579582 | GTGAATCTACTTCTCTTAACAAAGTCTCAATGTCCTATTTGCAATTTATGTGGTAAACACTGAA GACAATGGTCCTTAACCTTT |
| 2872 | WARS | 3579583 | AACTGCCCAGCGTGACCAGTGGCCACCTCTGCA |
| 2873 | WARS | 3579584 | GAAGAGTATTAAAGACCATTTCTGGC |
| 2874 | WARS | 3579585 | TTATAAGAAACCCTTAGCTGAATGC |
| 2875 | WARS | 3579586 | TGGCCCTCCCGGGAGTATCCTTAGAGCCCGGCTTGCTGCCCGCCGCGTTCTGGCACTGTGAG GCGCGGAGCCTGCCACCGACCCCTCGCCCCTTTCCTCTGAGCGCCGCCGACCCACCCCGTCTC CCTTTCCCACTGGCACCCTTCATCGTCTCCGCCTGTTCGCTTTTCCCGAGGAGAGAGGCCCCCA TTTTTATTTAGCGCCTGCCATGTGCCAGAGGCTTTGCGTAGTGTTGCACTTAGTCCCCTCAACG GTAATGTTAGCAGGCTTCTCCATGCCCATTCCACAGATGAGGAAACCGAAGGGGAAGCAGAA AAGTAATGCGACCCTTGCCCAAGGTTTCGAATAAGTCCAAGCTGGGATTGAAACCCAGGCGT CTGTGACCCCAGAACTCCTGATCTTTCCACTGCACTGTGCCGCCTCGGTGAACAGATGCGGGG AATTTACAGTTTCTCTTTTCCACCGCCCACGACTACACAAAATCAGTCACACTGACGCTGAGGGT GGGGAACGGGAAGAGGGTGGGGAGGTTATTTGGAGGCCAGCGGGGGGTGAGGGGTGGCT GATGCAATGACCAGCTAATGGCTCGATTCTCAAGA |
| 2876 | WARS | 3579587 | GTTGGTCCAAGGCACAGCGCTTTCTGAAGGAACAGGAAGTGAAAGGAAGGCGAGCGGCTAT GAGAGACCGCGTTAAGCGGCACGGGGCGCTTTAGGCGCTGCCCAGTCCCGGCCCCTCCAGCC CGGGGCCCGCCGCTCACCACACGCACCGGAAGCGTCGGTTCTCCCGGAGGCAGACCGGCCA GCACACTACCATCCAGTCACGTTCCGACGCGACGCCGCGGCCGCCAGCCAATCAGTGGCGGC CTCTGCCCCGCCCCCGCGCGAACAGCCAATGACGGCGCCGTCGGGCCGGAAGTTGTTCCGTC CGGACGGCGTTTCCACGGACGCCCAGGAGACA |
| 2877 | THBS1 | 3589468 | GATCCCTGCTGGGCACCAACAGCTCCACC |
| 2878 | THBS1 | 3589469 | GCCTGGGGACTAGGCGTCCTGTTCCTGATGCATGTGTGTGGCACCAACCGCATTC |
| 2879 | THBS1 | 3589470 | TTCCGCATCGAGGATGCCAACCTGATCCCCCCTGTGCCTGATGACAAGTTCCAAGACCTGGTG GATGCTGTGCGGGCAGAAAAGGGTTTCCTTCCTTCTGGCATCCCTGAGGCAGATGAAGAAGAC CCGGGGCACGCTGCTGGCCCTGGAGCGGAAAGACCACTCTGGCCAGGTCTTCAGCGTGGTGT CCAATGGCAAGGCGGGCACCCTGGACCTCAGCCTGACCGTCAAGGAAAGCAGCACGTGGT GTCTGTGGAAGAAGCTCTCCTGGCAACCGGCCAGTGGAAGAGCATCACCCTGTTTGTGCAGG AAGACAGGGCCCAGCTGTACATCGACTGTGA |
| 2880 | THBS1 | 3589474 | TGGCCAATGAGCTGAGGCGGCCTCCCCTATGCTATCACAACGGAGTTCAGTACAGAAATAAC GAGGAATGGACTGTTGATAGCTGCACTGAGTGTCA |
| 2881 | THBS1 | 3589475 | CTGCAAAAAGGTGTCCTGCCCCATCATGCCCTGCTCCAATGCCACAGTTCCTGATGGAGAA |
| 2882 | THBS1 | 3589477 | CTCACGGCCAGTTGGAGCCAGAACCAACAACAGCTCGGCTGCCTTCACACTCATCTGTCAAA CACATGGTGTATAGGCTCCCCTGACAGAAATGACTCCTATAAGCTTCCTCATACTCGCGCATTCT TGGAAGTCTGAGACTGGAAATGCCTACCCAGATATGTTAAGTCAGTAAAGGAAAACTCATTT GCAATGCTGAGAGGAGAAAGAAAATCAATGAATAGGAGAGCATACACTGTGGGAAGGCTCA GCTGTACTGAGCCAGGCAAAGCATCCGATTACCCACTGCTGTACACATCATGACCTGGGATA AACCCCTGGGCCGTTGGCCTAAGAAATATGTTGCTTTTCATCCTGTATAACTGCAACTTTGTGC CGGCTCATA |
| 2883 | THBS1 | 3589479 | CATGGTCCGAGTGGACCTCCTGTTCTACGAGCTGTGGCAATGGAATTCAGCAGCGCGGCCGC TCCTGCGATAGCCTCAACAACCGATGTGAGGGCTCCTCGGTCCAGACACGGACCTGCCACCATT CAGGAGTGTG |
| 2884 | THBS1 | 3589482 | GATGGTGTGATCACAAGGATCCGGCTCTGCAACTCTCCCAGCCCCCAGATGAACGGGAAACC CTGTGAAGGCGAAGCGCGGG |

TABLE 13-continued

Subtyping Target Sequences

| SEQ ID NO. | Gene | Affy Probeset ID | Sequence |
|---|---|---|---|
| 2885 | THBS1 | 3589483 | CCAGCTGGTTGCCTGGCATCTGCAGCCTGCAGTTCAGTGGGTCATAGAGCAGGAAGGTTACC<br>TACTAGAGAAACAAACAGAAGCAAAGTCCTGCAGGCTCAGCAACTTCTTTTAATGAAA |
| 2886 | THBS1 | 3589484 | GGTCACCATGGGACATCTGTTCTGTCACCTGTGGAGGAGGGGTACAGAAACGTAGTCGTCTC<br>TGCAACAACCCCACACCCCAGTTTGGAGGCAAGGACTGCGTTGGTGATGTAACAGAAAACCA<br>GATCTGCAACAAGCAGGACTGTCCA |
| 2887 | THBS1 | 3589485 | GCCACGCAGCCCAGGATGAAACGACCCAGG |
| 2888 | THBS1 | 3589486 | TGCTTTGCCGGCGTGAAGTGTACTAGCTACCCTGATGGCAGCTGGAAATGTGGTGCTTGTCCC<br>CCTGGTTACAGTGGAAATGGCATCCAGTGCACAGATG |
| 2889 | THBS1 | 3589487 | TCAACCACAATGGAGAGCACCGGTGTGAGAACACGGACCCCGGCTACAACTGCCTGCCCTGC<br>CCCCCACGCTTCACCGGCTCACAGCCCTTCGGCCAGGGTGTCGAACATGCCACGGCCAACAAA<br>CA |
| 2890 | THBS1 | 3589489 | GATGGGACCCACGACTGCAACAAGAACGCCAAGTGCAACTACCTGGGCCACTATAGCGACCC<br>CATGTACCGCTGCGAGTGCAAGCCTGGCTACGCTGGCAATGGCATCATCTGCGGGGAGGACA<br>CAGACCTGGATGGCTGGCCCAATGAGAACCTGGTGTGCGTGGCCAATGCGACTTACCA |
| 2891 | THBS1 | 3589491 | ATTGCCCCAACCTTCCCAACTCAGGGCAGGAAGACTATGACAAGGATGGAATTGGTGATGCC<br>TGT |
| 2892 | THBS1 | 3589493 | CATTCCATTACAACCCAGCTCAGTATGACTATGACAGAGATGATGTGGGAGACCGCTGTGAC<br>AACTGTCCCTACAACCACA |
| 2893 | THBS1 | 3589495 | TATCCTCAATGAACGGGACAACTGCCAGTACGTCTACAATGTGGACCAGAGAGACACTGATA<br>TGGATGGGGTTGGAGATCAGTGTGACAATTGCCCCTTGGAACACAATCCGGATC |
| 2894 | THBS1 | 3589497 | GGACTCTGACTCAGACCGCATTGGAGATACCTGTGACAACAATCAGGATATTGATGAAGATG<br>GCCACCAGAACAATCTGGACAACTGTCCCTATGTGCCCAATGCCAACCAGGCTGACCATGACA<br>AAGATGGCAAGGGAGATGCCTGTGACCACGATGATGACAACGATGGCATTCCTGATGACA |
| 2895 | THBS1 | 3589498 | TGACATCAGTGAGACCGATTTCCGCCGATTCCAGATGATTCCTCTGGACCCCAAAGGGACATC<br>CCAAAATGACCCTAACTGGGTTGTACGCCATCAGGGTAAAGAACTCGTCCAGACTGTCAACTG<br>TG |
| 2896 | THBS1 | 3589500 | TATGATGAGTTTAATGCTGTGGACTTCAG |
| 2897 | THBS1 | 3589501 | ACCGAAAGGGACGATGACTATGCTGGATTTGTCTTTGGCTACCAGTCCAGCAGCCGCTTTTAT<br>GTTGTGATGTGGAAGCAAGTCACCCAGTCCTACTGGGACACCAACCCCACGAGGGCTCAGGG<br>ATACTCGGGCCTTTCTGT |
| 2898 | THBS1 | 3589502 | GTAAGAAGCAAAGCCCTGGAACAGAGAGAGAGCTTATGG |
| 2899 | THBS1 | 3589503 | TGTGCTTTGACCAAGACTCTGACCAGGGAGTCTTAGAAAGTTCCCAGCATCACCAGCTGCAGC<br>ATTGAACTCTGCTTTGTAAAAACATAATAGTGTTGAAAAGGGAGCTTGACCAAGAATTGCCCT<br>GCAAATCCTAAGGTGCCTTCAGCCTTTTCAAACAAAAAAACCTCCTTCCCTCCTCTCTGTCTGCT<br>TTATATGTGTGCTCAGTGGCACACAACAAATATGAGAGGACTTGGAAAAATTCCCCATTGCAG<br>CCCTCTAACTTAGATCAGCTCAGTACCTTTCAAGCATTGTTTC |
| 2900 | THBS1 | 3589504 | CCTGTGGCATGACCCTCGTCACATAGGCTGGAAAGATTTCACCGCCTACAGATGGCGTCTCAG<br>CCACAGGCCAAAGACGGGTTTCATTA |
| 2901 | THBS1 | 3589505 | GCTGACTCAGGACCCATCTATGATAAAACCTATGCTGGTGGTAGACTAGGGTTGTTTGTCTTC<br>TCTCAA |
| 2902 | THBS1 | 3589509 | GCTGGTATTGCACCTTCTGGAACTATGGGCTTGAGAAAACCCCCAGGATCACTTCTCCTTGGC<br>TTCCTTCTTTTCTGTGCTTGCATCAGTGTGGACTCCTAGAACGTGCGACCTGCCTCAAGAAAAT<br>GCAGTTTTCAAAAACAGACTCAGCATTCAGCCTCCAATGAATAAGACATCTTCCAAGCATATA<br>AACAATTGCTTTGGTTTCCTTTTGAAAAAGCATCTACTTGCTTCAGTTGGGAAGGTGCCCATTC<br>CACTCTGCCTTTGTCACAGAGCAGGGTGCTATTGTGAGGCCATCTCTGAGCAGTGGACTCAAA<br>AGCATTTTCAGGCATGTCAGAGAAGGGAGGACTCACTAGAATTAGCAAACAAAACCACCCTG<br>ACATCCTCCTTCAGGAACACGGGGAGCAGAGGCCAAAGCACTAAGGGGAGGGCGCATACCC<br>GAGACGATTGTATGAAGAAAATATGGAGGAACTGTTACATGTTCGGTACTAAGTCATTTTCAG<br>GGGATTGAAAGACTATTGCTGGATTTCATGATGCTGACTGGCGTTAGCTGATTAACCCATGTA<br>AATAGGCACTTAAATAGAAGCAGGAAAGGGAGACAAAGACTGGCTTCTGGACTTCCTCCCTGA |
| 2903 | THBS1 | 3589510 | TGGCCAGAATTAGGGAATCAGAATCAAACCAGTGTAAGGCAGTGCTGGCT |
| 2904 | THBS1 | 3589511 | AGGGGCAGCCGTGCTTATATTTTTATGGTTACAATGGCACAAAATTATTATCAACCTAACTAA<br>AACATTCCTTTTCTCTTTTTTCCTGAATTATCATGGAGTTTTCTAATTCTCTCTTTTGGAATGTAG<br>ATTTTTTTTAAATGCTTTACGATGTAAAATATTTATTTTTACTTATTCTGGAAGATCTGGCTGA |

TABLE 13-continued

Subtyping Target Sequences

| SEQ ID NO. | Gene | Affy Probeset ID | Sequence |
|---|---|---|---|
| | | | AGGATTATTCATGGAACAGGAAGAAGCGTAAAGACTATCCATGTCATCTTTGTTGAGAGTCTT CGTGACTGTAAGATTGTAAATACAGATTATTTATTAACTCTGTTCTGCCTGGAAATTTAGGCTT CATACGGAAAGTGTTTGAGAGCAAGTAGTTGACATTTATCAGCAAATCTCTTGCAAGAACAGC ACAAGGAAAATCAGTCTAATAAGCTGCTCTGCCCCTTGTGCTCAGAGTGGATGTTATGGGATT CTTTTTTTCTCTGTTTTATCTTTTCAAGTGGAATTAGTTGGTTATCCATTTGCAAATGTTTTAAAT TGCAAAGAAAGCCATGAGGTCTTCAATACTGTTTT |
| 2905 | THBS1 | 3589512 | GTTCTCTACTGGCTTTATGTCATGAAGTATATGCGTAAATACCATTCATAAATCAATATAGCAT ATACAAAAATAAATTACAGTAAGTCATAGCAACATTCACAGTTTGTATGTGATTGAGAAAGAC TGAGTTGCTCAGGCCTAGGCTTAGAATTTGCTGCGTTTGTGGAATAAAAGAACA |
| 2906 | THBS1 | 3589513 | CATTAGCCTGCCATATCAAAAACATATAAAAGAGAAATTATCCCTAAGTCAAGGGCCCCCATA AGAATA |
| 2907 | THBS1 | 3589514 | TTAGATGTCATTGAATCCTTTTCAA |
| 2908 | THBS1 | 3589515 | AGCGACATTTTCTGACCCACGAATGATGCCTTGGGTGGGCAACACGATTGCATGTTGTGGAG ACACTTCGGAAGTAAATGTGGATGAGGGAGGAGCTGTCCTTGCAATGTTGAGCCAAGCATTA CAGATACCTCCTCTTGAAGAAGGAATAATAAGTTTAATCAAAAAAGAAGACTAAAAAATGTA AAATTTGGAAGGAATCCATAAATGCGTGTGTGTCTAAATACAAATTATCATGTGAAGAAAAG GCCCAAGTGTACCAATAAGCAGACCTTGATTTTTGGATGGGCTAATTATGAATGTGGAATACT GACCAGTTAATTTCCAGTTTTAATGAAAACAGATCAAAGAAGAAATTTTATGAGTAGGTTAAA GGTCTGGCTTTGAGGTCTATTAAACACTAGAAAGGACTGGCTGGGTGAGATAAAATCTTCTT GTTGATTTTCACTCTCATTCTATAAATACTCATCTTTCTGAGTAGCCATGATCACATACAAATGT AAATTGCCAAATCATTTTATAGTACCAAGGTGAAGAAGCAGGAACTAGAAAGTGTTGATAAT AGCTGTGGAGTTAGGAAAACTGATGTGAAGGAAATAATTCTTTGAAATGGCAAAGAATTAAA TACCATCATTCATTATCAGAAGAGTTCAACGTTTGAAGTGCTGGGAGATAATTCTAATTCATTC TTGGATAGTGAAGCAAAACTGATTGAAAATACCAAGATAAGACAGAAAAAGTGACTGGAAA GAGGGAGCTTTTCTTCCAGGCATGTTCCAGTTTCACC |
| 2909 | THBS1 | 3589516 | GTCATCGAGATGATAGCTTTTTTCCTCCTCCAACAGTTTATTGTCATGTGTTGTGGGAGAGCTC GAGTGAAGAGCAATAAACTCCAGGTCTTATAAGAATGTACATACAATAAAGGTGGTGCCAGC AGTTTTTTTTTTTCTAAAGAGTCACATGTAGAAAAGCCTCCAGTATTAAGCTCCTGA |
| 2910 | CYP1A1 | 3601834 | TCATCCTGGAGACCTTCCGACACTC |
| 2911 | ADAM10 | 3626562 | AAGGCGCTTCGCTTTTCAGACCTGGGCGTCTGTATCATGACTATCATAAATTTAGGATTAAGA CACCTAGCCTCCTACCAGGATGAATGAGGTGTCCATGTGACCTGCTGTGCCCTGGAATTTTAT ACATCTTTCTCTCATAGCACACACCATATTACAATATAATCCTGCCTCATCTAAGCCAAACTTTC GAGAGAATCATTTACACTCAGTGGCTACTTCAGCTCCCATTCACTTATCAACCTGCTGCAATTT TTCACAGCCCCCAAAGGACTGCAGTCTGTGCCTTCAGGGAGCTGAGGGTCTAGCGGAAGGAA AGAAACCAGCAGTTACAGTACAGAGGGGTTTGTGTTGGAAACTCTACAAACACAGGATGCCC TGGTAGCTCAGAGGAAGTGCATATCGAGCATGGTAGGTAGGTAGTGGGAAGAGCCAAGATG ACTTCCCAGAGGAGAAAAGCTGGACCTGAGTTTTGGAGTTTCGGTAAAAGTTTGCTCTAACTA GTCCAAGCTGCTGTCACAAGCTTTTAGAAATGATGTAACCATGGGGCAGTTGACTGTCGTCAT GTTCTTTGCTATTTTCATGACTCTGGATGTGCTTTTCCTATTCCCTGGATTGCCCTTTCCCTCGAT TCCTCTGCAGGACTGGGCTTTATTA |
| 2912 | ADAM10 | 3626563 | CAAAGTTTTGAATGCTAAGTACCTCATTTATTTTAAAAAGCCTAGTTTAATGATAAGTTTGTTT AAAATTTTGAGCCATCATTTTTCTCTTCATAGCAAATAAGGAGAGAATTGACATTTCAGTGTTA CCTAGAAAAGGAATTGTAAGCCCAGAATAATTCCCTGCATGAGGTAATCTGCTTCAAA |
| 2913 | ADAM10 | 3626564 | TACTCTTTGAACTCTGAGAACTATCACAAGAAGCTTCCCACAAGGCAGTGTTTTCTTACAGTTG TCTCTTCCTACAAAAGTATAGATTATCTTTATTCTTAATACTTTGGAATCCATGTAGAAAATTTC CAGTTAGATACTCTGCGTACACACAATAAACCTTTT |
| 2914 | ADAM10 | 3626565 | AAACTTGAAATGCATTAATAAATAG |
| 2915 | ADAM10 | 3626566 | GCTGCTACGGGCACAAGTGACTATACTGAAGAACACAGTTAAGTGTTGTGCAAACTGGACAT AGCAGCACATACTACTTCAGAGTTCATGATGTAGATGTCTGGTTTCTGCTTACGTCTTTTAAAC TTTCTAATTCAATTCCATTTTTCAATTAATAGGTGAAATTTTATTCATGCTTTGATAGAAATTAT GTCAATGAAATGATTCTTTTTATTTGTAGCCTACTTATTTGTGTTTTTCATATATCTGAAATATG CTAATTATGTTTTCTGTCTGATATGGAAAAGAAAAGCTGTGTCTTTATCAAAATATTTAAACGG TTTTTTCAGCATATCATCACTGATCATTGGTAACCACTAAAGATGAGTAATTTGCTTAAGTAGT AGTTAAAATTGTAGATAGGCCTTCTGACATTTTTTTTCCTAAAATTTTTAACAGCATTGAAGGT GAAACAGCACAATGTCCCATTCCAAATTTATTTTTGAAACAGATGTAAATAATTGGCATTTTAA AGAGAAAGCAAAACATTTAATGTATTAACAGGCTTATTGCTATGCAGAAAATAGAAGGGGC ATTACAAAAATTGAAGCTTGTGACATATTTATTGCTTCTGTTTTCCAACTACATCACTTCAACTA GAAGTAAAGCTATGATTTTCCTGACTTCACATAGGAGGCAAATTTAGAGAAAGTTGTAAAGAT TTCTATGTTTTGGGTTTTTTTTTTCCTTTTTTTTTTAAGAGTATAAGGTTTACACAATCATTCTC ATAATGTGACGCAAGCCAGCAAGGCCAAAAATGCTAGAGAAAATAACGGGATCTCTTCCTTG TAAACTTG |

TABLE 13-continued

Subtyping Target Sequences

| SEQ ID NO. | Gene | Affy Probeset ID | Sequence |
|---|---|---|---|
| 2916 | ADAM10 | 3626567 | GGCTCGACCACCTCAACATTGGAGACATCACTTGCCAATGTACATACCTTGTTATATGCAGAC ATGTATTTCTTACGTACACTGTACTTCTGTGTGCAATTGTAAA |
| 2917 | ADAM10 | 3626568 | TATATTTTTTTCAACTGCCAATCAAG |
| 2918 | ADAM10 | 3626569 | AGATCATATCCTCAGACCAGGTGGAATTACTTAAATTTTAAAGCCTGAAAATTCCAATTTGGG GGTGGGAGGTGGAAAAGGAACCCAATTTTCTTATGAACAGATATTTTTAACTTAATGGCACAA AGTCTTAGAATATTATTATGTGCCCCGTGTTCCCTGTTCTTCGTTGCTGCATTTTCTTCACTTGC AGGCAAACTTGGCTCTCAATAA |
| 2919 | ADAM10 | 3626570 | CCAAAGAGAAACCTATTAAGTCATCATCTCCAAACTAA |
| 2920 | ADAM10 | 3626571 | CTGCAGCTTTTGCCTTGGTTCTTCCTAG |
| 2921 | ADAM10 | 3626572 | CAGCGGCCCCGAGAGAGTTATCAAATGGGACACATGAGACGCTAA |
| 2922 | ADAM10 | 3626574 | CTCATTGGTGGGCAGTATTACTTATGGGAATTGCTCTGATCATGCTAATGGCTGGATTTATTAA GATATGCAGTGTTCATACTCCAAGTAGTAATCCAAAGTTGCCTC |
| 2923 | ADAM10 | 3626578 | TCTGTTTTACCGTGCTCCTTAGTTCATCTCCTGGATGGGTTACTTCTTTTGGTGCATATTATTAG GGCATTTTCATGGGACTTAAAAAACATTTTTTTTTGTTGTTTTTCAAGCAACTTATTTGCCCAA ATCGTGGACTAATTGGTGATTTTTCCTGATCTTTCAGTATAATCTCTGGGTCTTTATCTTGTTTG TAATAGGAAATGTTGAACAGAATAAGATCAGATACACAGCCTTTTGTAGATCTACTAATGATT ATGGATGTTCATCCAGCAGTAATCCACTGAACGCTTATTTTTAAGCCCACATATCTCCAAGTTG TACAAACACAGAATTACCTGATGTTTTCTTAAAAGATTGTCAAGATTGACTATCTCAACTTAAG TGTTCATGCTTTAAAAGTGATAACATTAAAATATCTATAGGAAGCTTGCAAATGATATATTTGA GAATGTGCTATAATTGAACTGAATGTAGTTTGCTTTGGAAATTGACTTATAACTCACATTCCCC TTTCTCAAATTAGTGTGTATGTGTGTGTGTGTATGTATGTATGTGTGTGTTCAGAACTATGG ATGCCTTAAAGCACAAAAGATGTTGTTTGTGTGGGATGTCAGCCTTTTTTGTACTCTTCTAATA ACATTCTAGAGTAAAAATTTTATAGTTAACCCCAGCATTTAAAATGATGTTTACCGTTCCTAGG ACACATTAGGATATGTGGTTTTTAGATATGTAATGATCATGGAGTAGAAGGATTGTTGAAATT GGATTTAGGAGATCTACCTAGGTTTCAAACCAAATACTTGAGCAGTTGACTTAACTTAGGTTT CCTTAAAACATGTTACTCTTTTTTAAATTCCTGTGCTTGTTGCGTGGTAAGTTC |
| 2924 | ADAM10 | 3626579 | TAGGCACTTCAGTGGTCGAACCATCACCCTGCAACCTGGATCCCCTTGCAACGATTTTAGAGG TTACTGTGATGTTTTCATGCGGTGCAGATTAGTAGATGCTGATGGTCCTCTAGCTAGGCTTAA AAAAGCAATTTTTAGTCCAGAGCTCTATGAAAACATTG |
| 2925 | ADAM10 | 3626580 | TGGACCCATCAACTTGTGCCAGTACAG |
| 2926 | ADAM10 | 3626581 | TGACCTACAGTTTGGCCAGATAATTTCCAGCTAAATCTGTCCTCTTGAGGAGATTATAAATGTA ACGTAGCATTGTGTCTCTATTATTATGGTCTCTACAATGTTTTAAAAATGATAAACTAGACAAA ACGTTGCCAGCTTTACAGCAGTAATTTACATAAACACTGTTAGACTTTAAGTCATCGTGGACAC TGAGTCAAGACTTGCTGGTTGCTTGTTTACATTGTAACATTTAATATGAATTACTGATGGCGTT ACCCAGCCTAACTAGAGA |
| 2927 | ADAM10 | 3626582 | TCTGTGAGAAATATGGCTTAGAGGAGTGTACGTGTGCCAGTTCTGATGGCAAAGATGATAAA GAATTATGCCATGTATGCTGTATATGAAGAAAA |
| 2928 | ADAM10 | 3626583 | CCATGTACATGTGGTTGATATTCTCTAGAGAAACATAGTTGTACAACTCGGCATGTGATTTGTC TATAATATTTAAGTTTTATAAAATAATATTTCAGTAGCCTAAATAAAAGAACTCTTTGGTCATCT TCTCTGAATATCAAACCTTCCAAAGCTTTTGTGGCTGAATATCACTTTGCTCTACAGGAAAAAA TTTAATTTTTCTTTCTTTATAGAAGAGCCGTAATAACCAACATAAAATCGATCCTCATCTAATCT CTTGCTCTGCTTTTATTTCATTTTTTTAAGTTGCCATTGCTTTAAAAGATTTACTATCTTTCTTGG ATTTACTGTTTTTCAAATTTTTTCAAATGTATTTATGTAATTCAGTTTTGATACTCATCTCTGTTT GTTTTTCACTTTCATTTCCATTTAAATATTTTGACATTGGAAGCTCATACTTGCCTGTCTGTTACT ATAA |
| 2929 | ADAM10 | 3626584 | GTCAAGGTCCTTGTTGTACAGCACAGTGTGCATTCAAGTCAAAGTCTGAGAAGTGTCGGGAT GATTCAGACTGTGCAAGGGAAGGAATATGTAATGGCTTCACAGCTCTCTGCCCAGCATCTGAC CCTAAACCAAACTTCACAGACTGTAATAGGCATACACAAGTGTGC |
| 2930 | ADAM10 | 3626585 | TGTAAAGATGAATGCTGCTTCGATGCAAATCAACCAGAGGGAAGA |
| 2931 | ADAM10 | 3626588 | ACATCATGTATGCAAGAGCAACATCTGGGGACAAACTTAACAACAATAAATTCTCACTCTGTA GTATTAGAAATATAAGC |
| 2932 | ADAM10 | 3626589 | CACTGGAATTATTACTGTTCAGAACTATGGGTCTCATGTACCTCCCAAAGTCTCTCACATTACT TTTGCTCACGAAGTTGGACATAACTTT |
| 2933 | ADAM10 | 3626590 | TCTGGAGGAATATGTGAAAAAGTA |
| 2934 | ADAM10 | 3626592 | GATTTTGATGATGGCGTACTTGGTCTGGCTTG |

TABLE 13-continued

Subtyping Target Sequences

| SEQ ID NO. | Gene | Affy Probeset ID | Sequence |
|---|---|---|---|
| 2935 | ADAM10 | 3626593 | TCCCAAATATTGGTGTGGAGAAGTTTCTGGAATTGAATTCTGAGCAGAATCATGATGACTACTGTTTGGCCTATGTCTTCACA |
| 2936 | ADAM10 | 3626595 | TCCAGTCATGTTAAAGCGATTGATACAATTTACCAGACCACAGACTTCTCCGGAATCCGTAACATCAGTTTCATG |
| 2937 | ADAM10 | 3626596 | CTGCTAATGGTCCAGAACTTCTGAGGAAAAACGTACAACTTCAGCTGAAAAAATACTTGTCAGCTTTATATTCAGACTGATCATTTGTTCTTTAAATATTACGGAACACGAGAAGCTGTGATTG |
| 2938 | ADAM10 | 3626602 | GCTTCCTGAGACCTCTCTAGAAGCCAAGCGGATGC |
| 2939 | ADAM10 | 3626607 | TGAGGAAATACCAGATGACTGGTGTAGAGGAAGTAACAC |
| 2940 | ADAM10 | 3626613 | GGCTTAGAAAACTTATGTCACTTGATTGTGGACCTCCTGTTCTTTACCCTGTGCTCTTCTGCTTCACTCATGGAAGAAAGC |
| 2941 | ADAM10 | 3626614 | GGAAGTTTTAGCCATGGGTCTGTTATTGATGGAAGATTTGAAGGATTCATCCAGACTCGTGGTGGCACATTTATGTTGAGCCAGCAGAGAGATATATTAAAGACC |
| 2942 | ADAM10 | 3626615 | CATTTCAACCTACGAATGAAGAGGGACACTTCCCTTTTCAG |
| 2943 | ADAM10 | 3626631 | CCATTAATCTCCAGCGTTCATTCGACTGATCTGG |
| 2944 | ADAM10 | 3626635 | AGGATTATCTTACAATGTGGATTCATTACACCAAAAACACCAGCGTGCCAAAAGAGCAGTCTCACATGAAGACCAATTTTTACGTCTAGATTTCCATGCCCATGG |
| 2945 | ADAM10 | 3626640 | ATTTCCAGAGTCCTTTATTGCATTAAGCATTGGTTAAAAGGCTAATTTTGGTGTTTTTGTTAAGCAGAACTTTTTCAAAAAACATAAGACAAGTTTTATTAGTTTTATTTTAAAATTAGTATCAAGATTCTAGCTTTTGGGTACTTGGAGATACTTGTAATTTTATTGTAACTATGGGGTATTTTTATCTACTAATCTGAGCTATTTTTGGTCACTTGTAAGATCTTTGTATGATGATTTGTAGACTTCAGCACATTGAGATTG |
| 2946 | ADAM10 | 3626641 | CATCAAGCAAGACACACATTATAGATTAAGAGCTGATAATAGATGTTTAGTTTTAAAAGGATTATGTGCGGGAGACTCTCTGTTAGAGGAGCCTTTTTCATCTGACATTTGTTATTTCTGTTCTAAACGTGGCTTTC |
| 2947 | ADAM10 | 3626642 | TTTCTGTCCTGTATTCTACCGAGTCCGAGGGTGGTA |
| 2948 | ADAM10 | 3626643 | GCTTTGGATGAGTGTCTGTAGCCTTTGATAATTTAGAAAATATCTATTTCATGTAATGTATTGTTTCTGTTTTTTTCTTTGCCACTTTGACTTATGACTGCAG |
| 2949 | ADAM10 | 3626644 | TCTCTTAGAGTAGAAGTTCGGTCCCTGGGTGACCCAACTTGAAGAGTTTCGTTAAACTTTCAGGTGGAGTAGATGTACAGTGTAGTTAGTGGATTGTCAAAA |
| 2950 | ADAM10 | 3626645 | ACCATTTGGGGATGTTCTTTGATTT |
| 2951 | ADAM10 | 3626646 | CTCGTGGGAAGTTGTGTTGTTTGCAGCTGGGCTCGTGTATTGTTCTTTACCCGGCGCGCCGGTCCTGACCGACCCCATTCTGCAGAGGGGCCGCCCGTGGAGTGGCAGCAGTCATCACCCGCTTATCTGAGACTAGTGGCCTCGGTTC |
| 2952 | ADAM10 | 3626648 | ATGGTGTTGCTGAGAGTGTTAATTCTGCTCCTCTCCTGGGCGGCGGGGATGG |
| 2953 | ADAM10 | 3626649 | CTTCTCCCTCCGGATCGATGTGCTGCTGTTAACCCGTGAGGAGGC |
| 2954 | ADAM10 | 3626650 | TCCCTGTTTTGGAGGAGCTAGGAGCGTTGCCGGCCCCTGAAGTGGAGCGAGAGGGAGGTGCTTCGCCGTTTCTCCTGCCAGGGGAGGTCCCGGCTTCCCGTGGAGGCTCCGGACCAA |
| 2955 | ADAM10 | 3626651 | CGGCAGGCCTAGCAGCACGGGAACCGTCCCCCGCGCGCATGCGCGCGCCCCTGAAGCGCCTGG |
| 2956 | ADAM10 | 3626653 | GCTAGGGTGAACTCTTGAAGCTATCAGTCATCCAGCAATCTTAGCAAGCAGGCCATTGGGTCCCTGTTTGCTCTGTCTCTCTCTCTCTCACTGTTGAAGGGCTTAGCTAACTACTTAAGTAAAATATTTGTTCTCTGTTAAACATGTCAAGGAGTATGGTCAGCTTATCCACATTAAGCCTGTGTGTCCCACGTTGGAGTAAATGTTAAGTAGCTCACTACAATAAACTAGATTCTTCTGCCCTCTCTTGTTTAAATGATCATGTTCCCTGGAGGTGGAAATAGATCTTTA |
| 2957 | ADAM10 | 3626654 | TGGCCAAGGCTGAGATAACTTTAGCATCAGCAAGGATAATATCTGCAAGAGATTGAAACTCATAGTATTGTATTTAACTCTGTGAGTTAATGATGGTAGTGGACAGAATTATAGTTACCTTTGGGATACGCTTTTAAAGAAATTCCAGGTAATAAGAGAAATGATAGAATTAGGATATCACCATTTTACCCCCCCCAACAATTTATGGATCTAGACAATAATCGCCAGTGACTGCTAACCTCACAAAGTGAGAGCAATCAGATTTTGTGCCTCCTAATGGAAGTACATATACCACCTATGAAGCAGTTCTGCCAAAAGTCACATCTCATCATGATGAAGCCTCCTGATCTAACTACC |

TABLE 13-continued

Subtyping Target Sequences

| SEQ ID NO. | Gene | Affy Probeset ID | Sequence |
|---|---|---|---|
| 2958 | ADAM10 | 3626655 | TTGATTGGGCAGACCCAGGGAAGTCAAATCCTAAACCAGCAGTGGGAACACAACAGAATGGT GTAGTTTGCACTGGTAAGATTTGGGTACC |
| 2959 | CYP1A1 | 3633082 | CAGCAGGCTGGCCTATGTGGTCTAAGGTTCAGCCTGAAACTCATAGACACTGATCTGGCTGCA GTTTTGCTATCTGGGCTGTGGGCAAGCCTAAGGGATCCTGCCTGCCCCTACCCTGGACTTGCC TCTGCACACCCTCCAGAGACAACAGGTAAAACAGGGCCACATAGATGCTGATGGAGCCTTCC CAAGTTGTGCTTGAGCCAGGAGGCCTGCTAGGGTTAGGAGGTCCTTAGGCCTCTGAGAAGCT CTGAAGAACTCTCTGGAAGCCCCTGGGCCCAGTACCTAGCTGGCTCTGTGAGGGTGCTGACT GGCTTCAGCAAGTTAGAACTAGCCAAACCAGGACCCTGTCCAATCTTTGACAATTGGGAGCTG CCAAGAGTGAAGGGAAGAGACAGCCCAGGATACTGGCACAGAGGTAGTCTCACTGCTTGAA CTAGGCTGA |
| 2960 | CYP1A1 | 3633083 | GTGAGCACTTCCAAATGCAGCTGCGCTCTTAG |
| 2961 | CYP1A1 | 3633084 | CCCTGATGGTGCTATCGACAAGGTGTTAAGTGAGAAGGTGATTATCTTTGGCATGGGCAAGC GGAAGTGTATCGGTGAGACCATTGCCCGCTGGGAGGTCTTTCTCTTCCTGGCTATCCTGCTGC AACGGGTGGAA |
| 2962 | CYP1A1 | 3633085 | ACACAAGTTTGAAAGGCTTTTACATCCCCAAGGGGCGTTGTGTCTTTGTAAACCAGTGGCAGA TCAACCATGACCA |
| 2963 | CYP1A1 | 3633087 | TCATCCTGGAGACCTTCCGACACTC |
| 2964 | CYP1A1 | 3633089 | GTTTGACACAGTCACAACTGCTATCTCCTGGAGCCTCATGTATTTGGTGATGAACCCCAGGGT ACA |
| 2965 | CYP1A1 | 3633090 | AAGCAGCTGGATGAGAACGCCAATGTCCAGCTGTCAGATGAGAAGATCATTAACATCGTCTT GGACCTCTTTGGAGC |
| 2966 | CYP1A1 | 3633091 | TGGCCTCTGATTGGGCACATGCTGACCCTGGGAAAGAACCCGCACCTGGCACTGTCAAGGAT GAGCCAGCAGTATGGGGACGTGCTGCAGATCCGAATTGGCTCCACACCCGTGGTGGTGCTGA GCGGCCTGGACACCATCCGGCAGGCCCTGGTGCGGCAGGGCGATGATTTCAAGGGCCGGCC CGACCTCTACACCTTCACCCTCATCAGTAATGGTCAGAGCATGTCCTTCAGCCCAGACTCTGGA CCAGTGTGGGCTGCCCGCCGGCGCCTGGCCCAGAATGGCCTGAAAAGTTTCTCCATTGCCTCT GACCCAGCCTCCTCAACCTCCTGCTACCTGGAAGAGCATGTGAGCAAGGAGGCTGAGGTCCT GATAAGCACGTTGCA |
| 2967 | CYP1A1 | 3633092 | ATGTCGGCCACGGAGTTTCTTCTGGCCTCTGTCATCTTCTGTCTGGTATTCTGGGTAATCAGGG CCTCA |
| 2968 | CYP1A1 | 3633093 | CACCTCCAAGATCCCTACACTGATC |
| 2969 | CYP1A1 | 3633094 | GTGATCCCAGGCTCCAAGAGTCCACCCTTCC |
| 2970 | CYP1A1 | 3633095 | GGAGGCGTGGCCACACGTACAAGCCCGCCTATAAAGGTGGCAGT |
| 2971 | SCNN1B | 3652907 | CAGTGTCACCAACACTCGGCCGCCGCCGCCAGCTTGGCGCGCACCGCCGCCTCCGCCACCGCC GACAGCGCGCATCCTCCGTGTCCCCGCTCC |
| 2972 | SCNN1B | 3652909 | ATCACCAGTTATCCATGCTGCTGCATATAAACCCAGCTTATTTATTTAAACTGCTGCATGGATT CCCGCCGTGGATAATGCCTACCGATGGGAATTTAGGTGACA |
| 2973 | SCNN1B | 3652921 | TGAAGGGCCTGCATCGGCTGCAGAAGGGCCCCGGCTACACGTACAAGGAGCTGCTGGTGTG GTACTGCGACAACACCAACACCCACGGCCCCAAGCGCATCATCTGTGAG |
| 2974 | SCNN1B | 3652922 | GTCTCCCTCTCCGTAGGCTTCAAGACCATGGACTTCCCTGCCGTCACCATCTGCAATGCTAGCCC |
| 2975 | SCNN1B | 3652924 | ATGCCAATGCCACCAGGAACCTGAACTTCTCCATCTGGAACCACACACCCCTGGTCCTTATTGA TGAACGGAACCCCACCACCCCATGGTCCTTGATCTCTTTGGAGACAACCACAATGGCTTAAC AAGCAGCTCAGCATCAGAAAAGATCTGTAATGCCCACGGGTGCAAAATGGCC |
| 2976 | SCNN1B | 3652925 | GTGGTCCCTGGGCACATATCAAGCAATGGGCCCCACCCAGTGAGGCTGATGGGTGTTTCTTTT CTGTAGTAATTTGAGTCTCGCTGGG |
| 2977 | SCNN1B | 3652926 | CGGAACTTCACCAGTGCTACCCAGGCATTG |
| 2978 | SCNN1B | 3652927 | CAGGTGCCACAGCAGGAGCTAGTAGAGATGAGCTACCCCGGCGAGCAGATGATCCTGGCCT GCCTATTCGGAGCTGAGCCCTGCAAC |
| 2979 | SCNN1B | 3652931 | ACTTCACGTCCATCTTCTACCCTCACTATGGCAACTGTTACATCTTCAACTGGGGCATGACAGA GAAGGCACTTCCTTCGGCCAACC |
| 2980 | SCNN1B | 3652933 | TTCCTTGCGTCCACGGCCGGGGTCAGGCTGATGCTTCACGAGCAGAGGTCATACCCCTTCATC AGAGATGAGGGCATCTACGCCATGTCGGGGACAGAGACGTCCATC |

TABLE 13-continued

Subtyping Target Sequences

| SEQ ID NO. | Gene | Affy Probeset ID | Sequence |
|---|---|---|---|
| 2981 | SCNN1B | 3652934 | CAAGCTTCAGCGCATGGGGGAGCCCTACAGCCCGTGCACCGTGAATGGTTCTGAGGTCCCCG TCCAAAACTTCTACAGTGACTACAACACGACCTACTCCAT |
| 2982 | SCNN1B | 3652935 | GCCAAGGCCTCAGTACTCCGGGAGAGCTGGCCCCAGCAAGTCTGGCTCTGCTGGGCCTTTGT AGGTTGCCACGGGGCACCCCGGGCCTGTGGGACCAGTCACTTTCCTGGGCTCTCTCACCAGG GCCTAGGGTTGGCCACTTCTCATCCCCACATTGGCAGGTGTACCCCTGGGGAAGCCCAGGGG ATTATGGGGATCTTACTCTGGGGTTTC |
| 2983 | SCNN1B | 3652938 | TGCTTCCAAGACCACATGATCCGTAACTGCAACTGTGGCCACTACCTGTACCCACTGCCCCGT GGGGAGAAATACTGCAACAACCGGGACTTCCCA |
| 2984 | SCNN1B | 3652940 | ATGAGCGTGGCGCAGAGAGAGACCTGCATTGGCATGTGCAAG |
| 2985 | SCNN1B | 3652944 | GAAGGGAATTGTCAAGCTCAACATCTACTTCCAAGAATTTAACTA |
| 2986 | SCNN1B | 3652945 | GGCTGCTCTCGAATCTGGGTGGCCAGTTTGGCTTCTGGATGGGGGGCTCTGTGCTGTGCCTC ATCGAGTTTGGGGAGATCATCATCGACTTTGTGTGGATCACCATCATCAAGCTGGTGGCCTTG GCCAAGAGCCTACGGCAGCGGC |
| 2987 | SCNN1B | 3652946 | GCCAAGACTGTTGCCCGAGGCCTCACTGTATGGTGCCCTCTCCAAAGGGTCGGGAGGGTAGC TCTCCAGGCCAGAGCTTGTGTCCTTCAACAGAGAGGCCAGCGGCAACTGGTCCGTTACTGGC CAAGGGCTCTGTAGAATCACGGTGCTGGTACAGGATGCAGGAATAAATTGTATCTTCACCTG GTTCCTACCCTCGTCCCTACCTGTCCTGATCCTGGTCCTGAAGACCCCTCGGAACACCCTCTCCT GGTGGCAGGCCACTTCCCTCCCAGTGCCAGTCTCCATCCACCCCAGAGAGGAACAGGCGGGT GGGCCATGTGGTTTTCTCCTTCCTGGCCTTGGCTGGCCTCTGGGCAGGGGTGGTGGAGAGA TGGAAGGGCATCAGGTGTAGGGACCCTGCCAAGTGGCACCTGATTTACTCTA |
| 2988 | SCNN1B | 3652948 | TAGCTGGCTGATGGGCCACTAAAACCCCCAAATATTGGCCACATAACTTCTGCCATGTGCGAG GGGTAGGGGGTAAGTGTAATGAAAGGGTCAAGGCTTGGGGTCTGGGGTTAGACCACCTAGA CTCAAATCCTGGCTCCATCTTACAAGCTGTGTG |
| 2989 | SCNN1B | 3652949 | TTATAGTTGCTGTAACCTGCCCAGAGAGGTTAAGTAACATCTCTGAAGTCACACAGTTGGTGA GTGGCAGAGCTAGCAGTCTGGGCCAGGCCCACCCCGCATCACTCTATTGCCTCA |
| 2990 | MMP2 | 3661686 | GCAAGCCAGATAGCTACAGTAATCGACAGACAGACAAACAAGAGCATCGTATGACCCAGGG GCCAACAAGTCCCACCCCAGTGACACCATCTCACTTTTGCAGAGCTCTTGCTCGCAAAGTGCA GCTAGGAGAACCCAGGCCTCCTGATGACAAATGCTCCTTCTTTTCTGCCCCCCACGTGCCAAGA GCGAGGAGGGAAGATAGCTGCTGGCTCACTG |
| 2991 | MMP2 | 3661687 | CTTGTTTCCGCTGCATCCAGACTTCCTCAGGCGGTGGCTGGAGGCTGCGCATCTGGGGCTTTA AACATACAAAGGGATTGCCAGGACCTGCGGCGGCGGCGGCGGCGGGGGCTGGGGCGC GGGGGCCGGACCATGAGCCGCTGAGCCGGGCAAACCCCAGGCCACCGAGCCAGCGGACCCT |
| 2992 | MMP2 | 3661688 | ACGGGTCCCCTGAGGGCGCTCTGTCTCCTGGGCTGCCTGCTGAGCCACGCCGCCGCGCGCC GTCGCCCATCATCAAGTTCCCCGGCGATGTCGCCCCCAAAACGGACA |
| 2993 | MMP2 | 3661691 | GCTGAAGGACACACTAAAGAAGATGCAGAAGTTCTTTGGACTGCCCCAGACAGGTGATCTTG ACCAGAATACCATCGAGACCATGCGGAAGCCACGCTGCGGCAA |
| 2994 | MMP2 | 3661694 | AGCATGGCGATGGATACCCCTTTGACGGTAAGGACGGACTCCTGGCTCATG |
| 2995 | MMP2 | 3661695 | GGAGACTCCCATTTTGATGACGATGAGCTATGGACCTTGGGA |
| 2996 | MMP2 | 3661697 | CCGATGGGGAGTACTGCAAGTTCCCCTTCTTGTTCAATGGCAAGGAGTACAACAGCTGCACTG ATACCGGCCGCAGCGATGGCTTCCTCTGGTGCTCCACCACCTACAACTTTGAGAAGGATGGCA AGTACGGCTTCTGTCCC |
| 2997 | MMP2 | 3661698 | CCGGTAGGGATTACATGTGGCGTTAACCCTTCCCTGTGTCACCCCTCTGATAGGAACAGAAAG CTTTGGTGATAGTTAGATGTGGAAACAGCTGTATTTCATAAATTTGGGAAGGGTTATTCCCTG CATTGGACATTAGCCATTTACTTTGTGCTTAGCCAGATGCAGATACGCACAACACGCACGTGT CTGGGTCTCGAGGCAGAGATTGTTGTTACTCAGCCCCTGCTGATGGCTGAGTCAGTGTCTGAT TCTTGCCATCCTTGTCAGGGGAATTTGGGAGGAGACAGGGGCTTCCTGGGTGGTAGAAATGA GAGGTCAGAGGCAGGGGCTGGCATTGGTCGAAGTTAACGCTTTGCCTTTCTCAACTCTGAG GCCACTAAGGTATCTGGACTCAGTCTTGCCTTTTCTCTAGGTGCCATTGTTTCTGGCATTGCAG GACAAGGTCTTTTGGTAGAGAGGGGAGTGGTGAGGATACAGGGCCTCGAGTTCTGTGGTGG GAGGCCAGGGACTGGGCTCATTCCGCCATGGTGGAGTTAACGGGGGCTGGTGAGGTCAC CTCTGGCGCCGTTGTGCACAGATGGTCCTTGTTA |
| 2998 | MMP2 | 3661699 | TGCAAGTTTCCATTCCGCTTCCAGGGCACATCCTATGACAGCTGCACCACTGAGGGCCGCACG GATGGCTACCGCTGGTGCGGCACCACTGAGGACTACGACCGCGA |
| 2999 | MMP2 | 3661700 | GTGGGTGCCACTCCCTCTCCCTCCCTCAGGGCCCAGCACCTGCTGTCTGAC |

TABLE 13-continued

Subtyping Target Sequences

| SEQ ID NO. | Gene | Affy Probeset ID | Sequence |
|---|---|---|---|
| 3000 | MMP2 | 3661701 | TGGGCAACAAATATGAGAGCTGCACCAGCGCCGGCCGCAGTGACGGAAAGATGTGGTGTGC GACCACAGCCAACTACGATGATGACC |
| 3001 | MMP2 | 3661702 | GGTACAGCCTGTTCCTCGTGGCAGCCCACGAGTTTGGCCACGCCATGGGGCTGGAGCACTCC CAAGACCCTGGGGCCCTGATGGCACCCATTTACACCTACACCAAGAACTTCCGTCTGT |
| 3002 | MMP2 | 3661703 | TGTCACTCCTGAGATCTGCAAACAGGACATTGTATTTGATGGCATCGCTCAGATCCGTGGTGA GATCTTCTTCT |
| 3003 | MMP2 | 3661704 | GTGACGCCACGTGACAAGCCCATGGGGCCCCTGCTGGTGGCCACATTCTGGCCTGAGCTCCC GGAAAAGATTGATGCGGTATACGAGGCCC |
| 3004 | MMP2 | 3661705 | CCTGGAGCGAGGGTACCCCAAGCCACTGACCAGCCTGGGACTGCCCCCTGATGTCCAGCGAG TGGATGCC |
| 3005 | MMP2 | 3661707 | CCAAGCTCATCGCAGATGCCTGGAATGCCATCCCCGATAACCTGGATGCCGTCGT |
| 3006 | MMP2 | 3661708 | CTTCTTCAAGGGTGCCTATTACCTGAAGCTGGAGAACCAAAGTCTGAAGAGCGTGAAGTTTG GAAGCATCAAATCCGACTGGCTAGGCTGCTG |
| 3007 | MMP2 | 3661709 | ACTGCCTTCGATACACCGGGCCTGGAGAACTAGAGAAGGACCCGGAGGGGCCTGGCAGCCG TGCCTTCAGCTCTACAGCTAATCAGCATTCTCACTCCTACCTG |
| 3008 | MMP2 | 3661710 | TAGATGCTGACTGTACTCCTCCCAGGCGCCCCTTCCCCCTCCAATCCCACCAACCCTCAGAGCC ACCCTAAAGAGATACTTTGATATTTTCAACGCAGCCCTGCTTTGGGCTGCCCTGGTGCTGCCA CACTTCAGGCTCTTCTCCTTTCACAACCTTCGTGGCTCACAGAACCCTTGGAGCCAATGGAGA CTGTCTCAAGAGGGCACTGGTGGCCCGACAGCCTGGCACAGGGCAGTGGGACAGGGCATGG CCAGGTGGCCACTCCAGACCCCTGGCTTTTCACTGCTGGCTGCCTTAGAACCTTTCTTA |
| 3009 | MMP2 | 3661711 | GTCTGAAGTCACTGCACAGTGCATCTCAGCCCACATAGTGATGGTTCCCCTGTTCACTCTACTT AGCATGTCCCTACCGAGTCTCTTCTCCACTGGATGGAGGAAAACCAAGCCGTGGCTTC |
| 3010 | MMP2 | 3661712 | CCTTCAACCATTCCCCATGGGAAATGTCAACAAG |
| 3011 | MMP2 | 3661713 | AGACCCAGCCAGAAGCGGAAACTTAAAAAGTCCGAATCTCTGCTCCCTGCAGGGCACAGGTG ATGGTGTCTGCTGGAAAGGTCAGAGCTTCCAAAGTAAACAGCAAGAGAACCTCAGGGAGAG TAAGCTCTAGTCCCTCTGTCCTGTAGAAAGAGCCCTGAAGAATCAGCAATTTTGTTGCTTTATT GTGGCATCTGTTCGAGGTTTGCTTCC |
| 3012 | MT1L | 3662135 | GCTCCTGTGCCAGCTCCTGCAAGTGCAAAGAG |
| 3013 | MT1L | 3662136 | TGCAAAGGGGCGTCGGAGAAGTGCAGCTGCTGTG |
| 3014 | MT1L | 3662137 | GTGGGGACAGCCCTGCTCCCAGATGTAA |
| 3015 | MT1L | 3662138 | TTTCATACAACCCTGAGCATTTGCTAC |
| 3016 | MT1E | 3662140 | GACTTCGGGAACACCGCGTACCTGCGGGGGCACAGCCCCACCCGAGCGAACGGGCTCCAAA GGGGAGGTCCCGCGGTGCCCACCGCGCAGAGCTCAGGGGGTGGTGCGCCCGGCCCTTCTGC GGCGCACAGCCCAGCCCAGGAACGCGGGCGGTGCGGACTCAGCGGGCCGGGTGCAGGCGC GGAGCTGGGCCTCTGCGCCCGGCCCGACCTCCGTCTATAAATAGAGCAGCCAGTTGCAGGGC TCCATTCTGCTTTCCAACTGCCTGACTGCTTGTTCGTCTCACTGGTGTGAGC |
| 3017 | MT1E | 3662143 | TGGCTCCTGCACGTGCGCCGGCTCCTGCAAGTGCAAAGAG |
| 3018 | MT1E | 3662145 | CCCTCATTGCCCGTGTCATTCCCTCTCCAGGCTTTCTGCCCTAAATTCAGATGGGGCAGGACA |
| 3019 | MT1E | 3662146 | CAGGGAGGTGCCCGGTCAAGTCTACTGCCACCTCTCACTCTC |
| 3020 | MT1E | 3662147 | CTGCGTCTGCAAAGGGGCATCGGAGAAGT |
| 3021 | MT1E | 3662148 | TGTGGGAACAGCTCTTCTCCCAGAT |
| 3022 | MT1E | 3662149 | TAAATAGAACAACCTGCACAACCTGGATTTTTTTAAAAATACAACACTGAGCCATTTGCTGCAT TTCTTTTTATACTAAATATGTGACTGACAAT |
| 3023 | MT1E | 3662161 | TGGCTCCTGCACGTGCGCCGGCTCCTGCAAGTGCAAAGAG |
| 3024 | CDH1 | 3666410 | AGTGGCGTCGGAACTGCAAAGCACCTGTGAGCTTGCGGAAGTCAGTTCAGACTCCAGCCCGC TCCAGCCCGGCCCGACCCGACCGCACCCGGCGCCTGC |
| 3025 | CDH1 | 3666411 | ATGGGCCCTTGGAGCCGCAGCCTCTCGGCGCTGCTGCTGC |

TABLE 13-continued

Subtyping Target Sequences

| SEQ ID NO. | Gene | Affy Probeset ID | Sequence |
|---|---|---|---|
| 3026 | CDH1 | 3666412 | GCCACCCTGGCTTTGACGCCGAGAGCTACACGTTCACGGTGCCCCGGCGCCACCTGGAGAGAGGCCGCGTCCTG |
| 3027 | CDH1 | 3666418 | CCTGGTTAGTACTAGTACTTGGATG |
| 3028 | CDH1 | 3666427 | GCACCGGTCGACAAAGGACAGCCTATTTTTCCCTCGACACCCGATTCAAAGTGGGCACAGATGGTGTGATTACAGTCAAAAGGCCTCTACGGTTTCATAACCCACAGATCCATTTCTTGGTCTACGCCTGGGACTCCACCTACAGAAAGTTTTCCACCAAAGTCACGCTGAATACAG |
| 3029 | CDH1 | 3666430 | CTGGAATCCAAGCAGAATTGCTCACATTTC |
| 3030 | CDH1 | 3666431 | AAGAGAGACTGGGTTATTCCTCCCATCA |
| 3031 | CDH1 | 3666432 | GAAGGCAAGGTTTTCTACAGCATCACTGGCCAAGGAGCTGACACACCCCTGTTGGTGTCTTTATTATTGAAAGAGAAACAGGATGGCTGAAGGTGACAGAGCCTCTGGATAGAGAACGCATTGCC |
| 3032 | CDH1 | 3666433 | CTCACGCTGTGTCATCCAACGGGAATGCAGTTGAGGATCCAATGGAGATTTTGATCACGGTAACCGATCAGAATGACAACAAGCCCGAATTCACCCAGG |
| 3033 | CDH1 | 3666435 | AGACGCGGACGATGATGTGAACACCTACAATGCCGCCATCGCTTACACCATCCTCAGCCAAGATC |
| 3034 | CDH1 | 3666436 | CTGACTTGGTTGTGTCGATCTCTCTGCAG |
| 3035 | CDH1 | 3666437 | CCTTCAAGGTGAGGGGTTAAGCACAACAGCAACAGCTGTGATCACAGTCACTGACACCAACGATAATCCTCCGATCTTCAATCCCA |
| 3036 | CDH1 | 3666438 | CGTCGTAATCACCACACTGAAAGTGACTGATGCTGATGCCCCCAATACCCCAGCGTGGGAGGCTGTATACACCATATTGAATGATGATGGTGGACAATTTGTCGTCACCACAAATCCAGTGAACAACGATGGCATTTTG |
| 3037 | CDH1 | 3666439 | CTCACAGCTGTTCATACCCTTGTCCCC |
| 3038 | CDH1 | 3666442 | TTTGAGGCCAAGCAGCAGTACATTCTACACGTAGCAGTGACGAATGTGGTACCTTTTGAGGTCTCTCTCACCACCTTCCACAGCCACCGTCACCGGGATGTGCTGGATGTGAATGAAGCCCCCATCTTTGTGCCTCCTGAAAAGAGAGTGGAAGTGTCCGAGGACTTTGGCGTGGGCCAGGAAATCACATCCTA |
| 3039 | CDH1 | 3666444 | CTGGCTGGAGATTAATCCGGACACTGGTGCCATTTCCACTCGGGCTGAGCTGGACAGGGAGGATTTTGAGCACGTGAAGAACAGCACGTACACAGC |
| 3040 | CDH1 | 3666445 | GTTGCTACTGGAACAGGGACACTTCTGCTGATCCTGTCTGATGTGAATGACAACGCCCCCATACCAGAACCTCGAACTATATTCTTCTGTGAGAGGAATCCAAAGCCTCAGGTCATAAACATCATTGATGCAGACCTTCCTCCCAATACATCTCCCTTCACAGCAGAACTAACACACGGGGCGAGTGCCAACTGGACCATTCA |
| 3041 | CDH1 | 3666447 | ACTATTCTACCGAGGTGGAGGCAGCTGTCAACTGCCTGGTCAATTTGCATATATGGGCTTCCTACACCTACTTCTCTCTGGGCTTCTATTTCCACCATGACGATGTGGATCTGGAAGGTGTGCACCACTTCTTCCACAAATTGGCCAAGGAGAAGCACAAGGGCGCTGAGTGTCCCTTGAAAATGCAAAACCAGTGTGGCGGCCGCACTGTCTTCCCGGACATCCAGAAGCCATGTAAAGATGAATGGGGTAAAACCCTGGGTGCGATGGAAGTCACTCTGGCCCTGGAGAAGAACCTGAACTGGACCCTTTTGGATCTTC |
| 3042 | CDH1 | 3666450 | CCCAAGAATCTATCATTTTGAAGCCAAAG |
| 3043 | CDH1 | 3666451 | GGTGGGTGACTACAAAATCAATCTCAAGCTCATGGATAACCAGAATAAAGACCAAGTGACCACCTTAGAGGTCAGCGTGTGTGACTGTGAAGGGGCCGCTGGCGTCTGTAGGAAGGCACAGCCTGTC |
| 3044 | CDH1 | 3666452 | TCTTGCTGTTTCTTCGGAGGAGAGCGGTGGTCAAAGAGCCCTTACTGCCCCAGAGGATGACACCCGGGACAACGTTATTACTATGATGAAGA |
| 3045 | CDH1 | 3666453 | ACGCTCGGCCTGAAGTGACTCGTAACGACGTTGCACCAACCCTCATGAGTGTCCCCCGGTATCTTCCCCGCCCTGCCAATCCCGATGAAATTGGAAATT |
| 3046 | CDH1 | 3666454 | CCCGCCTTATGATTCTCTGCTCGTGTTTGACTATGAAGGAAGCGGTTCCGAAGCTGCTAGTCTGAGCTCCCTGAACTCCTCAGAGTCAGACAAAGACCAGGACTATGACTACTTGAACGAATGGGGCAATCGCTTCAAGAAGC |
| 3047 | CDH1 | 3666455 | TCCCTTCCCTTGAGATGAGTTTCTGGGGAAAAAAAGAGACTGGTTAGTGATGCAGTTAGTATAGCTTTATACTCTCTCCACTTTATAGCTCTAATAAGTTTGTGTTAGAAAAGTTTCGACTTATTTCTTAAAGCTTTTTTTTTTTCCCATCACTCTTTACATGGTGGTGATGTCCAAAAGATACCCAAATTTTAATATTCCAGAAGAACAACTTTAGCATCAGAAGGTTCACCCAGCACCTTGCAGATTTTCTTA |

TABLE 13-continued

Subtyping Target Sequences

| SEQ ID NO. | Gene | Affy Probeset ID | Sequence |
|---|---|---|---|
| | | | AGGAATTTTGTCTCACTTTTAAAAAGAAGGGGAGAAGTCAGCTACTCTAGTTCTGTTGTTTTGT<br>GTATATAATTTTTTAAAAAAAATTTGTGTGCTTCTGCTCATTACTACACTGGTGTGTCCCTCTGC<br>CTTTTTTTTTTTTTAAGACAGGGTCTCATTCTATCGGCCAGGCTGGAGTGCAGTGGTGCAATC<br>ACAGCTCACTGCAGCCTTGTCCTCCCAGGCTCAAGCTATCCTTGCACCTCAGCCTCCCAAGTAG<br>CTGGGACCACAGGCATGCACCACTACGCATGACTAATTTTTTAAATATTTGAGACGGGGTCTC<br>CCTGTGTTACCCAGGCTGGTCTCAAACTCCTGGGCTCAAGTGATCCTCCCATCTTGGCCTCCCA<br>GAGTATTGGGATTACAGACATGAGCCACTGCACCTGCCCAGCTCCCCAACTCCCTGCCATTTTT<br>TAAGAGACAGTTTCGCTCCATCGCCCAGGCCTGGGATGCAGTGATGTGATCATAGCTCACTGT<br>AACCTCAAACTCTGGGGCTCAAGCAGTTCTCCCACCAGCCTCCTTTTTATTTTTTTGTACAGATG<br>GGGTCTTGCTATGTTGCCCAAGCTGGTCTTAAACTCCTGGCCTCAAGCAATCCTTCTGCCTTGG<br>CCCCCCAAAGTGCTGGGATTGTGGGCATGAGCTGCTGTGCCCAGCCTCCATGTTTTAATATCA<br>ACTCTCACTCCTGAATTCAGTTGCTTTGCCCAAGATAGGAGTTCTCTGATGCAGAAATTATTGG<br>GCTCTTTTAGGGTAAGAAGTTTGTGTCTTTGTCTGGCCACATCTTGACTAGGTATTGTCTACTC<br>TGAAGACCTTTAATGGCTTCCCTCTTTCATCTCCTGAGTATGTAACTTGCAATGGGCAGCTATC<br>CAGTGACTTGTTC |
| 3048 | MYH11 | 3682029 | TCTACAGTTTTGCACCACGGCAAGAAAACCAAAAACCAAAACAAACAAACAAAAAAAACCCA<br>ACAACAACCCAGAACAAAGCAAACCCAGCAGACTGTACTTAGCATTGTCTAAATCCATTCTC<br>AAATTCCAAATATCACAGACACCCCTCACACAAGGAATATAAAAACCACCACCCTCCAGCCTG<br>GGCAACGTAGTAAAACCTCATCTATACAAGAATTTAAAAATAAGCTGGGCGTGGTGGTACAC<br>ACCTGTGGTCCCAGCTACTAGGGAGGCTGAGCCAGGAAGAACGCTCCAGCCCAGGACTTCGA<br>GGCTGCAATGAGCTATAATTGCATCATTGCACTCCAGCCTGGGCAACAGAGACCCTGTCTCAA<br>CCACCACCACCACCACCCCCTACTACCCCTGTATTCAAGGTAAAAATTGAAGTTTGTATGAT<br>GTAAGAGATGAGAAAAACCCAACAGGAAACAGACACATCCTCCAGTTCTATCAATGGATT<br>GTGCAGACACTGAGTTTTTAGAAAAACATATCCACGGTAACCGGTCCCTGGCAATTCTGTTTA<br>CATGAAATGGGGAGAAAGTCACCGAAATGGGTGCCGCCGGCCCCACTCCCAATTCATTCCC<br>TAACCTGCAAACCTTTCCAACTTCTCACGTCAGGCTTTGAGAATTCTTTCCCCCTCTCCTGGTT<br>TCCACACCTCAGACACGCACAGTTCACCAAGTGCCTTCTGTAGTCACATGAATTGAAAAGGAG<br>ACGCTGCTCCCACGGAGGGGAGCAGGAATGCTGCACTGTTTACACCCTGACTG |
| 3049 | MYH11 | 3682030 | AAGGTCTGGAGGACGTAGAGTTATTGAAAATGCAGATGGTTCTGAGGAGGAAACGGACACT<br>CGAGACGCAGACTTCAATGGAACCAAGGC |
| 3050 | MYH11 | 3682031 | ACGAGACCTCTTTCGTTCCTTCTAG |
| 3051 | MYH11 | 3682032 | CCCCCCCACAGGAAACTTCGCAGTGA |
| 3052 | MYH11 | 3682034 | GGAGGAGTCCCAGCGCATCAACGCCAACCGCAGGAAGCTGCAGCGGGAGCTGGATGAGGCC<br>ACGGAGAGCAACGAGGCCATGGGCCGCGAGGTGAACGCACTCAAGAGC |
| 3053 | MYH11 | 3682035 | GGCGGCCACCAAGTCGCTGAAGCAGAAAGACAAGAAGCTGAAGGAAATCTTGCTGCAGGTG<br>GAGGACGAGCGCAAGATGGCCGAGCAGTACAAG |
| 3054 | MYH11 | 3682037 | GCAACGAGCTGGCCACAGAGCGCAGCACGGCCCAGAAGAATGAGAGTGCCCGGCAGCAGCT<br>CGAGCGGCAGAACAAGGAGCTCCGGAGCAAGCTCCACGAGATGGAGGGGGCCGTCAAGTCC<br>AAGTTCAAGTCCACCATCGCGGCGCTGG |
| 3055 | MYH11 | 3682038 | AGCTCTGACCTTATCCAGTGAGCCCTTGGTGATGTCACTGAGCACTAGTTCCATG |
| 3056 | MYH11 | 3682039 | GTGCAGGCCCTGGATTGAGGGACAAGAGGGTG |
| 3057 | MYH11 | 3682040 | AGGATCCTGCACCAGTCAACACACGCGTGGCGGCTTCCT |
| 3058 | MYH11 | 3682041 | AGGCCATGAGCGACCGGGTCCGCAAAGCCACACAGCA |
| 3059 | MYH11 | 3682042 | GAACGCACTCCAGGACGAGAAGCGCCG |
| 3060 | MYH11 | 3682043 | CCGCTGAGAGGGCTCGCAAACAAGCGGACCTCGAGAAGGAGGAACT |
| 3061 | MYH11 | 3682044 | GGAAGATGCCCGTGCCTCCAGAGATGAGATCTTTGCC |
| 3062 | MYH11 | 3682045 | GAGCTTCAGGCCGACTCTGCCATCAAGGGGAGGAGGAAGCCATCAAGCAGCTACGCAAAC<br>TGCAG |
| 3063 | MYH11 | 3682047 | GCCAAACTGCGGCTGGAAGTCAACATGCAGGCGCTCAAGGGCCAGTTCGAAAGGGATCTCC<br>AAGCCCGGGACGAGCAGAATG |
| 3064 | MYH11 | 3682048 | TTGAGCCTCATAGAATGGGGCTGCCCGCTCT |
| 3065 | MYH11 | 3682049 | TCTCTTCCAAATACGCGGATGAGAGGGACAGAGCTGAGGCAGAAGCCAGGGAGAAGGAAAC<br>CAAGGCCCTGTCCCTGGCTCGGGCCCTTGAAGAGGCCTTGGAAGCCAAAGAGGAACTCGAGC<br>GGACCAACAAAATGCTCAAAGCCGAAATGGAAGACCTGGTCAGCTCCAAGGATGACGTGGG<br>CA |

TABLE 13-continued

Subtyping Target Sequences

| SEQ ID NO. | Gene | Affy Probeset ID | Sequence |
|---|---|---|---|
| 3066 | MYH11 | 3682050 | TTGCCAGCACCGTGGAAGCTCTGGAAGAGGGGAAGAAGAGGTTCCAGAAGGAGATCGAGA<br>ACCTCACCCAGCAGTACGAGGAGAAGGCGGCCGCTTATGATAAACTGGAAAAGACCAAGAA<br>CAGGCTTCAGCAGGAGCTGGACGACCTGGTTGTTGATTTGGACAACCAGCGGCAACTCGTG |
| 3067 | MYH11 | 3682052 | TGCTTCAAGAAGAAACCCGGCAGAAGCTCAACGTGTCTACGAAGCTGCGCCAG |
| 3068 | MYH11 | 3682054 | TGAGAGCGTCACAGGGATGCTTAACGAGGCCGAGGGGAAGGCCATTAAGCTGGCCAAGGAC<br>GTGGCGTCCCTCAGTTC |
| 3069 | MYH11 | 3682055 | TGAACACCTCAAGTACTAGCCCATGTGTTTTGAGTAAAAAGGGCTCCTTTCAACGAGGATCCC<br>CTTCTAGAGGCTTTGACTAACCAGTCTCTTGGCACCCTTAG |
| 3070 | MYH11 | 3682062 | AGGTGACGGTGCTGAAGAAGGCCCTGGATGAAGAGACGCGGTCCCATGAGGCTCAGGTCCA<br>GGAGATGAGGCAGAAACACGCACAGGCGGT |
| 3071 | MYH11 | 3682066 | AAAGCAGAAGCGAGACCTCGGCGAGGAGCTGGAGGCCCTAAAGACAGAGCTGGAA |
| 3072 | MYH11 | 3682068 | GCTGAAACGGAAGCTGGAGGGTGATGCCAGCGACTTCCACGAGCAGATCGCTGACCTCCAG<br>GCGCAGATCGCAGAGCTC |
| 3073 | MYH11 | 3682069 | GAAAAGGCCAAGAATCTTACCAAGCTGAAAA |
| 3074 | MYH11 | 3682070 | CTCCTTGAGGAGAGGATTAGTGACTTAACGACAAATCTTGCAGAAG |
| 3075 | MYH11 | 3682071 | CTGCAACTTGAGAAGGTCACGGCTGAGGCCAAGATCAAG |
| 3076 | MYH11 | 3682072 | GGAGAAGAACCTGCTACAGGAACAGCTGCAGGCAGAGACAGAGCTGTATGCAGAGGCTGAG<br>GAGATGCGGGTGCGGCTGGCGGCCAAGAAGCAGGAGCTGGAGGAGATACTGCATGAGATG<br>GAGGCCCGCCTGGAGGAGGAGGAAGACAGGGGCCAGCAGCTACAGGCTGAAAGGAAG |
| 3077 | MYH11 | 3682074 | GAGAATGAGCTTAAGGAGCTGGAACAG |
| 3078 | MYH11 | 3682076 | GCAGCTGACCGCCATGAAGGTGATTCAGAGGAACTGCGCCGCCTACCT |
| 3079 | MYH11 | 3682078 | AGCAAAATCTTCTTCCGAACTGGCGTCCTGGCCCACCTAGAGGAGGAGCGAGATTTGAAGAT<br>CACCGATGTCATCATGGCCTTCCAGGCGATGTGTCGTGGCTACT |
| 3080 | MYH11 | 3682080 | CAAGCTGGATGCGTTCCTGGTGCTGGAGCAGCTGCGGTGCAATGGGGTGCTGGAAGGCATT<br>CGCATCTGCCGGCAGG |
| 3081 | MYH11 | 3682081 | AGGAAGTATTCACTGGGCTCTGCCCTGTCCTGGGTGCTGGGGAGCAGTGTTAGAAAAATTGT<br>AGCCCTTCCCTGTGGGTTTCTCATAATCTGGTGCAGGCATCTTCAGCTTGGGGCGATTGTGTC<br>CTCTATATGGACATGCTACAGACATTTTTGGTTGTCACAACCAGGAGGGGGCTGTTAGTCAGC<br>ATCTAGTGGGTAGGGGCCAGGGATGCCCTAAGCATTGTACA |
| 3082 | MYH11 | 3682082 | CCTGGACCAGATGGCCAAGATGACGGAGAGCTCGCTGCCCAGCGCCTCCAAGACCAAGAAG<br>GGCATGTTCCGCACAGTGGGGCAGCTGTACAAGGAGCAGCTGGGCAAGCTGATGACCACGC<br>TACGCAACACCACGCCCAACTTC |
| 3083 | MYH11 | 3682083 | CTATAATGCGAGTGCCTGGCTGACCAAGAATATGGACCCGCTGAATGACAACGTGACTTCCCT<br>GCTCAATGCCTCCTCCGACAAGTTT |
| 3084 | MYH11 | 3682084 | ACGGACAAGTCTTTCGTGGAGAAGCTGTGCACGGAGCAGGGCAGCCACCCCAAGTTCCAGA<br>AGCCCAAGCAGCTCAAGGACAAGACTGAGTTCTCCATCATCCATTATGC |
| 3085 | MYH11 | 3682086 | GGCTGGACCTACAGCCCTGCATCGAG |
| 3086 | MYH11 | 3682091 | TTTGGCCAAGGCAACATATGAGCGCCTTTTCCGCTGGATACTCACCCGCGTGAACAAAGCCCT<br>GGACAAGACCCATCGGCAAGGGGCTTCCTTCCTGGGGATCCTGGATATAGCTGGATTT |
| 3087 | MYH11 | 3682092 | TGCTCAGAAAGTTTGCCACCTCATGGGAATTAATGTGACAGATTTCACCAGATCCATCCTCACT<br>CCTCGTATCAAGGTTGGGCGAGATGT |
| 3088 | MYH11 | 3682094 | TGAAGGTGGTATCATCGGTCCTGCAGCTT |
| 3089 | MYH11 | 3682099 | GGAGGGCTTCAACAACTACACCTTCCTCTCCAATGGCTTTGTGCCCATCCCAGCAGCCCAGGA<br>TGATGAGATGTTCCAGGAAACCGTGGAGGCCATGGCAATCATGGGTTTCAGCGAGGAGGA |
| 3090 | MYH11 | 3682103 | CTGCTAGAAAAATCACGGGCAATTCGCCAAGCCAGAGAC |
| 3091 | MYH11 | 3682107 | CATCCGCATCAACTTCGACGTCACGG |
| 3092 | MYH11 | 3682109 | AAGCAGCTTCTACAAGCAAACCCGATTCTGGAGGCTTTCGGCAACGCCAAAACAGTGAAGAA<br>CGACAACTCCTCA |

TABLE 13-continued

Subtyping Target Sequences

| SEQ ID NO. | Gene | Affy Probeset ID | Sequence |
|---|---|---|---|
| 3093 | MYH11 | 3682110 | GGCCCAACTGCAGCCGCCATGTTTTAGGGCTAGGCCAAGAGCAGCTCGTTTGCTTTCCCAGCT TAACTTACCACATTGGCCCTTTCCTGCCATGATTAATCACGTGACCGCGTTTGTGCAAAGGCAT CCCGGCAGAGGGGGCCGGTGGGCTGTGTACAGTCTCAGCTTCCTTTAACCCAATGAATGGAG CTCAGGCAACCTGCTTTGAAGCTTTATTCCGCAGTCCGCTAAGAGGATTCCTGGTGGGTTTTG TGCATTCCTTACTTGTCTGCTGTAGAAGACTTCAGAAAACCAGTCCTGAGAAAGAAAAAATTG CAACTTAAAAAAAATTGCACTAAAATAATTAGAAGGAGGCTTGTAGTGGTTTAACTTGAAGAA GGCTGCTTGTTAAACATGAACAGCAGCACGACTGCCATGTACAGTGGGACAGGTGGTGCACT GCACAACTCCGGGGGGCACCATTCATCATGATGTAAATGACATCACCGACATTGTGCAAGGC AGTGGCTTTGAGTGGCAGTGATGTTGCACAGATGAGCAGGCCCTGGTCTTGAAAAAGTGAC CTTCCTAGGGAGCAGATGTCCTAGCTATTAGAGAGCTCAGACAGTTGCTTCTCTTCTGAAATC CTCCTGTAAATCTGAACATTAGCATCAGGGTCTAAGAGGAGGTAGGAGATAGGAGAGAACCT GTGGGTTAAGGGCAGAGTTTTGTGACAACATCCATCCAAGGTAGAACTGTCAGGACCTAGGT TGCTTTCTC |
| 3094 | MYH11 | 3682111 | TCCAGTGTTCGCCATTCCAGATGTCACTTTGCGTCCTCAGAGGGGACTCTGGGGCAGCCACCA TGGCCGGCTTGTCTGGAGGCCCTTGGAGATCTAGGATGGGCGCTGGTCGTGGCTTTGGAGAA CTTTCCTTCTCCAAACAAATGCAGGAAACTCAAGATTCAGCATCCTAGAATTGTCTCTGGCAAG TTGGTTTCCAGCCATAGTGAGTGGGAACAATGGCCCCAGAGGCTGTGTGGCAGTTTAAACAC AGTTTCCACTGCCTTCCCTTTCCCTAAAGAGTAAACACAGGAGATAATACTTTCTAACAACTCA TCGTTATCAAGGGCCTACTATGTGCTGCTTGTTTTGGCTGCATGCGTAAACACATCTC |
| 3095 | MYH11 | 3682112 | CAGCTTGCAGCCCAACCGAGATACAAACAGAACATCATTGCAAGAACTCAGGCCCCATCTGAC TACCCCTCCCCTGAAGACTCAAAGAGGGACCGTCTTTTTGGCGAGCAGGCCTGTTGAGTGTG GGTGATTTCTTGGCTCAGCTAGAAGCATCCCTCCAGAAGGGGGCCCGTTTTGTGAAATGAGA ATAAGCCCTTTCCTTCCATAGCGAGATCTTCCTCCACGTCGGG |
| 3096 | MYH11 | 3682113 | AGGTCATTCAGTACCTGGCCGTGGTGGCCTCCTCCCACAAGGGCAAGAAAGA |
| 3097 | MYH11 | 3682117 | TAAGGTCACCCAGGTAACTGGCAGAGGAGGGATTTGAACTTGAGCAACCTGGTCCTGGAGCC CATTATGCTATTCTGCCAATTGATGCTATAGGGGAGAGAGGCGTTGCTTCTGCCTGGGGTTTT GCAGGACGTGTAGGAGTTGTACAGTACAAAATGCCAGGGTGCTTTGCCAGTCA |
| 3098 | MYH11 | 3682122 | GCCTCTTCTGCGTGGTGGTCAACCCCTATAAACACCTGCCCATCTACTCGGAGAAGATCGTCG ACATGTACAAGGGCAAGAAGAGGCACGAGATGCCGCCTCACATCTACGCCATCGCAGACACG GCCTACCGGAGCATGCTTCAA |
| 3099 | MYH11 | 3682129 | CGCAGAAGGGCCAACTCAGTGACGATGAGAAGTTCCTCTTTGTGGACAAAAACTTCATCAAC AGCCCAGTGGCCCAGGCTGACTGGGCCGCCAAGAGACTCGTCTGGGTCCCCTCGGAGAAGC AGGGCTTCGAGGCAGCCAGCATTAAGGAGGAGAAGGGGGATGAGGTGGTTGTGGAGCTGG TGGAGAATGGCAAGAAGGTCACGGTTGGGAAAGATGACATCCAGAAGATGAACCCCACCCAA GTTCTCCAAGGTGGAGGACATGGCGGAGCTGACGTGCCTCAACGAAGCCTCCGTGCTACACA ACCTGAGGGAGCGGTACTTCTC |
| 3100 | MYH11 | 3682131 | GTCAGATCCGAGCTCGCCATCCAGTTTCCTCTCCACTAGTCCCCCCAGTTGGAGATCT |
| 3101 | TOX3 | 3691696 | TGGACTGTATTTTGATGCAACAACAAAG |
| 3102 | TOX3 | 3691698 | ACGTCCTCTCAAGTGTCTATTAGATAGGCAATAAGAACTGCAGTGTAGCTGAGTAACATCTT TTAGCTGACTATAAATCACTTTGTTTTTAAACAAGAAAAGCTGTGCTCTTTTATGTGATGCCTTT TTTATTTATTCAGGCTATACCTACAATATGTGAATCAAACTGTTTAATGAATCCTGGGACATAC TGATGACTATAAACTGGCCTCTCTGAGTCATAGAAAAATGCCTTATTTCTCCAGAAGTGAGT AAACCACACTTCCAGGCTATCTGAACTCCTGAAGCCCTAAAAATAAAAAGCACAGTTGTAACT ACCTGAAATATGAAGATCCAGTTTCATACAAACATTTGTATGACGTGAATAGTTGATGGCATT TTTTTGTCATGAAAAAATAATGTAAATCACAGACTTTTGCCAAAGCTCTTATTTTTTTTCCTAA ATCTCTCCAGAAAAAAAATGCAAGTGACTAAATTCAATTATTGACTAATTTCCACTTTTTATCCA TGACTTCTCCAAATCAAACCACAGTATATGTTGTAACAATATCTATGACCACTGTTAGCCCATT ATATTCATTCCAATTAGAAGAAATGTGAATACTATATTCCGTGTTTTGAGTGACAAGTTTC |
| 3103 | TOX3 | 3691700 | CCATCCCTGCCATCGGGAGCCCCCAGCCAGCCTCTCAGCAGCACCAGTCGCAAATACAGTCTC AGACACAGACTCAAGTATTATCGCAG |
| 3104 | TOX3 | 3691702 | CACCAGTCTCAGCCTTCTCCTCGGCAG |
| 3105 | TOX3 | 3691704 | AATGCATCAGCAAATCCAGCAGCAGATGCAGCAGCAGCATTTCCAGCACCACATGCAGCAGC ACCTGCAGCAGCAGCAGCAGCATCTCCAGCAGCAAATTAATCAACAGCAGCTGCA |
| 3106 | TOX3 | 3691706 | AGCAGCATCAGATGCAATTGCAGCAGCAGC |
| 3107 | TOX3 | 3691708 | CAGACCATCCGTTCTGTTCAGCAGACCCTGGCGTCGACCAATCTAACATCCTCTCTCCTTCTCA ACACTCCACTGTCTCAACATGGAACAGTGTCAGCATCACCTCAGACTCTCCAGCAATCCCTCCC TAGGTCAATCGCTCCCAAACCCTTAACCATGAGACTCCCCATGAACCAGATTGTCACATCAGTC ACCATTGCAGCCAACATGCCCTCGAACATTGGGGCTCCACTGATAAGCTCCATGGGAACGA |

TABLE 13-continued

Subtyping Target Sequences

| SEQ ID NO. | Gene | Affy Probeset ID | Sequence |
|---|---|---|---|
| 3108 | TOX3 | 3691710 | AAAGAATACCTGAAGGCCCTGGCGGCATACAGGGCCAGCCTCGTTTCTAA |
| 3109 | TOX3 | 3691712 | GTCTCATTATTGTCACCGGGCATTTGAAATTTTATTCCAAGTTCATTTTAAAGCAAGGCAGTAT<br>GAGAGGTATTCAGAAATTAGCCATGCTTGTGGGAGATACTTCCTTAGGGGCTTCGTCTCCTCT<br>CCTTCCCCTTGCAACTCCTCCACACAAATGAAGGGAAGAATGGGTTCCTTGGGGGTCGATCCC<br>CCCCTTACTCCTTGCATGAAACTCCAATTACCATTAAAAGAAGTTAACTTTTACATATCCACAG<br>AAGAATAGATCAACTCCTATGAGTGATAAAATAGAATAATTGTTTTCAAGAATGAAGAGTGG<br>AAAGTCCTTGATTTTGTTTACAAATCATGAACTTATTTCAGGAACTCATTCCTAGAAGCTTGTTT<br>TGTTGGGAAGGTGCAACATTAGAAATTTCTTTTTAGTTTGCACTGAGTTTATTACTGTAGATAG<br>CAGACTGATTTTCTGTCCCAGAAATATAATTCTGAGGGACTGGAAAAGTGCTGCACCTAACTT<br>TTAAACTCTGGAGAGAAAGATGCATGTTGACTGAACACCCAGCCATCAGACCACTTAGGAAA<br>AGGAGAAGCCCAAATCATGTTTAATATGCTGGAATTTTATTTATGTAACTCAGTGGGGTCACT<br>AATGGAAATCTC |
| 3110 | TOX3 | 3691714 | CAGCATATGCCCTGTTTTTCAGAGACACACAGGCTGCAATTAAAGGTCAAAACCCCAATGCAA<br>CCTTTGGAGAGGTCTCAAAAATTGTAGCATCTATGTGGGACAGCCTTGG |
| 3111 | TOX3 | 3691716 | ACACAAGTGTCCCAGTACCGGCAGGATCCCTCCCTGATCATGCGGTCCATCGTCCACATGACC<br>GATGCTGCGCGTTCTGGGGTCATGCCTCCTGCCCAGCTCACCACCATCAACCAGTCTCAGCTC<br>AGCGCCCAGTTGGGGTTGAATTTGGGAGGTGCCAGTATGCCTCACACATC |
| 3112 | TOX3 | 3691718 | CTTTCAAGCCCTCAGCGATCCATTGCCTTCCCAGGGAAGTGAATTCACACCCCAGTTTCCCCCT<br>CAAAGCCTGGACCTCCCTTCCATTACAATCTCAAGAAATCTCGTGGAACAAGATGGCGTGCTT<br>CATAGCAGTGGGTTGCATA |
| 3113 | TOX3 | 3691720 | TGGGGACGAGGAATTCGAAATTCCACCAATCA |
| 3114 | TOX3 | 3691722 | ATGGCTGAGGCGAACAATGCGTTCTTCGCTGCCA |
| 3115 | TOX3 | 3691729 | GCTAGAATCTGTGTTGTTCATTGCAGTTTGTGCTCAGCCACGGAAGGCACCTATCCCTAGCAC<br>CCAACCCCCATCCACCTAGGGCTCTATAAAA |
| 3116 | TOX3 | 3691736 | CTTCGGCATGGATGTGAGGTTCTACCCCGCGGCGGCCGGGGACCCTGCCAGCCTGGACTTCG<br>CGCAGTGCCTGGGGTACTACGGCTACAGCAAG |
| 3117 | TOX3 | 3691738 | CGCGCGCAGCGCTGCCTCGGTGCCCCGGCGGGGCGCGTCCCCCCGGCCGCCTCCCGCTCTCC<br>CGCGGCTCGCGTGGCCGCGCCTTTGTGTGCGGCGGCCGCGGCTCCCGAGCTCCTCGGGCTCT<br>GGGTCCCGGCGCCCCTCCGGCCGCGAGTCCCACGCGCCACCCCCGGGCGCCCTCGACGGTGG<br>ATCTAGCGGC |
| 3118 | NQO1 | 3696673 | CCCTTGCCGTGATAGCTTGCAACACCTTGG |
| 3119 | NQO1 | 3696675 | CTGGCCCTTGCAATCTTCTACTTTAAGGTTTGCAGAGATAAACCAATAAATCCACACCGTACAT<br>CTGCAATATGAATTCAAGAAAGGAAATAGTACCTTCAATACTTAAAAATAGTCTTCCACAAAA<br>AATACTTTATTTCTGATCTATACAAATTTTCAGAAGGTTATTTTCTTTATCATTGCTAAACTGAT<br>GACTTACTATGGGATGGGGTCCAGTCCCATGACCTTGGGGTACAATTGTAAACCTAGAGTTTT<br>ATCAACTTTGGTGAACAGTTTTGGCATAATAGTCAATTTCTACTTCTGGAAGTCATCTCATTCC<br>ACTGTTGGTATTATATAATTCAAGGAGAATATGATAAAACACTGCCCTCTTGTGGTGCATTGA<br>AAGAAGAGATGAGAAATGATGAAAAGGTTGCCTGAAAAATGGGAGACAGCCTCTTACTTGCC<br>AAGAAAATGAAGGGATTGGACCGAGCTGGAAAACCTCCTTTACCAGATGCTGACTGGCACTG<br>GTGGTTTTGCTCTCGACAGTATCC |
| 3120 | NQO1 | 3696676 | GGTACAGTTTGGCTAGGTATCATTCAACTCTCCAATGTTCTATTAATCACCTCTCTGTAGTTTAT<br>GGCAGAAGGGAATTGCTCAGAGAAGGAAAAGACTGAATCTACCTGCCCTAAGGGACTTAACT<br>TGTTTGGTAGTTAGCCATCTAATGCTTGTTTATGATATTTCTTGCTTTCAATTACAAAGCAGTTA<br>CTAATATGCCTAGCACAAGTACCACTCTTG |
| 3121 | NQO1 | 3696677 | AACATGTTATCAAATCTGGGTATCTTTCCAGGCTTCCCTGACTTGCTTTAGTTT |
| 3122 | NQO1 | 3696678 | TTTCTGTGGGCCATCACTTGGGCAAGTCCATCCCAACTGACAACCAGATCAAAG |
| 3123 | NQO1 | 3696679 | TGTGGCTTCCAAGTCTTAGAACCTCAACTGACATATAGCATTGGGCACACTCCAGCAGACGCC<br>CGAATTCAAATCCTGG |
| 3124 | NQO1 | 3696681 | GTGCTTTCCATCACCACTGGTGGCAGTGGCTCCATGTACTCTCTGCAAGGGATCCACGGGGAC<br>ATGAATGTCATTCTCTGGCCAATTCAG |
| 3125 | NQO1 | 3696683 | CATTCTGAAAGGCTGGTTTGAGCGAGTGTTCATAGGAGAGTTTGCTTACACTTACGCTGCCAT<br>GTATGACAAAGG |
| 3126 | NQO1 | 3696686 | GACCCTGCGAACTTTCAGTATCCTGCCGAGTCTGTTCTGGCTTATAAAGAAGGCCATCTGAGC<br>CCAGATATTGTGGCTGAACAAAAGAAGCTGGAAGCCGCAGACCTTGTGATATTCCAG |

TABLE 13-continued

Subtyping Target Sequences

| SEQ ID NO. | Gene | Affy Probeset ID | Sequence |
|---|---|---|---|
| 3127 | NQO1 | 3696687 | AGCACTGATCGTACTGGCTCACTCAGAGAGGACGTCCTTCAACTATGCCATGAAGGAGGCTGCTGCAGCGGCTTTGAAGAAGAAAGGATGGGAGGTGGTGGAGTCGGACCTCTATGCCATGAACTTCAAT |
| 3128 | NQO1 | 3696689 | TCAAACGGGCCGGACAGGATATATAAGAGAGAATGCACCGTGCACTACACACGCGACTCCCACAAGGTTGCAGCCGGAGCCGCCCAGCTCACCGAGAGCCTAGTTCCGGCCAGG |
| 3129 | CD68 | 3708859 | CTGGTGCAGACAGCCTAGCTGGACTTTGGGTGAGGCGGTTCAGCC |
| 3130 | CD68 | 3708860 | GGCTGTGCTTTTCTCGGGGGCCCTGCT |
| 3131 | CD68 | 3708861 | TTTGCTGCCATCCTTCACGGTGACACCCACGGTTACAG |
| 3132 | CD68 | 3708862 | TACCAAGAGCCACAAAACCACCACTCACAGGACAACCACCACAGGCACCACCAGCCACGGACCCACGACTGCCACTCACAA |
| 3133 | CD68 | 3708863 | AGCAATAGCACTGCCACCAGCCAGGGACCCTCAACTGCCACTCACAGTCCTGCCACCACTAGTCATGGAAATGCCACGGTTCATCCAACAAGCAACAGCACTGCCACCAGCCCAGGATTCACCAGTTCTG |
| 3134 | CD68 | 3708864 | ACCACCTCCACCCTCTCCGAGTCCTAG |
| 3135 | CD68 | 3708865 | AGGAGACCATTGGAGACTACACGTGGACCAATGGTTCCCAGCCCTGTGTCCACCTCCAAGCCCAGATTCAGATTCGAGTCATGTACACAACCCAGG |
| 3136 | CD68 | 3708867 | TCTCTGTACTGAACCCCAACAAAACCAAGGTCCAGGGAAGCTGTGAGGGTGCCCATCCCCACCTGCTTCTCTCATTCCCCTATGGACAC |
| 3137 | CD68 | 3708868 | AGCTACATGGCGGTGGAGTACAATGTGTCCTTCCCCCA |
| 3138 | CD68 | 3708869 | AGTGGACATTCTCGGCTCAGAATGCATCCCTTCGAGATCTCCAAGCACCCCTGGGGCAGAGCTTCAGTTGCAGCAACTCGAGCATCATTCTTTCACCAGCTGTCCACCTCGACCTGCTCTCCCTG |
| 3139 | CD68 | 3708870 | CCAGGCCCATAAGCCACTCATCTCTCTTCTTAACCCCCCAAATCTCGCTCTCCCAGCTTGTCATGGCTACAGGGCAGCTTTCTTTCCATCCTCTACAAGACTCTGCCAGTTTCCCCCTTTTATCACTGCTGAGTCACTGCGGTGAGCTCCTCACCAATCTCCTACTCCCCAGCATCCCCCCATTCCCTCCTCCCACCTTTATCCCAACCAGCACGTCACTGCAAATACCTACCTG |
| 3140 | CD68 | 3708871 | CAGTGACCGGTCCATCTTGCTGCCTCTCATCATCGGCCTGATCCTTCTTGGCCTCCTCGCCCTGGTGCTTATTGCTTTCTGCATCATCCGGAGACGCCCA |
| 3141 | CD68 | 3708872 | GGTACCCTTATTTCCTCGACACGCAACTGGCTCAAAGACAATGTTATTTTCCTTCCCTTTCTTGAAGAACAAAAGAAAGCCGGGCATGACGGCTCATGCCTGTAATCCCAGCACTTTGGGAGGCTGAGGCAGGTGGATCACTGGAGGTCAGGAGTTTGAGACCAGCCTGGCCAACATGGTGAAACCCTGTCTCTACTAAAAATACAATTAGCCAGGTGTGGCGGCGTAATCCCAGCTGGCCTGTAATCCCAGCTACTTGGGAGGCTGAGGCAGAACTGCTTGAACCCAGGAGGTGGAGGTTGCAGTGAGCCGTCATCGCGCCACTAAGCCAAGATC |
| 3142 | CD68 | 3708873 | TTTTATTAAATGTGACGAACTGCCCCCCCCCCCCCCCCAGCAGGAGAGCAGCAAAATTTATGCAAATCTTTGACGGGGTTTTCCTTGTCCTGCCAGGATTAAAAGCCATGAGTT |
| 3143 | ERBB2 | 3720403 | TTCCCGGATTTTTGTGGGCGCCTGCCCCGCCCCTCGTCCCCCTGCTGTGTCCATATATCGAGGCGATAGGGTTAAGGGAAGGCGGACGCCTGATGGGTTAATGAGCAAACTGAAGTGTTTTCCATGATCTTTT |
| 3144 | ERBB2 | 3720404 | CGCAATTGAAGTACCACCTCCCGAGGGTGATTGCTTCCCCATGCGGGGTAGAACCTTTGC |
| 3145 | ERBB2 | 3720406 | CCAGTGGTCTATACCTCCAGCAGCAAGTCGAGTGAGCAAGTGATGTCCTGAAAGGCCCAGTGGATCAGTGGAATGAAGCGGGCAGGAAGACTTAGTGCTCCTGAAACAAGGAATCCAGAATCCAGGAGAAGGATGGCTCAGTGGGGCTTTCAAGGGACAAGTATGGGGGTTGAAGGGGTCACTGTCCCTATACC |
| 3146 | ERBB2 | 3720407 | GGCAAAGCAAAGCTATATTCAAGACCACATGCAAAGCTACTCCCTGAGCAAAGAGTCACAGATAAAACGGGGGCACCAGTAGAATGGCCAGGACAAACGCAGTGCAGCA |
| 3147 | ERBB2 | 3720408 | GATGAGAGTGACATGTACTGTTGTGGACATGC |
| 3148 | ERBB2 | 3720410 | TGCCCCGGGGGTCCTGGAAGCCACA |
| 3149 | ERBB2 | 3720411 | AGAATGAAGTTGTGAAGCTGAGATTCCCCTCCATTGGGACCGGAGAAACCAGGGGAGCCCCCCGGGCAGCCGCGCGCCCCTTCCCACGGGGCCCTTTACTGCGCCGCG |
| 3150 | ERBB2 | 3720412 | CAGCCGGAGCCATGGGGCCGGAGCCG |

TABLE 13-continued

Subtyping Target Sequences

| SEQ ID NO. | Gene | Affy Probeset ID | Sequence |
|---|---|---|---|
| 3151 | ERBB2 | 3720413 | GAGCTGGCGGCCTTGTGCCGCTGGGGCTCCTCCTCG |
| 3152 | ERBB2 | 3720417 | TGTGCACCGGCACAGACATGAAGCTGCGGCTCCCTGCCAGTCCCGAGACCCACCTGGACATG CTCCGCCACCTCTACCAGGGCTGCCAGGTGGTGCAGGGAAACCTGGAACTCACCTACCTGCCC ACCAATGCCAGCCTGT |
| 3153 | ERBB2 | 3720419 | TTGGGAGCAGTTGTGAAGCTCAGAAGAGAAATGTCTGTGAAAAGGTTATGAACAGGAGGGA GAGTGGAAACCAACCTGCTGGATCGTGTCCACAGACCCTGGAATGGGGCCACATGCTTGGTT TGTCAAATTGCAGACGCCGGCCGGGT |
| 3154 | ERBB2 | 3720420 | CAGGGCTACGTGCTCATCGCTCACAACCAAGTGAGGCAGGTCCCACTGCAGAGGCTGCGGAT TGTGCGAGGCACCCAGCTCTTTGAGGACAACTATGCCCTGGCCGTGCTAGACAATGGAGACC CGCTGAACA |
| 3155 | ERBB2 | 3720421 | AGGGGAAAGGGTCCTCTGATCATTGCTCACCC |
| 3156 | ERBB2 | 3720422 | GGTCTTGATCCAGCGGAACCCCCAGCTCTGCTACCAGGACACGATTTTGTGGAAGGACATCTT CCACAAGAACAACCAGCTGGCTCTCACACTGATAGACACCAACCGCTCTCGGGCC |
| 3157 | ERBB2 | 3720425 | GCCACTGCCCACTGACTGCTGCCATGAGCAGTGTGCTGCCGGCTGCACGGGC |
| 3158 | ERBB2 | 3720427 | TGGTCACCTACAACACAGACACGTTTGAGTCCATGCCCAATCCCGAGGGCCGGTATACATTCG GCGCCAGCTGT |
| 3159 | ERBB2 | 3720428 | ACCTTTCTACGGACGTGGGATCCTGCACCCTCGTCTGCCCCCTGCACAACCAAGAGGTGACAG CAGAGGATGGAACACAGCGGTGTGAGAAGTGCAGCAAGCCCTGT |
| 3160 | ERBB2 | 3720429 | TGCAGTTCCTGTCCCTCTGCGCATGCAGCCTGGCCCAGCCCACCCTGTCCTATCCTTC |
| 3161 | ERBB2 | 3720430 | TACAAGTGTCCCTATATCCCCTGTCAGTGTGGGAGGGGCCCGGACCCTGATGCTCATGTGGC |
| 3162 | ERBB2 | 3720431 | GGCATGGAGCACTTGCGAGAGGTGAGGGCAGTTACCAGTGCCAATATCCAGGAGTTTGCTG GCTGCAAGAAGATCTTTGGGA |
| 3163 | ERBB2 | 3720432 | AACACTGCCCCGCTCCAGCCAGAGCAGCTCCAAGTGTTTGAGACTCTGGAAGAGATC |
| 3164 | ERBB2 | 3720434 | GGCGCCTACTCGCTGACCCTGCAAGGGCTGGGCATCAGCTGGCTGGGGCTGCGCTCACTGAG GGAACTGGGCAGTGGACTGGCCCTCATCCACCATAACACCCACCTCTGCTTCGTGCACACGGT GCCCTGGGACCAGCTCTTTCGGAACCCGCA |
| 3165 | ERBB2 | 3720435 | AGCAGCGTTCTTGGACTTGTGCAGACTGCCCGTCTCTGTGCACCCTTCTTGACTCAGCACAGCT CTGGCTGGCTTGGCCTCTTGGCATGGCTTCTCTAGCTGGGTCCTACCTGCCTTGGCATCCTTCC CTCCCCCTCTGTTTCTGAAATCTCAGAACTCTTCCTCTCCCTACATCGGCCCCACCTGTCCCCAC CCCTCCAGCCCACAGCCATGCCCACAGCCAGTTCCCTGGTTCACTTGGACCTG |
| 3166 | ERBB2 | 3720436 | GCCACCAGCTGTGCGCCCGAGGGCACTGCTGGGGTCCAGGGCCCACCCAGTGTGTCAACTGC AGCCAGTTCCTTCGGGGCCAGGAGTGCGTGGAGGAATGCCGA |
| 3167 | ERBB2 | 3720437 | TGGCTGGAGGGGTGCATGGGGCTCCTCTCAGACCCCCTCACCACTGT |
| 3168 | ERBB2 | 3720438 | GCTCCCCAGGGAGTATGTGAATGCCAGGCACT |
| 3169 | ERBB2 | 3720439 | ACTCGCTGTTACACCTTAGGTAATGCGTTTTCCTCTCTGGGTGCCTCCCATTTTCTGGCTCAAGT CCCTGCCCAGGATCAAGCTTGGAGGAGGGCCCCGAGGGAGGGGCCACAGAGACTGGGTGA AGAGCAAGGGTGTTTGTCCCAGGAGCATGGCGAAAATTGCTGCTGGGTGGCCTTGGGAAGC ACAAAGGGGACCCAACTAAGGGCCTGATCCTACTGCC |
| 3170 | ERBB2 | 3720440 | GTGGCCTGTGCCCACTATAAGGACCCTCCCTTCTGCGTGGCCCGCTGCCCCAGCGGTGTGAAA CCTGACCTCTCCTACATGCCCATCTGGAAGTTTCCAGATGAGGAGGGCGCATGCCA |
| 3171 | ERBB2 | 3720441 | GTGAGTCCAACGGTCTTTTCTGCAGAAAGGAGGACTTTCCTTTCAGGGGTCTTTCTGGGGCTC TTACTATAAAAG |
| 3172 | ERBB2 | 3720442 | GGGCTGCCCCGCCGAGCAGAGAGCC |
| 3173 | ERBB2 | 3720443 | TTCCACTGTGGAACCTCCTGTCATTTTCCACTTCACCAAGTGACAGAGGACCTGCTCAGATGCT GAGGGGAGGGACTGCAAGGAAAGATGGCTAGGAACCCAGTCCCTCCACACCCTAGAGTA ACTTGATGCCTTGTGAGGGACACAGGCAAAGTTCAATTC |
| 3174 | ERBB2 | 3720444 | GTGGTCTTTGGGATCCTCATCAAGCGACGGCAGCAGAAGATCCGGAAGTACACGATGCGGA GACTGCTGCAGG |
| 3175 | ERBB2 | 3720446 | AGCGATGCCCAACCAGGCGCAGATGCGGATCCTGAAAGAGACGGAGCTGAGGAAGGTGAA GGTGCTTGGATCTGGCGCTTT |

TABLE 13-continued

Subtyping Target Sequences

| SEQ ID NO. | Gene | Affy Probeset ID | Sequence |
|---|---|---|---|
| 3176 | ERBB2 | 3720447 | GCATCTGGATCCCTGATGGGGAGAATGTGAAAATTCCAGTGGCCATCAAAGTGTTGAGGGAA AACACATCCCCCAAAGCCAACAAAGAAATCTTAG |
| 3177 | ERBB2 | 3720449 | TGGGCATCTGCCTGACATCCACGGTGCAGCTGGTGACACAGCTTATGCCCTATGGCTGCCTCT TAGACCATGTCCGGGAAAACCGCGGACGCCTGGGCTCCCAGGACCTGCTGAACTGGTGTATG CAGATTGCCA |
| 3178 | ERBB2 | 3720452 | ATGTGCGGCTCGTACACAGGGACTTGGCCGCTCGGAACGTGCTGGTCAAGAGTCCCAACCAT GTCAAAATTACAGACTTCGGGCTGGCTCGGCTGCTGGACATTGACGAGACAGAGTA |
| 3179 | ERBB2 | 3720453 | CTGGGTGGAGTGGTGTCTAGCCCATGGGAGAACTCTG |
| 3180 | ERBB2 | 3720454 | CTGGAGTCCATTCTCCGCCGGCGGTTCACCCACCAGAGTGA |
| 3181 | ERBB2 | 3720455 | ACTGTGTGGGAGCTGATGACTTTTGGGGCCAAACCTTACGATGGGATCCCAGCCCGGGAGAT CCCTGACCTGCTG |
| 3182 | ERBB2 | 3720456 | GTGCGTGGCTGAGCTGTGCTGGCTGCCTGGA |
| 3183 | ERBB2 | 3720457 | GTTGGATGATTGACTCTGAATGTCGGCCAAGATTCCGGG |
| 3184 | ERBB2 | 3720458 | GTTGGTGTCTGAATTCTCCCGCATGGCCAGGGACCCCCAGCGCTTTGTGGT |
| 3185 | ERBB2 | 3720460 | TCTACCGCTCACTGCTGGAGGACGATGACATGGGGGACCTGGTG |
| 3186 | ERBB2 | 3720462 | GTGGGGACCTGACACTAGGGCTGGAGCCCTCTGAAGAGGAGGCCCCCAGGTCTCCACTGGC ACCCTCCGAAGGGGCTGGCTCCGATGTATTTGATGGTGACCTGGGAATGGGGGCAGCCAAG GGGCTGCAAAGCCTCCCCACACATGACCCCAGCCCTCTACAGCGGTACAGTGAGGACCCCAC AGTACCCCTGCCCTCTGAGACTGATGGCTACGTTGCCCCCCCTGA |
| 3187 | ERBB2 | 3720463 | ATGTGAACCAGCCAGATGTTCGGCCCCAGCCC |
| 3188 | ERBB2 | 3720464 | AGCCTTCGACAACCTCTATTACTGGGACCAGGACCCACCAGAGCGGGGGGCTCCACCCAGCA CCTTCAAAGGGACACCTACGGCAGAGAACCCAGAGTACCTGGGTCTGGACGTGCCAGTGT |
| 3189 | ERBB2 | 3720465 | AGAAGGCCAAGTCCGCAGAAGCCCT |
| 3190 | ERBB2 | 3720466 | CGACCACTTCCAGGGGAACCTGCCATGCCAGGAACCTGT |
| 3191 | ERBB2 | 3720467 | CTTCCTGCTTGAGTTCCCAGATGGCTGGAAGGGGTCCAGCCTCGTTGGAAGAGGAACAGCAC TGGGGAGTCTTTGTGGATTCTGAGGCCCTGCCCAATGAGACTCTA |
| 3192 | ERBB2 | 3720468 | GGTACTGAAAGCCTTAGGGAAGCTGGCCTGAGAGGGGAAGCGGCCCTAAGGGAGTGTCTAA GAACAAAAGCGACCCATTCAGAGACTGTCCCTGAAACCTAGTACTGCCC |
| 3193 | ERBB2 | 3720469 | AGTATCCAGGCTTTGTACAGAGTGCTTTTCT |
| 3194 | LRRC37A2 | 3724138 | CACAAGGGGCTTTTTCATCCTTAGGAGACCTGAGTCCTCAAGAAAACCCTTTTCTGGAAGTAT CTGCTCCTTCAGAACATTTTATAGAAAACAATAATACAAAACACACAACTGCAAGAAATGCCT TTGAAGAAAATGATTTTATGGAAAACACTAACATGCCAGAAGGAACCATCTCTGA |
| 3195 | CCL5 | 3753861 | GGCTTACCATTAAAGTTCTCAATGCAACCAT |
| 3196 | CCL5 | 3753862 | TCTGAGGCGCTGCTTTGTCAAAAGGAAGTCTCTAGGTTCTGAGCTCTGGCTTTGCCTTGGCTTT GCCAGGGCTCTGTGACCAGGAAGGAAGTCAGCATGCCTCTAGAGGCAAGGAGGGGAGGAA CACTGCACTCTTAAGCTTC |
| 3197 | CCL5 | 3753863 | AATGGGTTCGGGAGTACATCAACTCTTTGGAGATGAGCTAG |
| 3198 | CCL5 | 3753867 | CTTTGCCTACATTGCCCGCCCACTGCCCCGTGCCCACATCAAGGAGTATTTCTACACCAGTGGC AAGTGCTCCAACCCAG |
| 3199 | CCL5 | 3753868 | ATGAAGGTCTCCGCGGCAGCCCTCGCTGTCATCCTCATTGCTACTGCCCTCTGCGCTCCTGCAT CTGCC |
| 3200 | CCL5 | 3753869 | ATCAAGACAGCACGTGGACCTCGCACAGCCTCTCCC |
| 3201 | KRT23 | 3756592 | GGAAAGTCCTTGCACAGACACCAGTGAGTGAGTTCTAAAAGATACCCTTGGAATTATCAGACT CAGAAACTTTTATTTTTTTTTCTGTAACAGTCTCACCAGACTTCTCATAATGCTCTTAATATATT GCACTTTTCTAATCAAAGTGCGAGTTTATGAGGGTAAAGCTCTACTTTCCTACTGC |
| 3202 | KRT23 | 3756593 | TGAATGAAATCCAAAAGCACGCATGA |

TABLE 13-continued

Subtyping Target Sequences

| SEQ ID NO. | Gene | Affy Probeset ID | Sequence |
|---|---|---|---|
| 3203 | KRT23 | 3756594 | CAGGAGACCATCAACGGAAGATTAGTTCTTTGT |
| 3204 | KRT23 | 3756596 | CACGGGAAGAATCAAAGTCGAGCATGAAAG |
| 3205 | KRT23 | 3756597 | AGTCTCGGTACTCCTGCAAGCTCCAGGACATGCAAGAGATCATCTCCCACTATGAGGAGGAACTGACGCAGCTACGCCATGAACTGGAGCGGCAGAACAATGAATACCAAGTGCTGCTGGGCATCAAAACCCACCTGGAGAAGGAAATCACCACGTACCGACGGCTC |
| 3206 | KRT23 | 3756602 | GGTGACATCCACGAACTGAAGCGCACATTCCAGGCCCTGGA |
| 3207 | KRT23 | 3756603 | CAATGTCAATGTGAAGGTGGATACAGGTCCCAGGGAAGATCTGATTAAGGTCCTGGAGGATATGAGACAAGAATATGAGCTTATAATAAAGAAGAAGCATCGAGACTTGGACACTTGGTATA |
| 3208 | KRT23 | 3756604 | CTTGGAAATTGAAGTCGAGGGCCTCCGAAGGACCTTAGACAACCTGACCATTGTCACAACAGACCTAGAACAGGAGGTGGAAGGAATGAGGAAAGAGCTCATTCTCATGAAGAAGCACCATGAGCA |
| 3209 | KRT23 | 3756605 | CCAGGATGGCAGTGGATGACTTCAACCTCA |
| 3210 | KRT23 | 3756609 | AGGGCTCCCACCGTCCATGGCGGTGCGGGGGAGCCCGCATCTCCCTGTCCTTCACCACGCGGAGCTGCCCACCCCTGGAGGGTCTTGGGGTTCTGGAAGAAGCAGCCCCTACTAGGCGGAAATGGGAAGGCCACCATGCAGAATCTCAACGACCGCCTGGCCTCCTACCTGGAGAAGGTTCGCGCCCTGGAGGAGGCCAACATGAAGCTGGAAAGCCGCATCCTGAAATGGCACCAGCAGAGAGATCCTGGCAGTAAGAAAGATTATTCCCAGTATGAGGAAAACATCACA |
| 3211 | KRT23 | 3756610 | AATACCCGCCTGATGTCGTGGGCCACACCTCCGGGTTACCAGGGGAAGGGAGGAAGCAAACTGTCATATTGATGTGGCTCTAAACAACAACAGTGTGCGAAGGCCCAGGGGCACTTTGGGATTGACCA |
| 3212 | KRT23 | 3756611 | TAAGAGCGAGTCCTTTGAAAGTACTTTCCTTCAAACAGTGACTGCCACAAAGGCATCAGATATTCACCACCTTCTCGGCTGCCTCAGCACAGCAAGCTTTATTCTGGGACCTGAGATCCTGTTC |
| 3213 | KRT23 | 3756612 | TCAACCACATTTGACAGCCCATGGCAGGTTTCCTGTTTTCCATCGTCCCTCTGCAGGTCACAGACACACAGAGCCCAGCCGTGGCAGGCTCAGCCGGGTCCGGGGCTGCTAACAACGGCTACATTCCTCCCCCAGGGCCAAGGGAAATCCTGAGCGCAGGCC |
| 3214 | KRT19 | 3757109 | TCTGCTGTCCTTTGGAGGGTGTCTTCTGGGTAGAGG |
| 3215 | KRT19 | 3757110 | ACAATTTGTCTGCCTCCAAGGTCCTC |
| 3216 | KRT19 | 3757111 | GCCCAGCTGGCGCATATCCAGGCGCTGATCAGCGGTATTGAAGCCCAGCTGGGCGATGTGCGAGCTGATAGTGAGCGGCAGAATCAGGAGTACCAGCGGCTCATGGACATCAAGT |
| 3217 | KRT19 | 3757112 | CCTTGGAAGACACACTGGCAGAAACGGAG |
| 3218 | KRT19 | 3757113 | CGCTTCCCTGTGCAATTCACACTTATACCCTTGCAGCCTAGGGCAGCCTGGCCGGTGGCTGTGCCCATGCCCTCTCCGGGAACCAGGCTCTG |
| 3219 | KRT19 | 3757114 | CAGATGAGCAGGTCCGAGGTTACTGACCTGCGGCGCA |
| 3220 | KRT19 | 3757115 | AGGTGGATTCCGCTCCGGGCACCGATCTCGCCAAGATCCTGAGTGACATGCGAAGCCAATATGAGGTCATGGCCGAGCAGAACCG |
| 3221 | KRT19 | 3757116 | CCTGGGTGTGGGATCATGGATCCCAGGGTTCCAAGAGGAATCAGTGATGACCCAGTCTGTCCCCCAGTGCTAGTTACTAGGCCTGCACCTGAAAACTAAG |
| 3222 | KRT19 | 3757118 | TTTGAGACGGAACAGGCTCTGCGCATGAGCGT |
| 3223 | KRT19 | 3757119 | CCCTCACCTAGCCTAGATGGCCTGAAGCTAACCCCCCTATGGACTCCTGAACTCTGGGGAG |
| 3224 | KRT19 | 3757120 | GAACTCCAGGATTGTCCTGCAGATCGACAAT |
| 3225 | KRT19 | 3757121 | GGAAGAAAGTGAGTGGGCAGTGCCTGTGTGTTGAACTGGTACCAACC |
| 3226 | KRT19 | 3757122 | GGGGCAAAATATGCTTCGCATAGTGGGGGGGCAGGTATAGACAAAATCTACCCCCCATCTGGTTTATAGACCCCCTTCAGGCCATTTAGAGTTTCATTGCACACAGGTCTCAGAGATTTCCTCCCCAGGCTTGCCTTCCTGCCCTCCCCCACCCAAGTCCCCCTGGCTCCAGTTTTCTTCCTGCCCCAGCTTCTGGGCATGGACTGTTTGCAAGGCCTCCCAGAGAGCGGGCCAATGGGC |

TABLE 13-continued

Subtyping Target Sequences

| SEQ ID NO. | Gene | Affy Probeset ID | Sequence |
|---|---|---|---|
| 3227 | KRT19 | 3757124 | TATCGCCAGTCGTCGGCCACGTCGTCCTTCGGAGGCCTGGGCGGCGGCTCCGTGCGTTTTGG<br>GCCGGGGGTCGCCTTTCGCGCGCCCAGCATTCACGGGGGCTCCGGCGGCCGCGGCGTATCCG<br>TGTCCTCCGCCCGCTTTGTGTCCTCGTCCTCCTCGGGGGCCTACGGCGGCGGCTACGGCGGCG<br>TCCTGACCGCGTCCGACGGGCTGCTGGCGGGCAACGAGAAGCTAACCATGCAGAACCTCAAC<br>GACCGCCTGGCCTCCTACCTGGACAAGGTGCGCGCCCTGGAGGCGGCCAACGGCGAGCTAG<br>AGGTGAAGAT |
| 3228 | COL1A1 | 3762199 | TCCGCAGTGGCCTCCTAATTTCCTTCTTTGGAGTTGGGGGAGGGGTAGACATGGGGAAGGGG<br>CTTTGGGGTGATGGGCTTGCCTTCCATTCCTGCCCTTTCCCTCCCCACTATTCTCTTCTAGATCC<br>CTCCATAACCCCACTCCCCTTTCTCTCACCCTTCTTATACCGCAAACCTTTCTACTTCCTCTTTCAT<br>TTTCTATTCTTGCAATTTCCTTGCACCTTTTCCAAATCCTCTTCTCCCCTGCAATACCATACAGGC<br>AATCCACGTGCACAACACACACACACACTCTTCACATCTGGGGTTGTCCAAACCTCATACCCAC<br>TCCCCTTCAAGCCCATCCACTCTCCACCCCCTGGATGCCCTGCACTTGGTGGCGGTGGGATGCT<br>CATGGATACTGGGAGGGTGAGGGGAGTGGAACCCGTGAGGAGGACCTGGGGGCCTCTCCTT<br>GAACTGACATGAAGGGTCATCTGGCCTCTGCTCCCTTCTCACCCACGCTGACCTCCTGCCGAA<br>GGAGCAACGCAACAGGAGAGGGGTCTGCTGAGCCTGGCGAGGGTCTGGGAGGGACCAGGA<br>GGAAGGCGTGCTCCCTGCTCGCGTGTCCTGGCCCTGGGGGAGTGAGGGAGACAGACACCTGG<br>GAGAGCTGTGGGGAAGGCACTCGCACCGTGCTCTTGGGAAGGA |
| 3229 | COL1A1 | 3762200 | ATTATTTTGATTGCTGGAATAAAGCATGTGG |
| 3230 | COL1A1 | 3762201 | TTCTAAAGGTGCTATTTAACATGGGAGGAGAGCGTGTGCGGCTCCAGCCCAGCCCGCTGCTC<br>ACTTTCCACCCTCTCTCCACCTGCCTCTGGCTTCTCAGGCCTCTGCTCTCCGACCTCTCTCCTCTG<br>AAACCCTCCTCCACAGCTGCAGCCCATCCTCCCGGCTCCCTCCTAGTCTGTCCTGCGTCCTCTGT |
| 3231 | COL1A1 | 3762202 | TCCACTTGCTTGAAGACCCATGCGGGGGTAAGTCCCTTTCTGCCCGTTGGGCTTATGAAACCC<br>CAATGCTGCCCTTTCTGCTCCTTTCTCCACACCCCCCTTGGGGCCTCCCCTCCACTCCTTCCCAA<br>ATCTGTCTCCCCAGAAGACACAGGAAACAATGTATTGTCTGCCCAGCAATCAAAGGCAATGCT<br>CAAACACCCAAGTGGCCCCCACCCTCAGCCCGCTCCTGCCCGCCCAGCACCCCCAGGCCCTGG<br>GGGACCTGGGGTTCTCAGACTGCCAAAGAAGCCTTGCCATCTGGCGCTCCCATGGCTCTTGCA<br>ACATCTCCCCTTCGTTTTTGAGGGGGTCATGCCGGGGGAGCCACCAGCCCCTCACTGGGTTCG<br>GAGGAGAGTCAGGAAGGGCCACGACAAAGCAGAAACATCGGATTTGGGGAACGCGTGTCA<br>ATCCCTTGTGCCGCAGGGCTGGGCGGGAGAGACTGTTCTGTTCCTTGTGTAACTGTGTTGCTG<br>AAAGACTACCTCGTTCTTGTCTTGATGTGTCACCGGGGCAAC |
| 3232 | COL1A1 | 3762203 | GACAATTTCACATGGACTTTGGAAAATATTTTTTTCCTTTGCATTCATCTCTCAAACTTAGTTTTT<br>ATCTTTGACCAACCGAACATGACCAAAAACCAAAAGTGCATTCAACCT |
| 3233 | COL1A1 | 3762206 | AGCTGACCTTCCTGCGCCTGATGTCCACCGAGGCCTCCCAGAACATCACCTACCACTGCAAGA<br>ACAGCGTGGCCTACATGGACCAGCAGACTGGCAACCTCAAGAAGGCCCTGCTCCTCCAGGGC<br>TCCAACGAGATCGAGATCCGCGCCGAGGGCAACAGCCGCTTCACCTACAGCGTCACTGTCGA |
| 3234 | COL1A1 | 3762207 | AGACTGGTGAGACCTGCGTGTACCCCACTCAGCCCAGTGTGGCCCAGAAGAACTGGTACATC<br>AGCAAGAACCCCAAGGACAAGAGGCATGTCTGGTTCGGCGAGAGCATGACCGATGGATTCCA |
| 3235 | COL1A1 | 3762208 | AGCGCTGGTTTCGACTTCAGCTTCCTGCCCCAGCCACCTCAAGAGAAGGCTCACGATGGTGGC<br>CGCTACTACCGGGCTGATGATGCCAATGTGGTTCGTGACCGTGACCTCGAGGTGGACACCAC<br>CCTCAAGAGCCTGAGCCAGCAGATCGAGAACATCCGGAGCCCA |
| 3236 | COL1A1 | 3762209 | CCAAAGCACTTGGATGCCGGTAATCCCCACTCTCTT |
| 3237 | COL1A1 | 3762210 | CCTGGCAAAGATGGACTCAACGGTCTCCCTGGCCCCATTGGGCCCCCTGGTCCTCGCGGTCGC<br>ACTGGTGATGCTG |
| 3238 | COL1A1 | 3762211 | TGGTGAACAAGGTCCCTCTGGAGCCTC |
| 3239 | COL1A1 | 3762212 | TGAGACAGGCGAACAGGGCGACAGAGGCATAAAGGGTCACCGTGGCTTCTCTGG |
| 3240 | COL1A1 | 3762213 | TGCTGGTCCCACCGGTCCTGTCGGCCCTGTTGGCGCCCGTGG |
| 3241 | COL1A1 | 3762214 | TGACCGTGGTGAGACCGGCCCCGCTGGACCCCCTGGTGCTCCTGGTGCTCCTGGTGCCCCTG<br>GCCCCGTTGGCCCTGCTGGCAAGAGTGGTGATCGTGGTGAGACT |
| 3242 | COL1A1 | 3762215 | GCTCCTGGTGCCGAAGGTTCCCCTGGACGAGACGGTTCTCCTGGCGCCAAG |
| 3243 | COL1A1 | 3762216 | GGCAAACAAGGTCCCTCTGGAGCAAGTGGTGAACGTGGTCCCCCTGGTCCCATGGGCCCCCC<br>TGGATTGGCTGGACCCCCTGGTGAATCTGGA |
| 3244 | COL1A1 | 3762217 | GTACTCCCGGGCCTCAAGGTATTGCTGGACAGCGTGGTGTGGTCGGCCTGCCTGGTCAGAGA |
| 3245 | COL1A1 | 3762218 | GCTGGCAAAGAAGGCGGCAAAGGTCCCCGTGGTGAGACTGGC |
| 3246 | COL1A1 | 3762220 | GTGCTACTGGTTTCCCTGGTGCTGCTGGCCGAGTCGGTCCTCCTGGCCCCTCT |

TABLE 13-continued

Subtyping Target Sequences

| SEQ ID NO. | Gene | Affy Probeset ID | Sequence |
|---|---|---|---|
| 3247 | COL1A1 | 3762221 | CTGGAGCCAAAGGTGCTCGCGGCAGCGCT |
| 3248 | COL1A1 | 3762222 | TGCTGACGGCCAACCTGGTGCTAAAGGCGAACCTGGTGATGCTGGTGCTAAAGGCGATGCTGGTCCCCCTGG |
| 3249 | COL1A1 | 3762223 | GAGACCGTGGTGAGCCTGGTCCCCCCGGCCCTGCTGGCTTTGCTGGCCCCCCT |
| 3250 | COL1A1 | 3762224 | GTAAGTACAGAAGACCTGTTAAGACCCCATACTTGGCCCTTCCCTCCCTTCACACAGCACCCCTGGCCCTGTCTGTGCCTTCACCCCTTGCCTCTCCCCTCACCGCATCCCCGCCTTCCCTCCTGTCAGCGCATCTCTCCAATCTGACTCCTTTTCT |
| 3251 | COL1A1 | 3762226 | TGCTGGTCCCAAAGGTGCTGATGGCTCTCCTGGCAAAGATGGCGTCCGTGGTCTGACTGGCCCCATT |
| 3252 | COL1A1 | 3762227 | AGCTCCCGGTAGCCAGGGCGCCCCTGGCCTTCAGGGAATGCCTGGTGAACGTGGTGCAGCTGGTCTTCCAGGGCCTAAGGGTGACAG |
| 3253 | COL1A1 | 3762228 | CGAGCGTGGTGTGCAAGGTCCCCCTGGTCCTGCTGGTCCCCGAGGGGCCAACGGTGCTCCCGGCAACGATGGTGCTAAG |
| 3254 | COL1A1 | 3762229 | GGTGTTCCTGGAGACCTTGGCGCCCCTGGCC |
| 3255 | COL1A1 | 3762230 | CTGCTGGAATATGCTGTGACTTTCCCTCAACCCTTCTATTGATAAATCTTGGTCCATAGTTTGGGGAGGGGGGAAGCCTTTGACACATCCCTAGGAGGAAGAGAGGGGCTGTTTGGGATAATCTCAATTCAGTGCTGAGAAGGGGTTCCTCTCTAATCACGGCCAGACCCCAGGAGGAAGGACCGTGCTTTCCAGCAGAGTGGCCCCAGGTGGGTTTTGCTCACTGTCT |
| 3256 | COL1A1 | 3762231 | GTGAAGCAGGCAAACCTGGTGAACAG |
| 3257 | COL1A1 | 3762236 | CTGGAGAGCGAGGTGTTCCCGGACCC |
| 3258 | COL1A1 | 3762237 | AGAGCCAGGGACAAACACACCTGAGACTTGAAGGAGTCCTGGGCTCTGGGCTCAGCTGTGCCGCTGACCTGCCGTGTG |
| 3259 | COL1A1 | 3762238 | TGGGATTCCCTGGACCTAAAGGTGCTGCT |
| 3260 | COL1A1 | 3762239 | TCAAGATGGTCGCCCCGGACCCCCA |
| 3261 | COL1A1 | 3762240 | GTCCTCACTGCTGCTTTCGTGCCTCCCAT |
| 3262 | COL1A1 | 3762241 | CTGGTCCTGATGGCAAAACTGGCCC |
| 3263 | COL1A1 | 3762242 | TGAAGCTGGTCGTCCCGGTGAAGCTGGTCTGCCTGGT |
| 3264 | COL1A1 | 3762243 | GTCCCGCTGGTGAACGTGGTTCTCCTGGCCCTG |
| 3265 | COL1A1 | 3762244 | GTTTCCCTGGCGCAGATGGTGTTGCT |
| 3266 | COL1A1 | 3762245 | GGAGCTCGAGGTGAACCCGGACCCACTGGCCTGCCCGGACCCCCTG |
| 3267 | COL1A1 | 3762246 | GGCAGCAAAGGAGACACTGGTGCTAAGGGAGAGCCT |
| 3268 | COL1A1 | 3762247 | TGCTCCTGGTATTGCTGGTGCTCCTGGCTTCCCTGGTGCCCGAGGCCCCTCTGGACCCCAG |
| 3269 | COL1A1 | 3762250 | GGCCCCGAGGCTCTGAAGGTCCCCAGGGTGTGCGTGGTGAGCCTGGCCC |
| 3270 | COL1A1 | 3762251 | CCCACCGGCCCCGCTGGTCCTCCTGGCTTCCCTGGTGCTGTTGGTGCTAAG |
| 3271 | COL1A1 | 3762252 | GTGCTCGTGGAAATGATGGTGCTACTGGTGCTGCCGGGCCCCCT |
| 3272 | COL1A1 | 3762253 | GGCCCCGTGGCCTGCCTGGTGAGAGAGGTCGCCCTGGAGCCC |
| 3273 | COL1A1 | 3762254 | GCAGCCCTGGTGAAAATGGAGCTCCTGGTCAGATG |
| 3274 | COL1A1 | 3762255 | TCACTCATTATTCTCTGATCTACAG |
| 3275 | COL1A1 | 3762256 | TGGTTTGGATGGTGCCAAGGGAGATGCTGGTCCT |
| 3276 | COL1A1 | 3762258 | AGCTGGAAAACCTGGTCGTCCTGGTGAGCGTGGGCCTCCT |
| 3277 | COL1A1 | 3762259 | CCAGGTCCCCCTGGAAAGAATGGAGATGAT |
| 3278 | COL1A1 | 3762260 | CAAGGCTTCCAAGGTCCCCCTGGTGAG |

TABLE 13-continued

Subtyping Target Sequences

| SEQ ID NO. | Gene | Affy Probeset ID | Sequence |
|---|---|---|---|
| 3279 | COL1A1 | 3762263 | CCCAGCTGTCTTATGGCTATGATGAGAAATCAACCGGAGGAATTTCCGTGCCTGG |
| 3280 | COL1A1 | 3762264 | TGGACAGCCTGGACTTCCCGGACCC |
| 3281 | COL1A1 | 3762265 | AGGCCCCCCTGGCCGAGATGGCATCCC |
| 3282 | COL1A1 | 3762266 | CCAAGGGAGACACTGGCCCCCGAGGCCCAAGG |
| 3283 | COL1A1 | 3762267 | CGACCAAGAAACCACCGGCGTCGAG |
| 3284 | COL1A1 | 3762268 | CCTGCGTACAGAACGGCCTCAGGTACCATGACCGAGACGTGTGGAAACCCGAGCCCTGCCGGATCTGCGTCTGCGACAACGGCAAGGTGTTGTGCGATGACGTGATCTGTGACGAGACC |
| 3285 | COL1A1 | 3762269 | TCAGCTTTGTGGACCTCCGGCTCCTGCTCCTCTTAGCGGCCACCGCCCTCCTGACGCACGGCCAAGAGGAAGGCCAAGTCGAGGGCCAAGACGAAGACA |
| 3286 | ACOX1 | 3771216 | TGGTCTGTAACACCTGCACATCTTTTTATACGTGTAGAGGGTATGCCTGGGATATATAGGTTGTCTTCAAGCAGTAGCTGCTACTACAGCTAGAGAGAGGAGGAGTGCCAGGAAACTGATGACCTGAGACCAAGAGTCTTGTTGATGTTCTGACTTAGATAAAGGTTTTGATCATTTTCATGAAATAATGCAGGGAAGTCATTTCTGCTGTTTCTTTACTACTCCATTCTTGGAGGATTAGAACAAGTCACACTGTAATTGACTAAAACGACTTTTTATTTTAAAATATTGATGGTGGGGTTTTGCTTTTTTTTTTTTTTTTTTTGAGACGTTGTCTTGCTCTTTCACCCAGGGTAGAGTGCAGTGGCGAAATCTTGGCTCACTGCAACCTCTGCCTCCCGGGTTCAAGCAATTCTCTGCCTCAGCCTCCTGAGAAGCTGGGATTACAGCGCCTGCCACCATGCCTGTCTAGTTTTTTTGTATTTTTAGTAGAGACAGGGGTTTCACCAAGTTGGCCAGGCTGGTCTTGAACTCCTGACCTCGTGATCCACCCACCTCGGCCTCCCAAAGTGCTGGGATTACAGGCGTGAGCCACCGTGCCGGGCCAGTGTTTTTAACTGTCCACACTTACTAAATTTTCCAGTACTTCTTCCTATGGTTCATGATAGTAAACACAGAAACATATAAGGAACATTATTAGAGTTACCAGATGTTAGCTGTTGCATATGTGCACATTCCTAGATTCAAGGGTGTTTTTGCCTTAAATTTAAGTGGGTCATTGGTTGTCTTGGGAAGATCATGGAAAATTCGGGATTTTTTAGAATTCTGAACCAAAATATGTTTTGAGTGTTTCTTAGTAAATGTGTGATCTTCCACCTTCCACATTCAGACTGCGGACTACACTTCATAAATGCCTTTTATTTCCAGTTATGGATTCAACTAAATGACTGCCTTGGGAGCACATAATTACTTTGCTACCTTTTTCCCCCTTTGCTGTTGTGGCTCGAGTTTGGTTCTCACCTGAGAAGATGCATTGAGCATATGTTGTTACCCAGCCCTG |
| 3287 | ACOX1 | 3771217 | GCTCCAGTCACTTTAGGAGTCCTTGGAAGTACTTGGTACACATTGTTGGCTGTACCTTAAAGGAAGTGGCAAGTCCAGTTTGTTCTCTCTACCACACTAGACTGCCACTGACAAGTTTGGGTCTGTTGGATTCAAAATTTTGTAAGCCATTTTCACAAGTACAAAGATACATTTTAACCTTGTCTTCTCCAAAATTACTGAGTAGGAATTTTATTTTTATCTTTTTGAGACAGGGTATCACTGTCACCCAGACTGGAGTGCAGTGGTGGGATCTTGGCTTACTGTGACCTCTGCCTCCCGGGTTCAAATGGTCCTCCCTCCTCAGTCTCCTGAGTAGCTGGGACGACAGGCACGTGCCACCATGCCCAGCTAATTTGTTCTATTTTTTCTGTAGAGACGGGGTTTTGCCATGTTGCCCAGGCTGGTCTCAGACTCCTGGGCTCAAGCGATCATTTCGCCTCAGCCTCCCAAAGTGCTGAGATTATAGGTGTGAGCCACAGCATCTGGCCCAGAGTGAGGAGAATTAATGAGATTTTTGTGTGTGTTAGATAATATTGATTTAAGCCTTTTTTAAAAAGTACTCTCAACCAAATACAAAATTGAAAATGTGAGGTTTAATAGAAATGTGTTGGCTATTTGCAATGGATTTTCTTCTTGCCCAAGTGTTTGGAGTTCTACTTTATGCTCTGTATTTAAAAATTAGTGACCTCAAAGCAGAGTTGATGACACAGGCTTTGGGGCCCTCATGTTCTTGTCTTTAGAACATATCACTACTAAGTATCAGCTTATCTTCAGAACATTACAACATTCACCGTGTTCATATGCTTTCTGAGAAGTCACCACTTGTAATTTCAGATCACATACACCTGAAGGCATTTTATAGTTCCTAAAGTTAACATGTTAGATCTTTTTTTTCCACCCCATGAGGGTCTCACTCTCACCCAGGCTGGAATGCAGTGGTGTGATTGTAGCACACTTTGGCCACCAACTCCTGGGCTCAAGTGATCCTCCTGCTTTGGCCTCCTCTGAGAAGCTGGGATTACTGGTGCACACCACCACACCTGGCTAATTTTTATTCTTTTTATTTTTGGAAATAGGGTATGGCTATGTTGCCTTGGGCCCGTCATGAACTCCTAGCCTCAGGTGACCCTCCCACCTCAGGCCTCCCAAAGGGTTGGGATTACAGGAGTGAGCTACTGCACTGGGCCAACATG |
| 3288 | ACOX1 | 3771218 | AACTCCTATCTTGGGACCTGACATAATATCTATCTATCCTGGGGAACTGGTAATATGAGACTTATAGGTTACAGCAGAAATGCTACATGTTGACAAAAGCCTTAATCGTTCCACTGGGAGAACTAATTGATAATTGTGTTAAGATTGAAGATTAACCCTGTGTTAATCTCACTTGAGTCTATCCTGACAGTAGTTCAGATTCTGGAAAATGATAAACTGACCTGCTAGATGTAGAATTGTTTCAAAATTAGTGTTGAAATACCTTGTTCACAGATGAATATCTGGGCAGGATCTGAGGGTGTTTGGAATGACACCCCCCAATCCAGTTGCATAGATGGGATGTCTTTGCAGGTTTGAGGAGATCATCGACC |
| 3289 | ACOX1 | 3771219 | TGTCACTTAGGTCAGCACTCCCAGACGTAGCACAGAAAAACCCTTTGACACAAACCATGTGTTCTGATTTTTGGTTCAGAAAATATTGAAACTGTGAGTTGTTTTTTTTTTAACAACTGGGAAAAAACAAAAACAAAAACTATAGTTAGAAAATGGAAGTTCCATAGGTTCTATTTCTTACTCTATGTATGGCTTTGTTTTCAGTCTATTTCTAGGAGCTTTCTCTGAATCGCTAATTGTCC |
| 3290 | ACOX1 | 3771220 | GCTAGCATTTTTCCAACGAGGGAACTTATTCCGCACGGGCCTACTGTAGGACCATTGTCTCGTGTAATTAGGAATTTTCCATTTGAAGGATTGCTAAATTGTCACAGTAGTAGGAAGTATAGGGAAACCTCTCAGCTGTGGCACTG |
| 3291 | ACOX1 | 3771221 | TGGGGCCTGGCTTAAAAGCAGGATTG |

TABLE 13-continued

Subtyping Target Sequences

| SEQ ID NO. | Gene | Affy Probeset ID | Sequence |
|---|---|---|---|
| 3292 | ACOX1 | 3771222 | GCGCCTGTGTGCAACTCAAATTTTGTGGAATCTTTTTCGAATTCAAATAGCTATAGAGCAAAT GATAAATTGACCCCTTTTTATAAATGGAGGGAAAAAATGAACAGATTTCAGAGATTAAATGAA AAAAAGCAGATGTTTTAAGTGCAATTAACACTGAAAGAGACCTGTTAAACCATTCAGAAAAA GCTTAAGAAATGCGATATGACTTCCTTTTGTAATGCTGCTGATCCCAGTAGACTATGACTTTTG ATAATTAGCAGAATTTAACTACTGAGTAGTTGATTATTTTCACATTTTAATTGCTAATCACTGG CTATATAAGTGTTTTTAAGCAAAGGTATTTTTGAAGTGGTGTAGAACCCTTCCA |
| 3293 | ACOX1 | 3771224 | CAGCGTGTAAAGGAGTTACTCACTCTGATTCGCTCAGATGCTGTTGCTTTGGTTGATGCATTT GATTTTCAGGATGTGACACTTGGCTCTGTGCTTGGCCGCTATGATGGGAATGTGTAT |
| 3294 | ACOX1 | 3771226 | AAAGCAAGGAGGTAGCTTGGAACCTAACT |
| 3295 | ACOX1 | 3771227 | TTAGTAGAAATTGCTGCAAAAAACCTTCAAAAAGAAGTGATTCACAG |
| 3296 | ACOX1 | 3771228 | ATTTGAACGACCTGCCCAGTCAGCGCATCCAGCCACAGCAGGTAGCAGTCTGGCCAACCATG GTGGATATCAACAGCCCCGAAAGCCTAACCGAAGCATATA |
| 3297 | ACOX1 | 3771230 | GCCCTCACCGCTGGACTGAAGGCTTTCACCTCCTGGACTGCAAACACTGGCATTGAAGCATGT CGGATGGCTTGTGGTGGGCATGGCTATTCTCATTGCAGTGGTCTTCCAAATATTTATGTCAATT TCACCCCAAGCTGTACCTTTGAGGGAGAAAACACTGTCATGATGCTCCAGACGGCTA |
| 3298 | ACOX1 | 3771232 | GCAGTATAAACTCTTTCCACTCCTGGCCACTGCCTATGCCTTCCAGTTTGTGGGCGCATACATG AAGGAGACCTATCACCGGATTAACGA |
| 3299 | ACOX1 | 3771234 | TTCAGATCCCAGAATTCCCAAATGTCAATACAGAAGATGCATTAGCACTGCAAAATTGGCTAG GGTGATAACTGGGCCTGTAATTTCATATCTAGGCTTCCTTTTCTTAAGAGGAAAGACAGAAAT AACCACCCTTGCTATA |
| 3300 | ACOX1 | 3771235 | TGATGGCACATACGTGAAACCGCTGAGTAACAAGCTGACTTACGGGACCATGGTGTTTGTCA GGTCCTTCCTTGTGGGAGAAGCTGCTCGGGCTCTGTCTAAGGCGTGCACCATTGCCATCCGAT ACAGCGCTGTGAGGCACCAGTCTGAAATCAAGC |
| 3301 | ACOX1 | 3771238 | CATGCAATAGTTCTTGCCCAGCTCATCACTAAGGGGAAATGCTATGGATTACATGCCTTTATC GTACCTATTCGTGAAATCGGGACCCATA |
| 3302 | ACOX1 | 3771239 | GTAAGTGAATTTTTCAGCATTTATTGGATGTTTTGAAG |
| 3303 | ACOX1 | 3771241 | CCTCTGGATCTTCACTTGGGCATGTTCCTGCCCACCTTGCTTCACCAGGCAACTGCGGAGCAG CAGGAGCGCTTCTTCATGCCCGCCTGGAACTTGGAGATCATTGGCACTTATGCCCAGACAGAG ATGG |
| 3304 | ACOX1 | 3771244 | CCACCTCAGGACATCAGTTAACAGTGATTGCTGGCATTTGACTTTTTTCTGCTGCTACCTGTTT GGGATTCTATTTTTAAGTTGTTAAGTCAAAATTCAACTTCTTGTTTTCTCCTAGACATTTTCCCT GGAAACTGGTCCAGGGCTCTGGCCTATAAACGTCATTCACTG |
| 3305 | ACOX1 | 3771245 | ACCTGTGGGCCTCAATTACTCCATGTTATTCCTACCTTGCTGAATCAGGGCACCACTGCTCAG AAAGAGAAATGGCTGCTTTCATCCAAAGGACTCCAGATAATTGGCACCTACGCCCAGACGGA AATGGGCCACG |
| 3306 | ACOX1 | 3771252 | AGAGCAAGTGTTGTTAAGCCTAAACT |
| 3307 | ACOX1 | 3771253 | ATGAGGGAGTTTGGCATCGCTGACCCTG |
| 3308 | ACOX1 | 3771254 | GAACATGATCCTGAACGACCCAGACTTCCAGCATGAGGACTTGAACTTCCTCACTCGCAGCCA GCGTTATGAGGTGGC |
| 3309 | ACOX1 | 3771255 | ATGAACCCGGACCTGCGCAGGGAGCGGGATTCCGCCAGCTTCAACCCGGAGCTGCTTACACA CATCCTGGACGGCAG |
| 3310 | ACOX1 | 3771256 | GCCGCTGTCACTCACGCGCCAAAGGGCCACGGAGAAAGAAGGGGCGGGCCGGGGCGGGCC GGGCGAGCGGAGGCGGGACTTGCGCCGTCCTGAGGCTGCCTCCTAGGGTCCGGCCGGCGC TGGAGCTGCGGATTTAGATTGTCACTGCCACCTCGGTCGGTGCTTACTTCGCTGCCAGCTGGT CGTCG |
| 3311 | TIMP2 | 3772662 | TCGGTCCGTGGACAATAAACAGTATT |
| 3312 | TIMP2 | 3772663 | CTTGCTGCCGTAATTTAAAGCTCTGTTGATTTTGTTTCCGTTTGGATTTTTGGGGGAGGGGAG CACTGTGTTTATGCTGGAATATGAAGTCTGAGACCTTCCGGTGCTGGGAACACACAAGAGTT GTTGAAAGTTGACAAGCAGACTGCGCATGTCTCTGATGC |
| 3313 | TIMP2 | 3772664 | ACGGGGCTTTCTGCATGTGACGCCAGCTAAGCATAGTAAGAAGTCCAGCCTAGGAAGGGAA GGATTTTGGAGGTAGGTGGCTTTGGTGACACACTCACTTCTTTCTCAGCCTCCAGGACACTAT GGCCTGTTTTAAGAGACATCTTATTTTTCTAAAGGTGAATTCTCAGATGATAGGTGAACCTGA GTTGCAGATATACCAACTTCTGCTTGTATTTCTTAAATGACAAAGATTACCTAGCTAAGAAACT |

TABLE 13-continued

Subtyping Target Sequences

| SEQ ID NO. | Gene | Affy Probeset ID | Sequence |
|---|---|---|---|
| | | | TCCTAGGGAACTAGGGAACCTATGTGTTCCCTCAGTGTGGTTTCCTGAAGCCAGTGATATGGG GGTTAGGATAGGAAGAACTTTCTCGGTAATGATAAGGAGAATCTCTTGTTTCCTCACCTGT GTTGTAAAGATAAACTGACGATATACAGGCACATTATGTAAACATACACACGCAATGAAACC GAAGCTTGGCGGCCTGGGCGTGGTCTTGCAAAATGCTTCCAAAGCCACCTTAGCCTGTTCTAT TCAGCGGCAACCCCAAAGCACCTGTTAAGACTCCTGACCCCCAAGTGGCATGCAGCCCCCATG CCCACCGGGACCTGGTCAGCACAGATCTTGATGACTTCCCTTTCTAGGGCAGACTGGGAGGG TATCCAGGAATCGGCCCCTGCCCCACGGGCGTTTTCATGCTGTACAGTGACCTAAAGTTGGTA AGATGTCATAATGGACCAGTCCATGTGATTTCAGTATATACAACTCCACCAGACCCCTCCAACC CATATAACACCCCACCCCTGTTCGCTTCCTGTATGGTGATA |
| 3314 | TIMP2 | 3772665 | GCCTCCAAGGGTTTCGACTGGTCCAGCTCTGACATCCCTTCCTGGAAACAGC |
| 3315 | TIMP2 | 3772666 | TGCCTCTGGATGGACTGGGTCACAGAGAAGAACATCAACGGGCACCAGGCCAAGTTCTTCGC CTGCATCAAGAGAAGTGACGGCTCCTGTGCGTGGTACCGCGGCGCGGCGCCCCCCAAGCAG GAGTTTCTCGACATCG |
| 3316 | TIMP2 | 3772667 | GGCACTGCAGGCCTTACGCTGTTTCCAACATTCCCGACATTTTCACACCTGGGTTGGTGTCTAT GTGGGGTCTGTGTGTTGAGAATACCTGAACACCTGCTCCTCTTAAAATGAGCCCGGAGGTTGT GCCAGGCACAGCTGGAGCAGTGCAGCGCCTAGATGTGGCTGTGGAAGGTGAGATTACCGCC TCCAGGGCTCCCAGGCTGGCTCCTACCCTGTGGGCTCCTAGCACCCTATCCCCACCCTCCCTGC AGGAAGCATGGCTGAGTGCTGGGCACCTCCCACCCTGGGTCACTCCCAGTGAGTCTGGGACC AGGAGACTCTGGTGAGGCTGTGGGGATTGGCCTTCCCTGGGGAGCTGCCTGGGGCTGCCCTC CCTCCTGACGGCCCCCAGCCCCTTCTCCGCATGTTCAAAACAGGAATTCTGAACTCATAGTCTC CAGCCACACGTATGTTAAGCGAAACTCCTCTGTGCCCAGCATGAAATCAAAAGCAAGTTTTTC CTTTTTCTTTCCACGGTGGTGAAGGCGGTCATCCTCTTGTAGCCTAGGGTTCCTTGGCCAAATT GCTAGTTGCCGATGACCTCG |
| 3317 | TIMP2 | 3772668 | GTACCAGATGGGCTGCGAGTGCAAG |
| 3318 | TIMP2 | 3772669 | GCAAGATGCACATCACCCTCTGTGACTTCATCGTGCCCTGGGACAC |
| 3319 | TIMP2 | 3772672 | GGATATAGAGTTTATCTACACGGCCCCCTCCTCGGCAGTGTGTGGGGTCTCGCTGGACGTTGG AGGA |
| 3320 | TIMP2 | 3772675 | TGATCAGGGCCAAAGCGGTCAGTGAGAAGGAAGTGGACTCTGGAAACGACATTTATGGCAA CCCTATCAAGAGGATCCAGTATGAGATCAAGCAGATA |
| 3321 | TIMP2 | 3772676 | GCAGGCCTGGACGTCTTATCCCTCTCCTTAGCCCCAGGAGCGTGTTTCAGGAACTCTCCTCACC TCTGT |
| 3322 | TIMP2 | 3772677 | GAGGAGACGCCATGCCGGGGGCTGGGATCACCATGCCCCTTGCCCGTCTCGCACCTTGCTGCT |
| 3323 | TIMP2 | 3772695 | CCCACCCGGGGTAAATACATCACTGAT |
| 3324 | TIMP2 | 3772696 | GTTTCTTGAAGAAGCCCGGAAATGCTTGCGGGAGTTTCAGAACATATGCTAA |
| 3325 | TIMP2 | 3772697 | GGCTGAGCCTCTGTCCTGATAACGAAGACCTGCTTTGGAGGAAAAAGCACAAATTGCTACAA GCCCGGGGCAAAGGCGATCTCGCTCTGCAGAGAAGAGCGGATGCCAAGCTGTGGAAAAACT ACCAGCTCCAGCGCTTGGCTGAGGAGTTGAGGAGAGGGTATCAGGAGGCACAGCACCTGCA CGTCGGTGGCCTGGACAGGCTGCAGTCAGCACGTCGTTGGGCTGGGGAGGAGGACGGGCC AGGGAAAATGAGCCTGACTCGCAGGGGCCCATCCAGCGAAGATCAGCCAGGCCCCCGAGGG CCAAGGAGAAGCATAGAGCAGCCCTTAGTGAAGAGAGGAGTTGCAGGGAAGAGTTGGAGCC AGCAACACCCCAGGCACTCCAGGCCCCGGAAGACAGCAGCGAGTCCAGAGAAACCACAGAC TACAAAAGCCACGGGTCGGATGAATTCTCACCTGGCCCCGCCTGAGAAGAGAAAGGGAAGG CCAGAACCTTCGACCAAGTCTGGGGGTGGCCGCTGTGCCATCCATCCTCGGAGGAGCAAAGG GGCGGACCTAGAAAGGTCAAACCCACTCGTGGCTGCTGTGGGAGAAATCGGGCTTGTGGAG GAAAAAGAGAAAGGAACAGCTCGGGCGGGGAGGAGGCAACTGGGAAAGGGGGCAGTTTG CTTTGTTCCAGCCCTGACCAGTCGCTCTCAGGGACAGAGTCTGGAGGGGAAGCTGAGAGACC TCGGGCAGCTGTGGCCAGCTGATTCCAGCTGCAGAAGGGAAGCCGTGTCCCAGCATCTCAG TGCACGCTCCGGAGAAGAACAAGTGGCAGAAAGAGCTGGAGTTGGCCTTTGAAGAGTTGT TTAATATAAACAGAAAGCTGAAAAAACACCTGCTTGTACCTGGCACTGAAGCCCAGGATG GACCAGAGACCTGGGGAAGGGCATGCCTTCTCAGAGATGCAAGAGTGTGGCGCTGGGACCC CAAGAGGGAAGAAAATGGCAGACCCAGAGATGCTGCCTGCCGGGGAACCCAGGAGCCCAGC AGAGGAGGAGGCGCAGCAGGCAGCGTCCAAGACCGACTTGAAAACGTTCATGGGCAAGGCC CAGAACCAAAAATATCAGGGCACGGTCAAGCCCACGTTTAGAAATGGAAGTCAAACATTGTC TCCCGAGGCAGGTATATTTATCA |
| 3326 | TIMP2 | 3772698 | TTTGCTGTGGAACGTTGTGGCTTCGTGTGGCTCCTCAGGCCCGGGGCGCCCCTTGAACCCTCC ACTCTTGGCTCCAAGCACCTTCCCTGGGAAGCTGTATCTGCTGGGTTCGCAGACAGGAACAGA |
| 3327 | TIMP2 | 3772702 | AGGCACTTCGTAGCTGTTGACCATCATTTAGCTCCACGTCTGCCCGTCGGTTCCTCGTGCGTG GAATCCAGCACCACGTGGGTGTCTCTGCCGAGCTCTCGGCATTTCCTGAGCCCTCCCGGAAGC CAGACTCTGTTCTCGGCGCTTCACACGGGCCGTCTCGTCTGATG |

TABLE 13-continued

Subtyping Target Sequences

| SEQ ID NO. | Gene | Affy Probeset ID | Sequence |
|---|---|---|---|
| 3328 | TIMP2 | 3772703 | CCAGTGATTTCAAGACAGCCCTGGAGACAGTGCTTCCTGCCCTCCTGTCAGCTTCTGCCTCCCT<br>GTAATGTGTTCTGGGTGGTCTAGCTCAGTCATCTGG |
| 3329 | TIMP2 | 3772706 | CAGGTGGAGGCGGGGAAGCGATTCCGGCCA |
| 3330 | PTPRM | 3777471 | CGGCGAGCTCAGCAACCGGAACCGAGGGAAGATTTTGGCTCCGCGGGCTCGCCCTCCGCTCC<br>CTCTGCCAGCGGCGCCCAGACGCCGAGTGGGGCCAGGGACAGGGGAGGAGGACCCAGGACC<br>CTGTGCCCGCGCCCCTGGAGCCGCTGGAGTTCGGACTTCTGCAACTGTTGGCACTTTGGGGG<br>CTTGGCTTAGCGCTCTGCTGTTTAC |
| 3331 | PTPRM | 3777472 | GACTTGGGACTTGCCTGGCGACTTTGGCCGGACTTTTGCTAACTGCGGCGGGCGAG |
| 3332 | PTPRM | 3777522 | GCCGGAGCATGCTTCTCTAATCTTACCATTTATCACTGACCCTTCGGTGAAACTCTCTTCTGTTT<br>AAATTTACCAGGGTACACTTTGTAATACTTGGGACCAAGAATTTGAAGATAGTAATCAGACAA<br>ATCAAACAACTAGTAGTAGTGGAGAGACACGTAGCCCTACA |
| 3333 | PTPRM | 3777525 | GGCTGCCTCTTTGATGAGCCGTATAGCACATGTGGATATAGTCAATCTGAAGGTGATGACTTC<br>AATTGGGAGCAAGTGAACACCTTGACTAAACCGACTTCTGA |
| 3334 | PTPRM | 3777535 | CCTGCAACAAACTTGCTGGGGCCTGCTGTGTGTACACACTGTATCAGGCTGGGTGTACCTCGT<br>TAAGCACATAGGTGGTAAAATAAGTACCACGGTAAAATTATGGCTTAGGGCTCAGGGTAAAA<br>TTATAAAAAAGGAACAGATTACATCCCACTGTGGGCAATAAGAAACACTTTCTGCAGGATTCT<br>GAGATGGGCCTGGAAGAATGGATGATATTTCAACAGGGGGTAATGAGGAAATGCAGTTTCG<br>GTGTGGGCACCTGAACGGACAAAAGG |
| 3335 | PTPRM | 3777536 | CTGGGAAACCTGCATCACCTAATTCACTGGAGAGGGATAATAGTGATGCTATAAATAGCAAA<br>TGAAGTCAGTTGGGCTCTTATATGTGTTGAGCACCACCATCCATCTGAATAGTTGCTTAAGCC<br>AGAAACTGGGGAGTGGCCCCAGCTGCTTCTTCCTTCCCTTCATCCAGAAAGTTAGCAGTTCCT<br>GGATTTTCCTCCTCTAGAATGTCCCTCAAACCTGTCCTCTTTTGTCTTTTCTCATGTCTGCCACAC<br>TTGTCTTAGTCATTAGCGAAATATCCACATTTTATACTTCTGTTTTGAAACTGACGGAATTGTCC<br>CAGAAAACTGATGTTTATGGTTTCTTTTAAATAAGTACAGAAATTTACCCTCCCAGTCTTAAAT<br>CTTGAGAAAGTTACATTTATCTTATCTGAGTTCCTTTTTCAGGAAACCAATCATCAGTCCTCCCA<br>GTCTTAAATCTTGAGAAAGTTACATTTATCTTATCTGAGTTCCTTTTTCAGGAAACCAACCATCA<br>GTCCTCCCAGATAGTATCAAGGAACTGAAACTTTCCAGATCACAGCATCAGGACAGTGAGAC<br>ACCACACCCCTCACCCAACATGATTGCCTAGCCCACCACCTACTGCCTGTTGGCTAACTCCTCT<br>TCCTTACCCTTTCCTGGTCTTGTTTTCCCACATGTCATTACGTTTCTTTCCTGCTGTGTAAATCCT<br>TAATTTTAGTTGGCTTAGGAGATGGATTTGAGACTGATCTCCCATTCTCCTCTGCCGCAGTACC<br>CGAATAAAGCCTGGCAATACTCTTTGTCCTAGTAATTGGCCTCCTGTGCGGCAGCAGTGACAC<br>CTATCTGTACCATACCTTTGACGCTTTGGGGGCAGTTCTGTGAAGGTGGGAAAATTGATTGTG<br>GAATAAAGTGATACATTTGGTTTGGGGCATGTTTCTATCTTATTAATAGTATATTTTTCCTCATA<br>GAGATGTCTACTACACAGTTAGAAATAAAGGCCTAAGCTGGGCATCATTGCCCTTGCCTGCAA<br>TCCCAGCTACTAGGTAGGTTGAGGTGGAAAGATCGCTCGAGGCCAGGATTTTGAGACTGTAG<br>TGTGCAATGAGCATGCCTGTGAATAGCCACTGCGCTCTAGCCGGGCAATAATAATATTA |
| 3336 | PTPRM | 3777558 | ATGCTGGTGAATGCCTCTGGGAGACCTGAGGGGC |
| 3337 | PTPRM | 3777559 | CCTCCGGGGTTACTCAATGTCTACGTGAAGGTCAATAACGGGCCACTGGGGAATCCTATCTG<br>GAATATATCTGGAGACCCAACACGTACATGGA |
| 3338 | PTPRM | 3777565 | AGTGATAACTTCTGGACATCAAGGCTATCTCGCTATCGATGAGGTGAAGGTGTTA |
| 3339 | PTPRM | 3777567 | CACTTCCTGCGGATTCAGAATGTGGAAGTTAATGCTGGCCAGTTTGCTACCTTCCAGTGCAGT<br>GCCAT |
| 3340 | PTPRM | 3777570 | AGGAAGGGCTGAGCATGCCTAGCCCAGCCCCTTCTTTGGGGAGCTGACTGCCT |
| 3341 | PTPRM | 3777573 | TGTGCGAGATGCTCCTCTGAAGGAAATCAAGGTGACCAGCTCCCGACGCTTCATTGCTTCATT<br>TAATGTTGTGAATACCACCAAACGAGATGCTGGAAAGTACCGCTGCATGATTCGCACTGAAG<br>GA |
| 3342 | PTPRM | 3777575 | AGCTCGCCTCTGTAGGAGCCACCTACCTGTGGATACAGCTCAACGCCAACTCCATCAATGGGG<br>ATGGGCCCATTGTGGCCCGAGAGGTGGAGTACTGCACGGCCAGTGGGAGCTGGAATGACCG<br>GCAGCCAGTCGATTCCACGAGCTATAAAATTGGACACCTTG |
| 3343 | PTPRM | 3777592 | TAAGACGGAGAGCATGCAGTCTGAGT |
| 3344 | PTPRM | 3777611 | AAGCACAACAGAGATGTGAGTCACAACACAGAAACTTGGAAAGGCTTTTCACAGA |
| 3345 | PTPRM | 3777616 | TGCGAGGCCCAAGAAAACTAGAAGTAGTGGAGGTCAAATCTCGGCAAATCACTATCCGCTGG<br>GAGCCATTTGGATATAATGTAACTCGTTGCCACAGTTATAATCTCACTGTCCACTACTGTTACC<br>AAGTTGGAGGACAAGAACAAGTGCGAGAAGAAGTAAGCTGGGATACAGAAAACTCACACCC<br>TCAACACACGATCACTAACCTGTCACCATACACCAATGTCAGTGTGAAACTGATCCTCATGAAC<br>CC |

TABLE 13-continued

Subtyping Target Sequences

| SEQ ID NO. | Gene | Affy Probeset ID | Sequence |
|---|---|---|---|
| 3346 | PTPRM | 3777617 | GTGGAGAGAACCAACTCAAACATATGGTGTAATCACTTTA |
| 3347 | PTPRM | 3777620 | AAGCAGTCAGTTCCTTTGACCCAGAAATAGATTTATCCAATCAGAGTGGAAGAGTTTCAAAGC TGGGAAATGAAACCCATTTTCTGTTTTTTGGACTGTATCCGGGGACCACATACTCCTTTACCAT CCGAGCTAGCACAGCTA |
| 3348 | PTPRM | 3777621 | CCCTCTATGCCAGCTTATGAACTTGAGACACCTTTGAATCAAACTGACAATACCGTGACAGTC ATGCTGAAACCTGCCCA |
| 3349 | PTPRM | 3777626 | CGACAGAAATCTTAAAGTGCTACCCAGTGCCAATTCACTTCCAGAATGCTTCTCTGCTGAACTC ACAGTACTACTTTGCTGCAGAATTTCCTGCAGACAGCCTCCAAGCTGCGCAGCCTTTTACAATT GGTGATAATAAGACATATAATGGATACTGGAACACTCCCCTTCTCCCCTATAAAAGCTACAGA ATTTATTTCCAAGCTGCTAGTAGAGCCAATG |
| 3350 | PTPRM | 3777629 | GAAACCAAAATAGACTGTGTCCAAGTGGC |
| 3351 | PTPRM | 3777631 | TTTCAATTGGAAACACTGCTCAGTCTTCACCTTTATTTAGGATGAATGTTTTGGTTTTGTTTTC CTTTTTTCTTCTTCAGTTGATCTATCCAAGATCTCAGCCAAACCTTGCAACTGTGTCATAGTTA GAAATCCAACTGCCTGACTAGAGCTTGTTTAAGGGAAAAGAATTCAGAATATTCAGCACCTTG CTATGTTTTTTTTTCTTTTTTTCCTTTTCTTTTTGTTGTTGTTAGAACAAAGTTGAGACAATTTG ATATACTGATGGGGATTCTTCTTGCTAGCCTAGCTTCAGTCTGGCTTTTTTTTCCCTCATGCATG CTGACCTGGAAATCCTC |
| 3352 | PTPRM | 3777632 | CTGCGATAATCGTGACTCAGCTTACAACACCTTACATTCGCATCGCCCCCGCTGCAGGCGACG GCCAACTAACA |
| 3353 | PTPRM | 3777634 | CCAGAACCCGAGAAACAGACAGACCATACAGTTAAAATTGCTGGAGTCATCGCGGGCATCTT GCTGTTCGTGATTATATTTCTTGGAGTTGTGTTGGTAATGA |
| 3354 | PTPRM | 3777637 | GGGAGGCATTGTCAATTATTAGCTAAGATTGTTTTGTCTTCTGAAGAATTGGCCCTCTATAAAA AAATAGTTGTGGAAGGTGGGCTTTTAACAGAAAATGTAAAGTCTGTTCAGTTCATACTAATTA GTACATGGAATTATTTAACATATAGGCAATAATGGCTAAAAACTGACATGACCATCAGCTTTA TTTTAGGATGTTTTACAAACCTATCACAAAGCAACAACTAATTTTTTGTTCATGTATATTAATTC ATTTGGCCTTTACCTGGACTAATATCATCTGAAACCTTCTTTTCTTTGAAACATTTTATGAAATG TATACACTTATTTTTACTTTATTATGTAAGCAAAGCAATTTTTATTTTCCGTCCCACAAATTATG TGTTCC |
| 3355 | PTPRM | 3777664 | GAAACTGGCCAAGAAGCGGAAAGAGACC |
| 3356 | PTPRM | 3777665 | TGAGCAGCACCCGACAGGAGATGACTGTGATGGTGAACTCAATGGACAAGAGCTATGCTGA GCAGGGCACAAACTGCGACGAGGCTTTCTCATTCATGGACACGCACAATCTGAATGG |
| 3357 | PTPRM | 3777672 | CCACGTTGTAGTGATCCAGGTGCCATTTCAGCAACAGCAACATAGCTACACACTTGTGTACCA CCTTTCATACCATGCATCCCCAGGTGCTTTGCGATGCAGATAGAAGTGAGGTTCCCAAACCAG GCCCTGCTCATCAAGCACCCTTGGACTAAATTTTCTTCA |
| 3358 | PTPRM | 3777673 | GAAACCCACACAATGGCCAGCGATACCAGCAGCCTGGTGCAGTCCCATACTTACAAGAAGCG AGAGCCGGCCGACGTGCCCTATCAGA |
| 3359 | PTPRM | 3777688 | CTGCACCATGGGACTCGGCTAAGAAAGATGAGAAC |
| 3360 | PTPRM | 3777697 | ACGATCATTCCCGAGTGAGGCTGCAGACAATAGAAGGAGACACAAACTCAGACTATATCAAT GGCAATTATATCG |
| 3361 | PTPRM | 3777710 | GGATGGTGTGGCACGAAAACACTGCAAGTATCATCATGGTGACCAA |
| 3362 | PTPRM | 3777729 | TACCCTAATAGAAACAGAACTACTGGCAGAATATGTGAT |
| 3363 | PTPRM | 3777735 | CCGAGAGATCAGACAGTTTCACTTCACTGGCTGGCCGGATCATGGGGTCCCCTACCATGCCAC CGGCCTGCTGGGATTCGTGCGGCAAGTCAAGTCCAAGA |
| 3364 | PTPRM | 3777736 | ACTGGCTGTTTCATCGTCATTGATATCATGTTGGACATGGCCGAAAGGGAAGGGGTCGTAGA CATCTACAACTGCGTCAGGGAGC |
| 3365 | PTPRM | 3777737 | AGGGTTATCTCTGTGCACTTTGTTCTTCTCCCAGGGTCCTGGGAAGAACAGAAGCCTCCTGAC CCTAAAAATTCTGCCCAGTGTCTGGCGTCCTGGGGATTTGCCCATTTTGTGAAGTACTGTATAC TAACTAGTAACTCTGTAAGTGGAAATTCAAGGTATATCGGGAATTTCCATTTTTTCAGAAGCA ATGTTACATCCTGCTCTTAGGACATTCGTATTTTTACTCATATTTGATTGTTTTAAGTAGGCGTC ACACCGACCACCTGGAAAATGATTCATGAAGTGAAGTGAAGAAGAAGTAAGAATCCCTTACA TTTAGATGGTGCATTTAAGTTTATGAAAGCCTCTGGGAAACCTAATCCCATTTTTTTAGCTAAC ATAAAAATAACAGAAACTTTAAATGCTGCTTTCATGGGTTCTTTTCCTTAGAAAGGGGATACT GTGTTTGAAAGATAATAATCGTAATAATTTATCTTTTAATGTACTTTATAGTCAATCAAATGTT GCCACTCGCATTTCTCACTTGGATCTTCCATTTTCAGGTGTTGTTTACTGGTAGTGTGCTGTTTT TGGGAATCAATCTGTTGGACAAGAGGGTTGTTGAAAAAAAATAATTAAAGGTCATATTTATGTA |

TABLE 13-continued

Subtyping Target Sequences

| SEQ ID NO. | Gene | Affy Probeset ID | Sequence |
|---|---|---|---|
| | | | TAGAAAAAACCGAATTAACTGTAATAAGAGGCTTTTTAAACTTCCCATATAACTAAAGATTAAT<br>AATAAATATGATAAGACTCTACCAATGAATTTTAAGAAAAGTCAGTGCCAAATCAGAATTAGA<br>GGCCCCATATTTACACTGTGAACTCATTGAAGATATATATGAGAACAGCTCTCTGTACTTCTAA<br>GAGGTTTCATAATCATATTAACTTTTATGTTCTGAAATAAGAACTTCTAAGTACTTTTATGTTTT<br>GAATTAAGAACTTCCAGACTTCTTGTCTTCACAGTAATGCCAAGTTTTTCTGGACCTTCTTTGCA<br>CTATTATTTTGACCAGCAAATCCTACCATAGACAAAATTCTGCTCATTCCTCATGTGAAATACT<br>GAGTTCCAAGTGAGTAGGATCAGAATGACAGAGGTCTTCAGCCACAGTTTTCATGGTGCTGC<br>AGTGCGTGTGGTGGTTTGTATTGGGTCCGATTGGTTTTAATCAATCTGTGTAATATTTGGCATT<br>GCACCCCAGTCTCCTAGCACTTGAGCCCTTGGACCGTGTTTC |
| 3366 | PTPRM | 3777738 | TCCACGATGCGATCCTGGAAGCCTGTCTTTGTGGGGACACCTCTGTGCCTGCTTCCCAAGTTA<br>GGTCTCTGTATTATGACATGAACAAACTGGATCC |
| 3367 | PTPRM | 3777740 | CATGGTGACACCAACGCTGCGAGTAGAGGACTGCAGCATCGCACTGTTGCCCCGGAACCATG<br>AGAAAAACCGGTGCATGGAC |
| 3368 | PTPRM | 3777742 | TTTTATAGTCACCCAGCATCCTTTGCCAAACACAGTGAAAGACTTTTGGAGACTGGTCCTGGA<br>TTATCACTGCACATCCGTAGTTATGCTAAATGATGTGGA |
| 3369 | PTPRM | 3777747 | TGGATATCGGATGGTGCAGCAATTCCAGTTCCTGGGCTGGCCGATGTACAGGGACACACCAG<br>TGTCTAAGCGCTCCTTCTTGAAGCTCATTCGCCAGGTGGACA |
| 3370 | PTPRM | 3777749 | TCGTATGTGAGATGCTCCGGCACCAGAGAACCGTGGATGTCTTTCACGCTGTGAA |
| 3371 | PTPRM | 3777752 | CTGCTGATGTTCAACCACCCTACAAGGAGCCCCCAAGCTTTCTCCCAGCCTAGAGGCTGGAC<br>ACCAGCGGGGCTCTCAGGGTTCATGATGTGTG |
| 3372 | PTPRM | 3777758 | ATCAGTACAAGTTCTGCTACGAGGTGGCCCTGGAATACTTGAATTC |
| 3373 | PTPRM | 3777759 | TACCACAAAGCCAAGACGTTCCATGGTATTTGTGCAAAAGAGATGAAGACTTCTCAATATGCT<br>TATTTTGCTTTGCATAATTGGCTCTTTTTAAGAGCCCAAGAAAGTGTTTCTAAAATTGCTTGCA<br>CTGCCCAATCCCAGTAATGCTGCTGCCTGACAGAAACACACACAGCCACAGTTGCCAAATC<br>CCGTACTCCTTGCCACCGGCTTCCTAGAGCAGCTAGACAGCTGGTAAACTGAAGAGCACAA<br>CTATATTCTTATGAAGGAATTTGTACCTTTGGGGTATTATTTTGTGGCCCGTGACCCTCGTTAT<br>TGTTACAGCTGAGTGTATGTTTTTGTTCTGTGGAGAATGCTATCTGGCATTATGGTAATATATT<br>ATTTTAGGTAATATTTGTACTTTAACATGTTGCATAATATATGCTTATGTAGCTTTCCAGGACTA<br>ACAGATAAATGTGTAATGAACAAAGATATGTTGTATGAGTCGTCGTTTCTGTCAGATTTGTAT<br>TGTTTCCAAGGGAAAAGCTTGGGGGAGGACTCAGTTCACAAAATGCAAAACTCAACGATCAG<br>ATTCACGGACCCAGAGCTTTT |
| 3374 | PTPRM | 3777760 | TTTGATTTCATCAAATTATTTATTCATTAAAAG |
| 3375 | PTPRM | 3777780 | GGATGGTTAATAGGACCTCAGGCTCCTGGTCAGTGTGGGGCACTCAGACCCATGAGTCTAGA<br>AAGCAAAGAACAACTGGATTCATGTTTCCTATGTCAGAGTCCACCCAGTTGCAGTTCCACCTG<br>AGTCCTTCA |
| 3376 | PTPRM | 3777782 | TGGCTGCACCGTTTGACATTCCCTCCAGCCGTGTATGAGGGTTCGCTTTCTCCACGCCCTCGCT<br>AACACCTGCGATTTTCTTGTTATGTGAGCCTTCTCGTGAATGTTATTCCACTGACATTAATCTCA<br>TGGCACCGTCAGTGATTGAAATGATCTTCTTGTTCTCTGTCTTCGCCTCTGGATCATGACCTTC<br>CCGAGGACTGAATGTGTCATAAAATCCCCAGTCTCTAGCAGTACATGTGTA |
| 3377 | PTPRM | 3777784 | CTTCCAGTTGCTAAGGCTCTGTCCAGGGCCGGGCTCCTGCCAGGTGGCAGGCAGAGGCTTCC<br>TCAAGCCCTGCGTCCCTCTTCTGGGTTCAGAGACCACTCCCAGGCTTGGTTCTATCAGCACACT<br>CCATGCATACAGGTGCAGAATGCTCTCCCCGGCCACCCGAGACCACACCTCAGCCAGGACCTT<br>GTGCAGAGCTTGCTTGGGCCAAGGTACACGATCCAGGAAAGCTGAGCTCAA |
| 3378 | RALBP1 | 3778412 | GTTGGAACGACTAAAGCACGCTGGCGCAAGGAAAGCTCTCAACTTCGGGAGCTGAGGCGCA<br>GGCTGGCCAGAGCGTGGAGAGGAAAGCCCTTTCCATCCTCAAGGCCGTTGCAGGAGATGCCC |
| 3379 | RALBP1 | 3778416 | GTGCTGCGATCCTTCCTTCAGGTTTCAGTGGGAATGGACAGACAGATCTGAAGTTGAAAATTC<br>TTTTCACAACTCATGTTCAACTATGTGTGTTGTCAGAATGCTCTTAATG |
| 3380 | RALBP1 | 3778417 | ACCGCGCCCTGCCAACAGTAGTAGC |
| 3381 | RALBP1 | 3778421 | GTCTTAAACTTTGAGCTCAGGCAGTCCACCCTCCT |
| 3382 | RALBP1 | 3778422 | ATTGTCTTTATCAGTCTAGTATGGAAACAAAATAATTGTGTACCAGGAGAACATGGAAATGT<br>AGTATAGTATAACTTACAAATGTTGTAGGGGTGAATGATCAAAAGCCACCTGGCATTTTGCTG<br>CTGGTATTCCTGCCCTTACTCCTCTCTTAGCCCCAGTTTTGTCACTTTCTGGCTTTGGAATTGGT<br>AATGACTCCCACACCAGGTCTGAACTCAACATGACATTTAGTGTCTGAGCCCACCTTATCTTTTA |
| 3383 | RALBP1 | 3778423 | GTGCCATAGGTAGTGTTAAATTTTGGAGCTCACCATTAGCAAGGTGAACACATGCATATGTAA<br>TTGAAATACAGTATGGTAAGTGCTGTGAAGAGGTATGTTCAGGATGTTCTAGGACACAGAAA<br>AGGAGTATTTGTGGCTTATACTGGATGGGGTGGGTCACCAGGGAGGATTCTTGGAGAAGTGT |

TABLE 13-continued

Subtyping Target Sequences

| SEQ ID NO. | Gene | Affy Probeset ID | Sequence |
|---|---|---|---|
| | | | TGCTAGTGCTTGATTTTTTAAACAGCTTTATTGAGGTAGAACTCATATAAGATCCACTCACTC GAAGTGTATAATTTAATGATTTTTAGCCAGTTTATGGGTTTCTGCAACCATCACCATAATCCAA ATTTAGAATGTTTCCATCATCTACAAAATCATGCCCAATTGTAGGCCTAGTGTTA |
| 3384 | RALBP1 | 3778425 | GTAACAGAGAAGACCTCGTCCCTTCCTAGTCAGGGCATCAGC |
| 3385 | RALBP1 | 3778426 | AGCATGGCAGCGGGCTTACCCGGACCCCCAGCTCTGAAGAGATCAGCCCTACTAAGTTTCCTG GATTGTACCGCACTGGCGAGCCCTCA |
| 3386 | RALBP1 | 3778427 | GTAGTGTCTGATGATGAGAAAGATCATGGGAAGAAAAA |
| 3387 | RALBP1 | 3778429 | CTGAAGGCTATGCAGCCTTTCAGGA |
| 3388 | RALBP1 | 3778430 | GTCCTTCTAAAATGAAGAGGTCCAAGGGAATCCATGTTTTCAAGAA |
| 3389 | RALBP1 | 3778431 | AAGACTTGACAGCAGCTGATGTTGTTAAACAGTGGA |
| 3390 | RALBP1 | 3778432 | GCCAGAGGTGCCTCAGATTGATGTTCCAAATCTCAAACCCATTTTTGGAATTCCTTTGGCTGAT GCAG |
| 3391 | RALBP1 | 3778433 | CGTGAATGTATAGATTACGTAGAGA |
| 3392 | RALBP1 | 3778435 | GTTTATTCTCTAACCTGTGGCAATGTGCTGTAGTCAGCCCGACTTATGCTACTGTCATGGACAG TGCTAATAATAATACTGCCTTTTGCTGGAGATGTTAGTTCTCACTTATGCATTTTAAGACCTTTT GCTGGAAGTGTTAGTTCTTGCTTATC |
| 3393 | RALBP1 | 3778436 | TGCAGGAATTCCAGCGTTTACTCAAAGAACTGCCAGA |
| 3394 | RALBP1 | 3778437 | GAAACCTCTGCGATGGTCTAACATGGC |
| 3395 | RALBP1 | 3778438 | CTTTTGAATTGTTTACATCGAGATCTGCAGGGTGGGATAAAGGATTTGTCTAAAGAAGAAAG ATTATGGGAAGTACAAAGAATTTTGACAGCCC |
| 3396 | RALBP1 | 3778439 | GATTGCACAAGAGATAGCCAGTCTTTCAAAAGAGG |
| 3397 | RALBP1 | 3778440 | GAAGAGATTGAACGCCTCAGAGCTGAGATTGCTGA |
| 3398 | RALBP1 | 3778441 | GAGACTGAGGAGTACTCCTCCGAGAGCGA |
| 3399 | RALBP1 | 3778443 | CCCAGAGACGGCGTCCTTGAGCCAAAAGCAGCTAAAGAGCAGCCAAAGGCAGGCAAGGAGC CGGCAAAGCCATCGCCCAGCAG |
| 3400 | RALBP1 | 3778444 | AGGACCCGTGCATCTTACTGTAACCCGGGGGCCAGGCCGGCTCTCTCGCTGTACATTCTGTAA AGGTGTCTTCTCTTCTCAGACTCTTCCTCTGTCACACGTCTGACTCCTTCACGTCAGGCTCAGGT TCCATGGGAGGACGAAGCAGTGGACGCATTGTGGGCTTTAGGGACAGATGAGTTTTCCAGAT AGTGTCAGCTTA |
| 3401 | RALBP1 | 3778445 | CTGGGATCTCTGGTACCGTCACTCTTGCTTGTGCCTTCCACACCTTCTCGGTGCAGATCCCTAT GGGGGAGCTGCCTCACGTTCTCTGACTGGTCAGAGCAGCGCCTG |
| 3402 | RALBP1 | 3778446 | TGGGTGTTCCCTGGCCCACTCTCCTCTCTCCTTCT |
| 3403 | RALBP1 | 3778447 | TTCTAAACCACAGTCTATAAGCCCGAGTCACCAGGACGGCCTGTCTGGCCACAGACAGGGGC TGCCTGTGGAGCCTGCCCACCGGCCCCCGGCAGTGCAGTCCAGCGGGGAGGAGGCTGCCCG TTCCTGCCAGTTC |
| 3404 | RALBP1 | 3778448 | ATCCACAGAGGATGTTGTTCAAACCAGAAATCTTTTAAACGACTGACCTTCCTTAAAAACAGA ATGACTCCGATTGCTTGCTTGGGCTAGAATGTACACGTCTCCTTGCCTGAATAAGCCATATATA TGCTCTTAAACAAAAGTTTGAAATTATCCATATCATCTCAGTGAACCTACTGGTGGACTCCCAA TTGACAAGATTGAGCAATAGAAAAAAATTCCTTTCCTTTGAATGATAGCTGTGATTCACCCCAC CCCATTTTCTTGTTTCTGGTCCATCCGATGAGA |
| 3405 | RALBP1 | 3778449 | CTGTGAGGAGATTGAGTACTCTGCAGCTGGCGAGGAGTTGGTTGAGGCACTTCTTCAAGGCC |
| 3406 | RALBP1 | 3778450 | CATGCTGGCGGCGGCATGCCTCCCTTCCACAAGCCCATGCTGCTGCAGAGGGAGCCTGTGTTT GCAAAACCCAGTGGACTGGGCTGGGTCTG |
| 3407 | RALBP1 | 3778451 | TGGGAACTGCACACAAGTCCACTGGCCTGGCTTGGCCCCAGGCATTGCAATTGACAGACATTT GCATTTCATACGGTAAATGAGGACTCAGCACAGCCAACCATAATCAGCATGTCTGGGATAGA |
| 3408 | SLC14A1 | 3786883 | TGAGTATATAACTGTTAGGTGCCTCCCTCCAGCACCATCTCCTGAGAAGCACTCTCCCTTGTCG TGGAGGTGGGCAAATCTTTATCAGCCACTGC |
| 3409 | SLC14A1 | 3786884 | TCTCCTGCTACTTAAAATCAAAAACTA |

TABLE 13-continued

Subtyping Target Sequences

| SEQ ID NO. | Gene | Affy Probeset ID | Sequence |
|---|---|---|---|
| 3410 | SLC14A1 | 3786886 | TCCCTGTGTAGGATGGCTTCCCGTTATTTTTTTTTAAGCAAAGTAAATGAACATCAAATTTCC<br>ATAGTCAGCTGCTGTCTTTCTGCCCACTGAGAGCTCTTTGGTGAAGGCAAAGTCCTCCTTCTTC<br>ATTAGCGGTCTCCCATGTGGGGCCACATCTTCCCTCACCAGGAACCCAGTGGGCGCGCTCCAG<br>CCCCCCTCAGCTTGCCTTTTGCGTGGTCATTAGAGCTAGGGCACACGTCATGCTGATTC |
| 3411 | SLC14A1 | 3786887 | GTAAGGATGAATGGACGGTCTTTGATTGGCGGCGCTGGTGACGCCCGTCATGGTCCTGTTTG<br>GAAGGACCCTTTTGGAACTAAAGCTGGTGACGCAGCGCGCAGAGGCATCGCCCGGCTAAGC |
| 3412 | SLC14A1 | 3786889 | CAGGGTCTGATGATTTTGGCGTTTCCCTGCTTCCCAATTGACCTGGCTGTGCTGTTGGCTGTTC<br>TTGCACACTCAAGGTGGTTTTGCCATTGGCTTCCTCCCTCAGCCTGCCTCTGGGATTATGCCAC<br>TGCTATTCTTTTTTATCTACCATCAGCACAATGAAATCATCATTTTTGTCTTCAAGGTACCAAAT<br>TCTGGTGATATTGGTGCTTTCTTGCAGCTACTTATCATGAGAAGTGAATGGTCTCATAGTGAA<br>CACAGTCATGGTTATAGTGTTCATACGTTCCAGAGACATGTTTCCTATAATTATGCCCTGCACA<br>TTTTTCTATCATACAATCCTTAGATTACAGCTCTTTGGTTTTCAACAGCTTTGTCCAATTCCATCT<br>TTCCCAGTTTCTCTACCTTGATGAAATATCCTTCTTGCCTGGTTTTACATATTTAAATAACAAAT<br>TCCAAAAGTAAAGAGTATCTGAGGCAGTCACATGACATAAGGACAAATTCAAGCCATCTTGG<br>ACTTGCAGAGGGTGGGGAGACCGTGTCAACACACACAATTTTAAAAATTTCTTCCCTTTCAAT<br>CTTTTAAAAACAAAACTTTTTATAAAATAAAAATGTAATTTAAAAAGGCTACCTGTCTTGGCAA<br>GTAGCTGATCAGCCTGCATTGGTGAGCAGGCCATTCCATAACCTGGTTTCTTGCTCCTTAATTG<br>ACAGCATGGAGCTAACGTACTTAATTTCAGCTCTTTCTACGTGATTTGACTCATTCTGTTAACA<br>TTAACTGTTTTTCAGTCTTCTCAACTAGACTGAACTCCTTAAGTGCAAGAAATACACGCTTAGT<br>AAATGTTTGTTGGACCAGACACTGCACCTTATGAAATTAAAGACCAGAACATTCTCATGGTAG<br>CATTACAGACACTGATGGCAAAGGTACTGTGGGATTTGGGTTTGGCTAATAAGCTCTGTGGT<br>GGTGTTTCAGAAGGAAAATGGTGCTCTCTTAGTTCTATGGAACATAGTGGTCCAGATCTTCTA<br>CTGTAACCAGGCCCAAAGCTGGCTAATCTGGAGGGCTCTGCCTTAGGGATACTTATA |
| 3413 | SLC14A1 | 3786890 | GGTTAGAGTGGACAGCCCCACTATG |
| 3414 | SLC14A1 | 3786891 | CAGGTTTCGCCATGTCAAGGGAGAAGGTGCTTCCCCAAAGCTCTTGGCTATGTCACCGGTGAC<br>ATGAAAGAACTTGCC |
| 3415 | SLC14A1 | 3786893 | AACCCGTGGTGCTCCAGTTCATTGACTGGATTCTCCGGGGCATATCCCAAGTGGTGTTCGTCA<br>ACAACCCCGTCAGTGGAATCCTGATTCTGGTAGGACTTCTTG |
| 3416 | SLC14A1 | 3786894 | CATCTGGGCTCTATGGCTACAATGCCACCCTGGTGGGAGTACTCATGGCTGTCTTTTCGGACA<br>AGGGAGACTA |
| 3417 | SLC14A1 | 3786896 | AGTGCATTGAATTCCATGCTCAGCAAATGGGACCTCCCCGTCTTCACCCTCCCTTTCAACATGG<br>CGTTGTCAATGTACCTTTCAGCCACAGGACATTACAATCCATTCTTTCCAGCCAAACTGGTCAT<br>ACCTATAACTACAGCTCC |
| 3418 | SLC14A1 | 3786897 | GAGTTGGTCAGATCTATGGCTGTGATAATCCATGGACAGGGGGCATTTTCCTGGGAGCCATC<br>CTACTCTCCTCCCCACTCATGTGCCTGCATGCTGCCATAGGATCATTGCTG |
| 3419 | SLC14A1 | 3786898 | TTGAGGACATCTACTTTGGACTCTGGGGTTTCAACAGCTCTCTGGCCTGCATTGCAATGGGAG<br>GAATGTTCATGGCGCTCACCTGGCAAACC |
| 3420 | SLC14A1 | 3786899 | CAATCAAGGATAAGCAGTAAAAACGGACTGCATGAAAAATCAGGGCCAGGGTTCTGGCTTGA<br>GCCCACTTGCTGTCTAAGTGTGTGAACAGGACAAGTGACGTCCCCTCTCTGAGAGCA |
| 3421 | SLC14A1 | 3786902 | GTTGGATTGCCAGCTTGTACCTGGCCCTTCTGTTTGGCCACGCTATTGTTCCTCATCATGACCA<br>CAAAAAATTCCAACATCTACAAGATGCCCCTCAGTAAAGTTACTTATCCTGAAGAAAACCGCA<br>TCTTCTACCTGCAAGCCAAGAAAAGAATGGTGGAAAGCCCTTTGTGA |
| 3422 | SLC14A1 | 3786903 | TGCAGCCATGGTCACGAGTCATTTCTGCCTGACTGCTCCAGCTAACTTCCAGGGTCTCAGCAA<br>ACTGCTGTTTTTCACGAGTATCAACTTTCATACTGACGCGTCTGTAATCTGTTCTTATGCTCATT<br>TTGTATTTTCCTTTCAACTCCAGGAATATCCTTGAGCATATGAGAGTCACATCCAGGTGATGTG<br>CTCTGGTATGGAATTTGAAACCCCAATGGGGCCTTGGCACTAAGACTGGAATGTA |
| 3423 | SLC14A1 | 3786904 | GTGTGTGTGACATTCTCTCATGGGACAATGTTGGGGTTTTTCAGACTGACAGGACTGCAAGA<br>GGGAGAAAGGAATTTTGTCAATCAAAATTATTCTGTATTGCAACTTTTCTCAGAGATTGCAAA<br>GGATTTTTTAGGTAGAGATTATTTTTCCTTATGAAAATGATCTGTTTTAAATGAGATAAAATA<br>GGAGAAGTTCCTGGCTTAACCTGTTCTTACATATTAAAGAAAAGTTACTTACTGTATTTATGAA<br>ATACTCAGCTTAGGCATTTTTACTTTAACCCCTAAATTGATTTTGTAAATGCCACAAATGCATA<br>GAATTGTTACCAACCTCCAAAGGGCTCTTTAAAATCATATTTTTTATTCATTTGAGGATGTCTTA<br>TAAAGACTGAAGGCAAAGGTCAGATTGCTTACGGGTGTTATTTTTATAAGTTGTTGAATTCCT<br>TAATTTAAAAAGCTCATTATTTTTTGCACACTCACAATATTCTCTCTCAGAAATCAATGGCATT<br>TGAACCACCAAAAAGAAATAAAGGGCTGAGTGCGTCCACGCCTGTAATCCCAGCACTT<br>TGGGGAGCCCAGGCGGGCAGATTGCTTGAACCCAGGAGTTCAAGACCAGCCTGGGCAGCAT<br>GGTGAAACCCTGTATCTACAAAAAATACAAAAATTAGCCAGGCATGGTGGTGGGTGCCTGTA<br>GTTCCAGCTACTTGGGAGGCTGAGGTGGGAAAATGACTTGAGCCCAGGAGGAGGAGGCTGC<br>AGTGAGCTAAGATTGCACCACTGCACTCCAACCTGGGCGACAAGAGTGAAACTGTGTCTCTC<br>AAAAAAAAAAAAAAAACAAACAAAAACAAAACAAAACAAAACAAAACAGGT |

TABLE 13-continued

Subtyping Target Sequences

| SEQ ID NO. | Gene | Affy Probeset ID | Sequence |
|---|---|---|---|
| | | | AAGGATTCCCCTGTTTTCCTCTCTTTAATTTTAAAGTTATCAGTTCCGTAAAGTCTCTGTAACCA
AACATACTGAAGACAGCAACAGAAGTCACGTTCAGGGACTGGCTCACACCTGTAATCCCAGC
ACTTTGGGAGATGGAGGTAAAAGGATCTCTTGAGCCCAGGAGTTCAAGACCAGCTTGGGCAA
CATAGCAAGACTCCATCTCTTAAAAAATAAAAATAGTAACATTAGCCAGGTGTAGCAGCACAC
ATCTGCAGCAGCTACTCAGGAGGCTGAGGTGGAAAGATCGCTTGTGCACAGAAGTTCGAGG
CTGCAGTGAGCTATATGATCATGTCACTGCACTCCAGCCTGTGTGACCGAGCAAGACCCTATC
TCAAAAAAATTAATTAATTAATTAATTAATTTAAAAAGGAAGTCATGTTCATTTACTTTCC
ACTTCAGTGTGTATCGTGTAGTATTTTGGAGGTTGGAAAGTGAAACGTAGGAATCCTGAAGA
TTTTTTCCACTTCTAGTTTGCAGTGCTCAGTGCACAATATACATTTTGCTGAATGAATAAACAG
AAATAGGGAAGTAAACCTACAAATATTTTAGGGAGAAGCTCACTTCTTCCTTTTCTCAGGAAA
CCAAGCAAGCAAACATATCGTTCCAATTTTAAAACCCAGTGACCAAAGCCTTTGGAACTATGA
ATTTGCA |
| 3424 | SLC14A1 | 3786905 | AGTGAAGAATCTAGGCTGTGGCTGAGAGAACCAGAGGCCTCTAAAATGGACCCGAGTCGATC
TTCAGAACAGGGATCTACCATGCAGGAGCTTCTTGTGCTCACACAAATCTGTAAATGGGAACA
TTGTACATTGTCGAATTTAAATGATATTAATTTTCTCAAGCTATTTTGTTACTATTTTCCTAAAA
TTGAATATTTGCAGGGAGCACTTATACTTT |
| 3425 | SERPINB13 | 3791851 | TTGACTTATGCTTCCTAGTTCGTTGCCCAGCCACCAC |
| 3426 | SERPINB13 | 3791854 | ACTTGGCGCCGTCAGCACTCGACTTGGGTTTGATCTTTTCAAAGAGCTGAAGAAAACAAATGA
TGGCAACATCTTCTTTTCCCTGTGGGCATCTTGACTGCAATTGGCATGGTCCTCC |
| 3427 | SERPINB13 | 3791855 | ACTCTGAAAAGAGACGAAGAGCTCAAGAATAAAGGCTGA |
| 3428 | SERPINB13 | 3791856 | TAAGAATAAAGGCTGAAGGAAAAGAG |
| 3429 | SERPINB13 | 3791857 | CCCTTAATATTGAGAAGAGACCTTAGGTGTAATGGACAATACCGCTATGATAGAACTGGTAAA
GGCTAATAGACA |
| 3430 | SERPINB13 | 3791858 | ATAAGCAAACTCACTAATGATTATGAACTGAACATAACCAACAGGCTGTTTGGAGAAAAAAC
ATACCTCTTCCTTCA |
| 3431 | SERPINB13 | 3791859 | CATGCATCTCTGGAACCTGTTGATTTTGTAAATGCAGCCGATGAAAGTCGAAAGAAG |
| 3432 | SERPINB13 | 3791861 | TCCTCAGCTGATAAGAGGCAAACTGGATGCTAACAGAGGCATCTGACCCCAGAGTCTGGACT
CTTAACCATGAACCTTAATTTATCCACTGGGATAAATAGGCGATGGGCAAAATGAGAACCTCC
CCGTCGATTCTGCCAGCAAACCCTTTGTCAGCAAGGCCCTCA |
| 3433 | SERPINB13 | 3791863 | GATGGCTCTATTAGTAGCTCTACCAAGCTGGTGCTGGTGAACATGGTTTATTTTAAAGGGCAA
TGGGACAGGGAGTTTAAGAA |
| 3434 | SERPINB13 | 3791864 | CCATATAAAAACAACGACCTAAGCATGTTTGTGCTTCTGCCCAACGACATCGATGGCCTGGAG |
| 3435 | SERPINB13 | 3791866 | TTACGATCTAGAGGCGGTCCTGGCTGCCATGGGATGGGCGATGCCTTCAGTGAGCACAAAG
CCGACTACTCGGGAATGTCGTCAGGCTCCGGGTTGTACGCCCAGAAGTTCCTGCACAGTTCCT
TTGTGGCAGTAACTGAGGAAGGCACCGAGGCTGCAGCTGCCACCGGCATAGGCTTTACTGTC
ACATC |
| 3436 | SERPINB13 | 3791867 | GTGTTTATAACCATCCTCGAAAGTGAAATGTCCTTTTCTTTGTGCCATGCGTAAGGTGAGTCAA
ACCAAACCTCATTGATAATCTCCCTTTGGTTTCCTTTGAAAGTAAATTGGTATCTTGTAGTTTTG
TGCACACGAAAGGAGAAAAGTCTCTCCAGTAAAGAGTACGAACTAGTAATTTTGGGGGGTC
TCTCTAATTCTGGTATTTTGACATGTTATAATACGCAAGTAAAATAAAACAATAGTTTACTCAG
CTCATGTTACTATTCCCCAACAGATATTGTGGCAAATCACACATAGGAAAGAGAATTTGGGAA
TACAGTAGCAAAACATAAATTAAAACTCAAATGCCAGGACAAAATAAAACAATATACCAGAT
GGGAGAGGATGCCCGTATTTTCATCTTCCATTCATAACATTATCCATTGTTAGATGCATAAGCATT
TTGATATTGTGTAATAAATGTGGTATTTGAGAAGATAAATGATGTAGTTGATCAGTATTCCTCC
TCTATCACCTTTTTAGACTTTGTAAGGTAAATATTTGGACTAACTTTTAGAAAAGTTTCCCTTTT
TTTCTCCATTTACATTTTTCTGGTTTTTTTTTTTTTGAGTGAGGTACGAGTATTACCAAATGAT
ATTTTCTGAAGATGCTTTTTGGAAAGCTCTGAATCTATACCTAATGCTCTTAATTATTGGCTTGT
TTCATTTTTTTCCTCCAGTTTTTAACAAGATCACATAACTGGCTTATTTTTAACAGCTTTGTCAAA
CTACAATTTACATGCCGTAAAATGTACACACTGTAATTTTATAATTCATTGACTTTTAGTAAATT
TCTAGCGTTATGCATCGCCACAATCCAGTTTTAGAATATTTCCATGACCCTAAGAAGTTTCCTC
ATGTCTATTAATATTCCCAATCCTAGGCACCACTGAGTTGTTTTCTGTCTTTATAAGTTTTTCTTT
CTACATCTTATATAAATGGAATCATAATACATGTAGTATTTTGTGTCTGGCGTCTTGCACTTAG
CATGGTG |
| 3437 | SERPINB13 | 3791868 | TTGGGGAGATTCCTAGGCTAGAAATTGCTGGGCCATATGAAAAATCAATAGTTAGCTTTGTAA
GAAACAGTCAAACTGTTTTCCAACGTGACATTTTATATTCCCACCAGGAATGTTTAAAACTAGT
GTCTTCAAATCCTCACCAACATCCAGGATTGTGTCTTTATGATTATAGCCATTTTTGTAGGTAC
AAAGTGGCATCTCATGGTGGTTTTAATTTGCATTTCCATAATATCTAATTAGGTTGAGCTTTTTT
TATGTGCTTATTGGCCATTTGTTTGACTTTGTTTGGTGAAATGTATACAAATCATTTGCTCATTT
TTAATTTGGGTTGTCTGTCTTGTCTTCTCATTTTATTGAGTTAAATGAGTTCTTAATAATCTCTG
GCTTACAAGTCCTTAATTTATCAAATATATGATACGTGGACATTTCCTC |

TABLE 13-continued

Subtyping Target Sequences

| SEQ ID NO. | Gene | Affy Probeset ID | Sequence |
|---|---|---|---|
| 3438 | SERPINB13 | 3791869 | AGACTCAACTCTGGCAGTGGGGTTCAGACATCAGACAAATTGAGGACTAGCTAAAACAGGGA AGAGTTGGAAGCACCTCTCCAGAAGACATGCCCACCAGTGTGCCATATCAGTTTACCCTTGCC ATGGCTACACCCAGAAGTTATGGATGAAGCTGCTATGGATGAAGCTGGAGGACATTATGCTA AGTGAAAAGTAATACACAAAAAGAAAAGTACTGAATGATCTCACTTAAATGTGTAATATAAA AAAGTCAAATACATAGAGAAAGAGAATAAAATGGTAACTATCAGGGATTGGGGAGATGCAG GGAGAGGGAGAAAAAATAGAGAGATATAGGTCAAAGGATCCAAAGTTGAAGATATGTAGG ATGAACGAGTCTAGAGCTCTAACGTACAAGACAAGGATGATGGTTAATAATAATGTATTATAT ATAAGATTTTTGTGAAAATAGTAGATTTAAGGTGCTCTTGCCACACATCAAAAAGGATAACT ATGTGAGATGACGGATATATGTTAATTTACTTCACTAGAGCAACCATTTCACTGTGTACATG |
| 3439 | ATP8B1 | 3809827 | AAGTCCTATTATTCGGCCGGGCGTGGTGGCTCAGGTCTGTAATCCCAGCACTTTAGGAGGCTG AGGAGGGGAGATCACCTGAGGCCAGGAGTTCGAGACCAGCCCAGCCAACATGGTGAAACCC TGTCTCTACCATAAATTAAAAATTAGCCGGGCTTGGTGGTGGGCACCCGTAATCCCACCTATTT GAGAAGCTGAAGCAGAAGAATCGCTTGAACCTGGGAGATGGAGGTTACAGTGAGCCGAGAT TGCGCCACTGCACTCCAGCCTGGGTGACAGAGCAAGACTCTGTCTTAAGAAAAATTTAAAAAT AGGCCGGGCATGGTGGCTCATGCCTGTCATCCTAGCACTTTGGGAGGCCAAGGCAGGTGGAT CACTTGAGGTCAGGAGACCAGCCCGGCCAACATGGTGAAACCCCATCTCTACTAAAAATACA AAATTAGCTGGAAATCGCTTGAACCTGGGAGGTGGAGGTTCCAGTGAGCCGAGATCGTGG CACTGCACTCCAACCTGAGCAACAGAGTGAGACACCAGCTCAAAAAAATTTTTTAATAATAA TAAAAGTCCTATTATTCAACTGGTTATGTACATTATGGTTGAAAGGGAACGTTTTAATCCAGTC TCAATCCAGGGCAATAGAATTACAAAGCATGTTGTATTTCAGTTCAAATGGTATTGTATTATAA AATTACAGTTACATTTTCCTTTCGGTGATCTTCAGCATAATTTCCCAGAGGCCCCTTTTTCCTCC CTATAGGCCATCTTATTAACAGATTTTAAAATTTATAGTAATGACAAATGACTTATCAGTGTTC ATCATCTGAAAGCTAAGTGGTTCGTTCAATCACTTTTTCAAAGTTGATAGTAGATTGCATGGTT TCATGTTTCCTCATATTGGTTTATTAATTCTATTTAATCAAGGAAAATAACTTCAGATTCCATAA AGTTTCAGTTTATTTTTAGTTTACTACTAGGTGAGATAGCACATTACATACTTTTACTATCAAAT ATTATTTTAGCAGCTTCCCATAGTACCAAATGATTTGATTCCCTACTCTCATTTTTTAAAGCATA TAAATATTTATGGGCTTAAAAAGGGGGTTTTTAAAAACTGAGGATATCAGTAATAAATTGCAG AATATTTTGCAAAGCTTTCTTTTGGAAAGCAAACTTTTGTGCCTGCCTATATGCAAAGTATTTT ATCAGGGACTTGAACAAAGACCTCACTCTTTTTCACTTGTCTTATGTCGAGAGAAAAGGTTATT GGCAGCCACATTCCTAAGACTG |
| 3440 | ATP8B1 | 3809828 | ACAAAGCACGTCTATTTTTTTATGAAAGACTCTCAGGACTTTG |
| 3441 | ATP8B1 | 3809829 | GTACAGGCGCACCGGGGACAGCTGA |
| 3442 | ATP8B1 | 3809830 | CAGAAGCATCGCAAGCGGTTGAAGGCGGAGGAGCAGTGGCAGCGACGGCAGCAGGTGTTC CGCCGGGGCGTGTCAACGCGGCGCTCGGCCTACGCCTTCTCGCACCAGCGGGGCTACGCGGA CCTCATCTCCTCCGGGCGCAGCATCCGCAAGAAGCGCTCGCCGCTTGATGCCATCG |
| 3443 | ATP8B1 | 3809833 | TGGTTAACTATCATCCTGGCTGTTGCTGTGTGCTTACTACCCGTCGTTGCCATTCGATTCCTGTC AATGACCATCTGGCCATC |
| 3444 | ATP8B1 | 3809834 | GGCTTGGATACTTCTTATTGGACTTTTGTGAATGCTTTTTCAATTTTTGGAAGCATTGCACTTTA TTTTGGCATCATGTTTGACTTTCATAGTGCTGGAATACATGTTCTCTTTCCATCTGCATTTC |
| 3445 | ATP8B1 | 3809835 | TGAGCCTCCGATTCCCTGGGTTATACATAGTGGGACAAAGAGACTTACTATTCAACTATAAGA GATTCTTTGTAAGCTTGTTGCATGGGGTCCTAACATCGATGATCCTCTTCTTCATACCTCTTGG AGCTTATCTGCAAACCGTAGGGCAGGATGGAGAGGCACCTTCCGACTACCAGTCTTTTGCCGT CACCATTG |
| 3446 | ATP8B1 | 3809837 | CGAGTGACTATTCCTTTGCTCAGTTCCGATATCTGCAGAGGCTACTGCTGGTGCATGGCCGAT GGTCTTACATAAGGATGTGCAAGTTCCTACGATACTTCTTTTACAAAAACTTTGCCTTTACTTTG GTTCATTTCTGGTACTCCTTCTTCAATGGCTA |
| 3447 | ATP8B1 | 3809838 | GCCCACATTGGCGTTGGAATAAGTGGACAAGAAGGA |
| 3448 | ATP8B1 | 3809841 | TGAAATTCTTCTCGAGAAAAGACCAAGAGAAATAAGATTCTGAAGCTGAAGTTCCCAAGAA CAGAAGAAGAAAGACGGATGCGGACCCAAAGTAAAAGGAGGCTAGAAGCTAAGAAAGAGC AGCGGCAGAAAAACTTTGTGGACCTGGCCTGCGAGTCAGCGCAGTCATCTG |
| 3449 | ATP8B1 | 3809842 | ATAGAGGTGGCGTCTACGCAAAGTTTGCACCTCCTGTGCAGGAATCTTTTTTTCCACCCGGTG GAAACCGTGCCTTAATCATCACTGGTTCTTGGTTG |
| 3450 | ATP8B1 | 3809844 | AAATATAGGATTTGCTTGTGAACTTCTGACTGAAGACAC |
| 3451 | ATP8B1 | 3809846 | GCTACAGCTATTGAAGACAAGCTACAGGATGGAGTTCCAGAAACCATTTCAAAACTTGCAAA AGCTGACATTAAGATCTGGGTGCTTACTGGAGACAAAAAGG |
| 3452 | ATP8B1 | 3809847 | TCCACCAACCGGGACGAAGCTCTGGATAAAGTATATGAGG |
| 3453 | ATP8B1 | 3809848 | TCTTTGCAAATGAAACTCTTAGAACCCTATGCCTTTGCTACAAG |

TABLE 13-continued

Subtyping Target Sequences

| SEQ ID NO. | Gene | Affy Probeset ID | Sequence |
|---|---|---|---|
| 3454 | ATP8B1 | 3809849 | AGGCAATATCAAGCTTTACTGTAAAGGTGCTGACACTGTTATTTATGAACGGTTACATCGAATGAATCCTACTAAGCAAGAAACACAG |
| 3455 | ATP8B1 | 3809850 | GAAGGTGCCCTGGTAAACGCTGCCAGGAACTTTGGCTTTGCCTTCCTCGCCAGGACCCAGAACACCATCACCATCAGTGAACTGGGCACTGAAAGGACTTACAATGTTCTTGCCATTTTGGACTTCAACAGTGACCGGAAGCGAATGTCTATC |
| 3456 | ATP8B1 | 3809853 | GAAAGAGCCAGAAGTACGACAGTTCTTCTTCTTGCTCGCAGTTTGCCACACAGTCATGGTGGATAGGACT |
| 3457 | ATP8B1 | 3809855 | TCGGGATGCCTCTCAACACAACCACAACA |
| 3458 | ATP8B1 | 3809858 | GGGACCTGCAAATGTACTATGCTGAGAAGGACACACCCGCAAAAGCTAGAACCACCACACTCAATGAACAGCTCGGGCAGATCCATTATATCTTCTCTGATAAGACGGGGACACTC |
| 3459 | ATP8B1 | 3809860 | CTGGTCTTGCCATCGGCCATGCTTATTGGGAAGCACAGGTGGGCAATTCCTCTTGGTACCTCTATGATGGAGAAGACGATACACCCTCCTACCGTGGATTCCTCATTTTCTGGGGCTATATCATTGTTCTCA |
| 3460 | ATP8B1 | 3809864 | GAACACCGATTTCTGCCACGGCTTAGTCATTTTTGCAG |
| 3461 | ATP8B1 | 3809865 | TTGAATGTGAAGAACCCAATAACAGACTAGATAAGTTTACAGGAACACTATTTTGGAGAAACACAAGTTTTCCTTTGGATGCTGATAAAATTTTGTTACGTGGCTGTG |
| 3462 | ATP8B1 | 3809866 | TTTAAGATGTCACTTGAAATCACAGA |
| 3463 | ATP8B1 | 3809869 | GTCTAGCTCTGAGCCTAACAGCCTCTGCTATGTGGAAACAGC |
| 3464 | ATP8B1 | 3809871 | AATTCAAGTTGGAGACGTCATTCGTCTGAAAAAA |
| 3465 | ATP8B1 | 3809872 | AGGAAATCAACAATAGGACGTGTGAAGTCATTAAGGA |
| 3466 | ATP8B1 | 3809874 | TTAAACATACAAGTACAACGCATTTACCTTTATACCAATGAATCTGTTTGAGCAGTTTAAGAGAGCAG |
| 3467 | ATP8B1 | 3809875 | GGCAAGTCAAAGCAAACGATCGCAAGTACCACGAACAACCTCACTTTATGAACACAAAATTCTTGTGTATTAAGGAGA |
| 3468 | ATP8B1 | 3809880 | ACATTTGACGAGGATTCTCAGCCTAATGACGAAGTGGTTCCCTACAGTGATGATGAAACAGAAGATGAACTTGATGACCAGGGGTCTGCTGTTGAACCAGAACAAAACCGAGTC |
| 3469 | ATP8B1 | 3809881 | GCTTGATCACCCCAGTGTACTCCAGCCTAGGTGACAGAGCAAGAACTTGAATCAACAACCAAAAAAAAAAAAAAAGGAAGAAAAAAGAAGCAAACCACCTCATGTGTATGCCACACTCACAGGAAATTAA |
| 3470 | ATP8B1 | 3809912 | ATGCCCCAGCCGGGGCCCAGCGAACGCCAG |
| 3471 | SERPINB4 | 3811575 | TTTAGAAAATGTTCACCTAGAGGTGTTCTGGTAAACTGATTGCTGGC |
| 3472 | SERPINB4 | 3811576 | TGAATATCTTCAATGGGGATGCAGACCTCTCAGGCATGACCTGGAGCCACGGTCTCTCAGTATCTAAAGTCCTACACAAGGCCTTTGTGGAGGTCACTGAGGAGGGAGTGGAAGCTGCAGCTGCCACCGCTGTAGTAGTAGTCGAATTATC |
| 3473 | SERPINB3 | 3811576 | TGAATATCTTCAATGGGGATGCAGACCTCTCAGGCATGACCTGGAGCCACGGTCTCTCAGTATCTAAAGTCCTACACAAGGCCTTTGTGGAGGTCACTGAGGAGGGAGTGGAAGCTGCAGCTGCCACCGCTGTAGTAGTAGTCGAATTATC |
| 3474 | SERPINB4 | 3811577 | GAAATACCATACAAAGGCAAAGATCTAAGCATGATTGTG |
| 3475 | SERPINB3 | 3811577 | GAAATACCATACAAAGGCAAAGATCTAAGCATGATTGTG |
| 3476 | SERPINB4 | 3811578 | ATTCCTTTAATTTTGCCTTGCTGGAG |
| 3477 | SERPINB3 | 3811578 | ATTCCTTTAATTTTGCCTTGCTGGAG |
| 3478 | SERPINB4 | 3811580 | TGGCAATGATACGACACTGGTTCTTGTGAACGCAATCTATT |
| 3479 | SERPINB3 | 3811580 | TGGCAATGATACGACACTGGTTCTTGTGAACGCAATCTATT |
| 3480 | SERPINB4 | 3811584 | TTAGATGCCATCAAGAAATTTTACCAGACCAGTGTGGAATCTACTGATTTTGCAAATGCTCCAGAAGAAAGTCGAAAGAAGATTAACTCCTGGGTGGAAAGTCAAACGAATG |
| 3481 | SERPINB3 | 3811584 | TTAGATGCCATCAAGAAATTTTACCAGACCAGTGTGGAATCTACTGATTTTGCAAATGCTCCAGAAGAAAGTCGAAAGAAGATTAACTCCTGGGTGGAAAGTCAAACGAATG |

TABLE 13-continued

Subtyping Target Sequences

| SEQ ID NO. | Gene | Affy Probeset ID | Sequence |
| --- | --- | --- | --- |
| 3482 | SERPINB4 | 3811585 | GTTTCAAAAGCTTCTGACTGAATTCAACAAATCCACTGATGCATATGAGCTGAAGA |
| 3483 | SERPINB3 | 3811585 | GTTTCAAAAGCTTCTGACTGAATTCAACAAATCCACTGATGCATATGAGCTGAAGA |
| 3484 | SERPINB4 | 3811586 | TCAGCTTTAGATCCCTGAACAGGTC |
| 3485 | SERPINB3 | 3811586 | TCAGCTTTAGATCCCTGAACAGGTC |
| 3486 | SERPINB4 | 3811587 | CACAGAAAAGCTGCAACATATCAT |
| 3487 | SERPINB3 | 3811587 | CACAGAAAAGCTGCAACATATCAT |
| 3488 | SERPINB4 | 3811589 | CAACACTGCACAACAAATTAGCAAG |
| 3489 | SERPINB3 | 3811589 | CAACACTGCACAACAAATTAGCAAG |
| 3490 | SERPINB4 | 3811591 | TTCATTCCACAGACACACACAGCCTCTCTGCCC |
| 3491 | SERPINB3 | 3811591 | TTCATTCCACAGACACACACAGCCTCTCTGCCC |
| 3492 | SERPINB3 | 3811597 | AAAATGTTCACCTGCAGATGTTCTGGTAAACTGATTGCTGGC |
| 3493 | SERPINB3 | 3811598 | TAGGATTCGGATCATCACCTACTTCAACTAATGAAGAGTTCCATT |
| 3494 | SERPINB3 | 3811599 | ATGGTGGATATCTTCAATGGGATGCAGACCTCTCAGGCATGACCGGGAGCCGCGGTCTCGTGCTATCTGGAGTCCTACAC |
| 3495 | SERPINB4 | 3811600 | AATTGATGGAATGGACAAGTTTGCAGAATATGAGAGAGACACGTGTCGATTTACACTTACCTCGGTTCAAAGTGGAAGAGAGCTATGACCTCAAGGACACGTTGAGAAC |
| 3496 | SERPINB3 | 3811600 | AATTGATGGAATGGACAAGTTTGCAGAATATGAGAGAGACACGTGTCGATTTACACTTACCTCGGTTCAAAGTGGAAGAGAGCTATGACCTCAAGGACACGTTGAGAAC |
| 3497 | SERPINB4 | 3811601 | GAAATACCATACAAAGGCAAAGATCTAAGCATGATTGTG |
| 3498 | SERPINB3 | 3811601 | GAAATACCATACAAAGGCAAAGATCTAAGCATGATTGTG |
| 3499 | SERPINB3 | 3811602 | TGATGAGGCAATACACATCTTTTCATTTTGCCTCGCTGGAG |
| 3500 | SERPINB3 | 3811603 | GTAATATTGGCAGCAATACCACATTGGTTCTTGTGAACGCAATCTATT |
| 3501 | SERPINB4 | 3811608 | ATGCTCCAGAAGAAAGTCGAAAGAAGATTAACTCCTGGGTGGAAAGTCAAACGAATG |
| 3502 | SERPINB3 | 3811608 | ATGCTCCAGAAGAAAGTCGAAAGAAGATTAACTCCTGGGTGGAAAGTCAAACGAATG |
| 3503 | SERPINB4 | 3811609 | GTTTCAAAAGCTTCTGACTGAATTCAACAAATCCACTGATGCATATGAGCTGAAGA |
| 3504 | SERPINB3 | 3811609 | GTTTCAAAAGCTTCTGACTGAATTCAACAAATCCACTGATGCATATGAGCTGAAGA |
| 3505 | SERPINB3 | 3811610 | CCACAGGAAAAGCTGCAACATATCAT |
| 3506 | SERPINB3 | 3811612 | TGTTCGACCTGTTCCAACAGTTCAGAA |
| 3507 | SERPINB3 | 3811614 | GAGGAGAGGCATAAATTCAGGATCTCACCCTTCATTCCACAG |
| 3508 | CASP14 | 3822977 | GCCTTGAGGAACAGCTGCCTCTAGAGT |
| 3509 | CASP14 | 3822981 | GGTGCTGAGAGCCGGGACTCACAACCAAAG |
| 3510 | CASP14 | 3822984 | AAATATGATATGTCAGGTGCCCGCCTGGCCCTAATACTGTGTGTCACCAAAGCCCGGGAAGGTTCCGAAGAAGACCTGGATGCTCTGGAACACATGTTTCGGCAGCTGAGATTCGAAAGCACCATGAAAA |
| 3511 | CASP14 | 3822985 | CAATTCCAGGAAGAGCTGGAAAAATTCCAG |
| 3512 | CASP14 | 3822986 | CAGGCCATCGATTCCCGGGAAGATCCCGTCAGTTGTGCCTTCGTGGTACTCATGGCTCACGGGAGGGAAGGCTTCCTCAAGGGAGAAGATGGGGAGATGGTCAAGCTGGAGAATCTCTTCGAGGCCCTGAACAACAAGAACTGCCAGGCCCTGCGAGCTAAGCCCAAGGTGTACATCATACAGGCCTGTCGA |
| 3513 | CASP14 | 3822987 | TACCTTTCTCTCTGACTTTGCCTCCTCCTCTTCTTGTTGTTTCAG |

TABLE 13-continued

Subtyping Target Sequences

| SEQ ID NO. | Gene | Affy Probeset ID | Sequence |
|---|---|---|---|
| 3514 | CASP14 | 3822988 | GGTCATCAAAGACAGCCCACAAACCATCCCAACATACACAGATGCCTTGCACGTTTATTCCAC GGTA |
| 3515 | CASP14 | 3822989 | GAAAGGCTCATGCTTTATCCAGACCCTGGTG |
| 3516 | CASP14 | 3822992 | GTGACCCGGCGGATGGCAGAAGCAGAGCTGGTTCAAGAAGGAAAAGCAAGGAAAACGAAC CCTGAAATCCAAAGCACCCTCCGGAAACGGCTGTATCTGCAGTAG |
| 3517 | CASP14 | 3822993 | CTTCCAGCATTCTTTCTGTCTCACAGAAATTTAGAGGCAGCTCTTACCTCTCCCCAAGATCTTCT GTTCCCAAGGCCAAATGGCACCCAGTTTCTTTTCCATCACACCCTTCATGCAGGTCCTCCTGTC CTTATTAGAGCAAGCCAGCCAA |
| 3518 | CASP14 | 3822995 | ACTCCGTTCTCTTCCTAGCTCATGGCCTCTCTAGATAATAAAGTTGTCTCCTCCTTTCTGGATCT CTTCCTCCTAACACCCCTCCCCTGAAACCCTGGACTCTGCCCTCTCTCCAAGAAAATCCATCTAT TCAACTATTCTTGCATTCAATTACTCTAAATGAGAGCGTGTTGGAGCTATGGCAAATTCCCTGT TGTCACCTTGCTATTTTGCAGACAACATAATATTTAACCTCTCATAACCAGAGAGGTTAAATAA TTTGTCAAATGCAATACAGTAAGACAGAGGCAAGGACAAGGTTTGACTTCCAGCCCAGCCTCT TTTCCACAACCTGCTAAATCCTGATCCATCTGAAAACTTTTCTAATTAGTGAAGATGACTAATA AAAATTTTCCCTATCTCCAAGGTAGGAGCTTTCTGGAAGTTTCTAGAAATTTTCAATAACCACC AGCCAAGGTTACCTCCAGGTAACCTTGCAGCACCAGGCTGGAAGTCAGATCGGCTTCACTATC TTCCAACTCTACAGCCTGTATCTCTCCATCCCCAGCTTTGACCTTTCCTGCTCAAGTAACCTACG GGCACATCCAGCGTCACTAAAAA |
| 3519 | CASP14 | 3822997 | TAAGCCTTTGCTATCACCATTTCCCCAAGCTGGAGGGCCCTCCCTCTCCCTTTACCCCTCTTCC ACTACCTCCCACCCCTACTTTTTCCAGAAAGCCATTTCCTCTCTTTTTTCTGATTGATCCTTCCCT CTCACCCAGGATTAGATGCTGGAAATGACCACTTCTGGAGGGCAGGGAACAAGCCCTTAATC TG |
| 3520 | IFI30 | 3824875 | CCGCCGCCTGGTTAAAGGCGCTTATTTCCCAGGCAGCCGC |
| 3521 | IFI30 | 3824878 | CCCTGAAGAAGTCCAATGCACCGCTTGTCAATGTGACCCTCTACTATGAAGCACTGTGCGGTG GCTGCCGAGCCTTCCTGATCCGGGAGCTCTTCCCAACATGGCTGTTGGTCATGGAGATCCTCA ATGTCACGCTGGTGCCCTACGGAAAC |
| 3522 | IFI30 | 3824880 | GCCTGCGTGTTGGATGAACTTGACATGGAGCTAGCCTTCCTGACCATTGTCTG |
| 3523 | IFI30 | 3824881 | AGGGCTGTCGCCAGACACTATCATGGAGTGTGCAATGGGGGACCGCGGCATGCAGCTCATG CACGCCAACGCCCAGCGGACAGATGCTCTCCAGCCACCACACGAGTATGTGCCCTGGGTCAC CGTCAATG |
| 3524 | IFI30 | 3824882 | AGAATCTTTTTAGCCCTCAGCTTGACACTCATAGTCCCATGGAGTCAGGGATGGACAAGACAG AGGGACCAGAGATAAAGGAACCCAGGCGGAGGTTGCAGTGAGCTGAGATCATGCCACTGCA CTCCAGCCTGGGCAACAAGAGCAAAACTTGATAGCTTTGCATAGGGAAAGAGGGCATTGATG CTGGGGTTTTGAAAGGTGAGTAGGAGTCCATCAGGCAAAAAAGTATGTATTAATTCGAAGT ATTAAACATCCCTAGCCACCCCCATTGGGAAAGATGTGCCACTGATTTGCGAGGCGGGAGGC GGGGGCCAGACTTGGGAATATGTGCAGCCCTTTC |
| 3525 | IFI30 | 3824883 | AAACCCTTGGAAGATCAGACCCAGCTC |
| 3526 | IFI30 | 3824885 | CAAGAAGCCGGATGTCTGCCCTTCCTC |
| 3527 | IFI30 | 3824886 | GGCCGGTGAGCTGCGGAGAGCTCATGGAAGGCGAGTGG |
| 3528 | IFI30 | 3824887 | TCGGCACCTGCTACTTACCAACTGGAAAATTTTATGCATCCCATGA |
| 3529 | IFI30 | 3824888 | CAGATACACAAAATTCCACCCCATGATCAAGAATCCTGCTCCACTAAGAATGGTGCTAAAGTA AA |
| 3530 | ZNF486 | 3826181 | TCATTGCAATTTAGAGATGTGGCTGTAGAA |
| 3531 | ZNF486 | 3826182 | GTATTATTGTCTCTAAGCCAGACCTGATCACCTGTCTGGAGCAAGGAATAAAACCTCTGACT |
| 3532 | ZNF486 | 3826184 | TTGAAATATATAGAAGGTGACAAAGCT |
| 3533 | ZNF486 | 3826185 | AGTACTTCTCTAGCTTTACTACACATAAGAAAATTCATAGTGGAGAGAAACCCTACATTTGTG AAGAATGTGGCAAAGCCTTTATGTACCCCTATACCCTTACTACACATAAGATAATCCATACTGG AGAGCAACCCTACAAATGTAAAGAATGTGACAAAGCTTTTAACCATCCTGCAACTCTTTCTTCA CATAAGAAAATTCATACTGGAGAGAAACCGTACACGTGTGATAAATGTGGCAAAGCCTTTATT TCATCCTCGATCCTTAGTAAACATGAGAAGATTCATACGGGGAGAAAACCCTACAAATGTGAA GAATGTGGCAAAGCCTTCACCCGCTCCTCACACCTTACTATGCATAAGATAATTCATACTGGA GAGAAACCATACAAATGTGAAGAATGTGGCAAAGCCTTTACATGGTCTGCAGGCCTCCATAA ACATAGGAGAACTCATACTGGAGAGAAACCCTACAAATGTGAAGAATGTGGCAAAGCGTATA CTACATCCTCAAATCTAACTGAACATA |

TABLE 13-continued

Subtyping Target Sequences

| SEQ ID NO. | Gene | Affy Probeset ID | Sequence |
|---|---|---|---|
| 3534 | ZNF486 | 3826186 | GGTTCATAAAAGAGCAATTACTGTGACAAAAATCTTTCAGAAAATATAAGCCTTTAAGGTGAAGAAGAGTATTGATTCTGAAGACAAGCATTACAAATATAAAGAGGTTTGTAGTACCTTTGCTTGTATTACAGATCTTATTGCCCGCGTTTTGTATTAGAAGGAAACCCTAAAGCGGTTGCCAAACTTTGTG |
| 3535 | ZNF486 | 3826187 | TGAGATCAGACTGACCAAAACGGAGAAACCCAGTCTCTACTGAAAATATAAAATTAGCCATGCATGGTGGCACATGCCTGTAATCCCAGCTACTCAGGAGGCTTGAACCCTGGAGGCAGAGGTTGTGGTGAGTCGAGATCATTGCACTCCAGCCTGGGCAATAAGAGTGAAACTCTGTCTCCAGGAAAAAAAAAAATTTATTTGTGTATAACTTTAAAAGCAGATTTTTGGAAGCATTGTAATT |
| 3536 | UPK1A | 3830664 | GTCCCTGTTTGCTGAGACCATATGGGTGACAGCCGACCAGTACCGTGTATACCCACTGATGGGAGTCTCAGGCAAGGATGACGTCTTCGCTGGTGCCTGGATTGCCATCTTCTGCGGCTTCTCCTTCTTCATGGTAGCCAGTTTTGG |
| 3537 | UPK1A | 3830665 | TGGTGCTCATGCTCATCGTCTACATCTTCGAGTGCGCCTCCTGCATCACGTCCTACACCCACCGTGACTA |
| 3538 | UPK1A | 3830666 | ATGGTGTCCAACCCATCCCTGATCACCAAGCAGATGCTGACCTTCTACAGCGCGGACACCGACCAGGGCCAGGAGCTGACCCGCCTCTGGGACCGCGTCATGATT |
| 3539 | UPK1A | 3830668 | AGAATGCTGTGGCACATCTGGTCCCATGGACTGGGTGAACTTCACGTCAGCCTTCCGGGCGGCCACTCCGGAGGTGGTGTTCCCCTGGCCCCACTGTGCTGTCGCCGGACGGGAAACTTCATCCCCCTCAACGAGGAGGGCTGCCGCCTGGGGCACATGGACTACCTGTTCA |
| 3540 | UPK1A | 3830669 | ACGCCATCGACAGCTACACGTGGGGTATCTCGTGGTT |
| 3541 | UPK1A | 3830670 | GATAGCCATGTATTTCTACACCATGC |
| 3542 | UPK1A | 3830671 | GAGGGGAAGGCAACATACACACCCCGGACTCCTCCGCATC |
| 3543 | UPK1A | 3830672 | CCACTTCCAAGATCTTTTTCCAGGTTCCTGAGCCCTACTGTGTCTCAG |
| 3544 | UPK1A | 3830673 | GTGCACATATCCTTAGCCCATCTTTCAAGGGACCTCTCCATGATCCCACCTCCCATTCACAGATACCTCTCTTGTAGCTCTCTGACCTCCTC |
| 3545 | UPK1A | 3830674 | GCATCGCCATTCTTGCTGAACCGTTTGT |
| 3546 | UPK1A | 3830675 | TCTGGAAGCCTCTATTGCCATGAGAGTTCTGTCACGGTCACTTTACTGTCCCCATCATCACCCAGCACGGGGCTAAGCATATACTAGATAGTC |
| 3547 | IGFL1 | 3836693 | CCCATGACTCCTTACCTGATGCTGTGCCAG |
| 3548 | IGFL1 | 3836694 | AGATGTGGGGACAAGTTCTACGACCCCCTGCAGCACTGTTGCTATGATGATGCCGTCGTGCCCTTGGCCAGGACCCAGACGTGTGGAAACTGCACCTTCAGAGTCTGCTTTGAGCAGTGCTGCCCCTGGACCTTCATGGTGAAGCTGATAAACCAGAACTGCGACTCAGCCCGGACCTCGGATGACAGGCTTTGT |
| 3549 | IGFL1 | 3836695 | TTCTGTGACCTGTCTGAGGCCCACCCTGCAGCTGCCCTGAGGAGGCCCACAGGTCCCCTTCTAGAATTCTGGACAGCATGAGATGCGTGTGCTGATGGGGGCCCAGGGACTCTGAACCCTCCTGATGACCCCTATGCCAACATCAACCCGGCACCACCCCAAGGCTGGCTGGGGAACCCTTCACCCTTCTGTGAGATTTTCCATCATCTCAAGTTCTCTTCTATCCAGGAGCAAAGCACAGGATCATAATA |
| 3550 | CGB2 | 3838162 | CCTTCCAAGCCCATCCCGACTCCCGGGGCCCTCAGACACCCCGATCCTCCCACAATAAAGGCTTCTC |
| 3551 | MYADM | 3841081 | CTGCCGCTGTCGTCTTTGCTTCAGCCGCAGTCGC |
| 3552 | MYADM | 3841082 | CCCGCGGGGTTAAGATCACACACGCGCCCACGCCGGCCCGCGGGGCGTGCACTTTCGCTGGGTTCCGTCCGCCGCAG |
| 3553 | MYADM | 3841083 | TGCTGGGTTCCACGCCACGTTCCTGTCTCCGCAG |
| 3554 | MYADM | 3841084 | CGTTCGATCCCTAGAGGGAGGAGCCTGTCCAAACGGACGCTAACGGCCTACCTCCCCCTCAG |
| 3555 | MYADM | 3841085 | TGCTCTTACAGCCTGTTCCAAGTGTGGCTTAATCCGTCTCCACCACCAG |
| 3556 | MYADM | 3841088 | ATGCCAGTGACGGTAACCCGCACCACCATCACAACCACCACGACGTCATCTTCGGGCCTGGGGTCCCCCATGATCGTGGGGTCCCCTCGGGCCCTGACACAGCCCCTGGGTCTCCTTCGCCTGCTGCAGCTGGTGTCTACCTGCGTGGCCTTCTCGCTGGTGGCTAGCGTGGGCGCCTGGACGGGGTCCATGGGCAACTGGTCCATGT |
| 3557 | MYADM | 3841089 | TTCTCCGTGACCCTGATCATCCTCATCGTGGAGCTGTGCGGGCTCCA |

TABLE 13-continued

Subtyping Target Sequences

| SEQ ID NO. | Gene | Affy Probeset ID | Sequence |
|---|---|---|---|
| 3558 | MYADM | 3841090 | CTGCATCGCGTGTGTGGCTTACGCCACCGAAGTGGCCTGGACCCGGGCCCGGCCCGGCGAGA TCACTGGCTATATGGCCACCGTACCCGGGCTGCTGAAGGTGCTGGAGACCTTCGTTGCCTGCA TCATCTTCGCGTTCATCAGCGACCCCAACCTGTACCAGCACCAGCCGGCCCTGGAGTGGTGCG TGGCGGTGTACGCCATCTGCTTCATCCTAGCGGCCATCGCCATCCTGCTGAACCTGGGGGAGT GCACCAACGTGCTACCCATC |
| 3559 | MYADM | 3841091 | CCTCGGCGCTCGAGAGATGTAAGCTGCAGCCGCAGCCATGCCTACTACGTGTGTGCCTGGGA CCGCCGACTGGCTGTGGCCATCCTGACGGCCATCAACCTACTGG |
| 3560 | MYADM | 3841092 | ATGTGGCTGACCTGGTGCACTCTGCCCACCTGGTTTTTGTCA |
| 3561 | MYADM | 3841093 | ATGGAGTACTTCTTTCCTCCGCCTTTCCTCTGTTTTCCTCTTCCTGTCTCCCCTCCCTCCCACCTTT TTCTTTCCTTCCCAATTCCTTGCACTCTAACCAGTTCTTGGATGCATCTTCTTCCTTCCCTTTCCTC TTGCTGTTTCCTTCCTGTGTTGTTTTGTTGCCCA |
| 3562 | MYADM | 3841094 | TTGCCTGTCGGCTTTCTTATCTGCCTGTTTTGCAAGCACCTTCTCCTGTGTCCTTGGGAGCCCTG AGACTTCTTTCTCTCCTTGCCTCCACCCACCTCCAAAGGTGCTGAGCTCACATCCACACCCCTTG CAGCCGTCCATGCCACAGC |
| 3563 | MYADM | 3841095 | GGAGGAAGGTGTGCAGTGTACTTCCCCTTTAAAT |
| 3564 | MYADM | 3841096 | ATTTGGAGGTCAGTAATTTCCAATGGGCGGGAG |
| 3565 | MYADM | 3841097 | GTCCCTAGGCCCCGCCTGGCACTCAGCCTTGCCAGAGATTGGCTCCAGAATTTTTGCCAGGCT TACAGAACACCCACT |
| 3566 | MYADM | 3841098 | AACTATTCTCTGTGGTATCAAAAAGA |
| 3567 | MYADM | 3841099 | GGCCCTCTGTGTTAAGAATAACGTGTCCTGCTTTGGCAGAGAGAAGAAAATAGCCACTGCCC GCTTTCAAGGCAAGATCGACCTTTTCTGTTTTGTTTTGTTTTCTTTCTTTTTCCTGGCCATGAG GACAAAAATTACTGAGTGGCCCTTAAAGAGGGAAGTTTGTTTTCAGCTGTTCTCTTTTGCCCGT AGGTGGGAGGGTGGGATTGCTGCGTCCTAGCTAGAGGAATGGCTTTGCTTGAATGTGTAGT GCACACGCACGGGTGTTTCTGTGTGCTAGTTGCTTCTTGCTGCTGCTTCCTGCTTGTCTGGGAC TCACATACATAACGTGATATATATATATATATATATAAATGTATAAATATATATTTTATTTTTTTT TAAATCCCTGGAGCTTCTGGTTCCTATCAGTTC |
| 3568 | C3 | 3848041 | CTACATCATCGGGAAGGACACTTGGGTGGAGCACTGGCCCGAGGAGGACGAATGCCAAGAC GAAGAGAACCAGAAACAATGCCAGGACCTCGGCGCCTT |
| 3569 | C3 | 3848042 | TGAGTGCTTTCCCTGCGCGTGCGCGCGACCGCCCGACTGCCCCGCCCATGCCACGCCCACACC ATTGTCACGCCCCTGCGCC |
| 3570 | C3 | 3848043 | AGGTTGGACAGCAGCGCACGTTCATCAGCCCCATCAAGTGCAGAGAAGCCCTGAAGCTGGA GGAGAAGAAACACTACCTCATGTGGGGTCTCTCCTCCGATTTCTGGGGAGAG |
| 3571 | C3 | 3848044 | TTCAGCTGTCCAATGACTTTGACGAGTACATCATGGCCATTGAGCAGACCATCAAGTCAG |
| 3572 | C3 | 3848046 | GTGAGTTCCCTGGAGCCGGGAACAG |
| 3573 | C3 | 3848047 | AAGCTGTACCCGGTTCTACCATCCGGAAAAGGAGGATGGAAAGCTGAACAAGCTCTGCCGTG ATGAACTGTGCCGCTGTGCT |
| 3574 | C3 | 3848048 | TCTGATGGTTCCAGGGGCCTGAGAGTCCCAG |
| 3575 | C3 | 3848049 | CTCACACTCTGAGGATGACTGTCTAGCTTTCAAAGTTCACCAATACTTTAATGTAGAGCTTATC CAGCCTGGAGCAGTCAAGGTCTACGCCTATTACAACCTG |
| 3576 | C3 | 3848052 | TATGTCTATATTGGACATATCCATGATGACTGGCTTTGCTC |
| 3577 | C3 | 3848053 | GCAGGGTCAACATCACCATAGTCTGCTATTCTTTGATAACTCCATTTATGCTGTCTTTGAAGTT CACTTCTGGCATTATCACTTTTCATTTCTTTGCTGCATTTTTATCTTTGTTGGCCAGTTCCCTCTT TTCGTGATACATTGTTGTAAAATCTCATGGGAGTTAGCCACCTGGAGACAGGGAGGCAACAG AACTACACACTTTGCTGTCTGTGCATAAATTGAAGAGCAGAAGCTCAGTGACCAATCACTGAT GGACTTTGAAAGGAGTGACAGTAATTGGCCCTCAATTATGATGCTTATCTTTTATTTATGTCGT GATTTCTAGACTGAAGAGTTAGCAACAAAGTTTATACACATATGCAACTACTCGTGATCAATAT ACCAAGGTACTGAAAAAGAACCATGTCACTGGGCTACTAGTGTTATTTAACTGAATCATGCAG AGTGAGGGCTGCCTGTATTCTTGCCTTGTTTTCTAGAACTGAAGCATGGAGGGTCAAATAATG CATCCAATGTTATTTAGAGCTGGAATTTGAATCCATGCAGTTGGGTGCAGAGTCTGAGCTCTT AATCACCTTGACCATTACATTACCTTGCTTTTTAATTTCCTTTGGGGAAATGTTTCCTAAAAATG TAACGCCCCTCTGTGCTGCTATGTGGGAATCAGAAGTCTCAGTGCCTGATCAGACCTCCTTGTC |
| 3578 | C3 | 3848054 | TAAGAAGCTAGGTCACCGGGGTTCATCTTGGCCATCCCTCTATCTCTAGCAAGAATTCTTGCA AATAATATCCATGATATTCAGTACTTTCCAAGTACACTGTGTATCTGATACTGTT |

TABLE 13-continued

Subtyping Target Sequences

| SEQ ID NO. | Gene | Affy Probeset ID | Sequence |
|---|---|---|---|
| 3579 | C3 | 3848055 | AAAGAGGCCTCAGGATGCCAAGAACACTATGATCCTTGAGATCTGTACCAG |
| 3580 | C3 | 3848057 | CATGCTAAGGCCAAAGATCAACTCACCTGTAATAAATTCGACCTCAAGGTCACCATAAAACCAGCACCGGAAACA |
| 3581 | C3 | 3848059 | AGGAAAAGGCCAAGGCACCTTGTCG |
| 3582 | C3 | 3848061 | ACCTTCATGGTGTTCCAAGCCTTGGCTCAATACCAAAAGGACGCCCCTGACCACCAGGAACTGAACCTTGATGTGTCCCTCCAACTGCCCAGCCGCAGCTCCAAGATCACCCACCGTATCCACTGGGAATCTGCCAGCCTCCTGCGATCAGAAGAG |
| 3583 | C3 | 3848065 | CGTTGGCTCAATGAACAGAGATACTACGGTGGTGGCTATGGC |
| 3584 | C3 | 3848066 | ATAAGAACCGCTGGGAGGACCCTGGTAAGCAGCTCTACAACGTGGAGGCCACATCCTATGCCCTCTTGGCCCTACTGCAGCTAAAA |
| 3585 | C3 | 3848067 | GCCAAGCTGAGATGGATAGTCCTAAGGTATCAAGCTGGGATGCATAACCCTGAGCTGAGCTGGGATGCACGGCTCTAAGTTTTCGCAGGTCCTCATTGTAAACCACACGAGAAAGTTTGTTGCGTCATTTATTCAACAAATGCGTATTAAGCATTCATTTCAAAGGGAGAAGTGAGAGTTGATGAAACAAGAGAGGTAAGGCAGGAGCCAAGTAATTGAGAGCCTCGAATGTCAGCCAGGACACCCAAACACCAGGAAGTCTAGCATGCATCTC |
| 3586 | C3 | 3848068 | CCTTGAAGCCAACTACATGAACCTACAGAGATCCTACACTGTGGCCATTGCTGGCTATGCTCTGGCCCAGATGGGCAGGCTGAAGGGGCCTCTTCTTAACAAATTTCTGACCACAGC |
| 3587 | C3 | 3848074 | CCGCCTACGTGGTCAAGGTCTTCTCTCTGGCTGTCAACCTCATCGCCATCGACTCCCAAGTCCTCTGCGGGGCTGTTAAATGGCTGATCCTGGAGAAGCAGAAGCCCGACGGGGTCTTCCAGGAGGATGCGCCCGTGATACACCAAGAAATG |
| 3588 | C3 | 3848075 | AGCTCTGCCTTTGCGGCCTTCGTGAAACGGGCACCCAGCACCTG |
| 3589 | C3 | 3848076 | CGCGGAACGGCTGAAGCACCTCATTGTGACCCCCTCGGGCTGCGGGGAACAGAACATGATCGGCATGACGCCCACGGTCATCGCTGTGCATTACCTGGATGAAACGGAGCAGTGG |
| 3590 | C3 | 3848077 | TGCAGACCTCAGTGACCAAGTCCCGGACACCGAGTCTGAGACCAGAATTCTCCT |
| 3591 | C3 | 3848078 | ACAAAACTGTGGCTGTTCGCACCCTGGATCCAGAACGC |
| 3592 | C3 | 3848080 | CAAGAGGCGTCACCAGCAGACCGTAACCATCCCCCCCAAGTCCTCGTTGTCCGTTCCATATGTCATCGTGCCGCTAAAGACCGGCCTGCAGGAAGTGGAAGTCAAGGCTGCTGTCTACCATCATTTCATCAGTGACGGTGTC |
| 3593 | C3 | 3848081 | GGGTAGGTAGCCTGTTGCACACACACTTGCCCGGATCCTTTCTCTC |
| 3594 | C3 | 3848082 | GTGGAAATCCGAGCCGTTCTCTACAATTACCGGCAGAACC |
| 3595 | C3 | 3848083 | CTGTGTGGCAGACCCCTTCGAGGTCACAGTAATGCAGGACTTCTTCATCGACCTGCGGCTACCCTACTCTGTTGTTCGAAACGAGC |
| 3596 | C3 | 3848085 | TTGCAGAAGAGAACATCGTTTCCCGAAGTGAGTTCCCAGAGAGCTGGCTGTGGAACGTTGAGGACTTGAAAGAGCCACCGAAAAATGG |
| 3597 | C3 | 3848088 | GACGGCATGCGGGAGAACCCCATGAGGTTCTCGTGCCAGCGCCGGACCCGTTTCATCTCCCTGGGCGAGGCGTGCAAGAAGGTCTTCCT |
| 3598 | C3 | 3848089 | GACGCCGTTCCGTGCAGCTCACGGAGAAGCGAATGGACAAA |
| 3599 | C3 | 3848090 | AGGATTACGCCGGTGTCTTCTCCGACGCAGGGCTGACCTTCACGAGCAGCAGTGGCCAGCAGA |
| 3600 | C3 | 3848092 | CCAGTCAGAAGACCGGCAGCCTGTACCTGGGCAGCAGATGACCCTGAAGATAGAGGGTGACCACGGGGCCCGGTGGTACTGGTGGCCGTGGACAAGGGCGTGTTCGTGCTGAATAAGAAGACAAACTGACGCAGAGTAAG |
| 3601 | C3 | 3848093 | AACAAGGGCAGGCTGTTGAAGGCGGGACGCCAGGTGCGAGAGCCCGGCCAGGACCTGGTGTGCTGCCCCTGTCCATCACCACCGACTTCATCCCCTTCCTTCCGCCTGGTGGCGTACTACACGCTGATCGTGCCAGCGGCCAGAGGGAGGTGGTGGCCGACTCCGTGTGGGTGGACGTCAAGGACTCCT |
| 3602 | C3 | 3848094 | CATCCCGGATCCCTCCCTGCGTTCCCTGCCACTC |
| 3603 | C3 | 3848095 | AGGCTACCAGGACCATGCAGGCTCTGCCCTACAGCACCGTGGGCAACTCCAACAATTACCTGCATCTCTCAGTGCTACGTACAGAGCTCAGACCCGGGGAGACCCTCAACGTCAACTTCCTCCTGCGAATGGACCGCGCCCACGAGGCCAAGAT |

TABLE 13-continued

Subtyping Target Sequences

| SEQ ID NO. | Gene | Affy Probeset ID | Sequence |
|---|---|---|---|
| 3604 | C3 | 3848096 | TGTTCGTGACGAACCCTGATGGCTCTCCAGCCTACCGAGTCCCCGTGGCAGTCCAGGGCGAGGACACTGTGCAGTCTCTAACCCAGGGAGATGGCGTGGCCA |
| 3605 | C3 | 3848097 | CCCATCGTGACCTCTCCCTACCAGATCCACTTCACCAAGACACCCAAGTACTTCAAACCAGGAATGCCCTTTGACCT |
| 3606 | C3 | 3848098 | TTGTGCTGAGCCGGAAGGTACTGCTGGACGGGGTGCAGAACCCCGAGCAGAAGACCTGGTGGGGAAGTCTTTGTACGTGTCTGCCACCGTCATCTTGCACTCA |
| 3607 | C3 | 3848099 | AGAAAGTGGAGGGAACTGCCTTTGTCATCTTCGGGATCCAGGATGGCGAACAGAGGATTTCCCTGCCTGAATCCCTCAAG |
| 3608 | C3 | 3848100 | AGTTTCGAGGTCATAGTGGAGCCTACAGAGAAATTCTACTACATCTATAACGAGAAGGGCCTGGAGGTCACCATCACCGCCAG |
| 3609 | C3 | 3848101 | GGCCAGTGGAAGATCCGAGCCTACTATGAAAACTCACCACAGCAGGTCTTCTCCACT |
| 3610 | C3 | 3848102 | GTCAAGCAGGACTCCTTGTCTTCTCAGAACCAGCTTGGCGTCTTGCCCTTGTCTTGGGACATTCCGGA |
| 3611 | C3 | 3848103 | GTGCCAGCCAGAGGGGCCCCAGGGGAAGCAGGGGCACA |
| 3612 | C3 | 3848105 | CCAACAGGGAGTTCAAGTCAGAAAAGGGGCGCAACAAGTTCGTGACCGTGCAGGCCACCTTCGGGACCCAAGTGGTGGAGAAGGTGGTGCTGGTCAGCCTGCAGAGCGGGTACCTCTTCATCCAG |
| 3613 | C3 | 3848106 | CCCACGACGCGCAAGGGGATGTTCCAGTCACTGTTACTGTCCACGACTTCCCAGGCAAAAAACTAGTGCTGTCCAGTGAGAAGACTGTGC |
| 3614 | C3 | 3848107 | GCTGCTCCTGCTACTAACCCACCTCCC |
| 3615 | C3 | 3848108 | GTCCCTCTGACCCTGCACTGTCCCAGCACC |
| 3616 | C3 | 3848109 | TGCGCCTGGCAAGGGGATGCAGTTTCA |
| 3617 | C3 | 3848112 | GTCCGTGGATTCTGCTTTCAGTTAAACCCTGATCACTTCACCTCCCTGAGCCTCAGTTACCTTATCTGAATATCGGGATCATGACGGATAATTGTATGTCATCTATTCTACCGACGGCAGCCAGAGGACGCCTGTGAGCACCTGAGTCAGGGCCCATCCCTGCTCTGCCTACAGCCCTCCATGGCTCCCACCTTCCTATGCGTCAAAGCCCAAGTCCTCCCTGCAGTCCACAAGGCCCTGCACACCTTGCCCTGTCCCTTCCCTGCCCTCCCCTCCTCCCTCTCTCCCCCTCGTTCACTCTTTCTGGAGCCACACGGGCCATCCTCCCTGTTCCTCCAACACCCAGGTGCAGTCCTGCCTTGGCGCCTTGGCACGGGCTGTGCCCTCTTCTCAAGAAAACCCTCTTCTTCCAAATATCCACACAGCTTGTTCTCTCTCCTCCTTTAAGTCTTTGCTCAAATGTCACCAATGTCTCAATTTTACAATGAGGTCTCTCTGAGTAACCTATAAAGTCGCAAATACCCACCCTGAGCGTCCCCCCTCCCCGCTACACACTCCTCCTTCCTGCCATGTCCTGCAAATGAGATTTATTCATTTGATAATTGCTTCTCCCATCGCCTCGCCCTCTATTGAACCTAAATCCCTCCAGGAAGGAATTGTTATGTTTGTTGAGGGTTTTGTCACCTGAACTCAGC |
| 3618 | C3 | 3848119 | CTCCCTTCCAGCTATGTGTACAATAATGACCAATCTGTTTGGCTACGCCGTTGTCTTGCCTTTTTGGGGGTTGGGGTCTACACGGAGGTTGTGTTTACAATGTAGAAACCTGTTTTCGCTGTGTGTGGCGGGGGCGCGGGCACAGGGTCCGTGTCTTTGTATA |
| 3619 | C3 | 3848120 | ATCTCAGACCAAAGGGTCGTCCTCCCCCAGCATT |
| 3620 | C3 | 3848121 | ACAAAACAGCCAGCGGGCGGGAACTGTTATGA |
| 3621 | MUC16 | 3849299 | GTGCCTTTCCCCCAGCCAGGGTCCAAAGAAGCTTGGCTGGGGCAGAAATAAACCATAT |
| 3622 | MUC16 | 3849300 | TGACCACCCGCCGGCGGAAGAAGGAAGGAGAATACAACGTCCAGCAACAGTGCCCAGGCTACTACCAGTCACACCTAGACCTGGAGGATCTGC |
| 3623 | MUC16 | 3849301 | GGCTGTCATCCTCATCGGCTTGGCAGGACTCCTGGGAGTCATCACATGCCTGATCTGCGGTGTCCTG |
| 3624 | MUC16 | 3849302 | CCCAACAGAAATGAGCCCTTAACTGGGA |
| 3625 | MUC16 | 3849304 | GGTGGACTCCCTGTGTAACTTCTCGCCACTGGCTCGGAGAGTAGACAGAGTTGCCATCTATGAGGAATTTCTGCGGATGACCCGGAATGGTACCCAGCTGCAGAACTTC |
| 3626 | MUC16 | 3849306 | TTCTACCTGAATTTCACCATCACCAACCTACCATATTCCCAGGACAAAGCCCAGCCAGGCACCACCAATTACCAGAGGA |
| 3627 | MUC16 | 3849307 | ATGGAGTCATCAGTTTATCAACCAACAAGCAGCTCCA |

TABLE 13-continued

Subtyping Target Sequences

| SEQ ID NO. | Gene | Affy Probeset ID | Sequence |
|---|---|---|---|
| 3628 | MUC16 | 3849309 | CGTGTTGGTCACTGTCAAGGCATTGTTCTCCTCCAATTTGGACCCCAGCCTGGTGGAGCAAGTCTTTCTAGATAAGACCCTGAATGCCTCATTCCATTGGCTGGGCTCCACCTACCAGTTGGT |
| 3629 | MUC16 | 3849311 | AGGCAGTCAACTACATGACACATTCCGCTTCTGCCT |
| 3630 | MUC16 | 3849312 | CCCAGAATTTATCAATCCGGGGCGAGTACCAGATAAATTTCCACATTGTCAACTGGAACCTCAGTAATCCAGACCC |
| 3631 | MUC16 | 3849313 | CTATGTCCTGGACAGGGATAGCCTCTTCATCAA |
| 3632 | MUC16 | 3849315 | CAGCATGGGCCCCTTCTACTTGGGTTGCCAACTGATCTCCCTCA |
| 3633 | MUC16 | 3849316 | CATGGGGTACCACCTGAAGACCCTCACACTCAACTTCACCATCTCCAATCTCCAGTATTCACCAGATATGGGCAAGGGCTCAGCTACATTCAACTCCACCGAGGG |
| 3634 | MUC16 | 3849317 | GCCTCCTCTGTCAGAAGCCACAACAG |
| 3635 | MUC16 | 3849319 | AGACACGGGTGGACCTCCTCTGCACCTACCTGCAGCCCCTCAGCGGCCCAGGTCTGCCTATCAAGCAGGTGTTCCATGAGCTGAGCCAGCAGACCCATGGCATCACCCGGCTGGGCCCCTACTCTCTGGACAAAGACAGCCTCTACCTT |
| 3636 | MUC16 | 3849320 | GAGCAGCCTGGGTGCACGGTACACAGGCTGCAGGGTCATCGCACTAAG |
| 3637 | MUC16 | 3849321 | TCACACTGAACTTCACCATCAACAACCTGCGCTACATGGCGGACATGGGCCAACCCGGCTCCCTCAAGTTCAACATCACAG |
| 3638 | MUC16 | 3849324 | AGCTGACCCACAGCATCACTGAGCTGGGCCCCTACACACTGGACAGGGACAGTCTCTATGTCAATG |
| 3639 | MUC16 | 3849326 | GCCCTTGTTCAAGAACACCAGTGTTGGCCCTCTGTACTCTGGCTGCAG |
| 3640 | MUC16 | 3849327 | AACATGTGGCCTGGCTCCAGGAAGTTCAA |
| 3641 | MUC16 | 3849328 | TGGGAGCATCTAAGACTCCAGCCTCGATATTTGGCCCTTCAG |
| 3642 | MUC16 | 3849329 | ACTCATCGGAGCTCTGTGTCCACCACCAGC |
| 3643 | MUC16 | 3849330 | TATGCCCTGGACAACGACAGCCTCTTTGTCA |
| 3644 | MUC16 | 3849331 | TGTTCAAGAGCACCAGTGTTGGCCCTCTGTACTCTGGCTGCAGACT |
| 3645 | MUC16 | 3849332 | TCACCAACCTGCGGTATGAGGAGAACATG |
| 3646 | MUC16 | 3849333 | ACATCTGGGACTCCAGTTTCTAAACC |
| 3647 | MUC16 | 3849336 | AGCTGACCCACAGCATCACTGAGCTGGGCCCCTACACCCTGGACAGGGACAGTCTCTATGTCAATG |
| 3648 | MUC16 | 3849338 | TGTTCAAGAACACCAGTGTTGGCCCTCTGTACTCTGGCTGCAGACT |
| 3649 | MUC16 | 3849340 | CCTGGTGCTATTCACAATTAACTTCACCATCACTAACCTGCGGTATGAGGAGAACATGCATCACCCTGGCTCTAGAAAGTTTAACACCACGGAGAGA |
| 3650 | MUC16 | 3849341 | TGGCAACCTCGAGAACTCCAGCCTCCCTGT |
| 3651 | MUC16 | 3849342 | ACCCATCAGAGCTCTATGACGACCACCAGAA |
| 3652 | MUC16 | 3849343 | AGTGGATGCTGTCTGCACCCATCGTCCTGA |
| 3653 | MUC16 | 3849345 | TGCCCTTGTTCAAGAACACCAGTGTCAGCTCTCTGTACTC |
| 3654 | MUC16 | 3849347 | TTTTACCATCACTAACCTGCAGTAT |
| 3655 | MUC16 | 3849348 | CTTTCACAGTACAGCCGGAAACCTCTGAGACTCCATCATCC |
| 3656 | MUC16 | 3849350 | ATGGAGTAGCCACCAGAGTGGACGCCATCTG |
| 3657 | MUC16 | 3849351 | TGTTCAAGAGCACCAGTGTTGGCCCTCT |
| 3658 | MUC16 | 3849353 | TCCTTGGACTTCCACAGTTGACCTT |
| 3659 | MUC16 | 3849355 | CACCACCTTAACCCTCAAAGCCCTGGACTGGACA |
| 3660 | MUC16 | 3849357 | GGCCCTCTGTACTCTGGCTGCAGACT |

TABLE 13-continued

Subtyping Target Sequences

| SEQ ID NO. | Gene | Affy Probeset ID | Sequence |
|---|---|---|---|
| 3661 | MUC16 | 3849359 | TCTCCTGGTGCCGTTCACCCTCAACTTTACCATCACCAATCTGCAGTATGGGGAGGACATGCG<br>TCACCCTGGCTCCAGGAAGTTCAACACCAC |
| 3662 | MUC16 | 3849360 | GGGACCTCCACAGTGGACCTTGGGACCTCAGGG |
| 3663 | MUC16 | 3849362 | TGACCCATGGCATCAAAGAGCTGGG |
| 3664 | MUC16 | 3849363 | GGCCTTCTGTACTCTGGCTGCAGACT |
| 3665 | MUC16 | 3849365 | ATCACCAACCTGCAGTACGAGGAGGACATGCATCACCCAGGCTCCAGGAAGTTCAACACCAC<br>GGAG |
| 3666 | MUC16 | 3849366 | GGGACCTCCACAGTGGACCTTGGGACCTCAGGG |
| 3667 | MUC16 | 3849367 | CCCATCAGACCTCTGCGCCCAACACCAGCA |
| 3668 | MUC16 | 3849368 | TGGAGTGGATGCCATCTGCACCCACCGTCTTGACCCCAAAAGCCCTGGAGTGGACAGGGAGC<br>AGCTATACTGGGAGCTGAGCCAGCTGACCAATGGCATCA |
| 3669 | MUC16 | 3849370 | TGTTCAAGAACACCAGTGTTGGCCCTCTGTACTCTGGCTGCAGACT |
| 3670 | MUC16 | 3849372 | TCTCCTGGTGCCGTTCACCCTCAACTTCACCATCACCAACCTGAAGTACGAGGAGGACATGCA<br>TTGCCCTGGCTCCAGGAAGTTCAACACCAC |
| 3671 | MUC16 | 3849373 | TCCACAGTGGACCTTGGGTCAGGGACTCCATCCTCCCTCC |
| 3672 | MUC16 | 3849375 | TGGAGTGGATGCCATCTGCACCCACCGTCTTGACCCCAAAAGCCCTGGAGTGGACAGGGAGC<br>AGCTATACTGGGAGCTGAGCCAGCTGACCAATGGCATCAAAGAGCTGGGCCCCTACACCCTG<br>GACAGGAACAGTCTCTATG |
| 3673 | MUC16 | 3849377 | GGCCTTCTGTACTCTGGCTGCAGACT |
| 3674 | MUC16 | 3849379 | CCTGGCTCCAGGAAGTTCAACACCAC |
| 3675 | MUC16 | 3849380 | GGGACCTCCACAGTGGACCTTGGAACCTCAGGGACTCCATTCTCCCTCCCAAGCCCCGCA |
| 3676 | MUC16 | 3849381 | TTTCACCCATCGGACCTCTGTGCCCACCAGCA |
| 3677 | MUC16 | 3849382 | GGCATCAAAGAGCTGGGCCCCTACACCCTGGACAGGAACAGTCTCTATGTCAATG |
| 3678 | MUC16 | 3849383 | TGTTGGCCCTCTGTACTCTGGCTGCAGACT |
| 3679 | MUC16 | 3849384 | CCTGGCTCCAGGAAGTTCAACACCAC |
| 3680 | MUC16 | 3849385 | CCTCCACAGTGGATCTCAGAACCTCAGGGACTCCATCCTCCC |
| 3681 | MUC16 | 3849388 | TAAGCAAACTGACCAATGACATTGAAG |
| 3682 | MUC16 | 3849389 | GCCCTTGTTCAAGAACACCAGTGTTGGCCCTCTGTACTCTGGCTGCAGA |
| 3683 | MUC16 | 3849390 | ATCACCAACCTGCAGTACGAGGAGGACAT |
| 3684 | MUC16 | 3849391 | CCTGGGACCTCCACAGTGGATGTGGGAACCTCAGGGACTCCATCCTCCAG |
| 3685 | MUC16 | 3849393 | TTTCACCCATCGAAGCTCTATGCCCACCACCA |
| 3686 | MUC16 | 3849394 | GAAGGATAGCTCAGCCACGGCAGTGGATGCCATCTGCACACATCGCCCTGACCCTGAAGACC<br>TCGGACTGGACAGAGAGCGACTGTACTGGGAGCTGAGCAATCTGACAAATGGCATCAGGA |
| 3687 | MUC16 | 3849396 | CCTTGTTCAGGAATAGCAGTCTGGAATACCTCTATTCAGGCTGCAGACTAGCCTCACTC |
| 3688 | MUC16 | 3849397 | ATCACCAACCTGCAGTACGAGGAGGACAT |
| 3689 | MUC16 | 3849398 | GGATTTCCACATCCTCCATCCCCAGCTCCACAG |
| 3690 | MUC16 | 3849400 | CGTCGGTACTGGACCCCTGCCACCAGCA |
| 3691 | MUC16 | 3849403 | TCGCCTGCTGTATCACGGTTGGTGACCTCAATGGTCACCAGTTTGGCGGCAAAGACAAGTACA<br>ACTAATCGAGCTCTGACAAAACTCCCCTGGTGAACCAGCTACAACAGTTTCATTGGTCACGCAT<br>CCTGCACAGACCAGCCCAACAGTTCCCTGGACAACTTCCATTTTTTTCCATAGTAAATCAGACA<br>CCACACCTTCAATGACCACCAGTCATGGGCAGAATCCAGTTCAGCTGTTCCAACTCCAACTG<br>TTTCAACTGAGGTACCAGGAGTAGTGACCCCTTTGGTCACCAGTTCTAGGGCAGTGATCAGTA<br>CAACTATTCCAATTCTGACTCTTTCTCCTGGTGAACCAGAGACCACACCTTCAATGGCCACCAG |

TABLE 13-continued

Subtyping Target Sequences

| SEQ ID NO. | Gene | Affy Probeset ID | Sequence |
|---|---|---|---|
| | | | TCATGGGAAGAAGCCAGTTCTGCTATTCCAACTCCAACTGTTTCACCTGGGGTACCAGGAGT<br>GGTGACCTCTCTGGTCACTAGTTCTAGGGCAGTGACTAGTACAACTATTCCAATTCTGACTTTT<br>TCTCTTGGTGAACCAGAGACCACACCTTCAATGGCCACCAGTCATGGGACAGAAGCTGGCTC<br>AGCTGTTCCAACTGTTTTACCTGAGGTACCAGGAATGGTGACCTCTCTGGTTGCTAGTTCTAG<br>GGCAGTAACCAGTACAACTCTTCCAACTCTGACTCTTTCTCCTGGTGAACCAGAGACCACACCT<br>TCAATGGCCACCAGTCATGGGGCAGAAGCCAGCTCAACTGTTCCAACTGTTTCACCTGAGGTA<br>CCAGGAGTGGTGACCTCTCTGGTCACTAGTTCTAGTGGAGTAAACAGTACAAGTATTCCAACT<br>CTGATTCTTTCTCCTGGTGAACTAGAAACCACACCTTCAATGGCCACCAGTCATGGGGCAGAA<br>GCCAGCTCAGCTGTTCCAACTCCAACTGTTTCACCTGGGGTATCAGGAGTGGTGACCCCTCTG<br>GTCACTAGTTCCAGGGCAGTGACCAGTACAACTATTCCAATTCTAACTCTTTCTTCTAGTGAGC<br>CAGAGACCACACCTTCAATGGCCACCAGTCATGGGGTAGAAGCCAGCTCAGCTGTTCTAACT<br>GTTTCACCTGAGGTACCAGGAATGGTGACCTCTCTGGTCACTAGTTCTAGAGCAGTAACCAGT<br>ACAACTATTCCAACTCTGACTATTTCTTCTGATGAACCAGAGACCACAACTTCATTGGTCACCC<br>ATTCTGAGGCAAAGATGATTTCAGCCATTCCAACTTTAGCTGTCTCCCCTACTGTACAAGGGCT<br>GGTGACTTCACTGGTCACTAGTTCTGGGTCAGAGACCAGTGCGTTTTCAAATCTAACTGTTGC<br>CTCAAGTCAACCAGAGACCATAGACTCATGGGTCGCTCATCCTGGGACAGAAGCAAGTTCTG<br>TTGTTCCAACTTTGACTGTCTCCACTGGTGAGCCGTTTACAAATATCTCATTGGTCACCCATCCT<br>GCAGAGAGTAGCTCAACTCTTCCCAGGACAACCTCAAGGTTTTCCCACAGTGAATTAGACACT<br>ATGCCTTCTACAGTCACCAGTCCTGAGGCAGAATCCAGCTCAGCCATTTCAACAACTATTTCAC<br>CTGGTATACCAGGTGTGCTGACATCACTGGTCACTAGCTCTGGGAGAGACATCAGTGCAACTT<br>TTCCAACAGTGCCTGAGTCCCCACATGAATCAGAGGCAACAGCCTCATGGGTTACTCATCCTG<br>CAGTCACCAGCACAACAGTTCCCAGGACAACCCCTAATTATTCTCATAGTGAACCAGACACCA<br>CACCATCAATAGCCACCAGTCCTGGGGCAGAAACCACTTCAGATTTTCCAACAATAACTGTCT<br>CACCTGATGTACCAGATATGGTAACCTCACAGGTCACTAGTTCTGGGACAGACACCAGTATAA<br>CTATTCCAACTCTGACTCTTTCTTCTGGTGAGCCAGAGACCACAACCTCATTTATCACCTATTCT<br>GAGACACACACAAGTTCAGCCATTCCAACTCTCCCTGTCTCCCCTGGTGCATCAAAGATGCTG<br>ACCTCACTGGTCATCAGTTCTGGGACAGACAGCACTACAACTTTCCCAACACTGACGGAGACC<br>CCATATGAACCAGAGACAACAGCCATACAGCTCATTCATCCTGCAGAGACCAACACAATGGTT<br>CCCAGGACAACTCCCAAGTTTTCCCATAGTAAGTCAGACACCACACTCCCAGTAGCCATCACC<br>AGTCCTGGGCCAGAAGCCAGTTCAGCTGTTTCAACGACAACTATCTCACCTGATATGTCAGAT<br>CTGGTGACCTCACTGGTCCCTAGTTCTGGGACAGACACCAGTACAACCTTCCCAACATTGAGT<br>GAGACCCCATATGAACCAGAGACTACAGCCACGTGGCTCACTCATCCTGCAGAAACCAGCAC<br>AACGGTTTCTGGGACAATTCCCAACTTTTCCCATAGGGGATCAGACACTGCACCCTCAATGGT<br>CACCAGTCCTGGAGTAGACACGAGGTCAGGTGTTCCAACTACAACCATCCCACCCAGTATACC<br>AGGGGTAGTGACCTCACAGGTCACTAGTTCTGCAACAGACACTAGTACAGCTATTCCAACTTT<br>GACTCCTTCTCCTGGTGAACCAGAGACCACAGCCTCATCAGCTACCCATCCTGGGACACAGAC<br>TGGCTTCACTGTTCCAATTCGGACTGTTCCCTCTAGTGAGCCAGATACAATGGCTTCCTGGGTC<br>ACTCATCCTCCACAGACCAGCACACCTGTTTCCAGAACAACCTCCAGTTTTTCCCATAGTAGTC<br>CAGATGCCACACCTGTAATGGCCACCAGTCCTAGGACAGAAGCCAGTTCAGCTGTACTGACA<br>ACAATCTCACCTGGTGCACCAGAGATGGTGACTTCACAGATCACTAGTTCTGGGGCAGCAACC<br>AGTACAACTGTTCCAACTTTGACTCATTCTCCTGGTATGCCAGAGACCACAGCCTTATTGAGCA<br>CCCATCCCAGAACAGAGA |
| 3692 | MUC16 | 3849404 | AAAATACCCAATGAAGCAGCACACAGAGGTACCATAAGACCAGTCAAAGGCCCTCAGACATC<br>CACTTCGCCTGCCAGT |
| 3693 | MUC16 | 3849406 | GCAGCACTACTGAAGGACGCTTGGTTATGGTCAGTACTTTGGACACTTCAAGCCAACCAGGC<br>AGGACATCTTCATCACCCATTTTGGATACCAGAATGACAGAGAGCGTTGAGCTGGGAACAGT<br>GACAAGTGCTTATCAAGTTCCTTCACTCTCAACACGGTTGA |
| 3694 | MUC16 | 3849408 | CCTGGGGATGCTACTCTGTCCACCATTGCAGAGAGCCTGCCTTCATCCACTCCTGTGCCATTCT<br>CCTCTTCAACCTT |
| 3695 | MUC16 | 3849410 | TCATTTGCCACCACTGGAGTTCCACGAGCCATCTCAGGTTCAG |
| 3696 | MUC16 | 3849412 | TCCAAGGCTACATACCCAGTGGGTACTCCCTCTTCCATGGCTGAAACCTCTATTTCCACATCAA<br>TGCCTGCTAATTTTGAGACCACAGGATTTGAGGCTGAGCCATTTTCTCATTTGACTTCTGGATT<br>TAGGAAGACAAACATGTCCCTGGACACCAGCTCAGTCACACCAACAAATACACCTTCTTCTCCT<br>GGGTCCACTCACCTTTTACAGAGTTCCAAGACTGATTTCACCTCTTCTGCAAAAACATCATCCC<br>CAGACTGGCCTCCAGCCTCACAGTATACTGAAATTCCAGTGGACATAATCACCCCCTTTAATGC<br>TTCTCCATCTATTACGGAGTCCACTGGGATAACCTCCTTCCCAGAATCCAGGTTTACTATGTC |
| 3697 | MUC16 | 3849414 | TGGCCCGGCGACAACCACAGATATCTTGGGTACAAGCACAGAACCTGGAACCAGTTCATCTTC<br>AAGTTTGAGCACCACCTCCCATGAGAGACTGACCACTTACAAAGACACTGCACATACAGAAGC<br>CGTGCATCCTTCCACAAACACAGGAGGGACCAATGTGGCAACCACCAGCTCTGGATATAAATC<br>ACAGTCCTCTGTCCTAGCTGACTCATCTCCAATGTGTACCACCTCCACCATGGGGGATACAAGT<br>GTTCTCACATCAACTCCTGCCTTCCTTGAGACTAGGAGGATTCAGACAGAGCTAGCTTCCTCCC<br>TGACCCCTGGATTGAGGGAGTCCAGCGGCTCTGAAGGGACCAGCTCAGGCACCAAGATGAG<br>CACTGTCCTCTCTAAAGTGCCCACTGGTGCTACTACTGAGATTCCAAGGAAGACGTCACCTG<br>CATCCCAGGTCCCGCTCAATCCACAATATCACCAGACATCTCCACAAGAACCGTCAGCTGGTTC<br>TCTACATCCCTGTCATGACAGAATCAGCAGAATAACCATGAACACCCATACAAGTCCTTTA<br>GGGGCCACAACACAAGGCACCAGTACTTTGGACACGTCAAGCACAACCTCTTTGACAATGAC<br>ACACTCAACTATATCTCAAGGATTTTCACACTCACAGATGAGCACTCTTATGAGGAGGGTCC<br>TGAGGATGTATCATGGATGAGCCCTCCCCTTCTGGAAAAAACTAGACCTTCCTTTTCTCTGATG |

TABLE 13-continued

Subtyping Target Sequences

| SEQ ID NO. | Gene | Affy Probeset ID | Sequence |
|---|---|---|---|
| | | | TCTTCACCAGCCACAACTTCACCTTCTCCTGTTTCCTCCACATTACCAGAGAGCATCTCTTCCTC
TCCTCTTCCTGTGACTTCACTCCTCACGTCTGGCTTGGCAAAAACTACAGATATGTTGCACAAA
AGCTCAGAACCTGTAACCAACTCACCTGCAAATTTGAGCAGCACCTCAGTTGAAATACTGGCC
ACCTCTGAAGTCACCACAGATACAGAGAAAACTCATCCTTCTTCAAACAGAACAGTGACCGAT
GTGGGGACCTCCAGTTCTGGACATGAATCCACTTCCTTTGTCCTAGCTGACTCACAGACATCCA
AAGTCACATCTCCAATGGTTATTACCTCCACCATGGAGGATACGAGTGTCTCCACATCAACTCC
TGGCTTTTTTGAGACTAGCAGAATTCAGACAGAACCAACATCCTCCCTGACCCTTGGACTGAG
AAAGACCAGCAGCTCTGAGGGGACCAGCTTAGCCACAGAGATGAGCACTGTCCTTTCTGGAG
TGCCCACTGGTGCCACTGCTGAAGTCTCCAGGACAGAAGTCACCTCCTCTAGCAGAACATCCA
TCTCAGGCTTTGCTCAGCTCACAGTGTCACCAGAGACTTCCACAGAAACCATCACCAGACTCC
CTACCTCCAGCATAATGACAGAATCAGCAGAAATGATGATCAAGACACAAACAGATCCTCCTG
GGTCTACACCAGAGAGTACTCATACTGTGGACATATCAACAACACCCAACTGGGTAGAAACCC
ACTCGACTGTGACTCAGAGATTTTCACACTCAGAGATGACCACTCTTGTGAGCAGAAGCCCTG
GTGATATGTTATGGCCTAGTCAATCCTCTGTGGAAGAAACCAGCTCTGCCTCTTCCCTGCTGTC
TCTGCCTGCCACGACCTCACCTTCTCCTGTTTCCTCTACATTAGTAGAGGATTTCCCTTCCGCTT
CTCTTCCTGTGACTTCTCTTCTCAACCCTGGCCTGGTGATAACCACAGACAGGATGGGCATAA
GCAGAGAACCTGGAACCAGTTCCACTTCAAATTTGAGCAGCACCTCCCATGAGAGACTGACCA
CTTTGGAAGACACTGTAGATACAGAAGACATGCAGCCTTCCACACACACAGCAGTGACCAAC
GTGAGGACCTCCATTTCTGGACATGAATCACAATCTTCTGTCCTATCTGACTCAGAGACACCCA
AAGCCACATCTCCAATGGGTACCACCTACACCATGGGGGAAACGAGTGTTTCCATATCCACTT
CTGACTTCTTTGAGACCAGCAGAATTCAGATAGAACCAACATCCTCCCTGACTTCTGGATTGA
GGGAGACCAGCAGCTCTGAGAGGATCAGCTCAGCCACAGAGGGAAGCACTGTCCTTTCTGAA
GTGCCCAGTGGTGCTACCACTGAGGTCTCCAGGACAGAAGTGATATCCTCTAGGGGAACATC
CATGTCAGGGCCTGATCAGTTCACCATATCACCAGACATCTCTACTGAAGCGATCACCAGGCT
TTCTACTTCCCCCATTATGACAGAATCAGCAGAAAGTGCCATCACTATTGAGACAGGTTCTCCT
GGGGCTACATCAGAGGGTACCCTCACCTTGGACACCTCAACAACAACCTTTTGGTCAGGGACC
CACTCAACTGCATCTCCAGGATTTTCACACTCAGAGATGACCACTCTTATGAGTAGAACTCCTG
GAGATGTGCCATGGCCGAGCCTTCCCTCTGTGGAAGAAGCCAGCTCTGTCTCTTCCTCACTGT
CTTCACCTGCCATGACCTCAACTTCTTTTTTCTCCACATTACCAGAGAGCATCTCCTCCTCTCCTC
ATCCTGTGACTGCACTTCTCACCCTTGGCCCAGTGAAGACCACAGACATGTTGCGCACAAGCT
CAGAACCTGAAACCAGTTCACCTCCAAATTTGAGCAGCACCTCAGCTGAAATATTAGCCACGT
CTGAAGTCACCAAAGATAGAGAGAAAATTCATCCCTCCTCAAACACACCTGTAGTCAATGTAG
GGACTGTGATTTATAAACATCTATCCCCTTCCTCTGTTTTGGCTGACTTAGTGACAACAAAACC
CACATCTCCAATGGCTACCACCTCCACTCTGGGGAATACAAGTGTTTCCACATCAACTCCTGCC
TTCCCAGAAACTATGATGACACAGCCAACTTCCTCCCTGACTTCTGGATTAAGGGAGATCAGT
ACCTCTCAAGAGACCAGCTCAGCAACAGAGAAGTGCTTCTCTTTCTGGAATGCCCACTGGT
GCTACTACTAAGGTCTCCAGAACAGAAGCCCTCTCCTTAGGCAGAACATCCACCCCAGGTCCT
GCTCAATCCACAATATCACCAGAAATCTCCACGGAAACCATCACTAGAATTTCTACTCCCCTCA
CCACGACAGGATCAGCAGAAATGACCATCACCCCCAAAACAGGTCATTCTGGGGCATCCTCAC
AAGGTACCTTTACCTTGGACACATCAAGCAGAGCCTCCTGGCCAGGAACTCACTCAGCTGCAA
CTCACAGATCTCCACACTCAGGGATGACCACTCCTATGAGCAGAGGTCCTGAGGATGTGTCAT
GGCCAAGCCGCCCATCAGTGGAAAAAACTAGCCCTCCATCTTCCCTGGTGTCTTTATCTGCAG
TAACCTCACCTTCGCCACTTTATTCCACACCATCTGAGAGTAGCCACTCATCTCCTCTCCGGGT
GACTTCTCTTTTCACCCCTGTCATGATGAAGACCACAGACATGTTGGACACAAGCTTGGAACC
TGTGACCACTTCACCTCCCAGTATGAATATCACCTCAGATGAGAGTCTGGCCACTTCTAAAGCC
ACCATGGAGACAGAGGCAATTCAGCTTTCAGAAAACACAGCTGTGACTCAGATGGGCACCAT
CAGCGCTAGACAAGAATTCTATTCCTCTTATCCAGGCCTCCCAGAGCCATCCAAAGTGACATCT
CCAGTGGTCACCTCTTCCACCATAAAAGACATTGTTTCTACAACCATACCTGCTTCCTCTGAGA
TAACAAGAATTGAGATGGAGTCAACATCCACCCTGACCCCCACACCAAGGGAGACCAGCACC
TCCCAGGAGATCCACTCAGCCACAAAGCCAAGCACTGTTCCTTACAAGGCACTCACTAGTGCC
ACGATTGAGGACTCCATGACACAAGTCATGTCCTCTAGCAGAGGACCTAGCCCTGATCAGTCC
ACAATGTCACAAGACATATCCACTGAAGTGATCACCAGGCTCTCTACCTCCCCCATCAAGACA
GAATCTACAGAAATGACCATTACCACCCAAACAGGTTCTCCTGGGGCTACATCAAGGGGTACC
CTTACCTTGGACACTTCAACACTTTTATGTCAGGGACCCACTCAACTGCATCTCAAGGATTTT
CACACTCACAGATGACCGCTCTTATGAGTAGAACTCCTGGAGATGTGCCATGGCTAAGCCATC
CCTCTGTGGAAGAAGCCAGCTCTGCCTCTTTCTCACTGTCTTCACCTGTCATGACCTCATCTTCT
CCCGTTTCTTCCACATTACCAGACAGCATCCACTCTTCTTCGCTTCCTCTGTGACATCACTTCTCAC
CTCAGGGCTGGTGAAGACCACAGAGCTGTTGGGCACAAGCTCAGAACCTGAAACCAGTTCAC
CCCCAAATTTGAGCAGCACCTCAGCTGAAATACTGGCCATCACTGAAGTCACTACAGATACAG
AGAAACTGGAGATGACCAATGTGGTAACCTCAGGTTATACACATGAATCTCCTTCCTCTGTCC
TAGCTGACTCAGTGACAACAAAGGCCACATCTTCAATGGGTATCACCTACCCCACAGGAGATA
CAAATGTTCTCACATCAACCCCTGCCTTCTCTGACACCAGTAGGATTCAAACAAAGTCAAAGCT
CTCACTGACTCCTGGGTTGATGGAGACCAGCATCTCTGAAGAGACCAGCTCTGCCACAGAAA
AAAGCACTGTCCTTTCTAGTGTGCCCACTGGTGCTACTACTGAGGTCTCCAGGACAGAAGCCA
TCTCTTCTAGCAGAACATCCATCCAGGCCCTGCTCAATCCACAATGTCATCAGACACCTCCAT
GGAAACCATCACTAGAATTTCTACCCCCTCACAAGGAAAGAATCAACAGACATGGCCCATCAC
CCCCAAAACAGGTCCTTCTGGGGCTACCTCGCAGGGTACCTTTACCTTGGACTCATCAAGCAC
AGCCTCCTGGCCAGGAACTCACTCAGCTACAACTCAGAGATTTCCACAGTCAGTGGTGACAAC
TCCTATGAGCAGAGGTCCTGAGGATGTGCATGGCCAAGCCGCTGTCTGTGGAAAAAAACA
GCCCTCCATCTTCCCTGGTATCTTCATCTTCAGTAACCTCACCTTCGCCACTTTATTCCACACCAT
CTGGGAGTAGCCACTCCTCTCCTGTCCCTGTCACTTCTCTTTTCACCTCTATCATGATGAAGGCC
ACAGACATGTTGGATGCAAGTTTGGAACCTGAGACCACTTCAGCTCCCAATATGAATATCACC
TCAGATGAGAGTCTGGCCGCTTCTAAAGCCACCACGGAGACAGAGGCAATTCACGTTTTTGA
AAATACAGCAGCGTCCCATGTGGAAACCACCAGTGCTACAGAGGAACTCTATTCCTCTTCCCC |

TABLE 13-continued

Subtyping Target Sequences

| SEQ ID NO. | Gene | Affy Probeset ID | Sequence |
|---|---|---|---|
| | | | AGGCTTCTCAGAGCCAACAAAAGTGATATCTCCAGTGGTCACCTCTTCCTCTATAAGAGACAA
CATGGTTTCCACAACAATGCCTGGCTCCTCTGGCATTACAAGGATTGAGATAGAGTCAATGTC
ATCTCTGACCCCTGGACTGAGGGAGACCAGAACCTCCCAGGACATCACCTCATCCACAGAGAC
AAGCACTGTCCTTTACAAGATGCCCTCTGGTGCCACTCCTGAGGTCTCCAGGACAGAAGTTAT
GCCCTCTAGCAGAACATCCATTCCTGGCCCTGCTCAGTCCACAATGTCACTAGACATCTCCGAT
GAAGTTGTCACCAGGCTGTCTACCTCTCCCATCATGACAGAATCTGCAGAAATAACCATCACC
ACCCAAACAGGTTATTCTCTGGCTACATCCCAGGTTACCCTTCCCTTGGGCACCTCAATGACCT
TTTTGTCAGGGACCCACTCAACTATGTCTCAAGGACTTTCACACTCAGAGATGACCAATCTTAT
GAGCAGGGGTCCTGAAAGTCTGTCATGGACGAGCCCTCGCTTTGTGGAAACAACTAGATCTT
CCTCTTCTCTGACATCATTACCTCTCACGACCTCACTTTCTCCTGTGTCCTCCACATTACTAGACA
GTAGCCCCTCCTCTCCTCTTCCTGTGACTTCACTTATCCTCTCCCAGGCCTGGTGAAGACTACAGA
AGTGTTGGATACAAGCTCAGAGCCTAAAACCAGTTCATCTCCCAAATTTGAGCAGCACCTCAGT
TGAAATACCGGCCACCTCTGAAATCATGACAGATACAGAGAAAATTCATCCTTCCTCAAACAC
AGCGGTGGCCAAAGTGAGGACCTCCAGTTCTGTTCATGAATCTCATTCCTCTGTCCTAGCTGA
CTCAGAAACAACCATAACCATACCTTCAATGGGTATCACCTCCGCTGTGGACGATACCACTGT
TTTCACATCAAATCCTGCCTTCTCTGAGACTAGGAGGATTCCGACAGAGCCAACATTCTCATTG
ACTCCTGGATTCAGGGAGACTAGCACCTCTGAAGAGACCACCTCAATCACAGAAACAAGTGC
AGTCCTTTATGGAGTGCCCACTAGTGCTACTACTGAAGTCTCCATGACAGAAATCATGTCCTCT
AATAGAATACACATCCCTGACTCTGATCAGTCCACGATGTCTCCAGACATCATCACTGAAGTG
ATCACCAGGCTCTCTTCCTCATCCATGATGTCAGAATCAACACAAATGACCATCACCACCCAAA
AAAGTTCTCCTGGGGCTACAGCACAGAGTACTCTTA |
| 3698 | MUC16 | 3849416 | GGGCACATTTACCTTGGACACACCAACTACATCCTCCAGGGCAGGAACACACTCGATGGCGA
CTCAGGAATTTCCACACTCAGAAATGACCACTGTCATGAACAAGGACCCTGAGATTCTATCAT
GGACAATCCCTCCTTCTATAGAGAAAACCAGCTTCTCCTCTTCCCTGATGCCTTCACCAGCCAT
GACTTCACCTCCTGTTTCCTCAACATTACCAAAGACCATTCACACCACTCCTTCTCCTATGACCT
CACTGCTCACCCCTAGCCTAGTGATGACCACAGACACATTGGGCACAAGCCCAGAACCTACAA
CCAGTTCACCTCCAAATTTGAGCAGTACCTCACATGAGATACTGACAACAGATGAAGACACCA
CAGCTATAGAAGCCATGCATCCTTCCACAAGCACAGCAGCGACTAATGTGGAAACCACCAGTT
CTGGACATGGGTCACAATCCTCTGTCCTAGCTGACTCAGAAAAAACCAAGGCCACAGCTCCAA
TGGATACCACCTCCACCATGGGGCATACAACTGTTTCCACATCAATGTCTGTTTCCTCTGAGAC
TACAAAAATTAAGAGAGAGTCAACATATTCCTTGACTCCTGGACTGAGAGAGACCAGCATTTC |
| 3699 | MUC16 | 3849418 | CTCGTGTCCAGAGGATGAGCATCTCAGTTCCTGACATTTTAAGTACAAGTTGGACTCCCAGTA
GTACAGAAGCAGAAGATGTGCCTGTTTCAATGGTTTCTACAGATCATGCTAGTACAAAGACTG
ACCCAAATACGCCCTGTCCACTTTTCTGTTTGATTCTCTGTCCACTCTTGACTGGGACACTGG
GAGATCTCTGTCATCAGCCACAGCCACTACCTCAGCTCCTCAGGGGGCCACAACTCCCCAGGA
ACTCACTTTGGAAACCATGATCAGCCCAGCTACCTCACAGTTGCCCTTCTCTATAGGGCACATT
ACAAGTGCAGTCACACCAGCTGCAATGGCAAGGAGCTCTGGAGTTACTTTTTCAAGACCAGA
TCCCACAAGCAAAAGGCAGAGCAGACTTCCACTCAGCTTCCCACCACCACTTCTGCACATCC
AGGGCAGGTGCCCAGATCAGCAGCAACAACTCTGGATGTGATCCCACACACAGCAAAACTC
CAGATGCAACTTTTCAGAGACAAGGGCAGACAGCTCTTACAACAGAGGCAAGAGCTACATCT
GACTCCTGGAATGAGAAAGAAAAATCAACCCCAAGTGCACCTTGGATCACTGAGATGATGAA
TTCTGTCTCAGAAGATACCATCAAGGAGGTTACCAGCTCCTCCAGTGTATTAAGGACCCTGAA
TACGCTGGACATAAACTTGGAATCTGGGACGACTTCATCCCCAAGTTGGAAAAGCAGCCCATA
TGAGAGAATTGCCCCTTCTGAGTCCACCACAGACAAAGAGGCAATTCACCCTTCTACAAACAC
AGTAGAGACCACAGGCTGGGTCACAAGTTCCGAACATGCTTCTCATTCCACTATCCCAGCCCA
CTCAGCGTCATCCAAACTCACATCTCCAGTGGTTACAACCTCCACCAGGGAACAAGCAATAGT
TTCTATGTCAACAACCACATGGCCAGAGTCTACAAGGGCTAGAACAGAGCCTAATTCCTTCTT
GACTATTGAACTGAGGGACGTCAGCCCTTACATGGACACCAGCTCAACCACACAAACAAGTAT
TATCTCTTCCCCAGGTTCCACTGCGATCACCAAGGGGCCTAGAACAGAAATTACCTCCTCTAA
GAGAATATCCAGCTCATTCCTTGCCCAGTCTATGAGGTCGTCAGACAGCCCCTCAGAAGCCAT
CACCAGGCTGTCTAACTTTCCTGCCATGACAGAATCTGGAGGAATGATCCTTGCTATGCAAAC
AAGTCCACCTGGCGCTACATCACTAAGTGCACCTACTTTGGATACATCAGCCACAGCCTCCTG
GACAGGGACTCCACTGGCTACGACTCAGAGATTTACATACTCAGAGAAGACCACTCTCTTTAG
CAAAGGTCCTGAGGATACATCACAGCCAAGCCCTCCCTCTGTGGAAGAAACCAGCTCTTCCTC
TTCCCTGGTACCTATCCATGCTACAACCTCGCCTTCCAATATTTTGTTGACATCACAAGGGCAC
AGTCCCTCCTCTACTCCACCTGTGACCTCAGTTTTCTTGTCTGAGACCTCTGGCCTGGGGAAGA
CCACAGACATGTCGAGGATAAGCTTGGAACCTGGCACAAGTTTACCTCCCAATTTGAGCAGTA
CAGCAGGTGAGGCGTTATCCACTTATGAAGCCTCCAGAGATACAAAGGCAATTCATCATTCTG
CAGACACAGCAGTGACGAATATGGAGGCAACCAGTTCTGAATATTCTCCTATCCCAGGCCATA
CAAAGCCATCCAAAGCCACATCTCCATTGGTTACCTCCCACATCATGGGGACATCACTTCTTC
CACATCAGTATTTGGCTCCTCCGAGACCACAGAGATTGAGACAGTGTCCTCTGTGAACCAGGG
ACTTCAGGAGAGAAGCACATCCCAGGTGGCCAGCTCTGCTACAGAGACAAGCACTGTCATTA
CCCATGTGTCTAGTGGTGATGCTACTACTCATGTCACCAAGACACAAGCCACTTTCTCTAGCG
GAACATCCATCTCAAGCCCTCATCAGTTTATAACTTCTACCAACACATTTACAGATGTGAGCAC
CAACCCCTCCACCTCTCTGATAATGACAGAATCTTCAGGAGTGACCATCACCACCCAAACAGG
TCCTACTGGAGCTGCAACACAGGGTCCATATCTCTTGGACACATCAACCATGCCTTACTTGACA
GAGACTCCATTAGCTGTGACTCCAGATTTTACTGCAATCAGAGAAGACCACTCTCATAAGCAAA
GGTCCCAAGGATGTGTCCTGGACAAGCCCTCCCTCTGTGGCAGAAACCAGCTATCCCTCTTCC
CTGACACCTTTCTTGGTCACAACCATACCTCCTGCCACTTCCACGTTACAAGGGCAACATACAT
CCTCTCCTGTTTCTGCGACTTCAGTTCTTACCTCTGGACTGGTGAAGACCACAGATATGTTGAA
CACAAGCATGGAACCTGTGACCAATTCACCTCAAAATTTGAACAATTCATCAAATGAGATACT
GGCCACTTTGGCAGCCACCACAGATATAGAGACTATTCATCCTTCCATAAACAAAGCAGTGAC |

TABLE 13-continued

Subtyping Target Sequences

| SEQ ID NO. | Gene | Affy Probeset ID | Sequence |
|---|---|---|---|
| | | | CAATATGGGGACTGCCAGTTCAGCACATGTACTGCATTCCACTCTCCCAGTCAGCTCAGAACC |
| | | | ATCTACAGCCACATCTCCAATGGTTCCTGCCTCCAGCATGGGGGACGCTCTTGCTTCTATATCA |
| | | | ATACCTGGTTCTGAGACCACAGACATTGAGGGAGAGCCAACATCCTCCCTGACTGCTGGACG |
| | | | AAAAGAGAACAGCCACCCTCCAGGAGATGAACTCAACTACAGAGTCAAACATCATCCTCTCCAA |
| | | | TGTGTCTGTGGGGGCTATTACTGAAGCACAAAAATGGAAGTCCCCTCTTTTGATGCAACATT |
| | | | CATACCAACTCCTGCTCAGTCAACAAAGTTCCCAGATATTTTCTCAGTAGCCAGCAGTAGACTT |
| | | | TCAAACTCTCCTCCCATGACAATATCTACCCACATGACCACCACCCAGACAGGGTCTTCTGGAG |
| | | | CTACATCAAAGATTCCACTTGCCTTAGACACATCAACCTTGGAAACCTCAGCAGGGACTCCATC |
| | | | AGTGGTGACTGAGGGGTTTGCCCACTCAAAAATAACCACTGCAATGAACAATGATGTCAAGG |
| | | | ACGTGTCACAGACAAACCCTCCCTTTCAGGATGAAGCCAGCTCTCCCTCTTCTCAAGCACCTGT |
| | | | CCTTGTCACAACCTTACCTTCTTCTGTTGCTTTCACACCGCAATGGCACAGTACCTCCTCTCCTG |
| | | | TTTCTATGTCCTCAGTTCTTACTTCTTCACTGGTAAAGACCGCAGGCAAGGTGGATACAAGCTT |
| | | | AGAAACAGTGACCAGTTCACCTCAAAGTATGAGCAACACTTTGGATGACATATCGGTCACTTC |
| | | | AGCAGCCACCACAGATATAGAGACAACGCATCCTTCCATAAACACAGTAGTTACCAATGTGG |
| | | | GGACCACCGGTTCAGCATTTGAATCACATTCTACTGTCTCAGCTTACCCAGAGCCATCTAAAGT |
| | | | CACATCTCCAAATGTTACCACCTCCACCATGGAAGCACCACAATTTCCAGATCAATACCTAAA |
| | | | TCCTCTAAGACTACAAGAACTGAGACTGAGCAACTTCCTCCCTGACTCCTAAACTGAGGGAG |
| | | | ACCAGCATCTCCCAGGAGATCACCTCGTCACAGAGACAAGCACTGTTCCTTACAAAGAGCTC |
| | | | ACTGGTGCCACTACCGAGGTATCCAGGACAGATGTCACTTCCTCTAGCAGTACATCCTTCCCT |
| | | | GGCCCTGATCAGTCCACAGTGTCACTAGACATCTCCACAGAAACCAACACCAGGCTGTCTACC |
| | | | TCCCCAATAATGACAGAATCTGCAGAAATAACCATCACCACCCAAACAGGTCCTCATGGGGCT |
| | | | ACATCACAGGATACTTTTACCATGGACCCATCAAATACAACCCCCCAGGCAGGGATCCACTCA |
| | | | GCTATGACTCATGGATTTTCACAATTGGATGTGACCACTCTTATGAGCAGAATTCCACAGGAT |
| | | | GTATCATGGACAAGTCCTCCCTCTGTGGATAAAACCAGCTCCCCCTCTTCCTTTCTGTCCTCACC |
| | | | TGCAATGACCACACCTTCCCTGATTTCTTCTACCTTACCAGAGGATAAGCTCTCCTCTCCTATGA |
| | | | CTTCACTTCTCACCTCTGGCCTAGTGAAGATTACAGACATATTACGTACACGCTTGGAACCTGT |
| | | | GACCAGCTCACTTCCAAATTTCAGCAGCACCTCAGATAAGATACTGGCCACTTCTAAAGACAG |
| | | | TAAAGCACAAAGGAAATTTTTCCTTCTATAAACACAGAAGAGACCAATGTGAAAGCCAACA |
| | | | ACTCTGGACATGAATCCCATTCCCCTGCACTGGCTGACTCAGAGACACCCAAAGCCACAACTC |
| | | | AAATGGTTATCACCACCACTGTGGGAGATCCAGCTCCTTCCACATCAATGCCAGTGCATGGTT |
| | | | CCTCTGAGACTACAAACATTAAGAGAGCCAACATATTTCTTGACTCCTAGACTGAGAGAGA |
| | | | CCAGTACCTCTCAGGAGTCCAGCTTTCCCACGGACACAAGTTTTCTACTTTTCCAAAGTCCCCAC |
| | | | TGGTACTATTACTGAGGTCTCCAGTACAGGGGTCAACTCTTCTAGCAAAATTTCCACCCCAGA |
| | | | CCATGATAAGTCCACAGTGCCACCTGACACCTTCACAGGAGAGATCCCCAGGGTCTTCACCTC |
| | | | CTCTATTAAGACAAAATCTGCAGAAATGACGATCACCACCCAAGCAAGTCCTCCTGAGTCTGC |
| | | | ATCGCACAGTACCCTTCCCTTGGACACATCAACCACACTTTCCCAGGGAGGGACTCATTCAACT |
| | | | GTGACTCAGGGATTCCCATACTCAGAGGTGACCACTCTCATGGGCATGGGTCCTGGGAATGT |
| | | | GTCATGGATGACAACTCCCCCTGTGGAAGAAACCAGCTCTGTGTCTTCCCTGATGTCTTCACCT |
| | | | GCCATGACATCCCCTTCTCCTGTTTCCTCCACATCACCACAGAGCATCCCCTCCTCTCCTCTTCCT |
| | | | GTGACTGCACTTCCTACTTCTGTTCTGGTGACAACCACAGATGTGTTGGGCACAACAAGCCCA |
| | | | GAGTCTGTAACCAGTTCACCTCCAAATTTGAGCAGCATCACTCATGAGAGACCGGCCACTTAC |
| | | | AAAGACACTGCACACACAGAAGCCGCCATGCATCATTCCACAAACACCGCAGTGACCAATGT |
| | | | AGGGACTTCCGGGTCTGGACATAAATCACAATCCTCTGTCCTAGCTGACTCAGAGACATCGAA |
| | | | AGCCACACCTCTGATGAGTACCACCTCCACCCTGGGGGACAAGTGTTTCCACATCAACTCC |
| | | | TAATATCTCTCAGACTAACCAAATTCAAACAGAGCCAACAGCATCCCTGAGCCCTAGACTGAG |
| | | | GGAGAGCAGCACGTCTGAGAAGACCAGCTCAACAACAGAGACAAATACTGCCTTTTCTTATG |
| | | | TGCCCACAGGTGCTATTACTCAGGCCTCCAGAACAGAAATCTCCTCTAGCAGAACATCCATCT |
| | | | CAGACCTTGATCGGCCCACAATAGCACCCGACATCTCCACAGGAATGATCACCAGGCTCTTCA |
| | | | CCTCCCCCATCATGACAAAATCTGCAGAAATGACCGTCACCACTCAAACAACTACTCCTGGGG |
| | | | CTACATCACAGGGTATCCTTCCCTGGGACACATCAACCACACTTTTCCAGGGAGGGACTCATT |
| | | | CAACCGTGTCTCAGGGATTCCCACACTCAGAGATAACCACTCTTCGGAGCAGAACCCCTGGAG |
| | | | ATGTGTCATGGATGACAACTCCCCCTGTGGAAGAAACCAGCTCTGGGTTTTCCCTGATGTCAC |
| | | | CTTCCATGACATCCCCTTCTCCTGTTTCCTCCACATCACCAGAGAGCATCCCCTCCTCTCCTCTCC |
| | | | CTGTGACTGCACTTCTTACTTCTGTTCTGGTGACAACCACAAATGTATTGGGCACAACAAGCCC |
| | | | AGAGCCCGTAACGAGTTCACCTCCAAATTTAAGCAGCCCACACAGGAGAGACTGACCACTTA |
| | | | CAAAGACACTGCGCACACAGAAGCCATGCATGCTTCCATGCATACAAACACTGCAGTGGCCA |
| | | | ACGTGGGGACCTCCATTTCTGGACATGAATCACAATCTTCTGTCCCAGCTGATTCACACACATC |
| | | | CAAAGCCACATCTCCAATGGGTATCACCTTCGCCATGGGGGATACAAGTGTTTCTACATCAAC |
| | | | TCCTGCCTTCTTTGAGACTAGAATTCAGACTGAATCAACATCCTCTTTGATTCCTGGATTAAGG |
| | | | GACACCAGGACGTCTGAGGAGATCAACACTGTGACAGAGACCAGCACTGTCCTTTCAGAAGT |
| | | | GCCCACTACTACTACTACTGAGGTCTCCAGGACAGAAGTTTATCACTTCCAGCAGAACAACCAT |
| | | | CTCAGGGCCTGATCATTCCAAAATGTCACCCTACATCTCCACAGAAACCATCACCAGGCTCTCC |
| | | | ACTTTTCCTTTTGTAACAGGATCCACAGAAATGGCCATCACCAACCAAACAGGTCCTATAGGG |
| | | | ACTATCTCACAGGCTACCCTTACCCTGGACACATCAAGCACAGCTTCCTGGGAAGGGACTCAC |
| | | | TCACCTGTGACTCAGAGATTTCCACACTCAGAGGAGACCACTACTATGAGCAGAAGTACTAAG |
| | | | GGCGTGTCATGGCAAAGCCCTCCCTCTGTGGAAGAAACCAGTTCTCCTTCTTCCCCAGTGCCTT |
| | | | TACCTGCAATAACCTCACATTCATCTCTTTATTCCGCAGTATCAGGAAGTAGCCCCACTTCTGCT |
| | | | CTCCCTGTGACTTCCCTTCTCACCTCTGGCAGGAGGAAGACCATAGACATGTTGGACACACAC |
| | | | TCAGAACTTGTGACCAGCTCCTTACCAAGTGCAAGTAGCTTCTCAGGTGAGATACTCACTTCT |
| | | | GAAGCCTCCACAAATACAGAGACAATTCACTTTTCAGAGAACACAGCAGAAACCAATATGGG |
| | | | GACCACCAATTCTATGCATAAACTACATTCCTCTGTCTCAATCCACTCCCAGCCATCCGGACAC |
| | | | ACACCTCCAAAGGTTACTGGATCTATGATGGAGGACGCTATTGTTTCCACATCAACACCTGGT |
| | | | TCTCCTGAGACTAAAAATGTTGACAGAGACTCAACATCCCCTCTGACTCCTGAACTGAAAGAG |
| | | | GACAGCACCGCCCTGGTGATGAACTCAACTACAGAGTCAAACACTGTTTTCTCCAGTGTGTCC |

TABLE 13-continued

Subtyping Target Sequences

| SEQ ID NO. | Gene | Affy Probeset ID | Sequence |
|---|---|---|---|
| | | | CTGGATGCTGCTACTGAGGTCTCCAGGGCAGAAGTCACCTACTATGATCCTACATTCATGCCA<br>GCTTCTGCTCAGTCAACAAAGTCCCCAGACATTTCACCTGAAGCCAGCAGCAGTCATTCTAACT<br>CTCCTCCCTTGACAATATCTACACACAAGACCATCGCCACACAAACAGGTCCTTCTGGGGTGA<br>CATCTCTTGGCCAACTGA |
| 3700 | MUC16 | 3849421 | GTTCTCCAGAAACATGGGCAAGCTCTATTTCAGTTCC |
| 3701 | MUC16 | 3849422 | GCAAGGTCTGGTTCTAGTTCCTCTCCCATAAGCCTATCCACTGAGAAAGAAACAAGCTTCCTTT<br>CCCCCACTGCATCCACCTCCAGAAAGACTTCACTATTTCTTGGGCCTTCCATGGCAAGGCAGCC<br>CAACATATTGGTGCATCTTCAGACTTCAGCTCTGACACTTTCTCCAACATCCACTCTAAATATGT<br>CCCAGGAGGAGCCTCCTGAGTTAACCTCAAGCCAGACCATTG |
| 3702 | MUC16 | 3849423 | AACAGGGGACCCTAGATATGCCTCAGAGAGCATGTCTTATCCAGACCCAAGCAAGGCATCAT<br>CAGCTATGACATCGACCTCTCTTGCATCAAAA |
| 3703 | MUC16 | 3849424 | TACTCAATCAACAGCACCCAAAGGGATACCTGTGAAGCCCACCAGTGCTGAGTCAGGCCTCCT<br>AACACCTGTCTCTGCCTCCTCAAGCCCATCAAAGGCCTTTGCCTCACTGACTACAGCTCCCCCA<br>ACTTGGGGGATCCCACAGTCTACCTTGACATTTGAGTTTTCTGAGGTCCCAAGTTTGGATACTA<br>AGTCCGCTTCTTTACCAACTCCTGGACAGTCCCTGAACACCATTCCAGACTCAGATGCAAGCAC<br>AGCATCTTCCTCACTGTCCAAGTCTCCAGAAAAAAAACCCAAGGGCAAGGATGATGACTTCCAC<br>AAAGGCCATAAGTGCAAGCTCATTTCA |
| 3704 | MUC16 | 3849425 | TTGGCCAGTCCTACATCTTCGGTTGTGGGAAGAACCACCCAGTCTTTGGGGGTGATGTCCTCT<br>GCTCTCCCTGAGTCAACCTCTAGAGGAATGACACACTCCGAGCAAAGAACCAGCCCATCGCTG<br>AGTCCCCAGGTCAATGGAACTCCCTCTAGGAACTACCCTGCTACAAGCATGGTTTCAGGATTG<br>AGTTCCCCAAGGACCAGGACCAGTTCCACAGAAGGAAATTTTACCAAAGAAGCATCTACATAC<br>ACACTCACTGTAGAGACCACAAGTGGCCCAGTCACTGAGAAGTACACAGTCCCCACTGAGAC<br>CTCAACAACTGAAGGTGACAGCACAGAGACCCCCTGGGACACAAGATATATTCCTGTAAAAA<br>TCACATCTCCAATGAAAACATTTGCAGATTCAACTGCATCCAAGGAAAATGCCCCAGTGTCTAT<br>GACTCCAGCTGAGACCACAGTTACTGACTCACATACTCCAGGAAGGACAAACCCATCATTTGG<br>GACACTTTATTCTTCCTTCCTTGACCTATCACCTAAAGGGACCCCAAATTCCAGAGGTGAAACA<br>AGCCTGGAACTGATTCTATCAACCACTGGATATCCCTTCTCCTCTCCTGAACCTGGCTCTGCAG<br>GACACAGCAGAATAAGTACCAGTGCGCCTTTGTCATCATCTGCTTCAGTTCTCGATAATAAAA<br>TATCAGAGACCAGCATATTCTCAGGCCAGAGTCTCACCTCCCCTCTGTCTCCTGGGGTGCCCG<br>AGGCCAGAGCCAGCACAATGCCCAACTCAGCTATCCCTTTTTCCATGACACTAAGCAATGCAG<br>AAACAAGTGCCGAAAGGGTCAGAAGCACAATTTCCTCTCTGGGGACTCCATCAATATCCACAA<br>AGCAGACAGCAGAGACTATCCTTACCTTCCATGCCTTCGCTGAGACCATGGATATACCCAGCA<br>CCCACATAGCCAAGACTTTGGCTTCAGAATGGTTGGGAAGTCCAGGTACCCTTGGTGGCACC<br>AGCACTTCAGCGCTGACAACCACATCTCCATCTACCACTTTAGTCTCAGAGGAGACCAACACC<br>CATCACTCCACGAGTGGAAAGGAAACAGAAGGAACTTTGAATACATCTATGACTCCACTTGA<br>GACCTCTGCTCCTGGAGAAGAGTCCGAAATGACTGCCACCTTGGTCCCCACTCTAGGTTTTAC<br>AACTCTTGACAGCAAGATCAGAAGTCCATCTCAGGTCTCTTCATCCCACCCAACAAGAGAGCT<br>CAGAACCACAGGCAGCACCTCTGGGAGGCAGAGTTCCAGCACAGCTGCCCACGGGAGCTCT<br>GACATCCTGAGGGCAACCACTTCCAGCACCTCAAAAGCATCATCATGGACCAGTGAAAGCAC<br>AGCTCAGCAATTTAGTGAACCCCAGCACACACAGTGGGTGGAGACAAGTCCTAGCATGAAAA<br>CAGAGAGACCCCCAGCATCAACCAGTGTGGCAGCCCCTATCACCACTTCTGTTCCCTCAGTGG<br>TCTCTGGCTTCACCACCCTGAAGACCAGCTCCACAAAAGGGATTTGGCTTGAAGAAACATCTG<br>CAGACACACTCATCGGAGAATCCACAGCTGGCCCAACCACCCATCAGTTTGCTGTTCCCACTG<br>GGATTTCAATGACAGGAGGCAGCAGCACCAGGGGAAGCCAGGGCACAACCCACCTACTCAC<br>CAGAGCCACAGCATCATCTGAGACATCCGCAGATTTGACTCTGGCCACGAACGGTGTCCCAGT<br>CTCCGTGTCTCCAGCAGTGAGCAAGACGGCTGCTGGCTCAAGTCCTCCAGGAGGGACAAAGC<br>CATCATATACAATGGTTTCTTCTGTCATCCCTGAGACATCATCTCTACAGTCCTCAGCTTTCAGG<br>GAAGGAACCAGCCTGGGACTGACTCCATTAAACACTAGACATCCCTTCTCTTCCCCTGAACCA<br>GACTCTGCAGGACACACCAAGATAAGCACCAGCATTCCTCTGTTGTCATCTGCTTCAGTTCTTG<br>AGGATAAAGTGTCAGCGACCAGCACATTCTCACACCACAAAGCCACCTCATCTATTACCACAG<br>GGATTCCTGAAATCTCAACAAAGACAAAGCCCAGCTCAGCCGTTCTTTCCTCCATGACCCTAA<br>GCAATGCAGCAACAAGTCCTGAAAGAGTCAGAAATGCAACTTCCCCTCTGACTCATCCATCTC<br>CATCAGGGGAAGAGACAGCAGGGAGTGTCCTCACTCTCAGCACCTCTGCTGAGACTACAGAC<br>TCACCTAACATCCACCCAACTGGGACACTGACTTCAGAATCGTCAGAGAGTCCTAGCACTCTC<br>AGCCTCCCAAGTGTCTCTGGAGTCAAAACCACATTTTCTTCATCTACTCCTTCCACTCATCTATT<br>TACTAGTGGAGAAGAAACAGAGGAAACTTCGAATCCATCTGTGTCTCAACCTGAGACTTCTGT<br>TTCCAGAGTAAGGACCACCTTGGCCAGCACCTCTGTCCCTACCCCAGTATTCCCACCATGGAC<br>ACCTGGCCTACACGTTCAGCTCAGTTCTCTTCATCCCACCTAGTGAGTGAGCTCAGAGCTACG<br>AGCAGTACCTCAGTTACAAACTCAACTGGTTCAGCTCTTCCTAAAATATCTCACCTCACTGGGA<br>CGGCAACAATGTCACAGACCAATAGAGACACGTTTAATGACTCTGCTGCACCCCAAAGCACAA<br>CTTGGCCAGAGACTAGTCCCAGATTCAAGACAGGGTTACCTTCAGCAACAACCACTGTTTCAA<br>CCTCTGCCACTTCTCTCTCTGCTACTGTAATGGTCTCTAAATTCACTTCTCCAGCAACTAGTTCC<br>ATGGAAGCAACTTCTATCAGGGAACCATCAACAACCATCCTCACAACAGAGACCACGAATGG<br>CCCAGGCTCTATGCTGTGGCTTCTACCAACATCCCAATTGGAAAGGGCTACATTACTGAAGG<br>AAGATTGGACACAAGCCATCTGCCCATTGGAACCACAGCTTCCTCTGAGACATCTATGGATTT<br>TACCATGGCCAAAGAAAGTGTCTCAATGTCAGTATCTCCATCTCAGTCCATGGATGCTGCTGG<br>CTCAAGCACTCCAGGAAGGACAAGCCAATTCGTTGACACATTTTCTGATGATGTCTATCATTTA<br>ACATCCAGAGAAATTACAATACCTAGAGATGGAACAAGCTCAGCTCTGACTCCACAAATGACT<br>GCAACTCACCCTCCATCTCCTGATCCTGGCTCTGCTAGAAGCACCTGGCTTGGCATCTTGTCCT |

TABLE 13-continued

Subtyping Target Sequences

| SEQ ID NO. | Gene | Affy Probeset ID | Sequence |
|---|---|---|---|
| | | | CATCTCCTTCTTCTCCTACTCCCAAAGTCACAATGAGCTCCACATTTTCAACTCAGAGAGTCACC
ACAAGCATGATAATGGACACAGTTGAAACTAGTCGGTGGAACATGCCCAACTTACCTTCCACG
ACTTCCTTGACACCAAGTAATATTCCAACAAGTGGTGCCATAGGAAAAAGCACCCTGGTTCCC
TTGGACACTCCATCTCCAGCCACATCATTGGAGGCATCAGAAGGGGGACTTCCAACCCTCAGC
ACCTACCCTGAATCAACAAACACACCCAGCATCCACCTCGGAGCACACGCTAGTTCAGAAAGT
CCAAGCACCATCAAACTTACCATGGCTTCAGTAGTAAAACCTGGCTCTTACACACCTCTCACCT
TCCCCTCAATAGAGACCCACATTCATGTATCAACAGCCAGAATGGCTTACTCTTCTGGGTCTTC
ACCTGAGATGACAGCTCCTGGAGAGACTAACACTGGTAGTACCTGGGACCCCACCACCTACAT
CACCACTACGGATCCTAAGGATACAAGTTCAGCTCAGGTCTCTACACCCCACTCAGTGAGGAC
ACTCAGAACCACAGAAAACCATCCAAAGACAGAGTCCGCCACCCCAGCTGCTTACTCTGGAA
GTCCTAAAATCTCAAGTTCACCCAATCTCACCAGTCCGGCCACAAAAGCATGGAACCATCACAG
ACACAACTGAACACTCCACTCAATTACATTACACAAAATTGGCAGAAAAATCATCTGGATTTG
AGACACAGTCAGCTCCAGGACCTGTCTCTGTAGTAATCCCTACCTCCCCTACCATTGGAAGCA
GCACATTGGAACTAACTTCTGATGTCCCAGGGGAACCCCTGGTCCTTGCTCCCAGTGAGCAGA
CCACAATCACTCTCCCCATGGCAACATGGCTGAGTACCAGTTTGACAGAGGAAATGGCTTCAA
CAGACCTTGATATTTCAAGTCCAAGTTCACCCATGAGTACATTTGCTATTTTTCCACCTATGTCC
ACACCTTCTCATGAACTTTCAAAGTCAGAGGCAGATACCAGTGCATTAGAAATACAGATTCA
ACAACGTTGGATCAGCACCTAGGAATCAGGAGTTTGGGCAGAACTGGGGACTTAACAACTGT
TCCTATCACCCCACTGACAACCACGTGGACCAGTGTGATTGAACACTCAACACAAGCACAGGA
CACCCTTTCTGCAACGATGAGTCCTACTCACGTGACACAGTCACTCAAAGATCAAACATCTATA
CCAGCCTCAGCATCCCCTTCCCATCTTACTGAAGTCTACCCTGAGCTCGGGACACAAGGGAGA
AGCTCCTCTGAGGCAACCACTTTTTGGAAACCATCTACAGACACACTGTCCAGAGAGATTGAG
ACTGGCCCAACAAACATTCAATCCACTCCACCCATGGACAACACAACAACAGGGAGCAGTAG
TAGTGGAGTCACCCTGGGCATAGCCCACCTTCCCATAGGAACATCCTCCCCAGCTGAGACATC
CACAAACATGGCACTGGAAAGAAGAAGTTCTACAGCCACTGTCTCTATGGCTGGGACAATGG
GACTCCTTGTTACTAGTGCTCCAGGAAGAAGCATCAGCCAGTCATTAGGAAGAGTTTCCTCTG
TCCTTTCTGAGTCAACTACTGAAGGAGTCACAGATTCTAGTAAGGGAAGCAGCCCAAGGCTG
AACACACAGGGAAATACAGCTCTCTCCTCCTCTCTTGAACCCAGCTATGCTGAAGGAAGCCAG
ATGAGCACAAGCATCCCTCTAACCTCATCTCCTACAACTCCTGATGTGGAATTCATAGGGGGC
AGCACATTTTGGACCAAGGAGGTCACCACAGTTATGACCTCAGACATCTCCAAGTCTTCAGCA
AGGACAGAGTCCAGCTCAGCTACCCTTATGTCCACAGCTTTGGGAAGCACTGAAAATACAGG
AAAAGAAAAACTCAGAACTGCCTCTATGGATCTTCCATCTCCAACTCCATCAATGGAGGTGAC
ACCATGGATTTCTCTCACTCTCAGTAATGCCCCAATACCACAGATTCACTTGACCTCAGCCAT
GGGGTGCACACCAGCTCTGCAGGGACTTTGGCCACTGACAGGTCATTGAATACTGGTGTCAC
TAGAGCCTCCAGATTGGAAAACGGCTCTGATACCTCTTCTAAGTCCCTGTCTATGGGAAACAG
CACTCACACTTCCATGACTTACACAGAGAAGAGTGAAGTGTCTTCTTCAATCCATCCCCCGACCT
GAGACCTCAGCTCCTGGAGCAGAGACCACTTTGACTTCCACTCCTGGAAACAGGGCCATAAG
CTTAACATTGCCTTTTTCATCCATTCCAGTGGAAGAAGTCATTTCTACAGGCATAACCTCAGGA
CCAGACATCAACTCAGCACCCATGACACATTCTCCCATCACCCCACCAACAATTGTATGGACCA
GTACAGGCACAATTGAACAGTCCACTCAACCACTACATGCAGTTTCTTCAGAAAAAGTTTCTG
TGCAGACACAGTCAACTCCATATGTCAACTCTGTGGCAGTGTCTGCTTCCCCTACCCATGAGA
ATTCAGTCTCTTCTGGAAGCAGCACATCCTCTCCATATTCCTCAGCCTCACTTGAATCCTTGGAT
TCCACAATCAGTAGGAGGAATGCAATCACTTCCTGGCTATGGGACCTCACTACATCTCTCCCC
ACTACAACTTGGCCAAGTACTAGTTTATCTGAGGCACTGTCCTCAGGCCATTCTGGGGTTTCA
AACCCAAGTTCAACTACGACTGAATTTCCACTCTTTTCAGCTGCATCCACATCTGCTGCTAAGC
AAAGAAATCCAGAAACAGAGACCCATGGTCCCCAGAATACAGCCGCGAGTACTTTGAACACT
GATGCATCCTCGGTCACAGGTCTTTCTGAGACTCCTGTGGGGGCAAGTATCAGCTCTGAAGTC
CCTCTTCCAATGGCCATAACTTTCTAGATCAGATGTTTCTGGCCTTACATCTGAGAGTACTGCTA
ACCCGAGTTTAGGCACAGCCTCTTCAGCAGGGACCAAATTAACTAGGACAATATCCCTGCCCA
CTTCAGAGTCTTTGGTTTCCTTTAGAATGAACAAGGATCCATGGACAGTGTCAATCCCTTTGG
GGTCCCATCCAACTACTAATACAGAAACAAGCATCCCAGTAAACAGCGCAGGTCCACCTGGCT
TGTCCACAGTAGCATCAGATGTAATTGACACACCTTCAGATGGGGCTGAGAGTATTCCCACTG
TCTCCTTTTCCCCCTCCCCTGATACTGAAGTGACAACTATCTCACATTTCCCAGAAAAGACAACT
CATTCATTTAGAACCATTTCATCTCTCACTCATGAGTTGACTTCAAGAGTGACACCTATTCCTG
GGGATTGGATGAGTTCAGCTATGTCTACAAAGCCCACAGGAGCCAGTCCCTCCATTACACTGG
GAGAGAGAAGGACAATCACCTCTGCTGCTCCAACCACTTCCCCCATAGTTCTCACTGCTAGTTT
CACAGAGACCAGCACAGTTTCACTGGATAATGAAACTACAGTAAAAACCTCAGATATCCTTGA
CGCACGGAAAACAAATGAGCTCCCCTCAGATAGCAGTTCTTCTTCTGATCTGATCAACACCTCC
ATAGCTTCTTCAACTATGGATGTCACTAAAACAGCCTCCATCAGTCCCACTAGCATCTCAGGAA
TGACAGCAAGTTCCTCCCCATCTCTCTTCTTCAGATAGACCCCAGGTTCCCACATCTACAAC
AGAGACAAATCAGCCACCTCTCCATCTGTTTCCAGTAACACCTATTCTCTTGATGGGGGCTCC
AATGTGGGTGGCACTCCATCCACTTTACCACCCTTTACAATCACCCACCCTGTCGAGACAAGCT
CGGCCCTATTAGCCTGGTCTAGACCAGTAAGAACTTTCAGCACCATGGTCAGCACTGACACTG
CCTCCGGAGAAAATCCTACCTCTAGCAATTCTGTGGTGACTTCTGTTCCAGCACCAGGTACAT
GGACCAGTGTAGGCAGTACTACTGACTTACCTGCCATGGGCTTTCTCAAGACAAGTCCTGCAG
GAGAGGCACACTCACTTCTAGCATCAACTATTGAACCAGCCACTGCCTTCACTCCCCATCTCTC
AGCAGCAGTGGTCACTGGATCCAGTGCTACATCAGAAGCCAGTCTTCTCACTACGAGTGAAA
GCAAAGCCATTCATTCTTCACCACAGACCCCAACTACACCCACCTCTGGAGCAAACTGGGAAA
CTTCAGCTACTCCTGAGAGCCTTTTGGTAGTCACTGAGCACAACACTTACCTCAAA
GATTTTGGTCACAGATACCATCTTGTTTTCAACTGTGTCCACGCCACCTTCTAAATTTCCAAGTA
CGGGGACTCTGTCTGGAGCTTCCTTCCCTACTTTACTCCCGGACACTCCAGCCATCCCTCTCAC
TGCCACTGAGCCAACAAGTTCATTAGCTACATCCTTTGATTCCACCCCACTGGTGACTATAGCT
TCGGATA |

TABLE 13-continued

Subtyping Target Sequences

| SEQ ID NO. | Gene | Affy Probeset ID | Sequence |
|---|---|---|---|
| 3705 | MUC16 | 3849426 | GCAGGAGCACTAAAGCCACACCAGAAATGGATTCAGGACTGACAGGAGCCACCTTGTCACCT AAGACATCTACAGGTGCAATCGTGGTGACAGAACA |
| 3706 | MUC16 | 3849427 | CCTGGGTCATCTTCTCCCACCCGCT |
| 3707 | ZNF91 | 3857041 | TTGGCTTTTCTACCCCAATTCAAGAAGTCACTTCTTCAGTCAACCAAACCAATTACAAAATTGT GTTCCAATGTCACATGTTCAAAAATA |
| 3708 | ZNF91 | 3857045 | GGTTGATGGGCCCAGAGATATATCACATTGCCCCTTGTGGACAGGGACCAGGCAGGGGACTC ACATCACAATAGAGGTAGGACAAGGAATACATCACAATACGTTTTGAGAGCAGAACCAAAAA AGAGTAACATAATCTTTGTGTTGAGTGCAGCA |
| 3709 | ZNF91 | 3857047 | GAGAGAAGGGTCATATCACCTAAGCTCTGGATTCGCAGATAGGCCCCAATCTCTTTTTTGGGC AATGCTCGG |
| 3710 | ZNF91 | 3857049 | CACCCTAGTGGGCAGGTCCATTAAAGAGAAGGCTGTCAAAGCACATAGATGCTGGGCAAAGT GATATGTCATAATCCCCATGATGATAGGCCCAGAGACATGTCACAATGACCTCTTTAGGCAGA GACCAGGCAGAAGAATCACATCACTTGTGTGCTGGCCCTAGTGATAAGTCACTCTCATTTCTG TGGACATGGCCCAGGCAGAAGAGCAGAGTCACATTACCTAAGCGCTGGGTCAAGAGATATGT CACAATCTTTTACATGGGCAAAACCCAGGTAAAAAGAGGAGTAATATCAGATAGTAGGTGT TGCCAGAGATATGTCAAATGCCCCTGTATGAAAGACTCAGGCAGTCAAAACACATTAGTTG GTTTCTTAACCTAGTGATATGTTATAATCTTTCCTGTGGGTATGATGCAGGCAGAAGACGAGA GTCATGTGATGATGCAGAGACATGTCACAAGGTCTTCTGTGGGCAGGGTCCAGACTGAAGC CTTCCACCTGCTAGGGGTTGAGCCCAATGATATGTCACAATACCCAAATTATGCAGGGCCCAG GCAAAAAAACGAGAGGCACATCACCTGGGTTCTGGATCCAATGATATATCACAATTTTCTAT TTTGGCAAGACCCAGGCAGAAAGAAAAGTTACATCACCTAGGTGATGAATGAAAATACATAT TATAATAGTTTTGTGGGCAGGACCCATGCGGGAGAGTCACATCACCTAGGTGTTGGACCCAG AAATATGTCACAATATACAGTGTATACAGAGCTGAGGCATGAGACAATAGTAACTTCACTCAT TTGTTGAGCCCAGCTATACAATCCTTTTTTGGGCACAGCCGA |
| 3711 | ZNF91 | 3857051 | ATTATTCTCCTTTGGGCAGTGCTTCTGCAGAAAAGTTGCACCTTCTAGGTGTTGGACTCAGCAA TATATCACAATGTCTGCAGTATTTTGGAAGGAGAGGAGAGTCACCATTACTTA |
| 3712 | ZNF91 | 3857070 | GCCCAGTCTAGTGGTAATTAGTTTCCCCAGCATTTATTTGTCAGGGTAAGACTTTATATTCTTC ATTTGTGAAGGTTATTCTAGCTTGATATAAAATTTTTGGCTGGCAGTTTTCTTTTTTTTCAACAC TCTAAAAGTGCCATCCCATTCTCTTCTGGTCAGTAAAGTTTCTGCTGAGAAGTCTGCTTTTAAT CTAATGTGGTTTTCTTTATAAATTACTAGATGCTTTTCTTTTGCTTATTTTAGAATTACTTCCTTC ACTTTGACTTTAGATATTCTGATTATCATGTGCCATTATGATGTCTGTTTTGCAATATATTTTGT TTATATTTTGTTGTATTTTGTTTGCTGAGCTTCCTGTGTATGTATGTCTAATTCTATTGCTAGAG TTGGAAAGTTTTCA |
| 3713 | ZNF91 | 3857072 | ACCGCACCCAACCAAATCTATACATT |
| 3714 | ZNF91 | 3857074 | GCGCGATCTCGTCCCACTGCTCACTGC |
| 3715 | ZNF91 | 3857096 | TAATGGACTGACATCTCTAGTGATTTTTTTGCCAGTGAGTTTTAATTGCCATTAAGTTAAAGA ATATTGTTCCCATAGGCTAAATTTTTATTTTTATTTTCTCATTTAAATGTATTTGACTTAATTTTT GTGGATACCTAATATGTGTACATATTATGCCATATGTGGCATATTTTGATACGGACACACAAT ATATAACAATCGCATTAGACTAAATGCGGTCTCCATTACCTCTAGC |
| 3716 | ZNF91 | 3857098 | GCTTTGAACTAATGCTCACACCTTAATGCATAGGAAAGCATTTATGCTTGAGAAAAAGTGAAC AAATATAGACAAAAAGCCATTAATACCTGCTCACATCGTACTCAAATTCAGAGCGTTCATACTA AATAAGAAGTGTAATTACTGTCAAACGACTGATC |
| 3717 | ZNF91 | 3857100 | GATGTGCCAACGCTTTTGACAAGTCAAACTTT |
| 3718 | ZNF91 | 3857102 | GTGTGAATAATGTGGTAAAGTCTATAAAAAGTCCTGAATTCTTAACAG |
| 3719 | ZNF91 | 3857104 | GCAAATCCTTTTTCTGGTCCTCAGCCCTAACCAGACATAAGAAAATTCATACTGGACAGCAACC CTACAAACAGGAA |
| 3720 | ZNF91 | 3857106 | AGAAAATTCATACTATCACACCTGTA |
| 3721 | ZNF91 | 3857107 | GTCCTCAGCTCTTACTAAACATAAGATAAT |
| 3722 | ZNF91 | 3857108 | TTTATATCATCCTCAACCCTAAATG |
| 3723 | ZNF91 | 3857109 | CATTTAGCCAGCCTTCACACCTTACTACACATAAGAGGATGCACACTGGAGAGAAACCCTACA AATGTGAAGAATGTGGCAAAGCTTTTAGCCAATCCTCAACCCTTACTACACATAAGATAATTC ATACTGGAGAGAAACCCTACAAATGTGAAGAATGTGGCAAAGCTTTTAGGAAATCTTCAACTC TTACTGAACATAAGATAATTCATACTGGAGAGAAACCCTACAAATGTGAAGAATGTGGCAAA GCATTTAGCCAATCCTCAACCCTAACTAGACATACGAGGATGCACACTGG |
| 3724 | ZNF91 | 3857110 | AGAGAAAACCTACAAATGTGAAGAATGTG |

TABLE 13-continued

Subtyping Target Sequences

| SEQ ID NO. | Gene | Affy Probeset ID | Sequence |
|---|---|---|---|
| 3725 | ZNF91 | 3857111 | ATCAATCTTCAAATCTTACGACACATAAGATAATTCATACTAAAGAGAAACCTTCCAAGAGTGAAGAATGTGACAAAGCATTTATCTGGTCCTCAAC |
| 3726 | ZNF91 | 3857112 | GGCAAAGCTTTTAAGCACTCCTCAG |
| 3727 | ZNF91 | 3857113 | GGCAAAGCTTTTAGCCGTTCCTCAACCCTTACTAAGCATAAGACAATTC |
| 3728 | ZNF91 | 3857114 | AACTAGACATAAGAGGATACACACT |
| 3729 | ZNF91 | 3857115 | TGACAAAACTTTTAAGCGACTCTCAA |
| 3730 | ZNF91 | 3857116 | AACTAGACATAAGAGGATACACACT |
| 3731 | ZNF91 | 3857117 | TTTAGCCGTTCTTCAACCCTTGCTAAACATAAGAGAATTCATACTGGAGAGAAACCCTACAAATGTAAAGAATGTGGCAAAGCTTTTAGCAATTCCTCAACCCTTGCTAATCATAAGATAACTCATACTGAAGAGAAACCCTACAAATGTAAAGAATGTGACAAAGCTTTTAAGCGACTCTCAACCCTT |
| 3732 | ZNF91 | 3857118 | AACTAGACATAAGAGGATACACACT |
| 3733 | ZNF91 | 3857119 | ACCCAACATAAATGCGTTTATATTACA |
| 3734 | ZNF91 | 3857120 | GTGGGAAATATTTGAAAGTCTTCTATAAATTTTTAAATTCAAACAGACATACGATAAGACATACTGGAAAGAAATGCTTCAAATGTAAAAAATGTGTCAAGTCATTTTGCATCC |
| 3735 | ZNF91 | 3857121 | TTCAAAAAGTATTACTGAGAAAATATGAAAAATGTGGACATGAGAATTTACAGTTAAGAAAAGGTTGTAAAAGTGTGGATGAGTGTAAGGTGCACAAAGAAGGTTATAATAAACTTAACCAGTGTCTCACAACTGCCCA |
| 3736 | ZNF91 | 3857122 | CCTGATTACTTATCTGGAGCAAGGAAAAGAGCCCTGGAATATGAAGCAACATGAGATGGTGGATGAACCCAC |
| 3737 | ZNF91 | 3857123 | TCTCCGGAGGAGTGGCAATGTCTGGACACTGCACAGCAGA |
| 3738 | ZNF91 | 3857124 | CCGGAGTTTCCAGGTCTCGACTTCACTGCTC |
| 3739 | CXCL17 | 3863641 | TGTTTCCTTCAAATGGGGTCTGCCAATTCACAACCAGATGACCCATTTTACCCTATTCACTGCAGACTGAATCCAGATTCTACACATACTTATCCCCACCAAGACCCTCACTCTGTCTCCATTGGCCTACTTGTTCATC |
| 3740 | CXCL17 | 3863642 | GAGCGCCCACTCTTCCAATTAAACATTCTCAGCCAAGAAGACAGTGAGCACACCTACCAGACACTCTTCTTCTCCCACCTCACTCTCCCACTGTACCCACCCCTAAATCATTCCAGTGCTCTCAAAAAGCATGTTTTTCAAGATCATTTTGTTTGTTGCTCTCTCTAGTGTCTTCTTCTCTCGTCAGTCTTAGCCTGTGCCCTCCCCTTACCCAGGCTTAGGCTTAATTACCTGA |
| 3741 | CXCL17 | 3863643 | AGCCAAACAAGCATTCCAGAGCCTGCCAGCAATTTCTCAAACAATGTCAGCTAAGAAGCTTTGCTCT |
| 3742 | CXCL17 | 3863644 | ATTGGTTCCTGAGAGCCCCGAGAAGAAAATTCATGACAGTGTCTGGGCTGCCAAAGAAGCAGTGCCCCTGTGA |
| 3743 | CXCL17 | 3863647 | GCCACAGGGACCGAGGCCAGGCTTCTAGGAGATGGCTCCAGGAAGGCGGCCAAGAAT |
| 3744 | CXCL17 | 3863648 | CCTGTTGCTGCCACTAATGCTGATGTCCATGGTCTC |
| 3745 | CXCL17 | 3863649 | CCCTCAAATGGGAACGCTGGCCTGGGACTAAAGCATAGACCACCAGGCTGAGTATCCTGACCTGAGTCATCCCCAGGGATCAGGAGCCTCCAGCAGGGAACCTTCCATTATATTCTTCAAGCAACTTACAGCTGCACCGACAGTTGCG |
| 3746 | TPX2 | 3881448 | TCCTCCCGGAGTTTGGAACGGCTGAAGTTCACCTTCCAGCCCCTAGCGCCGTTCGCGCCGCTAGGCCTGGCTTCTGAGGCGGTTGCGGTGCTCGGTCGCCGCCTAGGCGGGGCAGGGTGCGAGCAGGGGCTTCGGGCCACGCTTCTCTTGGCGACAGGATTTTGCTGTGAAGTCCGTCCGGGAAACGGAGGAAAAAAAGAGTTGCGGGAGGCTGTCGGCTAATAAC |
| 3747 | TPX2 | 3881451 | TGATACATATTTGCCAGACTTCAAGATTTCAGAAAAGGGGTGAAAGAGAAGATTGCAACTTTGAGTCAGACCTGTAGGCCTGATAGACTGATTAAACC |
| 3748 | TPX2 | 3881454 | AAGGTGACCTGCTGAGAAAAGTGGTACAAATACTGGGAAAAACCTGCTCTTCTGC |
| 3749 | TPX2 | 3881455 | CACAAGTTAAAAGCTCTTATTCCTATGATGCCCCCTCGGATTTCATCAATTTTTCATCCTTGGATGATGAAGGAGATACTCAAAACATAGATT |
| 3750 | TPX2 | 3881457 | GGAACTGGAGGGCTTTTTCAGGGCAAAACTCCTTTGAGAAAGGCTAATCTTCAGCAAGCTATTGTCACACCTTTGAAAC |

TABLE 13-continued

Subtyping Target Sequences

| SEQ ID NO. | Gene | Affy Probeset ID | Sequence |
|---|---|---|---|
| 3751 | TPX2 | 3881458 | GACAACACTTACTACAAAGAGGCAGAAAAAGAAAATCTTGTGGAACAATCCATTCCGTCAAA TGCCTTGTTCTTCCCTGGAAGTTGAGGCAGCCATATCAAGAAAA |
| 3752 | TPX2 | 3881459 | CAAGAGATGTGCCACTCCTGTAATCATCGATGAAAT |
| 3753 | TPX2 | 3881462 | AGAAGGCAGTGCTCATCAAGATACTGCTGAAAAGAATGCATCTTCCCCAGAGAAAGCCAAGG GTAGACATACTGTGCCTTGTATGCCACCTG |
| 3754 | TPX2 | 3881463 | GAGAAGAGTATGAAAATGCAGCAAGAGGTGG |
| 3755 | TPX2 | 3881464 | ATCAGTGAGCCAGGTCACCAAATCAGTTGACTTCCACTTCCGCACAGATGAGCGAATCAAACA ACATCCTAAGAACCAGGAGGAATATAAGGAAGTGAACTTTACATCTGAACTACGAAAGCATC CTTC |
| 3756 | TPX2 | 3881467 | GCCCGAGTGACTAAGGGATGTACCATTGTTAAGCCTTTCAACCTGTCCCAAGGAAAGAAAAG AACATTTGATGAAACAGTTTCTACATATGTGCCCCTTGCACAGCAAGTTGAAGACTTCC |
| 3757 | TPX2 | 3881468 | ATGGCTCACTTCAGTGTCCAACTCCTGGGCT |
| 3758 | TPX2 | 3881472 | CTTGATCCCAGAATACTTGAAGGTGGGCCCATCTTGCCCAAGAAACCACCTGTGAAACCACCC ACCGAGCCTATTGGCTTTGATTTGGAAATTGAGAAAAGAATCCAGGAGCGAGAATCAAAGAA GAAAACAGAGGATGAACACTTTGAATTTCATTCCAGACCTTGCCCTACTAAGATTTTG |
| 3759 | TPX2 | 3881476 | TGTTCCTGAAAAGAAGGTACTTCCAATCACC |
| 3760 | TPX2 | 3881477 | CATTGAAGAACAGAATTCGAATGCCCACCAAAGA |
| 3761 | TPX2 | 3881478 | GACGAACCGGTAGTGATAAAAGCTCAACCTGTGCCACATTATGGGGTGCCTTTTAAGCCCCAA ATCCCAGAGGCAAGAACTGTGGAAATATGCCCTTTCTCGTTTGATTCTCGAGACAAAGAACGT CAGTTA |
| 3762 | TPX2 | 3881479 | GTGCCCAAGTTCAAGGCACTTCCCTTGCCTCATTTTGACACCATTAACCTGCCAGAGAAGAAG GTAAAGAATGTGACCCAGATTGAACCTTTCTGCTTGGAGACTGACAG |
| 3763 | TPX2 | 3881482 | CTTGTTTCAAGGCTCGTCCAAACACCGTCATCTCTCAGGAG |
| 3764 | TPX2 | 3881483 | TTCAGGAACCTTTTCAGCTGGCTACTGAGAAGAGAGCCAAAGAGCGGCAGGAGCTGGAGAA GAGAATGGCTGAGGTAGAAGCCCAGAAAGCCCAGCAGTTGGAGGAGGCCAGACTACAGGA GGAAGAG |
| 3765 | TPX2 | 3881487 | GTGCATAAGGCAAATCCAATACGCAAGTACCAGGGTCTGGAGATAAAGTCAAGTGACCAGCC TCTGACTGTG |
| 3766 | TPX2 | 3881488 | CCAAATTCTCCACTCGATTCCACTGCTAA |
| 3767 | TPX2 | 3881489 | TCAGCTGTGAGCTGCGGATACCGCCCGGCAATGGGACCTGCTCTTAACCTCAAACCTAGGACC GTCTTGCTTTGTCATTGGGCATGGAGAGAACCCATTTCTCCAGACTTTTACCTACCCGTGCCTG AGA |
| 3768 | TPX2 | 3881490 | CAGAAAATAAAGATAGTTAAATCCT |
| 3769 | TPX2 | 3881491 | GTCCTCTTCTCTGCATACCGTGAATTTATAGTTAAGGATCCCTTTGCTGTGAGGGTAGAAAACC TCACCAACTGCACCAGTGAGGAAGAAGACTGCGTGGATTCATGGGGAGCCTCACAGCAGCCA CGCAGCAGGCTCTGGGTGGGGCTGCCGTTAAGGCACGTTCTTTC |
| 3770 | TPX2 | 3881492 | GGAACCGTGCAGTGTGCATTTTAAGACC |
| 3771 | TPX2 | 3881493 | TGGCCTGGAATAAATACGTTTTGTC |
| 3772 | MYL9 | 3883925 | GGAAGCCCCACCCACCAGAAGCCAAG |
| 3773 | MYL9 | 3883926 | GACCACCAAGAAGCGGCCACAGCGGGCCACATCCAATGTCTTCGCAATGTTTGACCAGTCCCA GATCCAGGAGTTTAAGGAGGCTTTCAACATGATTGACCAGAACCGTGATGGCTTCATTGACA AGGAGGACCTGCACGACATGCTGG |
| 3774 | MYL9 | 3883929 | AGAACCCCACAGACGAATACCTGGAGGGCATGATGAGCGAGGCCCCGGGGCCCATCAACTTC ACCATGTTCCTCACCATGTTTGGGGAGAAGCTGAACGGCACGGACCCCGAGGATGTGATTCG CAACGCCTTTGCCTGCTTCGACGAGGAAGCCTCA |
| 3775 | MYL9 | 3883930 | AGGAAGTGGACGAGATGTACCGGGAGGCACCCATTGATAAGAAAGGCAACTTCAACTACGT GGAGTTCACCCGCATCCCTCAAACATGGCGCCAAGGATAAAGACGACTAG |

TABLE 13-continued

Subtyping Target Sequences

| SEQ ID NO. | Gene | Affy Probeset ID | Sequence |
|---|---|---|---|
| 3776 | MYL9 | 3883931 | CACCCGTCCATACCAGCTCCCTGCCCATGACCCTCGCTCAGGGATCCCCCTTTGAGGGGTTAG<br>GGTCCCAGTTCCCAGTGGAAGAAACAGGCCAGGAGAAGTGCGTGCCGAGCTGAGGCAGATG<br>TTCCCACAGTGACCCCAGAGCCCTGGGCTATAGTCTCTGACCCCTCCAAGGAAAGACCACCTT<br>CTGGGGACATGGGCTGGAGGGCAGGACCTAGAGGCACCAAGGGAAGGCCCCATTCCGGGG<br>CTGTTCCCCGAGGAGGAAGGGAAGGGGCTCTGTGTGCCCCCCAGGAGGAAGAGGCCCTGAG<br>TCCTGGGATCAGACACCCCTTCACGTGTATCCCCACACAAATGCAAGCTCACCAAGGTCCCCT<br>CTCAGTCCCCTTCCCTACACCCTGACCGGCCACTGCCGCACACCCACCCAGAGCACGCCACCC<br>GCCATGGGAGTGTGCT |
| 3777 | MYL9 | 3883932 | GGACATCTGTCCCAGAGGGGGCAGAATCTCCAAT |
| 3778 | MYL9 | 3883934 | AGCTCGGCTGAAACTCCTCATCCTGGCTCCAAACAGAGGCCCAAAAGTCCCTGGTATCAACTC<br>CAGAAGGGGCGAGACCCGAACAAGTTCCAAACCAGGCCCAAATAGTATCCCAAACTCAGTCC<br>CAAACACATTCTCACCCCCGGCAGCAGGCTGCAGGCCTCCAGCTACACACACGGCCCTGGGC<br>AACTCTCAGTCTGGCCACCCATTCGATGCTGCCAGCCCCAAGGGTGTGGGAGGGGGGTCTCA<br>GAGTGTCCCAGGGTACTGGCCACACATGCCCGACACCAGGGTCATAAGGTCCTCTCAGCA |
| 3779 | FLRT3 | 3898359 | TGCCACTGTCCTGATACTTTTTAAGGTGGTCTTTGAAAAACTGTTTTTTTAAAATAGCCTTTTAG<br>TAGAGTGAGTTGGCATTTGTGATACTGTGAAATACACACTTTCTCTTTGTCCCTGTTTCTGGCA<br>TACAACTCCTAAAATCCTTGCAATCTTCAAAGTGATATATTTTCATATGCTAATGAGTTCACTG<br>ATAGCTGGCAGGCCCTAGGTAGCTTCAAGATAAAGTCTGATCATTGAAAAGACCAAGACATG<br>ATTATAGGGTTGGGACTTACAACCCCAAACCCTAACCTCCAGAGAGGGCGAAGTGGATGAAG<br>ATTAAGTTGATCACCAGTGACCAGTGGTTTAATCAAGCATGCCTATGTAATCAAGCCTCCATA<br>AAAAAACAAAAGGTCAAGATTTGGAGAGCTTCCAGATTGCTGAACATGTGGTGGTTCCTGCA<br>GGATGGCATGCCTGGAGAGGGCATGGAAGCTCTGTGCCCACCTAGACCTCACCTTATGTTTCC<br>TGCCATCTGGATCCTTTGTAACATCCTTTATAATACGTCAGTAAATCTGTTTCCTTGCATTTTGT<br>GAGCTGTTGTAGCAAATTAATAGAACACAAAAAGGGGATCCTGGGAAACCAAACTTGAAGCT<br>GACTAGTCTTGCAACTGGTGTC |
| 3780 | FLRT3 | 3898360 | TGCTTGCTTTTTCAGGATTGTGTTACTATCACTAAGTAGCAAATTGCCCAGCACATTAGTCCTA<br>AACGTCCCATGTATT |
| 3781 | FLRT3 | 3898361 | TGCTGTGTCGAACAATCAGGACTGCATTCATATGAGATCCTTGTAGTATAAGCACAGGCCATT<br>TTTCACTTTGGTATTAATAAAATGTAAAAAAAAAAAACTGGCTGAATGGCTGAATGAGATAAA<br>ATTTAATTTTAAAAAATGGTTATGAAATAATGTTCCAATTATTAAATTTGTATTATCCCAGTGGT<br>ATTCAATAAATCAAAATGTGTGAAGTAATGGGCAATATCAAACTTCCTGCATATCTCCATTTTT<br>GCTCTAGGCAAATTAATTATCCTTAAAAAAGTTAAGCATATCTTCTGAACTGAATACATCAGCT<br>GGCATAAAAGGAGCATGAAGTCTGTTAAAGCCATTGTCAGCAAAGCTTTGAAAATAAAGGAC<br>TTCACAAAAACGGTAATGTAAATGTGCTTCCAAGTTGGGGGGAAAATGTGTACTTAGGAAAA<br>CATGGAAACTTAGACTTGTATAGTGTAATGAACACAAATACCAAAACTGCATTTTGGTTTTGC<br>CTATACCATCCTGATTTTTGAAAAGTGAATTATAAACACAAAATTGTTAGTGTTTATGATGTTT<br>TTATCATAAAGGATGTCAGAGAAACTTTATGCATATTAAAAATGTAATGTAATTATAAGCGAT<br>TCCCCTCAACAATCCAGAGAAAGTAGTTCTTTAAATAAGAGATAATTTAAAGAAAAATAAATA<br>CTAGACATCAAATTTAGATCTGGTTTATGTCAAAGGTTTTAACACTGTACATAAATGTTCAATT<br>TACTTTTACAAAGATCAAGAATACTGCCCATTACTGTCACAATTTTCCAGATATTATATAATGA<br>ACTCGTAATGTAACATTTCCTTCTAGCTTCCTACTGAATTGTGAGCTGTTACTTGTTGAAAAAC<br>CATATCACTTTTCTGTTGCCATGATTTTTTTTTTTCAACAAAAAACCAAAGTGCATTGTACGCC<br>CTTTGGCCAGTCTTGTATGTGCCTTGATCAACGCTACATGTATT |
| 3782 | FLRT3 | 3898362 | CCTCATCGGGACTAAAATTGGGCTGTTCCTTCAAGTAGCACCTCTATCAGTTATGGCTAAATCC<br>TGTCCATCTGTGTGTCGCTGCGATGCGGGTTTCATTTACTGTAATGATCGCTTTCTGACATCCA<br>TTCCAACAGGAATACCAGAGGATGCTACAACTCTCTACCTTCAGAACAACCAAATAAATAATG<br>CTGGGATTCCTTCAGATTTGAAAAACTTGCTGAAAGTAGAAAGAATATACCTATACCACAACA<br>GTTTAGATGAATTTCCTACCAACCTCCCAAAGTATGTAAAAGAGTTACATTTGCAAGAAAATA<br>ACATAAGGACTATCACTTATGATTCACTTTCAAAAATTCCCTATCTGGAAGAATTACATTTAGA<br>TGACAACTCTGTCTCTGCAGTTAGCATAGAAGAGGGAGCATTCCGAGACAGCAACTATCTCCG<br>ACTGCTTTTCCTGTCCCGTAATCACCTTAGCACAATTCCCTGGGGTTTGCCCAGGACTATAGAA<br>GAACTACGCTTGGATGATAATCGCATATCCACTATTTCATCACCATCTCTTCAAGGTCTCACTA<br>GTCTAAAACGCCTGGTTCTAGATGGAAACCTGTTGAACAATCATGGTTTAGGTGACAAAGTTT<br>TCTTCAACCTAGTTAATTTGACAGAGCTGTCCCTGGTGCGGAATTCCCTGACTGCTGCACCAGT<br>AAACCTTCCAGGCACAAACCTGAGGAAGCTTTATCTTCAAGATAACCACATCAATCGGGTGCC<br>CCCAAATGCTTTTTCTTATCTAAGGCAGCTCTATCGACTGGATATGTCCAATAATAACCTAAGT<br>AATTTACCTCAGGGTATCTTTGATGATTTGGACAATATAACACAACTGATTCTTCGCAACAATC<br>CCTGGTATTGCGGGTGCAAGATGAAATGGGTACGTGACTGGTTACAATCACTACCTGTGAAG<br>GTCAACGTGCGTGGGCTCATGTGCCAAGCCCCAGAAAAGGTTCGTGGGATGGCTATTAAGGA<br>TCTCAATGCAGAACTGTTTGATTGTAAGGACAGTGGGATTGTAAGCACCATTCAGATAACCAC<br>TGCAATACCCAACACAGTGTATCCTGCCCAAGGACAGTGGCCAGCTCCAGTGACCAAACAGC<br>CAGATATTAAGAACCCCAAGCTCACTAAGGATCACCAAACCACAGGGAGTCCCTCAAGAAAA<br>ACAATTACAATTACTGTGAAGTCTGTCACCTCTGATACCATTCATATCTCTTGGAAACTTGCTCT<br>ACCTATGACTGCTTTGAGACTCAGCTGGCTTAAACTGGGCATAGCCCGGCATTTGGATCTAT<br>AACAGAAACAATTGTAACAGGGGAACGCAGTGAGTACTTGGTCACAGCCCTGGAGCCTGATT<br>CACCCTATA |

TABLE 13-continued

Subtyping Target Sequences

| SEQ ID NO. | Gene | Affy Probeset ID | Sequence |
|---|---|---|---|
| 3783 | FLRT3 | 3898363 | TCTGAAGTAACGGAAGCTACCTTGTATAAAGACCTCA |
| 3784 | FLRT3 | 3898365 | TACCTGTTCTTGTATAACGTGACTGCACCAGACATTCTGAAAA |
| 3785 | FLRT3 | 3898369 | CTTTGTGTGGACTGGACGCAGAGCTTGGGAGACGGGGAGGGCTATTACTCCAATTCACTGT<br>CAATGGAATTACAGCTATAGCGGCAGTGTATATAGGATTGCTTTTTC |
| 3786 | TGM2 | 3905144 | TTACTTCCACGTTGGCCTATCTGTCCCCTTCTCCATCCTATCTGAAGCCCTCGAGGCAGGGACC<br>ACGTATCTCTTAAATACACTAATAAATGCTGAATTGGTAAATGAATGTTTCCTAACTCAACTCC<br>CACAAGACCTGTGCTGTCCCATAGAAATAATACATGAGCCACAAATGCAAGCCACATATGTAA<br>TTTAGAATTTTCTAGTGACCACATTGAAAACAGTAAAAAAGCCATAGGTGGAATTAGCTTTAA<br>TAATGTATTTTATTTAATCCAATATATCCAAAACATTATTTCAACATGTAATCAATATAAGAATT<br>AGTAAGGTATTTGACCTTCTTATTTTTGTACTCAATCTTTGAAATGTGGTGTGTGTTTTATACTG<br>ACAGCAGGTCTCAATTTGAACTAGCTGCATTTCAAGTGCTCGGTAGCCAGTCTGGCTAGTACT<br>GGATGAAGCAGGTCTAGACTGCGATTCCGTGGATGTG |
| 3787 | TGM2 | 3905146 | CCCAGCCTGACCTGAGACTGTCGGAGAGGCTGTCTGGGGCCTTTATCAAAAAAAGACTCAGC<br>CAAGACAAGGAGGTAGAGAGGGGACTGGGGGACTGGGAGTCAGAGCCCTGGCTGGGTTCA<br>GGTCCCACGTCTGGCCAGGCACTGCCTTCTCCTCTCTGGGCCTTTGTTTCCTTGTTGGTCAGAG<br>GAGTGATTGAACCAGCTCATCTCCAAGGATCCTCTCCACTCCATGTTTGCAATGCTTTTATATG<br>GCCCAGCCTTGTAAATAACCACAAGGTCCACTCCCTGCTCCACGAAGCCTTAAGCCATAGGCC<br>CAGGATATTTCTGAGAGTGAAACCATGACTGTGACCACCTTCTGTCCCCAGCCCTGTCCTGGTT<br>CCTTCCTATGCCCAGGTACCACCCTTCAGACCCCAGTTCTAGGGGAGAAGAGCCCTGGACACC<br>CCTGCTCTACCCATGAGCCTGCCCGCTGCAATGCCTAGACTTCCCAACAGCCTTAGCTGCCAGT<br>GCTGGTCACTAACCAACAAGGTTGGCACCCCAGCTACCCCTTCTTTGCAGGGCTAAGGCCCCC<br>AAACATAGCCCCTGCCCCGGAGGAAGCTTGGGGAACCCATGAGTTGTCAGCTTTGACTTTATC<br>TCCTGCTCTTTCTACATGACTGGGCCTCCCTTGGGCTGGAAGAATTGGGGATTCTCTATTGGA<br>GGTGAGATCACAGCCTCCAGGGCCCCCAAATCCCAGGGAAGGACTTGGAGAGAATCATGCT<br>GTTGCATTTAGAACTTTCTGCTTTGCACAGGAAAGAGTCACACAATTAATCAACATGTATATTT<br>TCTCTATACATAGAGCTCTATTTCTCTACGGTTTTATAAAAGCCTTGGGTTCCAACCAGGCAGT<br>AGATGTGCTTC |
| 3788 | TGM2 | 3905147 | CATTTAATCACCATGGGAAACTGTTGTGGGCGCTGCTTCCAGGATAAGGAGACTGAGGCTTA<br>GAGAGAGGAGGCAGCCCCCTCCACACCAGTGGCCTCGTGGTTATTAGCAAGGCTGGGTAATG<br>TGAAG |
| 3789 | TGM2 | 3905148 | GTCCCCTCCACATCCCAGCAGCCCAAG |
| 3790 | TGM2 | 3905149 | CCAAGCTAGTGAGCAAAATATGCCCCTTCTTGGGCCCCAGACCCCAGGGCAGGGTGGGCAGC<br>CTATGGGGGCTCTCGGAAATGGAATGTGCCCCTGGCCATCTCAGCCTCCTGAGCCTGTGGGT<br>CCCCACTCACCCCCTTTGCTGTGAGGAATGCTCTGTGCCAGAAACAGTGGGAGCCCTGACCTT<br>GGCTGACTGGGGCTGGGGTGAGAGAGGAAAGACCTACATTCCCTCTCCTGCCCAGATGCCCT<br>TTGGAAAGCCATTGACCACCCACCATATTGTTTGATCTACTTCATAGCTCCTTGGAGC |
| 3791 | TGM2 | 3905150 | TGCCGCTCCACATGGGCCTCCACAAGCTGGTGGTGAACTTCGAGAGCGACAAGCTGAAGGCT<br>GTGAAGGGCTTCCGGAATGTCATCATTGGCCC |
| 3792 | TGM2 | 3905151 | AAGGCTGCACCTTCACTGTGGAGGGGGCCGGCCTGACTGAGGAGCAG |
| 3793 | TGM2 | 3905152 | TCCTCTATGAGAAATACCGTGACTGCCTTACGGAGTCCAACCTCATCAAGGTGCGGGCCCTCC<br>TCGTGGAGCCAGTTATCAACAGCTACCTG |
| 3794 | TGM2 | 3905153 | TGGGGCTAAGAACCACACTTCAGTGGGTAGCTTTGTTCCTGCCATCTTCTTTCTCATCCCCATA<br>TCACTGTGCGGCTTTTGCTCTGCAACGACCCCTTGGTCTTACCTCTGCCCAGCAGGTGATAAGAT<br>CTGGGAACAGAGAGGAAACAGAGGGGAAACAGAGAGGGGAGGTCATCTCCCCGGGCTCAC<br>ACAGCCAGTGAGTGGCCAGACAGGGCCTGAGGCAAGTCTCCCAATCTGAGCACTTACTGGCA<br>GAGGTGATTCTTCATCTGTGCAACGGGTACAGCATCACGAGCCTCGTGGAGGGAAATGACCT<br>TATGTCCATGAGAGGCATTCTTCAGTGAGTGTGGACCATATTGTTGGACTCTAAGATCTGGAT<br>TATTAGTCCAGATGCCTGCACAGTACATATCAGCTGTGTGACCTAGGACAACGTTATTTCACCT<br>GCTGGAGACTCAGTTTTCTCATCTGTAAGTTGGGTGGTAATACACGTACAAGCCTTTTAGGGT<br>TGTCATGTAGGTGAAGTAGGAGCCCGCCGTGGGAAGTGCAGTGCCTGGTGCAGCAAGCAGA<br>TGTCGGCTCTGATCCTCCCCAGGATGAAGGGCCCGCGGCTCACACACCCTGAGTCCCGAGCG<br>CACCAGGCTCTTCCGGGACACTCGCTCAGCTCATCCTCCCACAGCCTTAGGAGTGCCTGTGCC<br>ACGCAGATCCAAACATCGAGGACCTGGAGGTGGAGTGGCTCACGCGGGTCACCCATTAG<br>AAGAGGCAAAGGCAGGATTAGAACCAAGGCCCGTGGGAGTCCAAGTGCGTCCTCTACC |
| 3795 | TGM2 | 3905161 | GTAAAGCCCTGTGTTCCTGGAGCATTTGTTGA |
| 3796 | TGM2 | 3905162 | GGGCGAACCACCTGAACAAACTGGCCGAGAAGGAGGAGACAGGGATGGCCATGCGGATCC<br>GTGTGGGCCAGAGCATGAACATGGGCAGTGACTTTGACGTCTTTGCCCACATCACCAACAAC<br>ACCGCTGAGGAGTACGTCTGCCGCCTCCTGCTCTGTGCCCGCACCGTCAGCTACAATGGGATC |

TABLE 13-continued

Subtyping Target Sequences

| SEQ ID NO. | Gene | Affy Probeset ID | Sequence |
|---|---|---|---|
| 3797 | TGM2 | 3905165 | GCCCAGTTCCAGTTCGTGCCATCAAGGAGGGCGACCTGAGCACCAAGTACGATGCGCCCTTT GTCTTTGCGGAGGTCAATGCCGACGTGGTAGACTGGATCCAGCAGGACGATGGGTCTGTGCA CAAATCCATCAACCGTTCCCTGATCGTTGGGCTGAA |
| 3798 | TGM2 | 3905167 | ACTTCCACTGCTGGGTGGAGTCGTGGATGACCAGGCCGGACCTGCAGCCGGGGTACGAGGG CTGGCAGGCCCTGGA |
| 3799 | TGM2 | 3905168 | CGCGTCGTGACCAACTACAACTCGGCCCATGACCAGAACAGCAACCTTCTCATCGAGTACTTC CGCAATGAGTTTGGGGAGATC |
| 3800 | TGM2 | 3905171 | TCAGCACAGAACCTAGCCCAGTGTCACTCTCGGCAAATATTAGCCAGTAATAACTGGATCCTA ACAGTAATATCAGTGTCAAGAAAGAAAGCATGTTCTAAAATGTAGAGGGGGAATATCGAGCA ATTTAAAACCAAAAAGTAAATAAATCTAAAACAAAATCTTCAAAATTTAAGGCCAGAAAA TGTCGATGATTGTTGCCAGGCTGATGATGGTGCTTATGAGAATGGGTTAGCATCACATGCTG GCTAAGAACGTAGACTCA |
| 3801 | TGM2 | 3905172 | CTGCACGCTGGGATGTGGGTCATGAGCCCTGGGAGGGGGCACGAAGAGCACTGGAGTAGG AATCAGGACATCCCTGCCCTGGTCCTGCCCCCTGCCACCAACACTCTCAATGCGCTATGTGGCC TAGAGCCTGTGACCACCCTCTCCGGTCCTTTATCCAATAGCCATCCCTCCAGTGG |
| 3802 | TGM2 | 3905173 | CGCTGGGACAACAACTACGGGGACGGCGTCAGCCCCATGTCCTGGATCGGCAGCGTGGACA TCCTGCGGCGCTGGAAGAACCACGGCTGCCAGCGCGTCAAGTATGGCCAGTGCTG |
| 3803 | TGM2 | 3905175 | AGATGGGATCCTAGACATCTGCCTGATCCTTCTAGATGTCAACCCCAAGTTCCTGAAGAACGC CGGCCGTGACTGCTCC |
| 3804 | TGM2 | 3905177 | TGCTGTGTACCTGGACTCGGAAGAGGAGCGGCAGGAGTATGTCCTCACCCAGCAGGGCTTTA TCTACCAGGGCTCGGCCAAGTTC |
| 3805 | TGM2 | 3905179 | TGACTGGACAGCCACCGTGGTGGACCAGCAAGACTGCACCCTCTCGCTGCAGCTCACCACCCC GGCCAACGCCCCCATCGGCCTGTATCGCCTCAGCCTGGAGGCCTCCACTGGCTACCAGGGATC CAGCTTTGTGCTGGGCCACTTCATTTTGCTCTTCAACGCCTGGTGCC |
| 3806 | TGM2 | 3905180 | CAAGGCCCGTTTTCCACTAAGAGATGC |
| 3807 | TGM2 | 3905184 | CTGGAGACCAATGGCCGAGACCACCACACGGCCGACCTGTGCCGGGAGAAGCTGGTGGTGC GACGGGGCCAGCCCTTCTGGCTGACCCTGCACTTTGAGGGCCGCAACTACGAGGCC |
| 3808 | TGM2 | 3905187 | CAGCCGCCAGTGGTCGCACTTGGAGGGTCTCGCCGCCAGTG |
| 3809 | TGM2 | 3905188 | GTTAGCGCCGCTCTCCGCCTCGGCAG |
| 3810 | TGM2 | 3905190 | CAAGAGACCAGAGATACCAGGATGAGAGATAGGACCCCTGGTTGCCAGGTTCGAGAAGTCC TAGGCTGAGTCCCTG |
| 3811 | TMPRSS2 | 3933041 | GCTTTGACAAAATGACTGGCTCCTGACTTAACGTTCTATAAATGAATGTGCTGAAGCAAAGTG CCCATGGTGGCGGCGAAGAAGAGAAAGATGTGTTTTGTTTTGGACTCTCTGTGGTCCCTTCCA ATGCTGTGGGTTTCCAACCAGGGGAAGGGTCCCTTTTGCATTGCCAAGTGCCATAACCATGAG CACTACTCTACCATGGTTCTG |
| 3812 | TMPRSS2 | 3933042 | CTGGTTTTGCTTCCCCGTGCATGATTTACTCTTAGAGATGATTCAGAGGTCACTTCATTTTTATT AAACAGTGAACTTGTCTGGC |
| 3813 | TMPRSS2 | 3933045 | CCTCTGGTCACTTCGAAGAACAATATCTGGTGGCTGATAGGGGATACAAGCTGGGGTTCTGG CTGTGCCAAAGCTTACAGACCAGGAGTGTACGGGAATGTGATGGTATTCACGGACTGGATTT ATCGACAAATG |
| 3814 | TMPRSS2 | 3933046 | GGTGGAGATTCGAAGCCCACACAGTCACTCGTAACTCACACTGCGACCCCCGCCCCCAACTC CTCTAGGCCTGGTCAGTGGTGTGCGGCAGATTGTGACTTGATTTTCTGCTCTCTGTACCTTGCT GTGTCCCACAG |
| 3815 | TMPRSS2 | 3933047 | TCAGAAGTGCTGAACGCTGCCAAGGTGCTTCTCATTGAGACACAGAGATGCAACAGCAGATA TGTCTATGACAACCTGATCACACCAGCCATGATCTGTGCCGGCTTCCTGCAGGGGAACGTCGA TTCTTGCC |
| 3816 | TMPRSS2 | 3933048 | TAGAGCCCTATAGTTTCAGAGCTGGGAATTTCTTTCCCTGAAGCTGAACTCCAGAGCTGCATT CAGCACAGGCACCGCCAGTTGTAAGGAGAATCCAGGTTTCCCAGGAGAGGGTTGGTGCTG GGATGAGCTGACCGGGCAGGGCTGGAAAATAGGGCTGTGACCATCTGTGTAGTGCGTGTG GAGGTCTCAGGGAGGGAAGTGTGCTCTCCCTGCGAGAGCTGCAGGCAACACTGGGAGCTCA ACA |
| 3817 | TMPRSS2 | 3933052 | AAACCAGTGTGTCTGCCCAACCCAGGCATGATGCTGCAGCCAGAACAGCTCTGCTGGATTTCC GGGTGGGGGGC |

TABLE 13-continued

Subtyping Target Sequences

| SEQ ID NO. | Gene | Affy Probeset ID | Sequence |
| --- | --- | --- | --- |
| 3818 | TMPRSS2 | 3933053 | AATCCATGGCATTGGACGGCATTTGCGGGGATTTTGAGACAATCTTTCATGTTCTATGGAGCCGGATACCAAGTAGAAAAGTGA |
| 3819 | TMPRSS2 | 3933056 | TGGCAGGTCAGCCTGCACGTCCAGAACGTCCACGTGTGCGGAGGCTCCATCATCACCCCCGAGTGGATCGTGACAGCCGCCCAC |
| 3820 | TMPRSS2 | 3933060 | AAAGCAGTGGTTTCTTTACGCTGTATAG |
| 3821 | TMPRSS2 | 3933061 | CCAAGGAATAGTGGATGACAGCGGATCCACCAGCTTTATGAAACTGAACACAAGTGCCGGCAATGTCGATATCTATAAAAAACTGTACCAC |
| 3822 | TMPRSS2 | 3933062 | AGGTGTACTCATCTCAGAGGAAGTCCTGGCACCCTGTGTGCCAAGACGACTGGAACGAGAACTACGGGCGGGCGGCCTGCAGGGACATGGGCTATAA |
| 3823 | TMPRSS2 | 3933070 | ATGGGCCTTACCTCATATACGTGTCTTATTAAGAACACATAAAACCTACTCTTGTAGTGATTTTCAAATATGCAACATATAGTTTATTAACTGCAGTCACTATGATGTACAATAGATTGCTCGAACTTATTCCTCCTGTCTAACTAAGATTTTGTGACCTCTGACCAACATCTCCCCAGTGTTGTCACCCCCCGCCCCCAGCCTCTGATAGCTGCCTTTCTACTCTCTGCTTCTGTGAGTTTGATGTTTATACATTCCACATGTAAGTGGCCTCATGCAGTGTTTCTGTCTCTGGCTTGTTCACTTAGCGTAATGTCCTCCAGCTTCATCTATGTTGTTGGAAATGACAGGATTTCCTTCTTTCTTGTGGCTGAATAGTATTGCCTTGTGCATATACACCACATTTTCTTTATCCCTTCATTCACTGATGGACTCTTAGGTTGATGTCATGTCTTGGCTGTTGTGAAAAATGCCGCAGTGAGCGTGGGCGTGCAGGTCCCTCTTCAACACACGGATTTCCTTTCCTTTGGATATAAACCCAGCAGTGAGATTGCTGGATCACATGGCAGTTCTGTTTCTCACCTTTTGAGGAAACTCCATACTGTTTTCCATAATGGCTGTAGCAACTTCCACTCCCACCCCCACGGTGCAAAGTCTCCATTTCTCTTCTACAACCTCACCAACTCCTGTTATTTTCCATCTTTCTGATAGTAGCCATTTGAAGAGGTATGAGATGATACCTCATTGTGGTTTTCATTTGCATTTTTATTTGTATTTTTCATGAATTTTTGAGGGTGATTTCAAGGGTAGTAGTGACTCGAACAGGGAAACGATCCTGAGTATGAGGGTTGTGCTAATCATCCCCCTCCTGCCAGCTGCGTACGGAATG |
| 3824 | TMPRSS2 | 3933071 | TGCATCAACCCCTCTAACTGGTGTGATGGCGTGTCACACTGCCC |
| 3825 | TMPRSS2 | 3933072 | CTCCAACTCTGGGATAGAGTGCGACTC |
| 3826 | TMPRSS2 | 3933074 | CTGCGCTGGCCGCTGGCCTACTCTGGAAGTTCA |
| 3827 | TMPRSS2 | 3933075 | TTGGACCTTACTATGAAAACCATGGATACCAACCGGAAAACCCCTATCCCGCACAGCCCACTGTGGTCCCCACTGTCTACGAGGTGCATCCGGCTCAGTACTACCCGTCCCCGTGCCCCAGTACGCCCCGAGGGTCCTGACGCAGGCTTCCAACCCCGTCGTCTGCACGCAGCCCAAATCCCCATCCGGGACAGTGTGCACCTCAA |
| 3828 | TMPRSS2 | 3933078 | CATTCCAGATACCTATCATTACTCGATGCTGTTGAT |
| 3829 | TMPRSS2 | 3933093 | CCGCCCGGAGGTGAAAGCGGGTGTGA |
| 3830 | TMPRSS2 | 3933099 | GTGACCCGTGCATCTTTCCAGCTTTTCCTTGGCCACCTGGGTGGCATGGGAGCTGGGAGTCAGAGTTCTGCTGAGCTGTAGGACCAAAGGCCACTGGCTCCGCTGCACCTGCGGACTGAGACACCCACCTGCTGAGTGAGACCCAGCCTCTGCGTGCTTAGGGGTCCCCTGCTACAGGGCATTGAGGTGAGGTCCGCCTTTGCCCAGTGTGAGAGCGCTGCTTTCAGAGCTTTGAGAAGGCTGTTATCATTTGTTTCTTTTTGAACTTGCCACCTCCCCACTTAGAGAATATTTCTGGGGACAGAGTTTCGTAACTCCTGCCGCATAGTTGGTGCCTGCTCTCGACTACATTAAA |
| 3831 | TMPRSS2 | 3933101 | CAAGTGGGGTCTGGACCACCGACCTTAGCTTCACCTCAACCCCCAAGAACACCTGCCCCGTTGGAG |
| 3832 | TIMP3 | 3943506 | GTCCCGCCGGGCACTCGGAGGGCAGCGCGCCGGAGGCCAAGGTTGCCCCGCACGGCCCGGCGGGCGAGCGAGCTCGGGCTGCAGCAGCCCCGCCGGCGGCGCGCACGGCAACTTTGGAGAGGCGAG |
| 3833 | TIMP3 | 3943507 | ATGACCCCTTGGCTCGGGCTCATCGTGCTCCTGGGCAGCT |
| 3834 | TIMP3 | 3943508 | GCGTGCACATGCTCGCCCAGCCACCCCC |
| 3835 | TIMP3 | 3943530 | ACTAGCCATCAGTGGAAGCGGGAAATAGGACTTCTATTTCTTGTTGTCACCCTCACCAGCACCCAACCCAATGTTCCAGACACCAACCTAGTTCATGCCTATGTTGGTTTGATTG |
| 3836 | TIMP3 | 3943531 | AGGTTCCAAGCTCAGGCTATTTGGG |
| 3837 | TIMP3 | 3943532 | CTCTTGTAAACACAATCATCTATTCCAGTTGGC |
| 3838 | TIMP3 | 3943533 | GGGGCCCTTCGGCACGCTGGTCTACACCATCAAGCAGATGAA |
| 3839 | TIMP3 | 3943534 | GCTTATCTGTCTAATACGGGCATGAGGGTGAGACCCCACAGGCCTGGAAACTCCCCAGAGGAGACAAGCCGCAATGTCCAGGTAGAAGGGAGTGGAGGAGTGACGCAGCCCACGGTGGTACCCAACCATCCCCAAGGCCAACCTCCAGGCTTTCTTATTCCTGTGTCCTGAGGCTGGATGTACTAAT |

TABLE 13-continued

Subtyping Target Sequences

| SEQ ID NO. | Gene | Affy Probeset ID | Sequence |
|---|---|---|---|
| | | | TTTGTGGAACCTGTTGCTTTGGATTCAATTTTGCAAACATCCACAGCCTTCTGGTTATGTAATG<br>TCCAGAGTCAGCCCTGGCCAGTTGCCCTTGGCTGCCTAAGCTTGGTCATG |
| 3840 | TIMP3 | 3943535 | CGGGACTCAGGTCCTAAGGTTGACAAAGAAAAAGGACCTTTGTCACAGCTACTTCTCTGGATT<br>TCTGAAAAGGTGCTGGGATGTCAGACATGTGTAGCCGAAGGAGTGTTGTGGGGCAGTTGGA<br>ATGGGGGGTATGGCTGGCTGCACAGGAAGGTTTCTCTGGGAAGGCACCAACCTGGCTAGTC<br>AAGAGGATCGGTGGCTTCATCTGGGGTGAAGGGGGCCCTGGGGTGGGTAGATCAGTGACCG<br>GCCACTGGACAGCTGAATAGGGGAGCGAGATTCCCTCAGATCCAATGTCAGC |
| 3841 | TIMP3 | 3943536 | CGCTTAGCAAAACGACCTCCAGTTCCAGCTGCATTGCCACAAATGACAAGATTTCATTCTTTTT<br>TCTGGATGAATCATATTCCATTGGGTATAGATACCAGGTTTTGTCTATCCATTCATCTGTTGAT<br>GGGCACTTAGGTTGATTTCATATCTTGGCTATTGTGAATATTGCTGCAGTCAACATGAGAGTG<br>CAGACCCCTCTTCCATATTCCGATTTCCTTTCCTTTGGATACATACCCAGCAGTGGGATTAGGG<br>ATCATACGGGTGTCCAAACTGG |
| 3842 | TIMP3 | 3943537 | CAAGATGCCCCATGTGCAGTACATCCATACGGAAGCTTCCGAGAGTCTCTGTGGCCTTAAGCT<br>GGAGGTCAACAAGTACCAGTACCTGC |
| 3843 | TIMP3 | 3943538 | GTCGCGTCTATGATGGCAAGATGTACACGGGGCTGTGCAACTTCGTGGAGAGGTGGGACCA<br>GCTCACCCTCTCCCAGCGCAAGGGGCTGAACTATCGGTATCACCTGGGTTGTAAC |
| 3844 | TIMP3 | 3943539 | CAGGTCTGAGCAGATATAGTAAGGATTGTTGCCCCAGGTGGGGCAGTGAGGAAGGCAGGGA<br>AGGAAGAATGCCTTTCTGCTGTAATCGGCTGCCTCCATGATGACCACTTGGAAGCTGCTGGG<br>GCATGAGGGCTCTTGAGTCCCTGGCCCCACCTGGCAGTTCAAGGCTGGAGG |
| 3845 | TIMP3 | 3943540 | TGTGACTTCCAAGAACGAGTGTCTCTGGACCGACATGCTCTCCAATTTCGGTTACCCTGGCTAC<br>CAGTCCAAACACTACGCCTGCATCCGGCAGAAGGGCGGCTACTGCAGCTGGTACCGAGGA |
| 3846 | TIMP3 | 3943541 | AAGGCCAACCATTTCAGGATCAGTCAAAGGCAGCAAGCAGATAGACTCAAGGTGTGTGAAA<br>GATGTTATACACCAGGAGCTGCCACTGCATGTCCCAACCAGACTGTGTCTGTCTGTGTCTGCA<br>TGTAAGAGTGAGGGAGGGAAGGAAGGAACTACAAGAGAGTCGGAGATGATGCAGCACACA<br>CACAATTCCCCAGCCCAGTGATGCTTGTGTTGACCAGATGTTCCTGAGTCTGGAGCAAGCACC<br>CAGGCCAGAATAACAGAGCTTTCTTAGTTGGTGAAGACTTAAACATCTGCCTGAGGTCAGGA<br>GGCAATTTGCCTGCCTTGTACAAAAGCTCAGGTGAAAGACTGAGATGAATGTCTTTCCTCTCC<br>CTGCCTCCCACCAGACTTCCTCCTGGAAAACGCTTTGGTAGATTTGGCCAGGAGCTTTCTTTTA<br>TGTAAATTGGATAAATACACACCATACACTATCCACAGATATAGCCAAGTAGATTTGGGTA<br>GAGGATACTATTTCCAGAATAGTGTTTAGCTCACCTAGGGGGATATGTTTGTATACACATTTG<br>CATATACCCACATGGGGACATAAGCTAATTT |
| 3847 | TIMP3 | 3943542 | CTCTTCCCTATCATGGGTCATCTGACCCCTGTCCGTCTCCTTGTCCCTGCTTCATGTTTGGGGGC<br>CTTTCTTTAACTGCCTTCCTGGCTTAGCTCAGATGGCAGATGAGAGTGTAGTCAAGGGCCTGG<br>GCACAGGAGGGAGAGCTGCAGAGTGTCCTGCCTGCCTTGGCTGGAGGGACACCTCTCCTGG<br>GTGTGGAGACAGCTTGGTTCCCTTTCCCTAGCTCCCTGGTGGGTGAATGCCACCTCCTGAGAT<br>CCTC |
| 3848 | TIMP3 | 3943543 | CGGCATCGGGTTTCCTTGGGATCAATTTCATTACCGTGTACCTTTCCCATTGTGGTCATGCCAT<br>TTGGCAGGGGGAGAATGGGAGGCTTGGCCTTCTTTGTGAGGCAGTGTGAGCAGAAGCTGAT<br>GCCAGCATGTCACTGGTTTTGAAGGGATGAGCCCAGACTTGATGTTTTGGGATTGTCCTTATT<br>TTAACCTCAAGGTCTCGCATGGTGGGGCCCCTGACCAACCTACACAAGTTCCCTCCCACAAGT<br>GGACATCAGTGTCTTCTCTGTGAGGCATCTGGCCATTCGCACTCCCTGGTGTGGTCAGCCTCT<br>CTCACACAAGGAGGAACTTGGGTGAAGGCTGAGTGTGAGGCACCTGAAGTTTCCCTGCGGA<br>GTCGATAAATTAGCAGAACCACATCCCCATCTGTTAGGCCTTGGTGAGGAGGCCCTGGGCAA<br>AGAAGGGTCTTTCGCAAAGCGATGTCAGAGGGCGGTTTTGAGCTTTCTATAAGCTATAGCTTT<br>GTTTATTTCACCCGTTCACTTACTGTATAATTTAAAATCATTTATGTAGCTGAGACACTTCTGTA<br>TTTCAATCATATCATGAACATTTTATTTTGCTAAATCTTGTGTCATGTGTAGGCTGTAATATGTG<br>TACATTGTGTTTAAGAGAAAAATGAAACCCACATGCCGCCATTTTCCTGAATCAAATTCTGCA<br>GTGGAATGGAGAGGAAAATACTTCTAGGCAAGCAGCTAGACTGGTGAATTGGGGGAAATAG<br>AAGGAACTAGTAACTGAGACTCCTCCAGCCTCCTCCCTATTGGAATCCCAATGGCTCCTGGAG<br>TAGGAAAAAGTTTAAACTACATTCATGTTCTTGTTCTGTGTCACTCGGCCCTGGGTAGTCTAC<br>CATTTACTTCACCCCAAGTCCTGCTGCCCATCCAGTTGGGAAGCCATGATTTTCCTAAGAATCC<br>AGGGCCATGGGAGATACAATTCCAAGTTCTCGCTTCCTCCTTTGGGCATCTCTTCTGCCTCCCA<br>ATCAAGGAAGCTCCATGCTCAGGCTCTCAGCTCTCGGGCCAGTGCTCTGCTCTGTCAGGGTA<br>GGTAATACTGGGAGACTCCTGTCTTTTACCCTCCCCTCGTTCCAGACCTGCCTCATGGTGGCAA<br>CATGGTTCTTGAACAATTAAAGAAACAAATGACTTTTTGGAATAGCCCTGTCTAGGGCAAACT<br>GTGGCCCCCAGGAGACACTACCCTTCCATGCCCCAGACCTCTGTCTTGCATGTGACAATTGAC<br>AATCTGGACTACCCCAAGATGGCACCCAAGTGTTTGGCTTCTGGCTACCTAAGGTTAACATGT<br>CACTAGAGTATTTTATGAGAGACAAACATTATAAAAATCTGATGGCAAAAGCAAAACAAAAT<br>GGAAAGTAGGGGAGGTGGATGTGACAACAACTTCCAAATTGGCTCTTTGGAGGCGAGAGGA<br>AGGGGAGAACTTGGAGAATAGTTTTTGCTTTGGGGGTAGAGGCTTCTTAGATTCTCCCAGCAT<br>CCGCCTTTCCCTTTAGCCAGTCTGCTGTCCTGTGAAACCCAGAAGTGATGGAGAGAAACCAACA<br>GAGATCTCGAACCCTGTCTAGAAGGAATG |
| 3849 | TIMP3 | 3943554 | TGGGAACAGATTTGCTGTCTGCAAAGGCTGCATCTGCGGGTCTGGCGTGCAAAGGAGGGTG<br>GTTCTTTGGCTAATGGTGGACTTGCTCCTAGGCCTATCCCAGAGTC |

TABLE 13-continued

Subtyping Target Sequences

| SEQ ID NO. | Gene | Affy Probeset ID | Sequence |
|---|---|---|---|
| 3850 | UPK3A | 3948530 | CCGCCCCGCGCTCTGGCGGCTCCTCCCGGGCG |
| 3851 | UPK3A | 3948532 | GCCAGTGTGACTTTCGCCACCAACAACCCCACACTTACCACTGTGGCCTTGGAAAAGCCTCTCT GCATGTTTGACAGCAAAGAGGCCCTCACTGGCACCCACGAGGTCTACCTGTATG |
| 3852 | UPK3A | 3948533 | CCAGGAATGCCTCAGTGCAAGACAGCACCAACACCCCACTGGGCTCAACGTTCCTACAAACA GAGGGTGGGAGGACAGGTCCCTACAAAGCTGTGGCCTTTGACCTGATCCCCTGCAGTGACCT GCCCAGCCTGGATGCCATTGGGGATGTGTCCAAGGCCTCACAGATCCTG |
| 3853 | UPK3A | 3948535 | TCCTGGTCAATATGTCCACGGGCTTGGTAGAGGACCAGACCCTGTGGTCAGACCCCATCCGCA CCAACCAG |
| 3854 | UPK3A | 3948538 | CTCGACGATCGACACGTGGCCAGGCCGGCGGAGCGGAGGCATGATCGTCATCACTTCCATCC TGGGCTCCCTGCCCTTCTTTCTACTTGTGGGTTTTGCTGGCGCCATTGCCC |
| 3855 | UPK3A | 3948540 | AGTTCTGATGGGGAAACGACTCACGACTCCCAAATCACTCAGGAGGCTGTTCCCAAGTCGCT GGGGGCCTCGGAGTCTTCCTACACGTCCGTGAAC |
| 3856 | UPK3A | 3948541 | GTGTATTCCAGCAAGCTCCAAGACTGA |
| 3857 | UPK3A | 3948542 | GCCCTGCAGCGGTGGTTGTCACACCCTGACTTCA |
| 3858 | PLXNB2 | 3965814 | GCTGCCTTGGGACATAGGTACCTGAGGTACCTGAGAGCCCCTCAGGGGAGGAGGCCGAGTG GCTGTGGCTGAGGCCCCCACCCTCCCCTGGAACGCGCCCCAAGCCGGAGTGGGTGCAGCCGG AACCCGCCCAGCGTCTAGACTGTAGCATCTTCCTCTGAGCAATACCGCCGGGCACCGCACCAG CACCAGCCCCAGCCCCAGCTCCCTCCGGCCGCAGAACCAGCATCGGGTGTTCACTGTCGAGTC TCCAGTGATTTGAAAATGTGCCTTACGCTGCCACGCTGGGGGCAGCTGGCCTCCGCCTCCGCC CACGCACCAGCAGCCGCCTCCATGCCCTAGGTTGGGCCCCTGGGGGATCTGAGGGCCTGTGG CCCCCAGGGCAAGTTCCCAGATCCTATG |
| 3859 | PLXNB2 | 3965816 | ACGGACTCCTTGAACACCCTCGTGGCACTCCACCAGCTCTACCAATACACGCAGAAGTACTAT GACGAG |
| 3860 | PLXNB2 | 3965819 | TACTACAAGGGGATCCGGCAGATGGTGCAGGTCAGCGACCAGGACA |
| 3861 | PLXNB2 | 3965820 | AGCTGCTGTACGCCAAGGAGATCTC |
| 3862 | STS | 3967692 | TTGGCCAAGCCTCCAGCAGCTGACGGGACCCAGCTGTAGTGAGGTTGCAGTGATTGAGTAGG ATTGGCCTGCTTCAAAGCAGAGGTTTCTCATGGGAATATGCTTATTAAACTCCCACTGGTGCA GAAACCATGAACAGAGGATGAACAAGTGAAGTTGCAATCTCCTCCATCACAG |
| 3863 | STS | 3967693 | AGTTCCCCAACAACAGGATCACAAGCTGGAG |
| 3864 | STS | 3967695 | TGGGAAGCCGAGAGCCACGCAGCATCAAGGCCGAACATCATCCTGGTGATGGCTGACGACCT CGGCATTGGA |
| 3865 | STS | 3967696 | CAATATCGACCGGTTGGCCAGTGGGGGAGTGAAACTCACTCAGCACCTGGCAGCATCACCGC TGTGCACACCAAGCAGGGCAGCCTTCATGACTGGCCGGTAC |
| 3866 | STS | 3967697 | GAATGGCATCTTGGTCCCGCACTGGAGTTTTCCTCTTCACAG |
| 3867 | STS | 3967698 | TCTTCGGGAGGACTTCCCACCGATGAGATTACCTTTGCTAAGCTTCTGAAGGA |
| 3868 | STS | 3967701 | TGAGCTGTCACAGCAAGACTGACTTCTGTCACCACCCTTTACATCACGGCTTCAATTATTTCTA TGGGATCTCTTTGACCAATCTGAGAGACTGCAAGCCCGGAGAG |
| 3869 | STS | 3967702 | GCTACTCCACGTGCCTCTAGGCGTTTTTTCAG |
| 3870 | STS | 3967708 | GAACACTGAGACTCCGTTCCTGCTTGTCTTG |
| 3871 | STS | 3967709 | CAAAAGTCAACACGGAGTCTACGGGGATG |
| 3872 | STS | 3967718 | GCTGAGATTGGCTAATGATACCCTCATCTACTTCACATCGGACCAGGGAGCACATGTAGAAG AAGTGTCTTCCAAAGGAGAAATTCATGGCGGAAGTAATGGGATCTA |
| 3873 | STS | 3967722 | CTTCGTTGGCCCAGGGTGATACAGGCTGGCCAGAAGATTGATGAGCCCACTAGCAACATGGA CATATTTCCTACAGTAGCCAAGCTGGCTGGAGCTCCCTTG |
| 3874 | STS | 3967725 | CATTGATGGACGTGATCTGATGCCCCTGCTTGAAGGAAAAAGCCAACGCTCCGATCATGAGTT TCTCTTCCATTACTGCAACGCCTACTTAAATGCTGTGCGCTGG |
| 3875 | STS | 3967735 | CATCTGGAAGGCCTTTTTCTTCACCCCCAACTTCAACCCCGTGGGTTCCAACGGATGCTTTGCC ACACACGTGTGCTTCTGTTTCGGGAGTTATGTCACCCATCACGAC |

TABLE 13-continued

Subtyping Target Sequences

| SEQ ID NO. | Gene | Affy Probeset ID | Sequence |
|---|---|---|---|
| 3876 | STS | 3967736 | GTGCCCGATCAGTTTTCATGGAACAACTTTCTTTGGAAGCCCTGGCTTCAGCTGTGCTGTCCTT<br>CCACCGGCCTGTCTTGCCAGTGTGATAGAGAAAAACAGGATAAGAGACTGAGCCGCTA |
| 3877 | STS | 3967737 | AGACAGACGCATGTGGCAAAGCTCACCATCTTCACTACAAACACGCCTGAGAGTGGCACTGG<br>GGAAACATAACTCCATCTACACCTTGGATTTGGACTGATTCTCCATTTTATCACCTGAAGGCTT<br>GGGCCAGAGCTCAACAGCTACTCAACTGGAGGGGTGAGGGGGATAAGGTCTGTAGTATACA<br>GACAGGAAGATGGTAGGTTTATGCCTTCTGTGGCCAGAGTCTTGGACTCATGGAAATAGAAT<br>GAATAGAGGGGCATTCACAAGGCACACCAGTGCAAGCAGATGACAAAAAGGTGCAGAAGGC<br>AATCTTAAAACAGAAAGGTGCAGGAGGTACCTTAACTCACCCCTCAGCAAATACCTATGTCAA<br>CAGTATAAGTTACCATTTACTCTATAATCTGCAGTGATGCAATAACCAGCATA |
| 3878 | STS | 3967738 | TTGGAAGGCAAGTCATTATTACTGGTATTAGTTAAAACACATATCAAATGCTTGCTCTTCATCA<br>TATATATAGTTATGCATACATACACACACACATACAGTATATTCTTTCCTCAAAAGGGTTAA<br>GATGTCTAAAATAGGGACCTAGAAGCTTAACACTATTTAAGTAAATACAGTAGAAGCTCACAA<br>ATAGATTTCTTTGCACAATGATTTTTTGCAAAATTTTACAGTAATAATAATCCCAAGGCAAATC<br>TCTCCTGAACTGCTTTCCATTCCATAATTTGTAGTATAATTCTTGGATTCCACTGTTTTCTTTGG<br>GGAATGGAAGTTCTGAATTAAAAGCCCACTGTGGAGATGCTGTGGTTCATGGAATCTCTTCCA<br>GTGTAATTCAGAATCATTGGCCTAGAAAGTCTCTG |
| 3879 | STS | 3967739 | ATGCAAGTTTTGTGACTGAGAAATTTCTGTGCTTCCAATCCACAATGAGATGCATGATTTTGTT |
| 3880 | STS | 3967740 | AATGCGCAACTGATCGCCTAGGAGAGGGCCTCGTAGTGGCACAGCTGGAGATAGTTTCAAAG<br>TCTAAACCACCAGCCCATCCTGAGGAAAGCCTCCTATGGAATGTAAAGTGCAATCATTTCTTC<br>AGATATAAGACTTTCCCCAACAATGTGATTGGATTCCTTTATGGCAAAATCGAGAGAAGCTGC<br>CATCCACCTGCTTATGCATTTATCTCTTTTGTGGACTTGTCTGACCACCTTCTATTTG |
| 3881 | STS | 3967741 | CCCACACAGCGGTTTGCAGAGAATGTTAGCCATGACTTGGGCTTTCTGAAAGTTGGCTATAAT<br>TTCTCTATCCCTACCCACAACCCTGGGAAGTTGGAGCAAGAGGGGCATACTATTGGGCTGGG<br>AGGATTTGACAGCATTTCCCCAGTTGCCCTTTAAGTTCTTCTATTTCAAACGTTAATTTTGCTTC<br>TCTTTCTAAAAAAAAAAAAAAAAAAGAAAGAGAAGAAAGAAGTGATTCCTACCCCCTACCTCC<br>AGAGTTGTTGAAAGCTGAAAAGCATACAAGATTCTTCCTTTTAACTTGGATTTCTCGTTCCAGA<br>AATTGTGGGATAATCTGTATTCTTGCTTTAGAAAACATTCTTAGAGAGGGTACTAGCTTACTG<br>ATGATGTGTTAGGATTGCTACTGATGCTGTCATGTGGAAACTATTTAAAGGCACTATTATAAA<br>TTTATCCTATAAGATGACAATGTTTACTCAAAGTCTAACATATTCAATGCAAGTAAGACTTTCT<br>GAAAACACTTTGATGATGTGGAAATGCTGCAGGATTAAATAACTTGAAGAGCCTTTATAGATTA<br>TATGAATGCCTATTTGTGTCTAGAACCAGTTATTTAACCTGTAAAATGTCAATAGCAAATGAA<br>GGATGAAGTATATCTCTAGATGCAAATACATTGAGTTTAAAAGTGCCTCAAAATAATTGAGAT<br>CACATTTCAGGACATTTGGAAATCAGGTCGATTTGTGGTAACTGTAGTCATCTTAAATTTCAAA<br>CCATTTACCATCTGAAAGTTTTGATTTGAATGTAAAACAGGAAATTGGAATTCCTTTGTCCAGG<br>AGAAACCTCACAAACCTTCTTTAAGGCATAGTTTTGTTGTTTGTTTGCTTGTTTGTTGCAGGCT<br>GTAAGGCATGGCTGCTTGTTTACAAAGCATCTCATTCATATTACCTGTGGAGTTGCATATCCAA<br>ACCTTAGTGA |
| 3882 | STS | 3967742 | CTCCGACCTCCATGATCCGAGAGTGGGAAAAGGCCCGATTATTACCCATAAGGCACACTCTCT<br>AAGGCCTTTTAAGGGGCCTACAAAAATGTTTTATTTTATAATCAGAAGAAAAGGAAATGAACA<br>TTGGGGATTGAAAATCATATTGGTATTTGCACCAACATAGTCATAAAATAGTATGTTAATATG<br>TTTTTACTTTATATATTTATATATTAAAATATATTTAATATGTTTTGCCTTTGTGGCCCATGAAAG<br>TCTTACTGGGCCCTGGGGAAGGTATCCTACCCTGGTGAAGCAGCTGCTTTGCTCTACAAATAC<br>CTGGGGCAGAAATTTGATTTGAAAAGTATTATTCTCTCTTCTCTTTGTTTCAACTGGATTCCTTT<br>GGAAAACCAAACTAGTATCAGAACAAACCCCGAAACAGTAAGAAATTGGAGTGAGAAGGGC<br>ATGGTATTGGGACTAGGATCGGCTCTCATTCGATCGAGCTATTCTTCTTAAAATGACAAAAAGT<br>GTCCATAAAGAGGCTGCTGGAGAGTGCGTGGCCATAGGGAGCCGACATGCCCGGGAGGAAA<br>GGTGTTGATTACATGGATACTTCTAAAAGCTAAAGCCTTGTTGCCTTCTCTTTAATGCCTAGAG<br>AATGGGATGTGTGATGCAAATGCTCAAAACCTCTTAAATCATAGCTGTCTGACCTCTACGGAC<br>CTCACATCCATCTGAGGCTTCATGGACAAAGATTCTCCACTTGGCCAAACTTTAGCCAAGCTCC<br>TCAACCTTCTCCCAGGCCCAATCTGGGCACTTCCTTGTAAAATCTAGTTTTGGCAAGAAGTCTA<br>TTAGGTCAGTTTAGCAAGAACACCTAACCCCCCCATATCTGTTCAACCTCAGTATCTGATCAGG<br>CTCCTCAGCCTCCACCATCCCCAGGTGATGTCTGGTCAACTGGCCTGCCTTCAGCTAGAATCC<br>TGTTAGGTCGGTTTAGATGAATGCTCCCTGATATTTCCTCTTGGTAATCTTCCATCCACTGCCCC<br>TGACCCTGTTCCCTGTCTATAAATCCCCAGTTTTCCATGGTGTATTCAGAGCTGAGTCCAGTCT<br>CTCTCCCCTACTACAAGTCCCCATTGCTGTGGTCCCCGTACCTGTCATGATGGTCCTAA |
| 3883 | STS | 3967743 | GAAACCTATTGGGACAGCATGACTGTGCAGGGTCTTTAGAGCTCAGCTTTCTGAGGCCCTGA<br>GCATTCTTGGTTTTCCGACATCGTGAACCTGTTCTG |
| 3884 | STS | 3967744 | GCTTCCTTGTTAGAATGCAAGCAGCTTAAAAACTACCCATGTCTTTCTGGAAAGGAAACATT<br>GCCATGTAACTATGTA |
| 3885 | SAT1 | 3971810 | CTCCTCCTACTGTTCAAGTACAGGGGCC |
| 3886 | SAT1 | 3971811 | CGCCCAGCCACTGCCGCCGACTGCAGTGACATACTGCGGCT |
| 3887 | SAT1 | 3971813 | ATGGAAGAACAAGTAATCTTAACTGAAA |

TABLE 13-continued

Subtyping Target Sequences

| SEQ ID NO. | Gene | Affy Probeset ID | Sequence |
|---|---|---|---|
| 3888 | SAT1 | 3971814 | CAACAGTGGCGGGACGGGGACAAGCGTTCGGTGCCTGTCACCTTCGCCAAGGCCATTACCG CCCCTGCTC |
| 3889 | SAT1 | 3971815 | CCTTTTACCACTGCCTGGTTGCAGAAGTGCCGAAAG |
| 3890 | SAT1 | 3971816 | GTCGGCTGTGTAGAACCACTGACTACACAGGCCGAAGTTACTGAGAACTTGGACAGAAAAAA TAGCCAGCAAGTGTTCAAACTACTGAGGAAAAAAAAAAATTAGATATGCTGCACTTAAGAAT ACTAGGGCAGGTTAAAAGAGCTG |
| 3891 | SAT1 | 3971817 | GACTCGGAAGTGTTTAAGCTGCTTAAGTAAGTATAAGTGCTGTGGAGACCCGGAAGAGTTAG ATATAATGTCATTTGTTGTAATTCAGTTTCATAAAATGGTTCTTGTTTGACCCTAACGTAACAGT TTTTGTAATTGTGTTAAATCACATTTTTTTCTTTAATTTGTCCCAATCTTCAG |
| 3892 | SAT1 | 3971818 | GTTACAGTCTCTAGCTTCGCCATGTACATGGCCCTTCCGTGT |
| 3893 | SAT1 | 3971819 | CTAAAAGATCCTTTACACAATAAAGTAGATGATCATGATAAATG |
| 3894 | SAT1 | 3971821 | GTGTGCTTTTTGCAAATACATGTTCTCAGAACAGTGAGATCATCCAGCAGTGGCCTGGACTGC ACTCACATAAAAATCATGAGACAGCCATGGCTACTTGTTTCTGTAATACATGCATGTGTGTTTT TTAAAACCTATGATAGGCCTCTGATTCTGCAGCTGCAACTTTTATGGAATGTT |
| 3895 | SAT1 | 3971822 | CTATTTTACCTATGACCCGTGGATTGGCAAGTTATTGTATCTTGAGGACTTCTTCGTGATGAGT GATTATAGA |
| 3896 | SAT1 | 3971823 | GTTCGGAGCAGAGGGTCTGAAGAGAGTTCAGAGTTATAAATGCTTACAATGACTTTT |
| 3897 | SAT1 | 3971824 | GCTTTGGCATAGGATCAGAAATTCTG |
| 3898 | SAT1 | 3971826 | TGCAATGAGGTGTCGCTGCAGCAGCATGCACTTCTTGGTAGCAGAATGGAATGAACCATCCA TCAACTTCTATAAAAGAAGAGGTGCTTCTGATCTGTCCAGTGAAGAGGGTTGGAGACTGTTCA AGATCGACAAGGAGTACT |
| 3899 | SAT1 | 3971827 | GGAGTGCTGCTGTAGATGACAACCTCCATTC |
| 3900 | SAT1 | 3971828 | TTCCAAAGCTTTATTACCAGTGGCGTTGTTGCATGTTTGAAATGAGGTCTGTTTAAAGTGGCA ATCTCAGATGCAGTTTGGAGAGTCAGATCTTTCTCCTTGAATATCTTTCGATAAACAACAAGGT GGTGTGATCTTAATATATTTGAAAAAAACTTCATTCTCGTGAGTCATTTAAATGTGTACAATGT ACACACTGGTACTTAGAGTTTC |
| 3901 | TIMP1 | 3976342 | TGAGTAATGCATCCAGGAAGCCTGGAGGCCTGTGGTTTCCGCACCCGCTGCCACCCCCGCCCC TAGCGTGGACATTTATCCTCTAGCGCTCAGGCCCTGCCGCCATCGCCGCAGATCCAGCGCCCA GAGAGA |
| 3902 | TIMP1 | 3976346 | ATCAGGGCCAAGTTCGTGGGGACACCAGAAGTCAACCAGACCACCTTATACCAGCGTTATGA GATCAAGATGA |
| 3903 | TIMP1 | 3976349 | ATGTATAAAGGGTTCCAAGCCTTAGGGGATGCCGCTGACATCCGGTTCGTCTACACCCCCGCC ATGGAGAGTGTCTGCGGATACTTCCACAG |
| 3904 | TIMP1 | 3976350 | GTCCCACAACCGCAGCGAGGAGTTTCT |
| 3905 | TIMP1 | 3976351 | CTGGGGCGCGGCCTAGCAACCACGAGGGGGCGAGGCTCTGATGGGAATGGTCCCACTGGAA ATGGGGACCACCCCAATTTCAGTCTATCAGAAGGCCGGGCCTTTGGCAGCTTGGCAGCTCAG CCAATCACAAGCTGCTTGTCGG |
| 3906 | TIMP1 | 3976352 | CTGCAGGATGGACTCTTGCACATCACTACCTGCAGTTTTGTGGCTCCCTGGAACAGCCTGAGC TTAGCTCAGCGCCGGGGCTTCACCAAGACCTACACTGTTG |
| 3907 | TIMP1 | 3976353 | TGGACCCTGACCTCCAACGGGAGATCCTTCCC |
| 3908 | TIMP1 | 3976354 | GCCCGAGACTGCTCCCTTACAAATTCTGGCTGCTCCCTTTCCCTGTGTCCAATACCGTGTGATC ACCTGTCCCTCCCTGGTCCCTCTAATTCTCCCTTGTGA |
| 3909 | TIMP1 | 3976356 | TTTCCCTGTTTATCCATCCCCTGCA |
| 3910 | TIMP1 | 3976357 | CTTCCAGTCCCGTCACCTTGCCTGCCT |
| 3911 | TIMP1 | 3976358 | AGTCCCTGCGGTCCCAGATAGCCTGA |
| 3912 | TIMP1 | 3976359 | GCCTGCACAGTGTCCACCCTGTTCCCACTCCCATCTTTCTTCCGGACAATGAAA |
| 3913 | PLP2 | 3977069 | ATGGCGGATTCTGAGCGCCTCTCGGCTCCTGGCTGCTGGGCCGCCTGCACCAACTTCTCGCGC ACTCGAAAGGGAATCCTCCTGTTTGCTG |

TABLE 13-continued

Subtyping Target Sequences

| SEQ ID NO. | Gene | Affy Probeset ID | Sequence |
|---|---|---|---|
| 3914 | PLP2 | 3977072 | TGATCTGCTTCAGTGCCTCCACACCAGGCTACTCCTCCCTGTCGGTGATTGAGATGATCCTTGC<br>TGCTATTTTCTTTGTTGTCTACATGTGTGACCTGCACACCAAGATACCATTCATCAACTGGCCC |
| 3915 | PLP2 | 3977073 | GATTTCTTCCGAACCCTCATAGCGGCAATCCTCTACCTGATCACCTCCATTGTTGTCCTTGTTG |
| 3916 | PLP2 | 3977074 | TTTGAGGAGCCAGGGACCATTTCTGCCTTTGCTTCTGGCAGAAATCGTGTGACCCACAGCAAG<br>TCACACTTGTCCTCAGACATGGAGGAAAGTCTGGCCCAGGACTTGGTTTTGCCTCCCAAGGTC<br>TTCATTTGCTG |
| 3917 | PLP2 | 3977075 | GTACTGGGCCTAATCGCTACGTGCCTCTTTGGCTATGATGCCTATGTCACCTTCCCCGTTCGGC<br>AGCCAAGACATACAGCA |
| 3918 | PLP2 | 3977076 | CCATATGTGTGTGCCTAGGTCCTCCTTCTGCACGATCCAATAGGAGACACCAGTTCTGACTGA<br>ACCATGCCCCCACCTAAGTCACAAAATGAGGGAAGTGGGGAGTTAGATTTCAGAGTCCAGGC<br>CCTAGGTTGGGACCCACTCCAAATAATCTCCTCGGTGTGGGTG |
| 3919 | PLP2 | 3977077 | TGGAGTGGAAACAGCTGGGCAAGGAGGCAAAGAAGCCAGGCCTGTTTTACAACAA |
| 3920 | KRT18 | 3983630 | ATGCGCCAGTCTGTGGAGAACGACATCCATGGGCTCCGCAAG |
| 3921 | BEX4 | 3985495 | CGGCGGCGCACCTCGCGTCAAGAATCCGGAGGAGGAGA |
| 3922 | BEX4 | 3985497 | TCCAAAGAGGAACTAGCGGCAAACAATCTCAACGGGAAAATGCCCAACAAGAAAACGAAG<br>GAGGGGAGCAGGCCCCCACGCAGAATGAAGAAGAATCCCGCCATTTGGGAGGGGTGAAG<br>GCCAGAAGCCTGGAGGAAATATCAGGCGGGGGCGAGTTAGGCGACTTGTCCCTAATTTTCGA<br>TGGGCCATACCTAATAGGCATATTG |
| 3923 | BEX4 | 3985498 | GCAGATGAGGCACTATATGCGCTTCCAAACTCCTGAACCTGACAACCATTATGACTTTTGCCTC<br>ATACCTTG |
| 3924 | BEX4 | 3985499 | TTGTCTCAGCCTAAAAGTTACGGTCAGCATGGCAATTCACCTATTTTAGGAAAAATACTCTTTT<br>CATAATATGAAATGCATAAAGCAGTTCAAAAAGCAGTCTGTATTCCATCATCTTCCTTTTTCAT<br>TCCAGTCCTTATTTTTGTAAGTATTACTTTTCCTCCTCCGGCTACCTGGACTCAAAATCTCAGTT<br>GTCTTTGACAGTTTTTTCTTGTCCCTGACCAAAAAGAATGATCATACCCAGAATTCAATGTT<br>TGATATTTTAAGAATGTATGTTCTAGTGTTTTTCAGAGTGAGTCTACCATCTGTATAAAAACAC<br>CTTGGGGGCAGGCAGGGGCATTTAAAAATGTAGGACCTATCGTCCAGACTCACAGAGTGGG<br>GCTC |
| 3925 | RNF128 | 3986262 | AGTGAAATAGAGCTGATGTATCCAGAGGTTATGTTGCTAG |
| 3926 | RNF128 | 3986263 | GTGAGATCAGTTACCTACGTGCAACTGAAATTTCAAACTTCTGTTCAGCAGGGACGTGAGTGG<br>ACAATGGTGACTGATAGTTGGAAATA |
| 3927 | RNF128 | 3986264 | ATGAACCAGGAGAATAGGTCCAGTTT |
| 3928 | RNF128 | 3986265 | TGGCGTTTATGGATTAGCTTCACCAGTGGCTAATGCTATGGGAGTGGTAGGCATCCCTAAGA<br>ACAATAACTACCAAGCTTGTGACCACAACACTGAGTTTAGTAATACTAAGAAGCCCTGGATTG<br>CGCTGATAGAAAGAGGTAATTGTACATTTTCAGAAAAAATTCAAACAGCGGGCAGAAGAAAT<br>GCTGATGCTGTTGTGATTTACAATGCTCCAGAGACTGGCAATCAGACGATA |
| 3929 | RNF128 | 3986267 | GGCAACCTGTGTGCTGACGCTACGTGCCTCCTGGCTCCGACGTAGCTCGCAGCTCCCCAGTCT<br>CACTCCATTCCTTCCCCACCTGGCGCGCACCTGCTCAAGACCAGGGTCCTGCCAAGCGCTAG |
| 3930 | RNF128 | 3986268 | GCGGTGGCTGCGGCTTTTCCAGATTGCTGG |
| 3931 | RNF128 | 3986269 | CGAATTTCACGGTGCCCACGGTTTGGGGAAGCACCGTGCAAGTCTCTTGGTTGGCCCTCATCC<br>AACGCGGCGGGGGCTGCACCTTCGCAGACAAGATCCATCTGGCTTATGAGAGAGGGGCGTC<br>TGGAGCCGTCATCTTTAACTTC |
| 3932 | RNF128 | 3986272 | GGCACAAAAATTCTGCAATCTATTCAAAGAGGCATACAAGTGACAATGGTCA |
| 3933 | RNF128 | 3986273 | AACATGGCCCTTGGGTGAATCACTATTCAATTTTTTTCGTTTCTGTGTCCTTTTTTATTATTACG<br>GCGGCAACTGTGGGCTATTTTATCTTTTATTCTGCTCGAAGGCTACGGAATGCAAGA |
| 3934 | RNF128 | 3986275 | AAGCTATTGGAAGGCTTCAACTACGCACACTGAAACAAGG |
| 3935 | RNF128 | 3986277 | ATGTGTTGACCCATGGCTGTTAGAACACAGGACTTGCCCCATGTGCAAATGTGACATACTCAA<br>AGC |
| 3936 | RNF128 | 3986278 | GTGTCTTTACAAGTCCCTGTATCCAATGAAATATCTAATAGTGCCTCCTCCCATGAAGAGGATA<br>ATCGCAGCGAGACCGCATCATCTGGATATGCTTCAGTACAGGGAACAGATGAACCGCCTCTG<br>GAGGAACACGTGCAGTCAACA |

TABLE 13-continued

Subtyping Target Sequences

| SEQ ID NO. | Gene | Affy Probeset ID | Sequence |
|---|---|---|---|
| 3937 | RNF128 | 3986279 | CTGTGGCAGTGGATGTTATTCCTCATGTTGACAACCCAACCTTTGAAGAAGACGAAACTCCTAATCAAGAGACTGCT |
| 3938 | RNF128 | 3986280 | GCCAATCAGGGCCTAGTTTCTATTAATAAATTGGATAAATTTAATAAAATAAGAGTGATACTGAAAGTGCTCAGATGACTAATATTATGCTATAGTTAAATGGCTTAAAATATTTAACCTGTTAACTTTTTTCCACAAACTCATTATAATATTTTTCATAGGCAAGTTTCCTCTCAGTAGTGATAACAACATTTTTAGACATTCAAAACTGTCTTCAAGAAGTCACGTTTTTCATTTATAACAATTTTCTTATAAAAACATGTTGCTTTTAAAATGTGGAGTAGCTGTAATCACTTTATTTTATGATAGTATCTTAATGAAAAATACTACTTCTTTAGCTTGGGCTACATGTGTCAGGGTTTTTCTCCAGGTGCTTATATTGATCTGGAATTGTAATGTAAAAGCAATGCAAACTTAGGCGAGTACTTCTTGAAATGTCTATTTAAGCTGCTTTAAGTTAATAGAAAAGATTAAAGCAAAATATTCATTTTTACTTTTTCTTATTTTTAAAATTAGGCTGAATGTACTTCATGTGATTTGTCAACCATAGTTTATCAGAGATTATGGACTTAATTGATTGGTATATTAGTGACATCAACTTGACACAAGATTAGACAAAAAATTCCTTACAAAATACTGTGTAACTATTTCTCAAACTTGTGGGATTTTTCAAAAGCTCAGTATATGAATCATCATACTGTTTGAAATTGCTAATGACAGAGTAAGTAACACTAATATTGGTCATTGATCTTCGTTCATGAATTAGTCTACAGAAAAAAATGTTCTGTAAAATTAGTCTGTTGAAAATGTTTTCCAAACAATGTTACTTTGAAAATTGAGTTTATGTTGACCTAAATGGGCTAAAATTACATTAGATAAACTAAAATTCTGTCCGTGTAACTATAAATTTTGTGAATGCATTTTCCTGGTGTTTGAAAAAGAAGGGGGGGAGAATTCCAGGTGCCTTAATA |
| 3939 | VGLL1 | 3992547 | GTGGGGGTACAAATCCTCAGCTCCTGCTTCCGCAAGCACTAACCTGCTCTGAAGTGAGCCAGGCAGCTC |
| 3940 | VGLL1 | 3992549 | CTGTCACCTGTGTCATTCACTCACA |
| 3941 | VGLL1 | 3992550 | GAAGACTGCCATCCGGCTGCCCAAAGGCAAACAGAAGCCTATAAAGACGGAATGGAATTCCCGGTGTGTCCTTTTCACCTACTTCCAAGGGGACATCAGCAGCGTAGTGGATGAACA |
| 3942 | VGLL1 | 3992554 | TGGCGTTACTCGTCTCCATGGACAAAGCCACAACCAGAAGTACCTGTCACAAACCGTGCCGCCAACTGCAACTTGCATGTGCCTGGTCCCATGGCTGTGAATCAGTTCTCACCGTCCCTG |
| 3943 | VGLL1 | 3992555 | AGCAAGACAGATGCCTAGCCCGTCCTCAGGAATCTGCCGCCAGGGAGAATGGCAACCCTGGCCAGATAGCTGGAAGC |
| 3944 | VGLL1 | 3992556 | AGGTCTTCATGCTCTACTCATGTTGACATGAGTTGTATTAATTGGTGACTGGAAGTCCAGGATCTGTTGAGGAAGTCAGTGACCCTTAATCAGGAACACTGCCTTGGAAGGTGGTGGACCTTTAAACAGAAGCTTCTCAGTTTTTGTAGCATCTGATATGAGAGAATATGCTAGATATTCATAAACTTAGGGCCAGGCAATGTGGGCCCCTGGAATGCTACTGGGCACTCTCTAACCTAGTCCTAGA |
| 3945 | VGLL1 | 3992557 | AGAAACTATATGTATCTCGTGGATCTGCCAGTACCAGCC |
| 3946 | VGLL1 | 3992563 | CCTGGGAAATACTCACTTACACCACCAAACCACTGGGGCCACCCACATCGATACCTGCAGCA |
| 3947 | VGLL1 | 3992564 | GAGAAAGACAACACTTGGTCTAAGACACGGCAGCAAGACATCCTGCATATTGTTCCAGA |
| 3948 | VGLL1 | 3992565 | ACTTGCCTCCCCAATCTGTTAAACAGCTTCGTGTCTAGTATGAGCTCAGTACTTGCCCTGTGAAATCCCAGAAGCCCCCGCTGTCAATGTTCCC |
| 3949 | BGN | 3995635 | AGTAGCTGCTTTCGGTCCGCCGGACACACCGGACAGATAGACGTGCGGACGGCCCACCACCCCAGCCCGCCAACTAGTCAGCCTGCGCCTG |
| 3950 | BGN | 3995641 | CCTGTGGCGCCTCGTGTCTCTGCTGGCCCTGAG |
| 3951 | BGN | 3995642 | GGACTTCACCCTGGACGATGGGCCATTCATGATGAACGATGAGGAAGCTTCGGGCGCTGACAC |
| 3952 | BGN | 3995643 | GGGCGTCCTGGACCCGGACTCTGTC |
| 3953 | BGN | 3995644 | GTGTCCTTTCGGCTGCCACTGCCACCTGCGGGTGGTTCAGTGCTCCGACCT |
| 3954 | BGN | 3995650 | AAAGAGATCTCCCCTGACACCACGCTG |
| 3955 | BGN | 3995651 | TGCAGAACAACGACATCTCCGAGCTCCGCAAGGATGA |
| 3956 | BGN | 3995652 | ACCAGCAGGCCTACAGCAGAGGGCAGG |
| 3957 | BGN | 3995654 | GCCCTCGTCCTGGTGAACAACAAGATCTCCAAGATCCATGAGAAGGCCTTCAGCCCACTGCGGAAG |
| 3958 | BGN | 3995657 | ATGGGCGGGAACCCACTGGAGAACAGTGGCTTTGAACCTGGAGCCTTCGATGGCCTGAAGCTCAACTACCTGCGCATCTCAGA |
| 3959 | BGN | 3995659 | AGACCCTGAATGAACTCCACCTAGACCACAACAAAATCCAGGCCATCGAACTGGAGGACCTGCTTCGCTACTCCAAGCTG |

TABLE 13-continued

Subtyping Target Sequences

| SEQ ID NO. | Gene | Affy Probeset ID | Sequence |
|---|---|---|---|
| 3960 | BGN | 3995660 | GGGCCTAGGCCACAACCAGATCAGGATGATCGAGAACGGGAGCCTGAGCTTCCTGCCCACCC<br>TCCGGGAGCTCCACTTGGACAACAACAAGTTGGCCAGGGTGCCCTCAGGGC |
| 3961 | BGN | 3995661 | GTGGTCTATCTGCACTCCAACAACATCACCAAAGTGGGTGTCAACGACTTCTGTCCCATGGGC<br>TTCGGGGTGAAGCGGGCCTACTACAACGGCATCAGCCTCTTCAACAACCCCGTGCCCTACTGG<br>GAGGTGCAGCCGGCCACTTT |
| 3962 | BGN | 3995662 | GGGGAACACAGCCAGACATCCTGATGGGGAGGCAGAGCCAGGAAGCTAAGCCAGGGCCCA<br>GCTGCGTCCAACCCAGCCCCCCACCTCGGGTCCCTGACCCCAGCTCGATGCCCCATCACCGCC<br>TCTCCCTGGCTCCCAAGGGTGCAGGTGGGCGCAAGGCCCGGCCCCCATCACATGTTCCCTTGG<br>CCTCAGAG |
| 3963 | BGN | 3995663 | TCCAGTCCTAGGAGAACAGTCCCTGGGTCAGCAGCCAGGAGGCGGTCCATAAGAATGGGGA<br>CAGTGGGCTCTGCCAGGGCTGCCGCACCTGTCCAGACACACATGTTCTGTTCCTCCTCCTCATG<br>CATTTCCAGCCTTTCAACCCTCCCCGACTCTGCGGCTCCCCTCAGCCCCCTTGCAAGTTCATGG<br>CCTGTCCCTCCCAGACCCCTGCTCCACTGGCCCTTCGACCAGTCCTCCCTTCTGTTCTCTCTTTC<br>CCCGTCCTTCCTCTCTCTCTCTCTCTCTCTCTCTTTCTGTGTGTGTGTGTGTGTGT<br>GTGTGTGTGTGTGTGTGTCTTGTGCTTCCTCAGACCTTTCTCGCTTCTGAGCTTGGTGGC<br>CTGTTCCCTCCATCTCTCCGAACCTGGCTTGCCTGTCCCTTTCACTCCACACCCTCTGGCCTTC<br>TGCCTTGAGCTGGGACTGCTTTCTGTCTGTCCGGCCTGCACCCAGCCCCTGCCCACAAAACCCC<br>AGGGACAGCAGTCTCCCCAGCCTGCCCTGCTCAGGCCTTGCCCCAAACCTGTACTGTCCCGG<br>AGGAGGTTGGGAGGTGGAGGCCCAGCATCCCGCGCAGATGACACCATCAACCGCCAGAGTC<br>CCAGACACCGGTTTTCCT |
| 3964 | BGN | 3995664 | GGGCTGCTTCTGAGGTCGGTGGCTGTCTTTCCATTA |
| 3965 | FLNA | 4027177 | CTGCCCTGTGCCGTGCTGCGCTCACCTGCCTCCCCAGCCAGCCGCTGACCTCTCGGCTTTCACT<br>TGGGCAGAGGGAGCCATTTGGTGGCGCTGCTTGTCTTCTT |
| 3966 | FLNA | 4027178 | GGACCCCCTGCGAGGAGATCCTGGTGAAGCACGTGGGCAGCCGGCTCTACAGCGTGTCCTAC<br>CTGCTCAAGGACAAGGGGGAGTACACACTGGTGGTCAAATGGGGGGACGAGCACATCCC |
| 3967 | FLNA | 4027179 | CTCCACGAGACATCATCAGTGTTTGTAGACTCTCTGACCAAGGCCACCTGTGCCCCCCAGCAT<br>GGGGCCCCGGGTCCTGGGCCTGCTGACGCCAGCAAGGTGGTGGCCAAGGGCCTGGGGCTGA<br>GCAAGGCCTACGTAGGCCAGAAGAGCAGCTTCACAGTAGACTGCAGCAAAGC |
| 3968 | FLNA | 4027180 | CGTGAACACGAGCAATGCGGGAGCTGGTGCCCTGTCGGTGACCATTGACGGCCCCTCCAAGG<br>TGAAGATGGATTGCAGGAGTGCCCTGAGGGCTACCGCGTCACCTATACCCCCATGGCACCT<br>GGCAGCTACCTCATCTCCATCAAGTACGGCGGCCC |
| 3969 | FLNA | 4027181 | GTAAGTCTGTCGGTGCGGCTGCACGTGTGCACACAGCTGCTAGGCCCTTGCCTCCAAGCTCTT<br>GGTGACAACAGGAGGCACCTGGAGGTGACAAGCCTGTGCTGGGTGGCCGAGGACAGGGAG<br>GCA |
| 3970 | FLNA | 4027182 | GAATGGCGTTTACCTGATTGACGTCAAGTTCAACGGCACCCACATCCCTGGAAGCCCCTTCAA<br>GATCCGAGTTGGGGAGCCTGGGCATGGAGGGGACCCAGGCTTGGTGTCTGCTTACGGAGCA<br>GGTCTGGAAGGCGGTGTCACAG |
| 3971 | FLNA | 4027183 | ACACCATCTGCTGGTTTGAGGAGGGGCCCCAGGCCCACAGCATGACTCCCTGCTCCTCAG |
| 3972 | FLNA | 4027184 | TGGCTCGCCACCCACAGCTATTAGGAAGGCCTTCTACCCTGCAGTACCATGCCATCTCCACAG<br>GGAAAGACTCAAAGTCCAGCCTCAGTGCTGCCCGGCCCTTCAGCCACGGCCATGGTACTTGT<br>GCACAGGCCTGGGGCAGCCTTGTGGGTAGGAGGAGCCCAGTGGGCTTCATTTCACGGCCTA<br>GTCCTGCCCTTCCCAGCTGCATGACCTGAAGCAAGTTCCTGCCCGTCTCTGAGCCTGTTAACAT<br>GCAGGGGATATGGTGTTCACGGTAACCTTTCTTAGGAGGCAGCAAGGCCTGGGTTTGGCTTG<br>TAAAAGATTTCCGTCCCAATGCACCCTGACGGTGGGCAGCTTGAGTGTCTAAACCTTCGGCCC<br>TCAGGA |
| 3973 | FLNA | 4027185 | AGGGCTAAAGGTCAACCAGCCAGCCTCTTTTGCAGTCAGCCTGAACGGGGCCAAGGGGGCG<br>ATCGATGCCAAGGTGCACAGCCCCTCAGGAGCCCTGGAGGAGTGCTATGTCACAGAAATTGA<br>CCAAG |
| 3974 | FLNA | 4027186 | GTAAGTGCGACCCGCGGGCCTCTTGCTCCTGGGGCCTTTCCGTCCTCCCTTGCCCTGGCTCAA<br>GCACCCCCATCTAACCATGTCTGCTGTG |
| 3975 | FLNA | 4027187 | ACCTGGGTGTGTGCGACGGCAGAGTGTGGGGCAGGGCGGGATGTGCGCCTGTGGCTT<br>GCTGCCCCTTGCAAATCAGTGGCTCTCCCTCTTTAAACCAAGTTGGACGCCAGATGG |
| 3976 | FLNA | 4027188 | GTGAGGCACCGAGAGAAACCGCCCACCTGGGGCTCCTGGGCCCGGACAGACCAGAGCCACC<br>GCAGAGACCAGGCCTTGGCCCTGTGTTCAGTGACCCCCCTGGCCCAGCTCTGGGTTCCAGGCC<br>TCTGCTCTGGCCGGGTGCAGCCCACGCTTGGGGTCGGCAGGAAATATCCTGCCCACCACGTG<br>GAGTTTTTCTCGTGTCTCA |
| 3977 | FLNA | 4027189 | TGTGGCTTCTCCGTCTGGCGACGCCCGCCGCCTCACTGTTTCTAGCCTTC |

TABLE 13-continued

Subtyping Target Sequences

| SEQ ID NO. | Gene | Affy Probeset ID | Sequence |
|---|---|---|---|
| 3978 | FLNA | 4027190 | CTACGAAGTCTCAGTCAAGTTCAACGAGGAACACATTCCCGACA |
| 3979 | FLNA | 4027191 | GCCTGAGTGTGGGTATTGGACCCAGGGCTGGCACAGATAGCCCTGCCTGGCACTCACTCTTC ACTTTGAGGTCACAGGGCCACCCAGGCTGTTCG |
| 3980 | FLNA | 4027192 | AATTCAGTATCTGGACCCGGGAAGCTGGTGCTGGAGGCCTGGCCATTGCTGTCGAGGGCCCC AGCAAGGCTGAGATCTCTTTTGAGGACCGCAAGGACGGCTCCTGTGGTGTGGCTTATGTGGT CCA |
| 3981 | FLNA | 4027194 | GGGCAAGACCCATGAGGCCGAGATCGTGGAAGGGGAGAACCACACCTACTGCATCCGCTTT GTTCCCGCTGAGATGGGCACACACACAGTCAGCGTGAAGTACAAGGGCCA |
| 3982 | FLNA | 4027196 | GGGCCGGGTGAAAGAGAGCATCACCCGCAGGCGTCGGGCTCCTTCAGTGGCCAACGTTGGT AGTCATTGTGACCTCAGCCTG |
| 3983 | FLNA | 4027197 | TCGGCAGCCCCCCTCACTACACCAG |
| 3984 | FLNA | 4027198 | TACATCATCAACATCAAGTTTGCCGACCAGCACGTGCCTG |
| 3985 | FLNA | 4027199 | GGCTCAGCCTGTCCATTGAGGGCCCCAGCAAGGTGGACATCAACACAGAGGACCTGGAGGA CGGGACGTGCAGGGTCACCTACTGCCC |
| 3986 | FLNA | 4027200 | ACCGAGGCTCAGGGGTATCCATCCCC |
| 3987 | FLNA | 4027201 | CCGGTGGTGATCAGCCAGTCGGAAATTGGGGATGCCAGTCGTGTTCGGGTCTCTGGTCAGGG CCTTCACGAAGGCCACACCTTTGAGCCTGCAGAGTTTATCATTGATACCCGCGATGCA |
| 3988 | FLNA | 4027202 | TCCCACCTAAAGGTCGGCTCTGCTGCCGACATCCCCATCAACATCTCAGAGACGGATCTCAGC CTGCTGACGGCCACTGTGGTCCCGCCCTCGGGCCGGGAGGAGCCCTGTTTGCTGAAGCGGCT GCGTAATGGCCAC |
| 3989 | FLNA | 4027203 | CATTGAGGGCCCGTCCAAAGCAGAAATCAGCTGCACTGACAACCAGGATGGGACATGCAGC GTGTCCTACCTGCCTGTGCTGCCGGGGGACTACAGCATTCTAGTCAAGTACAATGAACAGCAC GTCCCAGGCAGCC |
| 3990 | FLNA | 4027205 | TTCTATGTGGATTACGTCAACTGTGGCCATGTCACTGCCTATGGGCCTGGCCTCA |
| 3991 | FLNA | 4027206 | ACACACGAGGCTGCCATTCCACAAGG |
| 3992 | FLNA | 4027207 | GTGGCGCAGCCCACCATCACTGACAACAAAGACGGCACCGTGACCGTGCGGTATGCACCCAG CGAGGCTGGCCTGCACGAGATGGACATCCGCTATG |
| 3993 | FLNA | 4027208 | TTCACCATCAAGAAGGGCGAGATCACAG |
| 3994 | FLNA | 4027209 | CTGGCTGGGGACCAGCCCTCGGTGCAGCCCCTCTACGGTCTCAGCAGCTGGCCCCACAGTA CACCTACGCCCAGGGCGGC |
| 3995 | FLNA | 4027210 | CCACCATTCAGATTGGGGAGGAGACGGTGATCACTGTGGACACTAAGGCGGCAGGCAAAGG CAAAGTGACGTGCACCGTGTGCACGCCTGATGGCTCAGAGGTGGATGTGGACGTGGTGGAG AATGAGGACGGCACTTTCGACATCTTCTACACGGCCCCCCAGCCGGGCAAATACGTCATCTGT GTGCGCTTTGGTG |
| 3996 | FLNA | 4027215 | CAAGACAACCATGACGGCACGTATACAGTGGCCTACGTGCCAGACGTGACAGGTCGCTACAC CATCCTCATCAAGTACGGTGGTGACGAGATCCC |
| 3997 | FLNA | 4027216 | AAGGTGCTGCCTACTCATGATGCCAGCAAGGTGAAGGCCAGTGGCCCCGGGCTCAACACCAC TGGCGTGCCTGCCAGCCTGCCCGTGGAGTTCACCATCGATGCAAAGGACGCCGGGGA |
| 3998 | FLNA | 4027217 | AGCCAGTGGACGTGGTAGACAACGCTGATGGCACCCAGACCGTCAATTATGTGCCCAGCCGA GAA |
| 3999 | FLNA | 4027218 | GGAGGCCCAGGAGACTAGCTGATGCT |
| 4000 | FLNA | 4027220 | CCTGAGCCCAGGCATGGTTCGTGCCAACCTCCCTCAGTCCTTCCAGGTGGACACAAGCAAGGC TGGTGTGGCCCCATTGCAGGTCAAAGTGCAAGGGCCCAAAG |
| 4001 | FLNA | 4027221 | TTTCAAGGTCCCTGTGCATGATGTGACAGATGCGTCCAAGGTCA |
| 4002 | FLNA | 4027223 | ACGGCAGCTGCTCGGTCGAGTACATCCCTTATGAGGCTGGCACCTACAGCCTCAACGTCACCT ATGGTGGCCATCAAGTGCCAG |
| 4003 | FLNA | 4027227 | GCGCAGCTCGAGTGCTTGGACAATGGGGATGGCACATGTTCCGTGTCCTACGTGCCCACCGA GCCCGGGGACTACAACATCAACATCCTCTTCGCTGACACCCACATCCCTGGCTCCCCATTCAAG |

TABLE 13-continued

Subtyping Target Sequences

| SEQ ID NO. | Gene | Affy Probeset ID | Sequence |
|---|---|---|---|
| | | | GCCCACGTGGTTCCCTGCTTTGACGCATCCAAAGTCAAGTGCTCAGGCCCCGGGCTGGAGCG GGCCACCGCTGGGGAGGTGGGCCAATTCCAAGTGGACTGCTCGAGCGCGGGCAGCGCGGA GCTGACCATTGAGATCTGCTCGGAGGCGGGGCTTCCGGCCGAGGTGTACATCCAGGACCACG GTGATGGCACGCACACCATTACCTACATTCCCCTCTGCCCCGGGGCCTACACCGTCACCATCA AGTACGGCGGCCAGC |
| 4004 | FLNA | 4027229 | TCAAATCAAAGGGTGCTGGTGGTCAAGGCAAAGTGGCATCCAAGATTGTGGGCCCCTCGGGT GCAGCGGTGCCCTGCAAGGTGGAGCCAGGCCTGGGGGCTGACAACAGTGTGGTGCGCTTCC TGCCCCGTGAGGAAGGGCCCTATGAGGTGGAGGTGACCTATGACGGCGTGCCCGT |
| 4005 | FLNA | 4027230 | TAGGCGTCAATGTCACTTATGGAGGGGATCCCATCCCTAAGAGCCCTTTCTCAGT |
| 4006 | FLNA | 4027231 | CACAGTAAATGCCAAAGCTGCTGGCAAAGGCAAGCTGGACGTCCAGTTCTCAGGACTCACCA AGGGGGATGCAGTGCGAGATGTGGACATCATCGACCACCATGACAACACCTACACAGTCAAG TACACGCCTG |
| 4007 | FLNA | 4027232 | CCCATCCGAGTCAAGGTGGAGCCCTCTCATGACGCCAGTAAGGTGAAGGCCGAGGGCC |
| 4008 | FLNA | 4027233 | TAGGCCCCGCCGAAGCTGACATCGACTTCGACATCATCCGCAATGACAATGACACCTTCACGG TCAAGTACACGCCCCGGGGGGCTGGCAGCTACACCATTATGGT |
| 4009 | FLNA | 4027235 | CACCCCAACAAGGTCAAAGTATACGGCCCCGGAGTAGCCAAGACAGGGCTCAAGGCCCACG AGCCCACCTACTTCACTGTGGACTGCGCCGAGGCTG |
| 4010 | FLNA | 4027236 | CTGCCCTGTGGAGGCGTTGGTCAAGGACAACGGCAATGGCACTTACAGCTGCTCCTACGTGC CCAGGAAGCCGGTGAAGCACACAGC |
| 4011 | FLNA | 4027238 | AGAAGACAGGTGTGGCCGTCAACAAGCCAGCAGAGTTCACAGTGGATGCCAAGCACGGTGG CAAGGCCCCACTTC |
| 4012 | FLNA | 4027239 | GGCCATCGCAGGCTAAGATCGAATGTGACGACAAGGGCGACGGCTCCTGTGATGTGCGCTAC TGGCCGCAGGAGGCTGGCGAGTATGCCGTTCACGTGCTGTGCAACAGCGAAGACATCCGCC |
| 4013 | FLNA | 4027240 | CACCTGGGGACAGACGATGGCAAGGACGGCCCACCCTG |
| 4014 | FLNA | 4027242 | GGCGTGTATGGCTTCGAGTATTACCCCATGGTCCCTGGAACCTATATCGTCACCATCACGTGG GGTGGTCAGAACAT |
| 4015 | FLNA | 4027243 | CTGTAACCCGAGTGCCTGCCGGGCGGTTGGCCGGGGCCTCCAGCCCAAGGGTGTGCGGGTG AAGGAGACAGCTGACTTCAAGGTGTACACAAAGGGCGCTGGCA |
| 4016 | FLNA | 4027244 | AGGTCGAGGTTGTGATCCAGGACCCCATGGGACAGAAGGGCACGGTAGAGCCTCAGCTGGA GGCCCGGGGCGACAGCACATACCGCTGCAGCTACCAGCCCACCATGGAGGGCGTCCACACC GTGCACGTCACGTTTGCCGGCGTGCC |
| 4017 | FLNA | 4027245 | GCCCCTTCGAGGTGTACGTGGATAAGTCACAGGGTGACGCCAGCAAAGTGACAGCCCAAGG TCCCGGCCTGGAGCCCAGTGGCAACATCGCCAACAAGA |
| 4018 | FLNA | 4027246 | AAAGTGACCGCCAATAACGACAAGAACCGCACCTTCTCCGTCTGGTACGTCCCCGAGGTGA |
| 4019 | FLNA | 4027248 | ACGTGGACGAGCACTCTGTCATGACCTACCTGTCCCAGTTCCCCAAGGCCAAGCTGAAGCCAG GGGCTCCCTTGCGGCCCAAACTGAACCCGAAGAAAGCCCGTGCCTACGGGCCA |
| 4020 | FLNA | 4027250 | TGTGTCCTGACTGGGACTCTTGGGACGCCAGCAAGCCCGTTACCAATGCGCGAGAGGCCATG CAGCAGGCGGATGACTGGCTGGGCATCCCCCA |
| 4021 | FLNA | 4027252 | AGGCCATCGTGGACGGGAACCTGAAGCTGATCCTGGGCCTCATCTGGACCCTGATCCTGCAC TACTCCATCTCCATGCCCATGTGGGACGAGGAGGAGGATGAGGAGGCCAAGAAGCAGACCC CCAAGCAGAGGCTCCTGGGCTGGATCCAGAACAAGCTGCCGCAGCTGCCCATCACCAACTTC AGCCGGGACTGGCA |
| 4022 | FLNA | 4027256 | ATGAGTAGCTCCCACTCTCGGGCGGGCCAGAGCGCAGCAGGCGCGGCTCCGGGCGGCGGCG TCGACACGCGGGACGCCGAGATGCCGGCCACCGAGAAGGACCTGGCCGAGGACGCGCCGT GGAAGAAGATCCAGCAGAACACTTTCACGCGCTGGTGCAACGAGCACCTGAAGTGCGTGAG CAAGCGCATCGCCAACCTGCAGACGGACCTGAGCGACGGGCTGCGGCTTATCGCGCTGTTGG AGGTGCTCAGCCAGAAGAAGATGCACCGCAAGCACAACCAGCGGCCCACTTTCCGCCAAATG CAGCTTGAGAACGTGTCGGTGGCGCTCGAGTTCCTGGACCGCGAGAGCATCAAACTGGTGTC CA |
| 4023 | FLNA | 4027257 | CGCGCGCCTAGGTGCCTGCGACTTTAATTAAAGGGCCGTCCCCTCGCCGAGGCTGCAGCACC GCCCCCCGGCTTCTCGCGCCTCAA |
| 4024 | FLNA | 4027259 | GCGGACGCCGACAGAATCCCCGAGGCGCCTGGCGCGGGCGCGGGCGCGAAGGCGATCCGG GCGCCACCCCGCGGTCATCGGTCACCGGTCGCTCTCAGGAACAGCAG |

TABLE 13-continued

Subtyping Target Sequences

| SEQ ID NO. | Gene | Affy Probeset ID | Sequence |
|---|---|---|---|
| 4025 | KRT18 | 4028791 | CGGCGCCCGGCCGGTCAGCAGCGCGGCCAGCG |
| 4026 | KRT18 | 4028795 | ATGCGCCAGTCTGTGGAGAACGACATCCATGGGCTCCGCAAG |
| 4027 | HLA-DRB5 | 4048242 | TCATCTGTCCACCTGGCTCCAAAGACA |
| 4028 | HLA-DRB5 | 4048243 | GTACTCCCCCTGTGTGCCACAAATGCACTACGTTATTAAATT |
| 4029 | HLA-DRB5 | 4048245 | AGCACAGTCTGAATCTGCACAGAGCAAGATGCTGAGTGGAGTCGGGGGCTTTGTGCTGGGC CTGCTCTTCCTTGGGGCCGGGCTATTCATCTACTTCAAGAATC |
| 4030 | HLA-DRB5 | 4048247 | ATTGAAGTCAGGTGGTTCCGGAACAGCCAGGAAGAGAAGGCTGGGGTGGTGTCCACAGGCC TGATTCAGAATGGAGACTGGACCTTCCAGACCCTGGTGATGCTGGAAACAGTTCCTCGAAGT GGAGAGGTTTACACCTGCCAAGTGGAGCACCCAAGCGTGACGAGCCC |
| 4031 | HLA-DRB5 | 4048248 | ACCCTGCAGCACCACAACCTCCTGGTCTGCTCTGTGAATGGTTTCTATCCAG |
| 4032 | HLA-DRB5 | 4048249 | CTAAGGTGACTGTGTATCCTGCAAGGACCCAG |
| 4033 | HLA-DRB5 | 4048252 | GGTGCGGTTCCTGCACAGAGACATCTATAACCAAGAGGAGGACTTGCGCTTCGACAG |
| 4034 | HLA-DRB5 | 4048253 | GTTTCTTGCAGCAGGATAAGTATGAG |
| 4035 | HLA-DRB5 | 4048256 | ATGGCAAAGCTGACAGTGACACTGA |
| 4036 | HLA-DRB5 | 4048257 | GTGTGTCTGAAGCTCCCTGGAGGTTCCTAC |
| 4037 | HLA-DRB1 | 4048268 | CTGAAGTGCACATGACCACATTCAAGGAAGAACCTTCTGCCACAG |
| 4038 | HLA-DRB1 | 4048272 | AGATGCTGAGTGGAGTCGGGGGCTTTGTGCTGGGCCTGCTCTTCCTTGGGACAGGGCTGTTC ATCTACTTCAGGAATCAG |
| 4039 | HLA-DRB1 | 4048274 | TCAACCACCAAGAAGGGGACTGTGCTAATCCCTGAGC |
| 4040 | HLA-DRB1 | 4048275 | CTGCGGTGGTCTCCATAGGCCTGATCCAGAATGGAGATTGGACCTTCCAGACCCTGGTGATG CTGGAAACAGTTCCTCGGAGTGGAGAGGTTTACACCT |
| 4041 | HLA-DRB1 | 4048276 | CCATCCTAAGGTGACTGTGTATCCTGCAAAG |
| 4042 | HLA-DRB1 | 4048278 | ACTCGCTTCTGTGCCGGCCGCCAGAAGGTTTGCTGAGGGCAATCACTCCCTGGTGCCGGGCTC CTTGAGGTTATGCACTGGGACATCTAGAGCCTATTGTTTGAGGAATGCAGTCTTGCAAGCCTG CTCTGGATCAAGCCACAGACTGAAACACCCCGAAGAGCA |
| 4043 | HLA-DRB1 | 4048279 | TCTGTATTCACCCTGTATGACAAACACA |
| 4044 | HLA-DRB1 | 4048284 | GTGAGTGGTTTCTATCCAGGCAGCATT |
| 4045 | HLA-DRB1 | 4048285 | CTAAGGTGACTGTATATCCTTCAAAG |
| 4046 | HLA-DRB1 | 4048289 | TACTTCTATAACCAGGAGGAGTCCGTG |
| 4047 | HLA-DRB1 | 4048296 | CTGGAGGCTCCTGCATGACAGCGCTGACAGTGACACTGAT |
| 4048 | HLA-DRB1 | 4048297 | GGAGGGGTTCATAGTTCTCCCTGAGTGAGAC |
| 4049 | HLA-DRB1 | 4048299 | GACAAGATGGACGACTACTGCAGATACAATTACGGG |
| 4050 | HLA-DRB1 | 4048301 | GCTAAGTGTGAGTGTCATATCTTCAATGGGATGAAGCGGGTGCAGTACCTGAACAGATACAT CCATAAACGGGAGGAGAACCTGCGCTTCGACAGCAACGTGGAGGAGTTCCAGGCAGTTACG GAACTGGGGCGGCCTGTCGCAGAGAACTGGAACA |

Example 4

Univariate Analysis of a Genomic Subtyping Classifier to Predict Molecular Subtypes in Muscle-Invasive Bladder Cancer Univariate analysis for a genomic subtyping classifier to predict molecular subtypes in muscle-invasive bladder cancer patients was performed. P-values for individual genes in an exemplary Genomic Subtyping Classifier (GSC) were generated to predict four classes of subtypes (claudin-low, basal, luminal-infiltrated and luminal). P-values for the individual genes are shown in Table 14. These results showed that methods of the present invention are useful for predicting molecular subtypes for subject with muscle-invasive bladder cancer. These results suggested that the methods of the present invention may be useful for predicting benefit from neoadjuvant chemotherapy and treating a subject for bladder cancer.

TABLE 14

Univariate Analysis of Genes in Genomic Subtyping Classifier

|  | Luminal-Infiltrated | Luminal | Claudin-Low | Basal |
| --- | --- | --- | --- | --- |
| ACER2 | 0.157 | 0.000 | 0.000 | 0.000 |
| PPARG | 0.124 | 0.000 | 0.000 | 0.000 |
| TMPRSS2 | 0.289 | 0.000 | 0.000 | 0.000 |
| SCNN1B | 0.388 | 0.000 | 0.000 | 0.000 |
| ACOX1 | 0.142 | 0.000 | 0.000 | 0.000 |
| RNF128 | 0.119 | 0.000 | 0.000 | 0.000 |
| UPK2 | 0.107 | 0.000 | 0.000 | 0.000 |
| GRHL3 | 0.185 | 0.000 | 0.000 | 0.000 |
| TIMP2 | 0.020 | 0.000 | 0.000 | 0.126 |
| UPK3A | 0.323 | 0.000 | 0.000 | 0.000 |
| SNX31 | 0.053 | 0.000 | 0.000 | 0.000 |
| TNC | 0.185 | 0.000 | 0.000 | 0.101 |
| TGFBI | 0.100 | 0.000 | 0.000 | 0.139 |
| SULF1 | 0.040 | 0.000 | 0.000 | 0.235 |
| POSTN | 0.071 | 0.000 | 0.000 | 0.101 |
| VIM | 0.008 | 0.000 | 0.000 | 0.392 |
| GATA3 | 0.083 | 0.000 | 0.000 | 0.000 |
| PSCA | 0.119 | 0.000 | 0.000 | 0.001 |
| EFEMP1 | 0.128 | 0.000 | 0.000 | 0.044 |
| FBP1 | 0.137 | 0.000 | 0.001 | 0.000 |
| TMEM45B | 0.449 | 0.000 | 0.000 | 0.002 |
| MT1L | 0.742 | 0.000 | 0.000 | 0.080 |
| HPGD | 0.350 | 0.000 | 0.000 | 0.041 |
| DHRS2 | 0.032 | 0.000 | 0.000 | 0.000 |
| DCN | 0.011 | 0.000 | 0.001 | 0.107 |
| IFITM2 | 0.993 | 0.000 | 0.000 | 0.015 |
| CALD1 | 0.032 | 0.000 | 0.000 | 0.622 |
| BAMBI | 0.007 | 0.000 | 0.001 | 0.000 |
| TPM2 | 0.038 | 0.000 | 0.000 | 0.227 |
| ERBB2 | 0.209 | 0.000 | 0.000 | 0.000 |
| GBP5 | 0.810 | 0.000 | 0.000 | 0.008 |
| LAPTM5 | 0.132 | 0.000 | 0.001 | 0.064 |
| TBX3 | 0.100 | 0.000 | 0.000 | 0.001 |
| SEMA5A | 0.027 | 0.000 | 0.005 | 0.000 |
| EHF | 0.689 | 0.000 | 0.000 | 0.009 |
| LAMC2 | 0.168 | 0.000 | 0.000 | 0.309 |
| GSTM3 | 0.060 | 0.000 | 0.000 | 0.001 |
| IFI30 | 0.637 | 0.000 | 0.000 | 0.027 |
| HLA-DRA | 0.341 | 0.000 | 0.005 | 0.012 |
| ATP8B1 | 0.728 | 0.000 | 0.003 | 0.002 |
| SNCG | 0.012 | 0.000 | 0.000 | 0.000 |
| S100P | 0.428 | 0.000 | 0.000 | 0.042 |
| MYL9 | 0.016 | 0.000 | 0.000 | 0.314 |
| KRT5 | 0.236 | 0.000 | 0.005 | 0.000 |
| SNAI2 | 0.742 | 0.000 | 0.000 | 0.126 |
| SPINK1 | 0.051 | 0.000 | 0.001 | 0.000 |
| TOX3 | 0.439 | 0.000 | 0.000 | 0.015 |
| TIMP1 | 0.033 | 0.000 | 0.000 | 0.896 |
| BGN | 0.020 | 0.000 | 0.000 | 0.740 |
| COL1A2 | 0.060 | 0.000 | 0.000 | 0.493 |
| TWIST2 | 0.179 | 0.000 | 0.000 | 0.286 |
| VCAN | 0.033 | 0.000 | 0.000 | 0.658 |
| PVRL4 | 0.460 | 0.000 | 0.001 | 0.011 |
| ZNF91 | 0.119 | 0.000 | 0.014 | 0.000 |
| RALBP1 | 0.482 | 0.000 | 0.275 | 0.000 |
| ASPN | 0.179 | 0.000 | 0.037 | 0.021 |
| COL3A1 | 0.045 | 0.000 | 0.000 | 0.586 |
| LUM | 0.009 | 0.000 | 0.000 | 0.763 |
| SFRP2 | 0.203 | 0.000 | 0.000 | 0.928 |
| SLC14A1 | 0.369 | 0.000 | 0.009 | 0.002 |
| G0S2 | 0.922 | 0.000 | 0.000 | 0.375 |
| CYP4Z2P | 0.428 | 0.000 | 0.000 | 0.309 |
| SCCPDH | 0.551 | 0.000 | 0.001 | 0.023 |
| ELF3 | 0.624 | 0.000 | 0.000 | 0.053 |
| SYTL2 | 0.637 | 0.000 | 0.005 | 0.056 |
| KRT18 | 0.142 | 0.000 | 0.716 | 0.000 |
| CTSK | 0.036 | 0.000 | 0.000 | 0.615 |
| GABRP | 0.068 | 0.015 | 0.494 | 0.000 |
| AHR | 0.676 | 0.000 | 0.033 | 0.004 |
| UGT1A4 | 0.587 | 0.001 | 0.000 | 0.687 |
| MMP1 | 0.040 | 0.001 | 0.000 | 0.177 |
| UGT1A5 | 0.428 | 0.002 | 0.000 | 0.724 |
| ITGA6 | 0.880 | 0.001 | 0.000 | 0.856 |
| CD74 | 0.258 | 0.000 | 0.013 | 0.112 |
| ACTG2 | 0.017 | 0.000 | 0.000 | 0.968 |
| CD68 | 0.398 | 0.000 | 0.001 | 0.339 |
| PLP2 | 0.702 | 0.008 | 0.000 | 0.825 |
| KRT8 | 0.439 | 0.000 | 0.829 | 0.000 |
| UGT1A3 | 0.527 | 0.002 | 0.000 | 0.672 |
| AHNAK | 0.715 | 0.007 | 0.000 | 0.559 |
| TNFRSF21 | 0.493 | 0.000 | 0.005 | 0.023 |
| UGT1A10 | 0.408 | 0.007 | 0.000 | 0.880 |
| UPK1B | 0.032 | 0.000 | 0.001 | 0.008 |
| GBP1 | 0.796 | 0.000 | 0.000 | 0.156 |
| SAMD9 | 0.024 | 0.000 | 0.002 | 0.004 |
| OLFM4 | 0.243 | 0.022 | 0.352 | 0.000 |
| CCL5 | 0.769 | 0.000 | 0.006 | 0.042 |
| HLA-DRB5 | 0.323 | 0.000 | 0.119 | 0.023 |
| UGT1A1 | 0.637 | 0.002 | 0.000 | 0.672 |
| RNF138P1 | 0.539 | 0.000 | 0.001 | 0.095 |
| MMP12 | 0.076 | 0.000 | 0.067 | 0.000 |
| CFH | 0.243 | 0.000 | 0.002 | 0.420 |
| MAL | 0.216 | 0.000 | 0.006 | 0.013 |
| SAA1 | 0.191 | 0.000 | 0.001 | 0.034 |
| ADAM10 | 0.236 | 0.000 | 0.081 | 0.001 |
| PTPRM | 0.065 | 0.000 | 0.014 | 0.003 |
| FGFBP1 | 0.015 | 0.001 | 0.111 | 0.000 |
| ZNF486 | 0.041 | 0.000 | 0.030 | 0.001 |
| UGT1A8 | 0.369 | 0.006 | 0.000 | 0.615 |
| MMP2 | 0.031 | 0.000 | 0.000 | 0.786 |
| KRT7 | 0.378 | 0.000 | 0.189 | 0.002 |
| PAQR7 | 0.350 | 0.000 | 0.048 | 0.009 |
| C3 | 0.179 | 0.000 | 0.047 | 0.190 |
| DSP | 0.258 | 0.000 | 0.015 | 0.018 |
| THBS2 | 0.031 | 0.001 | 0.000 | 0.687 |
| CASP14 | 0.323 | 0.001 | 0.128 | 0.003 |
| KRT23 | 0.471 | 0.014 | 0.001 | 0.786 |

TABLE 14-continued

Univariate Analysis of Genes in Genomic Subtyping Classifier

|  | Luminal-Infiltrated | Luminal | Claudin-Low | Basal |
|---|---|---|---|---|
| STS | 0.223 | 0.001 | 0.065 | 0.006 |
| DDIT4 | 0.894 | 0.001 | 0.083 | 0.040 |
| HLA-A | 0.482 | 0.001 | 0.048 | 0.019 |
| AGR2 | 0.993 | 0.001 | 0.004 | 0.309 |
| IER3 | 0.922 | 0.001 | 0.005 | 0.300 |
| ANXA1 | 0.516 | 0.013 | 0.002 | 0.650 |
| NQO1 | 0.689 | 0.002 | 0.122 | 0.023 |
| SERPINB3 | 0.243 | 0.002 | 0.185 | 0.004 |
| CRISP3 | 0.060 | 0.002 | 0.007 | 1.000 |
| BTBD16 | 0.306 | 0.011 | 0.002 | 0.420 |
| GJB2 | 0.428 | 0.078 | 0.002 | 0.904 |
| CXCL17 | 0.702 | 0.127 | 0.003 | 0.319 |
| TACSTD2 | 0.922 | 0.003 | 0.275 | 0.027 |
| LYZ | 0.408 | 0.003 | 0.077 | 0.219 |
| SAT1 | 0.504 | 0.005 | 0.004 | 0.304 |
| IGFBP3 | 0.323 | 0.005 | 0.009 | 0.144 |
| TMSB10 | 0.993 | 0.006 | 0.007 | 0.462 |
| EPCAM | 0.964 | 0.009 | 0.956 | 0.007 |
| GSTM2 | 0.332 | 0.023 | 0.007 | 0.432 |
| MALL | 0.119 | 0.007 | 0.151 | 0.010 |
| MACC1 | 0.033 | 0.008 | 0.027 | 0.856 |
| FLRT3 | 0.009 | 0.200 | 0.040 | 0.231 |
| MUC16 | 0.439 | 0.009 | 0.128 | 0.047 |
| SPARCL1 | 0.010 | 0.029 | 0.022 | 0.329 |
| MYH11 | 0.011 | 0.072 | 0.012 | 0.118 |
| DUSP1 | 0.689 | 0.017 | 0.011 | 0.475 |
| CLDN1 | 0.323 | 0.016 | 0.427 | 0.012 |
| TIMP3 | 0.027 | 0.026 | 0.013 | 0.375 |
| MGP | 0.014 | 0.014 | 0.239 | 0.778 |
| PTN | 0.020 | 0.200 | 0.763 | 0.014 |
| IGFL1 | 0.223 | 0.021 | 0.158 | 0.044 |
| MMP13 | 0.173 | 0.030 | 0.292 | 0.025 |
| CGB2 | 0.428 | 0.181 | 0.030 | 0.904 |
| CPSF6 | 1.000 | 0.040 | 0.211 | 0.235 |
| SPP1 | 0.273 | 0.040 | 0.510 | 0.295 |
| LRRC37A2 | 0.715 | 0.056 | 0.057 | 0.475 |
| SPRR2F | 0.289 | 0.070 | 0.609 | 0.076 |
| PLXNB2 | 0.637 | 0.072 | 0.309 | 0.403 |
| TPX2 | 0.185 | 0.528 | 0.108 | 0.904 |
| HIST1H2BF | 0.852 | 0.656 | 0.134 | 0.397 |
| RARRES1 | 0.676 | 0.781 | 0.202 | 0.622 |
| NDRG1 | 0.428 | 0.725 | 0.230 | 0.888 |

Example 5

Molecular Subtypes in Muscle-Invasive Bladder Cancer

Tables 15 and 16 show subsets of markers based on the scores from Table 10.

TABLE 15

|  | Claudin-low | Basal | Luminal | Luminal-infiltrated |
|---|---|---|---|---|
| Score ≥0.75 | LAMC2; IFI30; SAA1; VIM; TGFBI | TMEM45A; GABRP | PTPRM |  |
| Score ≥0.5 | LAMC2; IFI30; SAA1; VIM; TGFBI; TIMP2; GBP1; SNAI2 | TMEM45A; GABRP; EFEMP1 | PTPRM; CPSF6; PTPN13; VGLL1; ELF3 | SNCG |
| Score ≥0.25 | LAMC2; IFI30; SAA1; VIM; TGFBI; TIMP2; GBP1; SNAI2; GBP5; POSTN; TNC; F3; BGN | TMEM45A; GABRP; EFEMP1; HIST1H2BF; IFI16; MALL; MMP12; SPRR1B; TGM2; TPX2 | PTPRM; CPSF6; PTPN13; VGLL1; ELF3; ACER2; ACOX1; CDH1; F11R; PPARG; RNF128; SCCPDH; SFN; STS; TACSTD2; TMEM45B | SNCG; AHR; INA; PM20D1; GRHL3 |
| Score ≥0.1 | LAMC2; IFI30; SAA1; VIM; TGFBI; TIMP2; GBP1; SNAI2; GBP5; POSTN; TNC; F3; BGN; CCL5; SULF1; WARS; MMP3; CXCL10; TIMP3; SERPINB1; DDIT4 | TMEM45A; GABRP; EFEMP1; HIST1H2BF; IFI16; MALL; MMP12; SPRR1B; TGM2; TPX2; CLDN1; GOS2; IFITM2; PTMS | PTPRM; CPSF6; PTPN13; VGLL1; ELF3; ACER2; ACOX1; CDH1; F11R; PPARG; RNF128; SCCPDH; SFN; STS; TACSTD2; TMEM45B; BTG2; GRHL1; IFI6; RALBP1; IGFBP3 | SNCG; AHR; INA; PM20D1; GRHL3; ACTA2; ACTG2; CYP1A1; DUSP1; HLA-DRB5; MAL; SPINK1; UPK1A |

TABLE 16

| Score ≥0.75 | Score ≥0.5 | Score ≥0.25 | Score ≥0.1 |
|---|---|---|---|
| LAMC2; IFI30; SAA1; VIM; TGFBI; TMEM45A; GABRP; PTPRM | LAMC2; IFI30; SAA1; VIM; TGFBI; TIMP2; GBP1; SNAI2; TMEM45A; GABRP; EFEMP1; PTPRM; CPSF6; PTPN13; VGLL1; ELF3; SNCG | LAMC2; IFI30; SAA1; VIM; TGFBI; TIMP2; GBP1; SNAI2; GBP5; POSTN; TNC; F3; BGN; TMEM45A; GABRP; EFEMP1; HIST1H2BF; IFI16; MALL; MMP12; SPRR1B; TGM2; TPX2; PTPRM; CPSF6; PTPN13; VGLL1; ELF3; ACER2; ACOX1; CDH1; F11R; PPARG; RNF128; SCCPDH; SFN; STS; TACSTD2; TMEM45B; SNCG; AHR; INA; PM20D1; GRHL3 | LAMC2; IFI30; SAA1; VIM; TGFBI; TIMP2; GBP1; SNAI2; GBP5; POSTN; TNC; F3; BGN; CCL5; SULF1; WARS; MMP3; CXCL10; TIMP3; SERPINB1; DDIT4; TMEM45A; GABRP; EFEMP1; HIST1H2BF; IFI16; MALL; MMP12; SPRR1B; TGM2; TPX2; CLDN1; GOS2; IFITM2; PTMS; PTPRM; CPSF6; PTPN13; VGLL1; ELF3; ACER2; ACOX1; CDH1; F11R; PPARG; RNF128; SCCPDH; SFN; STS; TACSTD2; TMEM45B; BTG2; GRHL1; IFI6; RALBP1; IGFBP3; SNCG; AHR; INA; PM20D1; GRHL3; ACTA2; ACTG2; CYP1A1; DUSP1; HLA-DRB5; MAL; SPINK1; UPK1A |

Although the invention has been described with reference to the above examples, it will be understood that modifications and variations are encompassed within the spirit and scope of the invention, Accordingly, the invention is limited only by the following claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11208697B2). An electronic copy of the "Sequence Listing" will also be available from the USPTO upon request and payment of the fee set forth in 37 CFR 1.19(b)(3).

What is claimed is:

1. A method for treating a subject with muscle-invasive bladder cancer, the method comprising:
  a) obtaining or having obtained an expression level of a plurality of genes in a biological sample obtained from a subject with muscle-invasive bladder cancer, wherein the plurality of genes are selected from Intercept, TMEM45B, ERBB2, TNFRSF21, FLRT3, SPINK1, LRRC37A2, SCCPDH, UGT1A3, ZNF486, UGT1A8, PPARG, UGT1A1, AHR, EPCAM, PVRL4, UGT1A4, IGFBP3, S100P, PTPRM, NQO1, RNF138P1, CPSF6, GATA3, UGT1A5, UGT1A10, ELF3, AGR2, EHF, SLC14A1, CXCL17, TMSB10, CCL5, MMP12, SAT1, CD68, ANXA1, IFITM2, KRT5, GJB2, MT1L, NDRG1, ASPN, SULF1, EFEMP1, G0S2, TIMP3, MUC16, GBP1, CGB2, SNAI2, DDIT4, CTSK, GBP5, C3, VIM, BGN, TGFBI, TIMP2, SAA1, LAMC2, FBP1, BAMBI, PAQR7, IGFL1, TMPRSS2, PLXNB2, MAL, TBX3, CRISP3, SCNN1B, RNF128, KRT7, KRT8, ADAM10, SNX31, KRT18, UPK3A, PSCA, UPK2, AHNAK, SPP1, TWIST2, SPARCL1, CASP14, MMP1, LAPTM5, MMP13, DUSP1, HIST1H2BF, GABRP, CFH, SFRP2, SERPINB3, MGP, FGFBP1, SAMD9, ITGA6, MALL, MYL9, IER3, SPRR2F, MMP2, HLA-DRA, DCN, TPM2, HLA-A, LYZ, LUM, COL3A1, POSTN, IFI30, CD74, VCAN, CALD1, COL1A2, HLA-DRB5, OLFM4, THBS2, KRT23, MYH11, CLDN1, RARRES1, HPGD, ACER2, RALBP1, GSTM3, BTBD16, MACC1, SEMASA, ACOX1, GSTM2, CYP4Z2P, ZNF91, STS, TOX3, PLP2, TACSTD2, ATP8B1, GRHL3, TNC, TPX2, DSP, TIMP1, UPK1B, DHRS2, PTN, SNCG, ACTG2, and SYTL2;

b) subtyping the muscle-invasive bladder cancer of the subject according to a genomic subtyping classifier based on the expression level of each of the plurality of genes, wherein said subtyping comprises assigning the muscle-invasive bladder cancer to one of four subtypes selected from the group consisting of a claudin-low subtype, a basal subtype, a luminal-infiltrated subtype, and a luminal non-infiltrated subtype; and c) administering neoadjuvant chemotherapy to the subject when the subtyping of step b) indicates that the subject has the basal subtype and administering an anti-cancer treatment other than the neoadjuvant chemotherapy to the subject when the subtyping of step b) indicates that the subject has the luminal-infiltrated subtype, the luminal non-infiltrated subtype, or the claudin-low subtype, wherein the anti-cancer treatment other than neoadjuvant chemotherapy is selected from the group consisting of surgery, radiation therapy, immunotherapy, biological therapy, hormonal therapy, and photodynamic therapy.

2. The method of claim 1, wherein the neoadjuvant chemotherapy comprises administering cisplatin.

3. The method of claim 1, wherein the biological sample is a biopsy.

4. The method of claim 1, wherein the biological sample is a urine sample or a bladder tumor sample.

5. The method of claim 1, wherein the biological sample is a transurethral resection (TUR) specimen.

6. The method of claim 1, wherein the subject is a human being.

7. The method of claim 1, wherein the level of expression is increased or reduced compared to a control.

8. The method of claim 1, wherein said level of expression is obtained by performing in situ hybridization, a PCR-based method, an array-based method, an immunohistochemical method, an RNA assay method, or an immunoassay method.

9. The method of claim 8, wherein said level of expression is obtained by using a reagent selected from the group consisting of a nucleic acid probe, one or more nucleic acid primers, and an antibody.

10. The method of claim 9, wherein said level of expression is obtained by measuring the level of an RNA transcript.

11. The method of claim 9, wherein after administering neoadjuvant chemotherapy to the subject when the subtyping of step b) indicates that the subject has the basal subtype, the method further comprises administering one cancer treatment selected from the group consisting of surgery, radiation therapy, immunotherapy, biological therapy, hormonal therapy, and photodynamic therapy.

* * * * *

UNITED STATES PATENT AND TRADEMARK OFFICE
CERTIFICATE OF CORRECTION

PATENT NO.      : 11,208,697 B2
APPLICATION NO. : 15/875871
DATED           : December 28, 2021
INVENTOR(S)     : Elai Davicioni et al.

It is certified that error appears in the above-identified patent and that said Letters Patent is hereby corrected as shown below:

In the Specification

At Column 5, Line 6, delete "SEMASA," and insert -- SEMASA --.

At Columns 51-52, Line 15 of "TABLE 1 – continued", delete "PT3/4" and insert -- pT3/4 --.

In the Claims

At Column 465, Line 56, delete "Intercept,".

At Column 466, Line 56, delete "SEMASA", and insert -- SEMA5A --.

Signed and Sealed this
Ninth Day of July, 2024

Katherine Kelly Vidal
*Director of the United States Patent and Trademark Office*